US012543982B2

(12) United States Patent
Shelton, IV et al.

(10) Patent No.: US 12,543,982 B2
(45) Date of Patent: Feb. 10, 2026

(54) METHOD OF ADJUSTING A SURGICAL PARAMETER BASED ON BIOMARKER MEASUREMENTS

(71) Applicant: Cilag GmbH International, Zug (CH)

(72) Inventors: Frederick E. Shelton, IV, Hillsboro, OH (US); Kevin M. Fiebig, Cincinnati, OH (US); Demetrius Harris, Cincinnati, OH (US); Jason L. Harris, Lebanon, OH (US); Chad Edward Eckert, Terrace Park, OH (US); Andréas N. Ward, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 603 days.

(21) Appl. No.: 17/156,287

(22) Filed: Jan. 22, 2021

(65) Prior Publication Data

US 2022/0233119 A1 Jul. 28, 2022

(51) Int. Cl.

| | |
|---|---|
| ***A61B 5/16*** | (2006.01) |
| ***A61B 5/117*** | (2016.01) |
| ***G16H 10/60*** | (2018.01) |
| ***G16H 80/00*** | (2018.01) |

(52) U.S. Cl.

CPC .............. *A61B 5/165* (2013.01); *A61B 5/117* (2013.01); *G16H 10/60* (2018.01); *G16H 80/00* (2018.01); *A61B 2560/0487* (2013.01)

(58) Field of Classification Search

CPC . A61B 5/165; A61B 5/117; A61B 2560/0487; G16H 10/60; G16H 80/00

USPC .......................................................... 600/300

See application file for complete search history.

(56) References Cited

U.S. PATENT DOCUMENTS

| | | | |
|---|---|---|---|
| 5,406,914 | A | 4/1995 | Hyppanen |
| 5,494,546 | A | 2/1996 | Horvath |
| 6,003,135 | A | 12/1999 | Bialick et al. |
| 6,036,446 | A | 3/2000 | Goodman |
| 6,317,731 | B1 | 11/2001 | Luciano |
| 6,491,701 | B2 | 12/2002 | Tierney et al. |

(Continued)

FOREIGN PATENT DOCUMENTS

| | | | |
|---|---|---|---|
| CA | 3032139 | A1 | 2/2018 |
| CA | 3080325 | A1 | 5/2019 |

(Continued)

OTHER PUBLICATIONS

U.S. Appl. No. 17/156,296, filed Jan. 22, 2021, Shelton, et al.

(Continued)

*Primary Examiner* — Michael T. Holtzclaw

(74) *Attorney, Agent, or Firm* — Condo Roccia Koptiw LLP

(57) ABSTRACT

A surgical computing system may receive usage data associated with movement of a surgical instrument and user inputs to the surgical instrument. The surgical computing system may receive motion and/or biomarker sensor data from sensing systems applied to the operator of the surgical instrument. The surgical computing system may determine, based on at least one of the usage data and/or the sensor data, a control feature for implementation by the surgical instrument. The surgical computing system may communicate the determined control feature(s) to the surgical instrument. The surgical instrument may modify its operation based on the control features.

20 Claims, 156 Drawing Sheets

(56) References Cited

U.S. PATENT DOCUMENTS

| | | | |
|---|---|---|---|
| 6,840,913 B2 | 1/2005 | Mansy et al. | |
| 7,321,862 B2 | 1/2008 | Rosenfeld et al. | |
| 8,210,411 B2 | 7/2012 | Yates et al. | |
| 8,417,342 B1 | 4/2013 | Abell | |
| 8,512,260 B2 | 8/2013 | Grudic et al. | |
| 8,583,224 B2 | 11/2013 | Lee et al. | |
| 8,591,459 B2 | 11/2013 | Clymer et al. | |
| 8,696,616 B2 | 4/2014 | Baynham et al. | |
| 8,864,009 B2 | 10/2014 | Shelton et al. | |
| 9,011,427 B2 | 4/2015 | Price et al. | |
| 9,028,407 B1 | 5/2015 | Bennett-guerrero | |
| 9,072,535 B2 | 7/2015 | Shelton et al. | |
| 9,123,155 B2 | 9/2015 | Cunningham et al. | |
| 9,345,481 B2 | 5/2016 | Hall et al. | |
| 9,456,779 B2 | 10/2016 | Clymer et al. | |
| 9,525,482 B1 | 12/2016 | Tse | |
| 9,621,357 B2 * | 4/2017 | Williams | H04L 63/101 |
| 9,700,317 B2 | 7/2017 | Aronhalt et al. | |
| 9,750,442 B2 | 9/2017 | Olsen | |
| 9,855,431 B2 | 1/2018 | Ternes et al. | |
| 9,974,903 B1 | 5/2018 | Davis et al. | |
| 10,065,658 B2 | 9/2018 | Deligianni et al. | |
| 10,194,873 B2 | 2/2019 | Colman et al. | |
| 10,335,031 B1 | 7/2019 | Kundu et al. | |
| 10,467,327 B1 | 11/2019 | Arazi | |
| 10,535,020 B2 * | 1/2020 | Experton | G06Q 10/06 |
| 10,653,368 B1 | 5/2020 | Mcnair | |
| 10,813,710 B2 | 10/2020 | Grubbs | |
| 10,943,692 B1 | 3/2021 | Lynn et al. | |
| 10,993,645 B2 | 5/2021 | Naseri et al. | |
| 11,099,647 B2 | 8/2021 | Ang et al. | |
| 11,182,576 B1 | 11/2021 | Bhushan et al. | |
| 11,238,012 B1 | 2/2022 | Liang et al. | |
| 11,240,404 B2 | 2/2022 | Bangs et al. | |
| 11,322,248 B2 | 5/2022 | Grantcharov et al. | |
| 11,328,806 B2 | 5/2022 | Vaccaro | |
| 11,543,887 B2 | 1/2023 | Ang et al. | |
| 11,564,620 B2 | 1/2023 | Clymer et al. | |
| 11,728,033 B2 | 8/2023 | Spenciner et al. | |
| 11,763,947 B2 | 9/2023 | Baronov et al. | |
| 2002/0111830 A1 * | 8/2002 | Tahan | G16H 10/65 705/3 |
| 2002/0183734 A1 | 12/2002 | Bommannan et al. | |
| 2003/0139942 A1 * | 7/2003 | Rakshit | G16H 10/60 705/2 |
| 2003/0157187 A1 | 8/2003 | Hunter | |
| 2004/0071323 A1 | 4/2004 | Darzi et al. | |
| 2004/0096817 A1 | 5/2004 | Diamond et al. | |
| 2005/0021369 A1 | 1/2005 | Cohen et al. | |
| 2005/0175703 A1 | 8/2005 | Hunter et al. | |
| 2005/0234612 A1 | 10/2005 | Bottomley et al. | |
| 2006/0085227 A1 | 4/2006 | Rosenfeld et al. | |
| 2007/0136218 A1 | 6/2007 | Bauer et al. | |
| 2007/0156624 A1 | 7/2007 | Palma | |
| 2007/0249949 A1 | 10/2007 | Hadley | |
| 2008/0064965 A1 | 3/2008 | Jay et al. | |
| 2008/0300915 A1 * | 12/2008 | Molmenti | G16H 10/60 705/2 |
| 2008/0306763 A1 | 12/2008 | James | |
| 2008/0319275 A1 | 12/2008 | Chiu et al. | |
| 2009/0299924 A1 | 12/2009 | Bauer et al. | |
| 2010/0228314 A1 | 9/2010 | Goetz | |
| 2011/0015942 A1 | 1/2011 | Oakley et al. | |
| 2011/0054290 A1 | 3/2011 | Derchak | |
| 2011/0152759 A1 | 6/2011 | Clymer et al. | |
| 2011/0319723 A1 | 12/2011 | Ziegler et al. | |
| 2011/0319746 A1 | 12/2011 | Kochba et al. | |
| 2012/0116365 A1 | 5/2012 | Price et al. | |
| 2012/0132211 A1 | 5/2012 | Halperin et al. | |
| 2012/0253360 A1 | 10/2012 | White et al. | |
| 2012/0259389 A1 | 10/2012 | Starkebaum et al. | |
| 2012/0265549 A1 | 10/2012 | Virolainen | |
| 2012/0310670 A1 * | 12/2012 | Pruitt | G06Q 10/10 705/2 |
| 2012/0323592 A1 | 12/2012 | Bechtel et al. | |
| 2013/0038707 A1 | 2/2013 | Cunningham et al. | |
| 2013/0137941 A1 | 5/2013 | Schardey | |
| 2013/0245481 A1 | 9/2013 | Tremper | |
| 2013/0265919 A1 | 10/2013 | Pochiraju et al. | |
| 2014/0051921 A1 | 2/2014 | Miller et al. | |
| 2014/0051950 A1 | 2/2014 | Clymer et al. | |
| 2014/0081659 A1 | 3/2014 | Nawana et al. | |
| 2014/0107504 A1 | 4/2014 | Stapelfeldt et al. | |
| 2014/0157288 A1 | 6/2014 | Wong | |
| 2014/0236159 A1 | 8/2014 | Haider et al. | |
| 2014/0263541 A1 | 9/2014 | Leimbach et al. | |
| 2014/0263551 A1 | 9/2014 | Hall et al. | |
| 2014/0263552 A1 | 9/2014 | Hall et al. | |
| 2014/0287393 A1 | 9/2014 | Kumar et al. | |
| 2014/0302509 A1 | 10/2014 | Moerman et al. | |
| 2014/0378500 A1 | 12/2014 | Cohen et al. | |
| 2015/0071909 A1 | 3/2015 | Rezaie et al. | |
| 2015/0123769 A1 | 5/2015 | Dalal et al. | |
| 2015/0126839 A1 | 5/2015 | Li et al. | |
| 2015/0173674 A1 | 6/2015 | Hayes et al. | |
| 2015/0173697 A1 | 6/2015 | Parks et al. | |
| 2015/0199010 A1 | 7/2015 | Coleman et al. | |
| 2015/0250445 A1 | 9/2015 | Spiegel et al. | |
| 2015/0289929 A1 | 10/2015 | Toth et al. | |
| 2015/0302536 A1 * | 10/2015 | Wahl | G06Q 50/00 705/2 |
| 2015/0302538 A1 | 10/2015 | Mazar et al. | |
| 2015/0302539 A1 | 10/2015 | Mazar et al. | |
| 2015/0317230 A1 | 11/2015 | Le Grand | |
| 2016/0000631 A1 | 1/2016 | Becker | |
| 2016/0030240 A1 | 2/2016 | Gonenc et al. | |
| 2016/0058380 A1 | 3/2016 | Lee et al. | |
| 2016/0110504 A1 * | 4/2016 | Fialkov | G16H 80/00 705/2 |
| 2016/0239611 A1 | 8/2016 | Heldt et al. | |
| 2016/0242646 A1 | 8/2016 | Obma | |
| 2016/0287184 A1 | 10/2016 | Diebold et al. | |
| 2016/0303340 A1 | 10/2016 | Sinderby et al. | |
| 2016/0331248 A1 | 11/2016 | Satish et al. | |
| 2017/0041688 A1 | 2/2017 | Pitigoi-aron et al. | |
| 2017/0068785 A1 * | 3/2017 | Experton | H04W 12/02 |
| 2017/0119300 A1 | 5/2017 | Conner | |
| 2017/0143268 A1 | 5/2017 | Kovacs et al. | |
| 2017/0228501 A1 * | 8/2017 | Turner, Jr. | G06Q 30/0277 |
| 2017/0231508 A1 | 8/2017 | Edwards et al. | |
| 2017/0258408 A1 | 9/2017 | Stapelfeldt | |
| 2017/0281064 A1 | 10/2017 | Bayon | |
| 2017/0296139 A1 | 10/2017 | Giaya et al. | |
| 2017/0296213 A1 | 10/2017 | Swensgard et al. | |
| 2017/0304400 A1 | 10/2017 | Poznansky et al. | |
| 2017/0311807 A1 | 11/2017 | Fu et al. | |
| 2017/0326190 A1 | 11/2017 | Ansell et al. | |
| 2017/0331881 A1 | 11/2017 | Chandramouli et al. | |
| 2017/0360358 A1 | 12/2017 | Amiot et al. | |
| 2018/0028088 A1 | 2/2018 | Garbey et al. | |
| 2018/0042681 A1 | 2/2018 | Jagga | |
| 2018/0090029 A1 | 3/2018 | Fisher | |
| 2018/0102960 A1 | 4/2018 | Rickert et al. | |
| 2018/0168579 A1 | 6/2018 | Aronhalt et al. | |
| 2018/0174680 A1 | 6/2018 | Sampath et al. | |
| 2018/0256051 A1 | 9/2018 | Stone et al. | |
| 2018/0262656 A1 | 9/2018 | Uchida et al. | |
| 2018/0286521 A1 | 10/2018 | Fong | |
| 2018/0353112 A1 | 12/2018 | Dassau et al. | |
| 2018/0360451 A1 | 12/2018 | Shelton, IV et al. | |
| 2018/0360452 A1 | 12/2018 | Shelton et al. | |
| 2019/0013099 A1 | 1/2019 | Esterberg et al. | |
| 2019/0014992 A1 | 1/2019 | Mestek et al. | |
| 2019/0048077 A1 | 2/2019 | Tsai et al. | |
| 2019/0059932 A1 | 2/2019 | Isosaki et al. | |
| 2019/0069957 A1 | 3/2019 | Barral et al. | |
| 2019/0076380 A1 | 3/2019 | Baron et al. | |
| 2019/0079916 A1 * | 3/2019 | Eyigoz | G06F 40/211 |
| 2019/0104919 A1 | 4/2019 | Shelton, IV et al. | |
| 2019/0113520 A1 | 4/2019 | Blume et al. | |
| 2019/0113973 A1 | 4/2019 | Coleman et al. | |
| 2019/0133497 A1 | 5/2019 | Moore | |
| 2019/0190635 A1 | 6/2019 | Goel et al. | |
| 2019/0192072 A1 | 6/2019 | Bailey et al. | |

(56) References Cited

U.S. PATENT DOCUMENTS

| | | | |
|---|---|---|---|
| 2019/0200844 A1 | 7/2019 | Shelton et al. | |
| 2019/0200981 A1 | 7/2019 | Harris et al. | |
| 2019/0201033 A1 | 7/2019 | Yates et al. | |
| 2019/0201043 A1 | 7/2019 | Shelton, IV et al. | |
| 2019/0201102 A1 | 7/2019 | Shelton, IV et al. | |
| 2019/0201104 A1 | 7/2019 | Shelton, IV et al. | |
| 2019/0201115 A1 | 7/2019 | Shelton, IV et al. | |
| 2019/0201129 A1 | 7/2019 | Shelton, IV et al. | |
| 2019/0201130 A1 | 7/2019 | Shelton, IV et al. | |
| 2019/0201136 A1 | 7/2019 | Shelton, IV et al. | |
| 2019/0201137 A1 | 7/2019 | Shelton et al. | |
| 2019/0201140 A1 | 7/2019 | Yates et al. | |
| 2019/0204201 A1 | 7/2019 | Shelton, IV et al. | |
| 2019/0206003 A1 | 7/2019 | Harris et al. | |
| 2019/0206050 A1 | 7/2019 | Yates et al. | |
| 2019/0206562 A1 | 7/2019 | Shelton, IV et al. | |
| 2019/0206563 A1 | 7/2019 | Shelton, IV et al. | |
| 2019/0206565 A1 | 7/2019 | Shelton, IV | |
| 2019/0206569 A1 | 7/2019 | Shelton et al. | |
| 2019/0216452 A1 | 7/2019 | Nawana et al. | |
| 2019/0223961 A1 | 7/2019 | Barral et al. | |
| 2019/0258672 A1* | 8/2019 | Sadrieh | G16H 40/20 |
| 2019/0259476 A1* | 8/2019 | Armijos | G06F 16/90335 |
| 2019/0283247 A1 | 9/2019 | Chang et al. | |
| 2019/0392162 A1* | 12/2019 | Stern | G06F 21/6245 |
| 2020/0022593 A1 | 1/2020 | Schardey | |
| 2020/0107781 A1 | 4/2020 | Navalgund et al. | |
| 2020/0131581 A1 | 4/2020 | Jain et al. | |
| 2020/0143594 A1 | 5/2020 | Lal et al. | |
| 2020/0168313 A1 | 5/2020 | Westerhoff | |
| 2020/0168334 A1 | 5/2020 | Mowery | |
| 2020/0184850 A1 | 6/2020 | Pugh | |
| 2020/0188028 A1 | 6/2020 | Feiner et al. | |
| 2020/0204631 A1 | 6/2020 | Subramaniam et al. | |
| 2020/0205900 A1 | 7/2020 | Buckland et al. | |
| 2020/0237452 A1 | 7/2020 | Wolf et al. | |
| 2020/0246081 A1 | 8/2020 | Johnson et al. | |
| 2020/0268472 A1 | 8/2020 | Wolf et al. | |
| 2020/0273575 A1 | 8/2020 | Wolf et al. | |
| 2020/0273581 A1 | 8/2020 | Wolf et al. | |
| 2020/0297422 A1 | 9/2020 | Gocho et al. | |
| 2020/0315454 A1 | 10/2020 | Gregg | |
| 2020/0315734 A1 | 10/2020 | El Amm | |
| 2020/0375433 A1 | 12/2020 | Polosky et al. | |
| 2020/0386772 A1 | 12/2020 | Noar | |
| 2020/0394334 A1* | 12/2020 | Bulut | G06N 5/048 |
| 2020/0397515 A1 | 12/2020 | Frimer et al. | |
| 2021/0000347 A1 | 1/2021 | Stump | |
| 2021/0000558 A1 | 1/2021 | Penny et al. | |
| 2021/0005321 A1 | 1/2021 | Hwang | |
| 2021/0007774 A1 | 1/2021 | Rodrigues et al. | |
| 2021/0015432 A1 | 1/2021 | Konno et al. | |
| 2021/0069513 A1 | 3/2021 | Beer et al. | |
| 2021/0077035 A1 | 3/2021 | Kayser et al. | |
| 2021/0098088 A1* | 4/2021 | Hashimoto | G16H 50/20 |
| 2021/0117868 A1 | 4/2021 | Sriharsha | |
| 2021/0137624 A1 | 5/2021 | Maret | |
| 2021/0158955 A1 | 5/2021 | Azizian et al. | |
| 2021/0196384 A1 | 7/2021 | Shelton, IV et al. | |
| 2021/0196423 A1 | 7/2021 | Shelton, IV et al. | |
| 2021/0196425 A1 | 7/2021 | Shelton, IV et al. | |
| 2021/0220064 A1 | 7/2021 | Kottenstette et al. | |
| 2021/0228276 A1 | 7/2021 | Giraldez et al. | |
| 2021/0241869 A1* | 8/2021 | Muse | G06F 9/542 |
| 2021/0257095 A1 | 8/2021 | Zacharia | |
| 2021/0259789 A1 | 8/2021 | Wright et al. | |
| 2021/0313052 A1 | 10/2021 | Makrinich et al. | |
| 2021/0346583 A1 | 11/2021 | Diaz-chiosa et al. | |
| 2021/0346853 A1 | 11/2021 | Hull et al. | |
| 2021/0378752 A1 | 12/2021 | Paul et al. | |
| 2021/0386489 A1 | 12/2021 | Wright et al. | |
| 2022/0022982 A1 | 1/2022 | Hares et al. | |
| 2022/0079675 A1 | 3/2022 | Lang | |
| 2022/0104896 A1 | 4/2022 | Shelton, IV et al. | |
| 2022/0193340 A1 | 6/2022 | Patel et al. | |
| 2022/0387995 A1 | 12/2022 | Kurabayashi et al. | |
| 2022/0409285 A1 | 12/2022 | Chow et al. | |
| 2023/0113555 A1 | 4/2023 | Dugan | |
| 2023/0145790 A1 | 5/2023 | Walker et al. | |
| 2023/0282339 A1 | 9/2023 | Flexman et al. | |
| 2024/0099647 A1 | 3/2024 | Pelssers et al. | |

FOREIGN PATENT DOCUMENTS

| | | | |
|---|---|---|---|
| CA | 3101092 | A1 | 10/2019 |
| CN | 109575143 | A | 4/2019 |
| CN | 111616803 | A | 9/2020 |
| CN | 112220562 | A | 1/2021 |
| EP | 3501459 | A2 | 6/2019 |
| EP | 3671305 | A1 | 6/2020 |
| EP | 3671759 | A1 * | 6/2020 |
| EP | 3895613 | A1 | 10/2021 |
| GB | 2333882 | A | 8/1999 |
| JP | 2019-525276 | A | 9/2019 |
| JP | 2019-177134 | A | 10/2019 |
| WO | 2007025218 | A2 | 3/2007 |
| WO | 2007/096931 | A2 | 8/2007 |
| WO | 2010017192 | A1 | 2/2010 |
| WO | 2016/046634 | A1 | 3/2016 |
| WO | 2017/098503 | A1 | 6/2017 |
| WO | 2017/147652 | A1 | 9/2017 |
| WO | 2018023037 | A1 | 2/2018 |
| WO | 2019084469 | A1 | 5/2019 |
| WO | 2019130075 | A1 | 7/2019 |
| WO | 2019130085 | A1 | 7/2019 |
| WO | 2019147718 | A1 | 8/2019 |
| WO | 2019181432 | A1 | 9/2019 |
| WO | 2019200222 | A1 | 10/2019 |
| WO | 2020075546 | A1 | 4/2020 |
| WO | 2020/092701 | A2 | 5/2020 |
| WO | 2020/180917 | A1 | 9/2020 |
| WO | 2020/191494 | A1 | 10/2020 |
| WO | 2021/007418 | A2 | 1/2021 |
| WO | 2021/126163 | A1 | 6/2021 |

OTHER PUBLICATIONS

U.S. Appl. No. 17/156,300, filed Jan. 22, 2021, Shelton, et al.
U.S. Appl. No. 17/156,304, filed Jan. 22, 2021, Shelton, et al.
U.S. Appl. No. 17/156,266, filed Jan. 22, 2021, Shelton, et al.
U.S. Appl. No. 17/156,318, filed Jan. 22, 2021, Shelton, et al.
U.S. Appl. No. 17/156,309, filed Jan. 22, 2021, Shelton, et al.
U.S. Appl. No. 17/156,306, filed Jan. 22, 2021, Shelton, et al.
U.S. Appl. No. 17/156,321, filed Jan. 22, 2021, Shelton, et al.
U.S. Appl. No. 17/156,281, filed Jan. 22, 2021, Shelton, et al.
U.S. Appl. No. 17/156,272, filed Jan. 22, 2021, Shelton, et al.
U.S. Appl. No. 17/156,279, filed Jan. 22, 2021, Shelton, et al.
U.S. Appl. No. 17/156,284, filed Jan. 22, 2021, Shelton, et al.
U.S. Appl. No. 17/156,282, filed Jan. 22, 2021, Shelton, et al.
U.S. Appl. No. 17/156,269, filed Jan. 22, 2021, Shelton, et al.
U.S. Appl. No. 17/156,286, filed Jan. 22, 2021, Shelton, et al.
U.S. Appl. No. 17/156,324, filed Jan. 22, 2021, Shelton, et al.
U.S. Appl. No. 17/156,329, filed Jan. 22, 2021, Shelton, et al.
U.S. Appl. No. 17/156,289, filed Jan. 22, 2021, Shelton, et al.
U.S. Appl. No. 17/156,293, filed Jan. 22, 2021, Shelton, et al.
U.S. Appl. No. 17/156,298, filed Jan. 22, 2021, Shelton, et al.
U.S. Appl. No. 17/156,274, filed Jan. 22, 2021, Shelton, et al.
U.S. Appl. No. 17/156,278, filed Jan. 22, 2021, Shelton, et al.
U.S. Appl. No. 17/062,509, filed Oct. 2, 2020, Shelton, et al.
U.S. Appl. No. 62/611,341, filed Dec. 28, 2017, Shelton, et al.
Aliverti, et al., "Wearable technology: role in respiratory health and disease", Breathe, 2017, 10 pages.
Kazamias, et al., "Blood pressure measurement with Doppler ultrasonic flowmeter", Journal of Applied Physiology vol. 30, No. 4, Apr. 1971, 1 page.
Cerfolio, et a., "Prospective Randomized Trial Compares Suction Versus Water Seal for Air Leaks", General Thoracic, May 1, 2001, 5 pages.
Brunelli, et al., "A Scoring System to Predict the Risk of Prolonged Air Leak After Lobectomy", General Thoracic, 2010, 6 pages.

(56) References Cited

OTHER PUBLICATIONS

Jacob, et al., "Clinical applications of magnets on cardiac rhythm management devices", European Society of Cardiology, May 26, 2011, 9 pages.
Carroll, et al., "Multi-Sensor Esophageal Temperature Probe Used During Radiofrequency Ablation for Atrial Fibrillation is Associated with Increased Intraluminal Temperature Detection and Increased Risk of Esophageal Injury Compared to Single-Sensor Probe", Journal of Cardiovascular Electrophysiology vol. 24, No. 9, Sep. 2013, 8 pages.
Singh, et al., "Esophageal Injury and Temperature Monitoring During Atrial Fibrillation Ablation", American Heart Association, Circulation: Arrhythmia and Electrophysiology, vol. 1, issue 3, Aug. 1, 2008, 7 pages.
Nair, et al., "Atrioesophageal Fistula: A Review", Journal of Atrial Fibrillation vol. 8, Issue 3, Oct. Nov. 2015, 6 pages.
Drewry, et al., "Body temperature patterns as a predictor of hospital-acquired sepsis in afebrile adult intensive care unit patients: a case-control study", Critical Care 2013, 11 pages.
Diduch, et al., "Synchronization of Data Streams in Distributed Realtime Multimodal Signal Processing Environments Using Commodity Hardware", 4 pages.
Kwon, et al., "Electrocardiogram Sampling Frequency Range Acceptable for Heart Rate Variability Analysis", The Korean Society of Medical Informatics, 2018 pages.
Pouchard, et al., "Open Standards for Sensor Information Processing", Oak Ridge National Laboratory, Jul. 2009, 49 pages.
Appelboom et al., "The Promise of Wearable Activity Sensors to Define Patient Recovery", Journal of Clinical Neuroscience, vol. 21, 2014, pp. 1089-1093.
Chen et al., "Type of Pelvic Disease as a Risk Factor for Surgical Site Infection in Women Undergoing Hysterectomy", Journal of Minimally Invasive Gynecology, vol. 26, No. 6, Sep. 1, 2019, pp. 1149-1156.
Erowele et al., "Treatment Options for Postoperative Ileus", U.S. Pharmacist, vol. 35, No. 12, 2010, 16 pages.
Fang et al., "Review of Colonic Anastomotic Leakage and Prevention Methods", Journal of Clinical Medicine, vol. 9, No. 4061, Dec. 16, 2020, 17 pages.
Jinbin, "Feedback Loops—Friend or Foe?", Available at <https://medium.com/unpackai/feedback-loops-friend-or-foe-81a552203228>, Oct. 19, 2020, pp. 1-3.
Li et al., "Attention-Aware Robotic Laparoscope for Human-Robot Cooperative Surgery", IEEE International Conference on Robotics and Biomimetics (ROBIO), 2013, 6 pages.
Machado, Lovina S. M., "Emergency Peripartum Hysterectomy: Incidence, Indications, Risk Factors and Outcome", North American Journal of Medical Sciences, vol. 3, No. 8, Aug. 2011, doi: 10.4297/najms.2011.358, pp. 358-361.
Sugino et al., "Surgical Task Analysis of Simulated Laparoscopic Cholecystectomy with a Navigation System", International Journal of Computer Assisted Radiology and Surgery, vol. 9, Jan. 14, 2014, pp. 825-836.
Clarke-Pearson, et al., "Complications of A Hysterectomy", Clinical Expert Series, vol. 121, No. 3, Mar. 2013, pp. 654-673.
Derbyshire, Philip J. et al., "Lactate in human sweat: a critical review of research to the present day", J Physio Sci 62, Jun. 2012, 12 pages.
Misic, Dragan et al., "Real-Time Monitoring of Bone Fracture Recovery by Using Aware, Sensing, Smart, and Active Orthopedic Devices", 8 pages.
Ewenighi, Chinwe O. et al., "Electrolyte changes and urinalysis pattern in patients with vesicovaginal fistula compared to their healthy controls", Journal of Experimental and Integrative Medicine; Oct.-Dec. 2014; vol. 4., Issue 4, 2014, 5 pages.
Szarka, Lawrence A. et al., "Methods for measurement of gastric mobility", American Journal of Physiology—Gastrointestinal and Liver Physiology 296.3, Jan. 15, 2009, 15 pages.
Gill, et al., "Urinary Leakage following hysterectomy", Cambridge University Press, 2014, pp. 261-262.
Johnston, et al., "Postoperative Hypoglycemia is Associated with Worse Outcomes After Cardian Surery", 2017, 526-532.
International Search Report and Written Opinion, received for PCT Application No. PCT/IB2022/050515, mailed on May 17, 2022, 17 pages.
Davies et al., "Preoperative Optimization of the High-Risk Surgical Patient", British Journal of Anaesthesia, vol. 93, No. 1, pp. 121-128, Apr. 30, 2004.
Foroutan et al., "An Increase in Heart Rate Variability Can Be an Index for End Point of Resuscitation in Trauma Patients", Chinese Journal of Traumatology, vol. 22, No. 3, pp. 134-137, Apr. 16, 2019.
Gehrich et al., "Risk of Postoperative Urinary Tract Infections Following Midurethral Sling Operations in Women Undergoing Hysterectomy", International Urogynecology Journal, vol. 27, No. 3, pp. 483-490, Oct. 14, 2015.
International Search Report and Written Opinion, received for PCT Application No. PCT/IB2022/050508, mailed on Mar. 24, 2022, 11 pages.
International Search Report and Written Opinion, received for PCT Application No. PCT/IB2022/050537, mailed on Apr. 7, 2022, 16 pages.
International Search Report and Written Opinion, received for PCT Application No. PCT/IB2022/050511, mailed on Mar. 25, 2022, 17 pages.
International Search Report and Written Opinion, received for PCT Application No. PCT/IB2022/050513, mailed on Mar. 25, 2022, 16 pages.
International Search Report and Written Opinion, received for PCT Application No. PCT/IB2022/050518, mailed on Mar. 25, 2022, 15 pages.
International Search Report and Written Opinion, received for PCT Application No. PCT/IB2022/050522, mailed on May 2, 2022, 17 pages.
International Search Report and Written Opinion, received for PCT Application No. PCT/IB2022/050524, mailed on Apr. 21, 2022, 19 pages.
International Search Report and Written Opinion, received for PCT Application No. PCT/IB2022/050525, mailed on May 4, 2022, 16 pages.
International Search Report and Written Opinion, received for PCT Application No. PCT/IB2022/050529, mailed on Apr. 20, 2022, 12 pages.
International Search Report and Written Opinion, received for PCT Application No. PCT/IB2022/050530, mailed on Apr. 25, 2022, 18 pages.
International Search Report and Written Opinion, received for PCT Application No. PCT/IB2022/050531, mailed on Apr. 13, 2022, 13 pages.
International Search Report and Written Opinion, received for PCT Application No. PCT/IB2022/050533, mailed on Apr. 13, 2022, 14 pages.
International Search Report and Written Opinion, received for PCT Application No. PCT/IB2022/050534, mailed on Apr. 22, 2022, 16 pages.
International Search Report and Written Opinion, received for PCT Application No. PCT/IB2022/050540, mailed on Jul. 26, 2022, 16 pages.
International Search Report and Written Opinion, received for PCT Application No. PCT/IB2022/050541, mailed on Jun. 7, 2022, 17 pages.
International Search Report and Written Opinion, received for PCT Application No. PCT/IB2022/050542, mailed on May 2, 2022, 17 pages.
International Search Report and Written Opinion, received for PCT Application No. PCT/IB2022/050543, mailed on Apr. 22, 2022, 20 pages.
International Search Report and Written Opinion, received for PCT Application No. PCT/IB2022/050544, mailed on Apr. 28, 2022, 17 pages.
Invitation to Pay Additional Fees, received for PCT Application No. PCT/IB2022/050540, mailed on Apr. 11, 2022, 12 pages.

(56) References Cited

OTHER PUBLICATIONS

Kirchhoff et al., "Complications in Colorectal Surgery: Risk Factors and Preventive Strategies", Patient Safety in Surgery, vol. 04, No. 1, 13 pages, Mar. 25, 2010.
Levine et al., "Computer Automated Total Periopertative Situational Awareness and Safety System", International Congress Series, vol. 1281, pp. 856-861, May 1, 2005.
Macefield et al., "Development of a Single, Practical Measure of Surgical Site Infection (SSI) for Patient Report or Observer Completion", Journal of Infection Prevention, vol. 18, No. 4, pp. 170-179, Jan. 1, 2017.
Petrella et al., "Predicting Prolonged Air Leak After Standard Pulmonary Lobectomy: Computed Tomography Assessment and Risk Factors Stratification", The Surgeon, vol. 9, pp. 72-77, 2011.
Schug et al., "Postoperative Pain Management of the Obese Patient", Best Practice & Research Clinical Anesthesiology, vol. 25, No. 1, pp. 73-81, Jan. 1, 2010.
Stoppelkamp et al., "Identification of Predictive Early Biomarkers for Sterile-SIRS after Cardiovascular Surgery", Plos One, vol. 10, No. 8, 20 pages, Aug. 11, 2015.
Veličković, Jelena V., "The Predictive Performance of the Possum Scoring System and Early Indicators of Peripheral Perfusion for Complications After Major Abdominal Surgery", University of Belgrade, School of Medicine, pp. 1-163, Dec. 31, 2019.

* cited by examiner

PATIENT SENSING - SIGMOID COLECTOMY-5

| Biomarker detectable with a wearable or environmental sensor | | Combinations |
|---|---|---|
| 1 – Blood pH | 17 – Bacteria in respiratory tract | 32 – Physical activity |
| 2 – Hydration state | 18 – Alcohol consumption | 33 – Autonomic tone |
| 3 – Oxygen saturation | 19 – Lactate (sweat) | 34 – Circadian rhythm |
| 4 – Core body temperature | 20 – Peripheral temperature | 35 – Menstrual cycle |
| 5 – Heart rate | 21 – Positivity and optimism 22 – Adrenaline (sweat) | 36 – Sleep |
| 6 – Heart rate variability | 23 – Cortisol | |
| 7 – Sweat rate | 24 – Edema | |
| 8 – Skin conductance | 25 – Mycotoxins | |
| 9 – Blood pressure | 26 – $VO_2$ max | |
| 10 – Light exposure | 27 – Pre-operative pain | |
| 11 – Environmental temperature | 28 – Chemicals in the air | |
| 12 – Respiratory rate | 29 – Circulating tumor cells 30 – Stress and anxiety | |
| 13 – Coughing and sneezing | 31 – Confusion and delirium | |
| 14 – Gastrointestinal motility 15 – Gastrointestinal tract imaging 16 – Tissue perfusion pressure | | |

FIG. 39E

PATIENT SENSING - SLEEVE GASTRECTOMY-2

ACCESS & PREP

1 Lift liver to gain access to stomach 2 Identify anatomy
3 Mobilize stomach - dissect mesentery
4 Identify and ligate blood vessels
5 Place bougie (via oral route)

- Damage to stomach and/or liver during mesentry disection and mobilization.
  - Strength of stomach tissue
  - Strength of liver tissue Harmonic scalpels, bipolar RF:

- Effective dissection of mesentery and adhesions.
  - Thickness of adhesions Fibrous
  - character of adhesions
  - Perfusion of adhesions
- Effective hemostasis.
  - Collagen levels of blood vessels
  - Blood pressure

FIG. 40B

PATIENT SENSING - SLEEVE GASTRECTOMY-3

GASTRIC TRANSECTION

1 Dissect adhesions
2 Transect fundus 3
Remove fundus

- Define staple line to preserve the antrum and ensure suitable blood supply.
  Blood supply of stomach

- Stapling through critical blood vessels, causing ischemia of the stomach.
  Blood supply of stomach Harmonic scalpels, bipolar RF:
- Effective dissection of mesentery and adhesions.
  see prev
- Effective hemostasis.
  see prev
- Accidental damage to stomach or spleen.
  How resilient are these organs in the patient?
  Strength of stomach tissue,
  Strength of spleen Linear stapler:
- Stapling of stomach tissue, aiming to achieve good compression and smooth firing of the stapler.
  - Stomach tissue thickness
  - Stomach tissue friability and Stomach
  - tissue viscoelastic properties

FIG. 40C

PATIENT SENSING - SLEEVE GASTRECTOMY-4

CONCLUSION

1 Check of staple line
2 Check the integrity and adequate form of the angle of His.
3 Endoluminal inspection to check for leaks
4 Remove transected stomach portion
5 Insert drainage tube

FIG. 40D

PATIENT SENSING - SLEEVE GASTRECTOMY-5

POST OP

- How much post operative pain is the patient experiencing?
- Has the patient recovered well?
  - Quality of life

- Leaking post-surgery resulting in slow healing or anastomosis.
  - Repair capacity of stomach tissue
  - pH of stomach acid
  - Volume of stomach acid produced
- Internal bleeding post-surgery.
  - Clotting capacity
  - Blood pressure
- Stricture post-surgery resulting from edema/chronic inflammation.
  - Risk of edema
  - Local and global
  - Inflammatory state of patient
- Infection/sepsis.
  - Risk of infection, compromised immunity Gastroparesis.

- Acute kidney injury.
  - Hydration state of patient
- Hypovolemic shock.
  - Hydration state of patient

FIG. 40E

25180

| Procedural Step | Effected Outcome | Potential Instruments Used During Procedural Step | Relevant Patient Biomarkers |
|---|---|---|---|
| Mobilize Colon | • Homeostasis | • Harmonic Scalpel<br>• Monopolar / Bipolar RF | • Blood Pressure |
| Resect Colon | • Homeostasis<br>• Friability of tissue | • Linear Stapler<br>• Circular Stapler | • Blood Pressure<br>• Edema<br>• Tissue Perfusion Pressure<br>• GI Tract Imaging |
| Anastomosis | • Homeostasis<br>• Friability of tissue | • Circular Stapler | • Blood Pressure<br>• Edema<br>• Tissue Perfusion Pressure<br>• GI Tract Imaging |

FIG. 53

25309

| Procedural Step | Effected Outcome | Potential Instruments Used During Procedural Step | Relevant Patient Biomarkers |
|---|---|---|---|
| Dissect parenchyma | • Homeostasis | • Monopolar Bovie<br>• Harmonic scalpel<br>• Advanced Bipolar RF | • Blood Pressure |
| Transect Arteries and Veins | • Homeostasis | • Harmonic scalpel<br>• Advanced Bipolar RF<br>• Staplers | • Blood Pressure<br>• Tissue perfusion pressure<br>• Edema<br>• Arterial stiffness<br>• Collagen content<br>• Thickness of connective tissue |
| Parenchyma transection | • Pneumostasis | • Staplers | • Edema<br>• Lung tissue thickness<br>• Lung tissue viscoelastic properties<br>• Lung tissue scarring/fibrous characterization |
| Lymph Node Dissection | • Homeostasis | • Monopolar Bovie<br>• Harmonic scalpel<br>• Advanced Bipolar RF | • Blood Pressure<br>• Edema<br>• Tissue Perfusion Pressure<br>• Urinary Tract Imaging |

FIG. 59

25670

| Procedural Step | Effected Outcome | Potential Instruments Used During Procedural Step | Relevant Patient Biomarkers |
|---|---|---|---|
| Trocar Placement | • Homeostasis<br>• Abdominal Adhesions | • Veress needle | • Blood Pressure<br>• Bowel Tract Imaging |
| Desiccate parametrial veins/ligaments | • Homeostasis | • Advanced Bipolar RF<br>• Harmonic Scalpel | • Blood Pressure |
| Mobilize bladder | • Homeostasis | • Harmonic Scalpel | • Blood Pressure |
| Resect uterus/cervix | • Homeostasis<br>• Friability of tissue | • Endopath<br>• Harmonic Scalpel | • Blood Pressure<br>• Edema<br>• Tissue Perfusion Pressure<br>• Urinary Tract Imaging |
| Vaginal cuff closure | • Homeostasis<br>• Friability of tissue | • Suture<br>• LapraTy Clip | • Blood Pressure<br>• Edema<br>• Tissue Perfusion Pressure<br>• Urinary Tract Imaging |

FIG. 70

25890

| Procedural Step | Effected Outcome | Potential Instruments Used During Procedural Step | Relevant Patient Biomarkers |
|---|---|---|---|
| Stomach Mobilization | • Homeostasis | • Harmonic Scalpel<br>• Monopolar / Bipolar RF<br>• Monopolar Bovie | • Blood Pressure |
| Gastric Transection | • Homeostasis<br>• Gastric Content Sealed | • Linear Stapler | • Blood Pressure<br>• Stomach Wall Thickness<br>• Stomach Wall Properties |

FIG. 76

28400
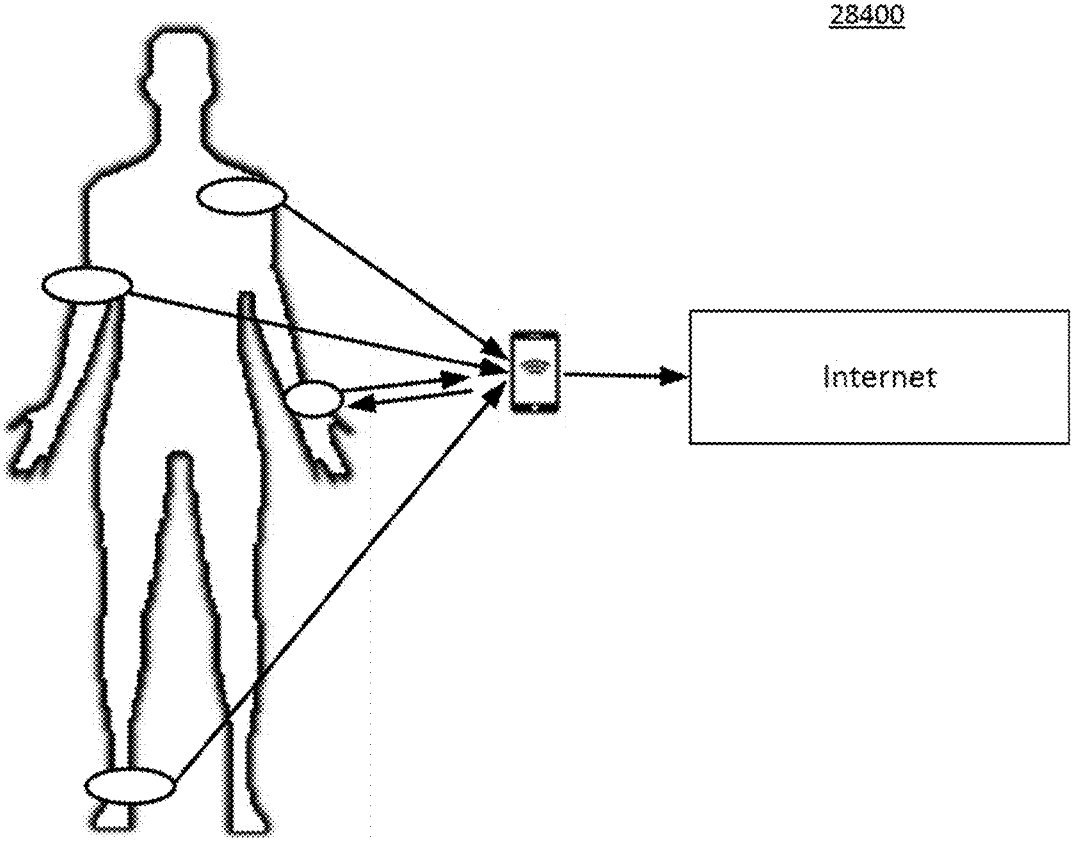
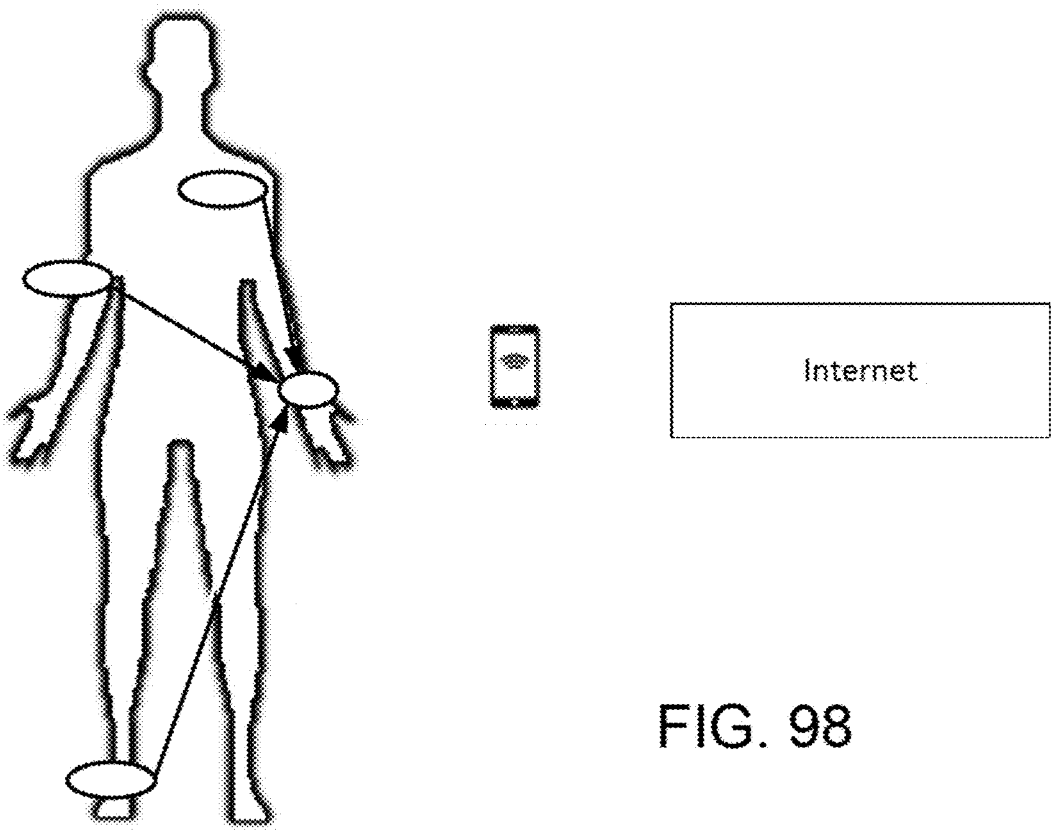
FIG. 98

29100

29618
Master Time Log 29620 29622 29624 29626 29628

| Sensing System ID | Measurement | Hub Receipt Time | Latency | Time Code |
|---|---|---|---|---|
| X | X1 | 6000 | 1800 | 4200 |
| Y | Y1 | 5400 | 1000 | 4400 |
| Z | Z1 | 5700 | 1100 | 4600 |

FIG. 120

METHOD OF ADJUSTING A SURGICAL PARAMETER BASED ON BIOMARKER MEASUREMENTS

CROSS-REFERENCE TO RELATED APPLICATIONS

This application is related to the following, filed contemporaneously, the contents of each of which are incorporated by reference herein:

- U.S. patent application Ser. No. 17/156,296, filed Jan. 22, 2021, titled ADAPTABLE SURGICAL INSTRUMENT CONTROL;
- U.S. patent application Ser. No. 17/156,300, filed Jan. 22, 2021, titled SITUATION ADAPTABLE SURGICAL INSTRUMENT CONTROL;
- U.S. patent application Ser. No. 17/156,304, filed Jan. 22, 2021, titled SURGICAL PROCEDURE MONITORING;
- U.S. patent application Ser. No. 17/156,266, filed Jan. 22, 2021, titled MULTI-SENSOR PROCESSING FOR SURGICAL DEVICE ENHANCEMENT;
- U.S. patent application Ser. No. 17/156,318, filed Jan. 22, 2021, titled PREDICTION OF ADHESIONS BASED ON BIOMARKER MONITORING;
- U.S. patent application Ser. No. 17/156,309, filed Jan. 22, 2021, titled PREDICTION OF BLOOD PERFUSION DIFFICULTIES BASED ON BIOMARKER MONITORING;
- U.S. patent application Ser. No. 17/156,306, filed Jan. 22, 2021, titled PREDICTION OF TISSUE IRREGULARITIES BASED ON BIOMARKER MONITORING;
- U.S. patent application Ser. No. 17/156,321, filed Jan. 22, 2021, titled PREDICTION OF HEMOSTASIS ISSUES BASED ON BIOMARKER MONITORING;
- U.S. patent application Ser. No. 17/156,281, filed Jan. 22, 2021, titled COLORECTAL SURGERY POST-SURGICAL MONITORING;
- U.S. patent application Ser. No. 17/156,272, filed Jan. 22, 2021, titled THORACIC POST-SURGICAL MONITORING AND COMPLICATION PREDICTION;
- U.S. patent application Ser. No. 17/156,279, filed Jan. 22, 2021, titled HYSTERECTOMY SURGERY POST-SURGICAL MONITORING;
- U.S. patent application Ser. No. 17/156,284, filed Jan. 22, 2021, titled BARIATRIC SURGERY POST-SURGICAL MONITORING;
- U.S. patent application Ser. No. 17/156,282, filed Jan. 22, 2021, titled PATIENT BIOMARKER MONITORING WITH OUTCOMES TO MONITOR OVERALL HEALTHCARE DELIVERY;
- U.S. patent application Ser. No. 17/156,269, filed Jan. 22, 2021, titled PRE-SURGICAL AND SURGICAL PROCESSING FOR SURGICAL DATA CONTEXT;
- U.S. patent application Ser. No. 17/156,286, filed Jan. 22, 2021, titled PRE-SURGERY AND IN-SURGERY DATA TO SUGGEST POST-SURGERY MONITORING AND SENSING REGIMES;
- U.S. patent application Ser. No. 17/156,324, filed Jan. 22, 2021, titled ACTIVE RECOGNITION AND PAIRING SENSING SYSTEMS;
- U.S. patent application Ser. No. 17/156,329, filed Jan. 22, 2021, titled AUDIO AUGMENTED REALITY CUES TO FOCUS ON AUDIBLE INFORMATION;
- U.S. patent application Ser. No. 17/156,289, filed Jan. 22, 2021, titled PREDICTIVE BASED SYSTEM ADJUSTMENTS BASED ON BIOMARKER TRENDING;
- U.S. patent application Ser. No. 17/156,293, filed Jan. 22, 2021, titled MACHINE LEARNING TO IMPROVE ARTIFICIAL INTELLIGENCE ALGORITHM ITERATIONS;
- U.S. patent application Ser. No. 17/156,298, filed Jan. 22, 2021, titled CONTEXTUAL TRANSFORMATION OF DATA INTO AGGREGATED DISPLAY FEEDS;
- U.S. patent application Ser. No. 17/156,274, filed Jan. 22, 2021, titled AD HOC SYNCHRONIZATION OF DATA FROM MULTIPLE LINK COORDINATED SENSING SYSTEMS; and
- U.S. patent application Ser. No. 17/156,278, filed Jan. 22, 2021, titled COOPERATIVE PROCESSING OF SURGICAL SENSOR-DATA STREAMS.

BACKGROUND

Healthcare professionals handle surgical instruments such as, for example, surgical staplers and surgical cutters while performing surgical procedures. A healthcare professional may handle an endocutter surgical instrument to position the endocutter surgical instrument at the appropriate location and orientation to engage tissue of a patient. The healthcare professional may interact with a surgical instrument's control components such as, for example, handles, triggers, and displays to position a surgical instrument and perform surgical operations.

Physiological issues may lead to complications in a surgical procedure. Adhesions, blood perfusion difficulties, tissue irregularities and/or hemostasis issues may lead to complications in a surgical procedure. For example, adhesions may form in the pleural space, such as between the parietal pleura and the visceral pleura and/or between the parietal pleura and the chest wall. In an example, in a lung segmentectomy procedure, the adhesions may need to be cut and released before a surgical site (e.g., a target lung lobe) may be reached and mobilized. In such example, fibrous and/or dense adhesions may have been formed and may have obliterated the pleural space, which may lead to convoluted tissue planes. Dissection of such adhesions may lead to unintended incisions to the underlying lung tissue, which may lead to uncontrollable bleeding during the procedure. Dissection of such adhesions may take meticulous and slow manipulation and hence may prolong a surgical procedure duration. Dissection of such adhesions may lead to prolonged air leaks that may persist beyond a normal hospitalization period. For example, similar surgical complications may occur in a colorectal procedure due to adhesions that form between the abdominal wall and the intestine, between bowel loops, and/or within the intestine.

Patients who undergo colorectal surgeries may experience latent post-surgical complications such as anastomosis leak. Anastomosis leak may occur when a patient's colon fails to heal properly and, in turn, develops a leak whereby intestinal fluid drips into surrounding bodily structures. This leak can cause serious health issues such as sepsis, shock, a loss in GI motility, etc. Symptoms of the leak may not be apparent to a patient or a healthcare provider (HCP) overseeing a patient, making early detection of the leak more difficult. The current state of technology for monitoring, detecting, and/or predicting an onset of anastomosis leak may not be adequate.

SUMMARY

Disclosed herein are techniques for adaptively controlling the operations of a surgical instrument. A surgical instrument may be configured to monitor user inputs to the surgical instrument. For example, a surgical instrument may monitor and collect usage data associated with the position and movement of the surgical instrument and associated with user inputs such as those relating to controlling jaws for clamping tissue. The surgical instrument may communicate usage data associated with operation of the surgical device to a surgical computing system. Healthcare professionals operating the surgical instrument may be monitored using sensing systems to collect sensor data such as, for example, data associated with movement, heartrate, respiration, temperature, etc. The sensing systems may communicate sensor data collected by the sensing systems to the surgical computing system.

Using a combination of patient-specific and/or surgical-environment-specific sensor inputs to determine a more optimal device setting may lead to better device perform and ultimately better patient outcomes.

A computing device may have a processor configured to receive two points of surgical sensor data from different sensors. The sensors may include wearable patient sensors and/or surgical theater environmental sensor system. The processor may be configured to determine a surgical device setting (e.g., a closure load for a powered surgical stapler, or for example, a power level of a surgical energy device). And the processor may send a signal indicative of the determined setting. A surgical device may receive the signal and perform a surgical action based on the determined setting. The device The surgical device may include any of a powered stapler, a powered stapler generator, an energy device, an energy device generator, an in-operating-room imaging system, a smoke evacuator, a suction-irrigation device, or an insufflation system, for example. The setting information may include an indication of any of a power level, an advancement speed, a closure speed, a closure load, or a wait time.

The processor may be configured to receive procedure information. The processor may be configured to determine the surgical-device setting based on first surgical sensor data, second surgical sensor data, and procedure information. And the signal sent from the processor may include information indicative of an alert. The alert may represent an identified patient complication associated with the surgical device being used with its existing settings, for example, without first switching to the determined surgical device setting.

BRIEF DESCRIPTION OF THE DRAWINGS

FIG. 39A-E illustrates example procedure steps of a sigmoid colectomy and example use of patient biomarker measurements.

FIG. 40A-E illustrates example procedure steps of a sleeve gastrectomy and example use of patient biomarker measurements.

FIG. 53 shows example correlation between relevant patient biomarkers and colorectal procedural steps.

FIG. 59 shows example correlation between relevant patient biomarkers and thoracis surgical procedural steps.

FIG. 70 shows example correlation between relevant patient biomarkers and hysterectomy procedural steps.

FIG. 76 shows example correlation between relevant patient biomarkers and bariatric procedural steps.

FIG. 98 illustrates an example a secondary computing system transitioning to a primary computing system to create a local computing system for low level analysis.

FIG. 105 depicts a block diagram of a system for controlling notification and/or calculating outcome probabilities.

FIG. 106 depicts a method for controlling notifications and/or calculating outcome probabilities.

FIG. 107 depicts a block diagram for applying machine learning to improve algorithms and/or controls of the one or more wearables.

FIG. 108 depicts a block diagram for applying machine learning to improve artificial intelligence algorithms and/or iterations of learning for artificial intelligence algorithms.

FIG. 109 depicts a method for applying machine learning to a data collection to improve a surgical outcome.

FIG. 110 depicts a flow diagram for applying machine learning to improve one or more patient monitoring measures.

FIG. 111 depicts a flow diagram for contextually transforming data from one or more data streams into an aggregated data feed, such as an aggregated display data feed.

FIG. 112 depicts a method for contextually transforming data from one or more data streams into an aggregated display feed.

FIG. 113 depicts a block diagram of a device for securing consent to share data with a health care provider.

FIG. 114 depicts a method for securing consent to share data with a health care provider.

FIG. 115 shows an example display that includes a visual representation of sensed measurements.

Figure 116A:
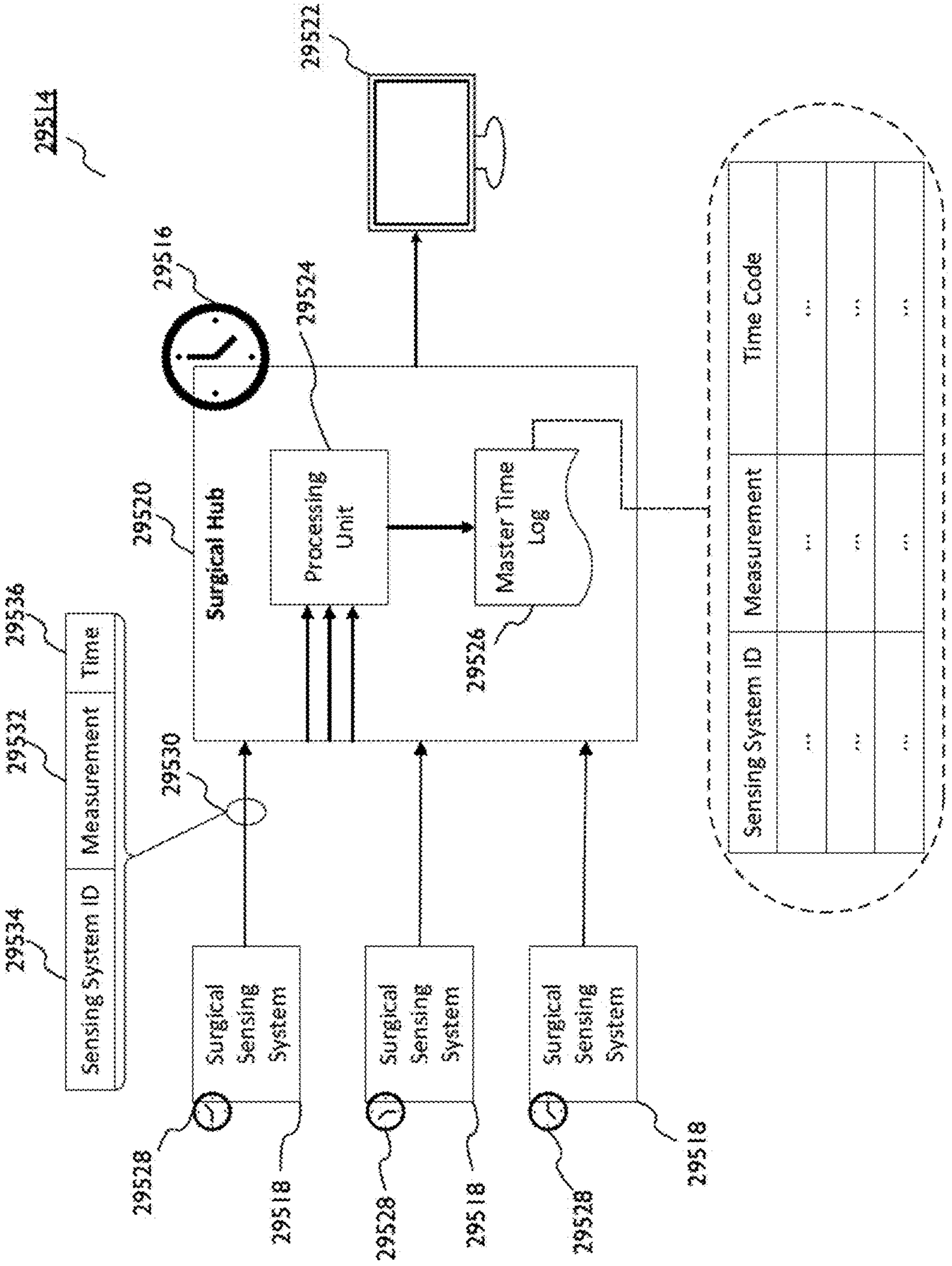
Figure 116B:
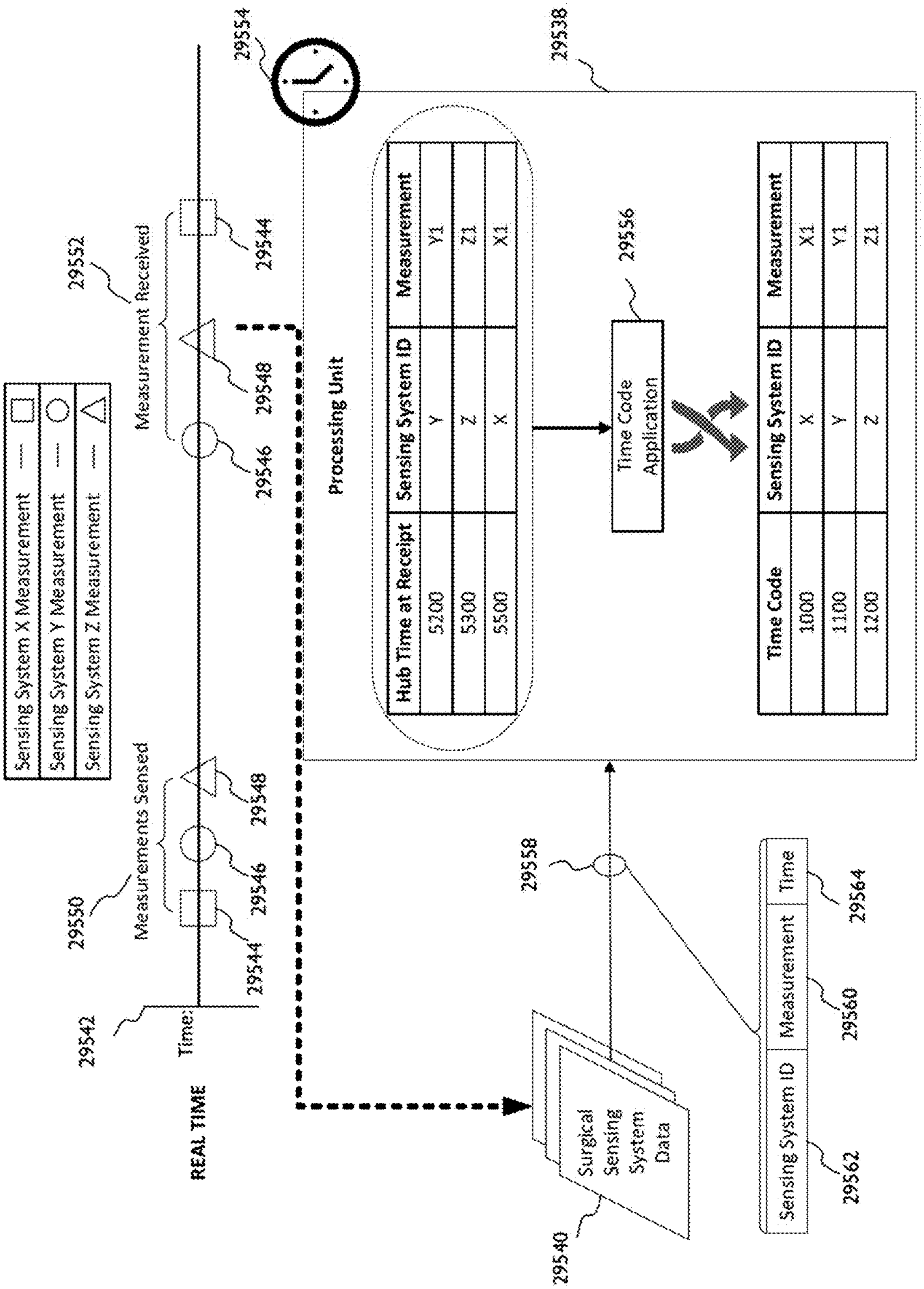

FIGS. 116A-B are functional block diagrams of an example surgical data ordering system and of an example processing unit, respectively.

Figure 117:
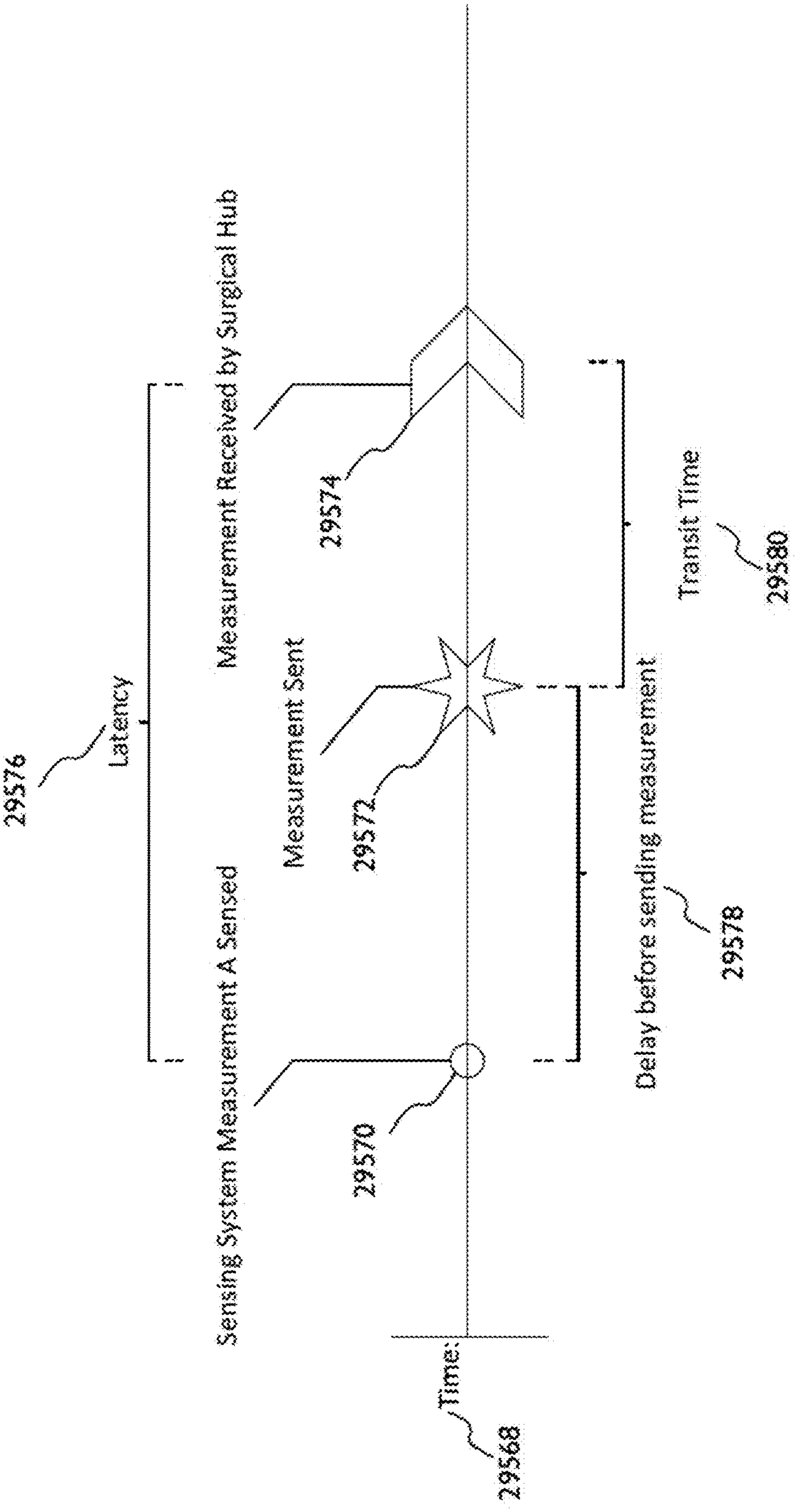

FIG. 117 shows a timeline illustrating an example method of obtaining a latency value associated with a surgical sensing system.

Figure 118:
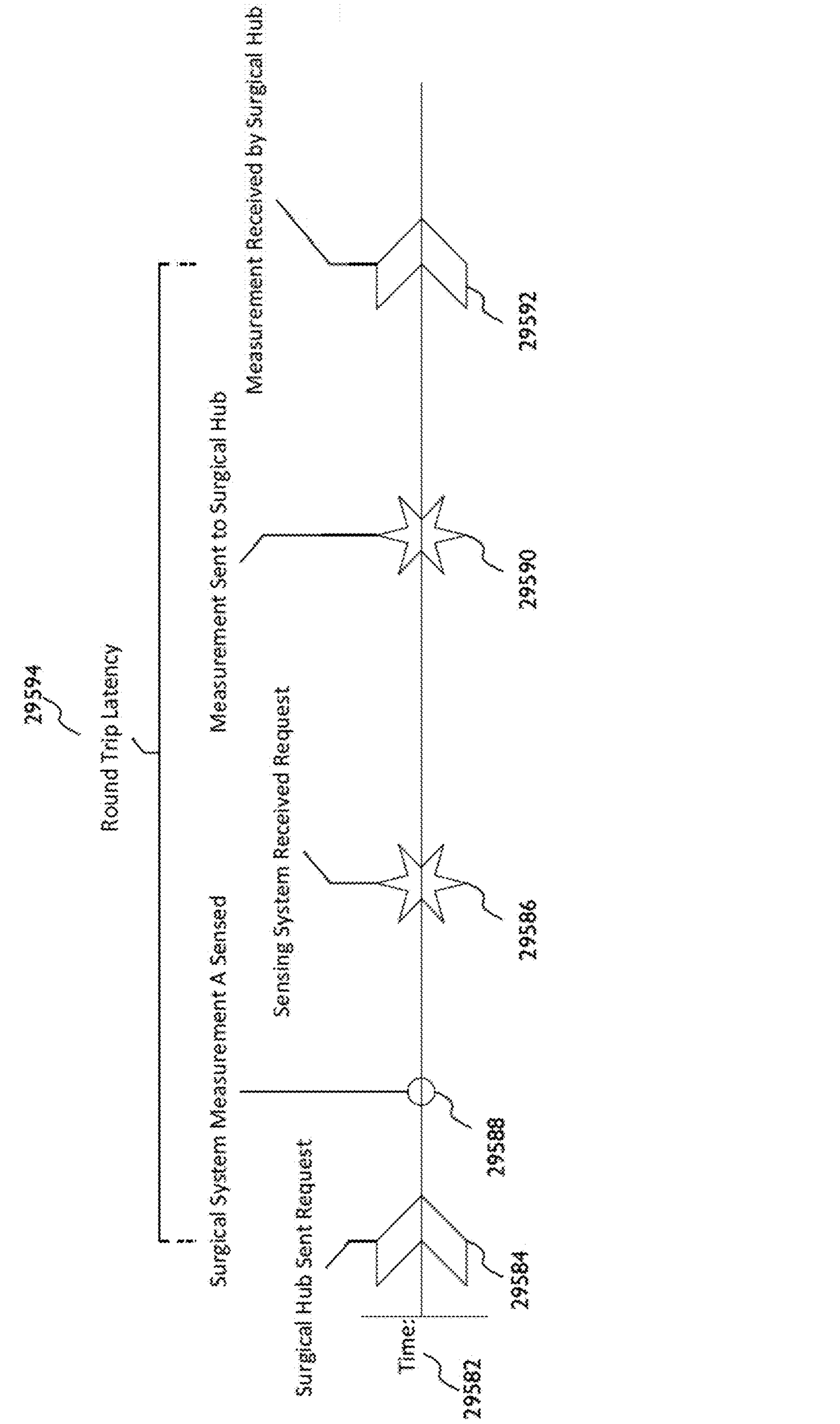

FIG. 118 shows a timeline illustrating an example method of obtaining a latency value associated with a surgical sensing system.

Figure 119:
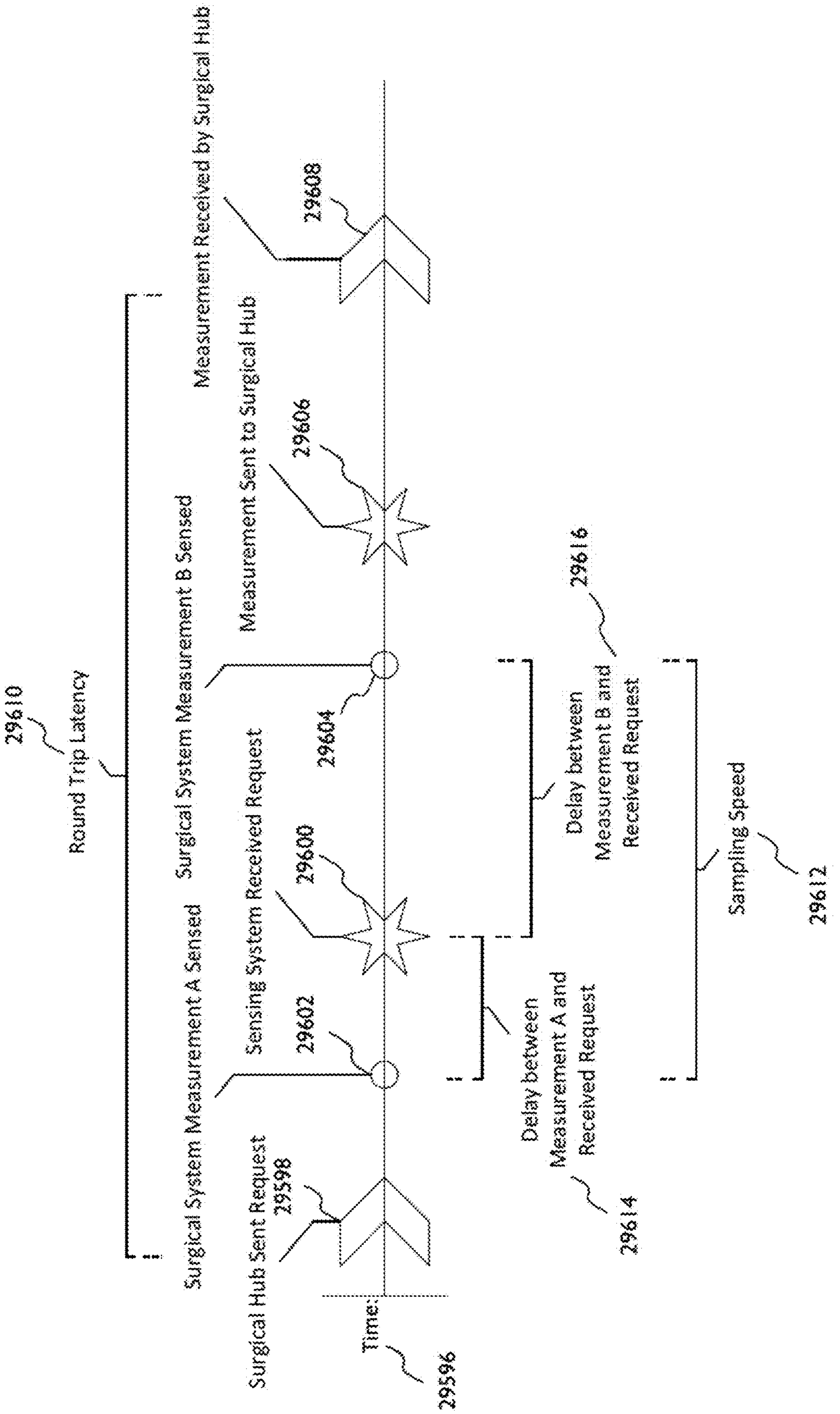

FIG. 119 shows a timeline illustrating an example method of selecting a sensed measurement.

FIG. 120 depicts an example master time log with surgical sensing system data.

Figure 121:
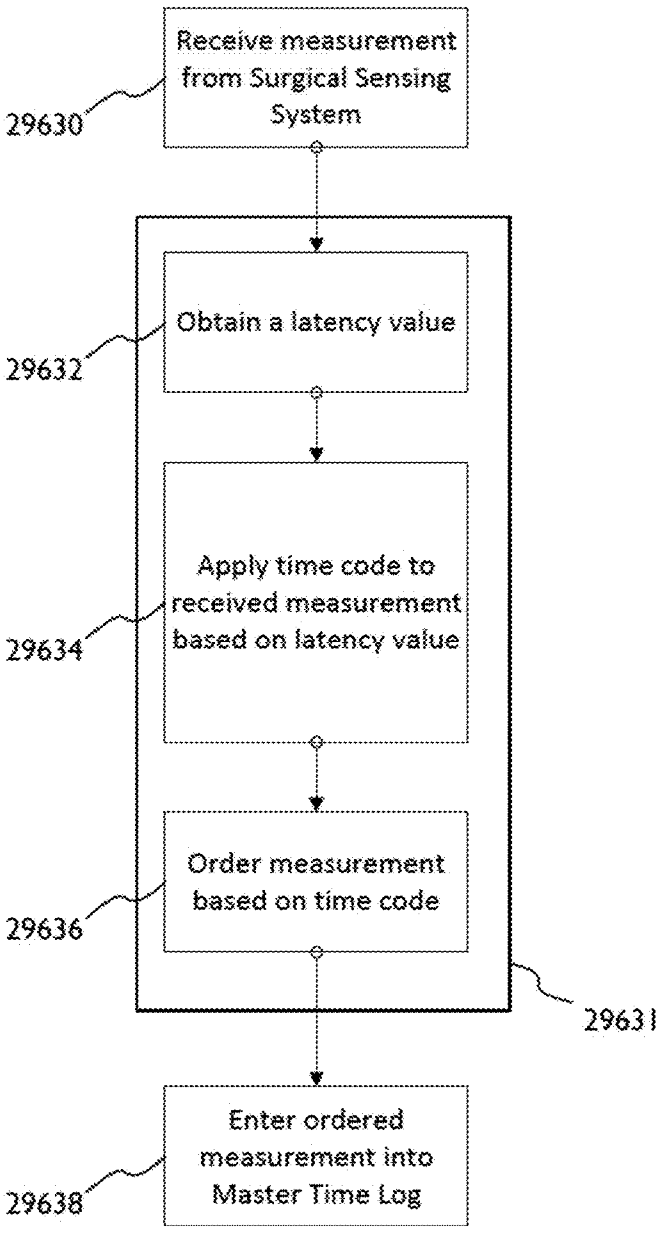

FIG. 121 illustrates an example method for ordering surgical sensing system data.

Figure 122:
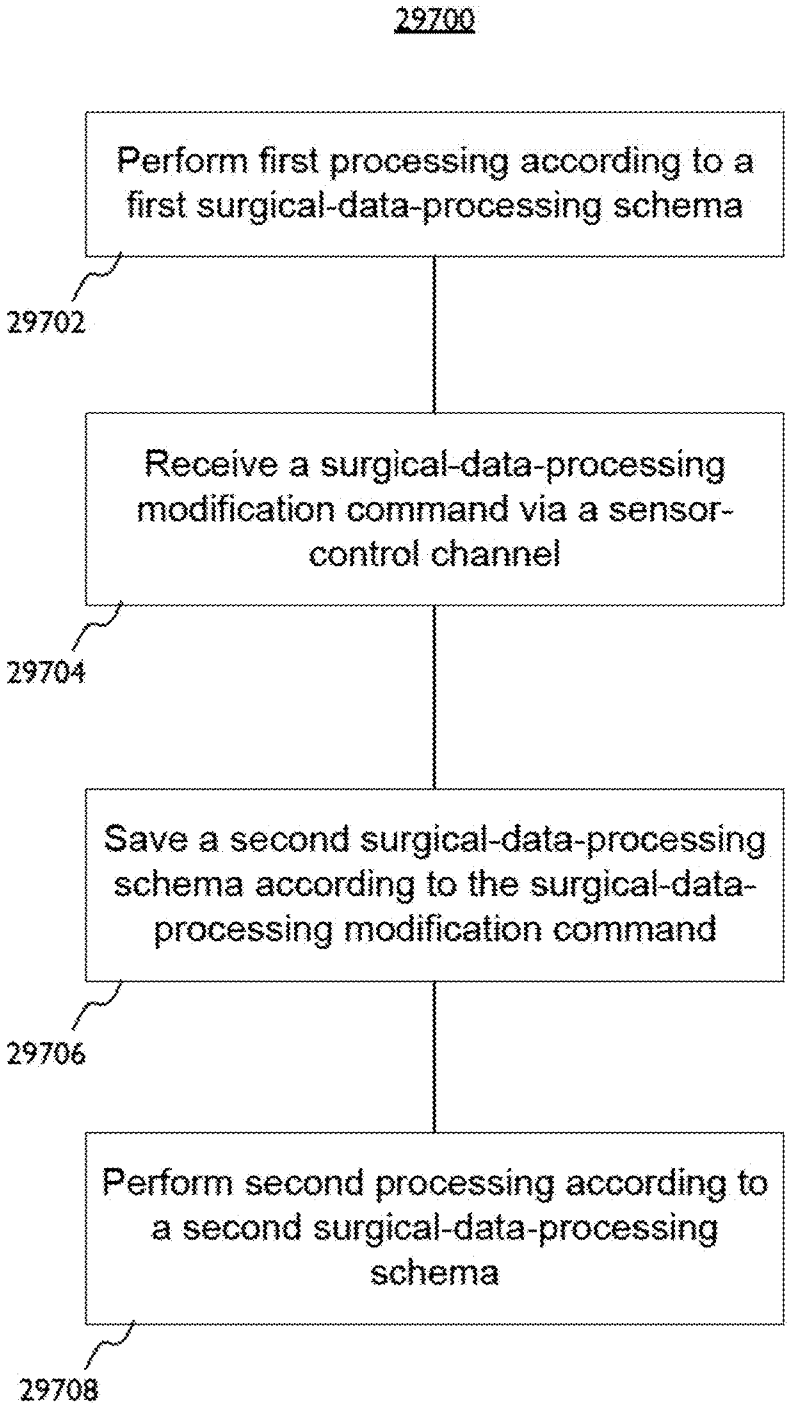

FIG. 122 is a flow diagram of an example method for processing surgical data during a surgical procedure.

Figure 123:
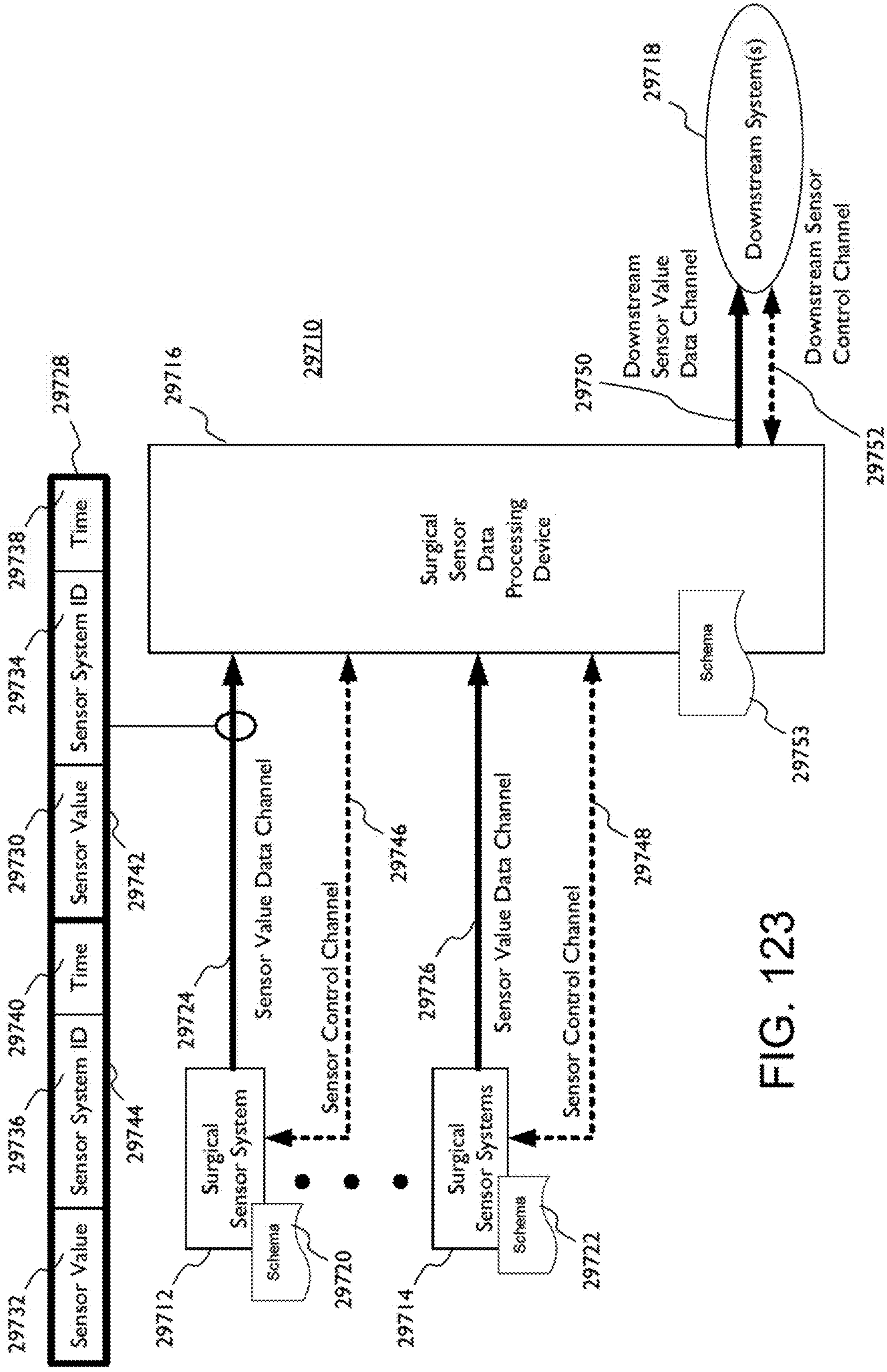

FIG. 123 is a block diagram of an example sensor data processing system.

Figure 124A:
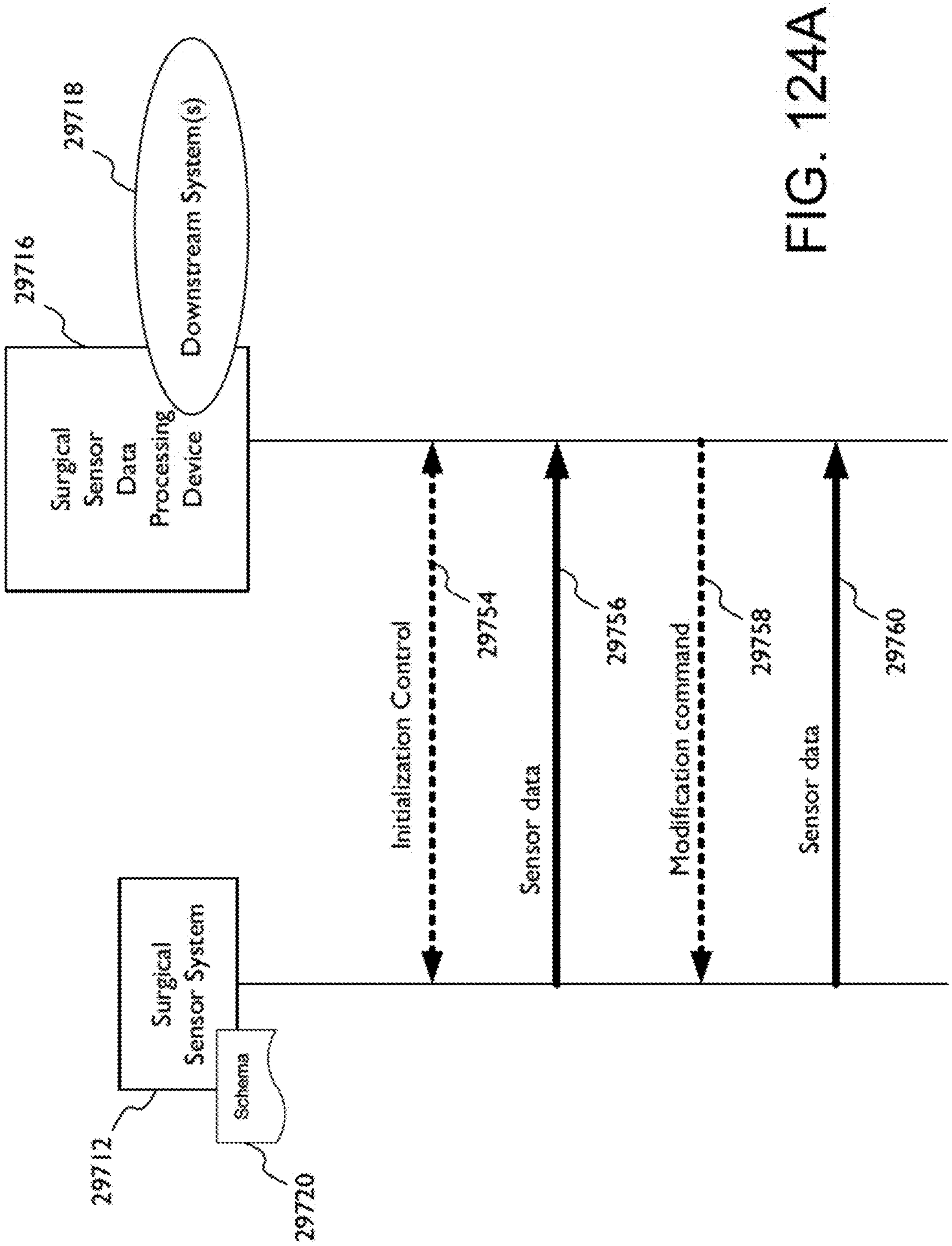
Figure 124B:
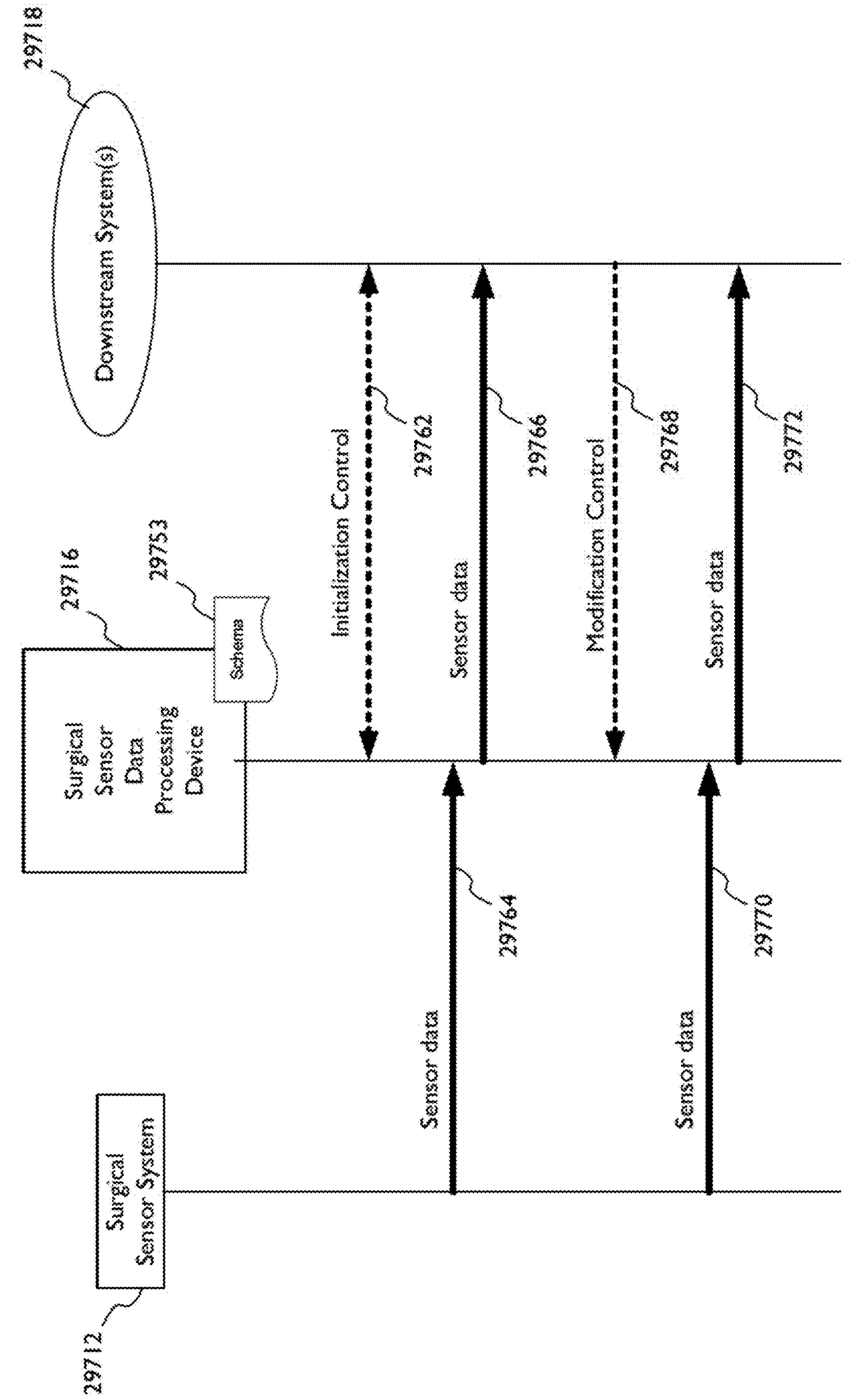
Figure 124C:
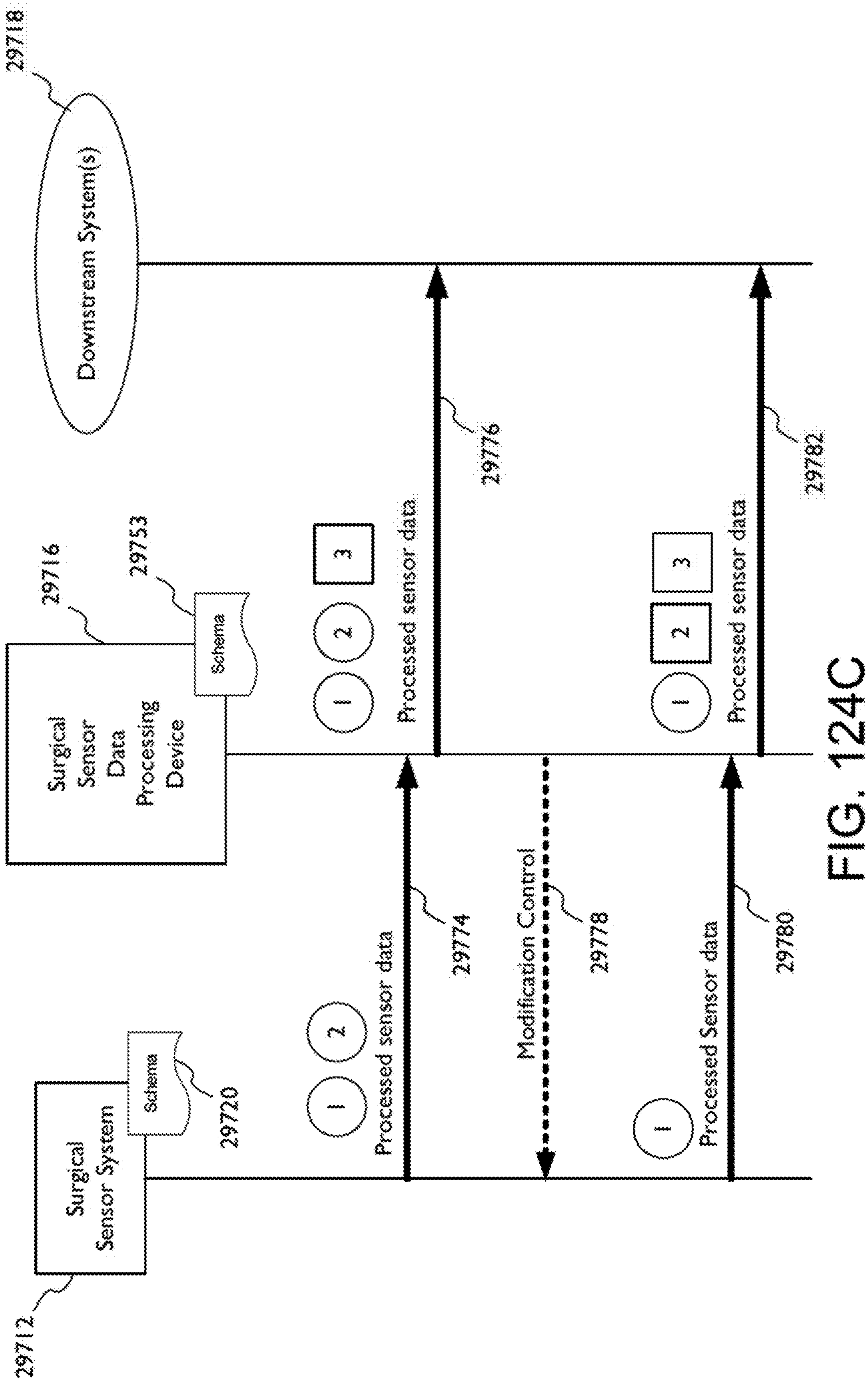

FIGS. 124A-C are example messaging diagrams illustrating, respectively, a processing modification at a surgical sensor system, a processing modification at a surgical sensor data processing device, and a processing modification at both a surgical sensor system and a surgical sensor data processing device.

Figure 125:
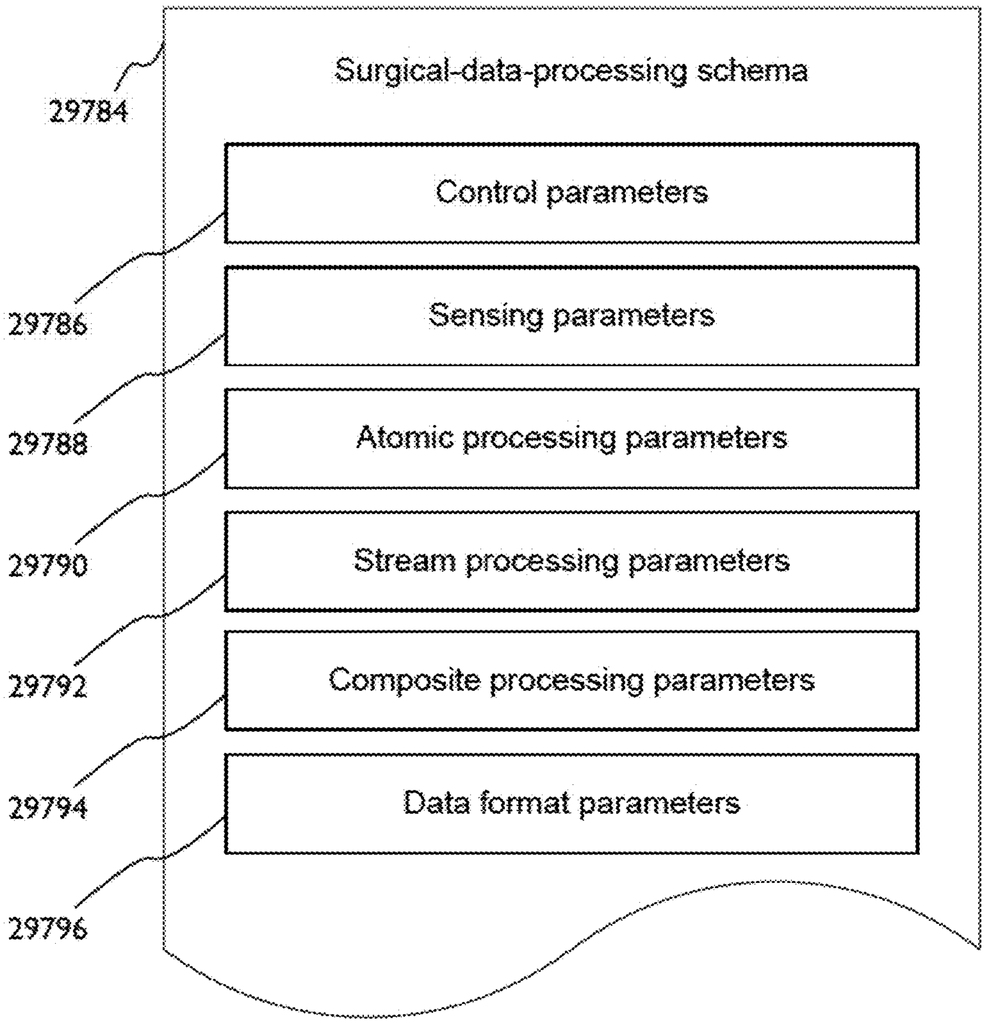

FIG. 125 is a block diagram of an example surgical-data-processing schema.

Figure 126:
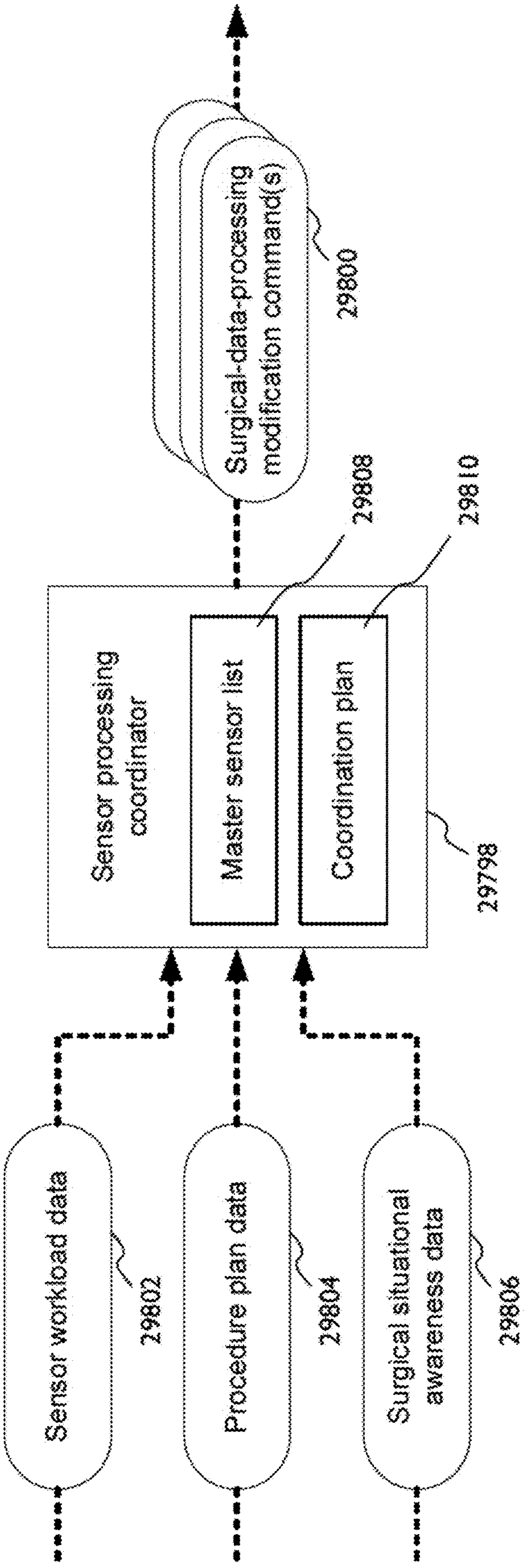

FIG. 126 is a block diagram of an example sensor processing coordinator.

DETAILED DESCRIPTION

Figure 1A:
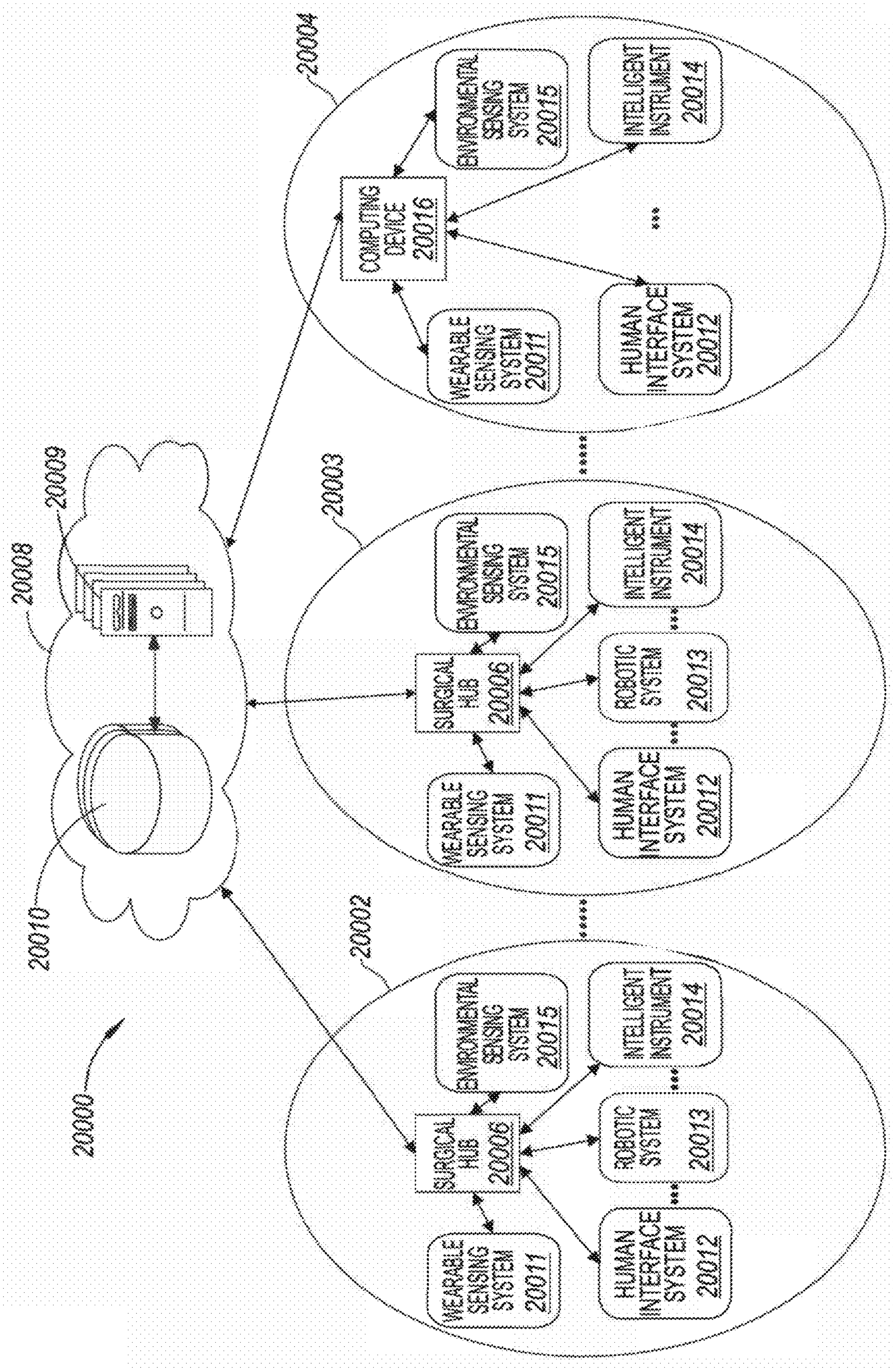
FIG. 1A is a block diagram of a computer-implemented patient and surgeon monitoring system.

FIG. 1A is a block diagram of a computer-implemented patient and surgeon monitoring system 20000. The patient and surgeon monitoring system 20000 may include one or more surgeon monitoring systems 20002 and a one or more patient monitoring systems (e.g., one or more controlled patient monitoring systems 20003 and one or more uncontrolled patient monitoring systems 20004). Each surgeon monitoring system 20002 may include a computer-implemented interactive surgical system. Each surgeon monitoring system 20002 may include at least one of the following: a surgical hub 20006 in communication with a cloud computing system 20008, for example, as described in FIG. 2A. Each of the patient monitoring systems may include at least one of the following: a surgical hub 20006 or a computing device 20016 in communication with a could computing system 20008, for example, as further described in FIG. 2B and FIG. 2C. The cloud computing system 20008 may include at least one remote cloud server 20009 and at least one remote cloud storage unit 20010. Each of the surgeon monitoring systems 20002, the controlled patient monitoring systems 20003, or the uncontrolled patient monitoring systems 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more surgeon sensing systems, and/or one or more patient sensing systems. The environmental sensing system 20015 may include one or more devices, for example, used for measuring one or more environmental attributes, for example, as further described in FIG. 2A. The robotic system 20013 (same as 20034 in FIG. 2A) may include a plurality of devices used for performing a surgical procedure, for example, as further described in FIG. 2A.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

Figure 1B:
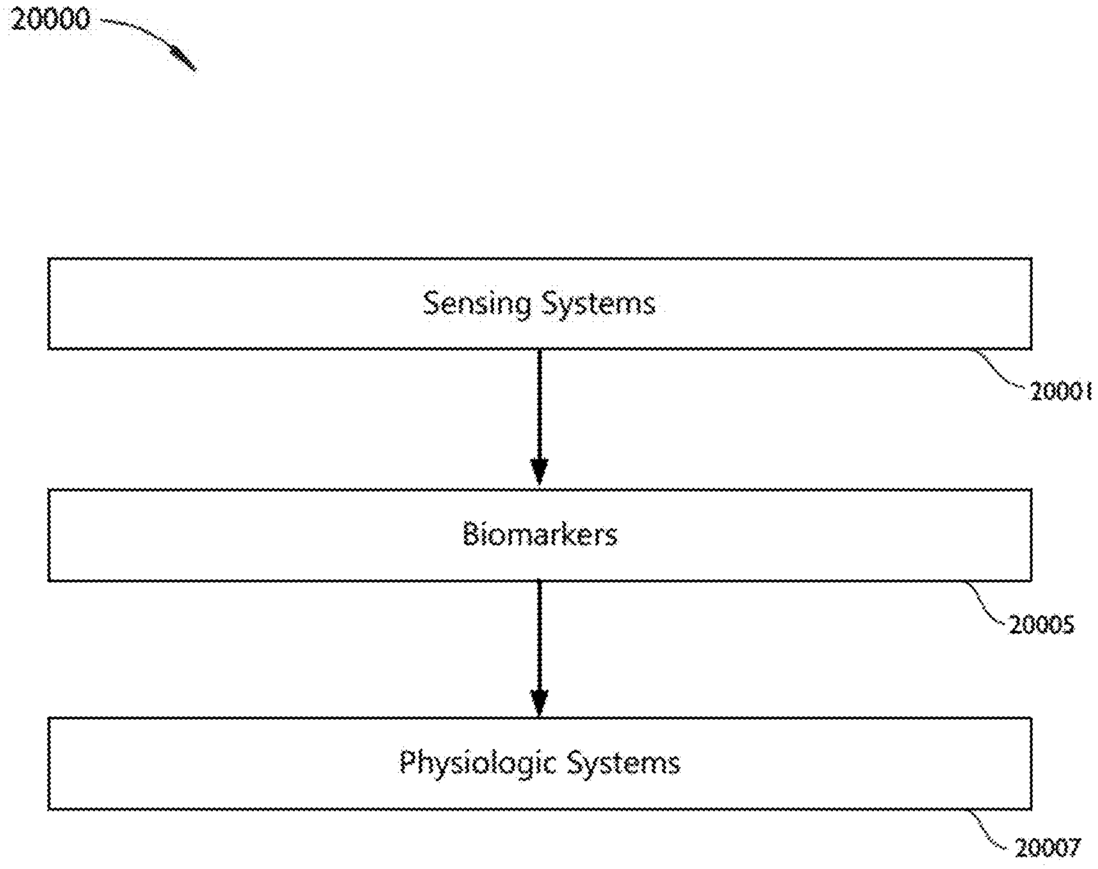
FIG. 1B is a block diagram of an example relationship among sensing systems, biomarkers, and physiologic systems.

FIG. 1B is a block diagram of an example relationship among sensing systems 20001, biomarkers 20005, and physiologic systems 20007. The relationship may be employed in the computer-implemented patient and surgeon monitoring system 20000 and in the systems, devices, and methods disclosed herein. For example, the sensing systems 20001 may include the wearable sensing system 20011 (which may include one or more surgeon sensing systems and one or more patient sensing systems) and the environmental sensing system 20015 as discussed in FIG. 1A. The one or more sensing systems 20001 may measure data relating to various biomarkers 20005. The one or more sensing systems 20001 may measure the biomarkers 20005 using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers 20005 as described herein using one of more of the following sensing technologies: photoplethysmography, electrocardiogramcephalography, colorimetry, impedimentary, potentiometry, amperometry, etc.

The biomarkers 20005 measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers 20005 may relate to physiologic systems 20007, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and surgeon monitoring system 20000, for example. The information from the biomarkers may be determined and/or used by the computer-implemented patient and surgeon monitoring system 20000 to improve said systems and/or to improve patient outcomes, for example.

The one or more sensing systems 20001, biomarkers 20005, and physiological systems 20007 are described in more detail below.

A sleep sensing system may measure sleep data, including heart rate, respiration rate, body temperature, movement, and/or brain signals. The sleep sensing system may measure sleep data using a photoplethysmogram (PPG), electrocardiogram (ECG), microphone, thermometer, accelerometer, electroencephalogram (EEG), and/or the like. The sleep sensing system may include a wearable device such as a wristband.

Based on the measured sleep data, the sleep sensing system may detect sleep biomarkers, including but not limited to, deep sleep quantifier, REM sleep quantifier, disrupted sleep quantifier, and/or sleep duration. The sleep sensing system may transmit the measured sleep data to a processing unit. The sleep sensing system and/or the processing unit may detect deep sleep when the sensing system senses sleep data, including reduced heart rate, reduced respiration rate, reduced body temperature, and/or reduced movement. The sleep sensing system may generate a sleep quality score based on the detected sleep physiology.

In an example, the sleep sensing system may send the sleep quality score to a computing system, such as a surgical hub. In an example, the sleep sensing system may send the detected sleep biomarkers to a computing system, such as a surgical hub. In an example, the sleep sensing system may send the measured sleep data to a computing system, such as a surgical hub. The computing system may derive sleep physiology based on the received measured data and generate one or more sleep biomarkers such as deep sleep quantifiers. The computing system may generate a treatment plan, including a pain management strategy, based on the sleep biomarkers. The surgical hub may detect potential risk factors or conditions, including systemic inflammation and/or reduced immune function, based on the sleep biomarkers.

A core body temperature sensing system may measure body temperature data including temperature, emitted frequency spectra, and/or the like. The core body temperature sensing system may measure body temperature data using some combination of thermometers and/or radio telemetry. The core body temperature sensing system may include an ingestible thermometer that measures the temperature of the digestive tract. The ingestible thermometer may wirelessly transmit measured temperature data. The core body temperature sensing system may include a wearable antenna that measures body emission spectra. The core body temperature sensing system may include a wearable patch that measures body temperature data.

The core body temperature sensing system may calculate body temperature using the body temperature data. The core body temperature sensing system may transmit the calculated body temperature to a monitoring device. The monitoring device may track the core body temperature data over time and display it to a user.

The core body temperature sensing system may process the core body temperature data locally or send the data to a processing unit and/or a computing system. Based on the measured temperature data, the core body temperature sensing system may detect body temperature-related biomarkers, complications and/or contextual information that may include abnormal temperature, characteristic fluctuations, infection, menstrual cycle, climate, physical activity, and/or sleep.

For example, the core body temperature sensing system may detect abnormal temperature based on temperature being outside the range of 36.5° C. and 37.5° C. For example, the core body temperature sensing system may detect post-operation infection or sepsis based on certain temperature fluctuations and/or when core body temperature reaches abnormal levels. For example, the core body temperature sensing system may detect physical activities using measured fluctuations in core body temperature.

For example, the body temperature sensing system may detect core body temperature data and trigger the sensing system to emit a cooling or heating element to raise or lower the body temperature in line with the measured ambient temperature.

In an example, the body temperature sensing system may send the body temperature-related biomarkers to a computing system, such as a surgical hub. In an example, the body temperature sensing system may send the measured body temperature data to the computing system. The computer system may derive the body temperature-related biomarkers based on the received body temperature data.

A maximal oxygen consumption (VO2 max) sensing system may measure VO2 max data, including oxygen uptake, heart rate, and/or movement speed. The VO2 max sensing system may measure VO2 max data during physical activities, including running and/or walking. The VO2 max sensing system may include a wearable device. The VO2 max sensing system may process the VO2 max data locally or transmit the data to a processing unit and/or a computing system.

Based on the measured VO2 max data, the sensing system and/or the computing system may derive, detect, and/or calculate biomarkers, including a VO2 max quantifier, VO2 max score, physical activity, and/or physical activity intensity. The VO2 max sensing system may select correct VO2 max data measurements during correct time segments to calculate accurate VO2 max information. Based on the VO2 max information, the sensing system may detect dominating cardio, vascular, and/or respiratory limiting factors. Based on the VO2 max information, risks may be predicted including adverse cardiovascular events in surgery and/or increased risk of in-hospital morbidity. For example, increased risk of in-hospital morbidity may be detected when the calculated VO2 max quantifier falls below a specific threshold, such as 18.2 ml kg-1 min-1.

In an example, the VO2 max sensing system may send the VO2 max-related biomarkers to a computing system, such as a surgical hub. In an example, the VO2 max sensing system may send the measured VO2 max data to the computing system. The computer system may derive the VO2 max-related biomarkers based on the received VO2 max data.

A physical activity sensing system may measure physical activity data, including heart rate, motion, location, posture, range-of-motion, movement speed, and/or cadence. The physical activity sensing system may measure physical activity data including accelerometer, magnetometer, gyroscope, global positioning system (GPS), PPG, and/or ECG. The physical activity sensing system may include a wearable device. The physical activity wearable device may include, but is not limited to, a watch, wrist band, vest, glove, belt, headband, shoe, and/or garment. The physical activity sensing system may locally process the physical activity data or transmit the data to a processing unit and/or a computing system.

Based on the measured physical activity data, the physical activity sensing system may detect physical activity-related biomarkers, including but not limited to exercise activity, physical activity intensity, physical activity frequency, and/or physical activity duration. The physical activity sensing system may generate physical activity summaries based on physical activity information.

For example, the physical activity sensing system may send physical activity information to a computing system. For example, the physical activity sensing system may send measured data to a computing system. The computing system may, based on the physical activity information, generate activity summaries, training plans, and/or recovery plans. The computing system may store the physical activity information in user profiles. The computing system may display the physical activity information graphically. The computing system may select certain physical activity information and display the information together or separately.

An alcohol consumption sensing system may measure alcohol consumption data including alcohol and/or sweat. The alcohol consumption sensing system may use a pump to measure perspiration. The pump may use a fuel cell that reacts with ethanol to detect alcohol presence in perspiration. The alcohol consumption sensing system may include a wearable device, for example, a wristband. The alcohol consumption sensing system may use microfluidic applications to measure alcohol and/or sweat. The microfluidic applications may measure alcohol consumption data using sweat stimulation and wicking with commercial ethanol sensors. The alcohol consumption sensing system may include a wearable patch that adheres to skin. The alcohol consumption sensing system may include a breathalyzer. The sensing system may process the alcohol consumption data locally or transmit the data to a processing unit and/or computing system.

Based on the measured alcohol consumption data, the sensing system may calculate a blood alcohol concentration. The sensing system may detect alcohol consumption conditions and/or risk factors. The sensing system may detect alcohol consumption-related biomarkers including reduced immune capacity, cardiac insufficiency, and/or arrhythmia. Reduced immune capacity may occur when a patient consumes three or more alcohol units per day. The sensing system may detect risk factors for postoperative complications including infection, cardiopulmonary complication, and/or bleeding episodes. Healthcare providers may use the detected risk factors for predicting or detecting post-operative or post-surgical complications, for example, to affect decisions and precautions taken during post-surgical care.

In an example, the alcohol consumption sensing system may send the alcohol consumption-related biomarkers to a computing system, such as a surgical hub. In an example, the alcohol consumption sensing system may send the measured alcohol consumption data to the computing system. The computer system may derive the alcohol consumption-related biomarkers based on the received alcohol consumption data.

A respiration sensing system may measure respiration rate data, including inhalation, exhalation, chest cavity movement, and/or airflow. The respiration sensing system may measure respiration rate data mechanically and/or acoustically. The respiration sensing system may measure respiration rate data using a ventilator. The respiration sensing system may measure respiration data mechanically by detecting chest cavity movement. Two or more applied electrodes on a chest may measure the changing distance between the electrodes to detect chest cavity expansion and contraction during a breath. The respiration sensing system may include a wearable skin patch. The respiration sensing system may measure respiration data acoustically using a microphone to record airflow sounds. The respiration sensing system may locally process the respiration data or transmit the data to a processing unit and/or computing system.

Based on measured respiration data, the respiration sensing system may generate respiration-related biomarkers including breath frequency, breath pattern, and/or breath depth. Based on the respiratory rate data, the respiration sensing system may generate a respiration quality score.

Based on the respiration rate data, the respiration sensing system may detect respiration-related biomarkers including irregular breathing, pain, air leak, collapsed lung, lung tissue and strength, and/or shock. For example, the respiration sensing system may detect irregularities based on changes in breath frequency, breath pattern, and/or breath depth. For example, the respiration sensing system may detect post-operative pain based on short, sharp breaths. For example, the respiration sensing system may detect an air leak based on a volume difference between inspiration and expiration. For example, the respiration sensing system may detect a collapsed lung based on increased breath frequency combined with a constant volume inhalation. For example, the respiration sensing system may detect lung tissue strength and shock including systemic inflammatory response syndrome (SIRS) based on an increase in respiratory rate, including more than 2 standard deviations. In an example, the detection described herein may be performed by a computing system based on measured data and/or related biomarkers generated by the respiration sensing system.

An oxygen saturation sensing system may measure oxygen saturation data, including light absorption, light transmission, and/or light reflectance. The oxygen saturation sensing system may use pulse oximetry. For example, the oxygen saturation sensing system may use pulse oximetry by measuring the absorption spectra of deoxygenated and oxygenated hemoglobin. The oxygen saturation sensing system may include one or more light-emitting diodes (LEDs) with predetermined wavelengths. The LEDs may impose light on hemoglobin. The oxygen saturation sensing system may measure the amount of imposed light absorbed by the hemoglobin. The oxygen saturation sensing system may measure the amount of transmitted light and/or reflected light from the imposed light wavelengths. The oxygen saturation sensing system may include a wearable device, including an earpiece and/or a watch. The oxygen saturation sensing system may process the measured oxygen saturation data locally or transmit the data to a processing unit and/or computing system.

Based on the oxygen saturation data, the oxygen saturation sensing system may calculate oxygen saturation-related biomarkers including peripheral blood oxygen saturation (SpO2), hemoglobin oxygen concentration, and/or changes in oxygen saturation rates. For example, the oxygen saturation sensing system may calculate SpO2 using the ratio of measured light absorbances of each imposed light wavelength.

Based on the oxygen saturation data, the oxygen saturation sensing system may predict oxygen saturation-related biomarkers, complications, and/or contextual information including cardiothoracic performance, delirium, collapsed lung, and/or recovery rates. For example, the oxygen saturation sensing system may detect post-operation delirium when the sensing system measures pre-operation SpO2 values below 59.5%. For example, an oxygen saturation sensing system may help monitor post-operation patient recovery. Low SpO2 may reduce the repair capacity of tissues because low oxygen may reduce the amount of energy a cell can produce. For example, the oxygen saturation sensing system may detect a collapsed lung based on low post-operation oxygen saturation. In an example, the detection described herein may be performed by a computing system based on measured data and/or related biomarkers generated by the oxygen saturation sensing system.

A blood pressure sensing system may measure blood pressure data including blood vessel diameter, tissue volume, and/or pulse transit time. The blood pressure sensing system may measure blood pressure data using oscillometric measurements, ultrasound patches, photoplethysmography, and/or arterial tonometry. The blood pressure sensing system using photoplethysmography may include a photodetector to sense light scattered by imposed light from an optical emitter. The blood pressure sensing system using arterial tonometry may use arterial wall applanation. The blood pressure sensing system may include an inflatable cuff, wristband, watch and/or ultrasound patch.

Based on the measured blood pressure data, a blood pressure sensing system may quantify blood pressure-related biomarkers including systolic blood pressure, diastolic blood pressure, and/or pulse transit time. The blood pressure sensing system may use the blood pressure-related biomarkers to detect blood pressure-related conditions such as abnormal blood pressure. The blood pressure sensing system may detect abnormal blood pressure when the measured systolic and diastolic blood pressures fall outside the range of 90/60 to 120-90 (systolic/diastolic). For example, the blood pressure sensing system may detect post-operation septic or hypovolemic shock based on measured low blood pressure. For example, the blood pressure sensing system may detect a risk of edema based on detected high blood pressure. The blood pressure sensing system may predict the required seal strength of a harmonic seal based on measured blood pressure data. Higher blood pressure may require a stronger seal to overcome bursting. The blood pressure sensing system may display blood pressure information locally or transmit the data to a system. The sensing system may display blood pressure information graphically over a period of time.

A blood pressure sensing system may process the blood pressure data locally or transmit the data to a processing unit and/or a computing system. In an example, the detection, prediction and/or determination described herein may be performed by a computing system based on measured data and/or related biomarkers generated by the blood pressure sensing system.

A blood sugar sensing system may measure blood sugar data including blood glucose level and/or tissue glucose level. The blood sugar sensing system may measure blood sugar data non-invasively. The blood sugar sensing system may use an earlobe clip. The blood sugar sensing system may display the blood sugar data.

Based on the measured blood sugar data, the blood sugar sensing system may infer blood sugar irregularity. Blood sugar irregularity may include blood sugar values falling outside a certain threshold of normally occurring values. A normal blood sugar value may include the range between 70 and 120 mg/dL while fasting. A normal blood sugar value may include the range between 90 and 160 mg/dL while not-fasting.

For example, the blood sugar sensing system may detect a low fasting blood sugar level when blood sugar values fall below 50 mg/dL. For example, the blood sugar sensing system may detect a high fasting blood sugar level when blood sugar values exceed 315 mg/dL. Based on the measured blood sugar levels, the blood sugar sensing system may detect blood sugar-related biomarkers, complications, and/or contextual information including diabetes-associated peripheral arterial disease, stress, agitation, reduced blood flow, risk of infection, and/or reduced recovery times.

The blood sugar sensing system may process blood sugar data locally or transmit the data to a processing unit and/or computing system. In an example, the detection, prediction and/or determination described herein may be performed by a computing system based on measured data and/or related biomarkers generated by the blood sugar sensing system.

A heart rate variability (HRV) sensing system may measure HRV data including heartbeats and/or duration between consecutive heartbeats. The HRV sensing system may measure HRV data electrically or optically. The HRV sensing system may measure heart rate variability data electrically using ECG traces. The HRV sensing system may use ECG traces to measure the time period variation between R peaks in a QRS complex. An HRV sensing system may measure heart rate variability optically using PPG traces. The HRV sensing system may use PPG traces to measure the time period variation of inter-beat intervals. The HRV sensing system may measure HRV data over a set time interval. The HRV sensing system may include a wearable device, including a ring, watch, wristband, and/or patch.

Based on the HRV data, an HRV sensing system may detect HRV-related biomarkers, complications, and/or contextual information including cardiovascular health, changes in HRV, menstrual cycle, meal monitoring, anxiety levels, and/or physical activity. For example, an HRV sensing system may detect high cardiovascular health based on high HRV. For example, an HRV sensing system may predict pre-operative stress, and use pre-operative stress to predict post-operative pain. For example, an HRV sensing system may indicate post-operative infection or sepsis based on a decrease in HRV.

The HRV sensing system may locally process HRV data or transmit the data to a processing unit and/or a computing system. In an example, the detection, prediction, and/or determination described herein may be performed by a computing system based on measured data and/or related biomarkers generated by the HRV sensing system.

A potential of hydrogen (pH) sensing system may measure pH data including blood pH and/or sweat pH. The pH sensing system may measure pH data invasively and/or non-invasively. The pH sensing system may measure pH data non-invasively using a colorimetric approach and pH sensitive dyes in a microfluidic circuit. In a colorimetric approach, pH sensitive dyes may change color in response to sweat pH. The pH sensing system may measure pH using optical spectroscopy to match color change in pH sensitive dyes to a pH value. The pH sensing system may include a wearable patch. The pH sensing system may measure pH data during physical activity.

Based on the measured pH data, the pH sensing system may detect pH-related biomarkers, including normal blood pH, abnormal blood pH, and/or acidic blood pH. The pH sensing system may detect pH-related biomarkers, complications, and/or contextual information by comparing measured pH data to a standard pH scale. A standard pH scale may identify a healthy pH range to include values between 7.35 and 7.45.

The pH sensing system may use the pH-related biomarkers to indicate pH conditions including post-operative internal bleeding, acidosis, sepsis, lung collapse, and/or hemorrhage. For example, the pH sensing system may predict post-operative internal bleeding based on pre-operation acidic blood pH. Acidic blood may reduce blood clotting capacity by inhibiting thrombin generation. For example, the pH sensing system may predict sepsis and/or hemorrhage based on acidic pH. Lactic acidosis may cause acidic pH. The pH sensing system may continuously monitor blood pH data as acidosis may only occur during exercise.

The pH sensing system may locally process pH data or transmit pH data to a processing unit and/or computing system. In an example, the detection, prediction and/or determination described herein may be performed by a computing system based on measured data and/or related biomarkers generated by the pH sensing system.

A hydration state sensing system may measure hydration data including water light absorption, water light reflection, and/or sweat levels. The hydration state sensing system may use optical spectroscopy or sweat-based colorimetry. The hydration state sensing system may use optical spectroscopy by imposing emitted light onto skin and measuring the reflected light. Optical spectroscopy may measure water content by measuring amplitudes of the reflected light from certain wavelengths, including 1720 nm, 1750 nm, and/or 1770 nm. The hydration state sensing system may include a wearable device that may impose light onto skin. The wearable device may include a watch. The hydration state sensing system may use sweat-based colorimetry to measure sweat levels. Sweat-based colorimetry may be processed in conjunction with user activity data and/or user water intake data.

Based on the hydration data, the hydration state sensing system may detect water content. Based on the water content, a hydration state sensing system may identify hydration-related biomarkers, complications, and/or contextual information including dehydration, risk of kidney injury, reduced blood flow, risk of hypovolemic shock during or after surgery, and/or decreased blood volume.

For example, the hydration state sensing system, based on identified hydration, may detect health risks. Dehydration may negatively impact overall health. For example, the hydration state sensing system may predict risk of post-operation acute kidney injury when it detects reduced blood flow resulting from low hydration levels. For example, the hydration state sensing system may calculate the risk of hypovolemic shock during or after surgery when the sensing system detects dehydration or decreased blood volume. The hydration state sensing system may use the hydration level information to provide context for other received biomarker data, which may include heart rate. The hydration state sensing system may measure hydration state data continuously. Continuous measurement may consider various factors, including exercise, fluid intake, and/or temperature, which may influence the hydration state data.

The hydration state sensing system may locally process hydration data or transmit the data to a processing unit and/or computing system. In an example, the detection, prediction, and/or determination described herein may be performed by a computing system based on measured data and/or related biomarkers generated by the hydration state sensing system.

A heart rate sensing system may measure heart rate data including heart chamber expansion, heart chamber contraction, and/or reflected light. The heart rate sensing system may use ECG and/or PPG to measure heart rate data. For example, the heart rate sensing system using ECG may include a radio transmitter, receiver, and one or more electrodes. The radio transmitter and receiver may record voltages across electrodes positioned on the skin resulting from expansion and contraction of heart chambers. The heart rate sensing system may calculate heart rate using measured voltage. For example, the heart rate sensing system using PPG may impose green light on skin and record the reflected light in a photodetector. The heart rate sensing system may calculate heart rate using the measured light absorbed by the blood over a period of time. The heart rate sensing system may include a watch, a wearable elastic band, a skin patch, a bracelet, garments, a wrist strap, an earphone, and/or a headband. For example, the heart rate sensing system may include a wearable chest patch. The wearable chest patch may measure heart rate data and other vital signs or critical data including respiratory rate, skin temperature, body posture, fall detection, single-lead ECG, R-R intervals, and step counts. The wearable chest patch may locally process heart rate data or transmit the data to a processing unit. The processing unit may include a display.

Based on the measured heart rate data, the heart rate sensing system may calculate heart rate-related biomarkers including heart rate, heart rate variability, and/or average heart rate. Based on the heart rate data, the heart rate sensing system may detect biomarkers, complications, and/or contextual information including stress, pain, infection, and/or sepsis. The heart rate sensing system may detect heart rate conditions when heart rate exceeds a normal threshold. A normal threshold for heartrate may include the range of 60 to 100 heartbeats per minute. The heart rate sensing system may diagnose post-operation infection, sepsis, or hypovolemic shock based on increased heart rate, including heart rate in excess of 90 beats per minute.

The heart rate sensing system may process heart rate data locally or transmit the data to a processing unit and/or computing system. In an example, the detection, prediction, and/or determination described herein may be performed by a computing system based on measured data and/or related biomarkers generated by the heart rate sensing system. A heart rate sensing system may transmit the heart rate information to a computing system, such as a surgical hub. The computing system may collect and display cardiovascular parameter information including heart rate, respiration, temperature, blood pressure, arrhythmia, and/or atrial fibrillation. Based on the cardiovascular parameter information, the computing system may generate a cardiovascular health score.

A skin conductance sensing system may measure skin conductance data including electrical conductivity. The skin conductance sensing system may include one or more electrodes. The skin conductance sensing system may measure electrical conductivity by applying a voltage across the electrodes. The electrodes may include silver or silver chloride. The skin conductance sensing system may be placed on one or more fingers. For example, the skin conductance sensing system may include a wearable device. The wearable device may include one or more sensors. The wearable device may attach to one or more fingers. Skin conductance data may vary based on sweat levels.

The skin conductance sensing system may locally process skin conductance data or transmit the data to a computing system. Based on the skin conductance data, a skin conductance sensing system may calculate skin conductance-related biomarkers including sympathetic activity levels. For example, a skin conductance sensing system may detect high sympathetic activity levels based on high skin conductance.

A peripheral temperature sensing system may measure peripheral temperature data including extremity temperature. The peripheral temperature sensing system may include a thermistor, thermoelectric effect, or infrared thermometer to measure peripheral temperature data. For example, the peripheral temperature sensing system using a thermistor may measure the resistance of the thermistor. The resistance may vary as a function of temperature. For example, the peripheral temperature sensing system using the thermoelectric effect may measure an output voltage. The output voltage may increase as a function of temperature. For example, the peripheral temperature sensing system using an infrared thermometer may measure the intensity of radiation emitted from a body's blackbody radiation. The intensity of radiation may increase as a function of temperature.

Based on peripheral temperature data, the peripheral temperature sensing system may determine peripheral temperature-related biomarkers including basal body temperature, extremity skin temperature, and/or patterns in peripheral temperature. Based on the peripheral temperature data, the peripheral temperature sensing system may detect conditions including diabetes.

The peripheral temperature sensing system may locally process peripheral temperature data and/or biomarkers or transmit the data to a processing unit. For example, the peripheral temperature sensing system may send peripheral temperature data and/or biomarkers to a computing system, such as a surgical hub. The computing system may analyze the peripheral temperature information with other biomarkers, including core body temperature, sleep, and menstrual cycle. For example, the detection, prediction, and/or determination described herein may be performed by a computing system based on measured data and/or related biomarkers generated by the peripheral temperature sensing system.

A tissue perfusion pressure sensing system may measure tissue perfusion pressure data including skin perfusion pressure. The tissue perfusion sensing system may use optical methods to measure tissue perfusion pressure data. For example, the tissue perfusion sensing system may illuminate skin and measure the light transmitted and reflected to detect changes in blood flow. The tissue perfusion sensing system may apply occlusion. For example, the tissue perfusion sensing system may determine skin perfusion pressure based on the measured pressure used to restore blood flow after occlusion. The tissue perfusion sensing system may measure the pressure to restore blood flow after occlusion using a strain gauge or laser doppler flowmetry. The measured change in frequency of light caused by movement of blood may directly correlate with the number and velocity of red blood cells, which the tissue perfusion pressure sensing system may use to calculate pressure. The tissue perfusion pressure sensing system may monitor tissue flaps during surgery to measure tissue perfusion pressure data.

Based on the measured tissue perfusion pressure data, the tissue perfusion pressure sensing system may detect tissue perfusion pressure-related biomarkers, complications, and/or contextual information including hypovolemia, internal bleeding, and/or tissue mechanical properties. For example, the tissue perfusion pressure sensing system may detect hypovolemia and/or internal bleeding based on a drop in perfusion pressure. Based on the measured tissue perfusion pressure data, the tissue perfusion pressure sensing system may inform surgical tool parameters and/or medical procedures. For example, the tissue perfusion pressure sensing system may determine tissue mechanical properties using the tissue perfusion pressure data. Based on the determined mechanical properties, the sensing system may generate stapling procedure and/or stapling tool parameter adjustment(s). Based on the determined mechanical properties, the sensing system may inform dissecting procedures. Based on the measured tissue perfusion pressure data, the tissue perfusion pressure sensing system may generate a score for overall adequacy of perfusion.

The tissue perfusion pressure sensing system may locally process tissue perfusion pressure data or transmit the data to a processing unit and/or computing system. In an example, the detection, prediction, determination, and/or generation described herein may be performed by a computing system based on measured data and/or related biomarkers generated by the tissue perfusion pressure sensing system.

A coughing and sneezing sensing system may measure coughing and sneezing data including coughing, sneezing, movement, and sound. The coughing and sneezing sensing system may track hand or body movement that may result from a user covering her mouth while coughing or sneezing. The sensing system may include an accelerometer and/or a microphone. The sensing system may include a wearable device. The wearable device may include a watch.

Based on the coughing and sneezing data, the sensing system may detect coughing and sneezing-related biomarkers, including but not limited to, coughing frequency, sneezing frequency, coughing severity, and/or sneezing severity. The sensing system may establish a coughing and sneezing baseline using the coughing and sneezing information. The coughing and sneezing sensing system may locally process coughing and sneezing data or transmit the data to a computing system.

Based on the coughing and sneezing data, the sensing system may detect coughing and sneezing-related biomarkers, complications, and/or contextual information including respiratory tract infection, infection, collapsed lung, pulmonary edema, gastroesophageal reflux disease, allergic rhinitis, and/or systemic inflammation. For example, the coughing and sneezing sensing system may indicate gastroesophageal reflux disease when the sensing system measures chronic coughing. Chronic coughing may lead to inflammation of the lower esophagus. Lower esophagus inflammation may affect the properties of stomach tissue for sleeve gastrectomy. For example, the coughing and sneezing sensing system may detect allergic rhinitis based on sneezing. Sneezing may link to systemic inflammation. Systemic inflammation may affect the mechanical properties of the lungs and/or other tissues. In an example, the detection, prediction, and/or determination described herein may be performed by a computing system based on measured data and/or related biomarkers generated by the coughing and sneezing sensing system.

A gastrointestinal (GI) motility sensing system may measure GI motility data including pH, temperature, pressure, and/or stomach contractions. The GI motility sensing system may use electrogastrography, electrogastroenterography, stethoscopes, and/or ultrasounds. The GI motility sensing system may include a non-digestible capsule. For example, the ingestible sensing system may adhere to the stomach lining. The ingestible sensing system may measure contractions using a piezoelectric device which generates a voltage when deformed.

Based on the GI data, the sensing system may calculate GI motility-related biomarkers including gastric, small bowel, and/or colonic transit times. Based on the gastrointestinal motility information, the sensing system may detect GI motility-related conditions including ileus. The GI motility sensing system may detect ileus based on a reduction in small bowel motility. The GI motility sensing system may notify healthcare professionals when it detects GI motility conditions. The GI motility sensing system may locally process GI motility data or transmit the data to a processing unit. In an example, the detection, prediction, and/or determination described herein may be performed by a computing system based on measured data and/or related biomarkers generated by the GI motility sensing system.

A GI tract imaging/sensing system may collect images of a patient's colon. The GI tract imaging/sensing system may include an ingestible wireless camera and a receiver. The GI tract imaging/sensing system may include one or more white LEDs, a battery, radio transmitter, and antenna. The ingestible camera may include a pill. The ingestible camera may travel through the digestive tract and take pictures of the colon. The ingestible camera may take pictures up to 35 frames per second during motion. The ingestible camera may transmit the pictures to a receiver. The receiver may include a wearable device. The GI tract imaging/sensing system may process the images locally or transmit them to a processing unit. Doctors may look at the raw images to make a diagnosis.

Based on the GI tract images, the GI tract imaging sensing system may identify GI tract-related biomarkers including stomach tissue mechanical properties or colonic tissue mechanical properties. Based on the collected images, the GI tract imaging sensing system may detect GI tract-related biomarkers, complications, and/or contextual information including mucosal inflammation, Crohn's disease, anastomotic leak, esophagus inflammation, and/or stomach inflammation. The GI tract imaging/sensing system may replicate a physician diagnosis using image analysis software. The GI tract imaging/sensing system may locally process images or transmit the data to a processing unit. In an example, the detection, prediction, and/or determination described herein may be performed by a computing system based on measured data and/or related biomarkers generated by the GI tract imaging/sensing system.

A respiratory tract bacteria sensing system may measure bacteria data including foreign DNA or bacteria. The respiratory tract bacteria sensing system may use a radio frequency identification (RFID) tag and/or electronic nose (e-nose). The sensing system using an RFID tag may include one or more gold electrodes, graphene sensors, and/or layers of peptides. The RFID tag may bind to bacteria. When bacteria bind to the RFID tag, the graphene sensor may detect a change in signal-to-signal presence of bacteria. The RFID tag may include an implant. The implant may adhere to a tooth. The implant may transmit bacteria data. The sensing system may use a portable e-nose to measure bacteria data.

Based on measured bacteria data, the respiratory tract bacteria sensing system may detect bacteria-related biomarkers including bacteria levels. Based on the bacteria data, the respiratory tract bacteria sensing system may generate an oral health score. Based on the detected bacteria data, the respiratory tract bacteria sensing system may identify bacteria-related biomarkers, complications, and/or contextual information, including pneumonia, lung infection, and/or lung inflammation. The respiratory tract bacteria sensing system may locally process bacteria information or transmit the data to a processing unit. In an example, the detection, prediction, and/or determination described herein may be performed by a computing system based on measured data and/or related biomarkers generated by the respiratory tract bacteria sensing system.

An edema sensing system may measure edema data including lower leg circumference, leg volume, and/or leg water content level. The edema sensing system may include a force sensitive resistor, strain gauge, accelerometer, gyroscope, magnetometer, and/or ultrasound. The edema sensing system may include a wearable device. For example, the edema sensing system may include socks, stockings, and/or ankle bands.

Based on the measured edema data, the edema sensing system may detect edema-related biomarkers, complications, and/or contextual information, including inflammation, rate of change in inflammation, poor healing, infection, leak, colorectal anastomotic leak, and/or water build-up.

For example, the edema sensing system may detect a risk of colorectal anastomotic leak based on fluid build-up. Based on the detected edema physiological conditions, the edema sensing system may generate a score for healing quality. For example, the edema sensing system may generate the healing quality score by comparing edema information to a certain threshold lower leg circumference. Based on the detected edema information, the edema sensing system may generate edema tool parameters including responsiveness to stapler compression. The edema sensing system may provide context for measured edema data by using measurements from the accelerometer, gyroscope, and/or magnetometer. For example, the edema sensing system may detect whether the user is sitting, standing, or lying down.

The edema sensing system may process measured edema data locally or transmit the edema data to a processing unit. In an example, the detection, prediction, and/or determination described herein may be performed by a computing system based on measured data and/or related biomarkers generated by the edema sensing system.

A mental aspect sensing system may measure mental aspect data, including heart rate, heart rate variability, brain activity, skin conductance, skin temperature, galvanic skin response, movement, and/or sweat rate. The mental aspect sensing system may measure mental aspect data over a set duration to detect changes in mental aspect data. The mental aspect sensing system may include a wearable device. The wearable device may include a wristband.

Based on the mental aspect data, the sensing system may detect mental aspect-related biomarkers, including emotional patterns, positivity levels, and/or optimism levels. Based on the detected mental aspect information, the mental aspect sensing system may identify mental aspect-related biomarkers, complications, and/or contextual information including cognitive impairment, stress, anxiety, and/or pain. Based on the mental aspect information, the mental aspect sensing system may generate mental aspect scores, including a positivity score, optimism score, confusion or delirium score, mental acuity score, stress score, anxiety score, depression score, and/or pain score.

Mental aspect data, related biomarkers, complications, contextual information, and/or mental aspect scores may be used to determine treatment courses, including pain relief therapies. For example, post-operative pain may be predicted when it detects pre-operative anxiety and/or depression. For example, based on detected positivity and optimism levels, the mental aspect sensing system may determine mood quality and mental state. Based on mood quality and mental state, the mental aspect sensing system may indicate additional care procedures that would benefit a patient, including paint treatments and/or psychological assistance. For example, based on detected cognitive impairment, confusion, and/or mental acuity, the mental aspects sensing system may indicate conditions including delirium, encephalopathy, and/or sepsis. Delirium may be hyperactive or hypoactive. For example, based on detected stress and anxiety, the mental aspect sensing system may indicate conditions including hospital anxiety and/or depression. Based on detected hospital anxiety and/or depression, the mental aspect sensing system may generate a treatment plan, including pain relief therapy and/or pre-operative support.

In an example, the detection, prediction, and/or determination described herein may be performed by a computing system based on measured data and/or related biomarkers generated by the mental aspect sensing system. The mental aspect sensing system may process mental aspect data locally or transmit the data to a processing unit.

A sweat sensing system may measure sweat data including sweat, sweat rate, cortisol, adrenaline, and/or lactate. The sweat sensing system may measure sweat data using microfluidic capture, saliva testing, nanoporous electrode systems, e-noses, reverse iontophoresis, blood tests, amperometric thin film biosensors, textile organic electrochemical transistor devices, and/or electrochemical biosensors. The sensing system may measure sweat data with microfluidic capture using a colorimetric or impedimetric method. The microfluidic capture may include a flexible patch placed in contact with skin. The sweat sensing system may measure cortisol using saliva tests. The saliva tests may use electrochemical methods and/or molecularly selective organic electrochemical transistor devices. The sweat sensing system may measure ion build-up that bind to cortisol in sweat to calculate cortisol levels. The sweat sensing system may use enzyme reactions to measure lactate. Lactate may be measured using lactate oxidase and/or lactate dehydrogenase methods.

Based on the measured sweat data, the sweat sensing system or processing unit may detect sweat-related biomarkers, complications, and/or contextual information including cortisol levels, adrenaline levels, and/or lactate levels. Based on the detected sweat data and/or related biomarkers, the sweat sensing system may indicate sweat physiological conditions including sympathetic nervous system activity, psychological stress, cellular immunity, circadian rhythm, blood pressure, tissue oxygenation, and/or post-operation pain. For example, based on sweat rate data, the sweat sensing system may detect psychological stress. Based on the detected psychological stress, the sweat sensing system may indicate heightened sympathetic activity. Heightened sympathetic activity may indicate post-operation pain.

Based on the detected sweat information, the sweat sensing system may detect sweat-related biomarkers, complications, and/or contextual information including post-operation infection, metastasis, chronic elevation, ventricular failure, sepsis, hemorrhage, hyperlactemia, and/or septic shock. For example, the sensing system may detect septic shock when serum lactate concentration exceeds a certain level, such as 2 mmol/L. For example, based on detected patterns of adrenaline surges, the sweat sensing system may indicate a risk of heart attack and/or stroke. For example, surgical tool parameter adjustments may be determined based on detected adrenaline levels. The surgical tool parameter adjustments may include settings for surgical sealing tools. For example, the sweat sensing system may predict infection risk and/or metastasis based on detected cortisol levels. The sweat sensing system may notify healthcare professionals about the condition.

In an example, the detection, prediction, and/or determination described herein may be performed by a computing system based on measured data and/or related biomarkers generated by the sweat sensing system. The sweat sensing system may locally process sweat data or transmit the sweat data to a processing unit.

A lactate sensing system may measure lactate level using electrochemical biosensors. The electrochemical biosensors may detect lactate oxidase and/or lactate dehydrogenase in various bodily fluids, including sweat. Based on the measured lactate level data, the lactate sensing system or processing unit may detect lactate-related biomarkers, complications, and/or contextual information including tissue oxygenation, ventricular failure, sepsis, hemorrhage, hyperlactemia, and/or septic shock. For example, the lactate sensing system may detect septic shock when serum lactate concentration exceeds a certain level, such as 2 mmol/L.

In an example, the detection, prediction, and/or determination described herein may be performed by a computing system based on measured data and/or related biomarkers generated by the lactate sensing system. The lactate sensing system may locally process lactate level data or transmit the lactate level data to a processing unit.

A sweat rate system may measure sweat rate data with microfluidic capture using a colorimetric or impedimetric method. The microfluidic capture may include a flexible patch placed in contact with skin. Based on the measured sweat rate data, the sweat rate sensing system or processing unit may detect sweat rate-related biomarkers, complications, and/or contextual information including sympathetic nervous system activity, psychological stress, post-operation infection and/or post-operation pain. For example, the sweat rate sensing system may detect psychological stress. Based on the detected psychological stress, the sweat rate sensing system may indicate heightened sympathetic activity. Heightened sympathetic activity may indicate post-operation pain.

In an example, the detection, prediction, and/or determination described herein may be performed by a computing system based on measured data and/or related biomarkers generated by the sweat rate sensing system. The sweat rate sensing system may locally process sweat rate data or transmit the sweat rate data to a processing unit.

A circulating tumor cell sensing system may detect circulating tumor cells. The circulating tumor cell sensing system may detect circulating tumor cells using an imaging agent. The imaging agent may use microbubbles attached with antibodies which target circulating tumor cells. The imaging agent may be injected into the bloodstream. The imaging agent may attach to circulating tumor cells. The circulating tumor cell sensing system may include an ultrasonic transmitter and receiver. The ultrasonic transmitter and receiver may detect the imaging agent attached to circulating tumor cells. The circulating tumor cell sensing system may receive circulating tumor cell data.

Based on the detected circulating tumor cells data, the circulating tumor cell sensing system may calculate metastatic risk. The presence of circulating cancerous cells may indicate metastatic risk. Circulating cancerous cells per milliliter of blood exceeding a threshold amount may indicate a metastatic risk. Cancerous cells may circulate the bloodstream when tumors metastasize. Based on the calculated metastatic risk, the circulating tumor cell sensing system may generate a surgical risk score. Based on the generated surgical risk score, the circulating tumor cell sensing system may indicate surgery viability and/or suggested surgical precautions.

In an example, the detection, prediction and/or determination described herein may be performed by a computing system based on measured data and/or related biomarkers generated by the circulating tumor cells sensing system. The circulating tumor cell sensing system may process the circulating tumor cell data locally or transmit the circulating tumor cells data to a processing unit.

An autonomic tone sensing system may measure autonomic tone data including skin conductance, heart rate variability, activity, and/or peripheral body temperature. The autonomic tone sensing system may include one or more electrodes, PPG trace, ECG trace, accelerometer, GPS, and/or thermometer. The autonomic tone sensing system may include a wearable device that may include a wristband and/or finger band.

Based on the autonomic tone data, the autonomic tone sensing system may detect autonomic tone-related biomarkers, complications, and/or contextual information, including sympathetic nervous system activity level and/or parasympathetic nervous system activity level. The autonomic tone may describe the basal balance between the sympathetic and parasympathetic nervous system. Based on the measured autonomic tone data, the autonomic tone sensing system may indicate risk for post-operative conditions including inflammation and/or infection. High sympathetic activity may associate with increase in inflammatory mediators, suppressed immune function, postoperative ileus, increased heart rate, increased skin conductance, increased sweat rate, and/or anxiety.

In an example, the detection, prediction, and/or determination described herein may be performed by a computing system based on measured data and/or related biomarkers generated by the autonomic tone sensing system. The autonomic tone sensing system may process the autonomic tone data locally or transmit the data to a processing unit.

A circadian rhythm sensing system may measure circadian rhythm data including light exposure, heart rate, core body temperature, cortisol levels, activity, and/or sleep. Based on the circadian rhythm data the circadian rhythm sensing system may detect circadian rhythm-related biomarkers, complications, and/or contextual information including sleep cycle, wake cycle, circadian patterns, disruption in circadian rhythm, and/or hormonal activity.

For example, based on the measured circadian rhythm data, the circadian rhythm sensing system may calculate the start and end of the circadian cycle. The circadian rhythm sensing system may indicate the beginning of the circadian day based on measured cortisol. Cortisol levels may peak at the start of a circadian day. The circadian rhythm sensing system may indicate the end of the circadian day based on measured heart rate and/or core body temperature. Heart rate and/or core body temperature may drop at the end of a circadian day. Based on the circadian rhythm-related biomarkers, the sensing system or processing unit may detect conditions including risk of infection and/or pain. For example, disrupted circadian rhythm may indicate pain and discomfort.

In an example, the detection, prediction, and/or determination described herein may be performed by a computing system based on measured data and/or related biomarkers generated by the circadian rhythm sensing system. The circadian rhythm sensing system may process the circadian rhythm data locally or transmit the data to a processing unit.

A menstrual cycle sensing system may measure menstrual cycle data including heart rate, heart rate variability, respiration rate, body temperature, and/or skin perfusion. Based on the menstrual cycle data, the menstrual cycle unit may indicate menstrual cycle-related biomarkers, complications, and/or contextual information, including menstrual cycle phase. For example, the menstrual cycle sensing system may detect the periovulatory phase in the menstrual cycle based on measured heart rate variability. Changes in heart rate variability may indicate the periovulatory phase. For example, the menstrual cycle sensing system may detect the luteal phase in the menstrual cycle based on measured wrist skin temperature and/or skin perfusion. Increased wrist skin temperature may indicate the luteal phase. Changes in skin perfusion may indicate the luteal phase. For example, the menstrual cycle sensing system may detect the ovulatory phase based on measured respiration rate. Low respiration rate may indicate the ovulatory phase.

Based on menstrual cycle-related biomarkers, the menstrual cycle sensing system may determine conditions including hormonal changes, surgical bleeding, scarring, bleeding risk, and/or sensitivity levels. For example, the menstrual cycle phase may affect surgical bleeding in rhinoplasty. For example, the menstrual cycle phase may affect healing and scarring in breast surgery. For example, bleeding risk may decrease during the periovulatory phase in the menstrual cycle.

In an example, the detection, prediction, and/or determination described herein may be performed by a computing system based on measured data and/or related biomarkers generated by the menstrual cycle sensing system. The menstrual cycle sensing system may locally process menstrual cycle data or transmit the data to a processing unit.

An environmental sensing system may measure environmental data including environmental temperature, humidity, mycotoxin spore count, and airborne chemical data. The environmental sensing system may include a digital thermometer, air sampling, and/or chemical sensors. The sensing system may include a wearable device. The environmental sensing system may use a digital thermometer to measure environmental temperature and/or humidity. The digital thermometer may include a metal strip with a determined resistance. The resistance of the metal strip may vary with environmental temperature. The digital thermometer may apply the varied resistance to a calibration curve to determine temperature. The digital thermometer may include a wet bulb and a dry bulb. The wet bulb and dry bulb may determine a difference in temperature, which then may be used to calculate humidity.

The environmental sensing system may use air sampling to measure mycotoxin spore count. The environmental sensing system may include a sampling plate with adhesive media connected to a pump. The pump may draw air over the plate over set time at a specific flow rate. The set time may last up to 10 minutes. The environmental sensing system may analyze the sample using a microscope to count the number of spores. The environmental sensing system may use different air sampling techniques including high-performance liquid chromatography (HPLC), liquid chromatography-tandem mass spectrometry (LC-MS/MS), and/or immunoassays and nanobodies.

The environmental sensing system may include chemical sensors to measure airborne chemical data. Airborne chemical data may include different identified airborne chemicals, including nicotine and/or formaldehyde. The chemical sensors may include an active layer and a transducer layer. The active layer may allow chemicals to diffuse into a matrix and alter some physical or chemical property. The changing physical property may include refractive index and/or H-bond formation. The transducer layer may convert the physical and/or chemical variation into a measurable signal, including an optical or electrical signal. The environmental sensing system may include a handheld instrument. The handheld instrument may detect and identify complex chemical mixtures that constitute aromas, odors, fragrances, formulations, spills, and/or leaks. The handheld instrument may include an array of nanocomposite sensors. The handheld instrument may detect and identify substances based on chemical profile.

Based on the environmental data, the sensing system may determine environmental information including climate, mycotoxin spore count, mycotoxin identification, airborne chemical identification, airborne chemical levels, and/or inflammatory chemical inhalation. For example, the environmental sensing system may approximate the mycotoxin spore count in the air based on the measured spore count from a collected sample. The sensing system may identify the mycotoxin spores which may include molds, pollens, insect parts, skin cell fragments, fibers, and/or inorganic particulate. For example, the sensing system may detect inflammatory chemical inhalation, including cigarette smoke. The sensing system may detect second-hand or third-hand smoke.

Based on the environmental information, the sensing system may generate environmental aspects conditions including inflammation, reduced lung function, airway hyper-reactivity, fibrosis, and/or reduce immune functions. For example, the environmental aspects sensing system may detect inflammation and fibrosis based on the measured environmental aspects information. The sensing system may generate instructions for a surgical tool, including a staple and sealing tool used in lung segmentectomy, based on the inflammation and/or fibrosis. Inflammation and fibrosis may affect the surgical tool usage. For example, cigarette smoke may cause higher pain scores in various surgeries.

The environmental sensing system may generate an air quality score based on the measured mycotoxins and/or airborne chemicals. For example, the environmental sensing system may notify about hazardous air quality if it detects a poor air quality score. The environmental sensing system may send a notification when the generated air quality score falls below a certain threshold. The threshold may include exposure exceeding 105 spores of mycotoxins per cubic meter. The environmental sensing system may display a readout of the environment condition exposure over time.

The environmental sensing system may locally process environmental data or transmit the data to a processing unit. In an example, the detection, prediction, and/or determination described herein may be performed by a computing system based on measured data generated by the environmental sensing system.

A light exposure sensing system may measure light exposure data. The light exposure sensing system may include one or more photodiode light sensors. For example, the light exposure sensing system using photodiode light sensors may include a semiconductor device in which the device current may vary as a function of light intensity. Incident photons may create electron-hole pairs that flow across the semiconductor junction, which may create current. The rate of electron-hole pair generation may increase as a function of the intensity of the incident light. The light exposure sensing system may include one or more photoresistor light sensors. For example, the light exposure sensing system using photoresistor light sensors may include a light-dependent resistor in which the resistance decreases as a function of light intensity. The photoresistor light sensor may include passive devices without a PN-junction. The photoresistor light sensors may be less sensitive than photodiode light sensors. The light exposure sensing system may include a wearable, including a necklace and/or clip-on button.

Based on the measured light exposure data, the light exposure sensing system may detect light exposure information including exposure duration, exposure intensity, and/or light type. For example, the sensing system may determine whether light exposure consists of natural light or artificial light. Based on the detected light exposure information, the light exposure sensing system may detect light exposure-related biomarker(s) including circadian rhythm. Light exposure may entrain the circadian cycle.

The light exposure sensing system may locally process the light exposure data or transmit the data to a processing unit. In an example, the detection, prediction, and/or determination described herein may be performed by a computing system based on measured data and/or related biomarkers generated by the light exposure sensing system.

The various sensing systems described herein may measure data, derive related biomarkers, and send the biomarkers to a computing system, such as a surgical hub as described herein with reference to FIGS. 1-12. The various sensing systems described herein may send the measured data to the computing system. The computing system may derive the related biomarkers based on the received measurement data.

The biomarker sensing systems may include a wearable device. In an example, the biomarker sensing system may include eyeglasses. The eyeglasses may include a nose pad sensor. The eyeglasses may measure biomarkers, including lactate, glucose, and/or the like. In an example, the biomarker sensing system may include a mouthguard. The mouthguard may include a sensor to measure biomarkers including uric acid and/or the like. In an example, the biomarker sensing system may include a contact lens. The contact lens may include a sensor to measure biomarkers including glucose and/or the like. In an example, the biomarker sensing system may include a tooth sensor. The tooth sensor may be graphene-based. The tooth sensor may measure biomarkers including bacteria and/or the like. In an example, the biomarker sensing system may include a patch. The patch may be wearable on the chest skin or arm skin. For example, the patch may include a chem-phys hybrid sensor. The chem-phys hybrid sensor may measure biomarkers including lactate, ECG, and/or the like. For example, the patch may include nanomaterials. The nanomaterials patch may measure biomarkers including glucose and/or the like. For example, the patch may include an iontophoretic biosensor. The iontophoretic biosensor may measure biomarkers including glucose and/or the like. In an example, the biomarker sensing system may include a microfluidic sensor. The microfluidic sensor may measure biomarkers including lactate, glucose, and/or the like. In an example, the biomarker sensing system may include an integrated sensor array. The integrated sensory array may include a wearable wristband. The integrated sensory array may measure biomarkers including lactate, glucose, and/or the like. In an example, the biomarker sensing system may include a wearable diagnostics device. The wearable diagnostic device may measure biomarkers including cortisol, interleukin-6, and/or the like. In an example, the biomarker sensing system may include a self-powered textile-based biosensor. The self-powered textile-based biosensor may include a sock. The self-powered textile-based biosensor may measure biomarkers including lactate and/or the like.

The various biomarkers described herein may be related to various physiologic systems, including behavior and psychology, cardiovascular system, renal system, skin system, nervous system, GI system, respiratory system, endocrine system, immune system, tumor, musculoskeletal system, and/or reproductive system.

Behavior and psychology may include social interactions, diet, sleep, activity, and/or psychological status. Behavior and psychology-related biomarkers, complications, contextual information, and/or conditions may be determined and/or predicted based on analyzed biomarker sensing systems data. A computing system, as described herein, may select one or more biomarkers (e.g., data from biomarker sensing systems) from behavior and psychology-related biomarkers, including sleep, circadian rhythm, physical activity, and/or mental aspects for analysis. Behavior and psychology scores may be generated based on the analyzed biomarkers, complications, contextual information, and/or conditions. Behavior and psychology scores may include scores for social interaction, diet, sleep, activity, and/or psychological status.

For example, based on the selected biomarker sensing systems data, sleep-related biomarkers, complications, and/or contextual information may be determined, including sleep quality, sleep duration, sleep timing, immune function, and/or post-operation pain. Based on the selected biomarker sensing systems data, sleep-related conditions may be predicted, including inflammation. In an example, inflammation may be predicted based on analyzed pre-operation sleep. Elevated inflammation may be determined and/or predicted based on disrupted pre-operation sleep. In an example, immune function may be determined based on analyzed pre-operation sleep. Reduced immune function may be predicted based on disrupted pre-operation sleep. In an example, post-operation pain may be determined based on analyzed sleep. Post-operation pain may be determined and/or predicted based on disrupted sleep. In an example, pain and discomfort may be determined based on analyzed circadian rhythm. A compromised immune system may be determined based on analyzed circadian rhythm cycle disruptions.

For example, based on the selected biomarker sensing systems data, activity-related biomarkers, complications, and/or contextual information may be determined, including activity duration, activity intensity, activity type, activity pattern, recovery time, mental health, physical recovery, immune function, and/or inflammatory function. Based on the selected biomarker sensing systems data, activity-related conditions may be predicted. In an example, improved physiology may be determined based on analyzed activity intensity. Moderate intensity exercise may indicate shorter hospital stays, better mental health, better physical recovery, improved immune function, and/or improved inflammatory function. Physical activity type may include aerobic activity and/or non-aerobic activity. Aerobic physical activity may be determined based on analyzed physical activity, including running, cycling, and/or weight training. Non-aerobic physical activity may be determined based on analyzed physical activity, including walking and/or stretching.

For example, based on the selected biomarker sensing systems data, psychological status-related biomarkers, complications, and/or contextual information may be determined, including stress, anxiety, pain, positive emotions, abnormal states, and/or post-operative pain. Based on the selected biomarker sensing systems data, psychological status-related conditions may be predicted, including physical symptoms of disease. Higher post-operative pain may be determined and/or predicted based on analyzed high levels of pre-operative stress, anxiety, and/or pain. Physical symptoms of disease may be predicted based on determined high optimism.

The detection, prediction, determination, and/or generation described herein may be performed by a computing system described herein, such as a surgical hub, a computing device, and/or a smart device based on measured data and/or related biomarkers generated by the biomarker sensing systems.

The cardiovascular system may include the lymphatic system, blood vessels, blood, and/or heart. Cardiovascular system-related biomarkers, complications, contextual information, and/or conditions may be determined and/or predicted based on analyzed biomarker sensing systems data. Systemic circulation conditions may include conditions for the lymphatic system, blood vessels, and/or blood. A computing system may select one or more biomarkers (e.g., data from biomarker sensing systems) from cardiovascular system-related biomarkers, including blood pressure, VO2 max, hydration state, oxygen saturation, blood pH, sweat, core body temperature, peripheral temperature, edema, heart rate, and/or heart rate variability for analysis.

For example, based on the selected biomarker sensing systems data, lymphatic system-related biomarkers, complications, and/or contextual information may be determined, including swelling, lymph composition, and/or collagen deposition. Based on the selected biomarker sensing systems data, lymphatic system-related conditions may be predicted, including fibrosis, inflammation, and/or post-operation infection. Inflammation may be predicted based on determined swelling. Post-operation infection may be predicted based on determined swelling. Collagen deposition may be determined based on predicted fibrosis. Increased collagen deposition may be predicted based on fibrosis. Harmonic tool parameter adjustments may be generated based on determined collagen deposition increases. Inflammatory conditions may be predicted based on analyzed lymph composition. Different inflammatory conditions may be determined and/or predicted based on changes in lymph peptidome composition. Metastatic cell spread may be predicted based on predicted inflammatory conditions. Harmonic tool parameter adjustments and margin decisions may be generated based on predicted inflammatory conditions.

For example, based on the selected biomarker sensing systems data, blood vessel-related biomarkers, complications, and/or contextual information may be determined, including permeability, vasomotion, pressure, structure, healing ability, harmonic sealing performance, and/or cardiothoracic health fitness. Surgical tool usage recommendations and/or parameter adjustments may be generated based on the determined blood vessel-related biomarkers. Based on the selected biomarker sensing systems data, blood vessel-related conditions may be predicted, including infection, anastomotic leak, septic shock and/or hypovolemic shock. In an example, increased vascular permeability may be determined based on analyzed edema, bradykinin, histamine, and/or endothelial adhesion molecules. Endothelial adhesion molecules may be measured using cell samples to measure transmembrane proteins. In an example, vasomotion may be determined based on selected biomarker sensing systems data. Vasomotion may include vasodilators and/or vasoconstrictors. In an example, shock may be predicted based on the determined blood pressure-related biomarkers, including vessel information and/or vessel distribution. Individual vessel structure may include arterial stiffness, collagen content, and/or vessel diameter. Cardiothoracic health fitness may be determined based on VO2 max. Higher risk of complications may be determined and/or predicted based on poor VO2 max.

For example, based on the selected biomarker sensing systems data, blood-related biomarkers, complications, and/or contextual information may be determined, including volume, oxygen, pH, waste products, temperature, hormones, proteins, and/or nutrients. Based on the selected biomarker sensing systems data, blood-related complications and/or contextual information may be determined, including cardiothoracic health fitness, lung function, recovery capacity, anaerobic threshold, oxygen intake, carbon dioxide ($CO_2$) production, fitness, tissue oxygenation, colloid osmotic pressure, and/or blood clotting ability. Based on derived blood-related biomarkers, blood-related conditions may be predicted, including post-operative acute kidney injury, hypovolemic shock, acidosis, sepsis, lung collapse, hemorrhage, bleeding risk, infection, and/or anastomotic leak.

For example, post-operative acute kidney injury and/or hypovolemic shock may be predicted based on the hydration state. For example, lung function, lung recovery capacity, cardiothoracic health fitness, anaerobic threshold, oxygen uptake, and/or CO2 product may be predicted based on the blood-related biomarkers, including red blood cell count and/or oxygen saturation. For example, cardiovascular complications may be predicted based on the blood-related biomarkers, including red blood cell count and/or oxygen saturation. For example, acidosis may be predicted based on the pH. Based on acidosis, blood-related conditions may be indicated, including sepsis, lung collapse, hemorrhage, and/or increased bleeding risk. For example, based on sweat, blood-related biomarkers may be derived, including tissue oxygenation. Insufficient tissue oxygenation may be predicted based on high lactate concentration. Based on insufficient tissue oxygenation, blood-related conditions may be predicted, including hypovolemic shock, septic shock, and/or left ventricular failure. For example, based on the temperature, blood temperature-related biomarkers may be derived, including menstrual cycle and/or basal temperature. Based on the blood temperature-related biomarkers, blood temperature-related conditions may be predicted, including sepsis and/or infection. For example, based on proteins, including albumin content, colloid osmotic pressure may be determined. Based on the colloid osmotic pressure, blood protein-related conditions may be predicted, including edema risk and/or anastomotic leak. Increased edema risk and/or anastomotic leak may be predicted based on low colloid osmotic pressure. Bleeding risk may be predicted based on blood clotting ability. Blood clotting ability may be determined based on fibrinogen content. Reduced blood clotting ability may be determined based on low fibrinogen content.

For example, based on the selected biomarker sensing systems data, the computing system may derive heart-related biomarkers, complications, and/or contextual information, including heart activity, heart anatomy, recovery rates, cardiothoracic health fitness, and/or risk of complications. Heart activity biomarkers may include electrical activity and/or stroke volume. Recovery rate may be determined based on heart rate biomarkers. Reduced blood supply to the body may be determined and/or predicted based on irregular heart rate. Slower recovery may be determined and/or predicted based on reduced blood supply to the body. Cardiothoracic health fitness may be determined based on analyzed VO2 max values. VO2 max values below a certain threshold may indicate poor cardiothoracic health fitness. VO2 max values below a certain threshold may indicate a higher risk of heart-related complications.

The detection, prediction, determination, and/or generation described herein may be performed by a computing system described herein, such as a surgical hub, a computing device, and/or a smart device, based on measured data and/or related biomarkers generated by the biomarker sensing systems.

Renal system-related biomarkers, complications, contextual information, and/or conditions may be determined and/or predicted based on analyzed biomarker sensing systems data. A computing system, as described herein, may select one or more biomarkers (e.g., data from biomarker sensing systems) from renal system-related biomarkers for analysis. Based on the selected biomarker sensing systems data, renal system-related biomarkers, complications, and/or contextual information may be determined including ureter, urethra, bladder, kidney, general urinary tract, and/or ureter fragility. Based on the selected biomarker sensing systems data, renal system-related conditions may be predicted, including acute kidney injury, infection, and/or kidney stones. In an example, ureter fragility may be determined based on urine inflammatory parameters. In an example, acute kidney injury may be predicted based on analyzed Kidney Injury Molecule-1 (KIM-1) in urine.

The detection, prediction, determination, and/or generation described herein may be performed by a computing system described herein, such as a surgical hub, a computing device, and/or a smart device based on measured data and/or related biomarkers generated by the biomarker sensing systems.

The skin system may include biomarkers relating to microbiome, skin, nails, hair, sweat, and/or sebum. Skin-related biomarkers may include epidermis biomarkers and/or dermis biomarkers. Sweat-related biomarkers may include activity biomarkers and/or composition biomarkers. Skin system-related biomarkers, complications, contextual information, and/or conditions may be determined and/or predicted based on analyzed biomarker sensing systems data. A computing system, as described herein, may select one or more biomarkers (e.g., data from biomarker sensing systems) from skin-related biomarkers, including skin conductance, skin perfusion pressure, sweat, autonomic tone, and/or pH for analysis.

For example, based on selected biomarker sensing systems data, skin-related biomarkers, complications, and/or contextual information may be determined, including color, lesions, trans-epidermal water loss, sympathetic nervous system activity, elasticity, tissue perfusion, and/or mechanical properties. Stress may be predicted based on determined skin conductance. Skin conductance may act as a proxy for sympathetic nervous system activity. Sympathetic nervous system activity may correlate with stress. Tissue mechanical properties may be determined based on skin perfusion pressure. Skin perfusion pressure may indicate deep tissue perfusion. Deep tissue perfusion may determine tissue mechanical properties. Surgical tool parameter adjustments may be generated based on determined tissue mechanical properties.

Based on selected biomarker sensing systems data, skin-related conditions may be predicted.

For example, based on selected biomarker sensing systems data, sweat-related biomarkers, complications, and/or contextual information may be determined, including activity, composition, autonomic tone, stress response, inflammatory response, blood pH, blood vessel health, immune function, circadian rhythm, and/or blood lactate concentration. Based on selected biomarker sensing systems data, sweat-related conditions may be predicted, including ileus, cystic fibrosis, diabetes, metastasis, cardiac issues, and/or infections.

For example, sweat composition-related biomarkers may be determined based on selected biomarker data. Sweat composition biomarkers may include proteins, electrolytes, and/or small molecules. Based on the sweat composition biomarkers, skin system complications, conditions, and/or contextual information may be predicted, including ileus, cystic fibrosis, acidosis, sepsis, lung collapse, hemorrhage, bleeding risk, diabetes, metastasis, and/or infection. For example, based on protein biomarkers, including sweat neuropeptide Y and/or sweat antimicrobials, stress response may be predicted. Higher sweat neuropeptide Y levels may indicate greater stress response. Cystic fibrosis and/or acidosis may be predicted based on electrolyte biomarkers, including chloride ions, pH, and other electrolytes. High lactate concentrations may be determined based on blood pH. Acidosis may be predicted based on high lactate concentrations. Sepsis, lung collapse, hemorrhage, and/or bleeding risk may be predicted based on predicted acidosis. Diabetes, metastasis, and/or infection may be predicted based on small molecule biomarkers. Small molecule biomarkers may include blood sugar and/or hormones. Hormone biomarkers may include adrenaline and/or cortisol. Based on predicted metastasis, blood vessel health may be determined. Infection due to lower immune function may be predicted based on detected cortisol. Lower immune function may be determined and/or predicted based on high cortisol. For example, sweat-related conditions, including stress response, inflammatory response, and/or ileus, may be predicted based on determined autonomic tone. Greater stress response, greater inflammatory response, and/or ileus may be determined and/or predicted based on high sympathetic tone.

The detection, prediction, determination, and/or generation described herein may be performed by a computing system described herein, such as a surgical hub, a computing device, and/or a smart device based on measured data and/or related biomarkers generated by the biomarker sensing systems.

Nervous system-related biomarkers, complications, contextual information, and/or conditions may be determined and/or predicted based on analyzed biomarker sensing systems data. A computing system, as described herein, may select one or more biomarkers (e.g., data from biomarker sensing systems) from nervous system-related biomarkers, including circadian rhythm, oxygen saturation, autonomic tone, sleep, activity, and/or mental aspects for. The nervous system may include the central nervous system (CNS) and/or the peripheral nervous system. The CNS may include brain and/or spinal cord. The peripheral nervous system may include the autonomic nervous system, motor system, enteric system, and/or sensory system.

For example, based on the selected biomarker sensing systems data, CNS-related biomarkers, complications, and/or contextual information may be determined, including post-operative pain, immune function, mental health, and/or recovery rate. Based on the selected biomarker sensing systems data, CNS-related conditions may be predicted, including inflammation, delirium, sepsis, hyperactivity, hypoactivity, and/or physical symptoms of disease. In an example, a compromised immune system and/or high pain score may be predicted based on disrupted sleep. In an example, post-operation delirium may be predicted based on oxygen saturation. Cerebral oxygenation may indicate post-operation delirium.

For example, based on the selected biomarker sensing systems data, peripheral nervous system-related biomarkers, complications, and/or contextual information may be determined. Based on the selected biomarker sensing systems data, peripheral nervous system-related conditions may be predicted, including inflammation and/or ileus. In an example, high sympathetic tone may be predicted based on autonomic tone. Greater stress response may be predicted based on high sympathetic tone. Inflammation and/or ileus may be predicted based on high sympathetic tone.

The detection, prediction, determination, and/or generation described herein may be performed by a computing system described herein, such as a surgical hub, a computing device, and/or a smart device based on measured data and/or related biomarkers generated by the biomarker sensing systems.

The GI system may include the upper GI tract, lower GI tract, ancillary organs, peritoneal space, nutritional states, and microbiomes. The upper GI may include the mouth, esophagus, and/or stomach. The lower GI may include the small intestine, colon, and/or rectum. Ancillary organs may include pancreas, liver, spleen, and/or gallbladder. Peritoneal space may include mesentry and/or adipose blood vessels. Nutritional states may include short-term, long-term, and/or systemic. GI-related biomarkers, complications, contextual information, and/or conditions may be determined and/or predicted based on analyzed biomarker sensing systems data. A computing system, as described herein, may select one or more biomarkers (e.g., data from biomarker sensing systems) from GI-related biomarkers, including coughing and sneezing, respiratory bacteria, GI tract imaging/sensing, GI motility, pH, tissue perfusion pressure, environmental, and/or alcohol consumption for analysis.

The upper GI may include the mouth, esophagus, and/or stomach. For example, based on the selected biomarker sensing systems data, mouth and esophagus-related biomarkers, complications, and/or contextual information, may be determined, including stomach tissue properties, esophageal motility, colonic tissue change, bacteria presence, tumor size, tumor location, and/or tumor tension. Based on the selected biomarker sensing systems data, mouth and esophagus-related conditions may be predicted, including inflammation, surgical site infection (SSI), and/or gastro-esophageal disease. The mouth and esophagus may include mucosa, muscularis, lumen, and/or mechanical properties. Lumen biomarkers may include lumen contents, lumen microbial flora, and/or lumen size. In an example, inflammation may be predicted based on analyzed coughing biomarkers. Gastro-esophageal reflux disease may be predicted based on inflammation. Stomach tissue properties may be predicted based on gastro-esophageal disease. In an example, esophageal motility may be determined based on collagen content and/or muscularis function. In an example, changes to colonic tissue may be indicated based on salivary cytokines. Inflammatory bowel disease (IBD) may be predicted based on changes to colonic tissue. Salivary cytokines may increase in IBD. SSI may be predicted based on analyzed bacteria. Based on the analyzed bacteria, the bacteria may be identified. Respiratory pathogens in the mouth may indicate likelihood of SSI. Based on lumen size and/or location, surgical tool parameter adjustments may be generated. Surgical tool parameter adjustments may include staple sizing, surgical tool fixation, and/or surgical tool approach. In an example, based on mechanical properties, including elasticity, a surgical tool parameter adjustment to use adjunct material may be generated to minimize tissue tension. Additional mobilization parameter adjustments may be generated to minimize tissue tension based on analyzed mechanical properties.

For example, based on the selected biomarker sensing systems data, stomach-related biomarkers, complications, and/or contextual information, may be determined including tissue strength, tissue thickness, recovery rate, lumen location, lumen shape, pancreas function, stomach food presence, stomach water content, stomach tissue thickness, stomach tissue shear strength, and/or stomach tissue elasticity. Based on the selected biomarker sensing systems data, stomach-related conditions may be predicted, including ulcer, inflammation, and/or gastro-esophageal reflux disease. The stomach may include mucosa, muscularis, serosa, lumen, and mechanical properties. Stomach-related conditions, including ulcers, inflammation, and/or gastro-esophageal disease may be predicted based on analyzed coughing and/or GI tract imaging. Stomach tissue properties may be determined based on gastro-esophageal reflux disease. Ulcers may be predicted based on analyzed *H. pylori*.

Stomach tissue mechanical properties may be determined based on GI tract images. Surgical tool parameter adjustments may be generated based on the determined stomach tissue mechanical properties. Risk of post-operative leak may be predicted based on determined stomach tissue mechanical properties. In an example, key components for tissue strength and/or thickness may be determined based on analyzed collagen content. Key components of tissue strength and thickness may affect recovery. In an example, blood supply and/or blood location may be determined based on serosa biomarkers. In an example, biomarkers, including pouch size, pouch volume, pouch location, pancreas function, and/or food presence may be determined based on analyzed lumen biomarkers. Lumen biomarkers may include lumen location, lumen shape, gastric emptying speed, and/or lumen contents. Pouch size may be determined based on start and end locations of the pouch. Gastric emptying speed may be determined based on GI motility. Pancreas function may be determined based on gastric emptying speed. Lumen content may be determined based on analyzed gastric pH. Lumen content may include stomach food presence. For example, solid food presence may be determined based on gastric pH variation. Low gastric pH may be predicted based on an empty stomach. Basic gastric pH may be determined based on eating. Buffering by food may lead to basic gastric pH. Gastric pH may increase based on stomach acid secretion. Gastric pH may return to low value when the buffering capacity of food is exceeded. Intraluminal pH sensors may detect eating. For example, stomach water content, tissue thickness, tissue shear strength, and/or tissue elasticity may be determined based on tissue perfusion pressure. Stomach mechanical properties may be determined based on stomach water content. Surgical tool parameter adjustments may be generated based on the stomach mechanical properties. Surgical tool parameter adjustments may be generated based on key components of tissue strength and/or friability. Post-surgery leakage may be predicted based on key components of tissue strength and/or friability.

The lower GI may include the small intestine, colon, and/or rectum. For example, based on the selected biomarker sensing systems data, small intestine-related biomarkers, complications, contextual information, and/or conditions may be determined, including caloric absorption rate, nutrient absorption rate, bacteria presence, and/or recovery rate. Based on the selected biomarker sensing systems data, small intestine-related conditions may be predicted, including ileus and/or inflammation. The small intestine biomarkers may include muscularis, serosa, lumen, mucosa, and/or mechanical properties. For example, post-operation small bowel motility changes may be determined based on GI motility. Ileus may be predicted based on post-operation small bowel motility changes. GI motility may determine caloric and/or nutrient absorption rates. Future weight loss may be predicted based on accelerated absorption rates. Absorption rates may be determined based on fecal rates, composition, and/or pH. Inflammation may be predicted based on lumen content biomarkers. Lumen content biomarkers may include pH, bacteria presence, and/or bacteria amount. Mechanical properties may be determined based on predicted inflammation. Mucosa inflammation may be predicted based on stool inflammatory markers. Stool inflammatory markers may include calprotectin. Tissue property changes may be determined based on mucosa inflammation. Recovery rate changes may be determined based on mucosa inflammation.

For example, based on the selected biomarker sensing systems data, colon and rectum-related biomarkers, complications, and/or contextual information may be determined, including small intestine tissue strength, small intestine tissue thickness, contraction ability, water content, colon and rectum tissue perfusion pressure, colon and rectum tissue thickness, colon and rectum tissue strength, and/or colon and rectum tissue friability. Based on the selected biomarker sensing systems data, colon and rectum-related conditions may be predicted, including inflammation, anastomotic leak, ulcerative colitis, Crohn's disease, and/or infection. Colon and rectum may include mucosa, muscularis, serosa, lumen, function, and/or mechanical properties. In an example, mucosa inflammation may be predicted based on stool inflammatory markers. Stool inflammatory markers may include calprotectin. An increase in anastomotic leak risk may be determined based on inflammation.

Surgical tool parameter adjustments may be generated based on the determined increased risk of anastomotic leak. Inflammatory conditions may be predicted based on GI tract imaging. Inflammatory conditions may include ulcerative colitis and/or Crohn's disease. Inflammation may increase the risk of anastomotic leak. Surgical tool parameter adjustments may be generated based on inflammation. In an example, the key components of tissue strength and/or thickness may be determined based on collagen content. In an example, colon contraction ability may be determined based on smooth muscle alpha-actin expression. In an example, the inability of colon areas to contract may be determined based on abnormal expression. Colon contraction inability may be determined and/or predicted based on pseudo-obstruction and/or ileus. In an example, adhesions, fistula, and/or scar tissue may be predicted based on serosa biomarkers. Colon infection may be predicted based on bacterial presence in stool. The stool bacteria may be identified. The bacteria may include commensals and/or pathogens. In an example, inflammatory conditions may be predicted based on pH. Mechanical properties may be determined based on inflammatory conditions. Gut inflammation may be predicted based on ingested allergens. Constant exposure to ingested allergens may increase gut inflammation. Gut inflammation may change mechanical properties. In an example, mechanical properties may be determined based on tissue perfusion pressure. Water content may be determined based on tissue perfusion pressure. Surgical tool parameter adjustments may be generated based on determined mechanical properties.

Ancillary organs may include the pancreas, liver, spleen, and/or gallbladder. Based on the selected biomarker sensing systems data, ancillary organ-related biomarkers, complications, and/or contextual information may be determined including gastric emptying speed, liver size, liver shape, liver location, tissue health, and/or blood loss response. Based on the selected biomarker sensing systems data, ancillary organ-related conditions may be predicted, including gastroparesis. For example, gastric emptying speed may be determined based on enzyme load and/or titratable base biomarkers. Gastroparesis may be predicted based on gastric emptying speed. Lymphatic tissue health may be determined based on lymphocyte storage status. A patient's ability to respond to an SSI may be determined based on lymphatic tissue health. Venous sinuses tissue health may be determined based on red blood cell storage status. A patient's response to blood loss in surgery may be predicted based on venous sinuses tissue health.

Nutritional states may include short-term nutrition, long-term nutrition, and/or systemic nutrition. Based on the selected biomarker sensing systems data, nutritional state-related biomarkers, complications, and/or contextual information may be determined, including immune function. Based on the selected biomarker sensing systems data, nutritional state-related conditions may be predicted, including cardiac issues. Reduced immune function may be determined based on nutrient biomarkers. Cardiac issues may be predicted based on nutrient biomarkers. Nutrient biomarkers may include macronutrients, micronutrients, alcohol consumption, and/or feeding patterns.

Patients who have had gastric bypass may have an altered gut microbiome that may be measured in the feces.

The detection, prediction, determination, and/or generation described herein may be performed by a computing system described herein, such as a surgical hub, a computing device, and/or a smart device based on measured data and/or related biomarkers generated by the biomarker sensing systems.

The respiratory system may include the upper respiratory tract, lower respiratory tract, respiratory muscles, and/or system contents. The upper respiratory tract may include the pharynx, larynx, mouth and oral cavity, and/or nose. The lower respiratory tract may include the trachea, bronchi, aveoli, and/or lungs. The respiratory muscles may include the diaphragm and/or intercostal muscles. Respiratory system-related biomarkers, complications, contextual information, and/or conditions may be determined and/or predicted based on analyzed biomarker sensing systems data. A computing system, as described herein, may select one or more biomarkers (e.g., data from biomarker sensing systems) from respiratory system-related biomarkers, including bacteria, coughing and sneezing, respiration rate, VO2 max, and/or activity for analysis.

The upper respiratory tract may include the pharynx, larynx, mouth and oral cavity, and/or nose. For example, based on the selected biomarker sensing systems data, upper respiratory tract-related biomarkers, complications, and/or contextual information may be determined. Based on the selected biomarker sensing systems data, upper respiratory tract-related conditions may be predicted, including SSI, inflammation, and/or allergic rhinitis. In an example, SSI may be predicted based on bacteria and/or tissue biomarkers. Bacteria biomarkers may include commensals and/or pathogens. Inflammation may be indicated based on tissue biomarkers. Mucosa inflammation may be predicted based on nose biomarkers, including coughing and sneezing. General inflammation and/or allergic rhinitis may be predicted based on mucosa biomarkers. Mechanical properties of various tissues may be determined based on systemic inflammation.

The lower respiratory tract may include the trachea, bronchi, aveoli, and/or lungs. For example, based on the selected biomarker sensing systems data, lower respiratory tract-related biomarkers, complications, and/or contextual information may be determined, including bronchopulmonary segments. Based on the selected biomarker sensing systems data, lower respiratory tract-related conditions may be predicted. Surgical tool parameter adjustments may be generated based on the determined biomarkers, complications, and/or contextual information. Surgical tool parameter adjustments may be generated based on the predicted conditions.

Based on the selected biomarker sensing systems data, lung-related biomarkers, complications, and/or contextual information may be determined, including poor surgical tolerance. Lung-related biomarkers may include lung respiratory mechanics, lung disease, lung surgery, lung mechanical properties, and/or lung function. Lung respiratory mechanics may include total lung capacity (TLC), tidal volume (TV), residual volume (RV), expiratory reserve volume (ERV), inspiratory reserve volume (IRV), inspiratory capacity (IC), inspiratory vital capacity (IVC), vital capacity (VC), functional residual capacity (FRC), residual volume expressed as a percent of total lung capacity (RV/TLC %), alveolar gas volume (VA), lung volume (VL), forced vital capacity (FVC), forced expiratory volume over time (FEVt), difference between inspired and expired carbon monoxide (DLco), volume exhaled after first second of forced expiration (FEV1), forced expiratory flow related to portion of functional residual capacity curve (FEFx), maximum instantaneous flow during functional residual capacity (FEFmax), forced inspiratory flow (FIF), highest forced expiratory flow measured by peak flow meter (PEF), and maximal voluntary ventilation (MVV).

TLC may be determined based on lung volume at maximal inflation. TV may be determined based on volume of air moved into or out of the lungs during quiet breathing. RV may be determined based on air volume remaining in lungs after a maximal exhalation. ERV may be determined based on maximal volume inhaled from the end-inspiratory level. IC may be determined based on aggregated IRV and TV values. IVC may be determined based on maximum air volume inhaled at the point of maximum expiration. VC may be determined based on the difference between the RV value and TLC value. FRC may be determined based on the lung volume at the end-expiratory position. FVC may be determined based on the VC value during a maximally forced expiratory effort. Poor surgical tolerance may be determined based on the difference between inspired and expired carbon monoxide, such as when the difference falls below 60%. Poor surgical tolerance may be determined based on the volume exhaled at the end of the first second of force expiration, such as when the volume falls below 35%. MVV may be determined based on the volume of air expired in a specified period during repetitive maximal effort.

Based on the selected biomarker sensing systems data, lung-related conditions may be predicted, including emphysema, chronic obstructive pulmonary disease, chronic bronchitis, asthma, cancer, and/or tuberculosis. Lung diseases may be predicted based on analyzed spirometry, x-rays, blood gas, and/or diffusion capacity of the aveolar capillary membrane. Lung diseases may narrow airways and/or create airway resistance. Lung cancer and/or tuberculosis may be detected based on lung-related biomarkers, including persistent coughing, coughing blood, shortness of breath, chest pain, hoarseness, unintentional weight loss, bone pain, and/or headaches. Tuberculosis may be predicted based on lung symptoms including coughing for 3 to 5 weeks, coughing blood, chest pain, pain while breathing or coughing, unintentional weight loss, fatigue, fever, night sweats, chills, and/or loss of appetite.

Surgical tool parameter adjustments and surgical procedure adjustments may be generated based on lung-related biomarkers, complications, contextual information, and/or conditions. Surgical procedure adjustments may include pneumonectomy, lobectomy, and/or sub-local resections. In an example, a surgical procedure adjustment may be generated based on a cost-benefit analysis between adequate resection and the physiologic impact on a patient's ability to recover functional status. Surgical tool parameter adjustments may be generated based on determined surgical tolerance. Surgical tolerance may be determined based on the FEC1 value. Surgical tolerance may be considered adequate when FEV1 exceeds a certain threshold, which may include values above 35%. Post-operation surgical procedure adjustments, including oxygenation and/or physical therapy, may be generated based on determined pain scores. Post-operation surgical procedure adjustments may be generated based on air leak. Air leak may increase cost associated with the post-surgical recovery and morbidity following lung surgery.

Lung mechanical property-related biomarkers may include perfusion, tissue integrity, and/or collagen content. Plura perfusion pressure may be determined based on lung water content levels. Mechanical properties of tissue may be determined based on plura perfusion pressure. Surgical tool parameter adjustments may be generated based on plura perfusion pressure. Lung tissue integrity may be determined based on elasticity, hydrogen peroxide (H2O2) in exhaled breath, lung tissue thickness, and/or lung tissue shear strength. Tissue friability may be determined based on elasticity. Surgical tool parameter adjustments may be generated based on post-surgery leakage. Post-surgery leakage may be predicted based on elasticity. In an example, fibrosis may be predicted based on H2O2 in exhaled breath. Fibrosis may be determined and/or predicted based on increased H2O2 concentration. Surgical tool parameter adjustments may be generated based on predicted fibrosis. Increased scarring in lung tissue may be determined based on predicted fibrosis. Surgical tool parameter adjustments may be generated based on determined lung tissue strength. Lung tissue strength may be determined based on lung thickness and/or lung tissue shear strength. Post-surgery leakage may be predicted based on lung tissue strength.

Respiratory muscles may include the diaphragm and/or intercostal muscles. Based on the selected biomarker sensing systems data, respiratory muscle-related biomarkers, complications, and/or contextual information may be determined. Based on the selected biomarker sensing systems data, respiratory muscle-related conditions may be predicted, including respiratory tract infections, collapsed lung, pulmonary edema, post-operation pain, air leak, and/or serious lung inflammation. Respiratory muscle-related conditions, including respiratory tract infections, collapsed lung, and/or pulmonary edema, may be predicted based on diaphragm-related biomarkers, including coughing and/or sneezing. Respiratory muscle-related conditions, including post-operation pain, air leak, collapsed lung, and/or serious lung inflammation may be predicted based on intercostal muscle biomarkers, including respiratory rate.

Based on the selected biomarker sensing systems data, respiratory system content-related biomarkers, complications, and/or contextual information may be determined, including post-operation pain, healing ability, and/or response to surgical injury. Based on the selected biomarker sensing systems data, respiratory system content-related conditions may be predicted, including inflammation and/or fibrosis. The selected biomarker sensing systems data may include environmental data, including mycotoxins and/or airborne chemicals. Respiratory system content-related conditions may be predicted based on airborne chemicals. Inflammation and/or fibrosis may be predicted based on irritants in the environment. Mechanical properties of tissue may be determined based on inflammation and/or fibrosis. Post-operation pain may be determined based on irritants in the environment. Airway inflammation may be predicted based on analyzed mycotoxins and/or arsenic. Surgical tool parameter adjustments may be generated based on airway inflammation. Altered tissue properties may be determined based on analyzed arsenic.

The detection, prediction, determination, and/or generation described herein may be performed by a computing system described herein, such as a surgical hub, a computing system, and/or a smart device based on measured data and/or related biomarkers generated by the biomarker sensing systems.

The endocrine system may include the hypothalamus, pituitary gland, thymus, adrenal gland, pancreas, testes, intestines, ovaries, thyroid gland, parathyroid, and/or stomach. Endocrine system-related biomarkers, complications, and/or contextual information may be determined based on analyzed biomarker sensing systems data, including immune system function, metastasis, infection risk, insulin secretion, collagen production, menstrual phase, and/or high blood pressure. Endocrine system-related conditions may be predicted based on analyzed biomarker sensing systems data. A computing system, as described herein, may select one or more biomarkers (e.g., data from biomarker sensing systems) from endocrine system-related biomarkers, including hormones, blood pressure, adrenaline, cortisol, blood glucose, and/or menstrual cycle for analysis. Surgical tool parameter adjustments and/or surgical procedure adjustments may be generated based on the endocrine system-related biomarkers, complications, contextual information, and/or conditions.

For example, based on the selected biomarker sensing systems data, hypothalamus-related biomarkers, complications, and/or contextual information may be determined, including blood pressure regulation, kidney function, osmotic balance, pituitary gland control, and/or pain tolerance. Based on the selected biomarker sensing systems data, hypothalamus-related conditions may be predicted, including edema. The hormone biomarkers may include antidiuretic hormone (ADH) and/or oxytocin. ADH may affect blood pressure regulation, kidney function, osmotic balance, and/or pituitary gland control. Pain tolerance may be determined based on analyzed oxytocin. Oxytocin may have an analgesic effect. Surgical tool parameter adjustments may be generated based on predicted edema.

For example, based on the selected biomarker sensing systems data, pituitary gland-related biomarkers, complications, and/or contextual information may be determined, including circadian rhythm entrainment, menstrual phase, and/or healing speed. Based on the selected biomarker sensing systems data, pituitary gland-related conditions may be predicted. Circadian entrainment may be determined based on adrenocorticotropic hormones (ACTH). Circadian rhythm entrainment may provide context for various surgical outcomes. Menstrual phase may be determined based on reproduction function hormone biomarkers. Reproduction function hormone biomarkers may include luteinizing hormone and/or follicle stimulating hormone. Menstrual phase may provide context for various surgical outcomes. The menstrual cycle may provide context for biomarkers, complications, and/or conditions, including those related to the reproductive system. Wound healing speed may be determined based on thyroid regulation hormones, including thyrotropic releasing hormone (TRH).

For example, based on the selected biomarker sensing systems data, thymus-related biomarkers, complications, and/or contextual information may be determined, including immune system function. Based on the selected biomarker sensing systems data, thymus-related conditions may be predicted. Immune system function may be determined based on thymosins. Thymosins may affect adaptive immunity development.

For example, based on the selected biomarker sensing systems data, adrenal gland-related biomarkers, complications, and/or contextual information may be determined, including metastasis, blood vessel health, immunity level, and/or infection risk. Based on the selected biomarker sensing system data, adrenal gland-related conditions may be predicted, including edema. Metastasis may be determined based on analyzed adrenaline and/or nonadrenaline. Blood vessel health may be determined based on analyzed adrenaline and/or nonadrenaline. A blood vessel health score may be generated based on the determined blood vessel health. Immunity capability may be determined based on analyzed cortisol. Infection risk may be determined based on analyzed cortisol. Metastasis may be predicted based on analyzed cortisol. Circadian rhythm may be determined based on measured cortisol. High cortisol may lower immunity, increase infection risk, and/or lead to metastasis. High cortisol may affect circadian rhythm. Edema may be predicted based on analyzed aldosterone. Aldosterone may promote fluid retention. Fluid retention may relate to blood pressure and/or edema.

For example, based on the selected biomarker sensing systems data, pancreas-related biomarkers, complications, and/or contextual information may be determined, including blood sugar, hormones, polypeptides, and/or blood glucose control. Based on the selected biomarker sensing systems data, pancreas-related conditions may be predicted. The pancreas-related biomarkers may provide contextual information for various surgical outcomes. Blood sugar biomarkers may include insulin. Hormone biomarkers may include somatostatin. Polypeptide biomarkers may include pancreatic polypeptide. Blood glucose control may be determined based on insulin, somatostatin, and/or pancreatic polypeptide. Blood glucose control may provide contextual information for various surgical outcomes.

For example, based on the selected biomarker sensing systems data, testes-related biomarkers, complications, and/or contextual information may be determined, including reproductive development, sexual arousal, and/or immune system regulation. Based on the selected biomarker sensing systems data, testes-related conditions may be predicted. Testes-related biomarkers may include testosterone. Testosterone may provide contextual information for biomarkers, complications, and/or conditions, including those relating to the reproductive system. High levels of testosterone may suppress immunity.

For example, based on the selected biomarker sensing systems data, stomach/testes-related biomarkers, complications, and/or contextual information may be determined, including glucose handling, satiety, insulin secretion, digestion speed, and/or sleeve gastrectomy outcomes. Glucose handling and satiety biomarkers may include glucagon-like peptide-1 (GLP-1), cholecystokinin (CCK), and/or peptide YY. Appetite and/or insulin secretion may be determined based on analyzed GLP-1. Increased GLP-1 may be determined based on enhanced appetite and insulin secretion. Sleeve gastrectomy outcomes may be determined based on analyzed GLP-1. Satiety and/or sleeve gastrectomy outcomes may be determined based on analyzed CCK. Enhanced CCK levels may be predicted based on previous sleeve gastrectomy. Appetite and digestion speeds may be determined based on analyzed peptide YY. Increased peptide YY may reduce appetite and/or increase digestion speeds.

For example, based on the selected biomarker sensing systems data, hormone-related biomarkers, complications, and/or contextual information may be determined, including estrogen, progesterone, collagen product, fluid retention, and/or menstrual phase. Collagen production may be determined based on estrogen. Fluid retention may be determined based on estrogen. Surgical tool parameter adjustments may be generated based on determined collagen production and/or fluid retention.

For example, based on the selected biomarker sensing systems data, thyroid gland and parathyroid-related biomarkers, complications, and/or contextual information may be determined, including calcium handling, phosphate handling, metabolism, blood pressure, and/or surgical complications. Metabolism biomarkers may include triiodothyronine (T3) and/or thyroxine (T4). Blood pressure may be determined based on analyzed T3 and T4. High blood pressure may be determined based on increased T3 and/or increased T4. Surgical complications may be determined based on analyzed T3 and/or T4.

For example, based on the selected biomarker sensing systems data, stomach-related biomarkers, complications, and/or contextual information may be determined, including appetite. Stomach-related biomarkers may include ghrelin. Ghrelin may induce appetite.

The detection, prediction, determination, and/or generation described herein may be performed by a computing system described herein, such as a surgical hub, a computing system, and/or a smart device based on measured data and/or related biomarkers generated by the biomarker sensing systems.

Immune system-related biomarkers may relate to antigens and irritants, antimicrobial enzymes, the complement system, chemokines and cytokines, the lymphatic system, bone marrow, pathogens, damage-associated molecular patterns (DAMPs), and/or cells. Immune system-related biomarkers, complications, and/or contextual information may be determined based on analyzed biomarker sensing systems data. A computing system, as described herein, may select one or more biomarkers (e.g., data from biomarker sensing systems) from immune system-related biomarkers, including alcohol consumption, pH, respiratory rate, edema, sweat, and/or environment for analysis. Antigens/irritants For example, based on the selected biomarker sensing systems data, antigen and irritant-related biomarkers, complications, and/or contextual information may be determined, including healing ability, immune function, and/or cardiac issues. Based on the selected biomarker sensing systems data, antigen and irritant-related conditions may be predicted, including inflammation. Antigen and irritant-related biomarkers may include inhaled chemicals, inhaled irritants, ingested chemicals, and/or ingested irritants. Inhaled chemicals or irritants may be determined based on analyzed environmental data, including airborne chemicals, mycotoxins, and/or arsenic. Airborne chemicals may include cigarette smoke, asbestos, crystalline silica, alloy particles, and/or carbon nanotubes. Lung inflammation may be predicted based on analyzed airborne chemicals. Surgical tool parameter adjustments may be generated based on determined lung inflammation. Airway inflammation may be predicted based on analyzed mycotoxin and/or arsenic. Surgical tool parameter adjustments may be generated based on determined airway inflammation. Arsenic exposure may be determined based on urine, saliva, and/or ambient air sample analyses.

For example, based on the selected biomarker sensing systems data, antimicrobial enzyme-related biomarkers, complications, and/or contextual information may be determined, including colon state. Based on the selected biomarker sensing systems data, antimicrobial enzyme-related conditions may be predicted, including GI inflammation, acute kidney injury, *E. faecalis* infection, and/or *S. aureus* infection. Antimicrobial enzyme biomarkers may include lysozyme, lipocalin-2 (NGAL), and/or orosomuccoid. GI inflammation may be predicted based on analyzed lysozyme. Increased levels in lysozyme may be determined and/or predicted based on GI inflammation. Colon state may be determined based on analyzed lysozyme. Surgical tool parameter adjustments may be generated based on analyzed lysozyme levels. Acute kidney injury may be predicted based on analyzed NGAL. NGAL may be detected from serum and/or urine.

For example, based on the selected biomarker sensing systems data, complement system-related biomarkers, complications, and/or contextual information may be determined, including bacterial infection susceptibility. Bacterial infection susceptibility may be determined based on analyzed complement system deficiencies.

For example, based on the selected biomarker sensing systems data, chemokine and cytokine-related biomarkers, complications, and/or contextual information may be determined, including infection burden, inflammation burden, vascular permeability regulation, omentin, colonic tissue properties, and/or post-operation recovery. Based on the selected biomarker sensing systems data, chemokine and cytokine-related conditions may be predicted, including inflammatory bowel diseases, post-operation infection, lung fibrosis, lung scarring, pulmonary fibrosis, gastroesophageal reflux disease, cardiovascular disease, edema, and/or hyperplasia. Infection and/or inflammation burden biomarkers may include oral, salivary, exhaled, and/or C-reactive protein (CRP) data. Salivary cytokines may include interleukin-1 beta (IL-1$\beta$), interleukin-6 (IL-6), tumor necrosis factor alpha (TNF-$\alpha$) and/or interleukin-8 (IL-8).

In an example, inflammatory bowel diseases may be predicted based on analyzed salivary cytokines. Increased salivary cytokines may be determined based on inflammatory bowel diseases. Colonic tissue properties may be determined based on predicted inflammatory bowel diseases. Colonic tissue properties may include scarring, edema, and/or ulcering. Post-operation recovery and/or infection may be determined based on predicted inflammatory bowel diseases. Tumor size and/or lung scarring may be determined based on analyzed exhaled biomarkers. Lung fibrosis, pulmonary fibrosis, and/or gastroesophageal reflux disease may be predicted based on analyzed exhaled biomarkers. Exhaled biomarkers may include exhaled cytokines, pH, hydrogen peroxide (H2O2), and/or nitric oxide. Exhaled cytokines may include IL-6, TNF-$\alpha$, and/or interleukin-17 (IL-17). Lung fibrosis may be predicted based on measured pH and/or H2O2 from exhaled breath. Fibrosis may be predicted based on increased H2O2 concentration. Increased lung tissue scarring may be predicted based on fibrosis. Surgical tool parameter adjustments may be generated based on predicted lung fibrosis. In an example, pulmonary fibrosis and/or gastroesophageal reflux disease may be predicted based on analyzed exhaled nitric oxide. Pulmonary fibrosis may be predicted based on determined increased nitrates and/or nitrites. Gastroesophageal disease may be predicted based on determined reduced nitrates and/or nitrites. Surgical tool parameter adjustments may be generated based on predicted pulmonary fibrosis and/or gastroesophageal reflux disease. Cardiovascular disease, inflammatory bowel diseases, and/or infection may be predicted based on analyzed CRP biomarkers. Risk of serious cardiovascular disease may increase with high CRP concentration. Inflammatory bowel disease may be predicted based on elevated CRP concentration. Infection may be predicted based on elevated CRP concentration. In an example, edema may be predicted based on analyzed vascular permeability regulation biomarkers. Increased vascular permeability during inflammation may be determined based on analyzed bradykinin and/or histamine. Edema may be predicted based on increased vascular permeability during inflammation. Vascular permeability may be determined based on endothelial adhesion molecules. Endothelial adhesion molecules may be determined based on cell samples. Endothelial adhesion molecules may affect vascular permeability, immune cell recruitment, and/or fluid build-up in edema. Surgical tool parameter adjustments may be generated based on analyzed vascular permeability regulation biomarkers. In an example, hyperplasia may be predicted based on analyzed omentin. Hyperplasia may alter tissue properties. Surgical tool parameter adjustments may be generated based on predicted hyperplasia.

For example, based on the selected biomarker sensing systems data, lymphatic system-related biomarkers, complications, and/or contextual information may be determined, including lymph nodes, lymph composition, lymph location, and/or lymph swelling. Based on the selected biomarker sensing systems data, lymphatic system-related conditions may be predicted, including post-operation inflammation, post-operation infection, and/or fibrosis. Post-operation inflammation and/or infection may be predicted based on determined lymph node swelling. Surgical tool parameter adjustments may be generated based on the analyzed lymph node swelling. Surgical tool parameter adjustments, including harmonic tool parameter adjustments, may be generated based on the determined collagen deposition. Collagen deposition may increase with lymph node fibrosis. Inflammatory conditions may be predicted based on lymph composition. Metastatic cell spread may be determined based on lymph composition. Surgical tool parameter adjustments may be generated based on lymph peptidome. Lymph peptidome may change based on inflammatory conditions.

For example, based on the selected biomarker sensing systems data, pathogen-related biomarkers, complications, and/or contextual information may be determined, including pathogen-associated molecular patterns (PAMPs), pathogen burden, *H. pylori*, and/or stomach tissue properties. Based on the selected biomarker sensing systems data, pathogen-related conditions may be predicted, including infection, stomach inflammation, and/or ulcering. PAMPs biomarkers may include pathogen antigens. Pathogen antigens may impact pathogen burden. Stomach inflammation and/or potential ulcering may be predicted based on predicted infection. Stomach tissue property alterations may be determined based on predicted infection.

For example, based on the selected biomarker sensing systems data, DAMPs-related biomarkers, complications, and/or contextual information may be determined, including stress (e.g., cardiovascular, metabolic, glycemic, and/or cellular) and/or necrosis. Based on the selected biomarker sensing systems data, DAMPs-related conditions may be predicted, including acute myocardial infarction, intestinal inflammation, and/or infection. Cellular stress biomarkers may include creatine kinase MB, pyruvate kinase isoenzyme type M2 (M2-PK), irisin, and/or microRNA. In an example, acute myocardial infarction may be predicted based on analyzed creatine kinase MB biomarkers. Intestinal inflammation may be predicted based on analyzed M2-PK biomarkers. Stress may be determined based on analyzed irisin biomarkers. Inflammatory diseases and/or infection may be predicted based on analyzed microRNA biomarkers. Surgical tool parameter adjustments may be generated based on predicted inflammation and/or infection. Inflammation and/ or infection may be predicted based on analyzed necrosis biomarkers. Necrosis biomarkers may include reactive oxygen species (ROS). Inflammation and/or infection may be predicted based on increased ROS. Post-operation recovery may be determined based on analyzed ROS.

For example, based on the selected biomarker sensing systems, cell-related biomarkers, complications, and/or contextual information may be determined, including granulocytes, natural killer cells (NK cells), macrophages, lymphocytes, and/or colonic tissue properties. Based on the selected biomarker sensing systems, cell-related conditions may be predicted, including post-operation infection, ulceratic colitis, inflammation, and/or inflammatory bowel disease. Granulocyte biomarkers may include eosinophilia and/or neutrophils. Eosinophilia biomarkers may include sputum cell count, eosinophilic cationic protein, and/or fractional exhaled nitric oxide. Neutrophil biomarkers may include S100 proteins, myeloperoxidase, and/or human neutrophil lipocalin. Lymphocyte biomarkers may include antibodies, adaptive response, and/or immune memory. The antibodies may include immunoglobulin A (IgA) and/or immunoglobulin M (IgM). In an example, post-operational infection and/or pre-operation inflammation may be predicted based on analyzed sputum cell count. Ulcerative colitis may be predicted based on analyzed eosinophilic cationic protein. Altered colonic tissue properties may be determined based on the predicted ulcerative colitis. Eosinophils may produce eosinophilic cationic protein which may be determined based on ulcerative colitis. Inflammation may be predicted based on analyzed fractional exhaled nitric oxide. The inflammation may include type 1 asthma-like inflammation. Surgical tool parameter adjustments may be generated based on the predicted inflammation. In an example, inflammatory bowel diseases may be predicted based on S100 proteins. The S100 proteins may include calprotectin. Colonic tissue properties may be determined based on the predicted inflammatory bowel diseases. Ulcerative colitis may be predicted based on analyzed myeloperoxidase and/or human neutrophil lipocalin. Altered colonic tissue properties may be determined based on predicted ulcerative colitis. In an example, inflammation may be predicted based on antibody biomarkers. Bowel inflammation may be predicted based on IgA. Cardiovascular inflammation may be predicted based on IgM.

The detection, prediction, determination, and/or generation described herein may be performed by a computing system described herein, such as a surgical hub, a computing device, and/or a smart device based on measured data and/or related biomarkers generated by the biomarker sensing systems.

Tumors may include benign and/or malignant tumors. Tumor-related biomarkers, complications, contextual information, and/or conditions may be determined and/or predicted based on analyzed biomarker sensing systems data. A computing system, as described herein, may select one or more biomarkers (e.g., data from biomarker sensing systems) from tumor-related biomarkers, including circulating tumor cells for analysis.

For example, based on the selected biomarker sensing systems data, benign tumor-related biomarkers, conditions, and/or contextual information may be determined, including benign tumor replication, benign tumor metabolism, and/or benign tumor synthesis. Benign tumor replication may include rate of mitotic activity, mitotic metabolism, and/or synthesis biomarkers. Benign tumor metabolism may include metabolic demand and/or metabolic product biomarkers. Benign tumor synthesis may include protein expression and/or gene expression biomarkers.

For example, based on the selected biomarker sensing systems data, malignant tumor-related biomarkers, complications, and/or contextual information may be determined, including malignant tumor synthesis, malignant tumor metabolism, malignant tumor replication, microsatellite stability, metastatic risk, metastatic tumors, tumor growth, tumor recession, and/or metastatic activity. Based on the selected biomarker sensing systems data, malignant tumor-related conditions may be predicted, including cancer. Malignant tumor synthesis may include gene expression and/or protein expression biomarkers. Gene expression may be determined based on tumor biopsy and/or genome analysis. Protein expression biomarkers may include cancer antigen 125 (CA-125) and/or carcinoembryonic antigen (CEA). CEA may be measured based on urine and/or saliva. Malignant tumor replication data may include rate of mitotic activity, mitotic encapsulation, tumor mass, and/or microRNA 200*c*.

In an example, microsatellite stability may be determined based on analyzed gene expression. Metastatic risk may be determined based on determined microsatellite stability. Higher metastatic risk may be determined and/or predicted based on low microsatellite instability. In an example, metastatic tumors, tumor growth, tumor metastasis, and/or tumor recession may be determined based on analyzed protein expression. Metastatic tumors may be determined and/or predicted based on elevated CA-125. Cancer may be predicted based on CA-125. Cancer may be predicted based on certain levels of CEA. Tumor growth, metastasis, and/or recession may be monitored based on detected changes in CEA. Metastatic activity may be determined based on malignant tumor replication. Cancer may be predicted based on malignant tumor replication. MicroRNA 200*c* may be released into blood by certain cancers. Metastatic activity may be determined and/or predicted based on presence of circulating tumor cells.

The detection, prediction, determination, and/or generation described herein may be performed by a computing system described herein, such as a surgical hub, a computing device, and/or a smart device based on measured data and/or related biomarkers generated by the biomarker sensing systems.

The musculoskeletal system may include muscles, bones, marrow, and/or cartilage. The muscles may include smooth muscle, cardiac muscle, and/or skeletal muscle. The smooth muscle may include calmodulin, connective tissue, structural features, hyperplasia, actin, and/or myosin. The bones may include calcified bone, osteoblasts, and/or osteoclasts. The marrow may include red marrow and/or yellow marrow. The cartilage may include cartilaginous tissue and/or chondrocytes. Musculoskeletal system-related biomarkers, complications, contextual information, and/or conditions may be determined and/or predicted based on analyzed biomarker sensing systems data. A computing system, as described herein, may select one or more biomarkers (e.g., data from biomarker sensing systems) from musculoskeletal-related biomarkers for analysis.

For example, based on the selected biomarker sensing systems data, muscle-related biomarkers, complications, and/or contextual information may be determined, including serum calmodulin levels, mechanical strength, muscle body, hyperplasia, muscle contraction ability, and/or muscle damage. Based on the selected biomarker sensing systems data, muscle-related conditions may be predicted. In an example, neurological conditions may be predicted based on analyzed serum calmodulin levels. Mechanical strength may be determined based on analyzed smooth muscle collagen levels. Collagen may affect mechanical strength as collagen may bind smooth muscle filament together. Muscle body may be determined based on analyzed structural features. The muscle body may include an intermediate body and/or a dense body. Hyperplasia may be determined based on analyzed omentin levels. Omentin may indicate hyperplasia. Hyperplasia may be determined and/or predicted based on thick areas of smooth muscles. Muscle contraction ability may be determined based on analyzed smooth muscle alpha-actin expression. Muscle contraction inability may result from an abnormal expression of actin in smooth muscle. In an example, muscle damage may be determined based on analyzed circulating smooth muscle myosin and/or skeletal muscle myosin. Muscle strength may be determined based on analyzed circulating smooth muscle myosin. Muscle damage and/or weak, friable smooth muscle may be determined and/or predicted based on circulating smooth muscle myosin and/or skeletal muscle myosin. Smooth muscle myosin may be measured from urine. In an example, muscle damage may be determined based on cardiac and/or skeletal muscle biomarkers. Cardiac and/or skeletal muscle biomarkers may include circulating troponin. Muscle damage may be determined and/or predicted based on circulating troponin alongside myosin.

For example, based on the selected biomarker sensing systems data, bone-related biomarkers, complications, and/or contextual information may be determined, including calcified bone properties, calcified bone functions, osteoblasts number, osteoid secretion, osteoclasts number, and/or secreted osteoclasts.

For example, based on the selected biomarker sensing systems data, marrow-related biomarkers, complications, and/or contextual information may be determined, including tissue breakdown and/or collagen secretion. Arthritic breakdown of cartilaginous tissue may be determined based on analyzed cartilaginous tissue biomarkers. Collage secretion by muscle cells may be determined based on analyzed chondrocyte biomarkers.

The detection, prediction, determination, and/or generation described herein may be performed by a computing system described herein, such as a surgical hub, a computing device, and/or a smart device based on measured data and/or related biomarkers generated by the biomarker sensing systems.

Reproductive system-related biomarkers, complications, contextual information, and/or conditions may be determined and/or predicted based on analyzed biomarker sensing systems data. A computing system, as described herein, may select one or more biomarkers (e.g., data from biomarker sensing systems) from reproductive system-related biomarkers for analysis. Reproductive system-related biomarkers, complications, and/or contextual information may be determined based on analyzed biomarker sensing systems data, including female anatomy, female function, menstrual cycle, pH, bleeding, wound healing, and/or scarring. Female anatomy biomarkers may include the ovaries, vagina, cervix, fallopian tubes, and/or uterus. Female function biomarkers may include reproductive hormones, pregnancy, menopause, and/or menstrual cycle. Reproductive system-related conditions may be predicted based on analyzed biomarker sensing systems data, including endometriosis, adhesions, vaginosis, bacterial infection, SSI, and/or pelvic abscesses.

In an example, endometriosis may be predicted based on female anatomy biomarkers. Adhesions may be predicted based on female anatomy biomarkers. The adhesions may include sigmoid colon adhesions. Endometriosis may be predicted based on menstrual blood. Menstrual blood may include molecular signals from endometriosis. Sigmoid colon adhesions may be predicted based on predicted endometriosis. In an example, menstrual phase and/or menstrual cycle length may be determined based on the menstrual cycle. Bleeding, wound healing, and/or scarring may be determined based on the analyzed menstrual phase. Risk of endometriosis may be predicted based on the analyzed menstrual cycle. Higher risk of endometriosis may be predicted based on shorter menstrual cycle lengths. Molecular signals may be determined based on analyzed menstrual blood and/or discharge pH. Endometriosis may be predicted based on the determined molecular signals. Vaginal pH may be determined based on analyzed discharge pH. Vaginosis and/or bacterial infections may be predicted based on the analyzed vaginal pH. Vaginosis and/or bacterial infections may be predicted based on changes in vaginal pH. Risk of SSI and/or pelvic abscesses during gynecologic procedures may be predicted based on predicted vaginosis.

The detection, prediction, determination, and/or generation described herein may be performed by any of the computing systems within any of the computer-implemented patient and surgeon monitoring systems described herein, such as a surgical hub, a computing device, and/or a smart device based on measured data and/or related biomarkers generated by the one or more sensing systems.

Figure 2A:
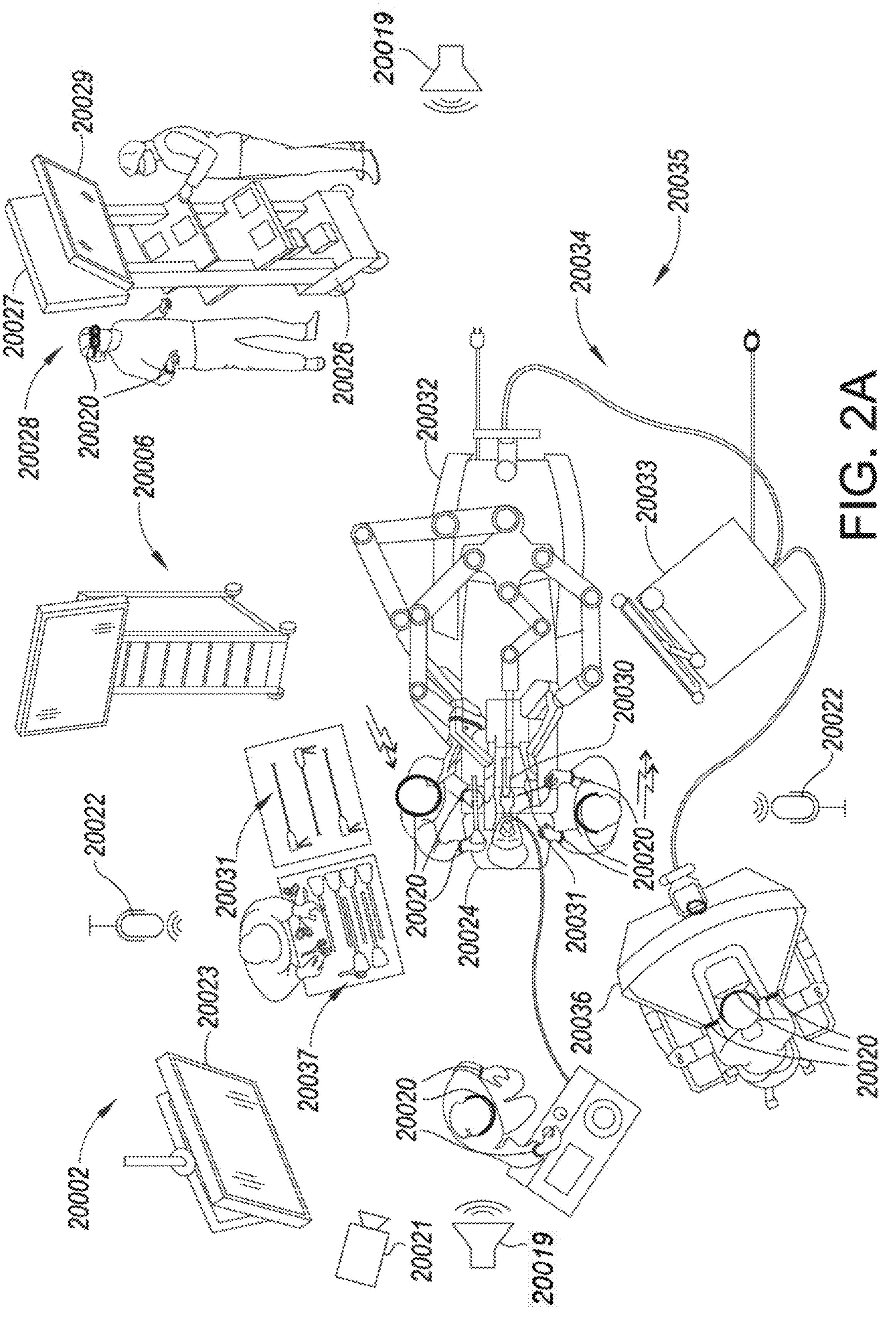
FIG. 2A shows an example of a surgeon monitoring system in a surgical operating room.

FIG. 2A shows an example of a surgeon monitoring system 20002 in a surgical operating room. As illustrated in FIG. 2A, a patient is being operated on by one or more health care professionals (HCPs). The HCPs are being monitored by one or more surgeon sensing systems 20020 worn by the HCPs. The HCPs and the environment surrounding the HCPs may also be monitored by one or more environmental sensing systems including, for example, a set of cameras 20021, a set of microphones 20022, and other sensors, etc. that may be deployed in the operating room. The surgeon sensing systems 20020 and the environmental sensing systems may be in communication with a surgical hub 20006, which in turn may be in communication with one or more cloud servers 20009 of the cloud computing system 20008, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2A, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2A, a surgical instrument 20031 is being used in the surgical procedure as part of the surgeon monitoring system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2A illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1 may include one or more sensing systems, for example, surgeon sensing systems 20020 as shown in FIG. 2A. The surgeon sensing systems 20020 may include sensing systems to monitor and detect a set of physical states and/or a set of physiological states of a healthcare provider (HCP). An HCP may be a surgeon or one or more healthcare personnel assisting the surgeon or other healthcare service providers in general. In an example, a sensing system 20020 may measure a set of biomarkers to monitor the heart rate of an HCP. In another example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the surgeon sensing systems 20020 may measure one or more surgeon biomarkers associated with an HCP and send the measurement data associated with the surgeon biomarkers to the surgical hub 20006. The surgeon sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 2B:
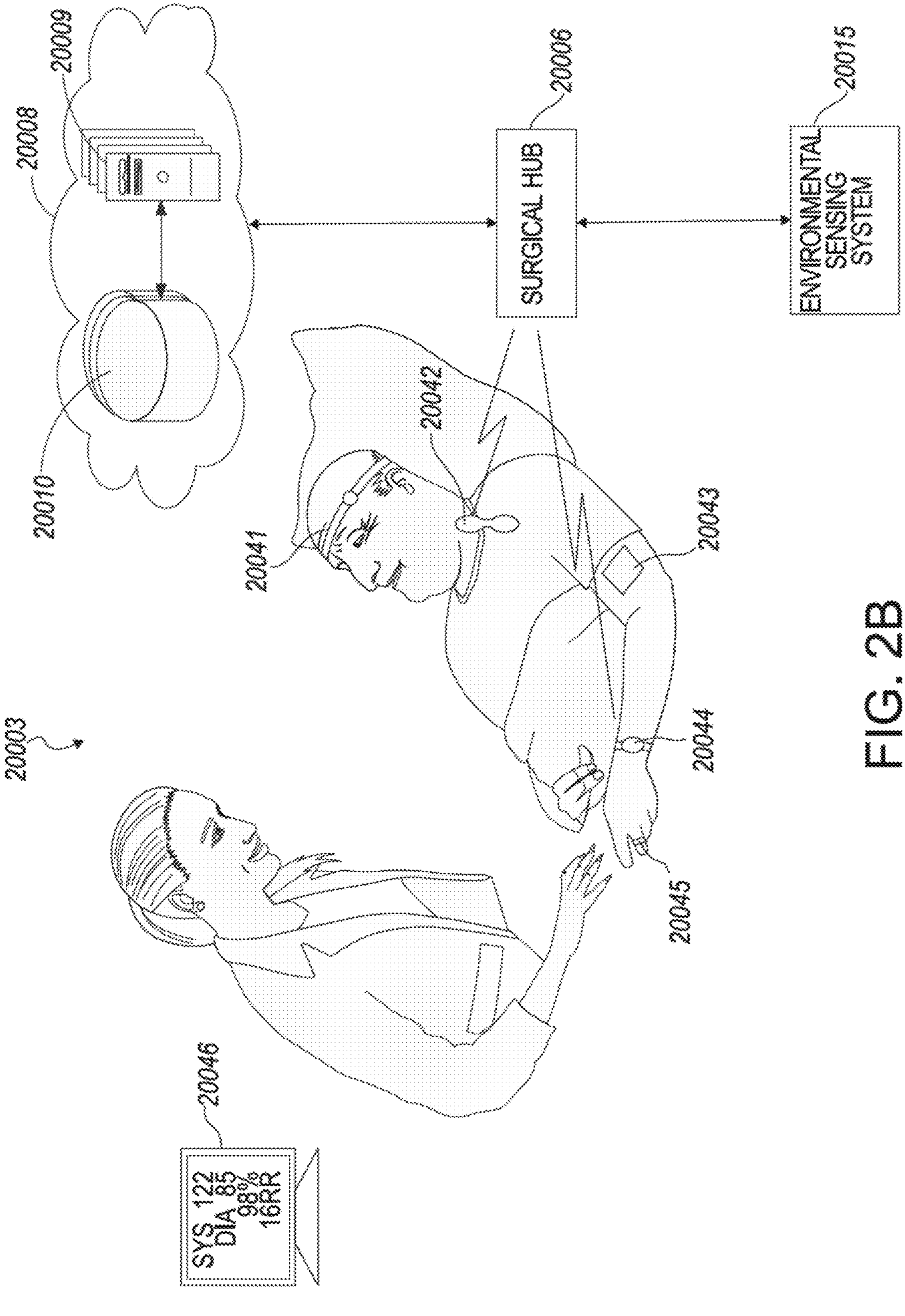
FIG. 2B shows an example of a patient monitoring system (e.g., a controlled patient monitoring system).

FIG. 2B shows an example of a patient monitoring system 20003 (e.g., a controlled patient monitoring system). As illustrated in FIG. 2B, a patient in a controlled environment (e.g., in a hospital recovery room) may be monitored by a plurality of sensing systems (e.g., patient sensing systems 20041). A patient sensing system 20041 (e.g., a head band) may be used to measure an electroencephalogram (EEG) to measure electrical activity of the brain of a patient. A patient sensing system 20042 may be used to measure various biomarkers of the patient including, for example, heart rate, VO2 level, etc. A patient sensing system 20043 (e.g., flexible patch attached to the patient's skin) may be used to measure sweat lactate and/or potassium levels by analyzing small amounts of sweat that is captured from the surface of the skin using microfluidic channels. A patient sensing system 20044 (e.g., a wristband or a watch) may be used to measure blood pressure, heart rate, heart rate variability, VO2 levels, etc. using various techniques, as described herein. A patient sensing system 20045 (e.g., a ring on finger) may be used to measure peripheral temperature, heart rate, heart rate variability, VO2 levels, etc. using various techniques, as described herein. The patient sensing systems 20041-20045 may use a radio frequency (RF) link to be in communication with the surgical hub 20006. The patient sensing systems 20041-20045 may use one or more of the following RF protocols for communication with the surgical hub 20006: Bluetooth, Bluetooth Low-Energy (BLE), Bluetooth Smart, Zigbee, Z-wave, IPv6 Low-power wireless Personal Area Network (6LoWPAN), Thread, Wi-Fi, etc.

The sensing systems 20041-20045 may be in communication with a surgical hub 20006, which in turn may be in communication with a remote server 20009 of the remote cloud computing system 20008. The surgical hub 20006 is also in communication with an HID 20046. The HID 20046 may display measured data associated with one or more patient biomarkers. For example, the HID 20046 may display blood pressure, Oxygen saturation level, respiratory rate, etc. The HID 20046 may display notifications for the patient or an HCP providing information about the patient, for example, information about a recovery milestone or a complication. In an example, the information about a recovery milestone or a complication may be associated with a surgical procedure the patient may have undergone. In an example, the HID 20046 may display instructions for the patient to perform an activity. For example, the HID 20046 may display inhaling and exhaling instructions. In an example the HID 20046 may be part of a sensing system.

As illustrated in FIG. 2B, the patient and the environment surrounding the patient may be monitored by one or more environmental sensing systems 20015 including, for example, a microphone (e.g., for detecting ambient noise associated with or around a patient), a temperature/humidity sensor, a camera for detecting breathing patterns of the patient, etc. The environmental sensing systems 20015 may be in communication with the surgical hub 20006, which in turn is in communication with a remote server 20009 of the remote cloud computing system 20008.

In an example, a patient sensing system 20044 may receive a notification information from the surgical hub 20006 for displaying on a display unit or an HID of the patient sensing system 20044. The notification information may include a notification about a recovery milestone or a notification about a complication, for example, in case of post-surgical recovery. In an example, the notification information may include an actionable severity level associated with the notification. The patient sensing system 20044 may display the notification and the actionable severity level to the patient. The patient sensing system may alert the patient using a haptic feedback. The visual notification and/or the haptic notification may be accompanied by an audible notification prompting the patient to pay attention to the visual notification provided on the display unit of the sensing system.

Figure 2C:
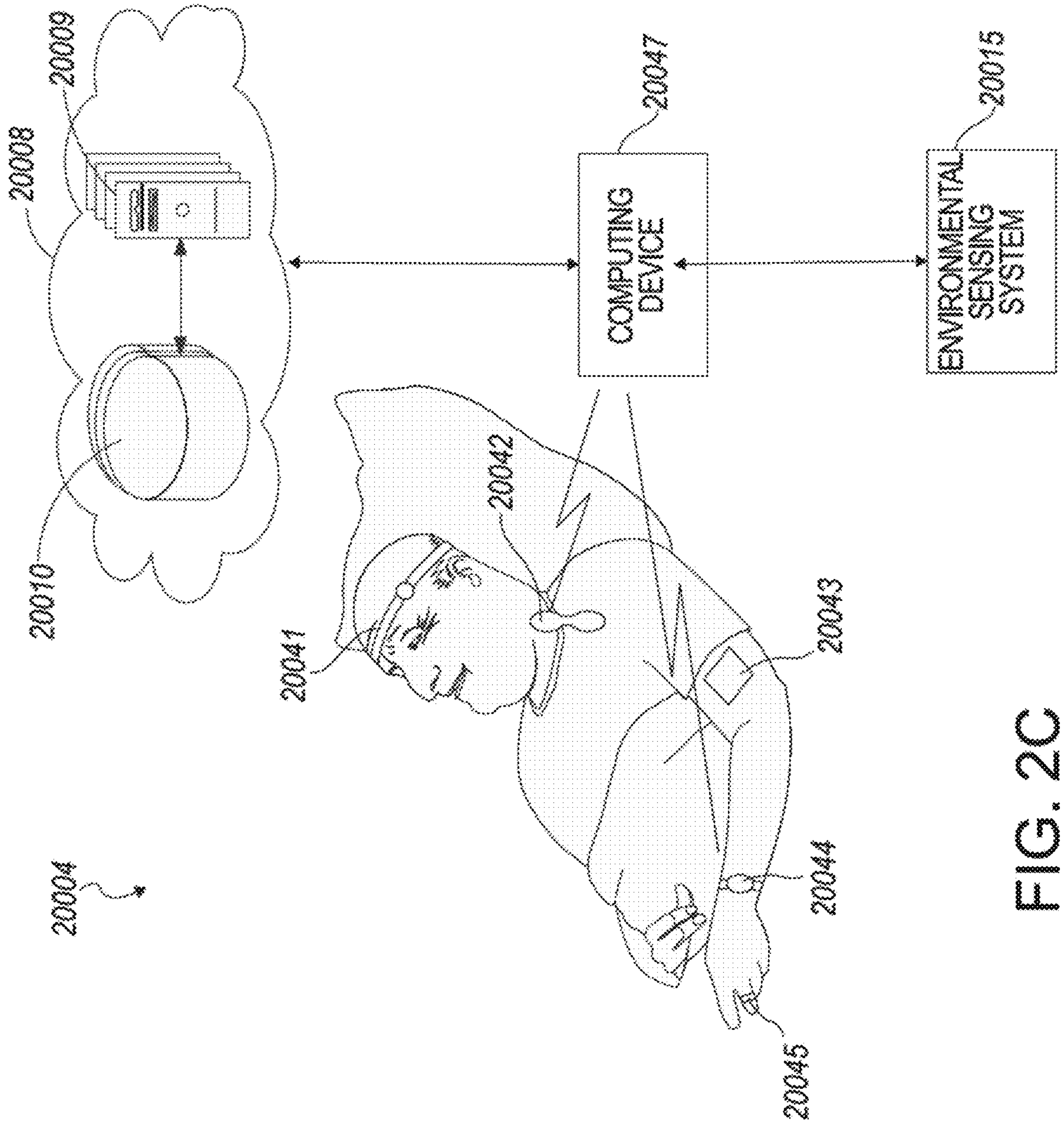
FIG. 2C shows an example of a patient monitoring system (e.g., an uncontrolled patient monitoring system).

FIG. 2C shows an example of a patient monitoring system (e.g., an uncontrolled patient monitoring system 20004). As illustrated in FIG. 2C, a patient in an uncontrolled environment (e.g., a patient's residence) is being monitored by a plurality of patient sensing systems 20041-20045. The patient sensing systems 20041-20045 may measure and/or monitor measurement data associated with one or more patient biomarkers. For example, a patient sensing system 20041, a head band, may be used to measure an electroencephalogram (EEG). Other patient sensing systems 20042, 20043, 20044, and 20045 are examples where various patient biomarkers are monitored, measured, and/or reported, as described in FIG. 2B. One or more of the patient sensing systems 20041-20045 may be send the measured data associated with the patient biomarkers being monitored to the computing device 20047, which in turn may be in communication with a remote server 20009 of the remote cloud computing system 20008. The patient sensing systems 20041-20045 may use a radio frequency (RF) link to be in communication with a computing device 20047 (e.g., a smart phone, a tablet, etc.). The patient sensing systems 20041-20045 may use one or more of the following RF protocols for communication with the computing device 20047: Bluetooth, Bluetooth Low-Energy (BLE), Bluetooth Smart, Zigbee, Z-wave, IPv6 Low-power wireless Personal Area Network (6LoWPAN), Thread, Wi-Fi, etc. In an example, the patient sensing systems 20041-20045 may be connected to the computing device 20047 via a wireless router, a wireless hub, or a wireless bridge.

The computing device 20047 may be in communication with a remote server 20009 that is part of a cloud computing system 20008. In an example, the computing device 20047 may be in communication with a remote server 20009 via an internet service provider's cable/FIOS networking node. In an example, a patient sensing system may be in direct communication with a remote server 20009. The computing device 20047 or the sensing system may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

In an example, a computing device 20047 may display information associated with a patient biomarker. For example, a computing device 20047 may display blood pressure, Oxygen saturation level, respiratory rate, etc. A computing device 20047 may display notifications for the patient or an HCP providing information about the patient, for example, information about a recovery milestone or a complication.

In an example, the computing device 20047 and/or the patient sensing system 20044 may receive a notification information from the surgical hub 20006 for displaying on a display unit of the computing device 20047 and/or the patient sensing system 20044. The notification information may include a notification about a recovery milestone or a notification about a complication, for example, in case of post-surgical recovery. The notification information may also include an actionable severity level associated with the notification. The computing device 20047 and/or the sensing system 20044 may display the notification and the actionable severity level to the patient. The patient sensing system may also alert the patient using a haptic feedback. The visual notification and/or the haptic notification may be accompanied by an audible notification prompting the patient to pay attention to the visual notification provided on the display unit of the sensing system.

Figure 3:
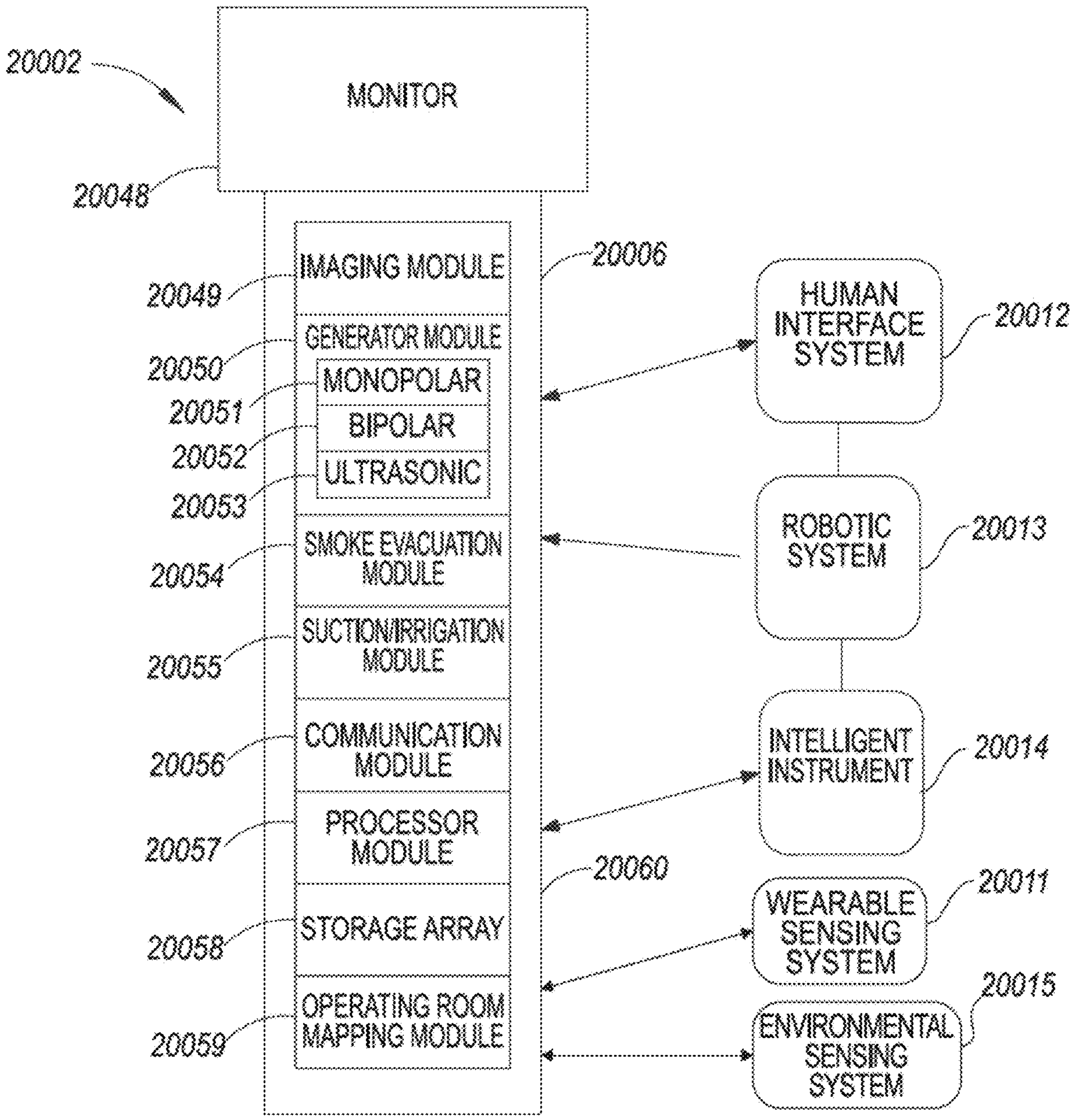
FIG. 3 illustrates an example surgical hub paired with various systems.

FIG. 3 shows an example surgeon monitoring system 20002 with a surgical hub 20006 paired with a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclosure 20060 further facilitates interactive communication between the modules 20059, 20054, and 20055. The generator module 20050 can be a generator module 20050 with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
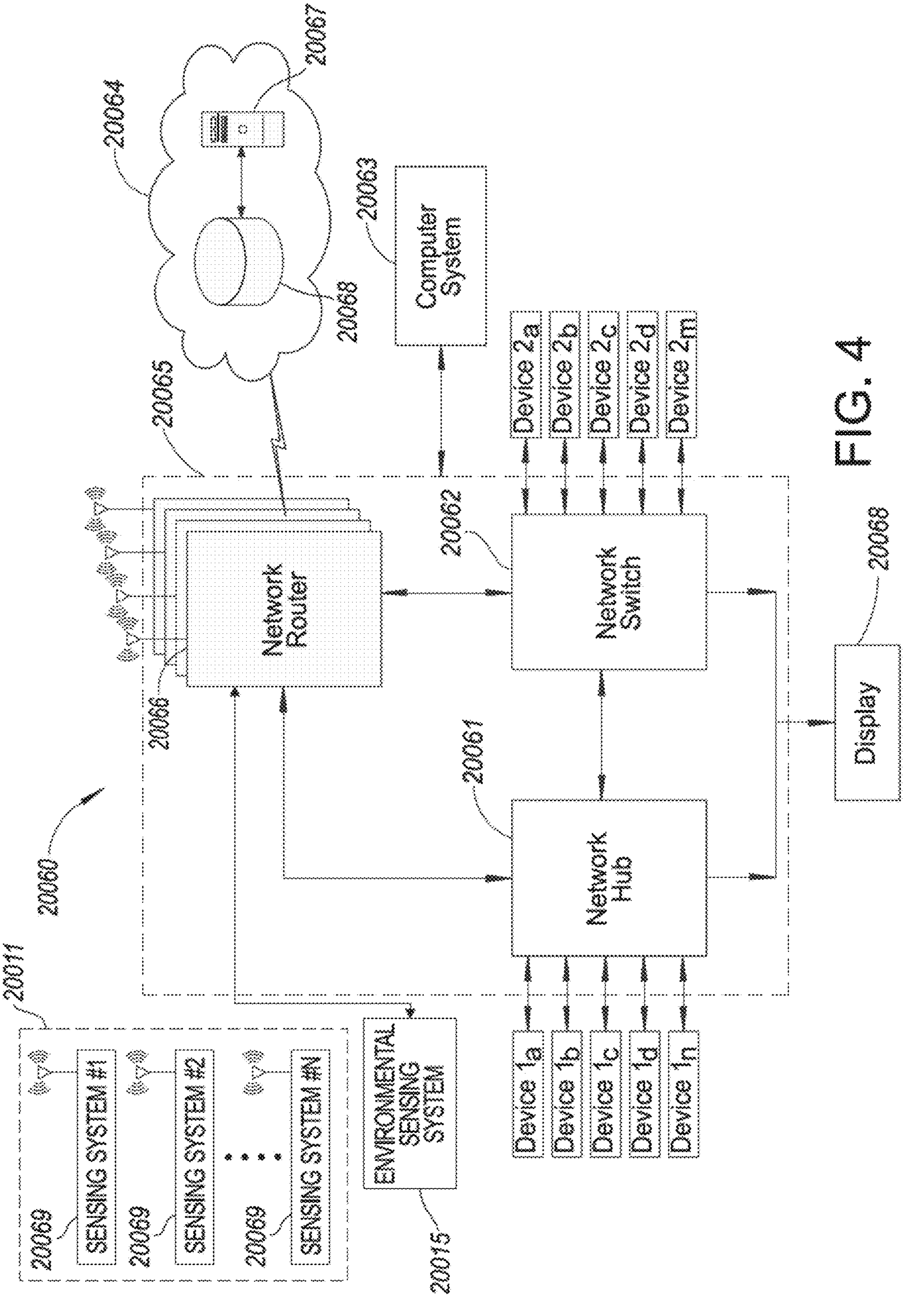
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, an environment sensing system, and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation. Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1*a*-1*n* located in the operating theater may be coupled to the modular communication hub 20065. The network hub 20061 and/or the network switch 20062 may be coupled to a network router 20066 to connect the devices 1*a*-1*n* to the cloud computing system 20064 or the local computer system 20063. Data associated with the devices 1*a*-1*n* may be transferred to cloud-based computers via the router for remote data processing and manipulation. Data associated with the devices 1*a*-1*n* may also be transferred to the local computer system 20063 for local data processing and manipulation. Modular devices 2*a*-2*m* located in the same operating theater also may be coupled to a network switch 20062. The network switch 20062 may be coupled to the network hub 20061 and/or the network router 20066 to connect the devices 2*a*-2*m* to the cloud 20064. Data associated with the devices 2*a*-2*m* may be transferred to the cloud computing system 20064 via the network router 20066 for data processing and manipulation. Data associated with the devices 2*a*-2*m* may also be transferred to the local computer system 20063 for local data processing and manipulation.

The wearable sensing system 20011 may include one or more sensing systems 20069. The sensing systems 20069 may include a surgeon sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1*a*-1*n*/2*a*-2*m*. The local computer system 20063 also may be contained in a modular control tower. The modular communication hub 20065 may be connected to a display 20068 to display images obtained by some of the devices 1*a*-1*n*/2*a*-2*m*, for example during surgical procedures. In various aspects, the devices 1*a*-1*n*/2*a*-2*m* may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1*a*-1*n*/2*a*-2*m* or the sensing systems 20069 to the cloud-base system 20064. One or more of the devices 1*a*-1*n*/2*a*-2*m* or the sensing systems 20069 coupled to the network hub 20061 or network switch 20062 may collect data or measurement data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services-such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1*a*-1*n*/2*a*-2*m* located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1*a*-1*n*/2*a*-2*m*, the surgical data network can provide improved surgical outcomes, reduced costs, and improved patient satisfaction. At least some of the devices 1*a*-1*n*/2*a*-2*m* may be employed to view tissue states to assess leaks or perfusion of sealed tissue after a tissue sealing and cutting procedure. At least some of the devices 1*a*-1*n*/2*a*-2*m* may be employed to identify pathology, such as the effects of diseases, using the cloud-based computing to examine data including images of samples of body tissue for diagnostic purposes. This may include localization and margin confirmation of tissue and phenotypes. At least some of the devices 1*a*-1*n*/2*a*-2*m* may be employed to identify anatomical structures of the body using a variety of sensors integrated with imaging devices and techniques such as overlaying images captured by multiple imaging devices. The data gathered by the devices 1*a*-1*n*/2*a*-2*m*, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, notify a patient of a complication during post-surgical period.

The operating theater devices 1*a*-1*n* may be connected to the modular communication hub 20065 over a wired channel or a wireless channel depending on the configuration of the devices 1*a*-1*n* to a network hub 20061. The network hub 20061 may be implemented, in one aspect, as a local network broadcast device that works on the physical layer of the Open System Interconnection (OSI) model. The network hub may provide connectivity to the devices 1*a*-1*n* located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1*a*-1*n* can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2*a*-2*m* may be connected to a network switch 20062 over a wired channel or a wireless channel. The network switch 20062 works in the data link layer of the OSI model. The network switch 20062 may be a multicast device for connecting the devices 2*a*-2*m* located in the same operating theater to the network. The network switch 20062 may send data in the form of frames to the network router 20066 and may work in full duplex mode. Multiple devices 2*a*-2*m* can send data at the same time through the network switch 20062. The network switch 20062 stores and uses MAC addresses of the devices 2*a*-2*m* to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1*a*-1*n*/2*a*-2*m* and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1*a*-1*n* and devices 2*a*-2*m* located in the operating theater.

In examples, the operating theater devices 1*a*-1*n*/2*a*-2*m* and/or the sensing systems 20069 may communicate to the modular communication hub 20065 via Bluetooth wireless technology standard for exchanging data over short distances (using short-wavelength UHF radio waves in the ISM band from 2.4 to 2.485 GHZ) from fixed and mobile devices and building personal area networks (PANs). The operating theater devices 1*a*-1*n*/2*a*-2*m* and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WIMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1*a*-1*n*/2*a*-2*m* and/or the sensing systems 20069 and may handle a data type known as frames. Frames may carry the data generated by the devices 1*a*-1*n*/2*a*-2*m* and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1*a*-1*n*/2*a*-2*m*.

Figure 5:
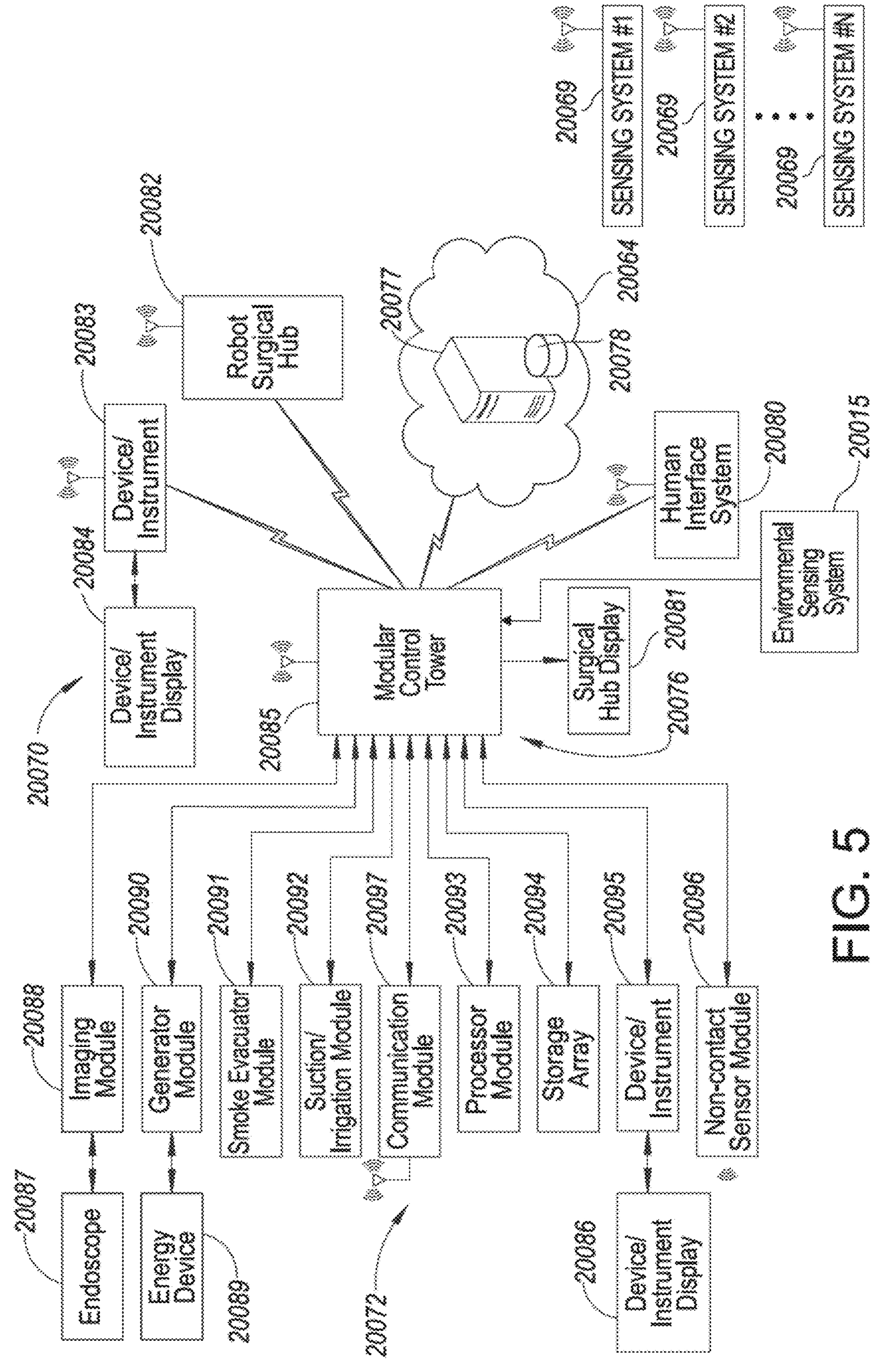
FIG. 5 illustrates an example computer-implemented interactive surgical system that may be part of a surgeon monitoring system.
Figure 6A:
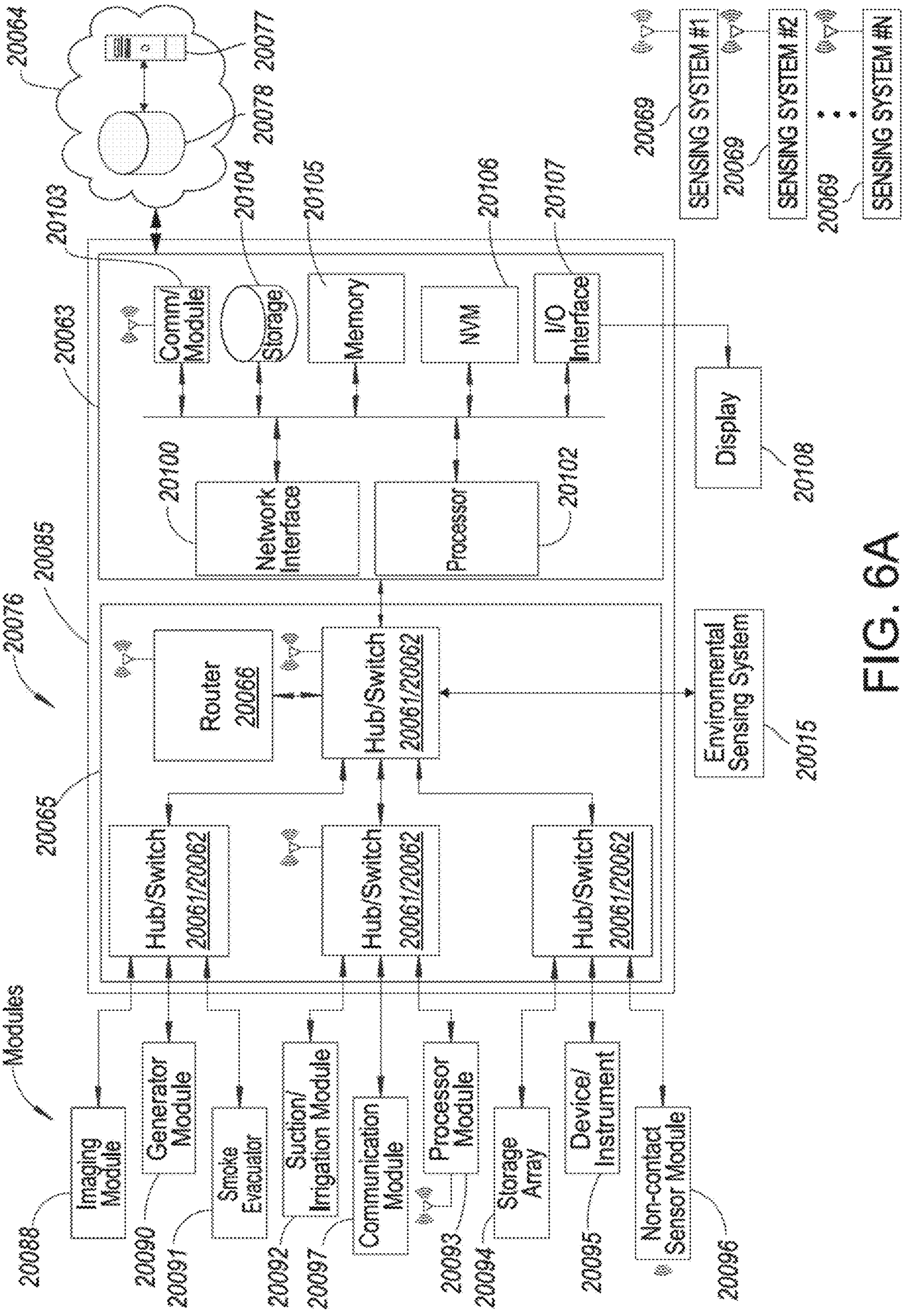
FIG. 6A illustrates a surgical hub comprising a plurality of modules coupled to a modular control tower.

FIG. 5 illustrates a computer-implemented interactive surgical system 20070 that may be a part of the surgeon monitoring system 20002. The computer-implemented interactive surgical system 20070 is similar in many respects to the surgeon sensing system 20002. For example, the computer-implemented interactive surgical system 20070 may include one or more surgical sub-systems 20072, which are similar in many respects to the surgeon monitoring systems 20002. Each sub-surgical system 20072 includes at least one surgical hub 20076 in communication with a cloud computing system 20064 that may include a remote server 20077 and a remote storage 20078. In one aspect, the computer-implemented interactive surgical system 20070 may include a modular control tower 20085 connected to multiple operating theater devices such as sensing systems (e.g., surgeon sensing systems 20002 and/or patient sensing system 20003), intelligent surgical instruments, robots, and other computerized devices located in the operating theater. As shown in FIG. 6A, the modular control tower 20085 may include a modular communication hub 20065 coupled to a local computing system 20063.

As illustrated in the example of FIG. 5, the modular control tower 20085 may be coupled to an imaging module 20088 that may be coupled to an endoscope 20087, a generator module 20090 that may be coupled to an energy device 20089, a smoke evacuator module 20091, a suction/irrigation module 20092, a communication module 20097, a processor module 20093, a storage array 20094, a smart device/instrument 20095 optionally coupled to a display 20086 and 20084 respectively, and a non-contact sensor module 20096. The modular control tower 20085 may also be in communication with one or more sensing systems 20069 and an environmental sensing system 20015. The sensing systems 20069 may be connected to the modular control tower 20085 either directly via a router or via the communication module 20097. The operating theater devices may be coupled to cloud computing resources and data storage via the modular control tower 20085. A robot surgical hub 20082 also may be connected to the modular control tower 20085 and to the cloud computing resources. The devices/instruments 20095 or 20084, human interface system 20080, among others, may be coupled to the modular control tower 20085 via wired or wireless communication standards or protocols, as described herein. The human interface system 20080 may include a display sub-system and a notification sub-system. The modular control tower 20085 may be coupled to a hub display 20081 (e.g., monitor, screen) to display and overlay images received from the imaging module 20088, device/instrument display 20086, and/or other human interface systems 20080. The hub display 20081 also may display data received from devices connected to the modular control tower 20085 in conjunction with images and overlaid images.

FIG. 6A illustrates a surgical hub 20076 comprising a plurality of modules coupled to the modular control tower 20085. As shown in FIG. 6A, the surgical hub 20076 may be connected to a generator module 20090, the smoke evacuator module 20091, suction/irrigation module 20092, and the communication module 20097. The modular control tower 20085 may comprise a modular communication hub 20065, e.g., a network connectivity device, and a computer system 20063 to provide local wireless connectivity with the sensing systems, local processing, complication monitoring, visualization, and imaging, for example. As shown in FIG. 6A, the modular communication hub 20065 may be connected in a configuration (e.g., a tiered configuration) to expand a number of modules (e.g., devices) and a number of sensing systems 20069 that may be connected to the modular communication hub 20065 and transfer data associated with the modules and/or measurement data associated with the sensing systems 20069 to the computer system 20063, cloud computing resources, or both. As shown in FIG. 6A, each of the network hubs/switches 20061/20062 in the modular communication hub 20065 may include three downstream ports and one upstream port. The upstream network hub/switch may be connected to a processor 20102 to provide a communication connection to the cloud computing resources and a local display 20108. At least one of the network/hub switches 20061/20062 in the modular communication hub 20065 may have at least one wireless interface to provided communication connection between the sensing systems 20069 and/or the devices 20095 and the cloud computing system 20064. Communication to the cloud computing system 20064 may be made either through a wired or a wireless communication channel.

The surgical hub 20076 may employ a non-contact sensor module 20096 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 20063 may comprise a processor 20102 and a network interface 20100. The processor 20102 may be coupled to a communication module 20103, storage 20104, memory 20105, non-volatile memory 20106, and input/output (I/O) interface 20107 via a system bus. The system bus can be any of several types of bus structure(s) including the memory bus or memory controller, a peripheral bus or external bus, and or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 20102 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with Stellaris Ware® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor 20102 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 20063 also may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface 20107. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

Figure 6B:
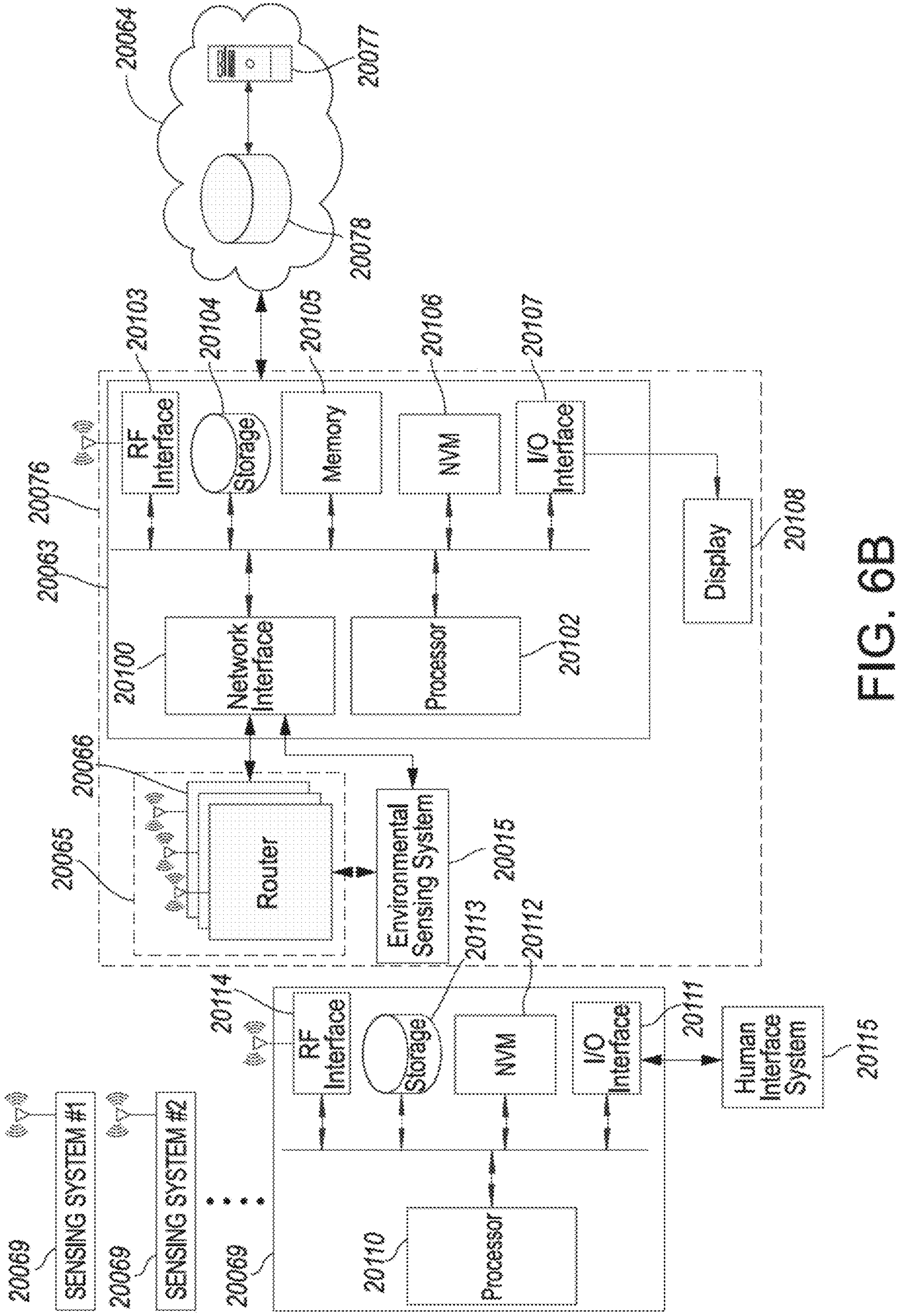
FIG. 6B illustrates an example of a controlled patient monitoring system.

In various examples, the computer system 20063 of FIG. 4, FIG. 6A and FIG. 6B, the imaging module 20088 and/or human interface system 20080, and/or the processor module 20093 of FIG. 5 and FIG. 6A may comprise an image processor, image-processing engine, media processor, or any specialized digital signal processor (DSP) used for the processing of digital images. The image processor may employ parallel computing with single instruction, multiple data (SIMD) or multiple instruction, multiple data (MIND) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

FIG. 6B illustrates an example of a wearable monitoring system, e.g., a controlled patient monitoring system. A controlled patient monitoring system may be the sensing system used to monitor a set of patient biomarkers when the patient is at a healthcare facility. The controlled patient monitoring system may be deployed for pre-surgical patient monitoring when a patient is being prepared for a surgical procedure, in-surgical monitoring when a patient is being operated on, or in post-surgical monitoring, for example, when a patient is recovering, etc. As illustrated in FIG. 6B, a controlled patient monitoring system may include a surgical hub system 20076, which may include one or more routers 20066 of the modular communication hub 20065 and a computer system 20063. The routers 20065 may include wireless routers, wired switches, wired routers, wired or wireless networking hubs, etc. In an example, the routers 20065 may be part of the infrastructure. The computing system 20063 may provide local processing for monitoring various biomarkers associated with a patient or a surgeon, and a notification mechanism to indicate to the patient and/or a healthcare provided (HCP) that a milestone (e.g., a recovery milestone) is met or a complication is detected. The computing system 20063 of the surgical hub system 20076 may also be used to generate a severity level associated with the notification, for example, a notification that a complication has been detected.

Figure 6C:
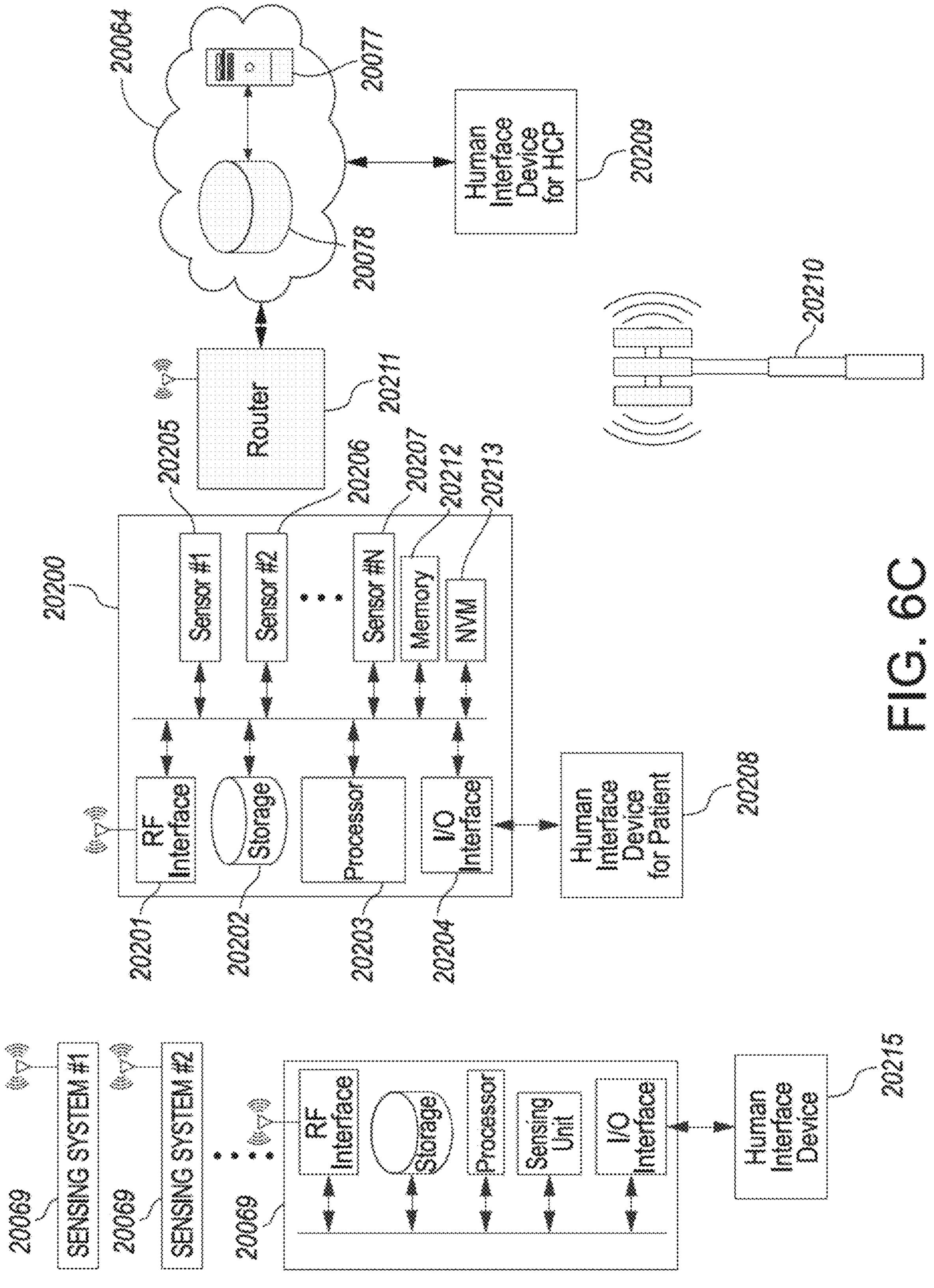
FIG. 6C illustrates an example of an uncontrolled patient monitoring system.
Figure 7A:
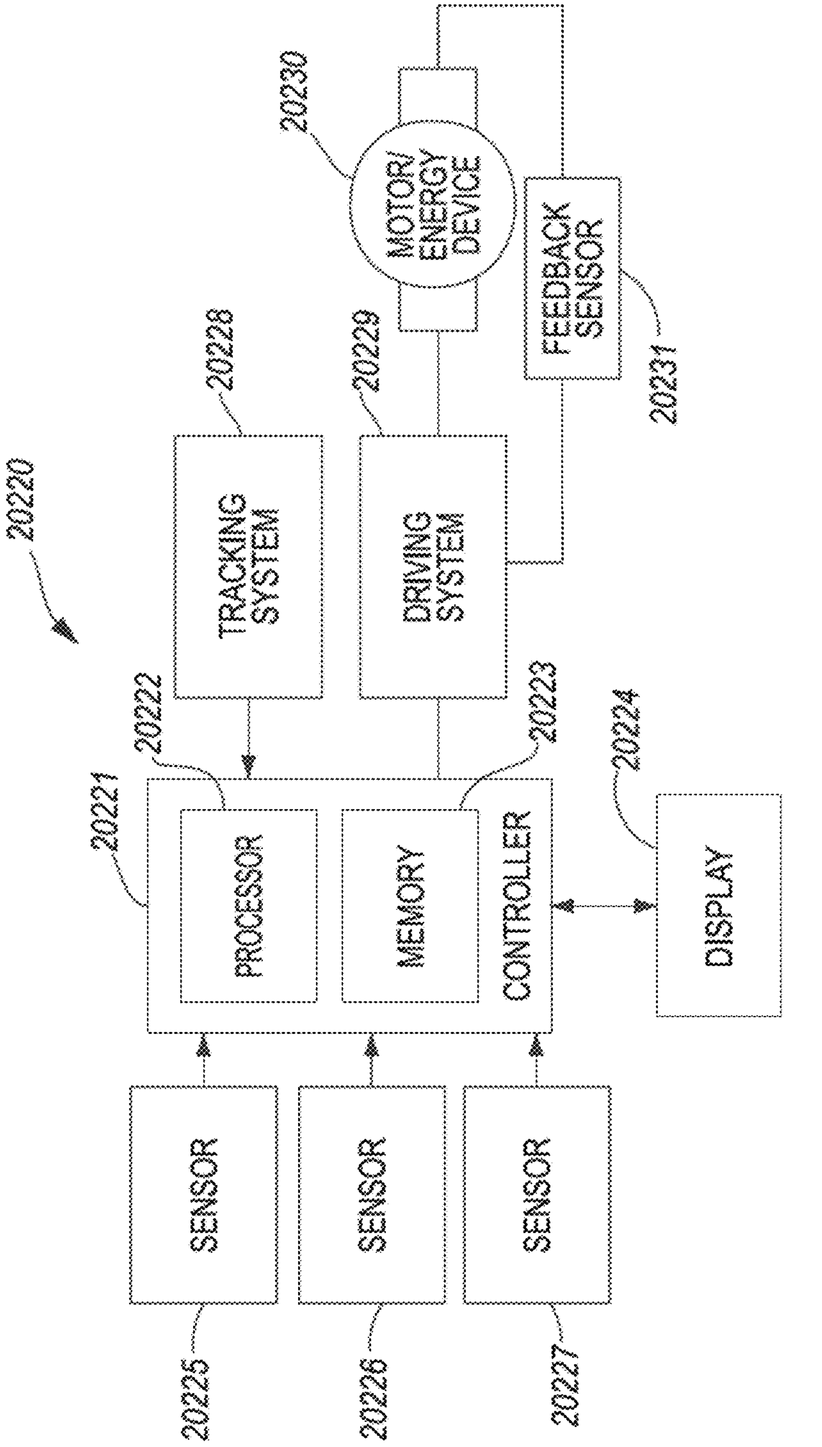
FIG. 7A illustrates a logic diagram of a control system of a surgical instrument or a tool.
Figure 7B:
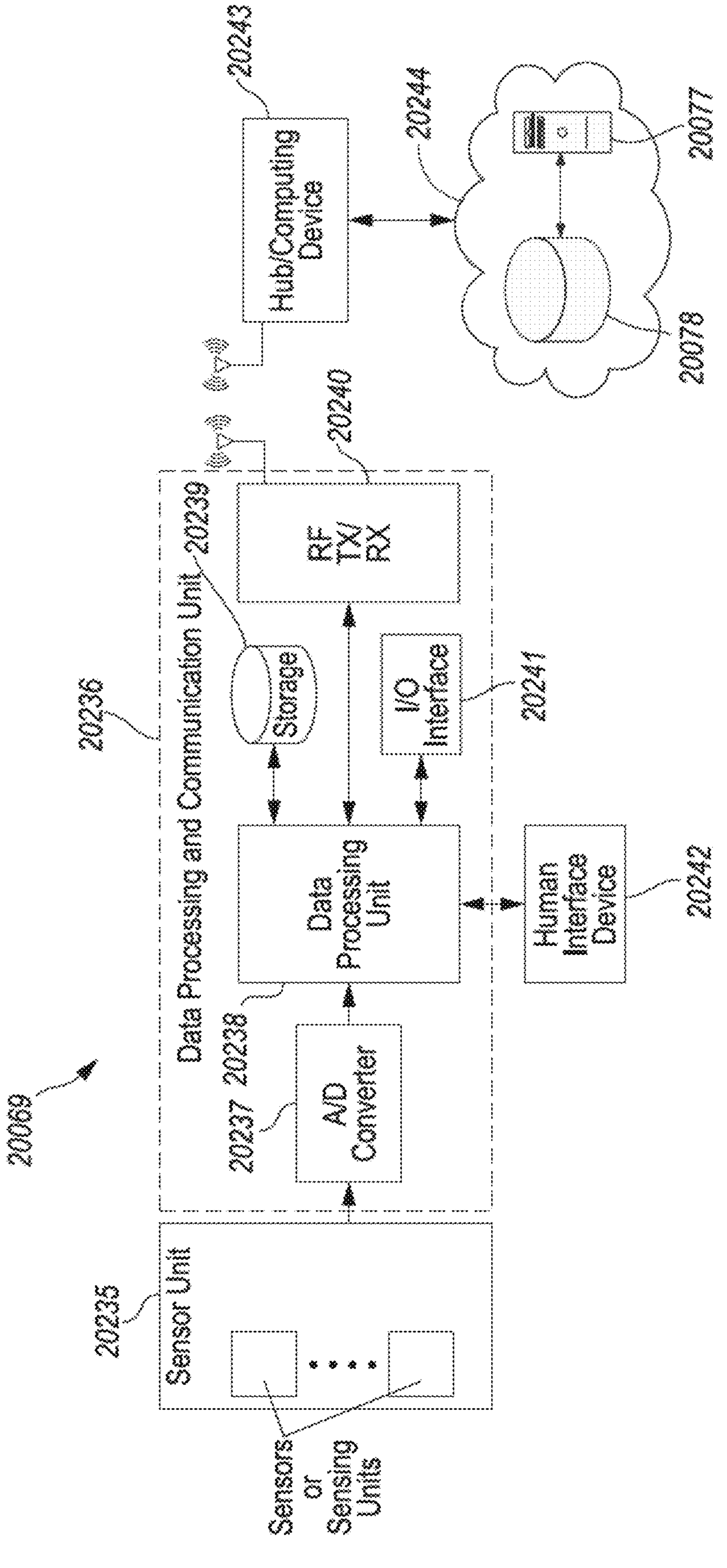
FIG. 7B shows an exemplary sensing system with a sensor unit and a data processing and communication unit.
Figure 7C:
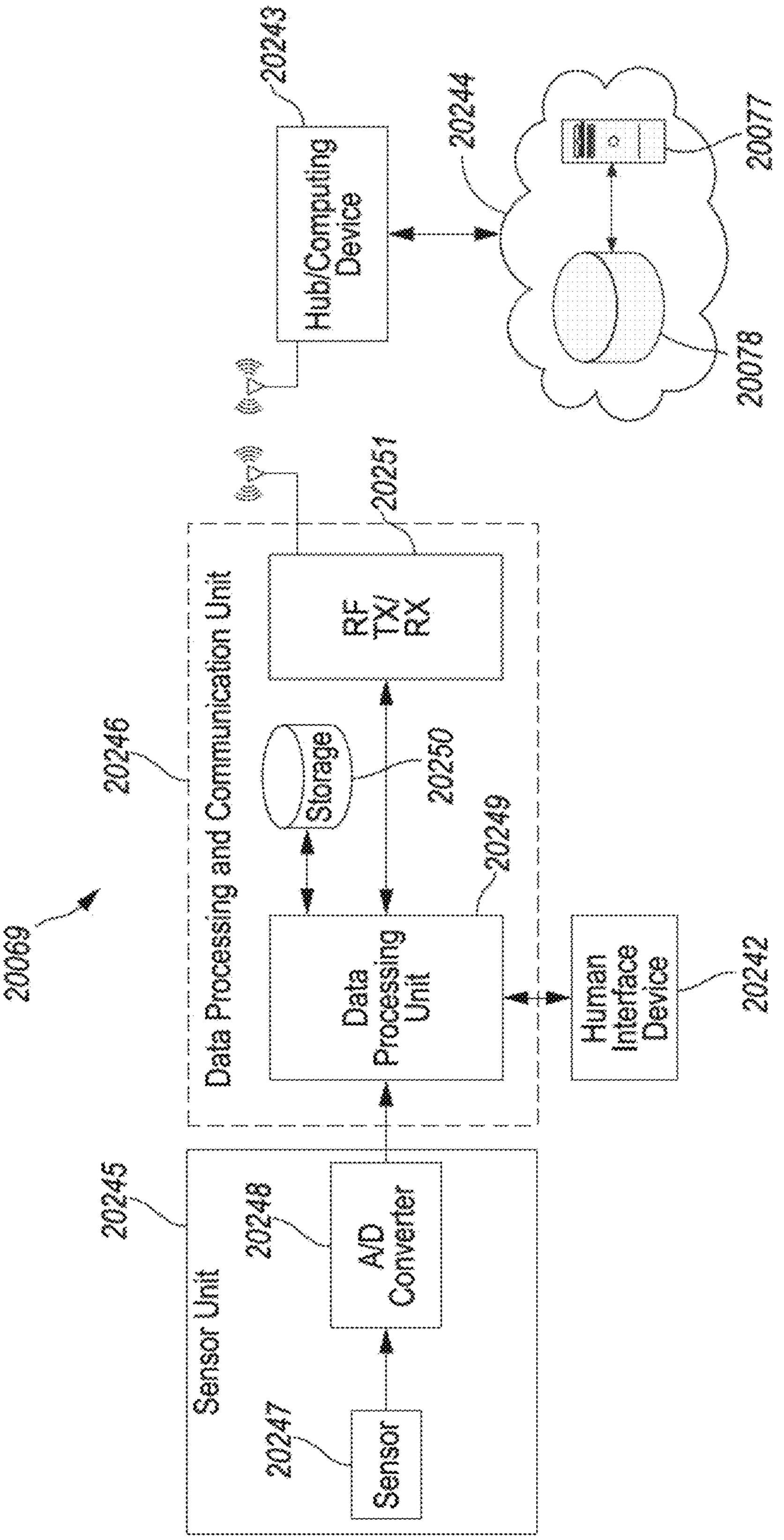
FIG. 7C shows an exemplary sensing system with a sensor unit and a data processing and communication unit.
Figure 7D:
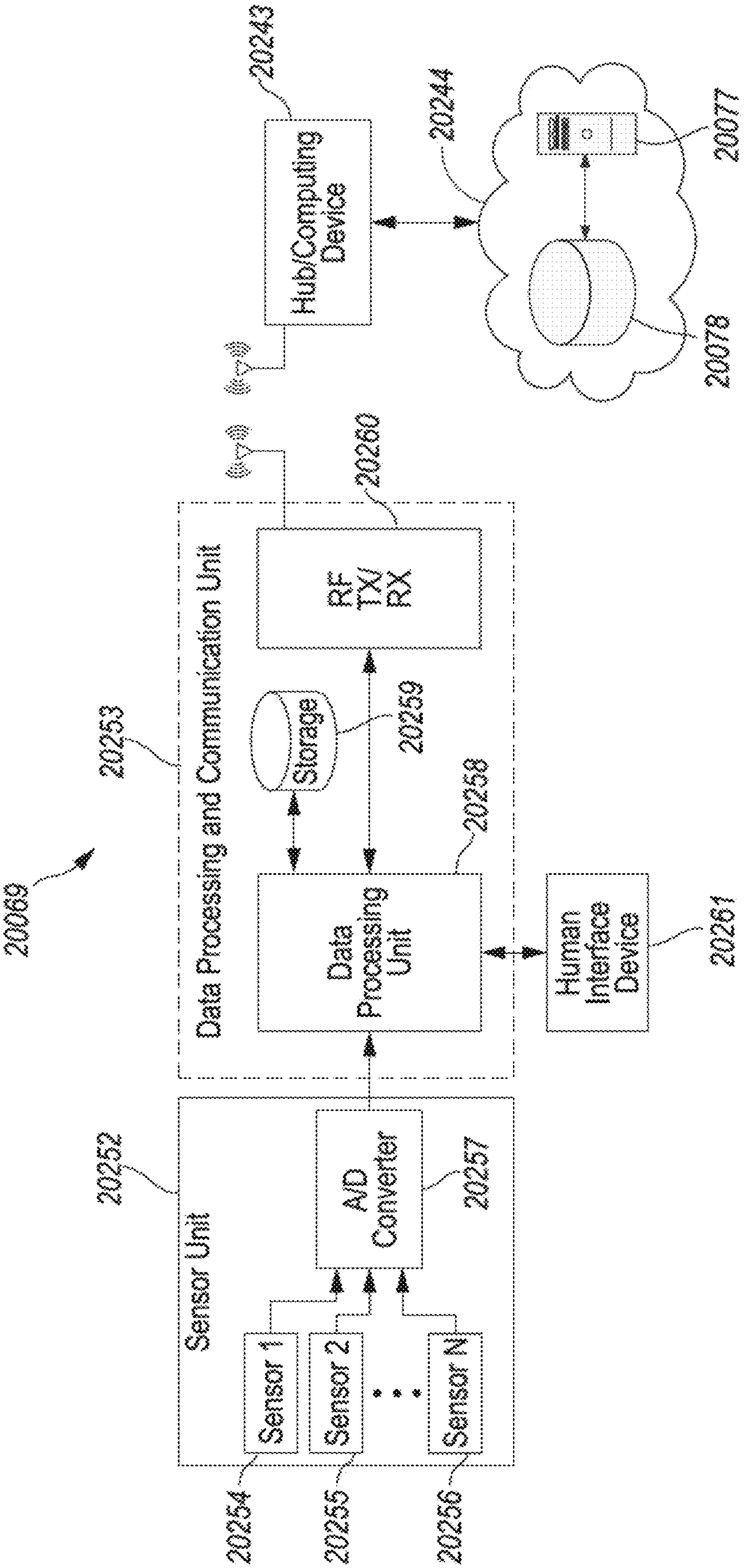
FIG. 7D shows an exemplary sensing system with a sensor unit and a data processing and communication unit.

The computing system 20063 of FIG. 4, FIG. 6B, the computing device 20200 of FIG. 6C, the hub/computing device 20243 of FIG. 7B, FIG. 7C, or FIG. 7D may be a surgical computing system or a hub device, a laptop, a tablet, a smart phone, etc.

As shown in FIG. 6B, a set of sensing systems 20069 and/or an environmental sensing system 20015 (as described in FIG. 2A) may be connected to the surgical hub system 20076 via the routers 20065. The routers 20065 may also provide a direct communication connection between the sensing systems 20069 and the cloud computing system 20064, for example, without involving the local computer system 20063 of the surgical hub system 20076. Communication from the surgical hub system 20076 to the cloud 20064 may be made either through a wired or a wireless communication channel.

As shown in FIG. 6B, the computer system 20063 may include a processor 20102 and a network interface 20100. The processor 20102 may be coupled to a radio frequency (RF) interface or a communication module 20103, storage 20104, memory 20105, non-volatile memory 20106, and input/output interface 20107 via a system bus, as described in FIG. 6A. The computer system 20063 may be connected with a local display unit 20108. In some examples, the display unit 20108 may be replaced by a HID. Details about the hardware and software components of the computer system are provided in FIG. 6A.

As shown in FIG. 6B, a sensing system 20069 may include a processor 20110. The processor 20110 may be coupled to a radio frequency (RF) interface 20114, storage 20113, memory (e.g., a non-volatile memory) 20112, and I/O interface 20111 via a system bus. The system bus can be any of several types of bus structure(s) including the memory bus or memory controller, a peripheral bus or external bus, and/or a local bus, as described herein. The processor 20110 may be any single-core or multicore processor as described herein.

It is to be appreciated that the sensing system 20069 may include software that acts as an intermediary between sensing system users and the computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

The sensing system 20069 may be connected to a human interface system 20115. The human interface system 20115 may be a touch screen display. The human interface system 20115 may include a human interface display for displaying information associated with a surgeon biomarker and/or a patient biomarker, display a prompt for a user action by a patient or a surgeon, or display a notification to a patient or a surgeon indicating information about a recovery millstone or a complication. The human interface system 20115 may be used to receive input from a patient or a surgeon. Other human interface systems may be connected to the sensing system 20069 via the I/O interface 20111. For example, the human interface device 20115 may include devices for providing a haptic feedback as a mechanism for prompting a user to pay attention to a notification that may be displayed on a display unit.

The sensing system 20069 may operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. The remote computer(s) may be logically connected to the computer system through a network interface. The network interface may encompass communication networks such as local area networks (LANs), wide area networks (WANs), and/or mobile networks. LAN technologies may include Fiber Distributed Data Interface (FDDI), Copper Distributed Data Interface (CDDI), Ethernet/IEEE 802.3, Token Ring/IEEE 802.5, Wi-Fi/IEEE 802.11, and the like. WAN technologies may include, but are not limited to, point-to-point links, circuit-switching networks like Integrated Services Digital Networks (ISDN) and variations thereon, packet-switching networks, and Digital Subscriber Lines (DSL). The mobile networks may include communication links based on one or more of the following mobile communication protocols: GSM/GPRS/EDGE (2G), UMTS/HSPA (3G), long term evolution (LTE) or 4G, LTE-Advanced (LTE-A), new radio (NR) or 5G, etc.

FIG. 6C illustrates an exemplary uncontrolled patient monitoring system, for example, when the patient is away from a healthcare facility. The uncontrolled patient monitoring system may be used for pre-surgical patient monitoring when a patient is being prepared for a surgical procedure but is away from a healthcare facility, or in post-surgical monitoring, for example, when a patient is recovering away from a healthcare facility.

As illustrated in FIG. 6C, one or more sensing systems 20069 are in communication with a computing device 20200, for example, a personal computer, a laptop, a tablet, or a smart phone. The computing system 20200 may provide processing for monitoring of various biomarkers associated with a patient, a notification mechanism to indicate that a milestone (e.g., a recovery milestone) is met or a complication is detected. The computing system 20200 may also provide instructions for the user of the sensing system to follow. The communication between the sensing systems 20069 and the computing device 20200 may be established directly using a wireless protocol as described herein or via the wireless router/hub 20211.

As shown in FIG. 6C, the sensing systems 20069 may be connected to the computing device 20200 via router 20211. The router 20211 may include wireless routers, wired switches, wired routers, wired or wireless networking hubs, etc. The router 20211 may provide a direct communication connection between the sensing systems 20069 and the cloud servers 20064, for example, without involving the local computing device 20200. The computing device 20200 may be in communication with the cloud server 20064. For example, the computing device 20200 may be in communication with the cloud 20064 through a wired or a wireless communication channel. In an example, a sensing system 20069 may be in communication with the cloud directly over a cellular network, for example, via a cellular base station 20210.

As shown in FIG. 6C, the computing device 20200 may include a processor 20203 and a network or an RF interface 20201. The processor 20203 may be coupled to a storage 20202, memory 20212, non-volatile memory 20213, and input/output interface 20204 via a system bus, as described in FIG. 6A and FIG. 6B. Details about the hardware and software components of the computer system are provided in FIG. 6A. The computing device 20200 may include a set of sensors, for example, sensor #1 20205, sensor #2 20206 up to sensor #n 20207. These sensors may be a part of the computing device 20200 and may be used to measure one or more attributes associated with the patient. The attributes may provide a context about a biomarker measurement performed by one of the sensing systems 20069. For example, sensor #1 may be an accelerometer that may be used to measure acceleration forces in order to sense movement or vibrations associated with the patient. In an example, the sensors 20205 to 20207 may include one or more of: a pressure sensor, an altimeter, a thermometer, a lidar, or the like.

As shown in FIG. 6B, a sensing system 20069 may include a processor, a radio frequency interface, a storage, a memory or non-volatile memory, and input/output interface via a system bus, as described in FIG. 6A. The sensing system may include a sensor unit and a processing and communication unit, as described in FIG. 7B through 7D. The system bus can be any of several types of bus structure(s) including the memory bus or memory controller, a peripheral bus or external bus, and/or a local bus, as described herein. The processor may be any single-core or multicore processor, as described herein.

The sensing system 20069 may be in communication with a human interface system 20215. The human interface system 20215 may be a touch screen display. The human interface system 20215 may be used to display information associated with a patient biomarker, display a prompt for a user action by a patient, or display a notification to a patient indicating information about a recovery millstone or a complication. The human interface system 20215 may be used to receive input from a patient. Other human interface systems may be connected to the sensing system 20069 via the I/O interface. For example, the human interface system may include devices for providing a haptic feedback as a mechanism for prompting a user to pay attention to a notification that may be displayed on a display unit. The sensing system 20069 may operate in a networked environment using logical connections to one or more remote computers, such as cloud computer(s), or local computers, as described in FIG. 6B.

FIG. 7A illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

In one aspect, the microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with Stellaris Ware® software, a 2 KB EEPROM, one or more PWM modules, one or more QEI analogs, and/or one or more 12-bit ADCs with 12 analog input channels, details of which are available for the product datasheet.

In one aspect, the microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

In some examples, the motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the of the displacement member, where d1 is the longitudinal linear distance that the displacement member moves from point “a” to point “b” after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder’s algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

In one form, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the modular communication hub 20065 as shown in FIG. 5 and FIG. 6A.

FIG. 7B shows an example sensing system 20069. The sensing system may be a surgeon sensing system or a patient sensing system. The sensing system 20069 may include a sensor unit 20235 and a human interface system 20242 that are in communication with a data processing and communication unit 20236. The data processing and communication unit 20236 may include an analog-to-digital converted 20237, a data processing unit 20238, a storage unit 20239, and an input/output interface 20241, a transceiver 20240. The sensing system 20069 may be in communication with a surgical hub or a computing device 20243, which in turn is in communication with a cloud computing system 20244. The cloud computing system 20244 may include a cloud storage system 20078 and one or more cloud servers 20077.

The sensor unit 20235 may include one or more ex vivo or in vivo sensors for measuring one or more biomarkers. The biomarkers may include, for example, Blood pH, hydration state, oxygen saturation, core body temperature, heart rate, Heart rate variability, Sweat rate, Skin conductance, Blood pressure, Light exposure, Environmental temperature, Respiratory rate, Coughing and sneezing, Gastrointestinal motility, Gastrointestinal tract imaging, Tissue perfusion pressure, Bacteria in respiratory tract, Alcohol consumption, Lactate (sweat), Peripheral temperature, Positivity and optimism, Adrenaline (sweat), Cortisol (sweat), Edema, Mycotoxins, VO2 max, Pre-operative pain, chemicals in the air, Circulating tumor cells, Stress and anxiety, Confusion and delirium, Physical activity, Autonomic tone, Circadian rhythm, Menstrual cycle, Sleep, etc. These biomarkers may be measured using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The sensors may measure the biomarkers as described herein using one of more of the following sensing technologies: photoplethysmography, electrocardiography, electroencephalography, colorimetry, impedimentary, potentiometry, amperometry, etc.

As illustrated in FIG. 7B, a sensor in the sensor unit 20235 may measure a physiological signal (e.g., a voltage, a current, a PPG signal, etc.) associated with a biomarker to be measured. The physiological signal to be measured may depend on the sensing technology used, as described herein. The sensor unit 20235 of the sensing system 20069 may be in communication with the data processing and communication unit 20236. In an example, the sensor unit 20235 may communicate with the data processing and communication unit 20236 using a wireless interface. The data processing and communication unit 20236 may include an analog-to-digital converter (ADC) 20237, a data processing unit 20238, a storage 20239, an I/O interface 20241, and an RF transceiver 20240. The data processing unit 20238 may include a processor and a memory unit.

The sensor unit 20235 may transmit the measured physiological signal to the ADC 20237 of the data processing and communication unit 20236. In an example, the measured physiological signal may be passed through one or more filters (e.g., an RC low-pass filter) before being sent to the ADC. The ADC may convert the measured physiological signal into measurement data associated with the biomarker. The ADC may pass measurement data to the data processing unit 20238 for processing. In an example, the data processing unit 20238 may send the measurement data associated with the biomarker to a surgical hub or a computing device 20243, which in turn may send the measurement data to a cloud computing system 20244 for further processing. The data processing unit may send the measurement data to the surgical hub or the computing device 20243 using one of the wireless protocols, as described herein. In an example, the data processing unit 20238 may first process the raw measurement data received from the sensor unit and send the processed measurement data to the surgical hub or a computing device 20243.

In an example, the data processing and communication unit 20236 of the sensing system 20069 may receive a threshold value associated with a biomarker for monitoring from a surgical hub, a computing device 20243, or directly from a cloud server 20077 of the cloud computing system 20244. The data processing unit 20236 may compare the measurement data associated with the biomarker to be monitored with the corresponding threshold value received from the surgical hub, the computing device 20243, or the cloud server 20077. The data processing and communication unit 20236 may send a notification message to the HID 20242 indicating that a measurement data value has crossed the threshold value. The notification message may include the measurement data associated with the monitored biomarker. The data processing and computing unit 20236 may send a notification via a transmission to a surgical hub or a computing device 20243 using one of the following RF protocols: Bluetooth, Bluetooth Low-Energy (BLE), Bluetooth Smart, Zigbee, Z-wave, IPv6 Low-power wireless Personal Area Network (6LoWPAN), Wi-Fi. The data processing unit 20238 may send a notification (e.g., a notification for an HCP) directly to a cloud server via a transmission to a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G. In an example, the sensing unit may be in communication with the hub/computing device via a router, as described in FIG. 6A through FIG. 6C.

FIG. 7C shows an example sensing system 20069 (e.g., a surgeon sensing system or a patient sensing system). The sensing system 20069 may include a sensor unit 20245, a data processing and communication unit 20246, and a human interface device 20242. The sensor unit 20245 may include a sensor 20247 and an analog-to-digital converted (ADC) 20248. The ADC 20248 in the sensor unit 20245 may convert a physiological signal measured by the sensor 20247 into measurement data associated with a biomarker. The sensor unit 20245 may send the measurement data to the data processing and communication unit 20246 for further processing. In an example, the sensor unit 20245 may send the measurement data to the data processing and communication unit 20246 using an inter-integrated circuit (I2C) interface.

The data processing and communication unit 20246 includes a data processing unit 20249, a storage unit 20250, and an RF transceiver 20251. The sensing system may be in communication with a surgical hub or a computing device 20243, which in turn may be in communication with a cloud computing system 20244. The cloud computing system 20244 may include a remote server 20077 and an associated remote storage 20078. The sensor unit 20245 may include one or more ex vivo or in vivo sensors for measuring one or more biomarkers, as described herein.

The data processing and communication unit 20246 after processing the measurement data received from the sensor unit 20245 may further process the measurement data and/or send the measurement data to the smart hub or the computing device 20243, as described in FIG. 7B. In an example, the data processing and communication unit 20246 may send the measurement data received from the sensor unit 20245 to the remote server 20077 of the cloud computing system 20244 for further processing and/or monitoring.

FIG. 7D shows an example sensing system 20069 (e.g., a surgeon sensing system or a patient sensing system). The sensing system 20069 may include a sensor unit 20252, a data processing and communication unit 20253, and a human interface system 20261. The sensor unit 20252 may include a plurality of sensors 20254, 20255 up to 20256 to measure one or more physiological signals associated with a patient or surgeon's biomarkers and/or one or more physical state signals associated with physical state of a patient or a surgeon. The sensor unit 20252 may also include one or more analog-to-digital converter(s) (ADCs) 20257. A list of biomarkers may include biomarkers such as those biomarkers disclosed herein. The ADC(s) 20257 in the sensor unit 20252 may convert each of the physiological signals and/or physical state signals measured by the sensors 20254-20256 into respective measurement data. The sensor unit 20252 may send the measurement data associated with one or more biomarkers as well as with the physical state of a patient or a surgeon to the data processing and communication unit 20253 for further processing. The sensor unit 20252 may send the measurement data to the data processing and communication unit 20253 individually for each of the sensors Sensor 1 20254 to Sensor N 20256 or combined for all the sensors. In an example, the sensor unit 20252 may send the measurement data to the data processing and communication unit 20253 via an I2C interface.

The data processing and communication unit 20253 may include a data processing unit 20258, a storage unit 20259, and an RF transceiver 20260. The sensing system 20069 may be in communication with a surgical hub or a computing device 20243, which in turn is in communication with a cloud computing system 20244 comprising at least one remote server 20077 and at least one storage unit 20078. The sensor units 20252 may include one or more ex vivo or in vivo sensors for measuring one or more biomarkers, as described herein.

Figure 8:
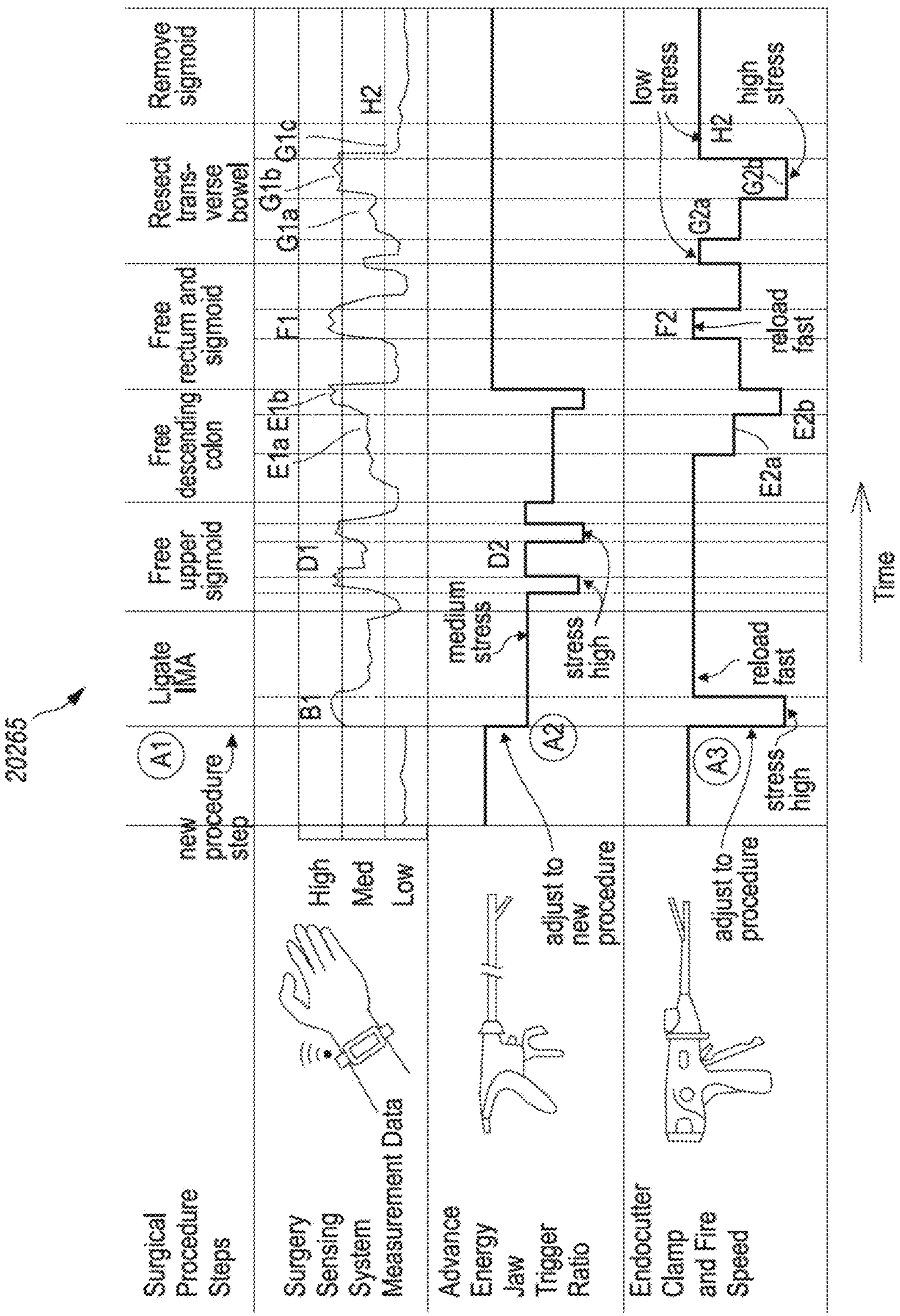
FIG. 8 illustrates an exemplary timeline of an illustrative surgical procedure indicating adjusting operational parameters of a surgical device based on a surgeon biomarker level.

FIG. 8 is an example of using a surgical task situational awareness and measurement data from one or more surgeon sensing systems to adjust surgical instrument controls. FIG. 8 illustrates a timeline 20265 of an illustrative surgical procedure and the contextual information that a surgical hub can derive from data received from one or more surgical devices, one or more surgeon sensing systems, and/or one or more environmental sensing systems at each step in the surgical procedure. The devices that could be controlled by a surgical hub may include advanced energy devices, endocutter clamps, etc. The surgeon sensing systems may include sensing systems for measuring one or more biomarkers associated with the surgeon, for example, heart rate, sweat composition, respiratory rate, etc. The environmental sensing system may include systems for measuring one or more of the environmental attributes, for example, cameras for detecting a surgeon's position/movements/breathing pattern, spatial microphones, for example to measure ambient noise in the surgical theater and/or the tone of voice of a healthcare provider, temperature/humidity of the surroundings, etc.

In the following description of the timeline 20265 illustrated in FIG. 8, reference should also be made to FIG. 5. FIG. 5 provides various components used in a surgical procedure. The timeline 20265 depicts the steps that may be taken individually and/or collectively by the nurses, surgeons, and other medical personnel during the course of an exemplary colorectal surgical procedure. In a colorectal surgical procedure, a situationally aware surgical hub 20076 may receive data from various data sources throughout the course of the surgical procedure, including data generated each time a healthcare provider (HCP) utilizes a modular device/instrument 20095 that is paired with the surgical hub 20076. The surgical hub 20076 may receive this data from the paired modular devices 20095. The surgical hub may receive measurement data from sensing systems 20069. The surgical hub may use the data from the modular device/instruments 20095 and/or measurement data from the sensing systems 20069 to continually derive inferences (i.e., contextual information) about an HCP's stress level and the ongoing procedure as new data is received, such that the stress level of the surgeon relative to the step of the procedure that is being performed is obtained. The situational awareness system of the surgical hub 20076 may perform one or more of the following: record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the FOV of the medical imaging device, change the energy level of an ultrasonic surgical instrument or RF electrosurgical instrument), or take any other such action described herein. In an example, these steps may be performed by a remote server 20077 of a cloud system 20064 and communicated with the surgical hub 20076.

As a first step (not shown in FIG. 8 for brevity), the hospital staff members may retrieve the patient's EMR from the hospital's EMR database. Based on select patient data in the EMR, the surgical hub 20076 may determine that the procedure to be performed is a colorectal procedure. The staff members may scan the incoming medical supplies for the procedure. The surgical hub 20076 may cross-reference the scanned supplies with a list of supplies that can be utilized in various types of procedures and confirms that the mix of supplies corresponds to a colorectal procedure. The surgical hub 20076 may pair each of the sensing systems 20069 worn by different HCPs.

Once each of the devices is ready and pre-surgical preparation is complete, the surgical team may begin by making incisions and place trocars. The surgical team may perform access and prep by dissecting adhesions, if any, and identifying inferior mesenteric artery (IMA) branches. The surgical hub 20076 can infer that the surgeon is in the process of dissecting adhesions, at least based on the data it may receive from the RF or ultrasonic generator indicating that an energy instrument is being fired. The surgical hub 20076 may cross-reference the received data with the retrieved steps of the surgical procedure to determine that an energy instrument being fired at this point in the process (e.g., after the completion of the previously discussed steps of the procedure) corresponds to the dissection step.

After dissection, the HCP may proceed to the ligation step (e.g., indicated by A1) of the procedure. As illustrated in FIG. 8, the HCP may begin by ligating the IMA. The surgical hub 20076 may infer that the surgeon is ligating arteries and veins because it may receive data from the advanced energy jaw device and/or the endocutter indicating that the instrument is being fired. The surgical hub may also receive measurement data from one of the HCP's sensing systems indicating higher stress level of the HCP (e.g., indicated by B1 mark on the time axis). For example, higher stress level may be indicated by change in the HCP's heart rate from a base value. The surgical hub 20076, like the prior step, may derive this inference by cross-referencing the receipt of data from the surgical stapling and cutting instrument with the retrieved steps in the process (e.g., as indicated by A2 and A3). The surgical hub 20076 may monitor the advance energy jaw trigger ratio and/or the endocutter clamp and firing speed during the high stress time periods. In an example, the surgical hub 20076 may send an assistance control signal to the advanced energy jaw device and/or the endocutter device to control the device in operation. The surgical hub may send the assistance signal based on the stress level of the HCP that is operating the surgical device and/or situational awareness known to the surgical hub. For example, the surgical hub 20076 may send control assistance signals to an advanced energy device or an endocutter clamp, as indicated in FIG. 8 by A2 and A3.

The HCP may proceed to the next step of freeing the upper sigmoid followed by freeing descending colon, rectum, and sigmoid. The surgical hub 20076 may continue to monitor the high stress markers of the HCP (e.g., as indicated by D1, E1*a*, E1*b*, F1). The surgical hub 20076 may send assistance signals to the advanced energy jaw device and/or the endocutter device during the high stress time periods, as illustrated in FIG. 8.

After mobilizing the colon, the HCP may proceed with the segmentectomy portion of the procedure. For example, the surgical hub 20076 may infer that the HCP is transecting the bowel and sigmoid removal based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. It should be noted that surgeons regularly switch back and forth between surgical stapling/cutting instruments and surgical energy (e.g., RF or ultrasonic) instruments depending upon the step in the procedure because different instruments are better adapted for particular tasks. Therefore, the sequence in which the stapling/cutting instruments and surgical energy instruments are used can indicate what step of the procedure the surgeon is performing.

The surgical hub may determine and send a control signal to surgical device based on the stress level of the HCP. For example, during time period G1*b*, a control signal G2*b* may be sent to an endocutter clamp. Upon removal of the sigmoid, the incisions are closed, and the post-operative portion of the procedure may begin. The patient's anesthesia can be reversed. The surgical hub 20076 may infer that the patient is emerging from the anesthesia based on one or more sensing systems attached to the patient.

Figure 9:
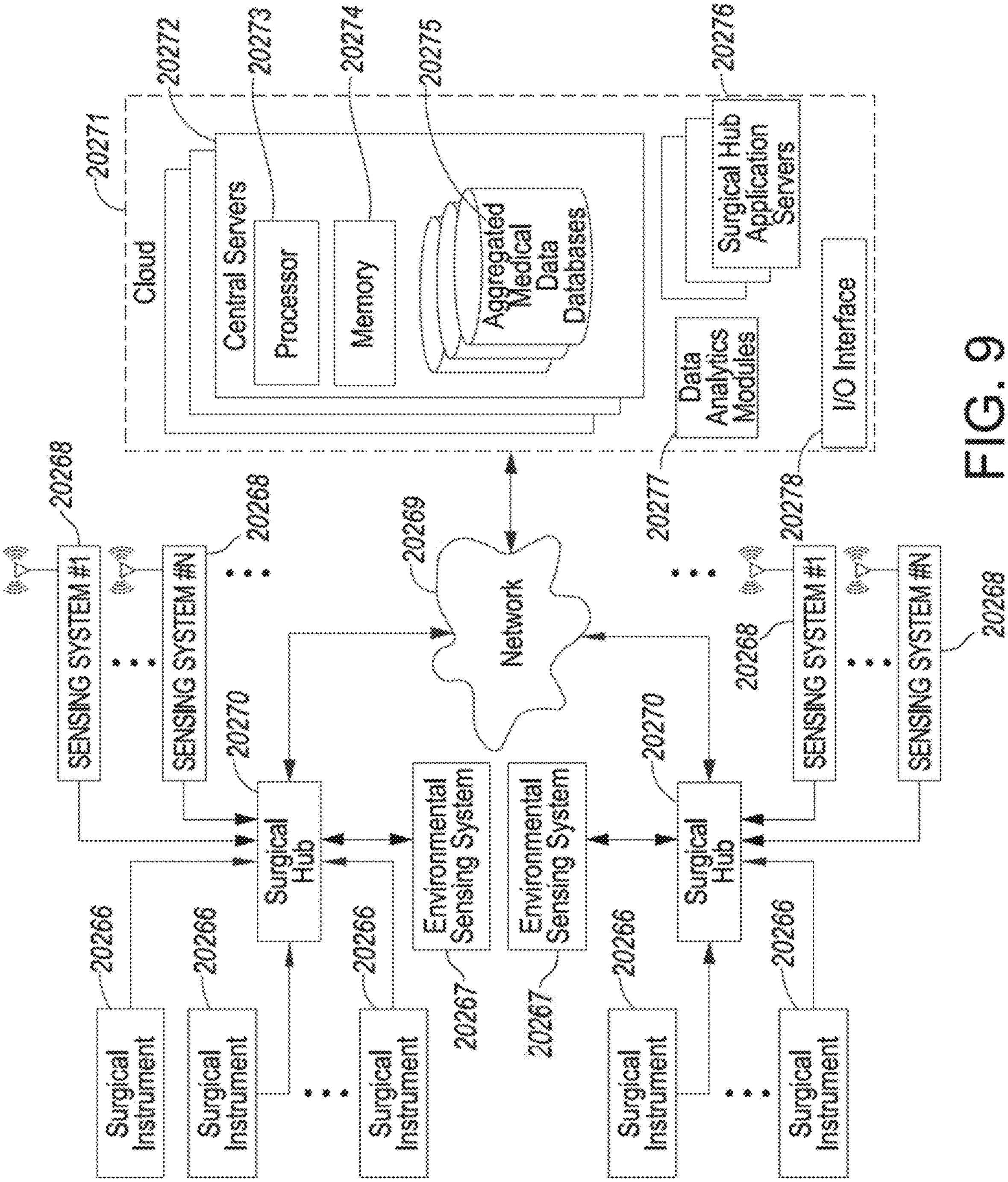
FIG. 9 is a block diagram of the computer-implemented interactive surgeon/patient monitoring system.

FIG. 9 is a block diagram of the computer-implemented interactive surgical system with surgeon/patient monitoring, in accordance with at least one aspect of the present disclosure. In one aspect, the computer-implemented interactive surgical system may be configured to monitor surgeon biomarkers and/or patient biomarkers using one or more sensing systems 20069. The surgeon biomarkers and/or the patient biomarkers may be measured before, after, and/or during a surgical procedure. In one aspect, the computer-implemented interactive surgical system may be configured to monitor and analyze data related to the operation of various surgical systems 20069 that include surgical hubs, surgical instruments, robotic devices and operating theaters or healthcare facilities. The computer-implemented interactive surgical system may include a cloud-based analytics system. The cloud-based analytics system may include one or more analytics servers.

As illustrated in FIG. 9, the cloud-based monitoring and analytics system may comprise a plurality of sensing systems 20268 (may be the same or similar to the sensing systems 20069), surgical instruments 20266 (may be the same or similar to instruments 20031), a plurality of surgical hubs 20270 (may be the same or similar to hubs 20006), and a surgical data network 20269 (may be the same or similar to the surgical data network described in FIG. 4) to couple the surgical hubs 20270 to the cloud 20271 (may be the same or similar to cloud computing system 20064). Each of the plurality of surgical hubs 20270 may be communicatively coupled to one or more surgical instruments 20266. Each of the plurality of surgical hubs 20270 may also be communicatively coupled to the one or more sensing systems 20268, and the cloud 20271 of the computer-implemented interactive surgical system via the network 20269. The surgical hubs 20270 and the sensing systems 20268 may be communicatively coupled using wireless protocols as described herein. The cloud system 20271 may be a remote centralized source of hardware and software for storing, processing, manipulating, and communicating measurement data from the sensing systems 20268 and data generated based on the operation of various surgical systems 20268.

As shown in FIG. 9, access to the cloud system 20271 may be achieved via the network 20269, which may be the Internet or some other suitable computer network. Surgical hubs 20270 that may be coupled to the cloud system 20271 can be considered the client side of the cloud computing system (e.g., cloud-based analytics system). Surgical instruments 20266 may be paired with the surgical hubs 20270 for control and implementation of various surgical procedures and/or operations, as described herein. Sensing systems 20268 may be paired with surgical hubs 20270 for in-surgical surgeon monitoring of surgeon related biomarkers, pre-surgical patient monitoring, in-surgical patient monitoring, or post-surgical monitoring of patient biomarkers to track and/or measure various milestones and/or detect various complications. Environmental sensing systems 20267 may be paired with surgical hubs 20270 measuring environmental attributes associated with a surgeon or a patient for surgeon monitoring, pre-surgical patient monitoring, in-surgical patient monitoring, or post-surgical monitoring of patient.

Surgical instruments 20266, environmental sensing systems 20267, and sensing systems 20268 may comprise wired or wireless transceivers for data transmission to and from their corresponding surgical hubs 20270 (which may also comprise transceivers). Combinations of one or more of surgical instruments 20266, sensing systems 20268, or surgical hubs 20270 may indicate particular locations, such as operating theaters, intensive care unit (ICU) rooms, or recovery rooms in healthcare facilities (e.g., hospitals), for providing medical operations, pre-surgical preparation, and/or post-surgical recovery. For example, the memory of a surgical hub 20270 may store location data.

As shown in FIG. 9, the cloud system 20271 may include one or more central servers 20272 (may be same or similar to remote server 20067), surgical hub application servers 20276, data analytics modules 20277, and an input/output ("I/O") interface 20278. The central servers 20272 of the cloud system 20271 may collectively administer the cloud computing system, which includes monitoring requests by client surgical hubs 20270 and managing the processing capacity of the cloud system 20271 for executing the requests. Each of the central servers 20272 may comprise one or more processors 20273 coupled to suitable memory devices 20274 which can include volatile memory such as random-access memory (RAM) and non-volatile memory such as magnetic storage devices. The memory devices 20274 may comprise machine executable instructions that when executed cause the processors 20273 to execute the data analytics modules 20277 for the cloud-based data analysis, real-time monitoring of measurement data received from the sensing systems 20268, operations, recommendations, and other operations as described herein. The processors 20273 can execute the data analytics modules 20277 independently or in conjunction with hub applications independently executed by the hubs 20270. The central servers 20272 also may comprise aggregated medical data databases 20275, which can reside in the memory 20274.

Based on connections to various surgical hubs 20270 via the network 20269, the cloud 20271 can aggregate data from specific data generated by various surgical instruments 20266 and/or monitor real-time data from sensing systems 20268 and the surgical hubs 20270 associated with the surgical instruments 20266 and/or the sensing systems 20268. Such aggregated data from the surgical instruments 20266 and/or measurement data from the sensing systems 20268 may be stored within the aggregated medical databases 20275 of the cloud 20271. In particular, the cloud 20271 may advantageously track real-time measurement data from the sensing systems 20268 and/or perform data analysis and operations on the measurement data and/or the aggregated data to yield insights and/or perform functions that individual hubs 20270 could not achieve on their own. To this end, as shown in FIG. 9, the cloud 20271 and the surgical hubs 20270 are communicatively coupled to transmit and receive information. The I/O interface 20278 is connected to the plurality of surgical hubs 20270 via the network 20269. In this way, the I/O interface 20278 can be configured to transfer information between the surgical hubs 20270 and the aggregated medical data databases 20275. Accordingly, the I/O interface 20278 may facilitate read/write operations of the cloud-based analytics system. Such read/write operations may be executed in response to requests from hubs 20270. These requests could be transmitted to the surgical hubs 20270 through the hub applications. The I/O interface 20278 may include one or more high speed data ports, which may include universal serial bus (USB) ports, IEEE 1394 ports, as well as Wi-Fi and Bluetooth I/O interfaces for connecting the cloud 20271 to surgical hubs 20270. The hub application servers 20276 of the cloud 20271 may be configured to host and supply shared capabilities to software applications (e.g., hub applications) executed by surgical hubs 20270. For example, the hub application servers 20276 may manage requests made by the hub applications through the hubs 20270, control access to the aggregated medical data databases 20275, and perform load balancing.

The cloud computing system configuration described in the present disclosure may be designed to address various issues arising in the context of medical operations (e.g., pre-surgical monitoring, in-surgical monitoring, and post-surgical monitoring) and procedures performed using medical devices, such as the surgical instruments 20266, 20031. In particular, the surgical instruments 20266 may be digital surgical devices configured to interact with the cloud 20271 for implementing techniques to improve the performance of surgical operations. The sensing systems 20268 may be systems with one or more sensors that are configured to measure one or more biomarkers associated with a surgeon perfuming a medical operation and/or a patient on whom a medical operation is planned to be performed, is being performed or has been performed. Various surgical instruments 20266, sensing systems 20268, and/or surgical hubs 20270 may include human interface systems (e.g., having a touch-controlled user interfaces) such that clinicians and/or patients may control aspects of interaction between the surgical instruments 20266 or the sensing system 20268 and the cloud 20271. Other suitable user interfaces for control such as auditory controlled user interfaces may also be used.

The cloud computing system configuration described in the present disclosure may be designed to address various issues arising in the context of monitoring one or more biomarkers associated with a healthcare professional (HCP) or a patient in pre-surgical, in-surgical, and post-surgical procedures using sensing systems 20268. Sensing systems 20268 may be surgeon sensing systems or patient sensing systems configured to interact with the surgical hub 20270 and/or with the cloud system 20271 for implementing techniques to monitor surgeon biomarkers and/or patient biomarkers. Various sensing systems 20268 and/or surgical hubs 20270 may comprise touch-controlled human interface systems such that the HCPs or the patients may control aspects of interaction between the sensing systems 20268 and the surgical hub 20270 and/or the cloud systems 20271. Other suitable user interfaces for control such as auditory controlled user interfaces may also be used.

Figure 10:
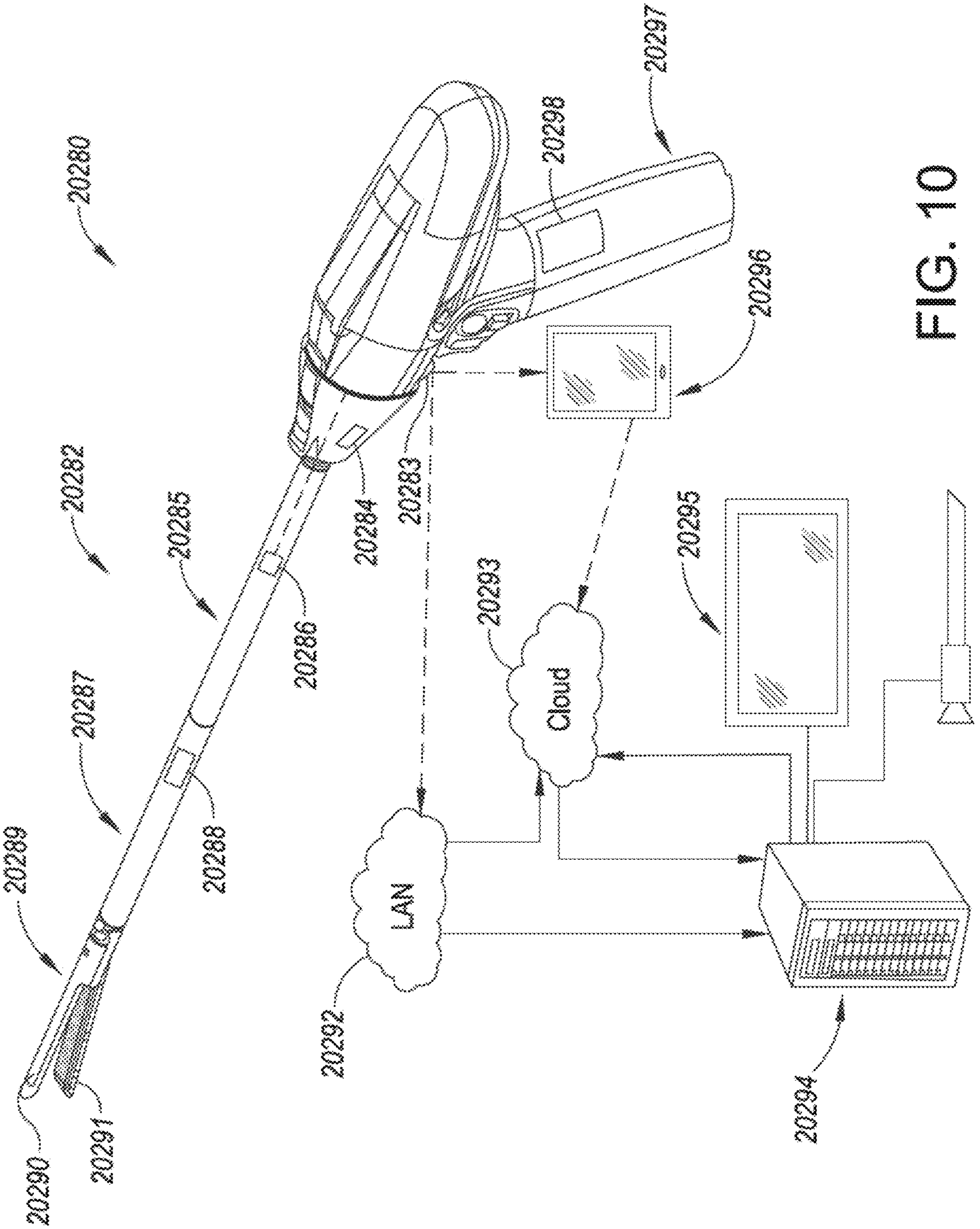
FIG. 10 shows an example surgical system that includes a handle having a controller and a motor, an adapter releasably coupled to the handle, and a loading unit releasably coupled to the adapter.

FIG. 10 illustrates an example surgical system 20280 in accordance with the present disclosure and may include a surgical instrument 20282 that can be in communication with a console 20294 or a portable device 20296 through a local area network 20292 or a cloud network 20293 via a wired or wireless connection. In various aspects, the console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub 20270, as illustrated in FIG. 9. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 11A:
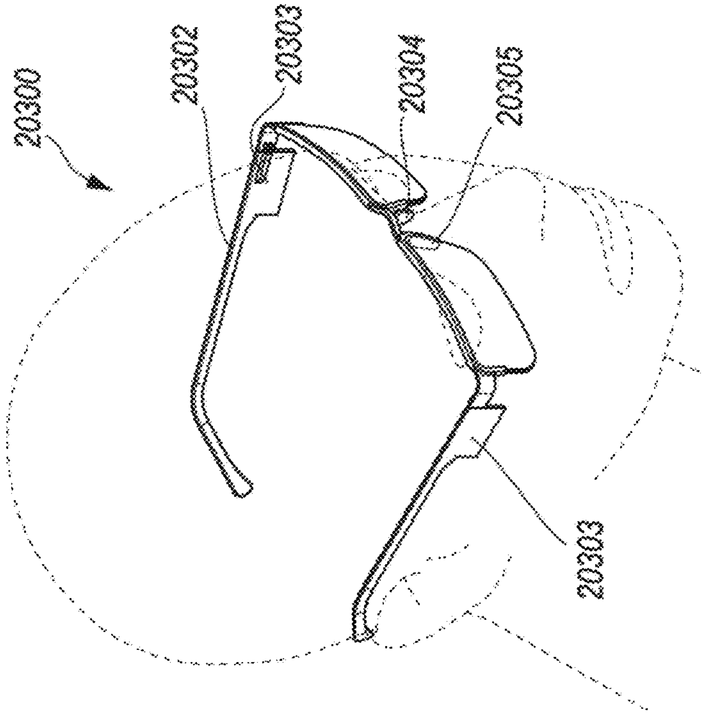
FIGS. 11A-11D illustrate examples of sensing systems that may be used for monitoring surgeon biomarkers or patient biomarkers.

FIG. 11A to FIG. 11D illustrates examples of wearable sensing systems, e.g., surgeon sensing systems or patient sensing systems. FIG. 11A is an example of eyeglasses-based sensing system 20300 that may be based on an electrochemical sensing platform. The sensing system 20300 may be capable of monitoring (e.g., real-time monitoring) of sweat electrolytes and/or metabolites using multiple sensors 20304 and 20305 that are in contact with the surgeon's or patient's skin. For example, the sensing system 20300 may use an amperometry based biosensor 20304 and/or a potentiometry based biosensor 20305 integrated with the nose bridge pads of the eyeglasses 20302 to measure current and/or the voltage.

The amperometric biosensor 20304 may be used to measure sweat lactate levels (e.g., in mmol/L). Lactate that is a product of lactic acidosis that may occur due to decreased tissue oxygenation, which may be caused by sepsis or hemorrhage. A patient's lactate levels (e.g., >2 mmol/L) may be used to monitor the onset of sepsis, for example, during post-surgical monitoring. The potentiometric biosensor 20305 may be used to measure potassium levels in the patient's sweat. A voltage follower circuit with an operational amplifier may be used for measuring the potential signal between the reference and the working electrodes. The output of the voltage follower circuit may be filtered and converted into a digital value using an ADC.

The amperometric sensor 20304 and the potentiometric sensor 20305 may be connected to circuitries 20303 placed on each of the arms of the eyeglasses. The electrochemical sensors may be used for simultaneous real-time monitoring of sweat lactate and potassium levels. The electrochemical sensors may be screen printed on stickers and placed on each side of the glasses nose pads to monitor sweat metabolites and electrolytes. The electronic circuitries 20303 placed on the arms of the glasses frame may include a wireless data transceiver (e.g., a low energy Bluetooth transceiver) that may be used to transmit the lactate and/or potassium measurement data to a surgical hub or an intermediary device that may then forward the measurement data to the surgical hub. The eyeglasses-based sensing system 20300 may use signal conditioning unit to filter and amplify the electrical signal generated from the electrochemical sensors 20305 or 20304, a microcontroller to digitize the analog signal, and a wireless (e.g., a low energy Bluetooth) module to transfer the data to a surgical hub or a computing device, for example, as described in FIGS. 7B through 7D.

Figure 11B:
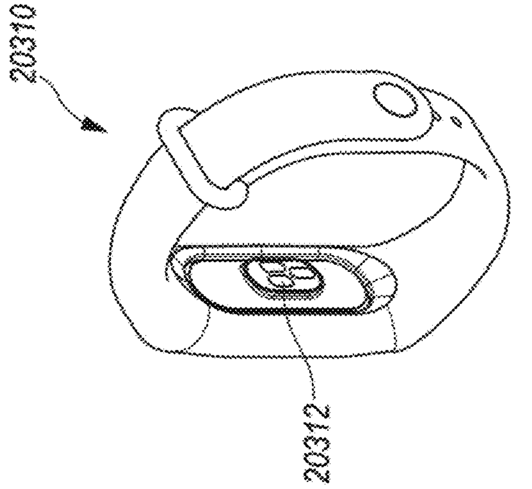

FIG. 11B is an example of a wristband-type sensing system 20310 comprising a sensor assembly 20312 (e.g., Photoplethysmography (PPG)-based sensor assembly or Electrocardiogram (ECG) based-sensor assembly). For example, in the sensing system 20310, the sensor assembly 20312 may collect and analyze arterial pulse in the wrist. The sensor assembly 20312 may be used to measure one or more biomarkers (e.g., heart rate, heart rate variability (HRV), etc.). In case of a sensing system with a PPG-based sensor assembly 20312, light (e.g., green light) may be passed through the skin. A percentage of the green light may be absorbed by the blood vessels and some of the green light may be reflected and detected by a photodetector. These differences or reflections are associated with the variations in the blood perfusion of the tissue and the variations may be used in detecting the heart-related information of the cardiovascular system (e.g., heart rate). For example, the amount of absorption may vary depending on the blood volume. The sensing system 20310 may determine the heart rate by measuring light reflectance as a function of time. HRV may be determined as the time period variation (e.g., standard deviation) between the steepest signal gradient prior to a peak, known as inter-beat intervals (IBIs).

In the case of a sensing system with an ECG-based sensor assembly 20312, a set of electrodes may be placed in contact with skin. The sensing system 20310 may measure voltages across the set of electrodes placed on the skin to determine heart rate. HRV in this case may be measured as the time period variation (e.g., standard deviation) between R peaks in the QRS complex, known as R-R intervals.

The sensing system 20310 may use a signal conditioning unit to filter and amplify the analog PPG signal, a microcontroller to digitize the analog PPG signal, and a wireless (e.g., a Bluetooth) module to transfer the data to a surgical hub or a computing device, for example, as described in FIGS. 7B through 7D.

Figure 11C:
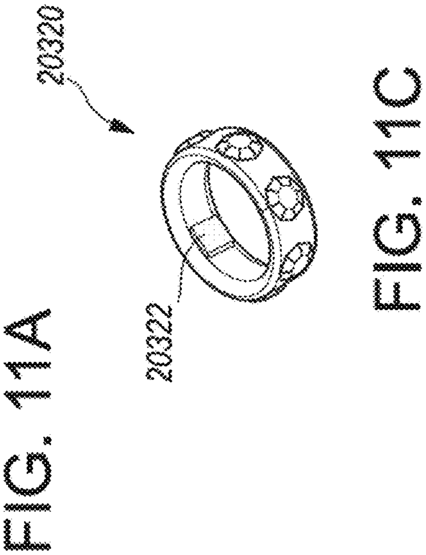

FIG. 11C is an example ring sensing system 20320. The ring sensing system 20320 may include a sensor assembly (e.g., a heart rate sensor assembly) 20322. The sensor assembly 20322 may include a light source (e.g., red or green light emitting diodes (LEDs), and photodiodes to detect reflected and/or absorbed light. The LEDs in the sensor assembly 20322 may shine light through a finger and the photodiode in the sensor assembly 20322 may measure heart rate and/or oxygen level in the blood by detecting blood volume change. The ring sensing system 20320 may include other sensor assemblies to measure other biomarkers, for example, a thermistor or an infrared thermometer to measure the surface body temperature. The ring sensing system 20320 may use a signal conditioning unit to filter and amplify the analog PPG signal, a microcontroller to digitize the analog PPG signal, and a wireless (e.g., a low energy Bluetooth) module to transfer the data to a surgical hub or a computing device, for example, as described in FIGS. 7B through 7D.

Figure 11D:
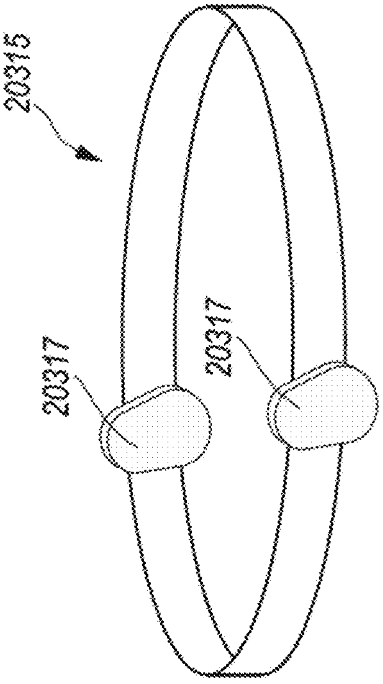

FIG. 11D is an example of an electroencephalogram (EEG) sensing system 20315. As illustrated in FIG. 11D, the sensing system 20315 may include one or more EEG sensor units 20317. The EEG sensor units 20317 may include a plurality of conductive electrodes placed in contact with the scalp. The conductive electrodes may be used to measure small electrical potentials that may arise outside of the head due to neuronal action within the brain. The EEG sensing system 20315 may measure a biomarker, for example, delirium by identifying certain brain patterns, for example, a slowing or dropout of the posterior dominant rhythm and loss of reactivity to eyes opening and closing. The ring sensing system 20315 may have a signal conditioning unit for filtering and amplifying the electrical potentials, a microcontroller to digitize the electrical signals, and a wireless (e.g., a low energy Bluetooth) module to transfer the data to a smart device, for example, as described in FIGS. 7B through 7D.

Figure 12:
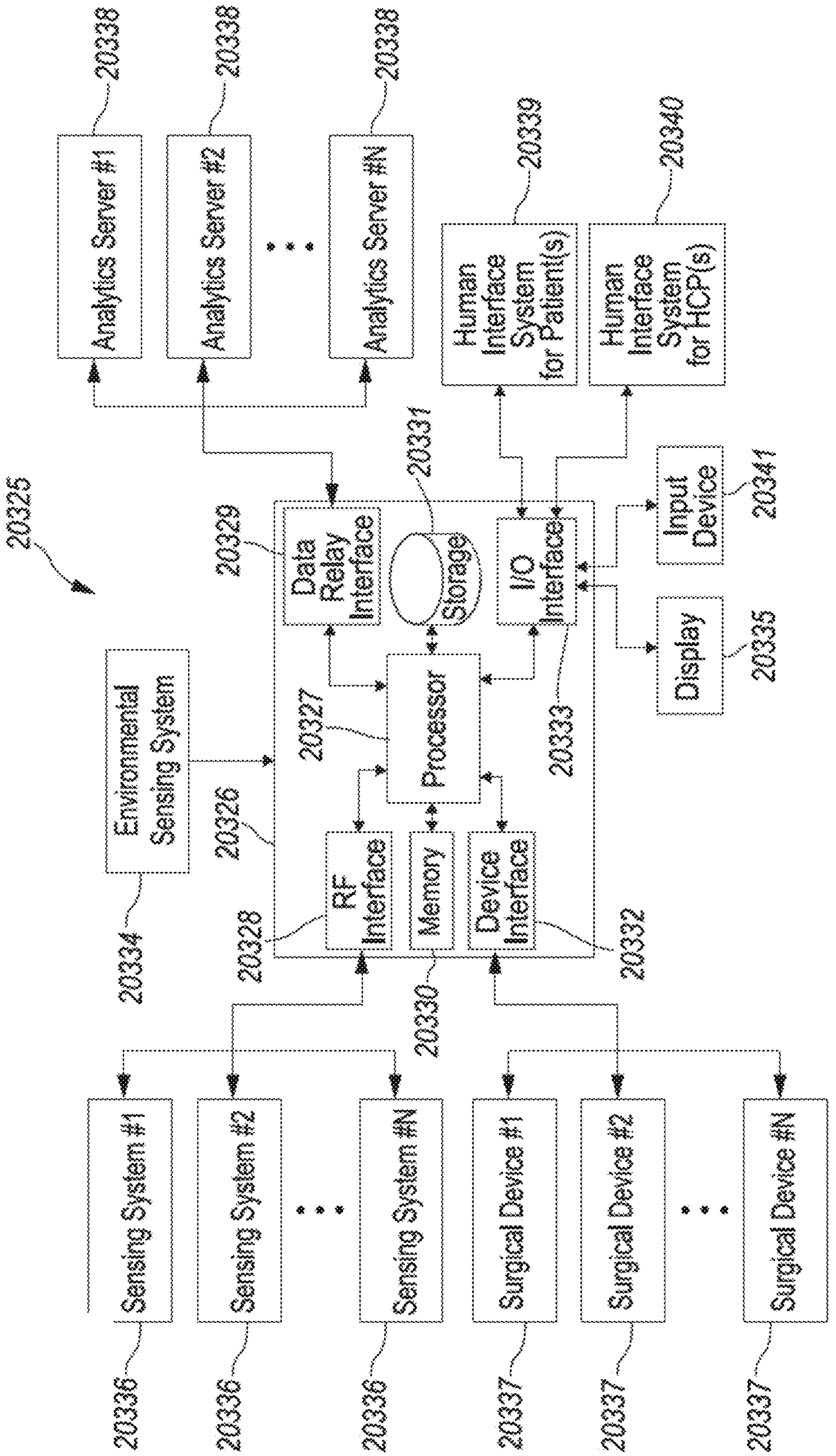
FIG. 12 is a block diagram of a patient monitoring system or a surgeon monitoring system.

FIG. 12 illustrates a block diagram of a computer-implemented patient/surgeon monitoring system 20325 for monitoring one or more patient or surgeon biomarkers prior to, during, and/or after a surgical procedure. As illustrated in FIG. 12, one or more sensing systems 20336 may be used to measure and monitor the patient biomarkers, for example, to facilitate patient preparedness before a surgical procedure, and recovery after a surgical procedure. Sensing systems 20336 may be used to measure and monitor the surgeon biomarkers in real-time, for example, to assist surgical tasks by communicating relevant biomarkers (e.g., surgeon biomarkers) to a surgical hub 20326 and/or the surgical devices 20337 to adjust their function. The surgical device functions that may be adjusted may include power levels, advancement speeds, closure speed, loads, wait times, or other tissue dependent operational parameters. The sensing systems 20336 may also measure one or more physical attributes associated with a surgeon or a patient. The patient biomarkers and/or the physical attributes may be measured in real time.

The computer-implemented wearable patient/surgeon wearable sensing system 20325 may include a surgical hub 20326, one or more sensing systems 20336, and one or more surgical devices 20337. The sensing systems and the surgical devices may be communicably coupled to the surgical hub 20326. One or more analytics servers 20338, for example part of an analytics system, may also be communicably coupled to the surgical hub 20326. Although a single surgical hub 20326 is depicted, it should be noted that the wearable patient/surgeon wearable sensing system 20325 may include any number of surgical hubs 20326, which can be connected to form a network of surgical hubs 20326 that are communicably coupled to one or more analytics servers 20338, as described herein.

In an example, the surgical hub 20326 may be a computing device. The computing device may be a personal computer, a laptop, a tablet, a smart mobile device, etc. In an example, the computing device may be a client computing device of a cloud-based computing system. The client computing device may be a thin client.

In an example, the surgical hub 20326 may include a processor 20327 coupled to a memory 20330 for executing instructions stored thereon, a storage 20331 to store one or more databases such as an EMR database, and a data relay interface 20329 through which data is transmitted to the analytics servers 20338. In an example, the surgical hub 20326 further may include an I/O interface 20333 having an input device 20341 (e.g., a capacitive touchscreen or a keyboard) for receiving inputs from a user and an output device 20335 (e.g., a display screen) for providing outputs to a user. In an example, the input device and the output device may be a single device. Outputs may include data from a query input by the user, suggestions for products or a combination of products to use in a given procedure, and/or instructions for actions to be carried out before, during, and/or after a surgical procedure. The surgical hub 20326 may include a device interface 20332 for communicably coupling the surgical devices 20337 to the surgical hub 20326. In one aspect, the device interface 20332 may include a transceiver that may enable one or more surgical devices 20337 to connect with the surgical hub 20326 via a wired interface or a wireless interface using one of the wired or wireless communication protocols described herein. The surgical devices 20337 may include, for example, powered staplers, energy devices or their generators, imaging systems, or other linked systems, for example, smoke evacuators, suction-irrigation devices, insufflation systems, etc.

In an example, the surgical hub 20326 may be communicably coupled to one or more surgeon and/or patient sensing systems 20336. The sensing systems 20336 may be used to measure and/or monitor, in real-time, various biomarkers associated with a surgeon performing a surgical procedure or a patient on whom a surgical procedure is being performed. A list of the patient/surgeon biomarkers measured by the sensing systems 20336 is provided herein. In an example, the surgical hub 20326 may be communicably coupled to an environmental sensing system 20334. The environmental sensing systems 20334 may be used to measure and/or monitor, in real-time, environmental attributes, for example, temperature/humidity in the surgical theater, surgeon movements, ambient noise in the surgical theater caused by the surgeon's and/or the patient's breathing pattern, etc.

When sensing systems 20336 and the surgical devices 20337 are connected to the surgical hub 20326, the surgical hub 20326 may receive measurement data associated with one or more patient biomarkers, physical state associated with a patient, measurement data associated with surgeon biomarkers, and/or physical state associated with the surgeon from the sensing systems 20336, for example, as illustrated in FIG. 7B through 7D. The surgical hub 20326 may associate the measurement data, e.g., related to a surgeon, with other relevant pre-surgical data and/or data from situational awareness system to generate control signals for controlling the surgical devices 20337, for example, as illustrated in FIG. 8.

In an example, the surgical hub 20326 may compare the measurement data from the sensing systems 20336 with one or more thresholds defined based on baseline values, pre-surgical measurement data, and/or in surgical measurement data. The surgical hub 20326 may compare the measurement data from the sensing systems 20336 with one or more thresholds in real-time. The surgical hub 20326 may generate a notification for displaying. The surgical hub 20326 may send the notification for delivery to a human interface system for patient 20339 and/or the human interface system for a surgeon or an HCP 20340, for example, if the measurement data crosses (e.g., is greater than or lower than) the defined threshold value. The determination whether the notification would be sent to one or more of the to the human interface system for patient 20339 and/or the human interface system for an HCP 2340 may be based on a severity level associated with the notification. The surgical hub 20326 may also generate a severity level associated with the notification for displaying. The severity level generated may be displayed to the patient and/or the surgeon or the HCP. In an example, the patient biomarkers to be measured and/or monitored (e.g., measured and/or monitored in real-time) may be associated with a surgical procedural step. For example, the biomarkers to be measured and monitored for transection of veins and arteries step of a thoracic surgical procedure may include blood pressure, tissue perfusion pressure, edema, arterial stiffness, collagen content, thickness of connective tissue, etc., whereas the biomarkers to be measured and monitored for lymph node dissection step of the surgical procedure may include monitoring blood pressure of the patient. In an example, data regarding postoperative complications could be retrieved from an EMR database in the storage 20331 and data regarding staple or incision line leakages could be directly detected or inferred by a situational awareness system. The surgical procedural outcome data can be inferred by a situational awareness system from data received from a variety of data sources, including the surgical devices 20337, the sensing systems 20336, and the databases in the storage 20331 to which the surgical hub 20326 is connected.

The surgical hub 20326 may transmit the measurement data and physical state data it received from the sensing systems 20336 and/or data associated with the surgical devices 20337 to analytics servers 20338 for processing thereon. Each of the analytics servers 20338 may include a memory and a processor coupled to the memory that may execute instructions stored thereon to analyze the received data. The analytics servers 20338 may be connected in a distributed computing architecture and/or utilize a cloud computing architecture. Based on this paired data, the analytics system 20338 may determine optimal and/or preferred operating parameters for the various types of modular devices, generate adjustments to the control programs for the surgical devices 20337, and transmit (or "push") the updates or control programs to the one or more surgical devices 20337. For example, an analytics system 20338 may correlate the perioperative data it received from the surgical hub 20) 236 with the measurement data associated with a physiological state of a surgeon or an HCP and/or a physiological state of the patient. The analytics system 20338 may determine when the surgical devices 20337 should be controlled and send an update to the surgical hub 20326. The surgical hub 20326 may then forward the control program to the relevant surgical device 20337.

Additional detail regarding the computer-implemented wearable patient/surgeon wearable sensing system 20325, including the surgical hub 30326, one or more sensing systems 20336 and various surgical devices 20337 connectable thereto, are described in connection with FIG. 5 through FIG. 7D.

The surgical computing system may receive the usage data from the surgical instrument and/or may receive sensor data from the sensing systems. The surgical computing system may determine, based on at least one of the usage data and/or the sensor data, that the operation of the surgical instrument should be modified and may instruct the surgical instrument implement a control feature. For example, if the received usage data indicates that a closure trigger has been held in a position for a period exceeding a threshold, the surgical computing system may determine that the surgical instrument should implement position control. If the usage data and/or the sensor data indicates that the jaws of an endocutter are substantially open and/or not engaged with patient tissue, the surgical computing system may determine that the surgical instrument may apply gross control in response to inputs to the closure trigger. If the usage data and/or the sensor data comprise data associated with user correction action, the surgical computing system may determine that the surgical instrument should implement over-correction control. If the usage data/or sensor data indicate the operator of the surgical instrument is experiencing tremors, the surgical computing system may determine that the surgical instrument should implement stability control. If the usage data and/or sensor data indicate the healthcare professional operating the surgical instrument is experiencing fatigue, the surgical computing system may determine that the surgical instrument should implement fatigue control. The surgical computing system may communicate the determined control feature(s) to the surgical instrument which implements the control feature(s).

The surgical instrument may receive the control feature and may modify its operation to implement the control feature. For example, if the received control feature indicates position control, the surgical instrument may modify or switch operation from load control of the clamping jaws to position control of the clamping jaws. If the received control feature indicates one of gross control or fine control, the surgical instrument may change the rate that an end effector is moved in response to user input controls. If the received control feature indicates over-correction control, the surgical instrument may slow reaction of the surgical instrument to user input controls. If the received control feature indicates stability control, the surgical instrument may minimize or lessen transmission of tremors to an end effector comprised in the surgical instrument. If the received control feature indicates fatigue control, the surgical instrument may adjust operation of user controls to compensate for fatigue.

Applicant of the present application owns the following U.S. patent applications, patent publications, and patents, each of which is herein incorporated by reference in its entirety:

- U.S. Patent Application Publication No. US20190200844 A1 (U.S. patent application Ser. No. 16/209,385, filed Dec. 4, 2018), titled "METHOD OF HUB COMMUNICATION, PROCESSING, STORAGE AND DISPLAY," published Jul. 4, 2019;
- U.S. Patent Application Publication No. US20190201137 A1 (U.S. patent application Ser. No. 16/209,407, filed Dec. 28, 2017), titled "METHOD OF ROBOTIC HUB COMMUNICATION, DETECTION, AND CONTROL," published Jul. 4, 2019;
- U.S. Patent Application Publication No. US20190206569 A1 (U.S. patent application Ser. No. 16/209,403 filed Dec. 4, 2018), titled "METHOD OF CLOUD BASED DATA ANALYTICS FOR USE WITH THE HUB," published Jul. 4, 2019;
- U.S. Provisional Patent Application Ser. No. 62/611,341, titled "INTERACTIVE SURGICAL PLATFORM," filed Dec. 28, 2017;
- U.S. Patent Application Publication No. US20170296213 A1 (U.S. patent application Ser. No. 15/130,590 filed Apr. 15, 2016), titled "SYSTEMS AND METHODS FOR CONTROLLING A SURGICAL STAPLING AND CUTTING INSTRUMENT," published Oct. 19, 2017;
- U.S. Pat. No. 9,345,481, titled "STAPLE CARTRIDGE TISSUE THICKNESS SENSOR SYSTEM," issued May 24, 2016;

U.S. Patent Application Publication No. US20140263552 (U.S. patent application Ser. No. 13/800,067 filed Mar. 13, 2013), titled "STAPLE CARTRIDGE TISSUE THICKNESS SENSOR SYSTEM," published Sep. 18, 2014;

U.S. Patent Application Publication No. US20180360452 (U.S. patent application Ser. No. 15/628,175, filed Jun. 20, 2017), titled "TECHNIQUES FOR ADAPTIVE CONTROL OF MOTOR VELOCITY OF A SURGICAL STAPLING AND CUTTING INSTRUMENT," published Dec. 20, 2018;

U.S. Patent Application Publication No. US20190200981 (U.S. application Ser. No. 16/209,423, filed Dec. 4, 2018), titled "METHOD OF COMPRESSING TISSUE WITHIN A STAPLING DEVICE AND SIMULTANEOUSLY DISPLAYING THE LOCATION OF THE TISSUE WITHIN THE JAWS," published Jul. 4, 2019;

U.S. Pat. No. 9,072,535, titled "SURGICAL STAPLING INSTRUMENTS WITH ROTATABLE STAPLE DEPLOYMENT ARRANGEMENTS," issued Jul. 5, 2015;

U.S. Patent Application Publication No. US20140263541 (U.S. application Ser. No. 13/803,086, filed Mar. 14, 2013), titled "ARTICULATABLE SURGICAL INSTRUMENT COMPRISING AN ARTICULATION LOCK," published Sep. 18, 2014; and U.S. Patent Application Publication No. US20140263551 (U.S. application Ser. No. 13/800,025, filed Mar. 13, 2013), titled "STAPLE CARTRIDGE TISSUE THICKNESS SENSOR SYSTEM," published Sep. 18, 2014.

Systems and techniques are disclosed for adaptively controlling the operations of a surgical instrument based on usage data associated with the surgical instrument and/or sensor data associated with the healthcare professional operating the surgical instrument. A surgical instrument may monitor and collect usage data associated with the position and movement of the surgical instrument and associated with user inputs such as those relating to operating the surgical instrument. Sensing systems applied to the healthcare provider operating the surgical instrument collect sensor data such as, for example, data associated with heartrate, respiration, temperature, etc. A surgical computing system may determine, based on at least one of the usage data and/or the sensor data, control features for implementation by the surgical instrument. The surgical instrument may modify its operation based upon the determined control features.

FIGS. 13 to 16 depict a motor-driven surgical instrument 150010 for cutting and fastening that may or may not be reused. Additional information regarding a motor-driven surgical instrument 150010 may be found in U.S. Patent Publication No. 20190200981 (from U.S. application Ser. No. 16/209,423, filed Dec. 4, 2018), titled "METHOD OF COMPRESSING TISSUE WITHIN A STAPLING DEVICE AND SIMULTANEOUSLY DISPLAYING THE LOCATION OF THE TISSUE WITHIN THE JAWS," published Jul. 4, 2019, the contents of which are hereby incorporated herein in their entirety. In the illustrated examples, the surgical instrument 150010 includes a housing 150012 that comprises a handle assembly 150014 that is configured to be grasped, manipulated, and actuated by the clinician. The housing 150012 is configured for operable attachment to an interchangeable shaft assembly 150200 that has an end effector 150300 operably coupled thereto that is configured to perform one or more surgical tasks or procedures. In accordance with the present disclosure, various forms of interchangeable shaft assemblies may be effectively employed in connection with robotically controlled surgical systems. The term "housing" may encompass a housing or similar portion of a robotic system that houses or otherwise operably supports at least one drive system configured to generate and apply at least one control motion that could be used to actuate interchangeable shaft assemblies. The term "frame" may refer to a portion of a handheld surgical instrument. The term "frame" also may represent a portion of a robotically controlled surgical instrument and/or a portion of the robotic system that may be used to operably control a surgical instrument. Interchangeable shaft assemblies may be employed with various robotic systems, instruments, components, and methods disclosed in U.S. Pat. No. 9,072,535, titled SURGICAL STAPLING INSTRUMENTS WITH ROTATABLE STAPLE DEPLOYMENT ARRANGEMENTS, which is herein incorporated by reference in its entirety.

Figure 13:
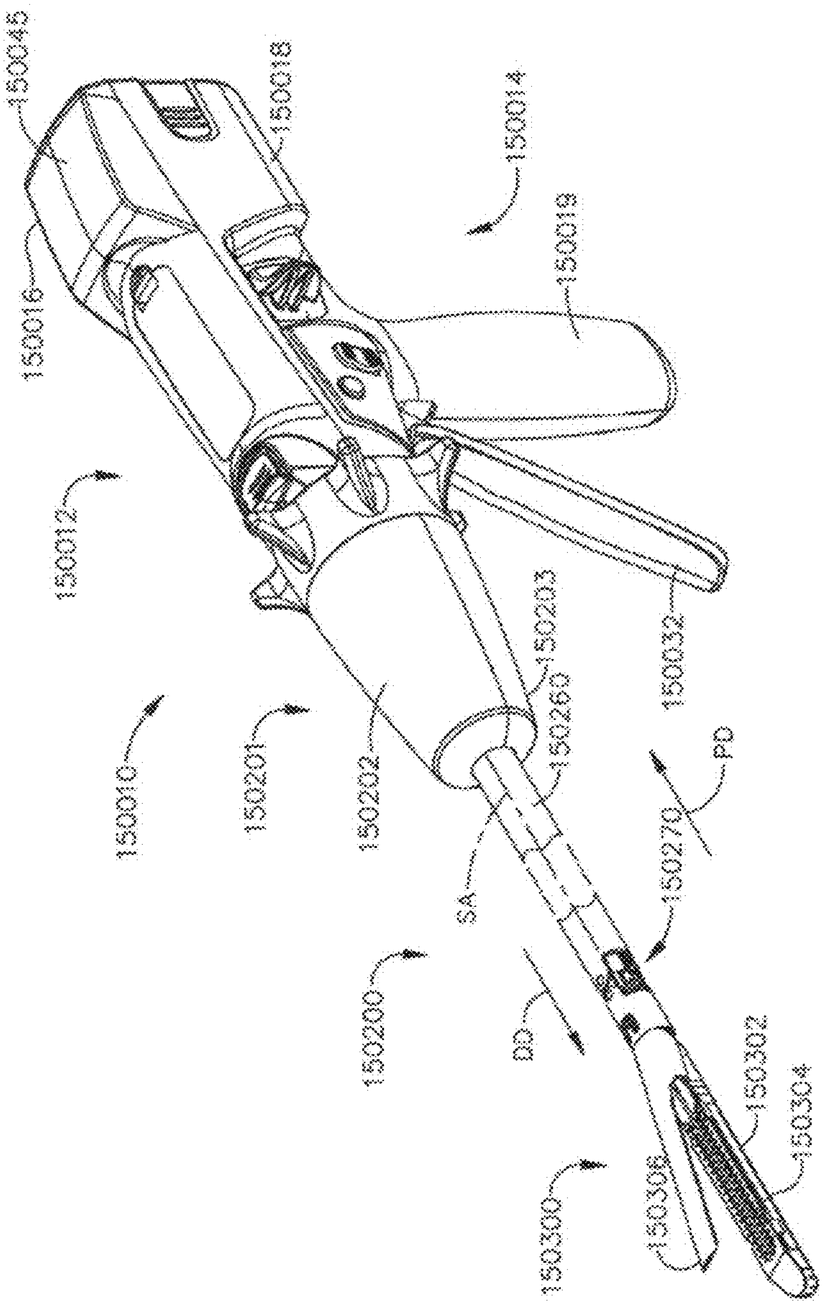
FIG. 13 illustrates a perspective view of an example surgical instrument that has an example interchangeable shaft assembly operably coupled thereto.

FIG. 13 is a perspective view of a surgical instrument 150010 that has an interchangeable shaft assembly 150200 operably coupled thereto, in accordance with at least one aspect of this disclosure. The housing 150012 includes an end effector 150300 that comprises a surgical cutting and fastening device configured to operably support a surgical staple cartridge 150304 therein. The housing 150012 may be configured for use in connection with interchangeable shaft assemblies that include end effectors that are adapted to support different sizes and types of staple cartridges, have different shaft lengths, sizes, and types. The housing 150012 may be employed with a variety of interchangeable shaft assemblies, including assemblies configured to apply other motions and forms of energy such as, radio frequency (RF) energy, ultrasonic energy, and/or motion to end effector arrangements adapted for use in connection with various surgical applications and procedures. The end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

The handle assembly 150014 may comprise a pair of interconnectable handle housing segments 150016, 150018 interconnected by screws, snap features, adhesive, etc. The handle housing segments 150016, 150018 cooperate to form a pistol grip portion 150019 that can be gripped and manipulated by the clinician. The handle assembly 150014 operably supports a plurality of drive systems configured to generate and apply control motions to corresponding portions of the interchangeable shaft assembly that is operably attached thereto. A display may be provided below a cover 150045.

Figure 14:
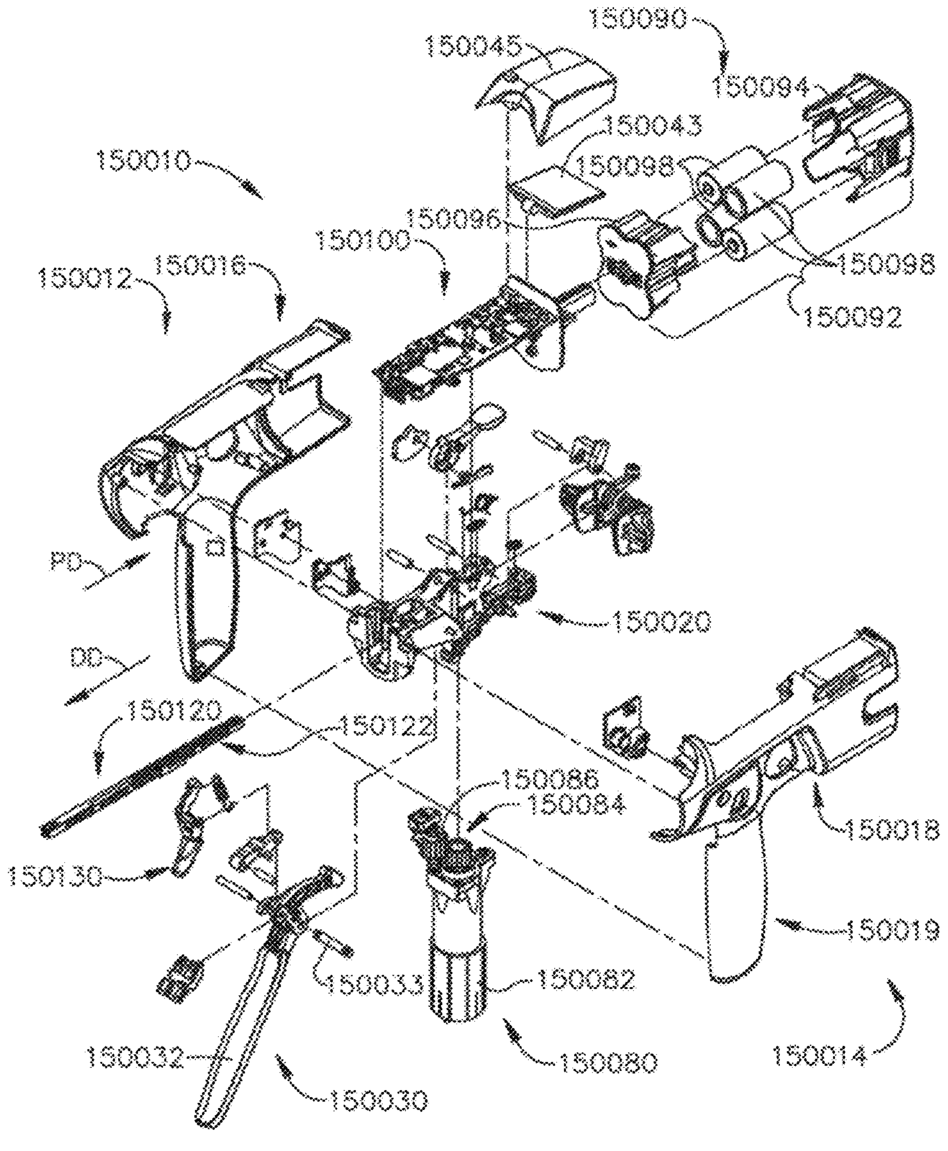
FIG. 14 illustrates an exploded assembly view of a portion of the example surgical instrument of FIG. 13.

FIG. 14 is an exploded assembly view of a portion of the surgical instrument 150010 of FIG. 13, in accordance with at least one aspect of this disclosure. The handle assembly 150014 may include a frame 150020 that operably supports a plurality of drive systems. The frame 150020 can operably support a "first" or closure drive system 150030, which can apply closing and opening motions to the interchangeable shaft assembly 150200. The closure drive system 150030 may include an actuator such as a closure trigger 150032 pivotally supported by the frame 150020. The closure trigger 150032 is pivotally coupled to the handle assembly 150014 by a pivot pin 150033 to enable the closure trigger 150032 to be manipulated by a clinician. When the clinician grips the pistol grip portion 150019 of the handle assembly 150014, the closure trigger 150032 can pivot from a starting or "unactuated" position to an "actuated" position and more particularly to a fully compressed or fully actuated position.

The handle assembly 150014 and the frame 150020 may operably support a firing drive system 150080 configured to apply firing motions to corresponding portions of the interchangeable shaft assembly attached thereto. The firing drive system 150080 may employ an electric motor 150082 located in the pistol grip portion 150019 of the handle assembly 150014. The electric motor 150082 may be a DC brushed motor having a maximum rotational speed of approximately 25,000 RPM, for example. In other arrangements, the motor may include a brushless motor, a cordless motor, a synchronous motor, a stepper motor, or any other suitable electric motor. The electric motor 150082 may be powered by a power source 150090 that may comprise a removable power pack 150092. The removable power pack 150092 may comprise a proximal housing portion 150094 configured to attach to a distal housing portion 150096. The proximal housing portion 150094 and the distal housing portion 150096 are configured to operably support a plurality of batteries 150098 therein. Batteries 150098 may each comprise, for example, a Lithium Ion (LI) or other suitable battery. The distal housing portion 150096 is configured for removable operable attachment to a control circuit board 150100, which is operably coupled to the electric motor 150082. Several batteries 150098 connected in series may power the surgical instrument 150010. The power source 150090 may be replaceable and/or rechargeable. A display 150043, which is located below the cover 150045, is electrically coupled to the control circuit board 150100. The cover 150045 may be removed to expose the display 150043.

The electric motor 150082 can include a rotatable shaft (not shown) that operably interfaces with a gear reducer assembly 150084 mounted in meshing engagement with a set, or rack, of drive teeth 150122 on a longitudinally movable drive member 150120. The longitudinally movable drive member 150120 has a rack of drive teeth 150122 formed thereon for meshing engagement with a corresponding drive gear 150086 of the gear reducer assembly 150084.

In use, a voltage polarity provided by the power source 150090 can operate the electric motor 150082 in a clockwise direction wherein the voltage polarity applied to the electric motor by the battery can be reversed in order to operate the electric motor 150082 in a counter-clockwise direction. When the electric motor 150082 is rotated in one direction, the longitudinally movable drive member 150120 will be axially driven in the distal direction "DD." When the electric motor 150082 is driven in the opposite rotary direction, the longitudinally movable drive member 150120 will be axially driven in a proximal direction "PD." The handle assembly 150014 can include a switch that can be configured to reverse the polarity applied to the electric motor 150082 by the power source 150090. The handle assembly 150014 may include a sensor configured to detect the position of the longitudinally movable drive member 150120 and/or the direction in which the longitudinally movable drive member 150120 is being moved.

Actuation of the electric motor 150082 can be controlled by a firing trigger 150130 that is pivotally supported on the handle assembly 150014. The firing trigger 150130 may be pivoted between an unactuated position and an actuated position.

Turning back to FIG. 13, the interchangeable shaft assembly 150200 includes an end effector 150300 comprising an elongated channel 150302 configured to operably support a surgical staple cartridge 150304 therein. The end effector 150300 may include an anvil 150306 that is pivotally supported relative to the elongated channel 150302. The interchangeable shaft assembly 150200 may include an articulation joint 150270. Construction and operation of the end effector 150300 and the articulation joint 150270 are set forth in U.S. Patent Application Publication No. 2014/0263541, titled ARTICULATABLE SURGICAL INSTRUMENT COMPRISING AN ARTICULATION LOCK, which is herein incorporated by reference in its entirety. The interchangeable shaft assembly 150200 may include a proximal housing or nozzle 150201 comprised of nozzle portions 150202, 150203. The interchangeable shaft assembly 150200 may include a closure tube 150260 extending along a shaft axis SA that can be utilized to close and/or open the anvil 150306 of the end effector 150300.

Turning back to FIG. 13, the closure tube 150260 is translated distally (direction "DD") to close the anvil 150306, for example, in response to the actuation of the closure trigger 150032 in the manner described in U.S. Patent Application Publication No. 2014/0263541. The anvil 150306 is opened by proximally translating the closure tube 150260. In the anvil-open position, the closure tube 150260 is moved to its proximal position.

Figure 15:
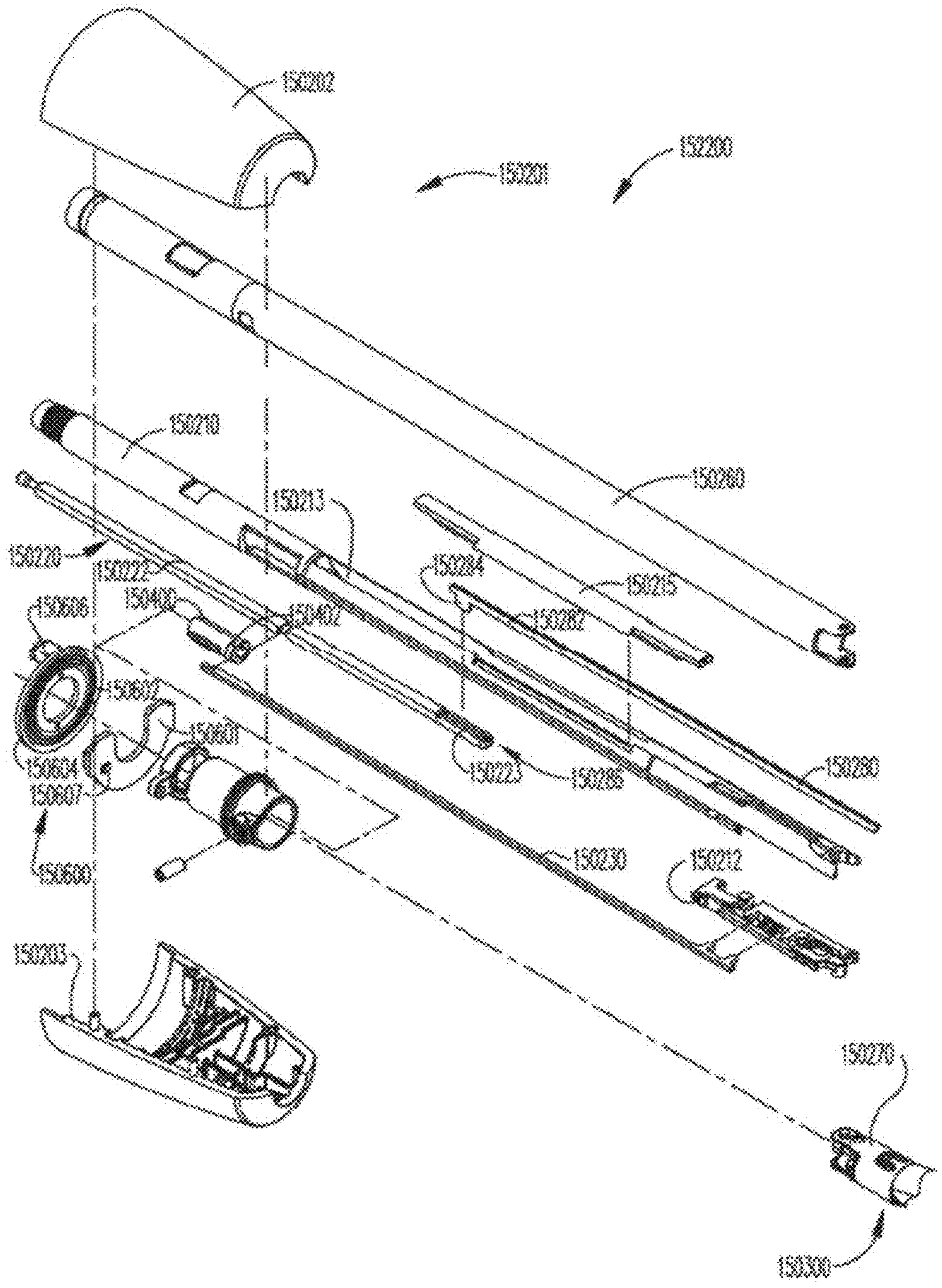
FIG. 15 illustrates an exploded assembly view of portions of the example interchangeable shaft assembly.

FIG. 15 is another exploded assembly view of portions of the interchangeable shaft assembly 150200, in accordance with at least one aspect of this disclosure. The interchangeable shaft assembly 150200 may include a firing member 150220 supported for axial travel within the spine 150210. The firing member 150220 includes an intermediate firing shaft 150222 configured to attach to a distal cutting portion or knife bar 150280. The firing member 150220 may be referred to as a "second shaft" or a "second shaft assembly". The intermediate firing shaft 150222 may include a longitudinal slot 150223 in a distal end configured to receive a tab 150284 on the proximal end 150282 of the knife bar 150280. The longitudinal slot 150223 and the proximal end 150282 may be configured to permit relative movement there between and can comprise a slip joint 150286. The slip joint 150286 can permit the intermediate firing shaft 150222 of the firing member 150220 to articulate the end effector 150300 about the articulation joint 150270 without moving, or at least substantially moving, the knife bar 150280. Once the end effector 150300 has been suitably oriented, the intermediate firing shaft 150222 can be advanced distally until a proximal sidewall of the longitudinal slot 150223 contacts the tab 150284 to advance the knife bar 150280 and fire the staple cartridge positioned within the channel 150302. The spine 150210 has an elongated opening or window 150213 therein to facilitate assembly and insertion of the intermediate firing shaft 150222 into the spine 150210. Once the intermediate firing shaft 150222 has been inserted therein, a top frame segment 150215 may be engaged with the shaft frame 150212 to enclose the intermediate firing shaft 150222 and knife bar 150280 therein. Operation of the firing member 150220 may be found in U.S. Patent Application Publication No. 2014/0263541. A spine 150210 can be configured to slidably support a firing member 150220 and the closure tube 150260 that extends around the spine 150210. The spine 150210 may slidably support an articulation driver 150230.

The interchangeable shaft assembly 150200 can include a clutch assembly 150400 configured to selectively and releasably couple the articulation driver 150230 to the firing member 150220. The clutch assembly 150400 includes a lock collar, or lock sleeve 150402, positioned around the firing member 150220 wherein the lock sleeve 150402 can be rotated between an engaged position in which the lock sleeve 150402 couples the articulation driver 150230 to the firing member 150220 and a disengaged position in which the articulation driver 150230 is not operably coupled to the firing member 150220. When the lock sleeve 150402 is in the engaged position, distal movement of the firing member 150220 can move the articulation driver 150230 distally and, correspondingly, proximal movement of the firing member 150220 can move the articulation driver 150230 proximally. When the lock sleeve 150402 is in the disengaged position, movement of the firing member 150220 is not transmitted to the articulation driver 150230 and, as a result, the firing member 150220 can move independently of the articulation driver 150230. The nozzle 150201 may be employed to operably engage and disengage the articulation drive system with the firing drive system in the various manners described in U.S. Patent Application Publication No. 2014/0263541.

The interchangeable shaft assembly 150200 can comprise a slip ring assembly 150600 which can be configured to conduct electrical power to and/or from the end effector 150300 and/or communicate signals to and/or from the end effector 150300, for example. The slip ring assembly 150600 can comprise a proximal connector flange 150604 and a distal connector flange 150601 positioned within a slot defined in the nozzle portions 150202, 150203. The proximal connector flange 150604 can comprise a first face and the distal connector flange 150601 can comprise a second face positioned adjacent to and movable relative to the first face. The distal connector flange 150601 can rotate relative to the proximal connector flange 150604 about the shaft axis SA-SA (FIG. 13). The proximal connector flange 150604 can comprise a plurality of concentric, or at least substantially concentric, conductors 150602 defined in the first face thereof. A connector 150607 can be mounted on the proximal side of the distal connector flange 150601 and may have a plurality of contacts wherein each contact corresponds to and is in electrical contact with one of the conductors 150602. Such an arrangement permits relative rotation between the proximal connector flange 150604 and the distal connector flange 150601 while maintaining electrical contact there between. The proximal connector flange 150604 can include an electrical connector 150606 that can place the conductors 150602 in signal communication with a shaft circuit board, for example. In at least one instance, a wiring harness comprising a plurality of conductors can extend between the electrical connector 150606 and the shaft circuit board. The electrical connector 150606 may extend proximally through a connector opening defined in the chassis mounting flange. U.S. Patent Application Publication No. 2014/0263551, titled STAPLE CARTRIDGE TISSUE THICKNESS SENSOR SYSTEM, is incorporated herein by reference in its entirety. U.S. Patent Application Publication No. 2014/0263552, titled STAPLE CARTRIDGE TISSUE THICKNESS SENSOR SYSTEM, is incorporated by reference in its entirety. Further details regarding slip ring assembly 150600 may be found in U.S. Patent Application Publication No. 2014/0263541.

The interchangeable shaft assembly 150200 can include a proximal portion fixably mounted to the handle assembly 150014 and a distal portion that is rotatable about a longitudinal axis. The rotatable distal shaft portion can be rotated relative to the proximal portion about the slip ring assembly 150600. The distal connector flange 150601 of the slip ring assembly 150600 can be positioned within the rotatable distal shaft portion.

Figure 16:
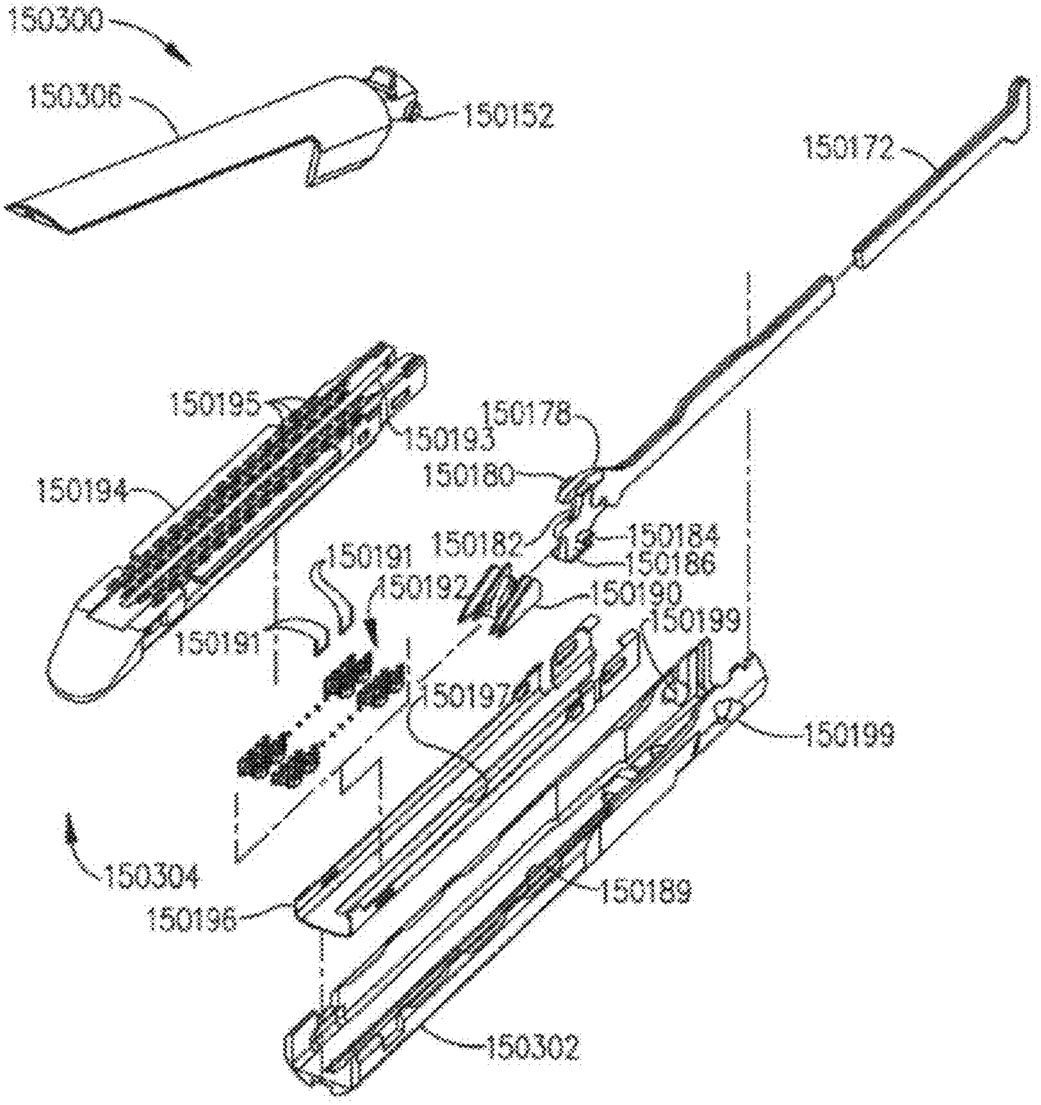
FIG. 16 illustrates an exploded view of an end effector of the example surgical instrument of FIG. 13.

FIG. 16 is an exploded view of one aspect of an end effector 150300 of the surgical instrument 150010 of FIG. 13, in accordance with at least one aspect of this disclosure. The end effector 150300 may include the anvil 150306 and the surgical staple cartridge 150304. The anvil 150306 may be coupled to an elongated channel 150302. Apertures 150199 can be defined in the elongated channel 150302 to receive pins 150152 extending from the anvil 150306 to allow the anvil 150306 to pivot from an open position to a closed position relative to the elongated channel 150302 and surgical staple cartridge 150304. A firing bar 150172 is configured to longitudinally translate into the end effector 150300. The firing bar 150172 may be constructed from one solid section, or may include a laminate material comprising a stack of steel plates. The firing bar 150172 comprises an I-beam 150178 and a cutting edge 150182 at a distal end thereof. A distally projecting end of the firing bar 150172 can be attached to the I-beam 150178 to assist in spacing the anvil 150306 from a surgical staple cartridge 150304 positioned in the elongated channel 150302 when the anvil 150306 is in a closed position. The I-beam 150178 may include a sharpened cutting edge 150182 to sever tissue as the I-beam 150178 is advanced distally by the firing bar 150172. In operation, the I-beam 150178 may, or fire, the surgical staple cartridge 150304. The surgical staple cartridge 150304 can include a molded cartridge body 150194 that holds a plurality of staples 150191 resting upon staple drivers 150192 within respective upwardly open staple cavities 150195. A wedge sled 150190 is driven distally by the I-beam 150178, sliding upon a cartridge tray 150196 of the surgical staple cartridge 150304. The wedge sled 150190 upwardly cams the staple drivers 150192 to force out the staples 150191 into deforming contact with the anvil 150306 while the cutting edge 150182 of the I-beam 150178 severs clamped tissue.

The I-beam 150178 can include upper pins 150180 that engage the anvil 150306 during firing. The I-beam 150178 may include middle pins 150184 and a bottom foot 150186 to engage portions of the cartridge body 150194, cartridge tray 150196, and elongated channel 150302. When a surgical staple cartridge 150304 is positioned within the elongated channel 150302, a slot 150193 defined in the cartridge body 150194 can be aligned with a longitudinal slot 150197 defined in the cartridge tray 150196 and a slot 150189 defined in the elongated channel 150302. In use, the I-beam 150178 can slide through the aligned longitudinal slots 150193, 150197, and 150189 wherein, as indicated in FIG. 16, the bottom foot 150186 of the I-beam 150178 can engage a groove running along the bottom surface of elongated channel 150302 along the length of slot 150189, the middle pins 150184 can engage the top surfaces of cartridge tray 150196 along the length of longitudinal slot 150197, and the upper pins 150180 can engage the anvil 150306. The I-beam 150178 can space, or limit the relative movement between, the anvil 150306 and the surgical staple cartridge 150304 as the firing bar 150172 is advanced distally to fire the staples from the surgical staple cartridge 150304 and/or incise the tissue captured between the anvil 150306 and the surgical staple cartridge 150304. The firing bar 150172 and the I-beam 150178 can be retracted proximally allowing the anvil 150306 to be opened to release the two stapled and severed tissue portions.

Figure 17A:
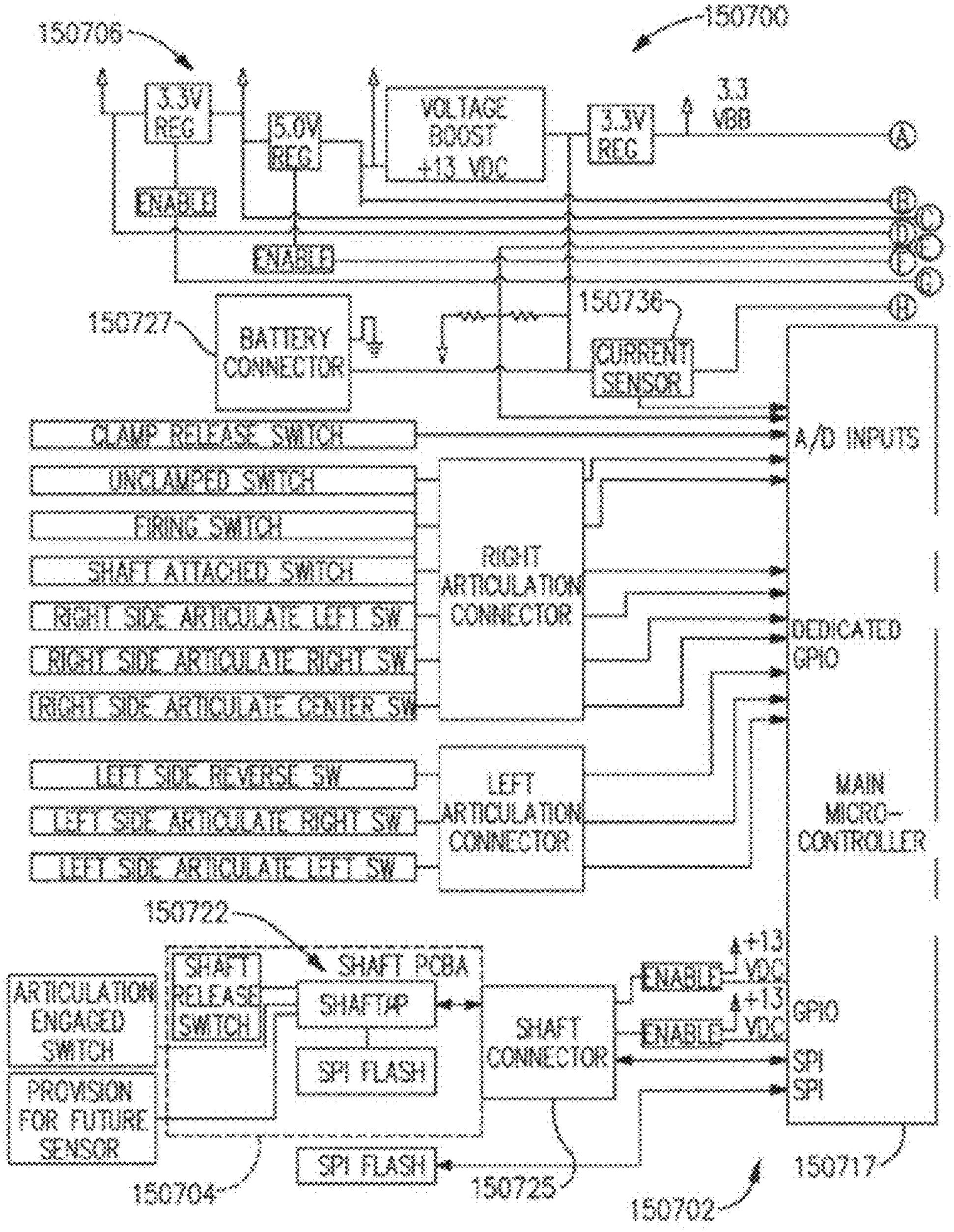
FIG. 17A illustrates a block diagram of a control circuit of the surgical instrument of FIG. 13 spanning two drawing sheets, in accordance with at least one aspect of this disclosure.
Figure 17B:
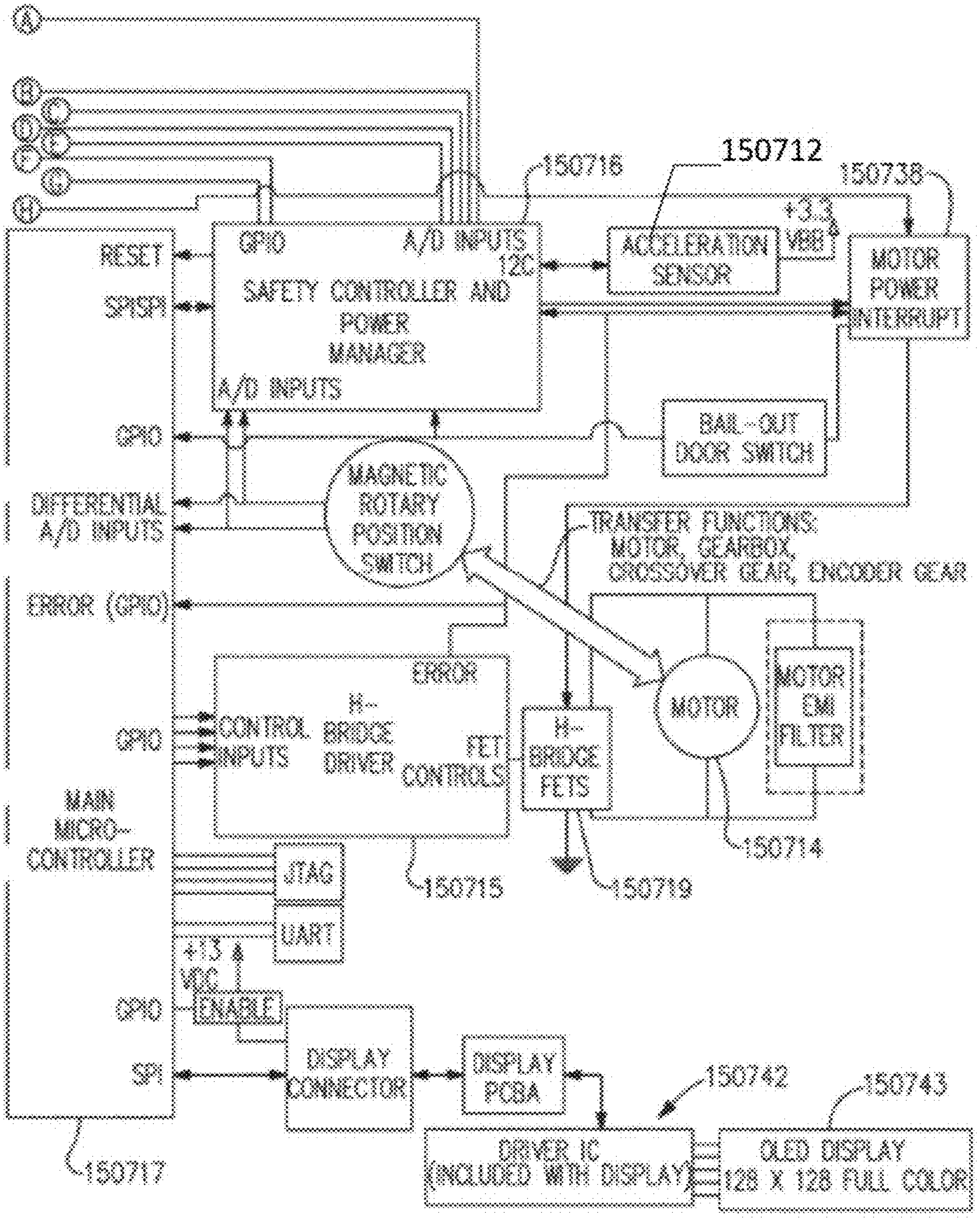
FIG. 17B illustrates a block diagram of a control circuit of the example surgical instrument of FIG. 13 spanning two drawing sheets.

FIGS. 17A and 17B is a block diagram of a control circuit 150700 of the surgical instrument 150010 of FIG. 13 spanning two drawing sheets, in accordance with at least one aspect of this disclosure. Referring primarily to FIGS. 17A and 17B, a handle assembly 150702 may include a motor 150714 which can be controlled by a motor driver 150715 and can be employed by the firing system of the surgical instrument 150010. In various forms, the motor 150714 may be a DC brushed driving motor having a maximum rotational speed of approximately 25,000 RPM. In other arrangements, the motor 150714 may include a brushless motor, a cordless motor, a synchronous motor, a stepper motor, or any other suitable electric motor. The motor driver 150715 may comprise an H-Bridge driver comprising field-effect transistors (FETs) 150719, for example. The motor 150714 can be powered by the power assembly 150706 releasably mounted to the handle assembly 150200 for supplying control power to the surgical instrument 150010. The power assembly 150706 may comprise a battery which may include a number of battery cells connected in series that can be used as the power source to power the surgical instrument 150010. In certain circumstances, the battery cells of the power assembly 150706 may be replaceable and/or rechargeable. In at least one example, the battery cells can be Lithium-Ion batteries which can be separably couplable to the power assembly 150706.

The shaft assembly 150704 may include a shaft assembly controller 150722 which can communicate with a safety controller and power management controller 150716 through an interface while the shaft assembly 150704 and the power assembly 150706 are coupled to the handle assembly 150702. For example, the interface may comprise a first interface portion 150725 which may include one or more electric connectors for coupling engagement with corresponding shaft assembly electric connectors and a second interface portion 150727 which may include one or more electric connectors for coupling engagement with corresponding power assembly electric connectors to permit electrical communication between the shaft assembly controller 150722 and the power management controller 150716 while the shaft assembly 150704 and the power assembly 150706 are coupled to the handle assembly 150702. One or more communication signals can be transmitted through the interface to communicate one or more of the power requirements of the attached interchangeable shaft assembly 150704 to the power management controller 150716. In response, the power management controller may modulate the power output of the battery of the power assembly 150706, as described below in greater detail, in accordance with the power requirements of the attached shaft assembly 150704. The connectors may comprise switches which can be activated after mechanical coupling engagement of the handle assembly 150702 to the shaft assembly 150704 and/or to the power assembly 150706 to allow electrical communication between the shaft assembly controller 150722 and the power management controller 150716.

The interface can facilitate transmission of the one or more communication signals between the power management controller 150716 and the shaft assembly controller 150722 by routing such communication signals through a main controller 150717 residing in the handle assembly 150702, for example. In other circumstances, the interface can facilitate a direct line of communication between the power management controller 150716 and the shaft assembly controller 150722 through the handle assembly 150702 while the shaft assembly 150704 and the power assembly 150706 are coupled to the handle assembly 150702.

The main controller 150717 may be any single core or multicore processor such as those known under the trade name ARM Cortex by Texas Instruments. In one aspect, the main controller 150717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with Stellaris Ware software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

The safety controller may be a safety controller platform comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 150706 may include a power management circuit which may comprise the power management controller 150716, a power modulator 150738, and a current sense circuit 150736. The power management circuit can be configured to modulate power output of the battery based on the power requirements of the shaft assembly 150704 while the shaft assembly 150704 and the power assembly 150706 are coupled to the handle assembly 150702. The power management controller 150716 can be programmed to control the power modulator 150738 of the power output of the power assembly 150706 and the current sense circuit 150736 can be employed to monitor power output of the power assembly 150706 to provide feedback to the power management controller 150716 about the power output of the battery so that the power management controller 150716 may adjust the power output of the power assembly 150706 to maintain a desired output. The power management controller 150716 and/or the shaft assembly controller 150722 each may comprise one or more processors and/or memory units which may store a number of software modules.

The surgical instrument 150010 (FIGS. 13 to 16) may comprise an output device 150742 which may include devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 150742 may comprise a display 150743 which may be included in the handle assembly 150702. The shaft assembly controller 150722 and/or the power management controller 150716 can provide feedback to a user of the surgical instrument 150010 through the output device 150742. The interface can be configured to connect the shaft assembly controller 150722 and/or the power management controller 150716 to the output device 150742. The output device 150742 can instead be integrated with the power assembly 150706. In such circumstances, communication between the output device 150742 and the shaft assembly controller 150722 may be accomplished through the interface while the shaft assembly 150704 is coupled to the handle assembly 150702.

The control circuit 150700 comprises circuit segments configured to control operations of the powered surgical instrument 150010. A safety controller segment (Segment 1) comprises a safety controller and the main controller 150717 segment (Segment 2). The safety controller and/or the main controller 150717 are configured to interact with one or more additional circuit segments such as an acceleration segment, a display segment, a shaft segment, an encoder segment, a motor segment, and a power segment. Each of the circuit segments may be coupled to the safety controller and/or the main controller 150717. The main controller 150717 is also coupled to a flash memory. The main controller 150717 also comprises a serial communication interface. The main controller 150717 comprises a plurality of inputs coupled to, for example, one or more circuit segments, a battery, and/or a plurality of switches. The segmented circuit may be implemented by any suitable circuit, such as, for example, a printed circuit board assembly (PCBA) within the powered surgical instrument 150010. It should be understood that the term processor as used herein includes any microprocessor, processors, controller, controllers, or other basic computing device that incorporates the functions of a computer's central processing unit (CPU) on an integrated circuit or at most a few integrated circuits. The main controller 150717 is a multipurpose, programmable device that accepts digital data as input, processes it according to instructions stored in its memory, and provides results as output. It is an example of sequential digital logic, as it has internal memory. The control circuit 150700 can be configured to implement one or more of the processes described herein.

The acceleration segment (Segment 3) may comprise an acceleration sensor 150712. The acceleration sensor 150712 may comprise, for example, an accelerometer. The acceleration sensor 150712 may be configured to detect movement or acceleration of the powered surgical instrument 150010. Data generated by the acceleration sensor 150712 may be associated with the acceleration, motion, and/or orientation of the surgical instrument 150010 or a portion of the surgical instrument. The acceleration sensor 150712 may communicate data within the surgical instrument 150010 and/or to systems external to the surgical instrument such as, for example, a surgical hub. Data generated by the acceleration sensor 150712 may be used to modify operations of the surgical instrument. Input from the accelerometer may be used, for example, to identify the location of the surgical instrument 150010, to transition to and from a an operational (e.g., sleep) mode, to identify an orientation of the powered surgical instrument 150010, and/or to identify when the surgical instrument has been dropped. The acceleration sensor 150712 may be communicatively coupled with the safety controller and/or the main controller 150717 and may communicate data to the controllers for processing and communication to outside of the surgical instrument 150010.

The acceleration sensor 150712 may be programmed to measure various forms of acceleration including, for example, coordinate acceleration as well as those that may not necessarily be coordinate acceleration (rate of change of velocity). The acceleration sensor 150712 may be programmed to determine the acceleration associated with the phenomenon of weight experienced by a test mass at rest in the frame of reference of the acceleration sensor 150712. For example, the acceleration sensor 150712 at rest on the surface of the earth may measure an acceleration g=9.8 m/s2 (gravity) straight upwards, due to its weight. The acceleration sensor 150712 may measure g-force acceleration. The acceleration sensor 150712 may comprise a single, double, or triple axis accelerometer. The acceleration sensor 150712 may comprise one or more inertial sensors to detect and measure acceleration, tilt, shock, vibration, rotation, and multiple degrees-of-freedom (DoF). A suitable inertial sensor may comprise an accelerometer (single, double, or triple axis), a magnetometer to measure a magnetic field in space such as the earth's magnetic field, and/or a gyroscope to measure angular velocity.

The display segment (Segment 4) comprises a display connector coupled to the main controller 150717. The display connector couples the main controller 150717 to a display through one or more integrated circuit drivers of the display. The integrated circuit drivers of the display may be integrated with the display and/or may be located separately from the display. The display may comprise any suitable display, such as, for example, an organic light-emitting diode (OLED) display, a liquid crystal display (LCD), and/or any other suitable display. In some examples, the display segment is coupled to the safety controller.

The shaft segment (Segment 5) comprises controls for an interchangeable shaft assembly 150200 (FIGS. 13 and 15) coupled to the surgical instrument 150010 (FIGS. 13 to 16) and/or one or more controls for an end effector 150300 coupled to the interchangeable shaft assembly 150200. The shaft segment comprises a shaft connector configured to couple the main controller 150717 to a shaft PCBA. The shaft PCBA comprises a low-power microcontroller with a ferroelectric random access memory (FRAM), an articulation switch, a shaft release Hall effect switch, and a shaft PCBA EEPROM. The shaft PCBA EEPROM comprises one or more parameters, routines, and/or programs specific to the interchangeable shaft assembly 150200 and/or the shaft PCBA. The shaft PCBA may be coupled to the interchangeable shaft assembly 150200 and/or integral with the surgical instrument 150010. In some examples, the shaft segment comprises a second shaft EEPROM. The second shaft EEPROM comprises a plurality of algorithms, routines, parameters, and/or other data corresponding to one or more shaft assemblies 150200 and/or end effectors 150300 that may be interfaced with the powered surgical instrument 150010.

The position encoder segment (Segment 6) comprises one or more magnetic angle rotary position encoders. The one or more magnetic angle rotary position encoders are configured to identify the rotational position of the motor 150714, an interchangeable shaft assembly 150200 (FIGS. 13 and 15), and/or an end effector 150300 of the surgical instrument 150010 (FIGS. 13 to 16). In some examples, the magnetic angle rotary position encoders may be coupled to the safety controller and/or the main controller 150717.

The motor circuit segment (Segment 7) comprises a motor 150714 configured to control movements of the powered surgical instrument 150010 (FIGS. 13 to 16). The motor 150714 is coupled to the main microcontroller processor 150717 by an H-bridge driver comprising one or more H-bridge field-effect transistors (FETs) and a motor controller. The H-bridge driver is also coupled to the safety controller. A motor current sensor is coupled in series with the motor to measure the current draw of the motor. The motor current sensor is in signal communication with the main controller 150717 and/or the safety controller. In some examples, the motor 150714 is coupled to a motor electromagnetic interference (EMI) filter.

The motor controller controls a first motor flag and a second motor flag to indicate the status and position of the motor 150714 to the main controller 150717. The main controller 150717 provides a pulse-width modulation (PWM) high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 150717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power intensive operations and prevent brownout or low-power conditions.

A plurality of switches are coupled to the safety controller and/or the main controller 150717. The switches may be configured to control operations of the surgical instrument 150010 (FIGS. 13 to 16), of the segmented circuit, and/or indicate a status of the surgical instrument 150010. A bail-out door switch and Hall effect switch for bailout are configured to indicate the status of a bail-out door. A plurality of articulation switches, such as, for example, a left side articulation left switch, a left side articulation right switch, a left side articulation center switch, a right side articulation left switch, a right side articulation right switch, and a right side articulation center switch are configured to control articulation of an interchangeable shaft assembly 150200 (FIGS. 13 and 15) and/or the end effector 150300 (FIGS. 13 and 16). A left side reverse switch and a right side reverse switch are coupled to the main controller 150717. The left side switches comprising the left side articulation left switch, the left side articulation right switch, the left side articulation center switch, and the left side reverse switch are coupled to the main controller 150717 by a left flex connector. The right side switches comprising the right side articulation left switch, the right side articulation right switch, the right side articulation center switch, and the right side reverse switch are coupled to the main controller 150717 by a right flex connector. A firing switch, a clamp release switch, and a shaft engaged switch are coupled to the main controller 150717.

Any suitable mechanical, electromechanical, or solid state switches may be employed to implement the plurality of switches, in any combination. For example, the switches may be limit switches operated by the motion of components associated with the surgical instrument 150010 (FIGS. 13 to 16) or the presence of an object. Such switches may be employed to control various functions associated with the surgical instrument 150010. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field such as Hall-effect devices, magneto-resistive (MR) devices, giant magneto-resistive (GMR) devices, magnetometers, among others. In other implementations, the switches may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). Other switches may include wireless switches, ultrasonic switches, accelerometers, inertial sensors, among others.

A surgical instrument may be adaptively controlled to modify operation of the surgical instrument based on usage data and sensor data. A surgical instrument may be configured to monitor user inputs to the surgical instrument. The surgical instrument may monitor and collect usage data associated with the position and movement of the surgical instrument and associated with user inputs such as those relating to controlling jaws for clamping tissue. Healthcare professionals operating the surgical instrument may be monitored using sensing systems to collect sensor data such as, for example, data associated with movement of body parts, heartrate, respiration, temperature, etc. The usage data and sensing data may be communicated to a surgical computing system.

The surgical computing system may determine, based on at least one of the usage data and/or the sensor data, a control feature for implementation by the surgical instrument. If the received usage data comprises data associated with controlling jaws of the surgical instrument, the surgical computing system may determine based on the received data that the control feature for implementation by the surgical instrument may comprise position control. The surgical computing system may communicate the determined control feature(s) to the surgical instrument.

The surgical instrument may receive the control features and may modify its operation based on the control feature. If the received control feature indicates position control, the surgical instrument may determine to modify or switch operation from load control of the clamping jaws to position control of the clamping jaws.

Figure 18:
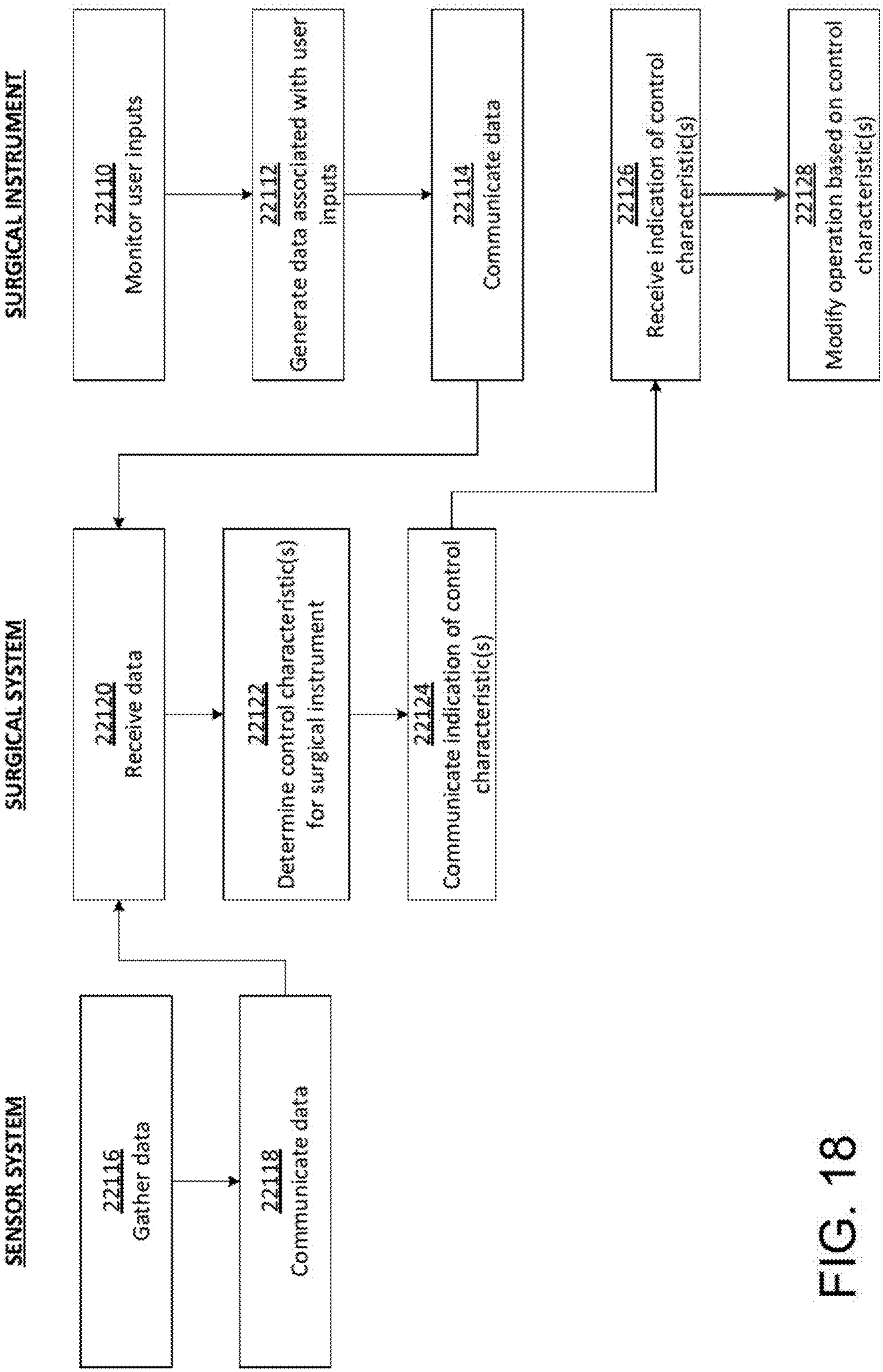
FIG. 18 depicts example processing for modifying control operations.

FIG. 18 depicts a flow diagram of example processing associated with determining control features for a surgical instrument based on usage data and/or sensor data. A surgical instrument, which may be, for example, a surgical instrument 20282 as described in connection with FIG. 10, may be programmed to operate in a surgical operating room as described in connection with FIGS. 2A and 12. The surgical instrument 20282 may comprise control systems with features as described, for example, in connection with FIGS. 7A and 17A-B. The surgical instrument 20282 may be configured to interface with a surgical hub as described, for example, in connection with FIG. 8.

The surgical instrument 20282 and the processors therein as described in connection with FIG. 7A may be programmed to monitor user inputs to the surgical instrument. Referring to FIG. 18, at 22110, the surgical instrument 20282 may monitor user input associated with movement and positioning of the surgical instrument. The surgical instrument 20282 may employ, for example, an acceleration sensor 150712, as described in connection with FIG. 17B, to monitor the movement and positioning of the surgical instrument. The surgical instrument 20282 may monitor the orientation of the surgical instrument 20282 and a length of time the surgical instrument 20282 is maintained in a particular position. The surgical instrument 20282 may monitor user inputs associated with operation of controls of the surgical instrument 20282. For example, the surgical instrument 20282 may monitor inputs associated with controlling the operation of claws for clamping patient tissue. The surgical instrument 20282 may monitor the degree that a control trigger is pressed, the speed at which the trigger is pressed, and a length of time a trigger is held in a particular control position.

At 22112, the surgical instrument 20282 may generate usage data associated with the user inputs monitored and detected by the surgical instrument 20282 at 22110. The surgical instrument 20282 may generate usage data associated with the movement and positioning of the surgical instrument 20282 and/or associated with the user inputs associated with controlling operations of the surgical instrument.

At 22114, the surgical instrument 20282 may communicate the usage data to a surgical computing system which may be, for example, a surgical hub 20006.

At 22116, data associated with the one or more healthcare professionals who operate the surgical instrument 20282 may also be gathered. Healthcare professionals operating the surgical instruments 20282 and/or who are in the area where the surgical procedure is being performed may have one or more sensing systems applied thereto. Sensing systems 20069 such as those described herein in connection with FIG. 2A may be applied to the healthcare professionals to collect sensor data. The sensing systems 20069 may sense and gather sensor data which may include biometric data such as, for example, data associated with heartrate, respiration, temperature, etc. The sensing systems 20069 may sense and gather sensor data associated with movement of the healthcare professional such as, for example, movement of the healthcare professional's arms, hands, legs, and/or torso.

At 22118, the surgical instrument 20282 may communicate the sensor data to the surgical computing system 20006.

The surgical computing system 20006 and the processors therein as described in connection with FIGS. 10 and 12 may be programmed to receive and process the usage and sensor data. At 22120, the surgical computing system 20006 may receive the sensor data from the sensing systems 20069 and may receive usage data from the surgical instrument 20282.

At 22122, the surgical computing system 20006 may process the received usage data and/or sensor data and may determine, based on the received data, one or more control features for implementation by the surgical instrument 20282. The surgical computing system 20006 may be configured to determine control features for the surgical instrument 20282 based on the indications from the usage and/or sensor data regarding the surgical procedure and the healthcare professionals performing the surgical procedure. For example, the surgical computing system 20006 may receive usage data comprising data associated with controlling the jaws 20290, 20291 of a surgical instrument 20282 to clamp tissue. The usage data may indicate that a closure trigger 150032 of the surgical instrument 20282 has been maintained in a clamped position for period of time. The surgical computing system 20006 may determine that the period indicated by the usage data exceeds a threshold. Based on determining that the period of time the closure trigger 150032 has been held in a position exceeding a threshold, the surgical computing system 20006 may determine that the surgical instrument 20282 may switch the closure trigger 150032 from operating under a load control mode to operate under a position control mode. The surgical computing system 20006 may determine that a control feature associated with operating in position control may be applied by the surgical instrument 20282.

At 22124, the surgical computing system 20006 may communicate an indication of the determined control feature to the surgical instrument 20282. The surgical computing system 20006 may communicate an indication, which may be an instruction, that position control may be implemented by the surgical instrument 20282.

At 22126, the surgical instrument 20282 may receive the indication of the determined control characteristic.

At 22128, the surgical instrument 20282 may be programmed to modify its operations based upon the received indication of the determined control feature. If the indication of the control feature indicates to implement position control, the surgical instrument 20282 may implement position control in connection with operation of a closure trigger 150032 and clamping of tissue. If the healthcare professional may have been applying a force to the closure trigger 150032 to maintain pressure on the patient's tissue, the surgical instrument 20282 switching to a position control may cause the surgical instrument 20282 to apply the same force to the patient tissue without the need for the healthcare provider to continue applying the same force to the closure trigger 150032.

The surgical computing system 20006 may receive usage data and sensor data associated with numerous different surgical procedures and situations. The control features determined by the surgical computing system may vary based on the received usage data and sensor data.

The surgical computing system 20006 may determine whether a surgical instrument 20282 may apply load control or position control in connection with operation of a mechanical device control. A surgical instrument may comprise a handle grip 150019 and a closure trigger 150032 that may be displaced toward the handle grip 150019. The surgical instrument 20282 may be configured so that displacement of the closure trigger 150032 toward the handle grip 150019 may control the operation of another portion of the surgical instrument 20282. For example, the surgical instrument 20282 may be an endocutter device and may comprise one or more jaws 20290, 20291 that is configured to receive tissue therein. The surgical instrument 20282 may be configured so that operation of the closure trigger 150032 controls operation of the jaws 20290, 20291. The surgical instrument 20282 may be configured so that the manner that the jaws respond to operation of the closure trigger 150032 varies depending upon the type of trigger mode that is employed. The surgical instrument 20282 may be configured to operate in a trigger mode that may be referred to as load control. While the surgical instrument 20282 operates in load control mode or configuration, compression of the closure trigger 150032 or displacement of the trigger 150032 toward the handle grip 150019 causes the jaws 20290, 20291 to close and to apply a force to tissue engaged by the jaws 20290, 20291. While the surgical instrument 20282 operates in load control mode, force may be applied to the closure trigger 150032 for pressure to be maintained by the jaws 20290, 20291.

The surgical instrument 20282 may be configured to operate in a trigger mode that may be referred to as position control. If the surgical instrument 20282 operates in position control mode, the surgical instrument 20282 may maintain the existing position of the jaws 20290, 20291 and the existing force applied by the jaws in response to little or no force applied by the healthcare professional to the closure trigger 150032. The surgical instrument 20282 may maintain the force associated with the corresponding position of the trigger without requiring a force be applied to the trigger.

Figure 19:
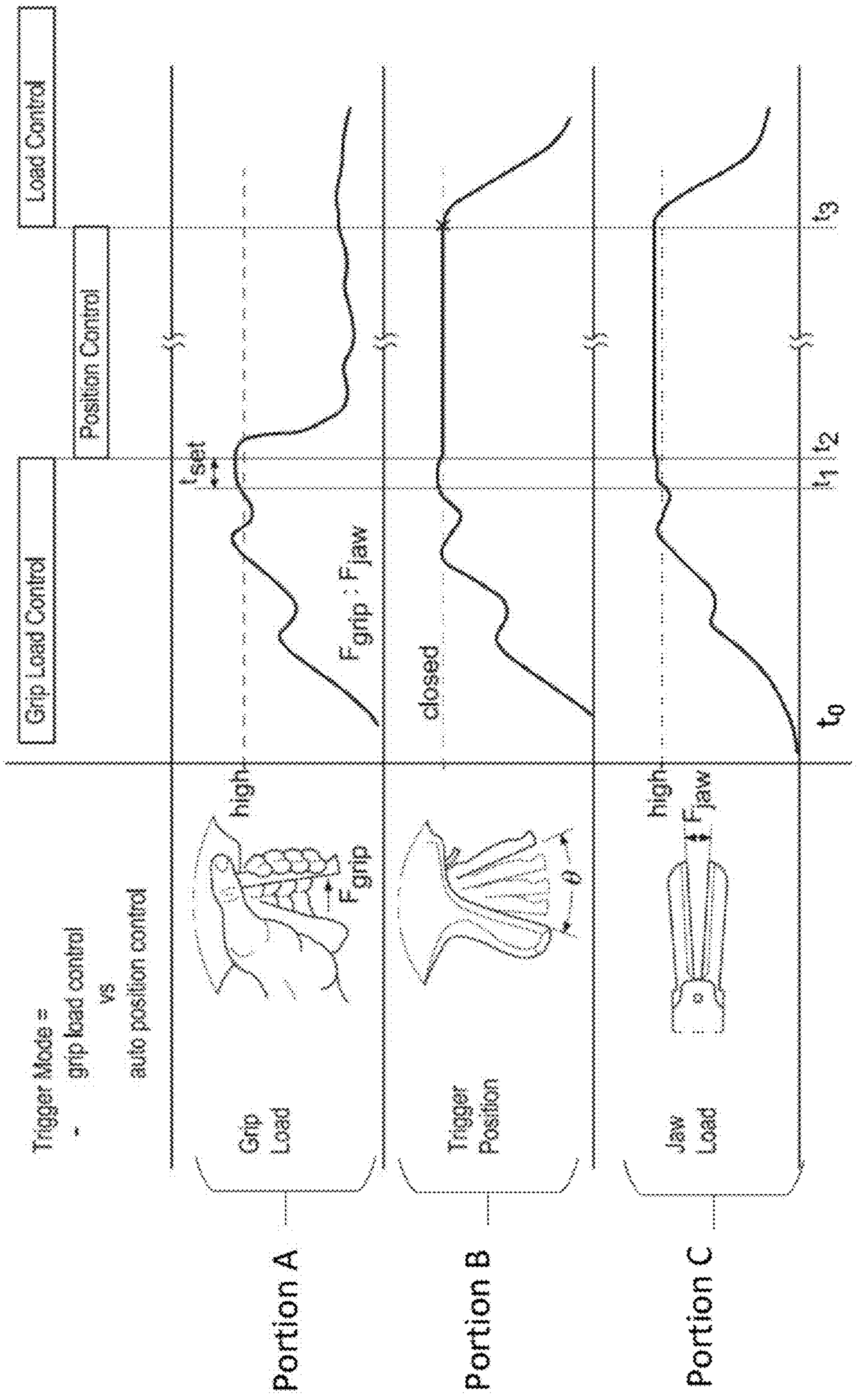
FIG. 19 depicts graphs illustrating example switching from load control processing to position control processing.

The surgical computing system 20006 may dynamically determine to have a surgical instrument 20282 switch between trigger control modes based upon usage data received from the surgical instrument 20282. FIG. 19 illustrates example forces associated with switching from operating in load control mode to position control mode. Portion A of FIG. 19 illustrates an example force (depicted on the y-axis) applied by the healthcare professional to the closure trigger 150032 across a period of time (depicted on the x-axis). Portion B of FIG. 19 illustrates the relative position of the closure trigger 150032 between an open position (associated with no force being applied) and a closed position (associated with a maximum force being applied) (depicted on the y-axis) across the same period of time (depicted on the x-axis). A third portion C of FIG. 19 illustrates example force applied by the jaws 20290, 20291 (depicted on the y-axis) across the same period of time.

During a time period beginning at time to, the surgical instrument 20282 may operate in load control mode. As illustrated in portion A, a healthcare professional may apply a generally increasing force to the closure trigger 150032 across time. As illustrated in portion B, in response to the force applied by the healthcare provider, the closure trigger 150032 moves to a closed position over time. As illustrated in portion C, in response to the force applied by the healthcare professional to the closure trigger 150032, the force applied by the jaws 20290, 20291 increases over time.

The healthcare professional operating the closure trigger 150032 may determine that sufficient force is being applied and may apply a substantially constant force to the closure trigger 150032. As illustrated in portion A, between the time $t_1$ and $t_2$, the force applied by the healthcare provider remains substantially constant. As illustrated in portion B, the closure trigger 150032 remains at a relatively fixed closed position. As shown in portion C, the force applied by the jaws 20290, 20291 likewise remain substantially constant during the period between time $t_1$ and $t_2$.

The processing of FIG. 18 may be applied to determining a control mode. At 22110, the surgical instrument 20282 may monitor the user inputs including the force applied to the closure trigger 150032, time associated with application of the force, displacement of the closure trigger 150032, time associated with displacement of the closure trigger 150032, force applied by jaws 20290, 20291, and time associated with the force applied by the jaws 20290, 20291. The surgical instrument 20282 may monitor and detect as illustrated in portion A of FIG. 19, that between the time t1 and t2, the force applied by the healthcare professional remains substantially constant, the closure trigger 150032 remains at a relatively fixed closed position, and the force applied by the jaws 20290, 20291 likewise remains substantially constant.

At 22112, the surgical instrument 20282 may generate usage data associated with the user inputs. The usage data may reflect that between the time t1 and t2, the force applied by the healthcare professional remains substantially constant, the closure trigger 150032 remains at a relatively fixed closed position, and the force applied by the jaws 20290, 20291 likewise remains substantially constant. At 22124, the surgical instrument 20281 may communicate the usage data to the surgical computing system 20006.

At 22120, the surgical computing system 20006 may receive the usage data and may process the received data at 22122 to determine control features for implementation by the surgical instrument 20282. The surgical computing system 20006 may determine that the usage data indicates that the force applied by the healthcare professional to the closure trigger 150032 remains substantially constant for period between t1 and t2. The surgical computing system 20006 may determine that the time period between t1 and t2 satisfies, e.g., meets or exceeds, a predetermined threshold. The surgical computing system 20006 may determine, based upon the time period exceeding the predetermined threshold, that the surgical instrument 20282 may switch from load control to position control. The surgical computing system 20006 may determine that a control feature, which may be, for example, an instruction, a parameter, or other indicator, may indicate that the surgical instrument 20282 may assume or switch to position control in connection with operation of the closure trigger 150032. At 22124, the surgical computing system 20006 may communicate an indication of the control feature, e.g., apply position control, to the surgical instrument 20282.

At 22126, the surgical instrument 20282 may receive an indication of control features from the surgical computing system 20006. At 22128, the surgical instrument 20282 may determine to modify its operation based on the received control feature to use position control in connection with the trigger. Referring to FIG. 19, at time t2, the surgical instrument 20282 may begin applying position control to the closure trigger 150032. Applying position control, the surgical instrument 20282 may maintain the force applied by the jaws 20290, 20291 while the healthcare professional may apply a lesser force to the closure trigger 150032. As shown in portion A, after time t2, the force applied to the closure trigger 150032 by the healthcare professional begins to be reduced. The healthcare professional may apply a relaxed grip. As shown in portion B of FIG. 19, after time t2, the closure trigger 150032 position remains substantially constant. The closure trigger 150032 maintains its closed position even though the force applied to the closure trigger 150032 may be reduced relative to its previous value. As shown in portion C, after time t2, the surgical instrument 20282 operates the jaws 20290, 20291 to maintain the clamping force even though the force applied by the healthcare professional to the closure trigger 150032 is reduced.

The healthcare professional controlling the surgical instrument 20282 may finish with a step in a surgical procedure and may wish to remove pressure from tissue presently acted upon by the surgical instrument 20282. The healthcare professional may wish to switch from position control of the closure trigger 150032 to load control. As shown in FIG. 19, at time t3, the healthcare professional may enter an input to the surgical instrument 20282 to indicate an intention to switch from position control of the trigger to load control. The input may be entered in any suitable manner such as, for example, by tapping, e.g., double tapping, on the side of the surgical instrument 20282, moving the trigger in a secondary direction, other input. The surgical instrument 20282 may be configured to receive the input and, in response, transition to load control of the closure trigger 150032. The surgical instrument 20282 may also be configured to perform the transition based on control features from the surgical computing system 20006. The surgical instrument 20282 may monitor the user inputs related to transitioning from position control and communicate associated data to the surgical computing system 20006. The surgical computing system 20006 may determine based upon the inputs to transition to position control and may communicate a control feature to the surgical instrument 20282. The surgical instrument 20282 may switch to load control of the closure trigger 150032 based on the received control feature. Referring to FIG. 19, after time t3, as shown in portion A, the pressure applied to the closure trigger 150032 remains substantially reduced. As shown in portion B, the closure trigger 150032 moves from a closed position to an open position. As shown in portion C, the force applied by the jaws 20290, 20291 lessens over time.

The adaptive switching from load control to position control may relieve the healthcare professional from having to apply a constant force to the closure trigger 150032 to maintain the contact force applied by the jaws 20290, 20291. This switch between control operations may improve the healthcare professional's stamina and preserve his or her fine motor skills as they may not need to use excess force to close the jaws 202290, 2020291 for an extended period of time. Aspects of the operation may be configurable. For example, the threshold time used by the surgical computing system 20006 in determining to switch to position control may be a value that may be changed and configured depending upon user preference.

A healthcare professional may employ a control device such as, for example, a closure trigger 150032, to control opening and closing an end effector, such as, for example, a pair of clamping jaws 20290, 20291, comprised in the surgical instrument 20282. It may be appropriate to vary the speed with which the jaws close in response to input applied to the closure trigger 150032 during a surgical procedure. The speed with which the jaws close in response to input may be scalable. If the jaws 20290, 20291 are in the initial stages of being positioned around a target portion of the patient, it may be appropriate to apply a first manner of control, which may be referred to as gross control, of the jaws 20290, 20291 whereby the jaws respond to the closure trigger 150032 by closing relatively quickly. If the jaws 20290, 20291 are in contact with the patient's flesh, it may be appropriate to apply a second manner of control, which may be referred to as fine control, of the jaws 20290, 20291 whereby the jaws respond to the closure trigger 150032 with slower speed to allow for greater precision. The outputs generated at the jaws 20290, 20291 in response to inputs received at the closure trigger 150032 may be scaled differently by the surgical instrument 20282 depending on the manner of control implemented by the surgical instrument 20282. If the surgical instrument 20282 is applying the first manner of control, e.g., gross control, the surgical instrument may scale or employ a first multiplier to the inputs received at the closure trigger 150032 to control the speed of movement of the jaws 20290, 2029. The first manner of control may be appropriate for operation of the surgical instrument 20282 when precision is not the primary concern. If the surgical instrument 20282 is applying a second manner of control, e.g., fine control, the surgical instrument 20282 may scale or employ a second multiplier to inputs received by the closure trigger 150032 to control the speed of movement of the jaws 20290, 20291. The second manner of control may be appropriate for instances when precision is a significant consideration. The surgical computing system 20006 may be configured to receive usage inputs from the surgical instrument 20282 and/or sensor data from sensing systems 20069 applied to the healthcare professional to determine whether the surgical instrument 20282 should be in one or the other of the first manner of scalable control, e.g., gross control, or the second manner of scalable control, e.g., fine control.

The processing depicted in FIG. 18 may be applied to determine whether a surgical instrument 20282 may apply a manner of scalable control including either gross control or fine control in response to user inputs. Referring to FIG. 18, at 22110, the surgical instrument 20282 may monitor user inputs to the surgical instrument including inputs to a closure trigger 150032 that controls the closing of the jaws 20290, 20291. The relative positions of the jaws 20290, 20291 and the degree that the jaws 20290, 20291 are opened and/or closed may be monitored. The surgical instrument 20282 may comprise an acceleration sensor 150712 which may provide data regarding the movement and orientation of the surgical instrument 20281. At 22112, the surgical instrument 20282 may generate usage data associated with the monitored user inputs. The usage data may indicate the inputs to the closure trigger 150032, the relative positions of the jaws 20290, 20291, the degree the jaws 20290, 20291 are open or closed, load experienced by the jaws 20290, 20291, movement of the surgical instrument 20282, orientation of the surgical instrument 20282, and timing data associated with the position and movement data. At 22114, the usage data may be communicated to the surgical computing system 20006.

Data may be collected from sensing systems 20069 that may be applied to the healthcare professional operating the surgical instrument 20282. For example, sensing systems 20069 comprising accelerometers may be applied to the healthcare professional's arms and/or wrists. The accelerometers may generate data regarding motion and orientation of the healthcare professional's arms and/or wrists. Sensing systems 20069 may collect biomarker data from the healthcare provider including data associated with heartbeat, respiration, temperature, etc. At 2216, data may be gathered by the sensing systems 20069 and at 2218, the gathered sensor data may be communicated to the surgical computing system 20006.

At 22120, the surgical computing system 20006 may receive usage data from the surgical instrument 20282 and may receive sensor data from the sensing systems 20069. At 22122, the surgical computing system 20006 may determine, based on the received usage data, whether to respond to inputs to the closure trigger 150032 with gross control or fine control mode of the jaws 20290, 20291. The surgical computing system 20006 may determine that the surgical instrument 20282 may operate in fine control mode based on the position and/or state of the components of the surgical instrument 20282. For example, if the usage data indicates the jaws 20290, 20291 are substantially open, e.g., completely or nearly completely open, the surgical computing system 20006 may determine the surgical instrument 20282 may apply gross control in response to closure trigger 150032 inputs. If the usage data indicates the jaws 20290, 20291 are partially closed or at least a predefined percentage (e.g., 50 percent or 75 percent) closed, the surgical computing system 20006 may determine the surgical instrument 20282 may apply fine control in response to the closure trigger 150032 inputs. If the usage data indicates the rate of closure is slowing, the surgical computing system 20006 may determine the surgical instrument 20282 may apply fine control.

The surgical computing system 20006 may determine that the surgical instrument 20282 may operate in fine control mode based on a sensed parameter such as, for example, the load experienced by the jaws 20290, 20291. The jaws 20290, 20291 might experience a load thereon when the jaws 20290, 20291 engage tissue of the patient. The surgical instrument 20282 may monitor and collect data regarding the load experienced by the jaws 20290, 20291 during closure. The load may correspond to a load placed on one or more motors employed to move the jaws 20290, 20291. If the data collected by the surgical instrument 20282 and processed by the surgical computing system 20006 indicates the jaws 20290, 20291 have not experienced a load, or a load of significance, the surgical computing system 20006 may determine that the surgical instrument 20282 may be configured to employ gross control in response to the inputs to the closure trigger 150032. If the data collected by the surgical instrument 20282 and processed by the surgical computing system 20006 indicates the jaws 20290, 20291 are experiencing a load, such as may be associated with engaging a patient's tissue, the surgical computing system 20006 may determine that the surgical instrument 20282 may be configured to employ fine control in response to the inputs to the closure trigger 150032.

The surgical computing system 20006 may determine that the surgical instrument 20282 may operate in fine control mode based on user inputs associated with activating fine control. One or more user inputs or a series of user inputs may be associated with activating fine control. For example, the healthcare professional operating the surgical instrument 20282 may cycle the closure trigger 150032 or handle grip 150019 twice in quick succession to request to activate fine control. The healthcare professional may tap (e.g., double tap in quick succession) the side of the surgical instrument 20282 to request to activate fine control. The usage data received by the surgical instrument 20282 may indicate such user inputs designated to indicate activation of fine control. If the data collected by the surgical instrument 20282 and processed by the surgical computing system 20006 indicates one or more user inputs associated with activating fine control, the surgical computing system 20006 may determine the surgical instrument 20282 may be configured to employ fine control in response to the inputs to the closure trigger 150032.

The surgical computing system 20006 may also consider sensor data collected by and received from sensing systems 20069 applied to the healthcare professional operating the surgical instrument 20282. For example, the surgical computing system 20006 may consider sensor data that indicates the position and movement of various portions of the healthcare professional. If the surgical computing system determines the sensor data indicates the healthcare professional's arms are positioned in an orientation typically associated with locating a surgical instrument 20282, the surgical computing system 20006 may determine the surgical instrument 20282 may be configured to employ gross control in response to closure trigger 150032 inputs. If the surgical computing system 20006 determines the sensor data indicates the healthcare professional's arms and hands are positioned in an orientation typically associated with performing a procedure, the surgical computing system 20006 may determine the surgical instrument 20282 may be configured to employ fine control in response to closure trigger 150032 inputs.

The surgical computing system 20006 may receive and consider both usage data and sensor data in determining a level of scalability to be applied in response to inputs to the surgical instrument 20282. If the usage data indicates that the jaws 20290, 20291 of the surgical instrument 20282 are in the process of being closed and the sensor data indicates the arms and hands of the healthcare provider operating the surgical instrument 20281 are positioned and/or moving consistent with performing a surgical procedure, the surgical computing system 20006 may determine that the surgical instrument 20282 may be configured to apply fine control in response to closure trigger 150032 inputs. If the usage data indicates the jaws 20290, 20291 are in an open position, and/or the sensor data indicates the arms and hands of the healthcare professional are moving and not in a position consistent with performing a surgical procedure, the surgical computing system may determine the surgical instrument 20282 may be configured to employ gross control in response to the closure trigger 150032 inputs.

The surgical computing system 20006 may store the received usage data and sensor data. The surgical computing system 20006 may analyze the stored data to develop a knowledge base regarding how the healthcare professional operates the surgical instrument 20282 and controls the end effector or jaws 20290, 20291. The surgical computing system 20006 may employ the knowledge base to determine whether fine control or gross control may be employed under a particular set of circumstances as indicated by the usage data and sensor data.

Referring to FIG. 18, at 22124, the surgical computing system may communicate an indication of a control feature associated with a manner of control for the surgical instrument to apply. The control feature may indicate one of gross control or fine control.

At 22126, the surgical instrument may receive the indication of control feature indicating one of gross control or fine control. At 22128, the surgical instrument may determine to operate consistent with the indication of gross control or fine control. If gross control is indicated, the surgical instrument 20282 may employ a first multiplier in controlling the speed of movement of the jaws 20290, 20291 in response to input at the closure trigger 150032. If fine control is indicated, the surgical instrument 20282 may employ a second multiplier in controlling the speed of movement of the jaws 20290, 20291 in response to input applied at the closure trigger 150032.

The surgical computing system 20006 may continuously receive usage data and sensor data and may determine to change the manner of control used by the surgical instrument 20282. If the healthcare professional implements one or more inputs, e.g., a predefined sequence of grips or taps, that are associated with deactivating fine control, the surgical computing system 20006 may determine based on data indicating the inputs to switch from fine control to gross control. If the usage data indicates opening of the jaws 20290, 20291 or heavy acceleration of the user movement of the controls which may be an attempt to compensate for fine control, the surgical computing system 20006 may determine to switch from fine control to gross control.

Automated control of the response of the surgical instrument jaws 20290, 20291 may improve user control of the jaws 20290, 20291 and the load experienced by the jaws. The automated control may lessen the need for the healthcare professional to apply fatiguing loads and hand muscle loading.

The surgical computing system 20006 may be configured to identify hand motions and/or arm motions for a healthcare professional using data received from sensing systems 20069 and the surgical instrument 20282. The surgical computing system 20006 may identify the healthcare professional based on the hand motions and/or arm motions and may communicate features to the surgical instrument 20282 to configure the instrument for the healthcare professional.

The surgical computing system 20006 may be configured to anticipate a healthcare professional's next or continued hand motions and/or arm motions using data received from the sensing systems 20069 and the surgical instrument 20282. The surgical computing system 20006 may combine accelerometer readings from the surgical instrument 20282 and one or motion tracking sensors affixed to the healthcare professional's arms to estimate future motions and to modify the selection of load control to be applied. If the surgical computing system 20006 determines based on the received data that the healthcare provider is entering a portion of a surgical procedure that requires delicate motions, the surgical computing system 20006 may determine that fine control may be activated.

In some scenarios, automatic supplementation of a healthcare professional's hand motions via scaling of trigger inputs may not be productive. For example, it may not be appropriate to scale inputs when switching between closed insertion and gross tissue spreading as may take place during an otomy. The surgical computing system 20006 may identify if such automated scaling of inputs may not be appropriate by monitoring previous uses over time and/or by monitoring for extreme switches in instrument actuation.

A surgical computing system 20006 may analyze usage data and/or sensor data to determine whether to activate over-correction control or compensation. Over-correction may refer to a healthcare professional controlling a surgical instrument to respond to a previously requested instrument action. For example, a healthcare professional who is controlling a surgical instrument 20282, after applying force to the closure trigger 150032 to close the jaws 20290, 20291, may determine that he/she has applied too much force too quickly and may discontinue applying any force to the trigger, when merely lessening (and not terminating) the applied force would have been an appropriate action. The healthcare professional may make too large of a change in input, which may be referred to as over-correction, for a perceived mistake. Repeated correction, over-correction, or oscillating reaction may be a leading indicator of fatigue.

Figure 20:
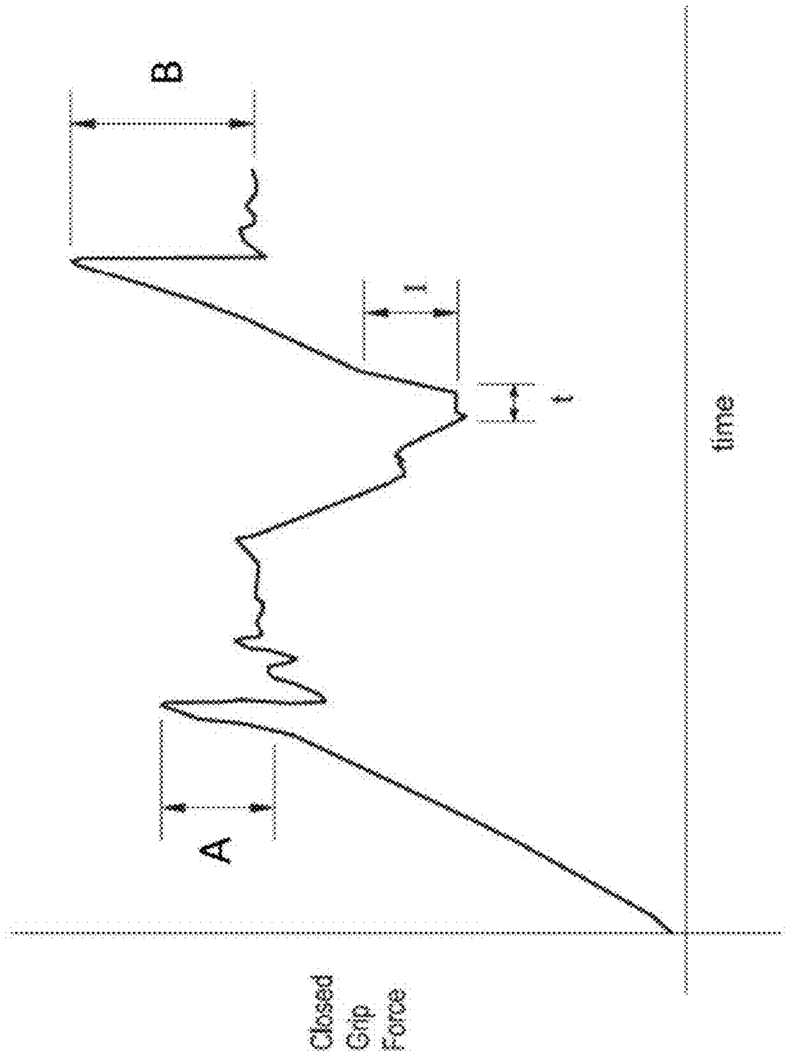
FIG. 20 depicts a graph illustrating example over-correction.

FIG. 20 depicts a chart of an example force curve illustrating example instances of over-correction. As shown, the force applied to a closure grip or trigger is plotted on the y-axis. Time is plotted on the x-axis. A healthcare professional may attempt to gently grasp lung tissue within the jaws 20290, 20291 of a surgical instrument 20282 which may be a surgical stapler. The healthcare professional may apply force to the closure trigger 150032, represented in the force curve by the increasing line, and may cause the jaws 20290, 20291 to close too quickly or forcefully, which may increase the risk of collateral tissue damage by inducing micro tissue tension around the perimeter of the anvil where the pressure gradient may be the greatest. The healthcare professional may realize that he or she commanded the surgical instrument 20282 to clamp too far and too fast and may release the trigger control as indicated in FIG. 20 by the initial quick drop in force. Gap A represents an amount of excess force that was applied (force overshoot) and the subsequent correction amount initiated by the healthcare provider. The force correction overshoots to the downside as it falls below the intended force. The healthcare provider may then apply varying force to reach the desired force level before the applied force eventually reaches an equilibrium. The healthcare professional may subsequently release pressure from the closure trigger 150032 as indicated by the downward sloping line. After a time interval "t," the healthcare professional may again apply force to the closure trigger 150032. The applied force may again exceed the intended value, and the healthcare provider may again attempt to correct for the error by quickly removing force from the closure trigger 150032. Repeated instances of overshooting the target force amount and subsequent overcorrections may be an indication that the healthcare professional is becoming fatigued and could benefit from an alteration of the reaction times for the forces applied to the closure trigger 150032.

A surgical computing system 20006 may be configured to analyze data from the surgical instrument 20282 and biometric data gathered from sensing systems 20069 attached to the healthcare professional to determine whether over-correction may be taking place. If over-correction is determined to be occurring, the surgical computing system 20006 may instruct the surgical instrument 20282 to implement overcorrection control or compensation. In response, the surgical instrument 20282 may slow the response time to user inputs and thereby provide additional time for a healthcare provider to react to their own inputs. The surgical instrument 20282 may slow an actuator advancement speed or lower a control load and thereby provide the healthcare professional with time to evaluate the operations of the surgical instrument 20282 and avoid over correction.

The techniques depicted in FIG. 18 may be applied to determine whether a surgical instrument 20282 may apply over-correction control. Referring to FIG. 18, at 22110, the surgical instrument 20282 may monitor user inputs including inputs to a closure trigger 150032 that controls the closing of the jaws 20290, 20291. The monitored input may comprise an indication of force applied to the closure trigger 150032 over time. The surgical instrument 20282 may comprise an accelerometer sensor 150712 which may provide data regarding the movement and orientation of the surgical instrument. At 22112, the surgical instrument 20282 may generate usage data associated with the monitored user inputs. The usage data may indicate the inputs to the closure trigger 150032 including the force applied to the jaws 20290, 20291, the relative positions of the jaws 20290, 20291, the degree the jaws 20290, 20291 are open or closed, load experienced by the jaws 20290, 20291, movement of the surgical instrument 20282, and orientation of the surgical instrument 20282. At 22114, the usage data may be communicated to the surgical computing system 20006.

Data may be collected from sensing systems 20069 that may be applied to the healthcare professional operating the surgical instrument 20282. For example, accelerometers may be applied to the healthcare professional's arms and/or wrists. The accelerometers may generate data regarding motion and orientation of the healthcare professional's arms and/or wrists. Sensing systems 20069 may collect biomarker data from the healthcare provider including data associated with heartbeat, respiration, temperature, etc. At 2216, sensor data may be gathered and at 2218, the gathered data may be communicated to the surgical computing system 20006.

At 22120, the surgical computing system 20006 may receive usage data from the surgical instrument 20282 and may receive sensor data from the sensing systems 20069. At 22122, the surgical computing system 20006 may determine, based on the received usage data and/or sensor data, whether the surgical instrument 20282 may implement overcorrection compensation. The surgical computing system 20006 may determine that the received usage data and/or sensor data indicate one or more instances whereby the operator attempted to correct for previous inputs or attempted user correction action. The usage data may be received across time and may indicate instrument actions over time. The surgical computing system 20006 is configured to compare user inputs to the surgical instrument 20282 to recently entered inputs. The surgical computing system 20006 may identify indications of over correction from the user inputs and/or sensor data. The surgical computing system 20006 may identify changes by comparing actions as indicated in the usage data and/or sensor data (e.g., accelerometer data) to previous actions. An intentional input may be consistent with previous actions, while inputs associated with over-compensation may be identified for being variable from prior inputs. The surgical computing system 20006 may differentiate between normal operation of the surgical instrument 20282 and over actuation and subsequent compensation by determining whether the data indicates repetition in action and the proportionality of an action relative to previous actions. Changes in magnitude and/or frequency of inputs that exceed a predetermined delta may be an indication that the operator has over-compensated in attempting to correct a previous action. The surgical computing system 20006 may be configured with a baseline control function and may adjust limits for determining over-compensation over time as additional inputs are received.

At 22124, the surgical computing system 20006 may communicate an indication of a control feature associated with a manner of control for the surgical instrument 20282 to apply. The control feature may indicate to implement over-correction control or compensation.

At 22126, the surgical instrument 20282 may receive the indication of a control feature indicating to implement over-correction control. At 22128, the surgical instrument 20282 may determine to operate consistent with the indication of over-correction control. If over-correction control is indicated, the surgical instrument 20282 may be configured to slow the response time to user inputs and thereby provide additional time for a healthcare professional to react to their own inputs. The surgical instrument 20282 may slow an actuator advancement speed or lower a control load and thereby provide the healthcare professional with time to evaluate the operations of the surgical instrument 20282 and avoid over correction and possible collateral damage. The surgical instrument 20282 may implement over-correction control by inserting a delimiter into processing to momentarily stop a requested action until the operator healthcare professional confirms the action or reproduces an action in acceptable range.

A healthcare professional operating a surgical instrument 20282 may be susceptible to fatigue which may result in tremors or shaking. Tremors experienced by the healthcare professional may negatively impact performance of procedures with the surgical instrument 20282. A surgical computing system 20006 may be configured to analyze usage data and/or sensor data to determine whether a healthcare professional is experiencing tremors and, if so, to activate stability control in the surgical instrument 20282.

A healthcare professional may wear gloves, a watch, wristband, or other wearable sensing systems 20069 that comprise one or more accelerometers. A surgical instrument 20282 may comprise one or more acceleration sensor 150712. The wearable sensing systems 20069 and/or the surgical instrument 20282 may be configured to employ the acceleration sensor to detect tremors or shaking, including detecting magnitude and frequency of shaking of the hands or arms. A surgical computing system 20006 may be configured to receive sensor data and/or usage data and may be configured to determine, based on the data, that the healthcare professional is experiencing shaking or tremors. The surgical computing system 20006 may be configured to determine to instruct the surgical instrument 20282 to implement stability control to compensate for tremors or shaking of the surgical instrument 20282.

The techniques depicted in FIG. 18 may be applied to determine whether a surgical instrument 20282 may implement stability control or compensation. Referring to FIG. 18, at 22110, the surgical instrument 20282 may monitor user inputs to the surgical instrument including inputs that result in shaking of the surgical instrument. Shaking, whether done intentionally or otherwise, may be detected by one or more acceleration sensors 150712 which provide data regarding the movement and orientation of the surgical instrument 20282. The detected data may indicate magnitude and frequency of any tremors. At 22112, the surgical instrument 20282 may generate usage data associated with the monitored user inputs. The usage data may indicate the inputs to the surgical instrument 20282 including movements of all or a portion of the surgical instrument 20282 including shaking movements. At 22114, the usage data may be communicated to the surgical computing system 20006.

Data may be collected from sensing systems 20069 that may be applied to the healthcare professional who operates the surgical instrument 20282. Sensing systems 20069 comprising accelerometers may be applied to the healthcare professional's hands, wrists, and/or arms. The accelerometers may generate data regarding motion and orientation of the healthcare professional's hands and/or arms. The data may indicate magnitude and frequency of movements including any shaking motion. Sensing systems 20069 may also collect biomarker data from the healthcare provider including data associated with heartbeat, respiration, temperature, etc. At 2216, sensor data may be gathered by the sensor systems and, at 2218, may be communicated to the surgical computing system 20006.

At 22120, the surgical computing system 20006 may receive usage data from the surgical instrument 20282 and may receive sensor data from the sensing systems 20069. At 22122, the surgical computing system 20006 may determine, based on the received usage data and/or sensor data, whether the surgical instrument 20282 may implement stability control. The surgical computing system 20006 may determine that the received usage data and/or sensor data indicate the healthcare professional who is operating the surgical instrument may be exhibiting tremors or shaking. The data may indicate movement associated with shaking or tremors and may indicate a magnitude and/or frequency of any tremors. The surgical computing system 20006 may determine based on the received usage data and/or sensor data that the surgical instrument 20282 may implement stability control to compensate for the tremors.

Referring to FIG. 18, at 22124, the surgical computing system 20006 may communicate an indication of a control feature associated with a manner of control for the surgical instrument to apply. The control feature may indicate to implement stability control.

At 22126, the surgical instrument 20282 may receive the indication of control feature indicating to implement stability control. At 22128, the surgical instrument 20282 may determine to operate consistent with the indication of stability control. The surgical instrument 20282 may attempt to dampen tremors originating from the healthcare professional from impacting the output of the surgical instrument 20282. The surgical instrument 20282 may modify its control algorithms to alter the output. The surgical instrument 20282 may introduce delay to a robotic interface to lessen or minimize tremors originating from the healthcare professional from being transmitted to an output tip or end effector of the surgical instrument. The surgical instrument 20282 may reduce the fineness and/or speed of instrument motions to lessen or minimize transmission of hand tremors to the surgical instrument output. The surgical instrument 20282 may correlate motion of the surgical instrument tip or end effector to micro hand motions to lessen or minimize transmitted harmonic oscillation of the device tip. The tremor frequency and/or magnitude may be used as a control means for adjustment of the tremor damping mechanism.

The surgical computing system may be configured to detect and provide notifications to healthcare professionals regarding possible future physical episodes such as tremors. Referring to FIG. 18, at 22120, received usage data and sensor data may be stored over time by the surgical computing system 20006. The sensor data may comprise data that may allow for detection of automatic tone. For example, the sensor data my comprise the following: skin conductance which may be found, for example, through variation of current between two electrodes; heart rate variability which may be measured from an electrocardiogram; activity measured using an accelerometer; peripheral body temperature measured by a thermometer; and/or blood pressure measured with pressure sensors that may be adapted to take oscillometeric measurements or perform photoplethysmography. The data may be stored correlated with time.

The surgical computing system 20006 may also store data indicating instances control features were identified based upon the data. The surgical computing system 20006 may store an indication that tremors were identified and may store the indication in relation to the usage data and sensor data on which the tremor indication was based. The data may also be correlated based on time.

At 22124, if a control feature such as, for example, tremor control is communicated to the surgical instrument 20282, the surgical computing system 20006 may also communicate feedback information to the healthcare professional regarding the corresponding sensor data readings, e.g., heart rate, body temperature, blood glucose, that existed when the tremors occurred. Coupling of tremors and biomarkers may be used as a metric to illustrate a correlation between performance and health. The feedback sensor data may allow health care professionals to monitor their lifestyle and possibly determine a cause of the tremors.

The surgical computing system 20006 may use the stored data as baseline data against which current data may be evaluated. The surgical computing system 20006 may be configured to compare currently received sensor and usage data to previously stored sensor and usage data. The surgical computing system 20006 may determine whether the current sensor data is similar to sensor data correlated to one or more prior tremor episodes. If so, the surgical computing system 20006 may determine that a tremor episode may be a possibility in the near future and may communicate a notification to the healthcare professional. The notification may be communicated to a user interface device associated with the healthcare professional and located in the operating room. The notification may suggest interventions to the healthcare professional. For example, the notification may suggest one or more of the following: a break from activities; obtaining ergonomic support; and/or hydration. The surgical computing system 20006 may subsequently determine that the sensor data has not improved as a consequence of a notification. The surgical computing system 20006 may determine to communicate an escalated notification. The escalated communication may be communicated to the healthcare professional as well as others with an interest. The escalated communication may be communicated if the monitored data indicates the task at hand may be impacted.

The surgical computing system 20006 may continuously monitor received sensor and usage data associated with a healthcare professional. The surgical computing system 20006 may determine to communicate feedback regarding how performance may be changing as it relates to tremors and possible correlation of the tremors with biomarker/wearable measurements. The surgical computing system 20006 may analyze data associated with an arterial transection in lobectomy performed by a physician. The surgical computing system 20006 may determine that the data indicates increased placement/transaction time. The sensor data may reveal that cases are the second or third such cases performed by the physician during the day. Data collected by an accelerometer may indicate increased average hand motion and/or arm motions compared to average hand motion and/or arm motion during a transection procedure performed on another day. The surgical computing system 20006 may determine that blood glucose is markedly decreased during these cases. The surgical computing system 20006 may communicate an indication linking possible decreased performance with physical readings such as tremor and biochemical readings such as, for example, reduced blood glucose. The surgical computing system 20006 may provide possible recommendations such as to eat a snack or change diet.

The healthcare professionals who operate surgical instruments 20282 may be susceptible to fatigue and inhibited dexterity. Healthcare professionals such as, for example, nurses who assist in the operating room may also be susceptible to fatigue. A surgical computing system 20282 may be configured to analyze usage data and/or sensor data to determine whether the healthcare professionals working in the operating room are experiencing fatigue and, if so, to modify operation of the surgical instrument 20282 and to provide notifications associated with the fatigue levels.

The techniques depicted in FIG. 18 may be applied to identifying fatigue, modifying operations of a surgical instrument 20282, and providing notifications associated with the fatigue. Referring to FIG. 18, at 22110, the surgical instrument 20282 may monitor user inputs to the surgical instrument 20282 including inputs that result in shaking of the surgical instrument. Shaking, whether done intentionally or otherwise, may be detected by one or more acceleration sensors 150712 which provide data regarding the movement and orientation of the surgical instrument 20282. The detected data may indicate magnitude and frequency of any tremors. At 22112, the surgical instrument 20282 may generate usage data associated with the monitored user inputs. The usage data may indicate the inputs to the surgical instrument 20282 including movements of all or a portion of the surgical instrument 20282 including shaking. At 22114, the usage data may be communicated to the surgical computing system 20006.

At 2216, data may be collected from sensing systems 20069 that may be applied to the healthcare professional operating the surgical instrument 20282 as well as other healthcare professionals who may assist in the operating room. Accelerometers may be applied to the healthcare professionals' hands, wrists, and/or arms. Accelerometers may also be applied to healthcare providers' torsos to gather data associated with the body movements including swaying and body tremors. The accelerometers may generate data regarding motion and orientation of the healthcare professional's hands and/or arms. The data may indicate magnitude and frequency of movements including shaking. Sensing systems 20069 may collect biomarker data from the healthcare professional including data associated with heartbeat, respiration, temperature, etc. The sensing systems 20069 may collect data associated with the hydration/dehydration of the healthcare professional operating the surgical instrument as well as the other healthcare professionals assisting in the operating room. At 2218, the gathered data may be communicated to the surgical computing system 20006.

At 22120, the surgical computing system 20006 may receive usage data from the surgical instrument 20282 and may receive sensor data from the sensing systems 20069. The surgical computing system 20006 may store the received data in association with time stamp data indicating time the data was collected.

At 22122, the surgical computing system 20006 may determine, based on the received usage data and/or sensor data, fatigue levels for the healthcare professionals operating the surgical instrument 20282 and assisting in the operating room. The surgical computing system 20006 may determine, based on the received usage data and sensor data, time periods associated with the surgical procedure. The surgical computing system 20006 may determine, for each healthcare professional, values associated with time in the operating room, time spent standing in the operating room, time spent physically exerting themselves. The surgical computing system may determine fatigue levels for the individual healthcare professionals based on the time spent in surgery.

The surgical computing system 20006 may determine, based on the received usage data and/or sensor data, physical indications of fatigue. The surgical computing system 20006 may determine, if the received data indicates a healthcare professional is swaying or unsteady, that the healthcare professional is fatigued. The surgical computing system may determine, if the received data indicates tremors are exhibited by a healthcare professional, that the healthcare professional is fatigued.

The surgical computing system 20006 may determine, based on the received usage data and sensor data, values associated with hydration/dehydration of the healthcare providers in the operating room. Dehydration may impact energy levels and make a person feel tired and fatigued. Less body fluid tends to increase heart rate. The surgical computing system 20006 may analyze heartbeat data in the context of hydration levels and differentiate between stress and other heart elevation events from hydration. The surgical computing system 20006 may employ a baseline measure to differentiate acute events from ongoing chronic events and to differentiate between fatigue and dehydration.

The surgical computing system 20006 may calculate a weighted measure of fatigue for the healthcare professional operating the surgical instrument as well as others in the operating room. The weighted measure of fatigue may be based on cumulative cooperative events and contributions. For example, the weighted measure of fatigue may be based on the intensity of stress experienced by a healthcare professional and the force exerted by the healthcare professional over time in controlling an actuator such as closure trigger 150032 over time.

If the surgical computing system 20006 determines that the healthcare professionals have experienced fatigue, the surgical computing system may determine to communicate control features to the surgical instrument to perform fatigue control or accommodation and adjust operation to compensate for fatigue. The control feature to perform fatigue control may indicate to reduce the force required to implement an action. For example, the control feature may indicate to reduce the force needed to be applied to a closure trigger 150032 to activate clamping jaws. The control feature may indicate to increase the sensitivity of the closure trigger 150032. The control features may indicate to increase delay or wait time responsive to user inputs. The control features may indicate to slow activation and provide additional time before acting.

If the surgical computing system 20006 determines the healthcare professionals have experienced fatigue, the surgical computing system 20006 may also determine to communicate control features to provide notifications regarding the fatigue. The surgical computing system 20006 may determine that notifications regarding fatigue may be provided by the surgical instrument 20282 to the healthcare professional. The surgical computing system 20006 may determine that the notifications may provide more steps-for-use to the operator. The surgical computing system 20006 may also determine that notifications regarding fatigue levels may be made to persons in the operating room other than the healthcare professional manning the surgical instrument 20282. Such notifications may be displayed on display systems such as display 20023.

At 22124, the surgical computing system 20006 may communicate an indication of a control features associated with fatigue control. The control features may be communicated to the surgical instrument 20282 and may also be communicated to other systems in the operating room such as display 20023 which may be employed to provide notifications.

At 22126, the surgical instrument 20282 and display 20023 may receive the indication of control features indicating to implement fatigue control and provide notifications. At 22128, the surgical instrument 20282 may determine to operate consistent with the indication of fatigue control. The surgical instrument 20282 may reduce the force required to activate and/or operate closure trigger 150032. The surgical instrument 20282 may increase the delay or wait time between requesting an action, e.g., applying force to the closure trigger 150032, and implementing the corresponding action, e.g., closing the jaws 20290, 20291. The surgical instrument 20282 may slow activation in response to inputs and thereby provide more time for the operator to position the surgical instrument 20282.

If the control features indicate to provide notifications, the surgical instrument 20282 may provide physical tactile feedback as well as visual feedback. The display 20023 may also provide visual feedback regarding fatigue. The notifications may provide steps-for-use to minimize overlooking of details.

Accordingly, systems and techniques are disclosed for adaptively controlling the operations of a surgical instrument based on usage data associated with the surgical instrument and/or sensor data associated with the healthcare professional operating the surgical instrument. A surgical instrument may monitor and collect usage data associated with the position and movement of the surgical instrument and associated with user inputs such as those relating to operating the surgical instrument. Sensing systems applied to the healthcare provider operating the surgical instrument collect sensor data such as, for example, data associated with heartrate, respiration, temperature, etc. A surgical computing system may determine, based on at least one of the usage data and/or the sensor data, control features for the surgical instrument. The surgical instrument may modify its operation based upon the determined control features.

Systems, methods and instrumentalities are disclosed for adaptively adjusting operation and/or control of a surgical instrument and/or adaptively communicating information to a healthcare professional. Adaptation of operation, control and/or communication may be based on, for example, situational awareness of a surgical procedure. Situational awareness may include, for example, an importance level as indicated by a detected stress level and/or focus of attention of a health care provider, possession of a controllable surgical instrument by a health care provider, and/or body positioning of a health care provider. Situational awareness may be determined, for example, based on information provided by one or more personnel (e.g., wearable) sensing systems, environmental sensing systems, and/or surgical instruments. The information may comprise, for example, one or more of healthcare provider data (e.g., position, posture, balance, motion, attention, physiologic states), environmental data (e.g., operating room noise level, patient data, healthcare provider data), and/or surgical instrument data (e.g., position, possession, motion, and/or usage). A surgical computing system and/or a surgical instrument may receive information, determine situational awareness and adapt instrument operation, control and/or information communication based on situational awareness.

Situational awareness may be monitored, for example, to assess the criticality of an operation in a surgical procedure. A surgical operation may be modified based on criticality. A surgical computing system may receive biomarker data from one or more sensing systems and/or environmental data from one or more environmental sensing systems. The biomarker data may be associated with a healthcare professional operating a surgical instrument. Biomarker data may include, for example, one or more of heart rate, blood pressure, sweat, physical activity, body movement, or eye movement. Environmental data may include, for example, one or more of noise level, healthcare professional attention (e.g., based on eye tracking, such as location and/or time of view), and/or patient biomarkers. The surgical computing system may determine an importance level, for example, based on one or more of biomarker data, environmental data, and/or data associated with a surgical procedure. The surgical computing system may determine, based on the importance level, one or more operational parameters for the surgical instrument. A surgical computing system may determine whether to modify one or more operational parameters based on a determination whether data such as, for example, biomarker data, is within an expected range for a step in a surgical procedure. The surgical computing system may communicate the one or more operational parameters to the surgical instrument.

Instrument motions and operator motions may be assessed to determine the operator of a surgical instrument. A surgical computing system may receive biomarker data which may include movement data from a plurality of sensing systems associated with one of a plurality of healthcare professionals. The surgical computing system may receive usage data which may include movement data from a surgical instrument. The surgical computing system may determine which one of the plurality of healthcare providers has possession of the surgical instrument based at least on the biomarker data and usage data. For example, a surgical computing system may determine whether a healthcare provider's biomarker data including movement data corresponds to usage data including movement data from the surgical instrument. The surgical computing system may determine information for communication to a healthcare provider, for example, based on possession of the surgical instrument. Information communicated to an assistant in possession of an instrument may include, for example, information associated with preparing the surgical instrument for operation. Information communicated to a physician in possession of an instrument may include, for example, information associated with previous use of the surgical instrument. Inconsistencies between data may be detected. The surgical computing system may determine the surgical instrument is not located in an area identified for performing a surgical procedure, for example, based at least on an inconsistency between the biomarker data and usage data. The surgical computing system may determine whether there is a correlation error based on an inconsistency.

Surgical instrument operation may be adjusted, for example, based on an assessment of the posture of a health care professional. A surgical computing system may receive biomarker data from one or more sensing systems associated with a healthcare professional operating a surgical instrument. The surgical computing system may receive usage data associated with user inputs from the surgical instrument. The surgical computing system may receive environmental data from one or more environmental sensing systems. The surgical computing system may determine an evaluation of body positioning of the healthcare professional based at least in part on the biomarker data, usage data, and/or environmental data. An evaluation of body positioning may include an evaluation of posture (e.g., body posture, arm posture, or wrist posture), balance, range of motion, and/or range of reach. The surgical computing system may determine one or more operational parameters for the surgical instrument based on the evaluation of body positioning of the healthcare professional. The surgical computing system may communicate the one or more operational parameters to the surgical instrument. Operational parameters may include, for example, parameters associated with one or more of the following: controls of the surgical instrument, stoke trigger points, an activation limit or a deactivation limit, and/or activating secondary controls. The surgical computing system may receive an indication to override one or more operational parameters from the surgical instrument.

A surgical computing system and/or a surgical instrument may determine situational awareness about a surgical procedure based on information provided by one or more sensors and dynamically adapt operation and/or control of surgical instruments and/or communication of information to healthcare professionals based on the determined situational awareness. Situational awareness may include, for example, an importance level (e.g., a stress level or attention) of a health care provider, possession of a controllable surgical instrument by a health care provider, and/or body positioning of a health care provider. Situational awareness may be determined based on information provided by one or more personnel (e.g., wearable) sensing systems, environmental sensing systems, and/or surgical instruments, such as one or more of healthcare provider data (e.g., position, posture, balance, motion, attention, physiologic states), environmental data (e.g., operating room noise level, patient data, healthcare provider data), and/or surgical instrument data (e.g., position, motion, possession, and/or usage).

Figure 21:
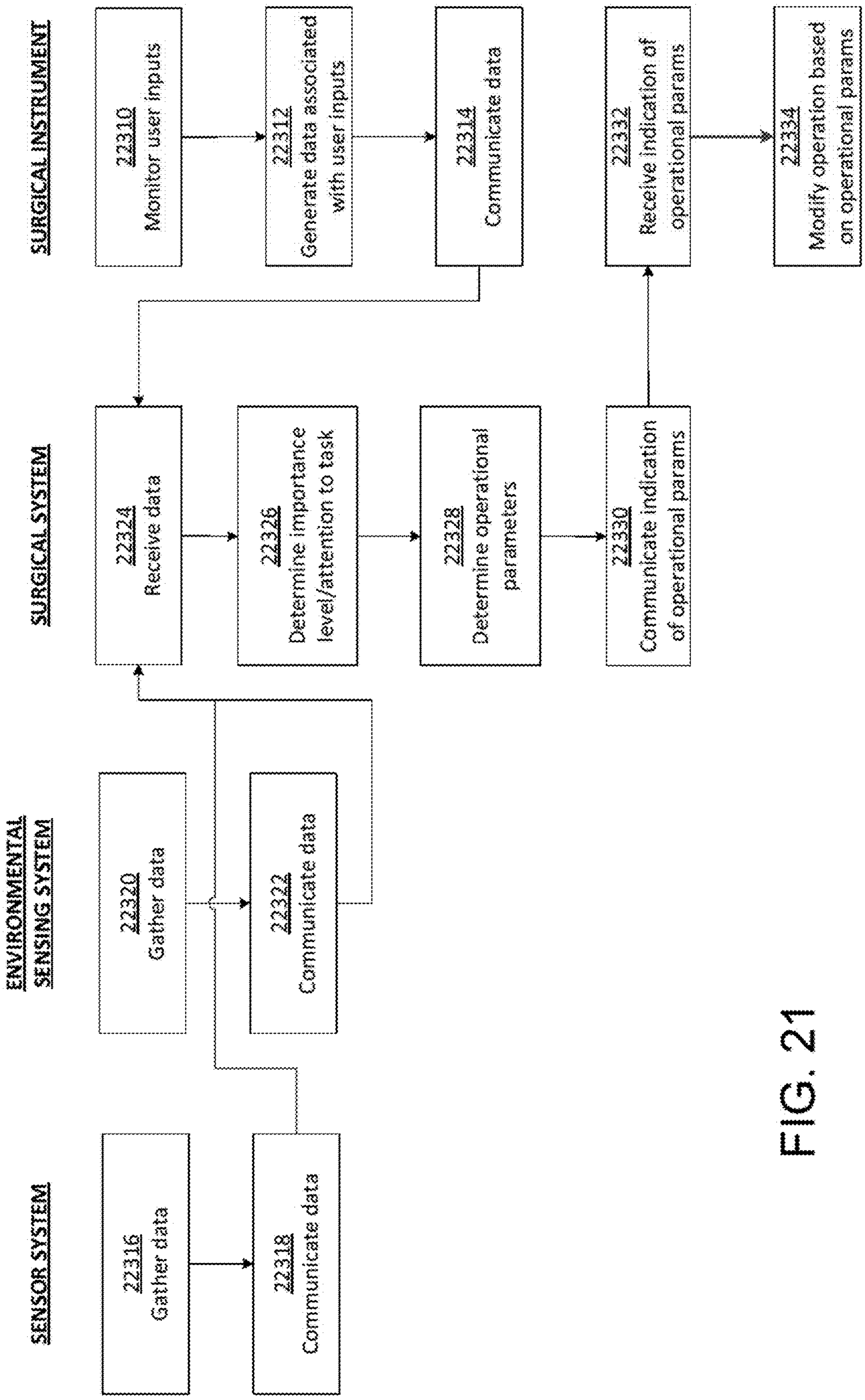
FIG. 21 illustrates example processing associated with determining operational parameters of a surgical instrument based on a determination of importance level and/or attention to a task.

FIG. 21 illustrates an example of processing associated with determining operational parameters of a surgical instrument based on a determination of criticality (e.g., importance level and/or attention to a task). Task criticality may be determined, for example, by monitoring surgeon biomarkers to develop (e.g., determine) situational awareness. Situational awareness monitoring may support (e.g., enable or provide) an understanding of a surgical task. One or more personnel and/or environmental sensors may monitor one or more biomarkers (e.g., user stress trigger biomarker levels, noise levels, physical action biomarkers, such as precision and/or minute hand motions) to determine task criticality. A determined task criticality level may be communicated to a surgical computing system and/or a surgical instrument, for example, to adjust operational parameters of a surgical instrument (e.g., to improve user control). Situational awareness may be used to adapt instrument control algorithms. Intercommunication between a surgical instrument, a surgical computing device, at least one (e.g., wearable) sensor and/or at least one environmental sensor may provide a surgical computing system and/or a surgical instrument with situational awareness of a task and/or task objectives (e.g., speed versus precision versus outcome). A surgical computing device and/or a surgical instrument may adjust the control of one or more surgical instrument actuators based on situational awareness. One or more HCP sensing systems may monitor one or more biomarkers to generate sensor data, which may be communicated from the HCP sensing system(s) to the surgical computing system and/or surgical instrument, for example, to provide (e.g., additional and/or alternative) context about the importance or criticality of a surgical task. HCP sensor data may support dynamic adaptation of surgical instrument operation and/or controls for an HCP. HCP biomarkers may include, for example, stress, heart rate, and/or the like. Environmental data (e.g., from an OR) may include, for example, noise level, staff movements, attention level, and/or the like.

As shown in FIG. 21, at 22310, a surgical instrument, which may be a surgical instrument 20282 (e.g., as described in connection with FIG. 10), may monitor user inputs to the surgical instrument. The surgical instrument 20282 may monitor user input associated with movement and positioning of the surgical instrument 20282. The surgical instrument 20282 may employ, for example, an acceleration sensor 150712 (e.g., as shown in FIG. 17B) to monitor the movement and positioning of the surgical instrument 20282. The surgical instrument 20282 may monitor the orientation of the surgical instrument 20282 and a length of time the surgical instrument 20282 is maintained in a particular position. The surgical instrument 20282 may monitor user inputs associated with operation of controls of the surgical instrument 20282. For example, the surgical instrument 20282 may monitor inputs associated with controlling the operation of jaws for clamping patient tissue. The surgical instrument 20282 may monitor, for example, the degree that a control trigger is pressed, the speed at which the trigger is pressed, and a length of time a trigger is held in a particular control position.

At 22312, the surgical instrument 20282 may generate usage data associated with the user inputs monitored and detected by the surgical instrument 20282 at 22110. The surgical instrument 20282 may generate usage data associated with the movement and positioning of the surgical instrument 20282 and/or associated with the user inputs associated with controlling operations of the surgical instrument 20282.

At 22314, the surgical instrument 20282 may communicate the usage data to a surgical computing system which may be, for example, a surgical hub 20006.

At 22316, data associated with the one or more healthcare professionals who operate the surgical instrument 20282 may (e.g., also) be gathered. Healthcare professionals operating the surgical instruments 20282 and/or who are in the area where the surgical procedure is being performed may have one or more sensing systems applied thereto. Sensing systems 20069, such as those described herein in connection with FIG. 6B, may be applied to the healthcare professionals to collect sensor data. The sensing systems 20069 may sense and gather sensor data, which may include biometric data such as, for example, data associated with heart rate, blood pressure, respiration, temperature, sweat rate, sweat composition, frequency of blinking, etc. The sensing systems 20069 may sense and gather sensor data associated with physical activity (e.g., position, movement) and/or lack thereof (e.g., static waits) of the healthcare professional alone and/or in the aggregate with other personnel, such as, for example, positions and/or movements of the healthcare professional's arms, hands, legs, and/or torso.

At 22318, the surgical instrument 20282 may communicate the sensor data to the surgical computing system 20006.

At 22320, environmental data associated with one or more conditions or attributes in a surgical environment may be gathered (e.g., to determine the importance of phases or steps in a surgical procedure). Conditions or attributes in a surgical environment may include, for example, one or more of a (e.g., an ambient) noise level, HCP positions, HCP movements, HCP attention location (e.g., based on eye tracking, such as location and/or time of view), and/or patient biomarker data (e.g., patient biomarker notifications and/or alarms). One or more environmental sensing systems 20015 may be deployed in a surgical environment as part of a surgical monitoring system 20000 to collect environmental data. Environmental sensing systems 20015, such as those described herein in connection with FIG. 6B, may be activated to collect sensor data. The environmental sensing system(s) 20015 may be systems for measuring one more of the environmental attributes and may include, for example, cameras (e.g., for detecting a surgeon's position, movements, and/or breathing pattern), spatial microphones (e.g., to measure ambient noise in the surgical theater and/or the tone of voice of a healthcare provider), climate sensor(s) (e.g., to measure temperature and/or humidity of the surroundings), etc. The environmental sensing systems 20015 may sense and gather environmental data, which may include data associated with, for example, the surgical environment, people in the surgical environment (e.g., healthcare professionals and patient), instruments in the surgical environment, etc. The environmental sensing systems 20015 may (e.g., also) sense and gather sensor data associated with, for example, positions and/or movements of the healthcare professional (e.g., position and/or movement of the healthcare professional's arms, hands, legs, and/or torso) and/or positions and/or movements of surgical instruments.

At 22322, the environmental sensing system 20015 may communicate the environmental sensor data to the surgical computing system 20006.

At 22324, the surgical computing system 20006 may receive the sensor data from the (e.g., personnel or wearable) sensing systems 20069, usage data from the surgical instrument(s) 20282, and/or environmental data from the environmental sensing system(s) 20015.

At 22326, the surgical computing system 20006 may process the received usage data, sensor data, and/or environmental sensor data (e.g., data set(s)) and may determine an importance level and/or attention to task based on the received data. The surgical computing system 20006 may be configured to determine an importance level and/or attention to task based on the indications from the sensor data, environmental data, and/or usage data regarding the surgical procedure and the healthcare professionals performing the surgical procedure. For example, the surgical computing system 20006 (e.g., situationally aware surgical hub 20076 shown in FIG. 5) may process the sensor data from the (e.g., personnel or wearable) sensing systems 20069, usage data from the surgical instrument(s) 20282, and/or environmental data from the environmental sensing system(s) 20015 to determine an importance level and/or attention to task. For example, the surgical computing system 20006 may translate or map one or more selected data items in the received data set(s) to an importance level and/or an attention to a task. In an example, a criticality level (e.g., low, medium, high) may be inferred from a stress level (e.g., low, medium, high) of an HCP using the surgical instrument(s) 20282, and/or surgical instrument usage data indicating a phase or portion of a surgical procedure. A determination (e.g., mapping) may be based on, for example, the surgical instrument determined to be in use (e.g., and by whom based on sensor and/or environmental data) during a determined stage of a surgical operation.

At 22328, the surgical computing system 20006 may determine one or more operational parameters for one or more surgical instruments based on the importance level and/or attention to task determined at 22326. The surgical computing system 20006 may be configured to determine (e.g., translate or map) the importance level and/or attention to task determined at 22326 to one or more operational parameters for a surgical instrument in use during the determined task. For example, operational parameters for an advanced energy jaw trigger ratio or an endocutter clamp and fire speed may be selected or adjusted based on the detected importance level and/or attention to task. In some examples, operational parameters may be adjusted in proportion to detected stress levels of a surgeon using the device.

At 22330, the surgical computing system 20006 may communicate an indication of the determined operational parameters to the surgical instrument 20282. The surgical computing system 20006 may be configured to communicate an indication to a surgical instrument 20282 determined to be in use during the determined task of the surgical procedure.

At 22332, the surgical instrument 20282 may receive the indication of the determined operational parameters. For example, an endocutter may receive operational parameters for clamp and fire speed or an advanced energy device may receive operational parameters for a jaw trigger ratio.

At 22334, the surgical instrument 20282 may modify operation based upon the received indication of the determined operational parameter(s). For example, an endocutter surgical instrument 20282 may reduce clamp and fire speed if the received operational parameter(s) indicate to reduce clamp and fire speed or the received clamp and fire speed is slower than an existing clamp and fire speed.

The surgical computing system 20006 may receive instrument usage data, sensor data, and/or environmental data associated with numerous different surgical procedures and situations. The importance level, attention to task, and/or operational parameters determined by the surgical computing system 20006 may vary based on the received usage data, sensor data, and/or environmental data.

For example, with reference to the timeline 20265 for a surgical (e.g., colorectal) procedure shown in FIG. 8, the surgical computing system 20006 (e.g., situationally aware surgical hub 20076 shown in FIG. 5) may receive data from various data sources throughout the course of the surgical procedure. The surgical hub 20076 may receive instrument usage data, which may be generated each time an HCP utilizes a modular device/instrument 20095 that is paired with the surgical hub 20076 (e.g., advanced energy device and/or endocutter used in the surgical procedure). The surgical hub 20076 may receive sensor data (e.g., measurement data) from one or more surgeon sensing systems 20069 for measuring one or more biomarkers associated with the surgeon, such as one or more of heart rate, sweat composition, respiratory rate, etc. The sensor data may be processed to determine, e.g., as shown in FIG. 8, low, mid and high stress levels of a surgeon during one or more phases or steps of a surgical (e.g., colorectal) procedure. An importance level may be inferred, at least in part, from a determined stress level.

The surgical hub 20076 may derive inferences (i.e., contextual information) about an HCP's stress level and/or the importance level of an ongoing procedure, e.g., at least in part, from the usage data from the modular device/instruments 20095 and sensed measurement data from the sensing systems 20069. The stress level of an HCP (e.g., surgeon) may be indicated or determined relative to the step of the procedure that is being performed. The surgical hub 20076 may perform one or more of the following (e.g., using a situational awareness system): provide data or prompts (e.g., via a display screen) that may be pertinent to a procedural step, adjust modular devices based on the context (e.g., activate monitors, adjust the FOV of the medical imaging device, change the energy level of an ultrasonic surgical instrument or RF electrosurgical instrument, change clamp and fire speed, change a jaw trigger ratio), etc.

FIG. 8 shows an example of an ongoing procedure from left to right, moving from dissection to ligating the inferior mesenteric artery (IMA) branches, etc. The surgical hub 20076 may infer procedural steps (e.g., start, end), at least based on usage data received from surgical instruments. The surgical hub 20076 may infer that the surgeon is ligating arteries and veins, for example, based on receiving data from the advanced energy jaw device and/or the endocutter indicating that the instrument is being fired. The surgical hub may (e.g., also) receive measurement data from one of the HCP's sensing systems, such as an indication of a higher stress level of the HCP (e.g., indicated by B1 mark on the time axis). A higher stress level may be indicated, for example, by a change in the HCP's heart rate (e.g., from a base value). The surgical hub 20076 may derive the inference of the ligate IMA step by cross-referencing the receipt of data from the surgical stapling and cutting instrument (e.g., as indicated by A2 and A3) with the retrieved steps in the known surgical process.

The surgical hub 20076 may determine one or more operational parameters for one or more surgical instruments 20282 based on the determined importance level (e.g., stress level). For example, the surgical hub 20076 may monitor (e.g., and control) the advance energy jaw trigger ratio and/or the endocutter clamp and fire speed based on stress levels, e.g., during high, medium and/or low stress time periods. In an example, the surgical hub 20076 may send an assistance control signal to the advanced energy jaw device and/or the endocutter device to control the device in operation (e.g., during high stress of the HCP). The surgical hub may send the assistance signal based on the stress level of the HCP that is operating the surgical device and/or situational awareness known to the surgical hub. For example, the surgical hub 20076 may send control assistance signals to an advanced energy device or an endocutter clamp, as indicated in FIG. 8 by A2 and A3. In an example (e.g., as shown in FIG. 8 at A2 and A3), the advanced energy jaw trigger ratio and the endocutter clamp and fire speed are reduced, respectively, based on detection of high stress from the surgery sensing system measurement data.

The HCP may proceed to the next step of freeing the upper sigmoid followed by freeing descending colon, rectum and sigmoid. The surgical hub 20076 may continue to receive inputs from the advanced energy jaw device and/or the endocutter device and may continue to monitor sensing system measurement data for high stress markers of the HCP (e.g., as indicated by D1, E1*a*, E1*b*, F1). The surgical hub 20076 may send assistance (e.g., adaptive control) signals to the advanced energy jaw device and/or the endocutter device, for example, during the high stress time periods, as illustrated in FIG. 8.

An HCP may mobilize the colon and resect the sigmoid, beginning with resecting the transverse bowel portion of the procedure. For example, the surgical hub 20076 may infer that the HCP is performing the transverse bowel resection and sigmoid removal based on data from the surgical stapling and cutting instrument, e.g., including data from the surgical stapling and cutting instrument cartridge. The cartridge data may correspond to the size or type of staple being fired by the instrument, for example. The cartridge data may indicate the type of tissue being stapled and/or transected, for example, as different types of staples are utilized for different types of tissues. An HCP (e.g., surgeon) may switch back and forth between surgical stapling/cutting instruments and surgical energy (e.g., RF or ultrasonic) instruments depending upon the particular step in the procedure because different instruments are better adapted for particular tasks. A sequence of use of the stapling/cutting instruments and surgical energy instruments may indicate what step of the procedure the surgeon is performing.

In some examples (e.g., as shown in FIG. 8), the surgical hub 20076 may determine and send (e.g., wirelessly communicate) a control signal to a surgical device 20282 based on the determined stress level of the HCP using the surgical instrument 20282. The stress level may be deemed or mapped to an importance level for a portion of a surgical procedure. For example, during time period G1*b*, a control signal G2*b* may be sent to an endocutter clamp to reduce endocutter clamp and fire speed in proportion to the determined high stress level (e.g., high importance level). During time period G1*c*, a control signal H2 may be sent to the endocutter clamp to increase endocutter clamp and fire speed in proportion to the determined low stress level (e.g., low importance level). The operation of the advanced energy jaw device and/or the endocutter device may be modified, for example, by implementing (e.g., executing) the control signal received from the surgical hub 20076. In various implementations, an importance level may be determined based, at least in part, on one or more biomarkers, such as one or more of heart rate, blood pressure, sweat, physical activity, body movement, or eye movement (e.g., with or without determining a stress level). In some examples, an importance level may be determined based at least in part on environmental data (e.g., with or without biomarker data). Determining criticality (e.g., stress level), receiving sensed biomarker data, environmental data, and usage data, analyzing received data, and determining instrument operational parameters, etc. (e.g., operations disclosed herein) may be performed by one or more surgical computing systems and/or surgical instruments.

Sensor data and/or environmental data may be derived from attention monitoring of one or more HCPs (e.g., using one or more surgical instruments). Attention monitoring may include, for example, one or more sensors providing data that tracks eye movements or a view (e.g., eye tracking) of an HCP to determine where an HCP attention is focused, and for how long, which may be referred to as time on target. Attention tracking may be used to determine criticality of a task and/or one or more specific portions thereof such as, for example, portions of a task or area of operation. The surgical hub 20076 may communicate more refined (e.g., more precise) information and/or parameters (e.g., feedback) to surgical instruments 20272 involved in a procedure and/or displays to improve the HCP's control of the surgical instruments 20272 (e.g., precision control of jaw actuation mechanisms), for example, by combining task criticality detection with HCP (e.g., surgeon) attention tracking and/or the time span of focus. HCP attention monitoring may be used, for example, to determine which displays and/or portions thereof an HCP may be focusing on. The hub 20076 may determine criticality (e.g., importance level) and/or change or update information displayed to an HCP on one or more monitors based (e.g., at least in part) on attention tracking. For example, sensed and/or environmental data may indicate that a surgeon's physical gestural behavior appears to show the surgeon having difficulty seeing the task/job. The hub 20076 may (e.g., in response), for example, improve the zoom and/or focus on the area of interest in a displayed image for as the surgeon and/or inquire (e.g., ask) the surgeon whether he/she would like the section magnified or overlaid with a multi-spectral feed to improve visualization.

Instrument motions and operator motions may be assessed, for example, to determine the operator of a surgical instrument. A surgical computing system 20006 may receive biomarker data (e.g., movement data) from a plurality of sensing systems. A sensing system may be associated with one of a plurality of healthcare professionals. The surgical computing system may receive usage data such as, for example, movement data, from a surgical instrument. The surgical computing system may determine which one of the plurality of healthcare providers has possession of the surgical instrument, for example, based at least on the biomarker data and usage data. For example, a surgical computing system may determine whether a healthcare provider's biomarker data (e.g., movement data) corresponds to usage data such as, for example, movement data, from the surgical instrument. The surgical computing system may determine information for communication to a healthcare provider, for example, based on possession of the surgical instrument. Information communicated to an assistant in possession of an instrument may include, for example, information associated with preparing the surgical instrument for operation. Information communicated to a physician in possession of an instrument may include, for example, information associated with previous use of the surgical instrument. Inconsistencies between data may be detected. The surgical computing system may determine the surgical instrument is not located in an area identified for performing a surgical procedure, for example, based at least on an inconsistency between the biomarker data and usage data. The surgical computing system may determine whether there is a correlation error based on an inconsistency.

Differentiation of the criticality of a task (e.g., the step at hand) in a surgical procedure (e.g., in the OR) may be implemented (e.g., used) with procedure step tracking. Procedure step tracking may be performed by the surgical computing system 20006, for example, to support (e.g., control) device operation, such as moving between "Fast and Efficient" and "Accurate and Precise" modes of operation. Fast and efficient operation may be reflected or distinguished, for example, by larger gross motions, faster clamp and release operations, accelerated articulation angle changes, higher advanced energy power levels, and/or faster firing of staplers. Accurate and precise operation may be reflected or distinguished, for example, by lower (e.g., reduced) advanced energy levels, which may result in slower operation and/or longer weld times, slower and/or finer articulation angle changes with larger delays in starting motion to minimize overshoot and/or inadvertent operation, slower stapler firing speeds, more gentle and/or slower clamp rates to improve tissue creep and/or minimize collateral tissue tension damage, etc.

Logging procedure step tracking with sensed data from the personnel (e.g., wearable) sensors and/or environmental sensors an HCP may support (e.g., allow) determination of trends and correlations. Deviations from the trends or correlations or irregularities from the trends may be highlighted to the healthcare professional, communicated to the surgical instrument, etc. In an example procedure such as, for example, a lobectomy procedure, there may be four primary jobs to perform including dissection and transection of the vessels, bronchus, parenchyma and lymph nodes. Transection of the vessels may be acritical step in the procedure. A heart rate monitor worn by the surgeon may indicate a heart rate increase as compared to a baseline heartrate around the transection of vessels portion of the procedure. The surgical computing system 20006 may determine to not react to an increased heartrate given a historical context, for example, unless the heart rate is higher than the historical average for the user. The surgical computing system 20006 may provide a communication to the healthcare provider and/or modify operation of a surgical instrument if it determines that a surgeon's heart rate for a parenchyma firing may be below the surgeon's heart rate for a vessel firing, but higher than historical heart rate data.

Speech patterns and/or a speech tone of a surgeon and/or operating room staff may be monitored by one or more sensing systems. Anxiety, stress and/or pressure may cause changes to breathing patterns, which may contribute to voice and/or speech difficulty for an HCP. An HCP's mood may change, for example, based on certain situations or agitates, which may affect an HCP's tone of speech. Anxiety, stress and/or pressure, mood changes, etc. may lead to physical behavior, such as shakiness, rapid breathing, dizziness, and/or frustration. A sensor, such as a microphone, may be used to monitor speech patterns and/or tones. The sensed data may be used by the surgical computing system 20006 to determine to adjust one or more environment variables to reduce stress and assist an HCP with maintaining focus.

The surgical computing system 20006 may determine to adjust one or more environmental characteristics or variables based on the received data. One or more operating room sounds may be changed (e.g., based on criticality), for example, to improve HCP perception and remove distractions. A monitoring system alarm and/or notification levels may be modified (e.g., reduced), for example, if an HCP is performing a critical (e.g., tense) task. Operating room lighting may be modified (e.g., based on criticality), for example, to improve contrast and/or focus while limiting distracting and/or overwhelming light intensity. One or more screens, displays, and/or content may be changed (e.g., based on criticality), for example, to alleviate pressure/stress of content displayed. For example, the surgical computing system may determine to enlarge important aspects and/or change contrast between acute elements relevant to a task or the situation at hand and/or allow secondary data to remain in a more semi-transparent state.

The surgical computing system 20006 may determine to notify an HCP regarding one or more biomarkers. The surgical computing system 20006 may determine one or more biomarkers are out of an expected range, which may indicate stress. The surgical computing system 20006 may communicate breathing instructions to the HCP to mitigate the effect. The surgical computing system 20006 may select music which may provide an audible rhythm to alter a respiratory pattern and/or other biomarker indicating HCP stress.

Figure 22:
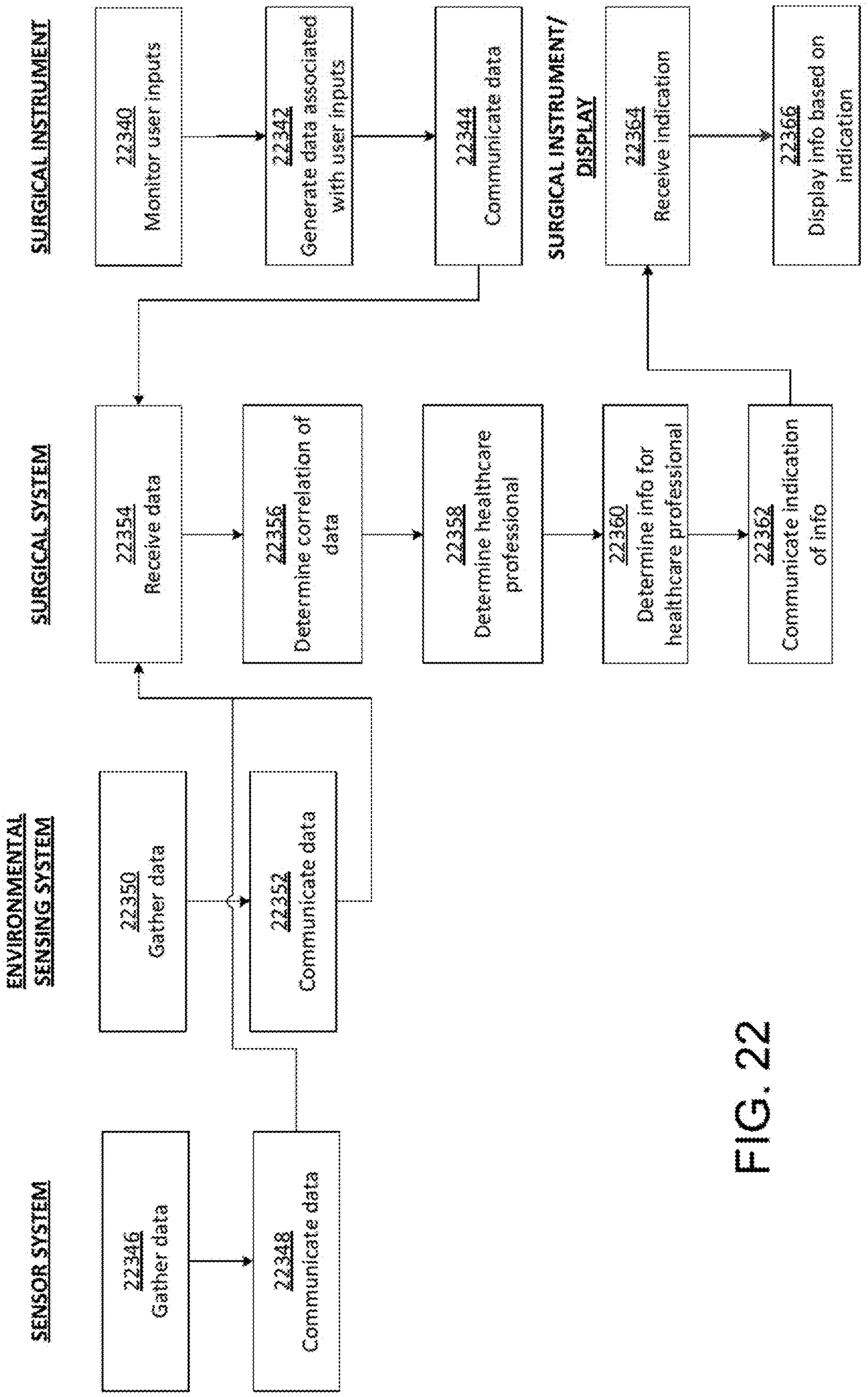
FIG. 22 illustrates example processing associated with determining possession of a surgical instrument and communication of information based on a correlation of instrument and healthcare professional motion.

FIG. 22 illustrates an example of processing associated with determining possession of a surgical instrument and communication of information based on a correlation of instrument and HCP motion. As shown in FIG. 22, at 22340, a surgical instrument, which may be a surgical instrument 20282 (e.g., as described in connection with FIG. 10), may monitor user inputs to the surgical instrument. The surgical instrument 20282 may monitor user input associated with movement and positioning of the surgical instrument 20282. The surgical instrument 20282 may employ, for example, an acceleration sensor 150712 (e.g., as shown in FIG. 17B) to monitor the movement and positioning of the surgical instrument 20282. The surgical instrument 20282 may monitor the orientation of the surgical instrument 20282 and a length of time the surgical instrument 20282 is maintained in a particular position. The surgical instrument 20282 may monitor user inputs associated with operation of controls of the surgical instrument 20282. For example, the surgical instrument 20282 may monitor inputs associated with controlling the operation of jaws for clamping patient tissue. The surgical instrument 20282 may monitor, for example, the degree that a control trigger is pressed, the speed at which the trigger is pressed, and a length of time a trigger is held in a particular control position.

At 22342, the surgical instrument 20282 may generate usage data associated with the user inputs monitored and detected by the surgical instrument 20282 at 22340. The surgical instrument 20282 may generate usage data associated with the movement and positioning of the surgical instrument 20282, and/or associated with the user inputs associated with controlling operations of the surgical instrument 20282.

At 22344, the surgical instrument 20282 may communicate the usage data to a surgical computing system which may be, for example, a surgical hub 20006.

At 22346, data associated with the one or more healthcare professionals who operate the surgical instrument(s) 20282 may (e.g., also) be gathered. Healthcare professionals operating the surgical instruments 20282 and/or who are in the area where the surgical procedure is being performed may have one or more sensing systems applied thereto. Sensing systems 20069, such as those described herein in connection with FIG. 6B, may be applied to the healthcare professionals to collect sensor (e.g., HCP biomarker) data. The sensing systems 20069 may sense and gather sensor data, which may include biometric data such as, for example, data associated with heart rate, blood pressure, respiration, temperature, sweat rate, sweat composition, frequency of blinking, etc. The sensing systems 20069 may sense and gather sensor data associated with physical activity (e.g., position, movement) and/or lack thereof (e.g., static waits) of the healthcare professional alone and/or in the aggregate with other personnel, such as, for example, position and/or movement of the healthcare professional's arms, hands, legs, and/or torso.

At 22348, the surgical instrument 20282 may communicate the sensor data to the surgical computing system 20006.

At 22350, environmental data associated with one or more conditions or attributes in a surgical environment may (e.g., also) be gathered. Conditions or attributes in a surgical environment may include, for example, one or more of a (e.g., an ambient) noise level, HCP positions, HCP movements, HCP attention location (e.g., based on eye tracking, such as location and/or time of view), surgical instrument movements, and/or patient biomarker data (e.g., patient biomarker notifications and/or alarms). One or more environmental sensing systems 20015 may be deployed in a surgical environment as part of a surgical monitoring system 20000 to collect environmental data. Environmental sensing systems 20015, such as those described herein in connection with FIG. 6B, may be activated to collect sensed environmental data. The environmental sensing system(s) 20015 may measure one more of the environmental attributes and may include, for example, cameras (e.g., for detecting an HCP's position, movements, and/or breathing pattern), spatial microphones (e.g., to measure ambient noise in the surgical theater and/or the tone of voice of a healthcare provider), climate sensor(s) (e.g., to measure temperature and/or humidity of the surroundings), etc. The environmental sensing systems 20015 may sense and gather environmental data, which may include data associated with, for example, the surgical environment, people in the surgical environment (e.g., healthcare professionals and patient), instruments in the surgical environment, etc. The environmental sensing systems 20015 may sense and gather sensor data associated with, for example, positions and/or movements of the healthcare professional including, for example, position and/or movement of the healthcare professional's arms, hands, legs, and/or torso, and/or positions and/or movements of surgical instruments.

At 22352, the environmental sensing system 20015 may communicate the environmental sensor data to the surgical computing system 20006.

At 22354, the surgical computing system 20006 may receive the sensor data from the (e.g., personnel or wearable) sensing systems 20069, usage data from the surgical instrument(s) 20282, and/or environmental data from the environmental sensing system(s) 20015.

At 22356, the surgical computing system 20006 may process the received usage data, sensor data, and/or environmental sensor data (e.g., data set(s)) and may determine whether there are one or more correlations based on the received data. The surgical computing system 20006 may be configured to determine whether the data sets indicate correlation of movements between one or more HCPs and one or more surgical instruments based on the sensor data, environmental data, and/or usage data regarding the surgical procedure and the healthcare professionals performing the surgical procedure. For example, the surgical computing system 20006, which may be, for example, situationally aware surgical hub 20076 shown in FIG. 5, may process the sensor data from the personnel or wearable sensing systems 20069, usage data from the surgical instrument(s) 20282, and/or environmental data from the environmental sensing system(s) 20015 to determine one or more correlations in movement data. For example, the surgical computing system 20006 may correlate movement of a surgeon with movement of an advanced energy device and/or an endocutter during performance of a task in a surgical procedure, as shown by example in FIG. 23. A correlation of movements may be based on, for example, environmental data from one or more operating room cameras tracking surgeon movements and instrument usage data, e.g., including accelerometer data generated by one or more accelerometer sensor(s) in the surgical instrument 20282 determined to be in use during a determined stage of a surgical operation. A surgical instrument 20282 may detect motions and orientations (e.g., by using built-in accelerometers). One or more correlations may be determined, for example, by comparing position, orientation and/or motion data for one or more surgical instruments 20282 with position and/or motion data from sensed data and/or environmental data pertaining to for one or more healthcare professionals who may be, for example, one or more surgeons, back-table nurses, assistants, and/or rotation nurses. One or more correlations may determine which healthcare professional is holding and/or using which instrument.

At 22358, the surgical computing system 20006 may determine one or more healthcare professionals in possession of and/or using one or more surgical instruments, for example, based on the one or more correlations determined at 22356. The surgical computing system 20006 may be configured to determine location, possession and/or use of surgical instruments based on correlation(s) and/or lack of correlation(s). For example, detected instrument motions and operating room detected personnel physical activities may be used to determine a location of a surgical instrument 20282 (e.g., in the operating room, not in the operating room, in the possession of a healthcare professional or not in the possession of a healthcare professional.

A surgical computing system 20006 may use detection of instrument motions and operating room personnel physical activities to determine whether there is a correlation or synchronization error in the system monitoring the sensors. For example, a surgical computing system 20006 may determine an alignment issue if instrument data indicates an instrument is moving or changing orientation in the operating room while sensor data and/or environmental data do not indicate any personnel are moving in a correlated manner. The surgical computing system 2006 may perform an analysis to determine whether there is a problem and, if so, a potential solution, for example, if the detected problem occurs over a pre-determined amount of time and/or number of motions. A surgical computing system 20006 may determine that an instrument is in a nearby operating room or storage room and is not being used in the current operating room. Solutions to a misalignment problem may include, for example, re-calibration, re-correlating, etc.

The surgical computing system 20006 may flag a synchronization issue with the data and/or may attempt to re-fuse and adjust "ad hoc" time stamping of operating room datasets, for example, if the surgical computing system 20006 determines that a healthcare professional's physical monitor appears to have similarly correlated motions that are out of sequence to the instrument motion(s).

The surgical computing system 20006 may re-calibrate and/or re-align the orientation of some or all in-room sensors to the main room coordinate system, for example, if the inverse of the motions detected by the instruments are correlated to a healthcare professional's physical biomarkers.

The surgical computing system 20006 may (e.g., visually) detect whether there are one or more healthcare professionals that are not wearing one or more sensors. The surgical computing system 20006 may attempt to re-index the room personnel, for example, if multiple (e.g., repeated) motions (e.g., over time) of a surgical instrument do not correlate to any operating room staff motions. The surgical computing system 20006 may assume that a surgical device is in another room and inadvertently paired to the incorrect surgical computing system, for example, if there are no additional detected personal. The surgical computing system 20006 may communicate with one or more adjacent operating room surgical computing systems, for example, to attempt to return monitoring of the inadvertently paired instrument to the room in which the surgical instrument is located.

At 22360, the surgical computing system 20006 may determine information for communication to one or more healthcare professionals. For example, the surgical computing system 20006 may determine information pertinent to communicate to an assistant. If the surgical device 20282 motion data correlates with motion by the assistant, such as may occur when an assistant may be preparing or reloading an instrument for a surgeon, the surgical computing system 20006 may determine based on correlated motion data that a back-table nurse has possession of a surgical instrument 20282. The usage data may indicate that the surgical device was recently fired and has not been reloaded. The surgical computing system 20006 may determine or select information to be displayed. The surgical computing system 20006 may determine the information should be displayed with emphasis, such as capitalization, highlighting, flashing or blinking. The information may indicate that the surgical device 20282 has a "used" cartridge in the jaws to minimize reintroduction of the surgical device 20282 without reloading. The surgical computing system 20006 may determine or select information to be displayed as steps-for-use. For example, the surgical computing system 20006 may determine information to be displayed associated with cleaning and/or reloading the surgical instrument 20282. Operational parameters may be adjusted in proportion to detected stress levels of a surgeon using the device. A surgical computing device 20006 may determine based on correlated motion data that a surgeon has possession of a surgical instrument 20282. The usage data may also indicate that the surgical instrument was recently fired and has not been reloaded. The surgical computing device 20006 may determine or select information to be displayed to the surgeon to indicate previous firing data and/or any notifications or alerts that occurred due to recent use of the surgical instrument 20282.

At 22362, the surgical computing system 20006 may communicate an indication of the determined information for display to the surgical instrument 20282 and/or an associated display unit such as, for example, display 20023 or other suitable display in the operating room.

At 22364, the surgical instrument 20282 and/or display unit 20023 may receive the indication of the determined information (e.g., display information). For example, a surgical stapler may receive information for a surgeon in possession of the stapler indicating previous firing data and/or any notifications or alerts that occurred due to recent use of the surgical instrument 20282.

At 22366, the surgical instrument 20282 and/or display unit 20023 may display the received information. For example, a surgical stapler and/or a related display may display information for a surgeon in possession of the stapler indicating previous firing data and/or any notifications or alerts that occurred due to recent use of the surgical instrument 20282.

The surgical computing system 20006 may receive instrument usage data, sensor data, and/or environmental data associated with numerous different surgical procedures and situations. The location, orientation, and/or motion of one or more surgical instruments, the location and/or motion of one or more healthcare professionals, and/or the possession of one or more surgical instruments determined by the surgical computing system 20006 may vary based on the received usage data, sensor data, and/or environmental data.

Figure 23:
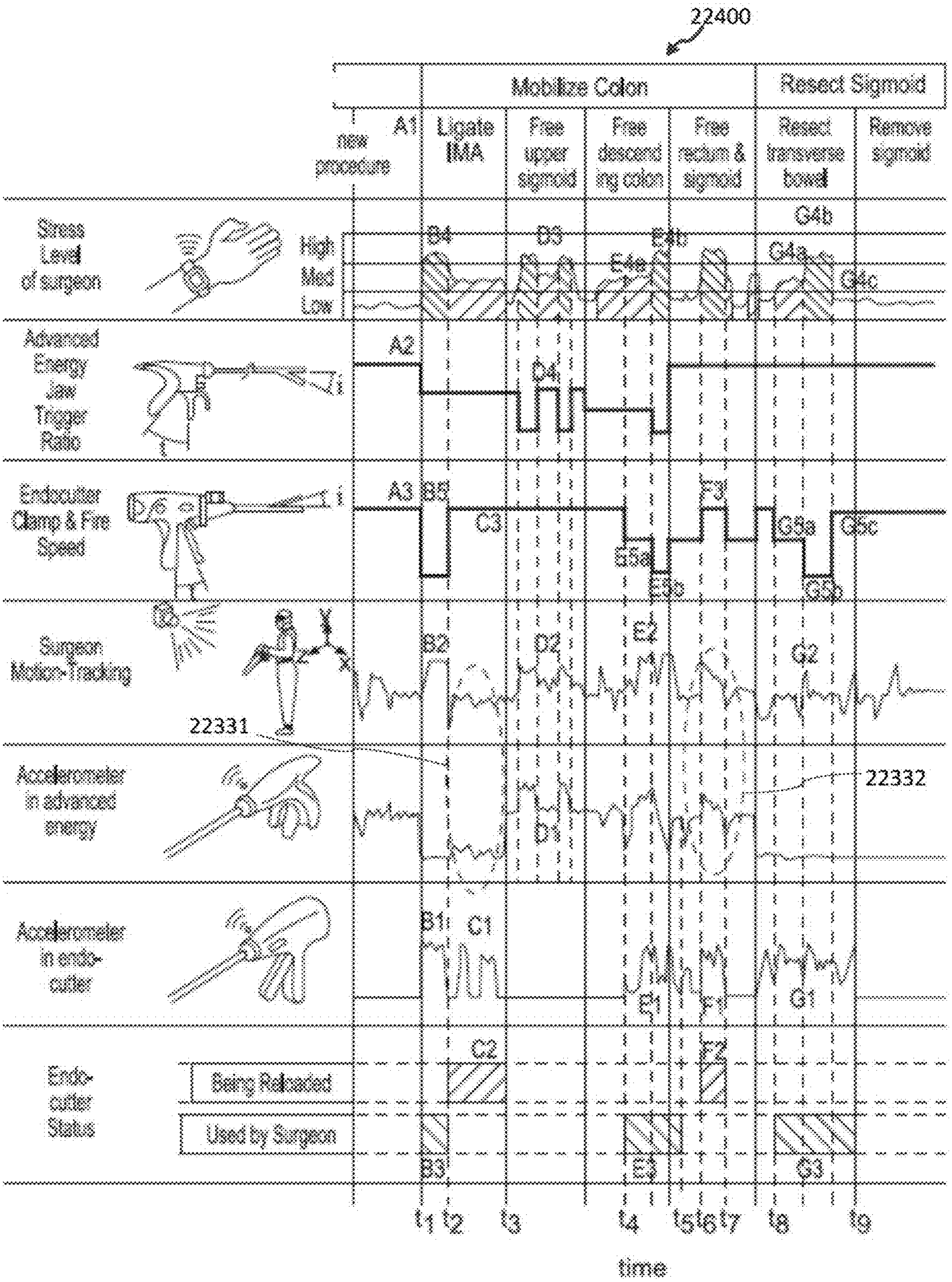
FIG. 23 illustrates an example timeline for a surgical procedure indicating possession of surgical instruments by one of multiple health care professionals based on correlation of motion data for instruments and health care professionals.

FIG. 23 depicts an example surgical procedure timeline and corresponding values associated with surgical instrument data, personnel sensor data, and/or environmental data during the surgical procedure. A surgical computing system may determine the particular healthcare professional who has possession of and is operating a surgical instrument at moments in time during the surgical procedure based upon the surgical instrument data, personnel sensor data, and/or environmental data.

A surgical computing system 20006, which may be a situationally aware surgical hub 20076 as described in connection with FIG. 5, may receive data from various data sources during the course of a surgical procedure. The surgical hub 20076 may receive instrument usage data, which may be generated by a surgical instrument such as, for example, a modular device/surgical instrument 20095, in response to a healthcare professional handling, operating, and/or utilizing the instrument. The surgical instrument may be, for example, an advanced energy device and/or endocutter. The surgical hub 20076 may receive motion data, which may be generated by accelerometer sensors within the surgical instruments. The surgical hub 20076 may receive sensor data, which may include measurement data, from one or more surgeon sensing systems 20069 for measuring one or more biomarkers associated with the surgeon, such as one or more of heart rate, sweat composition, respiratory rate, etc. The sensor data may be processed to determine, e.g., as shown in FIG. 23, low, mid and high stress (e.g., importance) levels of a surgeon during one or more phases or steps of a surgical procedure. The surgical hub 20076 may receive environmental data from one or more environmental sensing systems 20015, which may include motion data for one or more healthcare professionals and/or one or more surgical instruments 20272 from one or more motion sensing cameras 20021, which may indicate movement in multiple (e.g., three) dimensions.

The surgical hub 20076 may derive inferences, which may include contextual information, about movements in an ongoing procedure based at least in part on the usage data from the modular device/instruments 20095, motion data from the modular device/instruments 20095, sensed measurement data from the sensing systems 20069, and/or environmental data (e.g., including motion data). Motion may be indicated or determined relative to the step of the procedure that is being performed. The surgical hub 20076 may perform one or more of the following using, for example, a situational awareness system: provide data or prompts (e.g., via a display screen) that may be pertinent to a procedural step and/or the healthcare professional in possession of an instrument; adjust modular devices based on the context (e.g., activate monitors, adjust the FOV, focus and/or zoom of the medical imaging device, change the energy level of an ultrasonic surgical instrument or RF electrosurgical instrument, change clamp and fire speed, change a jaw trigger ratio); etc.

In FIG. 23, the timeline 22400 may correspond to an example colorectal surgical procedure performed using, for example, at least an advanced energy jaw device and an endocutter. Portions of the timeline that correspond to particular steps in the surgical procedure are designated using columns. As shown, columns are denoted for the following surgical procedure steps: Ligate IMA; Free upper sigmoid; Free descending colon; Free rectum & sigmoid; Resect transverse bowel; and Remove sigmoid. FIG. 23 depicts a plurality of vertically arranged rows, with each row depicting a value across time for various data items associated with the surgical procedure. Rows are designated to illustrate values for the following: stress level of the surgeon; advanced energy jaw trigger ratio; endocutter claim and fire speed; surgeon motion-tracking, accelerometer in advanced energy; accelerometer in the endocutter; and endocutter status. It will be appreciated that the top three rows, which are labelled stress level of surgeon, advanced energy jaw trigger ratio, and endocutter clamp and fire speed, generally correspond to the three rows depicted in and described in connection with FIG. 8.

Referring to FIG. 23, as shown, during the period of time before time t1, the surgical hub 20076 may derive a stress level from biomarker data received from sensing systems applied to the healthcare professional who is performing the surgical procedure. As shown, at the initial stages of the procedure prior to time t1, the surgeon's stress level is relatively low. The surgical hub 20076 may use received usage data from the advanced energy jaw device to determine an initial value for a trigger ratio as indicated in the second row. The surgical hub 20076 may rely upon received usage data from the endocutter device to determine an initial value for a clamp and fire speed for the endocutter as indicated in the third row. The surgical hub 20076 may use environment sensor data to track movements by the surgeon as depicted in a fourth row. As shown, in the period before time t1, the surgeon may be moving in preparation for the procedure. The surgical hub 20076 may use usage data including accelerometer data from the advanced energy jaw device to derive values of motion for the advanced energy jaw device as depicted in the fifth row from the top. As shown, in the period before time t1, the advanced energy jaw device may be moving, which may indicate the device may be used in the procedure. The surgical hub 20076 may use usage data including accelerometer data from the endocutter to derive values for motion associated with the endocutter as depicted in the sixth row from the top. As shown, in the period before time t1, the endocutter may not be moving indicating it is not in use or intended for imminent use. The surgical hub 20076 may use the received data to determine the status of the endocutter as indicated in a seventh row. The surgical hub 20076 may determine whether the endocutter is being reloaded or whether it is being used by the surgeon.

In FIG. 23, the steps in the surgical procedure are depicted from left to right, moving from dissection to ligating the IMA branches, etc. The surgical hub 20076 may infer procedural steps, at least based on usage data received from surgical instruments. The surgical hub 20076 may infer that the surgeon is ligating arteries and veins, for example, based on receiving data from the advanced energy jaw device and/or the endocutter indicating that the instrument is being fired. The surgical hub may receive measurement data from one of the healthcare professional's sensing systems, from which the surgical hub may derive a stress level for the healthcare provider as indicated in the top row depicted in FIG. 23. A surgical hub 20076 may determine that a healthcare professional is experiencing a higher stress level by determining the data indicates a change in the healthcare professional's heart rate from a base value. The surgical hub 20076 may derive the inference of the ligate IMA step by cross-referencing the receipt of data from the surgical stapling and cutting instrument (e.g., as indicated by A2 and A3) with the retrieved steps in the known surgical process.

The surgical hub 20076 may determine which instruments are in use and/or which HCP has possession of the instruments, for example, based on determined correlation of position and/or movement data for one or more HCPs and one or more surgical instruments 20282. For brevity, FIG. 23 shows motion tracking data for a surgeon HCP, but not an assistant HCP, who may, for example, clean and reload surgical instruments while a surgeon utilizes another surgical instrument. It will be understood that the surgical hub 20076 may receive and process data for multiple individuals in the operating room and process the information consistent with data associated with the surgeon.

As shown in FIG. 23, two phases are shown during the ligate IMA step. A phase B is depicted between times t1 and t2, and a phase C is depicted between time t2 and t3. During the phase B of the ligate IMA step of the procedure, the surgical hub 20076 may determine that the motion associated with the endocutter, as noted at B1, and which may be determined based on one or more accelerometers in the endocutter, is similar to or correlates to the motion of the surgeon, as noted at B2, which may be determined based on one or more environmental sensors. The surgical hub 20076 may determine based on the similarity or correlation, that the surgeon is using the endocutter in phase B phase of the ligate IMA step. The status of being used by the surgeon is noted at B3 in the endocutter status row.

During the period between t1 and t2, corresponding to the time that the endocutter is in use, the surgical hub 20076 may determine from biomarker data that the stress of the surgeon is elevated as noted at B4. The surgical hub 20076 may react by communicating with the endocutter to reduce the clamp and fire speed as noted at B5. While advanced energy device may not be in use, the surgical hub 20076 may anticipate per the procedure that the advanced energy device will soon be used and may adjust the jaw trigger ratio as shown in the second row. The surgical hub 20076 may determine, based on the correlation(s) of position and/or movement data, information to communicate to the surgeon via the endocutter during phase B phase of the ligate IMA step. The endocutter may display the information received from the surgical hub 20076. The information displayed may relate to the procedural steps and actions that may be taken.

Between times t1 and t2, the surgical hub 20076 may determine that advanced energy device motion shown in the fifth row is similar to or correlates with surgeon motion. The correlation is noted by the dashed oval 22331. The surgical hub 20076 may determine, based on the correlation, that the surgeon is using the advanced energy device during phase C in the ligate IMA step of the surgical procedure. The surgical hub 20076 may determine based on received biomarker data that the surgeon is experiencing medium levels of stress. The surgical hub 20076 may determine, based on the procedural step and the medium stress level, to maintain the jaw trigger ratio at its existing value. The surgical hub 20076 may determine, based on the correlation(s) of position and/or movement data, information to communicate to the surgeon via the advanced energy device during phase C of the ligate IMA step. The advanced energy device may display the information received from the surgical hub 20076.

Referring to the endocutter status row, during phase C, as indicated by C2, the surgical hub 20076 may determine that motion detected for another HCP such as, for example, a back table nurse, may correlate with endocutter motion C1. The surgical hub 20076 may determine that correlated motion alone and/or in combination with contextual information such as the endocutter usage data may indicate that the back table nurse is cleaning and reloading the endocutter while, for example, the surgeon uses the advanced energy device during phase C. The surgical hub 20076 may determine, based on the correlation(s) of position and/or movement data, information to communicate to the back table nurse via the endocutter or a related display during phase C of the ligate IMA step. The endocutter and/or related display may display the information received from the surgical hub 20076.

The HCP(s) may progress to the free upper sigmoid step of the surgical procedure which begins at time t3. During the upper sigmoid step, which may be referred to as phase D, the surgical hub 20076 may determine that the surgeon motion, indicated by D2, correlates with the motion of the advanced energy device, which is indicated by D1. The surgical hub 20076 may determine, based on the correlation, that the surgeon is using the advanced energy device during phase D. The surgical hub 20076 may determine based on received sensor data that the surgeon may be experiencing elevated stress levels during performance of the free upper sigmoid step as noted at D3. The surgical hub 20076 may communicate with the advanced energy device to adjust the advanced energy jaw trigger ratio during phase D as indicated at D4. During periods when the surgeon is experiencing high stress, the surgical hub 20076 may lower the jaw trigger ratio and may return the ratio to a second level during periods that the surgeon is experiencing medium levels of stress. The surgical hub 20076 may determine, based on the correlation(s) of position and/or movement data, information to communicate to the surgeon via the advanced energy device during phase D. The advanced energy device and/or an associated display may display the information received from the surgical hub 20076.

The healthcare professionals may progress to the free descending colon and free rectum and sigmoid steps of the procedure. During the period between time t4 and t5, which may be referred to as phase E, the surgical hub 20076 may determine that the surgeon motion, indicated at E2, correlates with the motion of the endocutter, indicated at E1. As noted at E3, the surgical hub 20076 may determine, based on the correlation, that the surgeon is using the endocutter during phase E which may span portions of the free descending colon and free rectum and sigmoid steps. The surgical hub 20076 may determine, based on the correlation(s) of position and/or movement data, information to communicate to the surgeon via the endocutter during phase E. The endocutter and/or a display may display the information received from the surgical hub 20076.

The surgical hub 20076 may determine from biomarker data that during a first portion of phase E, that the surgeon is experiencing an elevated level of stress as noted at E4*a*. The surgical hub 20076 may address the elevated stress level by communicating with the endocutter to reduce the clamping and firing speed configuration as noted at E5*a*. During a second portion of phase E, the surgical hub 20076 may determine from received biomarker data that the surgeon stress level as further increased as noted at E4*b*. The surgical hub may address the elevated stress level by communicating with the endocutter to further reduce the clamping and firing speed as noted at E5*b*.

During phase F of the free rectum and sigmoid steps of the procedure, between time t6 and t7, the surgical hub 20076 may determine that endocutter motion F1 is not similar to surgeon motion, indicating the surgeon is not using the endocutter as noted in endocutter status row of FIG. 23. The surgical hub 20076 may determine that advanced energy device motion is similar to surgeon motion, as noted in FIG. 23 by dashed oval 22332, indicating the surgeon is using the advanced energy device in performing the free rectum and sigmoid steps of the procedure. For brevity, the advanced energy status is not shown in FIG. 23. The surgical hub 20076 may determine, based on the correlation(s) of position and/or movement data, information to communicate to the surgeon via the advanced energy device.

During phase F, as indicated by F2 in FIG. 23, the surgical hub 20076 may determine that motion detected for another HCP (e.g., a back table nurse) may correlate with endocutter motion F1. The surgical hub 20076 may determine that correlated motion alone and/or in combination with contextual information (e.g., endocutter usage data) indicate the back table nurse is cleaning and reloading the endocutter while the surgeon uses the advanced energy device. While the endocutter is being reloaded, the surgical hub 20076 may communicate with the endocutter to have the clamping and firing speed reset to an initial value as indicated at F3. The surgical hub 20076 may determine, based on the correlation(s) of position and/or movement data, information to communicate to the back table nurse via the endocutter during the F phase of the free rectum and sigmoid steps of the procedure. The endocutter may display the information received from the surgical hub 20076. An HCP may progress to the resect transverse bowel step of the procedure, where the surgical hub 20076 may determine that the surgeon motion G2 between time t8 and t9 correlates with the motion of the endocutter G1, indicating the surgeon is using the endocutter as noted at G3. The surgical hub 20076 may (e.g., based on the correlation(s) of position and/or movement data) determine information to communicate to the surgeon via the endocutter and/or related display. The endocutter and/or display may display the information received from the surgical hub 20076. The surgical hub 20076 may determine, based on received biomarker data, stress levels for the surgeon during the process of resecting the transverse bowel. The surgical hub 20076 may determine that during the procedure the stress level of the surgeon may increase as noted at G4*a* and G4*b*. The surgical hub 20076 may communicate with the endocutter to adjust down the clamping and firing speed as noted at G5*a* and G5*b*. When the surgical hub 20076 determines the stress has returned to a low level, as shown at G4*c*, the speed of the endocutter returns to its initial values as shown at G5*c*.

As illustrated in FIG. 23, the surgical hub 20076 may determine and send (e.g., wirelessly communicate) information to a surgical device 20282 based on the determined correlation of position and/or motion of an HCP (e.g., based on biomarker and/or environmental data) and the surgical instrument 20282 (e.g., based on usage and/or motion data). Information determined (e.g., selected) for communication may be device-dependent, HCP-dependent, procedure-dependent, and/or procedural step-dependent. One or more surgical computing systems and/or surgical instruments may: determine instrument location, orientation, movement, and/or possession; receive sensed biomarker data, environmental data, and/or usage data; analyze received data; determine instrument information to communicate; communicate information, etc.

Instrument operation may be adjusted, for example, based on an assessment of the posture of a health care professional. A surgical computing system may receive biomarker data (e.g., from one or more sensing systems) associated with a healthcare professional operating a surgical instrument. The surgical computing system may receive usage data associated with user inputs from the surgical instrument. The surgical computing system may receive environmental data from one or more environmental sensing systems. The surgical computing system may determine an evaluation of body positioning of the healthcare professional, for example, based at least in part on the biomarker data, usage data, and/or environmental data. An evaluation of body positioning may include an evaluation of posture (e.g., body posture, arm posture, or wrist posture), balance, range of motion, and/or range of reach. The surgical computing system may determine one or more operational parameters for the surgical instrument based, for example, on the evaluation of body positioning of the healthcare professional. The surgical computing system may communicate the one or more operational parameters to the surgical instrument. Operational parameters may include, for example, parameters associated with one or more of the following: controls of the surgical instrument, stoke trigger points, an activation limit or a deactivation limit, and/or activating secondary controls. The surgical computing system may receive (e.g., from the surgical instrument) an indication to override one or more operational parameters.

Figure 24:
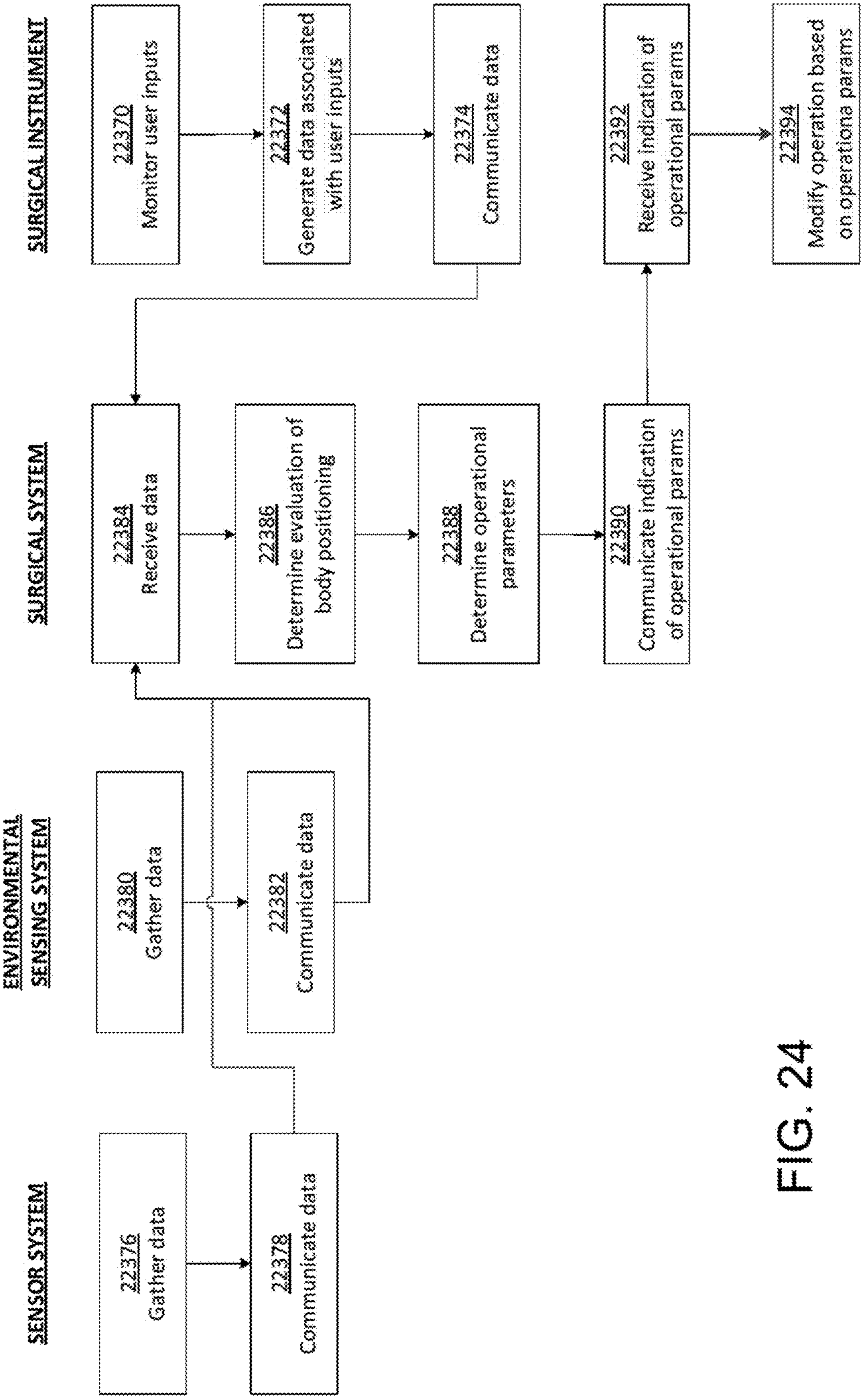
FIG. 24 illustrates example processing associated with determining operational parameters of a surgical instrument based on a determination of the positioning of a health care provider for a surgical task.

FIG. 24 illustrates example processing associated with determining operational parameters of a surgical instrument based on a determination of the positioning of a health care provider for a surgical task. FIGS. 24-27 illustrate examples of determining adjustment(s) to the operation and/or control of surgical instruments if/when an HCP using the surgical instruments exceeds one or more thresholds based on, for example, situational awareness data indicating the HCP's posture, reach, lift capacity, grip force capability, and/or other body mechanics and ergonomic limits, the position, motion and/or orientation of the surgical instruments. An HCP may be allocated a range of positions (e.g., for body, arm, wrist) between thresholds. Sensor data, environmental data, and/or instrument data, which may indicate HCP and/or instrument positioning, may be evaluated against one or more thresholds. Operational parameters of instruments may be determined, for example, based on exceeding and/or the magnitude of exceeding one or more thresholds.

Referring to FIG. 24, at 22370, a surgical instrument, which may be a surgical instrument 20282 (e.g., as described in connection with FIG. 10), may monitor user inputs to the surgical instrument. The surgical instrument 20282 may monitor user input associated with movement and positioning of the surgical instrument 20282. The surgical instrument 20282 may employ, for example, an acceleration sensor 150712 (e.g., as shown in FIG. 17B) to monitor the movement and positioning of the surgical instrument 20282. The surgical instrument 20282 may monitor the orientation of the surgical instrument 20282 and a length of time the surgical instrument 20282 is maintained in a particular position. The surgical instrument 20282 may monitor user inputs associated with operation of controls of the surgical instrument 20282. For example, the surgical instrument 20282 may monitor inputs associated with controlling the operation of jaws for clamping patient tissue. The surgical instrument 20282 may monitor, for example, the degree that a control trigger is pressed, the speed at which the trigger is pressed, and a length of time a trigger is held in a particular control position.

At 22372, the surgical instrument 20282 may generate usage data associated with the user inputs monitored and detected by the surgical instrument 20282 at 22110. The surgical instrument 20282 may generate usage data associated with the movement and positioning of the surgical instrument 20282 and/or associated with the user inputs associated with controlling operations of the surgical instrument 20282.

At 22374, the surgical instrument 20282 may communicate the usage data to a surgical computing system which may be, for example, a surgical hub 20006.

At 22376, data associated with the one or more healthcare professionals who operate the surgical instrument 20282 may (e.g., also) be gathered. Healthcare professionals operating the surgical instruments 20282 and/or who are in the area where the surgical procedure is being performed may have one or more sensing systems applied thereto. Sensing systems 20069, such as those described herein in connection with FIG. 6B, may be applied to the healthcare professionals to collect sensor data. The sensing systems 20069 may sense and gather sensor data, which may include biometric data such as, for example, data associated with heart rate, blood pressure, respiration, temperature, sweat rate, sweat composition, frequency of blinking, etc. The sensing systems 20069 may sense and gather sensor data associated with physical activity (e.g., movement) and/or lack thereof (e.g., static waits) of the healthcare professional alone and/or in the aggregate with other personnel, such as, for example, movement of the healthcare professional's arms (e.g., shoulders, elbows, wrists), hands, legs, feet, and/or torso.

At 22378, the surgical instrument 20282 may communicate the sensor data to the surgical computing system 20006.

At 22380, environmental data associated with one or more conditions or attributes in a surgical environment may be gathered and may be used to determine the importance of phases or steps in a surgical procedure. Conditions or attributes in a surgical environment may include, for example, one or more of a noise (e.g., ambient noise) level, HCP positions, HCP movements, HCP attention location, which may be based on eye tracking, such as location and/or time of view, and/or patient biomarker data, which may comprise patient biomarker notifications and/or alarms. One or more environmental sensing systems 20015 may be deployed in a surgical environment as part of a surgical monitoring system 20000 to collect environmental data. Environmental sensing systems 20015, such as those described herein in connection with FIG. 6B, may be activated to collect sensor data. The environmental sensing system(s) 20015 may include systems for measuring one more of the environmental attributes and may include, for example: cameras which may be configured to detect a surgeon's position, movements, and/or breathing pattern; spatial microphones which may be configured to measure ambient noise in the surgical theater and/or the tone of voice of a healthcare provider; and climate sensor(s) which may be configured to measure temperature and/or humidity of the surroundings. The environmental sensing systems 20015 may sense and gather environmental data, which may include data associated with, for example, the surgical environment, people in the surgical environment (e.g., healthcare professionals and patient), instruments in the surgical environment, etc. The environmental sensing systems 20015 may sense and gather sensor data associated with, for example, positions and/or movements of the healthcare professional (e.g., position and/or movement of the healthcare professional's arms, hands, legs, and/or torso) and/or movement of surgical instruments.

At 22382, the environmental sensing system 20015 may communicate the environmental sensor data to the surgical computing system 20006.

At 22384, the surgical computing system 20006 may receive the sensor data from the (e.g., personnel or wearable) sensing systems 20069, usage data from the surgical instrument(s) 20282, and/or environmental data from the environmental sensing system(s) 20015. For example, an HCP's wearable sensing system and/or an environmental sensing system may inform a surgical instrument 20082 and/or a surgical hub 20076 with sensor data and/or environmental data that may indicate the healthcare provider is exceeding one or more threshold limits of awkwardness, lack of balance, and/or over-extended reach. User body positioning (e.g., posture and balance precariousness) may be monitored, for example, to enable the surgical hub 20006 to compensate with operation and/or control adjustments for a surgical instrument 20282 to reduce or minimize the impact of awkward body positioning on the user.

At 22386, the surgical computing system 20006 may process the received usage data, sensor data, and/or environmental sensor data (e.g., data set(s)) and may evaluate the body positions of one or more HCPs based on the received data. The surgical computing system 20006 may be configured to determine body positions based on the indications from the sensor data, environmental data, and/or usage data regarding the surgical procedure and the healthcare professionals performing the surgical procedure. For example, the surgical computing system 20006, which may be, for example, a situationally aware surgical hub 20076 described in connection with FIG. 5, may process the sensor data from the personnel or wearable sensing systems 20069, usage data from the surgical instrument(s) 20282, and/or environmental data from the environmental sensing system(s) 20015 to determine HCP body positions which may comprise body positions relative to one or more surgical instruments. The surgical computing system 20006 may determine the position of one or more body parts for one or more HCPs, such as one or more of the following: head, face, body, chest, arms (e.g., shoulder, elbow, wrist), hands, legs (e.g., hips, knees, ankles), feet, etc. The surgical computing system 20006 may evaluate the determined positions of one or more body parts (e.g., alone or in combination) in comparison to one or more body thresholds Br and/or to other information, such as the time period one or more positions are held and/or out of range, the location, position, orientation, motion pertaining to one or more surgical instruments, the location, position, and/or motion of one or more HCPs, and/or the portion, step or phase of the surgical procedure. For example, an evaluation may assess body position relative to a body position range $B_{Trange}$ between body position thresholds Br. The surgical computing system 20006 may determine to make adjustments if/when a body (or a portion thereof) is out of a body position range $B_{Trange}$ in excess of a body position threshold Br. The center of a body position range $B_{Trange}$ may be a body position balance. An evaluation may assess arm (e.g., shoulder, elbow, wrist) position relative to an arm position range $A_{Trange}$ between arm position thresholds Ar. The surgical computing system 20006 may determine to make adjustments if/when an arm (e.g., or a portion thereof) is out of an arm position range $A_{Trange}$ in excess of an arm position threshold Ar. The center of an arm position range $A_{Trange}$ may be an arm position balance. An evaluation may be based on, for example, the surgical instrument determined to be in use (e.g., and by whom based on sensor and/or environmental data) during a determined stage of a surgical operation.

At 22388, the surgical computing system 20006 may determine one or more operational parameters for one or more surgical instruments based on the body position evaluation determined at 22386. The surgical computing system 20006 may be configured to determine (e.g., translate or map) the determined body position(s) (e.g., alone or relative to one or more surgical instruments) determined at 22386 to one or more operational parameters for one or more surgical instrument in use during the determined task. Surgical instrument operation and control may be adapted, for example, because body position and/or instrument position (e.g., momentary and over time) may impact fatigue, stress, balance, strength, range of motion, hand/arm reach and/or other capabilities of an HCP. Surgical hub 20006 and/or surgical instrument 20282 may determine (e.g., select and/or adjust) operational parameters, for example, to minimize inadvertent or unintentional actuation (e.g., activation, deactivation), incomplete strokes, bumping secondary controls, confusion due to inverted controls, and/or the like. In some examples, actuation (e.g., activation, deactivation) forces of a surgical instrument may be tracked and adjusted if/when a user (e.g., an HCP, such as a surgeon) is determined to be in an awkward position/orientation that may limit the user's capabilities. In some examples, the limits to activate and/or deactivate (e.g., engage and/or disengage) physical and/or virtual controls may be changed based on received position data. For example, surgical computing system 20006 and/or surgical instrument 20282 may complete control actuations that near the limits of the actuators range, and may implement wait times before activating opposing motions or deactivation trigger actuations to minimize the possibility of inadvertent micro-release causing unintended actions. A hub 20006 and/or surgical instrument 20282 may adjust instrument operation and/or control based on HCP body positioning, such as posture (e.g., body posture, arm posture, or wrist posture), balance, range of motion, range of reach (e.g., hand and/or arm reach), etc. Adjustment(s) may be applied to any suitable aspect of a surgical instrument including, for example: actuators, activation/deactivation positions, ranges, forces and/or stokes, and which controls are active/inactive including, for example, additional or alternative actuators such as a remote actuator.

The surgical hub 20006 and/or instrument 20282 may adjust operation parameters (e.g., stoke trigger points, an activation limit, a deactivation limit), activate/deactivate secondary controls, and/or adjust other operation and/or controls of the surgical instrument 20282 based, for example, on the HCP's compromised orientation/posture. Actuation controls in a surgical instrument 20282 such as, for example, a powered surgical stapler, may have hall effect sensors for monitoring a range (e.g., a full range) of actuator motion. Activation controls may have an "activation" stoke location and a "deactivation" stoke location on the actuator release action. Activation and deactivation stoke locations may be separate from each other, for example, to calibrate tolerance of the instrument control (e.g., to start and stop the motor uniformly/repeatably from one instrument to the next). Stokes trigger points may be adjusted to minimize stress on the user, for example, if the user is in awkward orientations with respect to the instrument control.

In some examples, the surgical hub 20006 and/or instrument 20282 may adjust the activation and deactivation limits of the controls for the surgical instrument 20282 independently, e.g., depending on the detected range-of-motion limits of the user being exceeded. For example, the hub 20006 and/or the surgical instrument 20282 may determine that the surgical instrument 20282 is at the limit of an HCP's arm reach. The hub 20006 and/or instrument 20282 may adjust (e.g., increase) the activation limit, for example, to minimize a false positive activation as may occur if the user inadvertently squeezed the trigger while extending reach to the control. The hub 20006 and/or the surgical instrument 20282 may (e.g., by contrast) adjust the "deactivation" limit to or near zero, for example, so that once the user has the actuator in motion, the actuator may continue to move until the user releases (e.g., fully releases) the trigger. The independent control of activation and deactivation may be based on one or more assumptions, which may be conditionally based on determined body positioning. For example, the hub 20006 and/or instrument 20282 may determine control of instrument 20282 based on an assumption that a user in one or more awkward body positions may inadvertently reduce pressure on the control over time and/or stop/pause, for example, due to fatigue of the spring load of the trigger during use.

The hub 20006 and/or instrument 20282 may control devices differently for similar body positioning. The control may be device specific. In some examples, the controls of a powered surgical instrument 20282 may be spring biased into the disengaged state and/or the stoke limit triggers for activation and deactivation may be adjustable. The amount of control displacement may be adjustable. The force to activate and/or deactivate the control may be adjustable. A user may be holding an endocutter in an inverted position relative to the user in order to get the correct angle of the end-effector to the transection site given the articulation and shaft rotation limitations. The endocutter may also be vertical to the patient due to the patient positioning on the table to get appropriate surgical site access. One or more sensing systems 20011 and/or environmental sensing systems 20015 that sense physical activity may indicate to the surgical hub 20006 and/or the endocutter that the HCP (e.g., surgeon) is at full arm reach with his/her hand upside down to the handle of the endocutter while leaning over the table and in a poorly balanced posture. The sensing systems 20011 and/or environmental sensing systems 20015 may communicate the ergonomic threshold limits to the hub 20006, which may communicate updated control algorithms to the endocutter. The updated control algorithms may reduce the force threshold on the actuators of the endocutter controls so that the HCP may pull the triggers with less force while at the limits of hand and/or arm reach. The updated control algorithms may create a larger delay between control actuation and actuator energizing, for example, to minimize inadvertent control actuation while the HCP may be in an extended or unbalanced state.

Operation and/or control adjustments for one or more actuator control algorithms for one or more surgical instruments may be based on general adjustments applicable to multiple HCPs and/or specific adjustments applicable to a specific HCP. Operation and control of surgical instruments 20282 may be situation-specific, device-specific and/or user-specific. For example, a surgical hub 20006 and/or surgical instrument 20282 may determine adjustments to instrument operation and/or controls (e.g., forces and strokes) based on the frame size or body type of the detected user. Adjustments for surgical instruments (e.g., based on position-based parameters) may be determined (e.g., selected) from user-specific categories based on one or more physical characteristics of HCPs, such as one or more of sex, age, height, weight, arm length, torso length, etc. Adjustment (e.g., of control loop) operation and/or controls of surgical instruments 20282 may be based on the situation-specific and/or user-specific unique needs of the user in the sensed situation.

A surgical computing system or hub 20006 and/or a surgical instrument 20282 may, in connection with determining operational parameters and based on body position data for a user, enable pairing or utilization of an additional and/or alternative actuator (e.g., a remote actuator) to operate the device in addition to or in place of the (e.g., built-in) actuator. A user may be unable, due to, for example, orientation and/or posture, to access one or more configured actuation controls, which may mean that adjusting the inaccessible controls may not assist the user. Additional and/or alternative controls may be (e.g., selectively) activated for a user, for example, based on user positional data. Additional and/or alternative controls may be on a surgical device 20282 and/or remote from the surgical device 20282. Additional and/or alternative controls may be dedicated and/or multi-purpose controls, which may be selectable and/or pairable with one or more operations of a surgical device 20282.

At 22390, the surgical computing system 20006 may communicate an indication of the determined operational parameters to the surgical instrument 20282. The surgical computing system 20006 may be configured to communicate an indication to a surgical instrument 20282 determined to be in use during the determined task of the surgical procedure.

At 22392, the surgical instrument 20282 may receive the indication of the determined operational parameters. For example, an endocutter may receive operational parameters that reduce the force threshold on the actuators of the endocutter controls so that the HCP may pull the triggers with less force.

One or more operational parameters and/or adjustments thereto may be overridden via, for example, a surgical instrument 20282 and/or a surgical hub 20006. A healthcare professional may reject one or more operational parameters such as, for example, adjusted operational parameters, and the surgical instrument 20282 may indicate the user's override to the surgical hub 20076. A user may reject/override operational parameters generally and/or specifically. An override indication provided by a user to a surgical hub 20006 and/or surgical instrument 20282 may be, for example, verbal, gestural, manual, etc.

At 22394, the surgical instrument 20282 may, if the operational parameters are not overridden, modify operation based upon the received indication of the determined operational parameter(s). For example, an endocutter surgical instrument 20282 may reduce the force threshold on the actuators of the endocutter controls so the HCP may pull the triggers with less force.

The surgical computing system 20006 may receive instrument usage data, sensor data, and/or environmental data associated with numerous different surgical procedures and situations. The importance level, attention to task, and/or operational parameters determined by the surgical computing system 20006 may vary based on the received usage data, sensor data, and/or environmental data.

For example, with reference to the timeline 20265 for a surgical colorectal procedure shown in FIG. 2A, the surgical computing system 20006, which may be, for example, situationally aware surgical hub 20076 described in connection with FIG. 5, may receive data from various data sources throughout the course of the surgical procedure. The surgical hub 20076 may receive instrument usage data indicating instrument location, positioning and/or orientation, which may be generated each time an HCP utilizes a modular device/instrument 20095 that is paired with the surgical hub 20076. A modular device/instrument 20095 may be, for example, an advanced energy device and/or endocutter. The surgical hub 20076 may receive sensor data, which may be measurement data, from one or more surgeon sensing systems 20069 indicating body positioning associated with the surgeon. The surgical hub 20076 may receive environmental sensor data from one or more environmental sensing systems 20015 indicating body positioning associated with the surgeon. The body positioning data may be processed by the surgical hub 20076 to determine one or more operational and/or control adjustments for one or more surgical instruments 20095 during one or more phases or steps of a surgical procedure to compensate for determined body positioning of an HCP.

Figures 25A, 25B:
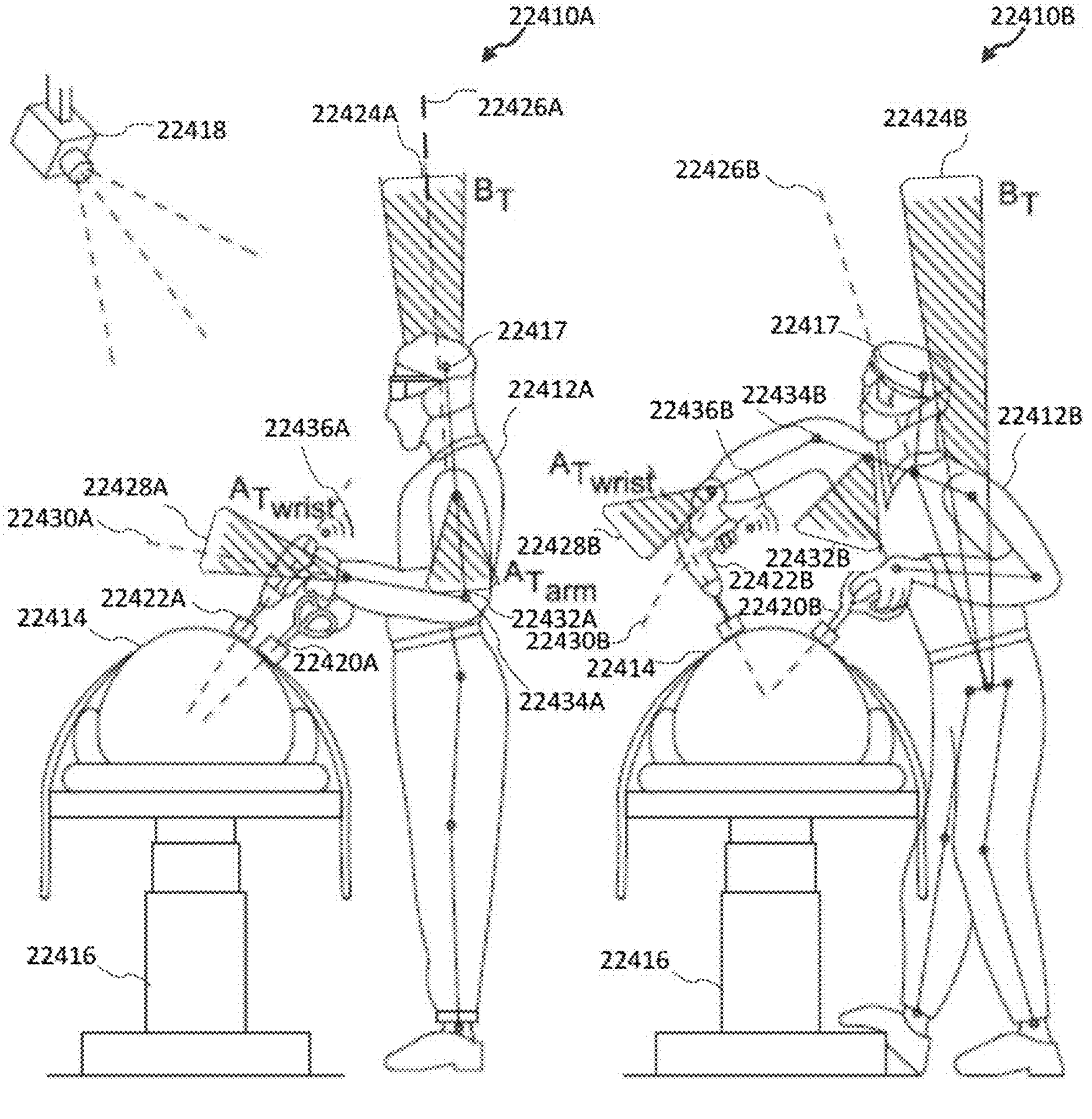
FIGS. 25A and 25B illustrate example body positioning of a health care professional in ergonomic range and out of ergonomic range, respectively, while performing surgical tasks.

FIGS. 25A and 25B illustrate example body positioning of a health care provider in ergonomic range (FIG. 25A) and out of ergonomic range (FIG. 25B), respectively, while performing surgical tasks. FIGS. 25A and 25B show examples of a surgeon 25412 in a first operating room (OR) scene 22410A and a second OR scene 22410B. In the first OR scene 22410A, the surgeon 25412A is shown with body, arm, and wrist positions within ergonomic ranges. In the second OR scene 22410B, the surgeon 25412B is shown with body, arm, and wrist positions outside ergonomic ranges. One or more monitored body parts may be in or outside respective ergonomic ranges.

Referring to FIG. 25A, a surgeon 25412A, a first instrument 22420A, and a second instrument 22422A are shown in first positions, which are designated by A, which may indicate the surgeon 22412A is performing a first portion of a surgical procedure on the patient 22414 positioned on operating table 22416. The first body positions/orientations of the surgeon 22412A may be tracked, for example, by one or more wearable sensors 22417 on the body of the surgeon 22412A and/or one or more environmental sensors (e.g., cameras) 22418 in the OR. The first positions of the first surgical instrument 22420A and the second surgical instrument 22422A may be tracked, for example, by one or more sensors (e.g., accelerometers) on or in the first and second surgical instruments 22420A, 22422A and/or by one or more environmental sensors (e.g., cameras) 22418 in the OR. The first surgical instrument 22420A may comprise a passive surgical instrument without positioning/orientation sensors, such as a clamp, and the second surgical instrument 22422A may comprise a powered instrument with positioning/orientation sensors such as, for example, an endocutter. The second instrument 22422A may wirelessly communicate 22436A usage, position, and/or orientation data, for example, with a surgical computing system.

As shown in scene 22410A, the surgeon's body (e.g., torso) position (e.g., body angle or balance) 22426A, which may be tracked by one or more sensors, is within an ergonomic body position range 22424A. The ergonomic body position range 22424A is indicated as the area between ergonomic body positioning thresholds Br. A surgical computing system 20006, which may be a situationally aware surgical hub 20076, may not adjust the operating parameters of the second surgical device 22422A based on a determination that the surgeon's body position 22426A is within the ergonomic body position range 22424A, which may be predefined (e.g., as a default and/or custom range).

The surgeon's arm position (e.g., arm angle) 22434A, which may be tracked by one or more sensors, is within an ergonomic arm position range 22432A. The ergonomic arm position range 22432A is indicated as the area between ergonomic arm positioning thresholds $A_{Tarm}$. A surgical computing system 20006, which may be a situationally aware surgical hub 20076, may not adjust the operating parameters of the second surgical device 22422A based on a determination that the surgeon's arm position 22434A is within the ergonomic arm position range 22432A, which may be predefined (e.g., as a default and/or custom range).

The surgeon's wrist position (e.g., wrist angle) 22430A, which may be tracked by one or more sensors, is within an ergonomic wrist position range 22428A. The ergonomic wrist position range 22428A is indicated as the area between ergonomic wrist positioning thresholds $A_{Twrist}$. A surgical computing system 20006 may not adjust the operating parameters of the second surgical device 22422A based on a determination that the surgeon's wrist position 22430A is within the ergonomic wrist position range 22428A, which may be predefined (e.g., as a default and/or custom range).

FIG. 25B shows an example of a second OR scene 22410B, where the surgeon 25412B, the first instrument 22420B, and the second instrument 22422B are in second positions designated B, which may indicate the surgeon 22412B is performing a second portion of a surgical procedure on the patient 22414 positioned on operating table 22416. The second body positions/orientations of the surgeon 22412B may be tracked, for example, by one or more wearable sensors 22417 on the body of the surgeon 22412B and/or one or more environmental sensors (e.g., cameras) 22418 in the OR. The second positions of the first surgical instrument 22420) Band the second surgical instrument 22422B may be tracked, for example, by one or more sensors (e.g., accelerometers) on or in the first and second surgical instruments 22420B, 22422B and/or by one or more environmental sensors (e.g., cameras) 22418 in the OR. In an example, the first surgical instrument 22420B may comprise a passive surgical instrument without positioning/orientation sensors, such as a clamp, and the second surgical instrument 22422B may comprise a powered instrument with positioning/orientation sensors (e.g., an endocutter). The second instrument 22422B may wirelessly communicate 22436B usage, position, and/or orientation data, for example, with a surgical computing system (not shown).

As shown in the second OR scene 22410B, the surgeon's body (e.g., torso) position (e.g., body angle or balance) 22426B, which may be tracked by one or more sensors, may be outside an ergonomic body position range 22424B. The ergonomic body position range 22424B is indicated as the area between ergonomic body positioning thresholds Br. A surgical computing system 20006, which may be a situationally aware surgical hub 20076, may adjust the operating parameters of the second surgical device 22422B based on a determination that the surgeon's body position 22426B is outside the ergonomic body position range 22424B, which may be predefined (e.g., as a default and/or custom range).

As shown in the second OR scene 22410B, the surgeon's arm position (e.g., arm angle) 22434B, which may be tracked by one or more sensors, is outside an ergonomic arm position range 22432B. The ergonomic arm position range 22432B is indicated as the area between ergonomic arm positioning thresholds $A_{Tarm}$. A surgical computing system 20006, which may be a situationally aware surgical hub 20076, may adjust the operating parameters of the second surgical device 22422B based on a determination that the surgeon's arm position 22434B is outside the ergonomic arm position range 22432B, which may be predefined (e.g., as a default and/or custom range).

As shown in the second OR scene 22410B, the surgeon's wrist position (e.g., wrist angle) 22430B (e.g., as tracked by one or more sensors) is outside an ergonomic wrist position range 22428B. The ergonomic wrist position range 22428B is indicated as the area between ergonomic wrist positioning thresholds $A_{Twrist}$. A surgical computing system 20006 (e.g., a situationally aware surgical hub 20076) may (e.g., as described herein) adjust the operating parameters of the second surgical device 22422B based on a determination that the surgeon's wrist position 22430B is outside the ergonomic wrist position range 22428B, which may be predefined (e.g., as a default and/or custom range).

Figure 26B:
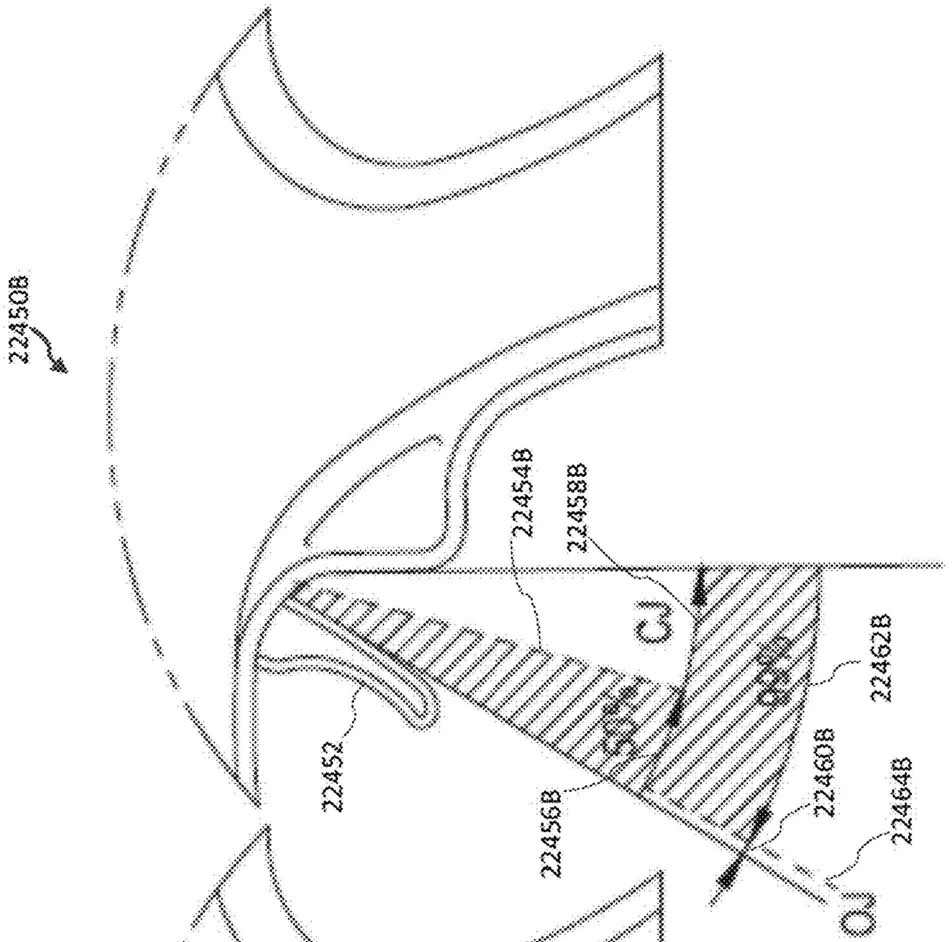
FIGS. 26A and 26B illustrate example adjustments to controls of a surgical instrument based on body positioning of a health care provider determined to be in ergonomic range and out of ergonomic range, respectively, while performing surgical tasks.
Figure 26A:
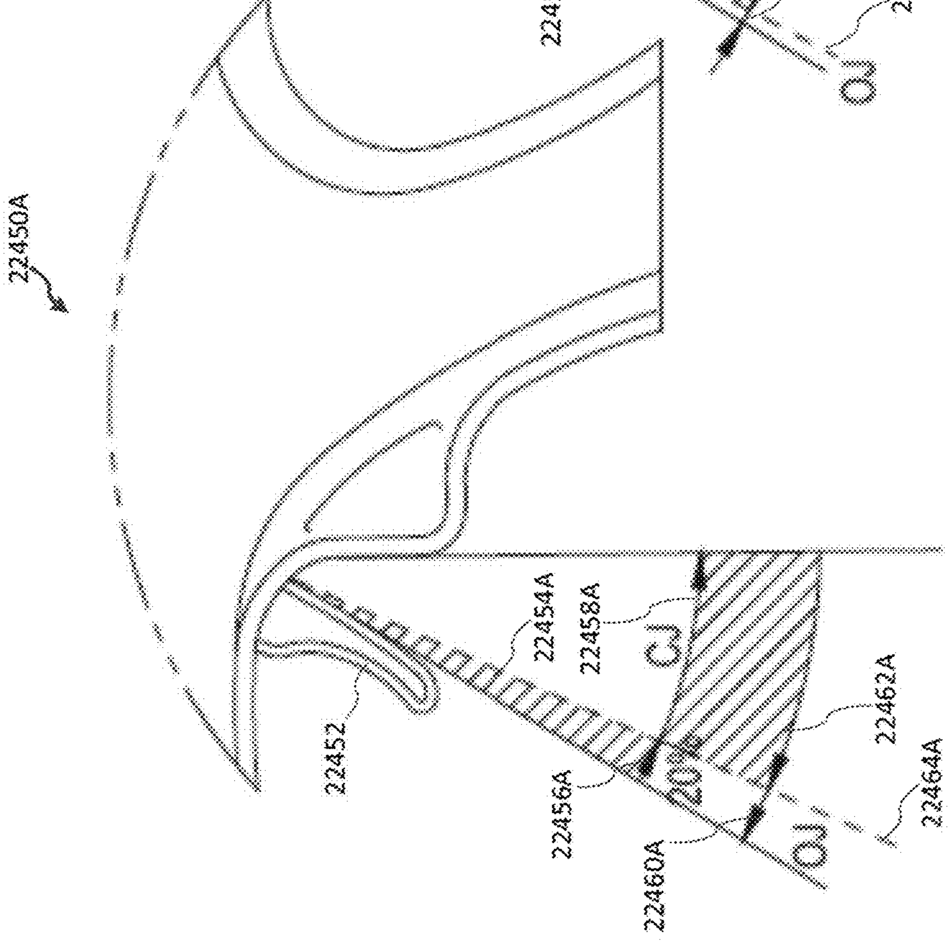

FIGS. 26A and 26B illustrate examples of determining adjustments to controls of a surgical instrument based on body positioning of a health care provider determined to be in ergonomic range and out of ergonomic range, respectively, while performing surgical tasks. FIG. 26A shows an example of an unadjusted (e.g., default or original) control parameter configuration of a surgical instrument and FIG. 26B shows an example of an adjusted (e.g., adapted) control parameter configuration of the surgical instrument. In the examples shown in FIGS. 26A and 26B, trigger activation and deactivation are independently controlled by automated adjustment based on determined body position/orientation and/or surgical device position/orientation. Trigger activation and deactivation may be dependently controlled by automated adjustment based on determined body position/orientation and/or surgical device position/orientation).

FIG. 26A shows an example of an unadjusted (e.g., default or original) trigger control parameter configuration 22450A of the second surgical instrument 22422A in the first OR scene 22410A shown in FIG. 25A, where the body position 22426A, arm position 22434A and wrist position 22430A of the surgeon 22412A are, respectively, within the ergonomic body position range 22426A, the ergonomic arm position range 22432A, and the ergonomic wrist position range 22430A.

As shown by example in the unadjusted control parameter configuration 22450A, a trigger 22452 for a surgical device, which may be, for example, an endocutter, may be configured (e.g., by control algorithm operating parameters) to close jaws (e.g., end effector 20289 jaws, such as a first jaw 20291 and a second jaw 20290) at a first jaw closure activation limit 22454A. As shown in FIG. 26A, the first jaw closure activation limit 22454A may be a 20% trigger stroke, where the jaws remain open during a first range 22456A (e.g., from 0% to 20% trigger stroke) and close in a second (close jaw (CJ) range 22458A (e.g., from 20% to 100% trigger stroke).

As shown by example in the unadjusted control parameter configuration 22450A, the trigger 22452 for the surgical device (e.g., an endocutter) may be configured (e.g., by control algorithm operating parameters) to open already closed jaws (e.g., end effector 20289 jaws, such as a first jaw 20291 and a second jaw 20290) at a first jaw closure deactivation limit 22464A. In an example (e.g., as shown in FIG. 26A), the first jaw closure deactivation limit 22464A may be a 20% trigger stroke, where the jaws remain closed during a first range 22462A (e.g., from 100% to 20% trigger stroke) and open in a second (open jaw (OJ) range 22460A (e.g., from 20% to 0% trigger stroke).

FIG. 26B shows an example of an adjusted (e.g., adapted) trigger control parameter configuration 22450B of the second surgical instrument 22422B in the second OR scene 22410B shown in FIG. 25B, where the body position 22426B, arm position 22434B and/or wrist position 22430B of the surgeon 22412B may be, respectively, outside the ergonomic body position range 22424B, the ergonomic arm position range 22432B, and the ergonomic wrist position range 22430B. A surgical computing system 20006, which may be a situationally aware surgical hub 20076, may adjust the operating parameters of the first surgical device 22422A (e.g., with the unadjusted trigger control parameter configuration 22450A) to the second surgical device 22422B (e.g., with the adjusted trigger control parameter configuration 22450B) based on a determination that the surgeon's body position 22424B, arm position 22434B, and/or wrist position 22428B is, respectively, outside the ergonomic body position range 22426B, the ergonomic arm position range 22432B, and/or the ergonomic wrist position range 22430B. The closure activation and/or closure deactivation limits may be adjusted, for example, to alleviate or compensate for limited capabilities of the surgeon 22412B in one or more awkward positions/orientations.

In the adjusted control parameter configuration 22450B, the trigger 22452 for the surgical device (e.g., an endocutter) may be configured (e.g., adjusted by control algorithm operating parameters) to close jaws (e.g., end effector 20289 jaws, such as a first jaw 20291 and a second jaw 20290) at a first jaw closure activation limit 22454B. In an example (e.g., as shown in FIG. 26B), the first adapted jaw closure activation limit 22454B may be a 50% trigger stroke, where the jaws remain open during a first adjusted range 22456B (e.g., from 0% to 50% trigger stroke) and close in a second adjusted (close jaw (CJ)) range 22458B (e.g., from 50% to 100% trigger stroke). The closure activation limit may be adjusted (e.g., increased from 20% to 50%), for example, to minimize unintended/false positive activation when the surgeon's hand and/or arm position is/are extended out of range.

In the adjusted control parameter configuration 22450B, the trigger 22452 for the surgical device (e.g., an endocutter) may be configured (e.g., by control algorithm operating parameters) to open already closed jaws (e.g., end effector 20289 jaws, such as a first jaw 20291 and a second jaw 20290) at a first jaw closure deactivation limit 22464B. In an example (e.g., as shown in FIG. 26B), the first jaw closure deactivation limit 22464B may be a 1% trigger stroke, where the jaws remain closed during a first adjusted range 22462B (e.g., from 100% to 1% trigger stroke) and open in a second adjusted (open jaw (OJ) range 22460B (e.g., from 1% to ( ) trigger stroke). The closure deactivation limit may be adjusted (e.g., decreased from 20% to 1%), for example, to account for the surgeon inadvertently releasing the trigger 22452 over time due to fatigue (e.g., in the surgeon's finger squeezing the trigger 22452).

Figure 27:
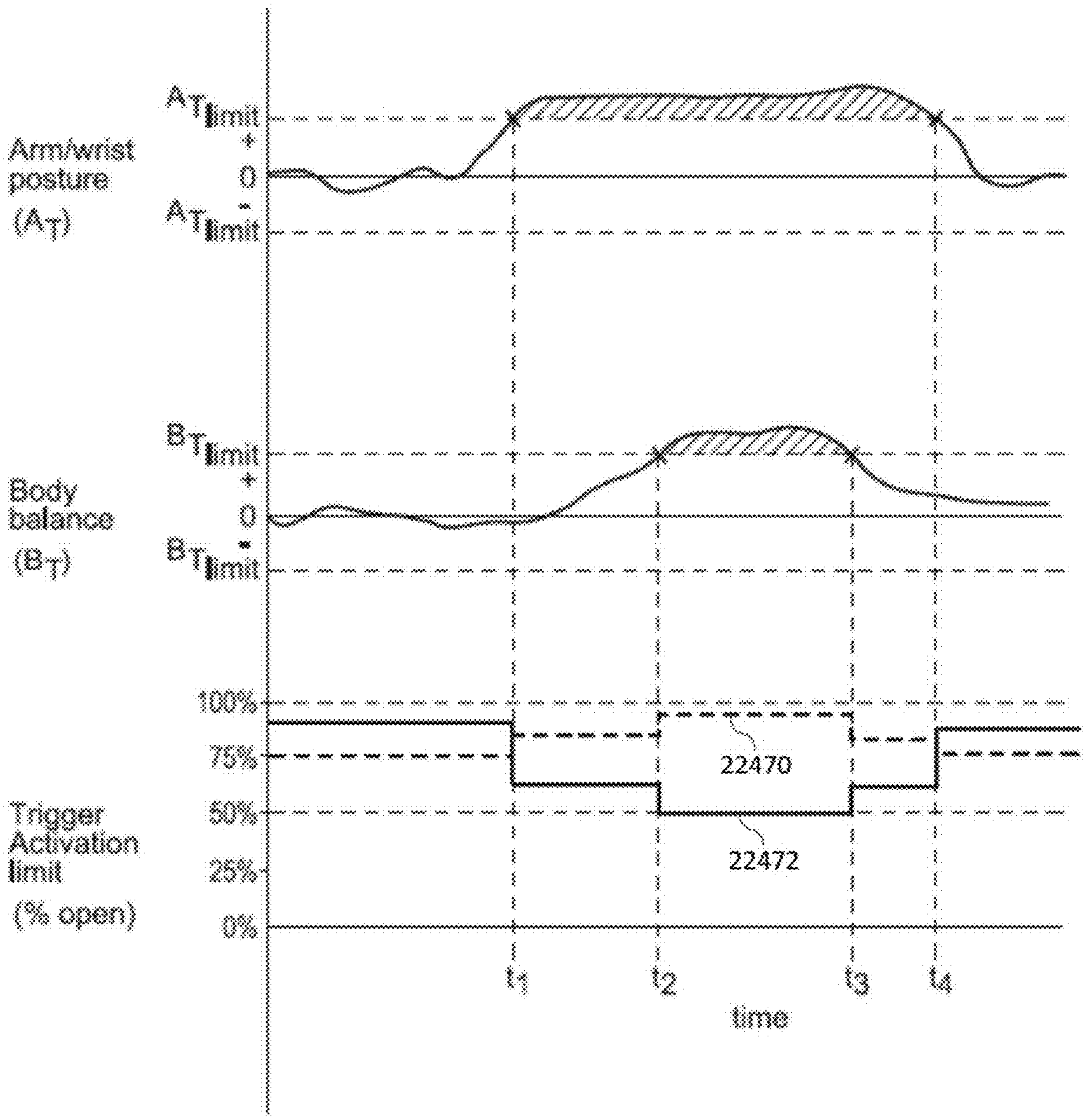
FIG. 27 illustrates example monitoring the body positioning of a health care provider performing surgical tasks with a surgical instrument and determining adjustments to operation or controls of the surgical instrument based on whether the body positioning is determined to be in ergonomic body positioning range.

FIG. 27 illustrates processing to modify operation controls of surgical instrument based on monitoring of body position and arm/wrist posture of a healthcare profession who is handling a surgical instrument. In the top portion of FIG. 27, a value representing arm/wrist posture of a healthcare professional is graphed across time. The healthcare professional may be handling a surgical instrument such as, for example, a surgical instrument 22422 as described in connection with FIGS. 25A, 25B, 23A, and 23B. Two thresholds are shown, a positive $A_{Tlimit}$ and a negative $A_{Tlimit}$, which together define an acceptable range for arm/wrist posture during a surgical procedure. The values representing the arm/wrist posture may be sensed by sensing systems and environment systems and communicated to a surgical computing system 20006.

A graph of a value representing the healthcare professional's body balance or posture across time is depicted below the arm/wrist posture data. Two thresholds are depicted, a positive $B_{Tlimit}$ and a negative $B_{Tlimit}$, which together define an acceptable range for the healthcare professional's body position while performing the surgical procedure. The values representing the body posture may be sensed by sensing systems and environment systems and communicated to a surgical computing system 20006.

Below the graph of the body balance is a graph of a trigger activation limit for jaw clamping and jaw unclamping across time that may be associated with the surgical instrument 22422 and its trigger 22452. The trigger activation limit is defined as a percentage of opening of the trigger, with zero percent corresponding to the trigger being fully closed and one hundred percent corresponding to the trigger being fully open. The trigger activation limit for jaw clamping is depicted by line 22472. The trigger activation limit for jaw unclamping is depicted by line 22740. The surgical computing system 20006 may determine to modify the jaw clamping and unclamping limits based upon the hand/wrist posture and body posture and whether they remain within defined thresholds.

As shown, in the time period before time t1, the arm/wrist posture is within the area defined by the thresholds $A_{Tlimit}$. The body balance is similarly within the values defined by the $B_{Tlimit}$ thresholds. Prior to time t1, the trigger activation limit for jaw clamping 22472 has a value between 75 percent open and 100 percent open. The trigger activation limit 22472 may be configured to activate (e.g., close endocutter jaws) at 90% open (e.g., 10% trigger stroke), for example, if/when the user's arm/wrist posture is within the ergonomic arm/wrist range and the user's body balance is within the ergonomic body balance range. The trigger activation limit for jaw unclamping 22470 has a value of approximately 75 percent open. The trigger deactivation limit 22470 may be configured to deactivate (e.g., open endocutter jaws) at 75% open (e.g., 25% trigger stroke), for example, if/when the user's arm/wrist posture is within the ergonomic arm/wrist range and the user's body balance is within the ergonomic body balance range.

Prior to the time t1, the arm/wrist posture value begins moving toward the upper limit $A_{Tlimit}$. At time t1, the value crosses over the $A_{Tlimit}$ threshold. The surgical computing system 20006 may monitor the arm/wrist posture and may determine, based on the arm/wrist posture exceeding threshold $A_{Tlimit}$, to modify the operation of the surgical instrument 22422. As shown, the surgical computing system 20006 may determine, at time t1, to reduce the trigger activation limit 22472 for jaw clamping from between 75 percent and 100 percent to between 50 percent and 75 percent. The trigger activation limit 22472 may be configured to activate (e.g., close endocutter jaws) at 60% open (e.g., 40% trigger stroke), for example, if/when the user's arm/wrist posture is outside the ergonomic arm/wrist range and the user's body balance is within the ergonomic body balance range.

The surgical computing system 20006 may determine to modify the trigger activation limit 22470 for jaw unclamping. As show, at time t1, the surgical computing system 20006 may determine to increase the jaw unclamping activation limit 22470 from 75 percent to between 75 percent and 100 percent. The trigger deactivation limit 22470 may be configured to deactivate (e.g., open endocutter jaws) at 85% open (e.g., 15% trigger stroke), for example, if/when the user's arm/wrist posture is outside the ergonomic arm/wrist range and the user's body balance is within the ergonomic body balance range.

The surgical computing system 20006 may communicate operational parameters corresponding to the modified limits to the surgical instrument 22422 which modifies its clamping and unclamping activation limits. Accordingly, in response to the healthcare professional assuming an arm/wrist posture that is outside the range considered ergonomically acceptable, the surgical computing system 20006 may adjust the operational parameters of the surgical instrument 22422 to accommodate the healthcare professional.

Between time t1 and t2, the posture of the healthcare professional's arm/wrist continues to exceed the $A_{Tlimit}$. The surgical computing system 20006 may maintain the modified trigger activation limits for the surgical instrument 22422. The surgical computing system 20006 may monitor the body posture and may determine, based on the body posture exceeding threshold $B_{Tlimit}$, to modify the operation of the surgical instrument 22422. As shown, the surgical computing system 20006 may determine, at time t2, to further reduce the trigger activation limit 22472 for jaw clamping from below 75 percent to 50 percent. The trigger activation limit 22472 may be configured to activate (e.g., close endocutter jaws) at 50% open (e.g., 50% trigger stroke), for example, if/when the user's arm/wrist posture is outside the ergonomic arm/wrist range and the user's body balance is outside the ergonomic body balance range.

The surgical computing system may determine to modify the trigger activation limit 22470 for jaw unclamping. As show, at time t1, the surgical computing system 20006 may determine to increase the jaw unclamping activation limit 22470 to approximately 99 percent. The trigger deactivation limit 22470 may be configured to deactivate (e.g., open endocutter jaws) at 99% open (e.g., 1% trigger stroke), for example, if/when the user's arm/wrist posture is outside the ergonomic arm/wrist range and the user's body balance is outside the ergonomic body balance range.

The surgical computing system 20006 may determine to communicate operational parameters to the surgical instrument 22422 so that trigger 22452 activates clamping or closure at 50 percent closure of the trigger 22452 and unclamping or release at 99 percent opening of the trigger 22452.

As shown in FIG. 27, at time t3, the body balance or posture of the healthcare professional may move below $B_{Tlimit}$ corresponding to the healthcare professional assuming a position that is more ergonomically correct. The surgical computing system 20006 may determine, at time t3, based on the data indicating improved posture, to modify operational parameters of the surgical instrument 22422 to increase the jaw clamping trigger activation limit 22472 to a value between 50 percent and seventy five percent. The surgical computing system 20006 may determine, based on the data indicating improved posture, to modify operational parameters of the surgical instrument 22422 to decrease the jaw unclamping limit 22470 to a value of 75 percent. The surgical computing system 20006 may determine to communicate operational parameters to the surgical instrument 22422 to modify the activation limits of the trigger 22452.

At time t4, the arm/wrist posture of the healthcare professional may move below $A_{Tlimit}$ corresponding to the arm/wrist of the healthcare professional assuming a posture that is more ergonomically sustainable. The surgical computing system 20006 may determine, at time t4, based on the data indicating improved arm/wrist posture, to modify operational parameters of the surgical instrument 22422 to restore the trigger activation limit for jaw clamping 22472 and jaw unclamping 22470) to their initial values. The surgical computing system 20006 may communicate the operational parameters to the surgical instrument 22422 which may implement the modifications.

Accordingly, systems and techniques are disclosed for adaptively adjusting operation and/or control of a surgical instrument and/or adaptively communicating information to a healthcare professional (e.g., surgeon, assistant). Adaptation of operation, control and/or communication may be based on, for example, situational awareness (e.g., of a surgical procedure). Situational awareness may include, for example, an importance level (e.g., a stress level) of a health care provider, possession of a controllable surgical instrument by a health care provider, and/or body positioning of a health care provider. Situational awareness may be determined, for example, based on information provided by one or more personnel (e.g., wearable) sensing systems, environmental sensing systems, and/or surgical instruments, such as one or more of healthcare provider data (e.g., position, posture, balance, motion, attention, physiologic states), environmental data (e.g., operating room noise level, patient data, healthcare provider data), and/or surgical instrument data (e.g., position, possession, motion, and/or usage). A surgical computing system (e.g., a hub) and/or a surgical instrument may receive (e.g., sensed) information, determine situational awareness and adapt instrument operation, control and/or information communication based on situational awareness.

Healthcare professionals operating the surgical instrument may be monitored using sensing systems to collect sensor data such as, for example, data associated with movement of the healthcare professional including movements of the arms, hands, and torso. Sensor data associated with heartrate, respiration, temperature, etc. may also be collected. The sensing systems may communicate sensor data to the surgical computing system.

The surgical computing system may receive the usage date from the surgical instrument and/or may receive sensor data from the sensing systems. The surgical computing system may determine, based on at least one of the usage data and/or the sensor data, one or more actions that have been performed by the healthcare professional. For example, the surgical computing system may determine, based on usage and/or sensor data, that the healthcare professional has positioned a surgical instrument in a particular manner for a length of time and/or that the healthcare professional has been moving the surgical instrument in a particular manner for a length of time. The surgical computing system may determine based on the received data that the healthcare professional has performed a series of actions with the surgical instrument in a particular period of time.

The surgical computing system may evaluate the actions of the healthcare professional. The surgical computing system may compare one or more actions performed by the healthcare professional with expected one or more actions. The surgical computing system may compare one or more movements performed by the healthcare professional with one or more expected movements. The expected movements may be movements for performing a surgical procedure that satisfy accepted standards. The surgical computing system may compare force applied by a healthcare professional to expected forces.

The surgical computing system may determine, based on the evaluation of the actions of the healthcare professional, to provide feedback to the healthcare professional. If the surgical computing system determines the one or more actions of the healthcare professional are inconsistent with the expected one or more actions, the surgical computing system may determine to provide feedback comprising instructions for the surgical instrument to modify its operation. For example, the feedback may comprise instructions for the surgical instrument to modify a rate that clamping jaws are closed in response to input to a closure trigger. The surgical computing system may determine to provide feedback comprising instructions to present notifications for the healthcare professional. The instructions to present notifications may comprise instructions to the surgical instrument to generate audible feedback and/or to provide tactile or haptic feedback such as, for example, a vibration. The instructions to present notifications may comprise instructions to present one or more notices on a display unit. The notifications may indicate suggested actions for the healthcare professional. The notification may indicate that the healthcare professional should cease operating the surgical instrument, alter movement associated with operating the surgical instrument, and/or take actions consistent with a surgical plan. The surgical computing system may communicate the feedback to the surgical instrument and/or display unit.

The surgical instrument may receive feedback and may proceed consistent with the feedback. If the feedback comprises instructions to provide specific tactile or haptic feedback, the surgical instrument may control the corresponding portions of the surgical instrument to generate the received feedback. If the feedback comprises instructions to modify the operation of the surgical instrument, the surgical instrument may modify the operation of a surgical instrument. For example, if the feedback comprises instructions to modify a rate that clamping jaws are closed in response to input to a closure trigger, the surgical instrument may implement the modified rate of clamping.

A display unit may receive feedback from the surgical computing system. The display unit may be configured to receive feedback comprising one or more notifications and may be configured to display the notifications. The notifications may comprise an indication for the healthcare professional to begin operating the surgical instrument in a different manner. The notifications may indicate for the healthcare professional to change his or her current procedures and/or to follow a prescribed procedure.

A surgical computing system may receive usage data associated with movement of a surgical instrument and user inputs to the surgical instrument. The surgical computing system may receive motion and biomarker sensor data from sensing systems applied to the operator of the surgical instrument. The surgical computing system may determine, based on at least one of the usage data and/or the sensor data, an evaluation of the actions of the operator of the surgical instrument. The surgical computing system may determine, based on the evaluation, to provide feedback. The feedback may comprise instructions for the surgical instrument to provide haptic feedback and/or to modify its configuration. The feedback may comprise instructions for a display unit to present notifications instructing the healthcare professional. The surgical computing system may communicate instructions for providing the feedback to the surgical instrument and/or the display unit.

Figure 28:
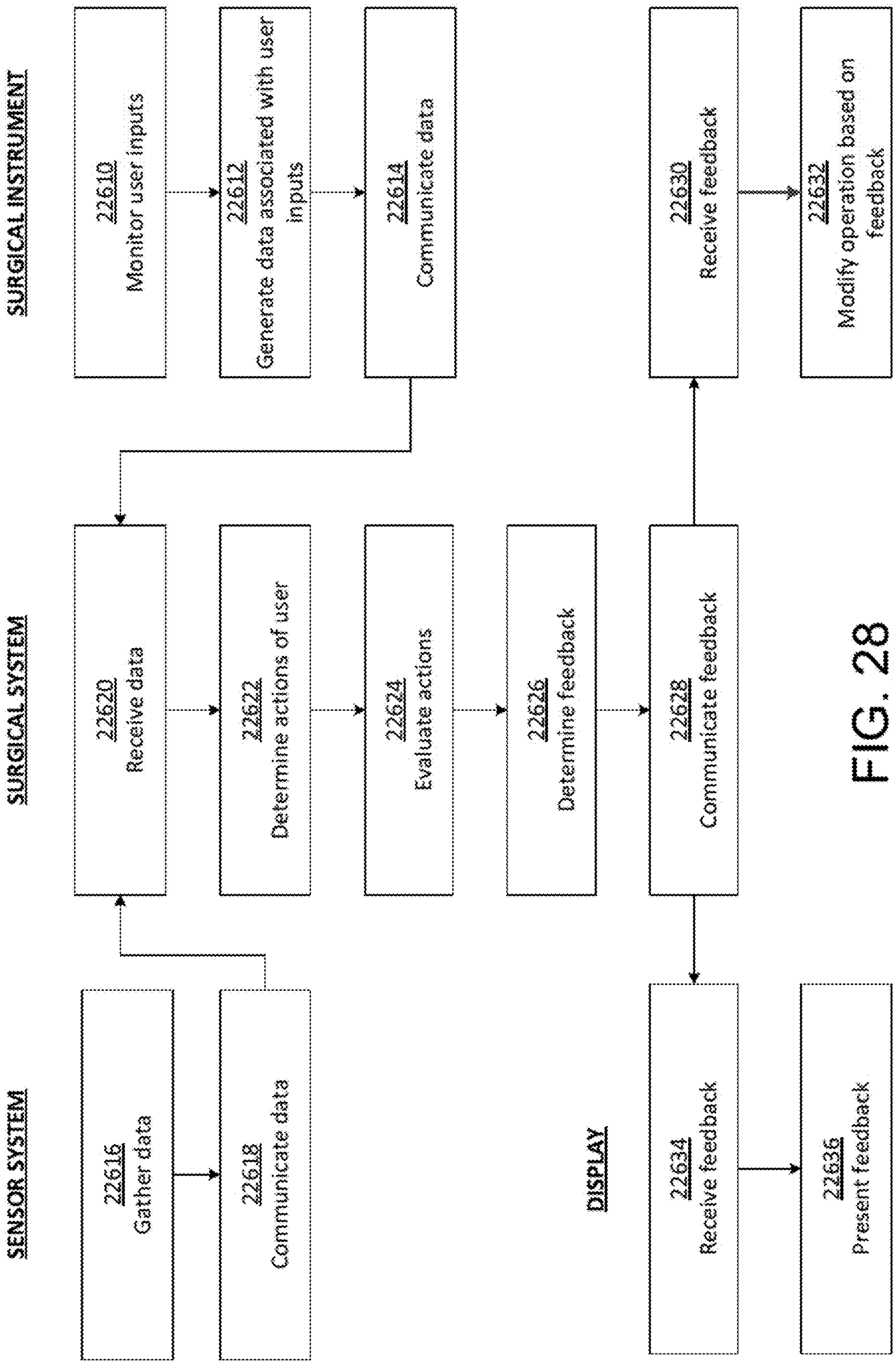
FIG. 28 depicts example processing for monitoring operation of a surgical instrument.

FIG. 28 depicts a flow diagram of example processing associated with monitoring a healthcare professional's operation of a surgical instrument and providing feedback. As shown, at 22610, a surgical instrument, which may be a surgical instrument 20282 as described in connection with FIG. 10, may monitor user inputs to the surgical instrument. The surgical instrument 29282 may monitor user input associated with movement and positioning of the surgical instrument. The surgical instrument 20282 may employ, for example, an acceleration sensor 150712 to monitor the movement and positioning of the surgical instrument. The surgical instrument 20282 may monitor the orientation of the surgical instrument 20282 and a length of time the surgical instrument 20282 is maintained in a particular position. The surgical instrument 20282 may monitor user inputs associated with operation of controls of the surgical instrument 20282. For example, the surgical instrument 20282 may monitor inputs associated with controlling the operation of claws for clamping patient tissue. The surgical instrument 20282 may monitor the degree that a closure trigger is pressed, the speed at which the trigger is pressed, and a length of time a trigger is held in a particular control position. The surgical instrument 20282 may monitor the force load applied by the healthcare professional to the control trigger and/or the force load applied by the surgical instrument to a patient.

At 22612, the surgical instrument 20282 may generate usage data associated with the user inputs monitored and detected by the surgical instrument 20282 at 22610. The surgical instrument 20282 may generate usage data associated with the movement and positioning of the surgical instrument 20282 and associated with the user inputs associated with controlling operations of the surgical instrument.

At 22614, the surgical instrument 20282 may communicate the usage data to a surgical computing system which may be, for example, a surgical hub 20006. The usage data may be continuously gathered and communicated during operation of the surgical instrument.

Data associated with the one or more healthcare professionals who operate the surgical instrument 20282 may also be gathered. Healthcare professionals operating the surgical instruments 20282 and/or who are in the area where the surgical procedure is being performed may have one or more sensing systems applied thereto. Sensing systems 20069 such as those described herein in connection with FIG. 6B may be applied to the healthcare professionals to collect sensor data. The sensing systems 20069 may sense and gather sensor data associated with movement of the healthcare professional such as, for example, movement of the healthcare professional's arms, hands, legs, and/or torso. The sensing systems 20069 monitor the healthcare professional's movement and/or lack of movement. Data associated with a force load, which may be referred to as the force, applied by the healthcare professional may be gathered. Data associated with an applied force may be gathered, for example, using force myography and/or compressive measurements. The sensing systems 20069 may employ kinematics to capture and describe the motion of the healthcare professional. The sensing systems 20069 may sense and gather sensor data which may include biometric data such as, for example, data associated with heartrate, respiration, temperature, etc.

At 22618, the surgical instrument 20282 may communicate the sensor data to the surgical computing system 20006. The sensor data may be continuously gathered and communicated during operation of the surgical instrument.

At 22620, the surgical computing system 20006 may receive the sensor data from the sensing systems 20069 and may receive usage data from the surgical instrument 20282.

At 22622, the surgical computing system 20006 may process the received usage data and/or sensor data and may determine one or more actions performed by the healthcare professional. The actions may comprise movements and/or lack of movement of particular portions of the healthcare professional. For example, the actions may comprise movements of the healthcare professional's hand, wrists, forearms, etc. The actions may comprise movements of the surgical instrument 20282. The actions may comprise inputs to the surgical instrument such as, for example, force applied to the closure trigger 150032 and/or the corresponding force applied by jaws of the surgical instrument 20282.

At 22624, the surgical computing system 20006 may evaluate the actions performed by the healthcare professional. The surgical computing system 20006 may be configured with data regarding accepted standards for performing surgical procedures. The accepted standards may specify actions that have been determined to be acceptable or expected during various surgical procedures. The surgical computing system 20006 may comprise data specifying for a surgical procedure, the various actions that are performed, the movements of the healthcare provider and the surgical instrument associated with the surgical procedure, the inputs to the controls of the surgical instrument that received, and the times that the various actions are to be performed. The parameters that may be assessed and evaluated may vary depending upon the surgical procedure and surgical instruments that are used. For example, for stapler instruments, wait times are significant and may be assessed. For powered devices, stroke limits and rate of actuations may be assessed. For wearables, patient heart rate, surgeon heart rate, and/or nerve stimulation may benefit from being hapotically communicated to the surgeon.

The surgical computing system 20006 may evaluate the determined actions, as indicated by the usage and sensor data, relative to the actions that have been determined to be acceptable or expected as indicated by accepted standards. For example, the surgical computing system 20006 may evaluate the actions relative to actions as specified in a surgical plan. The surgical computing system 20006 may determine whether the actions, which may include various movements performed by the healthcare professional, are consistent or inconsistent with the acceptable or expected actions. The surgical computing system 20006 may evaluate the force loads associated with the surgical instrument. The surgical computing system 20006 may evaluate the force loads applied by the healthcare professional to a closure trigger 150032 or applied by jaws of the surgical instrument to patient tissue.

At 22626, the surgical computing system 20006 may determine feedback. The feedback may comprise one or more notifications for communication to the healthcare professional using the surgical instrument 20282 and/or a display which may be, for example, a display 20023. The surgical computing system 20006, if it has determined the actions of the healthcare professional are inconsistent with accepted or expected courses of action, may determine to provide feedback comprising instructions to modify operation of the surgical instrument 20282. If the surgical computing system 20006 has determined the actions of the healthcare professional are inconsistent with accepted standards, the surgical computing system 20006 may determine suggested actions consistent with accepted standards. The surgical computing system 20006 may determine the feedback comprises one or more notifications to stop operating the surgical instrument 20282 and/or to alter movement associated with operating the surgical instrument. The feedback may comprise instructions to present suggested actions for the healthcare professional. If the surgical computing system 20006 determined an evaluation of force loads associated with a surgical instrument, the surgical computing system 20006 may determine to provide feedback comprising instructions for the surgical instrument to modify control associated with the force loads. For example, the surgical instrument 20006 may determine to provide instructions to change the scaling of the force applied by the jaws of an endocutter when a force is applied by the healthcare provider to a closure trigger 150032. The surgical computing system 20006 may determine to provide feedback comprising instructions to notify the healthcare professional to modify inputs used with the surgical instrument.

The surgical computing system 20006 may evaluate the actions indicated by the usage and sensor data and determine that the healthcare professional's, e.g., surgeon's, movements or lack of movements indicate that the healthcare professional should change his or her behavior. For example, the surgical computing system 20006 may determine that the healthcare professional should take a break from performing the procedure, change his or her position, and/or change his or her technique. The surgical computing system 20006 may determine that the healthcare professional has been hunched over an operating field for an extended period of time, e.g., three (3) hours, and may determine that the healthcare professional may benefit from reminders to stretch or move in order to avoid cramping or other complications. The surgical computing system 20006 may determine to provide feedback comprising instructions to provide notifications intended to remind the healthcare professional to break from performing the procedure. The instructions to provide notifications may comprise instructions to the surgical instrument 20282 to provide vibrations or audible tones to alert the healthcare professional.

The surgical computing system 20006 may process the actions indicated by the usage and sensor data to assess the techniques used by the healthcare professional and may determine suggested actions for an improved outcome. The surgical computing system 20006 may compare the actions and related data of the healthcare professional in performing the current surgical procedure with expected or accepted actions and related data which may have been derived from previously performed surgical procedures. The surgical computing system 20006 may evaluate the actions of the healthcare professional against one or more assessment characteristics such as, for example, the following: time to accomplish a surgical task which may be a time to mobilize and/or time to address bleeding events requiring intervention during mobilization; instrument bite size; instrument exchanges; number of instruments in use; number of staple cartridges used; delay in procedure time; number of secondary retraction instruments; and manual or device based suturing technique.

The surgical computing system 20006 may perform an assessment of suturing technique (e.g., whether manual suturing or device based suturing) by assessing suture selection and assessing suture technique. Suture selection assessment may comprise an assessment of the type of suture selected which may be defined by suture size, material, needle type, etc., and fixation style which may be, for example, barbed or traditional which may employ knots. The surgical computing system 20006 may assess and determine to provide feedback regarding the type of suture that may be appropriate.

The surgical computing system 20006 may perform an assessment of suturing technique by assessing and providing feedback regarding multiple aspects of suturing. The assessment and recommendation may be performed prior to an anticipated surgical procedure step. The assessment may comprise comparing variables and historical and/or current performance against general population for similar procedure steps. The timing of the assessment and feedback may be intraoperative or post-operative.

The surgical computing system 20006 may provide feedback regarding manual suturing verses device based suturing with associated recommendations. If historical surgical procedure data indicates that using a suturing device is faster or results in a better outcome for the healthcare professional, the surgical computing system 20006 may make the data available to the healthcare professional to inform the healthcare professional regarding device selection. Notifications providing this information may be communicated pre-operation, intra-operation, or post-operation.

The surgical computing system 20006 may perform an assessment and provide feedback regarding suturing technique selection, which may be one of interrupted sutures, running sutures, mattress sutures, etc., based on historical procedure data.

The surgical computing system 20006 may perform an assessment and provide feedback regarding a number and type of knots used during suturing. Different knot types may preferably be used with different suture types. For example, prolene (e.g., plastic monofilament) sutures may work well with alternating overhand knots to terminate a suture line as compared with Vicryl sutures (e.g., braided multifilament suture). Determining feedback regarding the number and type of knots may be performed in response to scissors being introduced to the patient and if an evaluation of the number of knots is determined not to be sufficient.

The surgical computing system 20006 may evaluate the actions indicated by the usage and sensor data and determine that the healthcare professional's loading of the surgical instrument 20282 controls deviates from expected or accepted loading values. The loads that a healthcare professional applies to the controls of the surgical instrument 20282 or the resulting loads and/or motions (e.g., displacements and/or rates) that the surgical instrument applies to patient tissue may be compared with values from previous procedures performed by the healthcare professional or compared with values associated with accepted practices, which may be based on aggregated values associated with other healthcare professionals who may have previously performed a similar surgical procedure. If the surgical computing system 20006 determines that the healthcare professional is clamping on a closure trigger 150032 with too much force, is moving the surgical instrument 20282 too quickly, or otherwise operating the surgical instrument 20282 out of synch with accepted or expected values, the surgical computing system 20006 may determine to provide feedback that may provide notice to the healthcare professional of the discrepancy and/or instruct the surgical instrument 20282 to adjust operations such as, for example, an actuation force or actuation rate associated with the closure trigger 150032 to conform the operation to accepted practice for actuation. The surgical computing system 20006 may determine that the feedback should adjust the operating characteristics of the surgical instrument 20282 so that the device surgical instrument operates as intended given the deviation of the inputs of the healthcare provider from expected inputs.

The surgical computing system 20006 may determine that the feedback may comprise instructions for the surgical device 20282 to provide haptic feedback to alert or instruct the healthcare professional. The haptic feedback may alert or remind the healthcare professional of alternative procedure options. The alternative options may be associated with improved outcomes. with potential better outcomes. While a healthcare professional is operating a surgical instrument 20282, haptic feedback may be activated to alert the healthcare professional to instances that more or less control actuation may improve surgical technique as indicated by aggregated data compiled over multiple surgical procedures by multiple healthcare professionals. In an example scenario, the surgical computing system may receive usage data indicating the healthcare professional may be releasing the closure trigger 150032 to activate the firing mechanism before a jaw compression wait period that the surgical computing system 20006 has determined to be most beneficial. The surgical computing system 20006 may determine that the feedback should include instructions to the surgical instrument 20282 to provide haptic feedback whereby the closure trigger 150032 or firing trigger may vibrate indicating a request that the healthcare provider pause for a longer period before proceeding to the next step. The healthcare provider may heed the alert and pause, or may over-ride the suggestion and proceed with the next step.

The surgical computing system 20006 may determine to provide haptic feedback to the healthcare professional meant to help to improve his or her technique. The haptic feedback may be made in combination with haptic feedback to control actuation. The haptic feedback intensity may be used to suggest more or less force may be employed. The haptic feedback may be employed to create a counter that allows the healthcare professional to have a better temporal understating of rates and wait times by allowing him or her to count the periodic haptic inputs.

The surgical computing system 20006 may determine to provide subtle haptic control indications to warn the healthcare professional and/or suggest adaptive techniques. For example, the surgical computing system 20006 may determine to provide a vibration when a particular control should be discontinued. The surgical computing system 20006 may determine to provide haptic feedback by utilizing two or more haptic generators that may not be aligned in the same plane relative to the device. Such an arrangement may allow for directionality tactile feedback or feedback in a specific portion of the device rather than throughout the device. This may be used to indicate various actions should be performed such as, for example, stop, increase, decrease, etc.

The surgical computing system 20006 may determine that the feedback may comprise one or more notifications indicating one or more steps that the healthcare professional may take consistent with accepted surgical practices which may have been derived or based on instances of previous surgical procedures. The one or more notifications may indicate information specifying operation of the surgical instrument consistent with accepted surgical procedures.

The surgical computing system 20006 may determine that the feedback may comprise one or more notifications associated with a probability that the patient may develop one or more complications as a result of the healthcare professional performing the surgical procedure. The surgical computing system 20006 may be configured to access historical procedure data associated with previous surgical procedures performed by the healthcare professional on previous patients. The historical procedure data regarding previous surgical procedures may comprise data associated with the previous patients in those procedures. The historical procedure data may comprise previous patient biomarker data measured before, during, and after the surgical procedure, along with data indicating results of the surgical procedure including complications experienced by the previous patients as a result of the surgical procedure.

The surgical computing system 20006 may also receive data in real time regarding the patient presently undergoing a surgical procedure. The present patient data may be collected from sensing systems applied to the patient and communicated to the surgical computing system 20006.

The surgical computing system 20006 may search the historical procedure data for previous patients that may have had similar biomarker data readings to the patient presently undergoing the surgical procedure. For the identified previous patients who had biomarker readings similar to those of the present patient, the surgical computing system 20006 may identify the complications and outcomes experienced by those previous patients. The surgical computing system 20006 may derive from the data regarding complications and outcomes experienced by previous patients, one or more probabilities regarding complications and outcomes that may be experienced by the present patient. The surgical computing system 20006 may determine feedback for the healthcare professional comprising one or more notifications regarding probabilities of complications the patient may experience based upon the patient's biometric data and the historical procedure data.

Accordingly, the surgical computing system 20006 may use a healthcare professional's historical procedure data associated with previous surgical procedures and the current patient's biomarker data and imaging data to adjust the probability of complications. The processing of the historical data set and the current biomarker data may allow a healthcare professional to determine where his or her skill levels and techniques are likely to have a high or lower probability of encountering procedural delays or other issues. Prior to, or at the initiation of a surgical procedure, the surgical computing system 20006 may estimate based on the patient's biomarker data and the historical data set that the patient may have a first percentage probability of developing complications. The surgical computing system 20006 may determine based on indications from the current biomarker data that the present procedure has proceeded smoothly and precautions were observed, and based on historical data comprising data for prior surgical procedures that had similar indications, that the procedures went smoothly and precautions were observed, that the potential for complications during the current procedure may have been reduced by a particular percentage. Indications that the procedure went smoothly may include the number of cuts that were needed, the amount of energy used, as well as other quantifiable data.

The surgical computing system 20006 may determine based on indications from the current data that the present procedure has not proceeded smoothly and may have involved complications. The surgical computing system 20006 may determine, based on historical data comprising data for prior surgical procedures that had similar indications, that the potential for complications during the current procedure may have increased by a particular percentage. Indications that the procedure has not proceeded smoothly and involved complications may include the presence of adhesions and associated dissections or cuts.

The surgical computing system 20006 may employ machine learning techniques on the historical data to determine probability of complications.

Feedback generated by the surgical computing system 20006 may provide notifications for healthcare professionals to understand how their average decrease in risk for specific procedures/complications may be linked to device specific usage, usage style, settings, etc.

At 22628, the surgical computing system 20006 may communicate the feedback to the surgical instrument 20282 and/or display 20023. If the surgical computing system 20006 has determined one or more notifications for the surgical instrument 20282, the surgical computing system 20006 may communicate instructions for the notifications to the surgical instrument 20282. The surgical computing system 20006 may communicate instructions for the surgical instrument to provide haptic feedback, tactile feedback, vibration feedback, and/or audible feedback. The feedback may be intended to direct the healthcare professional to perform an action and/or to cease performing an action. The surgical computing system 20006 may communicate instructions for the surgical instrument 20282 to modify its operation. The surgical computing system 20006 may communicate instructions for the surgical instrument to modify its response to the healthcare professional applying pressure to the closure trigger 150032.

The surgical computing system 20006 may communicate feedback to the display unit 20023. The surgical computing system 20006 may communicate one or more notifications to the display unit 20023. The one or more notifications may comprise instructions for presenting suggested actions for the healthcare provider to take. The suggested actions may comprise instructions for performing a surgical procedure or surgical plan; for operating the surgical instrument 20282 consistent with accepted standards, and/or to modify movement and/or posture. The one or more notifications may comprise notifications regarding probabilities of complications based upon historical data.

At 22630, the surgical instrument 20282 may receive the feedback from the surgical computing system 20006. The received feedback may comprise instructions to provide notifications which may be haptic and/or audio notifications and may comprise instructions for modifying the control algorithms for the surgical instrument.

At 22632, the surgical instrument 20282 may modify its operations based upon the received feedback. Consistent with received instructions to provide notifications, the surgical instrument 20282 may provide haptic feedback, tactile feedback, vibration feedback, and/or audible feedback. The feedback may be intended to direct the healthcare professional to perform an action and/or to cease performing an action. Consistent with the received instructions to modify operation, the surgical instrument 20282 may modify its response to operator inputs received at control inputs. For example, the surgical instrument 20282 may modify its response to the healthcare professional applying pressure to the closure trigger 150032.

At 22634, the primary display 20023 may receive the feedback from the surgical computing system 20006. The received feedback may comprise instructions to present one or more notifications.

At 22636, the display 20023 may present notifications consistent with the received feedback. The display 20023 may present one or more notifications including suggested actions for the healthcare provider to take. The suggested actions may comprise instructions for performing a surgical procedure or surgical plan; for operating the surgical instrument 20282 consistent with accepted standards, and/or to modify movement and/or posture. The one or more notifications may comprise notifications regarding probabilities of complications based upon historical data.

Accordingly, systems and techniques are disclosed for monitoring a healthcare professional's operation of a surgical instrument. The surgical instrument may collect usage data associated with the position and movement of the surgical instrument and/or associated with user inputs relating to operation of the surgical instrument. Sensing systems applied to the healthcare professional operating the surgical instrument may collect sensor data such as, for example, data associated with movements of the healthcare professional and/or data associated with biometrics such as heart-rate, respiration, temperature, etc. A surgical computing system may determine, based on at least one of the usage data and/or the sensor data, an evaluation of the actions of the healthcare professional. The surgical computing system may compare the actions of the healthcare professional with expected or acceptable actions. The surgical computing system may determine, based on the evaluation, to provide feedback. The feedback may comprise notifications to the healthcare professional to alter his or her actions. The feedback may comprise instructions for the surgical instrument to provide haptic feedback and/or to modify its configuration. The feedback may comprise instructions for a display unit to present notifications instructing the healthcare professional on how to proceed. The surgical computing system may communicate instructions for providing the feedback to the surgical instrument and/or the display unit. The surgical instrument may modify its operation based upon the feedback and/or provide haptic feedback to the healthcare professional. The display unit may display feedback notifications to the healthcare professional who may modify his or her actions based on the feedback.

Using a combination of patient-specific and/or surgical-environment-specific sensor inputs to determine a more optimal device setting may lead to better device perform and ultimately better patient outcomes.

A computing device may have a processor configured to receive two points of surgical sensor data from different sensors. The sensors may include wearable patient sensors and/or surgical theater environmental sensor system. The processor may be configured to determine a surgical device setting (e.g., a closure load for a powered surgical stapler, or for example, a power level of a surgical energy device). And the processor may send a signal indicative of the determined setting. A surgical device may receive the signal and perform a surgical action based on the determined setting. The device The surgical device may include any of a powered stapler, a powered stapler generator, an energy device, an energy device generator, an in-operating-room imaging system, a smoke evacuator, a suction-irrigation device, or an insufflation system, for example. The setting information may include an indication of any of a power level, an advancement speed, a closure speed, a closure load, or a wait time.

The processor may be configured to receive procedure information. The processor may be configured to determine the surgical-device setting based on first surgical sensor data, second surgical sensor data, and procedure information. And the signal sent from the processor may include information indicative of an alert. The alert may represent an identified patient complication associated with the surgical device being used with its existing settings, for example, without first switching to the determined surgical device setting.

A computing device may include an input, a processor, and an output. The device may be configured to receive two points of surgical sensor data from different sensors. The sensors may include wearable patient sensors and/or surgical theater environmental sensor system. The processor may determine a surgical device setting (e.g., a closure load for a powered surgical stapler, or for example, a power level of a surgical energy device). And the output may send a signal indicative of the determined setting. A surgical device may receive the signal and perform a surgical action based on the determined setting. Using a combination of patient-specific and/or surgical-environment-specific sensor inputs to determine a more optimal device setting may lead to better device perform and ultimately better patient outcomes.

Figure 29A:
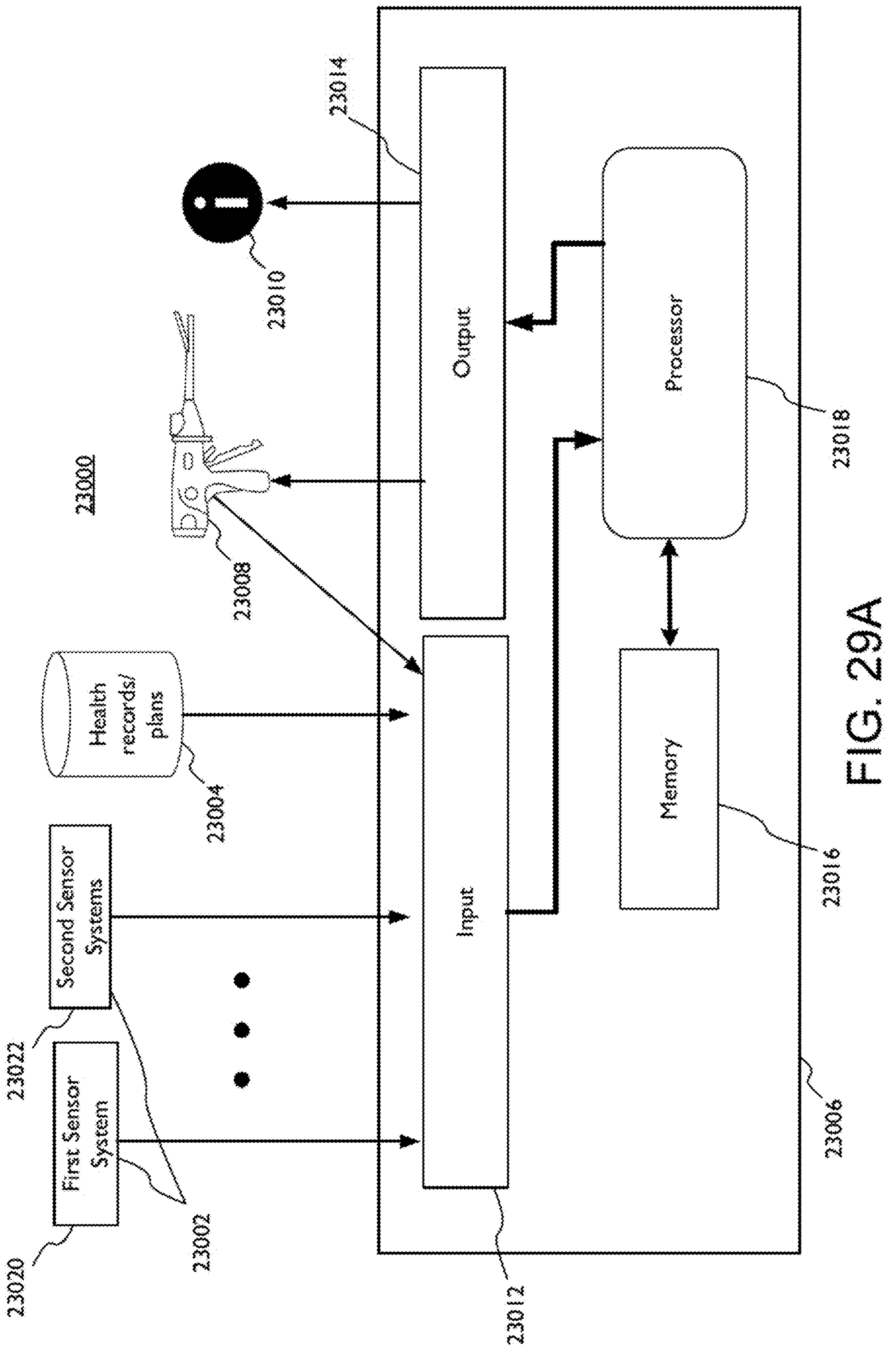
FIGS. 29A-B are block diagrams depicting an example system for determining surgical device settings and an example operation of the processor, respectively.
Figure 29B:
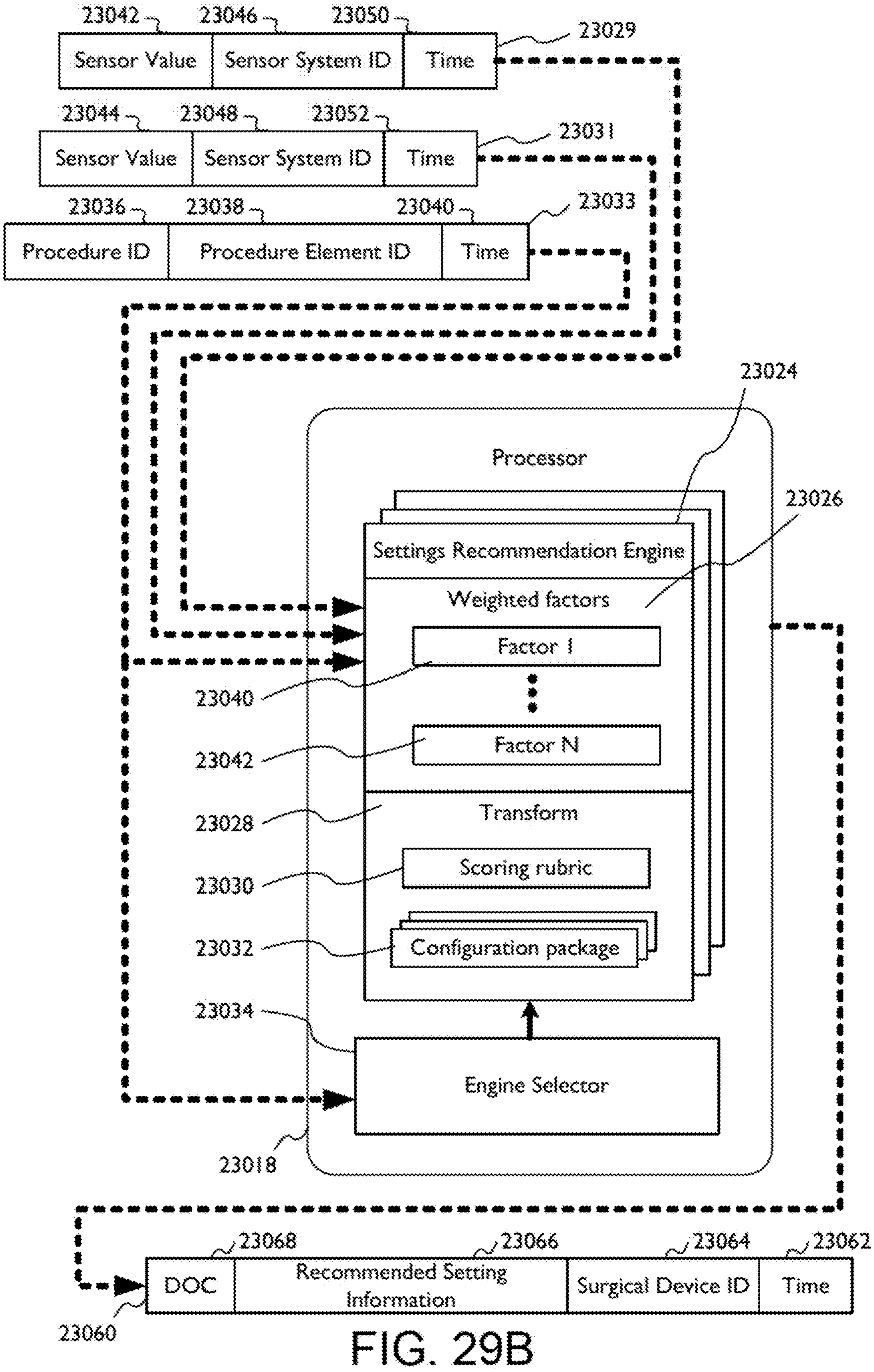

FIGS. 29A-B are block diagrams depicting an example system 23000 for determining surgical device settings and an example operation of the processor 23018, respectively. The example system 23000 may use sensor data and/or other relevant data (such as procedure plans, for example) to determine relevant notifications and recommended setting changes for surgical equipment. For example, the system 23000 may suggest that a particular surgical instrument be configured in a particular way to improve patient outcomes. In particular, the data may be used to identify complications and/or physiological comorbidities. Such complications and/or physiologic physiological comorbidities may affect a planned procedure and/or instrument use. And in turn, the system 23000 may notify the relevant health care professional. And the system 23000 may enable the adjustment of a set up and/or operation of surgical devices. The system 2300 may be a stand-alone system and/or may be incorporated into a broader computer-implemented patient and surgeon monitoring system, such as computer-implemented patient and surgeon monitoring system 20000, disclosed herein.

The system 23000 may make this notification and/or configuration-change recommendation based on data from a single source or based on data from multiple sources. When data is considered from multiple sources, the recommendation may be able to be made with a higher confidence than when a single source is considered. A health care professional may be more likely to consider and adopt the notification and/or the configuration change knowing that various sensor inputs have contributed to it.

The system 23000 may include one or more sensor systems 23002, one or more health record data sources 23004, a computing device 23006, configurable surgical equipment 23008, and/or a notification output system 23010.

The one or more one or more sensor systems 23002 may include any configuration of hardware and software devices suitable for sensing and presenting parameters relevant to a health procedure. Such surgical sensor systems 23002 may include the sensing and monitoring systems disclosed herein, including controlled patient monitoring systems, uncontrolled patient monitoring systems, surgeon monitoring systems, environmental sensing systems, and the like. For example, one or more one or more sensor systems 23002 may include any combination of surgical sensor systems, in particular, any combination of wearable patient sensor systems and/or surgical theater environmental sensor system.

The one or more one or more sensor systems 23002 may include any of those disclosed herein, such as those disclosed with reference to FIG. 1B for example.

The one or more health record data sources 23004 may include any data source relevant to a health procedure. For example, the health record data source 23004 may include patient records, procedure plans, situational awareness data, facility best practices, and the like. For example, the health record data source 23004 may include storage 20331 (e.g., storing an EMR database), as disclosed herein.

The configurable surgical equipment 23008 may include any equipment employed for a surgical procedure that has a configurable aspect to its operation. The configurable surgical equipment 23008 may include equipment in the surgical theater. The configurable surgical equipment 23008 may include any equipment employed in the surgical theater, such as that disclosed with reference to FIG. 1, FIG. 7A, FIG. 10, and throughout the present application, for example. The configurable surgical equipment 23008 may include surgical fixtures of a general nature, such as a surgical table, lighting, anesthesia equipment, robotic systems, and/or life-support equipment. The configurable surgical equipment 23008 may include surgical fixtures specific to the procedure at-hand, such as imaging devices, surgical staplers, energy devices, endocutter clamps, and the like. For example, the configurable surgical equipment 23008 may include any of a powered stapler, a powered stapler generator, an energy device, an energy device generator, an in-operating-room imaging system, a smoke evacuator, a suction-irrigation device, an insufflation system, or the like.

The configurable aspect of the equipment may include any adjustment or setting that has an influence on the operation of the equipment. For example, configurable surgical equipment 23008 may have software and/or firmware adjustable settings. Configurable surgical equipment 23008 may be hardware and/or structurally adjustable settings. In an example, the configurable surgical equipment 23008 may report its present settings information to the computing device 23006 via the input 23012.

An imaging device's settings may include placement, imaging technology, resolution, brightness, contrast, gamma, frequency range (e.g., visual, near-infrared), filtering (e.g., noise reduction, sharpening, high-dynamic-range), and the like.

A surgical stapler's settings may include placement, tissue precompression time, tissue precompression force, tissue compression time, tissue compression force, anvil advancement speed, staple cartridge type (which may include number of staples, staple size, staple shape, etc.), and the like.

An energy device's settings may include placement, technology type (such as harmonic, electrosurgery/laser surgery, mono-polar, bi-polar, and/or combinations of technologies), form-factor (e.g., blade, shears, open, endoscopic, etc.) coaptation pressure, blade amplitude, blade sharpness, blade type and/or shape, shears size, tip shape, shears knife orientation, shears pressure profile, timing profile, audio prompts, and the like.

The notification output system 23010 may include any human interface device suitable for producing a perceptible notification. The notification may include a visual indication, an audible indication, a haptic indication, and the like. The notification output system 23010 may include a computer display. The notification output system 23010 may include a text-to-speech device. The notification output system 23010 may include a wearable haptic device. For example, the notification may include a visual representation including text and/or images on a computer display. For example, the notification may include synthesized language prompt over an audio "smart" speaker. For example, the notification may include a haptic "tap" on a wearable device, such as a smartwatch worn by the surgeon.

The notification system 23010 may include an operative notification system and/or a pre-operative notification system. For example, an operative notification system may deliver recommendations and notifications during a surgery. For example, a pre-operative notification system may deliver recommendations and notifications before a surgery. To illustrate, the use of pre-operative sensor data and procedure data may be used to drive certain pre-operative recommendations to a health care professional, such as identifying potential instrument setup interactions and/or complications or physiologic co-morbidities that would affect the planned procedure or instrument use, and in turn, recommending procedures or procedure elements that might mitigate those issues (e.g., for example recommending among open surgery, laparoscopic surgery, and/or robotic surgery).

The computing device 23006 may any device suitable for processing sensor and health record data for purposes of determining corresponding notifications and recommended settings for configurable surgical equipment 23008. The computing device 23006 may be a stand-alone computing device. The computing device 23006 may be incorporated into a surgical hub, such as that disclosed in FIG. 1, for example. For example, the computing device may be incorporated in an element of surgical equipment itself.

The computing device 23006 may include an input 23012, and output 23014, memory 23016, and/or a processor 23018.

The input 23012 may be a communications interface suitable for receiving and or sending data. For example, the input 23012 may receive data from the one or more sensor systems 23002. For example, the input 23012 may receive data the health record data source 23004. The input 23012 may include one or more stand-alone interfaces. The input 23012 may be incorporated into an interface of a surgical data network, like the surgical data network 20060, shown in FIG. 3 and disclosed herein.

The output 23014 may be a communications interface suitable for receiving and or sending data. For example, the output may send data to one or more of the configurable surgical equipment 23008. The output 23014 may send configuration and/or settings information to one or more of the configurable surgical equipment 23008. For example, the output 23014 may send data the notification output system 23010. The output 23014 may include one or more stand-alone interfaces. The output 23014 may be incorporated into an interface of a surgical data network, like the surgical data network 20060, shown in FIG. 3 and disclosed herein.

The memory 23016 may include any device suitable for storing and providing stored data. The memory may include read-only memory (ROM) and/or random-access memory (RAM). The memory 23016 may an include non-volatile disk storage, such as hard-disk drive (HDD) and solid-state drive (SSD), for example. The memory 23016 may be suitable for providing one or more buffers, registers, and/or temporary storage of information. The memory 23016 may store programming code that when executed by the processor 23018 controls the operation of the computing device 23006. The memory 23016 may be suitable for storing programming code representing specific transforms between input data from the input 23012 and the output data from output 23014. For example, the memory 23016 may be suitable for storing data related to one or more settings recommendation engines, corresponding weighted factors, and an engine selector. The memory 23016 may be suitable for storing any intermediate data products in the operation of the computing device 23006 for example.

The processor 23018 may include any device suitable for handling the data processing required of the computing device as disclosed herein. For example, the processor 23018 may include a microprocessor, a microcontroller, a FPGA, and an application-specific integrated circuit (ASIC), a system-on-a-chip (SOIC), a digital signal processing (DSP) platform, a real-time computing system, or the like.

In operation, the processor 23018 may receive first sensor data from a first sensor system 23020. The processor 23018 may receive first sensor data from a first sensor system 23020 via the input 23012. The processor 23018 may receive second sensor data from a second sensor system 23022. The processor 23018 may receive second sensor data from a second sensor system 23022 via the input 23012. The second sensor system 23022 may be different than the first sensor system 23022. The processor 23018 may receive data from a health record data source 23004. The processor 23018 may receive data such as procedure information from a health record data source 23004. The processor 23018 may determine a surgical-device setting based on the first sensor data and the second sensor data. The processor 23018 may determine the surgical-device setting based on the first surgical sensor data, the second surgical sensor data, and the procedure information. Where the computing device may be incorporated in an element of surgical equipment itself, the computing device may further include a driver to perform a surgical action based on the determined surgical device setting.

For example, as shown in FIG. 29B, the processor 23018, in connection, for example, with the memory 23013, may implement one or more setting recommendation engines 23024. A setting recommendation engine 23024 may include one or more factors 23026 and a transform 23028. The setting recommendation engine 23024 represents the logic associated with translating data received at the input 23012 to data sent at the output 23014. For example, the setting recommendation engine 23024 may receive input, including for example sensor data 23029, 23031 and/or procedure data 23033. The setting recommendation engine 23024 may select, filter, and or weight the data according to one or more factors 23026. The setting recommendation engine 23024 may apply the result to the transform 23028. The transform 23028 may include a scoring rubric 23030 and one or more configuration packages 23032. The transform 23028 represents the logic associated with converting the data, as preprocessed by the one or more factors 23026, into a selection of a resultant configuration package 23032. The configuration package 23032 may include information for configuring the configurable surgical equipment 23008 and/or information for instructing a notification to be delivered via the notification output system 23010.

The conversion process is performed, at least in part, by the scoring rubric 23030. The scoring rubric 23030 may represent a specific logic structure. The scoring rubric 23030, for example, may be a summation and threshold analysis. The scoring rubric 23030, for example, may include a non-linear mathematical transform. The scoring rubric 23030, for example, may include a logic tree. The scoring rubric 23030, for example, may include a coded algorithm.

The engine selector 23034 may include a data table and management function to activate and/or deactivate one or more settings recommendation engines. The engine selector 23034 may activate and/or deactivate one or more settings recommendation engines 23024 according to a default or baseline condition without received procedure data 23033. The engine selector 23034 may activate and/or deactivate one or more settings recommendation engines 23024 in accordance with received procedure data 23033. For example, the procedure data 23033 may include a procedure ID 23036 that reflects a particular procedure being performed. The engine selector 23034 may include a lookup table to select one or more settings recommendation engines 23024 that are associated with the procedure ID 23036. The procedure data 23033 may include a procedure element ID 23036 that reflects a particular portion of the procedure being performed at a particular time 23040. The engine selector 23034 may include a lookup table to select one or more settings recommendation engines 23024 that are associated with the procedure element ID 23036 and/or associated with a particular time 23040. For example, certain settings recommendation engines 23024 may be selected for a particular procedure element at the start of the particular procedure activity and other settings recommendation engines 23024 may be selected for that same procedure activity in view of a lengthening duration of time in preforming that procedure activity.

In an example operation, the processor 23018 may receive first sensor data 23029, second sensor data 23031, and procedure data 23033. The sensor data 23029, 23031 may include respective sensor values 23042, 23044. The sensor data 23029, 23031 may include respective sensor system IDs 23046, 23048. The sensor data 23029, 23031 may include respective time stamps 23050, 23052.

The engine selector 23034 may have designated one or more settings recommendations engines 23024 as active. The engine selector 23034 may have designated one or more settings recommendations engines 23024 as inactive. An inactive settings recommendation engine 23024 may ignore incoming sensor and/or procedure data. An active settings recommendations engine 23024 may process incoming first sensor data 23029 and second sensor data 23031 in view of active settings recommendations engine's factors 23026. The active settings recommendations engine 23024 may scan incoming data for sensor values and sensor system IDs that filter according to the factors 23026. For example, the active settings recommendations engine 23024 may scan incoming data that matches specific sensor values, falls within a range of sensor values, exceeds a sensor value threshold, falls below a sensor value floor, presents the presence or absence of the sensor value itself. The active settings recommendations engine 23024 may pre-process incoming data for sensor values and sensor system IDs according to the factors 23026. For example, the active settings recommendations engine 23024 may pre-process incoming data by any type of signal processing technique, such as moving averages, absolute values, differences from a baseline, time within or outside a range, frequency analysis, noise reduction, compression, and the like. The factors 23026 may be applied to procedure data 23033. For example, the factors 23026 may be used to filter and/or pre-process on specific procedure IDs, on specific procedure element IDs, on time within a procedure, on time within a procedure element, on updated procedure IDs, on updated procedure elements, and on any other data included in the procedure data stream.

In an example operation, first sensor data 23029 may be filtered and/or pre-processed according to a first factor 23040 and the second sensor data 23031 may be filtered and/or pre-processed according to a second factor 23041. The resultant information, in this example, may include two values, one for each factor.

Figure 30A:
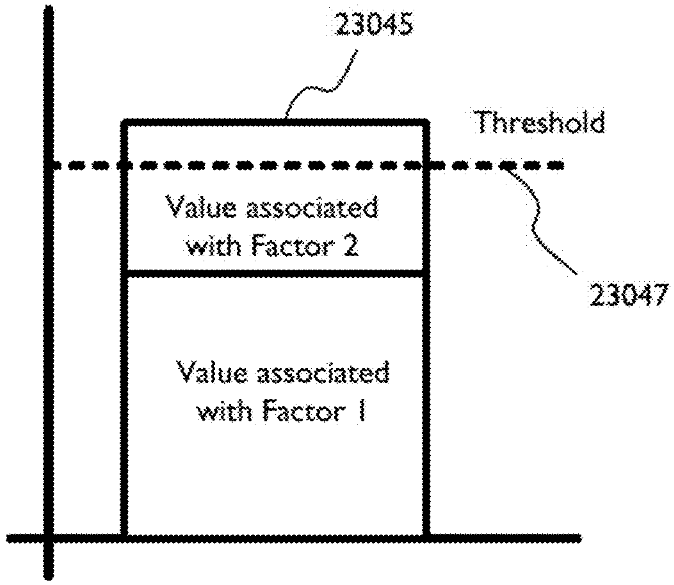
FIGS. 30A-B are plots depicting example adjustment score rubrics.

The resultant information from the factors 23026 of an active settings recommendation engine 23024 may be scored by the scoring rubric 23030 associated with that settings recommendation engine 23024. The scoring rubric 23030 takes as input the resultant information from the factors 23026 and outputs one or more scores that each may map to a respective configuration package 23032. In the example operation, and as illustrated in FIG. 30A, the information from the factors may be summed into a resultant score 23045. The resultant score 23045 is compared to a threshold 23047. If the threshold 23047 is exceeded, a corresponding configuration package 23032 may be selected. If the threshold 23047 is not exceeded, a different corresponding package 23032 may be selected. Or for example, if the threshold 23047 is not exceeded, no corresponding package 23032 or a null package may be selected. Having no corresponding package 23032 or a null package may result in no further substantive action being taken by the settings recommendation engine 23024.

The scoring rubric 23030 may engage complex decision making, including logic trees, look-up tables, non-linear thresholds, and the like. In one example, and illustrated in FIG. 30B, the information from the factors may combined into a vector 23049. The vector 23049 may be evaluated by one or more two-dimensional threshold functions 23051, 23053. The threshold functions 23051, 23053 may define evaluation zones 23054, 23056, 23058 within which the vector 23049 may fall. Each evaluation zone 23054, 23056, 23058 may be associated with a respective configuration package 23032. One or more evaluation zones 23054, 23056, 23058 may be associated with no configuration package 23032 and/or a null package.

Based on the evaluation of the scoring rubric 23030, one or more configuration packages 23032 may be selected for output. The processor may output information in accordance with the selected configuration package 23032 and the other available data, such as information from the scoring rubric 23030. For example, the processor may output a signal 23060 indicative of a determined surgical device setting. The signal may include a timestamp 23062, a surgical device ID 23064, recommended setting information 23066, a degree-of-confidence 23068, and/or any other information relevant to the operation of presenting a recommended surgical device setting.

The surgical device ID 23064 may be indicative of the specific surgical device for which the recommended setting and/or notification is relevant and/or intended.

The recommended setting information 23066 may include any information relevant in the operation of present surgical procedure as indicated by the settings configuration engine 23024. The recommended setting information 23066 may include a notification with information intended for presentation via a human interface device. The recommended setting information 23066 may include structured data with specific settings labels and values intended to be recommended and/or ingested by the identified surgical device. The recommended setting information 23066 may include computer code intended to be loaded and/or executed in connection with the operation of the identified surgical device. The recommended setting information 23066 may represent setting information in absolute terms. The recommended setting information 23066 may represent a departure from the present settings for the identified surgical device (e.g., as identified by the processor 23018 from setting information received from the configurable surgical equipment 23008 via the input 23012). The recommended setting information 23066 may represent setting information in relative terms. For example, recommended setting information 23066 may represent setting information in terms relative to the present settings for the identified surgical device.

Figure 30B:
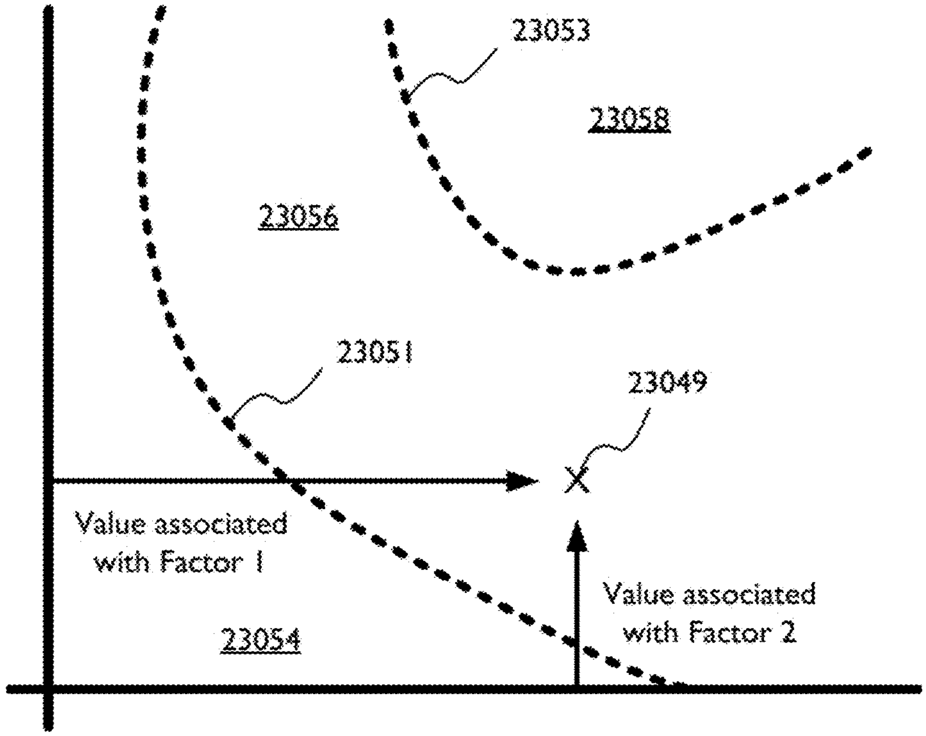

The degree-of-confidence 23068 may include any information indicative of the strength of the decision making associated with the settings recommendation engine 23024 and the scoring rubric 23030. For example, as shown in FIG. 30A, the degree-of-confidence 23068 may be associated with the extent to which the resultant score 23045 exceeds the threshold 23047. For example, as shown in FIG. 30B, the degree-of-confidence 23068 may be associated with the extent to which the vector 23049 is distant from a centroid of a respective evaluation zone 23054, 23056, 23058. The degree-of-confidence 23068 may be influenced by the specific settings recommendation engine 23024 itself. For example, settings recommendation engines 23024 may include a factor to normalize the degree-of-confidence 23068 across the active and/or all-available settings recommendation engines 23024. For example, a settings recommendation engine 23024 being serviced by many different sensor values (and corresponding factors) may amplify the degree-of-confidence 23024 otherwise generated by its scoring rubric 23030. For example, a settings recommendation engine 23024 being serviced by few different sensor values (and few corresponding factors) may amplify the degree-of-confidence 23024 otherwise generated by its scoring rubric 23030. The degree-of-confidence 23068 may include data intended for output to a human interface device, structure data (for output and for logging for example), and the like. The degree-of-confidence 23068 may include information that a surgeon and/or other health care professional may find relevant when evaluating the recommended surgical device setting 23066.

Figure 31:
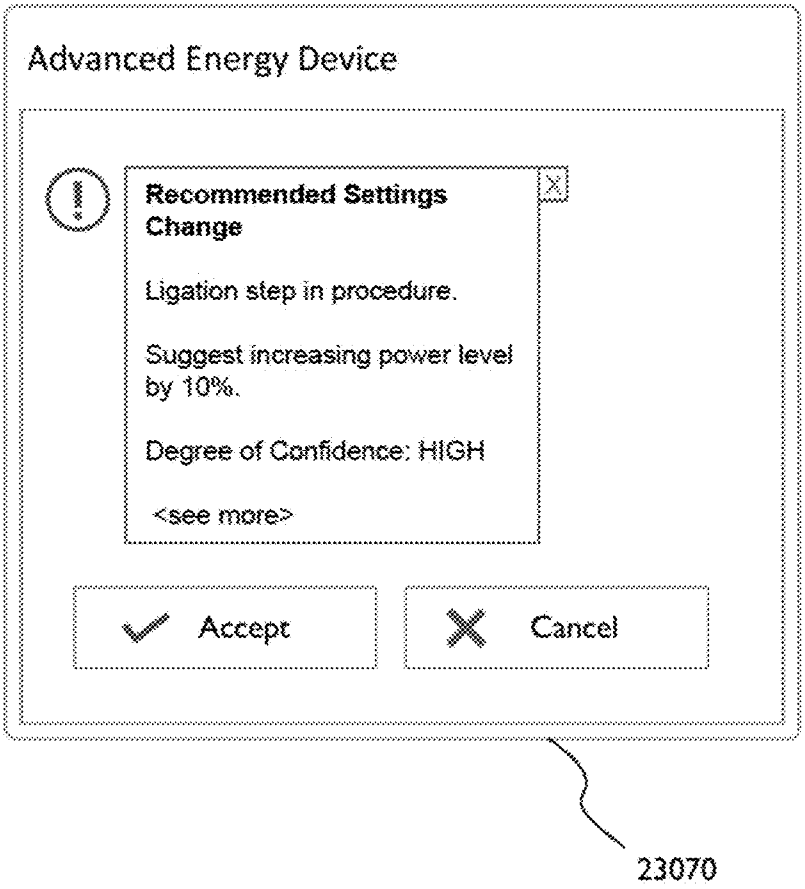
FIG. 31 illustrates an example user interface of notification and recommended device setting.

To illustrate, as shown in FIG. 31, an example user interface 23070 may be presented in connection with the system 23000. Here, based on one or more sensor values and procedure data, the processor 23018 outputs a signal 23060 that provides a recommended settings change to the health care professional. In this illustration, the relevant surgical device is an advanced energy device, the procedure element is a ligation, the recommended settings change is a relative increase in the power level of the advanced energy device.

Figure 32:
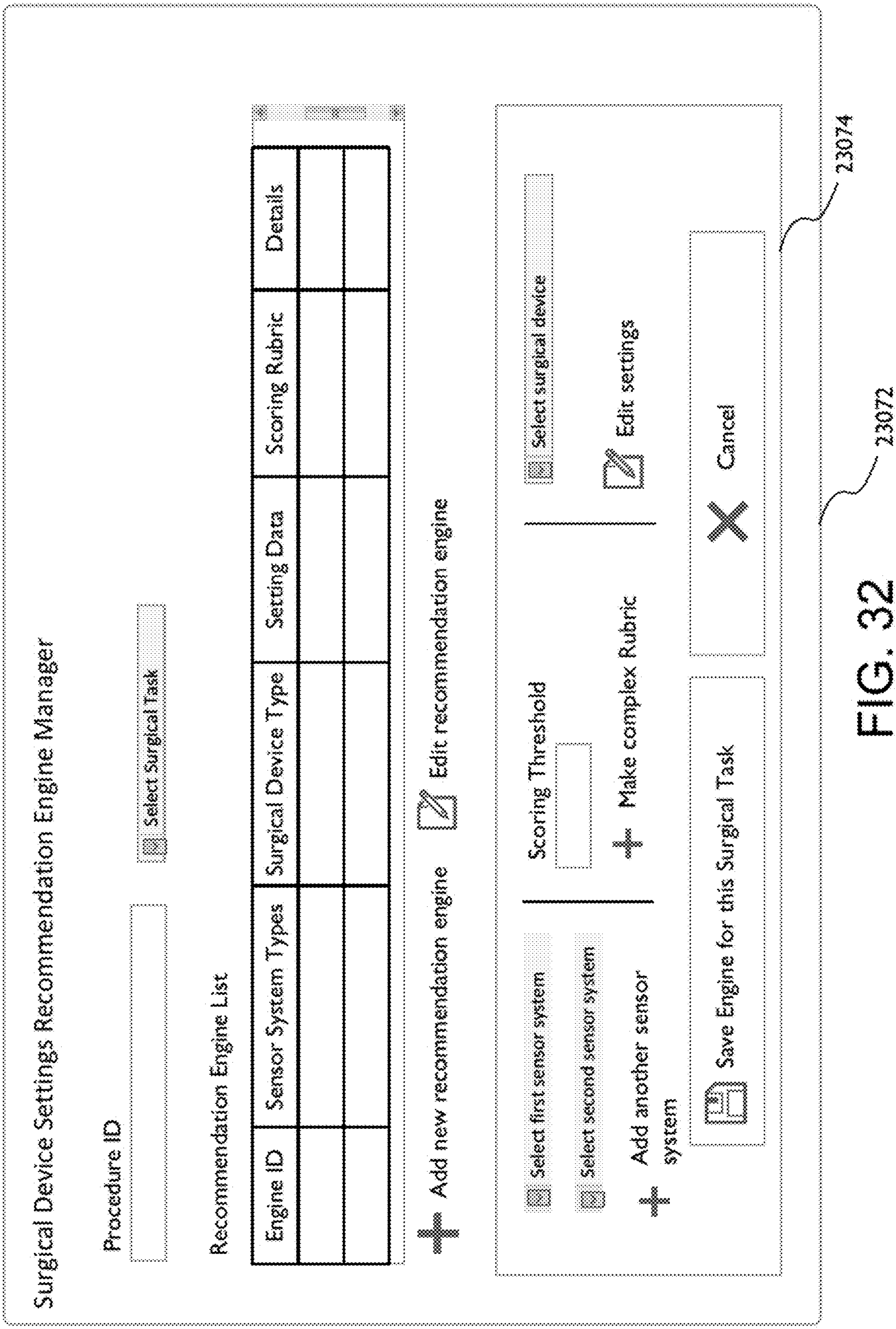
FIG. 32 illustrates an example user interface for managing a computing device for determining surgical device settings.

FIG. 32 is an example user interface 23072 for managing a computing device for determining surgical device settings. For example, the user interface 23072 may be used to manage at least a portion of the operation of the computing device 23006. The user interface may be used to create, delete, and/or modify the device settings recommendation engines.

A surgeon or other health care professional may start with a particular procedure ID and/or procedure element (e.g., a specific surgical task within a given procedure), for example. The procedure ID may refer to a procedure generally. The procedure ID may refer to a procedure for a particular patient.

The user interface 23072 may present one or more recommendation engines associated with the procedure ID in a recommendation engine list. The user may set the listed recommendation engines to be active or inactive for the procedure. The user may add new recommendation engines manually or input them from a data repository. The user may edit existing recommendation engines. The information associated with each engine, as illustrated in this example user interface 23072, may include an Engine ID, the relevant sensor system types, the surgical device types, the specific settings data (e.g., a representation of the configuration packages 23032), the scoring rubric, and other information.

When manually creating an engine or editing an existing engine, the surgeon may use the lower interface panel 23074. For example, the user may select one or more sensor systems for inclusion in the engine. For each sensor system a corresponding factor may established. The user may select certain procedure data (not shown) to be included with a corresponding factor.

The user may add or edit the scoring rubric. For example, the user may enter a simple scoring threshold. The user may use a subsequent user interface to enter a complex scoring rubric. The scoring rubric may include the previously selected sensor systems. The scoring rubric may include variables. For example, the scoring rubric may include a baseline level from a sensor to be used for calculating a threshold. The scoring rubric may take in account certain procedure data if so configured with a corresponding factor.

The user may then create one or more configurations. The user may select a surgical device for which the configuration would apply. The user may select that the configuration be a null configuration. The user may select that the configuration be associated with a notification.

Finally in this illustration, the individual engine may be saved and made active for the particular procedure ID. As a result, when the procedure is being performed, the settings recommendation manager 23024 may scan the incoming sensor and procedure data for matches to the sensor systems and procedure data entered via this interface 23072. The settings recommendation manager 23024 may process that sensor and procedure data according to the entered factors and evaluate it according to the entered scoring rubric 23030. The evaluation of the scoring rubric 23030 may indicate one or more applicable configuration packages 23032, as entered. The applicable configuration packages 23032 may then be triggered, as a signal output for example, to provide a recommended setting change and/or a notification for the relevant surgical device and/or relevant health care professionals, respectively.

Any of the relationships among sensing systems, biomarkers, and physiologic systems (e.g., those relationships disclosed herein, such as those with reference to FIG. 1B for example) may be used to inform differentiation among co-morbidities. Any of the relationships among sensing systems, biomarkers, and physiologic systems (e.g., those relationships disclosed herein, such as those with reference to FIG. 1B for example) may be used to inform a settings configuration engine.

Figure 33:
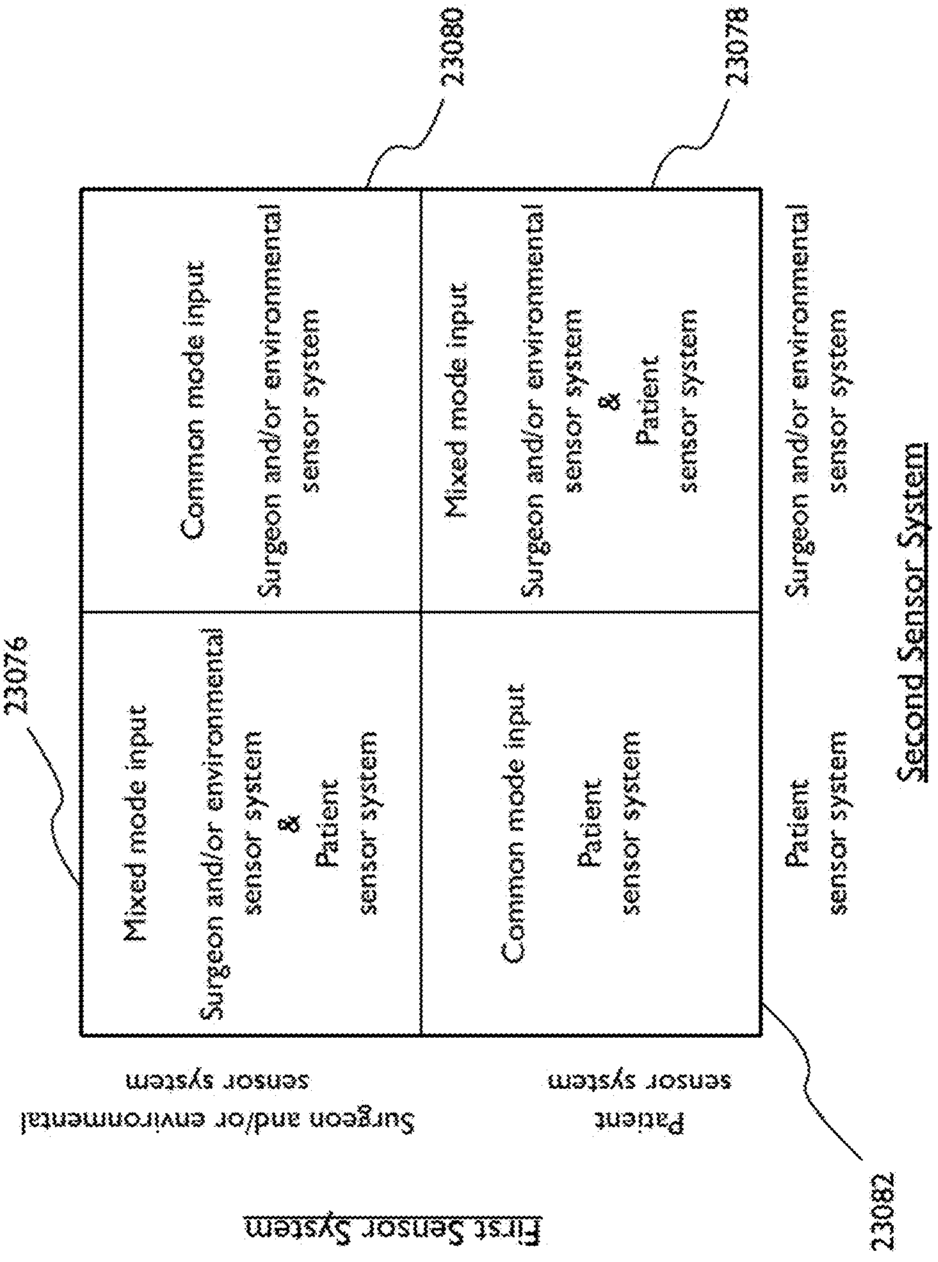
FIG. 33 is a diagram to illustrate common mode and mixed mode sensor inputs to an example computing device for determining surgical device settings.

FIG. 33 illustrates common mode and mixed mode sensor inputs to an example computing device for determining surgical device settings. As disclosed there are various modes of sensing systems, including for example controlled patient monitoring systems, uncontrolled patient monitoring systems, surgeon monitoring systems, environmental sensing systems, and the like. When considering patient related systems together with non-patient system (e.g., surgeon and/or environmental sensor systems), a resultant system synthesis framework may include a mixed mode and/or common mode systems (e.g., mixed mode and/or common mode settings recommendation engines). For example, at 23076, 23078, a mixed-mode input and/or system may include input from one or more surgeon and/or environmental sensor systems and input from one or more patient sensor systems. For example, at 23080, a common-mode input and/or system may include input from one or more surgeon and/or environmental sensor systems. For example, at 23082, a common-mode input and/or system may include input from one or more patient sensor systems.

The modality of resultant recommendation engine may influence the particular co-morbidities that are more likely to be differentiated. For example, convoluted causes based on a single monitored biomarker may be differentiated by a secondary external monitored parameter. For example, environmental air quality may be used in a lung resection procedure to differentiate emphysema. For example, obesity and activity issues may be differentiated from diabetes. For example, eating, stress, and other heart rate measures may be differentiated by monitoring physical activity level at the time.

In an example, a respiration rate monitor may be used to characterize breathing. The breathing such as shallow breathing, for example, may be indicative of a reduced lung volume utilization. Shallow breathing may also be indicative of externally induced physiological reaction. A second sensor such as an environmental monitor air quality may be used. The combination of the environmental monitor of air quality and the respiration rate monitor of the patient together (e.g., a mixed-mode system) may trigger recommendations that differentiate co-morbidities. For example, a recommendation and/or alert associated when the respiration rate is indicative of shallow breathing, but the environmental monitor air quality is low, may stress that the air quality is low may recommend improving air quality. However, a recommendation and/or alert associated when the respiration rate is indicative of shallow breathing, but the environmental monitor air quality is normal, may stress addressing the patient's airflow by factors other than improving air quality.

In an example, historical data and/or pre-operating patient measurements may be used to establish baselines against which analogous operative data may be compared (i.e., a common-mode analysis). The baseline comparison may be implemented in an appropriate scoring rubric. For example, baselines for breathing patterns may be assessed during an office visit and/or with an uncontrolled patient monitoring system before a scheduled surgery. This data may be incorporated into a settings recommendation engine. Then, during surgery, breathing measurements that deviate unexpectedly from this baseline may trigger the appropriate notifications and/or setting changes.

Figure 34:
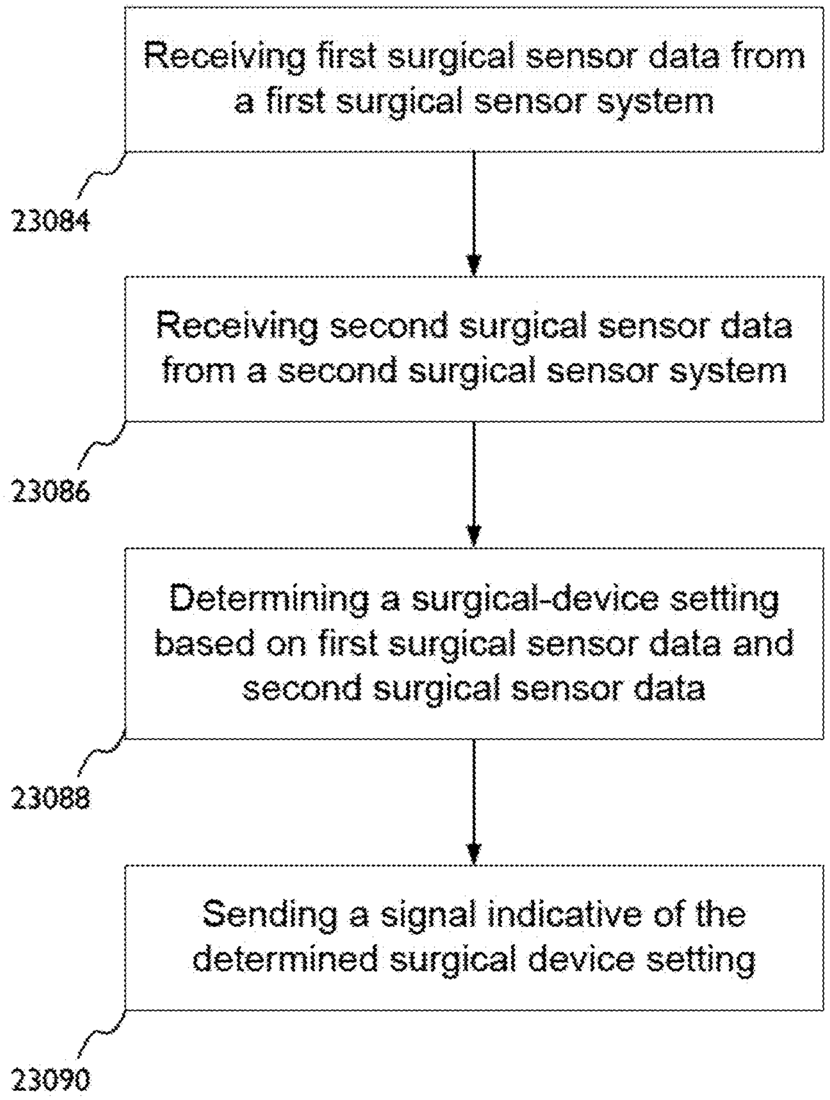
FIG. 34 is a diagram of an example process for determining surgical device settings.

FIG. 34 is a diagram of an example process for determining surgical device settings. The process may include a computer-implemented process for example. At 23084, first surgical sensor data may be received. For example, the first surgical sensor data may be received from a first surgical sensor system. The first surgical sensor system may include any of a first wearable patient sensor system, a first surgical theater environmental sensor system, or the like.

In an example, the first surgical sensor system may include a first wearable patient sensor system, and the second surgical sensor system may include a second wearable patient sensor system. In an example, first surgical sensor system may include a first wearable patient sensor system, and second surgical sensor system may include a second surgical theater environmental sensor system. In an example, the first surgical sensor system may include a first surgical theater environmental sensor system, and the second surgical sensor system may include a second surgical theater environmental sensor system.

At 23086, second surgical sensor data may be received. For example, the second surgical sensor data may be received from a second surgical sensor system. The second surgical sensor system may include any of a second wearable patient sensor system, a second surgical theater environmental sensor system, or the like.

At 23088, a surgical-device setting may be determined. For example, the surgical-device setting may be determined based on the first surgical sensor data and second surgical sensor data. The surgical-device setting may include a recommendation for a change in the surgical-device setting. For example, the surgical device may include any of a powered stapler, a powered stapler generator, an energy device, an energy device generator, an in-operating-room imaging system, a smoke evacuator, a suction-irrigation device, an insufflation system, or the like. For example, the surgical device setting may include any of a power level, an advancement speed, a closure speed, a closure load, a wait time, or the like.

In an example, a notification or recommendation without a surgical device setting, such as a notification that is independent of a surgical device setting, may be determined. Such a notification may be indicated by a corresponding signal (i.e., a signal indicative of the determined notification) at 23090.

At 23090, a signal indicative of the determined surgical device setting may be sent. The signal may represent information that, when received by a surgical device, enables the surgical device to perform in accordance with the determined surgical-device setting.

A computing system may be configured to monitor a patient's biomarkers and predict an adhesion complication before a surgery and/or during a surgery. The computing system may include a processor configured to obtain pre-surgical and/or in-surgical measurement data associated with one or more patient biomarkers via one or more sensing systems. The computing system may predict an adhesion complication based on the measurement data associated with the one or more patient biomarkers. For example, the computing system may determine a probability of a chronic inflammation response based on the measurement data associated with the one or more patient biomarkers. On the condition that the probability of a chronic inflammation response crosses a threshold, the computing system may predict an adhesion complication. The predicted adhesion complication may include convoluted tissue planes, internal scarring, and/or adhesion bands.

The computing system may generate an output based on the predicted adhesion complication. The generated output may include a control signal configured to indicate an adjustment to an instrument selection for dissecting capability. The adjustment may include selecting an improved dissection tool in place of an improved hemostasis tool. The generated output may include a control signal configured to indicate an adjustment to an instrument selection for access capability. The adjustment may include selecting a percutaneous instrument configured to combine with a 5 mm end effector, selecting a higher articulating surgical device with improved access capability, and/or selecting a percutaneous instrument to supplement a laparoscopic instrument. The generated output may include a control signal configured to display a probability of an adhesion complication on a pre-surgery imaging, display a probability of an adhesion complication via an augmented reality device, and/or display a probability of an adhesion complication in a surgical procedure plan along with an indication of an adjustment to the surgical procedure plan.

A computing system may monitor a patient's biomarkers pre-surgery and/or in-surgery and predict an adhesion complication. The computing system may obtain measurement data associated with one or more patient biomarkers via one or more sensing systems, predict an adhesion complication based on the measurement data associated with the one or more patient biomarkers, and generate an output based on the predicted adhesion complication. The adhesion complication may be predicted by determining a probability of a chronic inflammation response based on the measurement data associated with the one or more patient biomarkers. The generated output may include a control signal configured to indicate an adjustment to an instrument selection for dissecting capability and/or access capability. The generated output may include a control signal configured to notify a surgeon of a probability of an adhesion complication.

Figure 35:
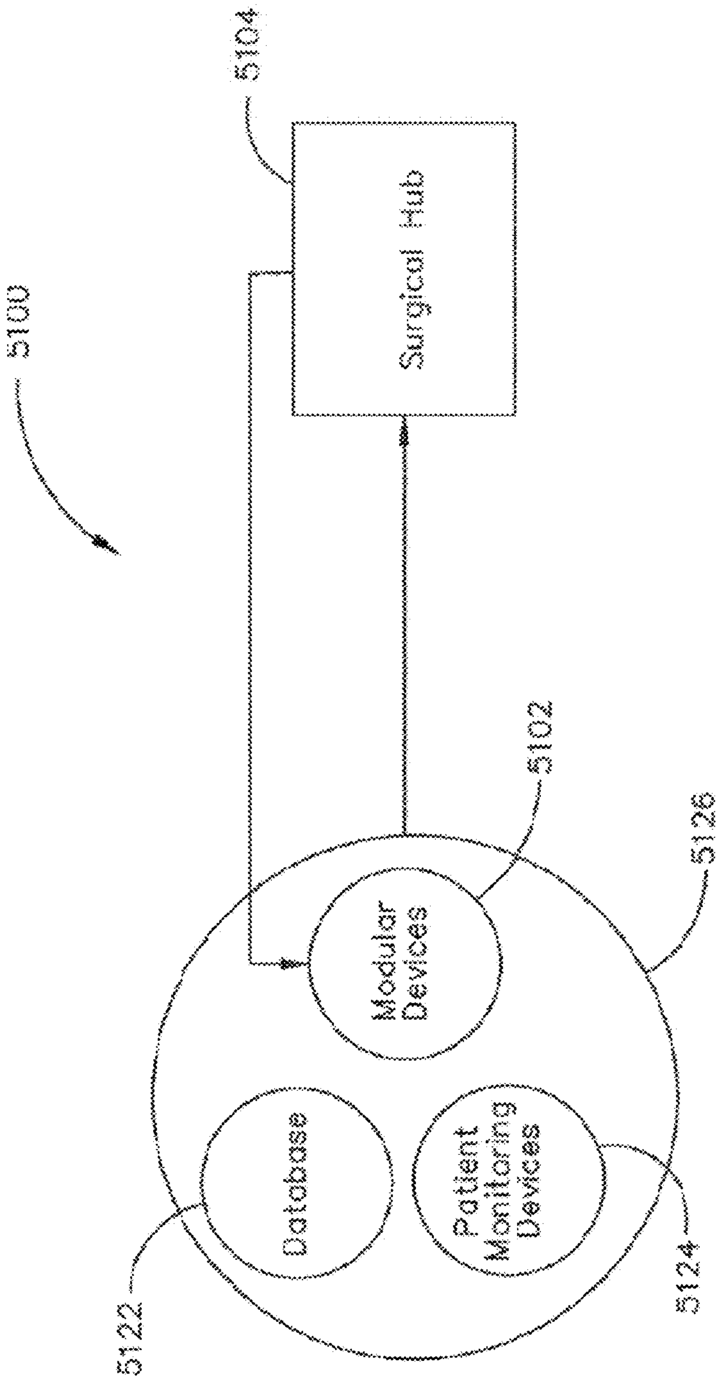
FIG. 35 is a diagram of an example situationally aware surgical system.

FIG. 35 illustrates a diagram of a situationally aware surgical system 5100, in accordance with at least one aspect of the present disclosure. In some exemplifications, the data sources 5126 may include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In an exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In an exemplification, the situational awareness system can include a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in an exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use a soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can be configured to compare the list of items for the procedure and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In some exemplifications, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In some exemplifications, the surgical hub 5104 can be configured to provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Figure 36:
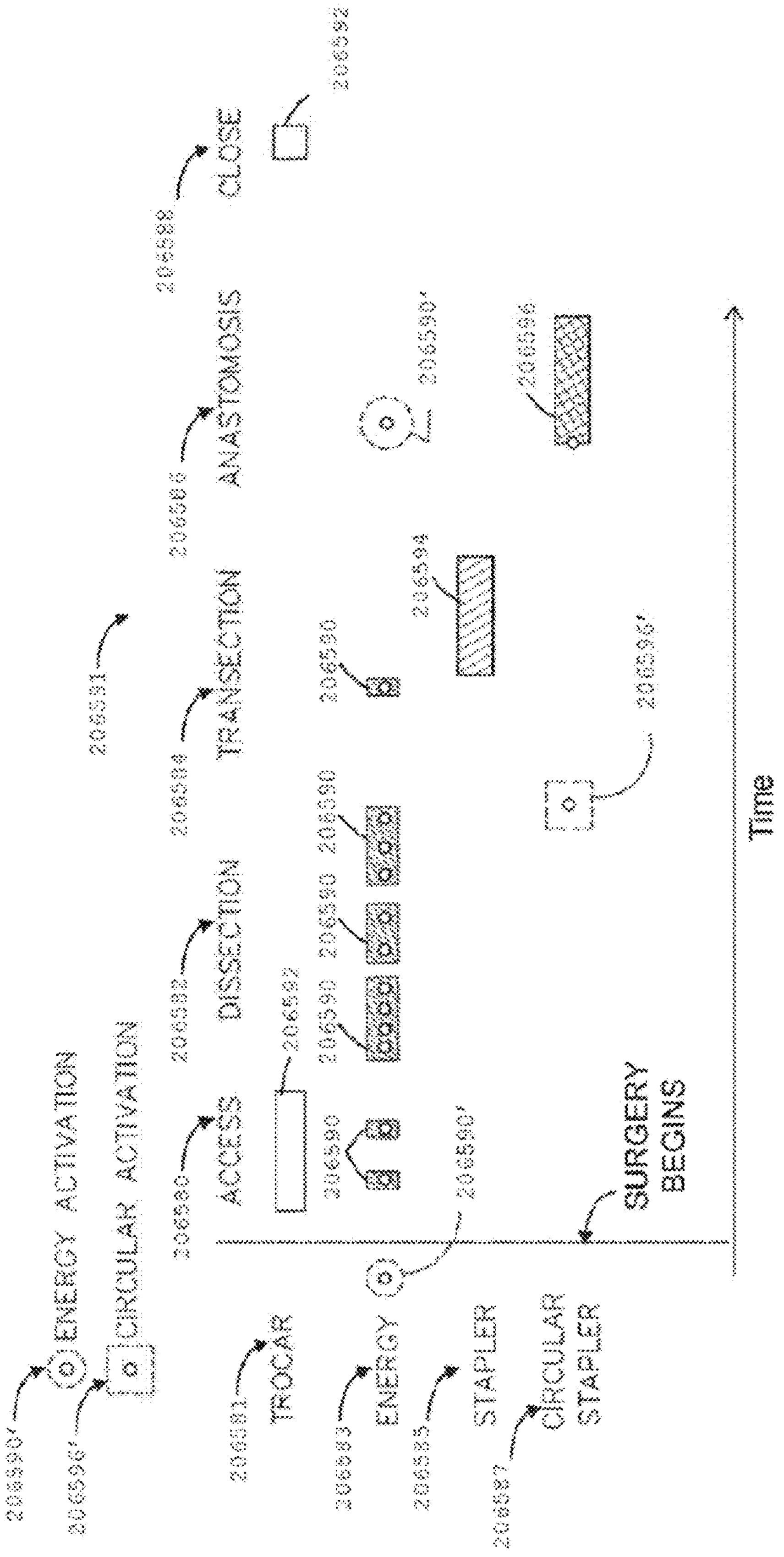
FIG. 36 illustrates example planned procedure steps of a colorectal procedure using various surgical devices.

FIG. 36, illustrates example planned procedure steps of a colorectal procedure using various surgical devices. As shown, planned procedure steps of a colorectal procedure may include access 206580, dissection 206582, transection 206584, anastomosis 206586, and closing 206588. The planned procedure steps may be associated with one or more modular devices such as a trocar 206581, a modular energy device 206583, a linear surgical stapler 206585, and a circular surgical stapler 206585. In various examples, the computing system may access a database of various surgeries, the identity and order of the planned surgical steps pertaining to the surgeries, and/or the identity and/or usage or activation frequency of the modular surgical devices to be used in the planned surgical steps.

Adhesions may lead to complications in a surgical procedure. For example, adhesions may form in the pleural space, such as between the parietal pleura and the visceral pleura and/or between the parietal pleura and the chest wall. In an example, in a lung segmentectomy procedure, the adhesions may need to be cut and released before a surgical site (e.g., a target lung lobe) may be reached and mobilized. In such example, fibrous and/or dense adhesions may have been formed and may have obliterated the pleural space, which may lead to convoluted tissue planes. Dissection of such adhesions may lead to unintended incisions to the underlying lung tissue, which may lead to uncontrollable bleeding during the procedure. Dissection of such adhesions may take meticulous and slow manipulation and hence may prolong a surgical procedure duration. Dissection of such adhesions may lead to prolonged air leaks that may persist beyond a normal hospitalization period. For example, similar surgical complications may occur in a colorectal procedure due to adhesions that form between the abdominal wall and the small and/or large intestine, between bowel loops (small and/or large intestine), and/or within the small and/or large intestine.

An adhesion complication may be predicted based on pre-surgical and/or in-surgical measurements of related biomarker(s). For example, an adhesion complication may be determined based on one or more chronic inflammation response-related biomarkers. Chronic inflammation response may lead to prolonged scar tissue forming, prolonged tissue remodeling, and/or scar tissues damaging and replacing healthy tissues. As a result, bands of scar tissues and adhesions may form. Biomarkers related to chronic inflammation response include tissue perfusion pressure, lactate, oxygen saturation, VO2Max, respiration rate, autonomic tone, sweat rate, heart rate variability, skin conductance, GI motility, and/or the like.

For example, an adhesion complication may be predicted based on biomarker(s) related to a chronic inflammation response associated with poor tissue oxygenation. Chronic poor tissue oxygenation may lead to cell death, the associated infection and chronic inflammation, and consequently adhesions. Biomarkers related to a chronic inflammation response associated with poor tissue oxygenation may include tissue perfusion pressure, lactate, oxygen saturation, and/or VO2Max. In an example, tissue perfusion pressure measures the sufficiency of blood flow through tissues. Insufficient tissue perfusion pressure may lead to chronic poor tissue oxygenation and consequently adhesions. In an example, lactate is a substance produced by cells during cell metabolism. A high lactate level may indicate chronic poor tissue oxygenation and consequently adhesions. In an example, oxygen saturation measures the oxygen level in the blood flow. A low oxygen level in the blood flow may lead to chronic poor tissue oxygenation and consequently adhesions. In example, VO2Max measures the maximum amount of oxygen the body can consume (e.g., from breathing in the air to tissue oxygenation) during a specified period of time (e.g., a period of incrementally intense exercise). A low VO2Max may indicate a poor oxygen consumption ability. Such poor oxygen consumption ability may lead to chronic poor tissue oxygenation and consequently adhesions.

For example, an adhesion complication may be predicted based on biomarker(s) related to a chronic inflammation response associated with increased respiration rate. Increased respiration rate may indicate a chronic lung inflammation condition and the presence of consequent adhesions. In an example, an increased respiration rate due to air leaks in lungs caused by an underlying chronic inflammation response may indicate the presence of adhesions.

For example, an adhesion complication may be predicted based on biomarker(s) related to a chronic inflammation response associated with an imbalanced autonomic tone. Autonomic tone describes the basal balance between the sympathetic and parasympathetic nervous system. In an example, an imbalanced autonomic tone, such as a high sympathetic tone, may indicate chronic inflammation and the presence of consequent adhesions. Autonomic tone may be associated with biomarkers related to the sympathetic nervous system, such as heart rate variability, skin conductance, or sweat rate. For example, a high sympathetic tone may be inferred from one or more of: an increased heart rate, an increased sweat rate, or a higher skin conductance (e.g., based on these biomarkers' association with heightened sympathetic activity). The inference of such high sympathetic tone may indicate a chronic inflammation response and the presence of consequent adhesions. The inference of such high sympathetic tone may be associated with pre-surgical and/or in-surgical pain and/or stress.

For example, an adhesion complication may be predicted based on biomarker(s) related to a chronic inflammation response associated with reduced GI motility. In an example, reduced small bowel motility due to small bowel obstruction may be caused by adhesions formed on the wall of a small bowel. Such adhesions may have resulted from a chronic inflammation response in the small bowel. In such example, the chronic inflammation response may have been caused by an underlying chronic inflammatory disease (e.g., Crohn's disease or irritable bowel syndrome (IBS)). In such example, the chronic inflammation response may have been caused by a chronic inflammation resulting from a prior colorectal procedure. In an example, the adhesion complication predicted based on reduced GI motility may be inferred from a high sympathetic tone indicated by one or more of: an increased heart rate, an increased sweat rate, or a higher skin conductance. The indication of such high sympathetic tone may be associated with pre-surgical and/or in-surgical pain and/or stress.

As described herein, various sensing systems (as described herein with reference to FIGS. 1A-B, 2A-C, 3, 4, 5, 6A-C, 7B-D, 9, 11A-D, and 12) may measure biomarkers that may be used to predict adhesion complication(s). For example, the sensing systems may perform pre-surgical and/or in-surgical measurement(s) of a patient's adhesion-related biomarkers, such as tissue perfusion pressure data, lactate data, oxygen saturation data, VO2Max data, respiration rate data, autonomic tone data, sweat rate data, heart rate variability data, skin conductance data, GI motility data, and/or the like. Such pre-surgical measurement(s) of adhesion-related biomarkers may be performed via the sensing system(s) in a clinical setting. In an example, as shown in FIG. 6A, one or more of sensing systems may perform pre-surgical measurement(s) of a patient's adhesion-related biomarker(s) before a surgical procedure in an operating room.

The sensing system(s) may process and/or store measurement data for predicting adhesion complication(s) locally, and/or send the measurement data to a computing system for further processing. The computing system may be or may include a surgical hub described herein, for example with reference to FIGS. 1A, 2A-B, 3, 5, 6A-B, 7B-D, 9, and 12. The computing system may include or be connected with a surgical hub/surgeon display interface described here, for example with reference to FIGS. 4, 5, 6A-B, and 12. In an example, as shown in FIG. 6A, the sensing system(s) may communicate with the computing system via a communication module 230. In an example, as shown in FIG. 6B, the sensing system(s) may communicate with the computing system via a local area network (LAN).

Pre-surgical measurement data and/or in-surgical measurement data associated with one or more patient biomarkers may be obtained from the sensing system(s). For example, the computing system may obtain, from the sensing system(s), measurement data associated with one or more adhesion-related biomarkers, such as tissue perfusion pressure, lactate, oxygen saturation, VO2Max, respiration rate, autonomic tone, sweat rate, heart rate variability, skin conductance, GI motility, and/or the like.

An adhesion complication may be predicted based on pre-surgical and/or in-surgical measurement data associated with biomarker(s) monitoring. For example, the sensing system(s) may perform the prediction based on the measurement data of adhesion-related biomarker(s). For example, the computing system may determine an adhesion complication based on the measurement data of adhesion-related biomarker(s) and the threshold(s) associated with the biomarker(s).

One or more thresholds may be obtained for a patient biomarker. For example, the computing system may determine respective threshold(s) associated with a patient's tissue perfusion pressure, hydration state, lactate, oxygen saturation, VO2Max, respiration rate, autonomic tone, sweat rate, heart rate variability, skin conductance, GI motility, and/or the like. The threshold(s) may be standard threshold(s). The threshold(s) may be pre-defined and/or set by an HCP. The threshold(s) may be customized for a patient based on the patient's medical history, health information, biographical information, family health information, and/or the like. A biomarker may be monitored by comparing the measurement data related to the biomarker against the corresponding threshold(s). A potential adhesion complication(s) may be detected when the measurement data related to one or more biomarkers crosses the corresponding threshold(s) for a predetermined amount of time. Crossing a threshold may include the measurement data associated with a biomarker increasing above the corresponding threshold value. Crossing the threshold may include the measurement data associated with a biomarker dropping below the corresponding threshold value. The predetermined amount of time may be used to mitigate erroneous measurement data. For example, the predetermined amount of time may reduce the number of false positive detections. The predetermined amount of time may be determined based on the one or more biomarkers being monitored.

The computing system may predict an adhesion complication by determining that a probability of a chronic inflammation response crosses a threshold. The probability of chronic inflammation response may be determined (e.g., calculated) based on the biomarker measurement data, such as tissue perfusion pressure, lactate, oxygen saturation, VO2Max, respiration rate, autonomic tone, sweat rate, heart rate variability, skin conductance, and/or GI motility data The computing system may determine an adhesion complication based on measurement data of one or more adhesion-related biomarker(s) deviating from the obtained threshold(s). For example, a tissue perfusion pressure sensing system (e.g., based on skin perfusion pressure) may measure blood volume changes to determine the skin perfusion pressure. The measured skin perfusion pressure may be compared against a skin perfusion pressure range threshold. An adhesion complication may be determined when a skin perfusion pressure measurement is below such range threshold. For example, a lactate sensing system may employ electrochemical biosensors to measure sweat lactate levels. The measured sweat lactate level may be compared against a sweat lactate level range threshold. An adhesion complication may be determined when a sweat lactate level measurement is above such range threshold. For example, a peripheral capillary oxygen saturation (SpO2) may be calculated as a ratio of pulsed signal to non-pulsed signal. The measured SpO2 may be compared against an SpO2 range threshold. An adhesion complication may be determined when a SpO2 measurement is above such range threshold. For example, VO2Max measures the body's oxygen consumption ability. The measured VO2Max score may be compared against a VO2Max score threshold. An adhesion complication may be determined when a SpO2 measurement is above such score threshold. For example, a respiration rate may measure the number of breaths per minute. The measured respiration rate may be compared against a respiration rate range threshold. An adhesion complication may be determined when a respiration rate measurement is above such range threshold. For example, a heart rate variability score measured by a heart rate sensing system may be compared against a heart rate variability score range threshold. An adhesion complication may be determined when a respiration rate measurement is above such range threshold. For example, a sweat rate measured by a sweat rate sensing system may be compared against a sweat rate range threshold. An adhesion complication may be determined when a sweat rate measurement is above such range threshold and hence indicates high sympathetic activity. For example, a skin conductance level (SCL) measured by a skin conductance sensing system may be compared against a SCL range threshold. An adhesion complication may be determined when a SCL measurement is above such range threshold and hence indicates high sympathetic activity. For example, an autonomic tone sensing system may be configured to employ a heart rate variability sensing sub-system, a sweat rate sensing sub-system, and/or a skin conductance sensing sub-system. An adhesion complication may be determined by an autonomic tone sensing system when an adhesion complication is determined by one or more such sub-systems. For example, a GI motility sensing system employing a wireless non-digestible capsule may measure gastric, small bowel, large bowel, and/or colonic transit times. The measured gastric transit time, small bowel transit time, large bowel transit time, and/or colonic transit time may be compared against a gastric transit time range threshold, a small bowel transit time range threshold, a large bowel transit time range threshold, and/or a colonic transit time range threshold, respectively. A reduced GI motility may be determined when one or more of such transit times are above their respective transmit time range threshold. Accordingly, an adhesion complication may be determined based on the determination of reduced GI motility. For example, a reduced GI motility may be determined when an autonomic tone-related biomarker (e.g., heart rate variability, sweat rate, or skin conductance) is determined to indicate high sympathetic activity. Accordingly, an adhesion complication may be determined based on the determination of the high sympathetic activity indication.

The determination of an adhesion complication may be based on the pre-surgical and/or in-surgical adhesion-related biomarker measurement data preprocessed by the sensing systems. For example, a tissue perfusion pressure sensing system (e.g., employing skin perfusion pressure measurement) may monitor a patient's skin perfusion pressure via continuous measurements. When the tissue perfusion pressure sensing system transmits the tissue perfusion pressure measurement data, the sensing system may calculate the mean of the measurements and transmit such mean to the computing system. The sensing system may calculate the mean of the measurements excluding outlier measurements and transmit such mean. The sensing system may calculate the mean of the measurements and standard deviation of the measurement data set, and transmit the mean and the standard deviation. The sensing system may calculate an average of the highest measurement and the lowest measurement and transmit such average. The sensing system may identify the highest measurement and the lowest measurement and transmit such measurement range. The sensing system may identify the highest measurement and the lowest measurement after excluding outlier measurements and transmit such measurement range. The sensing system may convert the preprocessed water content level measurement data to tissue perfusion pressure classifications, such as "high", "moderate", "low", or "severely low", and transmit such classifications to the computing system. The hydration state sensing system may transmit to the computing system identifiers for such classifications, e.g., "H", "M", "L", and "SL" for "high", "moderate", "low", and "severely low", respectively. Those of skill in the art will recognize other sensing systems described herein may also preprocess the biomarker measurement data and then transmit the preprocessed biomarker measurement data to the computing system as described.

The determination of an adhesion complication may be based on the pre-surgical and/or in-surgical adhesion-related biomarker measurement data as captured by the sensing systems (e.g., raw measurements). The computing system may process the raw measurements before making the determination. For example, a tissue perfusion pressure sensing system (e.g., employing skin perfusion pressure measurements) may monitor a patient's skin perfusion pressure via continuous measurements. The tissue perfusion pressure sensing system may transmit the raw measurements to the computing system. In response, the computing system may process the raw measurements as described in how the tissue perfusion pressure sensing system preprocesses the tissue perfusion pressure measurement data. Those of skill in the art will recognize other sensing systems described herein may transmit raw measurements to the computing system and in response the computing system may process the raw measurements as described.

The computing system may determine an adhesion complication associated with a pulmonary procedure based on the measurement data of a patient's pulmonary function. The pre-surgical measurement may be performed on the patient before an impending pulmonary procedure (e.g., in a clinical setting, such as in an operating room). In an example, forced expiratory volume in 1 second (FEV1) test may be performed. The measurement data may be entered into the computing system (e.g., via a user interface). The measurement data may be entered into a hospital record system (e.g., an EMR system) and obtained by the computing system. The computing system may determine an adhesion complication on the condition that the FEV1 measurement is below a FEV1 threshold and hence indicates the presence of a restrictive or obstructive pulmonary disease (e.g., emphysema). In an example, forced vital capacity (FVC) test may be performed. The measurement data may be entered into the computing system. The measurement data may be entered into a hospital record system and obtained by the computing system. The computing system may determine an adhesion complication on the condition that the FVC measurement is below a FVC threshold and hence may indicate the presence of a restrictive or obstructive pulmonary disease. In an example, the computing system may determine an adhesion complication on the condition that a ratio of the FEV1 measurement over the FVC measurement is below a FEV1/FVC ratio threshold and hence indicates the presence of a restrictive or obstructive pulmonary disease. In an example, a spirometry test may be performed. The measurement data may be entered into the computing system. The measurement data may be entered into a hospital record system and obtained by the computing system. The computing system may determine an adhesion complication on the condition that a spirometry test result is below a threshold.

The computing system may predict a higher likelihood of post-operative air leaks based on the indication of the presence of a restrictive or obstructive pulmonary disease (e.g., emphysema) and a patient's disease states and/or medical conditions. For example, a patient's EMR and/or other hospital records may indicate adhesions from prior surgerie(s), infection(s) (e.g., pneumonia), interstitial lung disease, and/or the like. Such disease states and/or medical conditions may indicate a higher likelihood of post-operative air leaks. Further, the computing system may provide such indication of a higher likelihood for post-operative air leaks to a post-operative chest tube management control program.

For example, the computing system may predict an adhesion complication by determining a probability of pleural adhesion based on measurement data of biomarkers such as a lung gliding movement and a chest wall motion. The measurement of the biomarkers may be via a piezoelectric and ultrasonic transducer test and a chest wall motion detection performed on the patient before an impending pulmonary procedure (e.g., in a clinical setting, such as in an operating room). In an example, a piezoelectric/ultrasound transducer sensing array may be placed at discrete locations on the chest wall to detect the presence of, the location of, and/or the severity of adhesions. The lung's (visceral pleura) gliding movements across the chest well (parietal pleura) may be sensed by the sensing array. A dense sensing array may be used for mapping out the density of adhesions. The chest wall motion due to lung inflation and deflation that correlate with the gliding movements may be sensed (e.g., using an accelerometer). The sensed data may be entered into the computing system. The sensed data may be entered into a hospital record system (e.g., an EMR system). The sensed data may be obtained by the computing system. The computing system may determine the presence of adhesions when the gliding movements data indicate a lack of or the absence of such gliding movements. The computing system may consider the chest wall motion data and discard the gliding movements data that correlate in time. The computing system may detect the location and/or the density of adhesions (e.g., when the sensed data was obtained via a dense sensing array).

The computing system may generate an output based on the predicted adhesion complication. The output may include a control signal configured to adjust a surgical parameter associated with a surgery for mitigating the predicted adhesion complication. For example, the computing system may generate one or more adjustments to an impending surgical procedure. The adjustment may include, but not limited to, an adjustment to a surgical approach, an adjustment to a surgical procedure step, an adjustment to a surgical procedure schedule, and/or an adjustment to a surgical instrument selection.

An impending surgical procedure may include planned procedure steps that may be stored and retrieved, or otherwise accessed on a computing device (e.g., the surgical hub 206 or 5104). For example, a list of planned procedure steps for a thoracic procedure (specifically, a lung segmentectomy procedure) may be retrieved or accessed.

Planned surgical instruments' (as shown in FIGS. 1A, 2A, 3, 4, 5, 6A, 7A, 8, 9, 10, 12) identification information may be obtained via a computing device (e.g., the surgical hub 206 or 5104). For example, planned surgical instruments' identification information may be obtained based on planned procedure steps and the associated surgical instruments information. For example, as described in FIG. 36, planned procedure steps of a colorectal procedure (e.g., access 206580, dissection 206582, transection 206584, anastomosis 206586, and closing 206588) may be retrieved from a surgical hub (e.g., the surgical hub 206 or 5104). A list of planned surgical instruments (e.g., trocar 206581, energy device 206583, linear surgical stapler 206585, and circular surgical stapler 206587) associated with the planned procedure steps may be retrieved from the surgical hub. Usage of planned surgical instruments at planned procedure steps may be detected and confirmed by the surgical hub (e.g., the surgical hub 206 or 5104). For example, activation instances 206592 illustrate the expected usage of trocar 206581 at planned procedure steps access 206580 and closing 206588. For example, activation instances 206590 illustrate the expected usage of energy device 206584 at planned procedure steps access 206580, dissection 206582, and transection 206584. For example, activation instance 206594 illustrates the expected usage of linear surgical stapler 206585 at planned procedure step transection 206584. For example, activation instance 206596 illustrates the expected usage of circular surgical stapler 206587 at planned procedure step anastomosis 206586.

Based on the predicted adhesion complication, the computing system may generate a control signal configured to indicate a suggestion for adjusting a surgical approach.

For example, a suggestion for adjusting the surgical approach may be a suggestion to opt for an open procedure in place of the planned laparoscopic procedure approach. In an example, the computing system may determine that adhesions are present in a large area in the pleural space based on the sensed data obtained from piezoelectric/ultrasonic transducer testing. In such example, the computing system may determine that adhesions are dense based on the sensed data. A suggestion for an open procedure approach may be indicated due to dense adhesions being present in a large area. Such adhesions may render complete visualization of anatomical structures of adhesions and the surrounding working space difficult or infeasible, access difficult or infeasible, and/or a higher probability of injury to the underlying tissue, laparoscopically.

For example, a suggestion for adjusting the surgical approach may be a suggestion to opt for a robotic procedure in place of a laparoscopic procedure. In an example, the computing system may determine that adhesions are present in a location of the pleural space that is hard to reach based on the sensed data obtained from piezoelectric/ultrasonic transducer testing. A suggestion for a robotic procedure approach may be indicated because robotic devices' dexterity to reach hard-to-reach areas laparoscopically.

Based on the predicted adhesion complication, the computing system may generate a control signal configured to indicate a suggestion for adjusting a surgical procedure step. For example, a suggestion for adjusting the use of trocars for an access step may be made. In an example, a suggestion may be made to adjust trocar placements and/or a quantity of trocars to be used at the access step of a laparoscopic colorectal procedure. The suggestion may be to add additional trocars (e.g., one or two more than the standard number of trocars) for inserting additional laparoscopes into the abdominal cavity to achieve improved visualization of the anatomical structures of the adhesions and the surrounding space. The suggestion may be to insert trocars away from surgical scars from previous abdominal procedure(s) (e.g., 5-10 cm away).

Based on the predicted adhesion complication, the computing system may generate a control signal configured to indicate a suggestion for adjusting an impending surgical procedure schedule. For example, pleural adhesions (e.g., dense adhesions) in the pleural space may take meticulous and slow manipulation to reach and dissect. A prolonged surgical procedure duration may result. The computing system may detect dense pleural adhesions based on piezoelectric/ultrasonic transducer testing data. The computing system may generate a control signal configured to indicate a suggestion for a longer procedure duration. Further, the computing system may generate a control signal configured to indicate a suggestion for reducing case load scheduled on the day associated the impending surgical procedure.

Based on the predicted adhesion complication, the computing system may generate a control signal configured to indicate a suggestion for adjusting a surgical instrument selection planned for one or more surgical procedure steps. In examples, a suggestion for adjusting a surgical instrument selection for a dissection step may be made. For example, a surgical instrument with an improved dissection capability (e.g., rather than an improved hemostasis capability) may be suggested (e.g., for when dense adhesions are present). In an example, a surgical instrument capable of simultaneous transection and coagulation (e.g., a harmonic scalpel) may be suggested to replace a radiofrequency (RF) energy device (e.g., a RF monopolar or a RF bipolar device). For example, a surgical instrument with a better articulation capability and/or improved access capabilities may be suggested (e.g., for when adhesions are in a confined working space). In an example, a powered dissector with improved access (e.g., ENDOPATH® electrosurgery PROBE PLUS® II Electrode Shafts with a curved dissector electrode) may be suggested. In an example, an articulating energy device (e.g., ENSEAL® G2 Articulating Tissue Sealer) may be suggested. In an example, a robotic device (e.g., a handheld robotic instrument with a user interface for controlling the tip of the instrument) may be suggested. For example, surgical instruments with improved access and retraction during dissection may be suggested. In an example, a percutaneous trocar-less 3 mm instrument configured to combine with a 5 mm end effector may be suggested. Such configuration may be for improved access in a confined working space and improved retraction of anatomical structures to create a clear view of the anatomy of adhesions at and/or surrounding the surgery site. Such end effector may be a retractor. Such end effector may be a dissector. For example, percutaneous instruments may be suggested to supplement standard laparoscopic instruments (e.g., in a laparoscopic colorectal procedure or a thoracoscopic lung procedure). In an example, percutaneous devices (e.g., mechanical graspers and electrosurgical probes of the Mini-Lap (® System) may be suggested to supplement a trocar inserted through a standard 5 mm access port for an imaging device (e.g., a laparoscope) for improved access in a confined working space to dissect adhesions.

Suggestions described herein may be provided via a user interface configured to interact with a surgeon (e.g., surgeon interface), such as a surgical planning interface, a surgeon pre-surgery imaging interface, a surgeon interface/console, surgical hub display 215 illustrated in FIG. 5, and/or a surgical device having a display. The suggestions may be generated by a computing system (e.g., the surgical hub 206 or 5104 described herein) and sent to the surgeon interface. A suggestion message may be displayed in a designated area on the surgeon interface, such as a suggestion overlay or a suggestion box at the bottom right corner of the surgeon interface.

Based on the predicted adhesion complication, the computing system may generate a control signal configured to indicate a notification of a probability of an adhesion complication. For example, a notification of the probability of an adhesion complication may be displayed as an overlay or a highlight in a surgical procedure plan on a surgical planning interface. In an example, the notification may be displayed in the procedure approach area, a procedure step area, a procedure's duration area, a surgical instrument selection area of the surgical procedure plan. Corresponding suggestion(s) for adjusting one or more of such areas of the surgical procedure plan may be displayed in the surgical procedure plan.

For example, a notification of the probability of an adhesion complication may be displayed as an overlay on top of pre-surgery imaging rendered on the surgeon interface.

For example, a notification of the probability of an adhesion complication may be presented as an augmented reality (AR) or mixed reality overlay on the surgeon interface that may be interrogated. An AR device may provide AR content to a user. For example, a visual AR device, such as safety glasses with an AR display, AR goggles, or head-mounted display (HMD), may include a graphics processor for rendering 2D or 3D video and/imaging for display. AR content may be overlaid onto the various displays described herein. For example, an audible AR device, such as an earbud, a headset, a headphone, or a speaker, may provide audible AR content. The audible AR device may provide auditory overlay, for example, in addition to hearing OR sounds. Audible overlay may be provided via an earbud set with pass through noise capabilities and/or via a bone conduction speaker system. The AR device may communicate certain information only to the targeted individual within the OR that could utilize the information. The AR device may include a processor, a non-transitory computer readable memory storage medium, and executable instructions contained within the storage medium that are executable by the processor to carry out methods or portions of methods disclosed herein. Examples of visual and audio AR devices can be found in more detail in U.S. patent application Ser. No. 17/062,509, titled INTERACTIVE INFORMATION OVERLAY ON MULTIPLE SURGICAL DISPLAYS, which was filed on Oct. 2, 2020, which is herein incorporated by reference in its entirety. Examples of visual and audio AR devices can be found in more detail are described in a patent application titled AUDIO AUGMENTED REALITY CUES TO FOCUS ON AUDIBLE INFORMATION, filed contemporaneously, which is herein incorporated by reference in its entirety.

Figure 37:
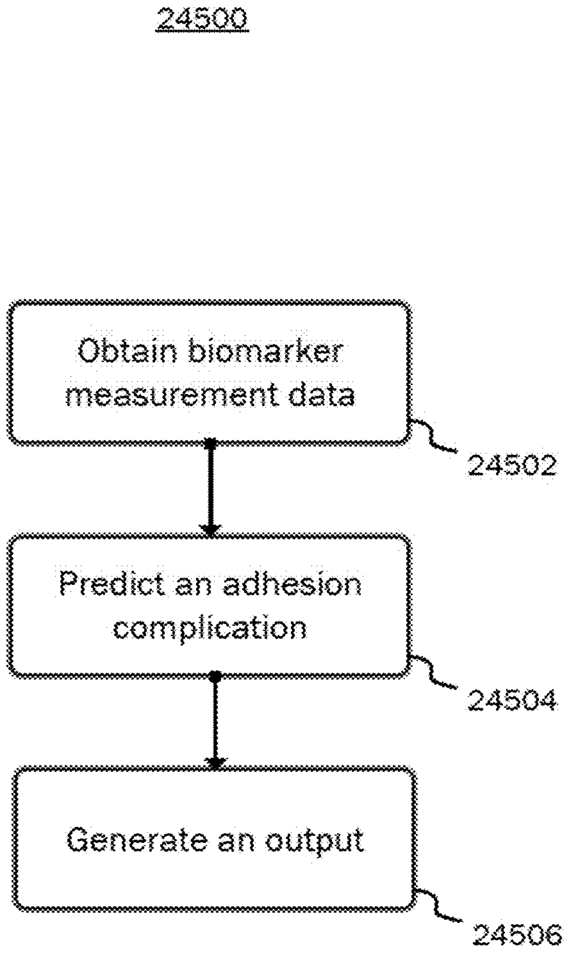
FIG. 37 illustrates an example process of predicting an adhesion complication.

FIG. 37 illustrates an example process 24500 of predicting an adhesion complication. The process may include a computer-implemented process. For example, a computing system may perform the process illustrated in FIG. 37. For example, a sensing system described herein may perform the process illustrated in FIG. 37.

At 24502, measurement data associated with one or more patient biomarkers may be obtained via one or more sensing systems. Measurement data may include measurement data obtained prior to a surgery, and/or biomarker measurements taken during a surgery. Pre-surgical measurements may be combined with in-surgical measurements. The patient biomarker(s) may include one or more of the following: tissue perfusion pressure, lactate, oxygen saturation, VO2Max, respiration rate, autonomic tone, sweat rate, heart rate variability, skin conductance, or GI motility.

At 24504, an adhesion complication may be predicted based on the measurement data associated with the one or more patient biomarkers. The adhesion complication may be predicted based on pre-surgical measurement data, in-surgical measurement data, or a combination of pre-surgical measurement data, in-surgical measurement data.

For example, the computing system may determine a probability of a chronic inflammation response based on the measurement data associated with the one or more patient biomarkers. On the condition that the probability of a chronic inflammation response crosses a threshold, the computing system may predict an adhesion complication. The predicted adhesion complication may include convoluted tissue planes, internal scarring, and/or adhesion bands.

At 24506, the computing system may generate an output based on the adhesion complication. The generated output may include a control signal configured to indicate an adjustment to an instrument selection for dissecting capability. The adjustment may include selecting an improved dissection tool in place of an improved hemostasis tool. The generated output may include a control signal configured to indicate an adjustment to an instrument selection for access capability. The adjustment may include selecting a percutaneous instrument configured to combine with a 5 mm end effector, selecting a higher articulating surgical device with improved access capability, and/or selecting a percutaneous instrument to supplement a laparoscopic instrument. The generated output may include a control signal configured to perform displaying a probability of an adhesion complication on a pre-surgery imaging, displaying a probability of an adhesion complication via an augmented reality device, and/or displaying a probability of an adhesion complication in a surgical procedure plan along with an indication of an adjustment to the surgical procedure plan.

FIG. 38A-D illustrates example procedure steps of a lung segmentectomy and example use of patient biomarker measurements. As shown in FIG. 38A-E, example steps of a lung segmentectomy may include pre-surgery, initiation, access and preparation, manage vessels, remove segment, manage lymph nodes, assessment, and post-surgery. As shown, patient biomarkers measurements may be used to inform various decisions, identify various risks pre-surgery, during surgery, after surgery, and/or determine operational parameters for various surgical tools.

Figure 38A:
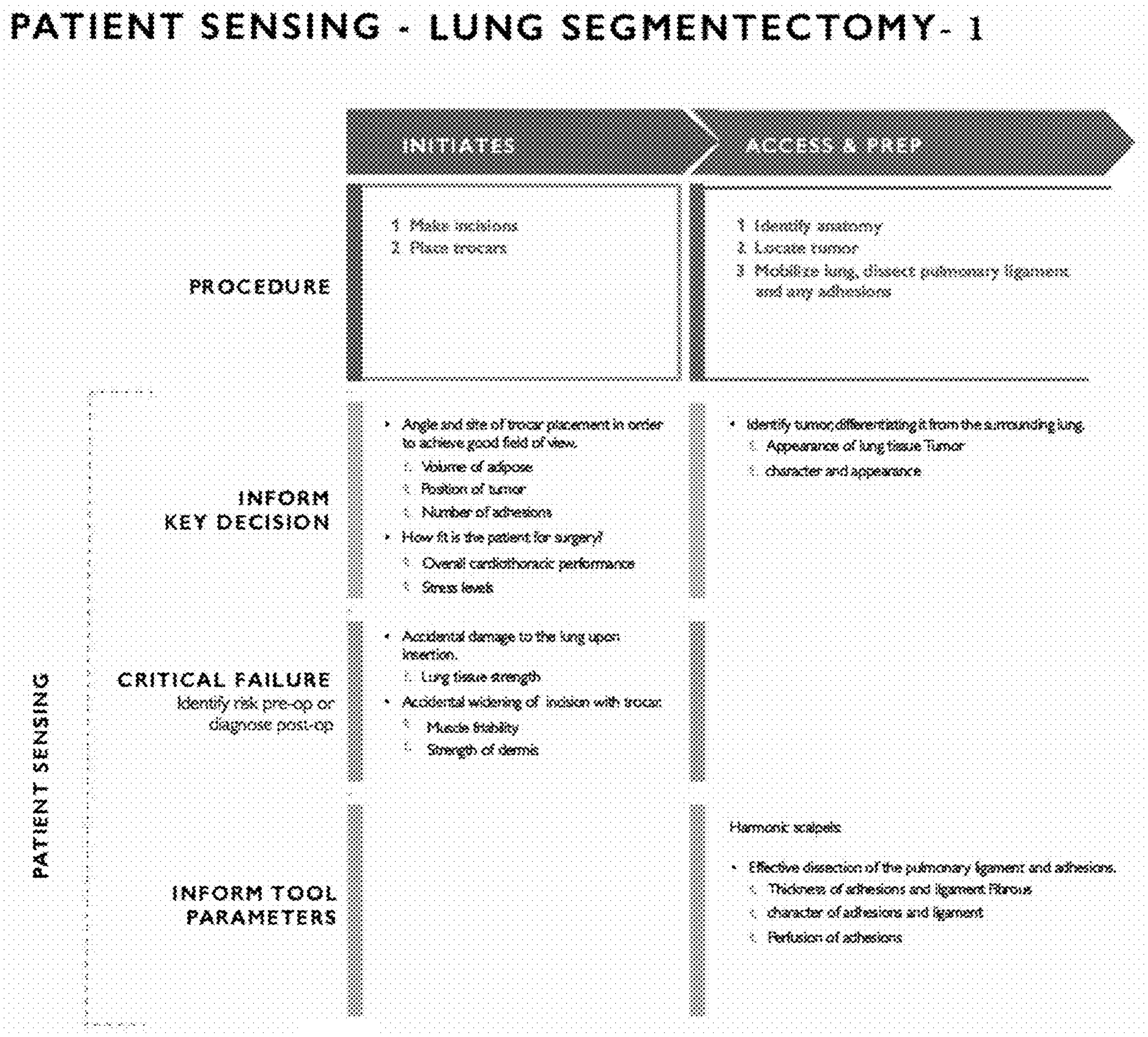
FIG. 38A-D illustrates example procedure steps of a lung segmentectomy and example use of patient biomarker measurements.

FIG. 38A illustrates example pre-surgery, initiation, and access and preparation procedural steps and example use of patient biomarkers during these steps.

As shown, during a pre-surgical period, patient biomarkers measurements may be used to inform various decisions related to lung segmentectomy. In an example, patient biomarkers measurements may be related to how fit the patient is to undergo surgery (e.g., lung segmentectomy). For example, the biomarkers measurements may be related to the patient's overall cardiothoracic performance and/or stress levels. The biomarkers measured may include oxygen saturation, blood pressure, cortisol level, and/or the like as described herein with reference to FIG. 1B. Pre-surgical biomarkers measurements may be used to determine the placement of one or more trocars. For example, the biomarker measurements may be related to the position of tumor, the volume of adipose, and/or the number of adhesions. A computing system may determine, based on the biomarker measurements, an angle and/or site for trocar placement (e.g., for an optimal field of view). Various sensing systems may be used to measure the biomarkers as described herein with reference to FIG. 1B.

As shown in FIG. 38A, a lung segmentectomy may include an initiation procedural step. Biomarkers measurements may be used to identify various risks associated with the initiation procedural step. For example, a risk associated with the initiation procedural step may be accidental damage to the lung upon insertion of the trocars. Biomarker measurements related to lung tissue strength, as described herein with reference to FIG. 1B, may be used to identify the risk that the lung may be accidentally damaged during the initiation procedural step. Biomarker measurements may be used post-op to diagnose or predict failure(s). For example, biomarker measurements related to lung tissue strength may be used to diagnose when the lung has been accidentally damaged. A risk may be accidentally widening the incision, and biomarker measurements related to muscle friability and/or dermis strength may be used to identify such accidental widening.

As shown in FIG. 38A, lung segmentectomy may include an access and preparation procedural step. Biomarkers measurements may be used to inform various decisions related to the access and preparation procedural step. For example, biomarker measurements related to the appearance and/or character of lung tissue tumor may be used to differentiate the tumor from the surrounding lung. The biomarker measurements may be lung tissue perfusion pressure and/or tissue friability as described herein with reference to FIG. 1B.

Biomarker measurements may be used to determine operational parameters for various surgical tools related to the access and preparation procedural step. During the access and preparation procedural step, the HCP may dissect the pulmonary ligament and/or adhesions using a harmonic scalpel. Biomarkers measurements related to the thickness, character, and/or perfusion of the adhesions and/or ligament may be used to determine the operational parameters of the harmonic scalpel. The biomarkers may include one or more of the biomarkers described with reference to FIG. 1B. A computing system may adjust the parameters of the harmonic scalpel based on the determined operational parameters. In examples, as described in FIG. 37, based on a predicted adhesion complication, such as a complication due to adhesions that are irregularly thick or fibrous, the computing system may generate control signals to improve dissection of adhesions. In an example, the computing system may generate a control signal configured to indicate a suggestion for using a surgical instrument capable of simultaneous transection and coagulation (e.g., a harmonic scalpel) may be suggested to replace a radiofrequency (RF) energy device (e.g., a RF monopolar or a RF bipolar device). In an example, the computing system may generate a control signal configured to increase an energy level. In an example, the computing system may generate a control signal configured to increase an energy application duration. In an example, the computing system may generate a control signal configured to increase a threshold (e.g., a desired resonant frequency threshold for starting a coagulation phase and/or desired resonant frequency threshold for starting a transection phase) for an energy generation associated with a subsequent energy application.

Figure 38B:
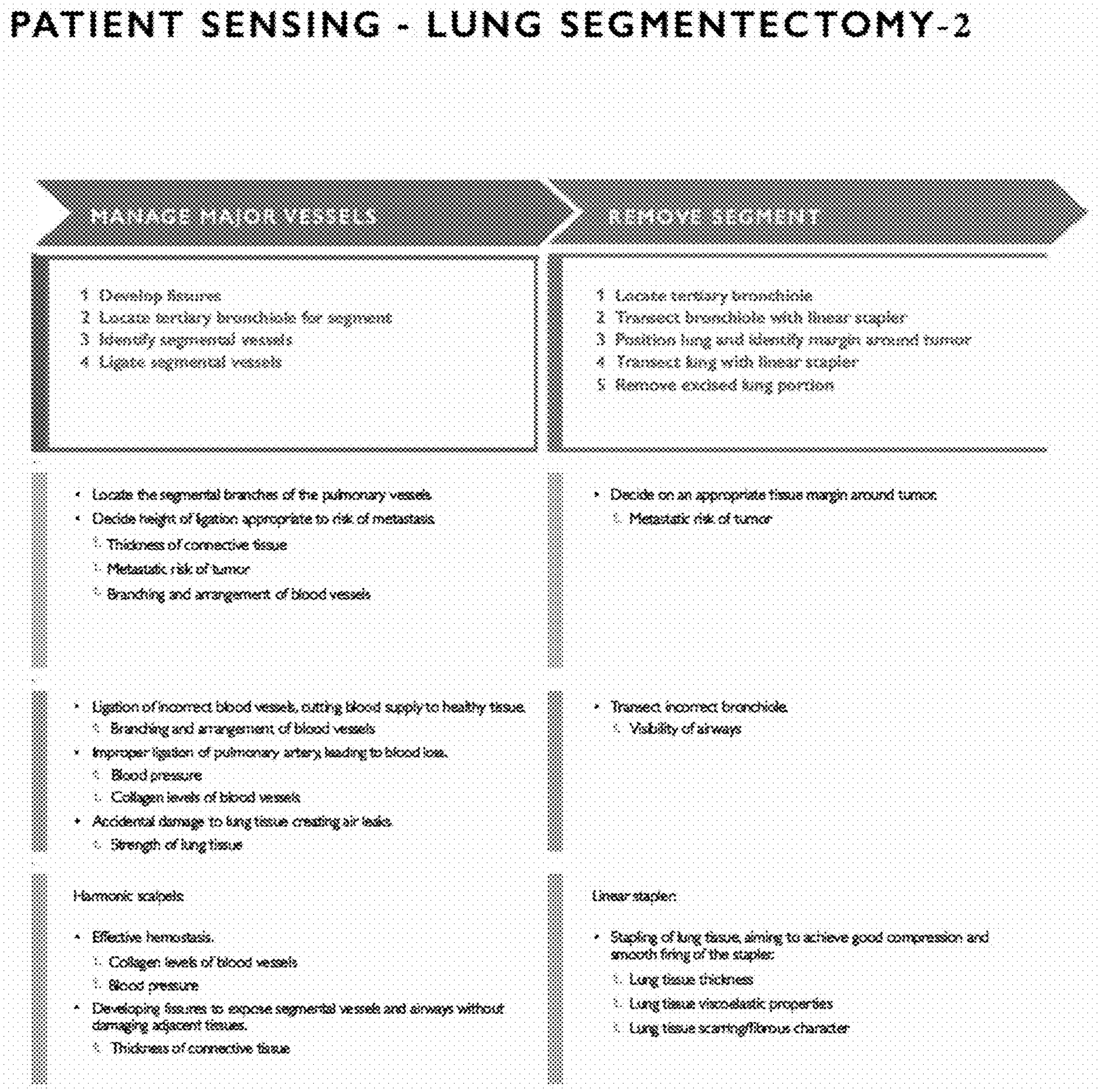

FIG. 38B illustrates example manage vessel and remove segment procedural steps and example use of patient biomarkers during these steps.

As shown, lung segmentectomy may include a manage vessel procedural step. Biomarkers measurements may be used to inform various decisions related to the manage vessel procedural step, such as locating segmental branches of the pulmonary vessels and deciding the height of ligation appropriate to risk of metastasis. Biomarker measurements related to the thickness of the connective tissue, the metastatic nature of the tumor, and/or the arrangement of the blood vessels may be used when deciding the ligation height.

As shown in FIG. 38B, biomarkers measurements may be used to identify various risks associated with the manage vessels procedural step. For example, a risk associated with the manage vessels procedural step may be ligating incorrect blood vessels and/or cutting off blood supply to healthy tissue. Biomarker measurements related to blood vessel arrangement, as described herein with reference to FIG. 1B, may be used to identify the risk that incorrect blood vessels may be ligated. Biomarker measurements related to blood vessel arrangement may be used post-op to diagnose when incorrect blood vessels have been ligated. A risk associated with the manage vessel procedural step may be improperly ligating the pulmonary artery and/or causing blood loss. Biomarker measurements related to blood pressure and/or blood vessel collagen level may be used to identify the risk of improper ligation and/or blood loss. These measurements may be used to diagnose improper ligation and/or blood loss. A risk associated with the manage vessel procedural step may be accidental damage to lung tissue and/or air leaks. Biomarker measurements related to lung tissue strength (e.g., lung tissue perfusion pressure) may be used to identify the risks.

As shown in FIG. 38B, biomarker measurements may be used to determine operational parameters for various surgical tools related to the manage vessels procedural step. During the manage vessels procedural step, the HCP may develop fissures to expose segmental vessels and/or airways using a harmonic scalpel. Biomarkers measurements related to the thickness of connective tissue may be used to determine the operational parameters of the harmonic scalpel. During the manage vessels procedural step, biomarker measurements related to effective homeostasis (e.g., blood vessel collagen level and/or blood pressure) may be used to determine the operational parameters of the harmonic scalpel. A computing system may adjust the parameters of the harmonic scalpel based on the determined operational parameters.

As shown in FIG. 38B, lung segmentectomy may include a remove segment procedural step. Biomarkers measurements may be used to inform various decisions related to the remove segment procedural step. For example, biomarker measurements related to the metastatic risk of tumor may be used to decide an appropriate tissue margin.

Biomarkers measurements may be used to identify various risks associated with the remove segment procedural step. For example, a risk associated with the remove segment procedural step may be transecting incorrect bronchiole. Biomarker measurements related to the visibility of airways, as described herein with reference to FIG. 1B, may be used to identify the risk that incorrect bronchiole may be transected. Biomarker measurements related to airway visibility may be used post-op to diagnose when incorrect bronchiole have been transected.

Biomarker measurements may be used to determine operational parameters for various surgical tools related to the remove segment procedural step. During the remove segment procedural step, the HCP may staple the tissue using a linear stapler. Biomarkers measurements related to lung tissue thickness, viscoelastic properties, and/or fibrous character may be used to determine the operational parameters of the linear stapler. For example, lung tissue friability, as described herein with reference to FIG. 1B, may be used to determine the operation parameters of the linear stapler. In examples, as described in FIG. 45, based on a predicted tissue irregularity complication, such as a complication due to a lung tissue that is irregularly thick or fibrous, the computing system may generate control signals to improve the optimal compression and/or firing of a linear stapler. In an example, the computing system may generate a control signal configured to reduce a clamping speed, increase a closure compression force, and/or prolong a tissue creep wait time prior to stapling. In an example, the computing system may generate a control signal configured to reduce a stapler firing speed.

Figure 38C:
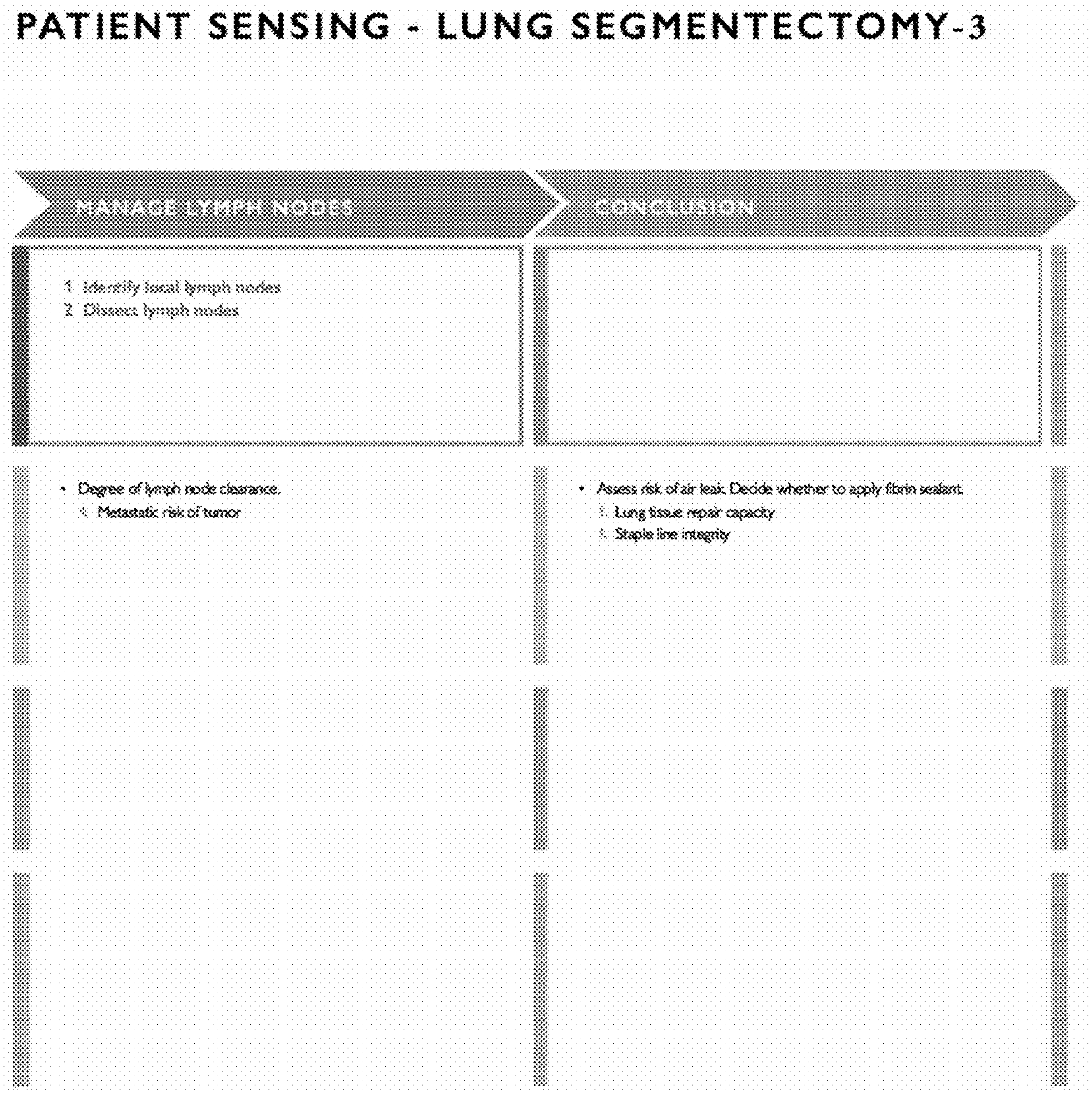

FIG. 38C illustrates example manage lymph nodes and assessment procedural steps and example use of patient biomarkers during these steps.

As shown, lung segmentectomy may include a manage lymph nodes procedural step. Biomarkers measurements may be used to inform various decisions related to the manage lymph nodes procedural step. For example, biomarker measurements related to the metastatic risk of tumor may be used to determine a degree of lymph node clearance.

As shown in FIG. 38C, lung segmentectomy may include an assessment procedural step. Biomarkers measurements related to lung tissue repair capacity and/or staple line integrity may be used to decide whether to apply fibrin sealant. Biomarkers measurements related to lung tissue repair capacity and/or staple line integrity may be used to decide the quantity of fibrin sealant to apply.

Figure 38D:
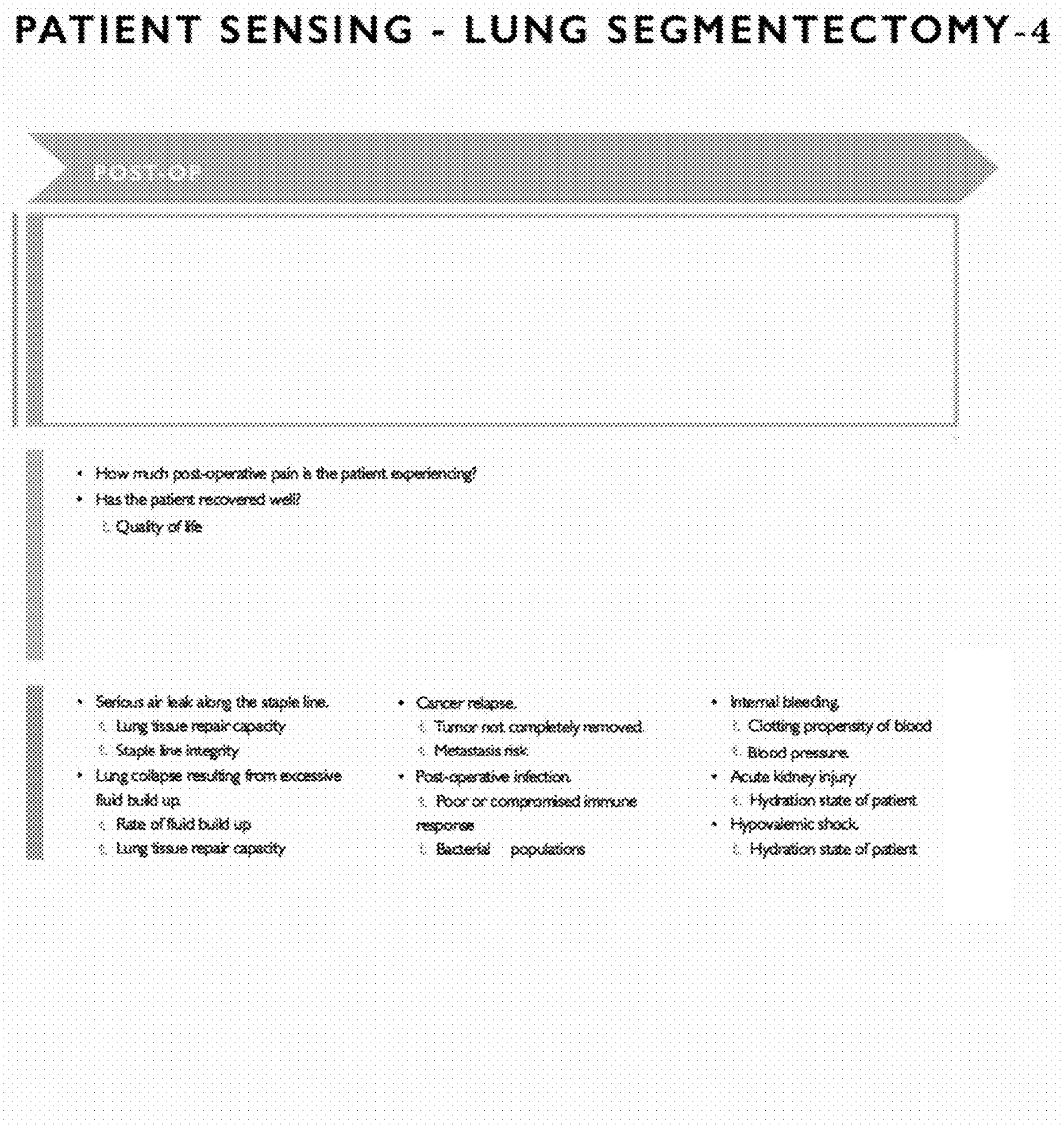

FIG. 38D illustrates example post-surgery and example use of patient biomarkers. Biomarker measurements may be used post-op to predict or detect post-surgical lung segmentectomy complications.

FIG. 39A-E illustrates example procedure steps of sigmoid colectomy and example use of patient biomarker measurements. As shown in FIG. 39A-E, example steps of a sigmoid colectomy may include pre-surgery, initiation, access and preparation, mobilize colon, resect sigmoid, anastomosis, assessment, and post-surgery. As shown, patient biomarkers measurements may be used to inform various decisions, identify various risks pre-surgery, during surgery, after surgery, and/or determine operational parameters for various surgical tools.

Figure 39A:
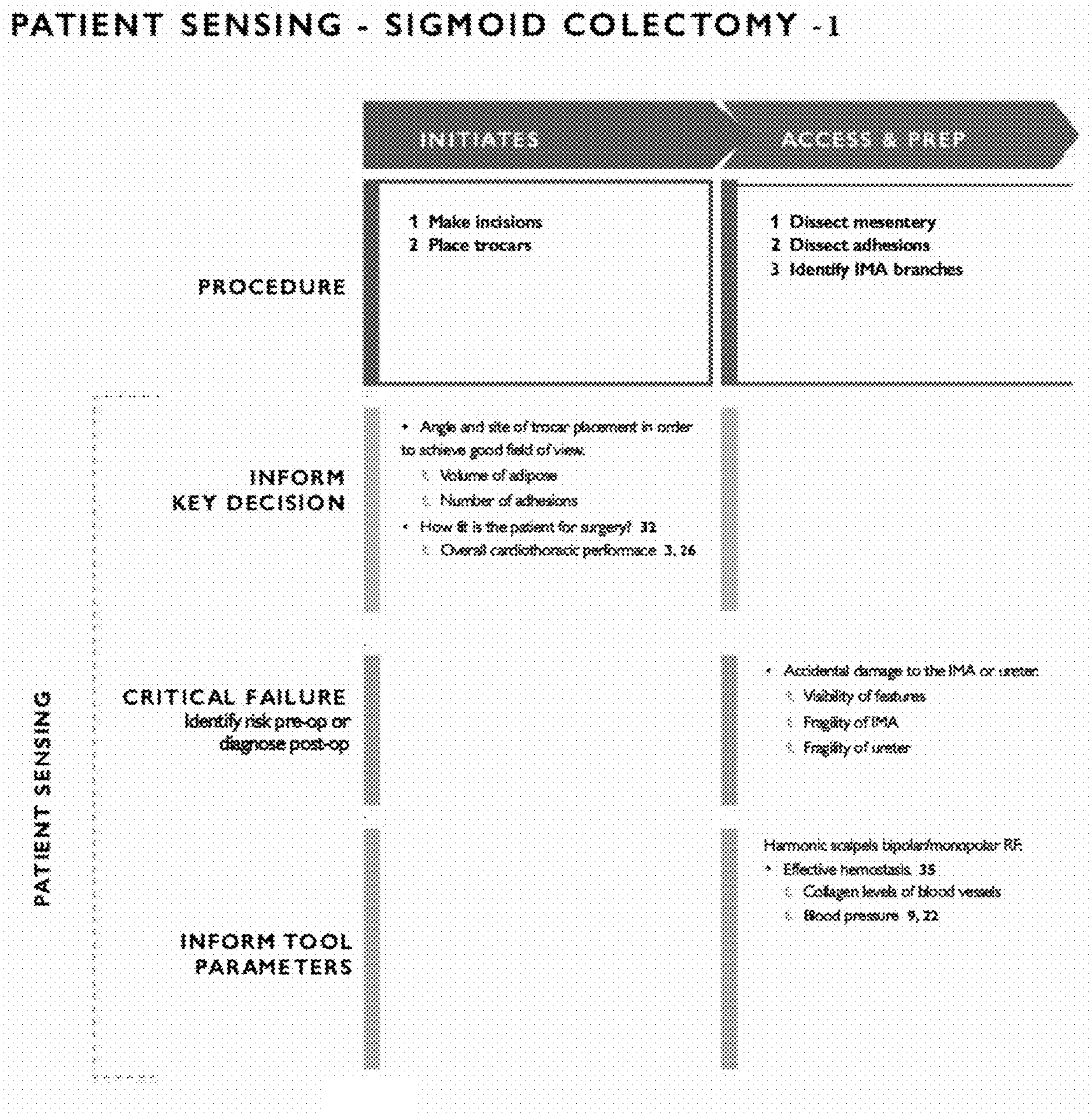

FIG. 39A illustrates example pre-surgery, initiation, and access and preparation procedural steps and example use of patient biomarkers during these steps.

As shown, during a pre-surgical period, patient biomarkers measurements may be used to inform various decisions related to sigmoid colectomy. In an example, patient biomarkers measurements may be related to how fit the patient is to undergo surgery (e.g. sigmoid colectomy). For example, the biomarkers measurements may be related to the patient's overall cardiothoracic performance. The biomarkers measured may include oxygen saturation, blood pressure, VO2 max, and/or the like as described herein with reference to FIG. 1B. Pre-surgical biomarkers measurements may be used to determine the placement of one or more trocars. For example, the biomarker measurements may be related to the volume of adipose and/or the number of adhesions. A computing system may determine, based on the biomarker measurements, an angle and/or site for trocar placement (e.g., for an optimal field of view). Various sensing systems may be used to measure the biomarkers as described herein with reference to FIG. 1B.

As shown in FIG. 39A, sigmoid colectomy may include an initiation procedural step. Biomarkers measurements may be used to identify various risks associated with the initiation procedural step.

As shown in FIG. 39A, sigmoid colectomy may include an access and preparation procedural step. Biomarkers measurements may be used to inform various decisions related to the access and preparation procedural step. Biomarkers measurements may be used to identify various risks associated with the surgery, such as accidental damage to the inferior mesenteric artery ("IMA") and/or ureter. Biomarker measurements related to visibility of features, IMA and/or ureter fragility, as described herein with reference to FIG. 1B, may be used to identify the risk that at least one of the bodily structures may be accidentally damaged during the access and preparation step. Biomarker measurements may be used post-op to diagnose or predict failure(s). For example, biomarker measurements related to IMA fragility may be used to diagnose when the IMA has been accidentally damaged. For example, biomarker measurements related to ureter fragility may be used to diagnose when the ureter has been accidentally damaged.

As shown in FIG. 39A, during the access and preparation step, biomarker measurements may be used to determine operational parameters for various surgical tools. The HCP may use a harmonic scalpel and/or bipolar and monopolar RF. Biomarker measurements related to homeostasis (e.g., blood vessel collagen level and/or blood pressure) may be used to determine the operational parameters of the harmonic scalpel and/or bipolar and monopolar RF. A computing system may adjust the parameters based on the determined operational parameters.

Figure 39B:
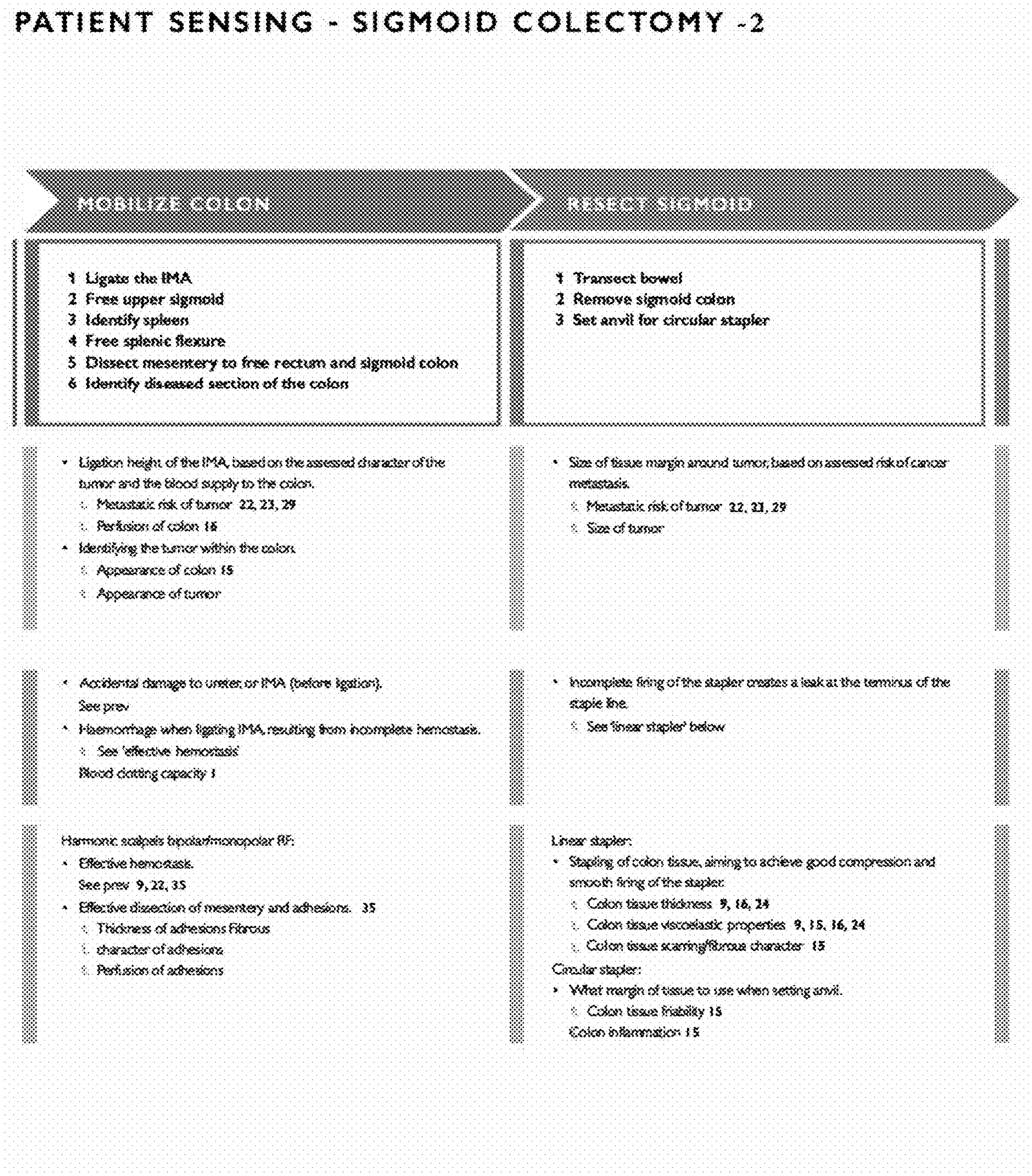

FIG. 39B illustrates example mobilize colon and resect sigmoid procedural steps and example use of patient biomarkers during these steps.

As shown, a sigmoid colectomy may include a mobilize colon procedural step. Biomarkers measurements may be used to inform various decisions related to the mobilize colon procedural step, such as deciding the ligation height of the IMA. Biomarker measurements related to the perfusion of the colon and/or the metastatic nature of the tumor may be used when deciding the ligation height. In such a case, the biomarker measurements may include sweat adrenaline, cortisol, colon tissue perfusion pressure, and/or circulating tumor cells. The mobilize colon procedure step may include identifying the tumor within the colon. Biomarker measurements related to the appearance of colon and/or tumor may be used when identifying the tumor. In such a case, the biomarker measurements may include gastrointestinal tract imaging.

As shown in FIG. 39B, biomarkers measurements may be used to identify various risks associated with the mobilize colon procedural step. For example, a risk associated with the mobilize colon procedural step may be accidental damage to the IMA and/or ureter. Biomarker measurements related to IMA and/or ureter fragility, as described herein with reference to FIG. 1B, may be used to identify the risk that at least one of the bodily structures may be accidentally damaged during the mobilize colon procedural step. Biomarker measurements may be used post-op to diagnose or predict failure(s). For example, biomarker measurements related to IMA fragility may be used to diagnose when the IMA has been accidentally damaged. For example, biomarker measurements related to ureter fragility may be used to diagnose when the ureter has been accidentally damaged. A risk associated with mobilize colon procedural step may be hemorrhage resulting from incomplete homeostasis. Biomarker measurements related to blood vessel collagen level and/or blood pressure, as described herein with reference to FIG. 1B, may be used to identify the risk of incomplete homeostasis.

As shown in FIG. 39B, biomarker measurements may be used to determine operational parameters for various surgical tools related to the mobilize colon procedural step. During the mobilize colon procedural step, the HCP may use a harmonic scalpel and/or bipolar and monopolar RF. Biomarker measurements related to homeostasis (e.g., blood vessel collagen level and/or blood pressure) may be used to determine the operational parameters of the harmonic scalpel and/or bipolar and monopolar RF. During the mobilize colon procedural step, the HCP may dissect mesentery and/or adhesions using a harmonic scalpel and/or bipolar and monopolar RF. Biomarkers measurements related to the thickness, character, and/perfusion of adhesions may be used to determine the operational parameters of the harmonic scalpel and/or bipolar and monopolar RF. A computing system may adjust the parameters based on the determined operational parameters. In examples, as described in FIG. 37, based on a predicted adhesion complication, such as a complication due to adhesions that are irregularly thick or fibrous, the computing system may generate control signals to improve dissection of adhesions. In an example, the computing system may generate a control signal configured to indicate a suggestion for using a surgical instrument capable of simultaneous transection and coagulation (e.g., a harmonic scalpel) may be suggested to replace a radiofrequency (RF) energy device (e.g., a RF monopolar or a RF bipolar device). In an example, the computing system may generate a control signal configured to increase an energy level. In an example, the computing system may generate a control signal configured to increase an energy application duration. In an example, the computing system may generate a control signal configured to increase a threshold (e.g., a desired resonant frequency threshold for starting a coagulation phase and/or desired resonant frequency threshold for starting a transection phase) for an energy generation associated with a subsequent energy application.

As shown in FIG. 39B, a sigmoid colectomy may include a resect sigmoid procedural step. Biomarkers measurements may be used to inform various decisions related to the resect sigmoid procedural step. For example, biomarker measurements related to the metastatic risk and/or size of the tumor may be used to decide an appropriate tissue margin.

As shown in FIG. 39B, biomarkers measurements may be used to identify various risks associated with the resect sigmoid procedural step. For example, a risk associated with the resect sigmoid procedural step may be colorectal leak. Biomarker measurements related to colon tissue thickness, viscoelastic properties, and/or fibrous character, as described herein with reference to FIG. 1B, may be used to identify the risk of colorectal leak. In such a case, the biomarkers measured may include blood pressure, gastrointestinal tract imaging, colon tissue perfusion pressure, and/or edema.

As shown, biomarker measurements may be used to determine operational parameters for various surgical tools related to the resect sigmoid procedural step. During the resect sigmoid procedural step, the HCP may staple the tissue using a linear and/or circular stapler. Biomarkers measurements related to colon tissue thickness, viscoelastic properties, and/or fibrous character may be used to determine the operational parameters of the linear stapler. Biomarker measurements related to colon tissue friability (e.g., gastrointestinal tract imaging) may be used to determine the operational parameters of the circular stapler. In examples, as described in FIG. 45, based on a predicted tissue irregularity complication, such as a complication due to a colon tissue that is irregularly thick or fibrous, the computing system may generate various control signals to improve the optimal compression and/or firing of a linear stapler. In an example, the computing system may generate a control signal configured to reduce a clamping speed, increase a closure compression force, and/or prolong a tissue creep wait time prior to stapling of a linear stapler. In an example, the computing system may generate a control signal configured to reduce a stapler firing speed.

Figure 39C:
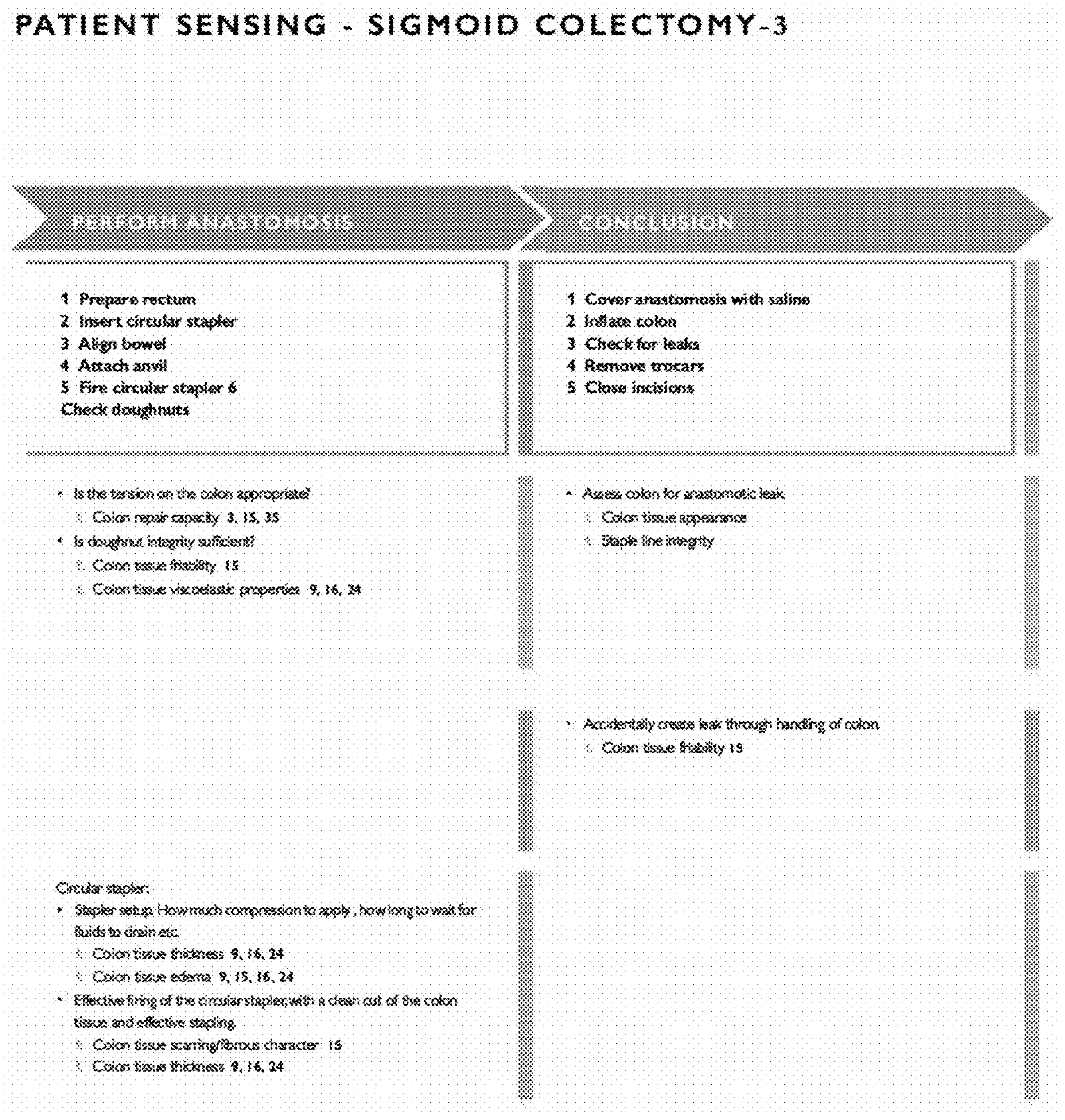

FIG. 39C illustrates example anastomosis and assessment procedural steps and example use of patient biomarkers during these steps.

As shown, sigmoid colectomy may include an anastomosis procedural step. Biomarkers measurements may be used to inform various decisions related to the anastomosis procedural step. For example, biomarker measurements related to colon repair capacity (e.g., oxygen saturation, gastrointestinal tract imaging, menstrual cycle) may be used to determine appropriate colon tension. Biomarker measurements related to colon tissue friability and/or viscoelastic properties may be used to determine whether the doughnut integrity is sufficient. In such a case, the biomarkers measured may include blood pressure, gastrointestinal tract imaging, colon tissue perfusion pressure, and/or edema.

As shown in FIG. 39C, biomarkers measurements may be used to identify various risks associated with anastomosis procedural step.

As shown in FIG. 39C, biomarker measurements may be used to determine operational parameters for various surgical tools related to the anastomosis procedural step. During the anastomosis procedural step, the HCP may staple the tissue using a circular stapler. Biomarkers measurements related to colon tissue thickness, edema, and/or fibrous character may be used to determine the operational parameters of the circular stapler. In examples, as described in FIG. 45, based on a predicted tissue irregularity complication, such as a complication due to a colon tissue that is irregularly thick or fibrous, the computing system may generate various control signals to improve the optimal compression and/or firing of a circular stapler. In an example, the computing system may generate a control signal configured to reduce a clamping speed, increase a closure compression force, and/or prolong a tissue creep wait time prior to stapling. In an example, the computing system may generate a control signal configured to reduce a stapler firing speed. In an example, the computing system may generate a control signal configured to shift upward a viable staple height range.

As shown, sigmoid colectomy may include an assessment procedural step. Biomarkers measurements may be used to inform various decisions related to the assessment procedural step. For example, biomarker measurements related to colon tissue appearance and/or staple line integrity may be used to determine an anastomosis leak.

As shown in FIG. 39C, biomarkers measurements may be used to identify various risks associated with the assessment procedural step. For example, a risk associated with the resect sigmoid procedural step may be anastomosis leak. Biomarker measurements related to colon tissue friability, as described herein with reference to FIG. 1B, may be used to identify the risk of anastomosis leak. In such a case, the biomarkers measured may include gastrointestinal tract imaging.

Figure 39D:
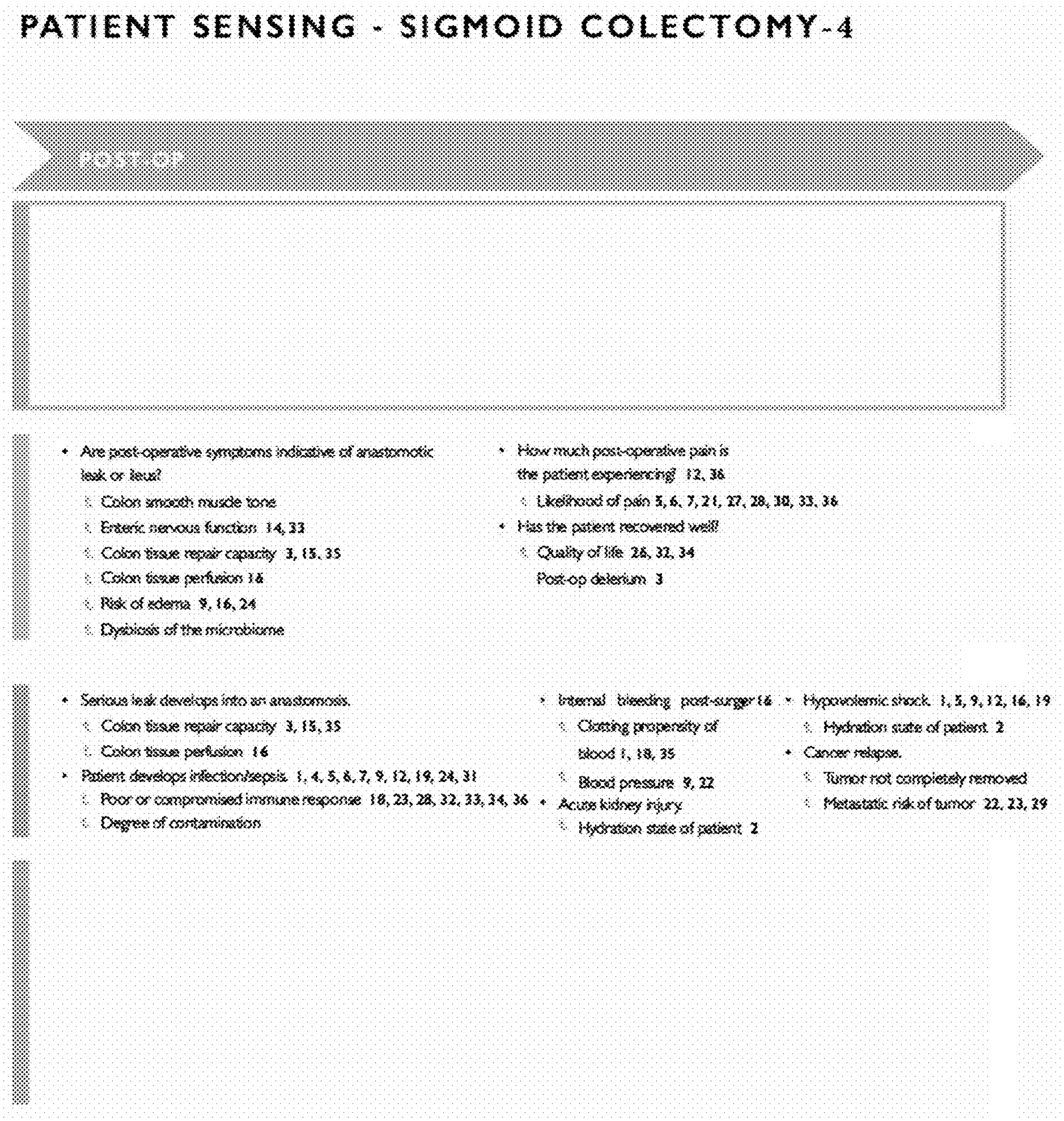

FIG. 39D illustrates example post-surgery and example use of patient biomarkers during this step.

Biomarker measurements may be used post-op to predict or detect post-surgical sigmoid colectomy complications.

FIG. 39E illustrates example patient biomarkers related to sigmoid colectomy. The various biomarkers and corresponding measurements using one or more sensing system(s) are described herein with reference to FIG. 1B.

FIG. 40A-E illustrates example procedure steps of sleeve gastrectomy and example use of patient biomarker measurements. As shown in FIG. 40A-E, example steps of a sigmoid colectomy may include pre-surgery, initiation, access and preparation, gastric transection, assessment, and post-surgery. As shown, patient biomarkers measurements may be used to inform various decisions, identify various risks pre-surgery, during surgery, after surgery, and/or determine operational parameters for various surgical tools.

Figure 40A:
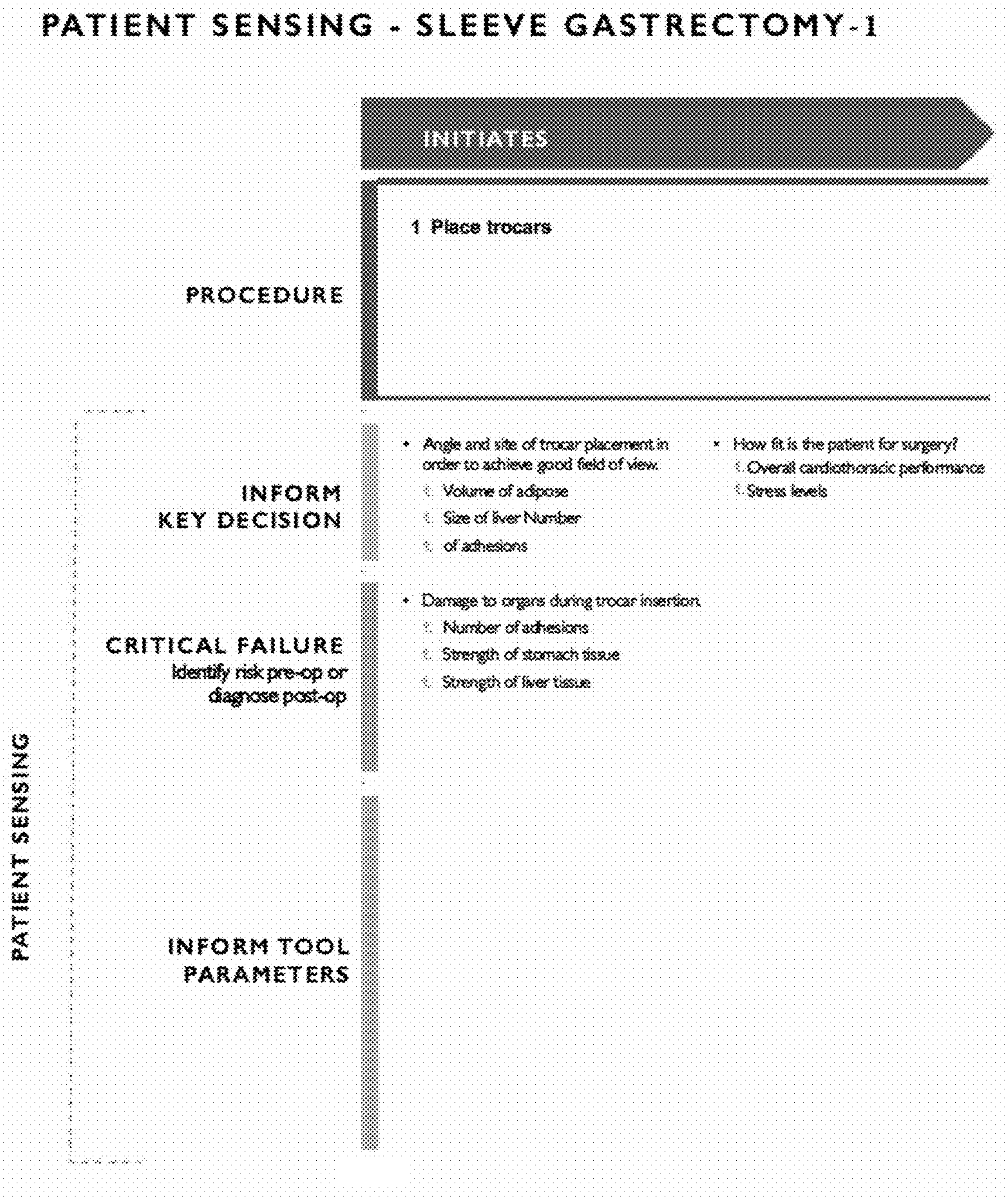

FIG. 40A illustrates example pre-surgery and initiation procedural steps and example use of patient biomarkers during these steps.

As shown, during a pre-surgical period, patient biomarkers measurements may be used to inform various decisions related to sleeve gastrectomy. In an example, patient biomarkers measurements may be related to how fit the patient is to undergo surgery (e.g., sleeve gastrectomy). For example, the biomarkers measurements may be related to the patient's overall cardiothoracic performance and/or stress levels. The biomarkers measured may include oxygen saturation, blood pressure, cortisol level, and/or the like as described herein with reference to FIG. 1B. Pre-surgical biomarkers measurements may be used to determine the placement of one or more trocars. For example, the biomarker measurements may be related to the size of the liver, the volume of adipose, and/or the number of adhesions. A computing system may determine, based on the biomarker measurements, an angle and/or site for trocar placement (e.g., for an optimal field of view). Various sensing systems may be used to measure the biomarkers as described herein with reference to FIG. 1B.

As shown in FIG. 40A, sleeve gastrectomy may include an initiation procedural step. Biomarkers measurements may be used to identify various risks associated with the initiation procedural step. For example, a risk associated with the initiation procedural step may be accidental damage to organs upon insertion of the trocars. Biomarker measurements related to number of adhesions, strength of stomach tissue, and/or strength of liver tissue, as described herein with reference to FIG. 1B, may be used to identify the risk that one or more organs may be accidentally damaged during the initiation procedural step. Biomarker measurements may be used post-op to diagnose or predict failures(s). For example, biomarker measurements related to number of adhesions, strength of stomach tissue, and/or strength of liver tissue may be used to diagnose when an organ has been accidentally damaged.

FIG. 40B illustrates an example access and preparation procedural step and example use of patient biomarkers during this step. As shown, biomarkers measurements may be used to inform various decisions related to the access and preparation procedural step. Biomarkers measurements may be used to identify various risks associated with the access and preparation procedural step. For example, a risk associated with the access and preparation procedural step may be accidental damage to the stomach and/or liver during mesentery dissection and/or mobilization. Biomarker measurements related to strength of stomach tissue and/or liver tissue, as described herein with reference to FIG. 1B, may be used to identify the risk that the stomach and/or liver may be accidentally damaged during the access and preparation procedural step. Biomarker measurements may be used post-op to diagnose or predict failure(s). For example, biomarker measurements related to stomach tissue strength and/or liver tissue strength may be used to diagnose when the stomach and/or liver has been accidentally damaged.

As shown in FIG. 40B, biomarker measurements may be used to determine operational parameters for various surgical tools related to the access and preparation procedural step. During the access and preparation procedural step, the HCP may use a harmonic scalpel and/or bipolar RF to dissect the mesentery and/or adhesions. Biomarker measurements related to the thickness, character, and/or perfusion of the adhesions may be used to determine the operational parameters of the harmonic scalpel and/or bipolar RF. Biomarker measurements related to homeostasis (e.g., blood vessel collagen level and/or blood pressure) may be used to determine the operational parameters of the harmonic scalpel and/or bipolar RF. A computing system may adjust the parameters based on the determined operational parameters. In examples, as described in FIG. 37, based on a predicted adhesion complication, such as a complication due to adhesions that are irregularly thick or fibrous, the computing system may generate control signals to improve dissection of adhesions. In an example, the computing system may generate a control signal configured to indicate a suggestion for using a surgical instrument capable of simultaneous transection and coagulation (e.g., a harmonic scalpel) may be suggested to replace a radiofrequency (RF) energy device (e.g., a RF monopolar or a RF bipolar device). In an example, the computing system may generate a control signal configured to increase an energy level. In an example, the computing system may generate a control signal configured to increase an energy application duration. In an example, the computing system may generate a control signal configured to increase a threshold (e.g., a desired resonant frequency threshold for starting a coagulation phase and/or desired resonant frequency threshold for starting a transection phase) for an energy generation associated with a subsequent energy application.

FIG. 40C illustrates an example gastric transection procedural step and example use of patient biomarkers during this step.

Figure 43:
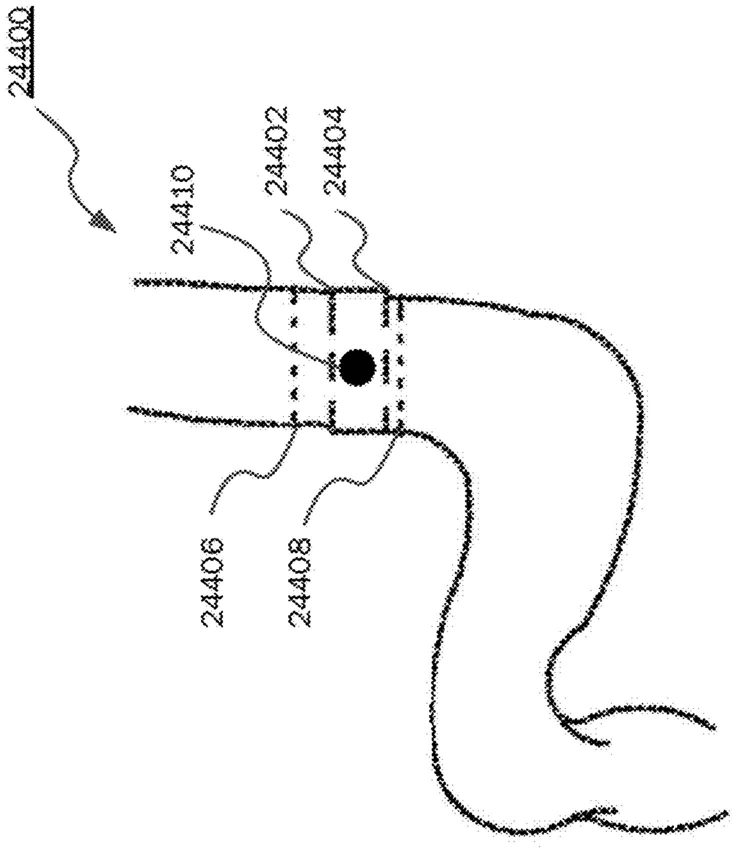
FIG. 43 illustrates an example resection template in a colorectal procedure.
Figure 44:
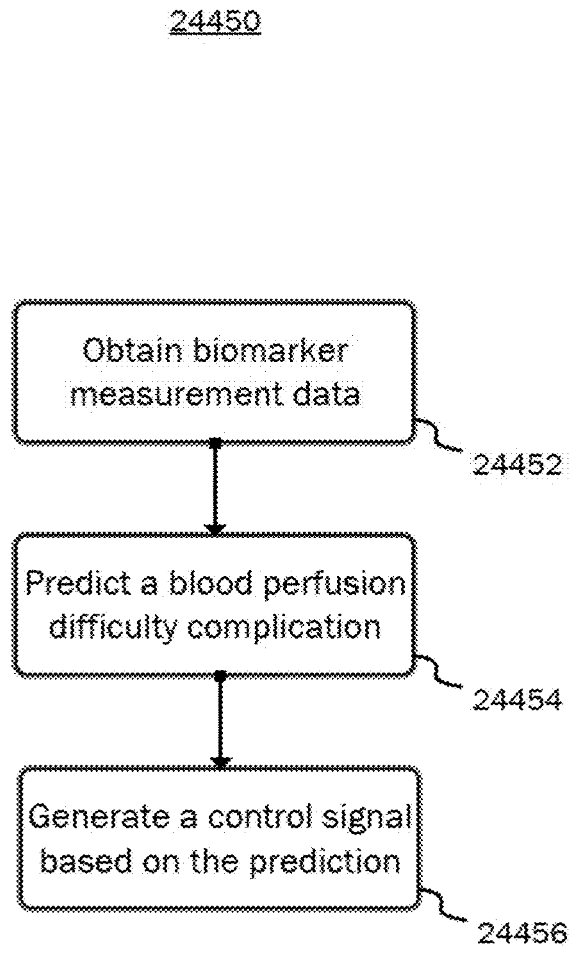
FIG. 44 illustrates an example process for predicting a blood perfusion difficulty complication.

As shown, sleeve gastrectomy may include a gastric transection procedural step. Biomarkers measurements may be used to inform various decisions related to the gastric transection procedural step, such as defining the staple line to preserve the antrum and ensure adequate blood supply to the stomach. Biomarker measurements related to stomach blood supply may be used when defining the staple line. In examples, as described herein, based on a predicted blood perfusion difficulty complication, such as a stomach blood perfusion difficulty complication, the computing system may generate various control signals to improve the stomach's post-surgical blood supply. For example, as shown in FIG. 43, the computing system may generate a control signal configured to enlarge a resection template of a surgical procedure plan (e.g., so as not to have poorly perfused remnant stomach tissue). For example, the computing system may generate a control signal configured to effect improved blood supply preservation. In an example, as shown in FIG. 44, a control signal may be generated and configured to control a surgical energy device to decrease an energy level at the transection step (e.g., to minimize collateral damage and associated blood loss). In an example, a control signal may be generated and configured to indicate to an HCP an adjustment to a surgical instrument selection for improved access capability at the transaction step (e.g., to avoid transecting site(s) that are better perfused). In an example, as shown in FIG. 44, a control signal may be generated and configured to indicate to HCP to add an adjunct to improve hemostasis.

As shown in FIG. 40C, biomarkers measurements may be used to identify various risks associated with gastric transection. For example, a risk associated with the gastric transection procedural step may be stapling through critical blood vessels and/or causing ischemia to the stomach. Biomarker measurements related to stomach blood supply, as described herein with reference to FIG. 1B, may be used to identify the risk of stapling through critical blood vessels and/or causing stomach ischemia during the gastric transection procedural step. Biomarker measurements may be used post-op to diagnose or predict failure(s). For example, biomarker measurements related to stomach blood supply may be used to diagnose when critical blood vessels have been stapled through and/or stomach ischemia.

As shown in FIG. 40C, biomarker measurements may be used to determine operational parameters for various surgical tools related to the gastric transection procedural step. During the gastric transection procedural step, the HCP may use a harmonic scalpel and/or bipolar RF to dissect the mesentery and/or adhesions. Biomarker measurements related to the thickness, character, and/or perfusion of the adhesions may be used to determine the operational parameters of the harmonic scalpel and/or bipolar RF. Biomarker measurements related to homeostasis (e.g., blood vessel collagen level and/or blood pressure) may be used to determine the operational parameters of the harmonic scalpel and/or bipolar RF. Biomarker measurements related to stomach tissue strength and/or spleen strength may be used to determine the operational parameters.

During the gastric transection procedural step, the HCP may use a linear stapler to staple the stomach tissue. Biomarker measurements related to the thickness, friability, and/or viscoelastic properties of the stomach may be used to determine the operational parameters of the linear stapler. In examples, as described in FIG. 45, based on a predicted tissue irregularity complication, such as a complication due to an irregularly thick stomach tissue, the computing system may generate various control signals to improve the optimal compression and/or firing of a linear stapler. In an example, the computing system may generate a control signal configured to reduce a clamping speed, increase a closure compression force, and/or prolong a tissue creep wait time prior to stapling. In an example, the computing system may generate a control signal configured to reduce a stapler firing speed.

FIG. 40D illustrates an example assessment procedural step and example use of patient biomarkers during this step. Biomarkers measurements may be used to inform various decisions related to the assessment procedural step. As shown, biomarkers measurements may be used to identify various risks associated with the assessment procedural step. For example, a risk associated with the assessment procedural step may be stomach leak. Biomarker measurements related to staple line integrity may be used to identify the risk of a stomach leak. Biomarker measurements related to staple line integrity may be used to diagnose or predict a stomach leak.

FIG. 40E illustrates example post-surgery and example use of patient biomarkers. As shown, biomarker measurements may be used post-op to predict or detect post-surgical sleeve gastrectomy complications.

Systems and techniques are disclosed for predicting a blood perfusion difficulty complication based on biomarker measurements obtained before and/or during a surgery, and adjusting a surgical parameter of the surgery based on the predicted complication.

For example, a computing system may monitor a patient's biomarkers and predict a potential blood perfusion difficulty complication. The computing system may include a processor configured to obtain pre-surgical and/or in-surgical measurement data associated with one or more patient biomarkers via one or more sensing systems. The computing system may predict a blood perfusion difficulty complication based on the biomarker measurement data. The patient biomarker(s) used for predicting a blood perfusion difficulty complication may include one or more of the following: core body temperature, peripheral temperature, blood sugar level, hydration state, and/or oxygen saturation data.

The computing system may predict blood perfusion complications based on whether the biomarker measurement data crosses a blood perfusion-related threshold. The blood perfusion difficulty complication may be predicted on the condition that the biomarker measurement data crosses the threshold. For example, a blood perfusion threshold associated with a differential between core temperature and peripheral temperature may be obtained. Whether the biomarker measurement data associated with the difference between core body temperature and peripheral temperature crosses the obtained blood perfusion threshold may be determined, and a blood perfusion difficulty complication may be predicted on the condition that the biomarker measurement data crosses the blood perfusion threshold. A blood perfusion threshold associated with oxygen saturation may be obtained. Whether the biomarker measurement data associated with a ratio of pulsed signals to non-pulsed signals measured via pulse oximetry oxygen saturation crosses the obtained blood perfusion threshold may be determined, and a blood perfusion difficulty complication may be predicted on the condition that the biomarker measurement data crosses the blood perfusion threshold.

Based on the predicted blood perfusion difficulty complication, a control signal associated with a surgical procedure may be generated. For example, the generated control signal may be configured to control a surgical energy device to decrease an energy level associated with a surgical step. The control signal configured to indicate an adjustment to a surgical procedure plan, such as adjustment(s) to surgical approach, to surgical instrument selection, to a resection template, and/or to adjunct utilization.

Blood perfusion difficulty complication(s) may be predicted based on biomarker measurements obtained before a surgery and/or during the surgery via one or more sensing systems. For example, a computing system may monitor the patient biomarker(s) including core body temperature, peripheral temperature, blood sugar level, hydration state data, and/or oxygen saturation data. Based on the prediction, the computing system may generate a control signal configured to alter a matter in which a surgical cutting and stapling device and/or a surgical energy operate, to adjust a surgical procedure plan, to adjust a surgical instrument selection, indicate a probability of the blood perfusion difficulty complication, and/or to indicate a suggested adjustment to surgical procedure plan, surgical approach, and/or surgical instrument selection.

Figure 41:
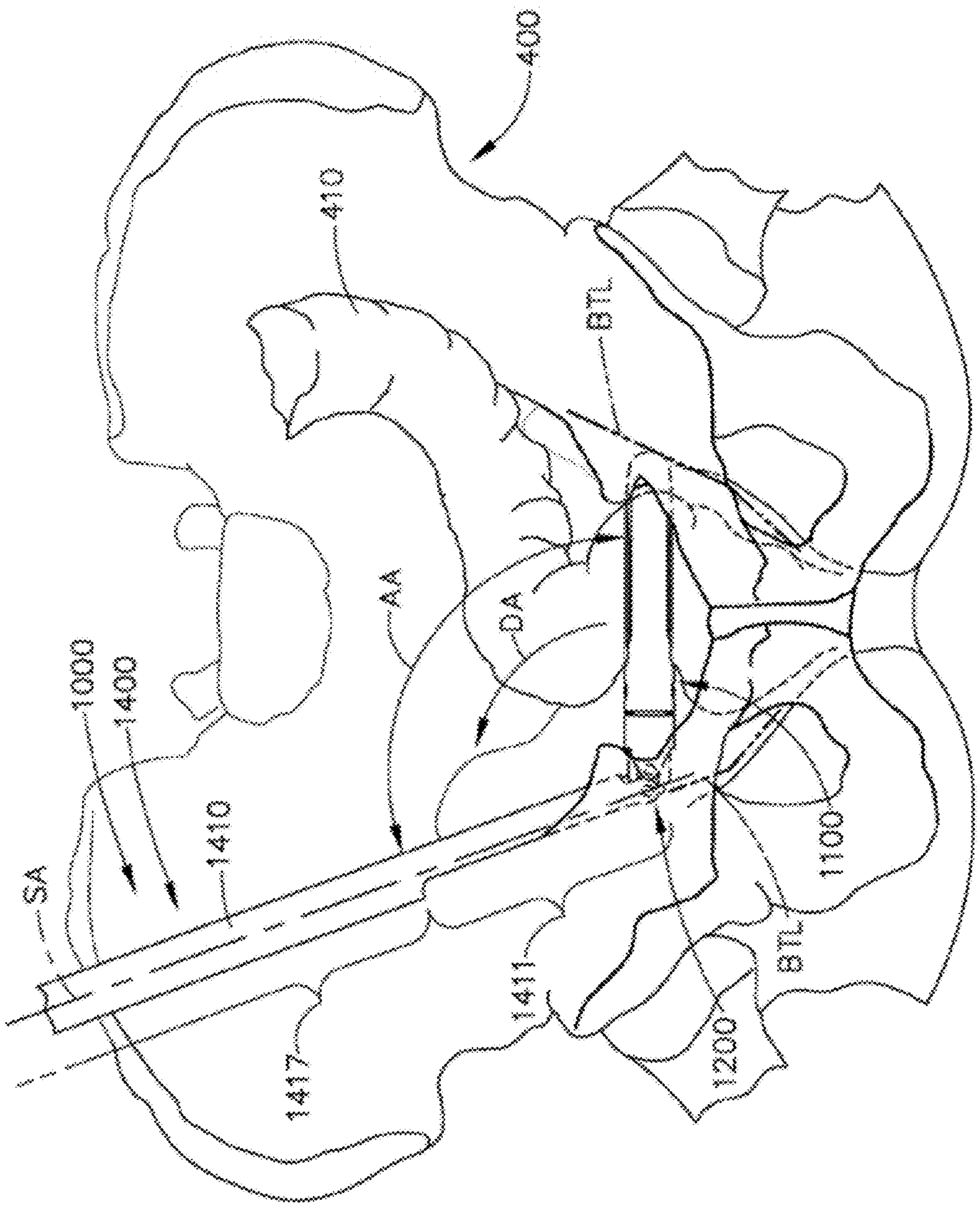
FIG. 41 illustrates use of an example surgical instrument designed with particular access capabilities to perform a medical procedure known as a lower anterior resection within a human pelvis area.

FIG. 41 illustrates an interchangeable surgical tool assembly 1000 that may be well-suited for use in connection with a medical procedure known as a lower anterior resection "LAR". Such procedure commonly involves removal of a diseased portion of the colon. For example, this procedure may comprise removal of the blood vessels and lymph nodes associated with this portion of the bowel. The surgeon then re-joins the remaining colon and the remaining part of the rectum (which may be referred to as an anastomosis). One challenge commonly facing the surgeon during this procedure is associated with getting the end effector into the pelvic area far enough to complete the procedure. FIG. 41 illustrates a desired position of the surgical end effector 1100 within the pelvis 400 of a patient during the resection of the patient's colon 410. Lines BTL in FIG. 41 may illustrate travel limits commonly created by the patient's pelvic bone structure and associated tissue. In the illustrated arrangement, the surgical tool assembly 1000 employs an "asymmetric" proximal closure member 1410 that is configured to provide additional clearance and maneuverability for the surgical tool assembly 1000 within that region.

As can be seen in FIG. 41, in one example, the proximal closure member 1410 of the shaft assembly 1400 includes an elongate proximal end portion 1417 and an elongate distal end portion 1411 that extends from the proximal end portion 1417. The shaft assembly 1400 includes an articulation point 1200. As can be seen in FIGS. 41, to facilitate more clearance between the shaft assembly 1400 and the pelvic structure for example, an asymmetric cut out or notched area 1418 is provided in the distal end portion 1411 of the proximal closure member 1410. In at least one example, the notched area 1418 extends for the entire distal end portion 1411. In such arrangement, an axial length of the distal end portion is less than an axial length of the proximal end portion 1417. For more details, see U.S. patent application Ser. No. 15/385,930, titled SURGICAL END EFFECTOR WITH TWO SEPARATE COOPERATING OPENING FEATURES FOR OPENING AND CLOSING END EFFECTOR JAWS, which was filed on Dec. 21, 2016, which is herein incorporated by reference in its entirety.

Figure 42B:
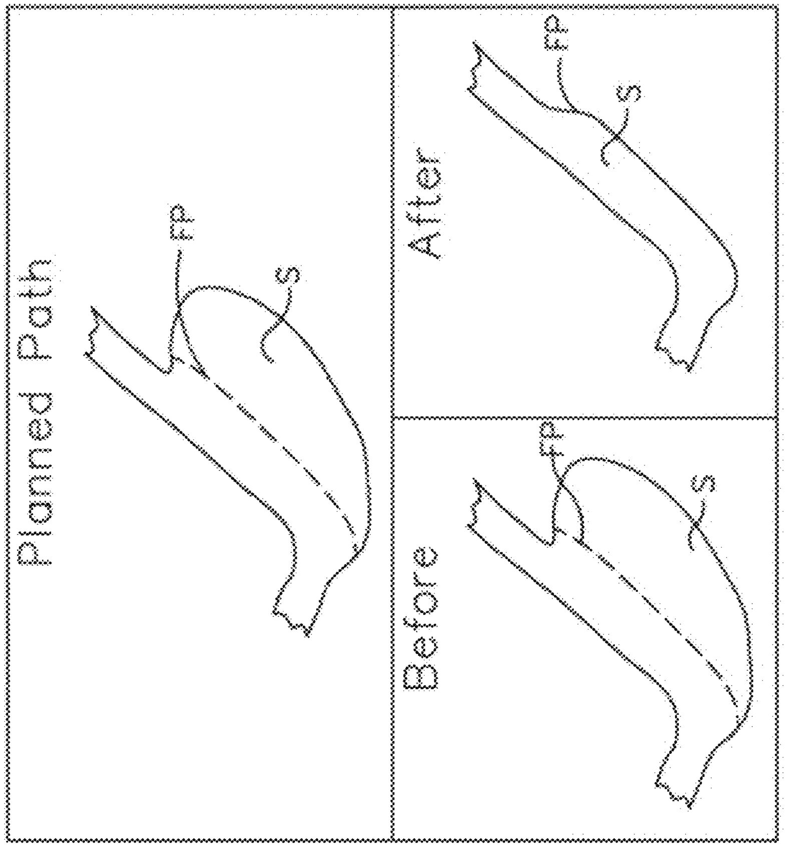
FIG. 42B illustrates a potential outcome of a stomach sleeve procedure using an example planned resection template.
Figure 42A:
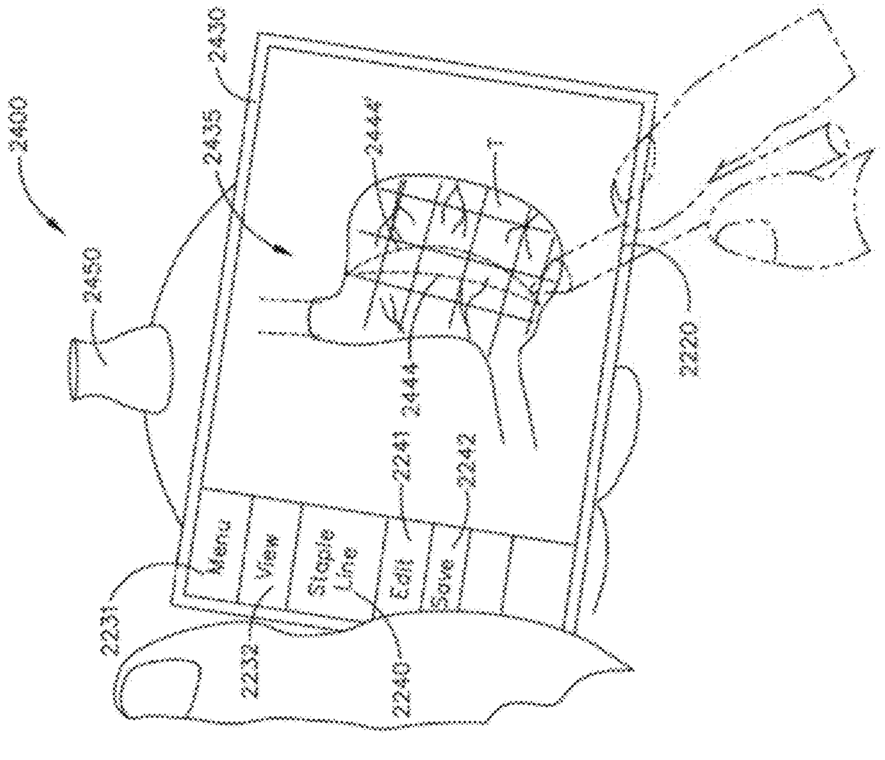
FIG. 42A illustrates a surgical instrument with a display for planning an example resection template in a stomach sleeve procedure.

FIG. 42A illustrates a surgical instrument 2400 comprises a display 2430. The stapling instrument 2400 is similar to the stapling instruments 2000 and 2200 in many respects and the display 2430 is similar to the displays 2130 and 2230 in many respects, most of which will not be discussed herein for the sake of brevity. The display 2430 is positioned above the surgical instrument 2400. The display 2430 comprises a touchscreen including an image display 2435. The image display 2435 provides an image of the patient tissue T that is to be stapled. The user of the stapling instrument 2400 can use a stylus 2220, for example, to draw one or more potential staple lines over the tissue T. For instance, the user can draw a first staple line 2444 and a second staple line 2444', both of which constitute a resection template. The controller of the stapling instrument 2400 can then require the user to choose between the two different staple lines 2444 and 2444' that is to be followed. Similarly, the user of the stapling instrument 2400 can use the stylus to modify a staple line 2444 into an alternate staple line 2444'. For more details, see Europe patent application Ser. No. 18/214,920.3, titled SURGICAL INSTRUMENT CONFIGURED TO DETERMINE FIRING PATH, which was filed on Dec. 20, 2018, which is herein incorporated by reference in its entirety.

FIG. 42B illustrates a potential outcome of a stomach sleeve procedure using a planned resection template. A staple firing path FP, which constitute a resection template, is used to cut the stomach sleeve SS from the patient's stomach S. For more details, see Europe patent application Ser. No. 18/214,920.3, titled SURGICAL INSTRUMENT CONFIGURED TO DETERMINE FIRING PATH, which was filed on Dec. 20, 2018, which is herein incorporated by reference in its entirety.

Physiological issues may lead to complications in a surgical procedure. For example, blood perfusion capabilities help supply oxygen to an organ. Blood perfusion difficulties such as insufficient blood perfusion or limited blood perfusion may lead to complications in a surgical procedure. For example, insufficient blood perfusion or limited blood perfusion in large intestine in the lower GI tract may lead to complications in a lower GI resection procedure.

Blood perfusion difficulty complications may be predicted based on pre-surgical and/or in-surgical measurements of related biomarkers. For example, a blood perfusion difficulty complication may be determined based on one or more biomarkers, such as core body temperature, peripheral temperature, oxygen saturation, blood sugar level, hydration state, and/or the like.

As described herein, various sensing systems (as described herein with reference to FIGS. 1A-B, 2A-C, 3, 4, 5, 6A-C, 7B-D, 9, 11A-D, and 12) may measure biomarkers that may be used to predict blood perfusion difficulty complication(s). For example, the sensing systems may perform pre-surgical and/or in-surgical measurement(s) of a patient's blood perfusion difficulty-related biomarkers, such as core body temperature, peripheral temperature, oxygen saturation, blood sugar level, hydration state, and/or the like. Such pre-surgical measurement(s) of blood perfusion difficulty-related biomarkers may be performed via the sensing system(s) in a clinical setting. In an example, as shown in FIG. 6A, one or more of sensing systems may perform pre-surgical measurement(s) of a patient's blood perfusion difficulty-related biomarker(s) before a surgical procedure in an operating room. An environmental temperature (e.g., an ambient temperature) may be measured to control for its influence on core body temperature measurements and/or peripheral temperature measurements.

The sensing system(s) may process and/or store measurement data for predicting blood perfusion difficulty complication(s) locally, and/or send the measurement data to a computing system for further processing. The computing system may be or may include a surgical hub described herein, for example with reference to FIGS. 1A, 2A-B, 3, 5, 6A-B, 7B-D, 9, and 12. The computing system may include or be connected with a surgical hub/surgeon display interface described here, for example with reference to FIGS. 4, 5, 6A-B, and 12. In an example, as shown in FIG. 6A, the sensing system(s) may communicate with the computing system via a communication module 230. In an example, as shown in FIG. 6B, the sensing system(s) may communicate with the computing system via a local area network (LAN).

Pre-surgical measurement data and/or in-surgical measurement data associated with one or more patient biomarkers may be obtained from the sensing system(s). For example, the computing system may obtain, from the sensing system(s), measurement data associated with one or more blood perfusion difficulty-related biomarkers, such as core body temperature, peripheral temperature, oxygen saturation, blood sugar level, hydration state, and/or the like.

A blood perfusion difficulty complication may be predicted based on pre-surgical and/or in-surgical measurement data associated with biomarker(s) monitoring. For example, the sensing system(s) may perform the prediction based on the pre-surgical and/or in-surgical measurement data of blood perfusion difficulty-related biomarker(s). For example, the computing system may determine a blood perfusion difficulty complication based on the pre-surgical and/or in-surgical measurement data of blood perfusion difficulty-related biomarker(s) and the threshold(s) associated with the biomarker(s).

The computing system may determine whether the biomarker measurement data associated with the one or more patient biomarkers crosses a threshold. The computing system may predict a blood perfusion difficulty complication on the condition that the biomarker measurement data associated with the one or more patient biomarkers crosses a threshold. The biomarker measurement data may include core body temperature data, peripheral temperature data, oxygen saturation data, blood sugar level data, and/or hydration state data.

One or more thresholds may be obtained for a patient biomarker, for example, for predicting blood perfusion difficulty complications. For example, the computing system may determine respective threshold(s) associated with a patient's core body temperature, peripheral temperature, oxygen saturation, blood sugar level, hydration state, and/or the like. The threshold(s) may be standard threshold(s). The threshold(s) may be pre-defined and/or set by an HCP. The threshold(s) may be customized for a patient based on the patient's medical history, health information, biographical information, family health information, and/or the like. A biomarker may be monitored by comparing the measurement data related to the biomarker against the corresponding threshold(s). A potential blood perfusion difficulty complication(s) may be detected when the measurement data related to one or more biomarkers crosses the corresponding threshold(s) for a predetermined amount of time. Crossing a threshold may include the measurement data associated with a biomarker increasing above the corresponding threshold value. Crossing the threshold may include the measurement data associated with a biomarker dropping below the corresponding threshold value. The predetermined amount of time may be used to mitigate erroneous measurement data. For example, the predetermined amount of time may reduce the number of false positive detections. The predetermined amount of time may be determined based on the one or more biomarkers being monitored.

In an example, an increased blood sugar level may correlate with decreased blood perfusion. High blood sugar level may damage blood vessels' lining and cause it to narrow, leading to poor blood perfusion. Blood sugar level measurement data may be compared against an obtained blood sugar level threshold. A blood perfusion difficulty complication may be determined when the blood sugar level measurement data is above such threshold.

In an example, a hydration state measures a water level in the body. Decreased water level in the body may lead to decreased blood perfusion. Dehydration may lead to poor blood perfusion. For example, hydration state sensing system employing optical spectroscopy may measure a water retention level of the blood. The water retention level of the blood measurement data may be compared against an obtained water retention level range threshold. A blood perfusion difficulty complication may be determined when the water content level of the blood measurement data is below such range threshold.

A differential between a peripheral temperature measurement and a core body temperature may correlate with peripheral perfusion changes (e.g., blood perfusion changes in peripheral tissues). An increased differential between a peripheral temperature measurement and a core body temperature may correlate with a decreased peripheral perfusion. A decreased peripheral perfusion may lead to blood perfusion difficulties in peripheral tissues.

For example, the computing system may determine whether a differential between a peripheral temperature measurement and a core body temperature crosses a threshold. The computing system may predict a blood perfusion difficulty complication on the condition that the biomarker measurement data associated with the peripheral temperature crosses the threshold. In an example, a blood perfusion difficulty complication may be determined when the differential between the measured peripheral temperature and the core temperature is above such threshold.

Oxygen saturation measures an oxygen level in the blood flow. A decreased oxygen level may correlate with a decreased blood perfusion. As such, blood perfusion difficulties may result. The computing system may determine whether the biomarker measurement data associated with oxygen saturation (SpO2) crosses a threshold associated with a ratio of pulsed signals to non-pulsed signals measured via pulse oximetry. The computing system may predict a blood perfusion difficulty complication on the condition that the biomarker measurement data associated with the SpO2 crosses the threshold. In an example, a measured ratio of pulsed signals to non-pulsed signals via pulse oximetry may be compared against a threshold ratio of pulsed signals to non-pulsed signals. A blood perfusion difficulty complication may be determined when the measured ratio is below the threshold ratio. In examples, a lower-than-threshold ratio may indicate vasoconstriction or lessened blood perfusion.

The determination of a blood perfusion difficulty may be based on the pre-surgical and/or in-surgical blood perfusion biomarker measurement data preprocessed by the sensing systems. For example, a hydration state sensing system (e.g., implemented using optical spectroscopy) may monitor a patient's water content level in the blood via continuous measurements. When the hydration state sensing system transmits the hydration state measurement data, the sensing system may calculate the mean of the measurements and transmit such mean to the computing system. The sensing system may calculate the mean of the measurements excluding outlier measurements and transmit such mean. The sensing system may calculate the mean of the measurements and standard deviation of the measurement data set, and transmit the mean and the standard deviation. The sensing system may calculate an average of the highest measurement and the lowest measurement and transmit such average. The sensing system may identify the highest measurement and the lowest measurement and transmit such measurement range. The sensing system may identify the highest measurement and the lowest measurement after excluding outlier measurements and transmit such measurement range. The sensing system may convert the preprocessed water content level measurement data to hydration state classifications, such as "well hydrated", "mildly dehydrated", or "severely dehydrated", and transmit such classifications to the computing system. The hydration state sensing system may transmit to the computing system identifiers for such classifications, e.g., "WH", "MD", "SD" for "well hydrated", "mildly dehydrated", or "severely dehydrated", respectively. Those of skill in the art will recognize other sensing systems described herein may also preprocess the biomarker measurement data and then transmit the preprocessed biomarker measurement data to the computing system as described.

The determination of blood perfusion difficulty may be based on the blood perfusion biomarker measurement data as captured by the sensing systems (e.g., raw measurements). The computing system may process the raw measurements before making the determination. For example, a hydration state sensing system (e.g., implemented using optical spectroscopy) may monitor a patient's water content level in the blood via continuous measurements. The hydration state sensing system may transmit the raw measurements to the computing system. In response, the computing system may process the raw measurements as described in how the hydration state sensing system preprocesses the hydration state measurement data described herein. Those of skill in the art will recognize other sensing systems described herein may transmit raw measurements to the computing system, and in response the computing system may process the raw measurements as described.

The computing system may generate an output based on the predicted blood perfusion difficulty complication. The output may include a control signal configured to adjust a surgical parameter associated with a surgery for mitigating the predicted blood perfusion difficulty complication. For example, the computing system may generate one or more adjustments to the impending surgical procedure. The adjustment may include, but not limited to, an adjustment to an adjustment to a surgical instrument's control program and/or an adjustment to a surgical procedure plan. The adjustment to a surgical procedure plan may include, but not limited to, an adjustment to a resection template, an adjustment to a surgical instrument selection, adding adjunct(s), and/or an adjustment to a surgical procedure approach.

A surgical procedure may include planned procedure steps that may be stored and retrieved, or otherwise accessed on a computing device (e.g., the surgical hub 206 or 5104). For example, a list of planned procedure steps for a thoracic procedure (specifically, a lung segmentectomy procedure) may be retrieved or accessed.

Planned surgical instruments' (as shown in FIGS. 1A, 2A, 3, 4, 5, 6A, 7A, 8, 9, 10, and 12) identification information may be obtained via a computing device (e.g., the surgical hub 206 or 5104). For example, planned surgical instruments' identification information may be obtained based on planned procedure steps and the associated surgical instruments information. For example, as described in FIG. 14, planned procedure steps of a colorectal procedure (e.g., access 206580, dissection 206582, transection 206584, anastomosis 206586, and closing 206588) may be retrieved from a surgical hub (e.g., the surgical hub 206 or 5104). A list of planned surgical instruments (e.g., trocar 206581, energy device 206583, linear surgical stapler 206585, and circular surgical stapler 206587) associated with the planned procedure steps may be retrieved from the surgical hub. Usage of planned surgical instruments at planned procedure steps may be detected and confirmed by the surgical hub (e.g., the surgical hub 206 or 5104). For example, activation instances 206592 illustrate the expected usage of trocar 206581 at planned procedure steps access 206580 and closing 206588. For example, activation instances 206590 illustrate the expected usage of energy device 206584 at planned procedure steps access 206580, dissection 206582, and transection 206584. For example, activation instance 206594 illustrates the expected usage of linear surgical stapler 206585 at planned procedure step transection 206584. For example, activation instance 206596 illustrates the expected usage of circular surgical stapler 206587 at planned procedure step anastomosis 206586.

Based on the predicted blood perfusion difficulty complication, a control signal configured to alter an operational parameter associated with a surgical device may be determined and generated as an output. The control signal may adjust the control program of a surgical instrument. The control signal may be configured to update an operational parameter, such as an operating parameter, a surgical parameter, or the like of the control program associated with a surgical instrument (e.g., during an activation instance).

For example, as described in FIG. 13, a computing system (e.g., the surgical hub 206 or 5104) may adjust operational parameters (e.g., energy level) of a control program of an energy device 206583. The control program of an energy device (e.g., an ultrasonic or a radio frequency energy device) may include adjustable operational parameters, such as an energy level for tissue separation or an energy level for tissue sealing/coagulation.

Based on the predicted blood perfusion difficulty complication, the computing system may generate a control signal configured to alter an energy device's operational parameter(s) at one or more procedure steps. For example, the control signal may indicate a lower energy level for tissue transection and/or tissue coagulation to minimize collateral damage and associated blood loss during dissection and mobilization. For example, the control signal may alter an energy device's operational parameter at a dissection step of a colorectal procedure. The control signal may decrease an energy level for tissue separation or decrease an energy level for tissue sealing and/or transection.

Based on the predicted blood perfusion complication, the computing system may generate a control signal configured to indicate a suggestion for adjusting a surgical instrument selection for improved dissection capability. The improved dissection capability may minimize collateral damage and associated blood loss and hence improve blood perfusion preservation. For example, a dissection tool having higher precision may be selected and suggested in place of a dissection tool having a lower precision. In an example, a smaller or more precise device, such as a curved tip stapler may replace a general-purpose stapler. In an example, an advanced energy device instead of a basic energy device may be suggested. In an example, a device with a more tapered dissection tool (e.g., a tapered jaw) such as in a HD1000 i harmonic device instead of a harmonic ACE+7 device may be suggested. For example, a dissection tool that minimizes the amount of dissection to enable less mobilization and more retention of blood perfusion, may be selected and suggested. In an example, a stapler with smaller end effector features (e.g., a narrow anvil) may be suggested. In an example, a stapler with a smaller staple line length may be suggested. In an example, a minimized end effector length distal to the articulation joint may be suggested. For example, a dissection tool that minimizes collateral damage during dissection and mobilization may be selected and suggested. In an example, a surgical device with a blunter dissection tool may be suggested. For example, a surgical device with a tool capable finer dissection may be suggested.

Based on the predicted blood perfusion difficulty complication, the computing system may generate a control signal configured to indicate a suggestion for adjusting a surgical instrument selection for improved access capability (e.g., to avoid transecting surgical site(s) that are better perfused). For example, a surgical instrument with better access characteristics that are better able to fit into a target space (e.g., at a transection step in a colorectal procedure described in FIG. 14) may be selected and suggested. In an example, a surgical instrument with characteristics such as a better articulation angle may be suggested. In an example, a surgical instrument with a capability of multi-axis articulation may be suggested. In an example, a surgical instrument with a minimal end effector length distal to the articulation joint may be suggested. In an example, a surgical instrument with a smaller anvil width may be suggested. In an example, as shown in FIG. 41, in a colorectal lower anterior resection (LAR) procedure, a surgical instrument 1000 end effector's travel limits in the surgical site (illustrated by lines BTL) are created by a patient's pelvic bone structure and associated tissue. To gain additional clearance and maneuverability, the surgical instrument 1000 may employ an "asymmetric" proximal closure member 1410. That is, closure member 1410 includes a distal end portion 1411 that includes a cut-out area that affords the surgical instrument 1000 more clearance at the transection site.

Based on the predicted blood perfusion difficulty complication, the computing system may generate a control signal configured to indicate a suggestion for adjusting a resection template of a surgical procedure (e.g., so as not to have poorly perfused remnant tissue(s)). For example, an adjustment to enlarge a resection template for a transection step may be generated. A resection template may define the contour and size of a portion of a targeted organ to be removed during a transaction step in a thoracic procedure, an abdominal procedure, or a colorectal procedure. For example, as described in FIG. 42A for a stomach reduction procedure, a surgeon may define a planned staple line/path 2444 (e.g., on a user display 2430). Such planned staple line/path may constitute a resection template. As further illustrated in FIG. 42B, the to-be-resected portion of the stomach S is the difference between the "Before" and the "After" drawings of the stomach S. An alternative staple line/path 2444' may define an alternative resection template. As shown in FIG. 42A, the alternative staple line/path 2444' may increase a resection number (e.g., a number of cuts required) of the resection template. Such resection templates for a transection step of an impending surgical procedure may be stored on a surgical hub (e.g., the surgical hub 206 or 5104) as a part of the stored procedure step information.

For example, an adjustment to a resection template for a transection step may include enlarging the stored resection template based on the severity of the determined blood perfusion difficulty complication (e.g., in colorectal procedure, such as LAR procedure). The enlarged resection may include an additional portion of a targeted organ that is in the surrounding area of the diseased part of the targeted organ in order to account for the prediction that the additional portion, if left remaining in the patient, would have poor blood perfusion. For example, as illustrated in FIG. 43, the planned resection template may be a portion of a colon 24400 defined between lines 24402 and 24404 surrounding a deceased part 24410. An enlarged resection template may be a portion of the colon 24400 defined between lines 24406 and 24408. In a severe case of blood perfusion difficulty, the surgical hub may enlarge the resection template by a predefined "large" enlargement amount (e.g., large additional resection areas between lines 24402 and 24406, and between lines 24404 and 24408). As shown in FIG. 43, the resection template's start locations have changed a part of lines 24406 and 24408. While in a mild case of blood perfusion difficulty, the surgical hub may enlarge the resection template by a predefined "small" enlargement amount (e.g., small additional resection areas between lines 24402 and 24406, and between lines 24404 and 24408). Such predefined enlargement amounts may be predefined values of a margin parameter of the resection template. Such margin parameter may correspond to the amount of tissue around the deceased part of the targeted organ.

Based on the predicted blood perfusion difficulty complication, the computing system may generate a control signal configured to indicate a suggestion for adding an adjunct at one or more procedure steps. For example, the computing system may generate a control signal configured to indicate a suggestion for adding an adjunct for a transection step. In an example, a suggestion may be made to use a buttress (e.g., an absorbable or permanent buttress) to supplement a surgical stapler to increase staple line strength and hence reduce staple line leaks and improve blood perfusion preservation. In an example, an absorbable biomaterial-based hemostatic adjunct (e.g., SURGICEL® Absorbable Hemostats) may be suggested to improve hemostasis and blood perfusion preservation. In an example, a drug-eluting implant (e.g., a drug-eluting stent) may be suggested to improve narrowness of blood vessels and hence improve blood perfusion.

Based on the predicted blood perfusion difficulty complication, the computing system may generate a control signal configured to indicate a suggestion for adjusting a surgical approach.

For example, a suggestion for adjusting the surgical approach may be a suggestion to opt for an open procedure in place of a planned laparoscopic procedure approach. In an example, when at least a partial visualization of a patient's anatomy is obtained (e.g., via one or more laparoscopes) during a colorectal surgery, poor blood perfusion may be observed in locations of a colon that make up a large area in the abdominal cavity. Accordingly, the enlargement of resection size at these locations may be challenging or infeasible laparoscopically. In such case, a suggestion to convert to an open procedure approach may be indicated.

For example, a suggestion for adjusting the surgical approach may be a suggestion to opt for a robotic procedure in place of a laparoscopic procedure. In an example, when at least a partial visualization of a patient's anatomy is obtained (e.g., via one or more laparoscopes) during a colorectal surgery, poor blood perfusion may be observed in a space of the abdominal cavity that is hard to reach laparoscopically. In such case, a suggestion to convert to a robotic procedure approach may be indicated to leverage robotic devices' dexterity to reach hard-to-reach areas.

Suggestions described herein may be provided via a user interface a surgeon interacts with ("surgeon interface"), such as a surgical planning interface, a surgeon interface/console, surgical hub display 215 illustrated in FIG. 5, and/or a surgical device having a display. The suggestions may be generated by a computing system (e.g., the surgical hub 206 or 5104) and sent to the surgeon interface. A suggestion message may be displayed in a designated area on the surgeon interface, such as a suggestion overlay or a suggestion box at the bottom right corner of the surgeon interface.

FIG. 44 illustrates an example process 24450 of predicting a blood perfusion difficulty complication. The process may include a computer-implemented process. For example, a computing system may perform the process illustrated in FIG. 44. For example, a sensing system described herein may perform the process illustrated in FIG. 44.

At 24452, measurement data associated with one or more patient biomarkers may be obtained via one or more sensing systems. Measurement data may include measurement data obtained prior to a surgery, and/or biomarker measurements taken during a surgery. Pre-surgical measurements may be combined with in-surgical measurements. The patient biomarker(s) may include one or more of the following: a difference between core body temperature and peripheral temperature, blood sugar level, hydration state, or oxygen saturation.

At 24454, a blood perfusion difficulty complication may be predicted based on the biomarker measurement data associated with the one or more patient biomarkers. The blood perfusion difficulty complication may be predicted based on pre-surgical measurement data, in-surgical measurement data, or a combination of pre-surgical measurement data, in-surgical measurement data.

For example, the computing system may determine whether the biomarker measurement data crosses a blood perfusion-related threshold. On the condition that the biomarker measurement data crosses the blood perfusion-related threshold, a blood perfusion difficulty complication may be predicted.

At 24456, an output associated with a surgical procedure may be generated based on the predicted blood perfusion difficulty complication. For example, a control signal configured to control a surgical energy device to decrease an energy level may be generated. A planned energy level associated with a surgical step for the surgical energy device may be obtained. A power level decrease for the surgical step based on the predicted blood perfusion difficulty may be determined. An indication of the determined power level decrease as part of the control signal configured to control a surgical energy device to decrease an energy level may be sent.

For example, a control signal configured to indicate an adjustment to a surgical procedure plan may be generated. For example, the adjustment to a surgical procedure plan may include an adjustment to a surgical approach, an adjustment to a surgical instrument selection, an adjustment to a resection template, and/or adding an adjunct.

For example, a control signal configured to indicate an adjustment to a surgical instrument selection for improved dissection capability may be generated. For example, the adjustment to a surgical instrument selection for improved dissection capability may include selecting a dissection tool having higher precision in place of a dissection tool having a lower precision, selecting a dissection tool that minimizes collateral damage, and/or selecting a dissection tool that minimizes amount of dissection.

Systems and techniques are disclosed for predicting a tissue irregularity complication based on biomarker measurements obtained before a surgery and/or during the surgery, and adjusting a surgical parameter of the surgery based on the predicted complication.

For example, a computing system may monitor a patient's biomarkers and predict a potential tissue irregularity complication. The computing system may include a processor configured to obtain pre-surgical and/or in-surgical measurement data associated with one or more patient biomarkers via one or more sensing systems. The computing system may predict a tissue irregularity complication based on the biomarker measurement data. The patient biomarker(s) used for predicting a tissue irregularity complication may include one or more of the following: tissue perfusion pressure, lactate, oxygen saturation, VO2Max, respiration rate, autonomic tone, sweat rate, heart rate variability, skin conductance, GI motility, edema or hydration state.

For example, the computing system may determine a probability of a chronic inflammation response based on the biomarker measurement data on one or more of: tissue perfusion pressure, lactate, oxygen saturation, VO2Max, respiration rate, autonomic tone, sweat rate, heart rate variability, skin conductance, or GI motility. On the condition that the probability of a chronic inflammation response crosses a threshold, the computing system may predict a tissue irregularity complication. For example, the computing system may determine a probability of an irregular water retention level based on measurement data associated with edema and/or hydration state. On the condition that the probability of an irregular water retention level crosses a threshold, the computing system may predict a tissue irregularity complication.

Based on the predicted tissue irregularity complication, a control signal associated with a surgical procedure may be generated. For example, the generated control signal may be configured to control a surgical cutting and stapling device to perform prolonging a tissue creep wait time prior to stapling, reducing a clamping speed, reducing a stapler firing speed, and/or increasing a closure compression force. The generated control signal may be configured to control a surgical energy device to perform increasing an energy level, increasing an energy application duration, and/or increasing a threshold for an energy generation associated with a subsequent energy application. The generated control signal may be configured to perform displaying a probability of a tissue irregularity complication on a pre-surgery imaging, displaying a probability of a tissue irregularity complication via an augmented reality device, and/or displaying a probability of a tissue irregularity complication in a surgical procedure plan along with an indication of an adjustment to the surgical procedure plan.

Tissue irregularity complication(s) may be predicted based on biomarker measurements obtained before a surgery and/or during the surgery via one or more sensing systems. For example, a computing system may monitor the patient biomarker(s) including tissue perfusion pressure, lactate, oxygen saturation, VO2Max, respiration rate, autonomic tone, sweat rate, heart rate variability, skin conductance, GI motility, edema and/or hydration state. Based on the prediction, the computing system may generate a control signal configured to alter a matter in which a surgical cutting and stapling device and/or a surgical energy operate, to adjust a surgical procedure plan, to adjust a surgical instrument selection, indicate a probability of the tissue irregularity complication, and/or to indicate a suggested adjustment to surgical procedure plan, surgical approach, and/or surgical instrument selection.

Tissue irregularity may lead to complications in a surgical procedure. For example, a failure to account for a thicker-than-normal tissue may lead to complications in a transection step of a surgical procedure. For example, a surgical stapler may compress a thicker-than-normal tissue ineffectively by applying a normal compression force during tissue compression. A sub-optimal compression on the thicker-than-normal tissue may be reached due to the thicker-than-normal tissue's reduced compressibility if the surgical stapler waits a normal tissue creep time before firing. A staple line may be poorly formed on the thicker-than-normal tissue if the surgical stapler uses staples with a normal staple height during firing. The complications may include staple-line air leaks in a thoracic surgery (e.g., a lung segmentectomy procedure) or staple-line leaks in a colorectal surgery (e.g., a lower anterior resection (LAR) procedure). For example, a failure to account for stiffer-than-normal tissue or a highly-variable-in-thickness tissue in a dissection, a transection, and/or an anastomosis step of a surgical procedure may lead to similar complications.

Tissue irregularity complication may be predicted based on pre-surgical and/or in-surgical measurements of related biomarker(s). For example, tissue irregularity may be determined based on one or more biomarkers, such as edema, tissue perfusion pressure, hydration state, lactate, oxygen saturation, VO2Max, respiration rate, autonomic tone, sweat rate, heart rate variability, skin conductance, GI motility, and/or the like.

For example, a tissue irregularity complication may be determined based on one or more biomarkers related to water retention level in tissues. Biomarkers related to irregular water retention level may include edema, hydration state, and/or the like. Edema is swelling caused by water content of the blood flow leaking into tissues and becoming trapped in tissues. Swelling in tissues may lead to thickened tissues. For example, hydration state indicates the water retention level of the body. Insufficient water retention may include insufficient blood flow through tissues and/or insufficient interstitial fluid (which may be referred to as tissue fluid). Such insufficiency of water retention may lead to stiffened tissues (e.g., with a higher density).

For example, a tissue irregularity complication may be determined based on one or more biomarkers related to chronic inflammation response. Chronic inflammation response may lead to prolonged scar tissue forming, prolonged tissue remodeling, and/or damaging healthy tissues. As such, fibrotic, stiffened, and/or thickened tissues may form. Biomarkers related to chronic inflammation response may include tissue perfusion pressure, lactate, oxygen saturation, VO2Max, respiration rate, autonomic tone, sweat rate, heart rate variability, skin conductance, GI motility, and/or the like.

For example, a tissue irregularity complication may be predicted based on biomarker(s) related to a chronic inflammation response associated with poor tissue oxygenation. Chronic poor tissue oxygenation may lead to cell death, the associated infection and chronic inflammation, and consequently thickened and/or stiffened tissues. Biomarkers related to a chronic inflammation response associated with poor tissue oxygenation may include tissue perfusion pressure, lactate, oxygen saturation, and/or VO2Max. In an example, tissue perfusion pressure measures the sufficiency of blood flow through tissues. Insufficient tissue perfusion pressure may lead to chronic poor tissue oxygenation and consequently thickened and/or stiffened tissues. Lactate is a substance produced by cells during cell metabolism. A high lactate level may indicate chronic poor tissue oxygenation and consequently thickened and/or stiffened tissues. In an example, oxygen saturation measures the oxygen level in the blood flow. A low oxygen level in the blood flow may lead to chronic poor tissue oxygenation and consequently thickened and/or stiffened tissues. VO2Max measures the maximum amount of oxygen the body can consume (e.g., from breathing in the air to tissue oxygenation) during a specified period of time (e.g., a period of incrementally intense exercise). A low VO2Max may indicate a poor oxygen consumption ability. Such poor oxygen consumption ability may lead to chronic poor tissue oxygenation and consequently thickened and/or stiffened tissues.

For example, a tissue irregularity complication may be predicted based on biomarker(s) related to a chronic inflammation response associated with increased respiration rate. Increased respiration rate may indicate a chronic lung inflammation condition and the presence of consequent thickened and/or stiffened tissues. In an example, an increased respiration rate due to air leaks in lungs caused by an underlying chronic inflammation response may indicate the presence of thickened and/or stiffened tissues.

For example, a tissue irregularity complication may be predicted based on biomarker(s) related to a chronic inflammation response associated with an imbalanced autonomic tone. Autonomic tone describes the basal balance between the sympathetic and parasympathetic nervous system. In an example, an imbalanced autonomic tone, such as a high sympathetic tone, may indicate chronic inflammation and the presence of consequent thickened and/or stiffened tissues. Autonomic tone may be associated with biomarkers related to the sympathetic nervous system, such as heart rate variability, skin conductance, or sweat rate. For example, a high sympathetic tone may be inferred from one or more of: an increased heart rate, an increased sweat rate, or a higher skin conductance (e.g., based on these biomarkers' association with heightened sympathetic activity). The inference of such high sympathetic tone may indicate a chronic inflammation response and the presence of consequent thickened and/or stiffened tissues. The inference of such high sympathetic tone may be associated with pre-surgical pain and/or stress.

For example, a tissue irregularity complication may be predicted based on biomarker(s) related to a chronic inflammation response associated with reduced GI motility. In an example, reduced small bowel motility due to small bowel obstruction may be caused by thickened and/or stiffened tissues formed on the wall of a small bowel. Such thickened and/or stiffened tissues may have resulted from internal scarring and/or remodeled tissues due to a chronic inflammation response in the small bowel. In such example, the chronic inflammation response may have been caused by an underlying chronic inflammatory disease (e.g., Crohn's disease or irritable bowel syndrome (IBS)). In such example, the chronic inflammation response may have been caused by a chronic inflammation resulting from a prior colorectal procedure. In an example, the tissue irregularity complication predicted based on reduced GI motility may be inferred from a high sympathetic tone indicated by one or more of: an increased heart rate, an increased sweat rate, or a higher skin conductance. The indication of such high sympathetic tone may be associated with pre-surgical pain and/or stress.

As described herein, various sensing systems may measure biomarkers that may be used to predict tissue irregularity complication(s). For example, the sensing systems may perform pre-surgical and/or in-surgical measurement(s) of a patient's tissue irregularity-related biomarkers, such as edema, hydration state, tissue perfusion pressure data, lactate data, oxygen saturation data, VO2Max data, respiration rate data, autonomic tone data, sweat rate data, heart rate variability data, skin conductance data, GI motility data, and/or the like. Such pre-surgical measurement(s) of tissue irregularity-related biomarkers may be performed via the sensing system(s) in a clinical setting. In an example, as shown in FIG. 6A, one or more of sensing systems may perform pre-surgical measurement(s) of a patient's tissue irregularity-related biomarker(s) before a surgical procedure in an operating room.

The sensing system(s) may process and/or store measurement data for predicting tissue irregularity complication(s) locally, and/or send the measurement data to a computing system for further processing. The computing system may be or may include a surgical hub described herein, for example with reference to FIGS. 1, 2, 2A, 2B, 3, 5, 6A, 6B, 7B, 7C, 7D, 9, and 12. The computing system may include or be connected with a surgical hub/surgeon display interface described here, for example with reference to FIGS. 4, 5, 6A-B, and 12. In an example, as shown in FIG. 6A, the sensing system(s) may communicate with the computing system via a communication module 230. In an example, as shown in FIG. 6B, the sensing system(s) may communicate with the computing system via a local area network (LAN).

Pre-surgical measurement data and/or in-surgical measurement data associated with one or more patient biomarkers may be obtained from the sensing system(s). For example, the computing system may obtain from the sensing system(s) measurement data associated with one or more tissue irregularity-related biomarkers, such as edema, hydration date, tissue perfusion pressure, lactate, oxygen saturation, VO2Max, respiration rate, autonomic tone, sweat rate, heart rate variability, skin conductance, GI motility, and/or the like.

A tissue irregularity complication may be predicted based on pre-surgical and/or in-surgical measurement data associated with biomarker(s) monitoring. For example, the sensing system(s) may perform the prediction based on the measurement data of tissue irregularity-related biomarker(s). For example, the computing system may determine a tissue irregularity complication based on the measurement data of tissue irregularity-related biomarker(s) and the threshold(s) associated with the biomarker(s).

One or more thresholds may be obtained for a patient biomarker. For example, the surgical computing system may determine respective threshold(s) associated with a patient's edema, hydration state, tissue perfusion pressure, lactate, oxygen saturation, VO2Max, respiration rate, autonomic tone, sweat rate, heart rate variability, skin conductance, GI motility, and/or the like. The threshold(s) may be standard threshold(s). The threshold(s) may be pre-defined and/or set by an HCP. The threshold(s) may be customized for a patient based on the patient's medical history, health information, biographical information, family health information, and/or the like. A biomarker may be monitored by comparing the measurement data related to the biomarker against the corresponding threshold(s). A potential tissue irregularity complication(s) may be detected when the measurement data related to one or more biomarkers crosses the corresponding threshold(s) for a predetermined amount of time. Crossing a threshold may include the measurement data associated with a biomarker increasing above the corresponding threshold value. Crossing the threshold may include the measurement data associated with a biomarker dropping below the corresponding threshold value. The predetermined amount of time may be used to mitigate erroneous measurement data. For example, the predetermined amount of time may reduce the number of false positive detections. The predetermined amount of time may be determined based on the one or more biomarkers being monitored.

The computing system may predict a tissue irregularity complication by determining that a probability of a water retention level crosses a threshold. The probability of an irregular water retention level may be determined (e.g., calculated) based on the biomarker measurement data, such as edema data or hydration state data.

The computing system may determine a tissue irregularity complication based on measurement data of a water retention level-related biomarker crossing the obtained threshold(s). For example, an edema sensing system (e.g., employing lower leg circumference measurements) may measure the lower leg circumference. The measured the lower leg circumference may be compared against a lower leg circumference threshold. A lower leg circumference measurement above such threshold may indicate thickened tissues. For example, a hydration state sensing system employing optical spectroscopy may measure a water retention level of the blood. The measured water retention level of the blood may be compared against a water retention level range threshold. A water retention level measurement below such range threshold may indicate stiffened tissues.

In examples, an edema severity may be determined based on an edema sensing system's measurement data described herein and/or other measurements/tests performed on a patient. For example, the computing system may determine an edema severity based on local edema, a weight change and an albumin level change. The computing system may detect a tissue irregularity complication when the determined edema severity exceeds a threshold. The weight change (e.g., increase in weight) may be obtained based on the patient's weight measurements before an impending surgical procedure and a baseline past weight. Weight data may be obtained from a patient's EMRs (e.g., hospital records) based on a weight measurement before an impending surgical procedure and a baseline past weight measurement. The albumin level change (e.g., a drop in albumin) may be obtained based on the patient's urine albumin test before an impending surgical procedure and a baseline past albumin. The albumin level data may be obtained from a patient's EMRs (e.g., other hospital records). In an example, the computing system may predict a tissue irregularity complication such as thickened tissues based on an edema sensing system's measurement data, an indication of an increase in weight, and/or a drop in albumin.

The computing system may predict a tissue irregularity complication by determining that a probability of a chronic inflammation response crosses a threshold. The probability of chronic inflammation response may be determined (e.g., calculated) based on the pre-surgical biomarker measurement data, such as tissue perfusion pressure, lactate, oxygen saturation, VO2Max, respiration rate, autonomic tone, sweat rate, heart rate variability, skin conductance, and/or GI motility data.

The computing system may determine a tissue irregularity complication based on measurement data of one or more chronic inflammation response-related biomarker(s) crossing the obtained threshold(s). For example, a tissue perfusion pressure sensing system (e.g., based on skin perfusion pressure) may measure blood volume changes to determine the skin perfusion pressure. The measured skin perfusion pressure may be compared against a skin perfusion pressure range threshold. A tissue irregularity complication may be determined when a skin perfusion pressure measurement is below such range threshold. For example, a lactate sensing system may employ electrochemical biosensors to measure sweat lactate levels. The measured sweat lactate level may be compared against a sweat lactate level range threshold. A tissue irregularity complication may be determined when a sweat lactate level measurement is above such range threshold. For example, a peripheral capillary oxygen saturation (SpO2) may be calculated as a ratio of pulsed signal to non-pulsed signal. The measured SpO2 may be compared against an SpO2 range threshold. A tissue irregularity complication may be determined when a SpO2 measurement is above such range threshold. For example, VO2Max measures the body's oxygen consumption ability. The measured VO2Max score may be compared against a VO2Max score threshold. A tissue irregularity complication may be determined when a SpO2 measurement is above such score threshold. For example, a respiration rate may measure the number of breaths per minute. The measured respiration rate may be compared against a respiration rate range threshold. A tissue irregularity complication may be determined when a respiration rate measurement is above such range threshold. For example, a heart rate variability score measured by a heart rate sensing system may be compared against a heart rate variability score range threshold. A tissue irregularity complication may be determined when a respiration rate measurement is above such range threshold. For example, a sweat rate measured by a sweat rate sensing system may be compared against a sweat rate range threshold. A tissue irregularity complication may be determined when a sweat rate measurement is above such range threshold and hence indicates high sympathetic activity. For example, a skin conductance level (SCL) measured by a skin conductance sensing system may be compared against a SCL range threshold. A tissue irregularity complication may be determined when a SCL measurement is above such range threshold and hence indicates high sympathetic activity. For example, an autonomic tone sensing system may be configured to employ a heart rate variability sensing sub-system, a sweat rate sensing sub-system, and/or a skin conductance sensing sub-system. A tissue irregularity complication may be determined by an autonomic tone sensing system when a tissue irregularity complication is determined by one or more such sub-systems. For example, a GI motility sensing system employing a wireless non-digestible capsule may measure gastric, small bowel, large bowel, and/or colonic transit times. The measured gastric transit time, small bowel transit time, large bowel transit time, and/or colonic transit time may be compared against a gastric transit time range threshold, a small bowel transit time range threshold, a large bowel transit time range threshold, and/or a colonic transit time range threshold, respectively. A reduced GI motility may be determined when one or more of such transit times are above their respective transmit time range threshold. Accordingly, a tissue irregularity complication may be determined based on the determination of reduced GI motility. For example, a reduced GI motility may be determined when an autonomic tone-related biomarker (e.g., heart rate variability, sweat rate, or skin conductance) is determined to indicate high sympathetic activity. Accordingly, a tissue irregularity complication may be determined based on the determination of the high sympathetic activity indication.

The determination of a tissue irregularity may be based on the pre-surgical and/or in-surgical tissue irregularity biomarker measurement data preprocessed by the sensing systems. For example, a hydration state sensing system (e.g., implemented using optical spectroscopy) may monitor a patient's water content level in the blood via continuous measurements. When the hydration state sensing system transmits the hydration state measurement data, the sensing system may calculate the mean of the measurements and transmit such mean to the computing system. The sensing system may calculate the mean of the measurements excluding outlier measurements and transmit such mean. The sensing system may calculate the mean of the measurements and standard deviation of the measurement data set, and transmit the mean and the standard deviation. The sensing system may calculate an average of the highest measurement and the lowest measurement and transmit such average. The sensing system may identify the highest measurement and the lowest measurement and transmit such measurement range. The sensing system may identify the highest measurement and the lowest measurement after excluding outlier measurements and transmit such measurement range. The sensing system may convert the preprocessed water content level measurement data to hydration state classifications, such as "well hydrated", "mildly dehydrated", or "severely dehydrated", and transmit such classifications to the computing system. The hydration state sensing system may transmit to the computing system identifiers for such classifications, e.g., "WH", "MD", "SD" for "well hydrated", "mildly dehydrated", or "severely dehydrated", respectively. Those of skill in the art will recognize other sensing systems described herein may also preprocess the biomarker measurement data and then transmit the preprocessed biomarker measurement data to the computing system as described.

The determination of a tissue irregularity may be based on the tissue irregularity biomarker measurement data as captured by the sensing systems (e.g., raw measurements). The computing system may process the raw measurements before making the determination. For example, a hydration state sensing system (e.g., implemented using optical spectroscopy) may monitor a patient's water content level in the blood via continuous measurements. The hydration state sensing system may transmit the raw measurements to the computing system. In response, the computing system may process the raw measurements as described in how the hydration state sensing system preprocesses the hydration state measurement data described herein. Those of skill in the art will recognize other sensing systems described herein may transmit raw measurements to the computing system, and in response the computing system may process the raw measurements as described.

The computing system may determine a tissue irregularity complication associated with a pulmonary procedure based on the measurement data of a patient's pulmonary function. The pre-surgical measurement may be performed on the patient before an impending pulmonary procedure (e.g., in a clinical setting, such as in an operating room). In an example, forced expiratory volume in 1 second (FEV1) test may be performed. The measurement data may be entered into the computing system (e.g., via a user interface). The measurement data may be entered into a hospital record system (e.g., an EMR system) and obtained by the computing system. The computing system may determine a tissue irregularity complication on the condition that the FEV1 measurement is below a FEV1 threshold and hence indicates the presence and/or the severity of a restrictive or obstructive pulmonary disease (e.g., emphysema). In an example, forced vital capacity (FVC) test may be performed. The measurement data may be entered into the computing system. The measurement data may be entered into a hospital record system (e.g., an EMR system) and obtained by the computing system. The computing system may determine a tissue irregularity complication on the condition that a pulmonary function metric crosses a threshold. In an example, the computing system may determine a tissue irregularity complication on the condition that FVC measurement is below a FVC threshold and hence indicates the presence and/or the severity of a restrictive or obstructive pulmonary disease. In an example, the computing system may determine a tissue irregularity complication on the condition that a ratio of the FEV1 measurement over the FVC measurement is below a FEV1/FVC ratio threshold and hence may indicate the presence and/or the severity of a restrictive or obstructive pulmonary disease. In an example, a spirometry test may be performed. The measurement data may be entered into the computing system. The measurement data may be entered into a hospital record system (e.g., an EMR system) and obtained by the computing system. The computing system may determine a tissue irregularity complication on the condition that a spirometry test result is below a threshold.

The computing system may determine a tissue irregularity based on the tissue irregularity biomarker measurement data received from the sensing systems described herein ("sensed biomarker data") and patient-related medical data. For example, the computing system may determine a tissue to be highly variable in thickness based on the sensed biomarker data and a patient's diseases state(s) data and/or medical condition(s) data obtained from the patient's EMRs or other hospital records. In an example, a determination of a thickened and/or stiffened tissue based on the sensed biomarker data may indicate a disease state such as a chronic obstructive pulmonary disease (e.g., emphysema). The computing system may determine the tissue to be highly variable in thickness on the condition that the patient's EMRs (or other hospital records) indicate one or more of the following: adhesions from a prior surgical procedure, a present infection (e.g., pneumonia or the like), a chronic lung disease (e.g., an interstitial lung disease), or the like. The computing system may determine a higher likelihood of post-operative air leaks on such above condition. Further, the computing system may provide such indication of a higher likelihood of post-operative air leaks to a post-operative chest tube management control program.

The computing system may generate an output based on the predicted tissue irregularity complication. The output may include a control signal configured to alter an operational parameter associated with a surgical device. For example, the computing system may generate one or more adjustments to an impending surgical procedure. The adjustment may include, but not limited to, an adjustment to a surgical instrument's control program, an adjustment to a surgical instrument's reload, adding an adjunct, and/or an indication of a probability of a tissue irregularity complication. An indication of a probability of tissue irregularity complication may be or may include a notification of a tissue irregularity complication in a surgical procedure plan. Such notification may include highlighting an affected area associated with the predicted tissue irregularity complication, enlarging a mobilization planned area, and/or displaying an improved access option.

An impending surgical procedure may include planned procedure steps that may be stored and retrieved, or otherwise accessed on a computing device (e.g., the surgical hub 206 or 5104). For example, a list of planned procedure steps for a thoracic procedure (specifically, a lung segmentectomy procedure) may be retrieved or accessed.

Planned surgical instruments' (as shown in FIGS. 1A, 2A, 3, 4, 5, 6A, 7A, 8, 9, 10, and 12) identification information may be obtained via a computing device (e.g., the surgical hub 206 or 5104). For example, planned surgical instruments' identification information may be obtained based on planned procedure steps and the associated surgical instruments information. For example, as described in FIG. 14, planned procedure steps of a colorectal procedure (e.g., access 206580, dissection 206582, transection 206584, anastomosis 206586, and closing 206588) may be retrieved from a surgical hub (e.g., the surgical hub 206 or 5104). A list of planned surgical instruments (e.g., trocar 206581, energy device 206583, linear surgical stapler 206585, and circular surgical stapler 206587) associated with the planned procedure steps may be retrieved from the surgical hub. Usage of planned surgical instruments at planned procedure steps may be detected and confirmed by the surgical hub (e.g., the surgical hub 206 or 5104). For example, activation instances 206592 illustrate the expected usage of trocar 206581 at planned procedure steps access 206580 and closing 206588. For example, activation instances 206590 illustrate the expected usage of energy device 206584 at planned procedure steps access 206580, dissection 206582, and transection 206584. For example, activation instance 206594 illustrates the expected usage of linear surgical stapler 206585 at planned procedure step transection 206584. For example, activation instance 206596 illustrates the expected usage of circular surgical stapler 206587 at planned procedure step anastomosis 206586.

Based on the predicted tissue irregularity complication, a control signal configured to alter an operational parameter associated with a surgical device may be determined and generated as an output. The control signal may adjust control program of a surgical instrument. The control signal may be configured to update an operational parameter, such as an operating parameter, a surgical parameter, or the like of the control program associated with a surgical instrument (e.g., during an activation instance).

For example, as described in FIG. 13, a computing system (e.g., the surgical hub 206 or 5104) may adjust operational parameters (e.g., energy level) of a control program of an energy device 206583. The control program of an energy device may include adjustable operational parameters, such as a power level for tissue separation, a power application duration for tissue separation, a power level for tissue sealing/coagulation, and/or a power application duration for tissue sealing/coagulation. The control program of an energy device may include an adjustable operational parameter, such as an ultrasonic blade's energy generation threshold for a subsequent energy application phase. In examples, an ultrasonic blade's energy generation threshold for a subsequent energy application phase may be a desired resonant frequency threshold for starting a tissue coagulation phase or an ultrasonic blade's desired resonant frequency threshold for starting a tissue transection phase.

Based on the predicted tissue irregularity complication, the computing system may generate a control signal configured to alter an energy device's operational parameter(s) at one or more procedure steps. Such alteration(s) may be due to a higher energy level and/or longer energy application duration needed for tissue transection and/or tissue coagulation. For example, based on predicted thickened and/or stiffened tissue, the control signal may alter an energy device's operational parameter at a dissection step of a colorectal procedure. The control signal may increase an energy level for tissue separation, increase an energy level for tissue sealing and/or transection, increase an energy application duration for tissue separation, increase an ultrasonic blade's desired resonant frequency threshold for starting a tissue coagulation phase, and/or increase an ultrasonic blade's desired resonant frequency threshold for a tissue transection phase.

Based on the predicted tissue irregularity complication, the computing system may generate a control signal configured to alter one or more operational parameters associated with a surgical stapling device at one or more procedure steps. For example, as described in FIG. 13, the computing system may update operational parameters (e.g., compression rate or load thresholds) of a control program of a surgical stapling and cutting instrument (e.g., 206585 or 206587). In an example, upon detecting a tissue irregularity, a control signal may be generated to adjust one or more closure parameters associated with a surgical stapling and cutting instrument, such as closure force (e.g., force-to-close (FTC) or closure compression force), closure velocity (e.g., closure rate or clamping speed), and/or tissue creep wait time (e.g., wait time before stapling). In an example, upon detecting a tissue irregularity, a control signal may be generated to adjust one or more firing parameters associated with a surgical stapling and cutting instrument, such as firing speed and/or viable staple height range.

The computing system may update a stapling and cutting instrument's control program operational parameter(s) at one or more procedure steps based on the predicted tissue irregularity complication. Such updates(s) may be due to a reduced compressibility and/or increased tissue impedance of thickened and/stiffened tissues. For example, the computing system may update the stapling and cutting instrument's (e.g., a linear stapler) control program to reduce the closure rate, prolong the tissue creep wait time (e.g., wait time before stapling), and/or reduce the firing speed associated with a transection step of a colorectal procedure. For example, the computing system may update the control program of a circular stapler to reduce the closure rate, increase the tissue creep wait time, and/or reduce the firing speed at an anastomosis step of a colorectal procedure. To form taller staples, the computing system may shift upward the viable staple height range of the circular surgical stapler.

Based on the predicted tissue irregularity complication, the computing system may generate a control signal configured to indicate a suggestion for changing a surgical instrument's reload. For example, a suggestion for changing a surgical instrument's reload may include changing a cartridge to be used for a linear surgical stapler in a transection step (e.g., in a colorectal procedure). In an example, to form taller staples to compensate for a predicted thickened and/or stiffened tissue, a cartridge including taller staples may be suggested. In an example, for a tissue predicted to be highly variable in thickness, a cartridge that compensates for such tissue may be suggested. For example, a cartridge with a gripping surface to minimize tissue slippage due to a highly variable tissue thickness (e.g., Echelon™ Gripping Surface Technology (GST)) may be suggested to replace a cartridge with a smooth surface (e.g., Echelon Endopath™ (ECR). For example, a cartridge including rows of staples with graduated staple heights (e.g., Endo GIA™ Tri-Staple™ technology) may be suggested to replace a cartridge including rows of staple with uniform staple heights (e.g., Endo GIA™). In an example, for a tissue predicted to be highly variable in thickness, a tissue thickness compensator may be suggested to be used with a general-purpose cartridge. Additional details are disclosed in U.S. Patent. No. U.S. Pat. No. 9,700,317, titled FASTENER CARTRIDGE COMPRISING A RELEASABLE TISSUE THICKNESS COMPENSATOR, issued Jul. 11, 2017 and U.S. Patent No. U.S. Pat. No. 8,864,009, titled TISSUE THICKNESS COMPENSATOR FOR A SURGICAL STAPLER COMPRISING AN ADJUSTABLE ANVIL, issued Oct. 21, 2014, which are herein incorporated by reference in their entirety.

Based on the predicted tissue irregularity complication, the computing system may generate a control signal configured to indicate a suggestion for adding an adjunct at one or more procedure steps. For example, the computing system may generate a control signal configured to indicate a suggestion for adding an adjunct for a transection step. In an example, a suggestion may be made to use a buttress (e.g., an absorbable or permanent buttress) to supplement a surgical stapler to increase staple line strength and hence reduce staple line leaks (e.g., when a tissue to be operated on is predicted to be highly variable in thickness). In an example, a suggestion may be made to use a lung sealant prophylactically in a lung segmentectomy procedure after transection is complete at a transection step to prevent prolonged post-operative air leaks (e.g., when a tissue to be operated on is predicted to be highly variable in thickness).

Suggestions described herein may be provided via a user interface a surgeon interacts with ("surgeon interface"), such as a surgical planning interface, a surgeon interface/console, surgical hub display 215 illustrated in FIG. 5, and/or a surgical device having a display. The suggestions may be generated by a computing system (e.g., the surgical hub 206 or 5104) and sent to the surgeon interface. A suggestion message may be displayed in a designated area on the surgeon interface, such as a suggestion overlay or a suggestion box at the bottom right corner of the surgeon interface.

Based on the predicted tissue irregularity complication, the computing system may generate a control signal configured to indicate a probability of the predicted tissue irregularity complication. The indication may be or may include a notification of predicted tissue irregularity complication.

For example, a notification of a tissue irregularity complication may be displayed in a surgical procedure plan on a surgical planning interface. In an example, the notification may be displayed as highlight(s) of affected area(s) associated with the tissue irregularity complication in a surgical procedure plan. The surgical plan may be based on the pre-surgery imaging (e.g., 2-D or 3-D ultrasound image(s) of a target surgical site and a surrounding area. Highlight(s) of potentially affected area(s) may be at the location(s) of the predicted tissue irregularity complication. The location(s) of the predicted tissue irregularity complications may be based on the pre-surgery imaging data from a patient's EMR data, such as location(s) of infection(s) (e.g., pneumonia) and/or interstitial lung disease. In an example, the notification may be displayed as enlarged mobilization area in the surgical plan to include working space potentially needed to work around the predicted tissue irregularity complication. Such enlarging of mobilization area may be based on increasing a pre-defined margin parameter's value to a higher threshold. In an example, the notification may be displayed as improved access option(s) during a dissection step in the surgical plan. Such improved access option(s) may be different trajector (ies) (e.g., path(s)) of a dissection instrument generated based on the patient's anatomical structure around the location of predicted potential thickened/stiffened tissue and/or adhesions from a prior surgery. Suggestion(s) described herein may be displayed in the surgical procedure plan.

For example, a notification of a tissue irregularity complication may be displayed as an overlay on top of pre-surgery imaging rendered on the surgeon interface.

For example, a notification of a tissue irregularity complication may be presented as an augmented reality (AR) or mixed reality overlay on the surgeon interface that may be interrogated. An AR device may provide AR content to a user. For example, the AR content may be the virtual anatomy of the target surgical site and its surrounding area generated based on pre-surgery imaging. The tissue irregularity complication(s) may be marked (e.g., highlighted, circled, and/annotated) in the virtual anatomy. For example, a visual AR device, such as safety glasses with an AR display, AR goggles, or head-mounted display (HMD), may include a graphics processor for rendering 2D or 3D video and/imaging for display. AR content may be overlaid onto the various displays described herein. For example, an audible AR device, such as an earbud, a headset, a headphone, or a speaker, may provide audible AR content. The audible AR device may provide auditory overlay, for example, in addition to hearing OR sounds. Audible overlay may be provided via an earbud set with pass through noise capabilities and/or via a bone conduction speaker system. The AR device may communicate certain information only to the targeted individual within the OR that could utilize the information. The AR device may include a processor, a non-transitory computer readable memory storage medium, and executable instructions contained within the storage medium that are executable by the processor to carry out methods or portions of methods disclosed herein. Examples of visual and audio AR devices can be found in more detail in U.S. patent application Ser. No. 17/062,509, titled INTERACTIVE INFORMATION OVERLAY ON MULTIPLE SURGICAL DISPLAYS, which was filed on Oct. 2, 2020, which is herein incorporated by reference in its entirety. Examples of visual and audio AR devices can be found in more detail are described in a patent application titled AUDIO AUGMENTED REALITY CUES TO FOCUS ON AUDIBLE INFORMATION, filed contemporaneously, which is herein incorporated by reference in its entirety.

Figure 45:
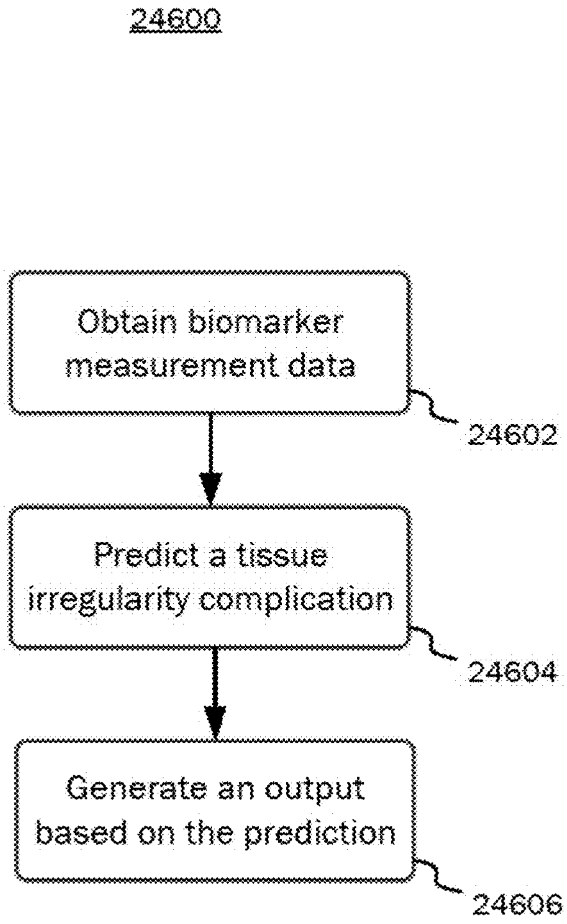
FIG. 45 illustrates an example process of predicting a tissue irregularity complication.

FIG. 45 illustrates an example process 24600 of predicting a tissue irregularity complication. The process may include a computer-implemented process. For example, a computing system may perform the process illustrated in FIG. 45. For example, a sensing system described herein may perform the process illustrated in FIG. 45.

At 24602, measurement data associated with one or more patient biomarkers may be obtained via one or more sensing systems. Measurement data may include measurement data obtained prior to a surgery, and/or biomarker measurements taken during a surgery. Pre-surgical measurements may be combined with in-surgical measurements. The patient biomarker(s) may include one or more of the following: tissue perfusion pressure, lactate, oxygen saturation, VO2Max, respiration rate, autonomic tone, sweat rate, heart rate variability, skin conductance, GI motility, edema or hydration state.

At 24604, a tissue irregularity complication may be predicted based on the biomarker measurement data associated with the one or more patient biomarkers. The tissue irregularity complication may be predicted based on pre-surgical measurement data, in-surgical measurement data, or a combination of pre-surgical measurement data, in-surgical measurement data.

For example, the computing system may determine a probability of a chronic inflammation response based on measurement data associated with the one or more of: tissue perfusion pressure, lactate, oxygen saturation, VO2Max, respiration rate, autonomic tone, sweat rate, heart rate variability, skin conductance, or GI motility. On the condition that the probability of a chronic inflammation response crosses a threshold, the computing system may predict a tissue irregularity complication.

The computing system may determine a probability of an irregular water retention level based on measurement data associated with the one or more of: edema or hydration state. On the condition that the probability of an irregular water retention level crosses a threshold, the computing system may predict a tissue irregularity complication.

At 24606, an output associated with a surgical procedure may be generated based on the predicted tissue irregularity complication. For example, a control signal configured to alter an operational parameter associated with a surgical device may be generated. For example, the control signal may control a surgical cutting and stapling device (e.g., a linear stapler or a circular stapler) to perform prolonging a tissue creep wait time prior to stapling, reducing a clamping speed, reducing a stapler firing speed, increasing a closure compression force, and/or shifting upward a viable staple height range. The control signal may be configured to control a surgical energy device to perform increasing an energy level, increasing an energy application duration, and/or increasing a threshold for an energy generation associated with a subsequent energy application. The control signal may be configured to perform displaying a probability of a tissue irregularity complication on a pre-surgery imaging, displaying a probability of a tissue irregularity complication via an augmented reality device, and/or displaying a probability of a tissue irregularity complication in a surgical procedure plan along with an indication of an adjustment to the surgical procedure plan. The output may be generated by a sensing system to indicate the predicted tissue irregularity complication.

Systems and techniques are disclosed for predicting a hemostasis-related complication based on measurements of related biomarker(s), and generating an adjustment of a surgical parameter associated with a surgery. For example, a hemostasis-related complication may be predicted by a computing device based on biomarker measurements of hemostasis-related biomarker(s) obtained before and/or during a surgery via one or more sensing systems. The hemostasis-related biomarker(s) measured pre-surgery and/or in-surgery for predicting a hemostasis-related complication may be or may include blood pressure, blood pH, edema, heart rate, blood perfusion rate, coagulation status and/or the like.

For example, the computing system may generate a control signal configured to alter a matter in which a surgical cutting and stapling device operates, to alter a matter in which an energy device operates, to adjust a surgical procedure plan, to adjust to a surgical instrument selection, indicate a probability of the hemostasis complication, and/or to indicate a suggested adjustment to surgical procedure plan, surgical approach, and/or surgical instrument selection.

A likelihood of clotting event associated with hemostasis complications may be predicted based on monitoring of patient biomarker(s). A likelihood of profusion rate associated with hemostasis complications may be predicted based on monitoring of patient biomarker(s). A hemostasis complication may be predicted based on the likelihood of clotting event associated with hemostasis complications and/or the likelihood of profusion rate associated with hemostasis complications. Upon predicting a hemostasis-related complication, surgical plan, choice of tools, and post-operational care may be adjusted based on the prediction. For example, devices, cartridges, and/or adjuncts that may have superior capabilities in creating hemostasis, may be suggested by the computing system.

The computing system, upon predicting a hemostasis complication may alter update the control program of an energy device to adjust power levels, adjust the time before transition point based on tissue impendence tracking, increase jaw compression, and/or instituting longer wait times between events, etc.

The computing system, upon predicting a hemostasis complication may update the control program of a surgical cutting and stapling device to increase pre-deployment compression, to slow firing actuator speed, to combine pauses in the advancement of actuators and/or to adjust viable staple height zones. For example, the control program may be updated to reduce the viable staple height zones for tighter staple form.

A computing system may predict a complication based on measurements of related biomarker(s) obtained via one or more sensing systems, and generate an adjustment of a surgical parameter associated with a surgery. The biomarker measurements may include pre-surgical and/or in-surigical measurements. The hemostasis-related biomarker(s) measured pre-surgery may include blood pressure, blood pH, edema, heart rate, blood perfusion rate, coagulation status and/or the like. Based on the prediction, the computing system may generate a control signal configured to alter a matter in which a surgical cutting and stapling device and/or a surgical energy operate, to adjust a surgical procedure plan, to adjust to a surgical instrument selection, indicate a probability of the hemostasis complication, and/or to indicate a suggested adjustment to surgical procedure plan, surgical approach, and/or surgical instrument selection.

Hemostasis issues may lead to complications in a surgical procedure. For example, blood clotting impacts or related hemostasis issues may lead to post-transection bleeding. Blood clotting impacts or related hemostasis issues may impact the intensity in surgery. Bleeding risk may be predicted based on blood clotting ability. Prediction of blood clotting impacts or related hemostasis issues may be used to reduce post-transection bleeding, reduce time in surgery, reduce blood loss, and/or reduce post-surgical complication(s).

A hemostasis complication may be predicted based on pre-surgical and/or in-surgical measurements of related biomarker(s). For example, a hemostasis complication may be determined based on one or more biomarkers related to blood clotting ability, such as blood pressure, blood pH, edema, heart rate and/or the like. Reduced blood clotting ability may be determined based on low fibrinogen content. Biomarkers related to hemostasis may include blood pressure, blood pH, edema, heart rate, blood perfusion rate, blood coagulation status, and/or the like.

The probability of clotting events and perfusion rates that may increase the likelihood of bleeding events or intensity in surgery may be determined based on pre-surgical monitoring of patient biomarker(s). If the probability of bleeding events exceeds a threshold, surgical plan, choice of tools, and post-op care may be adjusted towards devices, cartridges, and adjuncts that would have superior capabilities in creating hemostasis.

FIG. 4 (A illustrates example process 24700 of predicting a hemostasis complication. The process 24700 may be performed by a computing system, such as the computing system described herein with reference to FIG. 4. The computing system may be or may include a surgical hub described herein, for example with reference to FIGS. 1A, 2A-B, 3, 5, 6A-B, 7B-D, 9, and 12. The computing system may include or be connected with a surgical hub/surgeon display interface described here, for example with reference to FIGS. 4, 5, 6A-B, and 12. The process 24700 shown in FIG. 46A may be performed by a sensing system described herein with reference to FIGS. 1A-B, 2A-C, 3, 4, 5, 6A-C, 7B-D, 9, 11A-D, and 12.

At 24702, pre-surgical and/or in-surgical measurement data associated with one or more patient biomarkers may be obtained via one or more sensing systems. For example, one or more sensing system(s) described herein with reference to FIG. 1B may perform biomarker measurements before a surgery and may send the pre-surgical and/or in-surgical measurement data to the computing system. The computing system may retrieve pre-surgical and/or in-surgical measurement data from the sensing system(s). For example, biomarkers measured for predicting a potential hemostasis complication in an upcoming surgery may include biomarkers related to blood clotting capacity, such as blood pressure, blood pH, edema, heart rate, blood perfusion, blood coagulation status and/or the like.

A patient's blood coagulation status may be measured via a coagulation sensing system. For example, an optical system may measure the coagulation status of patients in vivo in a non-invasive manner. The coagulation sensing system may be based on a small optical sensor that may emit coherent light into the skin and collect the reflected light from the red blood cells in the blood vessels in the skin under the sensor. The sensor may be placed on the fingertip, and during a brief period of occlusion of blood flow by a small pneumatic cuff, red cell movement becomes Brownian in nature and may thereby be affected by the viscosity of the blood. In patients who have a bleeding tendency, red blood cell movement may be faster, while in patients with a hypercoagulable state the red cell movement may be slower.

Figure 46A:
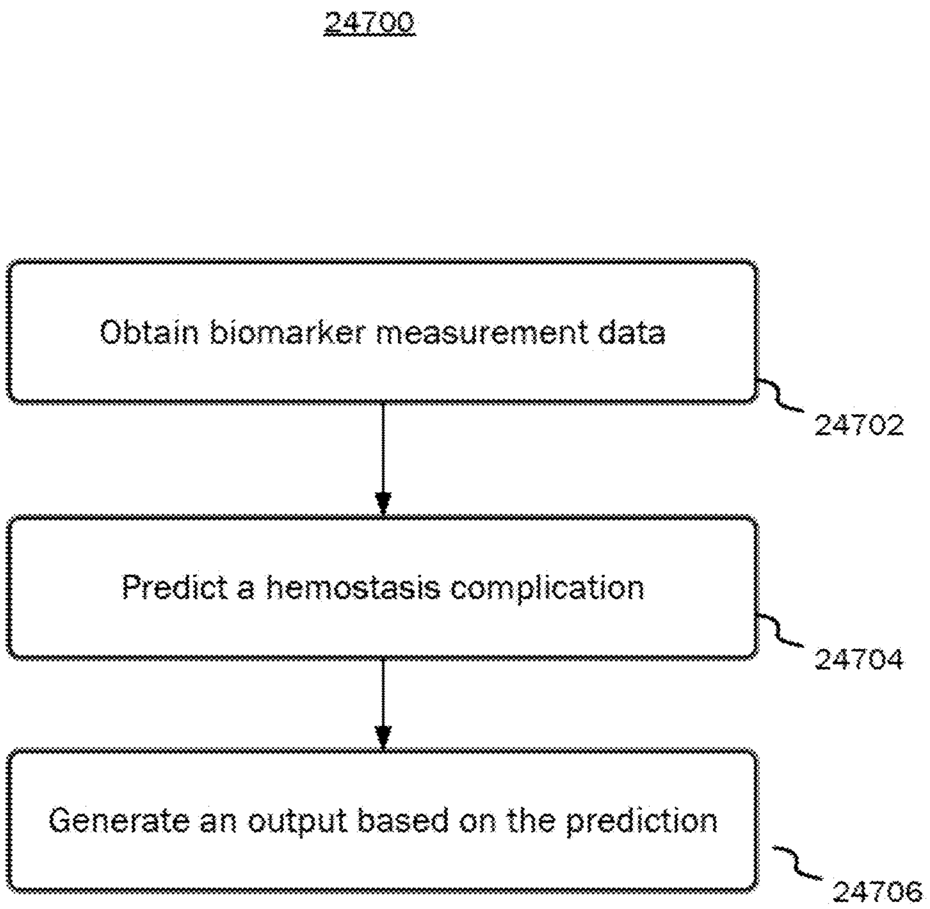
FIG. 46A illustrates example process of predicting a hemostasis complication.

As shown in FIG. 46A, at 24704, the computing system may predict a hemostasis complication based on the measurement data associated with the one or more patient biomarkers. Considering measurements for multiple biomarkers may improve the accuracy of complication prediction. The computing system may determine a probability of potential bleeding, oozing, and/or weeping from mobilization or transection based on the measurement data. The computing system may determine a probability of potential clot formation based on the biomarker measurement data.

A probability of potential bleeding events for a patient may be calculated based on the pre-surgical measurement data associated with one or more hemostasis-related biomarker(s). A bleeding event probability threshold may be obtained and compared against the calculated probability of potential bleeding events. Based on the probability of bleeding events exceeding the bleeding event probability threshold, a hemostasis complication may be predicted.

A probability of potential clotting events for a patient may be calculated based on the biomarker measurement data associated with the hemostasis-related biomarker(s). A clotting event probability threshold may be obtained and compared against the calculated probability of potential clotting events. Based on the probability of clotting events exceeding the clotting event probability threshold, a hemostasis complication may be predicted.

The thresholds described herein, such as the bleeding event probability threshold, the clotting event probability threshold, high blood pressure threshold, low blood pressure threshold, blood pH threshold and/or the thresholds associated with hemostasis-related biomarkers described herein may be pre-defined and/or set by an HCP. The threshold(s) may be customized for a patient based on the patient's medical history, health information, biographical information, family health information, and/or the like.

A biomarker may be monitored by comparing the measurement data related to the biomarker against the corresponding threshold(s). A biomarker threshold may be determined based on expected biomarker values, benchmark biomarker values, and/or the like. For example, a computing system and/or sensing system may determine a threshold associated with a patient's blood pressure. For example, a composite threshold may be used when multiple biomarkers are measured for complication prediction. A composite threshold may be associated with a combined value of multiple biomarkers, e.g., a patient's blood pressure, blood pH, edema, heart rate, blood perfusion, and/or blood coagulation status. The threshold may be adjusted based on measurement data received from one or more environmental sensing systems, for example, a video feed and/or a thermometer feed.

Measurement data associated with more than one biomarker may be combined into composite measurement data. For example, the computing system and/or sensing system may combine measurement data associated with a patient's blood pressure with measurement data associated with a patient's blood pH. The computing system and/or sensing system may compare this composite measurement data with a composite threshold. The measurement data associated with a biomarker may be associated with a biomarker weight. For example, the measurement data associated with a patient's blood pH may have a greater biomarker weight than the measurement data associated with a patient's heart rate. The computing system and/or sensing system may consider the biomarker weight(s) when predicting a potential complication. For example, the computing system and/or sensing system may be more likely to predict a complication when measurement data associated with high biomarker weight(s) crosses the corresponding threshold(s) compared to when measurement data associated with low biomarker weight(s) crosses the corresponding threshold(s). The computing system and/or sensing system may assign the biomarker weight(s). The biomarker weight(s) may be dynamic and adjusted based on the measurement data of another biomarker. The biomarker weight(s) may be selected by a healthcare provider overseeing the patient. For example, the healthcare provider may assign a high biomarker weight for a patient's blood pH and a low weight for a patient's blood pressure. The healthcare provider may adjust the one or more biomarker weights based on the medication that the patient intakes.

A potential hemostasis complication may be detected when the measurement data related to one or more biomarkers crosses the corresponding threshold(s) for a predetermined amount of time. Crossing a threshold may include the measurement data associated with a biomarker increasing above the corresponding threshold value. Crossing the threshold may include the measurement data associated with a biomarker dropping below the corresponding threshold value. The predetermined amount of time may be used to mitigate erroneous measurement data. For example, the predetermined amount of time may reduce the number of false positive detections. The predetermined amount of time may be determined based on the one or more biomarkers being monitored.

For example, a hemostasis complication may be predicted based on (e.g., in part on) pre-surgical and/or in-surgical measurement data for blood pressure. The computing system may predict a hemostasis complication, such as a potential bleeding event, based on measurements of blood pressure indicating high blood pressure. High blood pressure may be a symptom of thick blood, which may be associated with increased blood clotting ability. The computing system may predict a hemostasis complication, such as a potential clotting event, based on measurements of blood pressure indicating high blood pressure (e.g., exceeding a blood pressure threshold). Low blood pressure could be a risk factor for blood clotting. For example, if the heart cannot pump enough blood to meet the body's needs, slow blood flow may cause clots to form. The computing system may predict a hemostasis complication, such as a potential clotting event, based on measurements indicating low blood pressure (e.g., falling below a low blood pressure threshold). A blood pressure sensing system, as described herein, may measure blood pressure data.

For example, a hemostasis complication may be predicted based on (e.g., in part on) pre-surgical and/or in-surgical measurement data for blood ph. The computing system may predict a hemostasis complication, such as a potential bleeding event, based on measurements of blood pH indicating acidic blood (e.g., falling below a pH threshold). Acidic blood may reduce blood clotting capacity by inhibiting thrombin generation. For example, the pH sensing system may predict internal bleeding based on pre-operation acidic blood pH. A potential of hydrogen (pH) sensing system, as described herein, may measure pH data including blood pH.

For example, a hemostasis complication may be determined based on (e.g., in part on) pre-surgical and/or in-surgical measurement data for edema. Edema is swelling caused by water content of the blood flow leaking into tissues and becoming trapped in tissues. Swelling in tissues may be associated with an increased blood clotting ability, such as an irregular hyper ability to clot. The computing system may predict a hemostasis complication, such as a potential clotting event, based on measurements indicating edema.

For example, a hemostasis or bleeding complication may be determined based on (e.g., in part on) pre-surgical and/or in-surgical measurement data for heart rate. Excessive blood clotting, or hypercoagulation may be predicted based on heart rate data. Low heart rate could be a risk factor for blood clotting. For example, if heart rate data indicates that the heart cannot pump enough blood to meet the body's needs, slow blood flow may cause clots to form. The computing system may predict a hemostasis complication, such as a potential clotting event, based on measurements indicating low heart rate.

For example, a hemostasis complication may be predicted based on (e.g., in part on) pre-surgical and/or in-surgical measurement data for blood perfusion. The computing system may predict a hemostasis complication, such as a potential bleeding event, based on measurements of blood perfusion. Blood perfusion may be measured using one or more sensing system(s) described herein. Details on measuring blood perfusion can be found in patent application titled PREDICTION OF BLOOD PERFUSION DIFFICULTIES BASED ON PRE-SURGERY MONITORING, which is herein incorporated by reference in its entirety.

The computing system may consider physical activity measurement data received from a physical activity sensing system when processing measurement data of hemostasis-related biomarkers. For example, the computing system may receive heart rate variability measurement data from a heart rate variability sensing system and physical activity measurement data from a physical activity sensing system. In an example, the physical activity measurement data may be received from a sensing system employing an accelerometer. The received physical activity measurement data may indicate it is within the thresholds of a vigorous physical activity. In such case, the computing system may discard the heart rate variability data measured during the same period of the vigorous physical activity to ensure the heart rate variability data is measured at rest and is hence accurate. Those of skill in the art will recognize to consider physical activity measurement data as described when processing other hemostasis-related biomarkers.

The determination of a hemostasis complication may be based on the pre-surgical hemostasis-related biomarker measurement data preprocessed by the sensing systems. For example, a blood pressure sensing system may monitor a patient's blood pressure (e.g., via continuous, periodic measurements). When the blood pressure sensing system transmits the blood pressure measurement data, the sensing system may calculate the mean of the measurements and transmit such mean to the computing system. The sensing system may calculate the mean of the measurements excluding outlier measurements and transmit such mean. The sensing system may calculate the mean of the measurements and standard deviation of the measurement data set, and transmit the mean and the standard deviation. The sensing system may calculate an average of the highest measurement and the lowest measurement and transmit such average. The sensing system may identify the highest measurement and the lowest measurement and transmit such measurement range. The sensing system may identify the highest measurement and the lowest measurement after excluding outlier measurements and transmit such measurement range. The sensing system may convert the preprocessed water content level measurement data to blood pressure classifications, such as "high", "moderate", "low", or "severely low", and transmit such classifications to the computing system. The heart rate sensing system may transmit to the computing system identifiers for such classifications, e.g., "H", "M", "L", and "SL" for "high", "moderate", "low", and "severely low", respectively. Those of skill in the art will recognize other sensing systems described herein may also preprocess the biomarker measurement data and transmit the preprocessed biomarker measurement data to the computing system as described.

The determination of a hemostasis complication may be based on the pre-surgical and/or in-surgical hemostasis-related biomarker measurement data as captured by the sensing systems (e.g., raw measurements). The computing system may process the raw measurements before making the determination. For example, a blood pressure sensing system may transmit the raw measurements to the computing system. In response, the computing system may process the raw measurements as described in how the blood pressure sensing system preprocesses the blood pressure measurement data. Those of skill in the art will recognize other sensing systems described herein may transmit raw measurements to the computing system and in response the computing system may process the raw measurements as described.

The computing system may determine a hemostasis complication based on pre-surgical and/or in-surgical biomarker data obtained from tests performed on a patient.

Prescription anticoagulation medications can safely and effectively prevent blood clots. A side effect or complication associated with anticoagulation medications is bleeding. The computing system may detect that the patient's use of anticoagulation medication based on the biomarker measurements. In an example, the computing system may receive an indication of the patient's use of anticoagulation medication. The computing system may calculate the probability of clotting event and/or the probability of bleeding event based on the patient's use of anticoagulation medication in addition to the biomarker measurements obtained via the sensing system(s).

At 24706, an output may be generated based on the predicted hemostasis complication. The generated output may include a control signal configured to adjust a surgical parameter associated with a surgery for mitigating the predicted hemostasis complication. The generated output may include a control signal configured to display a probability of a hemostasis complication on a pre-surgery imaging, display a probability of a hemostasis complication via an augmented reality device, and/or display a probability of a hemostasis complication in a surgical procedure plan along with an indication of an adjustment to the surgical procedure plan. The generated output may include a control signal configured to change a surgical parameter associated with a surgical device for mitigating the predicted hemostasis complication, and to display the change to the surgical parameter (e.g., via a display associated with the surgical device).

For example, the sensing system may generate an indication of the predicted hemostasis complication. For example, the computing system may generate a control signal configured to alter a matter in which a surgical cutting and stapling device operates, to alter a matter in which an energy device operates, to adjust a surgical procedure plan, to adjust to a surgical instrument selection, indicate a probability of the hemostasis complication, and/or to indicate a suggested adjustment to surgical procedure plan, surgical approach, and/or surgical instrument selection. For example, the computing system may generate one or more adjustments to an impending surgical procedure.

The adjustment to surgical procedure plan and/or the adjustment to surgical instrument selection may be indicated as a suggested adjustment. The adjustment to surgical procedure plan and/or the adjustment to surgical instrument selection may be made to the surgical plan, and an indication of such adjustments may be generated as part of the output. The control signal may be configured to update an operational parameter, such as an operating parameter, a surgical parameter, or the like, of the control program associated with a surgical instrument (e.g., during an activation instance).

A surgical procedure plan may include planned procedure steps that may be stored and retrieved, or otherwise accessed on a computing device (e.g., the surgical hub 206 or 5104). For example, as shown in FIG. 14, a list of planned procedure steps for a thoracic procedure (specifically, a lung segmentectomy procedure) are described to be retrieved or accessed for comparison with procedure steps detected through hub situation awareness by the surgical hub 5104. At procedure step 5214, a detection of a patient's lung collapsing is compared with expected/planned steps of the procedure. Accordingly, a match is found with the first expected/planned procedure step of collapsing the lung, and a determination is made that the procedure has begun.

Planned surgical instruments' identification information may be obtained via a computing device (e.g., the surgical hub 206 or 5104). For example, planned surgical instruments' identification information may be obtained based on planned procedure steps and the associated surgical instruments information. For example, as described in FIG. 14, planned procedure steps of a colorectal procedure (e.g., access 206580, dissection 206582, transection 206584, anastomosis 206586, and closing 206588) may be retrieved from a surgical hub (e.g., the surgical hub 206 or 5104). A list of planned surgical instruments (e.g., trocar 206581, energy device 206583, linear surgical stapler 206585, and circular surgical stapler 206587) associated with the planned procedure steps may be retrieved from the surgical hub. Usage of planned surgical instruments at planned procedure steps may be detected and confirmed by the surgical hub (e.g., the surgical hub 206 or 5104). For example, activation instances 206592 illustrate the expected usage of trocar 206581 at planned procedure steps access 206580 and closing 206588. For example, activation instances 206590 illustrate the expected usage of energy device 206584 at planned procedure steps access 206580, dissection 206582, and transection 206584. For example, activation instance 206594 illustrates the expected usage of linear surgical stapler 206585 at planned procedure step transection 206584. For example, activation instance 206596 illustrates the expected usage of circular surgical stapler 206587 at planned procedure step anastomosis 206586.

Based on a prediction of hemostasis complication such as a bleeding event, a control signal may be generated to adjust a surgical parameter associated with a surgical cutting and stapling device (e.g., at one or more procedure steps). For example, as described in FIG. 13, the computing system may update operational parameters (e.g., compression rate or load thresholds) of a control program of a surgical stapling and cutting instrument (e.g., 206585 or 206587). Upon detecting a bleeding risk, a control signal may be generated to adjust one or more closure parameters associated with a surgical stapling and cutting instrument, such as clamp pressure, closure force (e.g., force-to-close (FTC) or closure compression force), closure velocity (e.g., closure rate or clamping speed), and/or tissue creep wait time (e.g., wait time). In an example, upon detecting a bleeding risk, a control signal may be generated to adjust one or more firing parameters associated with a surgical stapling and cutting instrument, such as creep threshold(s), advancement rates, firing speed, and/or viable staple height range.

For example, upon detecting a bleeding risk based on the biomarker measurement data, the computing system may generate a control signal to increase a pre-deployment compression, slow a firing actuator speed, prolong a tissue creep wait time prior to stapling, and/or combine pauses in the advancement of actuator(s) of a surgical stapling and cutting device. Wait time and/or compression may be improved. For example, upon detecting a bleeding risk, the computing system may generate a control signal to adjust viable staple height zones for tighter staple form (e.g., decrease the viable staple height range) of a surgical stapling and cutting device. For example, upon detecting a bleeding risk, the computing system may generate a control signal to provide a notification to suggest an adjunct to supplement the surgical stapling device.

Based on a prediction of a bleeding complication based on the biomarker measurement data, the computing system may generate a control signal configured to alter an energy device's operational parameters at one or more procedure steps. For example, the computing system may generate a control signal to adjust a power level, adjust a time before transition point based on tissue impendence tracking, increase a jaw compression, and/or prolong a wait time between surgical steps associated with an energy device.

The computing system, upon predicting a hemostasis complication may alter or update the control program of an energy device to adjust power levels, adjust the time before transition point based on tissue impendence tracking, increase jaw compression, and/or instituting longer wait times between events, etc.

For example, as described in FIG. 13, a computing system (e.g., the surgical hub 206 or 5104) may adjust operational parameters (e.g., energy level) of a control program of an energy device 206583. The computing system, based on a prediction of hemostasis complication such as a bleeding event, may alter an energy device's operational parameter at a dissection step of a colorectal procedure. Higher blood pressure may require a stronger seal to overcome bursting. For example, the computing system may increase the power level or energy level of an energy device such that a bleeding risk may be reduced. For example, the computing system may adjust an RF energy device's tissue impedance threshold (e.g., maximum tissue impedance) before increasing power level (e.g., voltage) to lower tissue temperature at the end of an issue treatment cycle for effective treatment. For example, the computing system may increase an energy device's jaw clamp force (e.g., with a motor to improve compression). For example, the computing system may reduce seal speed, or extend sealing time to improve hemostasis. For example, the computing system may increase jaw compression force such that a bleeding risk may be reduced. For example, the computing system may prolong a waiting period between surgical steps, such as prolong compression time (e.g., before activation of the energy generator), or prolong clamp time.

The computing system, upon predicting a hemostasis complication may generate a control signal configured to indicate a suggestion for adjusting a surgical instrument selection planned for one or more surgical procedure steps. Suggestions described herein may be provided via a user interface a surgeon interacts with ("surgeon interface"), such as a surgical planning interface, a surgeon pre-surgery imaging interface, a surgeon interface/console, surgical hub display 215 illustrated in FIG. 5, and/or a surgical device having a display. The suggestions may be generated by a computing system (e.g., the surgical hub 206 or 5104) and sent to the surgeon interface. A suggestion message may be displayed in a designated area on the surgeon interface, such as a suggestion overlay or a suggestion box at the bottom right corner of the surgeon interface.

For example, a notification of a hemostasis complication, a surgical plan adjustment, and/or a surgical adjustment suggestion may be presented as an augmented reality (AR) or mixed reality overlay on the surgeon interface that may be interrogated. An AR device may provide AR content to a user. For example, a visual AR device, such as safety glasses with an AR display, AR goggles, or head-mounted display (HMD), may include a graphics processor for rendering 2D or 3D video and/imaging for display. AR content may be overlaid onto the various displays described herein. For example, an audible AR device, such as an earbud, a headset, a headphone, or a speaker, may provide audible AR content. The audible AR device may provide auditory overlay, for example, in addition to hearing OR sounds. Audible overlay may be provided via an earbud set with pass through noise capabilities and/or via a bone conduction speaker system. The AR device may communicate certain information only to the targeted individual within the OR that could utilize the information. The AR device may include a processor, a non-transitory computer readable memory storage medium, and executable instructions contained within the storage medium that are executable by the processor to carry out methods or portions of methods disclosed herein. Examples of visual and audio AR devices can be found in more detail in U.S. patent application Ser. No. 17/062,509, titled INTERACTIVE INFORMATION OVERLAY ON MULTIPLE SURGICAL DISPLAYS, which was filed on Oct. 2, 2020, which is herein incorporated by reference in its entirety. Examples of visual and audio AR devices can be found in more detail are described in a patent application titled AUDIO AUGMENTED REALITY CUES TO FOCUS ON AUDIBLE INFORMATION, filed contemporaneously, which is herein incorporated by reference in its entirety.

The computing system, upon predicting a hemostasis complication may alter device selection, including trending to smaller stapler, selecting buttresses or force supplementing adjuncts, adding of hemostatic adjuncts to devices or procedure prophylactically, and/or the selecting improved hemostasis energy devices such as bipolar RF over other modes. The computing system may, based on the biomarker measurement data indicating a higher bleeding risk, adjust the surgical plan to direct the use or avoidance of certain modalities. For example, the computing system may direct the use of stapling in place of energy devices in lobectomies.

In examples, a suggestion for adjusting a surgical instrument selection for a dissection step may be made. For example, upon predicting a hemostasis complication, a surgical instrument with an improved hemostasis capability (e.g., rather than an improved dissection capability) may be suggested. For example, a radiofrequency (RF) bipolar energy device may be suggested.

Based on the predicted hemostasis complication, the computing system may generate a control signal configured to indicate a suggestion for adjusting the procedure plan. For example, upon detecting a bleeding risk based on the biomarker measurement data, the computing system may generate a control signal to indicate a surgical device/instrument selection adjustment. The adjustment may include one or more of selecting a small surgical cutting and stapling device in place of large surgical cutting and stapling device, selecting a surgical cutting and stapling device in place of an energy device, adding buttresses, adding force supplementing adjunct(s) to the instrument selection, adding hemostatic adjunct(s) to at surgical device prophylactically, or selecting an improved hemostasis energy device in place of an energy device associated with low hemostasis capability. The adjustment may include selecting a staple cartridge having smaller staple height. The adjustment may include selecting a fastener having a size associated with reduced post-transection bleeding (e.g., a size associated with tighter staple form). The surgical device/instrument selection adjustment may include adding bleeding maintenance adjuncts for use on the mechanical fasteners.

Based on the biomarker measurement data, the computing system may generate a control signal configured to indicate a suggestion for adding an adjunct at one or more procedure steps. For example, the computing system generate a control signal configured to indicate a suggestion for adding an adjunct for a transection step. In an example, a suggestion may be made to use a buttress (absorbable or permanent) to supplement a surgical stapler to increase staple line strength and hence improve hemostasis. In an example, an absorbable biomaterial-based hemostatic adjunct (e.g., SURGICEL® Absorbable Hemostats) may be suggested to address possible continuous oozing. In an example, a fibrin patch (e.g., EVARREST® Fibrin Sealant Patch) may be suggested to provide mechanical integrity and support clot formation independently of the patient coagulation profile. In an example, a flowable gelatin (e.g., SURGIFLO®) Hemostatic Matrix) may be suggested for bleeding that occurs in tight and difficult-to-access spaces. In an example, a fibrin sealant (EVICEL® Fibrin Sealant (Human) may be suggested to prevent potential post-operative re-bleeding risks prophylactically. These adjuncts and higher priced performance devices may not be considered due to surgical cost control. However, with the prediction of substantially increased hemostasis complication, the surgical instrument selection adjustment(s) described herein could reduce time in surgery, blood loss, and post-surgical complication by more than the increased cost of the selection.

For example, upon detecting a bleeding risk based on the biomarker measurement data, the computing system may generate a control signal to indicate a surgical procedure plan adjustment. The adjustment may include reducing a volume of anesthesia fluid, and/or reducing a volume to post-surgical fluid prescription. The changes to intra and/or post-op patient care can be adjusted. Part of anesthesia protocols may include the volume of fluids the patient receives intra-op and/or the volume of fluids the patient receives post-op. Based on the predicted bleeding risk, the computing system may reduce the volume of fluids the patient receives as part of the surgical procedure plan adjustment to help reduce blood pressure.

The computing system, upon predicting a hemostasis complication may update the control program of a surgical cutting and stapling device to increase pre-deployment compression, slow firing actuator speed, combine pauses in the advancement of actuators (e.g., to improve wait time and compression) and/or to adjust viable staple height zones. For example, the control program may be updated to reduce the viable staple height zones for tighter staple form.

For example, upon detecting a clotting risk (e.g., hypercoagulation, irregular blood clotting) based on the biomarker measurement data, the computing system may generate a control signal configured to adjust one or more surgical parameters to reduce the risk of blood clot formation. The computing system may adjust surgical parameters such as clamping duration, compression duration, the amount of power activation, or duration of power activation. For example, upon detecting increased risk of clotting (e.g., which may lead to thrombosis, thromboembolism), the computing system may increase the amount and duration of power activation associated with an energy device (e.g., in a coagulation mode). This may drive stabilization of clots. The computing system may, based on the biomarker measurement data indicating hypercoagulation, reduce the time and/or power (e.g., in a cutting mode) such that coagulative necrosis may be prevented or limited.

Measurement data related to a set of patient biomarkers for post-surgical monitoring may be received. For example, a computing system may be configured to receive the measurement data from one or more sensing systems. A sensing system may be or may include a patient wearable device. A sensing system may be or may include an environmental sensing system. A sensing system may include one or more sensors. The set of patient biomarkers may be monitored for detecting a post-surgical colorectal complication. For example, the set of patient biomarkers for detecting an anastomosis leak may include a patient's blood pH, sweat lactate, and/or GI motility. For example, the set of patient biomarkers for detecting internal bleeding may include a patient's blood pressure, heart rate, and/or heart rate variability. For example, the set of patient biomarkers for detecting a surgical site infection may include a patient's blood pH and/or edema. The measurement data received from the sensing system(s) may be in response to one or more requests for the measurement data. For example, the computing system may send a request to one or more sensing systems requesting respective measurement data.

One or more thresholds may be determined for a patient biomarker. For example, the surgical computing system may determine respective threshold(s) associated with a patient's blood pH, sweat lactate, GI motility, and/or other patient biomarkers for anastomosis leak detection. The threshold(s) may be standard threshold(s). The threshold(s) may be customized for a patient based on the patient's pre-surgical, in-surgical, and/or previously measured post-surgical patient biomarker measurements. A patient biomarker may be monitored in real-time by comparing the measurement data related to the patient biomarker against the corresponding threshold(s). For example, the computing system may monitor a patient's blood pH in real-time by comparing the measurement data related to the patient's blood pH against the threshold associated with the patient's blood pH. The computing system may compare the measurement data related to the patient's sweat lactate against the threshold associated with sweat lactate. The computing system may compare the measurement data related to the patient's GI motility against the threshold associated with GI motility. A potential post-surgical colorectal complication may be detected when the measurement data related to one or more patient biomarkers crosses the corresponding threshold (e.g., for a predetermined amount of time). For example, when the measurement data related to a patient's blood pH, sweat lactate, and/or GI motility crosses the respective threshold(s) associated with the patient, the computing system may detect a potential anastomosis leak.

In an example, the threshold(s) may be associated with a context. The computing system may consider the context when assessing whether the measurement data crosses the corresponding threshold(s). The context may be associated with a colorectal surgery recovery timeline and/or a set of environmental attributes.

An actionable severity level associated with the detected post-surgical colorectal complication may be determined. For example, the computing system may determine an actionable severity level associated with a detected anastomosis leak. A notification may be sent to the patient and/or the HCP indicating a potential post-surgical colorectal complication and the associated actionable severity level. For example, the computing system may send a real-time notification to a patient and/or an HCP indicating a potential anastomosis leak and the actionable severity level associated with the anastomosis leak. The real-time notification may include the medical name, medical details, actionable severity level and/or a recommended course of action associated with the detected post-surgical colorectal complication.

The computing system may determine type and/or content of the notification based on the determined actionable severity level. For example, when the detected complication is determined to be associated with low-risk actionable severity level, the computing system may generate a real-time notification to a device associated with the patient. When the detected complication is determined to be associated with high-risk actionable severity level, the computing system may generate a real-time notification to a device associated with the patient and a device associated with an HCP. For example, when the detected complication is determined to be associated with low-risk actionable severity level, the computing system may generate a real-time notification indicating the medical name of the complication and of the patient biomarker that crossed the corresponding threshold(s). When the detected complication is determined to be associated with high-risk actionable severity level, the computing system may generate a real-time notification indicating a recommended course of action.

A post-surgical colorectal complication may be predicted based on the measurement data. For example, the computing system may predict that, while a patient currently does not have an anastomosis leak, the patient may be likely to get an anastomosis leak in the future.

One or more thresholds may be received for each patient biomarker. For example, a wearable sensing system may receive, from a computing system, respective threshold(s) associated with a patient's blood pH, sweat lactate, GI motility, and/or other patient biomarkers for anastomosis leak detection.

A request for detecting a potential post-surgical colorectal complication may be received. For example, the wearable sensing system may receive a request for detecting a potential anastomosis leak. The computing system may send the request along with one or more thresholds associated with the patient biomarker(s) to be monitored by the wearable sensing system. For example, the computing system may send a request for detecting anastomosis leak along with blood pH, sweat lactate, and/or GI motility threshold(s).

Data related to the patient biomarker(s) may be measured. For example, the wearable sensing system may measure data related to a patient's blood pH, sweat lactate, and/or GI motility for detecting a potential anastomosis. The wearable sensing system may monitor patient biomarker(s) in real-time by comparing the measured data related to patient biomarker(s) against the corresponding threshold(s) received from the computing system. The wearable sensing system may detect a potential post-surgical colorectal complication when the measured data related to one or more patient biomarkers crosses the corresponding threshold(s) (e.g., for a predetermined amount of time). For example, when the measured data related to a patient's blood pH, sweat lactate, and/or GI motility crosses the respective threshold(s) associated with the patient, the wearable sensing system may detect an anastomosis leak (e.g., a potential anastomosis leak).

A patient actionable severity level and/or an HCP actionable severity level associated with the detected post-surgical colorectal complication may be determined. For example, a wearable sensing system may determine a patient actionable severity level and/or an HCP actionable severity level associated with a detected anastomosis leak. A notification may be sent to the patient and/or the HCP indicating a potential post-surgical colorectal complication and the associated actionable severity level. For example, the wearable sensing system may send a real-time notification to a patient and/or an HCP indicating a potential anastomosis leak and the actionable severity level associated with the anastomosis leak. The real-time notification may include the medical name, medical details (a patient's name, medical ID, etc.), actionable severity level and/or a recommended course of action associated with the detected post-surgical colorectal complication.

The wearable sensing system may determine type and/or content of the notification based on the determined actionable severity level. For example, when the detected complication is determined to be associated with low-risk patient actionable severity level, the wearable sensing system may generate a real-time notification to a device associated with the patient. When the detected complication is determined to be associated with high-risk patient actionable severity level, the wearable sensing system may generate a real-time notification to a device associated with the patient and a device associated with an HCP. For example, when the detected complication is determined to be associated with low-risk patient actionable severity level, the wearable sensing system may generate a real-time notification indicating the medical name of the complication and of the patient biomarker(s) that crossed the corresponding threshold(s). When the detected complication is determined to be associated with high-risk patient actionable severity level, the wearable sensing system may generate a real-time notification indicating a recommended course of action.

A computing system for measuring and monitoring patient biomarkers for detecting or predicting a post-surgical colorectal complication may be provided. A post-surgical colorectal complication may be predicted or detected by comparing measured/processed patient biomarker data with a corresponding determined threshold value. The comparison of the measured/processed patient biomarker data and the corresponding threshold may be performed in association with a context. The context may be based on at least one of a colorectal surgery recovery timeline, at least one situational attribute, or at least one environmental attribute. A notification message associated with a predicted or detected post-surgical colorectal complication may be sent (e.g., sent in real time) to a patient device or a healthcare provider's device. The notification message may be supplemented by a severity level message.

Figure 46B:
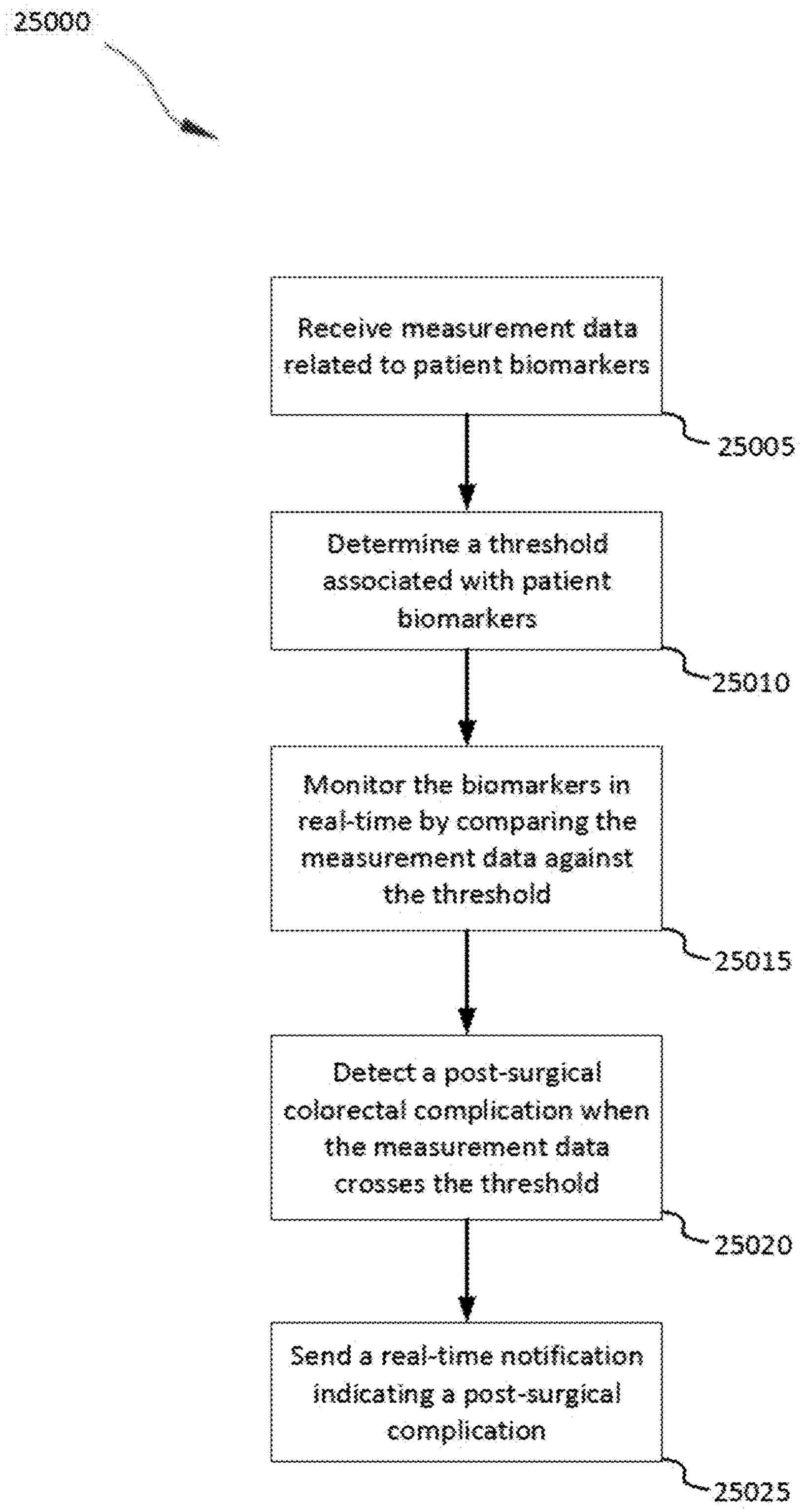
FIG. 46B shows example post-surgical colorectal complication prediction or detection.

FIG. 46B shows example 25000 post-surgical colorectal complication prediction or detection. One or more of 25005-25025 shown in FIG. 46B may be performed by a computing system, a sensing system, and/or another device described herein.

At 25005, measurement data related to patient biomarker(s) may be received. The patient biomarkers may be used for predicting or detecting a post-surgical colorectal complication. For example, the patient biomarkers may be used for detecting anastomosis leaks, internal bleeding, surgical site infection, and/or other post-surgical colorectal complications. The received measurement data may be raw measurement data that may be processed into processed measurement data. The processed measurement data may be in a different form than the raw measurement data. For example, the processed measurement data form may be better suited for analysis when compared to the raw measurement data form. The measurement data may be received from one or more patient sensing systems, such as a wristband patient sensing system, an ingestible pill patient sensing system, an ultra-thin catheter patient sensing system, an instrumented socks patient sensing system, and/or the like.

The measurement data may be related to one or more patient biomarkers associated with post-surgical signs used for predicting or detecting post-surgical colorectal complications. Prediction or detection of a post-surgical colorectal complication may be based on one or more of the following post-surgical signs: system sepsis, shock, GI motility, etc. One or more patient biomarkers may be related to the post-surgical signs and may be monitored to predict or detect a post-surgical colorectal complication. Such patient biomarkers may include patient intestinal microbiome composition, c-reactive protein production, intra-colonic pressure, core body temperature, colon tissue perfusion pressure, edema, colon tissue friability, white blood cell production, blood pressure, blood lactate, sweat lactate, blood pH, GI pH, physical mobility, heart rate, and/or heart rate variability.

Various sensing systems may perform patient biomarker measurements for post-surgical colorectal complication prediction or detection. For example, a wristband patient sensing system may measure patient biomarkers, including a patient's blood pressure, blood pH, blood lactate, sweat lactate, and/or heart rate. An ingestible pill patient sensing system may measure patient biomarkers such as GI pH, colon tissue perfusion pressure, colon tissue friability, and/or intestinal microbiome composition. An ultra-thin patient sensing system may measure patient biomarkers including c-reactive protein production, intra-colonic pressure, and/or white blood cell production. A patient sensing system (e.g., an instrumented socks patient sensing system) may send measurement data related to edema. Based on the measurement data, one or more patient biomarkers may be monitored for detecting anastomosis leak.

Measurement data associated with a patient may be obtained via one or more environmental sensing systems, for example, a video camera, a thermometer, etc. For example, a video camera may send measurement data (e.g., a video feed) related to a patient's physical attributes (e.g., physical mobility) to a computing system. A thermometer may send measurement data related to environmental temperature to the computing system.

The measurement data may be received in response to one or more requests for the measurement data. For example, a computing system may send a request to a patient sensing system requesting respective measurement data. The computing system may send the requests to different sensing systems at different time intervals or simultaneously. For example, the computing system may concurrently send requests to a wristband patient sensing system and an ingestible pill patient sensing system. For example, the computing system may send a request to an environmental sensing system at a first time interval and a request to an ingestible pill patient sensing system at a second time interval.

At 25010, a threshold associated with a patient biomarker may be determined. A patient biomarker threshold may be determined based on expected patient biomarker values, benchmark patient biomarker values, and/or the like. For example, a computing system and/or sensing system may determine a threshold associated with a patient's blood pressure and/or a threshold associated with a patient's GI motility. In an example, a composite threshold associated with a combined value of multiple patient biomarkers, e.g., a patient's blood pressure and/or GI motility, may be determined. The threshold may be (e.g., may further be) associated with measurement data received from one or more environmental sensing systems, for example, a video feed and/or a thermometer feed.

A patient biomarker threshold may be determined based on a standard threshold associated with a patient biomarker. A patient biomarker threshold may be customized for a patient. For example, patient biomarker threshold may be customized using a pre-surgical patient biomarker measurement, an in-surgical patient biomarker measurement, and/or a previously measured patient biomarker measurement. For example, a computing system and/or sensing system may determine a greater than normal threshold associated with a patient's blood pressure based on pre-surgical and/or in-surgical measurements that indicated the patient has high blood pressure. For example, a computing system and/or sensing system may determine a lesser than normal threshold associated with a patient's blood pressure based on pre-surgical and/or in-surgical measurements that indicated the patient has low blood pressure.

At 25015, one or more patient biomarkers may be monitored. For example, one or more patient biomarkers may be monitored in real-time. For example, a computing system and/or a sensing system may compare measurement data associated with each patient biomarker against a corresponding threshold(s). For example, measurement data associated with a patient's blood pressure and/or GI motility may be compared against a threshold associated with the patient's blood pressure and/or GI motility, respectively.

Measurement data associated with more than one patient biomarker may be combined into composite measurement data. For example, a computing system and/or sensing system may combine measurement data associated with a patient's blood pressure with measurement data associated with a patient's GI motility. The computing system and/or sensing system may compare this composite measurement data with a composite threshold. The measurement data associated with a patient biomarker may be associated with a patient biomarker weight. For example, the measurement data associated with a patient's blood pH may have a greater patient biomarker weight than the measurement data associated with a patient's GI motility. The computing system and/or sensing system may consider the patient biomarker weight(s) when predicting or detecting a potential post-surgical colorectal complication. For example, the computing system and/or sensing system may be more likely to detect a complication when measurement data associated with high patient biomarker weight(s) crosses the corresponding threshold(s) compared to when measurement data associated with low patient biomarker weight(s) crosses the corresponding threshold(s). The computing system and/or sensing system may assign the patient biomarker weight(s). The biomarker weight(s) may be dynamic and adjusted based on the measurement data of another biomarker. The patient biomarker weight(s) may be selected by a healthcare provider overseeing the patient. For example, the healthcare provider may assign a high patient biomarker weight for a patient's GI motility and a low weight for a patient's blood pressure. The healthcare provider may adjust the one or more patient biomarker weights during the patient's recovery.

At 25020, a post-surgical colorectal complication may be predicted or detected based on the measurement data. For example, a potential post-surgical colorectal complication may be identified on a condition that the measurement data related to a patient biomarker crosses a corresponding threshold for a predetermined amount of time. For example, a potential post-surgical colorectal complication may be identified on a condition that the measurement data related to multiple patient biomarkers cross their respective thresholds. For example, a potential post-surgical colorectal complication may be identified on a condition that composite measurement data related to a combination of patient biomarkers crosses a composite threshold. A computing system and/or sensing system may be used to check the condition. For example, the computing system may detect a potential anastomosis leak on condition that a patient's blood pressure and/or GI motility measurement data crosses a blood pH and/or GI motility threshold(s) for a predetermined amount of time. Crossing the threshold may include the measurement data associated with a patient biomarker increasing above the corresponding threshold value. Crossing the threshold may include the measurement data associated with a patient biomarker dropping below the corresponding threshold value. The predetermined amount of time may be used to mitigate erroneous measurement data. For example, the predetermined amount of time may reduce the number of false positive detections. The predetermined amount of time may be determined based on the one or more patient biomarkers being monitored. For example, the predetermined amount of time may be short when a patient's blood pH is being monitored and long when a patient's blood pressure is being monitored.

A patient biomarker threshold may be associated with one or more contexts. For example, a computing system and/or a sensing system may consider the context(s) when comparing the measurement data against the corresponding threshold(s). The context(s) may be associated with a colorectal surgery recovery timeline, a situational attribute, and/or a set of environmental attributes. For example, a context may be associated with a patient's motion. The computing system may consider the patient's motion when comparing the measurement data against the corresponding thresholds. For example, when comparing a patient's heart rate measurement data against a heart rate threshold, the computing system may consider the patient's motion (e.g., walking, sleeping, exercising, etc.). The situation attribute may be a patient's eating, sleeping status and/or the like. For example, when comparing a patient's heart rate measurement data against a heart rate threshold, a computing system may consider whether the patient is eating. The patient biomarker threshold(s) may be adjusted based on one or more contexts. In an example, the computing system may increase the heart rate threshold when the patient is eating. In an example, the computing system may decrease the heart rate threshold when the patient is sleeping.

Context data may be sent to the computing system from one or more patient biomarker sensing systems and/or one or more environmental sensing systems, for example, a video camera, a thermometer, etc. For example, a video camera may send context data (e.g., a video feed) related to a patient's physical mobility to the computing system. A thermometer may send measurement context data related to environmental temperature to the computing system. In an example, one or more environmental sensing systems may be a part of a patient biomarker sensing system. Environmental sensing system(s) and patient biomarker sensing system(s) may be associated with one device. For example, a smart mobile phone device may include one or more environmental sensing system(s) as well as one or more patient biomarker sensing(s).

The likelihood of a post-surgical colorectal complication occurring in the future may be predicted. For example, a computing system and/or sensing system may predict the likelihood of an anastomosis leak occurring by comparing a patient's blood pH measurement data against an expected value. The computing system may predict that an anastomosis leak may be highly likely to occur when a patient's blood pH crosses an expected value for a predetermined amount of time. The computing system and/or sensing system may assign a probability and a timeframe to the predicted complication. For example, the computing system may assign a probability of 0.9 out of 1 and a timeframe of 14 days to a predicted anastomosis leak. In such a case, the computing system has determined that the chances of an anastomosis leak occurring within the next 14 days is 0.9 out of 1.

Predictions of complications and/or recovery milestones may be generated, for example, by one or more machine learning (ML) models, such as predictive models, trained to make predictions after being trained on training data. For example, one or more ML classification algorithms may predict one or more types/classes of complications and/or recovery milestones by inference from input data. A model trained on vectorized training data may process vectorized input data. For example, a model may receive vectorized patient-specific data as input and classify the data as being indicative of one or more complications and/or one or more recovery milestones (e.g., each associated with a probability, likelihood, or confidence level). The model may receive updated patient-specific data to update predicted complications and probabilities and/or recovery milestones and probabilities. Complication mitigation (e.g., recommended actions or recommendations) may be based, at least in part, on one or more complications (e.g., and probabilities) generated by one or more models. A trained model may be any type of processing logic that performs an analysis and generates a prediction or determination derived from or generated based on empirical data, which may be referred to interchangeably as logic, an algorithm, a model, an ML algorithm or model, a neural network (NN), deep learning, artificial intelligence (AI), and so on.

A severity level (e.g., an actionable severity level) associated with the predicted or detected post-surgical colorectal complication may be determined. For example, a computing system and/or a sensing system may assign an actionable severity level to a detected anastomosis leak. In an example, the actionable severity level may be determined based on the degree by which the measurement data associated with a patient biomarker deviates from the corresponding threshold(s). For example, the computing system may determine that a patient's blood pressure has crossed the corresponding threshold by a minimal amount and may assign a low-risk actionable severity level to the detected complication. For example, the computing system may determine that the patient's blood pressure has crossed the corresponding threshold by a significant amount, which may be defined by a percentage of the threshold. In this case, a high-risk actionable severity level may be assigned to the detected complication. The actionable severity level may be determined based on the duration of the measurement data associated with a patient biomarker deviating from the corresponding threshold(s). Longer duration may be associated with higher severity level.

A severity level (e.g., an actionable severity level) may be indicated using an integer and/or a color code. For example, an integer 8 (on a scale of 1-10) and/or color red may indicate a high-risk actionable severity level, whereas an integer 2 using the same scale and/or color yellow may indicate a low-risk actionable severity level. In an example, the actionable severity level may be associated with a predicted post-surgical colorectal complication.

At 25025, a notification (e.g., a real-time notification) may be sent to the patient and/or the HCP indicating a potential post-surgical colorectal complication and the associated actionable severity level. For example, a computing system may send a real-time notification to a patient and/or an HCP indicating a potential anastomosis leak and the actionable severity level associated with the anastomosis leak. A real-time notification may be a notification sent remotely via a wireless connection and received, by a patient and/or HCP, within a determined timeframe. The notification (e.g., a real-time notification) may include the medical name, medical details (e.g., patient's name, patient's medical ID, etc.), actionable severity level, and/or a recommended course of action associated with the detected post-surgical colorectal complication.

Examples of notifications, recommendations, determinations, actions, and/or implementations (e.g., that may reduce or prevent one or more potential or predicted complications) may include, for example, one or more of the following: a selection or modification/change in a surgery plan, instrument choices, surgical approach, instrument configurations and/or schedule (e.g., of surgery and/or order of use of instruments during surgery). A notification may include, for example, one or more suggestions and/or determinations, such as one or more of the following: potential issue areas, procedure plan adjustments, alternative product mixes, and/or adjustment of control program parameters to interlinked smart instruments. The computing system may determine type and/or content of a notification based on the determined actionable severity level. For example, when the predicted or detected complication is determined to be associated with low-risk actionable severity level, the computing system may generate a real-time notification to a device associated with the patient. When the detected complication is determined to be associated with high-risk actionable severity level, the computing system may generate a real-time notification to a device associated with the patient and a device associated with an HCP. The content of the notification may be the amount of information included in the notification. For example, when the detected complication is determined to be associated with low-risk actionable severity level, the amount of information included in the notification may be minimal. When the predicted or detected complication is associated with a high-risk actionable severity level, the amount of information included in the notification may be significant. For example, when the detected complication is determined to be associated with low-risk actionable severity level, the computing system may generate a real-time notification indicating the medical name of the complication and of the patient biomarker that crossed the corresponding threshold(s). When the detected complication is determined to be associated with high-risk actionable severity level, the computing system may generate a real-time notification indicating the medical name of the complication and of the patient biomarker that crossed the corresponding threshold(s) as well as a recommended course of action.

Figure 47:
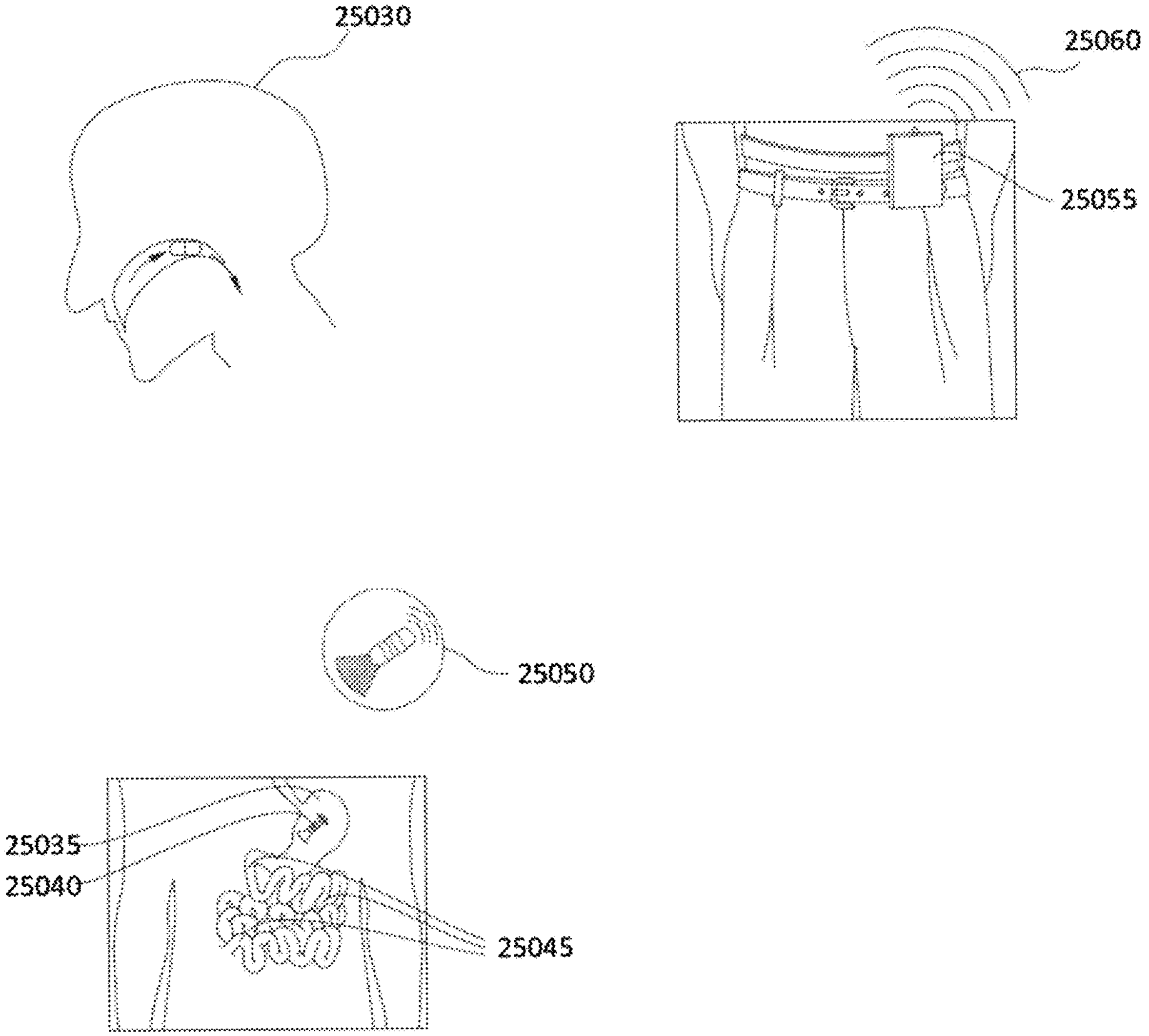
FIG. 47 shows an example wearable sensing system for detecting post-surgical colorectal complications.

FIG. 47 shows an example wearable sensing system for detecting post-surgical colorectal complications.

As illustrated, a patient may swallow a pill 25030. In an example, a surgeon may insert the pill in a target area in the body via invasive surgery. The pill may function as a sensor unit 25040 by measuring data related to one or more patient biomarkers to be monitored for detecting a post-surgical colorectal complication, for example, as described with reference to FIG. 7B and/or 7C. The pill may be a sensor unit and include multiple sensors as described with reference to FIG. 7D. The pill, as a sensor unit, may be associated with a sensing system. For example, the pill may be communicatively connected to a sensing system. The sensing system may be communicatively connected to a computing system (e.g., a surgical hub) and/or remote server(s) as described with reference to FIG. 2B and/or 2C. In an example, the pill may be a sensing system and may be communicatively connected to a computing system and/or remote sever(s). The sensing system may be or may include a wearable sensing system 25055. The wearable sensing system 25055 may receive, from a computing system, one or more thresholds associated with the patient biomarkers to be monitored, as described herein with reference to FIG. 48. The wearable sensing system 25055 may send, for example, to a computing system, measurement data related to the patient biomarkers to be monitored, as described herein with reference to FIG. 46B. The computing system may send the measurement data to one or more analytics servers as described with reference to FIG. 12. The computing system may receive environmental measurement data from one or more environmental sensing as described with reference to FIG. 12.

The pill, functioning as a sensor unit 25040, may travel through the GI tract 25045 of a patient and measure one or more patient biomarkers related to a post-surgical colorectal complication, for example an anastomosis leak, internal bleeding, surgical site infection, and/or other post-surgical colorectal complications. The pill may include one or more sensors as described with reference to FIG. 11B, 11C, and/or 11D. The pill may begin measuring the one or more patient biomarkers when it enters the stomach 25035, before it enters the stomach 25035, and/or after it exits the stomach 25035. Determining when the pill begins measuring may be based on the pill's capacity and/or power. The pill's size may conform to its surrounding environment. For example, the pill may expand in size when it lies in the stomach and shrink in size when it enters the GI tract 25045.

Figure 48:
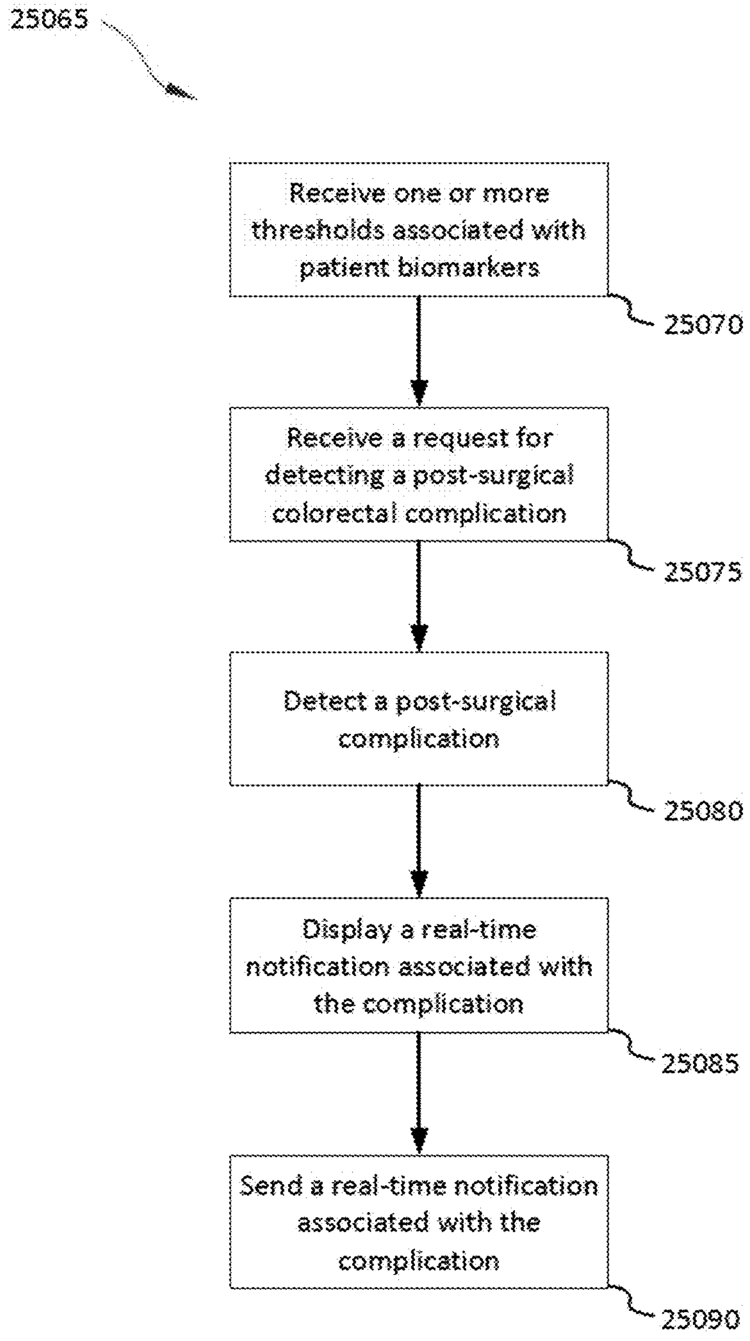
FIG. 48 shows example post-surgical colorectal complication wearable prediction or detection.

The pill may measure the patient biomarker(s) described herein with reference to FIG. 46B and/or FIG. 48. For example, the patient biomarker(s) measured may be GI pH and/or tissue perfusion pressure. The pill may travel through the GI tract 25045 and measure GI pH and/or tissue perfusion pressure. The pill may continuously measure GI pH and/or tissue perfusion pressure as it travels. The pill may measure GI pH and/or tissue perfusion pressure based on a periodic cycle, for example at three second intervals. The periodic cycle may be adjusted as the pill travels through the tract. For example, an HCP may identify a critical phase of the GI tract 25045 and shorten the period cycle so that the pill measures more frequently. The HCP may identify a non-critical phase of the tract 25045 and lengthen the periodic cycle in order to preserve the pill's energy source.

The pill measurements may be associated with pill measurement data. For example, the GI pH and/or tissue perfusion pill measurements may be associated with respective GI pH and/or tissue perfusion pill measurement data. The pill may transmit the pill measurement data (e.g., the GI pH and/or tissue perfusion pressure pill measurement data) to a wearable sensing system 25055 via RF signals 25050 using one of more RF protocols, as described herein. For example, the pill may transmit the pill measurement data using a Bluetooth protocol (e.g., a low energy Bluetooth protocol), a WiFi protocol, and/or using other wireless protocols, as described herein. The wearable patient sensing system 25055 may monitor the pill measurement data in real-time by comparing the pill measurement data to one or more corresponding thresholds. The wearable patient sensing system may obtain one or more thresholds associated with one or more patient biomarkers. In an example, the one or more thresholds may be received from a computing system or a computing device, as described herein with reference to FIG. 48. For example, the wearable patient sensing system 25055 may compare the GI pH and/or tissue perfusion pressure pill measurement data with a corresponding GI pH and/or tissue perfusion pressure threshold, respectively. Multiple comparisons may be performed simultaneously or at different time intervals. The wearable sensing system 25055 may detect a potential post-surgical colorectal complication when the pill measurement data related to at least one patient biomarker crosses the corresponding threshold for a predetermined amount of time. The predetermined amount of time may be received from the computing system and stored in the wearable sensing system 25055.

The wearable sensing system 25055 may transmit the pill measurement data to a computing system via RF signals 25060. In such an example, the computing system may monitor the pill measurement data (e.g., the GI pH and/or tissue perfusion pressure pill measurement data) in real-time by comparing pill measurement data to one or more corresponding thresholds. The computing system may detect a potential post-surgical colorectal complication when the pill measurement data related to at least one patient biomarker crosses the corresponding threshold for a predetermined amount of time, as described herein with reference to FIG. 46B.

FIG. 48 shows example 25065 post-surgical colorectal complication wearable prediction or detection. One or more of 25070-25090 shown in FIG. 48 may be performed by a computing system, a sensing system, and/or another device, as described herein.

At 25070, a threshold described herein with reference to FIG. 46B may be received. For example, a wearable sensing system may receive the threshold for predicting or detecting post-surgical colorectal complications, such as anastomosis leak, internal bleeding, surgical site infection, and/or other post-surgical colorectal complications.

The wearable sensing system may be or may include a wristband patient sensing system, an ingestible pill patient sensing system, an ultra-thin catheter patient sensing system, an instrumented socks patient sensing system, etc. One or more patient biomarkers described herein with reference to FIG. 46B may be monitored to predict or detect a post-surgical colorectal complication. Data described herein with reference to FIG. 46B may be measured by the wearable sensing system.

At 25075, a request may be received for predicting or detecting a potential post-surgical colorectal complication.

For example, the wearable sensing system may receive a request for detecting anastomosis leak. For example, a computing system may send the wearable sensing system the request. The request may include one or more thresholds associated with patient biomarkers related to the post-surgical complication. For example, a request to detect anastomosis leak may include GI motility and/or blood pH threshold(s).

The threshold(s) received by the wearable sensing may be associated with one or more contexts described herein with reference to FIG. 46B. The one or more contexts may be sent by a computing system to the wearable sensing system. The context(s) and/or threshold(s) may be sent simultaneously or at different time intervals.

At 25080, the wearable sensing system may monitor the set of patient biomarkers and detect a potential post-surgical colorectal complication described herein with reference to FIG. 46B. The wearable sensing system may predict the likelihood of a post-surgical colorectal complication described herein with reference to FIG. 46B.

A patient actionable severity level and an HCP actionable severity level associated with the predicted or detected post-surgical colorectal complication may be determined. For example, the wearable sensing system may assign a patient actionable severity level and HCP actionable severity level to a detected anastomosis leak. The actionable severity level(s) may be determined based on the degree by which measurement data associated with a patient biomarker deviates from the corresponding threshold(s). For example, the wearable sensing system may determine that a patient's blood pressure has crossed the corresponding threshold by a minimal amount and may assign a low-risk patient and/or HCP actionable severity level to the detected complication. The wearable sensing system may determine that a patient's blood pressure has crossed the corresponding threshold by a significant amount, which may be defined by a percentage of the threshold. A high-risk patient and/or HCP actionable severity levels may be assigned to the detected complication. The actionable severity level(s) may be determined based on the duration of the measurement data associated with a patient biomarker deviating from the corresponding threshold(s). Longer duration may be associated with higher severity level.

The actionable severity level(s) may be indicated using an integer and/or a color code. For example, an integer 8 (on a scale of 1-10) and/or color red may indicate a high-risk patient and/or HCP actionable severity level, whereas an integer 2 using the same scale and/or color yellow may indicate a low-risk patient and/or HCP actionable severity level. In an example, the actionable severity level may be associated with a predicted post-surgical colorectal complication.

At 25085, a notification may be displayed to the patient indicating a potential post-surgical colorectal complication and the associated actionable severity level. For example, the wearable sensing system may display a real-time notification to a patient indicating a potential anastomosis leak and the patient and the actionable severity level associated with the anastomosis leak.

At 25090, a notification (e.g., a real-time notification) indicating a potential post-surgical colorectal complication and the HCP actionable severity level associated with it may be sent to an HCP as described with reference to FIG. 46B.

Figure 49:
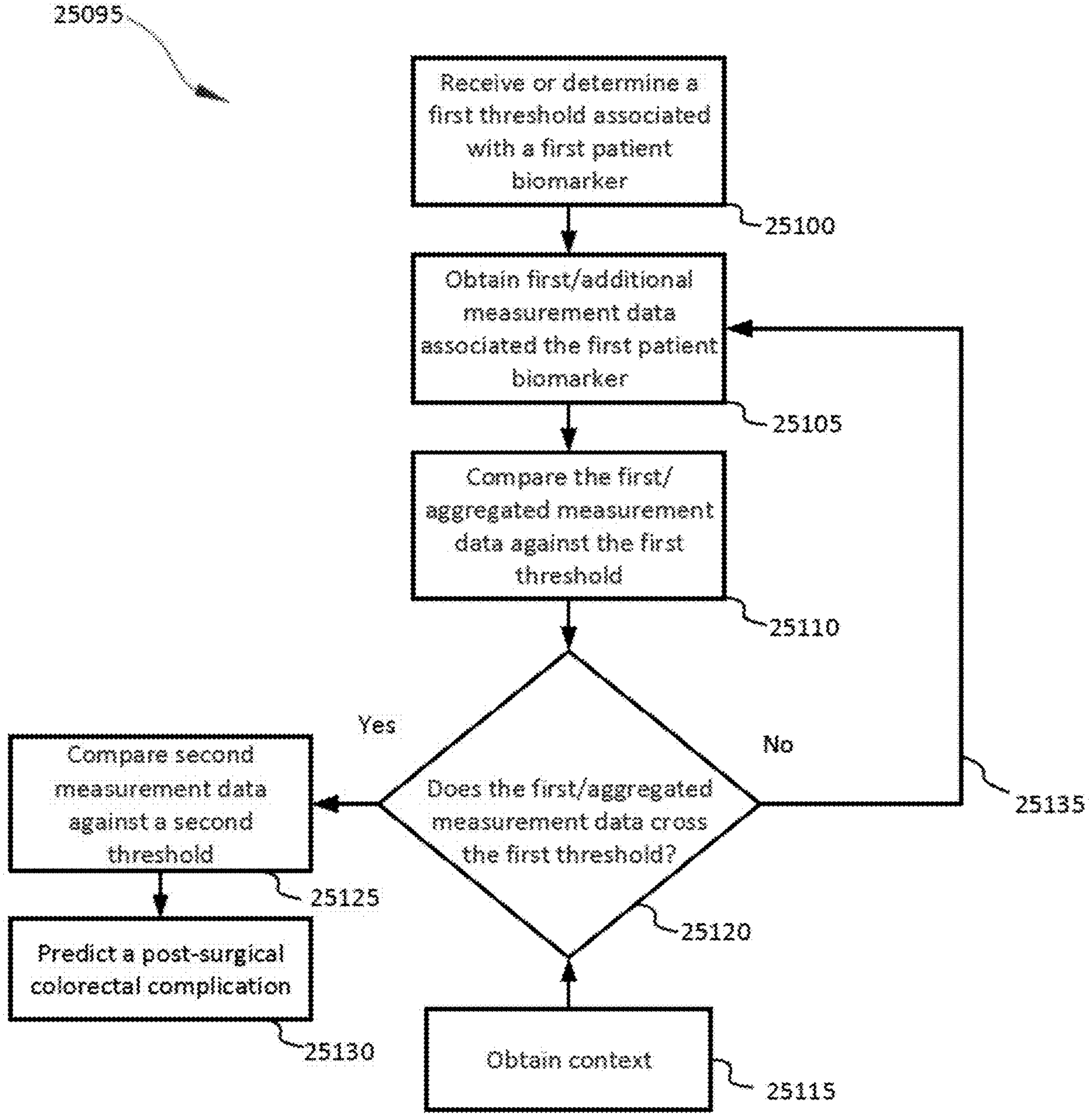
FIG. 49 shows example post-surgical colorectal complication wearable prediction or detection.

FIG. 49 shows example 25095 post-surgical colorectal complication wearable prediction or detection. One or more of 25100-25135 shown in FIG. 49 may be performed by a computing system, a sensing system, and/or another device described herein.

At 25100, a first threshold associated with a first patient biomarker may be received and/or determined described herein with reference to FIG. 46B and FIG. 48. For example, a threshold associated with blood pH may be received by a sensing system and/or determined by a computing system. The threshold may be used to predict or detect a post-surgical colorectal complication, for example an anastomosis leak.

At 25105, first measurement data associated with the first patient biomarker may be obtained described herein with reference to FIG. 46B and FIG. 48. For example, measurement data associated with blood pH may be obtained by a computing system and/or a sensing system for predicting or detecting post-surgical colorectal complication. The first measurement data may be obtained as a response to a request for the measurement data. For example, a computing system and/or a sensing system may request the first measurement data.

At 25110, the first measurement data may be compared against the first threshold described herein with reference to FIG. 46B and FIG. 48.

At 25115, a computing system and/or a sensing system may obtain context described herein with reference to FIG. 46B. The computing system may consider the context when determining whether the measurement data crosses the threshold. For example, the computing system may adjust the first threshold based on the received context. The computing system may use the received context as input context data. The input context data may influence the computing system as the computing system determines whether measurement data crosses the threshold.

At 25120, a computing system and/or a sensing system may compare the first measurement data against the first threshold by determining whether the measurement data crosses the threshold (e.g., for a predetermined amount of time) as described herein with reference to FIG. 46B and FIG. 48. The computing system or the sensing system may compare the first measurement against the first threshold based on a context.

Assuming that the first measurement data, for example, based on the context, crosses the first threshold, at 25125, second measurement data may be compared against a second threshold described herein with reference to FIG. 46B and FIG. 48. The second threshold may be associated with a second patient biomarker. The second threshold may be received and/or determined similar to how the first threshold may be received and/or determined. The second measurement data may be compared based on a condition that the first measurement data crosses the first threshold for a predetermined amount of time. A computing and/or sensing system may determine that the first measurement data crosses the first threshold for a predetermined amount of time and may compare the second measurement data against a second threshold. In an example, second measurement data may be compared on a condition that the first measurement data crosses the first threshold by a predetermined amount, for example 10% of the first threshold value. The computing system may request the second measurement data when the first measurement data crosses the first threshold.

At 25130, a post-surgical colorectal complication may be predicted described herein with reference to FIG. 46B and FIG. 48. A computing system and/or a sensing system may predict a post-surgical colorectal complication based on the first measurement data comparison and the second measurement data comparison. For example, the computing system may predict a complication when both the first measurement data and the second measurement data cross the respective first and second thresholds. The computing system may assign weight(s) to each comparison. The computing system may assign a high comparison weight to the first measurement data crossing the first measurement data and a low comparison weight to the second measurement data crossing the second threshold. Predicting a post-surgical colorectal complication may be based on the comparison weight(s). A computing system may be more likely to predict a complication when measurement data associated with a high comparison weight crosses a threshold compared to measurement data associated with low comparison weight crossing a threshold.

At 25135, a computing system and/or a sensing system may determine that the first measurement data does not cross the first threshold for a predetermined amount of time. The computing system may then continue at 25105. Additional or optionally at 25105, the computing system may obtain additional first measurement data. At 25105, the computing system may aggregate the additional first measurement data with the original first measurement data. The aggregated first measurement data may be compared against the first threshold. The computing system and/or sensing system may adjust the first threshold based on the additional first measurement data.

Figure 50:
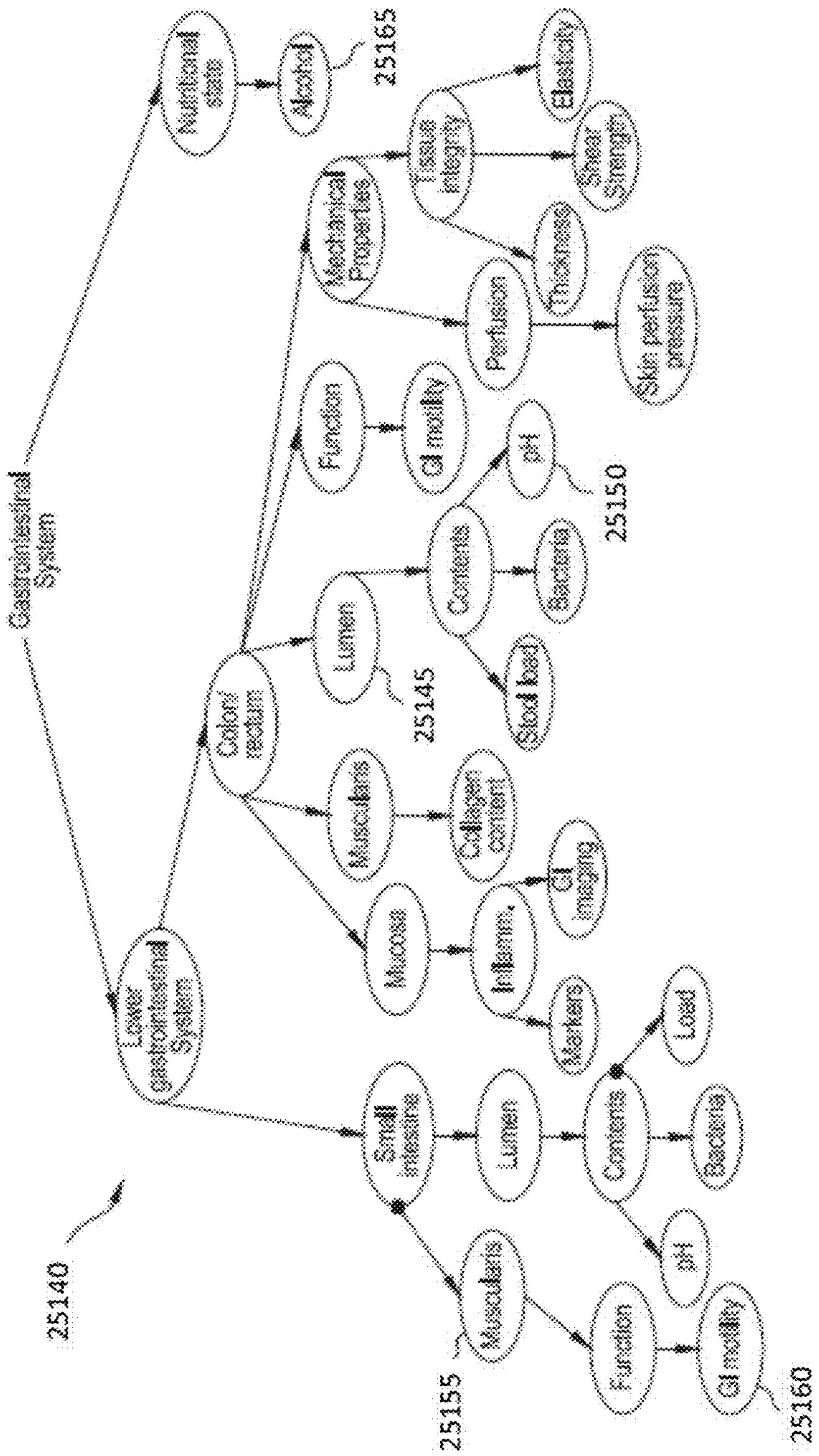
FIG. 50 shows example patient biomarkers related to the gastrointestinal (GI) system for predicting or detecting post-surgical colorectal complication.

FIG. 50 shows example patient biomarkers 25140 related to the GI system for predicting or detecting post-surgical colorectal complication.

For example, pH 25150 of the lumen 25145 may be set as a patient biomarker and monitored to detect anastomosis leak. After colorectal surgery, a patient may be instructed by an HCP to use a sensing system to measure lumen pH 25150 for a period of time following the surgery. The sensing system may include a sensor for measuring lumen pH 25150. During this period, the sensing system may send measurement data associated with the lumen pH 25150 to the computing system. The sensing system may send the measurement data as a response to a request for the measurement data. The sensing system may send the measurement data based on a periodic cycle, for example at twenty-minute intervals. The computing system may adjust the period cycle. For example, the computing system may identify a critical phase of recovery from colorectal surgery. During this phase, the computing system may shorten the periodic cycle. The computing system may identify a non-critical phase of recovery and may lengthen the period cycle. The computing system may compare the received measurement data with a corresponding lumen pH 25150 threshold and, if the measurement data crosses the corresponding lumen pH 25150 threshold for a predetermined amount of time, may predict or detect a potential anastomosis leak and send a real-time notification to the HCP and/or patient. The corresponding lumen pH 25150 threshold may have been determined by the computing system based on pre-surgical, in-surgical, and/or previously measured patient biomarker measurements. The predetermined amount of time may be determined based on the lumen pH 25150 biomarker.

A combination of patient biomarkers related to the lower GI system may be monitored to predict or detect a potential post-surgical colorectal complication. For example, pH 25150 of the lumen 25145 and GI motility 25160 of the muscularis 25155 may be set as patient biomarkers and monitored to detect anastomosis leak. A sensing system may include a sensor that may measure lumen pH 25150 and muscularis GI motility 25160. For example, the sensing system may include two sensors, the first of which may measure lumen pH 25150 and the second of which may measure muscularis GI motility 25160. During the post-surgical period, the sensing system may send the respective measurement data associated with the pH 25150 of the lumen 25145 and the muscularis GI motility 25160 to the computing system. The computing system may compare the measurement data with a corresponding lumen pH 25150 threshold and a corresponding muscularis GI motility 25160 threshold, respectively. The computing system may detect an anastomosis leak when either set of measurement data crosses the corresponding threshold for a predetermined amount of time and send a real-time notification to the HCP and/or the patient. For example, the computing system may only detect an anastomosis leak when both sets of measurement data cross the corresponding threshold. The patient biomarker threshold(s) may be associated with patient biomarker weights described herein with reference to FIG. 46B. For example, lumen pH 25150 may be associated with lumen pH 25150 weight. For example, muscularis GI motility 25160 may be associated with muscularis GI motility 25160 weight. The predetermined amount of time may be determined based on the lumen pH 25150 and the muscularis GI motility 25160 biomarkers.

A combination of patient biomarkers related to and/or unrelated to the lower GI system may be monitored to predict or detect a post-surgical colorectal complication. For example, GI motility 25160 of the muscularis 25155 and alcohol consumption 25165 may be set as patient biomarkers and monitored by a computing system to detect anastomosis leak. A sensing system may include a sensor that may measure GI motility 25160) of the muscularis 25155 and alcohol consumption 25165.

A patient biomarker may be monitored by the sensing system. The sensing system may be a patient wearable sensing system. For example, a sensor may measure lumen pH 25150 and transmit measurement data to the patient wearable sensing system using one or more RF protocols, as described herein with respect to FIG. 48. The patient wearable sensing system may store the measurement data. The patient wearable sensing system may compare the measurement data with a corresponding lumen pH 25150 threshold and, if the measurement data crosses the corresponding lumen pH 25150 threshold for predetermined amount of time, may detect anastomosis leak and send a real-time notification to the HCP and/or the patient. A combination of patient biomarkers related to and/or unrelated to the lower GI system may be monitored by the sensing system.

Figure 51:
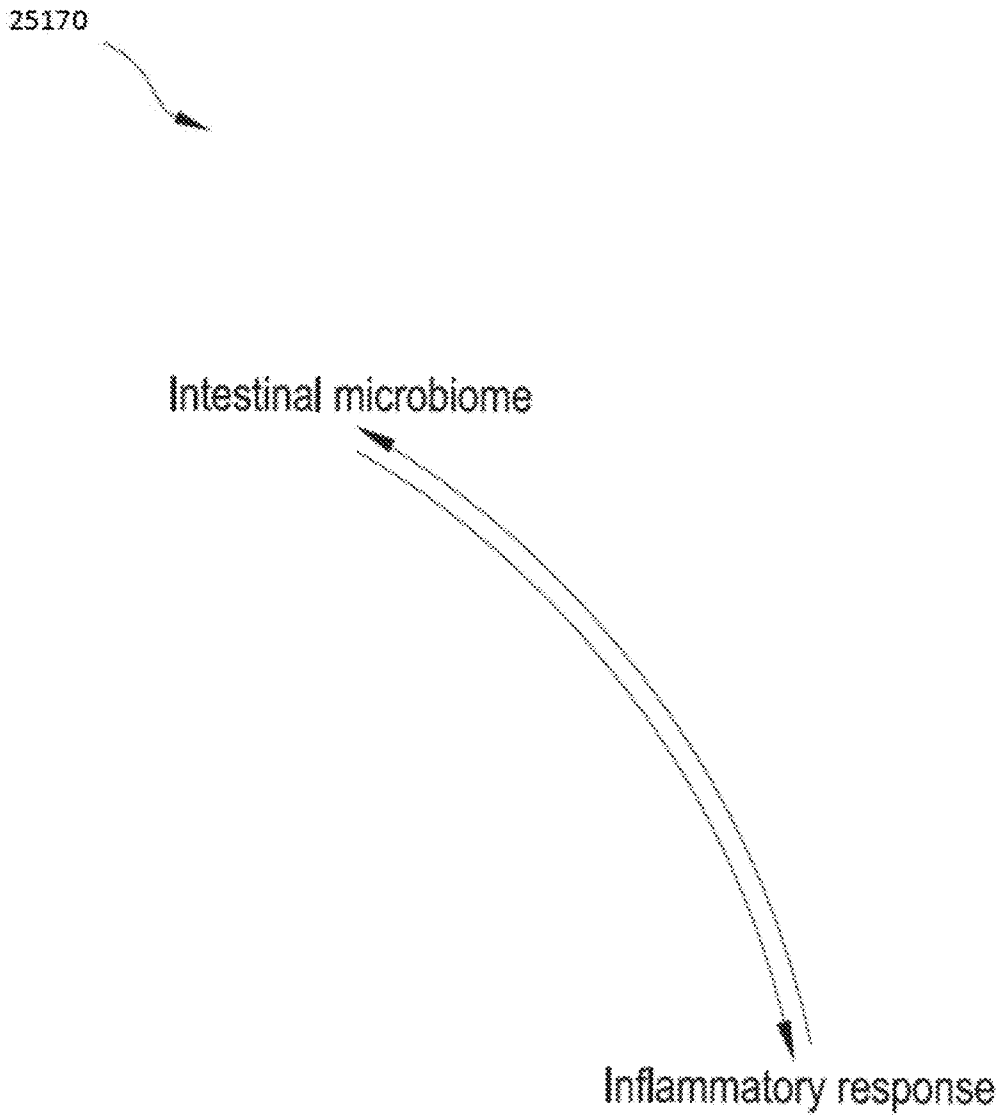
FIG. 51 shows an example relationship between intestinal microbiome and inflammation during anastomosis leak.

FIG. 51 shows an example relationship 25170 between intestinal microbiome and inflammation during anastomosis leak.

Referring to FIG. 51, one or more thresholds associated with a post-surgical colorectal complication may be determined based on the relationship between intestinal microbiome and inflammation. A computing system may determine one or more thresholds associated with anastomosis leak based on the relationship. A sensing system may receive one or more thresholds determined based on the relationship.

As shown in FIG. 51, the imbalance of intestinal microbiome and inflammation may be positively correlated during an anastomosis leak. The computing system may be aware of this relationship and determine high inflammation and intestinal microbiome thresholds. The computing system may determine low inflammation and intestinal microbiome thresholds. The sensing system may receive the determined high inflammation and intestinal microbiome thresholds.

The inflammation and intestinal microbiome threshold(s) may be adjusted based on the relationship. For example, the computing system may increase the inflammation threshold as the intestinal microbiome threshold increases. For example, the computing system may decrease the intestinal microbiome threshold as the inflammation threshold decreases.

The relationship between intestinal microbiome and inflammation may be used when predicting or detecting a potential post-surgical colorectal complication. For example, the intestinal microbiome and inflammation thresholds may be linked to detect or predict a complication. For example, the computing system may link the inflammation and intestinal microbiome thresholds when detecting or predicting for anastomosis leak. The computing system may determine that one or more patient biomarkers related to inflammation have crossed their respective inflammation thresholds for a predetermined amount of time. Based on this determination, the computing system may compare patient biomarkers related to intestinal microbiome against intestinal microbiome threshold. The inflammation and microbiome comparisons may occur sequentially. For example, a patient biomarker related to inflammation may be blood pH and a patient biomarker related to intestinal microbiome may be GI pH. In such a case, the computing system may determine a patient's blood pH has crossed a blood pH threshold. Based on this determination, the computing system may compare the patient's GI pH against a GI pH threshold. Measurement data may be requested based on the relationship. For example, the computing system may determine that a patient's blood pH has crossed a blood pH threshold and send a request for measurement data related to intestinal microbiome to one or more sensing systems. The sensing systems may be responsible for measuring intestinal microbiome biomarkers. For example, a sensing system may measure gas composition inside the colon. A sensing system may measure GI pH. A sensing system may measure more than one intestinal microbiome biomarkers. For example, a sensing system may measure both colon gas composition and GI pH.

One or more thresholds may be associated with corresponding weight(s) based on this relationship. For example, a computing system may assign greater threshold weight(s) to threshold(s) related to inflammation and/or intestinal microbiome compared to non-inflammation and/or non-intestinal microbiome threshold weight(s) when detecting anastomosis leak. The computing system may consider the threshold weight(s) when detecting a potential post-surgical colorectal complication. For example, a computing system may be more likely to detect potential anastomosis leak when a patient biomarker associated with a high threshold weight crosses a corresponding threshold as compared to a patient biomarker associated with a low threshold weight crossing a corresponding threshold.

The relationship between intestinal microbiome and inflammation may be used when predicting a potential post-surgical colorectal complication. For example, the computing system may assign a prediction weight to a threshold when predicting an anastomosis leak. The computing system may assign greater prediction weight(s) to inflammation and/or intestinal microbiome threshold(s) when compared to non-inflammation and/or non-intestinal microbiome threshold(s). For example, the prediction weight for an inflammation threshold may be 1.5 times greater than the prediction weight for a non-inflammation threshold. For example, the prediction weight for an intestinal microbiome threshold may be 0.8 times greater than the prediction weight for a non-intestinal threshold. The computing system may consider the prediction weight when predicting an anastomosis leak. For example, a computing system may be more likely to predict potential anastomosis leak when a patient biomarker associated with a high threshold weight crosses a corresponding threshold as compared to a patient biomarker associated with a low threshold weight crossing a corresponding threshold.

Figure 52A:
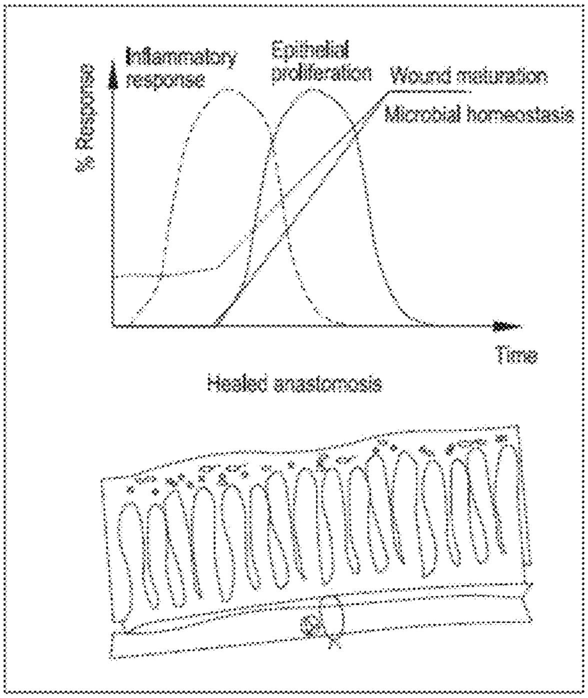
FIGS. 52A and 52B show example relationships between intestinal microbiome, inflammation, and epithelial proliferation during healed anastomosis and anastomosis leak.
Figure 52B:
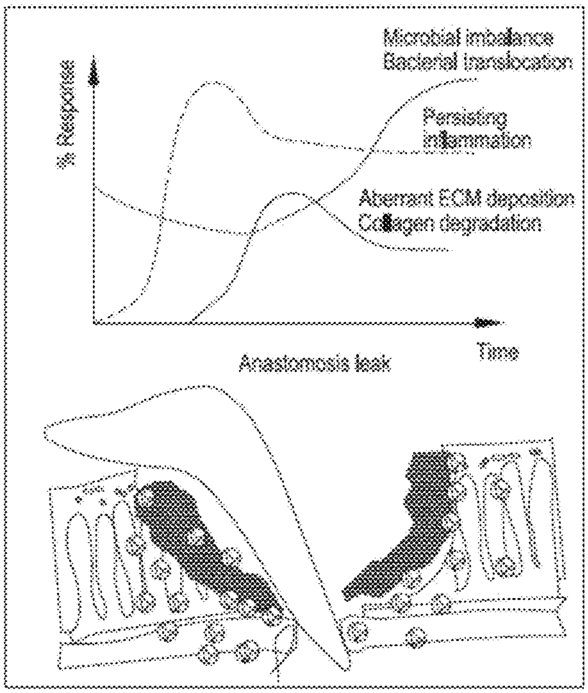

FIGS. 52A and 52B show example relationships 25175 between intestinal microbiome, inflammation, and epithelial proliferation during healed anastomosis and anastomosis leak. The relationships 25175 may be determined by a computing system, a patient sensing system, and/or other devices.

A computing system may be aware of the relationship during healed anastomosis, as depicted in the graph of FIG. 52A. For example, the computing system may be aware that during healed anastomosis, a patient's inflammation and epithelial proliferation should gradually drop in intensity over time while intestinal microbial homeostasis gradually increases over time. Data associated with this trend may be stored. For example, the trend data may reflect the rate at which inflammation and epithelial proliferation drops with respect to a given time. The trend data may reflect the rate at which microbial homeostasis increases with respect to a given time. The computing system may store the trend data and compare measurement data associated with a patient's biomarkers described herein with respect to FIG. 46B against the trend data. The computing system may determine a deviation number based on how much the measurement data deviates from the trend data. The deviation number may be compared to a deviation threshold. For example, the computing system may compare the deviation number to a deviation threshold for detecting anastomosis leak. An anastomosis leak may be identified on a condition that the deviation number crosses a deviation threshold for a predetermined amount of time. A deviation threshold may be received and compared against a deviation number. For example, a sensing system may receive a deviation threshold and compare a deviation number against the threshold for detecting anastomosis leak.

25175 shown in FIG. 52A may performed by a computing system, a sensing system, and/or another device described herein.

A computing system and/or sensing system may be aware of the relationship during an anastomosis leak, as depicted in the graph of FIG. 52B. For example, the computing system may be aware that during anastomosis leak, a patient's inflammation and epithelial proliferation remain near constant value(s) greater than zero over time while intestinal microbial imbalance gradually increases over time. Data associated with this trend may be stored. The computing system may store the trend data and compare measurement data associated with a patient's biomarkers described herein with respect to FIG. 46B against the trend data. The computing system may determine a deviation number based on how much the measurement data deviates from the trend data and compare the deviation number to a deviation threshold for detecting an anastomosis leak. An anastomosis leak may be identified on a condition that the deviation number crosses a deviation threshold for a predetermined amount of time.

25175 shown in FIG. 52B may performed by a computing system, a sensing system, and/or another device described herein.

FIG. 53 shows example correlation 25180 between relevant patient biomarkers and colorectal procedural steps. In the following description of FIG. 53, reference should also be made to FIG. 2 and FIG. 5. FIG. 2 provides the settings used in a patient monitoring system. FIG. 5 provides various components used in a surgical procedure.

A colorectal surgery may include multiple surgical procedural steps. For example, a colorectal surgery may include mobilizing the colon, resecting the colon, and anastomosis. Under each surgical procedural step, one or more tasks may be performed by an HCP (e.g., a surgeon). For example, under mobilizing the colon surgical procedural step, the HCP may cut-off the blood supply from bodily structures attached to the colon. For this task, the HCP may use a harmonic scalpel and/or a monopolar or bipolar RF instrument(s).

Under colon resection surgical procedural step, an HCP may cut out a segment of the colon that may be cancerous, infected, and/or impaired. During the colon resection surgical procedural step, the HCP may use a linear and/or circular stapler instrument(s).

Under anastomosis surgical procedural step, an HCP may reattach the remaining colon and puncture a hole at the point where the colon is reattached. During the anastomosis surgical procedural step, the HCP may use a circular stapler.

A patient biomarker may be correlated to a colorectal procedural step. For example, a patient's blood pressure may be correlated to mobilizing a patient's colon step, for example, in order to track blood supply after mobilization. A patient's colon tissue perfusion pressure may be correlated to resecting the colon since during resection the surgeon is causing trauma to the tissue by severing pieces of the infected colon. A patient's edema may be correlated to anastomosis since during anastomosis the surgeon is reattaching the colon in order to allow intestinal fluid to pass through the GI tract.

A patient biomarker may be monitored based on a procedural step. For example, an HCP may choose to monitor a patient's blood pressure due to a problem that arose when the surgeon was mobilizing the colon. A patient's tissue perfusion pressure may be monitored based on an observation made by the HCP during the colon resection surgical procedural step. Assigning patient biomarker weight(s) as described with reference to FIG. 46B may be assigned based on a surgical procedural step. For example, a patient's edema may be assigned a high patient biomarker weight when an HCP notices certain issues during the anastomosis surgical procedural step.

A patient biomarker threshold may be adjusted based on a surgical procedural step. For example, a blood pressure threshold may be decreased when an HCP notices issues regarding the colon mobilization surgical procedural step. The predetermined amount of time for detecting a complication as described with reference to FIGS. 46B and 48 may change based on a procedural step.

In an example, a computing system and/or sensing system may determine a relevant surgical procedural step based on the correlated patient biomarker crossing a corresponding threshold(s) for a predetermined amount of time. The relevant surgical procedural step may be associated with a detected colorectal complication. For example, when a patient's tissue perfusion pressure crosses a tissue perfusion pressure threshold, a computing system may detect an anastomosis leak and determine colon resection as the relevant procedural step associated with the anastomosis leak.

The relevant procedural step may indicate the procedural step that may be a cause of the detected complication. For example, the detected complication may be anastomosis leak and the relevant procedural step associated with the anastomosis leak may be colon resection surgical procedural step. In such a case, the manner in which the colon resection surgical procedural step was conducted may be a cause of the detected anastomosis leak.

A notification may be sent to the patient and/or HCP indicating a potential post-surgical colorectal complication and the associated relevant procedural step. For example, a computing system and/or sensing system may send a real-time notification to a patient and/or HCP indicating an anastomosis leak and colon resection as the relevant procedural step associated with the anastomosis leak. The relevant procedural step may be used when correcting the detected post-surgical colorectal complication. For example, an HCP may decide to perform a corrective surgery in order correct an anastomosis leak. A notification indicating colon resection as the surgical procedural step may be sent to the HCP before and/or during the corrective surgery. The HCP may use the use the information provided in the notification to develop a plan for a follow-up corrective surgery. In an example, the HCP may target an area that is involved in colon resection.

FIG. 39A-39E illustrates example procedure steps of sigmoid colectomy or a colorectal surgical procedure and example use of patient biomarker measurements. As shown, various post-operative or post-surgical patient biomarker measurements may be used to detect or predict various colorectal post-surgical complications and/or milestones, as described herein. The patient biomarker measurements may also be used to inform various decisions, identify various risks pre-surgery, during surgery, post-surgery, and/or determine operational parameters for various surgical tools.

FIG. 39E illustrates example patient biomarkers that may be monitored post-op to detect or predict post-surgical colorectal complications. The patient biomarkers may be monitored by a computing system as described herein with reference to FIG. 46B. The patient biomarkers may be monitored by a wearable sensing system as described herein with reference to FIG. 48. For example, a patient's blood pH and gastrointestinal motility may be monitored to detect or predict anastomosis leak.

As shown, the patient biomarkers may be measured using one or more wearable and/or environmental sensors as described herein with reference to FIG. 1B. For example, a patient's blood pH may be measured by a wearable patch sensor. A patient's physical activity may be measured by a video camera. Measurement data associated with the wearable and/or environmental sensors may be obtained by a computing system that may compare the data against corresponding threshold(s) as described herein with reference to FIG. 46B. In an example, the measurement data may be obtained by a sensing system that may compare the data against corresponding threshold(s) as described herein with reference to FIG. 48.

In an example, a post-surgical anastomosis leak may be detected or predicted by measuring patient biomarker(s) associated with a patient's oxygen saturation, GI tract imaging, and/or colon tissue perfusion pressure. Post-surgical sepsis may be detected by measuring patient biomarker(s) associated with blood pH, core body temperature, heart rate, heart rate variability, sweat rate, blood pressure, respiratory rate, sweat lactate, cortisol, physical mobility, autonomic tone, circadian rhythm, edema, and/or delirium. Post-surgical internal bleeding may be detected or predicted by measuring patient biomarker(s) associated with colon tissue perfusion pressure, blood pH, alcohol consumption, blood pressure, and/or sweat adrenaline. Post-surgical hypovolemic shock may be detected by measuring patient biomarker(s) associated with blood pH, heart rate, blood pressure, respiratory rate, colon tissue perfusion pressure, and/or sweat lactate. Post-surgical ileus may be detected by measuring patient biomarker(s) associated with GI motility, autonomic tone, oxygen saturation, GI tract imaging, menstrual cycle, colon tissue perfusion pressure, blood pressure, and/or edema. In an example, a post-surgical kidney injury may be detected by measuring a patient's hydration state. Post-surgical cancer relapse may be detected by measuring sweat adrenaline, cortisol, and/or tumor cell characteristics. In an example, patient biomarker measurements may be used post-op to assess a patient's quality of life following a sigmoid colectomy or colorectal surgery. For example, patient biomarkers associated with VO2 max, physical activity, and/or circadian rhythm may be measured to assess a patient's quality of life.

As shown in FIGS. 39A-39D, patient biomarker measurements may be used post-op to inform various decisions, identify various risks pre-surgery, during surgery, post-surgery, and/or determine operational parameters for various surgical tools. For example, post-op patient biomarker measurements may be used to determine a value (e.g., threshold) in which pre-surgical and/or in-surgical measurement data may be compared against.

The value may be used to inform various decisions during a pre-surgical and/or in-surgical procedural step. For example, during a mobilize colon procedural step, as shown in FIG. 39B, patient biomarker measurements associated with colon tissue perfusion pressure may be compared against a colon tissue perfusion pressure value to determine the ligation height of the IMA. The value may be used to identify risks associated with a pre-surgical and/or in-surgical procedural step. For example, during colon mobilization procedural step, a patient's blood pH may be compared against a blood pH value (e.g., for identifying the risk of hemorrhage). The value may be used to determine operational parameters for various surgical tools. During colon mobilization procedural step, a patient's blood pressure may be compared against a blood pressure value to determine the operational parameters of a harmonic scalpel. For example, the intensity of the harmonic scalpel may decrease when the patient's blood pressure crosses the blood pressure value as described herein with reference to FIG. 46B.

Multiple post-op patient biomarker measurements may be compared against multiple pre-surgical and/or in-surgical values simultaneously or at different time intervals. In an example, post-op patient biomarker measurements may increase or decrease the pre-surgical and/or in-surgical values.

Systems, methods, and instrumentalities are disclosed herein for a (e.g., pre-, in-, and/or post-operative) patient monitoring system. Patient biomarkers may be monitored before, during, and/or after thoracic surgery to predict complications, detect complications, track recovery, and/or make pre-, in- and/or post-surgery recommendations to avoid predicted complications and/or mitigate detected complications. Complications (e.g., prolonged air leak or esophageal stricture) may be predicted (e.g., by a model) based on patient parameters and/or patient biomarker measurements. Complications may be predicted or detected based on patient biomarker measurements compared to threshold values associated with a patient biomarker (e.g., developed from baselines) generated based on patient parameters, pre- and/or in-surgery patient biomarker measurements, and/or surgical details (e.g., decrease in lung capacity). Recovery milestones may be tracked based on patient biomarker measurements compared to predicted patient biomarker measurements for recovery stages. A recommendation (e.g., to avoid a predicted complication and/or mitigate a detected complication) may be a patient-specific selection and/or modification of more of the following: surgical preparation, in-surgery procedures, surgical instrument selection, surgical and/or post-surgical instrument settings (e.g., stapler force, suction control program), post-surgery procedures, in-surgery, and/or post-surgery monitoring, etc. Notifications (e.g., real-time notification) may be generated, for example, to indicate predictions, detections (e.g., of complications and/or milestones), recommendations (e.g., for manual and/or automated implementation), etc. Functionality may be variously implemented (e.g., distributed) among one or more of the following: wearable sensing system(s), hub(s), controllable device(s), display device(s), etc.

Thoracic surgery may refer to operations on organs in the chest, such as the heart, lungs, and esophagus, etc. Thoracic surgery may include, for example, coronary artery bypass surgery, heart transplant, lung transplant, and removal of parts of the lung (e.g., affected by cancer). Thoracic surgery may include procedural steps, such as dissect parenchyma, transect arteries and veins, transect parenchyma, and dissect lymph nodes. Patients may be monitored before, during, and/or after surgery. Pre-surgery and/or in-surgery monitoring may impact, for example, a surgical procedure and/or post-surgical monitoring. Post-surgery patient monitoring for recovery milestones and/or complications may be based on (e.g., adapted to), for example, a type of surgery, a surgical procedure, information derived from pre-surgery monitoring, and/or information derived from in-surgery monitoring.

Patient monitoring (e.g., post-surgical or recovery monitoring), such as thoracic surgery post-surgical monitoring, may (e.g., be used to) track recovery milestones, predict complications, and/or make recommendations (e.g., to reduce the severity of complications and/or to avoid complications). For example, an occurrence of a thoracic post-surgical complication may be predicted or detected by one or more computing systems (e.g., a surgical hub, a (wearable) sensing system, and/or the like). Monitoring (e.g., using one or more sensors) may be based on one or more (e.g., potential and/or actual) complications and/or recovery milestones (e.g., healing cascade milestones). Complications may include, for example, prolonged air leaks (PALs), infection, pulmonary insufficiency, arrhythmias, residual intrapleural air spaces, postpneumonectomy empyema, bronchopleural fistula, cardiac herniation, lobar gangrene, esophagopleural fistula, etc. For example, monitoring may (e.g., based on potential and/or actual complication and/or recovery milestones for a type of surgery) monitor for air leak incidence or progression, lung collapse, limited lung volume, irregular respiration, etc.

Monitoring (e.g., pre-, in- and/or post-surgical monitoring) may monitor one or more patient biomarkers. For example, post-surgical (e.g., recovery) monitoring may monitor patient biomarkers to track recovery metrics and/or complications for a surgery, such as lung surgery. Post-surgery monitoring of patient biomarkers may (e.g., be used to) track healing stage progress or recovery milestones and/or determine a probability of complications, which may, for example, result in PALs (e.g., after thoracic resection of a lung). Healing progress and/or development of one or more complications, for example, based on (e.g., using) one or more of baseline records (e.g., developed as described herein), monitored patient biomarkers (e.g., VO2 max, respiration rate, heart rate variability, physical reaction(s) such as coughing and/or sneezing, oxygen saturation), surgical results or modifications (e.g., lung volume reduction), and/or recovery milestones. Recovery milestones and/or complications may be based on (e.g., indicated by) one or more thresholds (e.g., threshold values associated with a patient biomarker), for example, relative to one or more time limits (e.g., predetermined amount(s) of time). For example, failure to achieve a recovery milestone (e.g., within a timeframe, such as a time relative to surgery) alone and/or in combination with patient biomarker values may indicate that one or more complications may be developing or have developed in the patient. Complication mitigation may be supported, for example, by reporting (e.g., of one or more patient biomarker values and/or results of one or more analyses), for example, to a health care provider (HCP). For example, one or more recommendations (e.g., behavioral, medication, bandaging) may be developed based on reporting of monitored patient biomarker values (e.g., measurements) and/or analyses.

Predictions of complications and/or recovery milestones may be generated, for example, by one or more machine learning (ML) models, such as predictive models, trained to make predictions after being trained on training data. For example, one or more ML classification algorithms may predict one or more types/classes of complications and/or recovery milestones by inference from input data. A model trained on vectorized training data may process vectorized input data. For example, a model may receive vectorized patient-specific data as input and classify the data as being indicative of one or more complications and/or one or more recovery milestones (e.g., each associated with a probability, likelihood, or confidence level). The model may receive updated patient-specific data to update predicted complications and probabilities and/or recovery milestones and probabilities. Complication mitigation (e.g., recommended actions or recommendations) may be based, at least in part, on one or more complications (e.g., and probabilities) generated by one or more models. A trained model may be any type of processing logic that performs an analysis and generates a prediction or determination derived from or generated based on empirical data, which may be referred to interchangeably as logic, an algorithm, a model, an ML algorithm or model, a neural network (NN), deep learning, artificial intelligence (AI), and so on.

Patient biomarkers may be monitored before, during, and/or after thoracic surgery to predict complications, detect complications, track recovery, and/or make pre-, in- and/or post-surgery recommendations to avoid predicted complications and/or mitigate detected complications. Complications (e.g., prolonged air leak or esophageal stricture) may be predicted (e.g., by a model) based on patient parameters and/or biomarker measurements. Complications may be predicted or detected based on biomarker measurements compared to thresholds associated with a biomarker (e.g., developed from baselines) generated based on patient parameters, pre- and/or in-surgery biomarker measurements, and/or surgical details (e.g., decrease in lung capacity). Recovery milestones may be tracked based on biomarker measurements compared to predicted biomarker measurements for recovery stages. A recommendation (e.g., to avoid a predicted complication and/or mitigate a detected complication) may be a patient-specific selection and/or modification of more of the following: surgical preparation, in-surgery procedures, surgical instrument selection, surgical and/or post-surgical instrument settings, post-surgery procedures, in-surgery and/or post-surgery monitoring, etc.

Figure 54:
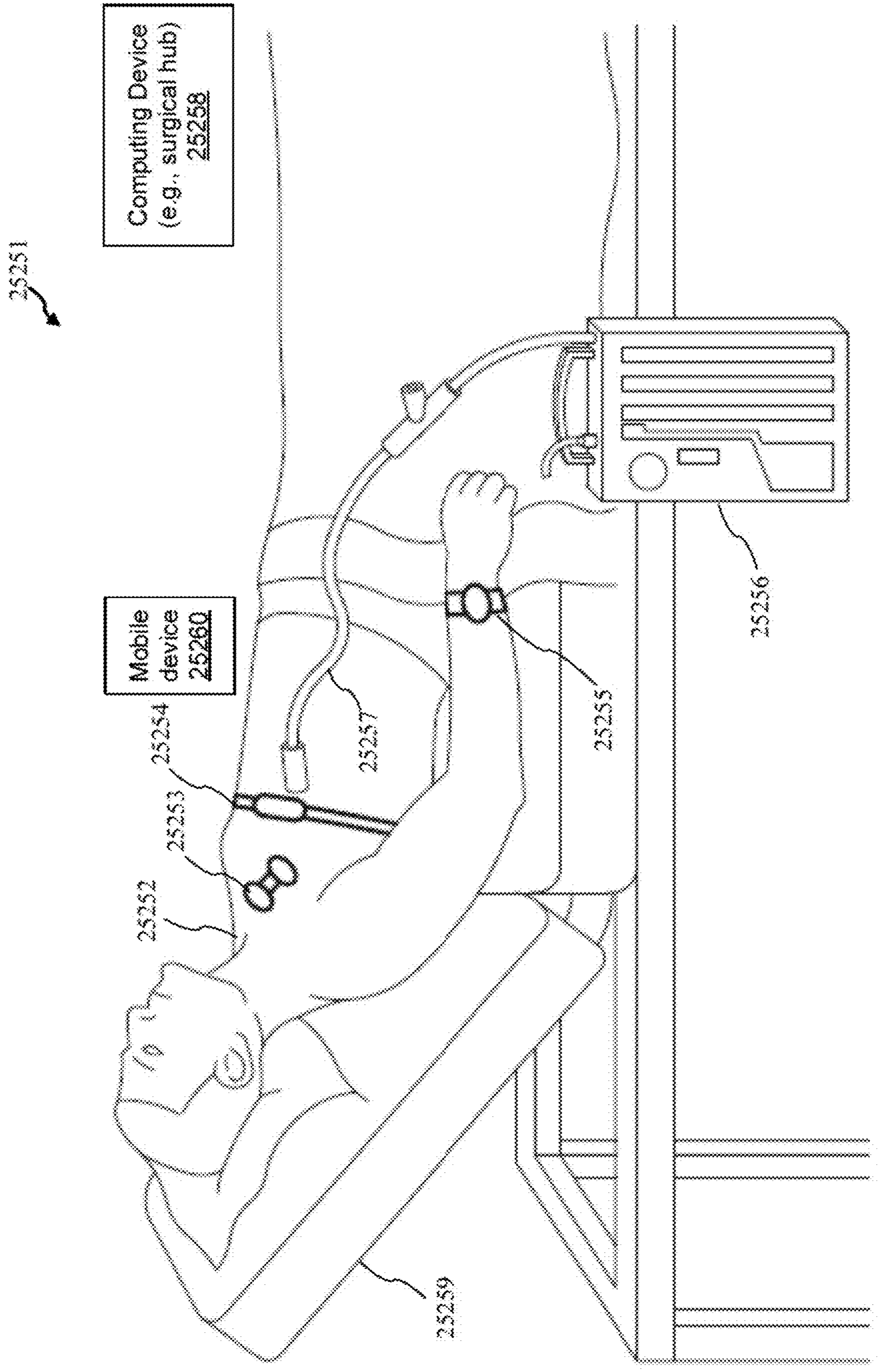
FIG. 54 shows an example of a patient monitoring system, in accordance with at least one aspect of the present disclosure.

FIG. 54 shows an example of a patient monitoring system, including patient wearable sensing systems, a controllable device, and a computing system or a computing device (e.g., a surgical hub), in accordance with at least one aspect of the present disclosure. Patient monitoring system 25251 may include (e.g., as shown by example in FIG. 54) first wearable sensing system 25253, second wearable sensing system 25254, third wearable sensing system 25255, controllable device 25256, and computing system or computing device (e.g., a surgical hub) 25258.

As discussed in various examples herein, a patient (e.g., patient 25252) may wear one or more devices with one or more sensors (e.g., first wearable sensing system 25253, second wearable sensing system 25254, and/or third wearable sensing system 25255) pre-, in-, and/or post-surgery to measure one or more patient biomarkers (e.g., VO2 max, respiration rate, heart rate variability (HRV), physical reaction(s) such as coughing and/or sneezing, oxygen saturation, respiratory rate, respiratory phase, diaphragmatic muscle tone, temperature, sweat, ECG, hydration state, tissue perfusion). Wearable sensing systems may include sensors that may be used to sense, monitor, or measure one or more patient biomarkers on and/or in any portion of a human body (e.g., wrist, arm, chest, waist, leg, foot, head, mouth) as discussed in FIGS. 11A-11D and FIGS. 7B-7D. For example, wearable sensor 25253 may be worn on the chest (e.g., near the clavicle), for example, to monitor one or more patient biomarkers (e.g., patient temperature, heart rate, HRV, coughing, sneezing, etc.). Second wearable sensor 25254 may be worn as a chest strap, for example, to monitor one or more of respiration information (e.g., respiratory rate, respiratory phase, such as inhale or exhale), diaphragmatic muscle tone (e.g., to provide a predictive value, such as ahead of a cough), temperature, heart rate, HRV, coughing, sweat, electrocardiogram (ECG), electromyography (EMG), mechanomyogram (MMG), hydration state, tissue perfusion, and/or other patient biomarkers. Third wearable sensing system 25255 is shown as a wrist strap (e.g., a watch or bracelet), which may be used to monitor, one or more patient biomarkers (e.g., heart rate, HRV, coughing, sweat, ECG, hydration state, tissue perfusion, and/or other patient biomarkers).

As discussed in various examples herein, one or more controllable devices (e.g., controllable device 25256) may be automatically and/or manually controlled by one or more recommendations generated based (e.g., at least in part) on one or more patient biomarkers monitored pre-, in- and/or post-surgery. The controllable device may also act as a sensing device that is communicatively coupled with the computing system or the surgical hub. In the example shown in FIG. 54, controllable device 25256 may be a portable pump controlled by a control program. Controllable device 25256 may control pressure or airflow (e.g., suction) in chest tube 25257 inserted into the chest of patient 25252 (e.g., to reduce pressure on an organ such as a lung and drain air, blood, or fluid from the pleural space around a lung). Controllable device 25256 and/or chest tube 25257 may incorporate one or more sensors and/or sensing systems (e.g., not shown). For example, one or more (e.g., in line sensors) in controllable device 25256 and/or chest tube 25257 may measure air flow or air volume in chest tube 25257 over time. One or more patient biomarkers may be measured and analyzed (e.g., to determine a phase of respiration) for use in regulating airflow in chest tube 25257. A control program in controllable device 25256 may be configured to modulate a suction level in chest tube 25257 connected to patient 25252, for example, based on the detected phase of respiration.

As discussed in various examples herein, one or more hubs (e.g., hub 25258) may be in communication with one or more of sensing systems (e.g., first, second and third sensing systems 25253, 25254, 25255) and one or more controllable devices (e.g., controllable device 25256), mobile device 25260, etc. In an example, the mobile device 25260 may perform all the functions of a sensing system and/or act as human interface device (HID) as described herein. In an example, the mobile device 25260 may be a computing device that may be an equivalent of the computing device 25258, as described herein in FIG. 2B. Hub 25258 may be configured to perform one or more of the following: receive and process patient biomarker measurements from one or more sensing systems, determine patient biomarker measurement thresholds, generate (e.g., patient-specific) predictions regarding potential complications, generate and transmit notifications and/or recommendations (e.g., to a patient sensing system 25255 or a mobile device 25260) for displaying to a patient and/or to controllable device 25256 to operate controllable device(s), and/or the like. For example, hub 25258 may receive measurement data associated with patient biomarker(s) from first, second and third sensing systems 25253, 25254, 25255, generate predicted complications to monitor patient for, determine patient monitoring thresholds for recovery milestones and/or complications, analyze patient biomarker measurements relative to the thresholds for the predicted complications and/or recovery milestones, generate and send (e.g., wirelessly transmit) recommendations, such as instructions to display to a patient or HCP and/or a control program or adjustments thereto for (e.g., patient specific) operation of controllable device 25256, etc.

Sensing system(s), hub(s), and/or controllable device(s) may be wired or wireless. Wireless sensing systems may communicate wirelessly with one or more other devices, such as one or more other sensing systems, controllable devices, and/or hubs.

As discussed in various examples herein, sensing system(s), hub(s), and/or controllable device(s) may perform one or more of the following operations in one or more procedures/methods that may be executed by one or more processors: take samples/measurements of patient biomarkers, process samples, generate information, transmit information, receive information, analyze information, generate thresholds, execute a patient model to generate predictions, generate recommendations, transmit recommendations, receive recommendations, display recommendations (e.g., to an HCP), select or control pre-, in-, and/or post-surgery device settings, etc.

The example scenario shown in FIG. 54 is one of many possible examples. In various implementations, there may be more or fewer sensing systems, controllable devices, and/or controllers. Although patient 25252 is shown in bed 25259, patient may be in other positions and environments (e.g., seated, standing, walking or otherwise mobile at home, in vehicle) at various times relative to surgery (e.g., pre-, in- and/or post-surgery). For example, patient 25252 may be immobile or mobile in a healthcare facility (e.g., near hub 25258) or away from a healthcare facility (e.g., away from hub 25258), as described in FIGS. 2B and 2C herein. A mobile patient may have one or more mobile devices (e.g., mobile device 25260), one of more sensing systems (e.g., as shown in FIG. 54 as 25253, 25254, 25255) each configured to communicate with the computing device (e.g., a hub or a surgical hub) 25258 (e.g., if hub 25258 is located remote from a mobile patient). For example, a mobile patient may have/carry a mobile device, such as a mobile phone, a wearable sensing system, a controllable device (e.g., controllable device 25256) and/or other device that may be configured with a patient monitoring application executed by a processor in the mobile device. In some examples, mobile device 25260 and a sensing system (e.g., third sensing system 25255) may be incorporated into a device, such as a watch with cellular phone capabilities and sensing system capabilities. The mobile device (e.g., running the patient monitoring application) may be configured to perform one or more of the following: receive and process patient biomarker measurements, determine patient biomarker measurement thresholds, generate and/or receive predictions regarding potential complications, generate, receive, display and/or apply notifications and/or recommendations to a patient and/or controllable device(s), and/or the like. For example, patient 25252 may carry a mobile phone configured (e.g., by executing a patient monitoring application) to receive patient biomarker measurements from first, second and third sensing systems 25253, 25254, 25255, receive predicted complications to monitor patient for, receive patient monitoring thresholds for recovery milestones and/or complications from the computing device 25258, analyze patient biomarker measurements relative to the received thresholds for received complications, send a notification with the patient biomarker measurements to the computing device 25258 if a threshold is reached (e.g., through a wireless telecommunications system and the internet), and receive from the computing device 25258 recommendations, such as instructions to display to a patient and/or a control program or adjustments thereto for operation of controllable device 25256.

In an example, a threshold associated with a patient biomarker may be determined. In some examples, a surgical hub (e.g., and/or a (wearable) sensing system) may include/comprise a processor configured to determine a first threshold associated with a first patient biomarker and/or a second threshold associated with a second patient biomarker. The first threshold and/or the second threshold may be determined, for example, based (e.g., at least) on baseline data associated with a patient. In an example, measurement data associated with a patient biomarker may be received or obtained. For example, the surgical hub (e.g., and/or a (wearable) sensing system) may receive, obtain, or utilize (e.g., from at least one sensing system) a first measurement data associated with the first patient biomarker and a second measurement data associated with the second patient biomarker. In an example, an occurrence of a thoracic post-surgical complication may be detected or predicted. For example, the surgical hub (e.g., and/or a (wearable) sensing system) may detect an occurrence of a thoracic post-surgical complication, for example, by comparing the first measurement data with the first threshold and the second measurement data with the second threshold. A notification (e.g., a real-time notification) may be generated and/or sent to a patient and/or an HCP. For example, the surgical bub (e.g., and/or a (wearable) sensing system) may generate a notification (e.g., a real-time notification) indicating the occurrence of the thoracic post-surgical complication if/when at least one of the first measurement data crosses the first threshold (e.g., for a predetermined amount of time) or the second measurement data crosses the second threshold (e.g., for a predetermined amount of time). The surgical hub (e.g., and/or a (wearable) sensing system) may generate an actionable notification associated with the occurrence of the thoracic post-surgical complication. The surgical hub (e.g., and/or a (wearable) sensing system) may send the notification (e.g., a real-time notification) and/or the actionable notification associated with the occurrence of the thoracic post-surgical complication to the patient or an HCP.

In some examples, a third threshold associated with a third patient biomarker may be determined or obtained. For example, a surgical hub (e g., and/or a (wearable) sensing system) may be configured to receive or obtain a third measurement data associated with the third patient biomarker. The occurrence of the thoracic post-surgical complication may be (e.g., further) detected or predicted, for example, by comparing the third measurement data with the third threshold. The notification (e.g., a real-time notification) may be generated, for example, if/when at least one of the first measurement data crosses the first threshold (e.g., for a predetermined amount of time), the second measurement data crosses the second threshold (e.g., for a predetermined amount of time), or the third measurement data crosses the third threshold (e.g., for a predetermined amount of time).

In some examples, a patient biomarker (e.g., the first patient biomarker, the second patient biomarker, or the third patient biomarker) may be, for example, VO2 Max, a respiration rate, a heart rate variability, a physical reaction, a diaphragmatic muscle tone, or an oxygen saturation, as described herein. In some examples, a threshold (e.g., to generate a notification, perform an analysis, make a determination, identify a complication, and/or the like) for a patient biomarker (e.g., the first patient biomarker, the second patient biomarker, or the third patient biomarker) may be determined based on, for example, one or more of VO2 Max, a respiration rate, a heart rate variability, a physical reaction, a diaphragmatic muscle tone, of oxygen saturation.

Monitoring (e.g., post thoracic surgery monitoring) of patient biomarkers may indicate (e.g., potential or actual thoracic post-surgical) complications, such as, for example, one or more of the following: PAL, a lung collapse (e.g., pneumothorax), pulmonary insufficiency (e.g., limited lung volume), irregular respiration, infection, arrhythmias, residual intrapleural air spaces, postpneumonectomy empyema, bronchopleural fistula, cardiac herniation, lobar gangrene, esophagopleural fistula and/or healing cascade milestones.

A PAL may be monitored and detected, for example, by measuring at least one of the following: an air volume, a respiratory rate, a phase of respiration, and/or the like. In some examples, an analysis of patient biomarker measurement values to one or more thresholds (e.g., via an algorithm, comparison and/or the like) and/or a determination relating thereto may be based on (e.g., may account for) patient-specific data/information, such as a surgical procedure (e.g., lung volume reduction), medication, time period after surgery, etc. For example, one or more thresholds involved in an analysis and/or determination may be adjusted based on patient-specific information, such as pre-surgery, in-surgery, and/or post-surgery generated data/information.

A lung collapse or pneumothorax may be monitored and detected, for example, if/when air leaks into space (e.g., pleural space) between a lung and a chest wall. The air may push on the outside of the lung, which may result in a lung collapse. A pneumothorax may be a complete lung collapse or a partial collapse of a portion of a lung. Pneumothorax may be indicated or detected, for example, by (e.g., common) signs of chest pain, and/or by monitoring one or more patient biomarkers, such as oxygen saturation, blood pressure reduction, and/or heart rate increase. For example, a thoracic post-surgical complication such as a lung collapse or pneumothorax may be predicted or detected based on one or more patient biomarkers reaching one or more (e.g., patient specific) threshold values. A patient biomarker (e.g., first, second and third patient biomarkers) may be, for example, a rate of change in a patient's Oxygen saturation, a rate of change in patient's blood pressure, or a rate of change in patient's heart rate.

Avoidance of a PAL complication may be balanced with avoidance a pneumothorax complication. An increase in suction may (e.g., be used to) remove a building pneumothorax. A leak (e.g., a PAL) may be worsened, for example, by an increase in suction in the pleural space (e.g., to prevent pneumothorax). Reduced suction may reduce stress on a lung (e.g., reduce inducement of a leak), but may allow air buildup (e.g., increasing the likelihood of pneumothorax), where severity may depend on a leak volume or rate.

Referring to the example shown in FIG. 54, a balance between avoiding a PAL and pneumothorax may be implemented, for example, by controlling suction in chest tube 25257. Flow or air volume (e.g., over a time period) in chest tube 25257 may be measured, for example, to determine negative pressure being applied to chest tube 25257. For example, a digital system (e.g., controllable device 25256) may (e.g., be used to) measure the air flow or air volume over a time period. Chest tube flow or air volume may be provided, for example, by a flow meter in line with chest tube 25257 (e.g., inside controllable device 25256). A balance may be achieved between suction of air and a leak rate or leak volume. Leak severity may be assessed (e.g., analyzed, detected), for example, by monitoring (e.g., analyzing or coupling) air flow or air volume (e.g., over a time period) in chest tube 25257 with one or more patient biomarkers, such as respiratory rate and a phase of respiration. Suction may be modulated, for example, based on a detected respiratory phase. Respiration phases may include inhaling and exhaling. Respiratory phases may be determined, for example, by monitoring diaphragmatic muscle tone. Diaphragmatic muscle tone may be monitored, for example, by a respiratory muscle mechanomyogram (MMG) generated by mechanomyography, e.g., to non-invasively assess mechanical activation of inspiratory muscles of a lower chest wall, and/or by electromyographic (EMG) monitoring. MMG and EMG may be measured, for example, using skin patches or a tocodynamometer-like belt (e.g., 25254 of FIG. 54).

An infection may be monitored and detected, for example, by monitoring at least one of the following patient biomarkers: core body temperature, heart rate, heart rate variability, sweat rate, coughing, bacteria in respiratory tract, peripheral temperature, circadian rhythm, and/or bacterial load in the lungs, as described herein. An arrhythmia is a problem with the rate or rhythm of heartbeat (e.g., heart beats too quickly, too slowly, and/or with an irregular pattern). In an example of heart rate and variability, an irregular heart function may indicate a reduced blood supply to the body, which may slow recovery.

A baseline may be established for each of one or more patient biomarkers. For example, a patient may wear one or more sensing devices with one or more sensors (e.g., first, second and/or third sensing systems 25253, 25254, 25255 shown in FIG. 54) pre-, in-, and/or post-surgery to measure one or more patient biomarkers (e.g., VO2 max, respiration rate, heart rate variability, physical reaction(s) such as coughing and/or sneezing, oxygen saturation). In some examples, pre-surgery patient biomarker monitoring may (e.g., be used to) establish a baseline for one or more patient biomarkers (e.g., for VO2 max, respiration rate, heart rate variability, physical reaction(s) such as coughing and/or sneezing, oxygen saturation). A baseline for one or more patient biomarker values may be compared to (e.g., real time) measured values (e.g., for VO2 max, respiration rate, heart rate variability, physical reaction(s) such as coughing and/or sneezing, oxygen saturation), for example, to monitor patient biomarkers in-surgery and post-surgery (e.g., during recovery). A threshold value may be obtained based on a baseline value associated with a patient biomarker. Comparison of measured patient biomarker values to baseline values and/or to threshold values (e.g., absolute value of measured value exceeds a threshold value) and/or comparison of derived metrics (e.g., difference/change between measured value and baseline value, normalized value, etc.) to a threshold value may (e.g., be used to) monitor a patient (e.g., detect one or more patient states), such as, for example, whether the patient reached one or more recovery milestones, whether the patient may be developing or has developed one or more complications, and/or other states (e.g., anxiety, physical activity, and/or other physiologic actions). One or more alarms and/or notifications may be based on (e.g., triggered by) one or more detected patient states. Measurement data/information may be obtained or collected from one or more sensing systems. A sensing system may include, for example, an environmental sensing system (e.g., a surgical sensing system with surgical sensors that generate sensor data during surgery on a patient), a patient sensing system, a personal sensing system, etc. For example, a surgical device/instrument (e.g., a surgical stapler, energy device) may have one or more environmental and/or personal/patient sensing systems with one or more sensors and/or one or more surgical device settings, which may be (e.g., automatically and/or manually) selected, for example, based on sensed data, processed data, feedback, recommendations, etc. A surgical device/instrument may be utilized in one or more surgical tasks, surgical procedures, and/or impending surgical actions. A surgical device/instrument may contextualize data associated with a surgical event, for example, to receive or generate a context action. A (e.g., personal) sensing system may include one or more wearable sensing systems (e.g., patient wearable sensing systems or patient sensing systems). A wearable sensing system may include, for example, a patient wearable sensing system, a health care professional (HCP) wearable sensing system, etc. A wearable sensing system may include one or more wearable devices. A wearable device may include one or more sensors and/or one or more sensing systems. A (e.g., patient) wearable sensing system may include one or more sensors. A patient wearable sensing system or one or more sensors (e.g., embedded) in a patient wearable sensing system may be used to measure one or more parameters (e.g., vital signs). Measured/measurement data may include, for example, pre-surgical measurement data, in-surgical measurement data, and/or post-surgical measurement data. Measured/measurement data may be, for example, raw data.

Measured/measurement data may be processed and/or transformed, for example, into (e.g., to determine) one or more patient biomarkers. An analysis may be performed, for example, using one or more patient biomarkers and/or measured/measurement data. Measurement data/information and/or patient biomarkers (e.g., detected or determined before, during, and/or after a surgical procedure) may be used to establish one or more thresholds for one or more patient biomarkers (e.g., to perform one or more analyses, make one or more determinations and/or recommendations). A patient biomarker is a measurable biological characteristic. A patient biomarker may be indicative of a physiologic property or a biologic state. A patient biomarker may be determined based on one or more other patient biomarkers. A biomarker may include, for example, a patient biomarker, a health care professional (HCP) biomarker, etc. A biomarker may include, for example, one or more values with or without metadata. Patient biomarker values may vary (e.g., over time, such as before, during, and/or after a surgical procedure). Patient biomarkers may include, for example, one or more of the following: a maximum amount of oxygen a person can utilize or consume (e.g., during exercise) (VO2 Max), respiration rate, heart rate variability, physical reaction (coughing and sneezing), and oxygen saturation, electroencephalogram (EEG), electrocardiogram (ECG or EKG), rapid eye movement sleep (REM sleep or REMS), gastrointestinal (GI) motility, etc.

A threshold value associated with a patient biomarker may be based on (e.g., established and/or adjusted), for example, one or more of the following: patient characteristics, a time of day, a time relative to surgery, an environment, biomarker measurements before, during, and/or after surgery, surgical details, baseline values etc. A device or sensing system may determine or receive one or more thresholds (e.g., from a hub). A hub may be used interchangeably with a computing system as described herein. A hub may include a surgical-related computing system. A hub or a surgical hub may include, for example, one or more of the following: a computing device, a server (e.g., a cloud server), a tablet, a smartphone, etc. A sensing system or a wearable sensing system may (e.g., selectively or routinely, such as periodically) process sensed/measured data (e.g., to generate one or more biomarkers), perform an analysis of sensed data and/or one or more biomarkers (e.g., based on one or more thresholds), and/or send/transmit (e.g., to a hub) sensed data, one or more biomarkers, and/or information (e.g., results, determinations) based on one or more analyses.

One or more thresholds may be processed, for example, based on (e.g., created relative to and/or used against) one or more baseline records. For example, threshold processing (e.g., creation and/or use) may account for surgical information (e.g., the amount of lung volume reduction in-surgery) that may result in an adjustment to a pre-surgical baseline. A measured biomarker value may be compared with a threshold value associated with a patient biomarker (e.g., based on an adjusted baseline) to determine recovery milestones, for example, to track healing progress and/or indication(s) of one or more complications. A baseline value for a biomarker may be created (e.g., and/or adjusted), for example, before, during and/or after surgery.

Figure 55:
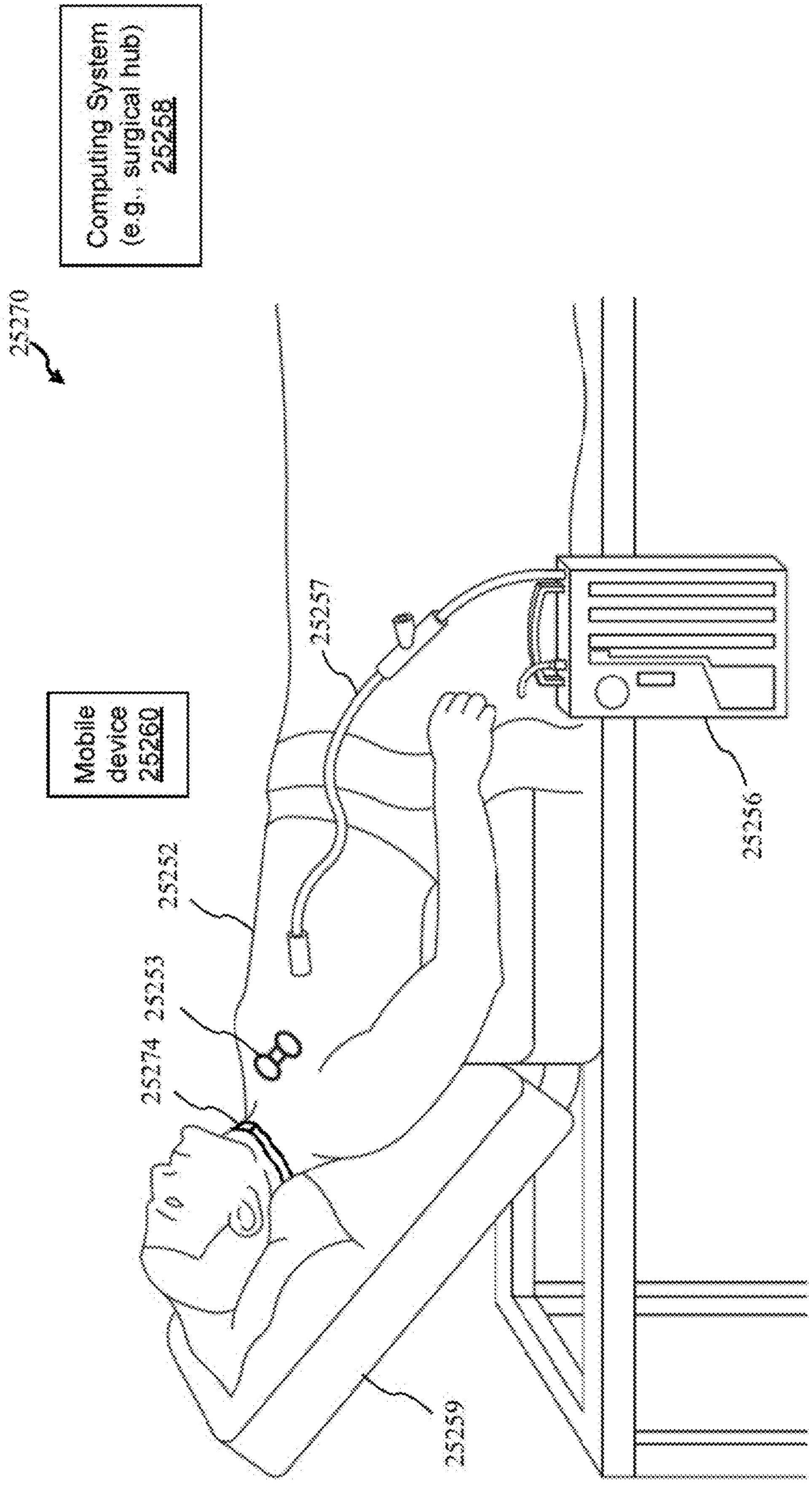
FIG. 55 shows an example of a patient wearing a patient wearable sensing system for detecting esophageal motion, in accordance with at least one aspect of the present disclosure.

A patient biomarker may be monitored by a sensing system. The sensing system may be a patient wearable sensing system. The sensing system may be communicatively coupled with a computing device or a hub or a surgical hub. In an example, a sensing system (e.g., as shown in FIGS. 54 and 55) may comprise one or more processors configured (e.g., by executing instructions in an executable program) to (e.g., at least) perform a method to receive (e.g., from a hub or a surgical hub), a first threshold associated with a first patient biomarker and/or a second threshold associated with a second patient biomarket. In an example, a post-surgical complication may be detected or predicted based on measurement data associated with the one or more of a set of patient biomarkers crossing respective threshold value(s). For example, a sensing system (e.g., via the one or more processors executing instructions) may be configured to receive a request for detecting a post-surgical complication based on at least one of a first measurement data associated with the first patient biomarker crossing a first threshold and/or a second measurement data associated with the second patient biomarker crossing a second threshold (e.g., for a predetermined amount of time). The sensing system (e.g. via the one or more processors executing instructions) may be configured to measure the first measurement data associated with the first patient biomarker and the second measurement data associated with the second patient biomarker. The sensing system (e.g., via the one or more processors executing instructions) may be configured to monitor the first measurement data and the second measurement data (e.g., in real-time), for example, by comparing each of the first measurement data and the second measurement data with the first threshold and the second threshold, respectively. The sensing system (e.g., via the one or more processors executing instructions) may be configured to generate a notification (e.g., real-time notification) indicating an occurrence of the post-surgical complication, for example, if/when the first measurement data crosses the first threshold, and/or if/when the second measurement data crosses the second threshold (e.g., for a predetermined amount of time). The sensing system (e.g., via the one or more processors executing instructions) may be configured to send the notification (e.g., to the surgical hub) indicating the occurrence of the post-surgical complication.

In some examples, the sensing system (e.g., via the one or more processors executing instructions) may be configured to determine a severity level associated with the thoracic post-surgical complication. In an example, the severity level may be determined based on a measurement data. A notification type associated with a notification (e.g., a real-time notification) may be determined based on the severity level. The sensing system (e.g., via the one or more processors executing instructions) may send the real-time notification and/or the severity level, for example, to a display unit for displaying to a patient, an HCP, etc. In an example, in some examples, the sensing system (e.g., via the one or more processors executing instructions) may be configured to send the notification and the severity level to a display unit for displaying to a patient if the severity level is low, and a display unit for displaying to an HCP if the severity level is high.

In various examples, the post-surgical complication may be any type of complication, such as a PAL. The first patient biomarker or the second patient biomarker may be any biomarker, such as one of the following: a blood lactate, a sweat lactate, an indication of GI motility, a heart rate variability, a blood pH value, a sweat pH value, etc.

A threshold (e.g., the first threshold or the second threshold) may be adjusted based on a context. For example, the sensing system (e.g., via the one or more processors executing instructions) may be configured to determine a context based at least on: a surgery recovery timeline, a set of situational attributes, or a set of environmental attributes or environmental aspects as described herein. An environment may be, for example, a controlled environment or an uncontrolled environment. The set of situational attributes may comprise, for example, a physical mobility state, a sleeping state, etc.

Patient biomarkers may be monitored pre-, in- and/or post-surgery. Post-surgery patient biomarker values may be monitored, for example, based on post-surgery data/information obtained/received from one or more sensors (e.g., in one or more sensing systems). Post-surgery measurement data/information (e.g., from sensors embedded in wearable sensing systems) may be collected (e.g., received, processed, and/or analyzed) to monitor or track one or more patient biomarkers. Data/information from one or more sensors may be measured, for example, instantaneously and/or tracked over a period of time. Post-surgery measurement data/information from the sensors may be measured or tracked in a controlled environment, for example, under supervision and/or at a location of an HCP, for example, as described in FIG. 2B herein. Post-surgery measurement data/information (e.g., from sensors) may be measured or tracked, for example, in an uncontrolled environment, such as a patient's (e.g., fixed or variable) location (e.g., house, vehicle, store) and/or while performing one or more (e.g., daily routine) tasks, such as eating, sleeping, walking, exercising, etc. as described in FIG. 2C herein.

Post-surgery measurement data/information from one or more sensors associated with a patient biomarker may be compared with respective threshold values associated with the patient biomarker. Post-surgery measurement data/information values achieving (e.g., equaling or exceeding) the (e.g., minimum) one or more thresholds within a time period (e.g., a predetermined time period) may indicate a progression to recovery. A failure to achieve one or more (e.g., established or defined) thresholds within a time period may indicate a slower recovery and/or one or more complications. One or more (e.g., relevant) healthcare providers (HCPs) may be notified about a failure to achieve one or more thresholds. Information and/or data provided (e.g., using one or more notifications) may enable (e.g., treatment) planning (e.g., by an HCP). For example, an HCP may plan alternative exploration and/or mitigation of a situation indicated by measurement data/information.

One or more recovery metrics may be tracked, for example, based on monitored post-surgical patient biomarkers. Complication development or progression (e.g., an advancing, stagnant or receding complication) may be tracked. For example, an esophageal stricture and/or other complications (e.g., non-lung complication(s) may be tracked (e.g., after an esophageal surgical procedure). Post-surgical monitoring may be performed (e.g., implemented) using one or more sensing systems (e.g., each with one or more sensors) to track various recovery milestones and/or complications. In some examples, recovery milestones may be used to detect the possibility (e.g., likelihood) of complications arising, developing, progressing, receding, and/or the like. Complications may include, for example, esophageal leakage or esophageal stricture.

FIG. 55 shows an example of a sensing system 25270 to predict or detect complications, such as esophageal leakage or esophageal stricture. FIG. 55 shows an example of a patient wearable sensing system for detecting esophageal motion, in accordance with at least one aspect of the present disclosure. Patient monitoring system 25271 may include (e.g., as shown by example in FIG. 55) first wearable sensing system 25253, fourth wearable sensing system 25274, controllable device 25256, and hub 25258.

FIG. 55, compared to FIG. 54, shows an additional and/or alternative sensing system, monitored patient biomarkers, and complication prediction or detection. To avoid repetition, discussion of FIG. 54 may be incorporated into discussion of FIG. 55 and vice versa. Post-surgery data/information may be collected by monitoring one or more (e.g., wearable) sensors for one or more patient biomarkers. Fourth wearable sensing system 25274 may monitor one or more patient biomarkers, whose measurements may be used to determine esophageal motion, which may (e.g., in turn) be used to detect one or more complications, such as esophageal leakage and/or an esophageal stricture. Muscle function and mechanics may be monitored/tracked (e.g., non-invasively), for example, by measuring vibrations produced in skeletal muscles, which may be referred to as mechanomyography. Mechanomyography may be implemented in one or more (e.g., wearable) sensors (e.g., a sensor array). Esophageal motion may be monitored, for example, by one or more sensors (e.g., in one or more devices) worn by a patient (e.g., on or near a patient's neck).

Fourth wearable sensing system 25274 may be worn, for example, around a patient's neck. Fourth wearable sensing system 25274 may monitor esophageal motion, for example, by performing mechanomyography on patient 25252. In some examples, first wearable sensing system 25253 may monitor one or more patient biomarkers that support detection of one or more complications, such as esophageal leakage or an esophageal stricture.

Data/information sensed and generated by first and/or fourth sensing systems 25253, 25274 may be tracked over a period of time, e.g., for hours or days during a post-surgical period of time. Data/information may (e.g., be used to) track esophageal stricture and/or other non-lung complications (e.g., infection, esophagopleural fistula). Abnormal waveforms of muscle motion (e.g., esophageal motion), which may be determined during analysis of one or more measured patient biomarkers, may indicate, for example, development of a stricture (e.g., during a healing process following surgery). Information/measurement data (e.g., collected from one or more wearable sensors, such as first and/or fourth sensing systems 25253, 25274) may be used (e.g., analyzed) to determine, for example, whether additional surgery may be required, whether to change the viscosity of food, whether to change or add to physical therapy and/or occupational therapy, etc. No action or one or more actions may be recommended (e.g., and taken automatically and/or manually), for example, based on one or more determinations resulting from one or more analyses of patient monitoring data/information provided by, for example, first and/or fourth sensing systems 25253, 25274. One or more notifications (e.g., real-time notifications) may be generated and/or sent (e.g., to an HCP, patient, and/or controllable device(s)), for example, based on one or more recommendations.

In some examples, hub 25258 may be configured to perform one or more of the following: receive and process patient biomarker measurement data from one or more sensing systems (e.g., first and/or fourth sensing systems 25253, 25274), determine patient biomarker measurement thresholds, generate (e.g., patient-specific) predictions regarding potential complications, generate and/or transmit notifications and/or recommendations for displaying to a patient and/or to controllable device 25256 to operate controllable device(s), and/or the like. For example, hub 25258 may receive patient biomarker measurement data from first and/or fourth sensing systems 25253, 25274, generate predicted complications to monitor patient for, determine patient monitoring thresholds for recovery milestones and/or complications, analyze patient biomarker measurements relative to the thresholds for the predicted complications and/or recovery milestones, generate and send (e.g., wirelessly transmit) recommendations, such as instructions to display to a patient or HCP and/or a control program or adjustments thereto for (e.g., patient specific) operation of a controllable device, etc.

In some examples, a patient biomarker monitoring/analysis system may be configured to communicably couple to a surgical hub. The surgical hub may be configured to communicably couple to one or more in-surgery and/or post-surgery (e.g., recovery) devices that may provide (e.g., display) one or more actionable notifications (e.g., to a patient and/or HCP). A patient biomarker monitoring/analysis system may comprise, for example: a processor and a memory coupled to the processor. The memory may store instructions that, when executed by the processor, cause the patient biomarker monitoring/analysis system to perform a method or procedure (e.g., as follows). A patient biomarker monitoring/analysis system may receive data/information indicative of one or more actions (e.g., recommendable actions). For example, the data/information may include one or more actions that may be taken after a surgical procedure (e.g., available actions may be based on general and/or specific details of one or more surgical procedures implemented on a patient). The patient biomarker monitoring/analysis system may receive patient biomarker data/information associated with the patient. The patient biomarker monitoring/analysis system may analyze the available or known actions and the patient's biomarker monitoring data/information to determine which action(s) may be optimal or suboptimal for the patient (e.g., to reduce the likelihood or impact of and/or avoid one or more potential complications). The patient biomarker monitoring/analysis system may generate an actionable notification indicating one or more selected actions (e.g., procedural steps, such as one or more exercises). The patient biomarker monitoring/analysis system may transmit the one or more selected actions, for example, to one or more devices that may provide to a patient and/or HCP (e.g., display at text, play as audio and/or video instruction).

A notification (e.g., an actionable notification) may be reported, for example, in real-time (e.g., real-time reporting). A notification (e.g., an actionable notification) may indicate, for example, a thoracic post-surgery complication or the achievement of a thoracic post-surgery milestone. Reports may be generated, provided, and/or received (e.g., by an HCP) periodically (e.g., hourly, daily, weekly) and/or aperiodically (e.g., ad hoc, on demand by sender and/or recipient, based on emergency or threshold detection, and/or the like). A report may include, for example, one or more values for one or more patient biomarkers, one or more results of one or more analyses performed based on one or more patient biomarker values, thresholds, baselines, etc., one or more threshold values, one or more baseline values, etc. A report may include, for example, data associated with an indication, such as data indicating that a thoracic post-surgery complication has been detected. A report may include, for example, data associated with therapy tracking, e.g., indicating patient therapy, whether a patient is performing therapy, the frequency of performance, whether the therapy is being performed correctly, etc.

An actionable notification may be selected or changed, modified or updated from a default or existing action (e.g., based on monitoring and/or analyses of one or more patient biomarkers), for example, to enable a patient or an HCP to perform at least one recommended action. The type of actionable notification may depend on the patient biomarker measurement(s) and/or processing (e.g., based on baseline value(s), types of notifications available). An actionable notification may include, for example, patient exercises.

An actionable severity level associated with the detected post-surgical thoracic complication may be determined. For example, the hub or the computing device or system may determine an actionable severity level associated with a detected or predicted PAL. A notification may be sent to the patient and/or the HCP indicating a potential thoracic post-surgical complication and the associated actionable severity level. The type and/or content of a notification may be determined based on the actionable severity level. For example, when the detected complication is determined to be associated with low-risk actionable severity level, the computing device or system or the hub may generate a real-time notification to a device associated with the patient. When the detected complication is determined to be associated with high-risk actionable severity level, the computing device or system may generate a real-time notification to a device associated with the patient and a device associated with an HCP. In an example, when the detected complication is determined to be associated with low-risk actionable severity level, the computing system may generate a real-time notification indicating the medical name of the complication and of the patient biomarker that crossed the corresponding threshold(s). When the predicted or detected complication is determined to be associated with high-risk actionable severity level, the computing system may generate a real-time notification indicating a recommended course of action. In some examples, an actionable notification may be associated with the occurrence of a thoracic post-surgical complication. An actionable notification may be selected or otherwise determined, for example, to assist a patient and/or an HCP with efforts to reduce or avoid one or more post-surgical complications. An actionable notification may, for example, support (e.g., enable) a patient and/or an HCP to perform at least one recommended action. For example, a recommended action may include (e.g., provide, such as for display) steps for performing one or more deep breathing exercises.

In some examples, a patent's inhale and exhale patterns may be monitored, for example, while performing a deep breathing exercise following a lung procedure. The deep breathing exercise may reduce the risk of pneumonia. A patient may be guided to perform a deep breathing exercise, for example, by monitoring chest wall motion. For example, a patient may perform a breathing exercise by inhaling and holding his/her breath for 3-5 seconds, repeating the exercise multiple times (e.g., 10-15 repetitions). A patient may be prompted to perform an exercise (e.g., periodically, at set intervals, such as once per hour. Patient compliance may be tracked, for example, by monitoring patient biomarkers.

Patient progress and compliance with post-operative protocols may be indicated to hospital caretakers, for example, by tracking the number, frequency, and duration of walks (e.g., and associated cardio and/or respiratory metrics).

Patient biomarkers may correlate to physiological states of a patient. Patient biomarkers may correlate to complications. Patient biomarkers may correlate to recovery milestones. Patient biomarkers may correlate to (e.g., map to) other patient biomarkers. For example, a first patient biomarker may predict or indicate the existence or value of a second patient biomarker (e.g., and/vice versa). Patient biomarkers may correlate to surgical procedures on one or more organs or tissues. For example, relevant patient biomarkers may be different in various portions of a surgical procedure.

Figure 56:
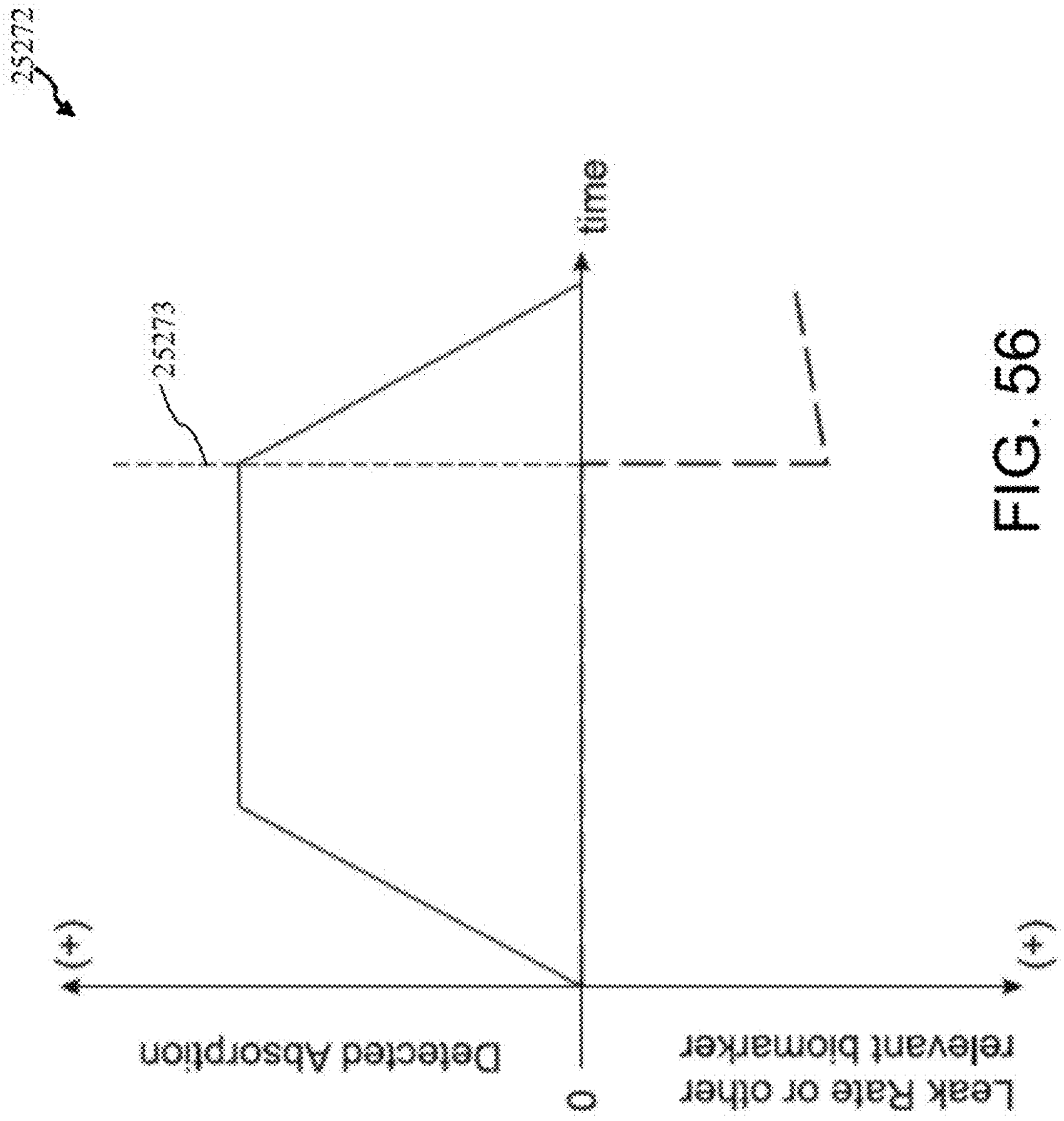
FIG. 56 shows an example relationship between a patient biomarker for bioabsorbable material with a patient biomarker indicative of healing.

FIG. 56 illustrates an example of a link between a patient biomarker for a bioabsorbable material and a patient biomarker indicative of healing. FIG. 56 shows an example of tracking changes in one or more patient biomarkers and identifying a link, e.g., by comparing tracked changes. A prediction may be based on a link or relationship (e.g., a link may support a prediction). For example (e.g., with respect to a prediction of recovery and/or complication), detection of a first patient biomarker may indicate the presence of a second patient biomarker and/or vice versa. In some examples, one or more patient biomarkers for bioabsorbable material may be linked with one or more patient biomarkers indicative of healing. The rate of detected absorption of a bioabsorbable material may provide an indication of an air leak rate or other relevant patient biomarker. For example, the rate of absorption of a bioabsorbable material (e.g., tracked by one or more patient biomarkers) may increase, remain the same and/or decrease or degrade (e.g., slow down). Comparative graph 25272 shows a relationship between multiple patient biomarkers as an example of determining (e.g., by measuring) a first patient biomarker (e.g., a detected absorption or resorbing rate) and determining (e.g., by a link or relationship) a second patient biomarker (e.g., a leak rate or other relevant patient biomarker) and/or vice versa. In some examples, a sealant (e.g., to avoid a leak) may degrade before the occurrence of full or complete healing, which may impact a relationship. As shown by example in FIG. 56, a decreasing absorption rate of a bioabsorbable material may be an indication of slow healing and/or a complication (e.g., an increasing leak rate with a potential for a PAL). For example, as shown in FIG. 56 beginning at time 25273, the leak rate or other patient biomarker value may increase if/when the detected absorption rate decreases, or vice versa.

Surgical procedural operations (e.g., steps) may correlate to one or more (e.g., relevant) patient biomarkers (e.g., post-surgery patient biomarkers). For example, measurement data and/or information generated (e.g., received, collected, processed, and so on) from monitoring one or more (e.g., post-surgical) patient biomarkers may be correlated with one or more surgical procedural operations (e.g., thoracic surgical procedure steps). In an example, a (e.g., thoracic) surgical procedure may include a dissection of parenchyma, a transection of arteries and/or veins, a transection of parenchyma, and a dissection of lymph node. A correlation (e.g., a relationship mapping) may be established between each portion (e.g., each operation) of a (e.g., thoracic) surgical procedure (e.g., dissection of parenchyma, transection of arteries and/or veins, transection of parenchyma, and dissection of lymph node) with one or more corresponding (e.g., post-surgical) patient biomarkers.

Figure 57:
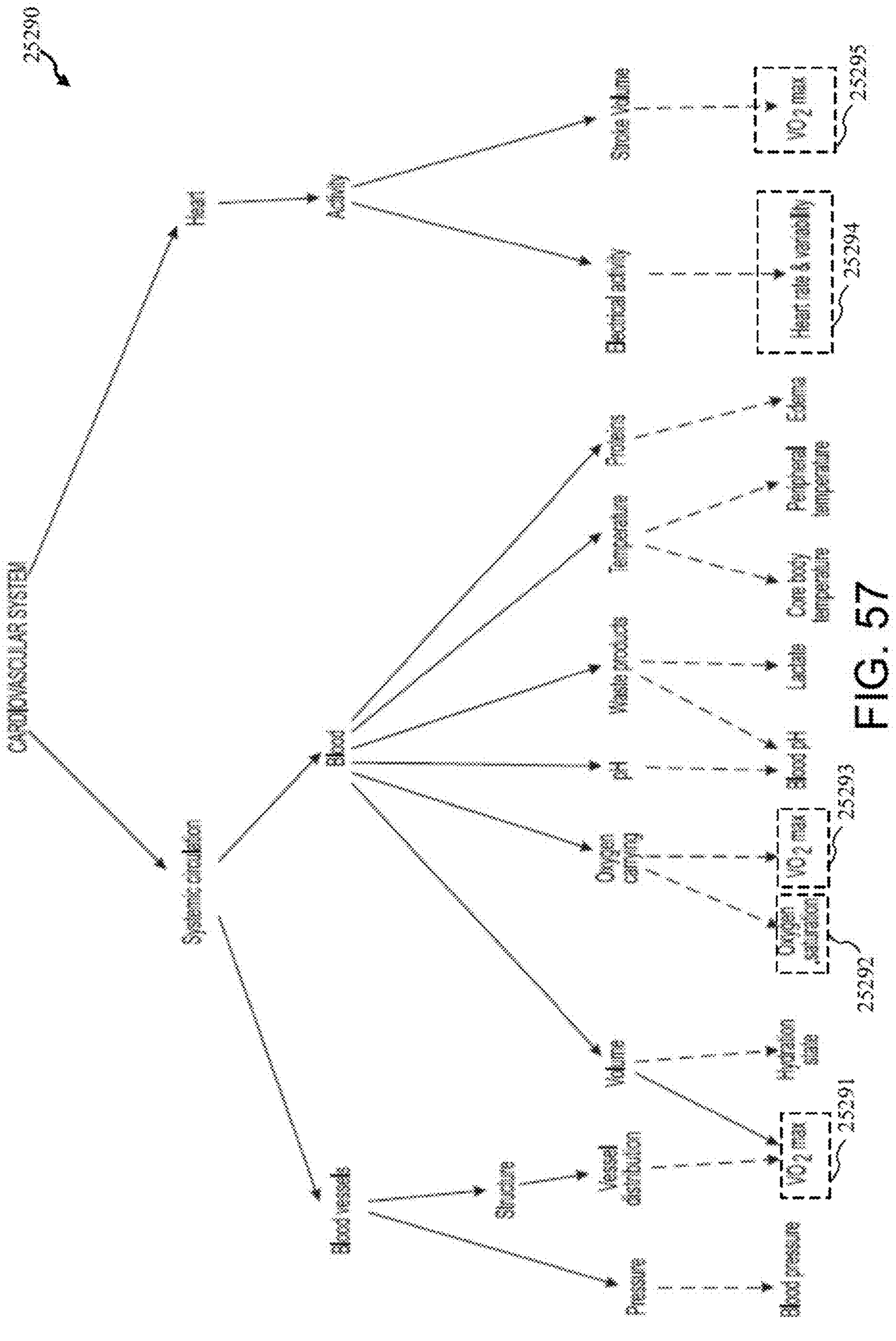
FIG. 57 illustrates example relationships between patient biomarkers relevant to the cardiovascular system that may be used to detect post-thoracic complications or milestones.
Figure 58:
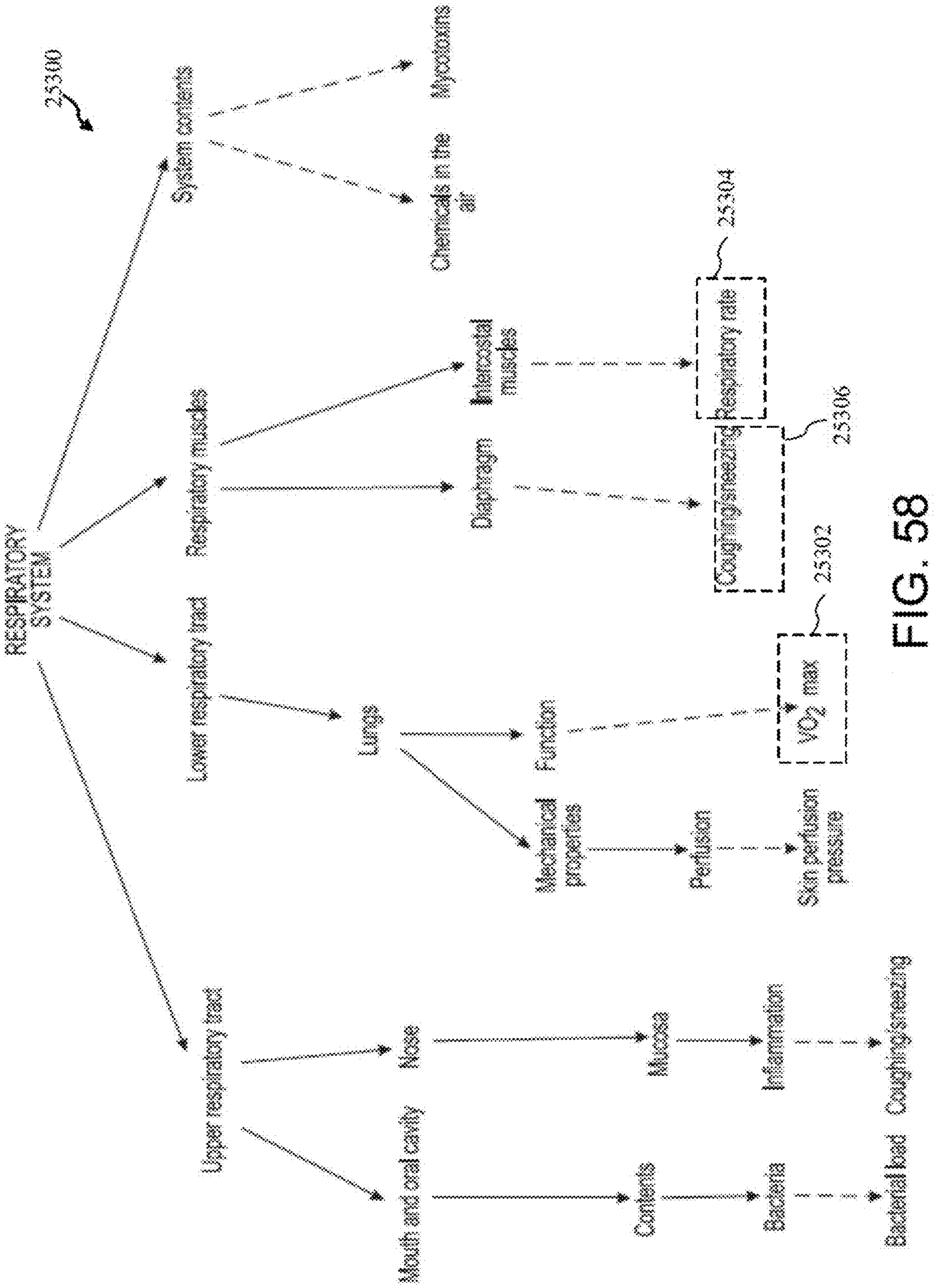
FIG. 58 illustrates example relationships between patient biomarkers relevant to the respiratory system that may be used to detect post-thoracic complications or milestones.

FIGS. 57 and 58 illustrate examples of relationships between patient biomarkers in the respiratory system and the cardiovascular system, respectively. FIG. 57 illustrates example relationships between patient biomarkers relevant to the cardiovascular system that may be used for detecting and/or predicting post-thoracic complications (e.g., prolonged air leaks) or milestones. In an example, one of more of the following patient biomarkers associated with the cardiovascular system 25290 may be measured. VO2 Max 25291, 25293, and 25295, heart rate variability (HRV) 25294, Oxygen saturation 25292 could be measured for detecting or predicting a complication (e.g., a prolonged air leak). As illustrated in FIG. 57, the VO2 Max 25295 may provide an indication of heart activity (e.g., stroke volume). VO2 Max 25291 may provide an indication of systemic circulation (e.g., blood volume and/or blood vessel distribution). VO2 Max 25293 may provide an indication of Oxygen carrying capacity of blood, HRV 25294 may provide an indication of heart activity (e.g., electrical heart activity). Oxygen saturation 25292 may provide an indication of Oxygen being carried in blood. As described herein, a combination of measurement data associated with these patient biomarkers may be used for detecting and/or predicting thoracic post-surgical complications (e.g., prolonged air leaks) and/or milestones by comparing the measurement data against the baseline records while accounting for the amount of lung volume reduction and compared against key recovery milestones to track healing progress or arising of complications.

FIG. 58 illustrates example relationships between patient biomarkers relevant to the respiratory system 25300. One or more patient biomarkers shown in FIG. 58 may be used to detect post-thoracic complications (e.g., prolonged air leaks) or recovery milestones, as described herein. In an example, one of more of the following patient biomarkers associated with the respiratory system 25300 may be measured. VO2 Max 25302, respiration rate 25304, physical reaction (coughing and sneezing) 25306 could be measured for detecting or predicting a complication (e.g., a prolonged air leak). As illustrated in FIG. 58, the VO2 Max 25302 may provide an indication of lung function related to the lower respiratory tract of the respiratory physiological system. Coughing/sneezing 25306 may indicate the state of respiratory muscles (e.g., the diaphragm). Respiratory rate 25304 may indicate the state of intercostal respiratory muscles of the respiratory physiological system. A combination of measurement data associated with these patient biomarkers may be used for detecting and/or predicting thoracic post-surgical complications (e.g., prolonged air leaks) and/or milestones by comparing the measurement data against the baseline records while accounting for the amount of lung volume reduction and compared against key recovery milestones to track healing progress or arising of complications.

In an example, thoracic post-surgical complications and/or milestones may be detected and/or predicted using measurement data associated with the patient biomarkers relevant to cardiovascular physiological system as shown in FIG. 57 and the patient biomarkers relevant to the respiratory physiological system as shown in FIG. 58.

FIG. 59 shows example correlation between relevant patient biomarkers and thoracic surgical procedural steps 25309. As illustrated in FIG. 59, a set of patient biomarkers may correlate to surgical procedures and/or a step thereof. For example, a parenchyma dissection step of a thoracic surgical procedure may be correlated with one or more (e.g., post-surgery) patient biomarkers, such as blood pressure. Surgical instruments associated with a parenchyma dissection step of a thoracic surgical procedure may include, for example, one or more of the following: a monopolar bovie, a harmonic scalpel, and/or an advanced bipolar radio frequency (RF) energy instrument. A step of a procedure may be associated with one or more outcomes (e.g., physiological states). An outcome related to a parenchyma dissection step of a thoracic surgical procedure may include, for example, hemostasis. The occurrence of hemostasis (e.g., due to dissection of parenchyma during a thoracic surgical procedure) may be monitored (e.g., and determined), for example, by measuring and/or monitoring a patient's blood pressure (e.g., in-surgery, during a post-surgical procedure, and/or during post-surgery monitoring).

A transection of arteries and/or veins step of a thoracic surgical procedure may be correlated with one or more (e.g., post-surgery) patient biomarkers, such as blood pressure, tissue perfusion pressure, edema, arterial stiffness, collagen content and/or thickness of connecting tissue. Surgical instruments associated with an artery and/or vein transection step of a thoracic surgical procedure may include, for example, one or more of the following: a harmonic scalpel, an advanced bipolar RF energy instrument, and/or a stapler. A thoracic surgical procedure step may be associated with one or more outcomes (e.g., physiological states). An outcome related to an artery and/or vein transection step of a thoracic surgical procedure may include, for example, hemostasis. The occurrence of hemostasis (e.g., due to transection of an artery and/or vein during a thoracic surgical procedure) may be monitored (e.g., and determined), for example, by measuring and/or monitoring blood pressure, tissue perfusion pressure, edema, arterial stiffness, collagen content, and/or thickness of connecting tissue (e.g., in-surgery, during a post-surgical procedure, and/or during post-surgery monitoring).

A parenchyma transection step of a thoracic surgical procedure may be correlated with one or more (e.g., post-surgery) patient biomarkers, such as pneumostasis, edema, lung tissue thickness, lung tissue viscoelastic properties, and/or lung tissue scarring and/or fibrous characterization. Surgical instruments associated with a parenchyma transection step of a thoracic surgical procedure may include, for example, a surgical stapler. A step of a thoracic surgical procedure may be associated with one or more outcomes (e.g., physiological states). An outcome related to a parenchyma transection step of a thoracic surgical procedure may include, for example, pneumostasis. The occurrence of pneumostasis (e.g., due to transection of parenchyma during a thoracic surgical procedure) may be monitored (e.g., and determined), for example, by measuring and/or monitoring edema, lung tissue thickness, lung tissue viscoelastic properties, and/or lung tissue scarring and/or fibrous characterization (e.g., in-surgery, during a post-surgical procedure, and/or during post-surgery monitoring).

A lymph node dissection step of a thoracic surgical procedure may be correlated with one or more (e.g., post-surgery) patient biomarkers, such as hemostasis and/or blood pressure. Surgical instruments associated with a lymph node dissection step of a thoracic surgical procedure may include, for example, one or more of the following: a monopolar bovie, a harmonic scalpel, and/or an advanced bipolar RF energy instrument. A step of a thoracic surgical procedure may be associated with one or more outcomes (e.g., physiological states). An outcome related to a lymph node dissection step of a thoracic surgical procedure may include, for example, hemostasis. The occurrence of hemostasis (e.g., due to dissection of a lymph node during a thoracic surgical procedure) may be monitored (e.g., and determined), for example, by measuring and/or monitoring blood pressure (e.g., in-surgery, during a post-surgical procedure, and/or during post-surgery monitoring).

One or more complications may develop from one or more portions of a surgical procedure, such as an issue with hemostasis or bleeding. For example, bronchial artery bleeding may occur. Bleeding may be reduced, for example, by pre-emptive clipping of a bronchial artery before bronchial dissection or lymph node dissection. Bronchial artery bleeding may be stopped, for example, by compression with a suction tip and/or by handling the vascular stump with energy devices or clips.

Bleeding may occur from large vessel stumps and bronchial stumps. Bronchial stump bleeding may occur from an accompanying bronchial artery, which may be clipped for hemostasis. Bleeding at a vascular stump may be reduced, for example, by compression for hemostasis, by using hemostatic materials, by stapling, by re-stapling, and/or by a suture.

Bleeding may occur from a lung parenchyma. Bleeding from a lung parenchyma may be reduced, for example, by coagulation hemostasis and/or suturing, e.g., for wounds with visible air leakage or an insufficient hemostatic effect of coagulation.

Bleeding may occur during (e.g., at the site of) lymph node dissection. Non-grasping en-bloc lymph node dissection may nourish vessels of a lymph node. Energy devices may be used for hemostasis (e.g., in combination with hemostatic materials), for example, if bleeding occurs at the site of lymph node dissection. Bleeding may occur from chest wall incisions. One or more chest wall incisions may be made along the upper edge of one or more ribs. Hemostasis may be applied layer by layer. An incision may be re-checked for hemostasis before closing the chest.

Bleeding may occur at an internal chest wall. Bleeding at an internal chest wall may be managed, for example, with electrocoagulation. Diffuse capillary bleeding with an undefined bleeding site may be reduced, for example, by compression of the wound with gauze.

Pre-surgery monitoring, in-surgery monitoring, and/or post-surgery monitoring of patient biomarkers may (e.g., be used to) influence (e.g., select, adjust or change) surgical procedures, device settings, post-surgery procedures, exercises, medications, and/or the like. One or more (e.g., patient-specific or customized) recommendations may be based on (e.g., patient-specific) patient biomarker monitoring. For example, pre-surgery and/or in-surgery patient biomarker monitoring may influence surgery preparation/planning and/or operations implemented during a surgical procedure, such as surgical plans, what patient biomarkers to monitor, baselines, thresholds, device settings, choice of tools, post-surgical care, etc. Pre-surgery, in-surgery, and/or post-surgery patient biomarker monitoring may influence post-surgery. Measurement data and/or information gathered during pre-surgery, in-surgery and/or post-surgical monitoring of one or more patient biomarkers (e.g., hemostasis) may be used to determine or select what patient biomarkers to monitor, baselines, thresholds, device settings, post-surgical care, etc. For example, hemostasis issues may be predicted (e.g., based on pre-surgery and/or in-surgery patient biomarker monitoring) and/or hemostasis may not be achieved (e.g., in-surgery and/or during post-surgery).

A prediction of a complication, such as a hemostasis issue, based on pre-surgery monitoring and/or in-surgery monitoring of patient biomarkers, may lead to a determination pertaining to surgery planning and/or implementation. A determination may be based on monitored patient biomarkers and/or a prediction. A determination may provide a patient-specific or customized improvement, such as a determination to implement a tighter staple form, add reinforcement, and/or adjust an energy device algorithm, e.g., to improve the probability of reducing (e.g., post-transection) bleeding. For example, an analysis of data/information received from patient sensors for monitoring pre-surgical patient biomarkers may result in a prediction of a surgical complication, e.g., a complication resulting from hemostasis or bleeding. In some examples, the one or more patient biomarkers may be one or more (e.g., any combination) of blood pressure, blood pH, edema, heart rate, etc. An indication (e.g., a notification) of the prediction (e.g., with a probability of the likelihood of complication), such as for potential bleeding, oozing, or weeping from mobilization or transection may be provided (e.g., for automated and/or manual analysis and/or determination. In some examples (e.g., based on automated analysis and/or determination), a recommendation (e.g., compensation) may be indicated (e.g., displayed) for automated and/or manual implementation. For example, a recommendation or compensation may indicate one or more operations (e.g., operational changes) for device operation to compensate for a predicted complication based on one or more monitored patient biomarkers. In some examples, one or more adaptive energy devices may be automatically and/or manually adjusted for one or more recommended power levels, clamp pressures, impendence thresholds, energy modality, and/or termination conditions. For example, an adaptive stapler may be set (e.g., adjust or change) to one or more wait times, clamp pressures, creep thresholds, advancement rates, etc., to compensate for one or more predicted possibilities for one or more complications. In some examples, an indication (e.g., recommendation) may (e.g., also) be provided for one or more post-surgery (e.g., adjunct) therapies (e.g., to compensate for the likelihood of a predicted complication). One or more (e.g., a set of) thresholds for patient biomarker monitoring (e.g., post-surgery monitoring thresholds) may be set, for example, based (e.g., at least) on (e.g., pre-surgery) patient biomarkers that may pertain to one or more complications, such as a prolonged air leak (PAL). A complication, such as a prolonged air leak (PAL), may occur, for example, after a pulmonary resection (e.g., pulmonary lobectomy). A prolonged PAL may increase the risk of one or more post-surgical complications. Patients may be monitored for a post-surgery PAL. Prediction modeling may (e.g., be utilized to) establish a post-surgery threshold setting to monitor one or more complications (e.g., a PAL). A post-surgery threshold setting may be established (e.g., selected, configured), for example, based on one or more data models and/or one or more patterns provided by the one or more data models. A post-surgery threshold setting to monitor (e.g., and detect) a PAL may be set, for example, to more than five (5) days of leakage postoperative day (POD). A post-surgery threshold setting to monitor (e.g., and detect) a PAL may be based on, for example, one or more pre-surgery patient biomarkers.

Pre-surgery patient monitoring may be used to predict (and attempt to reduce or avoid) in-surgery and/or post-surgery complications. Pre-surgical monitoring of patient physiologic parameters may support prediction (e.g., anticipation or identification) of potential tissue or physiologic issues (e.g., complications) that may be reduced or avoided, for example, by one or more surgical procedure or tool implementations (e.g., adjustments, such as modifications by changes, additions, and/or subtractions) to increase the probability of a more successful (e.g., complication-free) outcome. Pre-surgery patient biomarkers may include, for example, at least one of the following: VO2 Max, respiration rate, heart rate variability, physical reaction (coughing and sneezing), oxygen saturation, EEG, ECG or EKG, REM sleep (REMS), GI motility, blood sugar levels, hydration state, temperature, tissue perfusion pressure, etc.

VO2 Max may (e.g., be used to), for example, gauge general fitness, identify a risk of adverse cardiovascular events (e.g., complications) in-surgery and/or post-surgery, track recovery (e.g., post-surgical milestones), etc.

Respiration rate may (e.g., be used to) identify, for example, one or more complications, such as post-operative pain, an air leak (e.g., a PAL), a collapsed lung, lung inflammation, etc.

Heart rate variability (HRV) may (e.g., be used to) identify, for example, stress and/or blood supply rate (e.g., relative to a recovery rate). A wearable sensor (e.g., a watch, such as Apple Watch series 5) may monitor and report heart rate and/or heart rate variability. HRV may be determined (e.g., from an ECG), for example, as the time period variation (e.g., standard deviation) between R peaks in the QRS complex, known as R-R intervals.

A physical reaction (e.g., coughing and/or sneezing), may (e.g., be used to) identify, for example, one or more complications, such as respiratory tract infections, a collapsed lung, pulmonary edema, etc.

Oxygen saturation, may (e.g., be used to) gauge or identify, for example, lung functionality, recovery capacity, etc.

EEG, may (e.g., be used to) identify, for example, stress, anxiety, depression, sleep, confusion, delirium, and/or sepsis. An EEG headset with one or more sensors may measure electrical activity in the brain, which may be correlated with (e.g., used to infer) stress, anxiety, depression, confusion, delirium, and/or sepsis. Delirium/sepsis-associated encephalopathy (SAE) may indicate (e.g., post-surgery) sepsis. Delirium may be indicated by hyperactive brain activity and/or physical behavior (e.g., agitation, pulling out lines, hallucinating, etc.) and/or the hypoactive brain activity and/or physical behavior (e.g., sluggishness, drowsiness, inattention, etc.). Confusion and/or delirium may be measured, for example, by a frequency and/or severity of episodes. Confusion may be inferred from the location or movement of a patient, which may be tracked, for example, by a location monitor (e.g., GPS tracker). An unexpected location change or disruption to normal routine may indicate that the user is suffering from confusion or delirium. Delirium may be identified through characteristic brain patterns (e.g., slowing or dropout of the posterior dominant rhythm and loss of reactivity to eyes opening and closing).

A threshold for EEG measurements (e.g., sensed by a wearable EEG headset) may be, for example, increased triphasic waves (e.g., greater than three EEG grade using Synek 5-point scale).

ECG or EKG, may (e.g., be used to) identify, for example, heart rate, heart rate variability, stress or anxiety, sleep, etc. A wearable sensing system (e.g., a wristband, a watch, etc.) may monitor and report ECG.

Sleep (e.g., REM sleep (REMIS)), may (e.g., be used to) identify, for example, the number of hours of sleep and/or the quality of sleep. Disrupted pre-op sleep may predict post-op pain, which may be used to define a tailored/customized pain management strategy. Disrupted sleep may indicate elevated inflammation and/or reduced immune function. Different sleep cycles may be identified, for example, by changes in heart rate, respiration rate, temperature, movement, brain activity, etc. Sleep cycles may be recognized/identified and quantified, for example, using one or more sensors (e.g., to monitor heart rate, breathing or respiration rate, body temperature, movement, and/or brain activity). Heart rate (e.g., measured by ECG) may, for example, drop during deep sleep, rise during REM sleep, and (e.g., gradually) rise again before waking up. Breathing or respiration rate (e.g., measured acoustically by a microphone) may, for example, drop during deep sleep. Poor sleep quality may be indicated, for example, by episodes of apnea. Body temperature (e.g., measured by a thermometer) may drop during deep sleep. Movement (e.g., measured by an accelerometer and/or microphone) may be significantly suppressed, for example, in deep sleep. Sleep time and quality may be inferred from EEG readings. Brain signals may vary depending on the nature of sleep. Deep sleep may be indicated, for example, by slow, large amplitude brain waves. REM sleep may be indicated, for example, by fast, wake-like signals. In some examples, a headband worn by a patient may track EEG, heart rate and/or movement. In some examples, movement may be detected based on audible sounds detected by a microphone and/or by an accelerometer, which may be processed by an application (e.g., a smartphone app) to determine (e.g., infer) a sleep state.

GI motility, may (e.g., be used to) identify, for example, to determine pre- or post-op intestinal obstruction (e.g., ileus). GI motility may be measured, for example, by one or more sensors in a stomach patch, a band, an electrogastroenterography (EGGG) wearable stethoscope, ultrasound, and/or an ingestible capsule, which may measure, for example, pH, temperature, pressure, etc.

Blood sugar levels, may (e.g., be used to) identify, for example, a patient's ability to heal, diabetes, etc.

Hydration state, may (e.g., be used to) identify a patient's hydration level, such as dehydration, which may have a negative impact on health and healing. Hydration state may provide a context for one or more other patient biomarkers, such as heart rate. Dehydration may reduce blood volume. Hydration state may help predict a risk of post-op acute kidney injury (AKI). Reduced blood flow to the kidneys may cause AKI. Hydration state may predict whether a patient may be at risk of hypovolemic shock during or after surgery. Hydration state may be (e.g., continuously) measured outside a healthcare environment (e.g., in a home environment). Hydration state may be influenced by various factors throughout a day (e.g., exercise, fluid intake, temperature). Hydration state may be measured, for example, by a wearable sensor (e.g., a bracelet, watch, patch). Sensing/detection may include, for example, optical spectroscopy and/or sweat-based colorimetry. Water may have characteristic absorption peaks. Peaks may be detected, e.g., by optical spectroscopy, for example, by measuring the amount of incident light that is reflected when shone onto the skin. The water content may be inferred from the differential amplitudes of different wavelengths, e.g., 1720, 1750 and 1770 nm. Hydration state may (e.g., additionally and/or alternatively) be measured similar to the way in which sweat rate may be measured, e.g., by sweat-based colorimetry. Hydration may be inferred from the amount of sweat produced. Sweat-based colorimetry may be more indirect than optical spectroscopy. Sweat-based colorimetry may utilize user information (e.g., such as a user keeping track of activity and water intake), for example, to determine hydration.

Temperature (e.g., core body temperature), may (e.g., be used to) identify, for example, infection, menstrual cycle, etc. Core body temperature in healthy individuals may vary between 36.5-37.5° C. Core body temperature may help indicate signs of post-op infection/sepsis (e.g., abnormal temperatures greater than 38.5° C. or less than 35° C. and/or characteristic fluctuations, such as 0.4° C. fluctuations). Body temperature may be measured by a (e.g., wearable) sensor. Temperature may be influenced, for example, by activities, such as exercise, climate, etc. Temperature may be analyzed alone and/or in conjunction (e.g., combination) with activities, exercise, sleep, environmental temperature, for example, to provide context to temperature measurements. Temperature may be measured, for example, by a wearable device, such as a chest strap, and/or an ingestible sensor. For example, an ingestible thermometer system may directly measure core body temperature. The system may wirelessly transmit the temperature detected by a sensor as it passes through the digestive tract (e.g., over a period of 24-36 hours). The system may use, for example, a quartz-crystal temperature sensor, which may determine temperature via the crystal's vibrational frequency. A wearable antenna may be used to detect electromagnetic radiation in the microwave region which, unlike IR radiation, can pass through the skin from tissue several centimeters below the surface. People, like all matter, emit blackbody radiation with a frequency spectrum determined by temperature. Core temperature may be inferred by measuring emission spectra of the body.

Tissue perfusion pressure may (e.g., be used to) identify, for example, surgical tool parameters, hypovolemia, internal bleeding, etc. Skin perfusion pressure may be proportional to the perfusion of other, deeper, tissue (e.g., organ tissue). Water content may contribute to mechanical properties of tissue. Tissue perfusion pressure may be monitored, for example, pre-surgery, in-surgery, and/or post-surgery. Tissue perfusion pressure before surgery may indicate mechanical properties of tissue, which may be used to set or adjust surgical procedure and/or parameters. A drop in perfusion pressure (e.g., post-surgery) may indicate hypovolemia or internal bleeding. Skin perfusion pressure may (e.g., be used to) monitor the overall adequacy of perfusion. Patients may be discharged earlier, for example, by use of home monitoring. Tissue perfusion pressure may be measured by a (e.g., wearable) sensor, such as a wrist band (e.g., bracelet or watch) or armband. Skin perfusion pressure may be measured, for example, optically. Measurement may vary, for example, depending on the applicability of controlled occlusion. Photoplethysmography may be implemented without application of pressure, for example, if occlusion is not applied. A device may illuminate skin and measure the light transmitted and reflected to detect changes in blood flow. Skin perfusion pressure may be (e.g., additionally and/or alternatively) measured as the pressure to restore blood flow after occlusion (e.g., if occlusion is applied). Pressure may be measured, for example, with a strain gauge or laser doppler flowmetry, which may measure the change in frequency of light caused by movement of blood. The magnitude and distribution of the shift may be (e.g., directly) related to the number and velocity of red blood cells, from which pressure may be calculated.

One or more (e.g., pre-surgery) patient biomarkers may be utilized in one or more analyses (e.g., algorithms) for a surgical procedure, such as a thoracic surgical procedure, for example, to provide one or more recommendations, determinations, actions, and/or implementations that may reduce or prevent one or more potential or predicted complications (e.g., PAL), whether intra-operative (in-surgery) or post-operative (post-surgery) complications. A patient sensing system may communicate one or more patient biomarker measurements to a surgical hub or system. One or more patient biomarker measurements may be processed (e.g., in whole or in part) to determine complication probability, reduction and/or avoidance measures, for example, by one or more (e.g., wearable) devices associated with a patient (e.g., a device with one or more patient biomarker sensors, a device receiving information from one or more patient biomarker sensors, a sensing system, a computing device, such as a cellular phone or tablet) and/or by a surgical hub or a computing system that may (e.g., in turn) notify an HCP of the probabilities of one or more complications and/or remedial recommendations (e.g., recommended actions) and/or actions to reduce or avoid potential complications.

Examples of notifications, recommendations, determinations, actions, and/or implementations (e.g., that may reduce or prevent one or more potential or predicted complications) may include, for example, one or more of the following: a selection or modification/change in a surgery plan, instrument choices, surgical approach, instrument configurations and/or schedule (e.g., of surgery and/or order of use of instruments during surgery). A notification may include, for example, one or more suggestions and/or determinations, such as one or more of the following: potential issue areas, procedure plan adjustments, alternative product mixes, and/or adjustment of control program parameters to interlinked smart instruments.

An example of a notification or recommendation is a control program. A control program or a portion thereof may be selected or changed, modified or updated (e.g., based on monitoring and/or analyses of one or more patient biomarkers), for example, to select or alter operation of one or more devices, such as one or more surgical devices and/or other devices used in-surgery, and/or one or more monitoring and/or other devices used post-surgery. The type of control program(s), selection(s) and/or change(s) may depend on the patient biomarker measurement(s) and/or processing (e.g., based on baseline value(s), types of control available). A control program may include, for example, control parameters that may be selected or adjusted for a control program.

In some examples, a patient biomarker monitoring/analysis system may be configured to communicably couple to a surgical hub. The surgical hub may be configured to communicably couple to one or more in-surgery and/or post-surgery (e.g., recovery) devices that may be controlled by one or more control programs. A patient biomarker monitoring/analysis system may comprise, for example: a processor and a memory coupled to the processor. The memory may store instructions that, when executed by the processor, cause the patient biomarker monitoring/analysis system to perform a method or procedure (e.g., as follows). For example, a patient biomarker monitoring/analysis system may receive data/information indicative of an operational behavior of a device. For example, the data/information may include data detected by the device during and/or after a surgical procedure. The patient biomarker monitoring/analysis system may receive patient biomarker data/information associated with the patient. The patient biomarker monitoring/analysis system may analyze the data/information indicative of an operational behavior of the device and the patient's patient biomarker monitoring data/information to determine whether the operational behavior of the device is or may be suboptimal for the patient. The patient biomarker monitoring/analysis system may generate a control program update configured to alter the manner in which the control program operates the device(s) (e.g., in-surgery and/or post-surgery) for the operational behavior. The patient biomarker monitoring/analysis system may transmit the control program update to the device, which may execute the updated control program.

A control program may be sent (e.g., by a surgical hub) to a sensing and/or control system. A processor (e.g., in a surgical hub) may be configured, for example, to send a control program (e.g., an adjustment or update to a program). The control program may be configured to modulate a suction level of a chest tube system connected to the patient. The control program may be received (e.g., and implemented) by one or more devices in (e.g., sensing systems) that may communicatively be connected with the source of the control program. In some examples, the suction level may be modulated, for example, based (e.g., at least in part) on a (e.g., sensed/measured) phase of respiration. The suction level may be modulated, for example, based (e.g., at least in part) on one or more (e.g., sensed/measured) patient biomarkers, such as diaphragmatic muscle tone. The type of control program update that may be generated (e.g., by a patient biomarker monitoring/analysis system) and may depend upon the one or more suboptimal behaviors exhibited by the one or more devices identified by the patient biomarker monitoring/analysis system. For example, a patient biomarker monitoring/analysis system may determine that (e.g., based on one or more analyses of patient biomarker measurement data/information) a particular (e.g., default, preexisting, or preselected) force to fire a surgical stapling instrument may result in an increased rate of leaking staple lines. The patient biomarker monitoring/analysis system may select, generate, update or otherwise indicate a control program that adjusts the force to fire from a first value to a second value that corresponds to a lower rate of leaking staple lines (e.g., a higher rate of non-leaking staple lines). As another example, a patient biomarker monitoring/analysis system may determine (e.g., based on one or more analyses of patient biomarker measurement data/information) that a particular (e.g., default, preexisting, or preselected) energy level for an electrosurgical or ultrasonic instrument may produce a low rate of hemostasis, for example, if/when the instrument is used in a liquid-filled environment (e.g., due to the energy dissipating effects of the liquid). The patient biomarker monitoring/analysis system may select, generate, update or otherwise indicate a control program that adjusts the energy level of the instrument when it is utilized in a surgical procedure (e.g., if/when the instrument will be immersed in liquid) for a patient based on the patient's patient biomarker monitoring.

The type of control program update that is generated (e.g., by a patient biomarker monitoring/analysis system) may depend upon whether the suboptimal behavior exhibited by an in-surgery and/or post-surgery (e.g., recovery) device is a matter of manual control or automated control (e.g., by a control program of the device). A control program update may be configured (e.g., for manual control) to provide (e.g., for display and/or other indication) warnings, recommendations, or feedback to a user (e.g., a surgeon, nurse), for example, based upon the manner in which the user is operating the device. A control program update may change a manually controlled operation of a device to an (e.g., automated) operation that may be controlled by a control program of the device. The control program update may or may not permit the user to override the control program's control of the particular function. For example, patient biomarker monitoring/analysis system may determine that surgeons are manually setting an RF electrosurgical instrument to a suboptimal energy level for a particular tissue type or procedure type. The patient biomarker monitoring/analysis system may generate a control program update that provides an alert (e.g., on a surgical hub and/or on the RF electrosurgical instrument itself) recommending that the energy level be changed. In another example, the generated control program update may (e.g., automatically) set the energy level to a default or recommended level (e.g., given the particular detected circumstances), which may be changed as desired by the user (e.g., medical facility staff). In an (e.g., additional and/or alternative) example, the control program update may (e.g., automatically) set the energy level to a level determined by the patient biomarker monitoring/analysis system without permitting a user (e.g., the medical facility staff, such as an HCP) to change the energy level. The control program update may alter how the control program functions (e.g., under the particular set of circumstances), for example, if the suboptimal behavior is caused by the control program of the device.

Post-surgery monitoring of a patient may be established and/or adjusted, for example, based on a risk based predictive model of a patient, which may use one or more pre-, in-and/or post-surgery patient biomarker levels, one or more procedure impacts (e.g., removal of a portion of an organ, such as a lung), and/or (e.g., potential) complications to make patient-specific determinations. One or more criticality levels and/or responses or escalation points may be established (e.g., set or selected) and/or adjusted (e.g., increased or decreased), for example, based on a predictive model analysis of one or more pre-surgery patient biomarker levels, and/or one or more procedure impacts and/or complications. Surgical prep and/or in-surgery procedures may be established and/or adjusted, for example, based on one or more pre-, in-, and/or post-surgery patient biomarker levels, one or more procedure impacts, and/or (e.g., potential) complications.

In some examples, a surgical hub (e.g., and/or a (wearable) sensing system) may include/comprise a processor configured to perform a method. For example, one or more processors may be configured to receive measurement data from at least one sensing system. The measurement data may be associated with one or more (e.g., a set of) patient biomarkers. The surgical hub (e.g., and/or a (wearable) sensing system) may (e.g., be configured to) predict an occurrence of a complication (e.g., a prolonged air leak (PAL), for example, based (e.g., at least) on the measurement data associated with the set of patient biomarkers. The surgical hub (e.g., and/or a (wearable) sensing system) may (e.g., be configured to) generate a set of recommendations for preventing the PAL.

In various examples, one or more (e.g., all) patient biomarkers in the set of patient biomarkers may be pre-, in-and/or post-surgery patient biomarkers. A processor may be configured to generate one or more (e.g., a set of) thresholds (e.g., for one or more patient biomarker measurements) for monitoring a potential complication (e.g., an in-surgical PAL or a post-surgical PAL), for example, if an occurrence of the complication (e.g., PAL) is predicted (e.g., by a patient prediction model). Generation of one or more thresholds may be triggered, for example, if a likelihood of a predicted complication exceeds a threshold. A processor may be configured to send the one or more generated thresholds to a patient monitoring system and/or to an HCP.

An occurrence of a complication, such as a PAL, may be (e.g., additionally and/or alternatively) predicted or determined (e.g., by a model used for predicting a complication, such as a PAL) based on a set of patient parameters, such as one or more of the following variables (e.g., predictive or determinative variables): a patient's age, a patient's body-mass index (BMI), nutritional status, forced expiratory volume (FEV) in one (1) second (FEV1) percentage, and/or presence of pleural adhesions (e.g., as may be observed during operation).

The probability of a complication, such as a PAL, may vary based on one or more patient characteristics and/or patient biomarker measurements. For example, the probability of a PAL occurring in a patient older than 65 years of age may be 0.04 or 4%. The probability of a PAL occurring in a patient with a BMI of less than 25.5 m/kg^2 may be, for example, less than 0.0001 or 0.01%. A BMI of less than 25.5 m/kg^2 may be an indication of poor nutritional status and/or chest mechanics (e.g., the ratio of the size of lung space to the size of available chest space). Nutritional status may be (e.g., additionally and/or alternatively) determined, for example, based on one or more of the following patient biomarkers: sweat, tears, urine, alcohol use, blood/serum ratio, saliva, etc.

A sweat patient biomarker may be measured, for example, as a sweat rate, e.g., with units μL/hour/cm2. A threshold may be determined, for example, over time. Sweat rate may indicate activity of a sympathetic nervous system. Sweat rate may help indicate psychological stress (e.g., preoperative anxiety), which may be associated with heightened sympathetic activity that may (e.g., in turn) be correlated with post-op pain. Sweat rate may (e.g., in part) indicate post-op infection. Infection may cause secondary hyperhidrosis. Sweat rate may be measured, for example, through a wearable sensor (e.g., in a home environment). Sweat may be affected by various factors in the day (e.g., climate, exercise). Sweat rate may be combined with other (e.g., contextual) patient biomarkers, such as heartrate, breathing rate, and/or activity/exercise, which may place sweat rate in context. Sweat and sweat rate may be sensed (e.g., by a wearable sensor, such as a patch, pad, band, bracelet, watch, etc. in contact with the skin), for example, based on sweat captured from the surface of the skin (e.g., in microfluidic channels). Sweat rate may be calculated (e.g., from microfluidic capture), for example, by a colorimetric technique and/or an impedimetric technique. In an example of a colorimetric-based determination, a water-responsive chromogenic reagent within one or more microfluidic channels may cause sweat to change color (e.g., on contact). A sweat rate may be calculated, for example, by monitoring the position of the leading edge of the color change as a function of time. In an example of an impedimetric determination, sweat may (e.g., gradually) cover multiple electrodes (e.g., two spiral electrodes), for example, as the microfluidic channel is filled. A change in impedance may be detected between the multiple electrodes, for example, as a function of time.

A tear patient biomarker may be measured by a tear sensor, which may be implemented, for example, in a wearable sensor (e.g., a patch). A urine patient biomarker may be measured by a urine sensor, which may be implemented, for example, in a wearable sensor (e.g., in a diaper). A blood/serum ratio patient biomarker may be measured by a blood/serum ratio sensor, which may be implemented, for example, in a wearable sensor. A saliva patient biomarker may be measured by a saliva sensor, which may be implemented, for example, in a wearable sensor. Wearable (e.g., on person) sensors may be attached in place for sensing or may be moved to a sensor location (e.g., periodically, such as in response to an indication to use the sensor to take a measurement). For example, a saliva sensor worn on a necklace may be moved into position temporarily for a sample.

An alcohol patient biomarker may be measured, for example, as blood alcohol concentration (BAC). A threshold may be based on one or more characteristics (e.g., sex, weight). Patients who drink alcohol (e.g., three or more alcohol units (AUs) per day) may have a reduced immune capacity. For example, a BAC threshold (e.g., an average BAC threshold) for reduced immunity may be greater than 0.04 BAC for a male weighing 80 kilograms (kg) and greater than 0.07 BAC for a female weighing greater than 60 kg. Measuring alcohol consumption may provide information to make determinations and/or take actions (e.g., precautions) to reduce or avoid potential complications, such as post-surgery infections, cardiopulmonary complications, bleeding, etc. Monitoring patient alcohol consumption in natural environments (e.g., at home) may provide a more accurate measurements (e.g., compared to hospital measurements). An alcohol use patient biomarker may be measured by an alcohol sensor, which may be implemented, for example, in a wearable sensor (e.g., a patch, band, bracelet, watch). An alcohol sensor may include, for example, transdermal and/or microfluidic monitoring. Transdermal alcohol monitoring may provide continuous monitoring of alcohol consumption. A transdermal sensor (e.g., in a device such as a bracelet) may be worn next to the skin to sample (e.g., otherwise insensible) perspiration. A pump inside a device (e.g., bracelet) may take a sample (e.g., of sweat). The presence of alcohol in the sample (e.g., sweat) may be measured, for example, based on a reaction between ethanol in the sample and a fuel cell (e.g., similar to a fuel cell used in a breath sensor). A blood alcohol level may be calculated based on the measurement.

Patient biomarker (e.g., pre-, in-, and/or post-surgery patient biomarker) monitoring may provide information to an HCP and/or a patient (e.g., prior to a surgery), for example, to avoid a complication, such as a PAL. A patient with an FEV1 of less than 80% may have a low probability of developing a PAL (e.g., a probability of 0.0001 or 0.01%). A patient with pleural adhesions (e.g., confirmed during operation) may have a relatively low probability of developing a PAL (e.g., a probability of 0.01 or 1%). A likelihood that a patient may have pleural adhesions may be indicated (e.g., anticipated or predicted), for example, by a history of unusual menstrual cycles (e.g., short menstrual cycles).

A surgical hub (e.g., and/or a (wearable) sensing system) may include a processor configured to receive measurement data from at least one sensing system. The measurement data may be associated with one or more (e.g., a set of) patient biomarkers. The surgical hub (e.g., and/or a (wearable) sensing system) may (e.g., be configured to) predict an occurrence of a complication (e.g., a prolonged air leak (PAL), for example, based (e.g., at least) on the measurement data associated with the set of patient biomarkers. The surgical hub (e.g., and/or a (wearable) sensing system) may (e.g., be configured to) generate a set of recommendations for preventing the complication (e.g., PAL).

A recommendation may be a selection and/or adaptation (e.g., change or modification of a default or existing selection) of one or more of the following: surgical preparation, in-surgery procedures, surgical instrument selection, surgical and/or post-surgical instrument settings, post-surgery procedures, in-surgery and/or post-surgery monitoring (e.g., recovery), etc. A recommendation may be selected or adapted to reduce or avoid one or more predictable complications, for example, based on patient biomarker monitoring alone or in combination with other information before, during and/or after surgery. For example, one or more patient biomarkers may (e.g., be used to) determine one or more stapling recommendations and/or stapling settings to avoid or minimize one or more potential complications, such as a PAL. A recommendation may be based on patient biomarkers that pertain to the likelihood of a patient developing a PAL.

In some examples, a set of recommendations for preventing the PAL (e.g., predicted based on measurement data associated with one or more patient biomarkers) may include at least one of the following: one or more stapling recommendations or settings, one or more post-stapling recommendations, or one or more surgical procedural recommendations, and/or one or more post-surgical recommendations.

In some examples, the one or more stapling recommendations or settings may include at least one of: applying a buttressed staple line, avoiding overlapping parenchymal staple lines, and/or stapling using a cautious mode on a powered stapling device. For example, a recommendation may be generated and/or provided for a surgical stapling instrument used in a surgical procedure to use a buttress material to reinforce the fastening of tissue provided by staples. For example, a recommendation may be generated and/or provided to pay increased (e.g., additional or careful) attention (e.g., during a procedure) to avoid overlapping parenchymal staple lines. For example, a recommendation may be generated and/or provided to set a power stapler to operate using a Cautious Mode.

In some examples, a recommendation or setting may include a cautious mode. A recommendation and/or an implementation of the recommendation may include a modified speed setting and/or a modified force setting. A stapler may be set to operate (e.g., based on a recommendation to operate in a Cautious Mode) at a (e.g., selected or modified) speed and/or force, for example, for (e.g., critical) staple lines on (e.g., thicker) lung tissue. A Cautious Mode may be recommended/selected (e.g., for a surgical instrument, such as a power stapler), for example, for advanced hemostasis (e.g., for vessels with greater than 7 mm thickness). In some examples, the one or more post-stapling recommendations or settings may include at least one of: using a low inspiratory pressure if/when inflating a lung and/or using a sealant. For example, a recommendation may be generated and/or provided for an HCP and/or a surgical instrument used in a surgical procedure (e.g., a post-stapling procedure) to use a low inspiratory pressure if/when inflating a lung and/or if/when using a sealant.

In some examples, the one or more surgical procedural recommendations or settings may include at least one of: controlling a number of dissections, creating an apical tent, or creating a pneumoperitoneum. For example, a recommendation may be generated and/or provided for an HCP and/or a surgical instrument used in a surgical procedure to a specified number of dissections and/or to reduce, increase, or otherwise control the number of dissections. For example, a recommendation may be generated and/or provided for an HCP and/or a surgical instrument used in a surgical procedure to create an apical tent. For example, a recommendation may be generated and/or provided for an HCP and/or a surgical instrument used in a surgical procedure to create a pneumoperitoneum.

In some examples, the one or more post-surgical procedural recommendations or settings may include at least one of: whether or not to use a water seal, or whether or not to use suction. For example, a recommendation may be generated and/or provided for an HCP and/or a post-surgical instrument (e.g., used in a post-surgical procedure) to use or to not use a water seal. For example, a recommendation may be generated and/or provided for an HCP and/or a post-surgical instrument (e.g., used in a post-surgical procedure) to use or to not use suction.

Recommendations may be based on the likelihood of a patient developing a complication. A likelihood of a complication may be patient specific, e.g., based on patient information, including patient biomarker measurements. For example, a recommendation indicating whether or not to use a water seal and/or suction may be based on a degree of likelihood of a patient experiencing pneumothorax (e.g., determined based on patient-specific information, including patient biomarker measurements).

In some examples, a patient biomarker analysis and/or patient biomarker specific adjustment process may be implemented by a surgical hub and/or a wearable sensing system, for example, to customize patient surgery and/or treatment-based patient biomarker monitoring. In some examples (e.g., as shown in FIG. 59) a patient-specific process may be implemented at or near the end of a surgery and/or a portion thereof. For example, the process may occur after (post) stapling. In an example, a pre-surgery (pre-op) patient biomarker analysis may indicate a patient is at a higher risk of developing a PAL. A surgical procedure (e.g., on the patient's lung) may be completed (e.g., at least in part, such as after stapling). A determination may be made about an inspiratory pressure to re-inflate the lung. The lung may be submerged (e.g., in sterile saline), for example, to check for air leaks. A determination may be made whether there is an air leak. A determination may be made (e.g., if an air leak is detected), about the magnitude of the detected air leak. A surgical procedure may be completed or may end, for example, if a leak is not detected. One or more procedural recommendations may be made, for example, based on a detection of a leak and/or based on an analysis of patient biomarker monitoring indicating a probability of a complication, such as a PAL. A recommendation may include, for example, suturing, using/adding a sealant, and/or the like, e.g., to seal the leak and/or to reduce or avoid a complication.

One or more (pre-surgery, in-surgery, and/or post-surgery) procedural recommendations may be generated, for example, based on one or more analyses of one or more monitored patient biomarkers. The number of cuts (e.g., dissection) may be correlated with exposed raw parenchymal surface area, for example, to determine (e.g., output) a risk of a patient developing a PAL. In some examples, the right upper lobe may anatomically abut multiple (e.g., two) fissures. A minor fissure may be nearly complete. More dissection in the fissure may expose a larger parenchymal raw surface area. In some examples, a recommendation to reduce the likelihood of developing a complication, such as a PAL, may include, for example, creating an apical pleural tent, e.g., at the time of an upper lobectomy. In some examples, a recommendation to reduce the likelihood of developing a complication, such as a PAL, may include creating a pneumoperitoneum, e.g., at the time of a lower lobe resection.

A (e.g., post-op) recommendation (e.g., based on patient biomarker monitoring) to reduce the likelihood of developing a complication, such as a PAL, may include creating a water seal and/or suction. Recommendations may be patient-specific, e.g., based on patient biomarker monitoring. For example, a water seal may not be recommended for a patient indicated to have a likelihood for pneumothorax (e.g., based on an analysis of patient biomarkers). Suction may not be recommended for patients who may be at risk for impaired healing. Suction may delay parenchymal healing, may lead to the rupture of blebs/bullae, and/or may prolong an air leak.

Post-surgical patient monitoring may track one or more complications (e.g., infection). One or more treatment plans may be generated, selected, or adapted, for example, based on one or more analyses of one or more monitored patient biomarkers. One or more (e.g., a combination of) metrics may provide insight into early infection post-surgery. For example, tracking resting heart rate, body temperature, and respiratory rate in combination may provide a picture of health progression after a surgical procedure.

An acute response to a foreign body may be indicated or detected (e.g., over one or more time periods), for example, by detecting an increase in average resting heart rate (e.g., a 5-10% increase per day), an increase in average body temperature change (e.g., a 1-2 degree F. increase per day), and/or an increase in respiratory rate (e.g., a 15-30% increase per day).

An event (e.g., a complication) may be predicted with improved accuracy, for example, by determining baseline values for patient biomarkers prior to surgery. Patient-specific or tailored metric thresholds may improve predictions of the occurrence of an event.

Patient biomarker measurements may be performed with one or more devices, such as a single device (e.g., a ring) or multiple devices (e.g., a bracelet or a watch and a ring), for example, as illustrated in FIGS. 54 and 56, and also described in FIGS. 11A-11D.

Patient biomarker measurement data/information may provide an (e.g., earlier) opportunity to intervene before a patient's immune response becomes more substantial and/or an infection becomes more widespread (e.g., as may be indicated by a high body temperature).

Patient biomarker measurement data/information may reduce erroneous and/or incomplete data/information from spot measurements. A (e.g., discrete) spot measurement (e.g., once or twice per day) may be performed, for example, using a temple, no-contact thermometer, which may pick up transient aberrations and/or miss trends.

Post-surgical patient monitoring (e.g., including analyses of patient biomarker measurements) may (e.g., be used to) generate one or more pain management plans, which may include administration of analgesics/narcotics. Post-surgical patient monitoring may measure one or more parameters, such as skin conductance, hormone levels (e.g., cortisol), heart rate and heart rate variability, etc. Patient monitoring may indicate, for example, autonomic nervous system activity. Patient monitoring may provide quantitative and/or objective metrics to guide analgesic administration post-surgery.

Patient monitoring may guide duration of effect, for example, to indicate how long a given analgesic may provide a desired effect. Patient monitoring may guide dosage, for example, to provide an (e.g., optimal) effect with the lowest possible dosage. Patient logging of analgesics/narcotics taken over time may correspond to a timeline of changes in measured parameters, which may indicate or may be used to detect improvements in health.

Methods may be implemented (e.g., in whole or in part), for example, by one or more devices, apparatuses, and/or systems (e.g., a hub, a sensing system, and/or the like), which may comprise one or more processors configured to execute the methods (e.g., in whole or in part) as computer executable instructions that may be stored on a computer readable medium or a computer program product, that, when executed by the one or more processors, performs the methods. The computer readable medium or the computer program product may comprise (e.g., store) instructions that cause one or more processors to perform the methods by executing the instructions.

Figure 60:
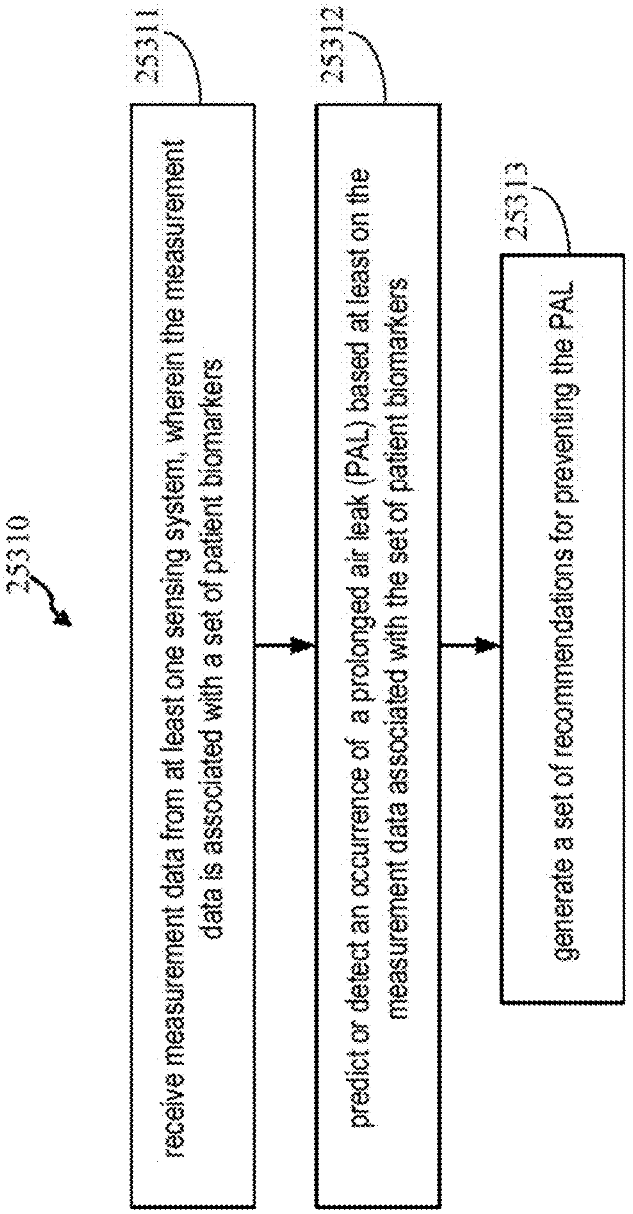
FIG. 60 illustrates an example of a logic flow diagram for predicting a PAL, in accordance with at least one aspect of the present disclosure.

FIG. 60 illustrates an example of a logic flow diagram of a process for predicting a complication (e.g., a PAL) and providing a recommendation (e.g., about use of a sealant) to attempt to avoid the complication, in accordance with at least one aspect of the present disclosure. In various examples, the process may be implemented (e.g., in whole or in part) in a surgical hub and/or a sensing system. Example process 25310 may be implemented, for example, by patient monitoring system 25251.

At 25311, measurement data may be received. For example, the measurement data may be received from at least one sensing system. The measurement data may be associated with a set of patient biomarkers. For example, hub 25258 may receive measurement data for one or more patient biomarkers shown in FIGS. 57 and 58 from first and as described herein, second or third sensing systems 25253, 25254, 25255 shown in FIG. 54 and for example in FIGS. 11A-11D. The measurement data may be pre-, in-, and/or post-surgery patient biomarker measurement data and/or one or more patient parameters. At 25312, an occurrence of a complication (e.g., a PAL) may be predicted, for example, based at least on the measurement data associated with the set of patient biomarkers. For example, a processor in hub 25258 may execute a patient prediction model that takes as input vectorized patient data generated from measurement data received at 25311 and generates an indication of one or more complications (e.g., a PAL) and associated probabilities of occurrence in the patient based on the vectorized patient data input. At 25313, a set of recommendations may be generated for preventing the complication (e.g., the PAL). For example, the probability of a complication (e.g., a PAL) predicted by hub 25258 may exceed a threshold probability and/or one or more patient biomarkers may exceed one or more thresholds. Hub 25258 may generate one or more recommendations, which may be provided, for example, to one or more of a surgical instrument, an HCP, and/or a patient to take one or more actions on (e.g., to prevent an occurrence of the complication). For example, the recommendation may be provided to a computer to display the recommendation to an HCP to use a sealant to prevent a PAL.

Figure 61:
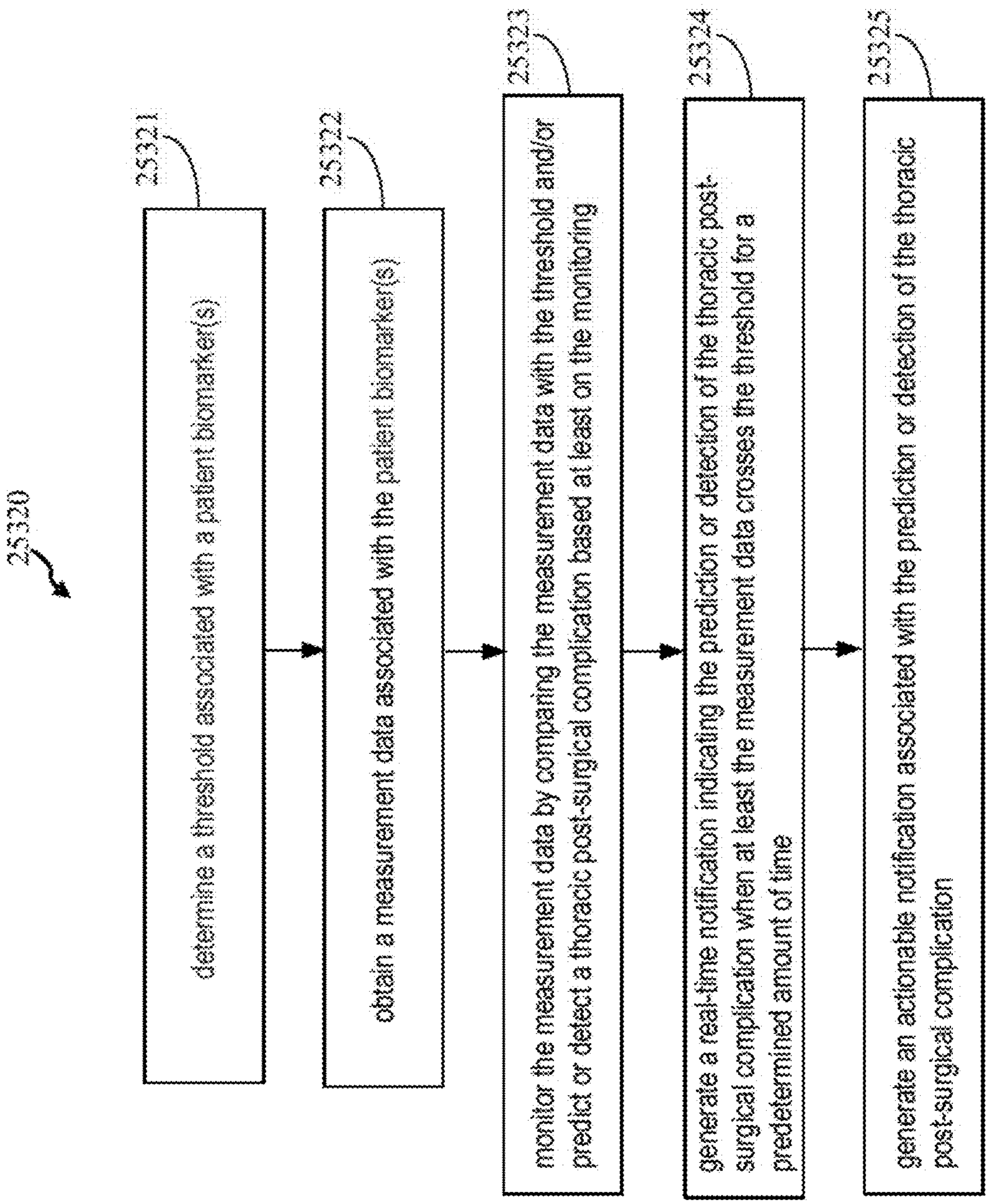
FIG. 61 illustrates an example of a logic flow diagram for detecting post-operative complication, in accordance with at least one aspect of the present disclosure.

FIG. 61 illustrates an example of a logic flow diagram of a process for a surgical hub for detecting a post-operative complication, in accordance with at least one aspect of the present disclosure. Example process 25320 may be implemented, for example, by patient monitoring system 25251.

At 25321, a threshold associated with a patient biomarker may be determined. For example, a first threshold associated with a first patient biomarker and/or a second threshold associated with a second patient biomarker may be determined. The first threshold and/or the second threshold may be determined, for example, based (e.g., at least) on baseline data associated with a patient. For example, hub 25258 may determine thresholds associated with measurement data (e.g., baseline data) for one or more (e.g., at least two) patient biomarkers shown in FIGS. 57 and 58 received from one or more of first, second or third sensing systems 25253, 25254, 25255 shown in FIG. 54.

At 25322, measurement data associated with a patient biomarker may be obtained. For example, a first measurement data associated with the first patient biomarker and a second measurement data associated with the second patient biomarker may be obtained (e.g., received from a sensing system). For example, hub 25258 may obtain (e.g., receive) measurement data for one or more patient biomarkers shown in FIGS. 57 and 58 from first, second or third sensing systems 25253, 25254, 25255 shown in FIG. 54.

At 25323, measurement data associated with the patient biomarkers may be monitored and a thoracic post-surgical complication may be predicted or detected based at least on the monitoring. For example, a thoracic post-surgical complication may be predicted or detected based at least on monitoring, which comprises comparing (e.g., in real time) the first measurement data with the first threshold and the second measurement data with the second threshold. For example, hub 25258 may detect an occurrence of a complication (e.g., PAL) based at least on monitoring, which comprises comparing (e.g., in real time) the received measurement data (e.g., with or without processing) obtained at 25322 to the first and second thresholds determined at 25321.

At 25324, a notification (e.g., a real-time notification) may be generated. The notification may indicate the occurrence of the thoracic post-surgical complication, for example, if/when at least one of the first measurement data crosses the first threshold and/or the second measurement data crosses the second threshold (e.g., for a predetermined amount of time). In an example, hub 23258 may generate a (e.g., real-time) notification indicating the occurrence of a complication, if/when the first measurement data crosses the first threshold and/or the second measurement data crosses the second threshold (e.g., for a predetermined amount of time).

At 25325, an actionable notification associated with the occurrence of the thoracic post-surgical complication may be generated. For example, hub 25258 may (e.g., based on the detected occurrence of the complication) generate one or more recommendations to take one or more actions.

The real-time notification and the actionable notification associated with the occurrence of the thoracic post-surgical complication may be sent to the patient and/or a healthcare provider (HCP). For example, hub 25258 may send an indication of the detected complication and an indication of the recommended action(s) to counteract the complication, for example, to an HCP and/or a patient to alert them to take one or more actions on (e.g., to counteract the detected occurrence of the complication). For example, the indications may be provided to one or more devices for visual, aural, touch, and/or other indication to a patient and/or HCP. In an example, the actionable notification associated with the occurrence of the thoracic post-surgical complication may be sent to the patient and/or a healthcare provider (HCP) based on a severity level of the real-time notification. For example, the actionable notification may be sent when the severity level of the corresponding real-time notification is high.

Figure 62:
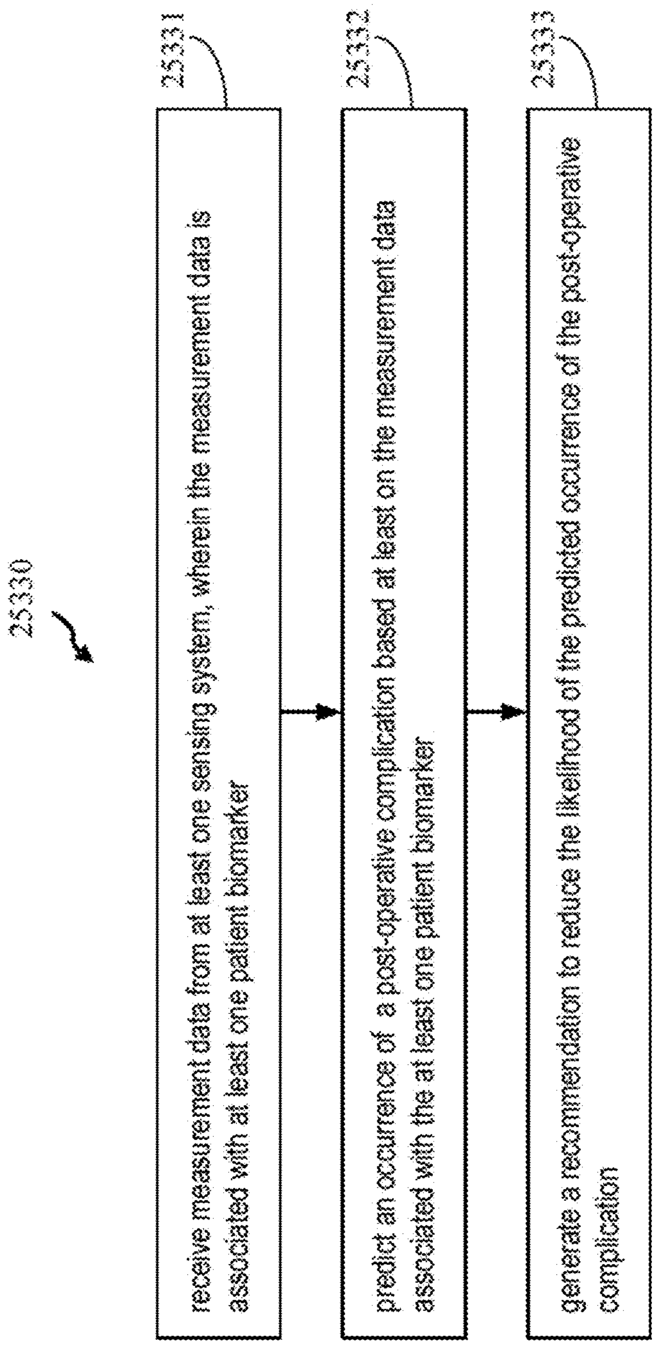
FIG. 62 illustrates an example of a logic flow diagram for predicting a post-operative complication, in accordance with at least one aspect of the present disclosure.

FIG. 62 illustrates an example of a logic flow diagram of a process for a surgical system for predicting a post-operative complication, in accordance with at least one aspect of the present disclosure. Example process 25330 may be implemented, for example, by patient monitoring system 25251.

At 25331, measurement data from at least one sensing system may be received. The measurement data may be associated with at least one patient biomarker. For example, hub 25258 may receive measurement data for one or more patient biomarkers, as shown in FIGS. 57 and 58 from first, second or third sensing systems 25253, 25254, 25255 shown in FIG. 54. At 25332, a post-operative complication may be predicted, for example, based on the measurement data associated with the at least one patient biomarker and/or based on one or more patient parameters. For example, a processor in hub 25258 may execute a patient prediction model that takes as input vectorized patient data generated from measurement data and/or patient parameters received at 25331 and generate an indication of one or more complications (e.g., a PAL) and associated probabilities of occurrence in the patient based on the vectorized patient data input. The measurement data may be pre-, in-, and/or post-surgery patient biomarker measurement data. The one or more patient parameters may be taken before, during, and/or after surgery. At 25333, a recommendation to reduce the likelihood of the predicted occurrence of the post-operative complication may be generated. For example, the probability of a complication (e.g., a PAL) predicted by hub 25258 may exceed a threshold probability, one or more patient biomarker measurements may exceed one or more thresholds, and/or one or more patient parameters may exceed one or more thresholds. Hub 25258 may generate one or more recommendations, which may be provided, for example, to one or more of a surgical instrument, an HCP, and/or a patient, e.g., to take one or more actions to reduce the likelihood of an occurrence of the predicted complication. For example, the recommendation may be provided to a computer to display the recommendation to an HCP to use a sealant to prevent a PAL.

Figure 63A:
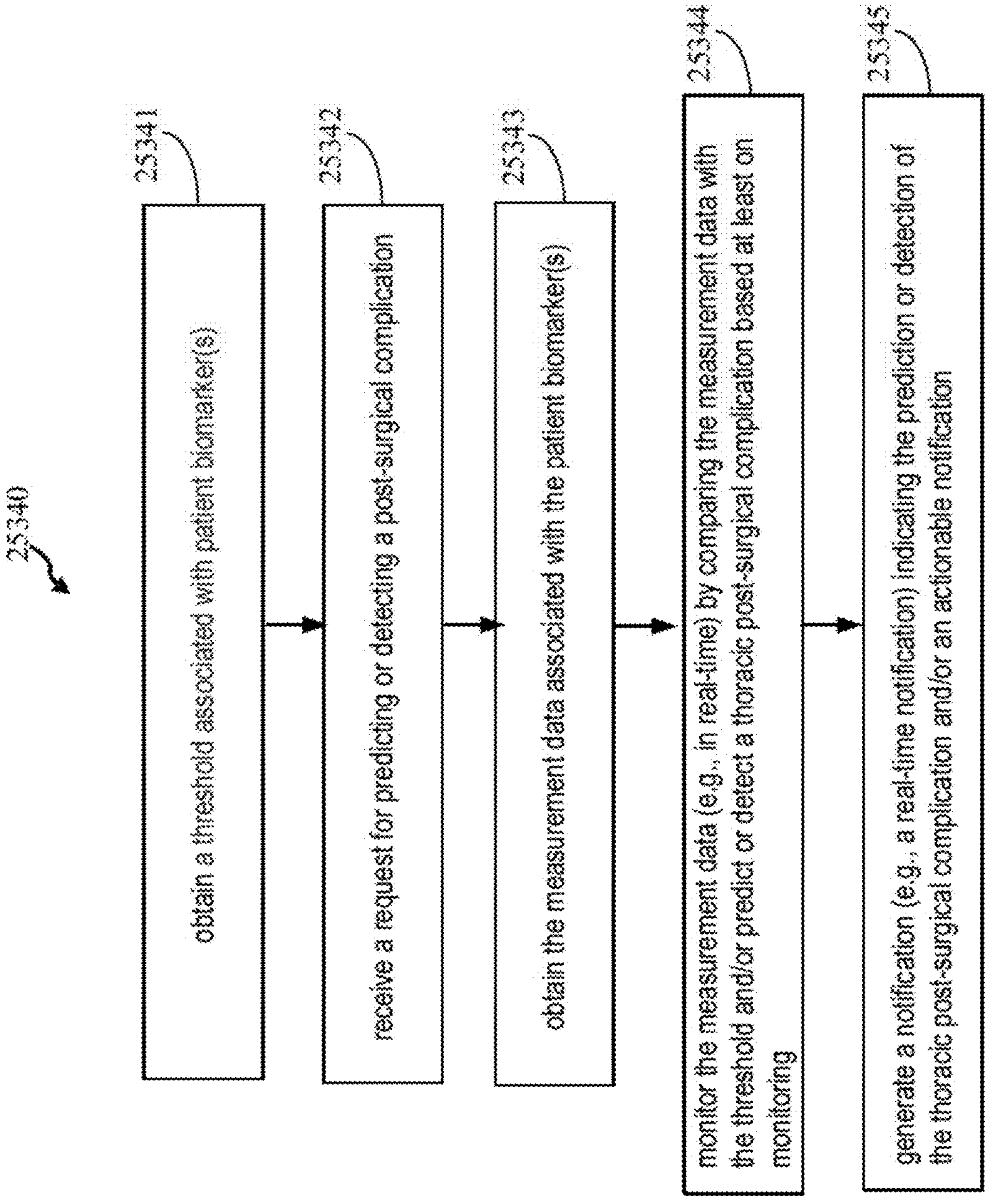
FIG. 63A illustrates an example of a logic flow diagram for detecting post-operative complication, in accordance with at least one aspect of the present disclosure.

FIG. 63A illustrates an example of a logic flow diagram of a process for a sensing system for detecting a post-operative complication, in accordance with at least one aspect of the present disclosure. Example process 25340 may be implemented, for example, by patient monitoring system 25251.

At 25341, a threshold associated with a patient biomarker may be obtained. For example, a first threshold associated with a first patient biomarker and a second threshold associated with a second patient biomarker may be received, for example, from a surgical hub. For example, hub 25258 may determine thresholds associated with at least two patient biomarkers shown in FIGS. 57 and 58. Hub 25258 may provide the thresholds to one or more sensing systems, e.g., first, second, and/or third sensing systems 25253, 25254, 25255 shown in FIG. 54.

At 25342, a request may be received for predicting or detecting a thoracis post-surgical complication. For example, a request may be received for predicting or detecting a post-surgical complication, for example, based on at least one of a first measurement data associated with the first patient biomarker crossing a first threshold or a second measurement data associated with the second patient biomarker crossing a second threshold (e.g., for a predetermined amount of time). For example, first, second, and/or third sensing systems 25253, 25254, 25255 may receive a request from hub 25258 to determine whether a patient is experiencing a complication.

At 25343, measurement data associated with a patient biomarker may be obtained. For example, the first measurement data associated with the first patient biomarker and the second measurement data associated with the second patient biomarker may be measured. For example, first, second, and/or third sensing systems 25253, 25254, 25255 may (e.g., in response to the request) measure at least two patient biomarkers shown in FIGS. 57 and 58.

At 25344, measurement data associated with a set of patient biomarkers may be monitored (e.g., monitored in real time) and/or a thoracic post-surgical complication or a milestone may be detected or predicted based at least on the monitoring. For example, the first measurement data and the second measurement data may be monitored (e.g., in real-time) by comparing each of the first measurement data and the second measurement data with the first threshold and the second threshold respectively. For example, first, second, and/or third sensing systems 25253, 25254, 25255 may (e.g., in response to the request) monitor the measurements of the at least two patient biomarkers shown in FIGS. 57 and 58 and compare the measurements to respective thresholds associated with patient biomarkers received from hub 25258.

At 25345, a notification (e.g., a real-time notification) and/or an actionable notification may be generated, as described, for example, in FIG. 61. For example, a notification indicating the post-surgical complication may be generated based at least on monitoring, which comprises determining (e.g., in real time) if/when the first measurement data crosses the first threshold, or the second measurement data crosses the second threshold (e.g., for a predetermined amount of time). In an example, first, second, and/or third sensing systems 25253, 25254, 25255 may (e.g., in response to the request) generate a notification if/when at least one of the comparisons indicate that at least one of the measured patient biomarkers crosses a respective threshold received from hub 25258.

The (e.g., real-time) notification indicating the occurrence of the post-surgical complication may be sent to the surgical hub. For example, first, second, and/or third sensing systems 25253, 25254, 25255 may (e.g., in response to detecting a post-surgical complication) send the notification of a post-surgical complication to hub 25258.

Figure 63B:
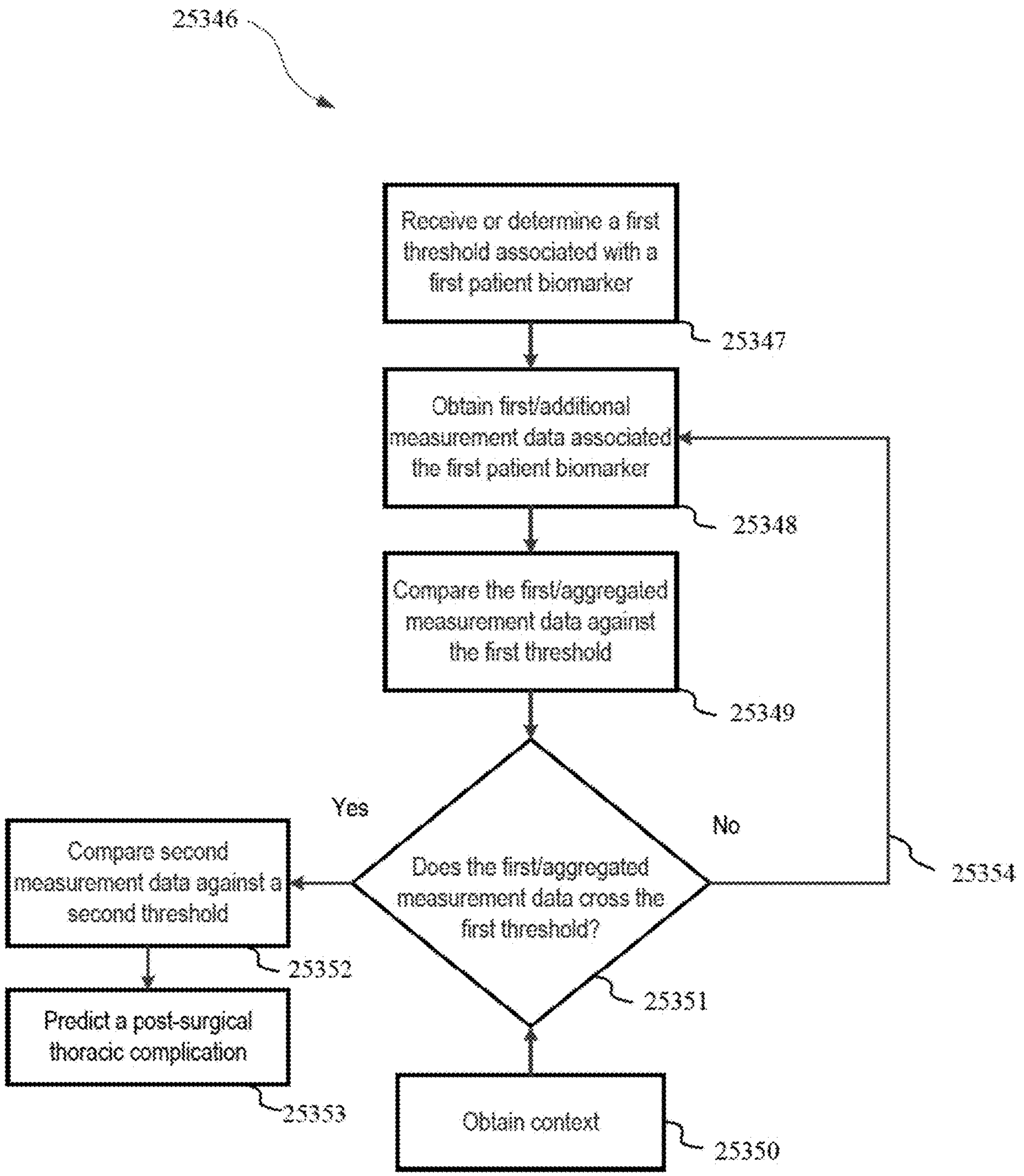
FIG. 63B shows example post-surgical thoracic complication wearable prediction or detection.

FIG. 63B shows example 25346 post-surgical thoracic complication wearable prediction or detection. One or more of 25347-25354 shown in FIG. 63B may be performed by a computing system, a sensing system, and/or another device described herein.

At 25347, a first threshold associated with a first patient biomarker may be received and/or determined described herein with reference to FIGS. 60-63A. For example, a threshold associated with blood pH may be received by a sensing system and/or determined by a computing system. The threshold may be used to predict or detect a post-surgical thoracic complication, for example an air leak.

At 25348, first measurement data associated with the first patient biomarker may be obtained described herein with reference to FIGS. 60-63A. For example, measurement data associated with blood pH may be obtained by a computing system and/or a sensing system for predicting or detecting post-surgical thoracic complication. The first measurement data may be obtained as a response to a request for the measurement data. For example, a computing system and/or a sensing system may request the first measurement data.

At 25349, the first measurement data may be compared against the first threshold described herein with reference to FIGS. 60-63A.

At 25350, a computing system and/or a sensing system may obtain context described herein with reference to FIGS. 60-63A. The computing system may consider the context when determining whether the measurement data crosses the threshold. For example, the computing system may adjust the first threshold based on the received context. The computing system may use the received context as input context data. The input context data may influence the computing system as the computing system determines whether measurement data crosses the threshold.

At 25351, a computing system and/or a sensing system may compare the first measurement data against the first threshold by determining whether the measurement data crosses the threshold (e.g., for a predetermined amount of time) as described herein with reference to FIGS. 60-63A. The computing system or the sensing system may compare the first measurement against the first threshold based on a context.

Assuming that the first measurement data, for example, based on the context, crosses the first threshold, at 25352, second measurement data may be compared against a second threshold described herein with reference to FIGS. 60-63A. The second threshold may be associated with a second patient biomarker. The second threshold may be received and/or determined similar to how the first threshold may be received and/or determined. The second measurement data may be compared based on a condition that the first measurement data crosses the first threshold for a predetermined amount of time. A computing and/or sensing system may determine that the first measurement data crosses the first threshold for a predetermined amount of time and may compare the second measurement data against a second threshold. In an example, second measurement data may be compared on a condition that the first measurement data crosses the first threshold by a predetermined amount, for example 10% of the first threshold value. The computing system may request the second measurement data when the first measurement data crosses the first threshold.

At 25353, a post-surgical thoracic complication may be predicted described herein with reference to FIGS. 60-63A. A computing system and/or a sensing system may predict a post-surgical thoracic complication based on the first measurement data comparison and the second measurement data comparison. For example, the computing system may predict a complication when both the first measurement data and the second measurement data cross the respective first and second thresholds. The computing system may assign weight(s) to each comparison. The computing system may assign a high comparison weight to the first measurement data crossing the first measurement data and a low comparison weight to the second measurement data crossing the second threshold. Predicting a post-surgical thoracic complication may be based on the comparison weight(s). A computing system may be more likely to predict a complication when measurement data associated with a high comparison weight crosses a threshold compared to measurement data associated with low comparison weight crossing a threshold.

At 25354, a computing system and/or a sensing system may determine that the first measurement data does not cross the first threshold for a predetermined amount of time. The computing system may then continue at 25348. Additional or optionally at 25348, the computing system may obtain additional first measurement data. At 25348, the computing system may aggregate the additional first measurement data with the original first measurement data. The aggregated first measurement data may be compared against the first threshold. The computing system and/or sensing system may adjust the first threshold based on the additional first measurement data.

FIGS. 38A-38D illustrates example procedure steps of a lung segmentectomy or a thoracic surgical procedure and example use of patient biomarker measurements. As shown, various post-operative or post-surgical patient biomarker measurements may be used to detect or predict various thoracic post-surgical complications and/or milestones, as described herein. The patient biomarker measurements may also be used to inform various decisions, identify various risks pre-surgery, during surgery, post-surgery, and/or determine operational parameters for various surgical tools.

FIG. 38D illustrates example patient biomarkers that may be monitored post-op to detect or predict post-surgical thoracic complications. The patient biomarkers may be monitored by a computing system or a wearable sensing system as described herein with reference to FIGS. 60-63A. For example, a patient's blood pressure may be monitored to detect or predict internal bleeding.

As shown, the patient biomarkers may be measured using one or more wearable and/or environmental sensors as described herein with reference to FIG. 1B. For example, a patient's hydration state may be measured by a wearable patch sensor. A patient's physical activity may be measured by a video camera. Measurement data associated with the wearable and/or environmental sensors may be obtained by a computing system that may compare the data against corresponding threshold(s) as described herein with reference to FIGS. 60-63A. In an example, the measurement data may be obtained by a sensing system that may compare the data against corresponding threshold(s).

In an example, a post-surgical air leak may be detected or predicted by measuring patient biomarker(s) associated with a patient's lung tissue repair capacity and/or staple line integrity. Post-surgical lung collapse may be detected by measuring patient biomarker(s) associated with rate of fluid build-up, and/or lung tissue repair capacity. Post-surgical cancer relapse may be detected or predicted by measuring patient biomarker(s) associated with tumor presence and/or metastatic risk. Post-surgical hypovolemic shock may be detected by measuring patient biomarker(s) associated with hydration state. Post-surgical acute kidney injury may be detected by measuring patient biomarker(s) associated with hydration state. In an example, a post-surgical internal bleeding may be detected by measuring patient biomarker(s) associated with blood clotting propensity and/or blood pressure. Post-surgical infection may be detected by measuring poor immune response and/or bacterial populations. In an example, patient biomarker measurements may be used post-op to assess a patient's quality of life following a lung segmentectomy or a thoracic surgery. For example, patient biomarkers associated with VO2 max, physical activity, and/or circadian rhythm may be measured to assess a patient's quality of life.

As shown in FIGS. 38A-38D, patient biomarker measurements may be used post-op to inform various decisions, identify various risks pre-surgery, during surgery, post-surgery, and/or determine operational parameters for various surgical tools. For example, post-op patient biomarker measurements may be used to determine a value (e.g., threshold) in which pre-surgical and/or in-surgical measurement data may be compared against.

The value may be used to inform various decisions during a pre-surgical and/or in-surgical procedural step. For example, during a manage major vessels procedural step, as shown in FIG. 38B, patient biomarker measurements associated with connective tissue thickness may be compared against a connective tissue thickness value to determine the ligation height. The value may be used to identify risks associated with a pre-surgical and/or in-surgical procedural step. For example, during manage major vessels procedural step, a patient's lung tissue strength may be compared against a lung tissue strength value (e.g., for identifying the risk of air leak). The value may be used to determine operational parameters for various surgical tools. During manage major vessels procedural step, a patient's blood pressure may be compared against a blood pressure value to determine the operational parameters of a harmonic scalpel. For example, the intensity of the harmonic scalpel may decrease when the patient's blood pressure crosses the blood pressure value.

Multiple post-op patient biomarker measurements may be compared against multiple pre-surgical and/or in-surgical values simultaneously or at different time intervals. In an example, post-op patient biomarker measurements may increase or decrease the pre-surgical and/or in-surgical values.

Measurement data related to a set of patient biomarkers for post-surgical monitoring may be received. For example, a computing system may be configured to receive the measurement data from one or more sensing systems. A sensing system may be or may include a patient wearable device. A sensing system may be or may include an environmental sensing system. A sensing system may include one or more sensors. The set of patient biomarkers may be monitored for detecting a post-surgical hysterectomy complication. For example, the set of patient biomarkers for detecting SSI may include a patient's body temperature, vaginal pH, and/or blood pH. For example, the set of patient biomarkers for detecting nerve damage may include a patient's luteinizing hormone and/or GI motility. For example, the set of patient biomarkers for detecting vaginal leak may include a patient's urinary motility and/or vaginal pH. The measurement data received from the sensing systems may be in response to one or more requests for the measurement data. For example, the computing system may send a request to one or more sensing systems requesting respective measurement data.

One or more thresholds may be determined for a patient biomarker. For example, the surgical computing system may determine respective threshold(s) associated with a patient's body temperature, vaginal pH, urinary pH, and/or other patient biomarkers for SSI. The threshold(s) may be standard threshold(s). The threshold(s) may be customized for a patient based on the patient's pre-surgical, in-surgical, and/or previously measured post-surgical patient biomarker measurements. A patient biomarker may be monitored in real-time by comparing the measurement data related to the patient biomarker against the corresponding threshold(s). For example, the computing system may monitor a patient's body temperature in real-time by comparing the measurement data related to the patient's body temperature against the threshold associated with the patient's body temperature. The computing system may compare the measurement data related to the patient's vaginal pH against the threshold associated with vaginal pH. The computing system may compare the measurement data related to the patient's urinary pH against the threshold associated with urinary pH. A potential post-surgical hysterectomy complication may be predicted or detected when the measurement data related to one or more patient biomarkers crosses the corresponding threshold (e.g., for a predetermined amount of time). For example, when the measurement data related to a patient's body temperature, vaginal pH, and/or urinary pH crosses the respective threshold(s) associated with the patient, the computing system may detect potential SSI.

In an example, the threshold(s) may be associated with a context. The computing system may consider the context when assessing whether the measurement data crosses the corresponding threshold(s). The context may be associated with a hysterectomy surgery recovery timeline and/or a set of environmental attributes.

An actionable severity level associated with the predicted or detected post-surgical hysterectomy complication may be determined. For example, the computing system may determine an actionable severity level associated with a detected SSI. A notification may be sent to the patient and/or the HCP indicating a potential post-surgical hysterectomy complication and the associated actionable severity level. For example, the computing system may send a real-time notification to a patient and/or an HCP indicating a potential SSI and the actionable severity level associated with the SSI. The real-time notification may include the medical name, medical details, actionable severity level, and/or a recommended course of action associated with the detected post-surgical hysterectomy complication.

The computing system may determine type and/or content of the notification based on the determined actionable severity level. For example, when the detected complication is determined to be associated with low-risk actionable severity level, the computing system may generate a real-time notification to a device associated with the patient. When the detected complication is determined to be associated with high-risk actionable severity level, the computing system may generate a real-time notification to a device associated with the patient and a device associated with an HCP. For example, when the detected complication is determined to be associated with low-risk actionable severity level, the computing system may generate a real-time notification indicating the medical name of the complication and of the patient biomarker that crossed the corresponding threshold(s). When the detected complication is determined to be associated with high-risk actionable severity level, the computing system may generate a real-time notification indicating a recommended course of action.

A post-surgical hysterectomy complication may be predicted based on the measurement data. For example, the computing system may predict that, while a patient currently does not have an SSI, the patient may be likely to get an SSI in the future.

One or more thresholds may be received for each patient biomarker. For example, a wearable sensing system may receive, from a computing system, respective threshold(s) associated with a patient's body temperature, vaginal pH, urinary pH, and/or other patient biomarkers for SSI detection.

A request for detecting a potential post-surgical hysterectomy complication may be received. For example, the wearable sensing system may receive a request for detecting a potential SSI. The computing system may send the request along with one or more thresholds associated with the patient biomarker(s) to be monitored by the wearable sensing system. For example, the computing system may send a request for detecting SSI along with body temperature, vaginal pH, and/or urinary pH threshold(s).

Data related to the patient biomarker(s) may be measured. For example, the wearable sensing system may measure data related to a patient's body temperature, vaginal pH, and/or urinary pH for detecting a potential SSI. The wearable sensing system may monitor patient biomarker(s) in real-time by comparing the measured data related to patient biomarker(s) against the corresponding threshold(s) received from the computing system. The wearable sensing system may detect a potential post-surgical hysterectomy complication when the measured data related to one or more patient biomarkers crosses the corresponding threshold(s) (e.g., for a predetermined amount of time.) For example, when the measured data related to a patient's body temperature, vaginal pH, and/or urinary pH crosses the respective threshold(s) associated with the patient, the wearable sensing system may detect SSI (e.g., potential SSI).

A patient actionable severity level and/or an HCP actionable severity level associated with the detected post-surgical hysterectomy complication may be determined. For example, a wearable sensing system may determine a patient actionable severity level and/or an HCP actionable severity level associated with a detected SSI. A notification may be sent to the patient and/or the HCP indicating a potential post-surgical hysterectomy complication and the associated actionable severity level. For example, the wearable sensing system may send a real-time notification to a patient and/or an HCP indicating a potential SSI and the actionable severity level associated with the SSI. The real-time notification may include the medical name, medical details (a patient's name, medical ID, etc.), actionable severity level and/or a recommended course of action associated with the detected post-surgical hysterectomy complication.

The wearable sensing system may determine type and/or content of the notification based on the determined actionable severity level. For example, when the detected complication is determined to be associated with low-risk patient actionable severity level, the wearable sensing system may generate a real-time notification to a device associated with the patient. When the detected complication is determined to be associated with high-risk patient actionable severity level, the wearable sensing system may generate a real-time notification to a device associated with the patient and a device associated with an HCP. For example, when the detected complication is determined to be associated with low-risk patient actionable severity level, the wearable sensing system may generate a real-time notification indicating the medical name of the complication and of the patient biomarker(s) that crossed the corresponding threshold(s). When the detected complication is determined to be associated with high-risk patient actionable severity level, the wearable sensing system may generate a real-time notification indicating a recommended course of action.

A computing system for measuring and monitoring patient biomarkers for detecting or predicting a post-surgical hysterectomy complication may be provided. A post-surgical hysterectomy complication may be predicted or detected by comparing measured/processed patient biomarker data with a corresponding determined threshold value. The comparison of the measured/processed patient biomarker data and the corresponding threshold may be performed in association with a context. The context may be based on at least one of a hysterectomy surgery recovery timeline, at least one situational attribute, or at least one environmental attribute. A notification message associated with a predicted or detected post-surgical hysterectomy complication may be sent (e.g., sent in real time) to a patient device or a healthcare provider's device. The notification message may be supplemented by a severity level message.

Figure 64:
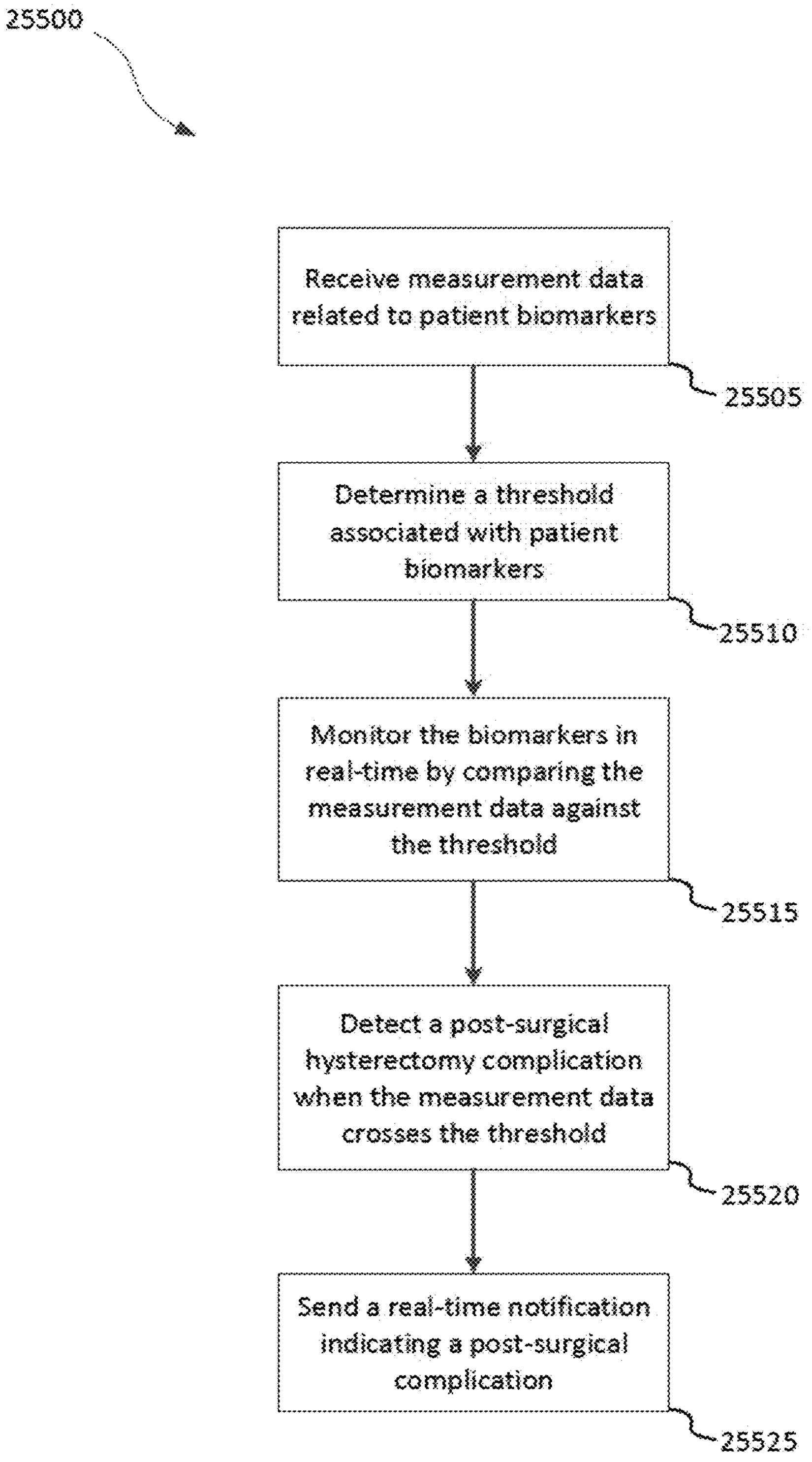
FIG. 64 shows example post-surgical hysterectomy complication prediction or detection.

FIG. 64 shows example 25500 post-surgical hysterectomy complication prediction or detection. One or more of 25505-25525 shown in FIG. 64 may be performed by a computing system, a sensing system, and/or another device, as described herein.

At 25505, measurement data related to patient biomarker(s) may be received. The patient biomarkers may be used for predicting or detecting a post-surgical hysterectomy complication. For example, the patient biomarkers may be used for detecting SSI, nerve damage, vaginal leak, and/or other post-surgical hysterectomy complications. The received measurement data may be raw measurement data that may be processed into processed measurement data. The processed measurement data may be in a different form than the raw measurement data. For example, the processed measurement data form may be better suited for analysis when compared to the raw measurement data form. The measurement data may be received from one or more patient sensing systems, such as a wristband patient sensing system, a patch patient sensing system, a tampon patient sensing system, a wearable brace patient sensing system, an instrumented socks patient sensing system, and/or the like.

The measurement data may be related to one or more patient biomarkers associated with post-surgical signs used for predicting or detecting post-surgical hysterectomy complications. Prediction or detection of a post-surgical hysterectomy complication may be based on one or more of the following post-surgical signs: system sepsis, shock, urination issues, etc. One or more patient biomarkers may be related to the post-surgical signs and may be monitored to predict or detect a post-surgical hysterectomy complication. Such patient biomarkers may include patient respiration rate, luteinizing hormone production, progesterone production, menstrual cycle, pelvis perfusion pressure, core body temperature, edema, urethra friability, blood glucose, blood pressure, blood lactate, sweat lactate, blood pH, vaginal pH, urinary pH, physical mobility, heart rate, urination rate, and/or heart rate variability.

Various sensing systems may perform patient biomarker measurements for post-surgical hysterectomy complication prediction or detection. For example, a wristband patient sensing system may measure patient biomarkers, including a patient's respiration rate, blood glucose, blood pressure, blood pH, blood lactate, sweat lactate, and/or heart rate. A patch patient sensing system may measure patient biomarkers such as luteinizing hormone production, progesterone production, menstrual cycle, and/or core body temperature. A tampon patient sensing system may measure patient biomarkers including vaginal pH, urinary pH, urination rate, pelvic perfusion pressure, and/or urethra friability. A wearable brace patient sensing system may measure physical mobility. A patient sensing system (e.g., an instrumented socks patient sensing system) may send measurement data related to edema. Based on the measurement data, one or more patient biomarkers may be monitored for detecting an SSI.

Measurement data associated with a patient may be obtained via one or more environmental sensing systems, for example, a video camera, a thermometer, etc. For example, a video camera may send measurement data (e.g., a video feed) related to a patient's physical attributes (e.g., physical mobility) to a computing system. A thermometer may send measurement data related to environmental temperature to the computing system.

The measurement data may be received in response to one or more requests for the measurement data. For example, a computing system may send a request to a patient sensing system requesting respective measurement data. The computing system may send the requests to different sensing systems at different time intervals or simultaneously. For example, the computing system may concurrently send requests to a patch sensing system and a tampon sensing system. For example, the computing system may send a request to an environmental sensing system at a first time interval and a request to a patch sensing system at a second time interval.

At 25510, a threshold associated with a patient biomarker may be determined. A patient biomarker threshold may be determined based on expected patient biomarker values, benchmark biomarker values, and/or the like. For example, a computing system and/or sensing system may determine a threshold associated with a patient's body temperature and/or a threshold associated with a patient's urinary pH. In an example, a composite threshold associated with a combined value of multiple patient biomarkers, e.g., a patient's body temperature and/or urinary pH, may be determined. The threshold may be (e.g., may further be) associated with measurement data received from one or more environmental sensing systems, for example, a video feed and/or a thermometer feed.

A patient biomarker threshold may be determined based on a standard threshold associated with a patient biomarker. A patient biomarker threshold may be customized for a patient. For example, patient biomarker threshold may be customized using a pre-surgical patient biomarker measurement, an in-surgical patient biomarker measurement, and/or a previously measured patient biomarker measurement. For example, a computing system and/or sensing system may determine a greater than normal threshold associated with a patient's body temperature based on pre-surgical and/or in-surgical measurements that indicated the patient has high body temperature. For example, a computing system and/or sensing system may determine a lesser than normal threshold associated with a patient's body temperature based on pre-surgical and/or in-surgical measurements that indicated the patient has low body temperature.

At 25515, one or more patient biomarkers may be monitored. For example, one or more patient biomarkers may be monitored in real-time. For example, a computing system and/or a sensing system may compare measurement data associated with each patient biomarker against a corresponding threshold(s). For example, measurement data associated with a patient's body temperature and/or urinary pH may be compared against a threshold associated with the patient's body temperature and/or urinary pH, respectively.

Measurement data associated with more than one patient biomarker may be combined into composite measurement data. For example, a computing system and/or sensing system may combine measurement data associated with a patient's body temperature with measurement data associated with a patient's urinary pH. The computing system and/or sensing system may compare this composite measurement data with a composite threshold. The measurement data associated with a patient biomarker may be associated with a patient biomarker weight. For example, the measurement data associated with a patient's body temperature may have a greater patient biomarker weight than the measurement data associated with a patient's urinary pH. The computing system and/or sensing system may consider the patient biomarker weight(s) when predicting or detecting a potential post-surgical hysterectomy complication. For example, the computing system and/or sensing system may be more likely to detect a complication when measurement data associated with high patient biomarker weight(s) crosses the corresponding threshold(s) compared to when measurement data associated with low patient biomarker weight(s) crosses the corresponding threshold(s). The computing system and/or sensing system may assign the patient biomarker weight(s). The patient biomarker weight(s) may be dynamic and adjusted based on the measurement data of another patient biomarker. The patient biomarker weight(s) may be selected by a healthcare provider overseeing the patient. For example, the healthcare provider may assign a high patient biomarker weight for a patient's body temperature and a low weight for a patient's urinary pH. The HCP may adjust the one or more patient biomarker weights during the patient's recovery.

At 25520, a post-surgical hysterectomy complication may be predicted or detected based on the measurement data. For example, a potential post-surgical hysterectomy complication may be identified on a condition that the measurement data related to a patient biomarker crosses a corresponding threshold for a predetermined amount of time. For example, a potential post-surgical hysterectomy complication may be identified on a condition that the measurement data related to multiple patient biomarkers cross their respective thresholds. For example, a potential post-surgical hysterectomy complication may be identified on a condition that composite measurement data related to a combination of patient biomarkers cross a composite threshold. A computing system and/or sensing system may be used to check the condition. For example, the computing system may detect a potential SSI on condition that a patient's body temperature and/or urinary pH measurement data crosses a body temperature and/or urinary pH threshold(s) for a predetermined amount of time. Crossing the threshold may include the measurement data associated with a patient biomarker increasing above the corresponding threshold value. Crossing the threshold may include the measurement data associated with a patient biomarker dropping below the corresponding threshold value. The predetermined amount of time may be used to mitigate erroneous measurement data. For example, the predetermined amount of time may reduce the number of false positive detections. The predetermined amount of time may be determined based on the one or more patient biomarkers being monitored. For example, the predetermined amount of time may be short when a patient's body temperature is being monitored and long when a patient's urinary pH is being monitored.

A patient biomarker threshold may be associated with one or more contexts. For example, a computing system and/or sensing system may consider the context(s) when comparing the measurement data against the corresponding threshold(s). The context(s) may be associated with a hysterectomy surgery recovery timeline, a situational attribute, and/or a set of environmental attributes. For example, a context may be associated with a patient's motion. The computing system may consider the patient's motion when comparing the measurement data against the corresponding thresholds. For example, when comparing a patient's heart rate measurement data against a heart rate threshold, the computing system may consider the patient's motion (e.g., walking, sleeping, exercising, etc.). The situation attribute may be a patient's eating, sleeping status and/or the like. For example, when comparing a patient's heart rate measurement data against a heart rate threshold, a computing system may consider whether the patient is eating. The patient biomarker threshold(s) may be adjusted based on one or more contexts. In an example, the computing system may increase the heart rate threshold when the patient is eating. In an example, the computing system may decrease the heart rate threshold when the patient is sleeping. Context data may be sent to the computing system from one or more patient biomarker sensing systems and/or one or more environmental sensing systems, for example, a video camera, a thermometer, etc. For example, a video camera may send context data (e.g., a video feed) related to a patient's physical mobility to the computing system. A thermometer may send measurement context data related to environmental temperature to the computing system. In an example, one or more environmental sensing systems may be a part of a patient biomarker sensing system. Environmental sensing system(s) and patient biomarker sensing system(s) may be associated with one device. For example, a smart mobile phone device may include one or more environmental sensing system(s) as well as one or more patient biomarker sensing(s).

The likelihood of a post-surgical hysterectomy complication occurring in the future may be predicted. For example, a computing system and/or sensing system may predict the likelihood of an SSI occurring by comparing a patient's body temperature measurement data against an expected value. The computing system may predict that an SSI may be highly likely to occur when a patient's body temperature crosses an expected value for a predetermined amount of time. The computing system and/or sensing system may assign a probability and a timeframe to the predicted complication. For example, the computing system may assign a probability of 9 out of 1 and a timeframe of 14 days to a predicted SSI. In such a case, the computing system has determined that the chances of an SSI occurring within the next 14 days is 0.9 out of 1.

Predictions of complications and/or recovery milestones may be generated, for example, by one or more machine learning (ML) models, such as predictive models, trained to make predictions after being trained on training data. For example, one or more ML classification algorithms may predict one or more types/classes of complications and/or recovery milestones by inference from input data. A model trained on vectorized training data may process vectorized input data. For example, a model may receive vectorized patient-specific data as input and classify the data as being indicative of one or more complications and/or one or more recovery milestones (e.g., each associated with a probability, likelihood, or confidence level). The model may receive updated patient-specific data to update predicted complications and probabilities and/or recovery milestones and probabilities. Complication mitigation (e.g., recommended actions or recommendations) may be based, at least in part, on one or more complications (e.g., and probabilities) generated by one or more models. A trained model may be any type of processing logic that performs an analysis and generates a prediction or determination derived from or generated based on empirical data, which may be referred to interchangeably as logic, an algorithm, a model, an ML algorithm or model, a neural network (NN), deep learning, artificial intelligence (AI), and so on.

A severity level (e.g., an actionable severity level) associated with the predicted or detected post-surgical hysterectomy complication may be determined. For example, a computing system and/or a sensing system may assign an actionable severity level to a detected SSI. In an example, the actionable severity level may be determined based on the degree by which the measurement data associated with a patient biomarker deviates from the corresponding threshold(s). For example, the computing system may determine that a patient's body temperature has crossed the corresponding threshold by a minimal amount and may assign a low-risk actionable severity level to the detected complication. For example, the computing system may determine that the patient's body temperature has crossed the corresponding threshold by a significant amount, which may be defined by a percentage of the threshold. In this case, a high-risk actionable severity level may be assigned to the detected complication. The actionable severity level may be determined based on the duration of the measurement data associated with a patient biomarker deviating from the corresponding threshold(s). Longer duration may be associated with higher severity level.

A severity level (e.g., an actionable severity level) may be indicated using an integer and/or a color code. For example, an integer 8 (on a scale of 1-10) and/or color red may indicate a high-risk actionable severity level, whereas an integer 2 using the same scale and/or color yellow may indicate a low-risk actionable severity level. In an example, the actionable severity level may be associated with a predicted post-surgical hysterectomy complication.

At 25525, a notification (e.g., a real-time notification) may be sent to the patient and/or the HCP indicating a potential post-surgical hysterectomy complication and the associated actionable severity level. For example, a computing system may send a real-time notification to a patient and/or an HCP indicating a potential SSI and the actionable severity level associated with the SSI. A real-time notification may be a notification sent remotely via a wireless connection and received, by a patient and/or HCP, within a determined timeframe. The notification (e.g., a real-time notification) may include the medical name, medical details (e.g., patient's name, patient's medical ID, etc.), actionable severity level, and/or a recommended course of action associated with the detected post-surgical hysterectomy complication.

Examples of notifications, recommendations, determinations, actions, and/or implementations (e.g., that may reduce or prevent one or more potential or predicted complications) may include, for example, one or more of the following: a selection or modification/change in a surgery plan, instrument choices, surgical approach, instrument configurations and/or schedule (e.g., of surgery and/or order of use of instruments during surgery). A notification may include, for example, one or more suggestions and/or determinations, such as one or more of the following: potential issue areas, procedure plan adjustments, alternative product mixes, and/or adjustment of control program parameters to interlinked smart instruments.

The computing system may determine type and/or content of a notification based on the determined actionable severity level. For example, when the predicted or detected complication is determined to be associated with low-risk actionable severity level, the computing system may generate a real-time notification to a device associated with the patient. When the detected complication is determined to be associated with high-risk actionable severity level, the computing system may generate a real-time notification to a device associated with the patient and a device associated with an HCP. The content of the notification may be the amount of information included in the notification. For example, when the detected complication is determined to be associated with low-risk actionable severity level, the amount of information included in the notification may be minimal. When the predicted or detected complication is associated with a high-risk actionable severity level, the amount of information included in the notification may be significant. For example, when the detected complication is determined to be associated with low-risk actionable severity level, the computing system may generate a real-time notification indicating the medical name of the complication and of the patient biomarker that crossed the corresponding threshold(s). When the detected complication is determined to be associated with high-risk actionable severity level, the computing system may generate a real-time notification indicating the medical name of the complication and of the patient biomarker that crossed the corresponding threshold(s) as well as a recommended course of action.

Figure 65:
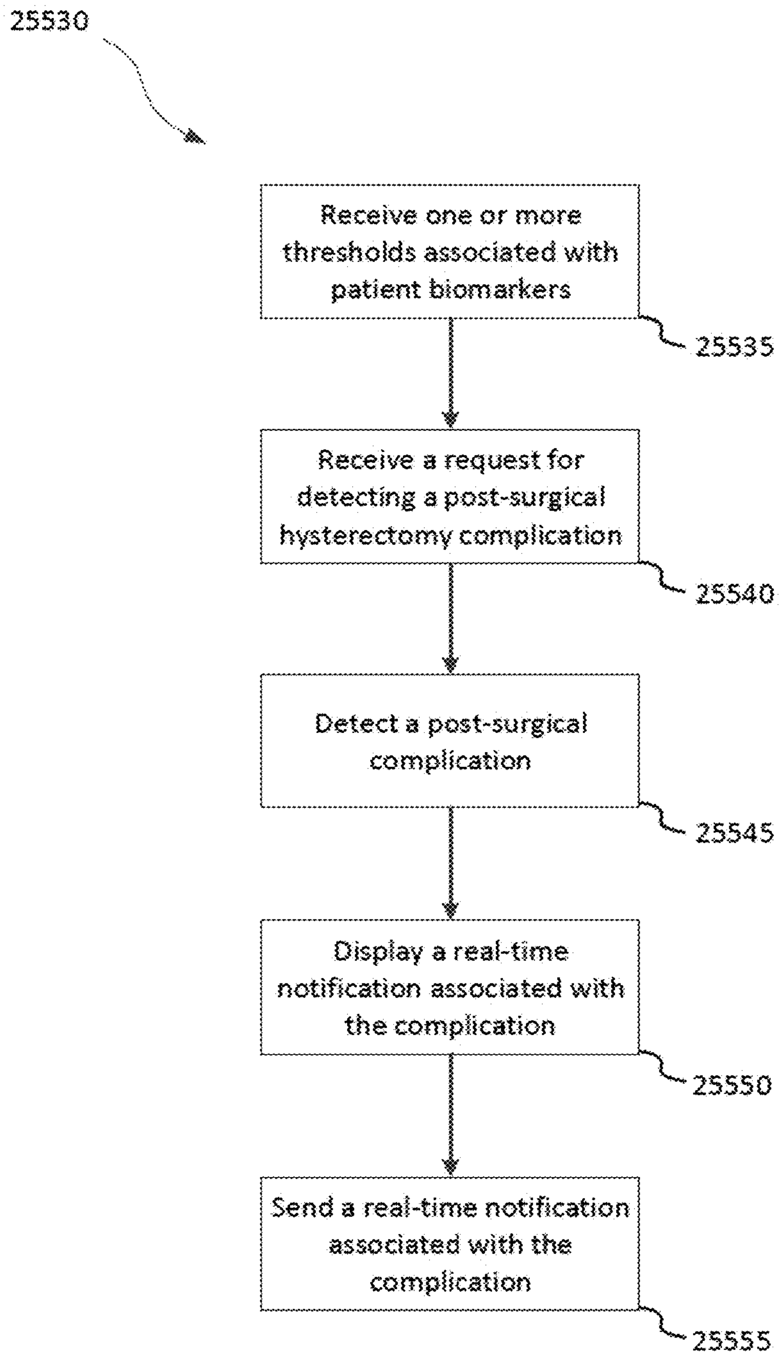
FIG. 65 shows example post-surgical hysterectomy complication wearable prediction or detection.

FIG. 65 shows example 25530 post-surgical hysterectomy complication wearable prediction or detection. One or more of 25535-25555 shown in FIG. 65 may be performed by a computing system, a sensing system, and/or another device, as described herein.

At 25535, a threshold as described herein with reference to FIG. 64 may be received. For example, a wearable sensing system may receive the threshold for predicting or detecting post-surgical hysterectomy complications, such as SSI, nerve damage, vaginal leak, and/or other post-surgical hysterectomy complications.

The wearable sensing system may be or may include a wristband patient sensing system, a patch patient sensing system, a tampon patient sensing system, a wearable brace patient sensing system, an instrumented socks patient sensing system, etc. One or more patient biomarkers as described herein with reference to FIG. 64 may be monitored to predict or detect a post-surgical hysterectomy complication. Data as described herein with reference to FIG. 64 may be measured by the wearable sensing system.

At 25540, a request may be received for predicting or detecting a potential post-surgical hysterectomy complication. For example, the wearable sensing system may receive a request for detecting SSI. For example, a computing system may send the wearable sensing system the request. The request may include one or more thresholds associated with patient biomarkers related to the post-surgical complication. For example, a request to detect SSI may include body temperature and/or urinary pH threshold(s).

The threshold(s) received by the wearable sensing may be associated with one or more contexts as described herein with reference to FIG. 64. The one or more contexts may be sent by a computing system to the wearable sensing system. The context(s) and/or threshold(s) may be sent simultaneously or at different time intervals.

At 25545, a post-surgical complication may be predicted or detected. For example, the wearable sensing system may monitor the set of patient biomarkers and detect a potential post-surgical hysterectomy complication as described herein with reference to FIG. 64. The wearable sensing system may predict the likelihood of a post-surgical hysterectomy complication as described herein with reference to FIG. 64.

A patient actionable severity level and an HCP actionable severity level associated with the predicted or detected post-surgical hysterectomy complication may be determined. For example, the wearable sensing system may assign a patient actionable severity level and HCP actionable severity level to a detected SSI. The actionable severity level(s) may be determined based on the degree by which measurement data associated with a patient biomarker deviates from the corresponding threshold(s). For example, the wearable sensing system may determine that a patient's body temperature has crossed the corresponding threshold by a minimal amount and may assign a low-risk patient and/or HCP actionable severity level to the detected complication. The wearable sensing system may determine that a patient's body temperature has crossed the corresponding threshold by a significant amount, which may be defined by a percentage of the threshold. A high-risk patient and/or HCP actionable severity levels may be assigned to the detected complication. The actionable severity level(s) may be determined based on the duration of the measurement data associated with a patient biomarker deviating from the corresponding threshold(s). Longer duration may be associated with higher severity level.

The actionable severity level(s) may be indicated using an integer and/or a color code. For example, an integer 8 (on a scale of 1-10) and/or color red may indicate a high-risk patient and/or HCP actionable severity level, whereas an integer 2 using the same scale and/or color yellow may indicate a low-risk patient and/or HCP actionable severity level. In an example, the actionable severity level may be associated with a predicted post-surgical hysterectomy complication.

At 25550, a notification may be displayed to the patient indicating a potential post-surgical hysterectomy complication and the associated actionable severity level. For example, the wearable sensing system may display a real-time notification to a patient indicating a potential SSI and the patient and the actionable severity level associated with the SSI.

At 25555, a notification (e.g., a real-time notification) indicating a potential post-surgical hysterectomy complication and the HCP actionable severity level associated with it may be sent to an HCP as described with reference to FIG. 64.

Figure 66:
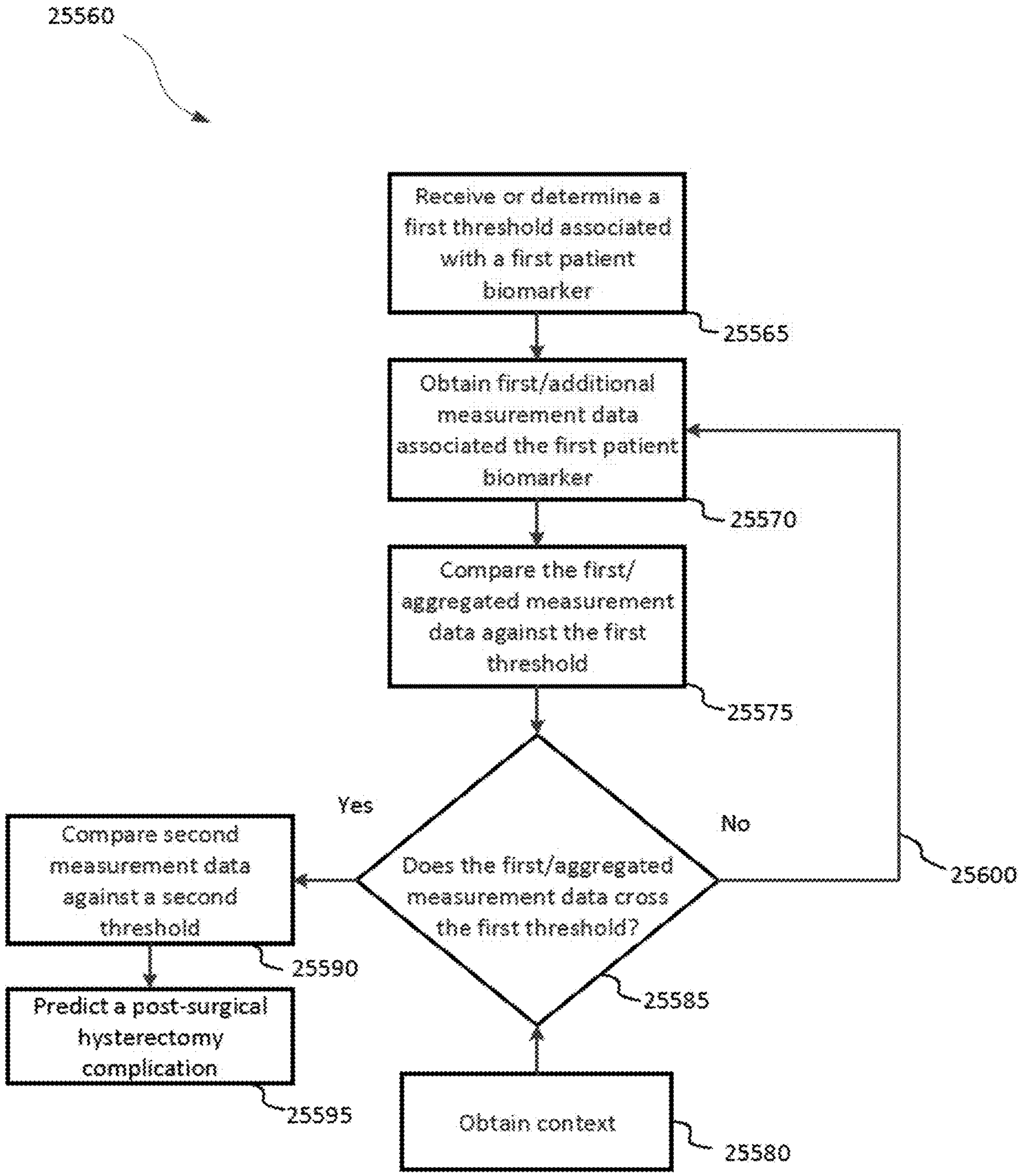
FIG. 66 shows example post-surgical hysterectomy complication wearable prediction or detection.

FIG. 66 shows example 25560) post-surgical hysterectomy complication wearable prediction or detection. One or more of 25565-25600 shown in FIG. 66 may be performed by a computing system, a sensing system, and/or another device described herein. At 25565, a first threshold associated with a first patient biomarker may be received and/or determined as described herein with reference to FIG. 64 and FIG. 65. For example, a threshold associated with body temperature may be received by a sensing system and/or determined by a computing system. The threshold may be used to predict or detect a post-surgical hysterectomy complication, for example an SSI.

At 25570, first measurement data associated with the first patient biomarker may be obtained, for example, as described herein with reference to FIG. 64 and FIG. 65. For example, measurement data associated with body temperature may be obtained by a computing system and/or a sensing system for predicting or detecting post-surgical hysterectomy complication. The first measurement data may be obtained as a response to a request for the measurement data. For example, a computing system and/or a sensing system may request the first measurement data.

At 25575, the first measurement data may be compared against the first threshold, for example, as described herein with reference to FIG. 64 and FIG. 65.

At 25580, a computing system and/or a sensing system may obtain context as described herein with reference to FIG. 64. The computing system/sensing system may consider the context when determining whether the measurement data crosses the threshold. For example, the computing system/sensing system may adjust the first threshold based on the received context. The computing system may use the received context in determining whether a measurement data crosses the threshold.

At 25585, a computing system and/or sensing system may compare the first measurement data against the first threshold by determining whether the measurement data crosses the threshold (e.g., for a predetermined amount of time) as described herein with reference to FIG. 64 and FIG. 65. The computing system or the sensing system may compare the first measurement against the first threshold based on a context.

Assuming that the first measurement data, for example, based on the context, crosses the first threshold, at 25590, second measurement data may be compared against a second threshold as described herein with reference to FIG. 64 and FIG. 65. The second threshold may be associated with a second patient biomarker. The second threshold may be received and/or determined similar to how the first threshold may be received and/or determined. The second measurement data may be compared based on a condition that the first measurement data crosses the first threshold for a predetermined amount of time. A computing and/or sensing system may determine that the first measurement data crosses the first threshold for a predetermined amount of time and may compare the second measurement data against a second threshold. In an example, second measurement data may be compared on a condition that the first measurement data crosses the first threshold by a predetermined amount, for example 10% of the first threshold value. The computing system may request the second measurement data when the first measurement data crosses the first threshold.

At 25595, a post-surgical hysterectomy complication may be predicted as described herein with reference to FIG. 64 and FIG. 65. A computing system and/or a sensing system may predict a post-surgical hysterectomy complication based on the first measurement data comparison and the second measurement data comparison. For example, the computing system may predict a complication when both the first measurement data and the second measurement data cross the respective first and second thresholds. The computing system may assign weight(s) to each comparison. The computing system may assign a high comparison weight to the first measurement data crossing the first measurement data and a low comparison weight to the second measurement data crossing the second threshold. Predicting a post-surgical hysterectomy complication may be based on the comparison weight(s). A computing system may be more likely to predict a complication when measurement data associated with a high comparison weight crosses a threshold compared to measurement data associated with low comparison weight crossing a threshold.

In case a computing system and/or sensing system determines that the first measurement data does not cross the first threshold (e.g., for a predetermined amount of time), the computing system and/or the sensing system may proceed at 25600 and continue at 25570.

Additional or optionally at 25570, the computing system may obtain additional first measurement data. For example, at 25570), the computing system may aggregate the additional first measurement data with the original first measurement data. The aggregated first measurement data may be compared against the first threshold. The computing system and/or sensing system may adjust the first threshold based on the additional first measurement data.

Figure 67:
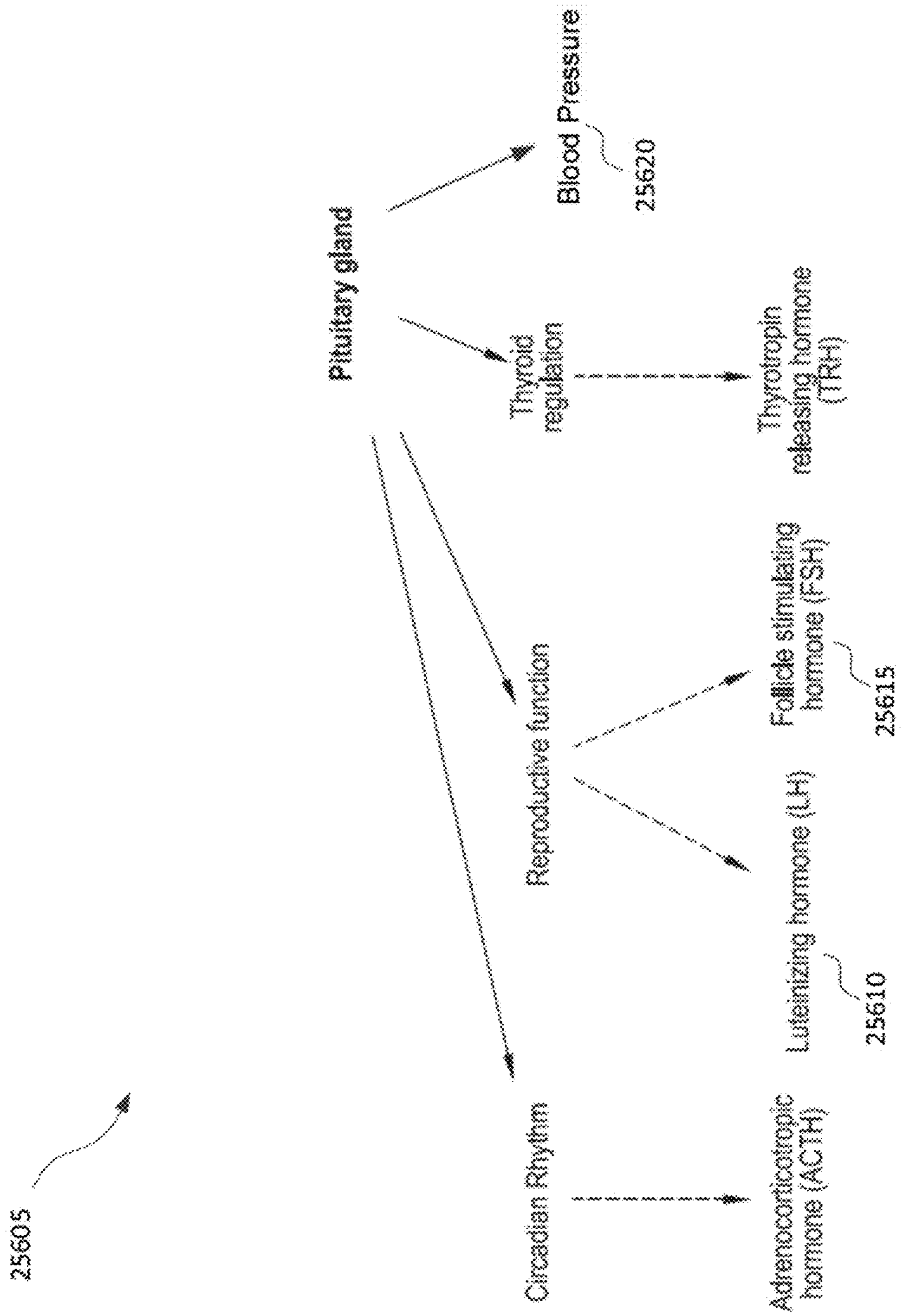
FIG. 67 shows example patient biomarkers related to the pituitary gland for predicting or detecting post-surgical hysterectomy complication.

FIG. 67 shows example patient biomarkers 25605 related to the pituitary gland for predicting or detecting post-surgical hysterectomy complication.

For example, luteinizing hormone 25610 may be set as a patient biomarker and monitored to detect fibroid development. After hysterectomy surgery, a patient may be instructed by an HCP to use a sensing system to measure luteinizing hormone 25610 for a period of time following the surgery. The sensing system may include a sensor for measuring luteinizing hormone 25610. During this period, the sensing system may send measurement data associated with the luteinizing hormone 25610 to the computing system. The sensing system may send the measurement data as a response to a request for the measurement data. The sensing system may send the measurement data based on a periodic cycle, for example at twenty-minute intervals. The computing system may adjust the period cycle. For example, the computing system may identify a critical phase of recovery from hysterectomy surgery. During this phase, the computing system may shorten the periodic cycle. The computing system may identify a non-critical phase of recovery and may lengthen the period cycle. The computing system may compare the received measurement data with a corresponding luteinizing hormone 25610 threshold and, if the measurement data crosses the corresponding luteinizing hormone 25610 threshold for a predetermined amount of time, may predict or detect a potential SSI and send a real-time notification to the HCP and/or patient. The corresponding luteinizing hormone 25610 threshold may have been determined by the computing system based on pre-surgical, in-surgical, and/or previously measured patient biomarker measurements. The predetermined amount of time may be determined based on the luteinizing hormone 25610 biomarker.

A combination of patient biomarkers related to the pituitary gland may be monitored to predict or detect a potential post-surgical hysterectomy complication. For example, luteinizing hormone 25610 and follicle stimulating hormone 25615 may be set as patient biomarkers and monitored to detect ovarian dysfunction. A sensing system may include a sensor that may measure luteinizing hormone 25610 and follicle stimulating hormone 25615. For example, the sensing system may include two sensors, the first of which may measure luteinizing hormone 25610 and the second of which may measure follicle stimulating hormone 25615. During the post-surgical period, the sensing system may send the respective measurement data associated with the luteinizing hormone 25610 and the follicle stimulating hormone 25615 to the computing system. The computing system may compare the measurement data with a corresponding luteinizing hormone 25610 threshold and a corresponding follicle stimulating hormone 25615 threshold, respectively. The computing system may detect an SSI when either set of measurement data crosses the corresponding threshold for a predetermined amount of time and send a real-time notification to the HCP and/or the patient. For example, the computing system may only detect an SSI when both sets of measurement data cross the corresponding threshold. The patient biomarker threshold(s) may be associated with patient biomarker weights as described herein with reference to FIG. 64. For example, luteinizing hormone 25610 may be associated with luteinizing hormone 25610 weight. For example, follicle stimulating hormone 25615 may be associated with follicle stimulating hormone 25615 weight. The predetermined amount of time may be determined based on the luteinizing hormone 25610 and the follicle stimulating hormone 25615 biomarkers.

A combination of patient biomarkers related to and/or unrelated to the pituitary gland may be monitored to predict or detect a post-surgical hysterectomy complication. For example, luteinizing hormone 25610 and blood pressure 25620) may be set as patient biomarkers and monitored by a computing system to detect fibroid development. A sensing system may include a sensor that may measure luteinizing hormone 25610 and blood pressure 25620.

A patient biomarker may be monitored by the sensing system. The sensing system may be a patient wearable sensing system. For example, a sensor may measure luteinizing hormone 25610 and transmit measurement data to the patient wearable sensing system using one or more RF protocols, as described herein with respect to FIG. 65. The patient wearable sensing system may store the measurement data. The patient wearable sensing system may compare the measurement data against a corresponding luteinizing hormone 25610 threshold and, if the measurement data crosses the corresponding luteinizing hormone 25610 threshold for predetermined amount of time, may detect fibroid development and send a real-time notification to the HCP and/or the patient. A combination of patient biomarkers related to and/or unrelated to the pituitary gland may be monitored by the sensing system.

Figure 68:
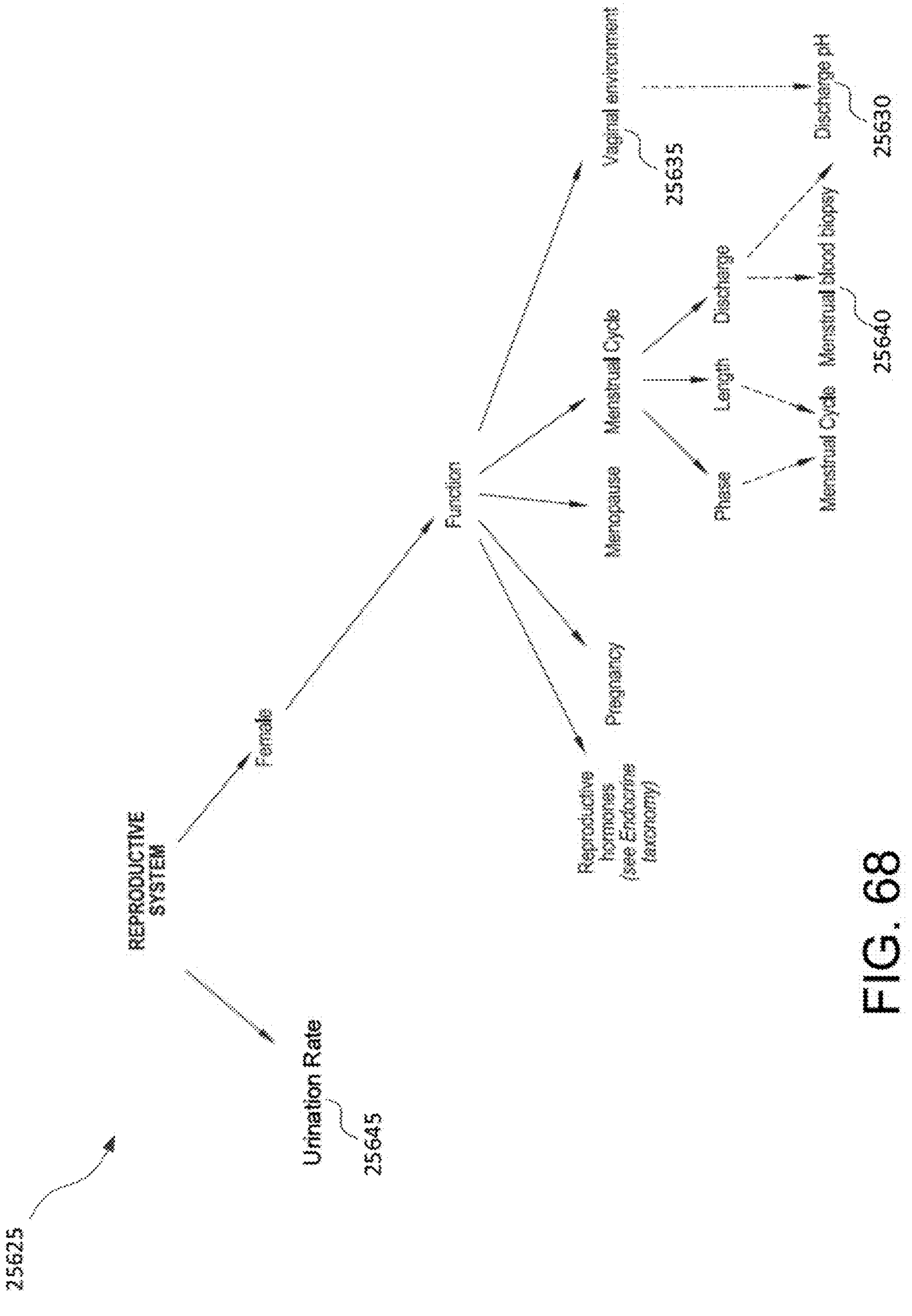
FIG. 68 shows example patient biomarkers related to the reproductive system for predicting or detecting post-surgical hysterectomy complication.

FIG. 68 shows example patient biomarkers 25625 related to the reproductive system for predicting or detecting post-surgical hysterectomy complication.

For example, pH (e.g., discharge pH) 25630 of the vagina or the vaginal environment 25635 may be set as a patient biomarker and monitored to detect SSI. After hysterectomy surgery, a patient may be instructed by an HCP to use a sensing system to measure vaginal pH 25630 for a period of time following the surgery. The sensing system may include a sensor for measuring vaginal pH 25630. During this period, the sensing system may send measurement data associated with the vaginal pH 25630 to the computing system. The sensing system may send the measurement data as a response to a request for the measurement data. The sensing system may send the measurement data based on a periodic cycle, for example at twenty-minute intervals. The computing system may adjust the period cycle. For example, the computing system may identify a critical phase of recovery from hysterectomy surgery. During this phase, the computing system may shorten the periodic cycle. The computing system may identify a non-critical phase of recovery and may lengthen the period cycle. The computing system may compare the received measurement data with a corresponding vaginal pH 25630 threshold and, if the measurement data crosses the corresponding vaginal pH 25630 threshold for a predetermined amount of time, may predict or detect a potential SSI and send a real-time notification to the HCP and/or patient. The corresponding vaginal pH 25630 threshold may have been determined by the computing system based on pre-surgical, in-surgical, and/or previously measured patient biomarker measurements. The predetermined amount of time may be determined based on the vaginal pH 25630 biomarker.

A combination of patient biomarkers related to the reproductive system may be monitored to detect a potential post-surgical hysterectomy complication. For example, vaginal pH 25630 and menstrual blood composition 25640 may be set as patient biomarkers and monitored to detect endometriosis. A sensing system may include a sensor that may measure vaginal pH 25630 and menstrual blood composition 25640. For example, the sensing system may include two sensors, the first of which may measure vaginal pH 25630 and the second of which may measure menstrual blood composition 25640. During the post-surgical period, the sensing system may send the respective measurement data associated with the vaginal pH 25630 and the menstrual blood composition 25640 to the computing system. The computing system may compare the measurement data with a corresponding vaginal pH 25630 threshold and a corresponding menstrual blood composition 25640 threshold, respectively. The computing system may detect an SSI when either set of measurement data crosses the corresponding threshold for a predetermined amount of time and send a real-time notification to the HCP and/or the patient. For example, the computing system may only detect an SSI when both sets of measurement data cross the corresponding threshold. The patient biomarker threshold(s) may be associated with patient biomarker weights as described herein with reference to FIG. 64. For example, vaginal pH 25630 may be associated with vaginal pH 25630 weight. For example, menstrual blood composition 25640 may be associated with menstrual blood composition 25640 weight. The predetermined amount of time may be determined based on the vaginal pH 25630 and the menstrual blood composition 25640 biomarkers.

A combination of patient biomarkers related to and/or unrelated to the reproductive system may be monitored to detect a post-surgical hysterectomy complication. For example, pH 25630 of the vagina 25635 and urination rate 25645 may be set as patient biomarkers and monitored by a computing system to detect SSI. A sensing system may include a sensor that may measure vaginal pH 25630 and urination rate 25645.

A patient biomarker may be monitored by the sensing system. The sensing system may be a patient wearable sensing system. For example, a sensor may measure vaginal pH 25630 and transmit measurement data to the patient wearable sensing system using one or more RF protocols, as described herein with respect to FIG. 65. The patient wearable sensing system may store the measurement data. The patient wearable sensing system may compare the measurement data against a corresponding vaginal pH 25630 threshold and, if the measurement data crosses the corresponding vaginal pH 25630 threshold for predetermined amount of time, may detect fibroid development and send a real-time notification to the HCP and/or the patient. A combination of patient biomarkers related to and/or unrelated to the reproductive system may be monitored by the sensing system.

Figure 69A:
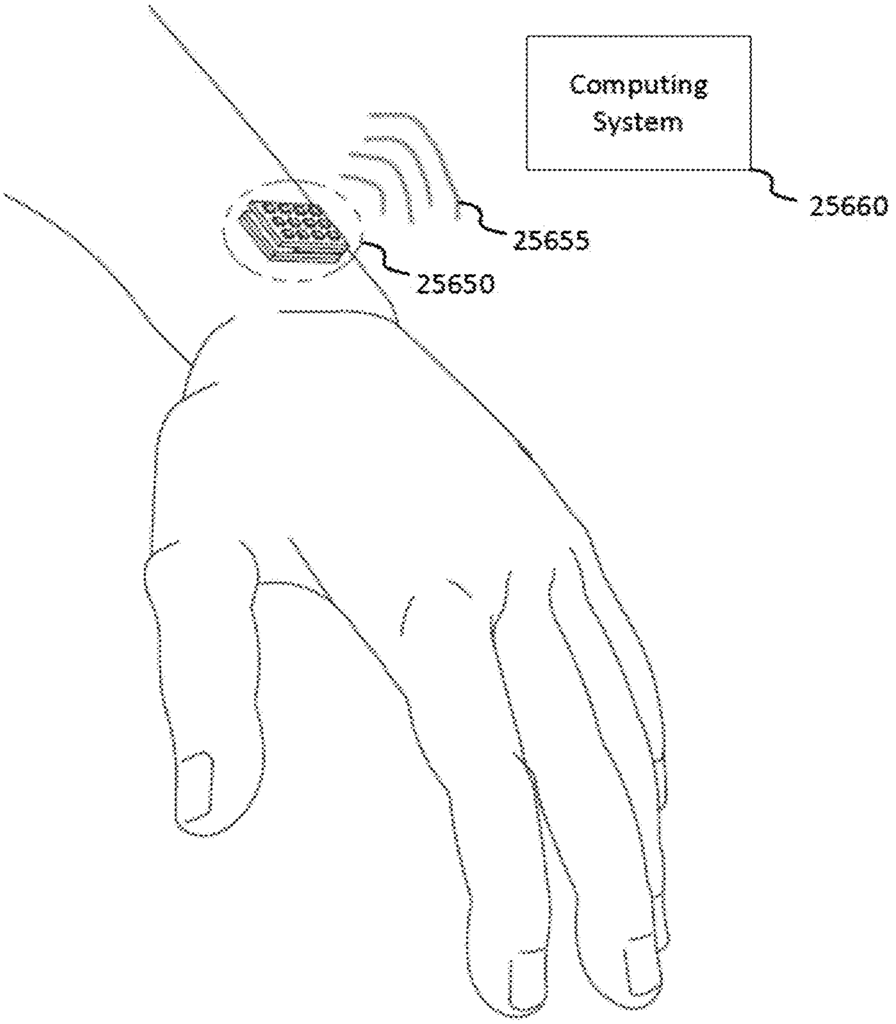
FIG. 69A shows an example wearable sensing system for detecting post-surgical hysterectomy complications.

FIG. 69A shows an example wearable sensing system for detecting post-surgical hysterectomy complications.

As illustrated, a patient may wear a patch sensing system 25650. In an example, an HCP may direct the patient to wear the patch sensing system 25650 on a target area of the body. The patch sensing system 25650 may include a sensor unit that measures data related to one or more patient biomarkers to be monitored for detecting a post-surgical hysterectomy complication, for example, as described herein with reference to FIG. 7B and/or 7C and FIGS. 11A-11D. In an example, the patch sensing system 25650 may be a sensor unit and include multiple sensors as described herein with reference to FIG. 7D and FIGS. 11A-11D. The patch sensing system 25650 may be communicatively connected to a computing system 25660 (e.g., a surgical hub, a mobile device, a tablet, etc.) and/or remote server(s) as described with reference to FIG. 2B and/or 2C. The patch sensing system 25650 may be or may include a wearable sensing system. The wearable sensing system may receive, from a computing system 25660, one or more thresholds associated with the patient biomarkers to be monitored, as described herein with reference to FIG. 65. The wearable sensing system may send, for example, to a computing system 25660, measurement data related to the patient biomarkers to be monitored, as described herein with reference to FIG. 64. The computing system 25660 may send the measurement data to one or more analytics servers as described with reference to FIG. 12. The computing system 25660 may receive environmental measurement data from one or more environmental sensing as described with reference to FIG. 12.

The patch sensing system 25650 may be used to measure one or more patient biomarkers related to a post-surgical hysterectomy complication, for example SSI, nerve damage, vaginal leak, and/or other post-surgical hysterectomy complications. The sensing system 25650 may include one or more sensors implementing various sensing mechanisms, as described herein with reference to FIGS. 11A-11D. The patch sensing system 25650 may begin measuring the one or more patient biomarkers when the patient attaches the patch sensing system 25650. The patch sensing system 25650 may begin measuring at a time after the patient attaches the patch sensing system 25650. Determining when the patch sensing system 25650 begins measuring may be based on the sensing system's capacity and/or power.

The patch measurements may be associated with patch measurement data. For example, the body temperature and/or blood lactate patch measurements may be associated with respective body temperature and/or blood lactate patch measurement data. The patch sensing system 25650 may monitor the patch measurement data in real-time by comparing the patch measurement data to one or more corresponding thresholds. The patch sensing system 25650 may obtain one or more thresholds associated with one or more patient biomarkers. In an example, the one or more thresholds may be received from a computing system 25660 or a computing device, as described herein with reference to FIG. 65. For example, the patch sensing system 25650 may compare the body temperature and/or blood lactate patch measurement data with a corresponding body temperature and/or blood lactate threshold, respectively. Multiple comparisons may be performed simultaneously or at different time intervals. The patch sensing system 25650 may detect or predict a potential post-surgical hysterectomy complication when the patch measurement data related to at least one patient biomarker crosses the corresponding threshold for a predetermined amount of time. The predetermined amount of time may be received from the computing system 25660 and stored in the patch sensing system 25650.

The patch sensing system 25650 may transmit the patch measurement data to a computing system 25660 using one or more RF protocols, as described herein. For example, the patch may transmit the patch measurement data using a Bluetooth protocol (e.g., a low energy Bluetooth protocol), a WiFi protocol, and/or using other wireless protocols, as described herein. In such an example, the computing system 25660 may monitor the patch measurement data (e.g., the body temperature and/or blood lactate patch measurement data) in real-time by comparing patch measurement data to one or more corresponding thresholds. The computing system 25660) may predict or detect a potential post-surgical hysterectomy complication when the patch measurement data related to at least one patient biomarker crosses the corresponding threshold for a predetermined amount of time, as described herein with reference to FIG. 64.

Figure 69B:
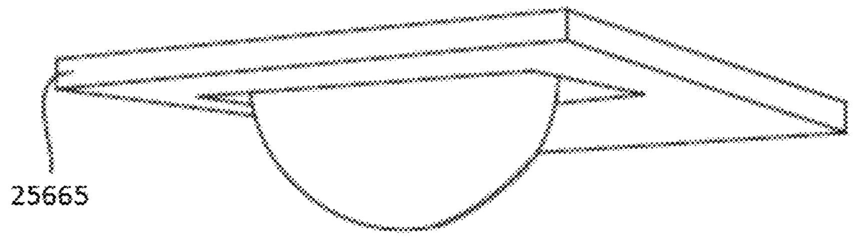
FIG. 69B shows an exemplary patch sensing system for detecting post-surgical hysterectomy complications.

FIG. 69B shows an exemplary patch sensing system for detecting post-surgical hysterectomy complications.

The exemplary patch sensing system 25665 may measure the patient biomarker(s) as described herein with reference to FIGS. 11A-11D, FIG. 64, and/or FIG. 65. For example, the patient biomarker(s) measured may be body temperature and/or blood lactate. The patient may wear the exemplary patch sensing system 25665 and the sensing system 25665 may measure body temperature and/or blood lactate. The patient biomarker(s) may be measured for a predetermined amount of time. For example, the sensing system 25665 may request sensor unit(s) to measure body temperature and/or blood lactate for 60 seconds. The sensor unit(s) may continuously measure body temperature and/or blood lactate as the patient wears the exemplary patch sensing system 25665. The sensor unit(s) may measure body temperature and/or blood lactate based on a periodic cycle, for example at three second intervals. The period cycle may be adjusted as the patient wears the exemplary patch sensing system. For example, a computing system and/or sensing system may shorten the periodic cycle to increase the frequency of the patient biomarker measurement(s). For example, a computing system and/or sensing system may lengthen the periodic cycle to decrease the frequency of the patient biomarker measurement(s).

FIG. 70 shows example correlation 25670 between relevant patient biomarkers and hysterectomy procedural steps. In the following description of FIG. 70, reference should also be made to FIG. 2 and FIG. 5. FIG. 2 provides the settings used in a patient monitoring system. FIG. 5 provides various components used in a surgical procedure.

A hysterectomy surgery may include multiple surgical procedural steps. For example, a hysterectomy surgery may include trocar placement, desiccating parametrial veins and ligaments, mobilizing the bladder, resecting the uterus and cervix, and vaginal cuff closure. Under each surgical procedural step, one or more tasks may be performed by an HCP (e.g., a surgeon). For example, under trocar placement surgical procedural step, the HCP may insert trocars through the abdomen. For this task, the HCP may use a Veress needle instrument.

Under desiccating parametrial veins and ligaments surgical procedural step, the HCP may apply heat to the parametrial veins and ligaments. For this task, the HCP may use an advanced bipolar RF and/or harmonic scalpel instrument(s)

Under mobilizing the bladder surgical procedural step, the HCP may cut-off the blood supply from bodily structures attached to the bladder. For this task, the HCP may use a harmonic scalpel instrument.

Under resecting the uterus and cervix surgical procedural step, the HCP may cut out a segment of the uterus and/or cervix that may be cancerous, infected, and/or impaired.

During this surgical procedural step, the HCP may use an endopath and/or harmonic scalpel instrument(s).

Under vaginal cuff closure surgical procedural step, the HCP may stitch together the top end of the vagina. During the vaginal cuff closure surgical procedural step, the HCP may use sutures and/or LapraTy Clip instrument(s).

A patient biomarker may be correlated to a hysterectomy procedural step. For example, a patient's blood pressure may be correlated to mobilizing a patient's bladder step, for example, to track blood supply after mobilization. A patient's uterus tissue perfusion pressure may be correlated to resecting the uterus since during resection the surgeon is causing trauma to the tissue by severing pieces of the infected uterus. A patient's edema may be correlated to vaginal cuff closure since during vaginal cuff closure the surgeon is stitching together the top end of vagina in order to allow the bowel to function properly.

A patient biomarker may be monitored based on a procedural step. For example, an HCP may choose to monitor a patient's blood pressure due to a problem that arose when the surgeon was mobilizing the bladder. A patient's tissue perfusion pressure may be monitored based on an observation made by the HCP during the uterus and cervix resection surgical procedural step. Assigning patient biomarker weight(s) as described with reference to FIG. 64 may be assigned based on a surgical procedural step. For example, a patient's edema may be assigned a high patient biomarker weight when an HCP notices certain issues during the vaginal cuff closure surgical procedural step.

A patient biomarker threshold may be adjusted based on a surgical procedural step. For example, a blood pressure threshold may be decreased when an HCP notices issues regarding the bladder mobilization surgical procedural step. The predetermined amount of time for detecting a complication as described with reference to FIGS. 64 and 66 may change based on a procedural step.

In an example, a computing system and/or sensing system may determine a relevant surgical procedural step based on the correlated patient biomarker crossing a corresponding threshold(s) for a predetermined amount of time. The relevant surgical procedural step may be associated with a detected hysterectomy complication. For example, when a patient's tissue perfusion pressure crosses a tissue perfusion pressure threshold, a computing system may detect a vaginal leak and determine uterus and cervix resection as the relevant procedural step associated with the vaginal leak.

The relevant procedural step may indicate the procedural step that may be a cause of the detected complication. For example, the detected complication may be a surgical site infection and the relevant procedural step associated with the SSI may be bladder mobilization surgical procedural step. In such a case, the way the bladder mobilization surgical procedural step was conducted may be a cause of the detected SSI.

A notification may be sent to the patient and/or HCP indicating a potential post-surgical hysterectomy complication and the associated relevant procedural step. For example, a computing system and/or sensing system may send a real-time notification to a patient and/or HCP indicating a vaginal leak and uterus and cervix resection as the relevant procedural step associated with the vaginal leak. The relevant procedural step may be used when correcting the detected post-surgical hysterectomy complication. For example, an HCP may decide to perform a corrective surgery in order correct a vaginal leak. A notification indicating uterus and cervix resection as the surgical procedural step may be sent to the HCP before and/or during the corrective surgery. The HCP may use the use the information provided in the notification to develop a plan for a follow-up corrective surgery. In an example, the HCP may target an area that is involved in uterus and cervix resection.

Measurement data related to a set of patient biomarkers for post-surgical monitoring may be received. For example, a computing system may be configured to receive the measurement data from one or more sensing systems. A sensing system may be or may include a patient wearable device. A sensing system may be or may include an environmental sensing system. A sensing system may include one or more sensors. The set of patient biomarkers may be monitored for detecting a post-surgical bariatric complication. For example, the set of patient biomarkers for detecting gastroparesis may include a patient's blood glucose, eating rate, and/or GI motility. For example, the set of patient biomarkers for detecting stomach leak may include a patient's blood lactate and/or sweat lactate. For example, the set of patient biomarkers for detecting absorption issues may include a patient's GI motility and/or GI pH. The measurement data received from the sensing system(s) may be in response to one or more requests for the measurement data. For example, the computing system may send a request to one or more sensing systems requesting respective measurement data.

One or more thresholds may be determined for a patient biomarker. For example, the surgical computing system may determine respective threshold(s) associated with a patient's blood glucose, eating rate, GI motility, and/or other patient biomarkers for gastroparesis. The threshold(s) may be standard threshold(s). The threshold(s) may be customized for a patient based on the patient's pre-surgical, in-surgical, and/or previously measured post-surgical patient biomarker measurements. A patient biomarker may be monitored in real time by comparing the measurement data related to the patient biomarker against the corresponding threshold(s). For example, the computing system may monitor a patient's blood glucose in real time by comparing the measurement data related to the patient's blood glucose against the threshold associated with the patient's blood glucose. The computing system may compare the measurement data related to the patient's eating rate against the threshold associated with eating rate. The computing system may compare the measurement data related to the patient's GI motility against the threshold associated with GI motility. A potential post-surgical bariatric complication may be detected when the measurement data related to one or more patient biomarkers crosses the corresponding threshold (e.g., for a predetermined amount of time). For example, when the measurement data related to a patient's blood glucose, eating rate, and/or GI motility crosses the respective threshold(s) associated with the patient, the computing system may detect potential gastroparesis.

In an example, the threshold(s) may be associated with a context. The computing system may consider the context when assessing whether the measurement data crosses the corresponding threshold(s). The context may be associated with a bariatric surgery recovery timeline and/or a set of environmental attributes.

An actionable severity level associated with the detected post-surgical bariatric complication may be determined. For example, the computing system may determine an actionable severity level associated with detected gastroparesis. A notification may be sent to the patient and/or the HCP indicating a potential post-surgical bariatric complication and the associated actionable severity level. For example, the computing system may send a real-time notification to a patient and/or an HCP indicating a potential gastroparesis and the actionable severity level associated with the gastroparesis. The real-time notification may include the medical name, medical details, actionable severity level and/or a recommended course of action associated with the detected post-surgical bariatric complication.

The computing system may determine type and/or content of the notification based on the determined actionable severity level. For example, when the detected complication is determined to be associated with low-risk actionable severity level, the computing system may generate a real-time notification to a device associated with the patient. When the detected complication is determined to be associated with high-risk actionable severity level, the computing system may generate a real-time notification to a device associated with the patient and a device associated with an HCP. For example, when the detected complication is determined to be associated with low-risk actionable severity level, the computing system may generate a real-time notification indicating the medical name of the complication and of the patient biomarker that crossed the corresponding threshold(s). When the detected complication is determined to be associated with high-risk actionable severity level, the computing system may generate a real-time notification indicating a recommended course of action.

A post-surgical colorectal complication may be predicted based on the measurement data. For example, the computing system may predict that, while a patient currently does not have a gastroparesis, the patient may be likely to get gastroparesis in the future.

One or more thresholds may be received for each patient biomarker. For example, a wearable sensing system may receive, from a computing system, respective threshold(s) associated with a patient's blood glucose, eating rate, GI motility, and/or other patient biomarkers for gastroparesis detection.

A request for detecting a potential post-surgical bariatric complication may be received. For example, the wearable sensing system may receive a request for detecting potential gastroparesis. The computing system may send the request along with one or more thresholds associated with the patient biomarker(s) to be monitored by the wearable sensing system. For example, the computing system may send a request for detecting gastroparesis along with blood glucose, eating rate, and/or GI motility threshold(s).

Data related to the patient biomarker(s) may be measured. For example, the wearable sensing system may measure data related to a patient's blood glucose, eating rate, and/or GI motility for detecting potential gastroparesis. The wearable sensing system may monitor patient biomarker(s) in real time by comparing the measured data related to patient biomarker(s) against the corresponding threshold(s) received from the computing system. The wearable sensing system may detect a potential post-surgical bariatric complication when the measured data related to one or more patient biomarkers crosses the corresponding threshold(s) (e.g., for a predetermined amount of time). For example, when the measured data related to a patient's blood glucose, eating rate, and/or GI motility crosses the respective threshold(s) associated with the patient, the wearable sensing system may detect gastroparesis (e.g., potential gastroparesis).

A patient actionable severity level and/or an HCP actionable severity level associated with the detected post-surgical bariatric complication may be determined. For example, the wearable sensing system may determine a patient actionable severity level and/or an HCP actionable severity level associated with detected gastroparesis. A notification may be sent to the patient and/or the HCP indicating a potential post-surgical bariatric complication and the associated actionable severity level. For example, the wearable sensing system may send a real-time notification to a patient and/or an HCP indicating potential gastroparesis and the actionable severity level associated with the gastroparesis. The real-time notification may include the medical name, medical details (a patient's name, medical ID, etc.), actionable severity level and/or a recommended course of action associated with the detected post-surgical bariatric complication.

The wearable sensing system may determine type and/or content of the notification based on the determined actionable severity level. For example, when the detected complication is determined to be associated with low-risk patient actionable severity level, the wearable sensing system may generate a real-time notification to a device associated with the patient. When the detected complication is determined to be associated with high-risk patient actionable severity level, the wearable sensing system may generate a real-time notification to a device associated with the patient and a device associated with an HCP. For example, when the detected complication is determined to be associated with low-risk patient actionable severity level, the wearable sensing system may generate a real-time notification indicating the medical name of the complication and of the patient biomarker(s) that crossed the corresponding threshold(s). When the detected complication is determined to be associated with high-risk patient actionable severity level, the wearable sensing system may generate a real-time notification indicating a recommended course of action.

A computing system for measuring and monitoring patient biomarkers for detecting or predicting a post-surgical bariatric complication may be provided. A post-surgical bariatric complication may be predicted or detected by comparing measured/processed patient biomarker data with a corresponding determined threshold value. The comparison of the measured/processed patient biomarker data and the corresponding threshold may be performed in association with a context. The context may be based on at least one of a bariatric surgery recovery timeline, at least one situational attribute, or at least one environmental attribute. A notification message associated with a predicted or detected post-surgical bariatric complication may be sent (e.g., sent in real time) to a patient device or a healthcare provider's device. The notification message may be supplemented by a severity level message.

Figure 71:
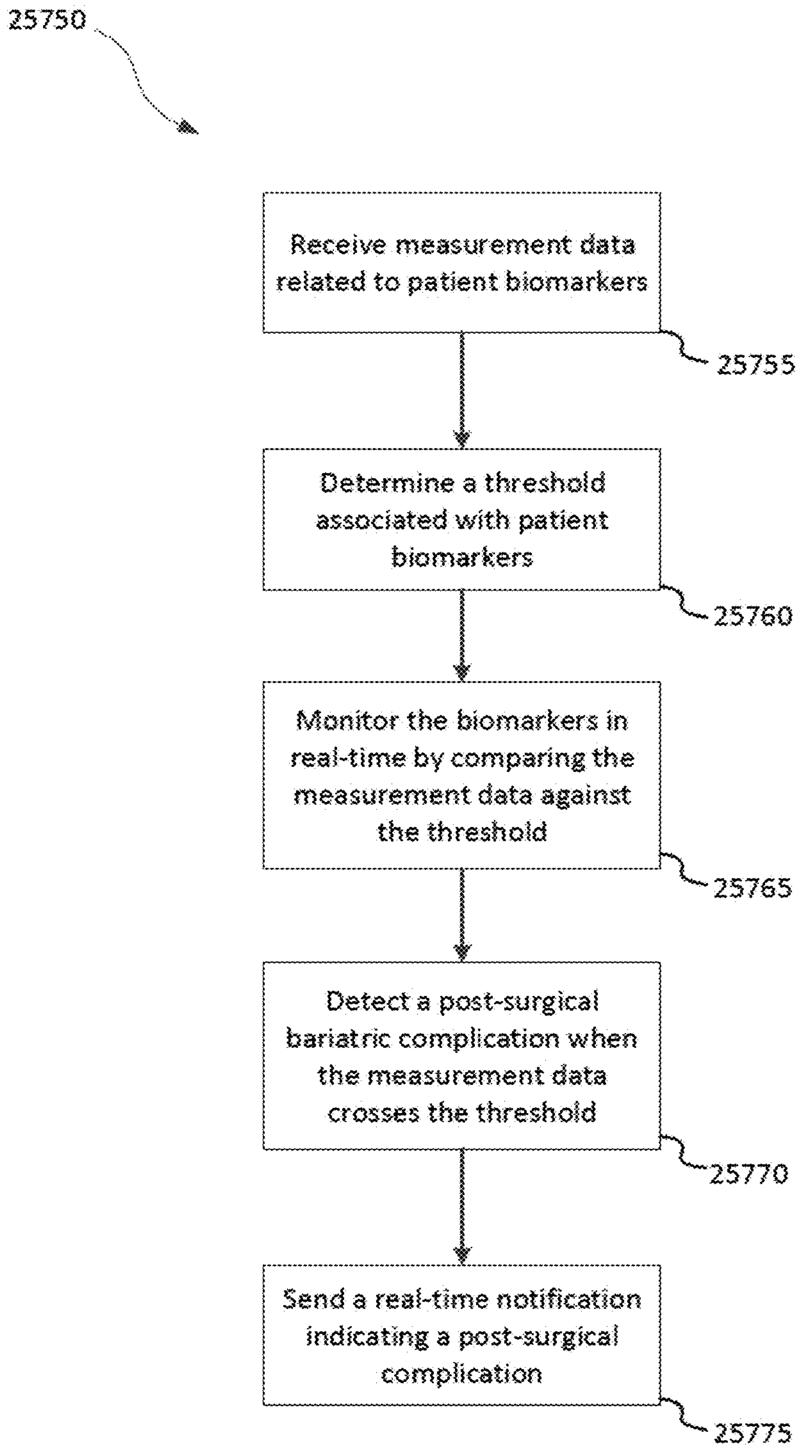
FIG. 71 shows example post-surgical bariatric complication prediction or detection.

FIG. 71 shows example 25750) post-surgical bariatric complication prediction or detection. One or more of 25755-25775 shown in FIG. 71 may be performed by a computing system, a sensing system, and/or another device, as described herein.

At 25755, measurement data related to patient biomarker(s) to be monitored may be received. The patient biomarkers may be used for predicting or detecting a post-surgical bariatric complication. For example, the patient biomarkers may be used for detecting gastroparesis, stomach leak, absorption issues, and/or other post-surgical bariatric complications. The received measurement data may be raw measurement data that may be processed into processed measurement data. The processed measurement data may be in a different form than the raw measurement data. For example, the processed measurement data form may be better suited for analysis when compared to the raw measurement data form. The measurement data may be received from one or more patient sensing systems, such as a wristband patient sensing system, an ingestible pill patient sensing system, a handheld patient sensing system, a wearable brace patient sensing system, an instrumented socks patient sensing system, and/or the like.

The measurement data may be related to one or more patient biomarkers associated with post-surgical signs used for predicting or detecting post-surgical bariatric complications. Prediction or detection of a post-surgical bariatric complication may be based on one or more of the following post-surgical signs: system sepsis, shock, GI motility, etc. One or more patient biomarkers may be related to the post-surgical signs and may be monitored to predict or detect a post-surgical bariatric complication. Such patient biomarkers may include patient intestinal microbiome composition, albumin production, intra-stomach pressure, core body temperature, caloric intake, body mass index, stomach tissue perfusion pressure, edema, stomach tissue friability, blood glucose, blood pressure, blood lactate, sweat lactate, blood pH, GI pH, physical mobility, heart rate, and/or heart rate variability.

Various sensing systems may perform patient biomarker measurements for post-surgical bariatric complication prediction or detection. For example, a wristband patient sensing system may measure patient biomarkers, including a patient's blood glucose, blood pressure, blood pH, blood lactate, sweat lactate, and/or heart rate. A wearable brace patient sensing system may measure physical mobility. An ingestible pill patient sensing system may measure patient biomarkers such as GI pH, stomach tissue perfusion pressure, stomach tissue friability, and/or intestinal microbiome composition. A handheld patient sensing system may measure patient biomarkers including caloric intake, body mass index, and/or albumin production. A patient sensing system (e.g., an instrumented socks patient sensing system may send measurement data related to edema. Based on the measurement data, one or more patient biomarkers may be monitored for detecting gastroparesis.

Measurement data associated with a patient may be obtained via one or more environmental sensing systems, for example, a video camera, a thermometer, etc. For example, a video camera may send measurement data (e.g., a video feed) related to a patient's physical attributes (e.g., physical mobility) to a computing system. A thermometer may send measurement data related to environmental temperature to the computing system.

The measurement data may be received in response to one or more requests for the measurement data. For example, a computing system may send a request to a patient sensing system requesting respective measurement data. The computing system may send the requests to different sensing systems at different time intervals or simultaneously. For example, the computing system may concurrently send requests to a wristband patient sensing system and a handheld patient sensing system. For example, the computing system may send a request to an environmental sensing system at a first time interval and a request to a handheld patient sensing system at a second time interval.

At 25760, a threshold associated with a patient biomarker may be determined. A patient biomarker threshold may be determined based on expected patient biomarker values, benchmark biomarker values, and/or the like. For example, a computing system and/or sensing system may determine a threshold associated with a patient's blood glucose and/or a threshold associated with a patient's caloric intake. In an example, a composite threshold associated with a combined value of multiple patient biomarkers, e.g., a patient's blood glucose and/or caloric intake, may be determined. The threshold may be (e.g., may further be) associated with measurement data received from one or more environmental sensing systems, for example, a video feed and/or a thermometer feed.

A patient biomarker threshold may be determined based on a standard threshold associated with a patient biomarker. A patient biomarker threshold may be customized for a patient. For example, patient biomarker threshold may be customized using a pre-surgical patient biomarker measurement, an in-surgical patient biomarker measurement, and/or a previously measured patient biomarker measurement. For example, a computing system and/or sensing system may determine a greater than normal threshold associated with a patient's blood glucose based on pre-surgical and/or in-surgical measurements that indicated the patient has high blood glucose. For example, a computing system and/or sensing system may determine a lesser than normal threshold associated with a patient's blood glucose based on pre-surgical and/or in-surgical measurements that indicated the patient has low blood glucose.

At 25765, one or more patient biomarkers may be monitored. For example, one or more patient biomarkers may be monitored in real-time. For example, a computing system and/or a sensing system may compare measurement data associated with each patient biomarker against a corresponding threshold(s). For example, measurement data associated with a patient's blood glucose and/or caloric intake may be compared against a threshold associated with the patient's blood glucose and/or caloric intake, respectively.

Measurement data associated with more than one patient biomarker may be combined into composite measurement data. For example, a computing system and/or sensing system may combine measurement data associated with a patient's blood glucose with measurement data associated with a patient's caloric intake. The computing system and/or sensing system may compare this composite measurement data with a composite threshold. The measurement data associated with a patient biomarker may be associated with a patient biomarker weight. For example, the measurement data associated with a patient's blood glucose may have a greater patient biomarker weight than the measurement data associated with a patient's caloric intake. The computing system and/or sensing system may consider the patient biomarker weight(s) when predicting or detecting a potential post-surgical bariatric complication. For example, the computing system and/or sensing system may be more likely to detect a complication when measurement data associated with high patient biomarker weight(s) crosses the corresponding threshold(s) compared to when measurement data associated with low patient biomarker weight(s) crosses the corresponding threshold(s). The computing system and/or sensing system may assign the patient biomarker weight(s). The patient biomarker weight(s) may be dynamic and adjusted based on the measurement data of another patient biomarker. The patient biomarker weights may be selected by an HCP overseeing the patient. For example, the HCP may assign a high patient biomarker weight to a patient's caloric intake and a low weight to a patient's blood glucose. The HCP may adjust the one or more patient biomarker weights during the patient's recovery.

At 25770, a post-surgical bariatric complication may be predicted or detected based on the measurement data. For example, a potential post-surgical bariatric complication may be identified on a condition that the measurement data related to a patient biomarker crosses a corresponding threshold for a predetermined amount of time. For example, a potential post-surgical bariatric complication may be identified on a condition that the measurement data related to multiple patient biomarkers cross their respective thresholds. For example, a potential post-surgical bariatric complication may be identified on a condition that composite measurement data related to a combination of patient biomarkers cross a composite threshold. A computing system and/or sensing system may be used to check the condition. For example, the computing system may detect potential gastroparesis on condition that a patient's blood glucose and/or caloric intake measurement data crosses a blood glucose and/or caloric intake threshold(s) for a predetermined amount of time. Crossing the threshold may include the measurement data associated with a patient biomarker increasing above the corresponding threshold value. Crossing the threshold may include the measurement data associated with a patient biomarker dropping below the corresponding threshold value. The predetermined amount of time may be used to mitigate erroneous measurement data. For example, the predetermined amount of time may reduce the number of false positive detections. The predetermined amount of time may be determined based on the one or more patient biomarkers being monitored. For example, the predetermined amount of time may be short when a patient's blood glucose is being monitored and long when a patient's caloric intake is being monitored.

A patient biomarker threshold may be associated with one or more contexts. For example, a computing system and/or a sensing system may consider the context when comparing the measurement data against the corresponding threshold(s). The context(s) may be associated with a bariatric surgery recovery timeline and/or a set of environmental attributes. For example, a context may be associated with a patient's motion. The computing system may consider the patient's motion when comparing the measurement data against the corresponding thresholds. For example, when comparing a patient's heart rate measurement data against a heart rate threshold, the computing system may consider the patient's motion (e.g., walking, sleeping, exercising, etc.). The context may be associated with a patient's eating, sleeping status, and/or the like. For example, when comparing a patient's heart rate measurement data against a heart rate threshold, a computing system may consider whether the patient is eating. The patient biomarker threshold(s) may be adjusted based on the context. In an example, the computing system may increase the heart rate threshold when the patient is eating. In an example, the computing system may decrease the heart rate threshold when the patient is sleeping.

Context data may be sent to the computing system from one or more patient biomarker sensing systems and/or one or more environmental sensing systems, for example, a video camera, a thermometer, etc. For example, a video camera may send context data (e.g., a video feed) related to a patient's physical mobility to the computing system. A thermometer may send measurement context data related to environmental temperature to the computing system. In an example, one or more environmental sensing systems may be a part of a patient biomarker sensing system. Environmental sensing system(s) and patient biomarker sensing system(s) may be associated with one device. For example, a smart mobile phone device may include one or more environmental sensing system(s) as well as one or more patient biomarker sensing(s).

The likelihood of a post-surgical bariatric complication occurring in the future may be predicted. For example, a computing system and/or sensing system may predict the likelihood of gastroparesis occurring by comparing a patient's blood glucose measurement data against an expected value. The computing system may predict that gastroparesis may be highly likely to occur when a patient's blood pH crosses an expected value for a predetermined amount of time. The computing system and/or sensing system may assign a probability and a timeframe to the predicted complication. For example, the computing system may assign a probability of 0.9 out of 1 and a timeframe of 14 days to a predicted gastroparesis. In such a case, the computing system has determined that the chances of gastroparesis occurring within the next 14 days is 0.9 out of 1.

Predictions of complications and/or recovery milestones may be generated, for example, by one or more machine learning (ML) models, such as predictive models, trained to make predictions after being trained on training data. For example, one or more ML classification algorithms may predict one or more types/classes of complications and/or recovery milestones by inference from input data. A model trained on vectorized training data may process vectorized input data. For example, a model may receive vectorized patient-specific data as input and classify the data as being indicative of one or more complications and/or one or more recovery milestones (e.g., each associated with a probability, likelihood, or confidence level). The model may receive updated patient-specific data to update predicted complications and probabilities and/or recovery milestones and probabilities. Complication mitigation (e.g., recommended actions or recommendations) may be based, at least in part, on one or more complications (e.g., and probabilities) generated by one or more models. A trained model may be any type of processing logic that performs an analysis and generates a prediction or determination derived from or generated based on empirical data, which may be referred to interchangeably as logic, an algorithm, a model, an ML algorithm or model, a neural network (NN), deep learning, artificial intelligence (AI), and so on.

A severity level (e.g., an actionable severity level) associated with the predicted or detected post-surgical bariatric complication may be determined. For example, a computing system and/or a sensing system may assign an actionable severity level to detected gastroparesis. In an example, the actionable severity level may be determined based on the degree by which the measurement data associated with a patient biomarker deviates from the corresponding threshold(s). For example, the computing system may determine that a patient's blood glucose has crossed the corresponding threshold by a minimal amount and may assign a low-risk actionable severity level to the detected complication. For example, the computing system may determine that the patient's blood glucose has crossed the corresponding threshold by a significant amount, which may be defined by a percentage of the threshold. In this case, a high-risk actionable severity level may be assigned to the detected complication. The actionable severity level may be determined based on the duration of the measurement data associated with a patient biomarker deviating from the corresponding threshold(s). Longer duration may be associated with higher severity level.

A severity level (e.g., an actionable severity level) may be indicated using an integer and/or a color code. For example, an integer 8 (on a scale of 1-10) and/or color red may indicate a high-risk actionable severity level, whereas an integer 2 using the same scale and/or color yellow may indicate a low-risk actionable severity level. In an example, the actionable severity level may be associated with a predicted post-surgical bariatric complication.

At 25775, a notification (e.g., a real-time notification) may be sent to the patient and/or the HCP indicating a potential post-surgical bariatric complication and the associated actionable severity level. For example, a computing system may send a real-time notification to a patient and/or an HCP indicating potential gastroparesis and the actionable severity level associated with the gastroparesis. A real-time notification may be a notification sent remotely via a wireless connection and received, by a patient and/or HCP, within a determined timeframe. The notification (e.g., a real-time notification) may include the medical name, medical details (e.g., patient's name, patient's medical ID, etc.), actionable severity level, and/or a recommended course of action associated with the detected post-surgical bariatric complication.

Examples of notifications, recommendations, determinations, actions, and/or implementations (e.g., that may reduce or prevent one or more potential or predicted complications) may include, for example, one or more of the following: a selection or modification/change in a surgery plan, instrument choices, surgical approach, instrument configurations and/or schedule (e.g., of surgery and/or order of use of instruments during surgery). A notification may include, for example, one or more suggestions and/or determinations, such as one or more of the following: potential issue areas, procedure plan adjustments, alternative product mixes, and/or adjustment of control program parameters to interlinked smart instruments.

The computing system may determine type and/or content of a notification based on the determined actionable severity level. For example, when the predicted or detected complication is determined to be associated with low-risk actionable severity level, the computing system may generate a real-time notification to a device associated with the patient. When the detected complication is determined to be associated with high-risk actionable severity level, the computing system may generate a real-time notification to a device associated with the patient and a device associated with an HCP. The content of the notification may be the amount of information included in the notification. For example, when the detected complication is determined to be associated with low-risk actionable severity level, the amount of information included in the notification may be minimal. When the predicted or detected complication is associated with a high-risk actionable severity level, the amount of information included in the notification may be significant. For example, when the detected complication is determined to be associated with low-risk actionable severity level, the computing system may generate a real-time notification indicating the medical name of the complication and of the patient biomarker that crossed the corresponding threshold(s). When the detected complication is determined to be associated with high-risk actionable severity level, the computing system may generate a real-time notification indicating the medical name of the complication and of the patient biomarker that crossed the corresponding threshold(s) as well as a recommended course of action.

Figure 72:
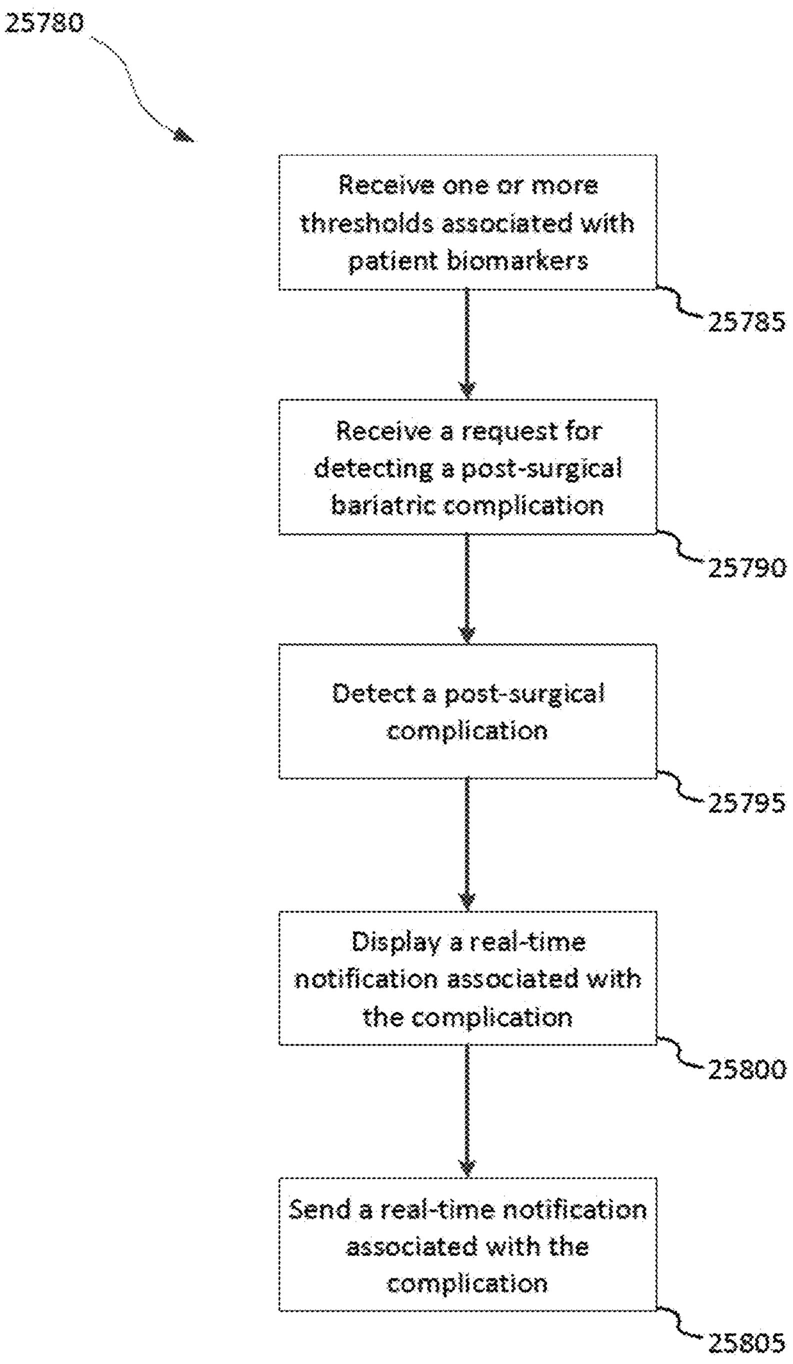
FIG. 72 shows example post-surgical bariatric complication wearable prediction or detection.

FIG. 72 shows example 25780) post-surgical bariatric complication wearable prediction or detection. One or more of 25785-25805 may be performed by a computing system, a sensing system, and/or another device, as described herein.

At 25785, a threshold described herein with reference to FIG. 71 may be received. For example, a wearable sensing system may receive the threshold for predicting or detecting post-surgical bariatric complications, such as gastroparesis, stomach leak, absorption issues, and/or other post-surgical bariatric complications.

The wearable sensing system may be or may include a wristband patient sensing system, an ingestible pill patient sensing system, a handheld sensing system, a wearable brace patient sensing system, an instrumented socks patient sensing system, and/or the like. One or more patient biomarkers described herein with reference to FIG. 71 may be monitored to predict or detect a post-surgical bariatric complication. Data described herein with reference to FIG. 71 may be measured by the wearable sensing system.

At 25790, a request may be received for predicting or detecting a potential post-surgical bariatric complication. For example, the wearable sensing system may receive a request for detecting gastroparesis. For example, a computing system may send the wearable sensing system the request. The request may include one or more thresholds associated with patient biomarkers related to the post-surgical complication. For example, a request to detect potential gastroparesis may include blood glucose and/or caloric intake threshold(s).

The threshold(s) received by the wearable sensing may be associated with one or more contexts described herein with reference to FIG. 71. The one or more contexts may be sent by a computing system to the wearable sensing system. The context(s) and/or threshold(s) may be sent simultaneously or at different time intervals.

At 25795, the wearable sensing system may monitor the set of patient biomarkers and detect a potential post-surgical bariatric complication described herein with reference to FIG. 71. The wearable sensing system may predict the likelihood of a post-surgical bariatric complication described herein with reference to FIG. 71.

A patient actionable severity level and an HCP actionable severity level associated with the predicted or detected post-surgical bariatric complication may be determined. For example, the wearable sensing system may assign a patient actionable severity level and HCP actionable severity level to detected gastroparesis. The actionable severity level(s) may be determined based on the degree by which measurement data associated with a patient biomarker deviates from the corresponding threshold(s). For example, the wearable sensing system may determine that a patient's blood glucose has crossed the corresponding threshold by a minimal amount and may assign a low-risk patient and/or HCP actionable severity level to the detected complication. The wearable sensing system may determine that a patient's blood glucose has crossed the corresponding threshold by a significant amount, which may be defined by a percentage of the threshold. A high-risk patient and/or HCP actionable severity levels may be assigned to the detected complication. The actionable severity level(s) may be determined based on the duration of the measurement data associated with a patient biomarker deviating from the corresponding threshold(s). Longer duration may be associated with higher severity level.

The actionable severity level(s) may be indicated using an integer and/or a color code. For example, an integer 8 (on a scale of 1-10) and/or color red may indicate a high-risk patient and/or HCP actionable severity level, whereas an integer 2 using the same scale and/or color yellow may indicate a low-risk patient and/or HCP actionable severity level. In an example, the actionable severity level may be associated with a predicted post-surgical bariatric complication.

At 25800, a notification may be displayed to the patient indicating a potential post-surgical bariatric complication and the associated actionable severity level. For example, the wearable sensing system may display a real-time notification to a patient indicating a potential gastroparesis and the patient actionable severity level associated with the gastroparesis.

At 25805, a notification (e.g., a real-time notification) indicating a potential post-surgical bariatric complication and the HCP actionable severity level associated with it may be sent to an HCP as described with reference to FIG. 71.

Figure 73:
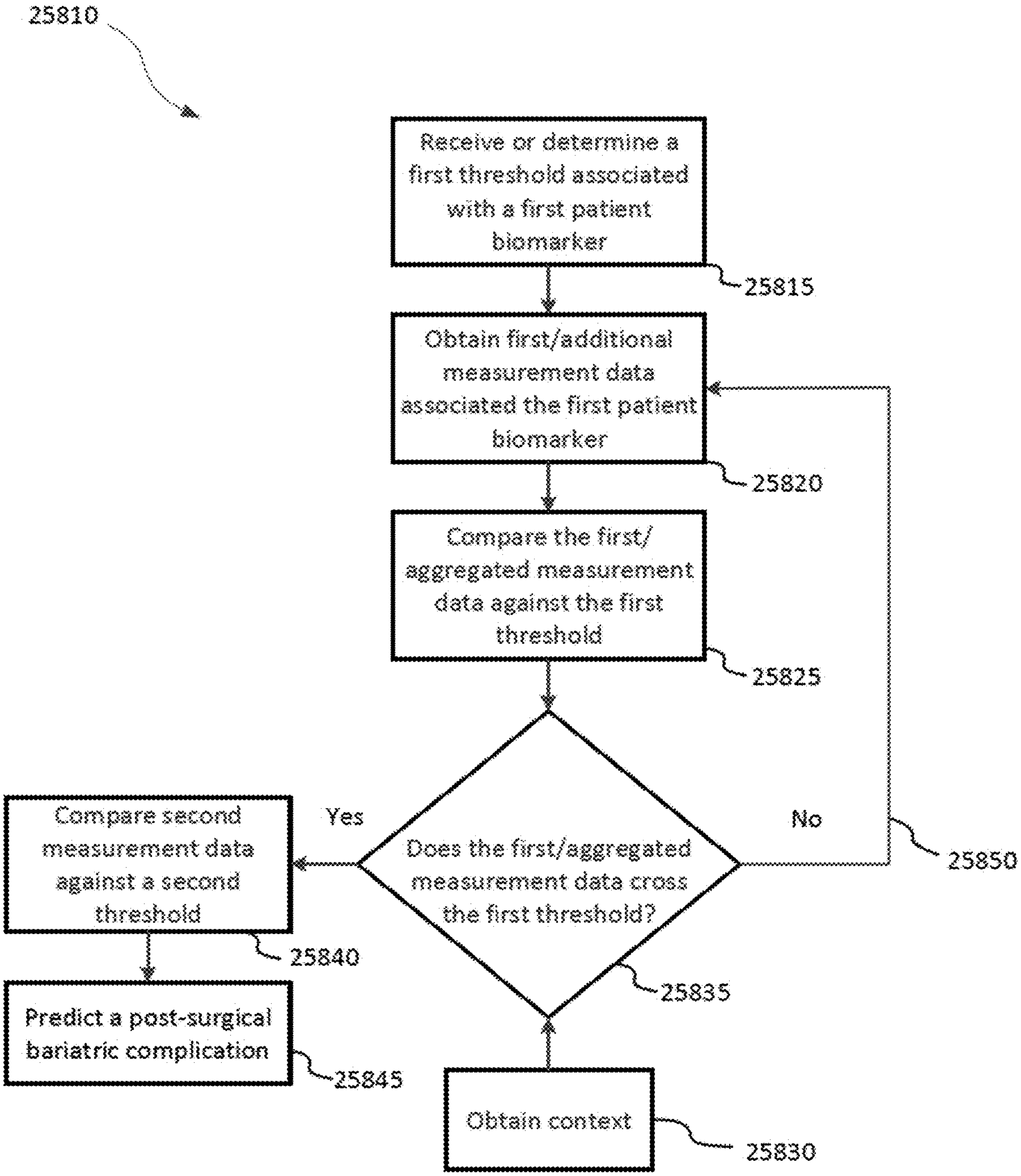
FIG. 73 shows example post-surgical bariatric complication wearable prediction or detection.

FIG. 73 shows example 25810 post-surgical bariatric complication wearable prediction or detection. One or more of 25815-25850 shown in FIG. 73 may be performed by a computing system, a sensing system, and/or another device described herein. At 25815, a first threshold associated with a first patient biomarker may be received and/or determined described herein with reference to FIG. 71 and FIG. 72. For example, a threshold associated with blood pH may be received by a sensing system and/or determined by a computing system. The threshold may be used to predict or detect a post-surgical bariatric complication, for example gastroparesis.

At 25820, first measurement data associated with the first patient biomarker may be obtained described herein with reference to FIG. 71 and FIG. 72. For example, measurement data associated with blood pH may be obtained by a computing system and/or a sensing system for predicting or detecting post-surgical bariatric complication. The first measurement data may be obtained as a response to a request for the measurement data. For example, a computing system and/or a sensing system may request the first measurement data.

At 25825, the first measurement data may be compared against the first threshold described herein with reference to FIG. 71 and FIG. 72.

At 25830, a computing system and/or a sensing system may obtain context described herein with reference to FIG. 71. The computing system may consider the context when determining whether the measurement data crosses the threshold. For example, the computing system may adjust the first threshold based on the received context. The computing system may use the received context as input context data. The input context data may influence the computing system as the computing system determines whether measurement data crosses the threshold.

At 25835, a computing system and/or a sensing system may compare the first measurement data against the first threshold by determining whether the measurement data crosses the threshold (e.g., for a predetermined amount of time) as described herein with reference to FIG. 71 and FIG. 72. The computing system or the sensing system may compare the first measurement against the first threshold based on a context.

Assuming that the first measurement data, for example, based on the context, crosses the first threshold, at 25840, second measurement data may be compared against a second threshold described herein with reference to FIG. 71 and FIG. 72. The second threshold may be associated with a second patient biomarker. The second threshold may be received and/or determined similar to how the first threshold may be received and/or determined. The second measurement data may be compared based on a condition that the first measurement data crosses the first threshold for a predetermined amount of time. A computing and/or sensing system may determine that the first measurement data crosses the first threshold for a predetermined amount of time and may compare the second measurement data against a second threshold. In an example, second measurement data may be compared on a condition that the first measurement data crosses the first threshold by a predetermined amount, for example 10% of the first threshold value. The computing system may request the second measurement data when the first measurement data crosses the first threshold.

At 25845, a post-surgical bariatric complication may be predicted described herein with reference to FIG. 71 and FIG. 72. A computing system and/or a sensing system may predict a post-surgical bariatric complication based on the first measurement data comparison and the second measurement data comparison. For example, the computing system may predict a complication when both the first measurement data and the second measurement data cross the respective first and second thresholds. The computing system may assign weight(s) to each comparison. The computing system may assign a high comparison weight to the first measurement data crossing the first measurement data and a low comparison weight to the second measurement data crossing the second threshold. Predicting a post-surgical bariatric complication may be based on the comparison weight(s). A computing system may be more likely to predict a complication when measurement data associated with a high comparison weight crosses a threshold compared to measurement data associated with low comparison weight crossing a threshold.

At 25850, a computing system and/or a sensing system may determine that the first measurement data does not cross the first threshold for a predetermined amount of time. The computing system may then continue at 25820. Additional or optionally, at 25280 the computing system may obtain additional first measurement data. At 25825, the computing system may aggregate the additional first measurement data with the original first measurement data. The aggregated first measurement data may be compared against the first threshold. The computing system and/or sensing system may adjust the first threshold based on the additional first measurement data.

Figure 74:
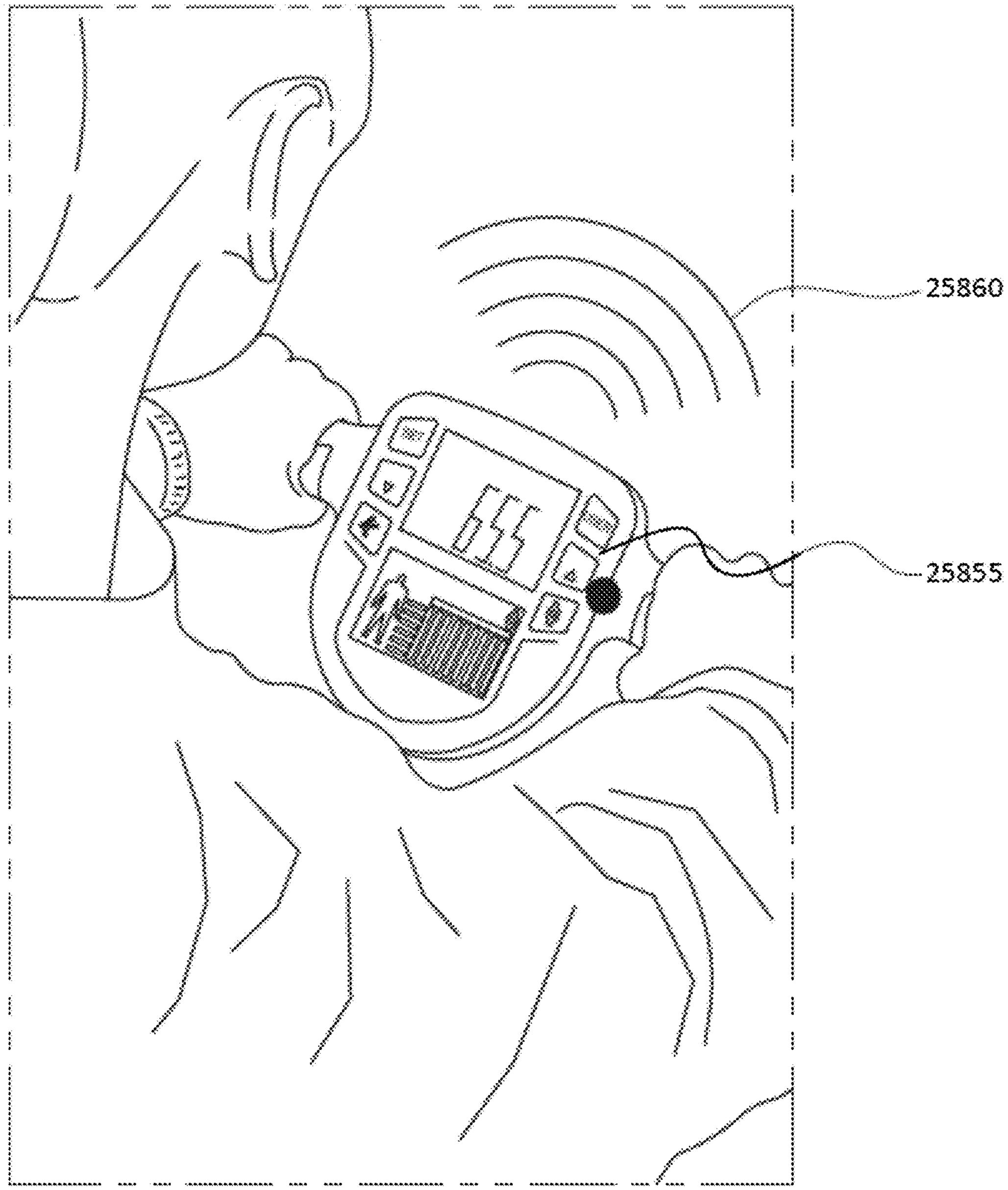
FIG. 74 shows an example wearable sensing system for detecting post-surgical bariatric complications.

FIG. 74 shows an example wearable sensing system for detecting post-surgical bariatric complications.

As illustrated, a patient may hold a sensing system 25855. In an example, a patient may place one or more fingers on a sensing system 25855. The sensing system 25855 may include arm(s) that function as a sensor unit by measuring data related to patient biomarker(s) to be monitored for detecting a post-surgical bariatric complication, as described with reference to FIG. 7B and/or 7C. The arm(s) may function as a sensor unit and include multiple sensors as described with reference to FIG. 7D. The arms(s), as a sensor unit, may be associated with a sensing system 25855. For example, the arm(s) may be communicatively connected to a sensing system 25855. The sensing system 25855 may be communicatively connected to a computing system (e.g., a surgical hub) and/or remote server(s) as described with reference to FIG. 2B and/or 2C. In an example, the arms(s) may be a sensing system 25855 and may be communicatively connected to a computing system and/or remote sever(s). The sensing system 25855 may receive, from a computing system, one or more thresholds associated with the patient biomarkers, as described herein with reference to FIG. 72. The sensing system 25855 may send, for example, to a computing system, measurement data related to the patient biomarkers to be monitored, as described herein with reference to FIG. 71. The computing system may send the measurement data to one or more analytics servers as described with reference to FIG. 12. The computing system may receive environmental measurement data from one or more environmental sensing as described with reference to FIG. 12.

The sensing system arm(s), functioning as a sensing unit, may be held by a patient and measure one or more patient biomarkers related to a post-surgical bariatric complication, for example gastroparesis, stomach leak, absorptions issues, and/or other post-surgical bariatric complications. The arm(s) may include one or more sensors as described with reference to FIG. 11B, 11C, and/or 11D. The arm(s) may begin measuring the one or more patient biomarkers when the patient grips the arms. The arm(s) may begin measuring at a time after the patient grips the arms. Determining when the arm(s) begin measuring may be based on the sensing system's capacity and/or power.

The arm(s) may measure the patient biomarker(s) described herein with reference to FIG. 71 and/or FIG. 72. For example, the patient biomarker(s) measured may be blood glucose and/or sweat lactate. The patient may hold the sensing system 25855 and the sensing system arm(s) may measure blood glucose and/or sweat lactate. The patient biomarker(s) may be measured for a predetermined amount of time. For example, the sensing system 25855 may request the arm(s) to measure blood glucose and/or sweat lactate for 60 seconds. The arms(s) may continuously measure blood glucose and/or sweat lactate as the patient holds the sensing system 25855. The arm(s) may measure blood glucose and/or sweat lactate based on a periodic cycle, for example at three second intervals. The period cycle may be adjusted as the patient holds the sensing system 25855. For example, a computing system and/or sensing system 25855 may shorten the periodic cycle in order to increase the frequency of the patient biomarker measurement(s). For example, a computing system and/or sensing system 25855 may lengthen the periodic cycle in order to decrease the frequency of the patient biomarker measurement(s).

The arm measurement(s) may be associated with arm measurement data. For example, the blood glucose and/or sweat lactate arm measurement(s) may be associated with respective blood glucose and/or sweat lactate arm measurement data. The sensing system 25855 may monitor the arm measurement data in real time by comparing the arm measurement data to one or more corresponding thresholds. The sensing system 25855 may obtain one or more thresholds associated with one or more patient biomarkers. In an example, the one or more thresholds may be received from a computing system or a computing device, as described herein with reference to FIG. 72. For example, the sensing system 25855 may compare the blood glucose and/or sweat lactate arm measurement data with a corresponding blood glucose and/or sweat lactate threshold(s), respectively. Multiple comparisons may be performed simultaneously or at different time intervals. The sensing system 25855 may detect a potential post-surgical bariatric complication when the arm measurement data related to at least one patient biomarker crosses the corresponding threshold for a predetermined amount of time. The predetermined amount of time may be received from the computing system and stored in the sensing system 25855.

The sensing system 25855 may transmit the arm measurement data to a computing system via RF signals 25860) using one or more RF protocols, as described herein. For example, the sensing system 25855 may transmit the arm measurement data using a Bluetooth protocol (e.g., a low energy Bluetooth protocol), a WiFi protocol, and/or using other wireless protocols, as described herein. In such an example, the computing system may monitor the arm measurement data (e.g., the blood glucose and/or sweat lactate arm measurement data) in real time by comparing arm measurement data to one or more corresponding thresholds. The computing system may detect a potential post-surgical bariatric complication when the arm measurement data related to at least one patient biomarker crosses the corresponding threshold for a predetermined amount of time, as described herein with reference to FIG. 71.

Figure 75:
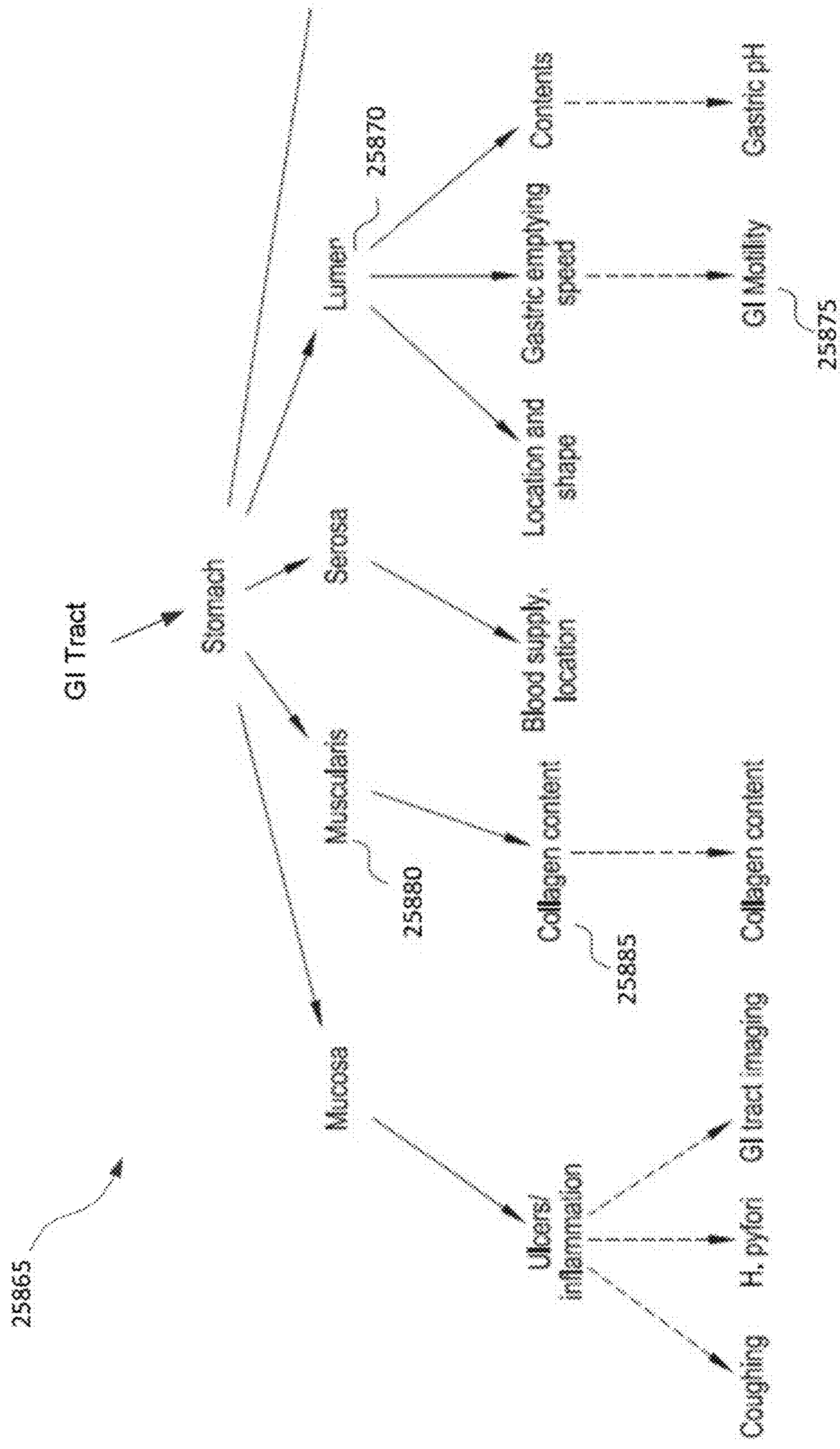
FIG. 75 shows example patient biomarkers related to the gastrointestinal (GI) system for predicting or detecting post-surgical bariatric complications.

FIG. 75 shows example patient biomarkers 25865 related to the GI system for predicting or detecting post-surgical bariatric complication.

For example, GI motility 27875 of the lumen 25870 may be set as a patient biomarker and monitored to detect gastroparesis. After bariatric surgery, a patient may be instructed by an HCP to use a sensing system to measure lumen GI motility 25875 for a period of time following the surgery. The sensing system may include a sensor for measuring lumen GI motility 25875. During this period, the sensing system may send measurement data associated with the lumen GI motility 25875 to the computing system. The sensing system may send the measurement data as a response to a request for the measurement data. The sensing system may send the measurement data based on a periodic cycle, for example at twenty-minute intervals. The computing system may adjust the period cycle. For example, the computing system may identify a critical phase of recovery from bariatric surgery. During this phase, the computing system may shorten the periodic cycle. The computing system may identify a non-critical phase of recovery and may lengthen the period cycle. The computing system may compare the received measurement data against a corresponding lumen GI motility 25875 threshold and, if the measurement data crosses the corresponding lumen GI motility 25875 threshold for a predetermined amount of time, may predict or detect potential gastroparesis and send a real-time notification to the HCP and/or patient. The corresponding lumen GI motility 25875 threshold may have been determined by the computing system based on pre-surgical, in-surgical, and/or previously measured patient biomarker measurements. The predetermined amount of time may be determined based on the lumen GI motility 25875 biomarker.

A combination of patient biomarkers related to the upper GI system may be monitored to predict or detect a potential post-surgical bariatric complication. For example, GI motility 25875 of the lumen 25870 and collagen 25885 of the muscularis 25880 may be set as patient biomarkers and monitored to detect gastroparesis. A sensing system may include a sensor that may measure lumen GI motility 25875 and muscularis collagen 25885. For example, the sensing system may include two sensors, the first of which may measure lumen GI motility 25875 and the second of which may measure muscularis collagen 25885. During the post-surgical period, the sensing system may send the respective measurement data associated with the GI motility 25875 of the lumen 25870 and the muscularis collagen 25885 to the computing system. The computing system may compare the measurement data against a corresponding lumen GI motility 25875 threshold and a corresponding muscularis collagen 25885 threshold, respectively. The computing system may detect gastroparesis when either set of measurement data crosses the corresponding threshold for a predetermined amount of time and send a real-time notification to the HCP and/or the patient. For example, the computing system may detect gastroparesis when both sets of measurement data cross the corresponding threshold(s). The patient biomarker threshold(s) may be associated with patient biomarker weight(s) described herein with reference to FIG. 71. For example, lumen GI motility 25875 may be associated with lumen GI motility 25875 weight. For example, muscularis collagen 25885 may be associated with muscularis collagen 25885 weight. The predetermined amount of time may be determined based on the lumen GI motility 25875 and the muscularis collagen 25885 biomarkers.

A combination of patient biomarkers related to, and unrelated to, the upper GI system may be monitored to predict or detect a post-surgical bariatric complication. For example, collagen 25885 of the muscularis 25880) and caloric intake may be set as patient biomarkers and monitored by a computing system to detect gastroparesis. A sensing system may include a sensor that may measure collagen 25885 of the muscularis 25880) and caloric intake.

A patient biomarker may be monitored by the sensing system. The sensing system may be a patient wearable sensing system. For example, a sensor may measure lumen GI motility 25875 and transmit measurement data to the patient wearable sensing system using one or more RF protocols, as described herein with respect to FIG. 72. The patient wearable sensing system may store the measurement data. The patient wearable sensing system may compare the measurement data against a corresponding lumen GI motility 25875 threshold and, if the measurement data crosses the corresponding lumen GI motility 25875 threshold for predetermined amount of time, may detect gastroparesis and send a real-time notification to the HCP and/or the patient. A combination of patient biomarkers related to and/or unrelated to the upper GI system may be monitored by the sensing system.

FIG. 76 shows example correlation 25890 between relevant patient biomarkers and bariatric procedural steps. In the following description of FIG. 76, reference should also be made to FIG. 2 and FIG. 5. FIG. 2 provides the settings used in a patient monitoring system. FIG. 5 provides various components used in a surgical procedure.

A bariatric surgery may include multiple surgical procedural steps. For example, a bariatric surgery may include mobilizing the stomach and gastric resection. Under each surgical procedural step, one or more tasks may be performed by an HCP (e.g., a surgeon). For example, under mobilizing the stomach surgical procedural step, the HCP may cut-off the blood supply from bodily structures attached to the stomach. For this task, the HCP may use a harmonic scalpel, a monopolar or bipolar RF, and/or a monopolar bovie instrument(s).

Under gastric resection surgical procedural step, an HCP may cut out a segment of the stomach that may be cancerous, infected, and/or impaired. During the gastric resection surgical procedural step, the HCP may use a linear stapler instrument.

A patient biomarker may be correlated to a bariatric procedural step. For example, a patient's blood pressure may be correlated to mobilizing a patient's stomach step, for example, in order to track blood supply after mobilization. A patient's stomach wall thickness may be correlated to gastric resection since during resection the surgeon is causing trauma to the tissue by severing pieces of the infected stomach.

A patient biomarker may be monitored based on a procedural step. For example, an HCP may choose to monitor a patient's blood pressure due to a problem that arose when the surgeon was mobilizing the stomach. A patient's stomach wall thickness may be monitored based on an observation made by the HCP during the gastric resection surgical procedural step. Assigning patient biomarker weight(s) as described with reference to FIG. 71 may be assigned based on a surgical procedural step. For example, a patient's blood pressure may be assigned a high patient biomarker weight when an HCP notices certain issues during the stomach mobilization surgical procedural step.

A patient biomarker threshold may be adjusted based on a surgical procedural step. For example, a blood pressure threshold may be decreased when an HCP notices issues regarding the stomach mobilization surgical procedural step. The predetermined amount of time for detecting a complication as described with reference to FIGS. 71 and 73 may change based on a procedural step.

In an example, a computing system and/or sensing system may determine a relevant surgical procedural step based on the correlated patient biomarker crossing a corresponding threshold(s) for a predetermined amount of time. The relevant surgical procedural step may be associated with a detected bariatric complication. For example, when a patient's blood pressure crosses a blood pressure threshold, a computing system may detect a gastroparesis and determine stomach mobilization as the relevant procedural step associated with the gastroparesis.

The relevant procedural step may indicate the procedural step that may be a cause of the detected complication. For example, the detected complication may be gastroparesis and the relevant procedural step associated with the gastroparesis may be gastric resection surgical procedural step. In such a case, the manner in which the gastric resection surgical procedural step was conducted may be a cause of the detected gastroparesis.

A notification may be sent to the patient and/or HCP indicating a potential post-surgical bariatric complication and the associated relevant procedural step. For example, a computing system and/or sensing system may send a real-time notification to a patient and/or HCP indicating gastroparesis and gastric resection as the relevant procedural step associated with the gastroparesis. The relevant procedural step may be used when correcting the detected post-surgical bariatric complication. For example, an HCP may decide to perform a corrective surgery in order correct gastroparesis. A notification indicating gastric resection as the surgical procedural step may be sent to the HCP before and/or during the corrective surgery. The HCP may use the use the information provided in the notification to develop a plan for a follow-up corrective surgery. In an example, the HCP may target an area that is involved in gastric resection.

FIGS. 40A-40E illustrates example procedure steps of a sleeve gastrectomy or a bariatric surgical procedure and example use of patient biomarker measurements. As shown, various post-operative or post-surgical patient biomarker measurements may be used to detect or predict various bariatric post-surgical complications and/or milestones, as described herein. The patient biomarker measurements may also be used to inform various decisions, identify various risks pre-surgery, during surgery, post-surgery, and/or determine operational parameters for various surgical tools.

FIG. 40E illustrates example patient biomarkers that may be monitored post-op to detect or predict post-surgical bariatric complications. The patient biomarkers may be monitored by a computing system as described herein with reference to FIG. 71. The patient biomarkers may be monitored by a wearable sensing system as described herein with reference to FIG. 72. For example, a patient's blood pH may be monitored to detect or predict a leak.

As shown, the patient biomarkers may be measured using one or more wearable and/or environmental sensors as described herein with reference to FIG. 1B. For example, a patient's blood pH may be measured by a wearable patch sensor. A patient's physical activity may be measured by a video camera. Measurement data associated with the wearable and/or environmental sensors may be obtained by a computing system that may compare the data against corresponding threshold(s) as described herein with reference to FIG. 71. In an example, the measurement data may be obtained by a sensing system that may compare the data against corresponding threshold(s) as described herein with reference to FIG. 72.

In an example, a post-surgical leak may be detected or predicted by measuring patient biomarker(s) associated with a patient's stomach tissue repair capacity, stomach pH, and/or stomach acid volume. Post-surgical sepsis may be detected by measuring patient biomarker(s) associated with compromised immunity and/or infection. Post-surgical internal bleeding may be detected or predicted by measuring patient biomarker(s) associated with clotting capacity and/or blood pressure. Post-surgical hypovolemic shock may be detected by measuring patient biomarker(s) associated with hydration state. In an example, a post-surgical kidney injury may be detected by measuring a patient's hydration state. Post-surgical stricture may be detected or predicted by measuring patient biomarker(s) associated with inflammatory state and/or edema. In an example, patient biomarker measurements may be used post-op to assess a patient's quality of life following a sleeve gastrectomy or a bariatric surgery. For example, patient biomarkers associated with VO2 max, physical activity, and/or circadian rhythm may be measured to assess a patient's quality of life.

As shown in FIGS. 40A-40D, patient biomarker measurements may be used post-op to inform various decisions, identify various risks pre-surgery, during surgery, post-surgery, and/or determine operational parameters for various surgical tools. For example, post-op patient biomarker measurements may be used to determine a value (e.g., threshold) in which pre-surgical and/or in-surgical measurement data may be compared against.

The value may be used to inform various decisions during a pre-surgical and/or in-surgical procedural step. For example, during a gastric transection procedural step, as shown in FIG. 40C, patient biomarker measurements associated with stomach blood supply may be compared against a stomach blood supply value to define the staple line. The value may be used to identify risks associated with a pre-surgical and/or in-surgical procedural step. For example, during gastric transection procedural step, a patient's stomach blood supply may be compared against a stomach blood supply value (e.g., for identifying the risk of ischemia). The value may be used to determine operational parameters for various surgical tools. During gastric transection procedural step, a patient's stomach tissue strength may be compared against a stomach tissue strength value to determine the operational parameters of a harmonic scalpel. For example, the intensity of the harmonic scalpel may decrease when the patient's stomach tissue strength crosses the stomach tissue strength value as described herein with reference to FIG. 71.

Multiple post-op patient biomarker measurements may be compared against multiple pre-surgical and/or in-surgical values simultaneously or at different time intervals. In an example, post-op patient biomarker measurements may increase or decrease the pre-surgical and/or in-surgical values.

Examples herein may include a computer system for outcome tracking of a plurality of patients, which may include a processor and a memory coupled to the processor. The memory may store instructions, that when executed by the processor, may cause the computer system to generate a respective expected patient biomarker dataset for each of the plurality of patients, wherein the expected patient biomarker dataset may represent the expected values of a patient biomarker over the duration of the patient's recovery. The computer system may receive respective actual patient biomarker data from respective patient sensor systems for each of the plurality of patients. The computer system may determine differences between the respective expected patient biomarker data and the respective actual patient biomarker data for each of the plurality of patients. The computer system may aggregate the differences. The computer system may generate a treatment notification based on the aggregation of the differences.

Examples herein may include a computer-implemented method for providing outcome tracking of a plurality patients, which may include generating a respective expected patient biomarker dataset for each of the plurality of patients, wherein the expected patient biomarker dataset may represent the expected values of a patient biomarker over the duration of the patient's recovery. The computer implementing method may include receiving respective actual patient biomarker data from respective patient sensor systems for each of the plurality of patients. The method may include aggregating the respective expected patient biomarker dataset and the respective actual patient biomarker data for each of the plurality of patients. The method may include determining differences between the respective expected patient biomarker data and the respective actual patient biomarker data. The method may include generating a treatment notification based on the differences.

Examples herein may include a facility analytics system for outcome tracking of a plurality of patients, which may include a processor and a memory coupled to the processor. The memory may store instructions, that when executed by the processor, may cause the facility analytics system to establish communication with a computing device. They facility analytics system may receive a treatment notification from the computing device, wherein the treatment notification may be based on differences of aggregated respective expected patient biomarker data and aggregated respective actual patient biomarker data for a plurality of patients. The facility analytics system may perform facility analytics based on the treatment notification.

Examples herein may include a computer-implemented method for providing outcome tracking of a plurality patients, which may include generating a respective expected patient biomarker dataset for each of the plurality of patients, wherein the expected patient biomarker dataset may represent the expected values of a patient biomarker over the duration of the patient's recovery. The computer implementing method may include receiving respective actual patient biomarker data from respective patient sensor systems for each of the plurality of patients. The method may include aggregating the respective expected patient biomarker dataset and the respective actual patient biomarker data for each of the plurality of patients. The method may include determining differences between the respective expected patient biomarker data and the respective actual patient biomarker data. The method may include generating a treatment notification based on the differences.

Figure 77:
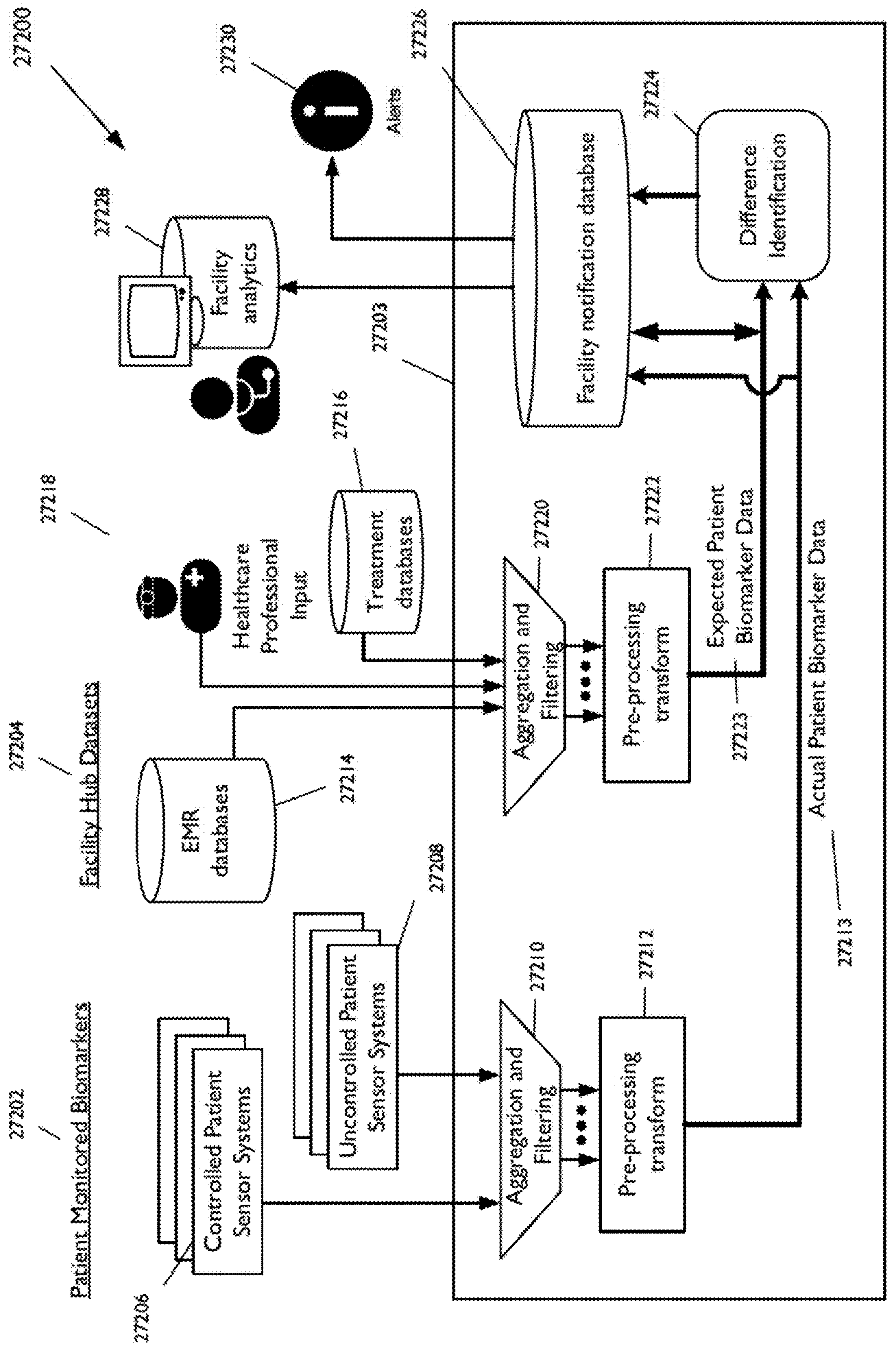
FIG. 77 shows an example of a computer implemented patient and surgeon monitoring system that aggregates biomarker data.

FIG. 77 shows an example of a computer implemented patient and surgeon monitoring system 27200 that aggregates biomarker data. The aggregation of biomarker data provides insights to the facility of care, compliance, follow-up metric, and intervention accuracies. The computer-implemented patient and surgeon monitoring system 27200 may include patient monitored biomarkers 27202, facility hub datasets 27204, a computing system 27203, and a facility analytics system 27228.

The patient monitored biomarkers 27202 may be used to measure actual patient biomarker data 27213. The patient monitored biomarkers 27202 may include one or more of the following: Blood pH, hydration state, oxygen saturation, core body temperature, heart rate, Heart rate variability, Sweat rate, Skin conductance, Blood pressure, Light exposure, Environmental temperature, Respiratory rate, Coughing and sneezing, Gastrointestinal motility, Gastrointestinal tract, imaging, Tissue perfusion pressure, Bacteria in respiratory tract, Alcohol consumption, Lactate (sweat), Peripheral temperature, Positivity and optimism, Adrenaline (sweat), Cortisol (sweat), Edema, Mycotoxins, VO2 max, Pre-operative pain, chemicals in the air, Circulating tumor cells, Stress and anxiety, Confusion and delirium, Physical activity, Autonomic tone, Circadian rhythm, Menstrual cycle, Sleep, etc. The patient monitored biomarkers 27202 may be measured by controlled patient sensor systems 27206 and uncontrolled patient sensor systems 27208. The controlled patient sensor systems 27206 may measure the patient monitored biomarkers 27202 in a controlled environment in close proximity to an HCP (e.g., in a hospital recovery room). The uncontrolled patient sensor systems 27208 may measure a patient in an uncontrolled environment not in close proximity to an HCP (e.g., a patient's residence). Each of the controlled patient sensor systems 27206 and uncontrolled patient sensor systems 27208 may be measured using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The sensors may measure the patient monitored biomarkers 27202 as described herein using one of more of the following sensing technologies: photoplethysmography, electrocardiography electroencephalography, colorimetry, impedimentary, potentiometry, amperometry, etc.

The facility hub datasets 27204 may provide information that is inputted into the computing system 27203 to compute expected patient biomarker data 27223. Facility hub datasets 27204 may include information from EMR databases 27214, treatment databases 27216, and HCP input 27218. EMR databases 27214 may include EMR information from specific patients from specific healthcare facilities. The EMR information may address certain issues unique to specific patients or specific groups of patients, such as patients with diabetes, patients with cancer, patients with a history of smoking, ext. Treatment databases 27216 may include treatment information related to specific treatments being performed. The treatment information may address certain issues unique to each specific treatment, such as issues related to heart surgery, issues related to bariatric surgery, and issues related to orthopedic procedures, ext. HCP input 27218 may allow for an HCP to input any changes to any specific patients and/or any specific procedures. For example, new developments in certain procedures and/or in a certain group of patients may impact the expected patient biomarker data 27223 that may not necessarily be reflected in the previous data stored in the EMR databases 27214 and/or in the treatment databases 27216. The HCP input 27218 may allow for the HCP to input any changes necessary into the computing system 27203.

At 27210, the computing system 27203 may aggregate and filter the patient monitored biomarkers 27202 measured by the controlled patient sensor systems 27206 and the uncontrolled patient sensor systems 27208 to compute the actual patient biomarker data 27213. For example, the computing system 27203 may aggregate and filter the measured heart rates of all patients on a recovery timeline after undergoing heart surgery. In examples, the data can be further aggregated and filtered by heart surgeries performed by certain HCPs. In examples, the data can be further aggregated and filtered by heart surgeries performed on patients with diabetes, patients with a history of smoking, and/or patients that have had multiple surgeries, ext. At 27212, the computing 27203 may perform a pre-processing transform before outputting the actual patient biomarker data 27213. For example, the pre-processing transform may use Gaussian process regression to make predictions based on similar patient data. The actual patient biomarker data 27213 may be stored in a facility notification database 27226.

At 27220, the computing system 27203 may aggregate and filter the information provided by the facility hub datasets 27204 to compute the expected patient biomarker data 27223. For example, the computing system may aggregate and filter the heart rates of all patients previously on a recovery timeline after undergoing heart surgery. The heart rate information may be provided by the EMR databases 27214 and/or treatment databases 27216. In examples, the data can be further aggregated and filtered by heart surgeries previously performed by certain HCPs, which may also be provided by the EMR databases 27214 and/or treatment databases 27216. In examples, the data can be further aggregated and filtered by heart surgeries previously performed on patients with diabetes, patients with a history of smoking, and/or patients that have had multiple surgeries, ext., which may also be provided by the EMR databases 27214 and/or treatment databases 27216. The data aggregated can be used to predict the expected patient biomarker data 27223 and compare it with the actual biomarker data 27213. At 27222, the computing system 27203 may perform a pre-processing transform before outputting the expected patient biomarker data 27213. For example, the pre-processing transform may use Gaussian process regression to make predictions based on similar patient data. The expected patient biomarker data 27223 may be stored in the facility notification database 27226.

At 27224, the computing system 27203 may compute the differences between the aggregated actual patient biomarker data 27213 and the aggregated expected patient biomarker data 27223. The differences may be stored in the facility notification database 27226. In examples, the facility notification database 27226 may output alerts 27230 to HCPs, healthcare facilities, and/or hospitals if the differences between the actual patient biomarker data 27213 and the expected patient biomarker data 27223 are over certain thresholds. In examples, the facility notification database 27226 may output alerts 27230 to HCPs, healthcare facilities, and/or hospitals if the differences between the actual patient biomarker data 27213 and the expected patient biomarker data 27223 are under a certain threshold and/or are negligible. In examples, the facility notification database 27226 may output alerts 27230 of the differences between the actual patient biomarker data 27213 and the expected patient biomarker data 27223 to HCPs, healthcare facilities, and/or hospitals at certain times, such as on a weekly, monthly, or semi-monthly basis for monitoring. In examples, the facility notification database 27226 may output the differences to a facility analytics system 27228. The facility analytics system 27228 may include a facility analytics server that may perform analytics regarding the data received. An HCP may view the analytics provided by the facility analytics system 27228 on a computing device to evaluate the care provided to the user and when used with outcomes data can be used to monitor trends of the facility and its HCPs. The data may be used to assess post-operative care, therapy compliance, and efficacy care from which the provider can update care path based on monitored data. The facility analytics system 27228 can perform the data analytics in real time. The facility analytics system 27228 is described further below in FIG. 80.

Figure 78A:
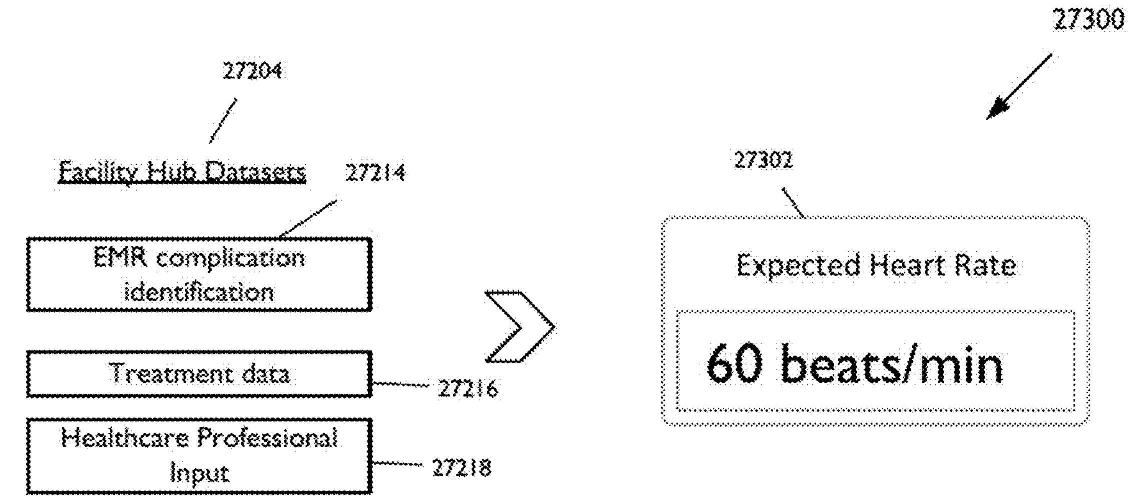
FIGS. 78A-78C show an example of a computer-implemented patient and surgeon monitoring system monitoring heart rate data of a group of patients.
Figure 78B:
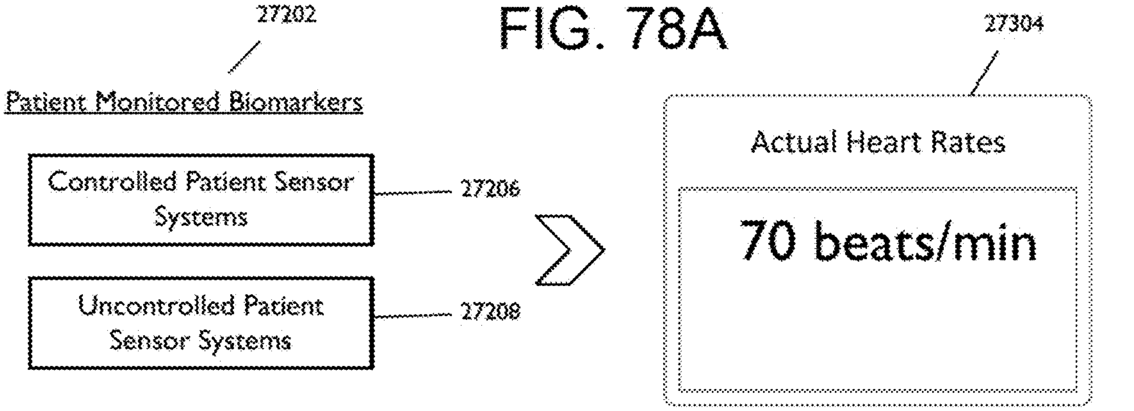
Figure 78C:
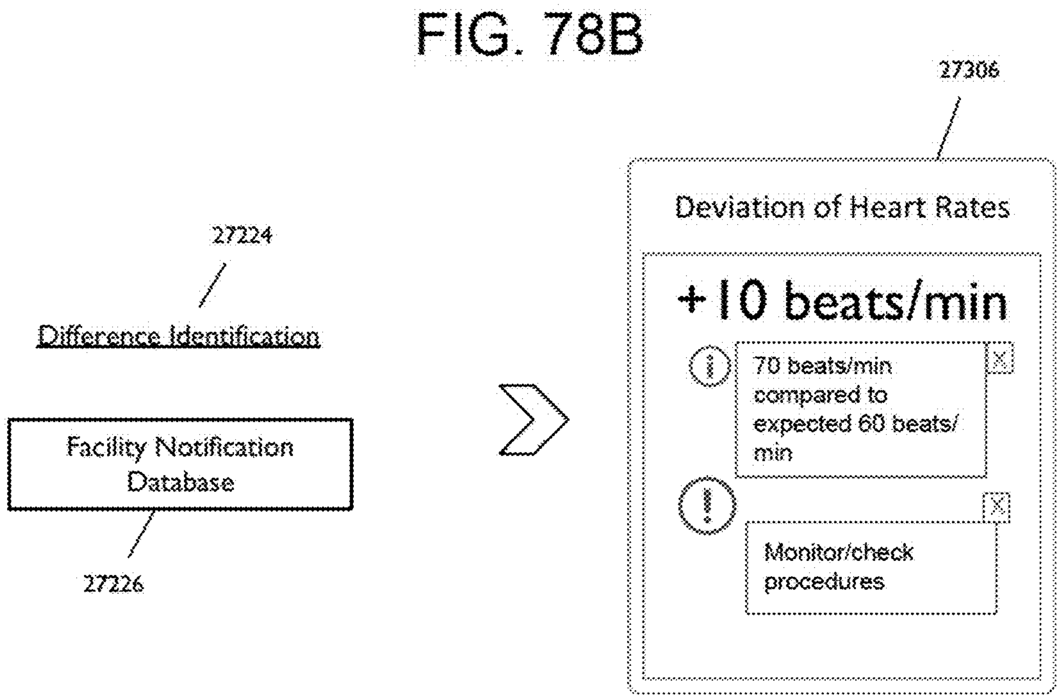

FIGS. 78A-78C show an example 27300 of the computer-implemented patient and surgeon monitoring system 27200 monitoring heart rate data of a group of patients. In FIG. 78A, the facility hub datasets 27204 may include information from the EMR databases 27214, the treatment databases 27216, and HCP input 27218 to send to the computing device 27203. As described in FIG. 77, the information from the facility hub datasets 27204 may be aggregated and filtered at 27220 by the computing system 27203 to compute expected patient biomarker data 27223. As shown in FIG. 78A, the expected patient biomarker data may be an expected heart rate 27302. In examples, the data from the facility hub datasets 27204 can be further aggregated and filtered by heart surgeries performed by certain HCPs and/or certain health care facilities. In examples, the data can be further aggregated and filtered by heart surgeries performed on patients with diabetes, patients with a history of smoking, and/or patients that have had multiple surgeries, ext. The expected heart rate 27302 may be stored in the facility notification database 27226. As shown in FIG. 78A, the expected heart rate 27302 may be 60 beats/min, for example. The expected heart rate 27302 can represent the expected heart rate for a specific group of patients, such as patients with diabetes, patients with a history of smoking, and/or patients that have had multiple surgeries, ext. The expected heart rate 27302 can represent the heart rates of patients over a recovery timeline for surgeries performed by certain HCPs or certain healthcare facilities, which can be used for monitoring HCPs and healthcare facilities, as described further below in FIG. 80.

In FIG. 78B, the patient monitored biomarkers 27202 may be patient heart rates. The patient heart rates may be measured by controlled patient sensor systems 27206 and uncontrolled patient sensor systems 27208. The controlled patient sensor systems 27206 may measure the patient heart rates in a controlled environment in close proximity to an HCP (e.g., in a hospital recovery room). The uncontrolled patient sensor systems 27208 may measure patient heart rates in an uncontrolled environment not in close proximity to an HCP (e.g., a patient's residence). As described in FIG. 77, the measurements from the controlled patient sensor systems 27206 and uncontrolled patient sensor systems 27208 may be aggregated and filtered at 27220 by the computing system 27203 to compute the actual heart rates 27304. For example, the computing system 27203 may aggregate and filter the measured heart rates of all patients on a recovery timeline after undergoing heart surgery. In examples, the data can be further aggregated and filtered by heart surgeries performed by certain HCPs. In examples, the data can be further aggregated and filtered by heart surgeries performed on patients with diabetes, patients with a history of smoking, and/or patients that have had multiple surgeries, ext. The actual heart rates 27304 may be stored in a facility notification database 27226. As shown in FIG. 78B, the actual heart rate 27304 may be 70 beats/min, for example. The actual heart rate 27304 can represent the actual heart rate for a specific group of patients, such as patients with diabetes, patients with a history of smoking, and/or patients that have had multiple surgeries, ext. The actual heart rate 27304 can represent the heart rates of patients over a recovery timeline for surgeries performed by certain HCPs or certain healthcare facilities, which can be used for monitoring HCPs and healthcare facilities, as described further below in FIG. 80.

In FIG. 78C, at 27224, the computing system 27203 may compute the differences between the aggregated actual heart rates 27304 and the aggregated expected heart rates 27302. The differences may be stored in the facility notification database 27226. In examples, the facility notification database 27226 may output alerts 27306 to HCPs, healthcare facilities, and/or hospitals if the differences between the actual heart rates 27304 and the expected heart rates 27302 are over certain thresholds. In examples, the facility notification database 27226 may output alerts of the differences between the actual patient heart rates 27304 and the expected patient heart rates 27302 to HCPs, healthcare facilities, and/or hospitals at certain times, such as on a weekly, monthly, or semi-monthly basis for monitoring. The alerts 27306 can be viewed on computing device displays within healthcare facilities. As shown in FIG. 78C, the alert 27306 may indicate the alert is regarding a "Deviation of Heart Rates" and show the deviation of the actual heart rate 27304 vs. the expected heart rate 27302, such as "+10 beats/min", indicating the actual heart rate 27304 is 10 beats/min over the expected heart rate 27302. As shown in FIG. 78C, the alert 273706 may also show the exact numbers, and display "70 beats/min compared to expected 60 beats/min", for example. The alert 27306 may provide suggested actions to take based on the deviations, such as to "monitor/check procedures" if the deviation is over a certain threshold amount, as shown in FIG. 78C.

In examples, the patient biomarker data may be absolute and relative temperature variations measured by temperature sensors. Measuring patient body temperatures and body temperature variations may give insights into infection risk and allow HCPs to more discriminately prescribe antibiotics or different antibiotics. In examples, the patient biomarker data may be orthopedic procedures such as knee replacement. The orthopedic procedures can be measured by sensors that can monitor motion (accelerometers) when possibly coupled with camera sensing, which could inform therapists of compliance of physical therapies. The range of motion data or other metrics could be computed to inform changes in therapy (increased repetitions, weights, etc.) to improve surgical care.

In various examples, the patient biomarker data may be heart variability can be measured for meal detection, as described in U.S. Pat. No. 8,696,616, titled OBESITY THERAPY AND HEART RATE VARIABILITY, filed Dec. 29, 2010, the disclosure of which is herein incorporated by reference in its entirety. Meal detection may be used to detect the frequency and duration of meals following bariatric surgery. Meal detection may be used to determine the difference between eating and drinking. Compliance to post-operative meal detection protocols can be assessed and the data used to provide feedback to patients. In other examples, alerts may alert the HCP of trends showing potential problems or complications that occur without initial symptoms but can later be life threatening. For example, monitoring patient biomarkers such as hematocrit, body temperature, and/or heart rate signal changes, can show trends suggestive of atrial-esophageal fistula after RF cardiac ablation, which can be life threatening after over 21 days without initial symptoms, allowing HCPs to take appropriate action preemptively to help save lives.

Figure 79A:
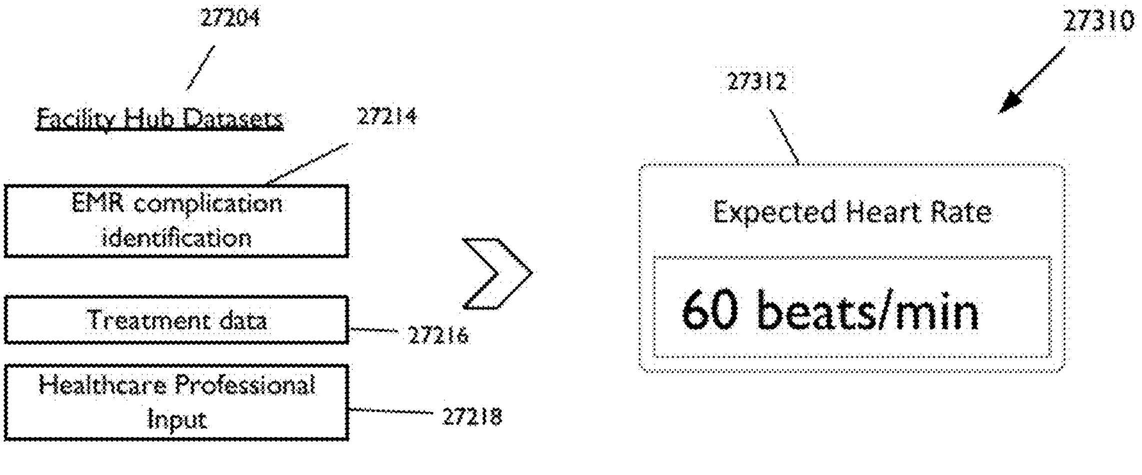
FIGS. 79A-79C show another example of the computer-implemented patient and surgeon monitoring system monitoring heart rate data of a group of patients.
Figure 79B:
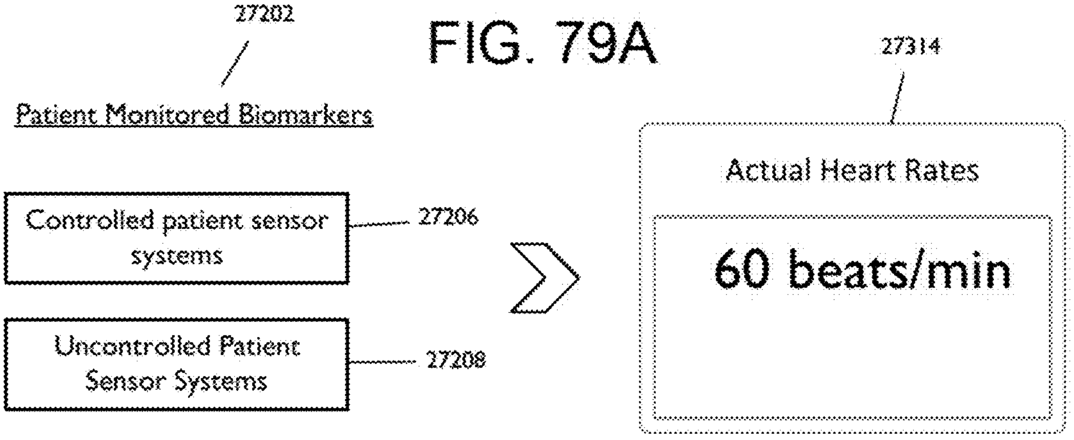
Figure 79C:
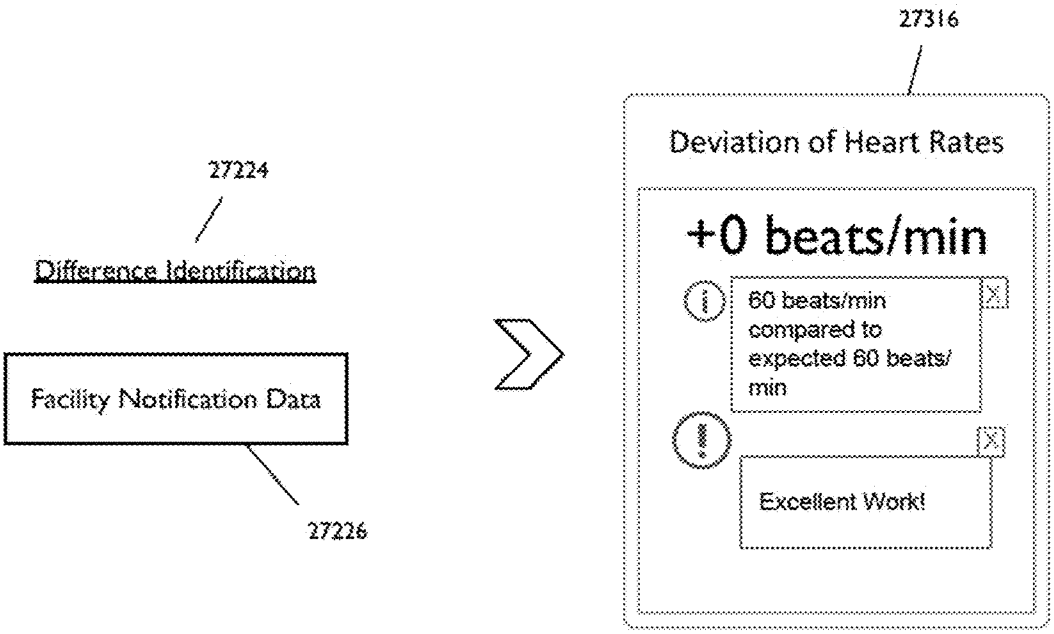

FIGS. 79A-79C show another example 27310 of the computer-implemented patient and surgeon monitoring system 27200 monitoring heart rate data of a group of patients.

In FIG. 79A, like FIG. 78A, the facility hub datasets 27204 may include information from the EMR databases 27214, the treatment databases 27216, and HCP input 27218 to send to the computing device 27203. The expected heart rate 27312 can represent the expected heart rate for a specific group of patients, such as patients with diabetes, patients with a history of smoking, and/or patients that have had multiple surgeries, ext. The expected heart rate 27312 may be stored in the facility notification database 27226. As shown in FIG. 79A, the expected heart rate 27312 may be 60 beats/min, for example.

In FIG. 79B, like FIG. 78B, the patient monitored biomarkers 27202 may be patient heart rates. The patient heart rates may be measured by controlled patient sensor systems 27206 and uncontrolled patient sensor systems 27208. As described in FIG. 77, the measurements from the controlled patient sensor systems 27206 and uncontrolled patient sensor systems 27208 may be aggregated and filtered at 27220 by the computing system 27203 to compute actual heart rates 27314. The actual heart rate 27314 can represent the expected heart rate for a specific group of patients, such as patients with diabetes, patients with a history of smoking, and/or patients that have had multiple surgeries, ext. The actual heat rate 27314 may be stored in a facility notification database 27226. As shown in FIG. 79B, the actual heart 27314 rate may be 60 beats/min, for example.

In FIG. 79C, at 27224, the computing system 27203 may compute the differences between the aggregated actual heart rates 27314 and the aggregated expected heart rates 27312. The differences may be stored in the facility notification database 27226. In the example shown in FIG. 79C, unlike in the example shown in FIG. 78C, the facility notification database 27226 may output alerts 27316 to HCPs, healthcare facilities, and/or hospitals if the differences between the actual heart rates 27314 and the expected heart rates 27312 are within a desired range. The alerts 27316 can be viewed on computing device displays within healthcare facilities. As shown in FIG. 79C, the alert 27316 may indicate the alert is regarding a "Deviation of Heart Rates" and show the deviation of the actual heart rate 27314 vs. the expected heart rate 27312, such as "+0 beats/min", indicating the actual heart rate 27314 is the same as the expected heart rate 27312. As shown in FIG. 79C, the alert 27316 may also show the exact numbers, and display "60 beats/min compared to expected 60 beats/min", for example. The alert 27316 may display a message to suggest the HCPs and/or the healthcare facilities are meeting certain outcome goals, such as "Excellent Work!" to provide encouragement, as shown in FIG. 79C.

Figure 80:
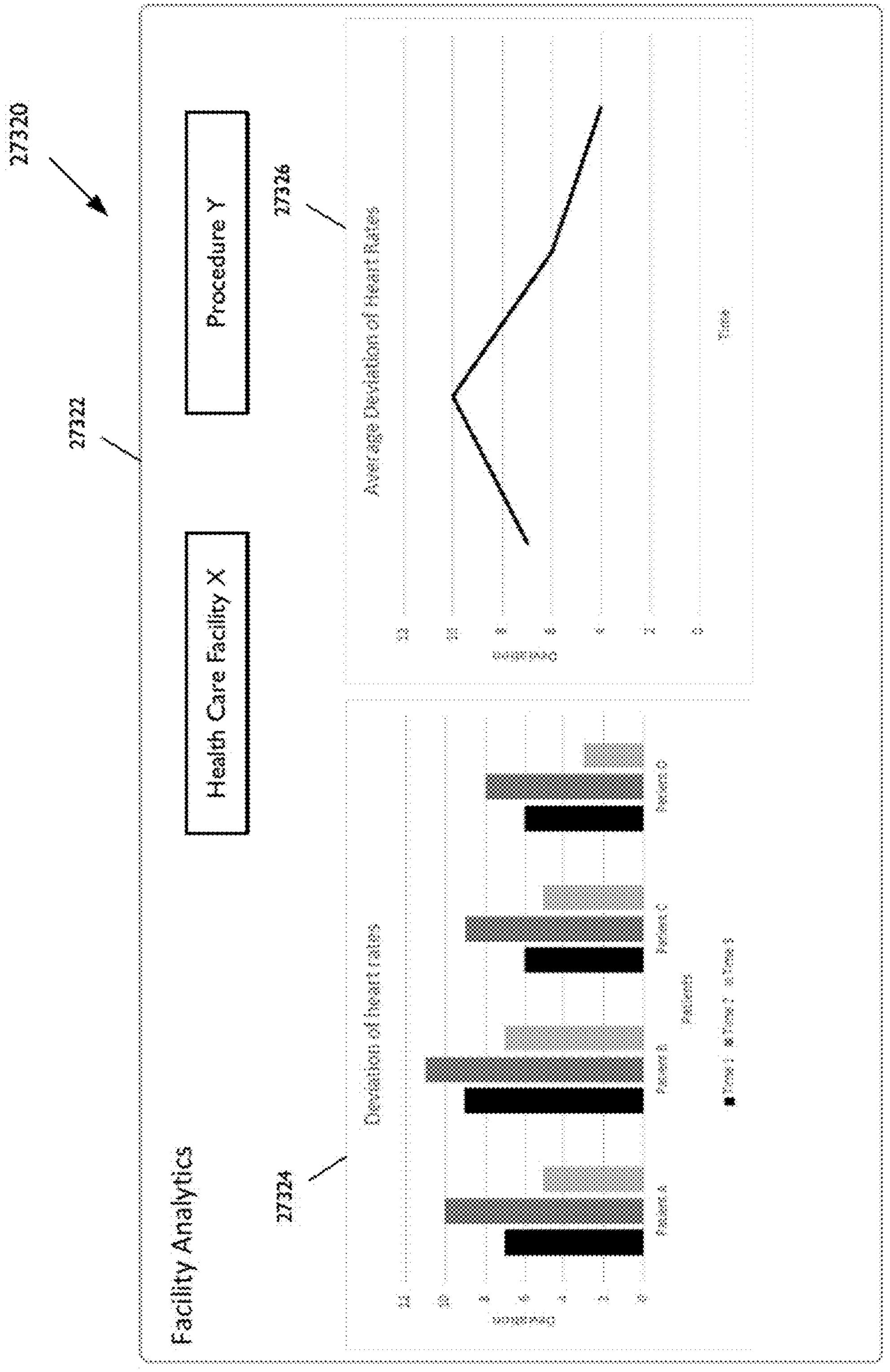
FIG. 80 shows example facility analytics system that can be viewed on a computing device by an HCP.

FIG. 80 shows example facility analytics data 27320 that can be viewed on a computing device 27322 by an HCP. The facility analytics data 27320 may be received from the facility analytics system 27228 within the computer-implemented patient and surgeon monitoring system 27200, as described above in FIG. 77. The facility analytics system 27228 may include a facility analytics server that may perform analytics regarding the data received. The facility analytics system 27228 may perform the data analytics in real time. For example, as shown in FIG. 80, the facility analysis data 27320 may be represented by graph 27324 and graph 27326. Also, shown in FIG. 80, the facility analytics data 27320 may be grouped based on certain procedures (represented by "Procedure Y" in FIG. 80) performed at certain health care facilities (represented by "Health Care Facility X" in FIG. 80). For example, graph 27324 may show the deviation of heart rates across different patients throughout the recovery timeline after surgery. The deviation of heart rates may be computed by the computing system 27203, which may compute the differences between the aggregated actual heart rates 27304, 27314 and the aggregated expected heart rates 27302, 27312, as described above in FIGS. 78A-78C and FIGS. 79A-79C.

In examples, the data in graph 27324 may represent the deviation of heart rates of all patients who underwent heart surgery at a certain health care facility and/or underwent heart surgery by a certain HCP. In examples, the data in graph 27324 may represent patients who underwent multiple heart surgeries at a certain health care facility. In examples, the data in graph 27324 may represent patients with diabetes, patients with a history of smoking, and/or patients with a history of irregular heartbeats. The data in graph 27324 may provide HCPs and/or health care facilities with beneficial data to monitor specific groups of patients. The data in graph 27324 may allow HCPs and/or health care facilities to analyze patients having surgery outcomes that are meeting expected outcomes and patients having surgery outcomes that are not meeting expected outcomes. The data in graph 27324 can also allow HCPs and/or healthcare facilities to monitor how the deviations of heart rates are changing throughout the recovery timeline after surgery for specific patients. For example, the deviation of heart rates at three different discrete times may be shown in bar graph format, which may be days, weeks, or months apart. If the recovery outcomes are not meeting expectations throughout certain times during the recovery timeline, healthcare facilities can use this data to improve certain procedures for all patients and/or a specific group of patients. Additionally, if certain HCPs and/or healthcare facilities are not meeting expectations throughout certain times during the recovery timeline, healthcare facilities can use this data to improve protocols performed at certain facilities or by certain HCPs by comparing protocols performed by healthcare facilities and/or HCPs having less heart rate deviations and achieving more expected outcomes.

In examples, the data in graph 27326 may show the average deviation of heart rates continuously for patients throughout a recovery timeline in line graph format. Graph 27326 may provide a quick, overall assessment for how certain health care facilities and/or HCPs are performing specific procedures, such as heart surgeries. Like graph 27324, graph 27326 may represent patients with diabetes, patients with a history of smoking, and/or patients with a history of irregular heartbeats. Like graph 27324, graph 27326 may provide data to monitor certain HCPs and/or healthcare facilities that are not meeting expectations throughout the recovery timeline. Healthcare facilities can use this data to improve protocols performed at certain facilities or by certain HCPs by comparing protocols performed by healthcare facilities and/or HCPs having less heart rate deviations and achieving more expected outcomes.

Figure 81:
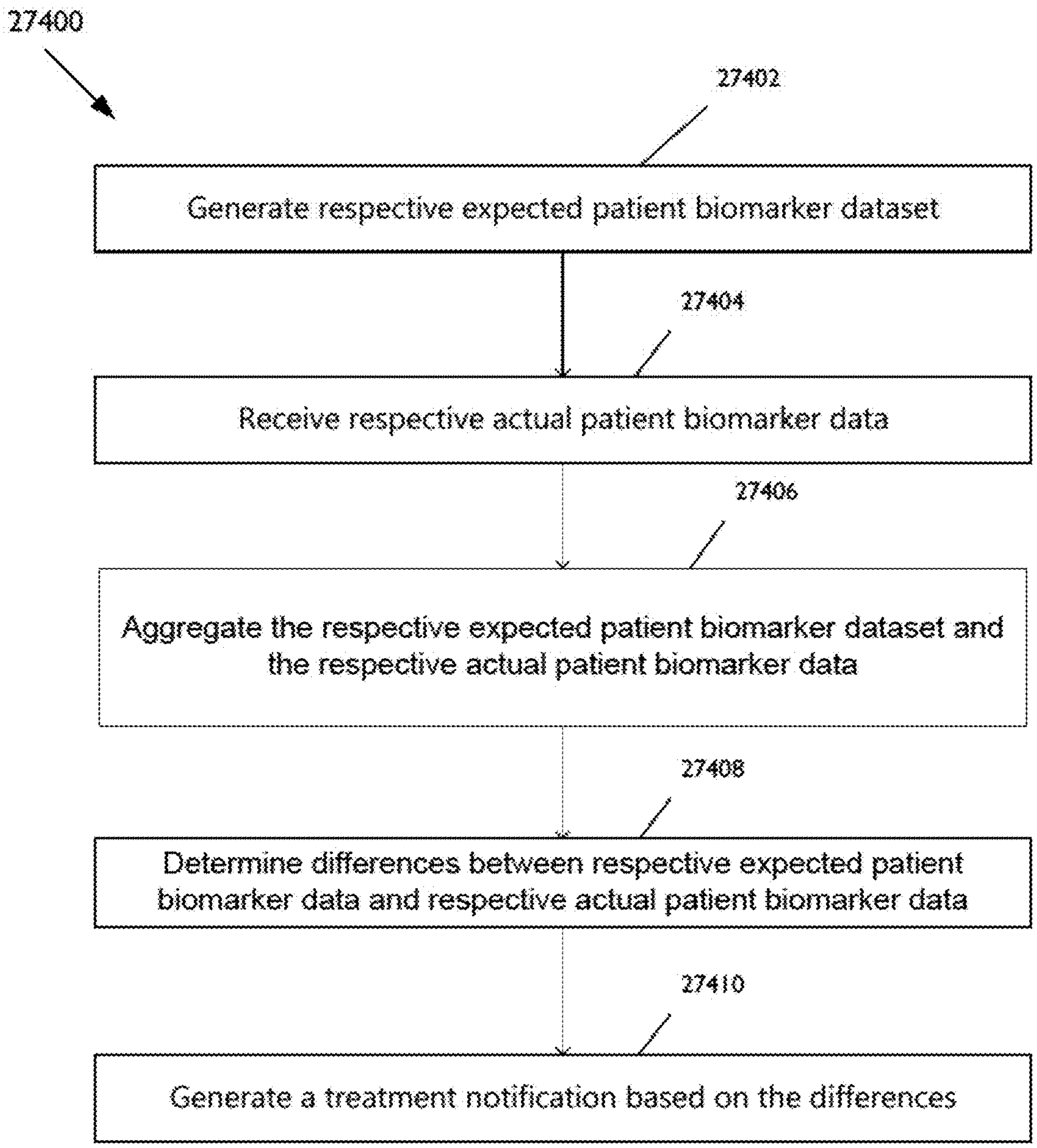
FIG. 81 illustrates a process for a computing-implemented patient and surgeon monitoring system that aggregates biomarker data.

FIG. 81 illustrates a process 27400 for a computing-implemented patient and surgeon monitoring system that aggregates biomarker data. The process 27400 may be performed by the computing device 27203 aggregating patient biomarker data described above in FIG. 77. At 27402, the computing device 27203 may compute the expected patient biomarker data 27223 for each of a plurality of patients. The expected patient biomarker data 27223 represents expected values of patient biomarkers over the duration of the patient's recovery after undergoing a surgery performed by an HCP at a healthcare facility. The expected patient biomarker data 27223 may be a set of values in a recovery timeline. At 27404, the computing device 27203 may receive respective actual patient biomarker data 27213 from respective patient sensor systems for each of the plurality of patients. The respective patient sensor systems may be the controlled patient sensor systems 27206 and the uncontrolled patient sensor systems 27208 described above. At 27406, the computing device 27203 may aggregate the respective expected patient biomarker data 27223 and the respective actual patient biomarker data 27213 for each of the plurality of patients. The aggregated respective expected patient biomarker data and the aggregated respective actual patient biomarker data may be by department or surgeon. The aggregated respective expected patient biomarker data and the aggregated respective actual patient biomarker data may be by procedure configuration, surgical instrument mix, complication type, re-admission rates, days of treatment, or time to intervention. At 27408, the computing device may determine the differences between the aggregated respective expected patient biomarker data 27223 and the aggregated respective actual patient biomarker data 27213 determined at 27406. The differences between the expected patient biomarker data 27223 and the actual patient biomarker data 27213 at any given time may be for the same time in the patient's recovery. At 27410, the computing device may generate a treatment notification based on the differences determined at 27408. The treatment notification is a unique notification tailored for a specific group of patients. The treatment notification may provide insights to follow-up metrics, facility of care, compliance, and intervention accuracies.

Figure 82:
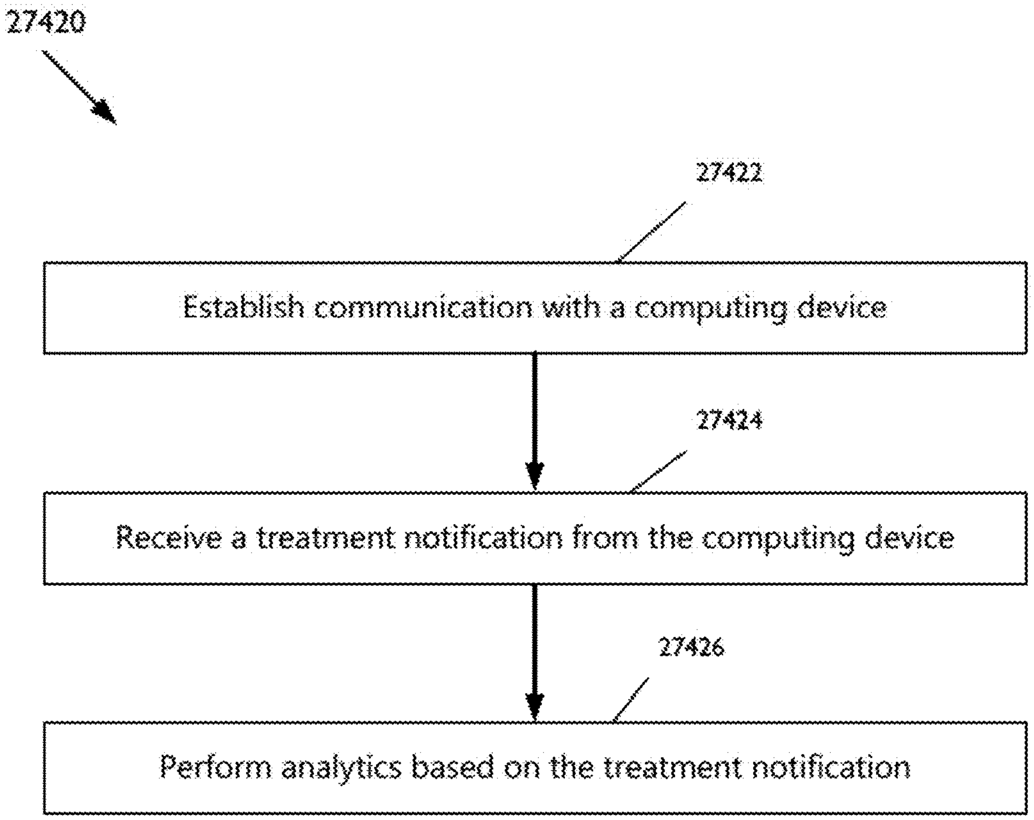
FIG. 82 illustrates a process for a facility analytics system for analyzing patient biomarker data.

FIG. 82 illustrates a process 27420 for a facility analytics system for analyzing patient biomarker data. The process 27420 may be performed by the facility analytics system 27320 analyzing patient biomarker data described above in FIG. 80. At 27422, the facility analytics system 27320 may establish communication with the computing device 27203. At 27424, the facility analytics system 27320 may receive a treatment notification from the computing device 27203. The treatment notification may be based on the differences of aggregated respective expected patient biomarker data 27223 and aggregated respective actual patient biomarker data for a plurality of patients. The expected patient biomarker data 27223 may be a set of values in a recovery timeline. The differences between the aggregated respective expected patient biomarker data 27223 and the aggregated respective actual patient biomarker data 27213 at any given time may be for the same time in the patient's recovery. The aggregated respective expected patient biomarker data 27223 and the aggregated respective actual patient biomarker data 27213 may be by department or surgeon. The aggregated respective expected patient biomarker data 27223 and the aggregated respective actual patient biomarker data 27213 may be by procedure configuration, surgical instrument mix, complication type, re-admission rates, days of treatment, or time to intervention. At 27426, the facility analytics system 27320 may perform analytics based on the treatment notification received. The treatment notification may provide insights to follow-up metrics, facility of care, compliance, and intervention accuracies.

The facility analytics system 27320 can provide many patient, HCP, and healthcare facility benefits. In examples, the facility analytics can be for escalation of user interaction based on monitored biomarkers, patient interactive responses, and HCP response, timing, and comparative best practices or facility improvement pre-set thresholds. In examples, the facility analytics can compare an expected event from an actual event. In the case where the expected event is occurring but does not match the user's input, a prompt to conduct a further investigation can occur. In examples, confirmation and verification of certain patient biomarker data can be compared with other related patient biomarker data to confirm the reliability of the inputted patient biomarker data. The patient biomarker data could be vetted against reliability markers to determine if the data is real or adjusted. The patient biomarker data could be plotted to determine if a normal distribution occurs. The patient biomarker data could be compared to previous data points looking for exact measures. The system could occasionally ask for re-imputing of the last data point of the patient biomarker data without showing the user the last data point they input for confirmation.

The facility analytics system 27320 can utilize the surgical data collected by the computing device 27203 to help provide healthcare inputs to medical billing, medical record keeping, and medication orders, for example. In examples, the facility analysis system 27320 can transfer the facility analytics data to the billing system and submitted the facility analytics data to insurance, Medicare, or other payers for reimbursement purposes. This could reduce resource required, inaccuracies and have documented evidence. The facility analytics system 27320 can provide facility analytics data that contributes to a medical records quality, such as improving physician documentation, lessening the need for handwriting legibility, and reducing duplication and inaccurate patient data. For example, if a clinical coder or HCP was extracting data from a medical record in which the principal diagnoses was unclear due to illegible handwriting, the health professional would have to contact the physician responsible for documenting the diagnoses in order to correctly assign the code. In these examples, the facility analytics system 27320 eliminates the need for a HCP to contact the physician responsible for documenting the diagnoses, and can simply access the data on the computing device of the facility analytics system 27320. The facility analytics system 27320 can provide medication orders based on the data received from the computing device 27203. The facility analytics system 27320 can offer a list of recommended medications that could be listed for the surgeon to select/approve, laboratory tests, imaging, and follow-up activities, based on task performed and the patient biomarker data received.

A device to output data associated with a surgical event of a surgery may include a processor. The processor may be configured to receive, before the surgery, first patient data that represents first information obtained before the surgery. For example, the first patient data may represent a baseline patient biomarker determined before the surgery. For example, the first patient data may represent a patient record information determined before the surgery.

The processor may be configured to generate a transform before the surgery. The transform may be based on the first information. The transform may include a condition. The condition may be based on second patient data. The second patient data may represent second information derived from an aspect of the surgical event.

The processor may be configured to receive the second patient data during the surgical event. And The processor may be configured to apply the transform based on the received second patient data satisfying the condition. The transform may be applied to the second patient data to derive third patient data. The third patient data may the second information and contextual information about the second information The processor may be configured to output the third data to a human-machine-interface device.

In an illustrative example, the first patient data may include a baseline value of a biomarker of the patient as determined based on wearable, un-controlled sensor measurements taken before surgery. The second patient data may include a present value of that biomarker obtained during the surgery. A transform may be applied on the condition that the present value deviates from the baseline by more than a threshold, such that the third data represents an alert to a health care professional with the value of the biomarker and an indication of the magnitude and/or nature of the present value's deviation from the baseline.

A device to output data associated a surgery may include a processor that may be configured to receive, before the surgery, first patient data. The processor may be configured to generate a transform before the surgery. The processor may be configured to receive second patient data during the surgery and to apply the transform based on the received second patient data satisfying a condition of the transform. The transform may be applied to the second patient data to derive third patient data. The third patient data may include the second information and contextual information about the second information. For example, the third patient data may include an alert to a health care professional with a present value of a biomarker and an indication of the magnitude and/or nature of the present value's deviation from a baseline.

Figure 83A:
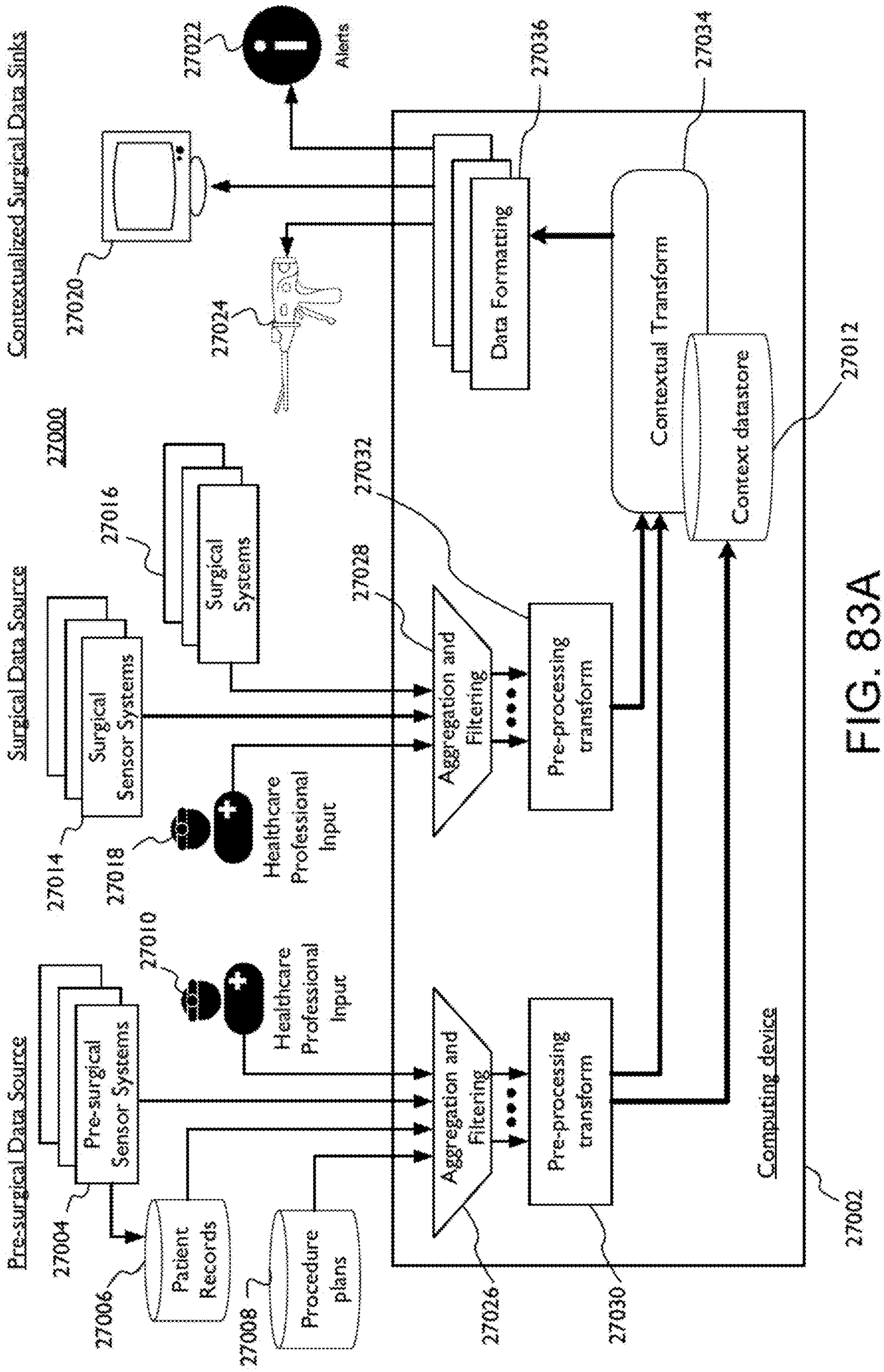
FIGS. 83A-B are block diagrams depicting an example system for contextualizing data associated with a surgical event and an example transform operation, respectively.

FIG. 83A is a block diagram depicting an example system 27000 processing for contextualizing data associated with a surgical event. The system 27000 may include a computing device 27002, one or more pre-surgical (e.g., pre-operative) collection sources, one or more surgical (e.g., intra-operative) collection sources, and or more of contextualized surgical data sinks.

The computing device 27002 may any device suitable for processing sensor, health record data, user input, and the like, before and during surgery, to transform the data and derive contextualized for output. The contextualized output may include a sensor measurement. The contextualized output may include context, for example, additional information relevant to the present understanding and/or interpretation of the sensor measurement. For example, the context may include pre-surgery and/or pre-therapy baselines. For example, the context may include situational awareness of incorrectly connected and/or incorrectly operating surgical and/or sensing systems. For example, the context may include adjustments to products, surgical plans, and/or margins.

The computing device 27002 may be incorporated into the system 27000 with any method suitable for implementation of the functionality disclosed herein. For example, the computing device 27002 may be incorporated as a stand-alone computing device. For example, the computing device may be incorporated into a surgical hub, such as that disclosed in FIG. 1, for example. For example, the computing device 27000 may be incorporated into a sensing system itself (e.g., sensing both pre-surgical and surgical data and providing contextualized data as an output). For example, the computing device 27000 may be incorporated into a surgical device itself (receiving both pre-surgical and surgical data and providing contextualized data and/or alerts as an output).

The pre-surgical data sources may include one or more pre-surgical sensor systems 27004, patient records 27006, procedure plans 27008, health care professional input 27010, and/or or the like.

The one or more one or more pre-surgical sensor systems 27004 may include any configuration of hardware and software devices suitable for sensing and presenting parameters patient biomarkers that may be relevant during a surgical procedure. Such pre-surgical sensor systems 27004 may include the sensing and monitoring systems disclosed herein, including uncontrolled patient monitoring systems, controlled patient monitoring systems, and the like. For example, one or more pre-surgical sensor systems 27004 may include wearable patient sensor systems. Such systems may be used by the patient for any amount of time prior to surgery, inside and outside of a medical facility. To illustrate, via an uncontrolled patient monitoring system, the patient may use a wearable heart-related sensor at home for four weeks prior to a surgical procedure. And/or, via a controlled patient monitoring system, a health care professional may monitor the same and/or analogous biomarkers using facility equipment during time the patient is prepped immediately before the surgical procedure. For example, the one or more pre-surgical sensor systems 27004 may provide data suitable for establishing baselines of patient biomarkers for use in contextual determination during and/or after surgery.

For example, the one or more one or more pre-surgical sensor systems 27004 may include any of those disclosed herein, such as those with reference to FIG. 1B for example.

The one or more patient records 27006 may include any data source relevant to a patient in view of a health procedure. The patient records 27006 may include information such as allergies and/or adverse drug reactions, chronic diseases, family medical history, illnesses and/or hospitalizations, imaging data, laboratory test results, medications and dosing, prescription record, records of surgeries and other procedures, vaccinations, observations of daily living, information collected by pre-surgical sensor systems 27004, and the like. For example, the patient records 27006 may be stored at storage 20331 (e.g., storing an EMR database), as disclosed herein.

The one or more procedure plans 27008 may include any data source relevant to a health procedure (e.g., relevant to a health procedure in view of a particular patient and/or facility). The procedure plan may include structured data indicative of the desired end result, the surgical tactics to be employed, the operation logistics, and the like. The procedure plan may include an accounting of the equipment to be used and/or the techniques to be used. The procedure plan may include an order. The procedure plan may include a timeline. The structured data may include defined fields and/or data tags associated corresponding values. The structured data may include codes associated with surgical steps.

The pre-surgical health care professional input 277010 may include any data relevant to the one or more pre-surgical sensor systems 27004; patient records 27006; procedure plans 27008; operation, configuration, and/or management of the computing device 27002, and the like. For example, the pre-surgical health care professional input 27010 may include managing a context datastore 27012. The pre-surgical health care professional input 27010 may include manually entering data not received directly for any relevant source (such as manually entering a manually taken biomarker reading, for example).

The surgical data sources may include one or more surgical sensor systems 27014, one or more surgical systems 27016, healthcare professional input 27018, and/or the like.

The one or more one or more surgical sensor systems 27014 may include any configuration of hardware and software devices suitable for sensing and presenting parameters patient biomarkers that may be relevant during a surgical procedure. Such surgical sensor systems 27014 may include the sensing and monitoring systems disclosed herein, including controlled patient monitoring systems, surgeon monitoring systems, environmental sensing systems, and the like.

The one or more surgical systems 27016 may include any surgical equipment suitable for providing operative data regarding its configuration, use, and/or present condition and/or status, for example. The surgical systems 27016 may include equipment in the surgical theater. The surgical systems 27016 may include any equipment employed in the surgical theater, such as that disclosed with reference to FIG. 1, FIG. 7A, FIG. 10, and throughout the present application, for example. The surgical systems 27016 may include surgical fixtures of a general nature, such as a surgical table, lighting, anesthesia equipment, robotic systems, and/or life-support equipment. The surgical systems 27016 may include surgical fixtures specific to the procedure at-hand, such as imaging devices, surgical staplers, energy devices, endocutter clamps, and the like. For example, the surgical systems 27016 may include any of a powered stapler, a powered stapler generator, an energy device, an energy device generator, an in-operating-room imaging system, a smoke evacuator, a suction-irrigation device, an insufflation system, or the like.

The surgical health care professional input 277010 may include any data relevant to the one or more surgical sensor systems 27014, the one or more surgical systems 27016; the operation, configuration, and/or management of the computing device 27002, and the like. For example, the pre-surgical health care professional input 27010 may include triggering a particular interaction with the context datastore 27012. The surgical health care professional input 27010 may include manually entering data not received directly for any relevant source (such as manually entering a manually taken biomarker reading, for example).

The contextualized surgical data sinks may include a human-interface device 27020, an alert system 27022, configurable surgical equipment 27024, and the like.

The human-interface device 27020 may include device suitable for producing a perceptible representation of the contextualize surgical data. The perceptible representation may include a visual indication, an audible indication, or the like. The human-interface device 27020 may include a computer display. For example, the human-interface device 27020 may include a visual representation including text and/or images on a computer display. The human-interface device 27020 may include a text-to-speech device. For example, the human-interface device 27020 may include synthesized language prompt over an audio "smart" speaker. The human-interface device 27020 may communicate the contextualized surgical data to the surgeon and/or surgical team. The human-interface device 27020 may include and/or be incorporated into any suitable device disclosed herein. For example, the human-interface device 27020 may include and/or be incorporated into any of the primary display 20023, a first non-sterile human interactive device 20027, and/or a second non-sterile human interactive device 20029, such as that disclosed in FIG. 2A for example. For example, the human-interface device 27020 may include and/or be incorporated into a human interactive device 20046, such as that disclosed in FIG. 2B. For example, the human-interface device 27020 may include and/or be incorporated into the display 20224 of a surgical instrument, such as that disclosed in FIG. 7A for example.

The alert system 27022 may include any device suitable for generating a perceptible indication that relevant contextual data is available and/or has changed. The indication may include a visual indication, an audible indication, a haptic indication, and the like. The alert system 270) 22 may incorporate any of the human-interface devices 27020 disclosed here. The alert system 27022 may include non-verbal and/or non-textual indications to represent contextual data is available and/or has changed. For example, the alert system may include audio tones, visual color changes, lights, and the like. For example, the notification may include a haptic "tap" on a wearable device, such as a smartwatch worn by the surgeon.

The configurable surgical equipment 27024 may include any equipment employed for a surgical procedure (such as surgical systems 27016) that has a configurable aspect to its operation. The configurable aspect of the equipment may include any adjustment or setting that has an influence on the operation of the equipment. For example, configurable surgical equipment 27024 may have software and/or firmware adjustable settings. Configurable surgical equipment 27024 may be hardware and/or structurally adjustable settings. In an example, the configurable surgical equipment 27024 may report its present settings information to the computing device 27002.

Example device settings may include placement, imaging technology, resolution, brightness, contrast, gamma, frequency range (e.g., visual, near-infrared), filtering (e.g., noise reduction, sharpening, high-dynamic-range), and the like for imaging devices; placement, tissue precompression time, tissue precompression force, tissue compression time, tissue compression force, anvil advancement speed, staple cartridge type (which may include number of staples, staple size, staple shape, etc.), and the like for surgical stapling devices; and placement, technology type (such as harmonic, electrosurgery/laser surgery, mono-polar, bi-polar, and/or combinations of technologies), form-factor (e.g., blade, shears, open, endoscopic, etc.) coaptation pressure, blade amplitude, blade sharpness, blade type and/or shape, shears size, tip shape, shears knife orientation, shears pressure profile, timing profile, audio prompts, and the like for energy devices, for example.

The computing device 27002 may include computing hardware including a processor, memory, input/output subsystems, and the like. The processor may be configured (via application specific hardware, software, firmware, or the like) to transform received data and to derive contextualized for output. For example, the processor may include a microprocessor, a microcontroller, a FPGA, and an application-specific integrated circuit (ASIC), a system-on-a-chip (SOIC), a digital signal processing (DSP) platform, a real-time computing system, or the like. For example, processor may be configured to implement computing functions and/or modules as disclosed herein. For example, the processor may be configured for aggregation and/or filtering 27026, 27028 of input, pre-processing 27030, 27032 of input, storage and/or management of a context datastore 27012, operation of a contextual transform 27034 (e.g., including real-time intra-operative processing), and/or data formatting 27036 of contextual output data as disclosed herein.

The data received from the pre-surgical data sources may be subject to aggregation and/or filtering 27026 and the corresponding pre-processing 27030. The data received from the surgical data sources may be subject to aggregation and/or filtering 27028 and the corresponding pre-processing 27032. The aggregation and/or filtering 27026, 27028 and/or pre-processing 27030, 27032 may be used to prepare and format the data for use in the context datastore 27012 and the contextual transform 27034, respectively.

For example, the aggregation and/or filtering 27026 and the corresponding pre-processing 27030 of the data received from the pre-surgical data sources may include filtering (e.g., to select specific sensor data from the stream of data from pre-surgical sensor systems 27004). For example, the aggregation and/or filtering 27026 and the corresponding pre-processing 27030 of the data received from the pre-surgical data sources may include averaging (e.g., to establish a baseline for a specific biomarker from pre-surgical sensor systems 27004). For example, the aggregation and/or filtering 27026 and the corresponding pre-processing 27030 of the data received from the pre-surgical data sources may include correlation analysis (e.g., to establish a baseline for relationships between and/or among specific biomarkers from pre-surgical sensor systems 27004). For example, the aggregation and/or filtering 27026 and the corresponding pre-processing 27030 of the data received from the pre-surgical data sources may include data translation (e.g., to coordinate format and/or datatype differences between a data source and the format and datatype expected by the context datastore 27012).

For example, the aggregation and/or filtering 27028 and the corresponding pre-processing 27032 of the data received from the surgical data sources may include filtering (e.g., to select specific sensor data from the stream of data from surgical sensor systems 27014). For example, the aggregation and/or filtering 27028 and the corresponding pre-processing 27032 of the data received from the surgical data sources may include averaging (e.g., to help reject noise in data from the surgical sensor systems 27014 and/or surgical systems 27016). For example, the aggregation and/or filtering 27028 and the corresponding pre-processing 27032 of the data received from the surgical data sources may include time mapping (e.g., to place received values from different sources in alignment with each other in regard to time). Time mapping may aid in correlation and ratio analysis in the contextual transform 27034. For example, the aggregation and/or filtering 27028 and the corresponding pre-processing 27032 of the data received from the surgical data sources may include data translation (e.g., to coordinate format and/or datatype differences between a data source and the format and datatype expected by the context datastore 27012).

The data formatting 27036 may include translating the output of the contextual transform 27034 into a format suitable for a specific data sink. For example, the data formatting 27036 may include translating the output into a textual notification for display on a visual human-interface device 27020. For example, the data formatting 27036 may include translating the output into a specific setting for the configurable surgical equipment 27024. For example, the data formatting 27036 may include translating the output into a trigger for triggering an alert of the alert system 27022.

Figure 83B:
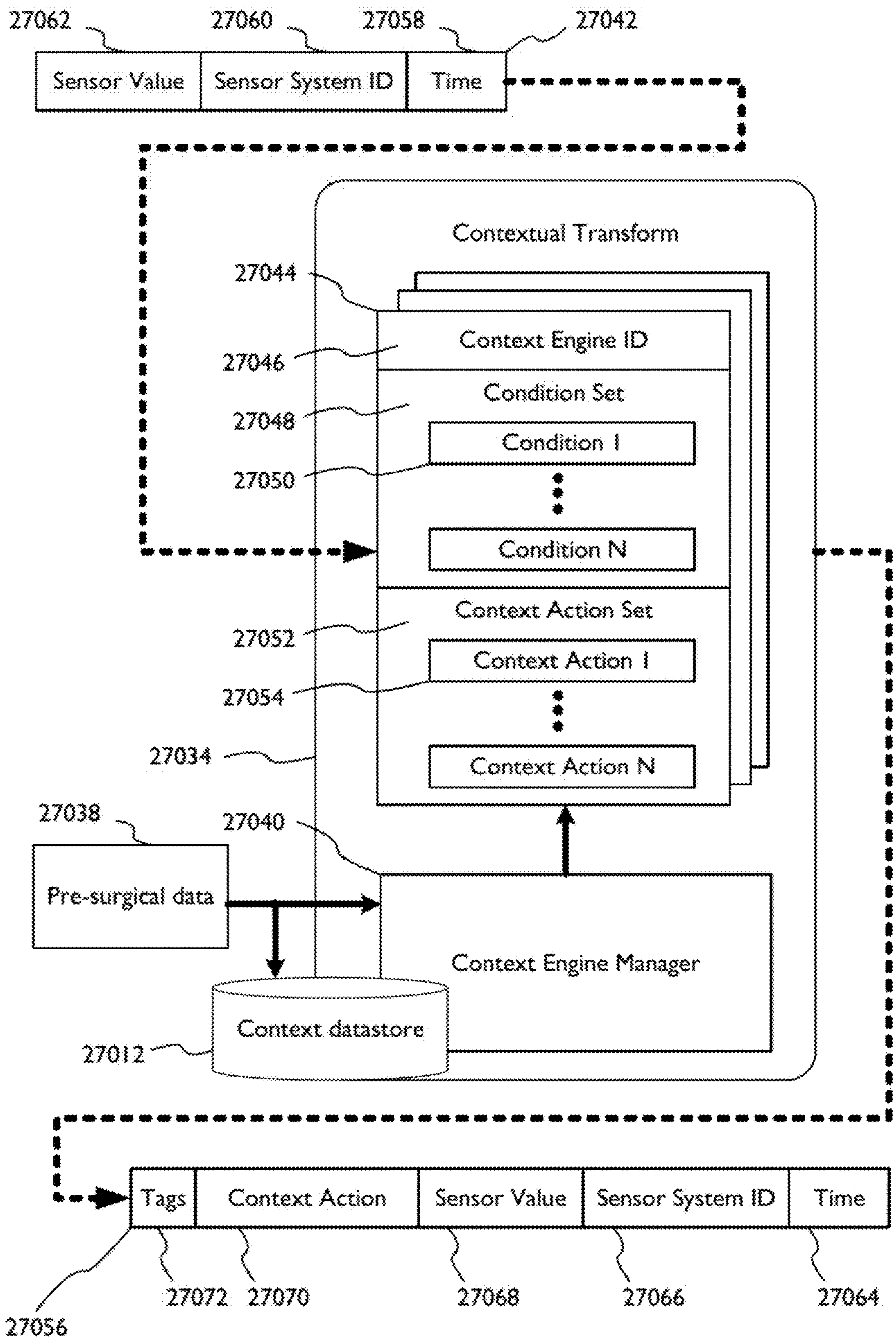

FIG. 83B is a block diagrams depicting an example transform operation. Pre-surgical data 27038 may be used to operate a context engine manager 27040 and/or a context datastore 27012. Surgical data (e.g., intra-surgical data) 27042 may be used to operate a one or more context engines 27044.

A context engine 27044 may include a context engine ID 27046, a condition set 27048 which may contain one or more conditions 27050, a context action set 27052 which may contain one or more context actions 27054.

The contextual transform 27034 may operate to transform the surgical input data 27042 into contextualized surgical data 27056. To illustrate, as an input the contextual transform may receive surgical data that includes, for example, a measurement time 27058, a sensor system identifier 27060, and a sensor value 27062. The contextual transform 27034 may output contextualized surgical data 27056. The contextualized surgical data 27056 may include a measurement time 27064, a sensor system identifier 27066, a sensor value 27068, and one or more context actions 27070. The outputted measurement time 27064, sensor system identifier 27066, and sensor value 27068 may be those values received at the input measurement time 27058, sensor system identifier 27060, and sensor value 27062 (such as a data pass-thru). The outputted measurement time 27064, sensor system identifier 27066, and sensor value 27068 may be themselves translated from the values received at the input measurement time 27058, sensor system identifier 27060, and sensor value 27062 (such as a data translation, data correction, and/or other processing defined by the contextual transform 27034). The context actions 27070 may include additional information that places the sensor value 27068 into a specific context for the health care professionals. For example, the context action 27070 may include instructions and/or information about a baseline value for the sensor value, an alert of a specific deviation, relevant information from the patient's record, relevant information to a specific procedural element of the surgery, surgical device settings, and/or any information the health care professional might find relevant to have at the moment of the sensor's measurement itself. The contextualized surgical data 27056 may include one or more data tags 27072. The data tags 27072 may include logging data (indicating that that a specific transform or other processing has occurred). For example, the data tag 27072 may include the context engine identifier 27046.

The value may take the form of any suitable unit of characterization. For example, the value may include a specific numerical value, such as an integer value, floating point value, or the like. The value may include an alphanumeric code. The value may include a logic value. The value may include multidimensional quantities, such as a vector, a time series, or the like.

The context engine manager 27040, in connection with the context datastore 27012, may serve to determine the content and/or active-inactive state of each context engine 27044. For example, the context engine manager 27040 may include data and/or instructions to create, edit, delete, import, export, and otherwise manage the one or more context engines 27044. The context engine manager 27040 may include triggers and/or other logic to activate and/or deactivate the one or more context engines 27044. The context engine manager 27040 may include logic to establish the data on which conditions and/or actions of each context engine 27044 may operate.

The context datastore 27012 may include a datastore for any information and/or instructions associated with the context engine manager 27040. For example, the context datastore 27012 may store the context engines 27044 themselves. The context datastore 27012 may store pre-surgical data 27038 that is relevant to the content and/or operation of one or more context engines 27044. To illustrate, the context datastore may receive weeks' worth of patient pre-surgical data (e.g., data obtained by one or more sensor systems). The context engine manager 27040 may be used to define a context engine 27044 that is used to provide the patient's baseline value for a particular biomarker (for example the patient's sleeping heartrate). The context datastore 27012 may process the pre-surgical data to determine this baseline value and have it available to the appropriate context engine 27044.

Each context engine 27044 may be identified by a corresponding context engine identifier 27046. For example, the context engine identifier 27046 may be a system-wide unique value. The context engine identifier 270) 46 may include a sequential serial number, a structured identification code, or the like. For example, the context engine identifier 27046 may include information such as creation data, creation source, last modified data, etc. that may be used to identify a specific context engine 27044 from the other context engines 27044 in the system 27000.

A context engine 27044 may include a corresponding condition set 27048. The condition set 27048 may include one or more conditions 27050. The conditions 27050 may be interrelated by logic statements, such as Boolean logic for example. The condition set 27048 may serve to trigger one or more context actions 27054 based on incoming surgical data 27042. For example, one or more conditions 27050 may define a range for a particular sensor system. And when surgical data 27042 is received with a sensor system ID 27060 that matches that set forth by a condition 27050 of the condition set 27048 of an active context engine 27044 and the corresponding sensor value 27062 is outside of the range established by one or more conditions 27044 of the condition set 27048, a corresponding context action 27054 may be triggered.

The context engine 27044 may include a corresponding context action set 27052. The context action set 27052 may include one or more context actions 27054. The context actions may each be associated with an outcome defined by the condition set 27048. For example, a condition set 27048 with three possible outcomes may be associated with three context actions 27054. The context action 27054 may include information and/or instructions that may be incorporated into the outputted contextualized surgical data.

The context actions may include, for example, notification and/or alarm information, additional display information, recommended device settings, and the like. The context actions may be defined and stored as part of the context engine 27044 and managed by the context engine manager 27040 and the context datastore 27012.

Context engines 270) 44 may be used to implement any number of context generating strategies related to pre-surgical information and surgical sensor input to provide timely and relevant additional information to health care professionals during a surgical procedure at the same time and in the same mechanism (e.g., same display) as the sensor input itself. This additional information may take any form suitable for informing a health care professional in view of the best practices, the professional's preferences, and patient and/or procedure specific details. For example, the contextual information may include information related to patient biomarker baselines, surgical plan information, flaws in surgery data collection, administered agents, patient sensitivities, potential interactions, instruction for use, surgical procedure baselines, and the like.

For example, the context engine 27044 may be used to present base line physiologic measures that can be displayed relative to the in-surgery feeds for context. Here, the display of a baseline measure of the same biomarker as that being measured and presented could help the surgeon understand the biomarker in the context of the norm for the specific patient. The context could be formatted as informing the health care professional of the baseline value itself, as the magnitude of deviation from the baseline, normalized by some other baseline metric, or the like. For example, alarms and/or notifications could be set to trigger when the absolute value of the sensor value 27062 crosses a threshold defined by one or more conditions 27050. For example, alarms and/or notifications could be set to trigger when a derived metric (e.g., change from baseline, normalized, etc.) of the sensor value 27062 crosses a threshold defined by one or more conditions 27050. To illustrate, where the blood pressure of a patient is naturally depressed, and the diastolic to systolic ratio is typically, for this specific patient, below normal, what may appear to be a mild elevation in blood pressure for the population may actually represent a much greater elevation for the present patient. Without the additional context, a healthcare professional might consider the elevation non-concerning. With the context, however, the healthcare professional may be able to make a more accurate assessment of the patient's situation in the moment. This elevation from the norm may be an indicator of felt pain or stress within the patient or their cardiovascular system. The context action 27070 may present information about this difference from the norm and/or may present recommendation on how to proceed.

For example, the context engine 27044 may be used to present surgical plan information. The importation of procedure plans, health record, pre-surgery imaging, pre-surgery testing, and the like into the context datastore may be part of context engines 27044 to present context and information related to anticipated aspects of the procedure. For example, a context engine 27044 may be used to identify an expansion of procedure plan margins, boundaries, starting locations, product selection (stapler type, staple cartridge color, re-enforcement, or staple strength) or the like. The context engine 27044 may be triggered based on input of surgical systems themselves (such as surgical systems 27016) as they indicate aspects of the procedure being carried out. The context engine 270) 44 may likely be triggered and/or activated in view of pre-surgery threshold violations, for example. Here, the context action 27054 may include the original plan and any suggested alterations with a highlight as to why the surgeon might want to follow the suggested alteration.

Similarly, when the surgical data 27042 indicates that the actual surgery is departing from the procedure plan (e.g., a unanticipated surgical device is engaged), a corresponding context action 27054 may update a displayed and/or alert the health care professional right away.

To illustrate, a diagnostic wedge resection is often performed prior to completing a lobectomy. If the intraoperative pathology of the lesion of interest comes up positive, the procedure may be converted to a lobectomy which would require different devices, procedure steps, post-op care, etc. If the pathology comes back negative, the procedure may be over with basic steps to close the patient required. Here, a context engine 270) 44 may be programmed and used to trigger the appropriate information based on the results of an intraoperative pathology.

A context engine 27044 may also be used to highlight potentially challenging dissection, mobilization, or transection due to pre-surgery biomarkers. Here, the aggregation of pre-surgery imaging with pre-surgery biomarkers may help to improve the classification of undetermined or un-classified areas. Accordingly, aspects of the procedure may trigger a context action 27054 to highlight of areas of the image that are challenging to classify. Aspects of the procedure may trigger a context action 27054 to highlight key patient data to better inform the surgeon in the moment.

For example, a context engine 27044 may be used to identify flaws in surgery data collection. For example, pre-surgery baselines could be incorporated with conditions related to surgical instrumentation initialization to highlight issues with monitoring hook-up. Here, surgical sensor feeds that appear to have clearly irregular reading based on the pre-surgery baselines could be identified. Such a context engine 27044 may include a condition 27050 based on the received time 27058 relative the beginning of the surgical sensor feed or other procedure information, such as a procedure start time, for example.

For example, a context engine 27044 may be used to improve the administration of agents. For example, a comparison of pre and in surgery datasets may be used to interpret therapy or medical agent progress. Here, patient baselines may be incorporated, via the context datastore 27012 and the corresponding conditions 27050. And surgical monitoring feeds together with surgical equipment input indicating aspects of the present therapy being delivered may received by the contextual transform 27034. If the patient's biomarkers deviate from the baseline expect by the current therapy administration, one or more context actions 27054 may be triggered to alert the health care professional and/or to suggest interpretations related to the therapy's or medical agent's progress.

For example, a context engine 27044 may be used identify, in the moment, patient allergies or conditions that may cause complications if a particular surgical event occurs. For example, a context engine 27044 may be established to trigger if a device and/or mediation is to be used or is presently being used that conflicts with a patient's allergy or other condition present in the patient records. To illustrate, cutaneous hypersensitivity to metal is not uncommon, affecting about 10-15% of the population. Metals known to be sensitizers (haptenic moieties in antigens) include beryllium, nickel, molybdenum, cobalt and chromium. Hypersensitivity to tantalum, titanium and vanadium has been reported only rarely. Metal allergy may be a factor in the failure of implants and complications in surgery. Accordingly, a context engine 27044 may be used to provide an indication when and/or before devices or medications are pulled from storage according to surgical equipment input and/or information from the procedure plan. Such a context engine 27044 may be used during surgery to trigger when a suspect device is activated and/or device activity is sensed. For example, a context engine 27044 could be used to trigger a warning (e.g., "Allergan alert: device contains Nickel") when such conditions 27050 are satisfied. Such an engine may provide timely insight to a health care professional that sees increased inflammation or rash. The corresponding context action 27054 may suggest a change in technique or approach based on location of surgery and potential contact of other critical functions like the lung or heart.

Also for example, a context engine 270) 44 may be used to avoid adverse interactions due to magnetism. Devices with magnets can cause adverse interactions with other implants. Unexpected device interactions could result in device damage and/or patient harm. A context engine 27044 could be triggered based on the activation of a device with magnets or a device that generates a magnetic field. To illustrate, some implantable cardiovert defibrillators and permanent pacemakers incorporate magnet-sensitive switches. Typically, a magnetic field effect of >10 Gauss is required to activate theses magnetic switches. A context engine 27044 may be established to trigger a warning whenever conditions 27050 related to a patient having a magnetically sensitive implant together with a device that has a problematic magnetic field are satisfied. The device with the problematic magnetic field may be identified by activation or operation of a device known to have a problematic magnetic field. The device with the problematic magnetic field may be identified by a surgical environment sensor (e.g., a magnetic field sensor). Additional conditions 27050 and corresponding context actions 27052 may be defined based on the proximity of the device to the patient's pacemaker or defibrillators.

For example, a context engine 27044 may be used present timely Instructions for Use (IFU) warnings. For example, the appropriate IFU warnings may be part of a context action 27054 that may be triggered when the surgical equipment input indicates the device is present, being used, being prepared for use, or the like. Moreover, further context actions 27054 may be defined to provide additional warnings or alerts based on a known contradictions, warning, or precaution that is particularly relevant in view of the procedural plan and/or patient data.

For example, a context engine 27044 may be used in connection with surgical procedure baselines. For example, certain critical physiologic events may be better highlighted with a baseline pre-surgery, pre-anaesthesia baseline. For example, such biomarkers may include blood sugar, stress markers, heart rate variability, heart rate, sweat rate, and the like. Baseline comparisons may enable the refined adjustment to procedural aspects, such as sedation level for example. To illustrate, conditions associated with pain level, stress indicators, heart rate and heart rate variability, for example, may be associate with a context action 27054 to suggest to the anesthesiologist a timely refinement to the sedation.

Figure 84A:
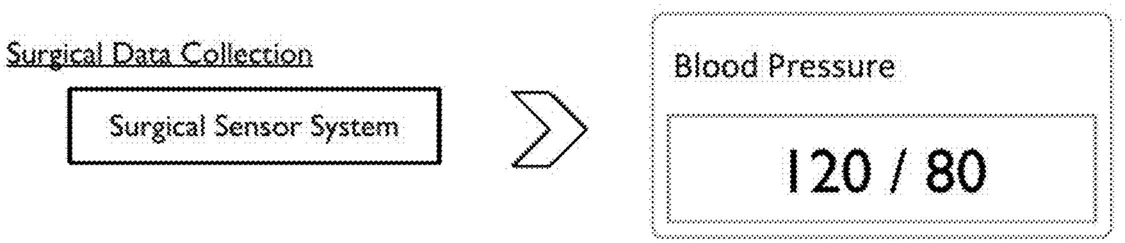
FIGS. 84A-F illustrates example user interfaces of contextualized data and the corresponding context sources.

FIGS. 84A-F illustrates example user interfaces of contextualized data and the corresponding context sources. To begin, a typical user interface for displaying surgical sensor data without context is shown in FIG. 84A. Here, the patient's blood pressure is displayed to the health care professional without additional context. Such an interface may result in system 27000 if no corresponding context engines 27044 were configured, active, or triggered, for example.

Figure 84B:
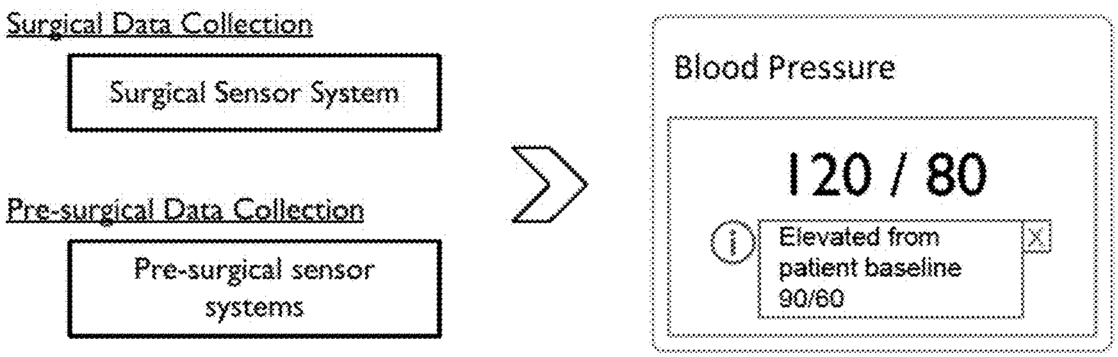

FIGS. 84B-F highlight contextual information in a user interface. In FIG. 84B, input from the surgical sensor systems and from the pre-surgical data collection may be used to present an interface displaying the patient's present blood pressure, together with contextual information. For example, here the contextual information is an indication of deviation from the patient's own baseline. Accordingly, a blood pressure that would appear normal in view of a particular population may actually be elevated with considered in the context of the specific patient's normal blood pressure.

Figure 84C:
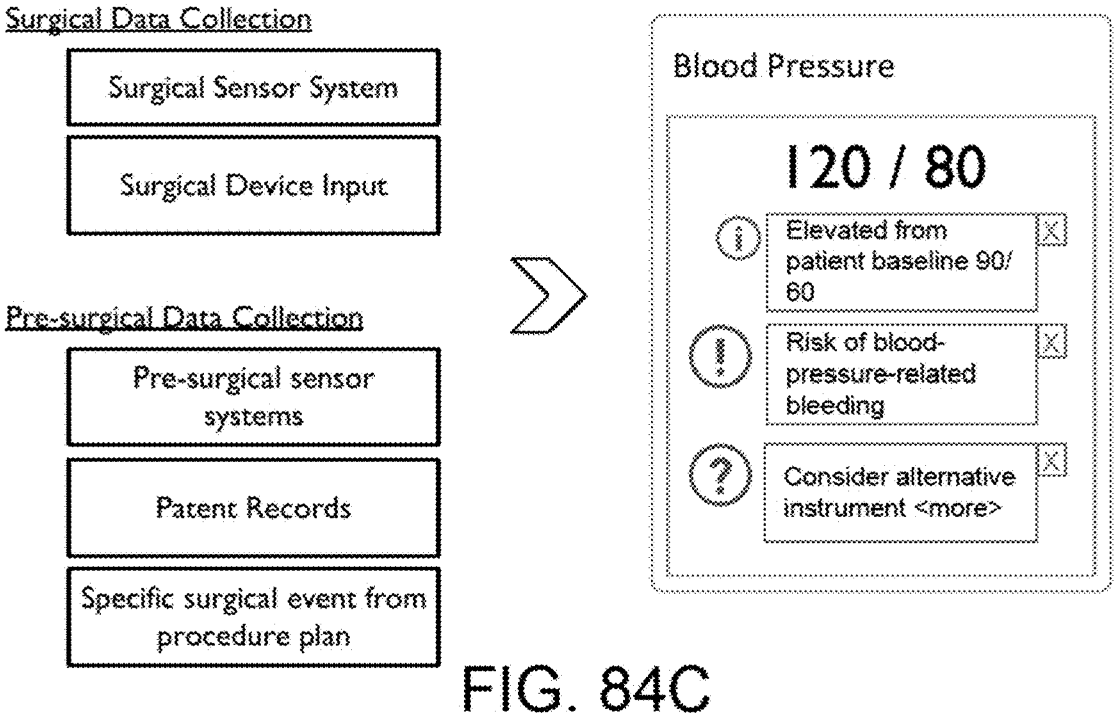

In FIG. 84C, the inclusion of data from surgical devices, patient records, and/or a specific event from a surgical procedure plan may be used to present an interface that further indicates a potential complication or risk of complication. Here, the elevated blood pressure together with a particular device and planned action may increase the risk of blood pressure-related bleeding. The interface may include suggestions to the health care professional on how to proceed.

Figure 84D:
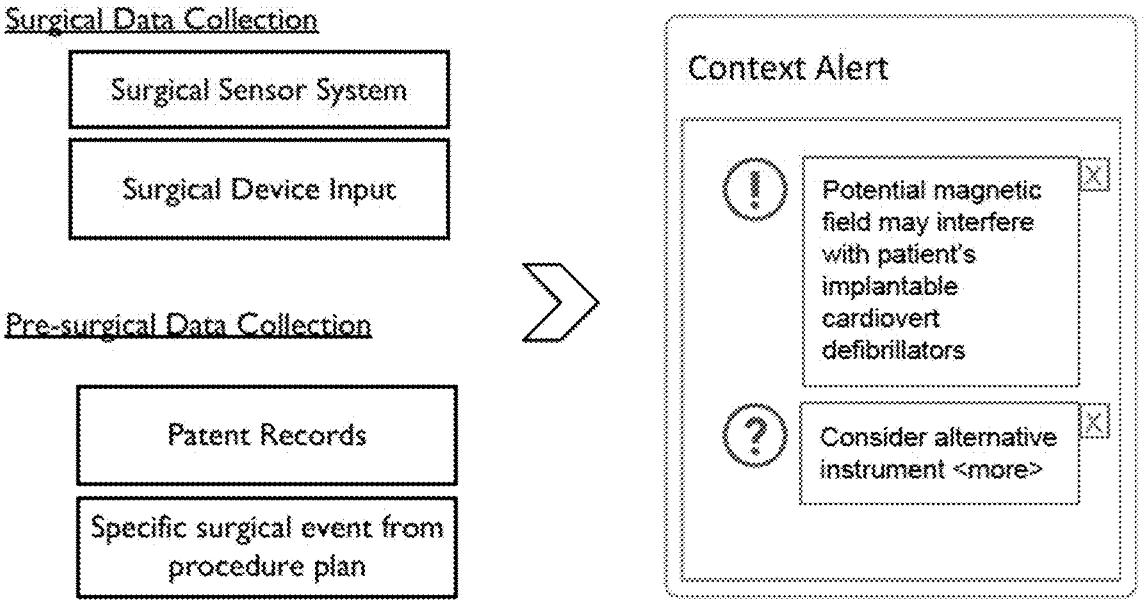

FIG. 84D illustrates an example interface associated with identifying a potential risk due to a potential patient-specific complication. Here, the patient records and events from the surgical plan may be used together with surgical data from sensor systems and/or the surgical devices themselves to indicate a potential conflict between a magnetically sensitive patient implant and magnetically problematic device or procedure. The interface may include suggestions to the health care professional on how to proceed. Such an interface may be beneficial when a real-time change is being made from an otherwise planned procedure. For example, a procedure plan to be appropriately distanced from a magnetically sensitive patient implant may be changed in the surgical theater to take place closer to the implant. Or for example, a procedure plan that calls for a particular device may be changed in the surgical theater to use a device with different magnetic properties. Here, a timely notification provided by the example interface upon detection of the change in plan and/or change in the device may help prevent a severe complication.

Figure 84E:
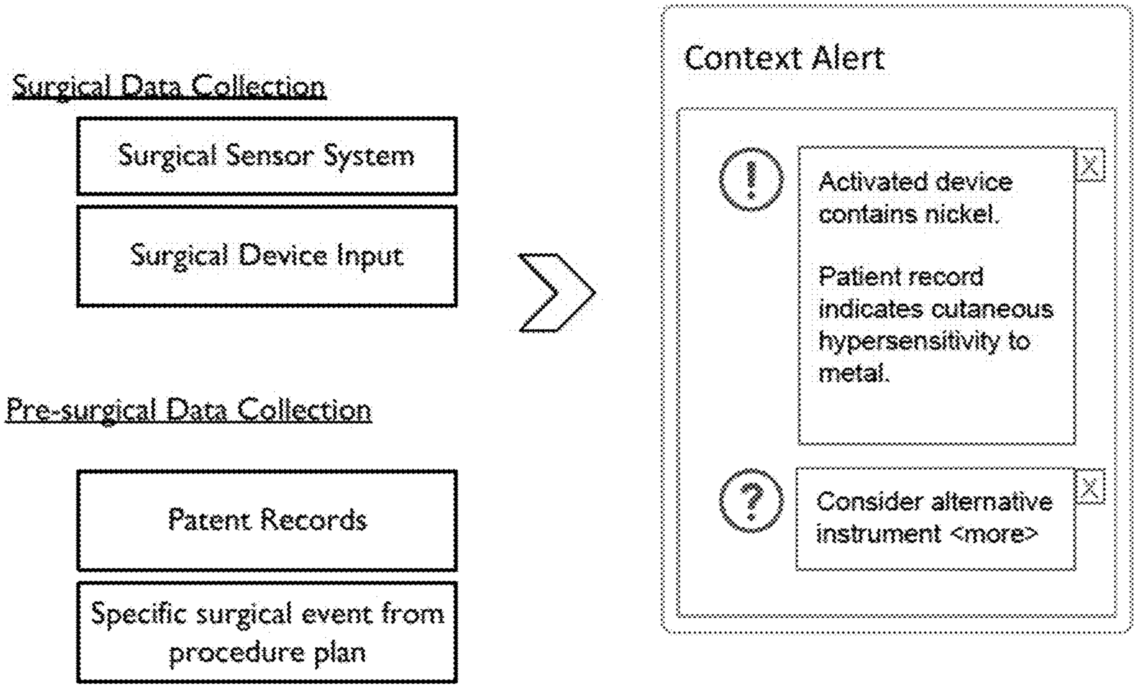

Similarly, FIG. 84E illustrates an example interface associated with identifying a potential risk due to a potential patient-specific complication. Here, the patient records and events from the surgical plan may be used together with surgical data from sensor systems and/or the surgical devices themselves to indicate a potential conflict between a device's material composition and a patient allergy. The interface may include suggestions to the health care professional on how to proceed. Like in FIG. 84D, the logic used to drive such an interface may be constructed to help prevent complications when there are changes to the procedure or to the device to be used.

Figure 84F:
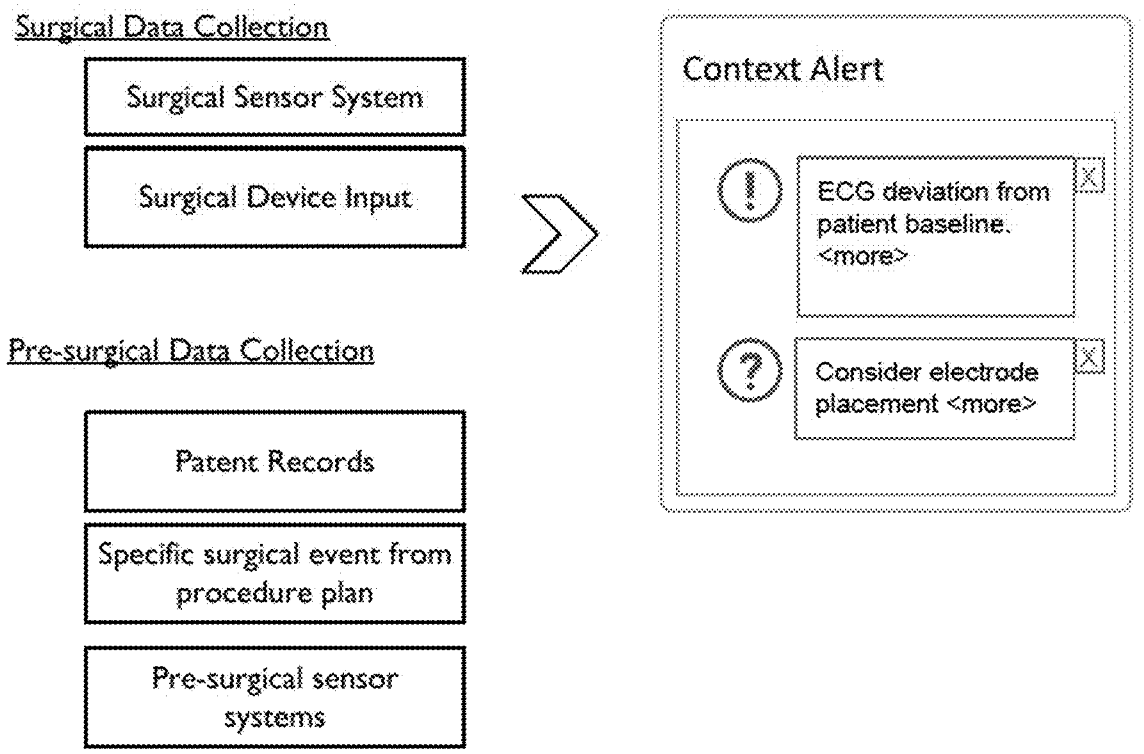

In FIG. 84F, data from surgical and/or pre-surgical sensing systems, surgical devices, patient records, and/or a specific event from a surgical procedure plan may be used to present an interface that indicates a potential issue with sensor hook-up and/or placement. Here, an initial or early ECG reading from a surgical sensing system may be determined to deviate widely from the patient's baseline (derived from pre-surgical data collection and/or patient records, for example). In view of the magnitude and/or timing of the deviation, the interface may suggest that the electrode placement be considered. The interface may include suggestions to the health care professional on how to proceed.

Figure 85:
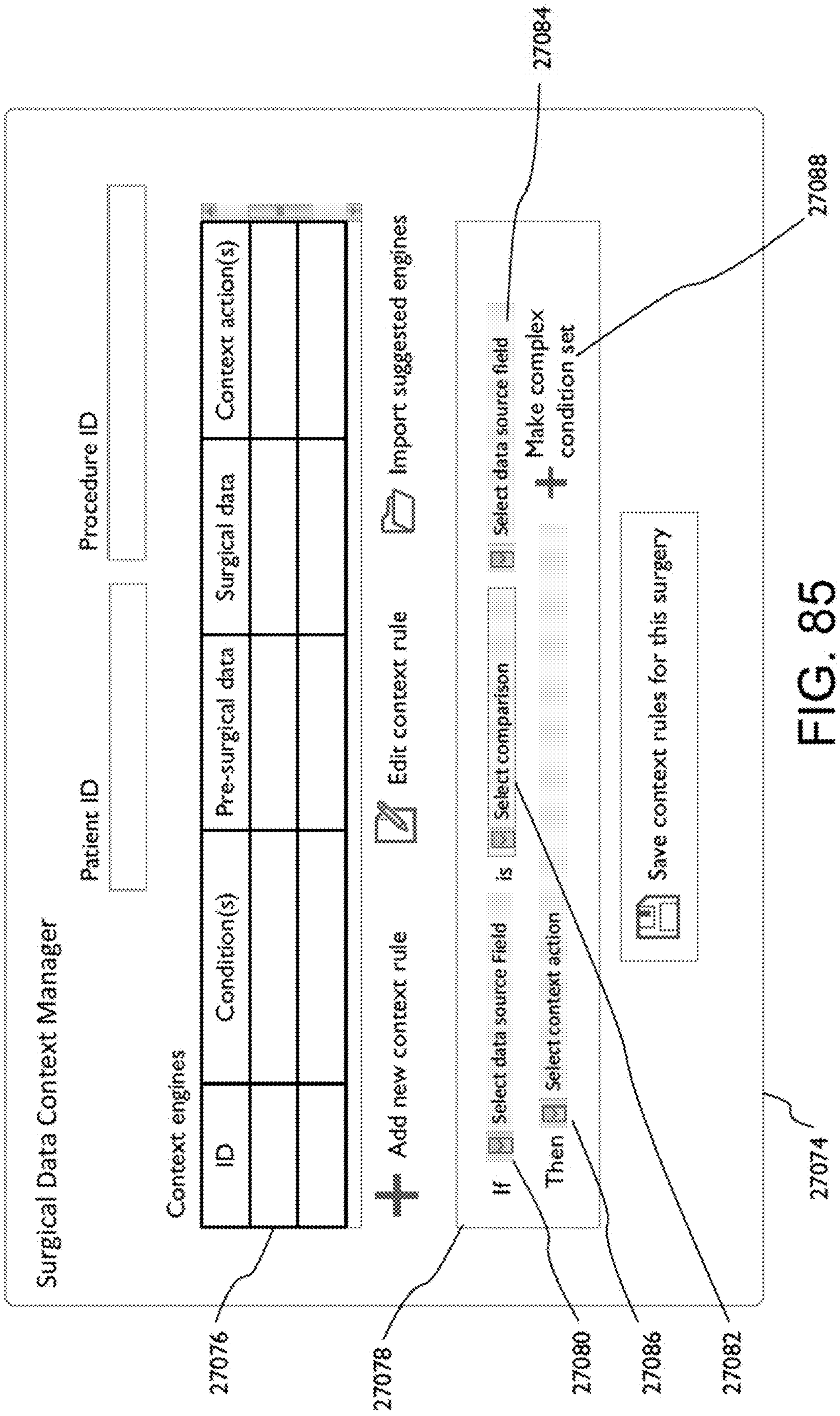
FIG. 85 illustrates an example user interface for managing a system for contextualizing data associated with a surgical event.

FIG. 85 illustrates an example user interface 27074 for managing a system (such as system 27000, for example) for contextualizing data associated with a surgical event. The user interface may enable context engine operations, such as to view, add, delete, change, and import/export, context engines. For example, the user interface enables searching by patient and/or procedure. For example, the user interface enables displaying the context engines associated with a particular patient and/or procedure within a grid element 27076. For example, the user interface may include core data regarding the context engines, such as the engine ID, a listing of the relevant pre-surgical and surgical data, the resultant context actions, and the conditions that would trigger particular context actions. The user interface may include any other data fields relevant to the operation of the context engines.

A if-than-styled interface element 27078 may be used to display, add, and/or edit an example context engine. The interface element 27078 presents the operation of the context engine as an if-than statement, where source data fields are selected with a corresponding comparison and a corresponding context action. For example, such an interface may be used to create an example baseline context engine, by selecting (from dropdown box or other search/selection interface for example) a particular biomarker 27080 (for example, "systolic blood pressure"), selecting a comparison operation 27082 (for example, "is 10% greater than"), selecting a related source biomarker data 27084 (for example, "the patient's average resting systolic blood pressure"), and finally selecting a resultant action 27086 (for example, "display a notification with the blood pressure information"). The user interface may enable condition sets with multiple if-statements, with Boolean logic, and/or other condition settings. For example, the user interface may enable such condition sets with a user interface icon 27088 that, when clicked, launches a condition set builder. The user interface 27074 may be used to set the operational state of a context engine (for example, making it active or inactive) for a particular patient and/or procedure.

Figure 86:
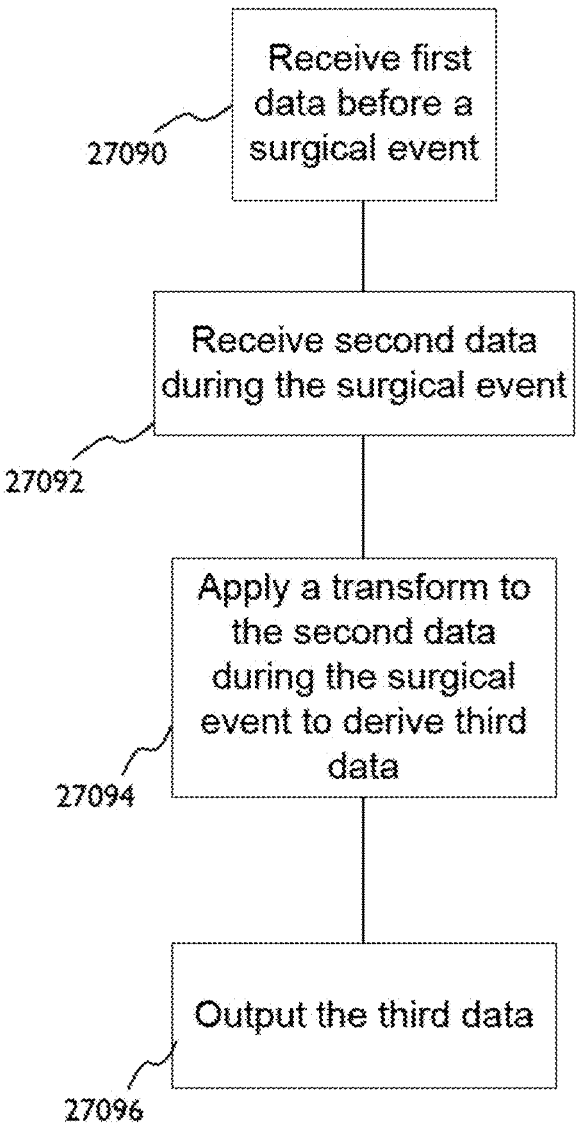
FIG. 86 is a diagram of an example process for contextualizing data associated with a surgical event.

FIG. 86 is a diagram of an example process for contextualizing data associated with a surgical event of a surgery. A surgery may include the procedures between a patient's surgical intake and surgical discharge. A surgery may include phases. For example, a surgery may include a preoperative phase, a pre-anesthesia phase, an intraoperative phase, a post-anesthesia phase, and a postoperative phase, and the like. For example, a surgery may include the intraoperative phase, where for example, phases such as a preoperative phase and a pre-anesthesia phase are considered pre-surgical phases and/or phases such as a post-anesthesia phase and a postoperative phase are considered post-surgical phases.

A surgical event may include any identifiable unit of a surgery. The identifiable unit may have a beginning, a duration, and an end. The identifiable unit may be identified relative to a clock (e.g., at 5 mins into the surgery). The identifiable unit may be identified relative to a procedure (e.g., the initial incision). The identifiable unit may be identified relative to a patient's response (e.g., bleeding).

At 27090, first data may be received. The first data may include first patient data. For example, the first patient data may be received before a surgical event. For example, the first data may represent a baseline patient biomarker determined before the surgical event. For example, the first data may represent a patient record information determined before the surgery. The first data may include information from sources such as procedure plans, patient records, pre-surgical sensor systems, healthcare professional input, and the like. The first data may include raw data containing granular measured values. The first data may include processed data containing broader metrics that have been processed from the raw data (e.g., an average, summation, true/false, and the like).

At 27092, second data may be received. The second data may include second patient data. The second patient data may be received during the surgical event. The second patient data may represent a biomarker. The second patient data may represent a corresponding value measured during the surgical event. The second patient data may represent a biomarker and a corresponding value measured during the surgical event. For example, the second patient data may represent a present patient biomarker collected from a surgical sensor system during the surgical event. For example, the second patient data may further represent information indicative of an impending surgical action. The surgical action may include any pre-surgical, intra-surgical, and/or post-surgical technique performed and/or applied in the surgery. A surgical action may be impending by nature of its order in the procedure plan, by its order and/or temporal relation to other surgical actions, and/or its temporal relation to the procedure as a whole. Surgical actions may include aseptic techniques (e.g., preparation of the patient's skin), sterility techniques (e.g., sterilization of instruments, set up of barriers), patient positioning, incisions, insufflation, dissection, drainage, haemostasis techniques (such as application of a haemostatic claim, suture ligation, diathermy coagulation, application of surgical coagulation materials, and the like), suturing, stapling, venipuncture, intravenous cannulation, central venous catheterization, tissue ligation, tissue excision, mobility of a particular structure or organ, imaging, wound closure, any techniques and/or surgical methods associated with the particular therapeutic procedure, and the like. For example, FIG. 8 and its accompanying description describes a number of surgical actions in an example colorectal surgical procedure.

At 27094, a transform may be applied to the second data. The transform may be applied to the second patient data. The transform may be applied during the surgical event. For example, the transform may include matching a condition of the second patient data and outputting an associated context action. The transform may derive third data. The third data may represent contextual information about the biomarker value measured during the surgical event. For example, the third data may include contextual information that may represent a deviation of the biomarker value measured during the surgical event from a baseline value obtained in the first patient data. For example, the third data third data may include contextual information that is associated with the patient record and that represents an adverse event indicated by the performing an impending surgical action on a patient represented by the patient record information.

The transform may be generated before the surgery. The transform may be based on the first data. The transform may be generated to contain a condition based on the second data. For example, the transform may be applied to the second data when the condition is satisfied by the second data. For example, incoming data during the surgery may be scanned for second data that satisfies the condition. And the incoming data having second data that satisfies the condition may be a trigger to apply the transform.

In an example, the received first patient data, at 27090, may include a baseline value of a biomarker of the patient as determined based on wearable, un-controlled sensor measurements taken before surgery. And the received second patient data, at 27092, may include a present value of that biomarker. And the third data, at 27094 and 27096, may include, for example, an indication of how much the present value has deviated from the baseline value.

At 27096, the third data may be outputted. For example, the third patient data may be outputted. The third patient data may be output to a human-machine-interface device. The third patient data may be output during the surgical event. The third patient data may be output to a human-interface device during the surgical event. For example, information derived from an aspect of the surgical event and its corresponding contextual information may be displayed. For example, information derived from an aspect of the surgical event and its corresponding contextual information may be displayed together.

In an example, the output may include displaying on a surgical display during the surgical event. And the displaying may include, together, a present value and a visual indication. The present value may include the present value of a biomarker that was received in an incoming surgical sensor data during the surgical event. The present value may include a present value that deviated more than a threshold value from its corresponding baseline value. And the visual indication may include an indication that the present value of the biomarker deviates more than the threshold value from its corresponding baseline value. The indication may include an indication of the magnitude by which the present value deviates from the baseline value.

Examples herein may include a computer system for outcome tracking of a patient, which may include a processor and a memory coupled to the processor. The memory may store instructions, that when executed by the processor, may cause the computer system to generate an event trigger for the patient, wherein during a duration of the patient's recovery, the event trigger may correspond to values of a patient biomarker over or under threshold values when the patient is performing a post-surgery activity related to the patient's recovery. The computer system may receive actual patient biomarker data from a patient sensor system for the patient when the patient is performing the post-surgery activity. If the actual patient biomarker data includes values over or under the threshold values when the patient is performing the post-surgery activity, the computer system may trigger the event trigger. The computer system may generate a notification alert corresponding to the event trigger.

Examples herein may include a computer-implemented method for providing outcome tracking of patients, which may include generating an event trigger for the patient, wherein during a duration of the patient's recovery, the event trigger may correspond to values of a patient biomarker over or under threshold values while the patient is performing a post-surgery activity related to the patient's recovery. The computer-implemented method may include receiving actual patient biomarker data from a patient sensor system for the patient while the patient is performing a post-surgery activity. If the actual patient biomarker data includes values over or under the threshold value while the patient is performing a post-surgery activity, the method may include triggering the event trigger. The method may include generating a notification alert corresponding to the event trigger.

Examples herein include a computer system for outcome tracking of a patient, which may include a processor and a memory coupled to the processor. The memory may store instructions, that when executed by the processor, may cause the computer system to generate a recovery threshold for the patient, wherein during a duration of the patient's recovery, the recovery threshold may correspond to values of a patient biomarker within a desired range when the patient is performing a post-surgery activity related to the patient's recovery. The computer system may receive actual patient biomarker data from a patient sensor system for the patient when the patient is performing the post-surgery activity. If the actual patient biomarker data includes values within the desired range of values over a period of a time when the patient is performing the post-surgery activity, the computer system may trigger the recovery threshold. The computer system may generate a notification alert corresponding to the recovery threshold.

Examples herein may include a computer-implemented method for providing outcome tracking of patients, which may include generating an event trigger for the patient, wherein during a duration of the patient's recovery, the event trigger may correspond to values of a patient biomarker over or under threshold values while the patient is performing a post-surgery activity related to the patient's recovery. The computer-implemented method may include receiving actual patient biomarker data from a patient sensor system for the patient while the patient is performing a post-surgery activity. If the actual patient biomarker data includes values over or under the threshold value while the patient is performing a post-surgery activity, the method may include triggering the event trigger. The method may include generating a notification alert corresponding to the event trigger.

Figure 87:
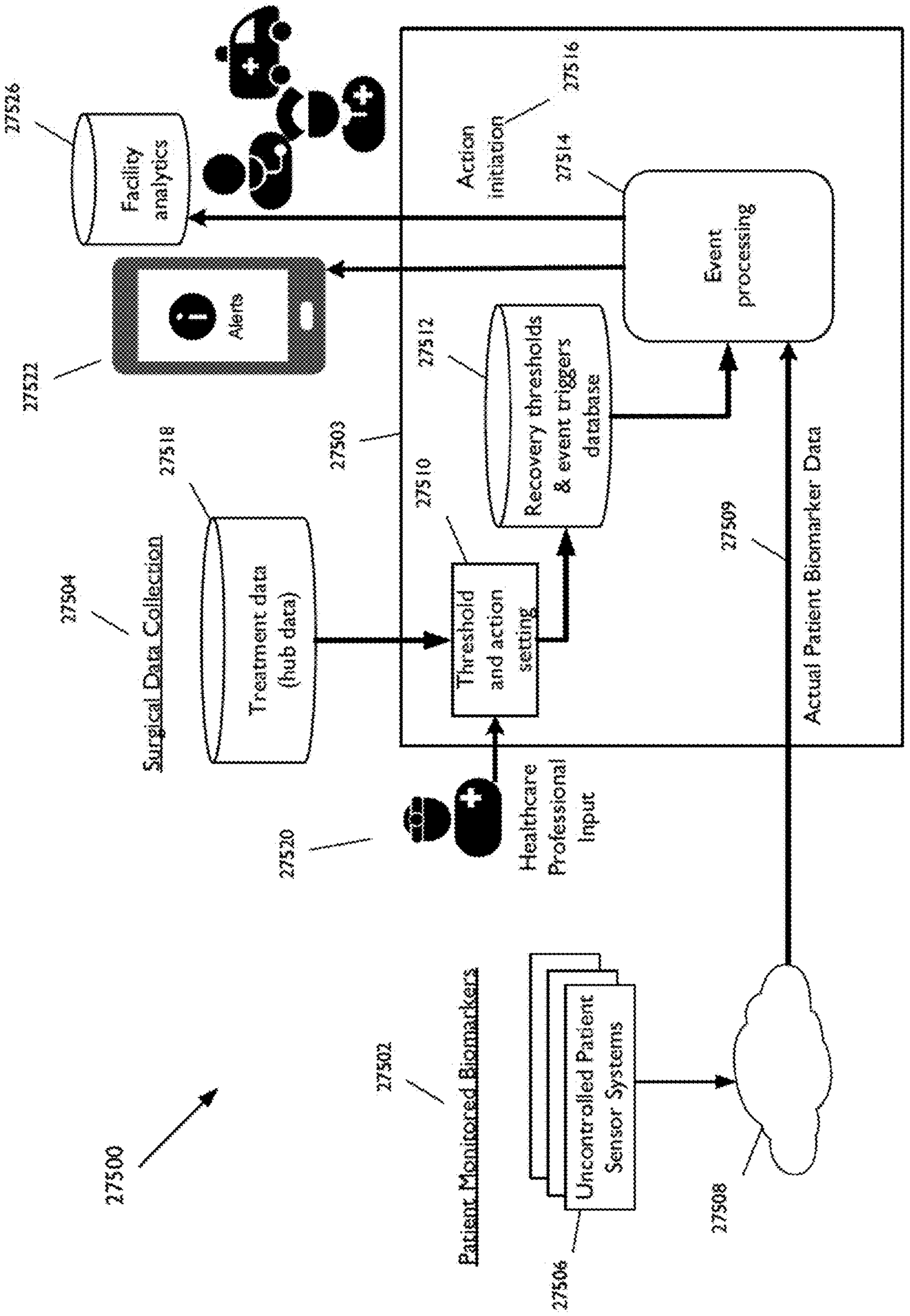
FIG. 87 shows an example of a computer-implemented patient and surgeon monitoring system that monitors post-surgery biomarkers.

FIG. 87 shows an example of a computer-implemented patient and surgeon monitoring system 27500 that monitors post-surgery biomarkers. The computer-implemented patient and surgeon monitoring system 27500 may include patient monitored biomarkers 27502, surgical data collection 27504, a computing system 27503, and a facility analytics system 27526.

The patient monitored biomarkers 27502 may used to measure actual patient biomarker data 27509. The patient monitored biomarkers 27502 may include one or more of the following: Blood pH, hydration state, oxygen saturation, core body temperature, heart rate, Heart rate variability, Sweat rate, Skin conductance, Blood pressure, Light exposure, Environmental temperature, Respiratory rate, Coughing and sneezing, Gastrointestinal motility, Gastrointestinal tract, imaging, Tissue perfusion pressure, Bacteria in respiratory tract, Alcohol consumption, Lactate (sweat), Peripheral temperature, Positivity and optimism, Adrenaline (sweat), Cortisol (sweat), Edema, Mycotoxins, VO2 max, Pre-operative pain, chemicals in the air, Circulating tumor cells, Stress and anxiety, Confusion and delirium, Physical activity, Autonomic tone, Circadian rhythm, Menstrual cycle, Sleep, etc. In examples, the patient monitored biomarkers 27502 may be measured by uncontrolled patient sensor systems 27506. The uncontrolled patient sensor systems 27506 may measure a patient in an uncontrolled environment not in close proximity to an HCP (e.g., a patient's residence). Each of the uncontrolled patient sensor systems 27506 may be measured using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The sensors may measure the patient monitored biomarkers 27502 as described herein using one of more of the following sensing technologies: photoplethysmography, electrocardiography, electroencephalography, colorimetry, impedimentary, potentiometry, amperometry, etc. The uncontrolled patient sensor systems 27506 may output the actual patient biomarker data 27509 to a cloud computing server 27508. The cloud computing server 27508 may send the actual patient biomarker data 27509 to an event processor 27514 within the computing device 27503.

The surgical data collection 27504 may provide information that is inputted into the computing system 27503 to compute threshold and action settings at 27510. Setting post-surgery thresholds for the uncontrolled patient sensor systems 27506 can provide useful data for HCP intervention or monitoring. Surgical data collection 27504 may include information from a treatment database 27518 and HCP input 27520. The treatment database 27518 may include information unique to specific patients or specific groups of patients, such as patients with diabetes, patients with cancer, patients with a history of smoking, ext. The treatment database 27518 may include treatment information related to specific treatments being performed. The treatment information may address certain issues unique to each specific treatment, such as issues related to heart surgery, issues related to bariatric surgery, and issues related to orthopedic procedures, ext. HCP input 27520) may allow for an HCP to input any changes to any specific patients and/or any specific procedures. For example, new developments in certain procedures and/or in a certain group of patients may impact the patient biomarker data that may not necessarily be reflected in the previous data stored in the treatment databases 27518. The HCP input 27520 may allow for the HCP to input any changes necessary into the computing system 27503 to compute the threshold and action settings at 27510. The threshold and action settings computed at 27510 may be stored in a recovery threshold and event trigger database 27512 within the computing device 27503. The threshold and action settings computed at 27510 may be sent to the event processor 27514.

In examples, the event processor 27514 may generate event triggers during a duration of the patient's recovery. The event trigger may correspond to values of a patient monitored biomarker 27502 over or under threshold values while the patient is performing a post-surgery activity, such as performing a physical activity or recovering after performing a physical activity, for example. The uncontrollable sensor systems 27506 could generate an event trigger for the patient if it detects an elevated or depressed patient monitoring biomarker 27502 while also detecting a post-surgery activity level or activity type that would not otherwise have trigger the event if not for the surgery. The thresholds could be a combination of situational awareness as well a key patient monitored biomarkers 27502 related to the surgical event. The interrogation could assess cognitive state, pain level, or other mental aspect. The post-surgery activity could be physical activity level, a fall, an apparent violation of a restricted action [i.e. operation of a vehicle, exceeding a bio-fenced area (leaving bed, a hospital room, etc.) or a physiologic perterbence (i.e. coughing, vomiting, eating, etc.)] The patient and monitoring system 27500 could use the baseline data, the procedure record and any in-surgery testing or imaging, to suggest to the surgeon threshold of monitoring the patient after surgery. These monitoring thresholds could have event triggers that initiate contact with an HCP for further interpretation or therapy adjustment. The event processor 27514 may receive the actual patient biomarker data 27509 for the patient while the patient is performing the post-surgery activity. In examples, if the actual patient biomarker data 27509 includes values over or under threshold values while the patient is performing the post-surgery activity, the event processor 27514 may trigger a threshold event trigger. The event processor 27514 may generate output action initiations at 27516 corresponding to the threshold event trigger.

In examples, the event processor 27514 may generate recovery thresholds during a duration of the patient's recovery. The recovery thresholds may correspond to values of a patient monitored biomarker 27502 within a desired range while the patient is performing a post-surgery activity, such as performing a physical activity or recovering after performing a physical activity, for example. The post-surgery activity may be uniquely related to the patient's recovery and may be monitored differently than it would if the patient was not recovering from surgery. Monitoring the post-surgery activity may be important in detecting how the patient is recovering from the surgery. The event processor 27514 may receive the actual patient biomarker data 27509 for the patient while the patient is performing the post-surgery activity. In examples, if the actual patient biomarker data 27509 includes values within the desired range while the patient is performing the post-surgery activity, the event processor 27514 may trigger a recovery event trigger. The event processor 27514 may generate output action initiations at 27516 corresponding to the recovery event trigger.

In examples, the patient and surgeon monitoring system 27500 could flag certain uncontrolled patient sensors 27506 to monitor for key physiologic events (i.e. eating, sleep quality, GI motility, physical activity) that are related to either key milestones of recovery or post-surgical events that require intervention from an HCP. Once these new targets are inputted, the patient, HCP, and/or healthcare facilities could be alerted when the target is achieved. These triggers could be meaningless to a patient biomarker sensor in its normal operation as the value could likely be within its normal operating range. However, within the context of the surgical event, the baselines data, and impacts of the surgical steps taken, these triggers could initiate additional HCP interaction.

The action initiations outputted at 27516 may send alerts 27522 to patients, HCPs, healthcare facilities, and/or hospitals to view on a computing device, such as a laptop or a smartphone. In examples, the alerts 27522 can allow the patients, HCPs, healthcare facilities, and/or hospitals to take action such as scheduling a follow up appointment, if necessary. In examples, the alerts 27522 may be sent back to the uncontrolled patient sensor systems 27506, which can be within a watch, phone, and/or wristband on patient. The alerts 27522 can be used to provide information to the patient on their progress of used for driving the patient to get to a target or goal setting for recovery. In examples, the alerts 27522 can allow the patients, HCPs, healthcare facilities, and/or hospitals to take immediate action in an emergency for example, if necessary. In examples, the alerts 27522 may notify patients, HCPs, healthcare facilities, and/or hospitals of certain recovery milestones. The action initiations outputted at 27516 may also be sent to a facility analytics system 27526. The facility analytics system 27526 may include a facility analytics server that may perform analytics regarding the data received regarding the patient. An HCP may view the analytics provided by the facility analytics system 27526 on a computing device for recording and monitoring. The facility analytics system 27526 can perform the data analytics in real time. The facility analytics system 27526 is described further below in FIG. 90.

Figure 88A:
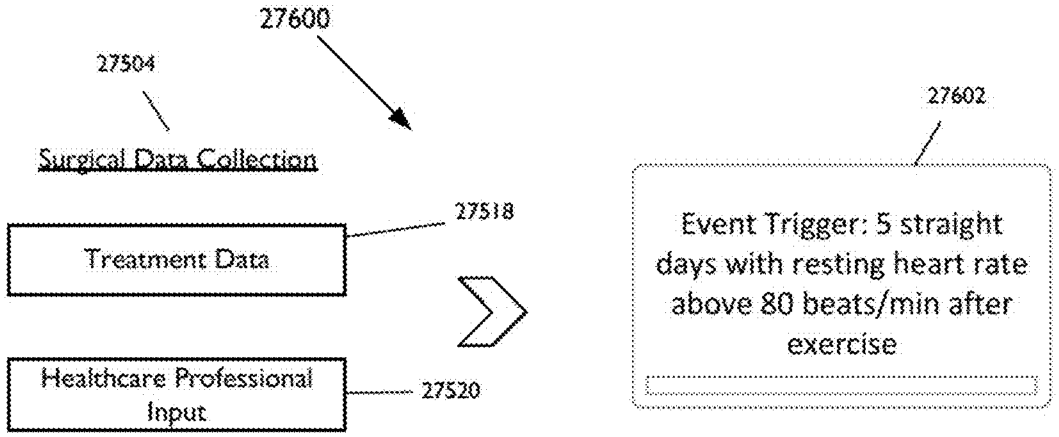
FIGS. 88A-88C show an example of the computer-implemented patient and surgeon monitoring system monitoring heart rate data after exercise during patient recovery.
Figure 88B:
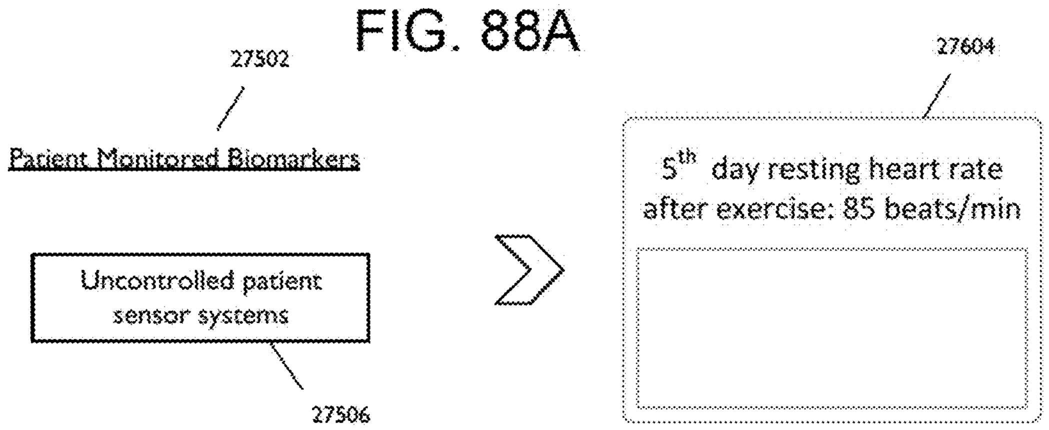
Figure 88C:
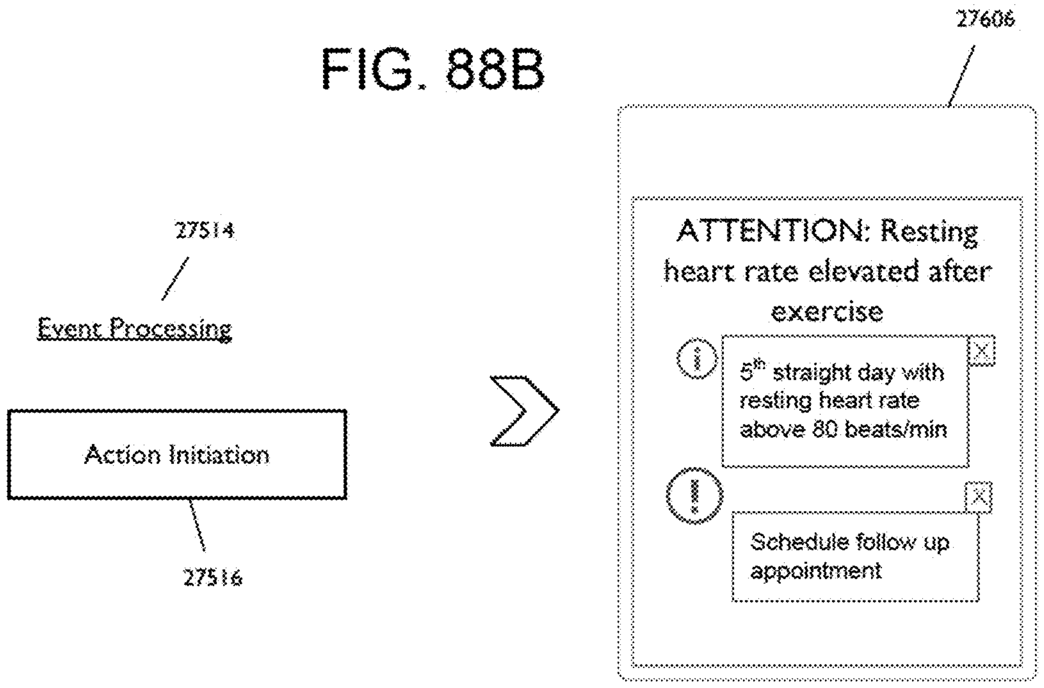

FIGS. 88A-88C show an example 27600 of the computer-implemented patient and surgeon monitoring system 27500 monitoring heart rate data after exercise during patient recovery. In FIG. 88A, the surgical data collection 27504 may include information from the treatment databases 27518 and HCP input 27520 to send to the computing device 27503. As described in FIG. 87, the information from the surgical data collection 27504 may be inputted into the computing system 27503 to compute threshold and action settings at 27510 corresponding to post-surgery activity for patients on a recovery timeline after undergoing different types of surgeries. The threshold and action settings computed at 27510 may be sent to the event processor 27514 which may generate a threshold event trigger 27602 corresponding to values of a patient monitored biomarker 27502 over or under threshold values while the patient is performing a post-surgery activity. As shown in FIG. 88A, the patient monitored biomarker may be heart rate and the post-surgery activity may be recovering from exercise. In FIG. 88A, the patient may be on a recovery timeline after undergoing heart surgery, as such, monitoring the patient's resting heart rate after exercise while recovering from surgery can be important for detecting how the patient is recovering. The patient's resting heart rate after exercise may be different when recovering from surgery than it would in normal circumstances. Therefore, the threshold event trigger 27602 may correspond to how a specific patient is expected to be recovering at a specific time in the recovery timeline after the surgery. In examples, the threshold event trigger 27602 generated by the event processor 27514 may be five straight days with a resting heart over 80 beats/min after recovering from exercise, such as 30 mins after recovering from exercise. In examples, the threshold event trigger 27602 may be altered to reflect patients with diabetes, patients with a history of smoking, and/or patients that have had multiple heart surgeries, ext.

In FIG. 88B, the actual biomarker data 27509 may be a patient heart rate. The patient heart rate may be measured by an uncontrolled patient sensor system 27506. The uncontrolled patient sensor systems 27506 may measure patient heart rates in an uncontrolled environment not in close proximity to an HCP (e.g., a patient's residence). As described in FIG. 87, the measurements from the uncontrolled patient sensor systems 27506 may be sent to the event processor 27514 which may input the values corresponding to values of the actual biomarker data 27509 while the patient is performing a post-surgery activity after undergoing different types of surgeries. As shown in FIG. 88B, the actual biomarker data may be heart rate and the post-surgery activity may be recovering from exercise. In FIG. 88B, the patient may be on a recovery timeline after undergoing heart surgery. In examples, the resting heart rate 27604 inputted into the event processor 27514 may be resting heart rate of 85 beats/min after exercise on the fifth day of performing exercise on a recovery timeline.

In FIG. 88C, the event processor 27514 may output an action initiation 27516 when the threshold event trigger 27602 is triggered. In FIG. 88C, the threshold event trigger 27602 may be triggered if the event processor receives the resting heart rate 27604 of 85 beats/min after exercise on the fifth day of performing exercise on a recovery timeline if the event processor 27514 received resting heart rates over 80 beats/min on the previous four days of performing exercise on the recovery timeline. As shown in FIG. 14A, since the threshold event trigger 27602 may be five straight days with resting heart rates above 80 beats/min after exercise, the threshold event trigger 27602 may be triggered when the event processor 27514 receives the resting heart rate 27604 of 85 beats/min on the fifth day of performing exercise as shown in FIG. 88B. In examples, when the threshold event trigger 27602 is triggered, the action initiation 27516 may send an alert 27606 corresponding to the threshold event trigger 27602. The alert 27606 can be viewed on computing devices such as on smartphones or laptops. The alert 27606 may be viewed by patients, HCPs, healthcare facilities, and/or hospitals. As shown in FIG. 88C, the alert 27606 may seek to get the attention of the viewer by displaying "ATTENTION: Resting heart rate elevated after exercise." The alert 27606 may show the exact numbers, such as that the patient has had a "5th straight day with resting heart rate above 80 beats/min." The alert 27606 may provide suggested actions to take based on the event trigger 27602, such as to "schedule follow up appointment."

In examples, a patient monitored biomarker may be measures of glucose handling and the post-surgery activity may be eating when recovering from surgery. For example, there are many measures of glucose handling that inform how the patient is metabolizing sugar. These measures can inform the diagnosis and treatment of Type 2 Diabetes Mellitus (T2DM). A real time glucose monitor can help establish a baseline for the patient in the time leading up to the procedure. Combined with meal detection, the glucose monitor can be used to determine fasting glucose levels as well as post-prandial glucose handling following every meal. In examples, a patient monitored biomarker may be measures of orthopedic or soft tissue repair procedures where reduced loading on the repaired/replaced location is desired post-surgery, which can be measured by an accelerometer or extensometer, providing feedback for when loading of a particular location exceeds a threshold. This threshold target may be within the typical range for the normal healthy population, but would be undesired for an immediate post-surgical patient. If the threshold is reached, the HCP can be alerted to evaluate the surgical site for any damage to the tissue or abnormal healing. In examples, a patient monitored biomarker may be measures of moisture exposure sensed by a moisture sensor. Monitoring for moisture exposure (amount, duration) may protect against infection or premature suture failure. A local moisture sensing wearable could track moisture exposure and alert the HCP if exposure reaches a defined threshold. This threshold may be within normal expected ranges for a person, but when elevated in a patient with suture, may indicate a higher risk. The HCP can be alerted to evaluate the suture site for any abnormal healing, infection, suture failure, etc.

In examples, Vertical Sleeve Gastrectomy patients often progress towards remission of T2DM, which often slowly and is linked to the weight loss that the patient undergoes. When this occurs, the patients T2DM is effectively in remission. The patient's progress towards remission of T2DM can be shared with the HCP and can be used to update the treatment for T2DM while it remains present. It can ultimately inform the HCP when treatment for T2DM is no longer required. In examples, a bariatric surgery candidate may have T2DM and wear an insulin pump with a glucose monitor. The pump may require attention from the patient to help administer the proper therapy. The uncontrollable patient sensor system 27506 can provide the HCPs access to real-time information on the patient's changes in glucose handling. The HCPs can be alerted when the changes cross milestone thresholds that warrant a change in the treatment strategy including the cessation of treatment once the T2DM has gone into remission.

In examples, a patient monitored biomarker may be calorie intake vs. calorie burned and the post-surgery activity may be sleep patterns and when the patient eats. The uncontrolled patient sensor system 27506 may use a bioelectrical impedance sensor to measure the fluid moving in and out of your skin cells-continuously, around the clock to monitor calorie intake. The uncontrolled patient sensor system 27506 may provide feedback when the patient should eat and if they need to eat less or more based on their allowable calorie consumption and calorie burn. If the patient has consumed more calories than required, the uncontrolled patient sensor system 27506 could indicate an activity level and have them do an activity until they reach the calorie burn to offset the calories consumed. The in-built HEALBE FLOW™ technology within the uncontrolled patient sensor system 27506 may use an advanced algorithm to analyze impedance data and calculate calorie intake based on your glucose curves, giving you a complete picture of your nutritional intake over time. This could act like a personal life coach where is continually monitoring and providing indication or moral support when a patient is required to do something.

Figure 89A:
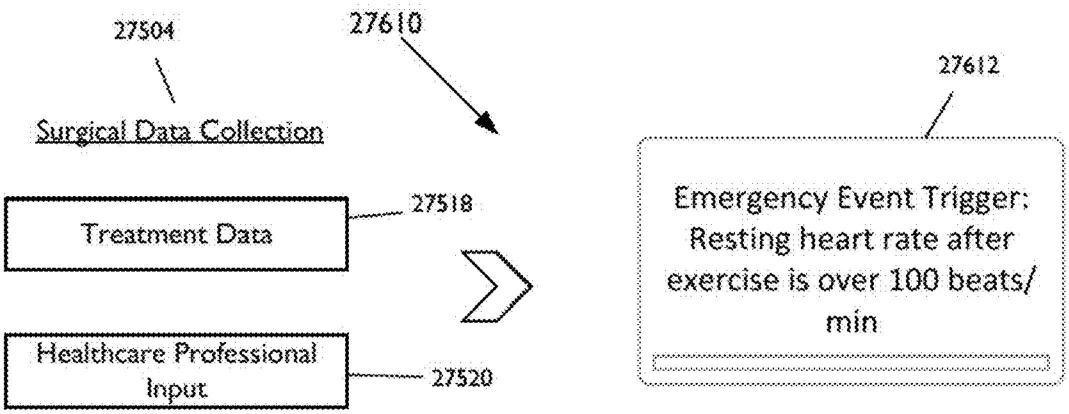
FIGS. 89A-89C show another example of the computer-implemented patient and surgeon monitoring system monitoring heart rate data after exercise during patient recovery.
Figure 89B:
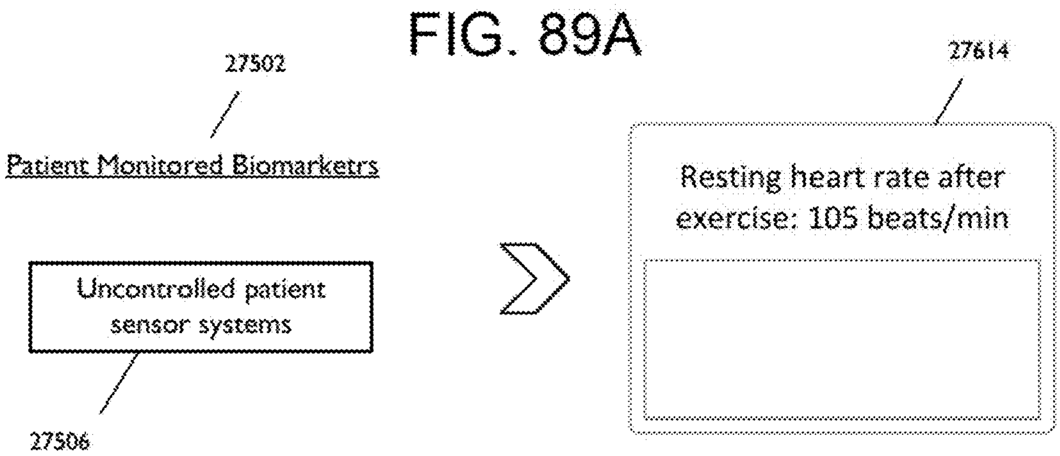
Figure 89C:
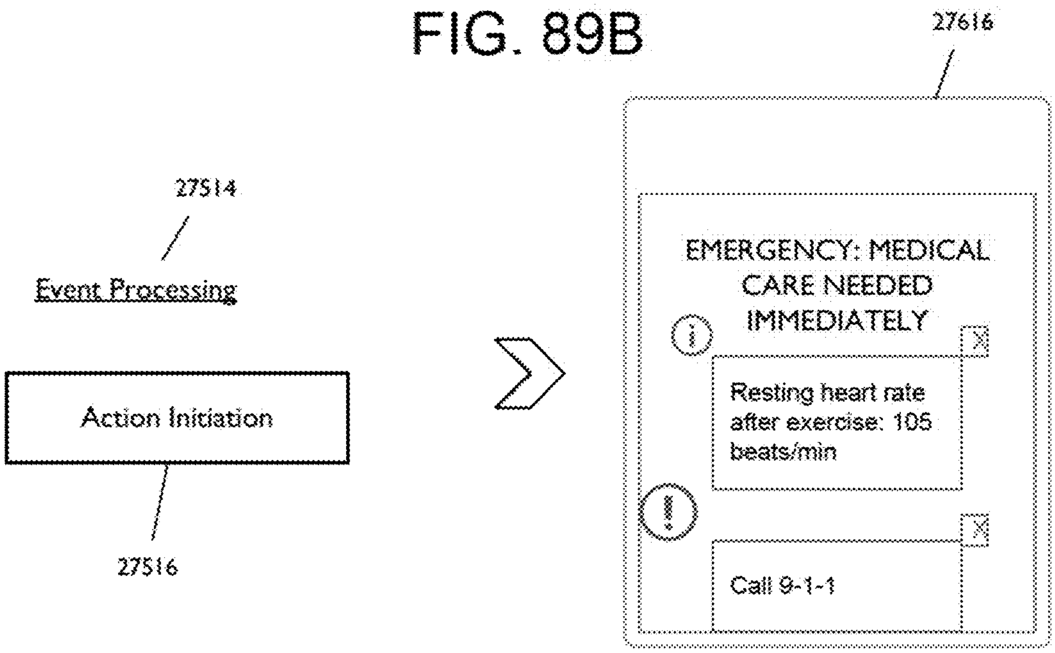

FIGS. 89A-89C show another example 27610 of the computer-implemented patient and surgeon monitoring system 27500 monitoring heart rate data after exercise during patient recovery. In FIG. 89A, like FIG. 88A, the surgical data collection 27504 may include information from the treatment databases 27518 and HCP input 27520 to send to the computing device 27503. As described in FIG. 87, the information from the surgical data collection 27504 may be inputted into the computing system 27503 to compute threshold and action settings at 27510 corresponding to post-surgery activity for patients on a recovery timeline after undergoing different types of surgeries. The threshold and action settings computed at 27510 may be sent to the event processor 27514 which may generate an emergency event trigger 27612 corresponding to values of a patient monitored biomarker 27502 over or under threshold values while the patient is performing a post-surgery activity. As shown in FIG. 89A, the patient monitored biomarker may be heart rate and the post-surgery activity may be recovering from exercise. In FIG. 89A, the patient may be on a recovery timeline after undergoing heart surgery. In examples, the emergency event trigger 27612 generated by the event processor 27514 anytime a patient's resting heart is over 100 beats/min after recovering from exercise, such as 30 mins after recovering from exercise. In examples, the emergency event trigger 27612 may be altered to reflect patients with diabetes, patients with a history of smoking, and/or patients that have had multiple heart surgeries, ext.

In FIG. 89B, like FIG. 88B, the actual biomarker data 27509 may be a patient heart rate. The patient heart rate may be measured by an uncontrolled patient sensor system 27506. The uncontrolled patient sensor systems 27506 may measure patient heart rates in an uncontrolled environment not in close proximity to an HCP (e.g., a patient's residence). As described in FIG. 87, the measurements from the uncontrolled patient sensor systems 27506 may be sent to the event processor 27514 which may input the values corresponding to values of the actual biomarker data 27509 while the patient is performing a post-surgery activity after undergoing different types of surgeries. As shown in FIG. 89B, the actual biomarker data may be heart rate and the post-surgery activity may be recovering from exercise. In FIG. 89B, the patient may be on a recovery timeline after undergoing heart surgery. In examples, the resting heart rate 27614 inputted into the event processor 27514 may be a resting heart rate of 105 beats/min after exercise on a recovery timeline.

In FIG. 89C, like FIG. 88C, the event processor 27514 may output an action initiation 27516 when the emergency event trigger 27612 is triggered. In FIG. 89C, the emergency event trigger 27612 may be triggered if the event processor receives the resting heart rate 27614 of over 100 beats/min after exercise on a recovery timeline. As shown in FIG. 89A, since the emergency event trigger 27612 may be triggered anytime the event processor receives a resting heart rate over 100 beats/min after exercise, the emergency event trigger 27612 may be triggered when the event processor 27514 receives the resting heart rate 27614 of 105 beats/min on the fifth day of performing exercise as shown in FIG. 89B. In examples, when the emergency event trigger 27612 is triggered, the action initiation 27516 may send an alert 27616 corresponding to the emergency event trigger 27612. The alert 27616 can be viewed on computing devices such as on smartphones or laptops. The alert 27616 may be viewed by patients, HCPs, healthcare facilities, and/or hospitals. As shown in FIG. 89C, the alert 27616 may seek to get the immediate attention of the viewer by displaying "EMERGENCY: MEDICAL CARE NEEDED IMMEDIATELY." The alert 27616 may show the exact numbers, such as that the patient has had a "Resting heart rate after exercise: 105 beats/min." The alert 27616 may provide suggested actions to take based on the emergency event trigger 27612, such as to "Call 9-1-1." FIG. 89A-89C, unlike FIG. 88A-88C may correspond to events that require immediate, emergency action.

In examples, a patient post-surgery could experience events that require HCP alerting and monitoring (i.e. falls, cognitive impairment, blood oxygen level, blood glucose level, prolonged coughing events, vomiting, stress, etc.) These events could trigger the system to alert an HCP and provide a captured portion of the data that caused the alert. These events could appear normal to the patient or go un-observed because they are within the patient's anticipated operation, however can allow an HCP to act if necessary. The HCP could request additional related or time-indexed data for context, could initiate interaction with the patient to expand assessment, and/or could adjust monitoring thresholds and event triggers.

Figure 90A:
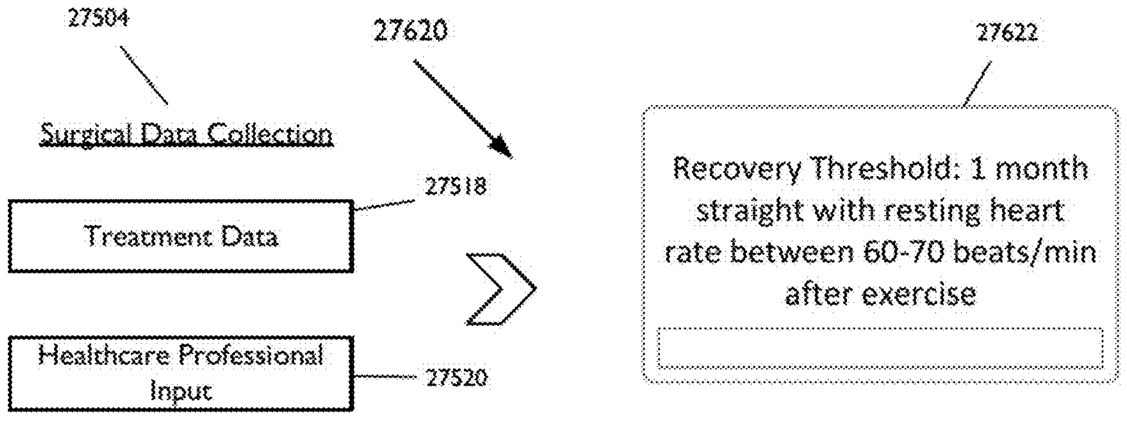
FIGS. 90A-90C show another example of the computer-implemented patient and surgeon monitoring system monitoring heart rate data after exercise during patient recovery.
Figure 90B:
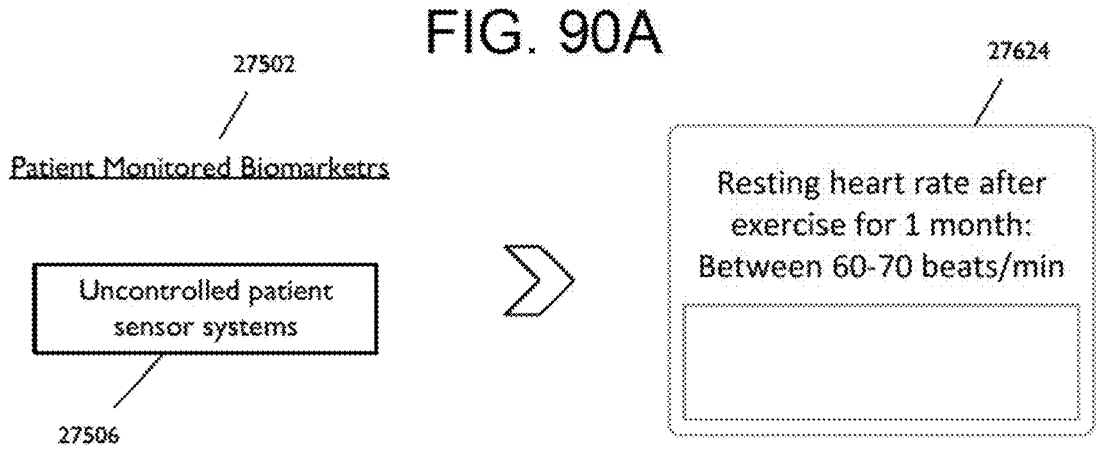
Figure 90C:
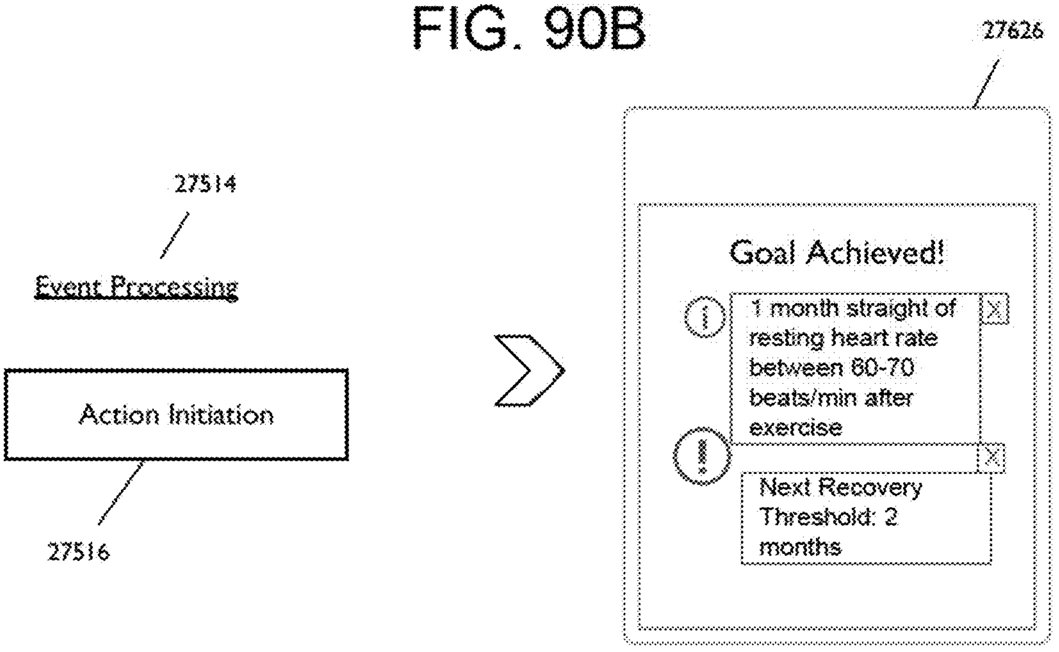

FIGS. 90A-90C show another example 27620 of the computer-implemented patient and surgeon monitoring system 27500 monitoring heart rate data after exercise during patient recovery. In FIG. 90A, like FIGS. 88A-89A, the surgical data collection 27504 may include information from the treatment databases 27518 and HCP input 27520 to send to the computing device 27503. As described in FIG. 87, the information from the surgical data collection 27504 may be inputted into the computing system 27503 to compute threshold and action settings at 27510 corresponding to post-surgery activity for patients on a recovery timeline after undergoing different types of surgeries. The threshold and action settings computed at 27510 may be sent to the event processor 27514 which may generate a recovery threshold 27622 corresponding to values of a patient monitored biomarker 27502 within a desired range of values while the patient is performing a post-surgery activity. Recovery thresholds 27622 could be set based on individual patients data prior to surgery or procedural data norms. The targets could be set to influence behaviors of patients or used to alter the targets as the patient shows progress and increase or change the targets to improve recovery. As shown in FIG. 90A, the patient monitored biomarker may be heart rate and the post-surgery activity may be recovering from exercise. In FIG. 90A, the patient may be on a recovery timeline after undergoing heart surgery. In examples, the recovery threshold 27622 generated by the event processor 27514 may be one month straight with a patient having a resting heart rate between 60-70 beats/min after recovering from exercise, such as 30 mins after recovering from exercise. In examples, the recovery threshold 27622 may be altered to reflect patients with diabetes, patients with a history of smoking, and/or patients that have had multiple heart surgeries, ext.

In FIG. 90B, like FIGS. 88B-89B, the actual biomarker data 27509 may be a patient heart rate. The patient heart rate may be measured by an uncontrolled patient sensor system 27506. The uncontrolled patient sensor systems 27506 may measure patient heart rates in an uncontrolled environment not in close proximity to an HCP (e.g., a patient's residence). As described in FIG. 87, the measurements from the uncontrolled patient sensor systems 27506 may be sent to the event processor 27514 which may input the values corresponding to values of the actual biomarker data 27509 while the patient is performing a post-surgery activity after undergoing different types of surgeries. As shown in FIG. 90B, the actual biomarker data may be heart rate and the post-surgery activity may be recovering from exercise. In FIG. 90B, the patient may be on a recovery timeline after undergoing heart surgery. In examples, the resting heart rates 27624 inputted into the event processor 27514 may be a resting heart rates between 60-70 beats/min after recovering from exercise for one month straight.

In FIG. 90C, like FIGS. 88C-89C, the event processor 27514 may output an action initiation 27516 when the recovery threshold 27622 is triggered. In FIG. 90C, the recovery threshold 27622 may be triggered if the event processor receives resting heart rates 27624 of between 60-70 beats/min after recovering from exercise for one straight month. As shown in FIG. 90A, since the recovery threshold 27622 may be triggered anytime the event processor 27514 receive resting heart rates 27624 between 60-70 beats/min after recovering from exercise for one straight month, the recovery threshold 27622 may be triggered when the event processor 27514 receives the resting heart rates 27624 between 60-70 beats/mins after recovering from exercise as shown in FIG. 90B. In examples, when the recovery threshold 27622 is triggered, the action initiation 27516 may send an alert 27626 corresponding to the recovery threshold 27622. The alert 27626 can be viewed on computing devices such as on smartphones or laptops. The alert 27626 may be viewed by patients, HCPs, healthcare facilities, and/or hospitals. As shown in FIG. 90C, the alert 27626 may seek to get the attention of the viewer by displaying "Goal Achieved!" The alert 27626 may show the exact numbers, such as that the patient has had "1 month straight of resting heart rates between 60-70 beams/min after exercise." The alert 27626 may provide a new recovery threshold based on the recovery threshold 27622, such as "Next Recovery: 2 months."

In examples, recovery milestone achievement or biomarker improvement could be used to inform the patient or other related HCPs (general practitioner, physical therapist, nurse or aide, etc) to change or initiate further rehab or recovery steps. Key milestones could also lower the need for post-surgery monitoring or change the key sensors being monitored as cone recovery event leads to the next. This could be done automatically or thru interaction with an HCP.

In examples, recovery thresholds 27622 could be set by the surgeon and the uncontrolled patient sensor systems 27506 could monitor and provide feedback. i.e. activity level of steps needed could be set and monitored throughout the day based on how many they have taken and the amount of time before they go to sleep, feedback could be driven through the uncontrollable sensor system 27506, such as within a smartphone, to indicate that they need more steps, "time for a walk", or if they are exceeding or will exceed their activity level based on how much activity they have done in the day verses when they typically fall asleep and it can indicate "time to rest" so the patient does not over do it. In examples, patients that are required to maintain certain heart rates or blood pressures, the uncontrolled patient sensor systems 27506 can monitor when limits shift in range or approach a target. The uncontrolled patient sensor systems 27506 can provide indicators to help calm and relax to reduce the heart rate or blood pressure. Indicators could be pulses on a smart watch, feedback to take deep breaths in which it can monitor and confirm actions were taken, could indicate to take a walk, meditate, or could play a song through their watch or phone to help calm, while confirming the patient is following direction by monitoring parameters.

Figure 91:
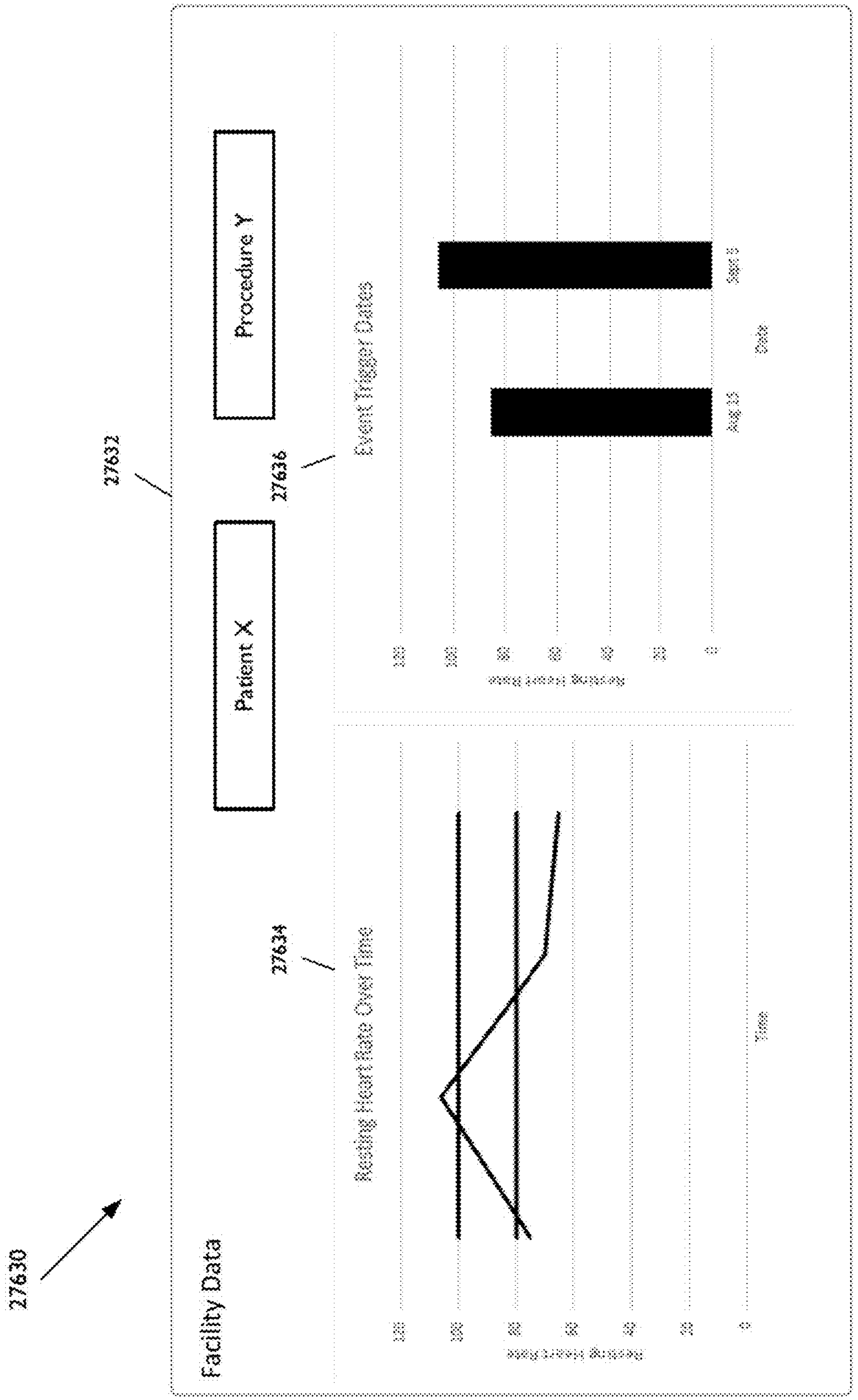
FIG. 91 shows example facility analytics data that can be viewed on a computing device by an HCP.

FIG. 91 shows example facility analytics data 27630 that can be viewed on a computing device 27632 by an HCP. The facility analytics data 27630 may be received from the facility analytics system 27526 within the computer-implemented patient and surgeon monitoring system 27500, as described above in FIG. 87. The facility analytics system 27526 may include a facility analytics server that may perform analytics regarding the data received. The facility analytics system 27526 may perform the data analytics in real time. For example, as shown in FIG. 91, the facility analysis data 27630 may be represented by graph 27634 and graph 27636. Also, shown in FIG. 91, the facility analytics data 27630 may be grouped based on the patient that received a procedure (represented by "Patient X" in FIG. 91) and the procedure performed (represented by "Procedure Y" in FIG. 91).

For example, as shown in FIG. 91, the graph 27634 may show the resting heart rate changing over time in line graph form after exercise during the recovery timeline for the patient after undergoing heart surgery. The resting heart rate shown in the graph 27634 may correspond to the resting heart rates 27604, 27614 discussed above in FIGS. 88A-88C and FIGS. 89A-89C. As shown in FIG. 91, the graph 27634 may show a threshold event trigger at 80 beats/min and an emergency event trigger at 100 beats/min. The threshold event trigger shown in the graph 27634 at 80 beats/min may correspond to the threshold event trigger 27602 as described above in FIGS. 88A-88C and the emergency event trigger shown in the graph 27634 at 100 beats/min may correspond to the emergency event trigger 27612 as described above in FIGS. 89A-89C. The graph 27634 may allow an HCP to easily view trends over time and how quickly the resting hearts rates went over or under certain thresholds, such as over the threshold event trigger at 80 beats/min and the emergency event trigger at 100 beats/min.

For example, as shown in FIG. 91, the graph 27636 may show event trigger dates for the patient during the recovery timeline for the patient after undergoing heart surgery and the resting heart rates of the patient on the event trigger date in bar graph form. As shown in FIG. 91, the trigger date of August 15 may correspond to the resting heart rate of a patient going above the threshold event trigger of 80 beats/mins and the trigger date of September 5 may correspond to the resting heart rate of a patient going above the emergency event trigger of 100 beats/min. The graph 27636 may allow an HCP to easily view the dates the resting hearts rates went over or under certain thresholds, such as over the threshold event trigger at 80 beats/min and the emergency event trigger at 100 beats/min. The graph 27636 may allow an HCP to easily view how much the resting hearts rates went over or under certain thresholds by giving the exact resting heart rate numbers. Both graphs 27634 and 27636 may allow HCPs, healthcare facilities, and/or hospitals to monitor patients during recovery timelines and review and monitor protocols in response to the data.

Figure 92:
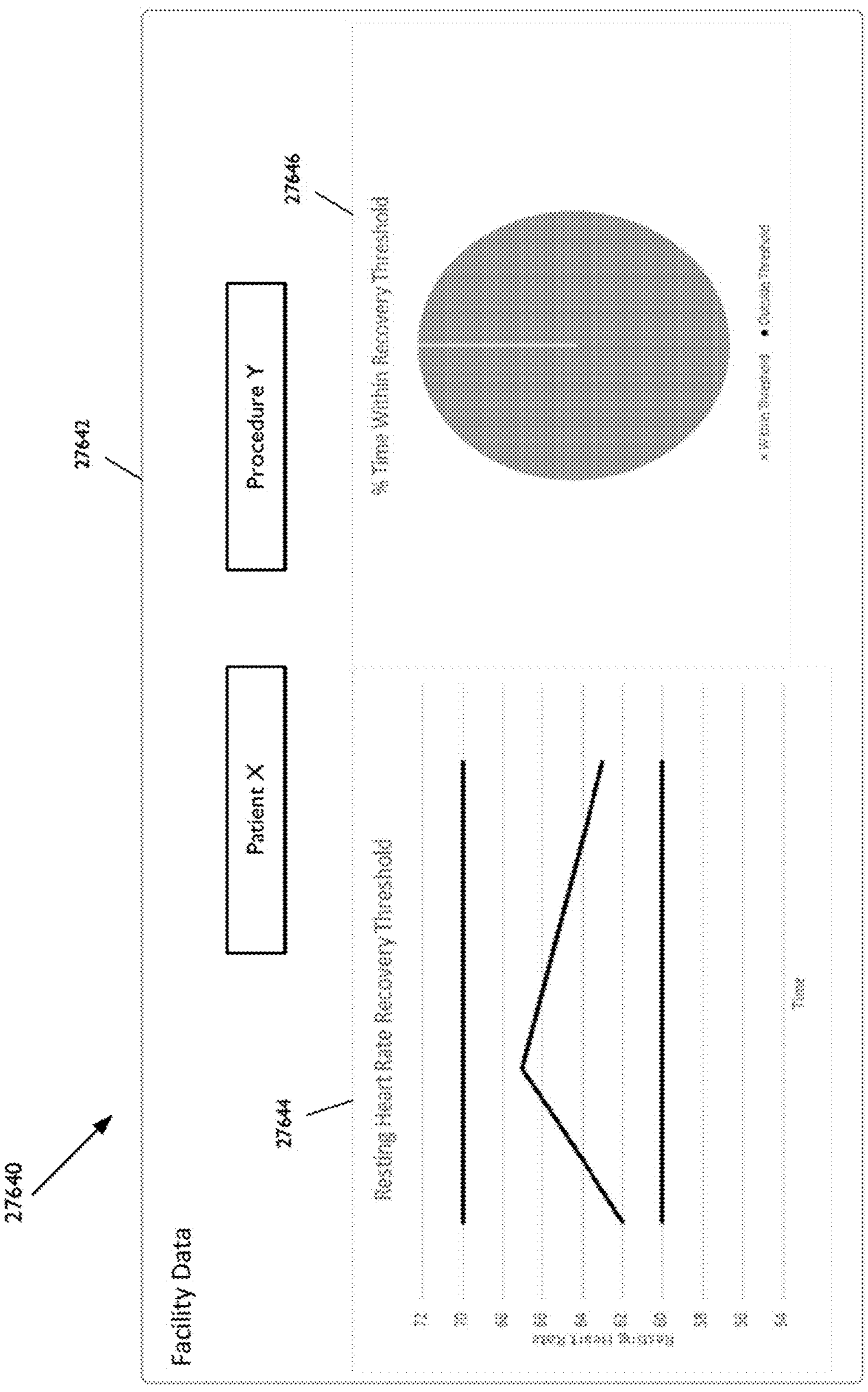
FIG. 92 shows example facility analytics data that can be viewed on a computing device by an HCP.

FIG. 92 shows example facility analytics data 27640 that can be viewed on a computing device 27642 by an HCP. The facility analytics data 27640 may be received from the facility analytics system 27526 within the computer-implemented patient and surgeon monitoring system 27500, as described above in FIG. 87. The facility analytics system 27526 may include a facility analytics server that may perform analytics regarding the data received. The facility analytics system 27526 may perform the data analytics in real time. For example, as shown in FIG. 92, the facility analysis data 27640 may be represented by graph 27644 and graph 27646. Also, shown in FIG. 92, the facility analytics data 27640 may be grouped based on the patient that received a procedure (represented by "Patient \" in FIG. 92) and the procedure performed (represented by "Procedure Y" in FIG. 92).

For example, as shown in FIG. 92, the graph 27644 may show the resting heart rate changing over time in line graph form after exercise during the recovery timeline for the patient after undergoing heart surgery. The resting heart rate shown in the graph 27644 may correspond to the resting heart rates 27624 discussed above in FIGS. 90A-90C. As shown in FIG. 92, the graph 27644 may show a recovery threshold window between 60 beats/min and 70 beats/min. The recovery threshold window shown in the graph 27644 between 60 beats/min and 70 beats/min may correspond to the recovery threshold 27622 as described above in FIGS. 90A-90C. The graph 27644 may allow an HCP to easily view trends over time and whether or not the resting heart rates stayed within the recovery threshold window. The graph 27644 may also allow an HCP to easily view how close the resting heart rates were from being outside the recovery threshold window.

For example, as shown in FIG. 92, the graph 27646 may show the percentage amount of time that the resting heart rate for the patient stayed within the recovery threshold window during the recovery timeline for the patient after undergoing heart surgery in pie graph form. As shown in FIG. 92, the resting heart rate stayed within the recovery threshold window between 60 beats/min and 70 beats/min during entire the recovery timeline, showing it was 100% within the recovery threshold window. The graph 27646 may allow an HCP to easily view how long the patients were within recovery thresholds, such as over the recovery threshold window. Both graphs 27644 and 27646 may allow HCPs, healthcare facilities, and/or hospitals to monitor patients during recovery timelines and review and monitor protocols in response to the data.

Figure 93:
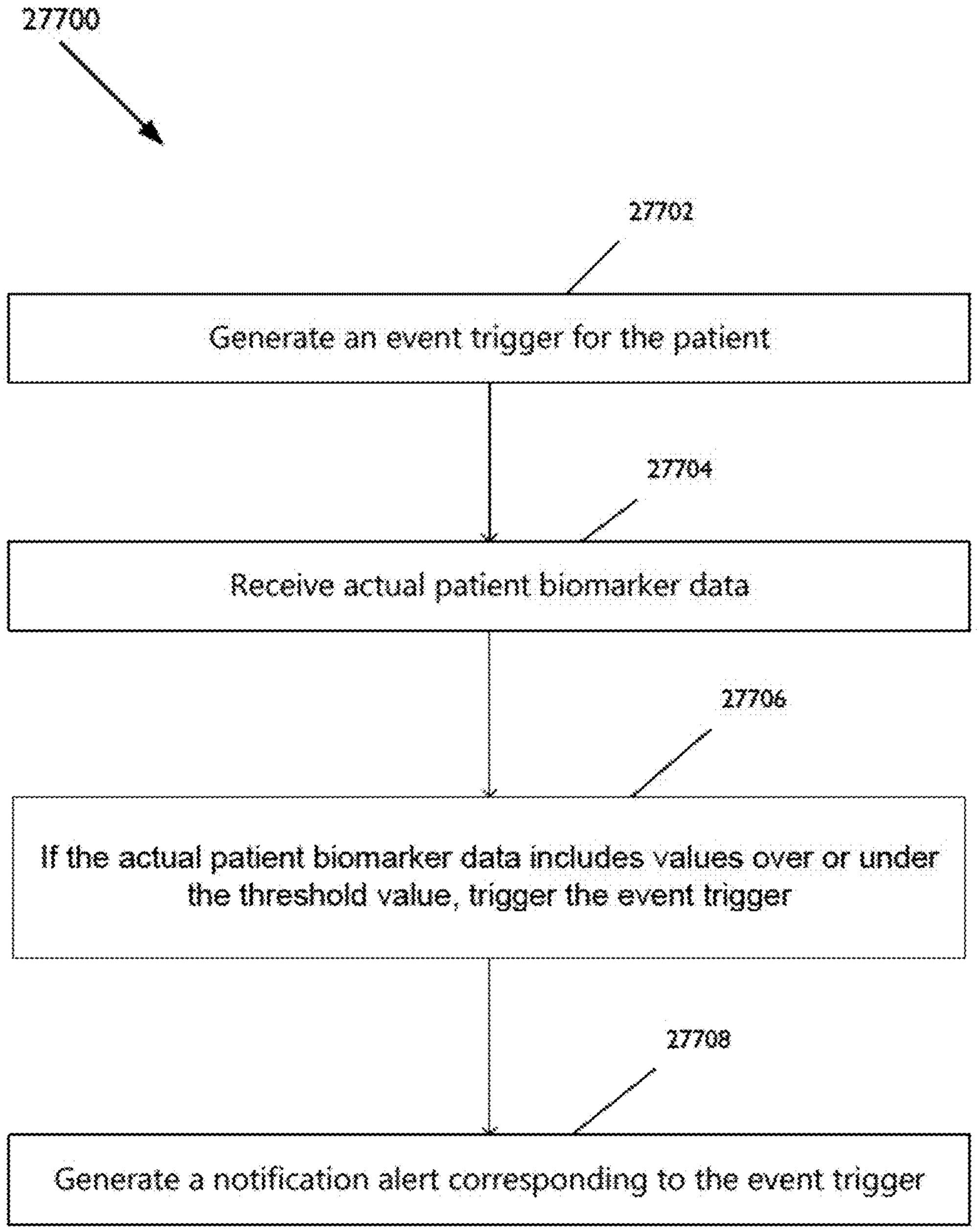
FIG. 93 illustrates a process for a computer-implemented patient and surgeon monitoring system that monitors post-surgery biomarkers.

FIG. 93 illustrates a process 27700 for a computer-implemented patient and surgeon monitoring system that monitors post-surgery biomarkers. The process 27700 may be performed by the computing device 27503 generating event triggers during a duration of the patient's recovery as described in FIG. 87. At 27702, the computing device 27503 may generate an event trigger for the patient. During the duration of the patient's recovery, the event trigger may correspond to values of a patient biomarker over or under threshold values while the patient is performing a post-surgery activity. The values of the patient biomarker may be a set of values in a recovery timeline. The event trigger may be a patient monitored event that initiates an elevated risk to the patient. The threshold values may correspond to the threshold event trigger 27602 as described in FIGS. 88A-88C or the emergency event trigger 27612 as described in FIGS. 89A-89C. The post-surgery activity may correspond to a patient resting heart rate after recovering from exercising during a recovery timeline after undergoing heart surgery. The values of the patient biomarker may be over or under the threshold values outside of an expected operating when the patient is performing the post-surgery activity. At 27704, the computing device 27503 may receive actual patient biomarker data from a patient sensor system for the patient while the patient is performing the post-surgery activity. The actual patient biomarker data may correspond to resting heart rates 27604, 27614, discussed above in FIGS. 88A-88C and FIGS. 89A-89C. At 27706, if the actual patient biomarker data includes values over or under the threshold values while the patient is performing the post-surgery activity, the computing device 27503 may trigger the event trigger. At 27708, the computing device 27503 may generate a notification alert corresponding to the event trigger. The notification alert may be accessed by multiple different caregivers to synchronize their handling of the patient. The notification alert may indicate an emergency and that immediate action be taken. The notification alert may be a unique notification tailored for a specific patient.

Figure 94:
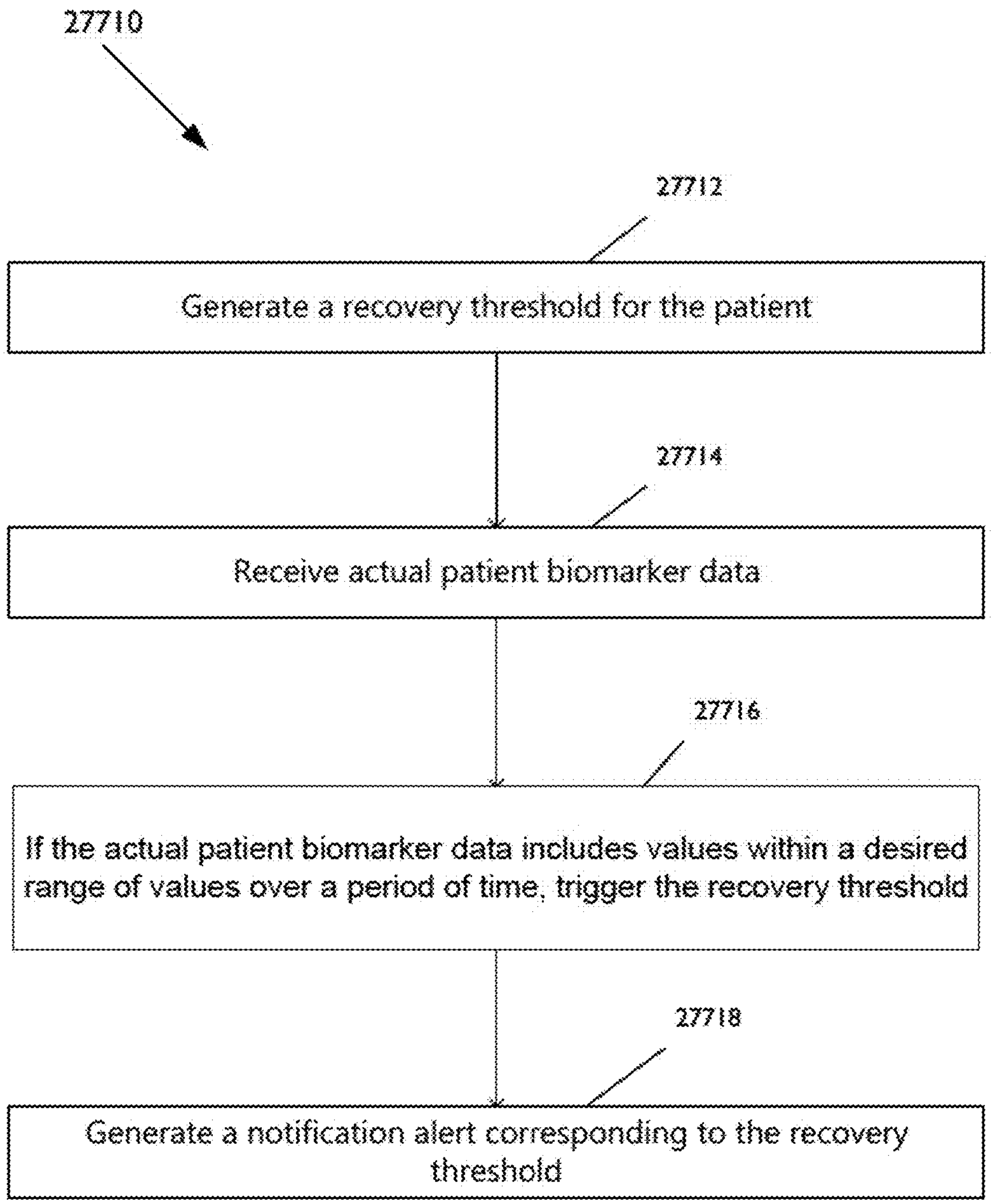
FIG. 94 illustrates a process for a computer-implemented patient and surgeon monitoring system that monitors post-surgery biomarkers.

FIG. 94 illustrates a process 27710 for a computer-implemented patient and surgeon monitoring system that monitors post-surgery biomarkers. The process 27710 may be performed by the computing device 27503 generating event triggers during a duration of the patient's recovery as described in FIG. 87. At 27712, the computing device 27503 may generate a recovery threshold for the patient. During the duration of the patient's recovery, the recovery threshold may correspond to values of a patient biomarker within a desired range while the patient is performing a post-surgery activity. The values of the patient biomarker may be a set of values in a recovery timeline. The desired range of values may be biomarker levels within an expected operating range when the patient is performing the post-surgery activity. The recovery threshold may be a patient monitored event that initiates an elevated risk to the patient. The recovery threshold 27622 may correspond to the recovery event trigger 27622 as described in FIGS. 90A-90C. The post-surgery activity may correspond to a patient resting heart rate after recovering from exercising during a recovery timeline after undergoing heart surgery. At 27714, the computing device 27503 may receive actual patient biomarker data from a patient sensor system for the patient while the patient is performing the post-surgery activity. The actual patient biomarker data may correspond to resting heart rates 27624 discussed above in FIGS. 90A-90C. At 27716, if the actual patient biomarker data includes values within the desired range of values over a period of time while the patient is performing the post-surgery activity, the computing device 27503 may trigger the recovery threshold. At 27718, the computing device 27503 may generate a notification alert corresponding to the recovery threshold. The notification alert may be accessed by multiple different caregivers to synchronize their handling of the patient. The notification alert may be a unique notification tailored for a specific patient.

A surgical computing system may scan for and detect a sensing system located in an operating room (OR). Based on the detection, the surgical computing system may establish a link with the sensing system. Using the established link between the surgical computing system and the sensing system, the surgical computing system may receive user role identification data from the sensing system. The user role identification data may be or may include information to identify a user role. The surgical computing system may identify a user role for a user in the OR based on the received user role identification data. The user role of a user in the OR may be or may include at least one of a surgeon, a nurse, a patient, a hospital staff, or a health care professional (HCP). Based on the identified user role, the surgical computing system may generate surgical aid information for the user in the OR. The surgical aid information may be or may include information associated with a surgical operation that is relevant to the identified user role. The surgical computing system described herein may be or may include a surgical hub.

The surgical computing system may receive different user role identification data from different sensing systems associated with multiple users in the OR. The computing system may identify various user roles and/or users based on the user role identification data received from the various sensing systems and provide different surgical aid information to the users based on their respective identified user role.

For example, the surgical computing system may receive user role identification data from a first sensing system associated with a first user and may receive user role identification data from a second sensing system associated with a second user. The surgical computing system may identify a user role for the first user and a user role for the second user. The surgical computing system may determine, generate, and/or send surgical aid information to the users (e.g., to the first user or to the second user) based on the corresponding user roles.

For example, the user role identification data may be or may include one or more of the following: a proximity of a user to a surgical instrument, locations and/or location tracking information of the users in the OR, interactions between the user and at least one healthcare professional, one or more surgical procedural activities, or visual data of the user in the OR. For example, the sensing system may be worn by the user such as a surgeon. The sensing system may monitor and/or store information about the proximity of the sensing system to a surgical instrument. The sensing system may store location tracking information of the surgeon during a surgical procedure. The sensing system may detect and/or store a surgical procedural activity of the surgeon. The sensing system may send such user role identification data to the surgical computing system.

For example, the surgical computing system may generate augmented reality (AR) content for a user based on the identified user role. Different AR content may be generated for different users based on their respective user roles identified via the sensing systems. The AR content may be or may include instructions on how to use a surgical instrument and/or an operation manual of the surgical instrument associated with the identified user role. The surgical computing system may send the generated AR content to the identified user. For example, the surgical computing system may send the AR content to an AR device associated with the user.

The surgical computing system may obtain surgical contextual data. The surgical computing system may identify a surgical instrument associated with the user based on the surgical contextual data and the identified user role. The surgical computing system may obtain an instruction on how to use the surgical instrument for inclusion in the surgical aid information.

For example, the surgical computing system may receive measurement data from a sensing system. The measurement data may include a stress level associated with a user and/or a fatigue level associated with the user. The surgical computing system may determine an elevated stress level and/or fatigue level associated with the user. The surgical computing system may generate and/or send the surgical aid information to the identified user that includes an instruction on how to use the surgical instrument if the surgical computing system detects an elevated stress level associated with the user. The surgical computing system may send an indication of fatigue control to the surgical instrument if the surgical computing system detects an elevated fatigue level associated with the user.

A computing system may scan for a sensing system located in an OR. The sensing system may include measurement data for a user. The computing system may determine whether the sensing system is compatible to establish a link with the computing system. Upon determining that the sensing system is compatible to establish a link with the computing system, the computing system may establish a link and receive the measurement data using the link with the sensing system.

Upon determining that the sensing system is incompatible to establish a link with the computing system, the computing system may generate a virtual computing system that is compatible to establish the link with the sensing system. The computing system may establish the link with the sensing system using the generated virtual computing system. The computing system may receive the measurement data using the link with the sensing system.

The computing system may establish an initial link with the sensing system before establishing a communication link with the sensing system. The computing system may send an initial link indication to a surgical computing system (e.g., a primary computing system). The initial link indication may request a user input to establish the link with the sensing system. The computing system may receive the user input from the surgical computing system. The computing system may establish the link with the sensing system.

The computing system may determine to generate AR content based on at least one of: the received measured data, locations of the sensing system in the OR, or surgical procedural activities of a surgical operation. The AR content may include display information associated with the measurement data. The computing system may send the generated AR content to an AR device associated with the user.

The computing system may detect one or more devices in the OR. For example, in the OR, there may be one or more surgeon sensing systems, patient sensing systems, computers, telephones, monitor screens, and/or other devices. The computing system may identify one or more sensing systems in the OR (e.g., to be paired with the computing system) from the detected devices in the OR. The computing system may establish a link with the identified sensing system.

A surgical computing system may scan for a sensing system located in an operating room. Upon detecting a sensing system in the operating room, the surgical computing system may establish a link with the sensing system. The surgical computing system may receive user role identification data from the sensing system using the established link. The surgical computing system may identify a user role for a user in the operating room based on the received user role identification data. The user role of a user may be or may include at least one of a surgeon, a nurse, a patient, a hospital staff, or a health care professional. Based on the identified user role, the surgical computing system may generate and send surgical aid information for the user in the operating room. The surgical aid information may include information associated with a surgical operation relevant to the identified user role.

Figure 95:
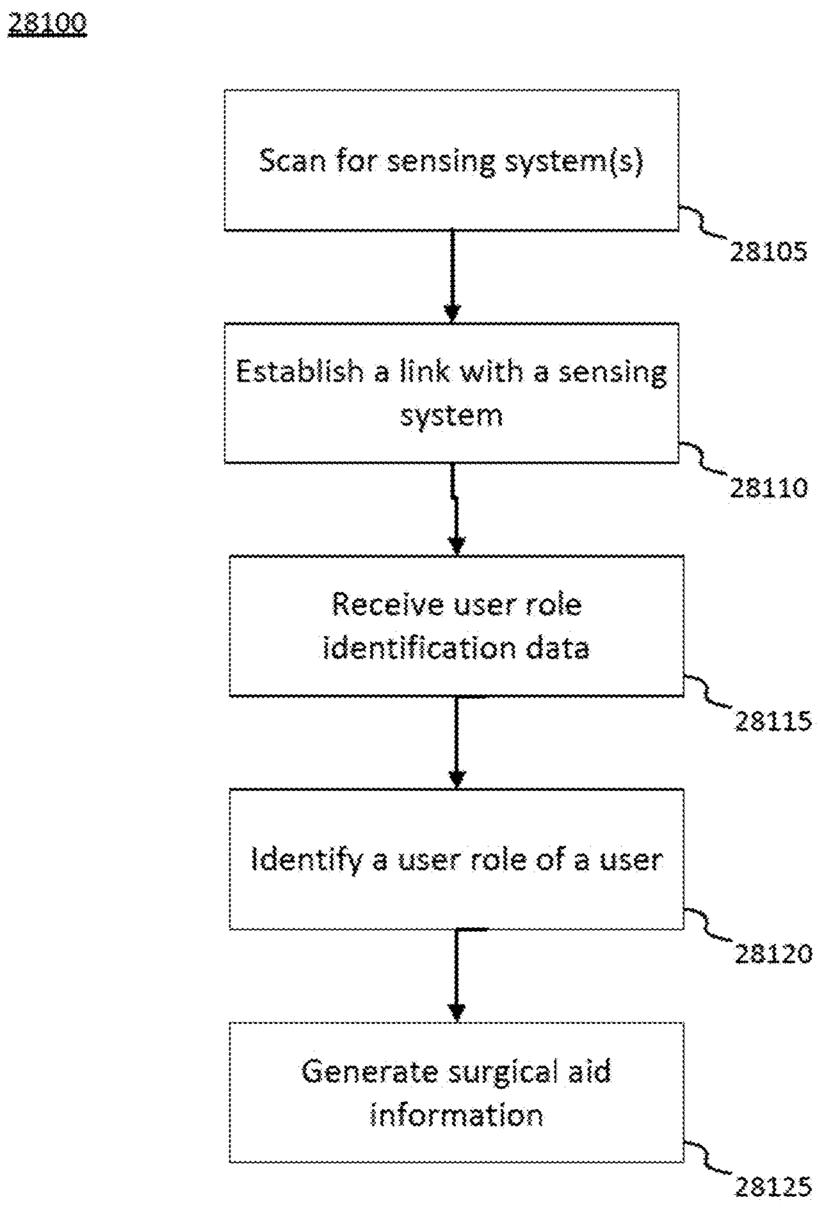
FIG. 95 illustrates an example flow for generating surgical aid information to a user in an operating room.

FIG. 95 illustrates an example flow for generating surgical aid information to a user in an operating room. At 28105, a computing system (e.g., such as a surgical computing system) may scan for a sensing system. The computing system may scan for a sensing system located in an operating room. As described herein, the sensing system may have measurement data associated with a user. For example, a user may be wearing the sensing system. The sensing system may monitor and/or sense measurement data of the user. As described herein, the sensing system may send user role identification data. The sensing system may send the user role identification data to the computing system. The user role identification data may be or may include data associated with identifying a user role of a user in an operating room.

At 28110, the computing system may establish a link with the sensing system. The computing system may communicate with the sensing system using the established link. The sensing system may send data, such as user role identification data and/or measurement data as described herein, using the established link.

At 28115, the computing system may receive user role identification data. The computing system may receive the user role identification data from the sensing system. The computing system may receive the user role identification data from the sensing system using the established link. The user role identification data may be or may include data for identifying a user role associated with a user. The user role associated with a user may be or may include a patient, a surgeon, a nurse, an HCP, a hospital staff, and/or the like. The user role identification data may be or may include a proximity of a user to one or more surgical instruments, location tracking information of the users in the operating room, interactions between the users, one or more surgical procedural activities, or visual data of the users in the operating room.

At 28120, the computing system may identify a user role of a user in the operating room based on the received user role identification data. As described herein, the computing system may identify that a user role associated with a user in the operating room is a surgeon, other user role associated with other user in the operating room is a nurse (e.g., a head nurse), another user role associated with another user in the operating room is a hospital staff and/or an HCP based on the user role identification data.

In examples, the user role identification data may be or may include data associated with proximities of a user to a surgical instrument(s). The computing system may identify a user role of a user in the operating room based on the proximities of the users to one or more surgical instruments. For example, the computing system may identify a user role of a user as a surgeon. The computing system may know that a surgeon will be in proximity to (e.g., next to) one or more surgical instruments. For example, as the surgeon will be using the one or more surgical instruments for a surgical procedure, the surgeon may be in proximity to (e.g., next to) the surgical instruments. The computing system may identify a user role of a user as a nurse (e.g., a head nurse) as the nurse will be assisting the surgeon and/or may be in proximity to (e.g., next to) the one or more surgical instruments. For example, the computing system may know that a nurse may hand the surgical instruments over to a surgeon based on a request from the surgeon, and the nurse may be in proximity to (e.g., next to) the surgical instruments. The computing system may determine a user role of a user as a hospital staff and/or an HCP. A hospital staff and/or an HCP may handle non-surgical related activities and may not be in proximity to the one or more surgical instruments. For example, the hospital staff and/or the HCP may be near an entrance of the operating room, a telephone, a clock, a music player, etc. that are not in proximity to (e.g., not next to) the one or more surgical instruments.

In examples, the user role identification data may be or may include data associated with location tracking information of the users in the operating room. For example, users in the operating room may be located and/or positioned at a particular location of the operating room. A patient may be located at a center of the operating room. The patient may be located under (e.g., directly under) a central lighting of the operating room. The patient may be stationary (e.g., not moving) throughout a surgical procedure. The computing system may identify a user in an operating room as a patient based on the user's position in the operating room (e.g., center, under a central lighting, etc.) and/or tracking information (e.g., lack of movement). A surgeon may be located in proximity to (e.g., next to) the patient. The surgeon may be located in proximity to a surgical table and/or to the patient. The surgeon may be located in proximity to (e.g., next to) one or more surgical instruments. The surgeon may be stationary and/or may not be moving (e.g., not walking around the operating room). The computing system may identify a user as a surgeon based on the location of the user being in proximity to at least one of a patient, a surgical table, or one or more surgical instruments and/or tracking information (e.g., lack of or little movement). A nurse assisting the surgeon (e.g., a head nurse) may be in proximity to (e.g., next to) the surgeon. The nurse may be next to a tray table that has one or more surgical instruments. The nurse may be moving from a surgical table to the tray table. The computing system may identify a user as a nurse based on the location information and/or the tracking information. A hospital staff and/or an HCPs may be located farther away from the surgical table, the surgeon, and/or the head nurse. For example, the hospital staff and/or other HCPs may be located closer to a door of the operating room and/or a phone located in the operating room. The computing system may identify a user as a hospital staff and/or an HCPs based on the location information and/or tracking information provided in the user role identification data.

In examples, the user role identification data may be or may include data associated with interactions between users in the operating room. A surgeon may communicate and/or instruct other users in the operating room. The surgeon may request a surgical instrument for a surgical procedure. The surgeon may make a request to increase, to decrease, and/or to change music playing in the operating room. A nurse assisting the surgeon may act in response to the request from the surgeon. For example, the nurse may hand a surgical instrument to the surgeon after the surgeon request the surgical instrument. The hospital staff and/or other HCPs may turn up, turn down, and/or change the music based on the request from the surgeon.

In examples, the user role identification data may be or may include data associated with one or more surgical procedural activities. A sensing system associated with a user may sense and/or monitor the user's activities. In examples, a surgeon may be wearing a sensing system on his/her wrist. The sensing system may detect, measure, and/or sense the surgeon's hand movements. The sensing system may send measurement data of the surgeon's hand movements to the computing system. Based on the measurement data of the surgeon's hand movements, the computing system may identify that the measurement data is associated with a user role for a surgeon. For example, the computing system may determine that the measurement data indicates a user role of a user using one or more surgical instruments and/or performing a surgical procedure. The computing system may identify a user role associated with the user as a surgeon. In examples, a nurse may be wearing a sensing system on his/her wrist. The sensing system may detect, measure, and/or sense the nurse's hand movements of carrying a surgical instrument and/or handing the surgical instrument. The sensing system may send measurement data of the nurse's hand movements to the computing system. Based on the measurement data of the nurse's hand movements, the computing system may identify that the measurement data is associated with a user role for a nurse. For example, the computing system may determine that the measurement data involves a user handing one or more surgical instruments to another user in the operating room. The computing system may identify a user role associated with the as a nurse assisting a surgeon. In examples, a hospital staff and/or an HCP may be wearing a sensing system on his/her wrist. The sensing system may detect, measure, and/or sense the hospital staff's and/or the HCP's hand movements. For example, the sensing system may detect the hospital staff and/or the HCP answering a phone in the operating room, adjusting volume of a music player in the operating room, and/or the like. Based on the measurement data from the sensing system, the computing system may identify that the user role of a user is a hospital staff and/or an HCP.

In examples, the user role identification data may be or may include data associated with visual data of the users in the operating room. An operating room may be equipped with a camera. The computing system may receive camera feed from the camera. Based on the camera feed, the computing system may determine/identify users in the operating room. In examples, the computing system may perform face recognitions of the users. In examples, the computing system may scan user badges and/or identification tags on the users and determine/identify the users in the operating room. The computing system may identify a user role of a user in the operating room based on the camera feed.

At 28125, the computing system may generate surgical aid information to the user based on the identified user role. In examples, if the computing system identifies a user role for a user as a surgeon, the computing system may generate surgical aid information for the surgeon. In examples, if the computing system identifies a user role for a user as a nurse, the computing system may generate surgical aid information for the nurse. In examples, if the computing system identifies a user role for a user as a hospital staff and/or an HCP, the computing system may generate surgical aid information for the hospital staff and/or the HCP. The surgical aid information may be augmented reality (AR) content. The computing system may generate AR content for identified user.

In examples, the computing system may generate AR content for a surgeon. The computing system may display the AR content to a computing system that is associated with the surgeon. The computing system associated with the user (e.g., a display AR device) may display the generated AR content from the surgical computing system. The AR content may aid the surgeon in a surgical procedure. In examples, the AR content may be or may include surgical steps that the surgeon is about to perform. In examples, the AR may include measured data of a patient. The generated AR content may be converted to audio and may be transmitted to an audio AR device that the surgeon is wearing.

In examples, the computing system may receive measurement data from the sensing system. The measurement data may be or may include stress level associated with a user. For example, the measurement data may be or may include stress level associated with a surgeon. The measurement data may be or may include an elevated stress level associated with the surgeon. As described herein, the computing system may determine an elevated stress level associated with a user (e.g., a surgeon). The computing system may obtain surgical contextual data. For example, a surgical instrument may send data associated with usage of the surgical instrument. The computing system determine whether the surgeon is operating a surgical instrument based on the surgical contextual data. The computing system may determine whether the surgeon is operating a surgical instrument based on the surgical contextual data and/or measurement data associated with the surgeon (e.g., measurement data associating with the surgeon's hand movement). If the computing system determines that the surgeon is not operating a surgical instrument and detects an elevated stress level, the computing system may generate and/or send surgical aid information to the surgeon. The surgical aid information may be or may include an operation manual of the surgical instrument. The surgical aid information may be or may include an instruction (e.g., video or audio) on how to use the surgical instrument.

In examples, the computing system may receive measurement data from the sensing system. The measurement data may be or may include stress level associated with a user. For example, the measurement data may be or may include stress level associated with a nurse. The measurement data may be or may include an elevated stress level associated with the nurse. The computing system may obtain surgical contextual data. For example, a surgical instrument may send data associated with usage of the surgical instrument. The computing system may determine whether the nurse is operating the surgical instrument. For example, the computing system may obtain the contextual data that indicates that a surgical staple gun has recently been fired and needs a reload. The computing system may determine whether the nurse is operating the surgical instrument based on the contextual data and/or measurement data associated with the nurse (e.g., measurement data associating with the nurse's hand movement). If the computing system determines that the nurse is not operating a surgical instrument and detects an elevated stress level, the computing system may generate and/or send surgical aid information to the nurse. The surgical aid information may be or may include an operation manual of the surgical instrument (e.g., reloading a staple gun). The surgical aid information may be or may include an instruction (e.g., video or audio) on how to use (e.g., reload) the surgical instrument.

In examples, the computing system may receive measurement data from the sensing system. The measurement data may be or may include fatigue level associated with a user. For example, the measurement data may be or may include fatigue level associated with a surgeon. The measurement data may be or may include an elevated fatigue level associated with the surgeon. As described herein, the computing system may determine an elevated fatigue level associated with a user (e.g., a surgeon). The computing system may obtain surgical contextual data. For example, a surgical instrument may send data associated with usage of the surgical instrument. The computing system may determine whether the surgeon is operating a surgical instrument. The computing system may determine whether the surgeon is operating a surgical instrument based on contextual data and/or measurement data associated with the surgeon (e.g., measurement data associating with the surgeon's hand movement). If the computing system determines that the surgeon is not operating a surgical instrument and detects an elevated fatigue level, the computing system may generate and/or send surgical aid information to the surgeon and/or a computing system associated with the surgeon. The surgical aid information may be or may include an indication of fatigue control for the surgical instrument.

A surgical computing system may identify (e.g., situationally identify) users in an operating room. As described herein, the surgical computing system may identify a user based on a sensing system and/or a computing system associated with a user. Based on the identification of the sensing system and/or the computing system associated with the user, the surgical computing system may determine who the person is, a user role in a surgical procedure (e.g., as a whole), and/or a user role in a current surgical procedure step.

In examples, a user may check in with a surgical computing system. The user may check in with the surgical computing system as the user is entering an operating room. The user may check in with the surgical computing system during a check in procedure.

A user may scan a sensing system and/or a computing system associated with a user as the user enters an operating room. For example, a user may scan and/or tag the sensing system and/or the computing system (e.g., an AR device) to a device, such as a scanning device, associated with the surgical computing system. The surgical computing system may receive the scanned information for the sensing system and/or the computing system associated with the user (e.g., wearing the sensing system and/or the computing system). The surgical computing system may identify and/or recognize the user based on the scanned information. The surgical computing system may determine what the user's role is with a surgical procedure.

In example, a user may be wearing a computing system and/or a sensing system on his/her wrist. As the user enters an operating room, the user may place the computing system and/or the sensing system in front of a scanning device and scan the computing system and/or the sensing system. A surgical computing system may receive the scanned information. The scanned information may be or may include employee identification associated with the user, such as a name, an occupation, a badge number, number of hours worked, and/or other personal data associated with the user. The surgical computing system may determine, based on the scanned information, a user role of the user. For example, the surgical computing system may determine that the user role of the scanned user is a surgeon, a nurse, a hospital staff, and/or an HCP for a surgical operation. If the surgical computing system need additional information, the surgical computing system may ask for additional information to the user. If the surgical computing system identifies a user in the operating room, the surgical computing system may select, identify, and/or assign a user role associated with the identified user. The selected, identified, and/or assigned user role may be associated with a task of the user for the surgical operation.

In example, a user may enter an operating room and go a designated spot (e.g., in front of a monitor, in proximity to and/or next to a surgical table, a surgical tray table, and/or a surgical instrument, etc.). A surgical computing system may detect and/or identify a computing system and/or a sensing system associated with the user based on location information and/or location tracking information of the users and/or proximities of the users to one or more surgical instruments as described herein. The surgical computing system may identify the computing system and/or the sensing system and/or identify a user role associated with the user.

In examples, a user may input (e.g., manually input) user identification information. For example, a user may enter the user identification information to a surgical computing system as the user enters an operating room, prior to a surgical procedure, and/or when prompted by the surgical computing system. The user may enter his/her name, employee ID, a badge number, and/or other user identifier information that identify the user.

In examples, a surgical computing system may have a list of users who will be in an operating room, e.g., from a pre operation plan submitted by a surgeon and/or a surgical plan submitted by an HCP related to a surgical procedure. The surgical computing system may prompt a user to select the user from the list to identify the user. The surgical computing system may identify a user role associated with the identified user for the surgical procedure.

A surgical computing system may identify a user in an operating room based on context information and may identify a user role associated with the user. For example, the context information may be or may include a procedure type, a procedure step, activities of a user, location tracking information of a user in the operating room, proximity of a user to one or more surgical instruments, etc.

In examples, a surgical computing system may identify users for a surgical procedure from an operation plan, e.g., from a pre operation plan and/or a surgical plan that a surgeon submitted prior to the surgery and/or an HCP submitted for a surgical procedure. The surgical computing system may know a type of surgical procedure for the surgical procedure. The surgical computing system may have a list of surgeons who may be able to perform the surgical procedure, e.g., based on expertise of the surgeons and/or shift schedules of the surgeons. The surgical computing system may have a list of nurses and/or HCPs who works with the surgeons, e.g., based on previous surgical plans and/or shift schedules. The surgical computing system retrieve the list from a hospital server. Based on the list, the surgical computing system may identify users for the surgical procedure.

In examples, a surgical computing system may identify a user in an operating room based on a current surgical procedure step. The surgical computing system may identify a user as a surgeon if the current surgical procedure step is performed (e.g., normally performed) by a surgeon. For example, the surgical computing system may identify the user as a surgeon if the current surgical procedure step is making an incision into a patient's chest. The surgical computing system may identify a user as a nurse if the current surgical procedure step needs a surgical instrument, such as a surgical staple gun, to be reloaded.

In examples, a surgical computing system may identify a user in an operating room based on measurement data received from a sensing system. The measurement data may be or may include activities of a user. For example, the measurement data may be or may include hand activities of the user. Based on the hand activities, e.g., performing a surgery, the surgical computing system may identify the user as a surgeon. In examples, the surgical computing system may identify the user as a nurse based on the hand activities involving loading a surgical staple gun and/or moving (e.g., handling) one or more surgical instruments.

In examples, a surgical computing system may identify a user in an operation room based on location tracking information of a user in the operating room, proximity of a user to one or more surgical instruments as described herein.

If a surgical computing system identifies a user in an operating room, the surgical computing system may generate and/or send surgical aid information associated with (e.g., dedicated to) the identified user. The surgical aid information may be or may include an instruction on a surgical procedure, an instruction on how to perform a surgical procedure, an instruction on how to use a surgical instrument, etc. The instruction may be audio and/or video. The surgical computing system may send the generated surgical aid information to a computing system associated with the identified user.

In examples, a surgical computing system may generate and/or surgical aid information including send an audio instruction on a surgical procedure to an audio AR device that a surgeon is wearing. The surgical computing system may send a video instruction on a surgical procedure to a video AR device that a surgeon is wearing. The surgeon may look at and/or listen to the surgical aid information and confirm the surgical procedure.

In examples, a surgical computing system may generate and/or send surgical aid information including an audio and/or a video instruction on how to reload a surgical staple gun to a computing system that a nurse is wearing. The nurse may look at and/or listen to the surgical aid information and properly load the surgical staple gun.

In examples, a surgical computing system may generate and/or send surgical aid information including an audio indication and/or a video indication to a speaker and/or a monitor connected to the operating room. The audio and/or the video indication may be or may include a critical step indication. For example, the surgical computing system may broadcast that a next surgical procedure of a surgical operation is a critical step. The surgical computing system may broadcast the surgical aid information and the users may stop talking, e.g., to help the surgeon to focus.

The users in the operating room may act in response to the surgical aid information (e.g., the indication) from the surgical computing system. For example, the indication may indicate the next surgical procedure step. A nurse may prepare a surgical instrument for the next surgical procedure step. The hospital staff and/or the HCPs may adjust the lighting in the operating, e.g., to provide a focus and/or highlight to a region for the surgical procedure.

A surgical computing system may provide surgical aid information that is or includes an indication of fatigue control of a surgical instrument based on information about identified users. For example, the surgical computing system may be aware of the user's experience levels, preferences, tendencies, outcomes, etc. Based on the information associated with the user, the surgical computing system may include and/or recommend device settings for a next surgical step using the surgical aid information.

In examples, the information associated with the user (e.g., experience levels, preferences, tendencies, outcomes, etc.) may be retrieved from a hospital database. For example, the surgical computing system may connect to the hospital database and retrieve information about the identified user.

In examples, the information associated with the user may be sent to (e.g., relayed to) the surgical computing system by a computing system associated with the user. For example, the computing system associated with the user may provide the user information to the surgical computing system during a check in procedure and/or after the surgical computing system and the computing system establish a link.

If the surgical computing system determines that a user, e.g., a surgeon, is a first year resident and/or new to a surgical step, the surgical computing system may provide the surgical aid information step-by-step. The surgical aid information may include recommendations based on nominal historical data from the hospital database and/or server. The surgical aid information may include recommendations based on nominal historical data from the hospital database and/or server instead of and/or in addition to the user's historical data.

If the surgical computing system determines that the user, e.g., a surgeon, is experienced and/or an expert on a surgical step, the surgical computing system may provide the surgical aid information less frequently.

As described herein, a surgical computing system may receive measurement data from a sensing system associated with a user. The surgical computing system may use the measurement data to adjust an indication of fatigue control to a surgical instrument.

In examples, the surgical computing system may receive measurement data of a surgeon. The measurement data may be or may include a stress level and/or a fatigue level. As described herein, the surgical computing system may determine whether the stress level and/or the fatigue level has been elevated. Based on a determination that the surgeon has an elevated stress level and/or a fatigue level, the surgical computing system may communicate an indication of fatigue control to a surgical instrument. For example, the surgical computing system may slow functions (e.g., speed of articulation, jaw closure, etc.), increase precision, etc. The surgical computing system may communicate an indication of fatigue control to a surgical instrument if the surgical computing system detects an elevated stress level and/or a fatigue level and if a surgical step is a critical step.

Determination of a stress level and/or a fatigue level is further described in ADAPTABLE SURGICAL INSTRUMENT CONTROL, filed contemporaneously, which is incorporated by reference herein in its entirety.

A surgical computing system may communicate with a computing system and/or a sensing system associated with a user. A surgical computing system may communicate with one or more other surgical computing systems in an operating room. For example, one or more surgical computing systems may exist in an operating room. A surgical computing system (e.g., a master surgical computing system or a primary surgical computing system) may have more processing capabilities (e.g., has the highest processing capability) in comparison to one or more surgical computing systems in the operating room. The primary surgical computing system may be connected a network (e.g., Internet, a hospital server and/or database, and/or a hospital cloud).

In examples, the primary surgical computing system may configure one or more other surgical computing systems (e.g., slave surgical computing systems and/or secondary surgical computing systems). For example, one or more secondary surgical computing systems may be in idle modes and/or may have processing power. If the primary surgical computing system determines that the primary surgical computing system needs additional processing power and/or needs to offload processing power (e.g., to perform additional analysis and/or providing additional steps and/or procedures during the operation), the primary surgical computing system may configure one or more secondary surgical computing systems to perform the processing tasks. For example, the primary surgical computing system may identify one or more secondary surgical computing systems that are in idle mode (e.g., not being used during a current surgical step) and/or have processing power. The primary surgical computing system may instruct the one or more idle secondary surgical computing systems to perform offloaded processing tasks.

In examples, the primary surgical computing system may configure one or more secondary surgical computing systems to acquire measurement data from one or more sensing systems associated with users in an operating room. For example, the primary surgical computing system may establish a link with a sensing system and/or a computing system associated with a user. The primary surgical computing system may assign a secondary surgical computing system to receive the measurement data from the linked sensing system and/or data from the linked computing system. The primary surgical computing system may configure other secondary surgical computing system to send an indication of fatigue control to a surgical instrument as described herein.

In examples, the primary surgical computing system may provide measurement data received by the primary surgical computing system to one or more secondary surgical computing systems. The primary surgical computing system may provide access to the received measurement data to the one or more secondary surgical computing systems.

As described herein, a surgical computing system may pair with one or more sensing systems and/or computing systems in an operating room. For example, a surgical computing system may interrogate (e.g., actively interrogate) other sensing systems and/or computing systems in the operating room to establish links and/or to access data. The surgical computing system may seek compatible system to establish a link and obtain access to data (e.g., measurement data and/or used identification data) stored in the sensing systems and/or computing systems.

Based on the established links with one or more compatible sensing systems and/or computing systems, the surgical computing system may index and/or record the locations and/or formats of the data. The surgical computing system (e.g., the primary surgical computing system) may send the information (e.g., the locations and/or formats of the data) to one or more secondary surgical computing systems.

A surgical computing system may store connections (e.g., network connection of other surgical computing systems, computing systems, and/or sensing systems in an operating room). For example, the surgical computing system may reuse stored connections (e.g., past network connections). The surgical computing system may use historic connection data as a setup for a new surgical procedure.

In examples, a surgical computing system may establish a link with a sensing system and/or a computing device associated with a user, such as a surgeon. Based on the link with the sensing system and/or the computing device, the surgical computing system may remember the past list of sensing systems and/or the computing systems that the surgical computing system established connection with. The surgical computing system may prompt a user to confirm a list of sensing systems and/or computing systems uploaded from the past list of systems. The user may select and/or deselect one or more sensing systems and/or computing systems from the past list.

The surgical computing system may use the past list to scan for the sensing systems and/or the computing systems that may be used for a current surgical procedure. The surgical computing system may update the list if one or more sensing systems and/or computing systems do not exist. The surgical computing system may update the list if one or more additional sensing systems and/or computing systems are detected.

The surgical computing system may retrieve a known list of systems that a user may frequently use. For example, if a surgeon has a known list of sensing systems (e.g., heart rate monitor, stress sensor, location identification, etc.) and the surgical computing system establishes a link with one of the known list of systems, the surgical computing system may prompt a connection and/or search other sensing systems from the known list. The sensing systems from the list may be or may include one or more previously connected sensing systems to the surgical computing system.

In examples, the surgical computing system may receive a known list of systems if the surgical computing system establishes a link with a sensing system and/or a computing system. For example, a surgical computing system may send a connection request message and/or a connection prompt to a sensing system. The sensing system may send a response to the connection request message and/or the connection prompt of the sensing system. The sensing system may include a list of other sensing systems and/or computing systems that the user used in previous surgical operations and/or established connections with the surgical computing system. The surgical computing system may use the list from the sensing system and scan for and/or establish connections with other systems based on the list.

In examples, if a sensing system and/or a computing system associated with a user, such as a surgeon, has a known list of systems (e.g., sensing systems and/or computing systems), the identification of a system may trigger a surgical computing system to prompt connections and/or search for other sensing systems and/or computing systems (e.g., specific to a patient). For example, a surgeon may prefer a particular array of sensing systems on patients. The surgical computing system may use information about the surgeon's preference and pre-populate a list of sensing systems for the patient. The surgical computing system may scan for and/or prompt connections to the pre-populated list of sensing systems on the patient.

A computing system may seek one or more sensing systems in an operating room. For example, a computing system may actively seek one or more sensing systems that are in proximity to the computing system. The computing system may be located in an operating room. The one or more sensing systems may include measurement data associated with a user. For example, the sensing systems may be surgeon sensing systems that may include measurement data associated with the surgeon. The sensing systems may be patient sensing systems that may include measurement data associated with the patient.

Figure 96:
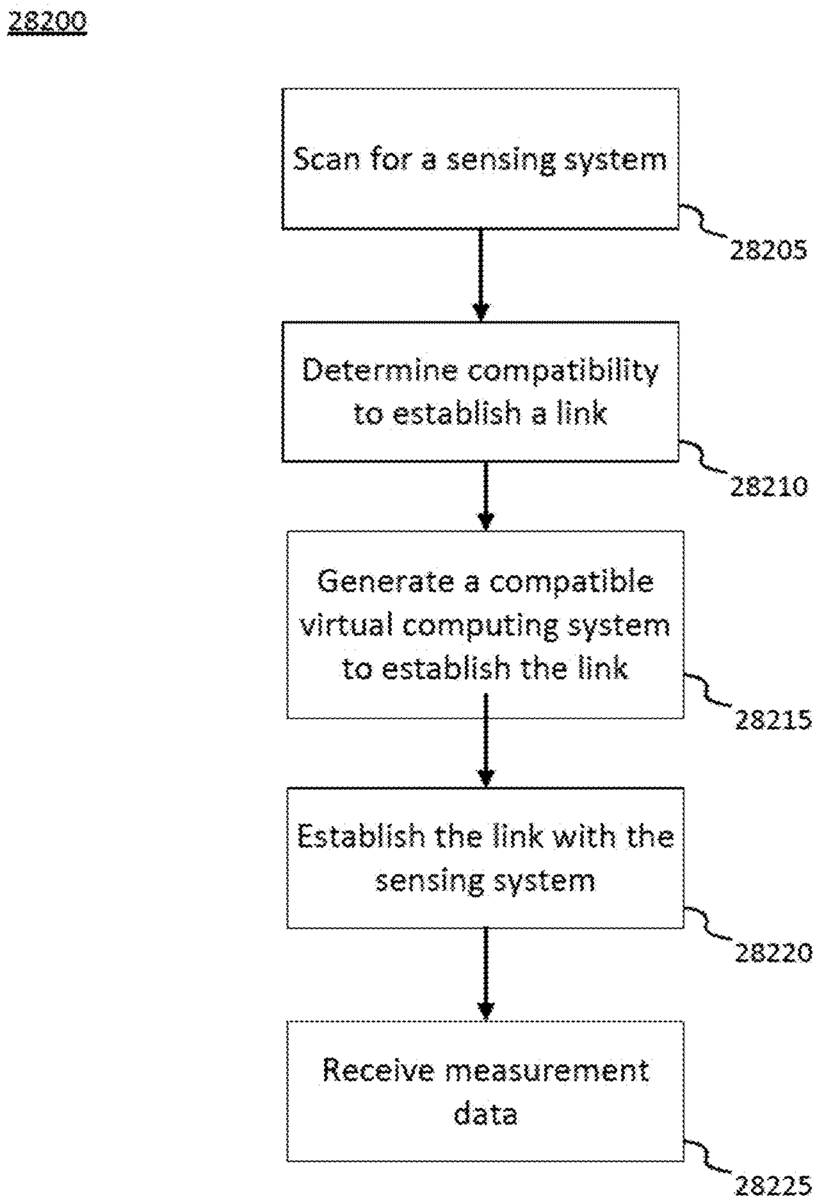
FIG. 96 illustrates an example flow of a computing system establishing a link with compatible and/or incompatible sensing system and/or computing system.

FIG. 96 illustrates an example flow of a computing system establishing a link with compatible and/or incompatible sensing system and/or computing system. At 28205, a computing system may scan an operating room and identify one or more devices that are located in the operating room and are in proximity to the computing system. The computing system may determine whether the detected devices are sensing systems.

In examples, the computing system may request device identifications associated with the detected devices. The computing system may look up the device identifications and determine whether the detected devices are sensing systems. In examples, the computing system may receive sensing system indications from the sensing systems. In examples, the computing system may establish links with other computing systems in an operating room. The other computing systems may have a list of one or more sensing systems in the operating room. The computing system may attempt to establish links with one or more sensing systems from the list.

At 28210, a computing system may determine compatibility to establish a link with a detected sensing system. If the computing system detects/identifies one or more sensing systems, the computing system may determine whether the detected/identified sensing systems are compatible to the computing system. For example, the computing system may determine whether the one or more sensing systems are compatible with the computing system to establish connections and/or share data.

At 28215, a computing system may generate a compatible virtual computing system to establish a link with the incompatible sensing system. If the computing system determines that the computing system and the one or more sensing systems are incompatible to establish links (e.g., connections), the computing system may generate a virtual computing system that is compatible to establish links with the one or more sensing systems. In examples, the virtual computing system may be or may include an intermediate computing system (e.g., virtual computing system configured to run by the computing system) that is compatible with one or more sensing system. In examples, the virtual computing system may be configured to act as a bridge or a tunnel to establish a connection between the computing system and one or more incompatible sensing system. The computing system may establish links with the one or more incompatible sensing systems via the virtual computing system and receive measurement data as described herein. If the computing system determines that the computing system and the one or more sensing systems are incompatible to establish links, the computing system may generate a virtual computing system that is compatible to establish links with the one or more sensing systems. The computing system may establish links with the one or more incompatible sensing systems via the virtual computing system and receive measurement data as described herein.

At 28220, the computing system may establish the link with the sensing system. If the computing system determines that the computing system and the one or more sensing systems are compatible to establish links (e.g., using the virtual computing system), the computing system may establish links (e.g., pair) with the one or more sensing system. The computing system may receive measurement data from the one or more linked/paired sensing systems. In examples, the computing system may receive the measurement data from the one or more paired sensing systems. In examples, the computing system may monitor (e.g., passively monitor) the measurement data from the one or more paired sensing systems. The computing system may send a list of measurement data and/or monitored measurement data from the one or more paired sensing systems to other computing system(s). For example, the computing system may send the list of measurement data and/or monitored measurement data from the one or more paired sensing systems to a primary computing system (e.g., a central computing system and/or a master computing system). In examples, the computing system may communicate paired information to other computing system(s), e.g., a primary computing system. The computing system may communicate the paired information to other computing system(s) periodically, if the computing system pairs with the other computing system(s) and/or when requested.

At 28225, the computing system may receive measurement data from one or more linked sensing systems. In examples, the computing system may store received measurement data from the one or more paired sensing systems. The computing system may send the stored measurement data to other computing system(s). The computing system may perform analysis of the measurement data and/or the other computing system(s) may perform analysis of the measurement data.

In examples, the computing system may send an indication to one or more paired sensing systems. The indication may be or may include a request and/or instructions to send (e.g., directly send) the measurement data to other computing systems (e.g., to a primary computing system and/or secondary computing system).

The computing system may determine whether to connect with a new sensing system after establishing the links with one or more sensing systems. For example, the computing system may determine whether a new sensing system has entered an operating room. Based on a determination that a new sensing system has entered the operating room, the computing system may determine whether to pair with the new sensing system.

In examples, the computing system may determine whether to include and pair with the new sensing system or exclude and skip pairing with the new sensing system based on historic set data. For example, based on the historic set data, the computing system may recognize that a user, such as a circulating nurse from the next operating room, may stop by the current operating room at a time interval (e.g., every hour or every few minutes). Based on the historic set data that the user leaves the current operating room after few minutes, the computing system may exclude the new sensing system associated with the user (e.g., the circulating nurse) and skip pairing with the sensing system. For example, the computing system may determine that a sensing system is associated with a user from a different operating room. If the one or more sensing systems associated with the user from different operating rooms are detected by the computing system, the computing system may exclude the one or more sensing systems associated with the user from the different operating rooms (e.g., a circulating nurse) from establishing a link with the computing system. Based on the data, if a circulating nurse enters the current operating room (e.g., at a time interval), the computing system may exclude (e.g., automatically exclude) the one or more sensing systems associated with the circulating nurse from establishing a link with the computing system.

In examples, the computing system may look up a list of sensing systems. For example, the computing system may query a hospital central supply database and/or cloud database to determine whether the new sensing system belongs to (e.g., associated with) users in the current operating room. Based on a determination that the new sensing system does not belong the identified users in the current operating room, the computing system may exclude the new sensing system from the pairing list and skip pairing with the new sensing system.

In examples, the computing system may determine whether the new sensing system is associated with commercial sensing systems. For example, the computing system may recognize that the new sensing system is associated with non-patients and/or non-HCP. The computing system may determine that the new sensing system does not match with a list of sensing systems listed and/or approved by the hospital. The computing system may exclude the new sensing system from the paring list and skip pairing with the new sensing system.

One or more HCPs may enter an operating room for a surgical procedure. The HCPs may check in with a computing system, such as a surgical computing system (e.g., a primary surgical computing system). In examples, the HCPs may check in with the computing system as the HCPs are entering the room. In examples, the HCPs may check in with the computing system after entering the room and prior to the surgical procedure.

In examples, as described herein, the HCPs may enter their names directly to the computing system. In examples, the HCPs may select/click their names displayed in the computing system. In examples, the HCPs may tag badges, identification cards, and/or other identifiers. The computing system may retrieve one or more sensing systems associated with the HCPs based on the check in information provided/performed by the HCPs.

As described herein, the computing system may identify the HCPs based on a camera feed in the operating room. For example, the computing system may have access to the camera feed in the operating room. Based on the camera feed, the computing system may identify the HCPs in the operating room. In examples, the computing system may identify the HCPs based on their locations in the operation room. In examples, the computing system may identify the HCPs based on their proximities to surgical instruments in the operating room.

In examples, if the computing system detects that a person is lying on an operating table, the computing system may identify the person as a patient. In examples, if the computing system detects a user standing next to and/or moving around near the patient and/or the operating table, the computing system may identify the user as a surgeon. In examples, if the computing system detects a user near a monitor and/or a phone, the computing system may identify the user as a nurse.

The computing system may retrieve one or more sensing systems associated with the identified users/HCPs. For example, the computing system may access database, such as a hospital central database, to retrieve one or more sensing systems that are associated with the identified patient, identified surgeon, and/or identified nurses. The hospital database may have a list of sensing systems and assignment of the sensing systems to one or more HCPs. For example, the hospital database may have a list of sensing systems that is assigned and/or associated with a surgeon. The hospital database may have a list of sensing systems that is assigned to and/or associated with a patient. The computing system may retrieve the list from the hospital database and aware of one or more sensing systems associated with the users in the operating room.

In examples, the computing system may determine the one or more sensing systems in an operating room based on connectivity to a network. The one or more sensing systems may attempt to establish a network connection when the sensing systems enter the operating room. For example, the one or more sensing systems may be connected to a Wifi that is assigned to the operating room. Based on the connection to the Wifi or attempted connection to the Wifi, the computing system may detect one or more sensing systems located in the operating room. As described herein, the computing system may identify and/or associate with the detected one or more sensing systems to corresponding users in the operating room.

In examples, the computing system may scan one or more sensing systems in an operating room. For example, the one or more sensing systems may have Bluetooth and/or Zigbee connection capability. The one or more sensing systems may be discoverable. The computing system may detect one or more sensing systems. As described herein, the computing system may identify and/or associate the discovered one or more sensing systems to corresponding users in the operating room.

The computing system may have information on one or more surgical instruments in an operating room. For example, the computing system may have a list of surgical instruments in an operating room. In examples, the computing system may retrieve a list of instruments in an operating room for a current operation from a pre-operation plan submitted by a surgeon and/or HCPs associated with the surgeon. The pre-operation plan may provide a list of instruments to be used for the surgical operation. The surgeon and/or the HCPs may upload the list to the computing system, to a hospital network, to hospital database. The computing system may retrieve the list.

In examples, an HCP, such as a nurse who is preparing the surgery, may have requested and/or uploaded the list of surgical instruments for an operation. The HCP may upload a surgical plan for the surgical procedure. The computing system may retrieve the list of one or more surgical instruments and/or the surgical plan.

A computing system described herein may handle offline data. A sensing system and/or a network of sensing systems may be connected to a network. For example, one or more sensing systems may be connected to the network through Wifi or the Internet on a mobile device. The Wifi or the Internet on the mobile device may go offline. The Wifi or the Internet may go offline due to one or more of the following: lack of connection, fault, a dead battery, and/or power fault. The computing system may handle the data (e.g., the reservoir of data or data transfer to process that data) based on the last online interaction with the Wifi or the Internet.

Predicted values may be uploaded to one or more sensing systems and/or a mobile device periodically. For example, predicted values may be uploaded to the one or more sensing systems and/or a mobile device daily. The computing system may operate locally within a closed network of the devices. For example, the computing system may learn pattern associated with a user. The computing system may learn timing of the user, sleep schedule, and/or normal marker values for the user. The measured data and/or values may provide contexts for at certain events. For example, eating may result in a spike of blood sugar within a range. For example, a workout may increase heart rate (HR) by 20-30%.

Figure 97:
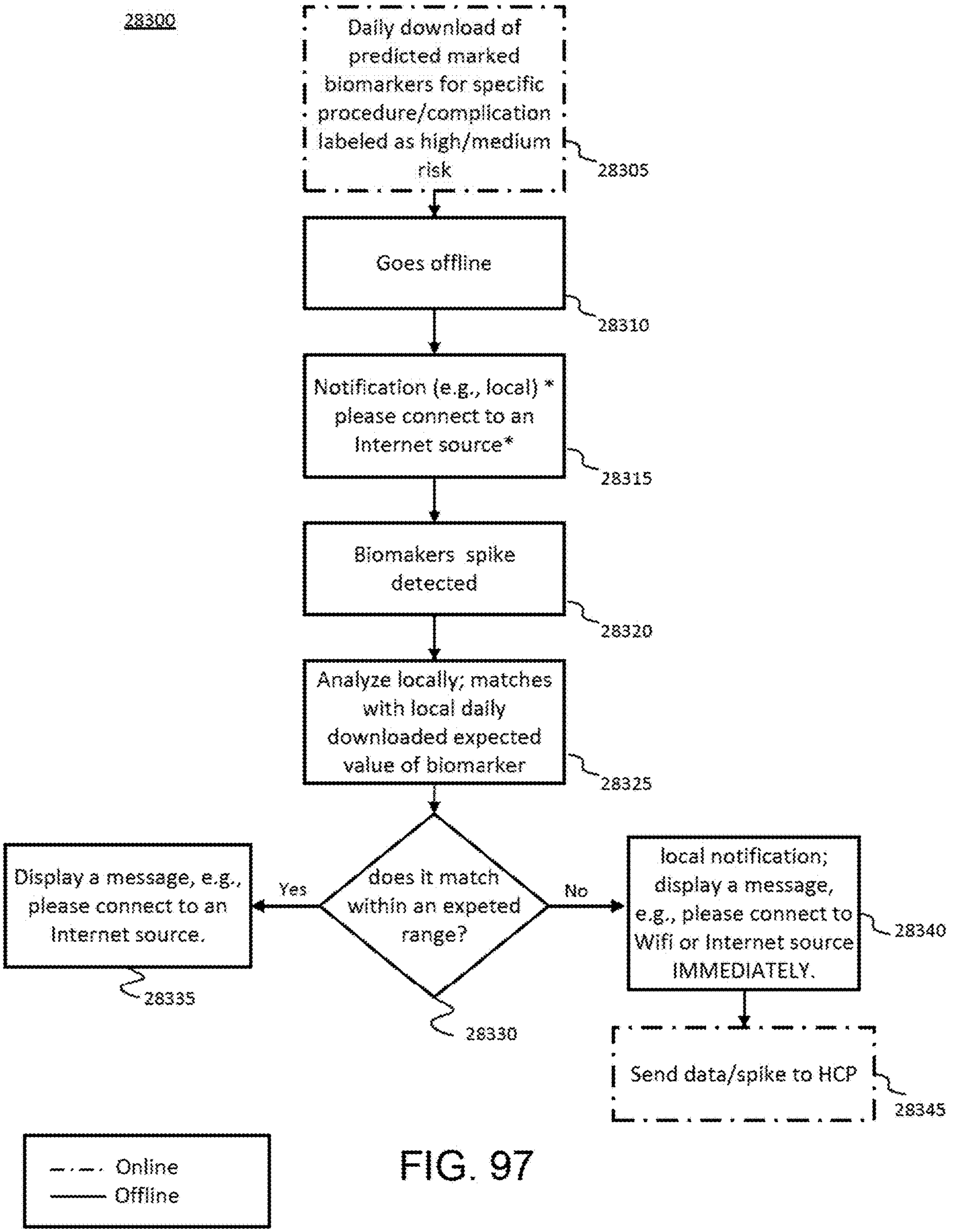
FIG. 97 illustrates an example flow of a computing system operating when online and offline.

FIG. 97 illustrates an example flow of a computing system operating when online and offline. At 28305, the computing system may receive daily download of predicted measurement data (e.g., marked biomarkers) for a specific surgical procedure and/or complication labeled as a high and/or a medium risk. At 28310, the computing system may go offline. The computing system may send a notification (e.g., a local notification). The notification may be or may include "Please connect to an Internet source." At 28315, the computing system may detect an elevated measurement data from a sensing system (e.g., spiked biomarkers). At 28325, the computing system may analyze locally. For example, the computing system may determine whether the elevated measurement data matches with daily downloaded expected value of the measurement data (e.g., local daily downloaded expected value of biomarker). At 28330, the computing system may determine whether the elevated measurement data is within an expected range. At 28335, the computing system may determine that elevated measurement data is within an expected range. The computing system may display a message. The message may be or may include "Please connect to an Internet source." At 28340, the computing system may determine that the elevated measurement data is outside of an expected range. The computing system may send a local notification. For example, the computing system may display a message. A message may be or may include "Please connect to Wifi and/or Internet source IMMEDIATELY." At 28345, the computing system may go online. The computing system may send data and/or elevated measurement data to an HCP.

The computing system may backlog when the computing system is back online. The computing system may provide a prompt to a user to identify one or more specific flags/concerns. The computing system may ask about what event was occurring at that time (e.g., eating, sleeping, etc.) when back online. The provided information may indicate whether a problem existed or is occurring.

The computing system may have an offline mode. In the offline mode, the computing system may look for a trigger (e.g., specific spikes) in measurement data (e.g., biomarkers). The computing system may perform analysis on the trigger when coming back online. The computing system may prioritize data storage and/or prioritize analysis at specific time markers. The analysis may use more power and/or drain the battery faster. The computing system may switch the analysis to the computing device, e.g., from a cloud, etc.

One or more computing systems (e.g., slave computing systems) may transition to one or more master computing systems. The transitioned master computing system may create a hub (e.g., a local hub) for analysis (e.g., low level analysis). FIG. 98 illustrates an example of a secondary computing system transitioning to a primary computing system to create a local computing system for low level analysis. A level 2 computing system (e.g., a primary computing system and/or a master computing system) may receive data and/or may receive 48-bit address of one or more computing systems that have been connected to a mobile device (e.g., from the mobile device). If Internet connection is lost and/or Bluetooth connection with the mobile device is disconnected, the level 2 computing system may page one or more level 1 computing systems (e.g., secondary computing systems and/or slave computing systems) to connect (e.g., automatically connect) to the level 2 computing system. The level 2 computing system may have unique address of other level 1 computing systems. A local network of computing systems may be created and may perform low level analysis and/or give a local notification via level 2 computing system if an emergency is detected and/or if something is wrong. A level 2 computing system may receive data and/or may receive 48-bit address of one or more computing systems that have been connected to a mobile device (e.g., from the mobile device). If Internet connection is lost and/or Bluetooth connection with the mobile device is disconnected, the level 2 computing system may page one or more level 1 computing systems to connect (e.g., automatically connect) to the level 2 computing system. The level 2 computing system may have unique address of other level 1 computing systems. A local network of computing systems may be created and may perform low level analysis and/or give a local notification via level 2 computing system if an emergency is detected and/or if something is wrong.

One or more sensing systems (e.g., wearable systems) may be dependent on an externally supplied piece of data for an operation on how the sensing systems would respond. For example, the sensing systems may operate to the absence of that data in a short-term. The reaction of the system to lack of external connection may be time dependent. For example, in the short-term, the sensing system may use the last communicated value. If the sensing system is offline long enough (e.g., longer than pre-configured short-term time interval), the sensing system may start notifying the user. The sensing system may default into a safe mode operation and/or other protected state.

If a recording capacity of a sensing system is reaching a maximum capacity and the sensing system cannot connect to an external system to upload measurement data, the sensing system may overwrite older data. The sensing system may keep every other or every tenth old data point and overwrite the other data to keep recording (e.g., and/or create space for further measurement data).

A sensing system may have one or more triggers to increase a criticality of connecting to an external system. The triggers may include irregularities and/or exceeding critical thresholds. If the sensing system cannot connect to the external system (e.g., the outside world) when the sensing system needs to report back, the sensing system may intensify a notification to a user (e.g., a wearer) and/or may provide an instruction to the user on how to get access and/or seek other ways to gain access to a communication path.

A surgical instrument (e.g., a smart surgical instrument) may include one or more of the following: a stapler, an energy device (e.g., an advanced energy device), a biologic adjunct, and/or a computing system.

An energy device may send a notification to an HCP, such as a surgeon. An energy device may send potentially problematic data, upcoming steps, and/or complications to the HCP.

For example, an energy device may detect bleeding and send a notification to the surgeon to adjust instrument operation. An example notification to the surgeon may include hemorrhage (IMA-sigmoid colectomy)—Warning: as the surgeon approaches IMA—the patient has a Low/High pH, Power Level x harmonic is suggested due to the risk of hemorrhage.

Examples of what measures may trigger a notification for an energy device as the energy device approaches a large vessel transection and coagulation may include one or more of the following: blood pH greater than 7.45; alcohol consumption; and/or menstrual cycle.

A biologic adjunct may provide an identification of patient escalation parameters that suggest adjunct or supplementary systems to be used.

A computing system may provide adjustments of operational thresholds. A computing system may highlight one or more surgical instruments (e.g., a combination surgical instruments) and patient irregularities. For example, the computing system may identify one or more surgical devices that may provide superior outcomes, access, and/or function based on the detected patent irregularities. A computing system may provide coordination of data streams. For example, the computing system may link one or more sensing systems to measure parameters (e.g., measurement data) with one or more surgical measurement devices (e.g., OR surgical measurement devices) to provide comparisons and/or baseline data.

An audible augmented reality (AR) computing system may receive audio data, such as audible information, from a sensing system in an operating room (OR). In examples, the audio data may be or may include measurement data associated with a user. A user may be or may include a health care professional (HCP), such as a surgeon, or a patient. In examples, the audio data may be or may include ambient noise of the OR. In examples, the audio data may block and/or cancel the ambient noise of the OR. In examples, the audio data may be or may include music, such as calming music, audible feedback information, audible information associated with a surgical step and/or task, and/or other audible information associated with a surgical procedure.

The audio AR computing system may generate AR content. For example, the audio AR computing system may generate the AR content based on the audible data. The AR content may be or may include audible information associated with the audio data. The AR content may be or may include audible AR information that is to be transmitted to a user who is wearing the audio AR computing system and/or a headset controlled by the audio AR computing system. For example, the audible AR computing system may be or may include a surgeon sensing system and/or patient sensing system.

The audio AR computing system may obtain an adjustment indication. The adjustment indication may be or may include adjustment information for the AR content. For example, the adjustment indication may be or may include one or more of a surgical task indication, a task importance indication, an audio insertion indication, an audio translation indication, an audio source location indication. The surgical task indication may indicate a surgical task being performed or to be performed. The task importance indication may indicate an importance of the surgical task. The audio insertion indication may indicate a calming audio and/or music insert. The audio translation indication may indicate an audio translation of the audio data. The audio source location indication may indicate an audio source location of the audio data. For example, the adjustment indication may be obtained (e.g., received) from a surgical computing system, such as a surgical hub.

The audio AR computing system may adjust the generated AR content, e.g., based on the adjustment indication. In examples, the audio AR computing system may adjust the generated AR content based on the adjustment indication indicating an importance of a surgical step. The audio AR computing system may identify an audio AR setting associated with the importance of the surgical step. The audio AR setting may include a volume associated with the audible information (e.g., that is associated with the surgical step), a frequency of transmission of the audible information, and/or a voice associated with the audible information. The audio AR computing system may adjust the generated AR content in accordance with the audio AR setting. For example, the audio AR computing system may adjust the volume of the AR content based on the AR setting. The audio AR computing system may increase or decrease the volume of the AR content based on the AR setting. The audio AR computing system may increase or decrease the frequency of receiving the generated content. The audio AR computing system may alter the voice of the generated AR content based on the AR setting.

In examples, the audio AR computing system may adjust the generated AR content based on the adjustment indication indicating audio information for a critical surgical step. The audio AR computing system may silence the audio data from the sensing system. For example, the audio AR computing system may adjust the AR content by blocking (e.g., temporarily blocking) the audio data from the sensing system and allowing audible information associated with the critical surgical step. The audio AR computing system may increase the volume of the audio information for the critical surgical step. The user of the audio AR computing system may receive the audible information for the critical surgical step and may listen to and/or focus on the audible information associated with the critical surgical step.

In examples, the audio AR computing system may adjust the generated AR content based on the audio information for the critical surgical step. The audio information for the critical surgical step may be or may include an increase frequency indication or a decrease frequency indication (e.g., such as an AR setting). The audio AR computing system may increase the frequency of the audible information for the critical surgical step based on the increase frequency indication. The audio AR computing system may send an increase frequency request to other computing system (e.g., a surgical computing system and/or a central computing system) and may request increase a frequency of sending the audible information. The audio AR computing system may decrease the frequency of the audible information for the critical surgical step based on the decrease frequency indication. The audio AR computing system may send a decrease frequency request to other computing system (e.g., a surgical computing system, a central computing system, and/or a surgical hub) and may request decrease a frequency of sending the audible information for the critical surgical step.

In examples, the audio AR computing system may adjust the generated AR content based on a surgical task indication included (e.g., comprised) in the adjustment indication. The surgical task indication may indicate a surgical task that is being performed or that is to be performed. The audio AR computing system may identify an audio AR setting associated with audible information associated the surgical task. The audio AR computing system may adjust the AR content in accordance with the identified audio AR setting. For example, as described herein, the audio AR computing system may adjust the AR content by increasing or decreasing the volume of the audible information associated with the surgical task and/or increasing or decreasing the frequency of receiving the audible information.

In examples, the audio AR computing system may adjust the generated AR content based on a surgical task indication included (e.g., comprised) in the adjustment indication. The surgical task indication may indicate a surgical task that is being performed or that is to be performed. The audio AR computing system may identify a relevance of the audio data from the sensing system to the surgical task indicated in the surgical task indication. For example, the audio AR computing system may receive one or more measurement data from the one or more sensing systems in the OR. The audio AR computing system may identify (e.g., determine) the relevance of the audio data associated with the measurement data from the sensing systems. The audio AR computing system may determine whether to block the audio data from the sensing system. For example, the audio AR computing system may determine whether to block the audio data from the one or more sensing systems based on the identified relevance to the surgical task indicated in the surgical task indication. If the audio AR computing system determines that one or more audio data from the one or more sensing system are irrelevant to the surgical task indicated in the surgical task indication, the audio AR computing system may block the one or more audio data. If the audio AR computing system determines that one or more audio data from the one or more sensing system are relevant to the surgical task indicated in the surgical task indication, the audio AR computing system may allow the one or more audio data and play the audio data.

In examples, the audio AR computing system may adjust the generated AR content by blocking an ambient noise of the OR. For example, the audio AR computing system may receive audio data that may include ambient noise of the OR (e.g., HCPs talking to one another, sounds of surgical instruments, and/or the like). The audio AR computing system may cancel and/or block the ambient noise.

In examples, the audio AR computing system may receive audible data with ambient noise blocked. The audio AR computing system may generate AR content without the ambient noise.

In examples, the audio AR computing system may receive an ambient noise level indication. The ambient noise level indication may indicate an ambient noise level of the OR. In examples, the audio AR computing system may detect the ambient noise level of the OR. If the audio AR computing system determines that the ambient noise level of the OR is below a threshold ambient noise level, the audio AR computing system may be aware and/or determine that a critical step and/or task is to be performed. The audio AR computing system may send a critical task indication to other computing system (e.g., a surgical computing system). The critical task indication may indicate a critical surgical task is to be performed. The audio AR computing system may adjust the AR content and may receive audible information for a critical surgical task.

In examples, the audio AR computing system may request a user input for adjusting the AR content. For example, the audio AR computing system may request a user input prior to adjusting the AR content. The audio AR computing system may send a user input request to other computing system (e.g., a surgical computing system). The user input request may request a user input before adjusting the generated AR content. The audio AR computing system may wait for a response for the user input for a preconfigured time. If the audio AR computing system does not receive a response for the user input, the audio AR computing system may send a reminder user input request and/or send a user input request to other HCPs in the OR.

In examples, the audio AR computing system may receive one or more audio data. For example, the audio AR computing system may receive audible information from a sensing system and receive another audible information from another sensing system. The audio AR computing system may obtain the adjustment indication. The adjustment indication may be or may include a user preference setting associated with a surgical operation. Based on the user preference setting, the audio AR computing system may adjust the AR content by selecting and/or receiving the audio information from the sensing system (e.g., the first audible information from the first sensing system). The audio AR computing system may block the other audio information from the other sensing system (e.g., the second audible information from the second sensing system).

The user preference setting may indicate a preferred audio data if the AR computing system receives audible data from multiple sensing systems. The AR computing system may adjust the AR content by increasing a volume of the selected and/or preferred audio data. The audio AR computing system may reduce the volume of the unselected audio data. The audio AR computing system may cancel and/or block the unselected audio data. The audio AR computing system may request an increase frequency of receiving the selected and/or preferred audio data. The audio AR computing system may send a decrease frequency of receiving the unselected audio data.

In examples, the audio AR computing system may adjust the AR content based on the adjustment indication indicating a surgical step indication. The surgical step indication may indicate a current surgical step associated with the surgical operation. The audio AR computing system may receive audio data associated with an HCP role in the OR. The audio AR computing system may receive other audio data associated with other HCP role in the OR. The audio AR computing system may adjust the AR content to allow the audio data (e.g., the first audio data) associated with the HCP role (e.g., first HCP role) and may block the other audio data (e.g., the second audio data) associated with the other HCP role (e.g., second HCP role)

An audible augmented reality (AR) computing system may receive audio data such as audible information, from a sensing system in an operating room (OR), ambient noise in the OR. The audio AR computing system may generate AR content. For example, the audio AR computing system may generate AR content based on the audible data. The AR content may be or may include audible information associated with the audio data. The audio AR computing system may receive an adjustment indication. The adjustment indication may be or may include one or more of adjustment information for the AR content. For example, the adjustment indication may be or may include one or more of a surgical task indication, a task importance indication, an audio insertion indication, an audio translation indication, an audio source location indication. The audio AR computing system may adjust the AR content based on the received adjustment indication.

Figure 99:
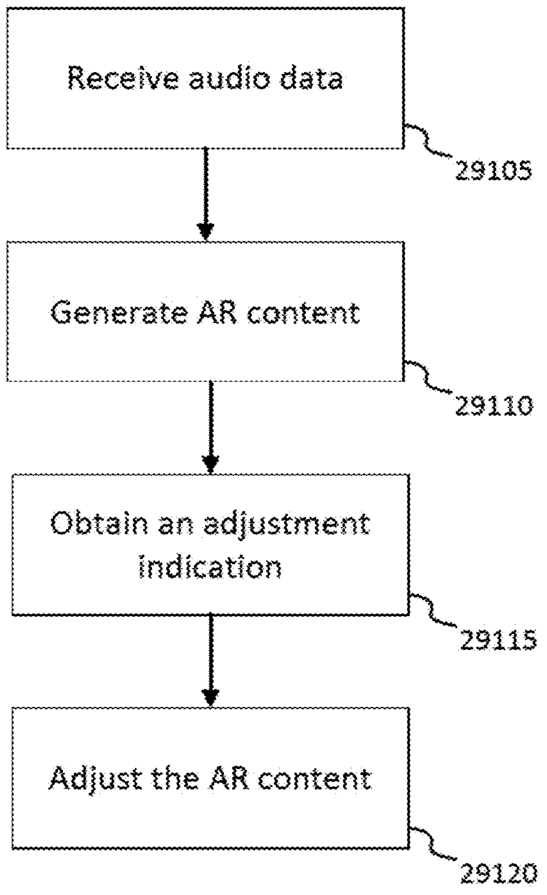
FIG. 99 illustrates an example flow for an audio augmented reality (AR) computing system adjusting the AR content.

FIG. 99 illustrates an example flow of a computing system, such as an audio augmented reality (AR) computing system adjusting an AR content. In examples, an audio AR computing system may be or may include an earbud, a headset, a headphone, etc., or a computing system that controls the audio played via an earbud, a headset, a headphone, etc. The audio AR computing system may receive audio data. The audio data may be or may include one or more of audio data of measurement data associated with a user, ambient noise of the OR, audible feedback, audible information, and/or the like. The audio AR computing system may generate an AR content. For example, the audio AR computing system may generate the AR content based on the received audio data. The AR content may be or may include audible data, such as audible augmented feedback from one or more computing devices and/or other computing systems. The audio AR computing system may obtain an adjustment indication (e.g., from other computing system and/or a surgical computing system). The audio AR computing system may adjust the generated AR content based on the adjustment indication.

At 29105, an audio AR computing system may receive audio data from one or more sensing systems and/or computing system(s) in an operating room (OR). The audio data may be or may include audio data of measurement data associated with a user, ambient noise of the OR, audible feedback, audible information, and/or the like. The audio data may be adjusted, filtered and/or blocked. For example, the audio data may have filtered ambient noise of the OR.

At 29110, the audio AR computing system may generate AR content. For example, the audio AR computing system may generate the AR content based on the received audio data. The generated AR content may be or may include audible AR information. The audible AR may enhance what a user, such as a surgeon, hears. The audio AR computing system may allow a user to listen to the generated AR that may be or may include audible AR information associated with the received audio data.

Generating AR content is further described in U.S. patent application Ser. No. 17/062,509 titled INTERACTIVE INFORMATION OVERLAY ON MULTIPLE SURGICAL DISPLAYS, filed Oct. 2, 2020, which is incorporated by reference herein in its entirety.

At 29115, the audio AR computing system may obtain an adjustment indication. The adjustment indication may indicate adjustment information for the generated AR content. In examples, the adjustment indication may indicate to adjust the AR content by altering voice of the AR content and/or blocking noise (e.g., ambient noise) of the OR that may be included in the AR content. In examples, the adjustment indication may indicate to adjust an audio AR setting associated with an important surgical step and/or a critical surgical step. For example, the audio AR computing system may amplify and/or increase volume of the AR content (e.g., associated with the important surgical step and/or the critical surgical step). The audio AR computing system may reduce and/or decrease the volume of the other AR content (e.g., non-important surgical step and/or the non-critical surgical step). The audio AR computing system may increase or decrease frequency of transmitting the generated AR content to the user. In examples, if the audio AR computing system receives two or more audio data from other devices (e.g., other sensing systems and/or computing systems), the adjustment indication may indicate preferred audio data to be transmitted based on one or more of a preference of the user, priority information, and/or relevance to the current task and/or step of the operation. For example, the AR adjustment indication may be received from one or more computing systems (e.g., such as a surgical computing system and/or a surgical hub) in the OR.

At 29115, the audio AR computing system may adjust the generated AR content. In examples, based on the adjustment indication, the audio AR computing system may adjust the generated AR content. The audio AR computing system may alter the voice of the AR content. The audio AR computing system may block ambient noise of the OR. The audio AR computing system may amplify and/or increase volume of the AR content, reduce and/or reduce volume of the AR content, and/or increase or decrease frequency of transmitting the generated AR content to the user. The audio AR computing system may select audio data from two or more audio data from the sensing systems and/or the computing systems.

The audio AR computing system skip adjusting the generated AR content. For example, the audio AR computing system may allow the AR content (e.g., audible information) to pass through the AR content without filtering and/or adjusting. The audio AR computing system may determine (e.g., based on the adjustment indication) that a surgical operation is about to begin and/or a non-critical task and/or non-critical step of the surgical operation. The audio AR computing system may allow the AR content to pass through (e.g., skip adjusting) and allow the user, such as a surgeon, to listen to ambient noises of the OR.

In examples, the audio AR computing system may adjust the generated AR content by canceling and/or blocking ambient noises and/or other audible data, e.g., based on the adjustment indication. For example, the audio AR computing system may determine that an upcoming step (e.g., task) of a surgical operation is a critical step. The audio AR computing system may cancel and/or block the ambient noises of the OR and/or other audible data to provide a quiet environment for the user. The user of the audio AR computing system, such as a surgeon, may be focused on the critical step. The audio AR computing system may allow the user to experience a quiet environment, such as diminished interactions with other HCPs in the OR and/or the surrounding OR. The audio AR computing system may remove distractions and/or overwhelming sounds (e.g., distracting sounds) from the AR content.

The audio AR computing system may adjust the AR content and insert calm music and/or voice to help the user stay calm, e.g., based on the adjustment indication. For example, the audio AR computing system may adjust the AR content to provide white noise, calm music, and/or music preferred and/or preconfigured by the user. The audio AR computing system may send the adjusted AR content with calming music or white noise to help the user focused on the current step associated with a surgical operation.

In examples, the audio AR computing system may adjust the generated AR content by adjusting an audio AR setting associated with the generated AR content. The audio AR computing system may adjust audio AR setting associated with the generated AR content. In examples, the audio AR computing system may amplify and/or increase volume of the generated AR content. In examples, the audio AR computing system may reduce and/or decrease volume of the generated AR content. In examples, the audio AR computing system may increase a frequency of the generated AR content transmitted to the user or decrease the frequency of the generated AR content transmitted to the user.

The audio AR computing system may adjust the AR content, such as the audio AR setting, based on the adjustment indication. The adjustment indication may be or may include a surgical task indication and/or a task importance indication. The surgical task indication may indicate a surgical task, such as the current surgical task being performed or a pending/upcoming surgical task to be performed. The task importance indication may indicate an importance and/or a criticality of the surgical task.

In examples, the audio AR computing system may amplify and/or increase the volume of the AR content based on the surgical task indication and/or the task importance indication indicating that the surgical task is an important and/or a critical task. The user may listen to the amplified and/or increased volume of the AR content and may be focus.

In examples, the audio AR computing system may reduce and/or decrease the volume of the AR content based on the surgical task indication and/or the task importance indication indicating that the surgical task is a non-important (e.g., less important) and/or a non-critical task. The user may listen to the reduced and/or decreased volume of the AR content and may relax.

The AR content may include multiple audio streams from multiple data sources. In examples, the audio AR computing system may identify an importance of an audio stream to a surgical step. The audio AR computing system may adjust the volume of the audio stream based on the current surgical step and the important of the audio stream to the surgical step. For example, when the audio stream is important to the surgical step, the volume of the audio stream may be increased; when the audio stream is not important to the surgical step, the volume of the audio stream may be decreased.

In examples, the AR content may include multiple audio streams from multiple data sources. For example, the AR content may be or may include multiple audio data from multiple sensing systems. The audio AR computing system may receive audio data from a sensing system in the OR. The audio AR computing system may receive the adjustment indication indicating a user preference setting associated with a surgical operation.

For example, the user preference setting may be or may include preferred measurement data for the surgical operation. The audio AR computing system may receive other audio data from other sensing system in the OR. The audio AR computing system may select a preferred audio data. For example, the audio AR computing system may select the preferred audio data between the multiple audio data from the multiple sensing systems indicated in the user preference setting. As described herein, the audio AR computing system may adjust the AR content by reducing (e.g., decreasing) a volume of unselected audio data from the sensing system and/or amplifying (e.g., increasing) a volume of selected audio data from the sensing system. The audio AR computing system may adjust the AR content by increasing the frequency of the selected AR content, and/or decreasing frequency of the unselected AR content. The audio AR computing system may adjust the AR content by blocking the unselected audio data.

In examples, the audio AR computing system may increase the frequency of the generated AR content played for the user based on the surgical task indication and/or the task importance indication. The task importance indication may indicate that the surgical task is an important (e.g., critical) task. In examples, the audio AR computing system may increase the frequency of the generated AR content if an emergency arises (e.g., a measurement data of a patient falls below a threshold level or reaches above a threshold level). For example, if the measurement data associated with the heartbeat of the patient suddenly changes, the audio AR computing system may increase the frequency of notifying the heartbeat measurement data to the user, such as the surgeon. The user may listen to the increased frequency of the heartbeat measurement data and know real-time measurement data.

In examples, the audio AR computing system may decrease the frequency of the AR content transmitted to the user based on the surgical task indication and/or the task importance indication indicating that the surgical task is an important (e.g., critical) task. In examples, the audio AR computing system may decrease the frequency of the AR content transmitted to the user if the emergency passes (e.g., if the measurement data of the patient goes back to normal level). For example, if the measurement data is associated with the heartbeat of the patient and if the heartbeat data goes back to normal (e.g., if an emergency was averted), the audio AR computing system may decrease the frequency of notifying the heartbeat measurement data to the user of the audio AR computing system. As the emergency is averted and/or the patient is stable, the user, such as the surgeon, may listen to and/or focus on other AR content.

In examples, the audio AR computing system may adjust the AR content, such as voice associated with the AR content. For example, the adjustment indication may be or may include a user preference and/or a user setting. Based on the user preference and/or the user setting, the audio AR computing system may alter the voices of the AR content to different voices. For example, different voices may be or may include Morgan Freeman, Denzel Washington, Darth Vader, and/or other voices that the user prefers to listen to.

In examples, the audio AR computing system may adjust the AR content by translating languages. For example, the adjustment indication may indicate that the AR content is in different language, e.g., non-English AR content. The audio AR computing system may translate the AR content in English or the language that the user may understand in real time and may facilitate better communication. In examples, a user, such as a surgeon, may travel to a foreign country and/or may work with HCPs who are not fluent with the language that the user speaks. For example, the surgeon may travel to other locations (e.g., based on the specialty and/or a global program, such as doctors without borders). The surgeon may not be fluent in the local language and may be unable to understand what is being said in the OR and/or ambient conversations. The audio AR computing system may adjust the AR content that is associated with the audio data of the OR and/or audio data in other language and may adjust the AR content by translating the AR content into the language that the user may understand, e.g., in real time.

In examples, the audio AR computing system may adjust the AR content based on an audio source location indication in the adjustment indication. For example, the audio source location indication may indicate an audio source location of the audible data associated with the AR content. The audio AR computing system may adjust the AR content based on the audio source location indication. In example, if the audio source location indication indicates that the audible data originates from outside of an area of interest (e.g., outside of the OR), the audio AR computing system may adjust the AR content by canceling the audible data originating from the outside of the OR. In examples, the audio AR computing system may expect audible data originating from the outside of the OR. For example, the user of the audio AR computing system may expect a phone call from an organ transplant personnel, other surgeons, HCPs in different ORs, experts located in different location (e.g., different countries), a technician from a surgical instrument company, and/or the like. The audio AR computing system may adjust the AR content by allowing the audio data originating from outside of the OR, upon determining that the audio source location associated with audio data is an expected source location.

In examples, the audio AR computing system may adjust the AR content by selecting and/or prioritizing the AR content, e.g., based on the adjustment indication. For example, the AR content may be or may include audible information from one or more computing devices and/or computing systems. The adjustment indication may be or may include a prioritization indication indicating a priority of audible data. If the audio AR computing system determines that the generated AR content is or includes two or more audible data and/or audible information, the audio AR computing system may adjust the AR content by selecting an audible data and/or audible information based on the indicated prioritization information. The audio AR computing system may amplify and/or increase volume of the prioritized audible data. In examples, the audio AR computing system may cancel other audible data. In examples, the audio AR computing system may reduce and/or decrease the volume of the non-priority audible data. The priority of audio data/audible information may be set via a user preference indication indicating a preference for audible data.

In examples, an audio AR computing system may receive an ambient noise level indication. The ambient noise level indication may indicate an ambient noise level of the operating room. In examples, the audio AR computing system may determine an ambient noise level of an OR. If the audio AR computing system determines that the ambient noise level is below a threshold ambient noise level, the audio AR computing system may determine that a critical surgical task is to be performed or is being performed. In examples, the audio AR computing system may adjust the AR content based on the ambient noise level dropping below a threshold ambient noise level. For example, the audio AR computing system cancel certain audible data in the AR content. For example, the audio AR computing system may provide a quiet and/or calm environment for the user to focus. In examples, the audio AR computing system may send a critical task indication to a surgical computing system. For example, the critical task indication may indicate a critical surgical task is to be performed in the OR (or is being performed). The computing system may send an alert(s) to other HCPs in the OR that an upcoming task involves a critical surgical task.

In examples, an audio AR computing system may send a user input request to a surgical computing system. The audio AR computing system may send the user input request to the surgical computing system before adjusting the AR content. If the user does not provide an input (e.g., confirmation of a suggest AR adjustment) to the user input request, the audio AR computing system may skip adjusting the AR content. In examples, the audio AR computing system determines that the user input is unregistered for a period of time (e.g., a preconfigured time), the audio AR computing system may send a reminder to the user about the user input request. In examples, if the audio AR computing system determines that the user input is unregistered for a period of time, the audio AR computing system may refer to a preconfigured setting (e.g., a default setting). The user may have preselected and/or preconfigured the default setting (e.g., the volume level for the AR content and/or the frequency of receiving the AR content). For example, the user may preconfigure the audio AR computing system to adjust the AR content to the default setting if the audio AR computing system does not register the user input after a preconfigured time (e.g., after 20 seconds) and/or after the audio AR computing system sends a reminder.

The audio AR computing system may receive the user input associated with (e.g., in response to) the user input request. If the audio AR computing system receives the user input, the audio AR computing system may adjust the AR content (e.g., adjust the AR content further) based on the user input. For example, as described herein, based on the user input, the audio AR computing system may further adjust the AR content by amplifying (e.g., increasing) volume of the AR content, reducing (e.g., decreasing) the volume of the AR content, increasing frequency of the AR content, and/or decreasing frequency of the AR content.

An audio AR computing system may adjust generated AR content based on an adjustment indication, e.g., that may be or may include a surgical step indication. For example, the surgical step indication may indicate a current and/or an upcoming surgical step associated with a surgical operation. The audio AR computing system may detect and/or may be aware of the current and/or the upcoming surgical step, e.g., based on the surgical step indication. In examples, the audio AR computing system may adjust the AR content based on a determination (e.g., situational awareness) that audio data of an HCP role that is relevant to the current and/or the upcoming surgical step. As described herein, the audio AR computing system may adjust the AR content by allowing the audio data of the relevant HCP role (e.g., a head nurse) and canceling the audio data associated with other HCP roles (e.g., and/or ambient noise).

Determination of a user or an HCP role is further described in ACTIVE RECOGNITION AND PAIRING SENSING SYSTEMS, filed contemporaneously, which is incorporated by reference herein in its entirety. For example, as described herein, an AR computing system may receive user role identification data from one or more sensing systems in an OR. The user role identification data may be or may include information to identify a user role. The surgical computing system may identify a user role for a user in the OR based on the received user role identification data. The user role of a user in the OR may be or may include at least one of a surgeon, a nurse, a patient, a hospital staff, or an HCP.

In examples, the audio AR computing system may receive audio data associated with an HCP role (e.g., a resident) in the OR. The audio AR computing system may receive another audio data associated with another HCP role (e.g., a head nurse) in the OR. The audio AR computing system may determine whether the audio data is relevant to the surgical step indicated in the surgical step indication. For example, the audio AR computing system may determine whether the audio data of the resident and/or the head nurse in the OR is relevant to the surgical step indicated in the surgical step indication. If the audio AR computing system determines that the audio data is relevant to the surgical step, the audio AR computing system may adjust the AR content by allowing the relevant audio data. For example, if the audio AR computing system determines that the audio data of the resident is relevant to the surgical step and the audio data of the head nurse is irrelevant to the surgical step, the audio AR computing system may adjust the AR content by passing through (e.g., allowing) the audio data of the resident and blocking the audio data of the head nurse.

Determination of a user or an HCP role is further described in ACTIVE RECOGNITION AND PAIRING SENSING SYSTEMS, filed contemporaneously, which is incorporated by reference herein in its entirety.

For example, an AR computing system may receive user role identification data from one or more sensing systems in an OR. The user role identification data may be or may include information to identify a user role. The surgical computing system may identify a user role for a user in the OR based on the received user role identification data. The user role of a user in the OR may be or may include at least one of a surgeon, a nurse, a patient, a hospital staff, or an HCP. Based on the identified user role, the surgical computing system may generate surgical aid information for the user in the OR. The surgical aid information may be or may include information associated with a surgical operation that is relevant to the identified user role. The AR computing system may transmit relevant information to the identified user, e.g., via AR content as described herein.

The user role identification data may be or may include one or more of the following: a proximity of a user to a surgical instrument, locations and/or location tracking information of the users in the OR, interactions between the user and at least one HCP, one or more surgical procedural activities, or visual data of the user in the OR. For example, the sensing system may be worn by the user such as a surgeon. The sensing system may monitor and/or store information about the proximity of the sensing system to a surgical instrument. The sensing system may store location tracking information of the surgeon during a surgical procedure. The sensing system may detect and/or store a surgical procedural activity of the surgeon. The sensing system may send such user role identification data to the surgical computing system.

For example, as described herein, the AR computing system may generate AR content for a user based on the identified user role. Different AR content may be generated for different users based on their respective user roles identified via the sensing systems. The AR content may be or may include instructions on how to use a surgical instrument and/or an operation manual of the surgical instrument associated with the identified user role. The surgical computing system may send the generated AR content to the identified user. For example, the surgical computing system may send the AR content to an AR device associated with the user.

In examples, the audio AR computing system may adjust the AR content by amplifying (e.g., increasing) volume of the audio data associated with the HCP role that is relevant to the surgical step, reducing (e.g., decreasing) the volume of the audio data associated with the HCP role that is irrelevant to the surgical step, increasing frequency of the audio data associated with the HCP role that is relevant to the surgical step, and/or decreasing frequency of the audio data associated with the HCP role that is irrelevant to the surgical step.

As described herein, the audio AR computing system may adjust the AR content based on awareness of an OR, e.g., based on an ambient noise level indication. If the audio AR computing system determines that the ambient noise level indication is below a threshold noise level, the audio AR computing system may determine that a current and/or an upcoming surgical step (e.g., task) is a critical step (e.g., task). The audio AR computing system may adjust the AR content by allowing the relevant audible data associated with the critical surgical task and/or block other audible data associated with non-critical surgical task (e.g., ambient noise). The audio AR computing system may adjust the AR content by amplifying (e.g., increasing) volume of the audio data associated with the critical surgical task, increasing frequency of the audio data associated with the critical surgical task, reducing (e.g., decreasing) volume of the audio data associated with the non-critical surgical task, and/or decreasing frequency of the audio data associated with the non-critical surgical task.

The audio AR computing system may adjust the AR content-based awareness of a user condition. For example, the audio AR computing system may determine that a stress level of a user has increased, e.g., based on measurement data associated with the user. Based on the increased stress level, the audio AR computing system may derive that a current and/or an upcoming surgical task is a critical task. If the audio AR computing system determines that the current and/or the upcoming surgical task is the critical task, the audio AR computing system may adjust the AR content. For example, as described herein, the audio AR computing system may adjust the AR content by allowing the relevant audible data associated with the critical surgical task to pass through and/or block other audible data associated with non-critical surgical task (e.g., ambient noise). Upon detecting the user's increased stress level, the audio AR computing system may adjust the AR content by amplifying (e.g., increasing) volume of the audio data associated with the critical surgical task, increasing frequency of the audio data associated with the critical surgical task, reducing (e.g., decreasing) volume of the audio data associated with the non-critical surgical task, and/or decreasing frequency of the audio data associated with the non-critical surgical task. Upon detecting the user's increased stress level, the audio AR computing system may adjust the AR content by inserting calming audio.

Determination of a stress level is further described in ADAPTABLE SURGICAL INSTRUMENT CONTROL, filed contemporaneously, which is incorporated by reference herein in its entirety.

For example, the computing system may receive measurement data from one of the sensing systems associated with the users in the operating room (e.g., sensing system associated with a surgeon). The computing system may also receive measurement data from one of the sensing systems associated with the users in the operating room indicating higher stress level of the users. For example, higher stress level may be indicated by change in the users' heart rate from a base value. The computing system may derive this inference by cross-referencing the receipt of data from the corresponding sensing systems. The computing system may send surgical aid information to the identified user as described herein.

The audio AR computing system may adjust the AR content based on awareness of a user condition. For example, the audio AR computing system may determine that a fatigue level of a user (e.g., the user wearing the audio AR computing system) has increased, e.g., based on measurement data associated with the user. Based on the increased fatigue level, the audio AR computing system may be aware and/or determine that the user may need to be focused. If the audio AR computing system determines that the user needs to be focused, the audio AR computing system may adjust the AR content. For example, as described herein, the audio AR computing system may adjust the AR content by allowing the relevant audible data associated with a current surgical task and/or block other audible data that are not associated with the current surgical task (e.g., ambient noise). The audio AR computing system may adjust the AR content by one or more of amplifying (e.g., increasing) volume of the audio data associated with the current surgical task and/or increase frequency of the audio data associated with the current surgical task. The audible AR component may adjust the AR content by one or more of reducing (e.g., decreasing) volume of the audio data that is not associated with the current surgical task and/or decrease frequency of the audio data that is not associated with the current surgical task.

Determination of a fatigue level is further described in ADAPTABLE SURGICAL INSTRUMENT CONTROL, filed contemporaneously, which is incorporated by reference herein in its entirety.

For example, the AR computing system may receive measurement data from one of the sensing systems associated with the users in the OR (e.g., sensing system associated with a surgeon). The measurement data may indicate the users, such as a surgeon, make too large of a change in input, which may be referred to as over-correction, for a perceived mistake. The AR computing system may interpret repeated correction, over-correction, or oscillating reaction as an indicator of fatigue and/or elevated fatigue level associated with the identified user.

The AR computing system may be configured to analyze usage data and/or measurement data to determine whether a user working in the OR is experiencing fatigue and, if so, to modify operation of the surgical instrument and/or to provide notifications associated with the fatigue levels. For example, the AR computing system may monitor user inputs to a surgical instrument (e.g., from the surgical instrument and/or from sensing systems). The user inputs to the surgical instrument may include inputs that result in shaking of the surgical instrument. Shaking, whether done intentionally or otherwise, may be detected by one or more sensing systems (e.g., acceleration sensors) which provide data regarding the movement and orientation of the surgical instrument. The detected data may indicate magnitude and frequency of any tremors. The surgical instrument may generate usage data associated with the monitored user inputs. The usage data may indicate the inputs to the surgical instrument, e.g., including movements of all or a portion of the surgical instrument including shaking. The usage data may be communicated to the AR computing system.

Data may be collected from sensing systems that may be applied to the users of the surgical instrument as well as other HCPs who may assist in the OR. Accelerometers may be applied to the users' hands, wrists, and/or arms. Accelerometers may also be applied to users' torsos to gather data associated with the body movements including swaying and body tremors. The accelerometers may generate data regarding motion and orientation of the users' hands and/or arms. The data may indicate magnitude and frequency of movements including shaking. Sensing systems (e.g., that may be or may include accelerometers) may collect biomarker data from the users including data associated with heartbeat, respiration, temperature, etc. The sensing systems may collect data associated with the hydration/dehydration of the corresponding users operating the surgical instrument as well as the other users assisting in the OR. The gathered data may be communicated to the AR computing system.

The AR computing system may receive usage data from the surgical instrument and may receive sensor data from the sensing systems corresponding to the users in the OR. The AR computing system may identify and/or store the received data in association with time stamp data indicating time the data was collected corresponding to the user.

The AR computing system may determine, based on the received usage data and/or sensor data, fatigue levels for the users operating the surgical instrument and assisting in the OR. The AR computing system may determine, based on the received usage data and sensor data, time periods associated with the surgical procedure. The AR computing system may determine, for each users, values associated with time in the OR, time spent standing in the OR, time spent physically exerting themselves. The AR computing system may determine fatigue levels for the users based on the time spent in surgery.

The AR computing system may determine, based on the received usage data and/or sensor data, physical indications of fatigue. The AR computing system may determine, if the received data indicates a user is swaying or unsteady, that the user is fatigued. The AR computing system may determine, if the received data indicates tremors are exhibited by a user, that the user is fatigued.

The AR computing system may determine, based on the received usage data and sensor data, values associated with hydration/dehydration of the users in the OR. Dehydration may impact energy levels and make a person feel tired and fatigued. Less body fluid tends to increase heart rate. The AR computing system may analyze heartbeat data in the context of hydration levels and differentiate between stress and other heart elevation events from hydration. The AR computing system may employ a baseline measure to differentiate acute events from ongoing chronic events and to differentiate between fatigue and dehydration associated with each users in the OR.

The AR computing system may calculate a weighted measure of fatigue for the user operating the surgical instrument as well as others in the OR. The weighted measure of fatigue may be based on cumulative cooperative events and contributions. For example, the weighted measure of fatigue may be based on the intensity of stress experienced by a user and the force exerted by the user over time in controlling an actuator such as closure trigger over time.

If the AR computing system determines that the users have experienced fatigue, the AR computing system may determine to communicate control features to the surgical instrument, to other AR computing systems associated with HCPs in the OR, and/or the AR computing system of the user whose fatigue level has been elevated. The communicated control features may be or may include fatigue control or accommodation and adjustment to compensate for fatigue. The control feature to perform fatigue control may indicate to reduce the force required to implement an action. For example, the control feature may indicate to reduce the force needed to be applied to a closure trigger to activate clamping jaws of a surgical instrument. The control feature may indicate to increase the sensitivity of the closure trigger. The control features may indicate to increase delay or wait time responsive to user inputs. The control features may indicate to slow activation and provide additional time before acting.

If the computing system determines the users have experienced fatigue, the AR computing system may also determine to communicate control features to provide notifications regarding the fatigue. The AR computing system may determine that notifications regarding fatigue may be provided by the surgical instrument to the user. The AR computing system may determine that the notifications may provide more steps-for-use to the operator. The AR computing system may also determine that notifications regarding fatigue levels may be made to persons in the OR other than the HCP manning the instrument. Such notifications may be displayed on display systems in or near the OR.

The AR computing system may communicate an indication of a control features associated with fatigue control. The control features may be communicated to the surgical instrument, the AR computing system, and/or may also be communicated to other systems in the OR such as display which may be employed to provide notifications.

The surgical instrument and display may receive the indication of control features indicating to implement fatigue control and provide notifications. The surgical instrument may determine to operate consistent with the indication of fatigue control. The instrument may reduce the force required to activate and/or operate closure trigger. The surgical instrument may increase the delay or wait time between requesting an action, e.g., applying force to the closure trigger, and implementing the corresponding action, e.g., closing the jaws. The surgical instrument may slow activation in response to inputs and thereby provide more time for the operator to position the surgical instrument.

If the control features indicate to provide notifications, the surgical instrument may provide physical tactile feedback as well as visual feedback. The display may also provide visual feedback regarding fatigue. The notifications may provide steps-for-use to minimize overlooking of details.

In examples, if an audio AR computing system receives critical audible information associated with a patient (e.g., sudden changes in the condition of the patient), the audio AR computing system may allow the critical audible information associated with the patient condition to be transmitted. For example, the audio AR computing system may exclude the critical audible information associated with the patient condition from being adjusted (e.g., canceled).

A computing system, such as an audio AR computing system and/or a visual AR computing system, may interpolate data, such as AR data and/or AR content, to be overlaid with an augmented array. In example, an audio AR computing system may interpolate audible AR content and the user of the audio AR computing system may listen to overall changes to the AR content (e.g., patient's measurement data associated with conditions of the patient). In examples, a visual AR computing system may interpolate visual AR content and the user of the visual AR computing system may view overall changes to the AR content (e.g., the measurement data associated with conditions of the patient).

In examples, the audio AR computing system may provide audible information associated with gradients of a marker over a patient (e.g., a body of the patient) or gradients over time to improved condition for the patient. The user of the audio AR computing system may understand the condition of the patient through the audio AR computing system and/or audible AR content.

In examples, the visual AR computing system may provide visual information associated with gradients of a marker over a patient (e.g., a body of the patient) or gradients over time to improved condition for the patient. The user of the visual AR computing system may understand the condition of the patient through the visual AR computing system and/or visual AR content.

The audible AR content and/or visual AR content may be or may include one or more information from a camera in an OR, an image of the patient's body (e.g., MRI, MRA, and/or the like), a camera inside the body of the patient, and/or the like.

The audible AR content and/or visual AR content may be or may include one or more information associated with temperatures of a patient, such as core temperature of the patient and/or peripheral temperatures of the patient. The audible AR content and/or visual AR content may be or may include gradient of the temperature that are plotted onto the body the patient. The audio AR computing system may provide an audible AR content and the user, such as a surgeon, may listen to the audible AR content (e.g., temperature information of the patient and/or the gradient temperature information of the patient). The visual AR computing system may provide a visual AR content, such as an overlay gradient temperature information of the patient. The user of the visual AR computing system may look at the visual AR content and/or monitor variations in patterns for the temperature of the patient.

In examples, an AR computing system (e.g., an audio AR computing system and/or a visual AR computing system) may receive AR contents, such as measurement data of a patient, from one or more other computing systems and/or computing devices. The AR computing system may receive and/or gather the measurement data of the patient and generate an AR content associated with the measurement data of the patient. The AR computing system may transmit the audible information associated with the measurement data of the patient. The AR computing system may show the visual information associated with the measurement data of the patient. The AR content may be or may include gradient information of the patient and/or changes in the measurement data of the patient over time.

An AR computing system (e.g., an audio AR computing system and/or a visual AR computing system) may provide AR content that may be or may include measurement data. In examples, an audio AR computing system may provide audible AR content for measurement data of a patient, e.g., locally to a user who is wearing the audio AR computing system. In examples, a visual AR computing system may provide visual AR content for measurement data of a patient, e.g., locally to a user who is wearing the visual AR computing system. The AR content may be information overlay of the measurement data of the patient. The AR content may provide data depth to the user, e.g., via the AR overlays.

An AR computing system may receive one or more measurement data from one or more sensing systems. For example, the AR computing system may receive one or more measurement data from one or more sensing systems located in an OR. The measurement data may be or may include measurement data of a patient and/or a user, such as a surgeon.

In examples, the audio AR computing system may generate an audible AR content based on the measurement data. As described herein, the audio AR computing system may overlay audible information of the measurement data and may generate and/or adjust the AR content. For example, the audio AR computing system may overlay audible AR content associated with the monitored and/or real-time measurement data of the patient and/or the user (e.g., such as the surgeon). In examples, the audio AR computing system may transmit the AR content using an audio output associated with the audio AR computing system and provide the AR content locally to a user. In examples, the audio AR computing system may share the audible AR content to a speaker and/or an audio output connected to an OR (e.g., to broadcast) and/or other audio AR computing systems associated with other HCPs in the OR.

In examples, the visual AR computing system may generate a visual AR content based on the measurement data. As described herein, the visual AR computing system may overlay visual information of the one or more measurement data and may generate and/or adjust the AR content. For example, the visual AR computing system may overlay the visual AR content associated with the monitored and/or real-time measurement data of the patient and/or the user (e.g., such as the surgeon). In examples, the visual AR computing system may transmit the AR content using a display associated with the visual AR computing system and provide the AR content locally to a user. In examples, the visual AR computing system may share the visual AR content to a display and/or a monitor connected to an OR (e.g., to broadcast) and/or other visual AR computing systems of other users (e.g., HCPs) in the OR.

In examples, as described herein, the audio AR computing system and/or the visual AR computing system may request a user input prior to sharing the information. If the audio AR computing system and/or the visual AR computing system does not receive the user input, the audio AR computing system and/or the visual AR computing system may send a reminder user input request and/or defer to a preconfigured setting (e.g., a default setting). In examples, the preconfigured setting may be or may include skip sharing the information to other HCPs and/or skip broadcasting to the OR. In examples, the preconfigured setting may be or may include sharing the measurement data to the HCPs and/or broadcast to the OR.

In examples, if the audio AR computing system and/or the visual AR computing system does not receive the user input (e.g., from the primary user, such as a surgeon), the audio AR computing system and/or the visual AR computing system may send a user input request to one or more other HCPs in the operating room. For example, if the audio AR computing system and/or the visual AR computing system does not receive an input from the surgeon, the audio AR computing system and/or the visual AR computing system may send the user input request to a head nurse. The head nurse may provide the user input. The surgeon may work with the list of HCPs, such as the head nurse. The head nurse may remember the surgeon's preference and/or prior instruction from the surgeon. Based on the instruction and/or known preference of the surgeon, the other HCPs, such as the head nurse, may provide the user input for the surgeon. The audio AR computing system and/or the visual AR computing system may share the AR content locally and/or broadcast the AR content in the OR and/or to other HCPs in the OR.

In examples, the audio AR computing system and/or the visual AR computing system may receive measurement data from one or more sensing systems and/or from a surgical computing system. As described herein, the audio AR computing system and/or the visual AR computing system may adjust the AR content (e.g., audible AR content or visual AR content) The AR device may display the received data (e.g., wearable data). In examples, the audio AR computing system and/or the visual AR computing system may highlight a particular measurement data (e.g., an important information such as blood pressure and/or heart monitor information of a patient).

In examples, the audio AR computing system may adjust the AR content and may amplify (e.g., increase volume) of the audible information associated with the particular measurement data that is relevant and/or important to a current surgical procedure. The audio AR computing system may adjust the AR based on awareness of the surgical procedure, atmosphere of the OR, and/or interactions between HCPs as described herein. The audio AR computing system may adjust the AR content based on an adjustment indication received from a surgical computing system that indicates important and/or relevant measurement data associated with a current surgical task.

In examples, the visual AR computing system may adjust the AR content and may increase the resolution on the visual information associated with the particular measurement data that is relevant and/or important to a current surgical procedure. For example, the visual AR computing system may provide a higher resolution on the relevant and/or the important measurement data for the current surgical procedure. The visual AR computing system may adjust the AR based on the awareness of the surgical procedure, atmosphere of the OR, and/or interactions between HCPs as described herein. The visual AR computing system may adjust the AR content based on an adjustment indication received from a surgical computing system that indicates important and/or relevant measurement data associated with a current surgical task.

The audio AR computing system and/or the visual AR computing system may provide the measurement data simultaneously and/or continuously. For example, the audio AR computing system may adjust the AR content that may be or may include measurement data and continuously provide the audible information associated with the measurement data. In examples, the audio AR computing system may provide the audible information in the same tone. In examples, the audio AR computing system may adjust the AR content and may highlight important and/or relevant measurement data in a different tone, volume, and/or voice.

The visual AR computing system may adjust the AR content and may display one or more (e.g., all) measurement data from the sensing systems simultaneously. In examples, the visual AR computing system may display the measurement data in the same resolution. In examples, the visual AR computing system may adjust the AR content and may provide a higher resolution and/or different resolution to highlight the important and/or the relevant measurement data. In examples, the visual AR computing system may adjust AR content and may enlarge the important and/or the relevant measurement data and/or truncate other measurement data.

In examples, the AR computing system may select audible information and/or visual information to adjust AR content based on a current step of the operation. For example, as described herein, the AR computing system may be situationally aware of the current step and/or task of the operation. The AR computing system may select relevant AR information for adjusting the AR content. The AR may send the unselected audible AR information and/or the visual AR information to the HCPs. For example, a surgeon may receive the AR content with the relevant AR information that is associated with the current step of the surgical operation. In examples, other HCPs in the OR may receive the same information. In examples, other HCPs in the OR may receive other AR information and may monitor the information.

An AR computing system may send a request to one or more sensing systems and/or a surgical computing system. The request may be or may include additional measurement data and/or updated data. For example, based on the current step and/or task, the AR computing system may prioritize AR content and may skip receiving updates on the AR information. In examples, during an emergency, the AR computing system may skip receiving heartbeat tracing information, electrocardiogram (EKG) information, and/or heart rate variability information of the patient. After the emergency, the AR computing system may resume receiving such information. For example, the AR system may send an update request for the skipped measurement data to one or more sensing systems and/or to the surgical computing system. The AR computing system may receive the updated and/or monitored measurement data.

In examples, the AR computing system may receive one or more measurement data from corresponding one or more sensing systems that are associated with a patient. The sensing system may have been tracking measurement data associated with the patient. For example, the measurement data may be or may include heartbeat tracing information, EKG information, and/or heart rate variability information of the patient. The sensing systems may have measurement data of the patient over a period of time (e.g., prior to the surgery) and may show history of the measurement data. The measurement data may be and/or may include real-time measurement data of the patient.

A user of the AR computing system may preconfigure (e.g., preset) AR settings associated with receiving audible AR information and/or visual AR information in an AR content. For example, the user may configure the frequency of receiving the audible AR information and/or the visual AR information (e.g., every 5 seconds or every minute). The user may configure the volume and/or the resolution of the audible AR information and/or the visual AR information. The user may configure the AR setting associated with the audible AR information and/or the visual AR information prior to the surgery, based on history data of the user preference, and/or during the surgery.

Measurement data from a sensing system may be used for risk assessment and may be applied to a surgical procedure (e.g., compatible surgical procedure). A computing system may use data to assess risk for a surgical procedure. The computing system may use the data to inform go/no go surgical decision.

A sensing system may gather measurement data. For example, a sensing system may gather measurement data (e.g., sensor data) prior to a surgical procedure. The sensing system may monitor one or more variables (e.g., specific variables) and may provide frequency updates to an HCP, such as a surgeon, prior to surgery. The measurement data may help inform the surgeon if acceptable conditions are in place prior to a scheduled surgery. In examples, international normalized ration (INR) may be a metric used to assess coagulation of blood, e.g., in a patient on coumadin (e.g., fairly common anti-coagulant). Elevated levels (e.g., elevated levels of measurement data) may be common for a patient on anti-coagulant therapy. The elevated levels may be associated with bleeding complications in elective and/or emergent surgical procedures.

A computing system may monitor an absolute value of INR and/or any change in the value of INR (e.g., trend) prior to a surgery. The absolute INR value, the INR value, and/or a trend of INR value may indicate readiness of a patient for a surgery. A guideline (e.g., a surgical guideline) may recommend stopping coumadin 5-6 days prior to the surgery and/or administration of reversal treatment approximately 6 hours prior to the surgery. If the patient is in the hospital, the patient's vitals and/or other information may be easily tracked. If the patient is not in the hospital, the patient's vitals and/or other information may not be easily tracked. If the patient is not in the hospital, the patient's vitals and/or other information may be tracked the day prior or day of the surgery. Having patient's vitals and/or other information the day prior to or the day of the surgery may lead to planning challenges and/or increased bleeding risk in the OR (e.g., and/or increased procedure costs).

One or more computing systems and one or more sensing systems may communicate and share measurement data (e.g., lab testing) and provide an overall analysis (e.g., improved overall analysis). A computing device may interact with other data sources (e.g., a hub and/or a sensing system) and/or may impact patient pre-operative or post-operative care.

Combination of multiple data sources may provide a patient care directive (e.g., an optimal patient care directive). For example, pre op care change of change in diet and/or change in medications for renal function may be implemented. For example, post op care (e.g., particular diet modifications and/or stratified risk for dialysis) may be implemented. In examples, low serum albumin levels may be associated with poor surgical outcomes (e.g., increased morbidity and/or mortality). The low serum albumin levels may or may not be related to nutrition. In examples, coupling serum albumin measurements with change in weight (e.g., measurement data from a wireless scale) may help control for low albumin from malnutrition, low albumin from kidney disease, and/or other pathologic condition. In examples, bioimpedance analysis may be combined with measurement data from a scale. The combined bioimpedance analysis and the measurement data from the scale may help elucidate water changes in body weight on a patient.

A computing system may monitor preconditioning of a patient. For example, a computing system may monitor and/or look for readiness thresholds from the monitored preconditioning of the patient. Preconditioning of a patient may prepare the patient for a surgery and/or may monitor for the patient to achieve a thresholds set by an HCP, such as a surgeon.

A computing system may use pre-operative patient monitoring data and/or conditioning to train a body based on surgery time. A sensing system may collect measurement data. For example, the measurement data may include: heart rate, respiration rate, temp, sleep, mental state, and/or the like. The computing system may determine when a patient should have a surgery performed based on the measurement data.

In (e.g., addition to and/or alternative to) examples, the computing system may use the measurement to train the body and/or subconscious mind to be conditioned for a certain time. Based on the monitored data, a computing system may set one or more triggers at certain times to lower anxiety, reduce heart rate and breathing rate to minimize inflammation, provide indication to a user to rest, and/or the like. The computing system may tier the triggers to a certain time. For example, the computing system may tier the triggers to a certain time, and the mind and body was conditioned and could be more relaxed at the time of surgery.

In (e.g., addition to and/or alternative to) examples, the computing system may utilize the measurement data and/or based on one or more triggers. The one or more triggers may pop up a video on the patient's device, such as a phone, to watch. The patient may watch the video to relax, lower pulse rate, and/or alter breathing. The patient may listen to an audio recording, e.g., deliberately altering the frequency of patient's brainwaves. For example, brainwaves of a patient may fall into a specific frequency depending on what the patient is doing at a given time. The brainwaves may be gamma if the patient is engaged in certain motor functions. The brainwaves may be beta if the patient is fully conscious and/or actively concentrating. The brainwaves may be alpha if the patient is relaxed. The brainwaves may be theta if the patient is drowsy and/or lightly sleeping. The brainwaves may be delta if the patient is in deep sleep.

Binaural beats may result if two tones are played at differing frequencies. The binaural beats may trigger brainwaves of the patient to follow a different pattern. For example, if a computing device (e.g., using the measurement data) wants to shift a patient's state from stressed to relaxed, the computing device may play audio and the patient may listen to an audio that triggers the alpha state.

An audio program may help reprogram subconscious mind of a patient, e.g., by creating a more receptive forum for installing positive messages. A subconscious mind may be more receptive to new information if a patient/body is relaxed, such as in the alpha or theta states.

Using a brain entrainment audio program and/or affirmations or visualization may be a powerful combination. Subconscious mind of a patient may let down its defenses and may easily absorb a message that an HCP and/or a computing device may wish to program in.

If more than one HCP is involved and the HCPs are one or more sites communication of data between HCPs, coordination and/or treatments between HCPs may be adjusted (e.g., improved).

A computing device (e.g., a wearable device) may provide a reminder(s) to a user. For example, a computing device may provide a reminder to a user of information that a HCP gave, e.g., at the time of discharged. If the reminder does not help resolve a confusion, the computing device may link to a mobile phone, WIFI, and/or other network and allow the HCP to interact with the user in real-time. The reminder may act as a reminder and a means to clear up things that a user needs to improve compliance and/or recovery. In examples, a reminder may be or may include an exercise(s) that is supposed to be done daily and/or a medication(s) that should be taken a certain time. The computing device may remind the user and/or detect that the user is engaging in the recommended exercise and/or taking the medicine. If the computing device does not detect an event and/or an underlying measurement data (e.g., biomarker) indicates a lack of improvement, a computing system may be used to understand if the user is doing the exercise correctly and/or taking the medicine on time. The computing system may notify the HCP and/or the computing system may help the user to remember to do the activities.

After a surgery, a surgeon may provide a primary care physician, physiotherapist, and/or other HCPS information on mobility restrictions and/or exercises that are needed. Other HCPs may modify the medications that the user is taking (e.g., temporarily or depending on measured parameters). Other HCPs may monitor and/or ensure compliance to a pre-surgery and/or post-surgery regiment, such as eating, resting, etc. Other HCPs may have one or more measurement data (e.g., biomarker) thresholds that now hold a higher importance and/or that may trigger an intervention if the measurement data (e.g., the biomarker) does not change over time as expected.

One or more supporting HCPs may record progress and/or compliance of the user. The primary surgeon may have the progress and/or compliance data available when the surgeon review recovery with the patient.

A computing system may include an antenna (e.g., a flexible antenna) and may isolate detection and a communication system. In examples, a computing system may use signal intensity, noise, and/or directional antennas to selectively engage one or more computing devices if a number of computing devices in roman operating room exceeds a threshold number. In examples, a computing device (e.g., a wearable computing device and/or an environmental computing device) may indicate compatibility and/or adjust signal output to be compatible with an unknown computing system. A computing device may move through a range of viable frequencies and/or communication modalities to determine if the computing device may pair to a computing system that the computing device detects.

One or more computing systems and/or other computing devices may communicate with one another. In examples, a computing system may communicate with one or more computing devices (e.g., wearable computing devices). In examples, one or more digital devices may exist. A computing system may detect a surgeon by physical actions and/or automated setup. In example, a computing system may setup one or more instrument operational parameters, e.g., based on the detection of a technique used by the surgeon.

In example, a computing system may detect a user, such as a surgeon in an operating room (OR), based on a physical action by the user. For example, the surgeon may be wearing one or more computing devices, such as a wearable, that may communicate with the computing system. The computing system, based on the information from the one or more computing devices, may determine what action the user is performing. For example, a surgeon may wear a computing device (e.g., a wearable) on his/her wrist. The computing device may detect the surgeon holding an instrument, such as a surgical staple gun. The computing system may receive the information, from the computing device, that the surgeon is holding a surgical staple gun. The computing system may determine one or more steps that the surgeon may take.

A computing system may hybridize one or more static imaging techniques with continuous data monitoring (e.g., from one or more measurement data).

Telemedicine may be interconnected with a computing system. In example, telemedicine appointment scheduling may be based on an intra-operative event. For example, based on intra-op measured data (e.g., parameters), one or more relevant telemedicine providers may be queued and/or booked in the computing system for regular follow-ups.

Single or combination of intraoperative computing devices (e.g., sensors) may flag a patient if the measurement data (e.g., monitored measurement data and/or variables) fall outside of desired values. If the computing devices flag based on the measurement data, an HCP, such as a surgeon, may be alerted, e.g., after a case that telemedicine follow-up is needed in a given specialty. In examples, the telemedicine may be alerted (e.g., automatically) to setup relevant follow-ups.

In example, a computing system and/or a computing device may monitor measurement data, such as serum albumin. If the computing device detects drop in serum albumin (e.g., below a preconfigured threshold serum albumin level), the computing device may prompt a need for scheduled nutritionist intervention post-op. The updates may be conditioned on one or more suitable criterion and/or set of criteria. In examples, an update may be conditioned on one or more hardware capabilities of a computing system, such as processing capability, bandwidth, resolution, and/or the like. In examples, the update may be conditioned on one or more software aspects, such as a purchase of certain software code. In examples, the update may be conditioned on a purchased service tier. The service tier may represent a feature and/or a set of features that the user is entitled to use in connection with the computer-implemented interactive surgical system. The service tier may be determined by a license code, an e-commerce server authentication interaction, a hardware key, a username/password combination, a biometric authentication interaction, a public/private key exchange interaction, and/or the like.

Disclosed herein are methods, systems, and apparatus for predictive based system adjustments based on biomarker trending. The embodiments disclosed herein may allow control of one or more notification associated with a biomarker to improve the quality of the one or more notifications and/or prevent a health care provided (HCP) from being distracted by the one or more notifications. For example, notifications associated with a biomarker may be control such that notification may bring to the biomarker and/or a probability associated with the biomarker to the attention of the HCP. The embodiments disclosed herein, may allow for an adjustment of calculated outcome probabilities. For example, one or more outcome probabilities that may be associated with a surgical procedure may be calculated, and one or more biomarkers may be used to adjust the one or more calculated outcome probabilities.

A computing system and/or a method may be provided for using a risk assessment to provide a notification. The computing system may comprise a processor. The processor may be configured to perform the method. A biomarker may be received for a patient from a sensing system. A data collection that includes pre-surgical data may be received for a patient. A probability of a patient outcome due to a surgery performed on the patient may be determined using the biomarker and the data collection. A notification may be sent to a user. The notification may indicate that the probability of the surgical complication may exceed a threshold.

A computing system and/or a method may be provided for using a risk assessment to provide a notification. The computing system may comprise a processor that may be configured to perform the method. A biomarker for a patient may be received from a sensing system. A data collection may be received. The data collection may include pre-surgical data and surgical data for the patient. A risk assessment model may be determined using the data collection. The risk assessment model may be for a patient outcome associated with a surgery performed on the patient. A probability of a medical issue may be determined using the risk assessment model and the biomarker.

A computing system and/or a method may be provided for using a risk assessment to provide a notification. The computing system may comprise a processor. The processor may be configured to perform a method. A biomarker may be received for a patient from a sensing system. A data collection may be received for the patient. A probability of a patient outcome due to a surgery perform on the patient may be determined using at least the biomarker and the data collection. An escalation level may be determined based on the probability of the patient outcome. A notification may be sent to a user based on the escalation level.

A computing system and/or a method may be provided for using a risk assessment to provide a notification. The computing system may comprise a processor. The processor may be configured to perform the method. A biomarker may be received for a patient from a sensing system. A data collection that includes pre-surgical data may be received for a patient. A probability of a patient outcome due to a surgery performed on the patient may be determined using the biomarker and the data collection. A notification may be sent to a user. The notification may indicate that the probability of the surgical complication may exceed a threshold.

Machine learning is a branch of artificial intelligence that seeks to build computer systems that may learn from data without human intervention. These techniques may rely on the creation of analytical models that may be trained to recognize patterns within a dataset, such as a data collection. These models may be deployed to apply these patterns to data, such as biomarkers, to improve performance without further guidance.

Machine learning may be supervised (e.g., supervised learning). A supervised learning algorithm may create a mathematical model from training a dataset (e.g., training data). The training data may consist of a set of training examples. A training example may include one or more inputs and one or more labeled outputs. The labeled output(s) may serve as supervisory feedback. In a mathematical model, a training example may be represented by an array or vector, sometimes called a feature vector. The training data may be represented by row(s) of feature vectors, constituting a matrix. Through iterative optimization of an objective function (e.g., cost function), a supervised learning algorithm may learn a function (e.g., a prediction function) that may be used to predict the output associated with one or more new inputs. A suitably trained prediction function may determine the output for one or more inputs that may not have been a part of the training data. Example algorithms may include linear regression, logistic regression, and neutral network. Example problems solvable by supervised learning algorithms may include classification, regression problems, and the like.

Machine learning may be unsupervised (e.g., unsupervised learning). An unsupervised learning algorithm may train on a dataset that may contain inputs and may find a structure in the data. The structure in the data may be similar to a grouping or clustering of data points. As such, the algorithm may learn from training data that may not have been labeled. Instead of responding to supervisory feedback, an unsupervised learning algorithm may identify commonalities in training data and may react based on the presence or absence of such commonalities in each train example. Example algorithms may include Apriori algorithm, K-Means, K-Nearest Neighbors (KNN), K-Medians, and the like. Example problems solvable by unsupervised learning algorithms may include clustering problems, anomaly/outlier detection problems, and the like Machine learning may include reinforcement learning, which may be an area of machine learning that may be concerned with how software agents may take actions in an environment to maximize a notion of cumulative reward. Reinforcement learning algorithms may not assume knowledge of an exact mathematical model of the environment (e.g., represented by Markov decision process (MDP)) and may be used when exact models may not be feasible. Reinforcement learning algorithms may be used in autonomous vehicles or in learning to play a game against a human opponent.

Machine learning may be a part of a technology platform called cognitive computing (CC), which may constitute various disciplines such as computer science and cognitive science. CC systems may be capable of learning at scale, reasoning with purpose, and interacting with humans naturally. By means of self-teaching algorithms that may use data mining, visual recognition, and/or natural language processing, a CC system may be capable of solving problems and optimizing human processes.

The output of machine learning's training process may be a model for predicting outcome(s) on a new dataset. For example, a linear regression learning algorithm may be a cost function that may minimize the prediction errors of a linear prediction function during the training process by adjusting the coefficients and constants of the linear prediction function. When a minimal may be reached, the linear prediction function with adjusted coefficients may be deemed trained and constitute the model the training process has produced. For example, a neural network (NN) algorithm (e.g., multilayer perceptrons (MLP)) for classification may include a hypothesis function represented by a network of layers of nodes that are assigned with biases and interconnected with weight connections. The hypothesis function may be a non-linear function (e.g., a highly non-linear function) that may include linear functions and logistic functions nested together with the outermost layer consisting of one or more logistic functions. The NN algorithm may include a cost function to minimize classification errors by adjusting the biases and weights through a process of feedforward propagation and backward propagation. When a global minimum may be reached, the optimized hypothesis function with its layers of adjusted biases and weights may be deemed trained and constitute the model the training process has produced.

Data collection may be performed for machine learning as a first stage of the machine learning lifecycle. Data collection may include steps such as identifying various data sources, collecting data from the data sources, integrating the data, and the like. For example, for training a machine learning model for predicting surgical complications and/or post-surgical recovery rates, data sources containing pre-surgical data, such as a patient's medical conditions and biomarker measurement data, may be identified. Such data sources may be a patient's electronical medical records (EMR), a computing system storing the patient's pre-surgical biomarker measurement data, and/or other like datastores. The data from such data sources may be retrieved and stored in a central location for further processing in the machine learning lifecycle. The data from such data sources may be linked (e.g., logically linked) and may be accessed as if they were centrally stored. Surgical data and/or post-surgical data may be similarly identified, collected. Further, the collected data may be integrated. In examples, a patient's pre-surgical medical record data, pre-surgical biomarker measurement data, pre-surgical data, surgical data, and/or post-surgical may be combined into a record for the patient. The record for the patient may be an EMR.

Data preparation may be performed for machine learning as another stage of the machine learning lifecycle. Data preparation may include data preprocessing steps such as data formatting, data cleaning, and data sampling. For example, the collected data may not be in a data format suitable for training a model. In an example, a patient's integrated data record of pre-surgical EMR record data and biomarker measurement data, surgical data, and post-surgical data may be in a rational database. Such data record may be converted to a flat file format for model training. In an example, the patient's pre-surgical EMR data may include medical data in text format, such as the patient's diagnoses of emphysema, pre-operative treatment (e.g., chemotherapy, radiation, blood thinner). Such data may be mapped to numeric values for model training. For example, the patient's integrated data record may include personal identifier information or other information that may identifier a patient such as an age, an employer, a body mass index (BMI), demographic information, and the like. Such identifying data may be removed before model training. For example, identifying data may be removed for privacy reasons. As another example, data may be removed because there may be more data available than may be used for model training. In such case, a subset of the available data may be randomly sampled and selected for model training and the remainder may be discarded.

Data preparation may include data transforming procedures (e.g., after preprocessing), such as scaling and aggregation. For example, the preprocessed data may include data values in a mixture of scales. These values may be scaled up or down, for example, to be between 0 and 1 for model training. For example, the preprocessed data may include data values that carry more meaning when aggregated. In an example, there may be multiple prior colorectal procedures a patient has had. The total count of prior colorectal procedures may be more meaningful for training a model to predict surgical complications due to adhesions. In such case, the records of prior colorectal procedures may be aggregated into a total count for model training purposes.

Model training may be another aspect of the machine learning lifecycle. The model training process as described herein may be dependent on the machine learning algorithm used. A model may be deemed suitably trained after it has been trained, cross validated, and tested. Accordingly, the dataset from the data preparation stage (e.g., an input dataset) may be divided into a training dataset (e.g., 60% of the input dataset), a validation dataset (e.g., 20% of the input dataset), and a test dataset (e.g., 20% of the input dataset). After the model has been trained on the training dataset, the model may be run against the validation dataset to reduce overfitting. If accuracy of the model were to decrease when run against the validation dataset when accuracy of the model has been increasing, this may indicate a problem of overfitting. The test dataset may be used to test the accuracy of the final model to determine whether it is ready for deployment or more training may be required.

Model deployment may be another aspect of the machine learning lifecycle. The model may be deployed as a part of a standalone computer program. The model may be deployed as a part of a larger computing system. A model may be deployed with model performance parameters(s). Such performance parameters may monitor the model accuracy as it is used for predicating on a dataset in production. For example, such parameters may keep track of false positives and false positives for a classification model. Such parameters may further store the false positives and false positives for further processing to improve the model's accuracy.

Post-deployment model updates may be another aspect of the machine learning cycle. For example, a deployed model may be updated as false positives and/or false positives are predicted on production data. In an example, for a deployed MLP model for classification, as false positives occur, the deployed MLP model may be updated to increase the probably cutoff for predicting a positive to reduce false positives. In an example, for a deployed MLP model for classification, as false negatives occur, the deployed MLP model may be updated to decrease the probably cutoff for predicting a positive to reduce false negatives. In an example, for a deployed MLP model for classification of surgical complications, as both false positives and false negatives occur, the deployed MLP model may be updated to decrease the probably cutoff for predicting a positive to reduce false negatives because it may be less critical to predict a false positive than a false negative.

For example, a deployed model may be updated as more live production data become available as training data. In such case, the deployed model may be further trained, validated, and tested with such additional live production data. In an example, the updated biases and weights of a further-trained MLP model may update the deployed MLP model's biases and weights. Those skilled in the art recognize that post-deployment model updates may not be a one-time occurrence and may occur as frequently as suitable for improving the deployed model's accuracy.

Disclosed herein are methods, systems, and apparatus for predictive based system adjustments based on biomarker trending. The embodiments disclosed herein may allow control of one or more notification associated with a biomarker to improve the quality of the one or more notifications and/or prevent a health care provided (HCP) from being distracted by the one or more notifications. For example, notifications associated with a biomarker may be control such that notification may bring to the biomarker and/or a probability associated with the biomarker to the attention of the HCP. The embodiments disclosed herein, may allow for an adjustment of calculated outcome probabilities. For example, one or more outcome probabilities that may be associated with a surgical procedure may be calculated, and one or more biomarkers may be used to adjust the one or more calculated outcome probabilities.

A computing system and/or a method may be provided for using a risk assessment to provide a notification. The computing system may comprise a processor. The processor may be configured to perform the method. A biomarker may be received for a patient from a sensing system. A data collection that includes pre-surgical data may be received for a patient. A probability of a patient outcome due to a surgery performed on the patient may be determined using the biomarker and the data collection. A notification may be sent to a user. The notification may indicate that the probability of the surgical complication may exceed a threshold.

A computing system and/or a method may be provided for using a risk assessment to provide a notification. The computing system may comprise a processor that may be configured to perform the method. A biomarker for a patient may be received from a sensing system. A data collection may be received. The data collection may include pre-surgical data and surgical data for the patient. A risk assessment model may be determined using the data collection. The risk assessment model may be for a patient outcome associated with a surgery performed on the patient. A probability of a medical issue may be determined using the risk assessment model and the biomarker.

A computing system and/or a method may be provided for using a risk assessment to provide a notification. The computing system may comprise a processor. The processor may be configured to perform a method. A biomarker may be received for a patient from a sensing system. A data collection may be received for the patient. A probability of a patient outcome due to a surgery perform on the patient may be determined using at least the biomarker and the data collection. An escalation level may be determined based on the probability of the patient outcome. A notification may be sent to a user based on the escalation level. Decision-making algorithms may be provided. Automated system decision-making algorithms may be provided. Decision-making algorithms may be provided based on biomarker monitoring. Decision-making algorithms may include decision-making. Decision-making algorithms may include risk assessment. Decision-making algorithms may include notification. Decision-making algorithms may include escalation procedure. Decision-making may include any combination of decision-making, risk assessment, notification, and escalation procedure. Automated systems may be used. Learning automated systems may be used. The automated systems may include a wearable. Decision-making may be performed. Decision-making may be risk based. Decision-making may include a risk assessment. Decision-making may be tasked based. Decision-making may include an escalation procedure. Decision-making may be performed based on biomarker information, for example. The biomarker information may include biomarker-related data and/or medical record information, for example. Biomarker information may be received from local devices, such as other wearable sensing systems, surgical equipment, surgical instruments, visualization systems, and the like, for example. Decision-making may be performed based on contextual information. Contextual information may be determined. Contextual information may be determined based on the biomarker information. Contextual information may be received from local devices.

Risk assessment may be performed. Risk assessment may be performed based on biomarker information. The biomarker information may be received from local devices, such as other wearable sensing systems, surgical equipment, surgical instruments, visualization systems, and the like, for example. For example, risk assessment may be performed based on blood pressure of a patient. A wearable may monitor blood pressure and blood pressure-related biomarkers, for example. The wearable may receive blood pressure-related biomarkers from local devices. The wearable may detect an increase in blood pressure. The wearable may detect the presence of blood pressure medicine. The wearable may determine a blood pressure threshold for normal values. The wearable may determine a risk assessment. The wearable may determine a risk assessment based on at least one of the increased blood pressure, presence of blood pressure medicine, and the blood pressure threshold. In an example, the wearable may determine the blood pressure is not at a critical level. The wearable may determine the blood pressure is not at a critical level based on the risk assessment. The blood pressure may be at a critical level if blood pressure falls outside a predetermined threshold. The predetermined threshold may consider blood pressure medication.

In an example, risk assessment may be updated. Risk assessment may be updated based on updated biomarker information. For example, risk assessment may indicate a higher risk if biomarker information show that biomarkers are continuing to stray from a normal predetermined threshold. A higher risk may be indicated based on increasingly abnormal blood pressure-related biomarkers, for example. Risk assessment may indicate a higher risk based on HCP inattentiveness, for example. Risk assessment may flag biomarker-related information. Risk assessment may flag biomarker-related information based on an indicated risk. The flags may be stored in a patient medical record.

Notification may be provided. Notification may be provided based on biomarker information. Notification may be provided based on risk assessment. Notification may be provided to at least one of a user, patient, HCP, and the like. Notification may include alerts. Notification may include alerts relating to biomarkers, surgical instruments, surgical procedure, and the like. Alerts may include at least one of a sound, a vibration, a flash, and the like. For example, notification may be provided based on an abnormal biomarker information. Notification may be provided based on a detected surgical complication, for example.

Notifications may include a request for a response. Notifications may include a request for a response from a user, patient, HCP, and the like. The request for a response may include a request for confirmation of receipt. The request for a response may include a request for a verification of the notification. The verification of the notification may include a confirmation that the notification is indicative (e.g., accurately indicative) of a surgical scenario. In an example, a notification may be sent to one or more HCPs. The notification may relate to abnormal biomarker information. The notification may request confirmation from the HCPs. The confirmation may include verification for the accuracy of detected abnormal biomarker information.

Notifications may be provided using a wearable. Notifications may be provided using local devices. Notifications may be provided on a plurality of devices. In an example, a notification may be provided to a wearable and a display device at the same time.

An escalation procedure may be provided. An escalation procedure may be provided based on one or more of a biomarker information, a risk assessment, a notification, and the like. An escalation procedure may include sending prioritized notifications. An escalation procedure may include a hierarchy of priority for notifications. The hierarchy of priority may include a scale of notification priorities. A higher prioritized notification may be provided based on the severity of biomarker information and/or a risk assessment. For example, a notification based on a detection of a slightly abnormal heart rate may indicate lower priority than a notification based on a detection of a heart attack.

The prioritized notifications may include one or more escalated notifications. The one or more escalated notifications may include louder audible alerts and/or stronger vibrational alerts, for example. The one or more escalated notifications may include a greater number of notifications. The one or more escalated notifications may include sending notifications to multiple devices. The one or more escalated notifications may include notifications to different users, patients, and/or HCPs. For example, an escalated notification may be sent to a more knowledgeable and/or higher-ranking HCP based on a higher priority.

An escalation procedure may be provided when monitored biomarker information exceeds normal thresholds. Blood pressure falling out of a normal threshold range may trigger escalation procedure, for example. An escalation procedure may be provided when abnormal biomarker information continues beyond normal thresholds. For example, blood pressure rising at an accelerating rate may trigger more prioritized notifications to be sent. An escalation procedure may be provided when a request for confirmation sent by a notification is ignored. For example, a higher priority notification may be sent when a previously sent notification is ignored for 30 minutes. The higher priority notification may escalate the notification to notify other users, patients, and/or HCPs. The higher priority notification may escalate the notification and sent a prioritized notification to other devices, such as local devices including wearables, monitors, display devices, sound systems, and the like. An escalation procedure may continue until a response is received.

In an example, decision-making algorithms may be provided relative to a surgical instrument. The surgical instrument may include surgical tools, monitors, displays, and the like. The decision-making algorithms may involve communication between one or more of a wearable, a surgical instrument, a surgical hub, and the cloud. A monitor with a visualization system may indicate that a surgical tool is located close to a vital organ, for example. The decision-making algorithms may send a notification based on the indication from the monitor. For example, the decision-making algorithms may learn that an advanced cutting instrument is being used. The decision-making algorithms may provide notifications based on the use of the advanced cutting instrument. The notifications provided may include noise from a wearable, based on the use of the advanced cutting instrument. The notifications provided may include a louder noise based on the volume of the advanced cutting instrument. The notifications provided may include turning the power down on the advanced surgical cutter based on the proximity to a vital organ.

In an example, decision-making algorithms may be provided to determine who to notify about detected information. The decision-making algorithms may determine a user, patient, and/or HCP to notify about detected information. The decision-making algorithms may determine the user, patient, and/or HCP to notify based on the priority of the notification. For example, the decision-making algorithm may notify a patient based on a low priority notification, such as low blood sugar. For example, the decision-making algorithm may notify a high-ranking HCP based on a high priority notification, such as signs pointing to a heart attack.

In an example, the decision-making algorithms may be provided in a wearable. The wearable may have access to patient information, such as biomarker information and/or electronic medical records. The wearable may monitor biomarkers, such as blood sugar, for example. The wearable may detect that a patient is a type-1 diabetic, based on electronic medical records. The wearable may send notifications based on a risk assessment. The risk assessment may be based on the blood sugar monitoring and the type-1 diabetes information, for example. The wearable may send a notification to the patient. The wearable may send a notification to the patient based on the risk assessment. The notification may notify the patient that blood sugar is low. The notification may direct a patient to receive insulin to mitigate the low blood sugar. The wearable may continue to monitor the patient after the notification. The wearable may determine that the notification was ignored. The wearable may determine that the notification was ignored based on the continued low blood sugar levels. The wearable may escalate the notification. The wearable may emit an audible notification, for example. The audible notification may alert other people in the same room as the patient. The wearable may continue to monitor the patient and escalate the procedure accordingly.

In an example, the wearable may communicate with local devices, such as other wearables, a surgical hub, and/or a cloud. The wearable may access information from the local devices. The accessed information may include biomarkers and healthcare records. The wearable may perform risk assessments based on the accessed information. The wearable may create models based on the access information. The created models may include one or more recovery modes (e.g., which may include a best recovery mode). The created models may include suggested procedural actions. The created models may include suggested surgical devices. The wearable may determine procedural actions based on the models and/or accessed information. The wearable may determine comorbidities based on the models and/or accessed information. The wearable may determine drug usage based on the models and/or accessed information. The wearable may determine pre-treatments based on the models and/or accessed information. The wearable may determine pre-scans based on the models and/or accessed information.

In an example, the wearables may include a memory. The memory may include a history of previous risk assessments, notifications, alerts, and/or models. The wearable may determine that a user, patient, and/or HCPs is not responsive to a certain alert based on the memory. The wearable may automatically elevate notifications based on the knowledge that the user, patient, and/or HCPs are not responsive to a specific notification.

Figure 100:
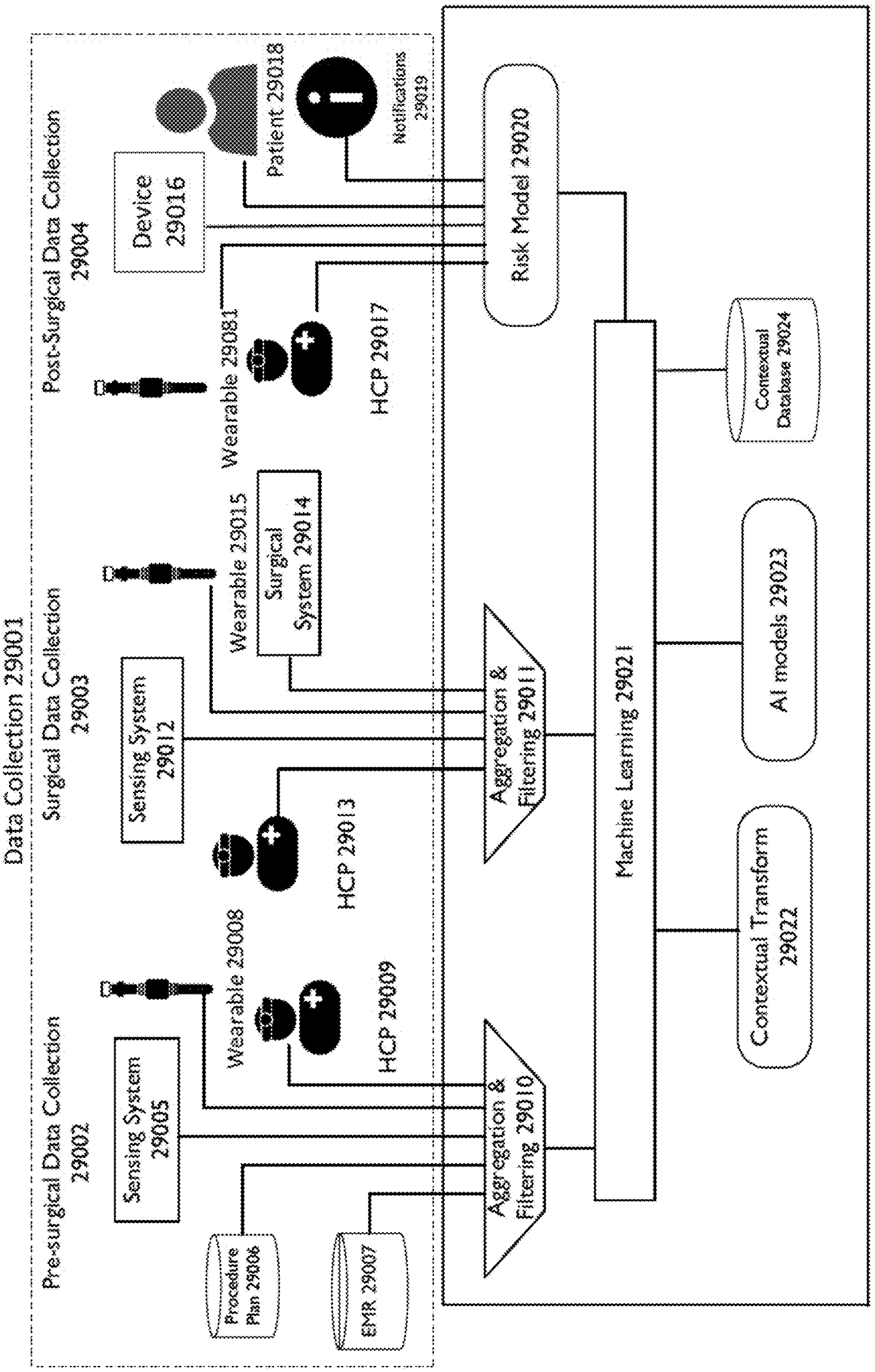
FIG. 100 depicts a block diagram of a system for providing a risk model analysis.

FIG. 100 depicts a block diagram of a system for providing a risk model analysis. The risk model analysis may include a data collection 29001. The risk model analysis may include aggregation and filtering, 29010 and 29011. The risk model analysis may include a risk model 29020. The risk model analysis may include machine learning 29021. The risk model analysis may include contextual transform 29022. The risk model analysis may include AI models 29023. The risk model analysis may include a contextual database 29024. The risk model analysis may include any combination of the data collection 29001, aggregation and filtering, 29010 and 29011, machine learning 29021, contextual transform 29022, AI models 29023, and contextual database 29024, for example.

Data collection 29001 may be provided. Data collection may include receiving data. Data collection 29001 may include one or more of pre-surgical data collection 29002, surgical data collection 29003, post-surgical data collection 29004, and the like. Data collection may include receiving data from one or more of a sensing system, 29005 and 29012, procedure plan 29006, electronic medical record (EMR) 29007, a wearable, 29008, 29015, and 29081, an HCP, 29009, 29013, and 29017, a surgical system 29014, a device 29016, a patient 29018, and notifications 29019. The pre-surgical data collection 29002 may include data collection from at least one the sensing system 29005, procedure plan 29006, EMR 29007, wearable 29008, and HCP 29009. The surgical data collection 29003 may include data collection from at least one of the sensing system 29012, HCP 29013, surgical system 29014, and wearable 29015. The post-surgical data collection 29004 may include data collection from at least one of the device 29016, HCP 29017, patient 29018, notifications 29019, and wearable 29081.

For example, the one or more sensing system, 29005 and 29012, may include one of a wearable, surgical sensing system, and the like, for example. The one or more sensing system, 29005 and 29012, may include any configuration of hardware and software devices suitable for sensing and presenting parameters, such as patient biomarkers, that may be relevant during a surgical procedure. The sensing system, 29005 and 29012, may measure and/or monitor biomarker data relating to a patient. The sensing system, 29005 and 29012, may be configured to measure and/or monitor heart-rate data, for example. The sensing system, 29005 and 29012, may include a wearable. For example, the sensing system, 29005 and 29012, may include a wristband, for example. The sensing system, 29005 and 29012, may incorporate or be incorporated into the sensing system 20001 as shown in FIG. 1B.

For example, the one or more wearable, 29008, 29015, and 29081, may include a sensing system. The one or more wearable may include a medical device, such as an insulin pump, for example. In an example, the wearable may be a wristband. The wearable may include a wristband configured to monitor blood sugar levels. The wearable may include a surgical sensing system, such as an IV machine, for example.

For example, the procedure plan 29006 may include data relating to a planned surgical procedure. The procedure plan 29006 may include procedural steps relating to the planned surgical procedure, for example. The procedure plan 29006 may include treatment plans relating to the planned surgical procedure, for example. The procedure plan 29006 may include surgical instruments relating to the planned surgical procedure, for example.

For example, the EMR 29007 may include patient medical records. The EMR 29007 may include any data source relevant to a patient in view of a health procedure. The patient medical records may include at least one of medical history of the patient, patient demographics, past procedures, medications, treatment plans, immunization dates, allergies, radiology images, laboratory and test results, notes, and the like, for example.

Data collection 29001 may include collecting data from the HCP, 29009 29013, and 29017. Data from the HCP, 29009, 29013, and 29017, may include any data relevant to the one or more surgical sensor systems, 29005 and 29012, surgical system 29014, and the like. Data from the HCP, 29009, 29013, and 29017, may include one or more inputs from the HCP. The inputs from the HCP may include a confirmation of the condition of a patient. The inputs from the HCP may include a confirmation of the biomarker data/vitals information of a patient.

Data collection 29001 may include collecting data from the surgical system 29014. The surgical system may include at least one of a surgical instrument, surgical visualization system, monitor, sound system, energy device, a wearable, and the like. For example, the surgical system may include a surgical hub. For example, the surgical system may include a surgical stapler. For example, the surgical system may include an endocutter, for example. Data from the surgical instrument may include surgical instrument parameters. The surgical instrument parameters may include surgical instrument power, for example. Data from the surgical visualization system may include location of surgical instruments in relation to a patient surgical site and/or organ. For example, data may include the distance between a surgical stapler and a close vital organ.

Data collection 29001 may include collecting data from the device 29016. The device 29016 may include a display device, for example. The device 29016 may include a surgical hub, for example. The device 29016 may include a wearable, for example. The device 29016 may include a display. The device 29016 may include a speaker. The device 29016 may be configured to show a notification.

Notifications 29019 may be provided. Notifications may include alerts. Notifications may include alerts relating to biomarkers, surgical instruments, surgical procedure, and the like. Alerts may include at least one of a sound, a vibration, a flash, and the like. For example, notifications may be provided based on an abnormal biomarker information. Notification may be provided based on a detected surgical complication, for example. Notifications may be provided based on a risk model analysis, for example. Notifications may be provided based on a risk model assessment for example.

Aggregation and filtering, 29010 and 29011, may be provided. Aggregation and filtering, 29010 and 29011, may be provided based on the data collection 29001. Aggregation and filtering, 29010 and 29011, may include transforming data. Aggregation and filtering, 29010 and 29011, may include deriving contextualized information. Aggregation and filtering, 29010, and 29011, may include data preparation. The data preparation may include data transforming steps, such as scaling, aggregating, and filtering. For example, the data preparation may include aggregating data received from at least one of the sensing system, procedure plan, EMR, wearables, HCP, surgical system, device, patient, and/or notification. For example, the data preparation may include filtering data received from at least one of the sensing system, procedure plan, EMR, wearables, HCP, surgical system, device, patient, and/or notification. The aggregation and filtering, 29010 and 29011, may be used to prepare and format the data for use in the contextual database 29024 and contextual transform 29022, respectively.

For example, the aggregation and filtering, 29010, may include filtering (e.g., to select specific sensor data from the stream of data from the pre-surgical data collection 29002). For example, the aggregation and filtering, 29010, may include averaging (e.g., to establish a baseline for a specific biomarker from the pre-surgical data collection 29002). For example, the aggregation and filtering, 29010, may include correlation analysis (e.g., to establish a baseline for relationships between and/or among specific biomarkers from the pre-surgical data collection 29002). For example, the aggregation and filtering, 29010, may include data translation (e.g., to coordinate format and/or datatype differences between a data source and the format and datatype expected by the contextual database 29024).

For example, the aggregation and filtering, 29011, may include filtering (e.g., to select specific sensor data from the stream of data from the surgical data collection 29003). For example, the aggregation and filtering, 29011, may include averaging (e.g., to establish a baseline for a specific biomarker from the surgical data collection 29003). For example, the aggregation and filtering, 29011, may include correlation analysis (e.g., to establish a baseline for relationships between and/or among specific biomarkers from the surgical data collection 29003). For example, the aggregation and filtering, 29011, may include data translation (e.g., to coordinate format and/or datatype differences between a data source and the format and datatype expected by the contextual database 29024).

A risk model 29020 may be generated. In an example, the risk model 29020 may include an analytical model. The analytical model may include computer implemented software, a series of parameters, or a probability, for example. The analytical model may include an artificial intelligence model. The artificial intelligence model may be trained. The analytical model may be trained to recognize patterns within a dataset, such as the data collection. The analytical model may be deployed. The analytical model may be deployed to apply the recognized patterns to data, such as biomarkers, to improve performance without human guidance. The analytical model may be deployed as a computer implemented program. The analytical model may be deployed as a part of a larger computing system. The analytical model may be deployed with a model performance parameter.

In an example, the analytical model may be deployed to an embedded device, such as a wearable. The analytical model may analyze received data, such as incoming patient data. The analytical model may perform an analysis. The analytics model may perform an analysis based on the received patient data. The analysis may generate an output, including but not limited to, a diagnosis, a notification, surgical complication, and the like. For example, a wearable may use an analytics model to analyze incoming heart rate data. The wearable may determine the heart rate indicates sepsis based on the analytics model and the heart rate data. The wearable may send a notification to the HCP based on the indicated sepsis.

In an example, the risk model 29020 may include a risk model assessment. The risk model assessment may be generated. The risk model assessment may be generated based on an analytical model. The risk model assessment may be generated based on the data collection. The risk model assessment may be generated based on the analytical model and the data collection. The risk model assessment may include a probability of a patient outcome, such as probability of sepsis, for example. For example, a risk model assessment may be calculated for the probability of sepsis based on an analytical model and received heart rate data.

Machine learning 29021 may be provided. Machine learning 29021 may be supervised and/or unsupervised as disclosed herein. Machine learning 29021 may include contextual transform 29022. Machine learning 29021 may include an AI model 29023. Machine learning 29021 may include a contextual database 29024. Machine learning 29021 may create analytical models, such as a risk model, that may be trained to recognize patterns within a dataset. The risk model may be deployed to apply the recognized patterns to data, such as biomarkers. The risk model may be deployed to a one or more device, such a wearable device, a cloud, a local server, a surgical hub, an edge computing device, and the like.

Machine learning 29021 may include training. The training may include receiving datasets, such as the data collection. The training may use the received datasets to improve the analytical model. For example, sepsis may be indicated based on an analytical model and received data. The HCP may be notified based on the indicated sepsis. The HCP may receive the notification and determine that the sepsis indication was incorrect. The HCP may input feedback to the analytical model. The analytical model may be trained based on the HCP feedback. The deployed analytical model may be updated as more live production data becomes available as training data.

Machine learning may include contextual transform 29022. The contextual transform 29022 may include transforming received data. The contextual transform 29022 may include transforming received data into contextual information. For example, the contextual transform 29022 may include transforming one or more patient data, such as biomarker data, into contextual information. The contextual information may include one or more of a medical complication, physiologic function, and the like.

In an example, analytical models may be trained using the contextual transform 29022. For example, contextual information determined based on the contextual transform 29022 may be applied to update the analytical models.

The contextual database 29024 may include a data storage medium. The contextual database 29024 may include a data storage medium for contextual information, such as any information relating to patient information and/or physiologic function. The contextual database 29024 may include the data transformed based on the contextual transform 29022. Datasets may be trained based on the contextual information stored in the contextual database 29024.

An artificial intelligence (AI) model storage 29023 may be provided. The AI model storage 29023 may include a storage medium. The storage medium may store analytical models, such as risk models. The analytical models may be generated. The analytical models may be generated based on the machine learning 29021. The analytical models stored may be deployed.

Figure 101A:
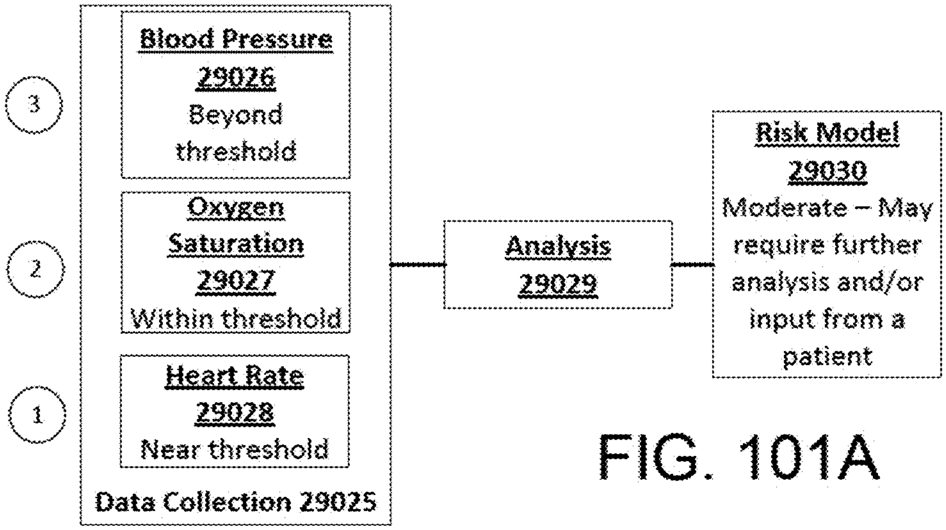
FIG. 101A depicts an example risk assessment performed by a wearable device using a risk model analysis.

FIG. 101A depicts an example risk assessment performed by a wearable device using a risk model analysis. The risk assessment may be performed based on data collection 29025. The risk assessment may be performed based on an analysis 29029. The risk assessment may be performed based on a risk model 29030. The risk assessment may be performed using a combination of data collection 29025, analysis 29029, and risk model 29030.

The data collection 29025 may include collecting data. The data collection 29025 may include collecting data from data streams from at least one of a sensing system, procedure plan, EMR, wearable, HCP, surgical system, device, patient, notification, and the like. The data collection 29025 may include a data stream of biomarker-related data, for example. As shown in FIG. 101A, the data streams may include blood pressure 29026, oxygen saturation 29027, and heart rate 29028 data, for example. The data collection 29025 may include data preparation. The data collection

29025 may include data preparation, such as aggregating and filtering, as shown in FIG. 100.

In an example, the analysis 29029 may include deploying a risk model. The selected risk model may include an analytical model. The analytical model may include a computer implemented program configured to generate an output based on received data. For example, the analytical model may include a program configured to generate a probability for patient outcomes based on patient data. The risk model may be selected based on available risk models.

In an example, the analysis 29029 may include creating a risk model. The risk model may be created based on a dataset. For example, a risk model may be created based on one or more biomarker datasets. The risk model may be trained. The risk model may be trained using machine learning.

In an example, the analysis 29029 may include calculating a risk assessment. The risk assessment may include a probability. The risk assessment may include a probability of a patient outcome. The risk assessment may be calculated based on the selected risk model. The risk assessment may be calculated based on the received patient data. The risk assessment may be calculated based on applying the selected risk model to the received patient data.

In an example, the analysis 29029 may include analyzing biomarker data in relation to one or more predefined thresholds. The one or more predefined thresholds may include a range indicating normal measurements for the measured biomarkers, for example. For example, the measured blood pressure 29026 may indicate the measured blood pressure is beyond a blood pressure threshold. For example, the measured oxygen saturation 29027 may indicate the measured oxygen saturation is within an oxygen saturation threshold. For example, the measured heart rate 29028 may indicate the measured heart rate is near a heart rate threshold. A risk assessment may be calculated based on the analyzed biomarker data in relation to the one or more predefined thresholds.

In an example, the data collection 29025 may include prioritization of the data streams. For example, the data collection 29025 may apply a weight to the data based on the prioritization. The data collection 29025, analysis 29029, and/or risk model 29030 may rank the incoming data streams in numerical order based on the prioritization, as shown in FIG. 101A. The heart rate 29028 may be prioritized as the most important data over other data streams and ranked with a number one, for example. The oxygen saturation 29027 may be prioritized as the second most important data and ranked with a number two, for example. The blood pressure 29026 may be prioritized as the third most important data and ranked with a number three, for example. The weight may be applied to the data based on the numerical ranking. The prioritization may be incorporated into a risk model.

In an example, the analysis 29029 may be provided based on the data collection 29025. For example, the analysis 29029 may be provided based on the collected blood pressure 29026, oxygen saturation 29027, and heart rate 29028. The analysis 29029 may be provided based on the one or more predetermined thresholds for the data streams. The analysis 29029 may be provided based on the prioritization of the data streams.

The risk model 29030 may be provided. The risk model 29030 may include a risk assessment. The risk assessment may be provided based on the data collection 29025. The risk assessment may be provided based on the analysis 29029. The risk assessment may be provided based on patient data. The risk assessment may be provided based on pre-surgical, surgical data, and/or post-surgical data. The risk model 29030 may be provided as shown in FIG. 100.

In an example, a severity of risk may be indicated, such as a risk of post-operation complication. The severity of risk may be indicated based on the risk assessment. The risk assessment may indicate a low, moderate, or high risk of post-operation complication, for example. A moderate risk assessment may include a request further analysis and/or an input from a patient. A high risk assessment may include contacting HCPs about the risk.

In an example, as shown in FIG. 101A, a risk assessment indicating a moderate risk may be provided. The risk assessment may be provided based on data collection 29025, analysis 29029, and the risk model 29030. The data collection 29025 may include blood pressure 29026, oxygen saturation 29027, and heart rate 29028 data streams. The moderate risk may be determined based on the measured blood pressure 29026, oxygen saturation 29027, and heart rate 29028. The moderate risk may be determined based on the measured biomarkers in relation to their respective predefined thresholds. For example, the moderate risk may be based on the combination of the blood pressure measuring beyond the predefined threshold, the oxygen saturation measuring within the predefined threshold, and the heart rate measuring near the predefined threshold. The analysis 29029 may be provided based on the biomarkers, the prioritization of the biomarkers, and the biomarkers in relation to the predefined thresholds. The risk assessment may be performed based on the analysis 29029 and the risk model 29030. The risk assessment for the blood pressure 29026, oxygen saturation 29027, and heart rate 29028, may indicate a moderate risk, for example. The risk assessment may prioritize the near normal heart rate measurement and the normal oxygen saturation measurement over the abnormal blood pressure measurement. The moderate risk determination may include a further analysis. The moderate risk determination may include a request for input from the patient.

Figure 101B:
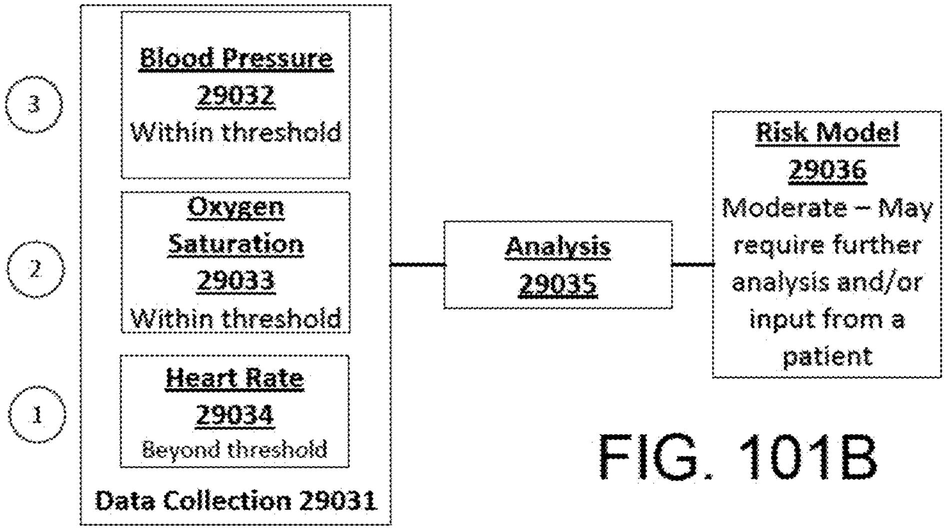
FIG. 101B depicts another example risk assessment performed by a wearable device using a risk model analysis.

FIG. 101B depicts another example risk assessment performed by a wearable device using a risk model analysis. The risk model analysis may include one of a data collection 29031, analysis 29035, and risk model 29036. The data collection 29031 may incorporate or be incorporated into the data collection 29025. The analysis 29035 may incorporate or be incorporated into the analysis 29029. The risk model 29036 may incorporate or be incorporated into the risk model 29030.

The data collection 29031 may include collecting data. The data collection 29031 may include collecting data from data streams from at least one of a sensing system, procedure plan, EMR, wearable, HCP, surgical system, device, patient, notification, and the like. The data collection 29031 may include a data stream of biomarker-related data, for example. As shown in FIG. 101B, the data streams may include blood pressure 29032, oxygen saturation 29033, and heart rate 29034 data, for example. The data collection 29031 may include data preparation. The data collection 29031 may include data preparation, such as aggregating and filtering, as shown in FIG. 100.

In an example, the analysis 29035 may include deploying a risk model. The selected risk model may include an analytical model. The analytical model may include a computer implemented program configured to generate an output based on received data. For example, the analytical model may include a program configured to generate a probability for patient outcomes based on patient data. The risk model may be selected based on available risk models.

In an example, the analysis 29035 may include creating a risk model. The risk model may be created based on a dataset. For example, a risk model may be created based on one or more biomarker datasets. The risk model may be trained. The risk model may be trained using machine learning.

In an example, the analysis 29035 may include calculating a risk assessment. The risk assessment may include a probability. The risk assessment may include a probability of a patient outcome. The risk assessment may be calculated based on the selected risk model. The risk assessment may be calculated based on the received patient data. The risk assessment may be calculated based on applying the selected risk model to the received patient data.

In an example, the analysis 29035 may include analyzing biomarker data in relation to one or more predefined thresholds. The one or more predefined thresholds may include a range indicating normal measurements for the measured biomarkers, for example. For example, the measured blood pressure 29032 may indicate the measured blood pressure is beyond a blood pressure threshold. For example, the measured oxygen saturation 29033 may indicate the measured oxygen saturation is within an oxygen saturation threshold. For example, the measured heart rate 29034 may indicate the measured heart rate is near a heart rate threshold. A risk assessment may be calculated based on the analyzed biomarker data in relation to the one or more predefined thresholds.

In an example, the data collection 29031 may include prioritization of the data streams. For example, the data collection 29031 may apply a weight to the data based on the prioritization. The data collection 29031, analysis 29035, and/or risk model 29036 may rank the incoming data streams in numerical order based on the prioritization, as shown in FIG. 101B. The heart rate 29034 may be prioritized as the most important data over other data streams and ranked with a number one, for example. The oxygen saturation 29033 may be prioritized as the second most important data and ranked with a number two, for example. The blood pressure 29032 may be prioritized as the third most important data and ranked with a number three, for example. The weight may be applied to the data based on the numerical ranking. The prioritization may be incorporated into a risk model.

In an example, the analysis 29035 may be provided based on the data collection 29031. For example, the analysis 29035 may be provided based on the collected blood pressure 29032, oxygen saturation 29033, and heart rate 29034. The analysis 29035 may be provided based on the one or more predetermined thresholds for the data streams. The analysis 29035 may be provided based on the prioritization of the data streams.

The risk model 29036 may be provided. The risk model 29036 may include a risk assessment. The risk assessment may be provided based on the data collection 29031. The risk assessment may be provided based on the analysis 29035. The risk assessment may be provided based on patient data. The risk assessment may be provided based on pre-surgical, surgical data, and/or post-surgical data. The risk model 29036 may be provided as shown in FIG. 100.

In an example, as shown in FIG. 101B, a risk assessment indicating a moderate risk may be provided. The risk assessment may be provided based on the data collection 29031, analysis 29035, and risk model 29036. The data collection 29031 may include blood pressure 29032, oxygen saturation 29033, and heart rate 29034 data streams. The moderate risk may be determined based on the analysis 29035. The moderate risk may be determined based on the measured biomarkers in relation to their respective predefined thresholds. For example, the moderate risk may be based on the combination of the blood pressure measuring within the predefined threshold, the oxygen saturation measuring within the predefined threshold, and the heart rate measuring beyond the predefined threshold. The moderate risk assessment may be determined based on a deployed risk model.

Figure 101C:
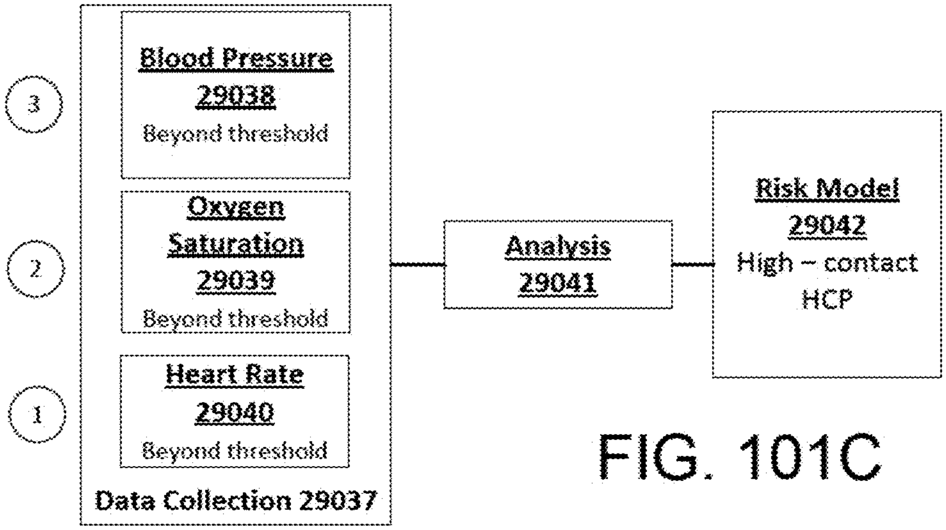
FIG. 101C depicts another example risk assessment performed by a wearable device using a risk model analysis.

FIG. 101C depicts another example risk assessment performed by a wearable device using a risk model analysis. The risk model analysis may include one of a data collection 29031, analysis 29035, and risk model 29036. The data collection 29031 may incorporate or be incorporated into the data collection 29025. The analysis 29035 may incorporate or be incorporated into the analysis 29029. The risk model 29036 may incorporate or be incorporated into the risk model 29030.

The data collection 29037 may include collecting data. The data collection 29037 may include collecting data from data streams from at least one of a sensing system, procedure plan, EMR, wearable, HCP, surgical system, device, patient, notification, and the like. The data collection 29037 may include a data stream of biomarker-related data, for example. As shown in FIG. 101C, the data streams may include blood pressure 29038, oxygen saturation 29039, and heart rate 29030 data, for example. The data collection 29037 may include data preparation. The data collection 29037 may include data preparation, such as aggregating and filtering, as shown in FIG. 100.

In an example, the analysis 29041 may include deploying a risk model. The selected risk model may include an analytical model. The analytical model may include a computer implemented program configured to generate an output based on received data. For example, the analytical model may include a program configured to generate a probability for patient outcomes based on patient data. The risk model may be selected based on available risk models.

In an example, the analysis 29041 may include creating a risk model. The risk model may be created based on a dataset. For example, a risk model may be created based on one or more biomarker datasets. The risk model may be trained. The risk model may be trained using machine learning.

In an example, the analysis 29041 may include calculating a risk assessment. The risk assessment may include a probability. The risk assessment may include a probability of a patient outcome. The risk assessment may be calculated based on the selected risk model. The risk assessment may be calculated based on the received patient data. The risk assessment may be calculated based on applying the selected risk model to the received patient data.

In an example, the analysis 29041 may include analyzing biomarker data in relation to one or more predefined thresholds. The one or more predefined thresholds may include a range indicating normal measurements for the measured biomarkers, for example. For example, the measured blood pressure 29038 may indicate the measured blood pressure is beyond a blood pressure threshold. For example, the measured oxygen saturation 29039 may indicate the measured oxygen saturation is within an oxygen saturation threshold. For example, the measured heart rate 29030 may indicate the measured heart rate is near a heart rate threshold. A risk assessment may be calculated based on the analyzed biomarker data in relation to the one or more predefined thresholds.

In an example, the data collection 29037 may include prioritization of the data streams. For example, the data collection 29037 may apply a weight to the data based on the prioritization. The data collection 29037, analysis 29041, and/or risk model 29042 may rank the incoming data streams in numerical order based on the prioritization, as shown in FIG. 101C. The heart rate 29030 may be prioritized as the most important data over other data streams and ranked with a number one, for example. The oxygen saturation 29039 may be prioritized as the second most important data and ranked with a number two, for example. The blood pressure 29038 may be prioritized as the third most important data and ranked with a number three, for example. The weight may be applied to the data based on the numerical ranking. The prioritization may be incorporated into a risk model.

In an example, the analysis 29041 may be provided based on the data collection 29037. For example, the analysis 29041 may be provided based on the collected blood pressure 29038, oxygen saturation 29039, and heart rate 29030. The analysis 29041 may be provided based on the one or more predetermined thresholds for the data streams. The analysis 29041 may be provided based on the prioritization of the data streams.

The risk model 29042 may be provided. The risk model 29042 may include a risk assessment. The risk assessment may be provided based on the data collection 29037. The risk assessment may be provided based on the analysis 29041. The risk assessment may be provided based on patient data. The risk assessment may be provided based on pre-surgical, surgical data, and/or post-surgical data. The risk model 29042 may be provided as shown in FIG. 100.

In an example, as shown in FIG. 101C, a risk assessment indicating a high risk may be provided. The risk assessment may be provided based on the data collection 29037, analysis 29041, and risk model 29042. The data collection 29037 may include blood pressure 29038, oxygen saturation 29039, and heart rate 29040 data streams. The high risk may be determined based on the analysis 29041. The high risk may be determined based on the measured biomarkers in relation to their respective predefined thresholds. For example, the high risk may be based on the combination of the blood pressure, oxygen saturation, and heart rate measuring beyond each of their respective thresholds. The high risk assessment may be determined based on a deployed risk model.

Figure 102:
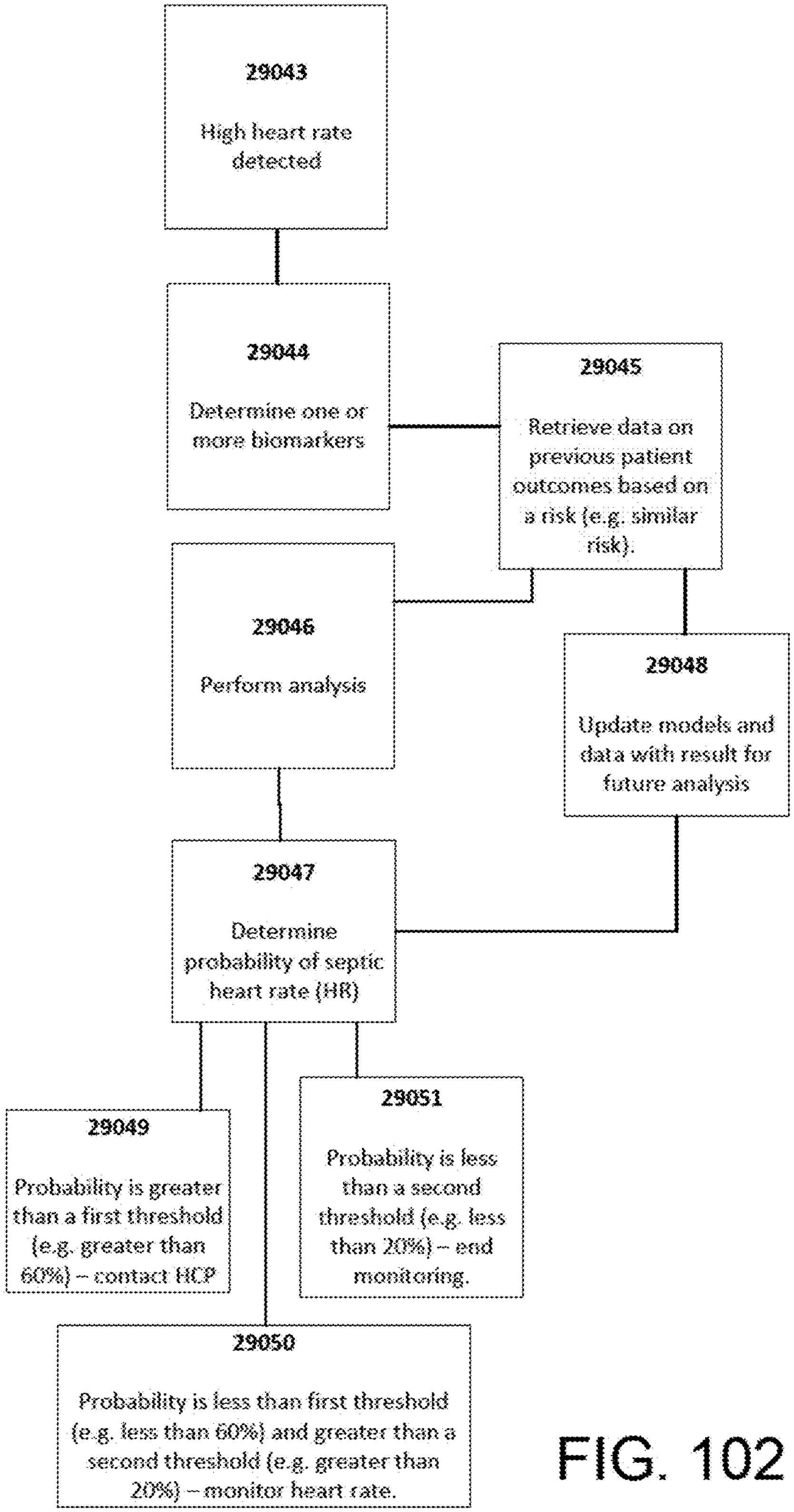
FIG. 102 depicts a block diagram of a system for analyzing one or more biomarkers using machine learning and a data collection.

FIG. 102 depicts a block diagram of a system for analyzing one or more biomarkers using machine learning and a data collection. At 29043, a first biomarker may be measured, such as heart rate, for example. The measured biomarker may indicate a risk of complication, such as septic heart rate, for example. At 29044, one or more biomarkers associated with the first biomarker and the complication may be determined. At 29045, previous patient outcome data and/or risk models based on a risk may be retrieved. At 29046, an analysis may be performed. At 29047, the risk of complication may be determined, such as probability of septic heart rate, for example. An output may be generated based on the risk of complication. At 29048, the previous patient outcome data and/or risk models may be updated.

In an example, a heart rate may be monitored. The heart rate may be monitored by a sensing system and/or wearable, for example. At 29043, based on the heart rate monitoring, an abnormal heart rate may be detected, such as a high heart rate, for example. A risk of a complication, such as septic heart rate, may be indicated. Risk of septic heart rate may be determined based on the heart rate measurement.

In an example, the risk of the complication may be determined by other related biomarkers. At 29044, the other related biomarkers may be determined. Risk of septic heart rate may be determined based on other related biomarkers, including but not limited to, menstrual cycle, blood pressure, blood pH, lactate (sweat), body temperature, heart rate variability, and/or oxygen saturation, for example. Risk of septic heart rate may be determined based on the combination of heart rate and the other related biomarkers.

In an example, data on previous patient outcomes may be retrieved. The previous patient outcomes may be retrieved based on a risk. The previous patient outcomes may be retrieved based on a similar risk. For example, the previous patient outcomes may include the one or more scenarios where risk of septic heart rate was indicated. The one or more scenarios may include when the risk of septic heart rate was similarly indicated and/or the same. The one or more scenarios may include when a high heart rate was measured. The previous patient outcomes may include a risk model. For example, previous patient outcomes may include data relating to risk of septic heart rate. The data relating to risk of septic heart rate may include previous scenarios of risk of septic heart rate. The data may include heart rate measurements and/or other related biomarker measurements.

In an example, an analysis of a risk of complication may be performed. The analysis may include the first biomarker, such as heart rate, for example. The analysis may include the determined one or more other related biomarkers. The analysis may include the retrieved previous patient data and/or risk models. The analysis may include any combination of the first biomarker, one or more other related biomarkers, and previous patient data.

In an example, the risk of complication may be determined. The risk of a septic heart rate may be determined, for example. The risk of complication may be determined based on the performed analysis. The risk of complication may include a probability. The risk of complication may include the probability of the complication occurring.

In an example, the previous patient outcomes and/or risk models may be trained. The trained risk models may provide more accurate data for analysis. Machine learning may be provided to train the previous patient outcomes and/or risk models. The machine learning may be supervised and/or unsupervised, for example. The machine learning may include updating the previous patient outcomes data and risk models with recent analyses. The machine learning's training process may update the risk model for predicting an outcome on new data set. For example, previous patient outcomes data and risk models may be updated with new analyses and determinations relating to risk of septic heart rate. The machine learning may use the determined risk of complication to train the risk model, for example. After an analysis, the previous patient outcomes and/or risk models may be updated to provide more accurate data for future analysis.

In an example, an output may be generated based on the determined risk of complication. The output may include a notification. The output may include a notification to contact the HCP, for example. The output may include an instruction to monitor a biomarker. The output may include an instruction to change the frequency of monitoring a biomarker. The output may include an instruction to end monitoring of a biomarker. The output may be generated based on the determined risk of complication in relation to one or more predefined thresholds.

At 29049, an output may be generated based on the probability of a complication exceeding a first threshold. The first threshold may be set at 60%, for example. For example, HCPs may be contacted based on a determined probability of septic heart rate exceeding 60%. At 29050, an output may be generated based on the determined probability of a complication exceeding a second threshold but falling below the first threshold. The second threshold may be set at 20%, for example. For example, an instruction to monitor heart rate may be generated based on the determined probability of a complication exceeding 20% but falling below 60%. At 29051, an output may be generated based on the probability of a complication falling below the second threshold. For example, an instruction to end monitoring may be generated based on the determined probability of a complication falling below 20%.

Figure 103:
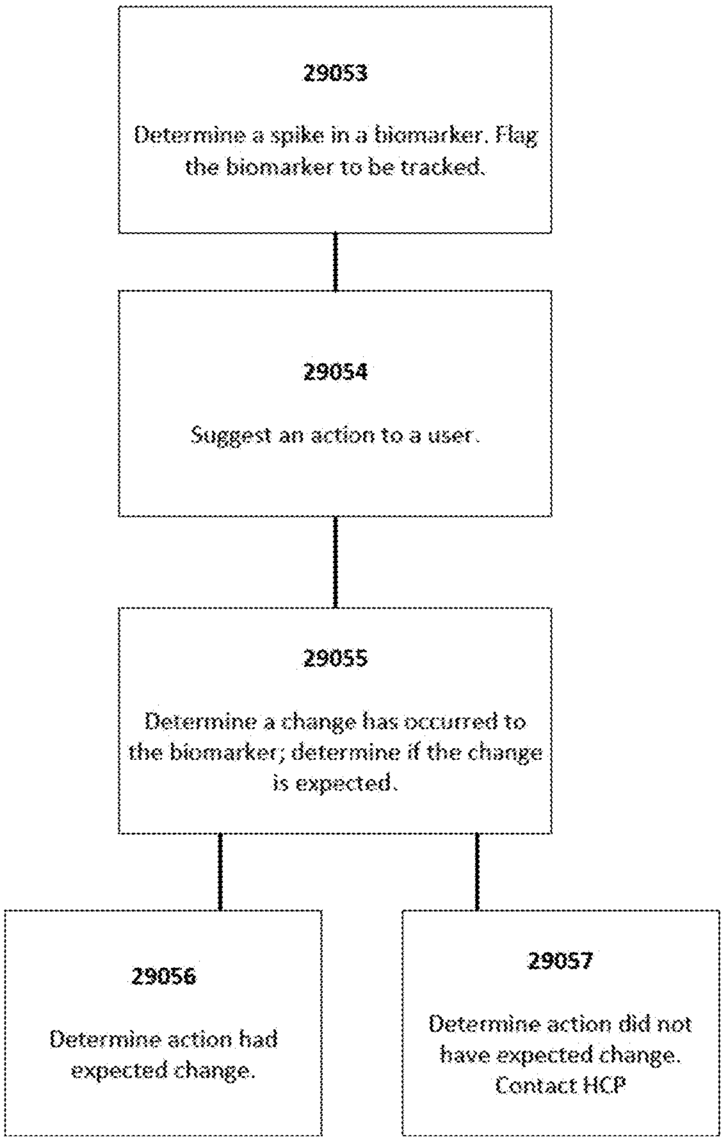
FIG. 103 depicts an example method for analyzing one or more biomarkers using machine learning and a data collection.

FIG. 103 depicts an example method for analyzing one or more biomarkers using machine learning and a data collection. The method may include determining a spike in a biomarker. The method may include flagging the biomarker to be tracked. The method may include suggesting an action to a user. The method may include determining that a change has occurred to the biomarker. The method may include determining whether the change is expected. The method may include determining the action had an expected change. The method may include determining the action did not have the expected change. The method may include contacting an HCP.

At 29053, a spike in may be determined from one or more biomarker measurements. For example, a spike in heart rate may be determined. Based on the determined spike, the biomarker may be flagged. For example, heart rate may be flagged. The biomarker flag may indicate instructions to track the biomarker.

At 29054, an action may be suggested. The action may be suggested based on the biomarker measurement spike. In an example, the suggested action may include an activity designed to normalize a biomarker spike. The action may include physical activity, such as walking, running, sitting, exercise, and the like. The action may include drug intake, such as intaking blood pressure medication, for example. The blood pressure medication may bring an expected change to a spike in blood pressure measurements. The action may include eating. Eating may bring an expected change to a spike in blood sugar level measurements. In an example, the action may be suggested to a user. The action may be suggested to HCPs.

At 29055, the monitored biomarker may be reassessed. The monitored biomarker may be reassessed to determine whether a change occurred to the biomarker. The monitored biomarker may be reassessed to determine whether a measured change was expected. For example, at 29056, an expected change may be determined to have occurred based on the suggested action. For example, at 29057, an expected change may be determined to have not occurred regardless of suggested action. HCPs may be contacted based on the lack of expected change.

In an example, an action may be suggested to normalize a biomarker spike. For example, a user may be suggested to eat to normalize a low blood sugar measurement. Eating may correlate with an increase in blood sugar measurement. Blood sugar levels may be monitored to determine whether the change in blood sugar levels occurred. Blood sugar levels may be monitored to determine whether the change in blood sugar levels was expected. Blood sugar levels may be monitored to determine whether an expected change in blood sugar levels occurred based on the suggested eating. The HCPs may be notified based on a determination that the suggested action did not have the expected change.

Figure 104:
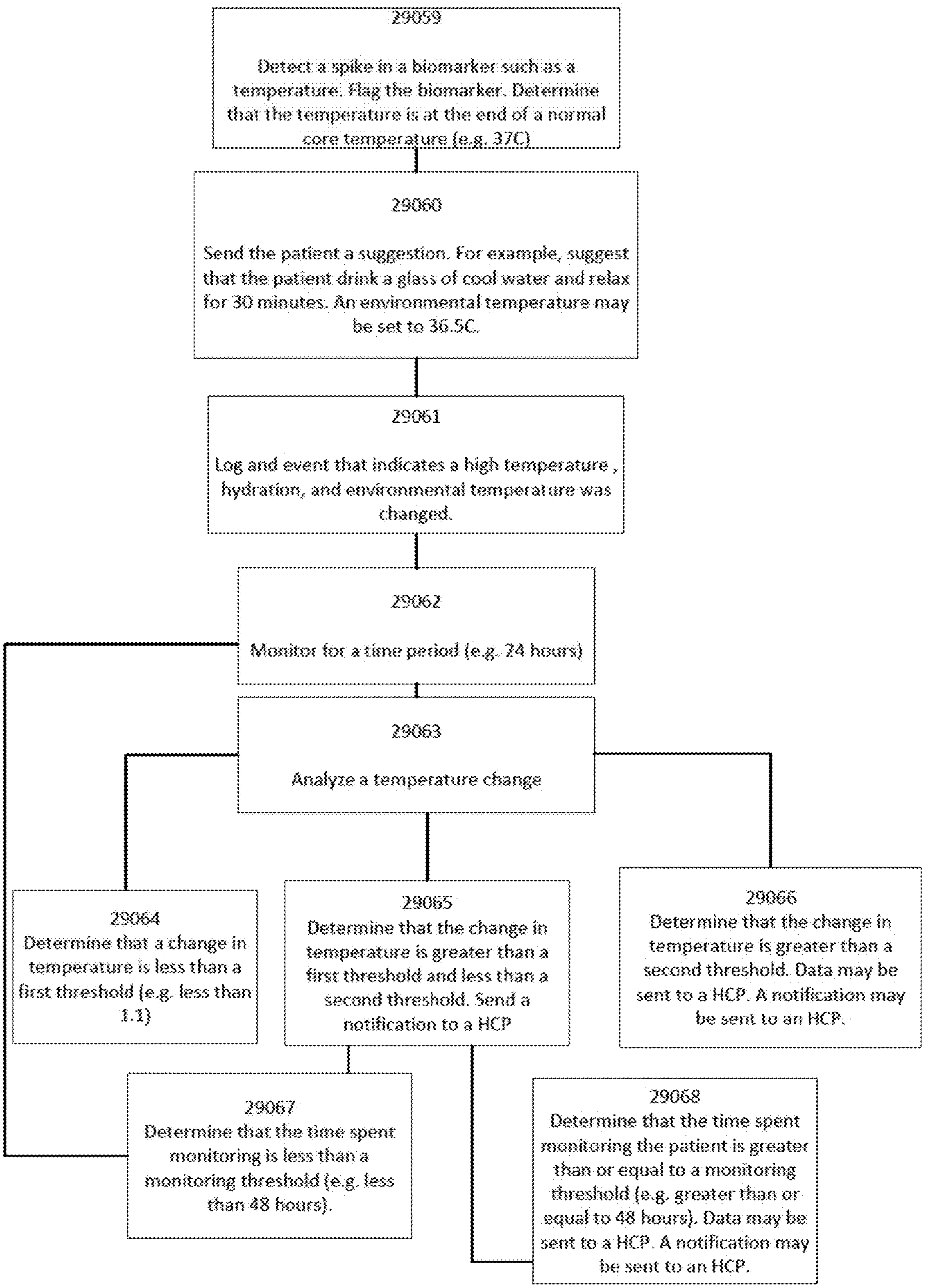
FIG. 104 depicts an example method for analyzing one or more biomarkers to determine whether to notify a patient and/or a health care provider.

FIG. 104 depicts an example method for analyzing one or more biomarkers to determine whether to notify a patient and/or a health care provider. For example, the one or more biomarkers analyzed may indicate a surgical complication, such as sepsis. A biomarker may be monitored, such as temperature, for example. At 29059, a spike in the monitored biomarker may be detected. The biomarker may be flagged. The biomarker may be flagged based on the detected spike. The abnormality of the biomarker spike may be determined. The abnormality of the biomarker spike may be determined based on a predefined range of values. For example, a measurement of 37 degrees Celsius for core body temperature may indicate that the core body temperature is at the end of a normal core temperature.

At 29060, a suggestion may be sent. The suggestion may be sent to a patient. The suggestion may include an action. The suggestion may include an action predicted to resolve abnormal biomarker measurements. For example, the suggestion may include a recommendation that the patient drink a glass of cool water. Drinking a glass of cool water may reduce core body temperature. For example, the suggestion may include a recommendation that the patient relax for 30 minutes. Relaxation may reduce core body temperature. For example, the suggestion may include a recommendation that the patient set environmental temperature to 36.5 degrees Celsius. Exposure to an environmental temperature below core body temperature may reduce core body temperature.

At 29061, an event may be logged. The event may be logged based on a biomarker measurement. The event may be logged based on a biomarker measurement spike. For example, an event may be logged based on a high core body temperature. For example, an event may be logged based on a measured hydration. The event may be logged based on an environment. For example, an event may be logged based on a measured environment temperature. The event may be logged based on a change in environment. For example, an event may be logged based on a change in environmental temperature. The logged event may indicate at least one of a biomarker measurement and an environment at a point in time. The logged event may include a timestamp based on the time of event logging.

At 29062, the patient may be monitored. The biomarkers of the patient may be monitored. The environment of the patient may be monitored. The patient may be monitored after a biomarker measurement spike. The patient may be monitored for a predefined set of time. The patient may be monitored for a predefined set of time after a biomarker measurement spike. For example, the patient may be monitored for 24 hours after a detected core body temperature spike.

At 29063, a change in biomarker measurement may be analyzed. The change in biomarker measurement may be analyzed based on an initial logged event. The change in biomarker measurement may be analyzed based on a current measurement. The change in biomarker measurement may be analyzed after a monitoring period. For example, the change in biomarker measurement may be analyzed after a 24-hour monitoring period.

In an example, at 29064, the analysis of the change in biomarker measurement may be determined to be less than a first threshold. The first threshold may be a predefined value. For example, the first threshold for change in temperature may include 1.1 degrees Celsius. For example, the change in temperature may be determined to be less than 1.1 degrees Celsius.

In an example, at 29065, the analysis of the change in biomarker measurement may be determined to be greater than the first threshold and less than a second threshold. The second threshold may be a predefined value. For example, the second threshold for change in temperature may include 1.5 degrees Celsius. For example, the change in temperature may be determined to be greater than 1.1 degrees Celsius and less than 1.5 degrees Celsius. A notification may be sent to an HCP. The notification may be sent based on the determination that the change in temperature is greater than 1.1 degrees Celsius and less than 1.5 degrees Celsius, for example.

The biomarker may continue to be monitored. The biomarker may continue to be monitored based on the length of time spent monitoring the threshold. The length of time spent monitoring the threshold may be determined. For example, at 29067, the length of time spent monitoring the threshold may be determined to be less than a predefined time, such as 48 hours, for example. The biomarker may continue to be monitored based on the length of time spent monitoring the threshold being less than 48 hours, for example.

For example, at 29068 the length of time spent monitoring the threshold may be determined to be greater than or equal to the predefined time. The biomarker measurements may be sent to an HCP. The biomarker measurements may be sent to the HCP based on the determined change in measurement being between the first and second threshold. The biomarker measurements may be sent to an HCP based on the length of time spent monitoring the threshold being greater than the predefined time. The HCP may be contacted. The HCP may be contacted based on the determined change in measurement being between the first and second threshold. The HCP may be contacted based on the length of time spent monitoring the threshold being greater than the predefined time.

In an example, at 29066, the analysis of the change in biomarker measurement may be determined to be greater than the second threshold. For example, the change in temperature may be determined to be greater than 1.5 degrees Celsius. The biomarker measurement data may be sent to the HCP based on the determination that the change in temperature is greater than the second threshold. The HCP may be notified based on the determination that the change in temperature is greater than the second threshold.

Figure 105:
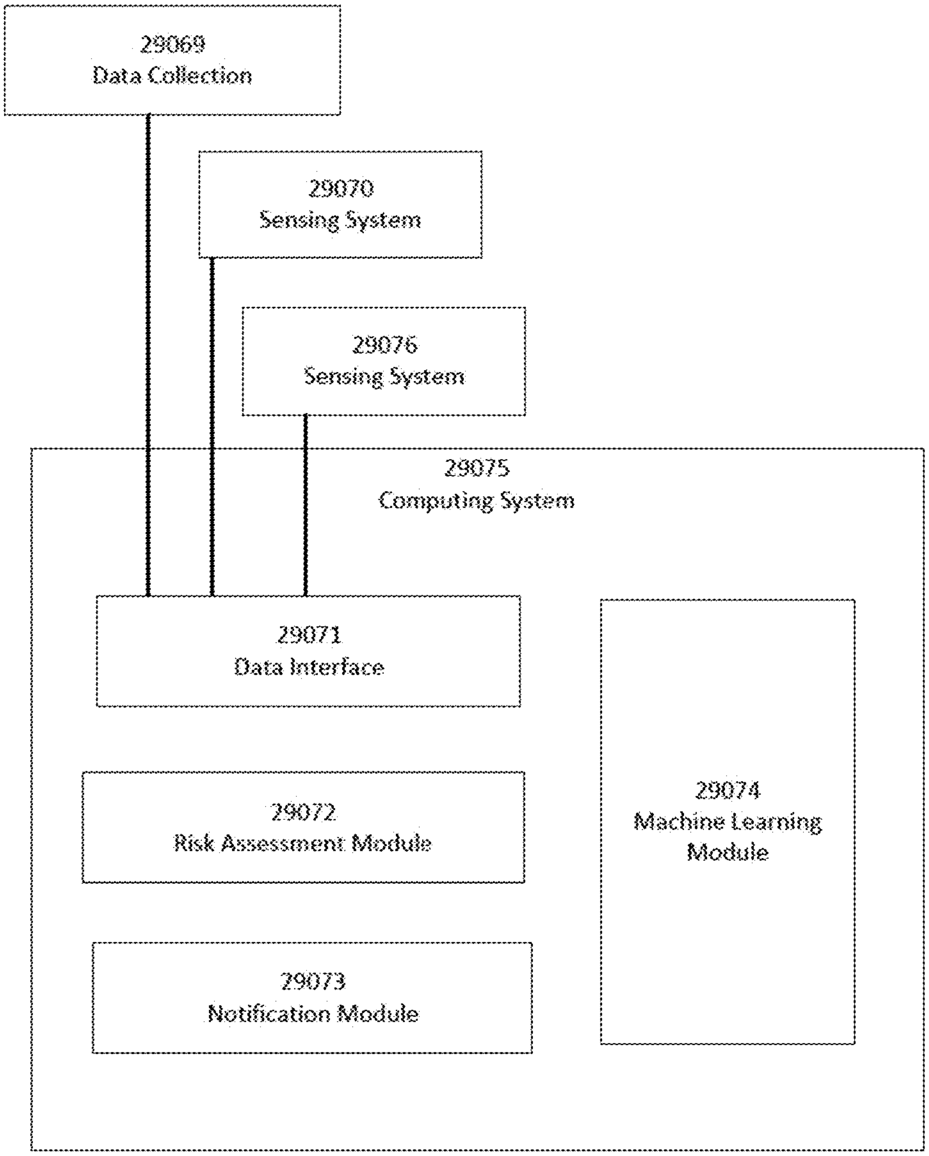

FIG. 105 depicts a block diagram of a system for controlling notification and/or calculating outcome probabilities. The system may include a computing system 29075. The computing system 29075 may include a wearable. The computing system 29075 may include at least one of a data interface 29071, risk assessment module 29072, notification module 29073, and machine learning module 29074.

The computing system 29075 may send and receive data streams. The computing system 29075 may communicate with a data collection 29069. The data collection 29069 may include medical data. The data collection 29069 may include biomarker data. The data collection 29069 may include EMR. The computing system 29075 may communicate with one or more sensing systems, 29070 and 29076. The computing system 29075 may send and receive data streams with at least one of a data collection 29069 and one or more sensing systems, 29070 and 29076, through the data interface 29071.

In an example, the data interface 29071 may aggregate data. The data interface 29071 may aggregate data received from the data collection 29069 and/or the one or more sensing systems, 29070 and 29076. The data interface 29071 may filter data. The data interface 29071 may filter data received from the data collection 29069 and/or the one or more sensing systems, 29070 and 29076. The data interface 29071 may communicate with at least one of the risk assessment module 29072, notification module 29073, and machine learning module 29074.

In an example, the data interface 29071 may include data preparation. Data preparation may include data preprocessing procedures, such as data formatting, data cleaning, and data sampling. Data preparation may include data transforming procedures.

In an example, the risk assessment module 29072 may calculate outcome probabilities. The outcome probabilities may include a probability of a medical complication. The outcome probabilities may include a probability of a physiologic condition. The outcome probabilities may include a probability of a surgical outcome. The risk assessment module 29072 may calculate outcome probabilities based on data from the data collection 29069. The risk assessment module 29072 may calculate outcome probabilities based on data from the sensing systems, 29070 and 29076. The risk assessment module 29072 may calculate outcome probabilities based on data from the data interface 29071.

In an example, the risk assessment module 29072 may calculate outcome probabilities based on a risk model. The risk model may include a data trend, table, artificial intelligence model, and the like. The risk model may be obtained. The risk model may be obtained based on at least one of patient data, biomarker data, EMR, and the like. The risk model may provide a situation awareness.

In an example, the notification module 29073 may control notification. The notification module 29073 may provide notifications. The notification module 29073 may provide notifications based on the data interface 29071. The notification module 29073 may provide notifications based on the risk assessment module 29072. The notification module 29073 may provide notifications based on the machine learning module 29074. The notification module may provide notifications based on the data collection 29069. The notification module may provide notifications based on the one or more sensing systems, 29070 and 29076.

The notifications may include alerts, for example. The notifications may include a sound, vibration, display, and the like. The notifications may include suggested actions. The suggested actions may include actions predicted to resolve abnormal data. The suggested actions may include a recommendation to eat food to resolve low blood sugar, for example. In an example, the notification module 29073 may provide flags. For example, the notification module 29073 may provide flags for detected abnormal data.

The notifications may be sent. For example, the notifications may be sent to a patient, HCP, user, and the like. The notifications may be sent to other devices. For example, the notifications may be sent to a surgical hub. For example, the notifications may be sent to a sensing system. For example, the notification may be sent to a wearable. For example, the notification may be sent to a surgical system.

In an example, the notification module 29073 may include escalation procedure. The escalation procedure may include increasing the intensity of a notifications based on the notification importance. For example, the escalation procedure may provide a more intense notification, such as an alarm, when it detects an imminent heart attack. For example, the escalation procedure may provide a minor notification, such as a vibration on a wrist wearable, when it detects low blood sugar. The escalation procedure may include sending notifications to people based on the notification importance. A notification with higher importance may be sent to the HCP, for example. A notification with lower importance may be sent to the user, for example The machine learning module 29074 may provide machine learning. Machine learning may be supervised and/or unsupervised. Machine learning may include training models, such as risk models for example. Machine learning may include training models based on a dataset. For example, models may be trained based on one or more of a data collection and a sensing system. The models may be trained to recognize patterns within a dataset. The models may be deployed to apply the recognized patterns to data, such as biomarkers. The trained model may be deployed to one or more devices, such as a wearable device, a cloud, a local server, a surgical hub, and the like.

The machine learning module 29074 may include model updates. For example, a deployed model may be updated as false positives and/or false negatives are predicted on live production data. For example, a deployed model may be updated as more live production data becomes available as training data. The deployed model may be further trained, validated, and tested with such additional live production data.

Figure 106:
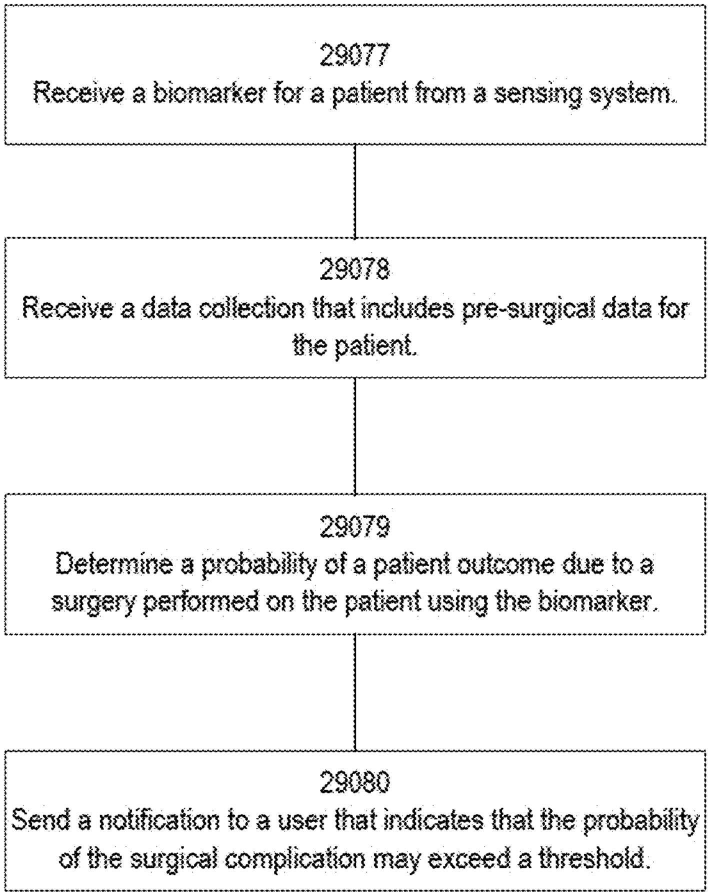

FIG. 106 depicts a method for controlling notifications and/or calculating outcome probabilities. The method may include receiving a biomarker for a patient from a sensing system. The method may include receiving a data collection that includes pre-surgical data for the patient. The method may include determining a probability of a patient outcome due to a surgery performed on the patient using the biomarker. The method may include sending a notification to a user that indicates that the probability of the surgical complication may exceed a threshold.

At 29077, a biomarker may be received. A biomarker for a patient may be received. The biomarker for a patient may be received from a sensing system. The sensing system may include one or more of a wearable, surgical system, and the like.

At 29078, a data collection may be received. The data collection may include pre-surgical data. The data collection may include pre-surgical data associated with a patient. The data collection including pre-surgical data for the patient may be received.

At 29079, an outcome probability may be determined. The outcome probability may include the probability of a patient outcome occurring. The patient outcome may include a surgical complication, medical condition, physiologic function, and the like. The outcome probability may be determined based on a performed surgery. The outcome probability may be determined based on the received biomarker. For example, the outcome probability of a patient outcome may be determined based on the surgery performed on the patient using the biomarker.

At 29080, a notification may be sent. The notification may be sent to a user. The notification may indicate the determined outcome probability. The notification may indicate that the determine outcome probability may exceed a threshold. For example, a notification may be sent to a user that indicates the probability of the surgical complication may exceed a threshold.

Automated system decision-making algorithms based on biomarker monitoring may include local reaction response and/or notification determination. Local response and notification determination may include interactive algorithm control on notification and calculated outcome probabilities between a wearable and a hub system. Adjustment of wearable notification and algorithms may be provided. The adjustment of wearable notification and algorithms to display functional combinations of wearable collected data streams may be provided. The adjustment of wearable notification and algorithms to display functional combinations of wearable collected data streams may be provided based on intercommunication of a remote system and a wearable device. The remote system may include data not solely monitored by the wearable device. Notification and display of at least one probability, risk, and resulting physiologic parameter may be provided. The notification and display may be provided based on a predefined threshold. The threshold may include at least one of a baseline, a goal, a minimum adjustment for an improved outcome, and a guideline.

Local response and notification determination may include predictive decision-making. Local response and notification determination may include risk assessment modeling. Local response and notification determination may include escalation of reaction. Local response and notification determination may include user interaction. Local response and notification determination may include situational severity analysis. Local response and notification determination may include interpreting multi-parameter longitudinal records.

Predictive decision-making may be provided. Predictive decision-making may draw conclusions. Predictive decision-making may provide system adjustments. Predictive decision-making may use previous trends and/or data conclusion. Predictive decision-making may provide system adjustments before data trends suggest an adjustment. Predictive decision-making may include predicted based system adjustments based on biomarker trends, for example.

Predictive based system adjustments based on biomarker trending may include prediction predicated decision-making. Prediction predicated decision-making may use a created model. Prediction predicated decision-making may use the created model to understand a situational awareness. Prediction predicated decision-making may use the created model to understand the situational awareness based on currently measured patient biomarkers. Prediction predicated decision-making may be used in combination with other biomarker indicators. The other biomarker indicators may include leading indicators of trends. Control systems may be preemptively adjusted based on the combination of prediction predicated decision-making and other biomarkers. The preemptive adjustment may avoid a biomarker from moving outside a normal range value.

In an example, predictive based system adjustments may include supervised learning. Predictive based system adjustments may include feature extraction, training, and/or testing procedures. The feature extraction, training, and/or testing procedures may be used during the prediction of data behavior. Predictive decision-making may control another system. Predictive decision-making may influence parameters of other systems. For example, predictive decision-making may influence the sampling rate, data collection type, or notification to a user of the other systems.

For example, the predictive models may include blood glucose level prediction, mortality prediction by clustering electronic health data, stress level prediction, and the like. Predictive models may be used in a predictive decision making system for dialysis patients, for example.

Peri-operative (e.g., surgical) predictive based system adjustments may be provided. In an example, the amount of fluids delivered to a patient during and after a procedure may be provided. The amount of fluids delivered to a patient during and after a procedure may have acute effects on blood pressures and the potential for hemostasis related complications. Intra-op measurements of blood pressure may be controlled through methods controlled by the anesthesiologist. The measurement of patient blood pressure, within the context of information about procedure duration, patient blood loss, medications delivered that may affect blood pressure, and the like, may be used to inform the deliver rate and volume of fluids intraoperatively. Understanding the full context of the situation and history with the patient blood pressure may inform the anesthesiologist pull the correct lever to keep blood pressure in the targeted range without the excessive use of fluids. The peri-operative predictive based system adjustments may be important for patients requiring special drug therapies to deal with clotting and the like that would increase the likelihood of hemostasis related complications.

Pre-operative (e.g., pre-surgical) and post-operative (e.g., post-surgical) predictive based system adjustments may be provided. For example, pre-operative and post-operative predictive based system adjustments may be provided for pain management drug administration, cognitive impacting drug distribution, stress level and other affected biomarker monitoring, and the like. In an example, insulin distribution may be adjusted. The insulin distribution may be adjusted before blood glucose levels become critical. The insulin distribution may be preemptively adjusted based on blood glucose level monitoring and control of an insulin pump. Blood glucose level monitoring and control of an insulin pump may use heart rate variability and/or physical activity monitoring to determine eating and calorie burn rates. The insulin distribution may be preemptively adjusted based on the eating and calorie burn rates.

Risk assessment modeling may be provided. Risk assessment modeling may indicate a probability of issue development from a surgery. The probability of issue development from a surgery may be indicated based on measured biomarkers of a patient before and after surgery. The risk assessment modeling may include a wearable that incorporates pre-operative and/or post-operative data in a risk model with post-operative data. The risk assessment modeling may include coupling biomarkers for discernment between a healthy and concerning output of a biomarker.

In an example, the wearable incorporating pre-operative and/or post-operative data in a risk model with post-operative data may include hub communication of wearable risk model analysis. The hub communication of wearable risk model analysis may enable on-the-fly monitoring for complications. In an example, HCPs may be alerted to a potential problem based on hub communication of the wearable risk model analysis.

In an example, a wearable may incorporate intra-operative esophagus temperature measurement with post-operatively measured metrics. The post-operatively measured metrics may include heart rate signal changes, hematocrit, and the like. Patient risk of atrial-esophageal fistula may be determined. The patient risk of atrial-esophageal fistula may be determined based on the intra-operative esophagus temperature measurement and post-operatively measured metrics. Post-operative data weight may be determined based on the intra-operative esophagus temperature measurement and post-operatively measured metrics. Whether the post-operative data weight is greater than without intra-operative measurement abnormalities may be determined. Esophageal temperature excursion during ablation may indicate high risk for atrial-esophageal fistula. Post-surgical monitoring may be performed based on atrial-esophageal fistula risk. For example, temperature excursions above 39 degrees Celsius may indicate increased risk of esophageal injury. For example. temperature excursions of 2 degrees Celsius or more above baseline may indicate increased esophageal risk.

The post-surgical monitoring may include computed tomography (CT) scans, radiographs, occult blood stool testing, upper endoscopy, and the like. Changes to diet may be recommended to reduce excessive force on esophagus during healing. Diet changes may include a semi-solid diet, liquid diet, and the like.

In an example, a risk level may be output to HCPs based on hub communication of the wearable risk model analysis. The associated risk level may be calculated. The associated risk level may be calculated based on weighting of a biomarker to fit specific post-operation risk. For example, a scenario may include monitoring biomarkers, such as blood pressure, oxygen saturation, and heart rate. The biomarkers may include a weighting scale, such as heart rate ranking the most important, oxygen saturation the next more important, and blood pressure the least important, for example. An analysis may be performed on the monitored biomarkers based on the weighting scale.

For example, an analysis may determine that blood pressure levels are in an abnormal range. The analysis may determine that the oxygen saturation levels are in a normal range. The analysis may determine that the heart rate is near an abnormal range. The analysis may generate an output. The output may include the risk level. The risk level may indicate a moderate risk. The risk level may indicate a moderate risk based on the weighted biomarker analysis. Further analysis may be provided. Further analysis may be provided based on the indicated moderate risk. Input from the patient may be requested. Input from the patient may be requested based on the indicated moderate risk.

For example, an analysis may determine that blood pressure levels are in a normal range. The analysis may determine that the oxygen saturation levels are in a normal range. The analysis may determine that the heart rate levels are in an abnormal range. The analysis may generate a risk level based on the weighted biomarker analysis. The risk level may indicate a moderate risk. The risk level may indicate a moderate risk based on the weighted biomarker analysis.

For example, an analysis may determine that blood pressure levels are in an abnormal range. The analysis may determine that oxygen saturation levels are in an abnormal range. The analysis may determine that the heart rate levels are in an abnormal range. The analysis may generate a risk level based on the weighted biomarker analysis. The risk level may indicate a high risk. The HCP may be contacted. The HCP may be contacted based on the high risk level.

In an example, the coupling of biomarkers for discernment between a healthy and concerning output of a biomarker may include machine learning. The machine learning may use previous patient data. The coupling of biomarkers for discernment between a healthy and concerning output of a biomarker may include a system automated discrimination between poor data and unhealthy biomarkers.

For example, a first biomarker, such as heart rate may be monitored. A spike of a high heart rate may be detected. Data associated with the first biomarker may be retrieved. For example, data associated with a heart rate biomarker may include biomarkers such as menstrual cycle, blood pressure, blood pH, lactate (sweat), body temperature, heart rate variability, oxygen saturation, and the like. A database on previous patient outcomes may be accessed. The database on previous patient outcomes based on the same risk may be accessed. An analysis may be provided. The analysis may generate an output. The analysis may generate an output based on one or more of the first biomarker, the related biomarkers, and the previous patient outcomes. The output may include a probability. The output may include a probability of a patient outcome, such as risk probability for septic heart rate, for example. The output may be fed into the database on previous patient outcomes for future analysis. Based on the generated probability of the patient outcome, the HCP may be contacted. For example, the HCP may be contacted if the risk percentage chance of septic heart rate exceeds 60%. Based on the generated probability of the patient outcome, the biomarker may be monitored. For example, heart rate may be monitored if the risk percentage chance of septic heart rate falls between 20% and 60%.

Escalation of reaction may be provided. Escalation of reaction may be provided based on number of events, severity, monitoring frequency of the HCP, and the like. In an example, escalation of reaction may include system flagging for automated monitoring. System flagging for automated monitoring may include a marker flag to a patient and a light flag to HCPs to monitor, for example.

For example, a biomarker may be monitored, such as blood pressure. A spike in the biomarker may be detected, such as a spike of blood pressure. The spike in the biomarker may be flagged. A first pass suggestion may be generated. The first pass suggestion may include a suggested action. The suggested action may include an action that may resolve the spiked biomarker, such as taking a walk. A change in biomarker data may be analyzed. The analysis may include determining whether the change in biomarker data matches an expected change in biomarker data. An HCP may be contacted based on the determination whether the change in biomarker data matches the expected change.

For example, a biomarker may be monitored, such as core body temperature. A spike in the core body temperature may be detected. The spike may be flagged. The spike may indicate a surgical complication, such as sepsis. Body temperature patterns may predict hospital-acquired sepsis in non-feverish adult intensive care unit patients. The spike may be flagged based on the core body temperature in relation to a normal core body temperature threshold. The spike may be flagged when core body temperature exceeds 37 degrees Celsius, for example. A first pass suggestion may be generated, such as a recommendation to drink a glass of cool water, relax for 30 minutes, set environmental temperature to 36.5 degrees Celsius, and the like, for example. An event may be logged. The event may include the biomarker spike. The event may include related biomarker data, such as hydration data. The event may include related environmental data, such as environmental temperature. The biomarker may be monitored. The biomarker may be monitored for a set time, such as 24 hours. The biomarker may be analyzed after the monitoring period. The change in biomarker, such as temperature change, may be analyzed. An HCP may be contacted based on the analyzed biomarker change. Data may be sent to the HCP based on the analyzed biomarker change. The HCP may be contacted and/or data may be sent to the HCP when the greatest change in temperature equals or exceeds 1.5 degrees Celsius. The HCP may be notified based on the analyzed biomarker change. The HCP may be notified when the greatest change in temperature falls between 1.1 degrees Celsius and 1.5 degrees Celsius.

In an example, the escalation may be keyed off of number of occurrences. The escalation may be keyed off of number of occurrences within a predefined time frame. The escalation may be keyed off of a severity of occurrence. The escalation may be keyed off of an increasingly detrimental indication of the biomarker. The escalation may be keyed off a time since the event occurred. The escalation may be keyed off of a time since the event occurred without HCP review. The escalation may be keyed off of a key threshold. The scalation may be keyed off of a key threshold which have a higher weighted issue value than lower.

Escalation may be increased if previous escalations recently occurred. For example, a temperature threshold may be flagged as a first marker requiring an HCP review. The attending HCP may respond quickly. The HCP response may include the determination that the flagged temperature threshold is a non-critical issue. A second more severe threshold may be exceeded. The second more severe threshold may include a critical threshold value. The second more severe threshold may be exceeded within a predefined time of the first flag. The notification for the second threshold may be escalated. The escalated notification may include sending the flag to the physician in addition to the attending HCP. The escalated notification may include data associated with the flagged measurements. The data associated with the flagged measurements may include current values and/or treatment progression data. A system may recognize that the situation includes escalating issues. The escalating issues may indicate the situation is not under control.

User interaction may be provided. User interaction may be provided as a response means. User interaction may be provided as a response means for monitored markers. User interaction may be provided as a response means for suggestions of handle ability. User interaction may be provided as response means for accommodating actions to mitigate responses for low risk, low severity events.

For example, daily user feedback may be provided. Daily user feedback generated by wearable analysis to improve correction may be provided. On-the-fly and/or daily feedback may be provided. On-the-fly and/or daily feedback may be provided to a user. On-the-fly and/or daily feedback may be provided on monitored changes. On-the-fly and/or daily feedback may be provided on events for low probability and low severity risk events and/or triggers. On-the-fly and/or daily feedback may be provided to encourage correction of the measure issue or minimization of its effects on upcoming procedures.

For example, the user feedback may include daily suggestions. The user feedback may include daily suggestions based on biomarkers. For example, disruptions in sleep may be detected. A daily suggestion to sleep with the tv off may be provided. The daily suggestion to sleep with the tv off may be provided based on detected disruptions of sleep. Disruptions in sleep may increase risk of infection. For example, change in circadian rhythm may be detected. A daily suggestion may include a notification to keep a consistent bedtime and/or adjust bedtime. The notification to keep a consistent bedtime and/or adjust bedtime may include a notification to the user of upcoming consistent bedtime and/or display averages of the previous week's normal time with the outlier also shown, for example. A daily suggestion to sleep with light exposure between two thresholds may be provided. Changes in circadian rhythm may weaken the immune system. For example, potential for weakened immune system based on other biomarkers may be detected. A daily suggestion for physical activity may be provided. The daily suggestion for physical activity may be provided based on the detected potential for weakened immune system based on other biomarkers.

Interpreting multi-parameter longitudinal records may be provided. Interpreting multi-parameter longitudinal records may include labeling vector values of datasets indicative of health status changes over time. Interpreting multi-parameter longitudinal records may include reduction of vector datasets to underlining physiologic mechanisms.

In an example, a computing system for using a risk assessment to provide a notification may be provided. The computing system may include a processor. The processor may be configured. The processor may be configured to receive a biomarker from a sensing system. The processor may be configured to receive a data collection that includes pre-surgical data for the patient. The processor may determine a probability of a patient outcome due to a surgery performed on the patient using the biomarker and the data collection. The processor may be configured to send a notification to a user that indicates that the probability of the surgical complication exceeds a threshold. The processor may be configured to any combination of the receiving, determining, or sending as described herein.

In an example, the user may include one or more of the patient, a care giver of the patient, a surgeon, a doctor, a nurse, and a health care provider.

In an example, the notification may include one or more of the probability, a physiologic parameter, the biomarker, a patient instruction, and contact information for a health care provider.

In an example, the threshold may include one or more of a baseline for the patient, a goal for the patient, an amount of adjustment to improve an outcome, and a guideline.

In an example, the data collection may include one or more of surgical data and post-surgical data.

In an example, the processor may be configured to determine the probability of the patient outcome due to the surgery performed on the patient using the biomarker, the data collection and a model. In an example, the model may provide a situational awareness. The model may provide a situational awareness based on the biomarker. The processor may be configured to train the model. The processor may be configured to train the model using at least one of machine learning and the data collection.

In an example, the biomarker may include a first biomarker. The processor may be configured to receive a second biomarker. The processor may be configured to receive a second biomarker for the patient from the sensing system. The processor may be configured to determine a trend indicator. The processor may be configured to determine the trend indicator using the first biomarker and the second biomarker. The processor may be configured to determine a data conclusion. The processor may be configured to determine a data conclusion using the trend indicator and the probability of the patient outcome. The processor may be configured to send a device instruction. The processor may be configured to send the device instruction to a device to adjust the device. The processor may be configured to send the device instruction to a device to adjust the device using the data conclusion.

In an example, the processor may be configured to determine a data trend. The processor may be configured to determine the data trend using the data collection. The processor may be configured to determine a data conclusion. The processor may be configured to determine the data conclusion using the data trend. The data conclusion may indicate that a device may be adjusted to prevent a second biomarker from moving outside an acceptable range. The processor may be configured to determine a device instruction. The processor may be configured to determine the device instruction to adjust the device using the data conclusion.

In an example, the processor may be configured to determine a device adjustment for a device to prevent a second biomarker from moving outside a range using the data collection.

In an example, the processor may be configured to send a message. The processor may be configured to send the message to a device. The message may include one or more of a request to increase a sampling rate, a request to provide a data collection type, a request to notify a user of a sensing system error, and a request to notify a user of a data collection error.

In an example, the processor may be configured to determine a predictive outcome model. The processor may be configured to determine a predictive outcome model using the probability of the patient outcome.

In an example, the biomarker may include a first biomarker. The sensing system may include a first sensing system. The processor may be configured to determine a second biomarker from a second sensing system. The processor may be configured to determine that the second biomarker confirms the probability of the patient outcome.

In an example, the biomarker may include a first biomarker. The sensing system may include a first sensing system. The processor may be configured to determine that a second biomarker from a second sensing system may be used to confirm the probability of the patient outcome. The processor may be configured to determine that a second biomarker from a second sensing system may be used to change the probability of the patient outcome. The processor may be configured to send a message to the second sensing system that instructs the second sensing system to provide a second biomarker for the patient. The processor may be configured to receive the second biomarker for the patient from the second sensing system.

In an example, the processor may be configured to determine a data display. The processor may be configured to determine a data display to provide a context of the patient outcome. The processor may be configured to determine a data display to provide a context of the patient outcome using the data collection and the biomarker when the probability of the surgical complication exceeds the threshold.

In an example, a computing system for using a risk assessment to provide a notification may be provided. The computing system may include a processor. The processor may be configured to receive a biomarker. The processor may be configured to receive a biomarker for a patient from a sensing system. The processor may be configured to receive a data collection. The processor may be configured to receive a data collection that includes pre-surgical data. The processor may be configured to receive a data collection that includes surgical data. The processor may be configured receive a data collection that includes pre-surgical data and surgical data for the patient. The processor may be configured to determine a risk assessment model. The processor may be configured to determine a risk assessment model for a patient outcome. The processor may be configured to determine a risk assessment model for a patient outcome associated with a surgery performed on the patient. The processor may be configured determine a risk assessment model for a patient outcome associated with a surgery performed on the patient using the data collection. The processor may be configured to determine a probability. The processor may be configured to determine a probability of a medical issue. The processor may be configured to determine a probability of a medical issue using the risk assessment model. The processor may be configured to determine a probability of a medical issue using the biomarker. The processor may be configured to determine a probability of a medical issue using the risk assessment model and the biomarker.

In an example, the processor may be configured to determine that biomarker is a healthy biomarker. The processor may be configured to determine that the biomarker is a healthy biomarker using the risk assessment model. In an example, the processor may be configured to determine that a biomarker is a concerning biomarker. The processor may be configured to determine that a biomarker is a concerning biomarker using the risk assessment model.

In an example, the processor may be configured to send a notification. The processor may be configured to send a notification to a user. The processor may be configured to send a notification to a user to alert the user of a potential medical issue. The processor may be configured to send a notification to a user to alert the user of a potential medical issue when the probability of the medical issue exceeds a threshold.

In an example the processor may be configured to determine a risk assessment model. The processor may be configured to determine a risk assessment model for a patient outcome. The processor may be configured to determine the risk assessment model for the patient outcome by training the risk assessment model. The processor may be configured to determine the risk assessment model for the patient outcome by training the risk assessment model using machine learning. The processor may be configured to determine the risk assessment model for the patient outcome by training the risk assessment model using the data collection. The processor may be configured to turn to determine the risk assessment model for the patient outcome by training the risk assessment model using machine learning and the data collection. In an example, the processor may be configured to determine the risk assessment model for the patient outcome by receiving the risk assessment model. The processor may be configured to determine the risk assessment model for the patient outcome by receiving the risk assessment model from a server.

In an example, the threshold may include a risk assessment threshold.

In an example, the patient outcome may include one or more of a reduced surgical complication for the patient. The patient outcome may include one or more of an increased surgical complication for the patient. The patient outcome may include one or more of an improved recovery rate for the patient. The patient outcome may include one or more of a decreased recovery rate for the patient.

In an example, a computing system for using a risk assessment to provide a notification may be provided. The computing system may include a processor. The processor may be configured to receive a biomarker. The processor may be configured to receive a biomarker for a patient from a sensing system. The processor may be configured to receive a data collection. The processor may be configured to determine a probability. The processor may be configured to determine the probability of a patient outcome. The processor may be configured to determine the probability of the patient outcome due to a surgery performed on the patient. The processor may be configured to determine the probability of the patient outcome due to a surgery performed on the patient using the biomarker. The processor may be configured to determine the probability of the patient outcome due to a surgery performed on the patient using the data collection. The processor may be configured to determine the probability of the patient outcome due to a surgery performed on the patient using the biomarker and the data collection. The processor may be configured to determine an escalation level. The processor may be configured to determine an escalation level based on the probability of the patient outcome. The processor may be configured to send a notification. The processor may be configured to send a notification to the user. The processor may be configured to send a notification to the user based on the escalation level.

In an example, the escalation level may indicate that the patient should be notified wherein the user is the patient. In an example, the escalation level may indicate that a health care provider should be notified wherein the user is the health care provider.

In an example, the notification may include a first notification. The processor may be configured to send a second notification. The processor may be configured to send a second notification to the patient.

In an example, the escalation level may be determined based on one or more of a number of concerning biomarkers. The escalation level may be determined based on one or more of the number of concerning biomarkers within a time frame. The escalation level may be determined based on a severity. The escalation level may be determined based on the severity of the one or more concerning biomarkers. The escalation level may be determined based on a detrimental implication. The escalation level may be determined based on a detrimental implication of the biomarker. The escalation level may be determined based on a time that has elapsed. The escalation level may be determined based on a time that has elapsed since a health care provider has provided a review. The escalation level may be determined based on a threshold. The escalation level may be determined based on at least one or more of a number of concerning biomarkers detected within a time frame, a severity of a concerning biomarker, a detrimental implication of the biomarker, a time that has elapsed since a health care provider has provided a review, and a threshold.

In an example, the processor may be configured to determine a weight. The processor may be configured to determine a weight associated with the biomarker. The escalation level may be determined based on the weight. The escalation level may be determined based on the weight of the biomarker.

In an example, the processor may be configured to determine the escalation level based on the probability of the patient outcome by training an escalation model. The processor may be configured to determine the escalation level based on the probability of the patient outcome by training an escalation model using machine learning. The processor may be configured to determine the escalation level based on the probability of the patient outcome by training an escalation model using the data collection. The processor may be configured to determine the escalation level based on the probability of the patient outcome by training an escalation model using the machine learning and data collection. The processor may be configured to determine the escalation level based on the probability of the patient outcome by determining the escalation level using the escalation model.

In an example, the escalation level may include a first escalation level. The notification may include a first notification. The processor may be configured to determine that the user did not respond to the first notification. The processor may be configured to determine a second escalation level. The processor may be configured to determine a second escalation level based on the first escalation level. The processor may be configured to determine a second escalation level based of the probability of the patient outcome. The processor may be configured to determine a second escalation level based on the probability of the first escalation level and the probability of the patient outcome. The processor may be configured to send a second notification. The processor may be configured to send the second notification to the user. The processor may be configured to send the second notification to the user based on the second escalation level.

In an example, the user may include a first user. The processor may be configured to send a third notification. The processor may be configured to send the third notification to a second user. The processor may be configured to send the third notification to the second user based on the second escalation level.

Disclosed herein are methods, systems, and apparatus to provide machine learning that may be used to improve artificial intelligence algorithms, may reduce the iterations used to train artificial intelligence algorithms, and/or may make training machine learning less timing consuming. Adaptive learning algorithms may be used to aggregation one or more data streams. Adaptive learning algorithms may be used to generate and/or determine meta-data from a data collection. Adaptive learning algorithms may be used to process data, determine an efficient way to transport data, determine an efficient way to store data, and the like. Adaptive learning may be used to determine one or more improvements from a previous machine learning analysis. Improvements in the collection and or processing of sensor feeds, data feeds, and or biomarker feeds may be used to produce improved power instrument algorithms. For example, improvements may be used to produce improved power instrument algorithms based on a desired outcome.

A computing system and/or a method may be used for applying machine learning to a data collection to improve a surgical outcome. The computing system may comprise a processor that may perform the method. A data collection that includes one or more biomarkers may be determined. The data collection and/or the one or more biomarkers may indicate that an operational behavior of a surgical device may be suboptimal. A model may be determined using machine learning and the data collection. The model may optimize and/or improve the operational behavior of the surgical device to improve a surgical outcome. The model may be updated using a feedback given by a healthcare provider (HCP) to improve the model. A control program update may be determined using the model and the collection data. The control program update may be configured to alter a manner in which a control program operates the surgical device during a surgical procedure. The control program update may be sent to the surgical device.

A computing system and/or method may be used for applying machine learning to a data collection to improve a surgical outcome. The computing system may comprise a processor that may perform the method. It may be determined from a data collection that includes one or more biomarkers that an operational behavior of a surgical advice may be suboptimal. A model that optimizes and/or improves the operational behavior of the surgical device and may predict a surgical complication may be determined using machine learning and the data collection. The model may be updated using a feedback given by a healthcare provider (HCP) to improve the model. The control program update may be determined using the model and the data collection. The control program update may be configured to alter a manner in which a control program may operate the surgical device during a surgical procedure to prevent the surgical complication. The control program update may be sent to the surgical device.

A computing system and or a method may be used for applying machine learning to a data collection to improve a surgical outcome. The computing system may comprise a processor that may perform the method. It may be determined that an operational behavior of a surgical device may be suboptimal using a surgical device data and a biomarker from a sensing system. A model that optimizes and/or improves the operational behavior of a surgical device to improve the surgical outcome may be determined using machine learning, the surgical device data, and the biomarker. The model may be updated using a feedback given by a healthcare provider (HCP) to improve the model. A control program update may be determined using the biomarker and the surgical device data. The control program update may be configured to alter a manner in which a control program may operate the surgical device during a surgical procedure. The control program update may be sent to the surgical device.

A computing system may be provided for applying machine learning to a data collection to improve a surgical outcome. The computing system may comprise a processor. The processor may be configured to perform a number of actions. An indication that an operational behavior of a surgical device may be suboptimal may be determined from a data collection that may include one or more biomarkers. A model that may optimize and/or improve the behavioral operation of the surgical device to improve a surgical outcome may be determined using machine learning and the data collection. The model may be updated using feedback given by a healthcare provider to improve the model. The control program update may be determined using the model and the data collection. The control program update may be configured to alter a manner in which a control program operates the surgical device during the surgical procedure. The control program update may be sent to the surgical device.

The computing system may perform a learned behavior, such as a learned behavior determined using artificial intelligence and/or machine learning. Computing systems, such as cloud computing systems, may be provided to provide learning and/or adaptive system behavior to improve local data collection algorithms and control functions. A computing system may provide machine learning adaptation of one or more wearable devices and/or sensor collections of data to improve operability. For example, the operability of a wearable device, a sensor system, a surgical system, and the like may be improved by a computing system that may use machine learning.

A computing system may use an adaptive learning algorithm, which may be cloud based, to aggregate one or more data streams. A computing system may use an adaptive learning algorithm to aggregate meta-data from data collection. Machine learning and/or an adaptive learning algorithm may be used to improve the processing of data, the transportation of data, the storage of data. A computing system may use machine learning to determine one or more improvements that may be made in the collection and/or processing of data from one or more sensor feeds. For example, a computing system may use machine learning improved data collection to produce an improved power instrument algorithm that may contribute to a desired outcome, such as a surgical outcome. The desired outcome, which may be a surgical outcome, may include reduced complications, improved recovery rates, low false positive sensing issues, faster learning cycle of machine learning and/or artificial intelligence algorithms, a creation of advanced instrument operations, and the like.

The computing system may perform predictive or prognostic model generation. The computing system may generate one or more improvements to an algorithm and/or control of a wearable device, which may improve the relevancy of data that may come from the wearable device. The computing system may employ one or more machine learning techniques to improve one or more sensed data streams.

The computing system may generate one or more improvements to the learned efficiency and effectiveness of one or more machine learning algorithms. The computing system may employ machine learning to improve the artificial intelligence (AI) algorithm iterations. For example, the computing system may use machine learning to improve the training of another machine learning algorithm.

The computing system may allow user input, such as user feedback, to a random dataset generated based on data in the field for machine learning, such as continuous machine learning. The computing system may generate random dataset. The generated random dataset may improve a round (e.g., each round) the user or HCP runs a program. An HCP, such as a surgeon, may set what he/she would flag as high risk, medium risk, or low risk. The surgeon may mark what level of notification he/she would like to receive based on that specific generated dataset and/or whether he/she would like to be notified in one case versus another. Another HCP may handle the flag. One or more improvements may occur over time with datasets from patients (e.g., actual patients) and a HCP's (e.g., a surgeon) activity level of machine teaching and/or model training sessions. One or more improvements to a model may be made by receiving feedback from an HCP, which may occur when the HCP is on break, in between surgeries, and/or after an initial number of runs, when starting the program to teach the system, and the like. At a point, the machine learning and/or the dataset may transition from surgeon input to verification from the surgeon that the proper notifications and risk levels that the machine learning model may execute are correct. The computing system may output an overlay of the knowledge or understanding from the machine learning of how to react verses the surgeon's input(s). Such output may guide determining the need for more machine learning training and/or teaching sessions. The output may be used as a teaching tool for residents and nurses under a surgeon to give a visual representation on how to handle certain cases and overlay the output with the surgeon's input(s). Under such an approach, the computing system may minimize an overload of notifications and/or resources that may have bene used to annotate the data. The computing system may personalize the machine learning for a surgeon such that a surgical device and/or the machine learning may be tailored to the surgeon.

The computing system may perform machine learning and may adjust a sensitivity of the machine learning. The computing system may perform dynamic learning of a magnitude of conservation regarding given one or more complications and one or more predicted complications. For example, a false positive may be weighed similarly to a false negative with regards to whether the machine was correct or not, which may influence the machine learning algorithm. The weight of the false negative may be adjusted to be scrutinized in the machine learning algorithm to lean toward a false positive in output versus a false negative that may be tailored to one or more complications.

Machine learning may be used to generate one or more datasets. The generation of the one or more datasets may be based on prioritizing areas, cases, situations, and the like that machine learning may not be familiar with. The generation of the one or more data sets may be based on a situation that the machine learning may not have seen yet. As such, the machine learning may generate a dataset, the machine learning may be trained, or the machine learning may be prepared when case such area, cases, and situations may occur.

The computing system may provide and/or perform one or more improvements to the aggregating of data. The computing system may provide and/or may perform a prediction of surgical complications, patient complications, recovery milestones, and the like. The computing system may employ machine learning to improve one or more patient monitoring measures. Machine learning adaptation of sensing and/or indications may be performed. Risk probability aggregation may be provided. For example, risk probability aggregation may be used to choose a system response.

A machine learning database may be provided. The machine learning database may include a data collection, one or more artificial intelligence models, and the like. Data used by the machine learning may include one or more contexts that may be associated with or tailored to a predictive model. For example, a machine learning model for <3 days post-op may be generated. For example, a machine learning model for patient with an underlying condition may be generated. For example, a machine learning model for one or more biomarkers during exercise may be generated. For example, a machine learning model for one or more biomarkers of patients with hypertension while eating may be generated.

The computing system may improve wearable milestone(s), threshold(s), and/or interrelationship(s). As the data for any of the procedure types (e.g., colorectal, Bariatric, Thoracic, GYN) may be processed for procedure steps and instrument use, the wearables pre-cursor information may be integrated and may allow the machine learning system to identify other interrelated wearable datasets that may provide indicators of the procedural complications (e.g., one or more surgical complications). Thresholds and algorithms associated with the data may be downloaded back to the computing system (e.g., a surgical hub) and may be sent to the wearables through the computing system with improved monitoring algorithms of threshold points to indicate complications on future procedures.

The computing system may improve communication and interconnecting methods. As the automated pairing systems may identify systems with which that may interact with or may not interact with, the machine learning may identify one or more ways for the systems to interact or spoof the wearable into believing the wearable was attached to a system that the wearable may interact with and provide data to. Example machine learning systems may be include distributed training, Jupyter Notebooks, continues integration/continuous delivery (CI/CD), hyperparameter optimization, feature stores, and the like.

Disclosed herein are methods, systems, and apparatus to provide machine learning that may be used to improve artificial intelligence algorithms and may reduce the iterations used to train artificial intelligence algorithms. Adaptive learning algorithms may be used to aggregate one or more data streams. Adaptive learning algorithms may be used to generate and/or determine meta-data from a data collection. Adaptive learning algorithms may be used to process data, determine an efficient way to transport data, determine an efficient way to store data, and the like. Adaptive learning may be used to determine one or more improvements from a previous machine learning analysis. Improvements in the collection and or processing of sensor feeds, data feeds, and/or biomarker feeds may be used to produce improved power instrument algorithms. For example, improvements may be used to produce improved power instrument algorithms based on a desired outcome (e.g., a surgical outcome).

A computing system and/or a method may be used for applying machine learning to a data collection to improve a surgical outcome. The computing system may comprise a processor that may perform the method. A data collection that includes one or more biomarkers may be determined. The data collection and/or the one or more biomarkers may indicate that an operational behavior of a surgical device may be suboptimal. A model may be determined using machine learning and the data collection. The model may optimize and/or improve the operational behavior of the surgical device to improve a surgical outcome. The model may be updated using a feedback given by a healthcare provider (HCP) to improve the model. A control program update may be generated using the model and the collection data. The control program update may be configured to alter a manner in which a control program operates the surgical device during a surgical procedure. The control program update may be sent to the surgical device.

A computing system and/or method may be used for applying machine learning to a data collection to improve a surgical outcome. The computing system may comprise a processor that may perform the method. It may be determined from a data collection that includes one or more biomarkers that an operational behavior of a surgical device may be suboptimal. A model that optimizes and/or improves the operational behavior of the surgical device and may predict a surgical complication may be determined using machine learning and the data collection. The model may be updated using a feedback given by a healthcare provider (HCP) to improve the model. The control program update may be generated using the model and the data collection. The control program update may be configured to alter a manner in which a control program may operate the surgical device during a surgical procedure to prevent the surgical complication. The control program update may be sent to the surgical device.

A computing system and/or a method may be used for applying machine learning to a data collection to improve a surgical outcome. The computing system may comprise a processor that may perform the method. It may be determined that an operational behavior of a surgical device may be suboptimal using a surgical device data and a biomarker from a sensing system. A model that optimizes and/or improves the operational behavior of a surgical device to improve the surgical outcome may be determined using machine learning, the surgical device data, and the biomarker. The model may be updated using a feedback given by a healthcare provider (HCP) to improve the model. A control program update may be generated using the biomarker and the surgical device data. The control program update may be configured to alter a manner in which a control program may operate the surgical device during a surgical procedure. The control program update may be sent to the surgical device.

Machine learning models may be generated from various data sources, such as patient EMR data, pre-surgical biomarker measurement data, surgical biomarker measurement data, surgical sensor measurement data, post-surgical biomarker measurement data, and biomarker sensor thresholds data. The machine learning models may predict surgical complications and/or post-surgical recovery milestones related to a patient's surgical procedure.

For example, such machine learning models may be created and trained locally at a computing system (e.g., a surgical hub) using data sources that may be connected with the computing system.

For example, machine learning models may be created and/or trained by a group of interconnected computing systems (e.g., surgical hubs) that may be at a physical location (e.g., in an operating room). Machine learning models be created and/or trained using data sources that may be collected by a group of computing systems. A group of interconnected computing systems may communicate with one another to detect an unused processing capacity and/or an unused data storage capability on another computing system and may distribute processing tasks to an underutilized computing system. The of processing tasks may include data collection, data preparation, model training, model validation, and/or model testing.

Embodiments disclosed herein may use distributed processing. Distributed processing may be coordinated by a first computing system, which may be in the operating room. The first computing system may direct a second computing system. The distributed processing may be coordinated using a peer-to-peer communication protocol.

Machine learning models may be created and/or trained at a server, at a cloud system, and the like. A cloud system that may have trained a machine learning model may be connected with one or more computing systems, which may be in various geographical locations. The cloud computing system may provide the one or more computing systems with access to one or more data sources.

One or more sensing systems may be located in an operating room and may be used to distribute the processing of sensor measurement data. For example, a first sensing system may not have sufficient capacity to process measurement data locally and may rely on a second sensing system and/or a computing system to process the measurement data. In an example, a first sensing system and/or a first computing system may be able to detect a second computing system and/or a second sensing system that may have an unused processing capacity. And the first sensing system and/or the first computing system may distribute processing to the second computing system and/or the second sensing system. For example, a first surgical hub in an operating room may determine that a second surgical hub in the operating room may have an unused processing capacity and the first surgical hub may distribute one or more processing tasks to the second surgical hub.

The computing system (e.g., a surgical hub) may adjust a data sampling rate and/or a data precision of a sensing system during a surgical procedure. For example, in a procedure step, the computing system may determine that it may not be necessary for the data sampling rate and/or data precision for biomarker measurement data from sensing system A to remain the same as that of the previous procedure step. In such case, the computing system may request sensing system A to scale down the data sampling rate and/or data precision. The computing system may determine the biomarker measurement data from a sensing system B to be more relevant. The computing system may request sensing system A to scale up the data sampling rate and/or data precision. The sensing system B may have sufficient processing capacity to scale up the data sampling rate and/or data precision as requested. The sensing system B may have insufficient processing capacity and may share processing tasks with the sensing system A and/or with the computing system.

The computing system may scale up data sampling rate and/or data precision of a sensing system during a surgical procedure based on a machine learning model's prediction(s). In an example, a machine learning model may be created and/or trained to predict probabilities of surgical complications. In such example, the machine learning model may predicate a probability of a surgical complication. Based on the predicted probability of the surgical complication, the computing system may determine request a sensing system C to scale up its data sampling rate and/or data precision based on the sensing system C biomarker measurement data's relevance with the predicted complication. The request may be to scale up a heart rate variability measurement from one measurement per minute (e.g., on an Apple Watch) to one measurement per second. The request may be to scale up a heart rate variability measurement from one decimal place to three decimal places. The request may be to scale up the complexity of a heart rate variability measurement from a mean score to a mean score with an associated standard deviation.

In response to the request to scale up data sampling rate, data precision, and/or data complexity, the sensing system C may scale up as requested. The sensing system C may not have sufficient processing capacity to scale up as data may be more frequently collected. The sensing system C may not have sufficient processing capacity to scale up as more data is being collected. The sensing system C may indicate to the computing system that sensing system C may lack processing capacity and the computing system may request the sensing system C to transmit raw measurement data without processing to the computing system for further processing at the computing system. The computing system request one or more other sensing systems (e.g., sensing system A and/or sensing system B) to scale down a data sampling and/or a data precision to reduce an amount of bandwidth that may be used within an operating room. (e.g., to mitigate the potential communication bandwidth bottlenecks).

Figure 107:
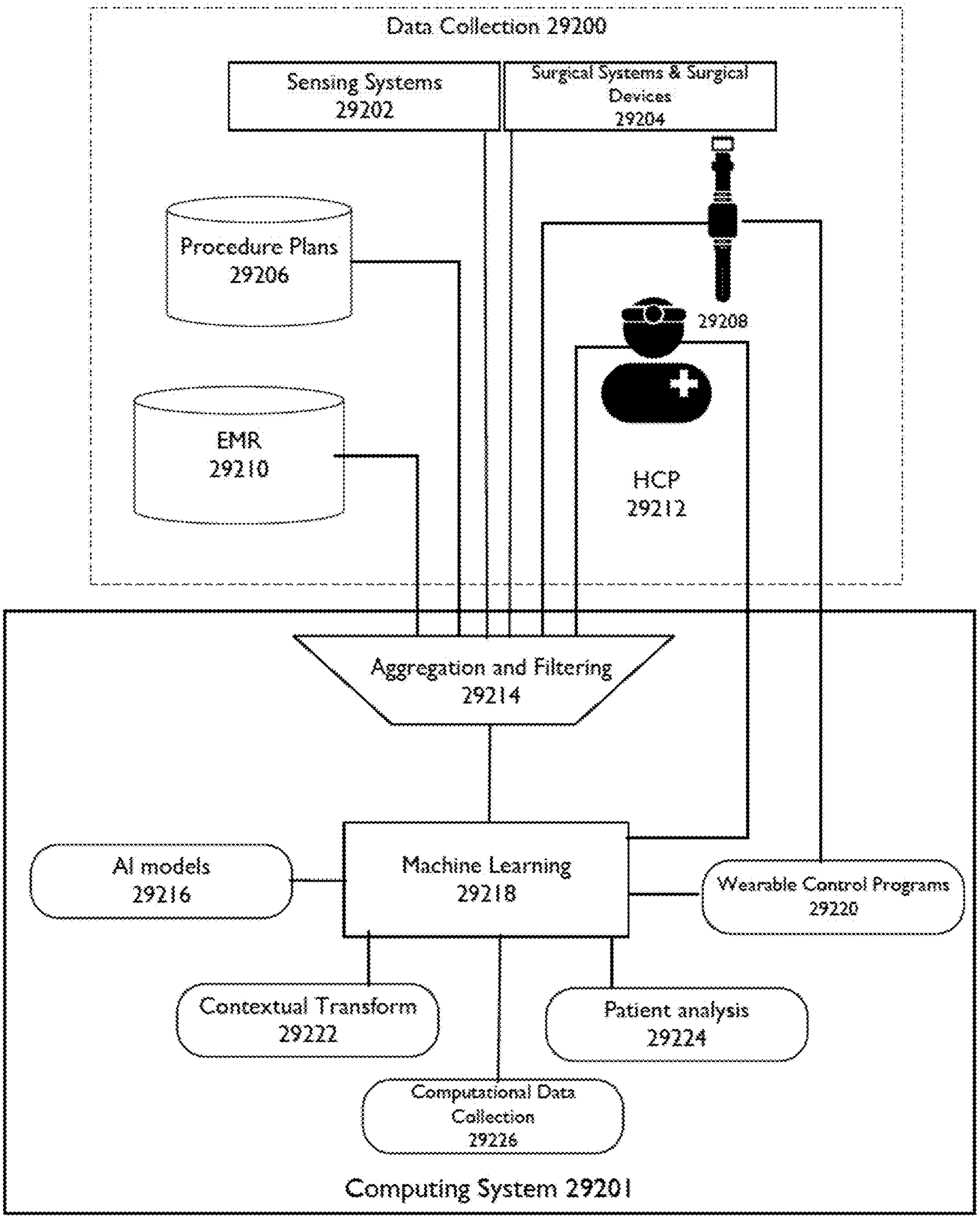

FIG. 107 depicts a block diagram for applying machine learning to improve algorithms and/or controls of one or more wearables.

The computing system 29201 may include computing hardware including a processor, memory, input/output subsystems, and the like. The processor may be configured (via application specific hardware, software, firmware, or the like) to transform received data and to derive contextualized for output. For example, the processor may include a microprocessor, a microcontroller, a FPGA, and an application-specific integrated circuit (ASIC), a system-on-a-chip (SOIC), a digital signal processing (DSP) platform, a real-time computing system, or the like. For example, processor may be configured to implement computing functions and/or modules as disclosed herein. For example, the processor may be configured for aggregation and/or filtering 29214, machine learning 29218, contextual transform 29222 (e.g., including real-time intra-operative processing), artificial intelligence models 29216, patient analysis 29224, wearable control programs 29220, wearable device data collection 29226, and the like.

The computing system 29201 may be any device suitable for processing sensor, health record data, EMR data, user input, training a machine learning model, deploying a machine learning model, creating a machine learning model, and the like. The computing system 29201 may be any device suitable for using a machine learning model to determine and/or predict one or more surgical outcomes, one or more surgical complications, and the like.

The computing system 29201 may be any device suitable to transform data and derive computational data for output, such as computational data collection 29226. Computational data collection 29226 may include contextualized data. Computational data collection 29226 may include a prediction, a machine learning model, and artificial intelligence model, pre-surgical data, surgical data, post-surgical data, a biomarker, a sensor measurement, and the like. Computational data collection 29226 may include contextualized data that may include a context. A context, for example, may be additional information that may be relevant to an understanding and/or interpretation of the sensor measurement. For example, the context may include pre-surgery and/or pre-therapy baselines. For example, the context may include situational awareness of incorrectly connected and/or incorrectly operating surgical and/or sensing systems. For example, the context may include adjustments to products, surgical plans, and/or margins.

The computing system 29201 may be incorporated with any method suitable for implementation of the functionality disclosed herein. For example, the computing system 29201 may be incorporated as a stand-alone computing system. For example, the computing system may be incorporated into a surgical hub, such as that disclosed in FIG. 1. For example, the computing system 29201 may be incorporated into a sensing system itself (e.g., sensing both pre-surgical and surgical data and providing contextualized data as an output). For example, the computing system 29201 may be incorporated into a surgical device itself (e.g., receiving, pre-surgical, surgical data, and post-surgical data and providing computational data, contextualized data, and/or alerts as an output).

A data collection, such as data collection 29200 may be provided. Machine learning may use the data collection, such as data collection 29200. Data collection 29200 may be used by machine learning to train a model, verify a model, determine a model, and the like.

Data collection 29200 may include one or more data sources. For example, data collection 29200 may include a pre-surgical data collection, a surgical data collection, a post-surgical data collection, contextualized surgical data collection, and the like. Data collection 29294 may include one or more biomarkers. The one or more biomarkers may come from one or more computing systems, surgical sensing systems, wearable devices, displays, surgical instruments, surgical devices, sensor systems, devices, and the like. The data collection 29200 may include electronic medical records for a patient, data for a patient, data for other patients, data regarding past procedures, data regarding research for procedures, medical data, instructions from a health care provider, plans for a surgical procedure, and the like.

Data collection 29200 may include data from a one or more data sources. For example, the sources may include procedure plans database 29206, EMR 29210, sensing systems 29202, surgical systems & surgical devices 29204, wearable device 29208, and data from HCP 29212.

Data collection 29294 may include a pre-surgical data collection. The pre-surgical data collection may include data from one or more data sources. The pre-surgical data collection may include data that is related to a patient that may be recorded prior to a surgery. The pre-surgical data collection may include one or more biomarkers they may have been recorded for a patient prior to a surgery. For example, a heart rate and blood glucose level for a patient may be recorded for a patient prior to a surgery.

The pre-surgical data collection may include data from sensing systems 29202, such as pre-surgical sensing system. The pre-surgical sensing system may include any configuration of hardware and software devices suitable for sensing and presenting patient parameters and/or biomarkers that may be relevant before, during, or after a surgical procedure. Such a pre-surgical sensing system may include any of the sensing and monitoring systems disclosed herein, including uncontrolled patient monitoring systems, controlled patient monitoring systems, and the like. For example, pre-surgical sensing system may include a wearable patient sensor system. The pre-surgical sensing system may provide data suitable for establishing baselines of patient biomarkers for use in contextual determination during and/or after surgery. The pre-surgical sensing system may incorporate or be incorporated into the sensing system 20001 as shown in FIG. 1B.

The pre-surgical data collection may include data from wearable device 29208. Wearable device 29208 may include any configuration of hardware and software devices suitable for sensing and presenting patent parameters and/or biomarkers that may be relevant before, during, or after a surgical procedure. Such systems may be used by the patient for any amount of time prior to surgery, inside and outside of a medical facility. To illustrate, via an uncontrolled patient monitoring system, the patient may use a wearable heart-related sensor at home for four weeks prior to a surgical procedure. And/or, via a controlled patient monitoring system, an HCP may monitor the same and/or analogous biomarkers using facility equipment during time the patient is prepped immediately before the surgical procedure. For example, the wearable device 29208 may provide data suitable for establishing baselines of patient biomarkers for use in contextual determination during and/or after surgery. Wearable device 29208 may include any of those disclosed herein, such as those with reference to FIG. 1B for example.

The pre-surgical data collection may include procedure plans 29206. Procedure plans 29206 may include any data source relevant to a health procedure (e.g., relevant to a health procedure in view of a particular patient and/or facility). Procedure plan 29206 may include structured data indicative of the desired end result, the surgical tactics to be employed, the operation logistics, and the like. Procedure plan 29206 may include an accounting of the equipment to be used and/or the techniques to be used. Procedure plan 29206 may include an order. Procedure plan 29206 may include a timeline. The structured data may include defined fields and/or data tags associated corresponding values. The structured data may include codes associated with one or more processes of a surgical procedure (e.g., surgical procedure steps).

The pre-surgical data collection may include EMR 29210. EMR 29210 may include any data source relevant to a patient in view of a health procedure, such a surgical procedure. EMR 29210 may include information such as allergies and/or adverse drug reactions, chronic diseases, family medical history, illnesses and/or hospitalizations, imaging data, laboratory test results, medications and dosing, prescription record, records of surgeries and other procedures, vaccinations, observations of daily living, information collected by sensing system 29202 (e.g., pre-surgical), information collected by wearable device 29208, and the like.

The pre-surgical data collection may include data from a pre-surgical healthcare provider, such as HCP 29212. Data from HCP 29212 may include any data relevant to a pre-surgical sensing system, a patient record, a procedure plan, and the like. Data from HCP 29212 may include data that may be relevant to an operation, configuration, and/or management of a computing system, such as computing system 29201. For example, data from HCP 29212 include feedback that may be provided to a machine learning module, such a machine learning 29218. The data from HCP 29212 may include manually entering data that may not be received directly for a relevant source (such as manually entering a manually taken biomarker reading, for example).

Data collection 29294 may include a surgical data collection. The surgical data collection may include data from one or more data sources. The surgical data collection may include data that may be related to a patient that may be recorded during a surgery. The surgical data collection may include one or more biomarkers they may have been recorded for a patient during a surgery. For example, a heart rate and blood glucose level for a patient may be recorded for a patient during a surgery.

The surgical data collection may include one or more data sources. The surgical data collection may include data from sensing systems 29202, HCP 29212, surgical systems & surgical devices 29204, and wearable device 29208.

The surgical data collection may include data from sensing system 29202, such as a surgical sensing system. The surgical sensing system may include any configuration of hardware and software devices suitable for sensing and presenting parameters patient biomarkers that may be relevant during a surgical procedure. The surgical sensing system may include the sensing and monitoring systems disclosed herein, including controlled patient monitoring systems, surgeon monitoring systems, environmental sensing systems, and the like.

The surgical data collection may include data from wearable device 29208. Wearable device 29208 may include any configuration of hardware and software devices suitable for sensing and presenting patent parameters and/or biomarkers that may be relevant before, during, or after a surgical procedure. Such systems may be used by the patient for any amount of time prior to surgery, inside and outside of a medical facility. To illustrate, via an uncontrolled patient monitoring system, the patient may use a wearable heart-related sensor at during a surgical procedure. And/or, via a controlled patient monitoring system, an HCP may monitor the same and/or analogous biomarkers using facility equipment during time of the surgical procedure. For example, the wearable device 29208 may provide data suitable for use in a contextual determination during and/or after surgery. Wearable device 29208 may include any of those disclosed herein, such as those with reference to FIG. 1B for example.

Surgical systems & surgical devices 29204 may include any surgical equipment suitable for providing operative data regarding its configuration, use, and/or present condition and/or status, for example. Surgical systems & surgical devices 29204 may include equipment in the surgical theater. Surgical systems & surgical devices 29204 may include any equipment employed in the surgical theater, such as that disclosed with reference to FIG. 1, FIG. 7A, FIG. 10, and throughout the present application, for example. The surgical systems & surgical devices 29204 may include surgical fixtures of a general nature, such as a surgical table, lighting, anesthesia equipment, robotic systems, and/or life-support equipment. Surgical systems & surgical devices 29204 may include surgical fixtures that may be related to the procedure at-hand, such as imaging devices, surgical staplers, energy devices, endocutter clamps, and the like. For example, surgical systems & surgical devices 29204 may include be one or more of a powered stapler, a powered stapler generator, an energy device, an energy device generator, an in-operating-room imaging system, a smoke evacuator, a suction-irrigation device, an insufflation system, or the like.

The surgical systems & surgical devices 29204 may include at least one of a surgical instrument, surgical visualization system, monitor, sound system, energy devices, a wearable, and the like. For example, the surgical system may include a surgical hub. For example, the surgical system may include a surgical stapler. For example, the surgical system may include an endocutter, for example. Data from the surgical instrument may include surgical instrument parameters. The surgical instrument parameters may include surgical instrument power, for example. Data from the surgical visualization system may include the location of surgical instruments in relation to a patient surgical site and/or organ. For example, data may include the distance between a surgical stapler and a close vital organ.

Surgical data collection may include data from a surgical HCP, such as HCP 29212. Data from HCP 29212 may include any data relevant to a surgical sensing system, a wearable device, a surgical system, a machine learning, a patient analysis, a surgical device control program, a wearable control program, a contextual transform, an artificial intelligence model, and the like. For example, HCP 29212 may provide data that may be associated with surgical systems & surgical devices 29204, wearable device 29208, sensing system 29202, machine learning 29218, and the like. For example, the HCP 29212 may provide data that may trigger an interaction with the context transform 29222 and/or machine learning 29218. The data from HCP 29212 may include manually entering data not received directly for any relevant source (such as manually entering a manually taken biomarker reading, for example).

The data received from data collection 29200 may be subject to aggregation and/or filtering 29214. Aggregation and/or filtering 29214 may perform pre-processing on data received from data collection 29200. Aggregation and/or filtering 29214 may be used to prepare and format the data for use by computing system 29201. For example, aggregation and/or filtering 29214 may prepare data to be processed by machine learning 29218, contextual transform 29222, artificial intelligence models 29218, patient analysis 29224, wearable device data collection 29226, and wearable control programs 29220.

002024 Processing the data received from data collection 29200 by aggregation and/or filtering 29214 may include filtering (e.g., to select sensor data from the stream of data from pre-surgical sensing system). Aggregation and/or filtering 29214 may use filtering to help reject noise in data from data collection 29200. Aggregation and/or filtering 29214 may use a method to establish a baseline for a biomarker from data collection 29200. Aggregation and/or filtering 29214 may perform time mapping on data from data collection 29200 (e.g., to place received values from different sources in alignment with each other in regard to time). Time mapping may aid in correlation and ratio analysis, which may occur in contextual transform 29222.

Aggregation and/or filtering 29214 may translate data from data collection 29200. The translation of data may include coordinating formats, coordinating data types, translating from one format to another format, translating from one data type, to another data type, accounting for a difference between a data source data format, and accounting for a data type expected by another module, such as machine learning 29218. Translating may include translating the data into a format suitable for machine learning, for artificial intelligence models, for patient analysis, for use by a surgical device control program, and/or for use by a wearable control program.

Contextual transform 29222 may operate to provide a context for data from data collection 29200. For example, contextual transform 29266 may transform data into contextualized surgical data. To illustrate, as an input the contextual transform may receive surgical data that includes, for example, a measurement time, a sensor system identifier, and a sensor value. Contextual transform 29222 may output contextualized surgical data. Contextual transform 29222 may output data that may be modified and/or enhanced by machine learning 29218, patient analysis 29224, wearable control programs 29220, wearable device data collection 29226, and artificial intelligence models 29216.

Contextual transform 29222 may determine and/or store data that may be related. Contextual transform 29222 may determine how data may be related. For example, contextual transform 29222 may determine that data from the surgical data collection may be related to data from the pre-surgical data collection. Contextual transform 29222 may determine a context for the data. Context, for example, additional information relevant to the present understanding and/or interpretation of the sensor measurement.

Computational data collection 29266 may be determined and/or generated by machine learning 29218. For example, machine learning 29218 may receive data from data collection 29200, may apply a machine learning model, and may use the machine learning model to generate the computational data collection 29226.

Computational data collection 29226 may include one or more biomarkers that may be augmented and/or enhanced by a machine learning model. For example, one or more biomarkers may be modified to make the one or more biomarkers more accurate using the machine learning model. Computational data collection 29226 may include one or more predictions and/or probabilities That may be associated with a patient, a surgical outcome, a diagnosis, a morbidity, and the like.

Computational data collection 29226 may include feedback from an HCP, such as HCP 29212. The feedback may be regarding a training of an artificial intelligence model, an accuracy of a biomarker, an accuracy of a prediction, A modification of a control program for a wearable device, a modification of a control program for a surgical device, and the like. For example, computational data collection 29226 may include feedback that indicates that an artificial intelligence model may be improving surgical outcomes when a surgical device is used with the modified control program generated by the artificial intelligence model. The computational data collection 29226, may include correlation analysis (e.g., to establish a baseline for relationships between and/or among biomarkers from the data collection 29200).

Computation data collection 29226 may include context, for example, additional information relevant to the present understanding and/or interpretation of the sensor measurement. For example, the context may include pre-surgery and/or pre-therapy baselines. For example, the context may include situational awareness of incorrectly connected and/or incorrectly operating surgical and/or sensing systems. For example, the context may include adjustments to products, surgical plans, and/or margins. Computational data collection 29226 may include data sent to or received from surgical systems & surgical devices 29204, wearable device 29208, sensing systems 29202, procedure plans 29206, EMR 29210, and/or HCP 29212. Computational data collection 29226 may be created, modified, received by and/or sent by machine learning 29218, contextual transform 29222, artificial intelligence models 29216, patient analysis 29224, wearable control programs 29220, and/or any combination thereof.

Computational data collection 29226 may include data that may provide a context. The context may include additional information that may have been created and/determined by machine learning 29218 that may place a biomarker into a specific context for the healthcare providers. For example, computational data collection 29226 may include instructions and/or information about a baseline value for a sensor value, an alert of a deviation, relevant information from the patient's record, relevant information to a procedural element of the surgery, surgical device settings, and/or any information the healthcare provider might find relevant to have at the moment of the sensor's measurement itself. Computational data collection 29226 may include one or more data tags. The data tags may include logging data (indicating that that a specific transform or other processing has occurred).

Computational data collection 29226 may include data that may be provided by HCP 29212 and may have been modified and/or augmented by machine learning 29218. For example, HCP 29212 may provide feedback regarding data provided by machine learning 29218. Computational data collection 29226 may include data that may be sent to HCP 29212. For example, HCP 29212 may receive data provided by machine learning 29218. Data from HCP 29212 may include any data relevant to a surgical sensing system, a wearable device, a surgical system, a machine learning, a patient analysis, a surgical device control program, a wearable control program, a contextual transform, an artificial intelligence model, and the like.

Computational data collection 29226 may include data from wearable device 29208. For example, device may be received from wearable device 29208 and may be processed by machine learning 29208. Machine learning 29218 may modify the data received from wearable device 29208 and may I put that data as computational data collection 29226. Machine learning 29208 may augment the data received from wearable device 29208. For example, one or more biomarkers received from 29208 may be improved by machine learning 29218 by augmenting the one or more biomarkers Machine learning 29218 may create, generate, train, and/or determine artificial intelligence (AI) models. The AI models may be stored in AI models 29216. Machine learning 29218 may create, generate, train, and/or determine artificial AI models using data collection 29200. Machine learning 29218 may generate data, such as computational data collection 29226, using one or more AI models.

Machine learning 29218 may use data collection 29200 to create and/or training a model for wearable device 29208. Machine learning 29218 may create, train, generate, and/or determine a model to improve an algorithm or control of wearable device 29208. For example, machine learning 29218 may train a model using data from data collection 29200. The model may indicate that an operation of wearable device 29208 may be improved. The model may determine one or more parameters of wearable device 29208 that may be adjusted to improve the operation of wearable device 29208. The model may determine that a wearable control program, which may be a firmware associated with wearable device 29208, may be created, updated, or modified to improve an operational of the wearable device 29208. Machine learning 29218 may determine train a model using data collection 29200 and may deploy that model to wearable device 29208 to improve an operational of wearable device 29208, such as an ability of wearable device 29208 to predict a surgical complication and/or measure one or more biomarkers.

Machine learning 29218 may prepare data from data collection 29200 (which may be processed by aggregation and filtering 29214). For example, machine learning 29218 use one or more machine learning algorithms to prepare data for contextual transform 29222, computational data collection 29226, patient analysis 29224, wearable control programs 29220, and AI models 29216.

In an example, machine learning 29218 may create a data field and appending it to each data record in a dataset. The data field may indicate whether there was a surgical bleeding complication during a respective surgical procedure derived from surgical data from collected from surgical systems & surgical devices 29204. The data field may serve as a desired output label for training a surgical wearable AI model, such as a model from AI models 29216 and/or machine learning 29218, with supervised machine learning for adjusting a wearable control program 29220, which may be deployed to wearable device 29208.

Machine learning 29218 may perform model training, model validation, model testing for a wearable device AI model and/or a wearable control program associated with wearable device 29208. For example, machine learning 29218 may train a decision tree algorithm-based wearable AI model. Those of skill in the art will recognize any other suitable machine learning algorithm may be used to build and/or train a model. The model may learn a pattern (e.g., among other patterns) that a surgical bleeding complication occurs (e.g., at a dissection/mobilization procedure step) when at least two condition occur as part of a patent analysis process, such as may occur with patient analysis 29224. A condition may be that pre-surgical data from wearable device 29208 may indicate at least one of a heart rate elevated above a threshold, blood pressure above a threshold, blood pH below a threshold, or an edema measurement above a threshold. A condition may be that surgical data from wearable device 29208 conform another conditional identified using the pre-surgical data.

AI models 29216 may be a database of one or more models. AI models 29216 may be a software module that may execute one or more models. AI models 29216 may include one or more models that may have been created, generated, and/or determined by machine learning 29218. Ai models 29216 may include one or more models that may have been or may be trained by machine learning 29218. AI models 29216 may include one or more models that may be deployed to machine learning 29218, wearable device 29208, surgical systems & surgical devices 29204, and sensing systems, 29202.

AI models 29216 may include models that may be specific to a context. For example, AI models 29216 may include a first model that may predict a surgical complication for a patient with high blood pressure and AI models 29216 may include a second model that may predict a surgical complication for a patient with normal blood pressure.

Machine learning 29218 may be configured to update to wearable control program 29220, which may be sent to wearable device 29208. Machine learning 29218 may run a model that may determine that the wearable control program associated with 29208 may need to be updated to monitor a patient to detect and/or prevent a surgical complication. For example, the model may determine that a surgical procedure (e.g., a sigmoid colectomy procedure) may have entered a dissection/mobilization procedure step. It may be determined that the wearable control program associated with wearable device 29208 may be updated to increase a data sampling rate (e.g., from once per minute to once per second). The update to the wearable control program may be generated by machine learning 29218 and/or by wearable control programs 29220 and may be sent to wearable device 29208. The update to may be to increase the data sampling rate (e.g., from once per minute to once per second). Machine learning 29218 may be configured to send an update to a second wearable control program for a second wearable device (e.g., configured for measuring biomarkers for determining tissue thickness irregularities) when the sigmoid colectomy procedure is detected to have entered an access procedure step. The update to the second wearable control program may be to decrease the data sampling rate (e.g., from once per five seconds to once per minute).

When an AI model has been deployed to a wearable device (e.g., as a part of machine learning 29218 in production) biomarker measurement data related to a surgical complication (e.g., bleeding complications) may be sent to the HCP 29212 to equip the HCP 29212 with more relevant data to prevent/mitigate potential bleeding complications. Additionally, such the AI model may prevent biomarker measurement data that may be unrelated to bleeding complications from being reported to reduce distractions by less relevant data to the HCP 29212.

Patient analysis 29224 may include an analytical model. The analytical model may include computer implemented software, a series of parameters, or a probability, for example. The analytical model may include an artificial intelligence model. The artificial intelligence model may be trained. For example, the AI model may be trained at machine learning 29218. The analytical model may be trained to recognize patterns within a dataset, such as the data collection. The analytical model may be deployed. The analytical model may be deployed to apply the recognized patterns to data, such as biomarkers, to improve performance without human guidance. The analytical model may be deployed as a computer implemented program. The analytical model may be deployed as a part of a larger computing system. The analytical model may be deployed with a model performance parameter.

In an example, the analytical model may be deployed to an embedded device, such as a wearable. The analytical model may analyze received data, such as incoming patient data. The analytical model may perform an analysis. The analytics model may perform an analysis based on the received patient data. The analysis may generate an output, including but not limited to, a diagnosis, a notification, surgical complication, and the like. For example, a wearable may use an analytics model to analyze incoming heart rate data. The wearable may determine the heart rate indicates sepsis based on the analytics model and the heart rate data. The wearable may send a notification to the HCP based on the indicated sepsis.

Figure 108:
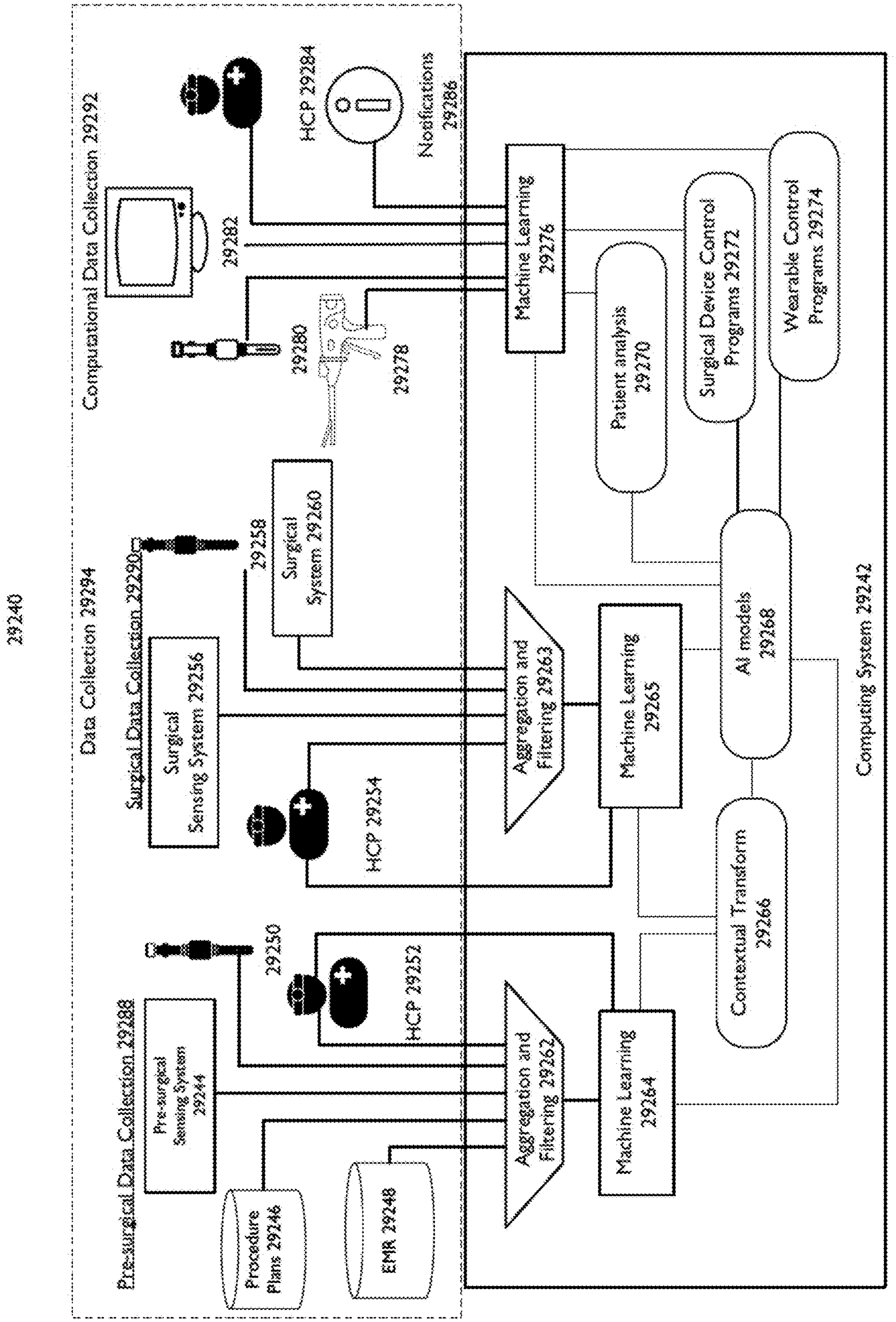

FIG. 108 depicts a block diagram for applying machine learning to improve artificial intelligence algorithms and/or iterations of learning for artificial intelligence algorithms. The computing system 29242 may include computing hardware including a processor, memory, input/output sub-systems, and the like. The processor may be configured (via application specific hardware, software, firmware, or the like) to transform received data and to derive contextualized for output. For example, the processor may include a microprocessor, a microcontroller, a FPGA, and an application-specific integrated circuit (ASIC), a system-on-a-chip (SOIC), a digital signal processing (DSP) platform, a real-time computing system, or the like. For example, processor may be configured to implement computing functions and/or modules as disclosed herein. For example, the processor may be configured for aggregation and/or filtering 29262, aggregation and/or filtering 29263, machine learning 29264, machine learning 29265, machine learning 29276, contextual transform 29266 (e.g., including real-time intra-operative processing), artificial intelligence models 29268, patient analysis 29270, surgical device control programs 29272, wearable control programs 29274, and the like.

The computing system 29242 may be any device suitable for processing sensor, health record data, user input, and the like, to transform the data and derive computational data for output. The computational output may include a sensor measurement. The computational output may include contextual information or a context, for example, which may include additional information relevant to the present understanding and/or interpretation of the sensor measurement. For example, the context may include pre-surgery and/or pre-therapy baselines. For example, the context may include situational awareness of incorrectly connected and/or incorrectly operating surgical and/or sensing systems. For example, the context may include adjustments to products, surgical plans, and/or margins.

The computing system 29242 may be incorporated into the system 29240 with any method suitable for implementation of the functionality disclosed herein. For example, the computing system 29242 may be incorporated as a stand-alone computing system. For example, the computing system may be incorporated into a surgical hub, such as that disclosed in FIG. 1. For example, the computing system 29242 may be incorporated into a sensing system itself (e.g., sensing both pre-surgical and surgical data and providing contextualized data as an output). For example, the computing system 29242 may be incorporated into a surgical device itself (receiving both pre-surgical and surgical data and providing contextualized data, computational data, and/or alerts as an output).

A data collection, such as data collection 29294 may be provided. Machine learning may use the data collection, such as data collection 29294. Data collection 29294 may be used by machine learning to train a model, verify a model, create a model, determine a model, and the like.

Data collection 29294 may include one or more data sources. For example, data collection 29294 may include pre-surgical data collection 29290, surgical data collection 29290, and computational surgical data 29292. Data collection 29294 may include one or more biomarkers. The one or more biomarkers may come from one or more computing systems, surgical sensing systems, wearable devices, displays, surgical instruments, surgical devices, sensor systems, devices, and the like. The data collection 29294 may include electronic medical records for a patient, data for a patient, data for other patients, data regarding past procedures, data regarding research for procedures, medical data, instructions from a health care provider, plans for a surgery, and the like.

Data collection may include data from a number of different sources. For example, the sources may include procedure plans database 29246, EMR 29248, pre-surgical sensing system 29244, wearable device 29250, data from health care provider 29252, surgical sensing system 29256, health care provider 29254, wearable device 29258, surgical system 29260, wearable device 29280, surgical instrument 29278, human-interface device 29282, data from health care provider 29284, and data related to notifications 29286.

Data collection 29294 may include pre-surgical data collection 29288. Pre-surgical data collection 29288 may include data from one or more data sources. Pre-surgical data collection 29288 may include data that is related to a patient that may be recorded prior to a surgery. Pre-surgical data collection 29288 may include one or more biomarkers they may have been recorded for a patient prior to a surgery. For example, a heart rate and blood glucose level for a patient may be recorded for a patient prior to a surgery.

Pre-surgical data collection 29288 may include data from pre-surgical sensing system 29244. Pre-surgical sensing system 29244 may include any configuration of hardware and software devices suitable for sensing and presenting patient parameters and/or biomarkers that may be relevant before, during, or after a surgical procedure. Such a pre-surgical sensing system 29244 may include any of the sensing and monitoring systems disclosed herein, including uncontrolled patient monitoring systems, controlled patient monitoring systems, and the like. For example, pre-surgical sensing system 29244 may include a wearable patient sensor system. The pre-surgical sensing system 29244 may provide data suitable for establishing baselines of patient biomarkers for use in contextual determination during and/or after surgery. The pre-surgical sensing system 29244 may provide data suitable for establishing baselines of patient biomarkers for use in making predications and/or creating computational data. The pre-surgical sensing system 29244 may incorporate or be incorporated into the sensing system 20001 as shown in FIG. 1B.

Pre-surgical data collection 29288 may include data from wearable device 29250. Wearable device 29250 may include any configuration of hardware and software devices suitable for sensing and presenting patient parameters and/or biomarkers that may be relevant before, during, or after a surgical procedure. Such systems may be used by the patient for any amount of time prior to surgery, inside and outside of a medical facility. To illustrate, via an uncontrolled patient monitoring system, the patient may use a wearable heart-related sensor at home for four weeks prior to a surgical procedure. And/or, via a controlled patient monitoring system, an HCP may monitor the same and/or analogous biomarkers using facility equipment during time the patient is prepped immediately before the surgical procedure. For example, the wearable device 29250 may provide data suitable for establishing baselines of patient biomarkers for use in contextual determination and/or for use in creating computational data. Wearable device 29250 may include any of those disclosed herein, such as those with reference to FIG. 1B for example.

Pre-surgical data collection 29288 may include procedure plans 29248. Procedure plans 29248 may include any data source relevant to a health procedure (e.g., relevant to a health procedure in view of a particular patient and/or facility). Procedure plan 29248 may include structured data indicative of the desired end result, the surgical tactics to be employed, the operation logistics, and the like. Procedure plan 29248 may include an accounting of the equipment to be used and/or the techniques to be used. Procedure plan 29248 may include an order. Procedure plan 29248 may include a timeline. The structured data may include defined fields and/or data tags associated corresponding values. The structured data may include codes associated with surgical steps.

Pre-surgical data collection 29288 may include EMR 29248. EMR 29248 may include any data source relevant to a patient in view of a health procedure, such a surgical procedure. EMR 29248 may include information such as allergies and/or adverse drug reactions, chronic diseases, family medical history, illnesses and/or hospitalizations, imaging data, laboratory test results, medications and dosing, prescription record, records of surgeries and other procedures, vaccinations, observations of daily living, information collected by pre-surgical sensing system 29244, information collected by wearable device 29250, and the like.

Pre-surgical data collection 29288 may include data from a pre-surgical healthcare provider, such as HCP 29252. Data from HCP 29252 may include any data relevant to a pre-surgical sensing system, a patient record, a procedure plan, and the like. Data from HCP 29252 may include data that may be relevant to an operation, configuration, and/or management of a computing system, such as computing system 29242. For example, data from HCP 29252 include feedback that may be provided to a machine learning module, such a machine learning module 29264. The data from HCP 29252 may include manually entering data that may not be received directly for a relevant source (such as manually entering a manually taken biomarker reading, for example).

Data collection 29294 may include surgical data collection 29290. Surgical data collection 29290 may include data from one or more data sources. Surgical data collection 29290 may include data that may be related to a patient that may be recorded during a surgery. Surgical data collection 29290 may include one or more biomarkers they may have been recorded for a patient during a surgery. For example, a heart rate and blood glucose level for a patient may be recorded for a patient during a surgery.

Surgical data collection 29290 may include one or more data sources. Surgical data collection 29290 may include data from surgical sensing system 29256, HCP 2954, surgical system 29260, and wearable device 29258.

Surgical data collection 29290 may include data from surgical sensing system 29256. Surgical sensing system 29256 may include any configuration of hardware and software devices suitable for sensing and presenting parameters patient biomarkers that may be relevant during a surgical procedure. Surgical sensing system 29256 may include the sensing and monitoring systems disclosed herein, including controlled patient monitoring systems, surgeon monitoring systems, environmental sensing systems, and the like.

Surgical data collection 29290 may include data from surgical sensing system 29256. Surgical sensing system 29256 may include any configuration of hardware and software devices suitable for sensing and presenting parameters patient biomarkers that may be relevant during a surgical procedure. Surgical sensing system 29256 may include one or more of the sensing and monitoring systems disclosed herein, including controlled patient monitoring systems, surgeon monitoring systems, environmental sensing systems, and the like.

Surgical data collection 29290 may include data from wearable device 29258. Wearable device 29258 may include any configuration of hardware and software devices suitable for sensing and presenting patent parameters and/or biomarkers that may be relevant before, during, or after a surgical procedure. Such systems may be used by the patient for any amount of time prior to surgery, inside and outside of a medical facility. To illustrate, via an uncontrolled patient monitoring system, the patient may use a wearable heart-related sensor at during a surgical procedure. And/or, via a controlled patient monitoring system, a healthcare provider may monitor the same and/or analogous biomarkers using facility equipment during time of the surgical procedure. For example, the wearable device 29258 may provide data suitable for use in a contextual determination and/or in a creation of computational data. Wearable device 29258 may include any of those disclosed herein, such as those with reference to FIG. 1B for example.

Surgical system 29260 may include any surgical equipment suitable for providing operative data regarding its configuration, use, and/or present condition and/or status, for example. Surgical system 29260 may include equipment in the surgical theater. Surgical system 29260 may include any equipment employed in the surgical theater, such as that disclosed with reference to FIG. 1, FIG. 7A, FIG. 10, and throughout the present application, for example. The surgical system 29260 may include surgical fixtures of a general nature, such as a surgical table, lighting, anesthesia equipment, robotic systems, and/or life-support equipment. Surgical system 29260 may include surgical fixtures that may be related to the procedure at-hand, such as imaging devices, surgical staplers, energy devices, endocutter clamps, and the like. For example, surgical system 29260 may include be one or more of a powered stapler, a powered stapler generator, an energy device, an energy device generator, an in-operating-room imaging system, a smoke evacuator, a suction-irrigation device, an insufflation system, or the like.

The surgical system 29260 may include at least one of a surgical instrument, surgical visualization system, monitor, sound system, energy devices, a wearable, and the like. For example, the surgical system may include a surgical hub. For example, the surgical system may include a surgical stapler. For example, the surgical system may include an endocutter, for example. Data from the surgical instrument may include surgical instrument parameters. The surgical instrument parameters may include surgical instrument power, for example. Data from the surgical visualization system may include location of surgical instruments in relation to a patient surgical site and/or organ. For example, data may include the distance between a surgical stapler and a close vital organ.

Surgical data collection 29290 may include data from a surgical HCP, such as HCP 29254. Data from HCP 29254 may include any data relevant to a surgical sensing system, a wearable device, a surgical system, a machine learning, a patient analysis, a surgical device control program, a wearable control program, a contextual transform, an artificial intelligence model, and the like. For example, HCP 29254 may provide data that may be associated with surgical system 29260, wearable device 29258, surgical sensing system 29256, machine learning 29265, and the like. For example, the HCP 29254 may provide data that may trigger an interaction with the context transform 29266 and/or machine learning 29265. The data from HCP 29254 may include manually entering data not received directly for any relevant source (such as manually entering a manually taken biomarker reading, for example).

The data received from the pre-surgical data sources, such as pre-surgical data collection 29288, may be subject to aggregation and/or filtering 29262. Aggregation and/or filtering 29262 may perform pre-processing on data received from pre-surgical data collection 29288. The data received from the surgical data sources, such as surgical data collection 29290, may be subject to aggregation and/or filtering 29263. Aggregation and/or filtering 29263 may perform per-processing on data received from surgical data collection 29290. Aggregation and/or filtering 29262 and aggregation and/or filtering 29263 may be used to prepare and format the data for use by computing system 29242. For example, aggregation and/or filtering 29262 and aggregation and/or filtering 29263 may prepare data to be processed by machine learning 29264, machine learning 29265, machine learning 29276, contextual transform 29266, artificial intelligence models 29268, surgical device control programs 29272, and wearable control programs 29274.

Processing the data received from the pre-surgical data collection 29288 by aggregation and/or filtering 29262 may include filtering (e.g., to select sensor data from the stream of data from pre-surgical sensing system 29244). Aggregation and/or filtering 29262 may use filtering to help reject noise in data from pre-surgical data collection 29244. Aggregation and/or filtering 29262 may use a method to establish a baseline for a biomarker from pre-surgical data collection 29288. Aggregation and/or filtering 29262 may perform time mapping on data from pre-surgical data collection 29288 (e.g., to place received values from different sources in alignment with each other in regard to time). Time mapping may aid in correlation and ratio analysis, which may occur in contextual transform 29266.

Aggregation and/or filtering 29262 may translate data from pre-surgical data collection 29288. The translation of data may include coordinating formats, coordinating data types, translating from one format to another format, translating from one data type, to another data type, accounting for a difference between a data source data format, and accounting for a data type expected by another module, such as machine learning 29264. Translating may include translating the data into a format suitable for machine learning, for artificial intelligence models, for patient analysis, for use by a surgical device control program, and/or for use by a wearable control program. Data from the pre-surgical data collection 29288 may be translated into a notification for display, such as display on a human-interface device 29282. Data from pre-surgical data collection 29288 may be translated into a setting for the surgical device 29278. Data from surgical collection 29290 may be translated into data that may be included and/or used for notifications 29287.

Processing the data received from surgical data collection 29290 by aggregation and/or filtering 29263 may include filtering (e.g., to select sensor data from the stream of data from surgical system 29260). Aggregation and/or filtering 29263 may use a method to establish a baseline for a biomarker from surgical data collection 29290. Aggregation and/or filtering 29263 may use filtering to help reject noise in data from surgical data collection 29290. Aggregation and/or filtering 29263 may perform time mapping on data from surgical data collection 29290 (e.g., to place received values from different sources in alignment with each other in regard to time). Time mapping may aid in correlation and ratio analysis, which may occur in contextual transform 29266.

Aggregation and/or filtering 29263 may translate data from surgical data collection 29290. The translation of data may include coordinating formats, coordinating data types, translating from one format to another format, translating from one data type, to another data type, accounting for a difference between a data source data format, and accounting for a data type expected by another module, such as machine learning 29265. Translating may include translating the data into a format suitable for machine learning, for artificial intelligence models, for patient analysis, for use by a surgical device control program, and/or for use by a wearable control program. Data from the surgical data collection 29290 may be translated into a notification for display, such as display on a human-interface device 29282.

Data from surgical data collection 29290 may be translated into a setting for the surgical device 29278. Data from surgical collection 29292 may be translated into data that may be included and/or used for notifications 29287.

Contextual transform 29266 may operate to provide a context for data, such as pre-surgical data collection 29288 and/or surgical data collection 29290. For example, contextual transform 29266 may transform data into contextualized surgical data, which may be included in computational data collection 29292. To illustrate, as an input the contextual transform may receive surgical data that includes, for example, a measurement time, a sensor system identifier, and a sensor value. Contextual transform 29266 may output contextualized surgical data. Contextual transform 29266 may output data that may be modified and/or enhanced by machine learning 29264, machine learning 29265, machine learning 29276, patient analysis 29270, surgical device control programs 29272, wearable control programs 29274, and artificial intelligence models 29268.

Contextual transform 29266 may determine and/or store data that may be related to each other. Contextual transform 29266 may determine how data may be related to each other. For example, contextual transform 29266 may determine that data from surgical data collection 29290 may be related to data from pre-surgical data collection 29290. Contextual transform 29266 may determine a context for the data. Context, for example, additional information relevant to the present understanding and/or interpretation of the sensor measurement.

Computational data collection 29292 may include data that may be generated, created, determined, and/or computed by computing system 29242. For example, computational data collection 29292 may include models output from machine learning, data generated by machine learning, biomarkers processed by computing system 29242, augmented data, predictive probabilities, firmware, firmware updates, parameters for surgical devices, surgical device control program, updates to surgical device control programs, wearable control programs, parameters for wearable devices, parameters for controlling surgical devices, electronic medical records, contextual data, contextual surgical data, notifications, requests for feedback, messages to healthcare providers, and the like.

Computational data collection 29292 may include context, for example, additional information relevant to the present understanding and/or interpretation of the sensor measurement. For example, the context may include pre-surgery and/or pre-therapy baselines. For example, the context may include situational awareness of incorrectly connected and/or incorrectly operating surgical and/or sensing systems. For example, the context may include adjustments to products, surgical plans, and/or margins. Computational data collection 29292 may include data sent to or received from surgical device 29278, wearable device 29280, human-interface device 29282, health care provider 29284, and notifications 29286. Computational data collection 29292 may be created, modified, received by and/or sent by machine learning 29264, machine learning 29265, machine learning 29276, contextual transform 29266, artificial intelligence models 29268, patient analysis 29270, surgical device control programs 29272, wearable control programs 29274, and/or any combination thereof.

Computational data collection 29292 may include data that provides a context. The context may include additional information that may place a biomarker into a specific context for the healthcare providers. For example, computational data collection 29292 may include instructions and/or information about a baseline value for a sensor value, an alert of a deviation, relevant information from the patient's record, relevant information to a procedural element of the surgery, surgical device settings, and/or any information the healthcare provider might find relevant to have at the moment of the sensor's measurement itself. The context may be determined by machine learning, such as by machine learning 29264, machine learning 29265, and/or machine learning 29276. Computational data collection 29292 may include one or more data tags. The data tags may include logging data (indicating that that a specific transform or other processing has occurred).

Computational data collection 29292 may include data that may be provided by HCP 29284. For example, HCP 29284 may provide feedback regarding data provided by machine learning 29276. Computational surgical data 29292 may include data that may be sent to HCP 29284. For example, HCP 29284 may receive data provided by machine learning 29276. Data from HCP 29284 may include any data relevant to a surgical sensing system, a wearable device, a surgical system, a machine learning, a patient analysis, a surgical device control program, a wearable control program, a contextual transform, an artificial intelligence model, and the like. For example, HCP 29284 may provide data that may be associated with surgical device 29278, wearable device 29280, a patent, human-interface device 29282, notifications 29286, computing system 29242, and/or any combination thereof. For example, the HCP 29284 may provide data that may trigger an interaction with the context transform 29266 and/or machine learning 29276. The data from HCP 29284 may include manually entering data not received directly for any relevant source (such as manually entering a manually taken biomarker reading, for example).

Human-interface device 29282 may include any device suitable for producing a perceptible representation of computational data, such as computational data collection 29292. The perceptible representation may include a visual indication, an audible indication, or the like. The human-interface device 29282 may include a computer display. For example, the human-interface device 29282 may include a visual representation including text and/or images on a computer display. The human-interface device 29282 may include a text-to-speech device. For example, the human-interface device 29282 may include synthesized language prompt over an audio speaker. The human-interface device 29282 may communicate the computational data to the surgeon and/or surgical team. The human-interface device 29282 may include and/or be incorporated into any suitable device disclosed herein. For example, the human-interface device 29282 may include and/or be incorporated into any of the primary display 20023, a first non-sterile human interactive device 20027, and/or a second non-sterile human interactive device 20029, such as that disclosed in FIG. 2A for example. For example, the human-interface device 29282 may include and/or be incorporated into a human interactive device 20046, such as that disclosed in FIG. 2B. For example, the human-interface device 29282 may include and/or be incorporated into the display 20224 of a surgical instrument, such as that disclosed in FIG. 7A for example.

The notifications 29286 may include any device suitable for generating a perceptible indication that relevant computational data is available and/or has changed. The indication may include a visual indication, an audible indication, a haptic indication, and the like. The notifications 29286 may incorporate any of the human-interface devices 27020 disclosed here. The notifications 29286 may include non-verbal and/or non-textual indications to represent contextual data is available and/or has changed. For example, the alert system may include audio tones, visual color changes, lights, and the like. For example, the notification may include a haptic tap on a wearable device, such as a smartwatch worn by the surgeon. Notifications 29286 may include computational data, pre-surgical data, surgical data, and/or post-surgical data. Notifications 29286 may include a request from a machine learning algorithm for a HCP to provide feedback regarding data, a recommendation, an accuracy of an artificial intelligence model, an accuracy of training data, an accuracy of machine learning, a diagnosis, an indication of a problem, data generated by machine learning, a patient analysis, a conclusion regarding a patient analysis, a modification to a surgical device control program, a surgical device control program, wearable control program, any combination thereof, and the like. For example, notifications 29286 may request that HCP 29284 provide feedback regarding a surgical device control program that may be sent to surgical device 29278.

The surgical device 29278 may include any equipment employed for a surgical procedure (such as surgical systems 29260) that may have a configurable aspect to its operation. The configurable aspect of the equipment may include any adjustment or setting that may influence the operation of the equipment. For example, surgical device 29278 may have software and/or firmware adjustable settings. Surgical device 29278 may be hardware and/or structurally adjustable settings. In an example, the surgical device 29278 may report its present settings information to the computing system 29242. In an example, the surgical device 29278 may include an artificial intelligence model that may be deployed by computing system 29242, trained at computing system 29242, modified by computing system 29242, any combination thereof, and the like.

Example device settings for surgical device 29278 may include placement, imaging technology, resolution, brightness, contrast, gamma, frequency range (e.g., visual, near-infrared), filtering (e.g., noise reduction, sharpening, high-dynamic-range), and the like for imaging devices; placement, tissue precompression time, tissue precompression force, tissue compression time, tissue compression force, anvil advancement speed, staple cartridge type (which may include number of staples, staple size, staple shape, etc.), and the like for surgical stapling devices; and placement, technology type (such as harmonic, electrosurgery/laser surgery, mono-polar, bi-polar, and/or combinations of technologies), form-factor (e.g., blade, shears, open, endoscopic, etc.) coaptation pressure, blade amplitude, blade sharpness, blade type and/or shape, shears size, tip shape, shears knife orientation, shears pressure profile, timing profile, audio prompts, and the like for energy devices, for example.

Computational data collection 29292 may include data from wearable device 29280. Wearable device 29280) may include any configuration of hardware and software devices suitable for sensing and presenting patent parameters and/or biomarkers that may be relevant before, during, or after a surgical procedure. Such systems may be used by the patient for any amount of time prior to surgery, inside and outside of a medical facility. To illustrate, via an uncontrolled patient monitoring system, the patient may use a wearable heart-related sensor at during a surgical procedure. And/or, via a controlled patient monitoring system, a healthcare provider may monitor the same and/or analogous biomarkers using facility equipment during time of the surgical procedure. For example, the wear able device 29280 may provide data suitable for use in a contextual determination during and/or after surgery. Wearable device 29280 may include any of those disclosed herein, such as those with reference to FIG. 1B for example.

Computational data collection 29292 may include a wearable control program that may have been sent by wearable control programs 29274 wearable device 29280. Computational data collection 29292 may include an artificial intelligence model that may be sent to wearable device 29280.

The machine learning module 29264 may perform data preparation as described herein with the pre-surgical data collection 29288 (e.g., a dataset). In an example, the data preparation may further include the machine learning module 29264 receiving input from an HCP 29252 labeling a subset of the data records in the dataset for training a pre-surgical patient analysis model (e.g., a training dataset). The pre-surgical patient analysis model may be stored at and/or or included within AI model 29268. The pre-surgical patient analysis model may be a training data set with supervised machine learning for patient analysis 29270 (e.g., a probability of surgical complications during a surgical procedure). For example, machine learning 29264 may receive data to from pre-surgical data collection 29288 that may be used to train a model that may be stored at AI model 29268 and may be deployed at patient analysis 29270.

Those of skill in the art will recognize any suitable machine learning algorithm may be used to build the model 29268. For example, the input from HCP 29252 may include a "high risk" label when a patient's data record from patent records 29248 indicates a risk of surgical complications related to adhesions due to a history of multiple prior colorectal surgical procedures and pre-surgical biomarker measurement data from a pre-surgical sensing system 29244 or a wearable device 29250 indicating a probability of presence of chronic inflammation response. For example, the input from HCP 29252 may include a "medium risk" label when a patient's data record indicates a risk of surgical complications related to adhesions due to a history of multiple prior colorectal surgical procedures without any indication from pre-surgical biomarker measurement data that there is a probability of presence of chronic inflammation response. For example, the input from HCP 29252 may include label "low risk" a when a patient's data record indicates a risk of surgical complications related to adhesions due to a history of a single prior colorectal surgical procedure without any another indication of a probability of adhesion. The labels provided by HCP 29252 may be machine learning 29264 to train one or more models that may be used for patient analysis, modification and/or creation of surgical device control programs, and modification and/or creation of wearable control programs. The model may be stored at AI models 29268 and may be deployed at machine learning 29264, patient analysis 29270, surgical device control programs 29272, and/or warble control programs 29274.

Further, the input from HCP 29252 may include a notification level setting associated with each high-risk label, medium-risk label, or low-risk label. For example, a notification level setting may be used by machine learning module 29264 to train a model to send a notification to HCP 29252 and/or HCP 29284 when the model may predict a high risk of surgical complication. In an example, a notification level may be used by the model when deployed at machine learning 29264 to send a notification to HCP 29252 when the model predicts a high risk of surgical complication. The HCP 29252 may respond to the notification with feedback, and the model may further be trained using the feedback. In an example, a notification level may be used by the model when deployed at patient analysis 29270 to send a notification to HCP 29284 and/or notifications 29286 when the model predicts a high risk of surgical complication. The HCP 29284 may respond to the notification with feedback, and the model may further be trained using the feedback.

The data preparation may also include the machine learning module 29264 receiving input from an HCP 29252 labeling a second subset of the data records in the dataset for validating a model (e.g., a validation dataset) with supervised machine learning.

The machining learning process 29264 may perform model training for the model. The machining learning process 29264 may perform model validation with the validation dataset after model may be deem trained (e.g., when a neutral network-based model's cost function has reached a global minimum).

Upon completing model validation, the machine learning module 29264 may perform model testing using a third subset of the data records in the dataset (e.g., an unlabeled dataset) for testing a model. The machine learning module 29264 may send predictions produced by the model to HCP 29252 for verification and/or HCP 29284. For example, the model may predict a high risk of surgical complication and an associated notification level of high-risk surgical complications. The machine learning module 29264 may send the high-risk prediction, notification level of high risk only, and decision points that may have led to such prediction (e.g., from the model 29268 trained with a decision tree machine learning algorithm).

In an example, based on the training dataset labeled by the HCP 29252, the model that may have been trained with a decision tree machine learning algorithm may learn a pattern (e.g., among other patterns) that a high-risk level of surgical complications may correlate with the combination of three or more prior colorectal surgical procedures and pre-surgical measurement data for at least one biomarker associated with a probability of chronic inflammation response (e.g., a high skin conductance level, a low tissue oxygenation level, and the like). Such a pattern may be a decision point in a decision tree algorithm-based model. The machine learning module 29264 may send a decision point along with the high-risk prediction and the notification level of high risk to the HCP 29252 and/or HCP 29284. machine learning module 29264 may send a decision point along with the high-risk prediction and the notification level of high risk to notifications 29286. In response, the HCP 29252 and/or HCP 29284 may provide a response verifying that the prediction is accurate. The verification may contribute to a success metric for meeting an accuracy parameter for deploying the model in a production environment (e.g., may be used on patients without supervision). A response from the HCP 29252 and/or HCP 29284 indicating the predication may be inaccurate may contribute to a failure metric for preventing model deployment due to inaccurate model predictions (e.g., may be used on patients with supervision).

The machine learning module 29264 may output the decision tree from the model. For example, the decision tree may be stored in AI models 29268. The decision tree may be sent to HCP 29252 and/or HCP 29284 to allow the decision tree to be verified holistically as opposed to one predication at a time.

Upon successful model testing with the test dataset, the computing system 29242 may deploy the model to a production environment production. For example, the model may be deployed to machine learning 29264, machine learning 29265, machine learning 29276, and patient analysis 29270. The deployed model 29268 may be further improved (e.g., for patient analysis purposes) in production. For example, patient analysis 29270, machine learning 29264, and/or machine learning 28276 may use feedback from an HCP to improve the model.

For example, the model may produce false negative predictions and/or false positive predictions. Feedback for such false negative and/or false positive predictions may be sent to the machine learning module 29276. In an example, the model may incorrectly predict a high risk of surgical complication. When the machine learning module 29276 sends an associated notification 29286, which may be sent to HCP 29284, the HCP 29284 may provide a response to the machine learning module 29276 indicating the prediction is a false positive. In such case, the machine learning module 29276 may not update the model threshold for predicting a positive prediction for surgical complications. The model may be stored and/or updated in AI models 29268 such that another deployment of the model may benefit from the feedback improvements.

In an example, the model may incorrectly predict no risk of a surgical complications. The machine learning module 29276 may fail to send a notification, such as notifications 29286, to HCP 29284. HCP 29284 may not be provided with an opportunity to provide feedback. In such a case, the machine learning module 29276 may detect the error by checking the model prediction against the surgical outcome data from surgical system 29260 (e.g., which may be a surgical hub). The machine learning module 29276 may lower the model threshold for predicting a positive prediction for surgical complications to reduce the possibility of predicting false negatives. The model may be stored and/or updated in AI models 29268 such that another deployment of the model may benefit from the feedback improvement and/or detection of the error.

The machine learning module 29265 may perform data preparation as described herein with the surgical data collection 29290 (e.g., a dataset) for creating and training a model, which may be a surgical device control program model. The model may be stored and/or deployed at AI models 29268. The model may be deployed at machine learning 29265, machine learning 29276, and/or surgical device control programs 29272. In an example, the data preparation may further include creating a data field and appending it to a (e.g., each) data record in the dataset. The data field may indicate whether there was a surgical complication during a respective surgical procedure derived from surgical data from collected from a surgical system 29260 (e.g., a surgical hub).

The data field may indicate whether an operation of a surgical device or a wearable device may be improved (e.g., the device may have sub-optimally operated). The data field may serve as a desired output label for training the model with supervised machine learning for improving a model and/or a surgical device control program that may be determined and/or deployed at device control program 29272 to improve a surgical outcome. For example, the model may be deployed at surgical device control program 29272 and may be used to improve a surgical device program associated with surgical device 29278.

The machine learning module 29265 may perform model training, model validation, model testing for an artificial intelligence algorithm that may be used to create a model, such as a decision tree algorithm model. Those of skill in the art will recognize any other suitable machine learning algorithm may be used to build the model. The model may learn a pattern (e.g., among other patterns) that a surgical complication (e.g., a bleeding complication) occurs when a first condition and a second condition occur. The first condition may be that data from surgical sensing system 29256 and/or wearable device 29258 indicates at least one of: heart rate elevated above a threshold A, blood pressure above a threshold B, blood pH below a threshold C, or an edema measurement above a threshold D. The second condition may be that a control program associated with surgical device 29278 (e.g., a linear stapler) may be configured to compress tissue with a compression force below a threshold E. The model may learn another pattern (e.g., among other patterns) that a surgical complication (e.g., a bleeding complication) does not occur when the first condition and the second condition occur. A third condition may be that a control program associated with surgical device 29278 (e.g., a linear stapler) may be configured to compress tissue with a compression force above the threshold E.

Upon model testing using a test dataset, the computing system 29242 may deploy model to a production environment as a part of the machine learning module 29276. For example, the model may be deployed at machine learning 29264, machine learning 29265, machine learning 29276, AI models 29268, patient analysis 29272, surgical device control programs 29272, and/or wearable control programs 29274. During an operation in production, the model may detect a data pattern that the model may have learned during model training. For example, the model may receive input data indicating heart rate elevated above threshold A and indicating that a control program for surgical device 29278 is configured to apply a compression force below threshold E. In response, the model may predict a surgical complication and the machine learning module 29276 may update a deployed model, may update a model for generating a surgical device control program, may send updated parameters to the surgical device, or may send an updated surgical device control program to the surgical device to, for example, increase the compression force to be above threshold E.

The machine learning module 29265 may perform data preparation as described herein for creating and training a model, which may be a model for a wearable device such as wearable device 29258, using the pre-surgical data collection 29288 (e.g., a pre-surgical dataset) and the surgical data collection 29290 (e.g., a surgical dataset). In an example, the data preparation may further include creating a data field and appending it to a (e.g., each) data record in the dataset. The data field may indicate whether there may have been a surgical bleeding complication during a respective surgical procedure derived from surgical data from collected from a surgical system 29260 (e.g., a surgical hub). The data field may serve as a desired output label for training the model with supervised machine learning for adjusting a wearable control program, which may be stored at wearable control program 29272 and may be deployed at wearable device 29280, for improved sensed data relevancy.

For example, the machine learning module 29265 may perform model training, model validation, model testing for a model, such as a decision tree algorithm model. Those of skill in the art will recognize any other suitable machine learning algorithm may be used to build the model. The model may learn a pattern (e.g., among other patterns) that a surgical bleeding complication occurs (e.g., at a dissection/mobilization procedure step) when at least two conditions occur. One condition may be that pre-surgical data from pre-surgical sensing system 29244 and/or wearable device 29250 indicates at least one of: heart rate elevated above a threshold A, blood pressure above a threshold B, blood pH below a threshold C, or an edema measurement above a threshold D. Another condition may be that surgical data from surgical sensing system 29256 and/or wearable device 29258 indicates at least one of: heart rate elevated above a higher threshold A' (e.g., as compared to threshold A), blood pressure above a higher threshold B' (e.g., as compared to threshold B), blood pH below a lower threshold C' (e.g., as compared to threshold C), or an edema measurement above a higher threshold D' (e.g., as compared to threshold D).

The machine learning module 29265 may be configured to send update a model for a wearable control program. For example, machine learning module 29265 may update a model that may be deployed at machine learning 29264, machine learning 29265, machine learning 29276, wearable control programs 29274, wearable device 29250, wearable device 29258, wearable device 29280 and the like. The machine learning module 29265 may be configured to update a wearable control program that may be stored and/or deployed at wearable control programs 29274, wearable device 29250, wearable device 29258, and/or wearable device 29280. For example, an update may be sent to update the wearable control program of wearable device 29280) (e.g., configured for measuring heart rate, blood pressure, blood pH, and/or edema) when a surgical procedure (e.g., a sleeve gastrectomy procedure) is detected to have entered a dissection/mobilization procedure step. The update to the wearable control program may be to increase the data sampling rate (e.g., from once per minute to once per second). During the model operation (e.g., after model deployment) as a part of the machine learning module 29276 in production, such increased data sampling rate (e.g., during the dissection/mobilization) of biomarker measurement data related to bleeding complications may be sent to the HCP 29254 and/or HCP 29284 (e.g., via device 29282) to equip the HCP 29284 with more relevant data to prevent/mitigate potential bleeding complications.

Patient analysis 29270 may include software that may be used to provide analysis on a patient. For example, the analysis may indicate a probability of a surgical complication, a probability of surgical success, a diagnosis of a disease, a probability of a disease, a probability of a patient recovery, and the like. Patient analysis 29270 may include a model. The model may be stored outpatient analysis 29270 and/or deployed at patient analysis 29270. Patient analysis 29270 may include a number of models. For example, patient analysis 29270 may include one model for high blood pressure, a second model for normal blood pressure, and the third model for patients with diabetes. A model deployed at patient analysis 29270 may be from machine learning 29264, machine learning 29265, machine learning 29276, and/or AI models 29268. Patient analysis 29270 may include computational data.

Surgical device control programs 29272 may include software that may be used to provide control programs for surgical devices. Surgical device control programs 29272 may include device control programs, such as firmware, that may be stored for surgical devices. Surgical device control programs 29272 may include one or more parameters that may be used to configure, modify, operate, or control a surgical device. Surgical device control programs 29272 may include a model. For example, surgical device control programs 29272 may store a model that may be used for a surgical device, may deploy a model that may be used for a surgical device, or may update a model that may be used for a surgical device. A model deployed at surgical device control programs 29272 may be from machine learning 29264, machine learning 29265, machine learning 29276, and/or AI models 29268. Surgical device control programs 29272 may include computational data.

Wearable control programs 29274 may include software that may be used to provide control programs for wearable devices. Wearable control programs 29274 may include device control programs, such as firmware, that may be stored for wearable devices. Wearable control programs 29274 may include one or more parameters that may be used to configure, modify, operate, or control a wearable device. Wearable control programs 29274 may include a model. For example, wearable control programs 29274 may store a model that may be used for a wearable device, may deploy a model that may be used for a wearable device, or may update a model that may be used for a wearable device. A model deployed at wearable control programs 29274 may be from machine learning 29264, machine learning 29265, machine learning 29276, and/or AI models 29268. Wearable control programs 29274 may include computational data.

Figure 109:
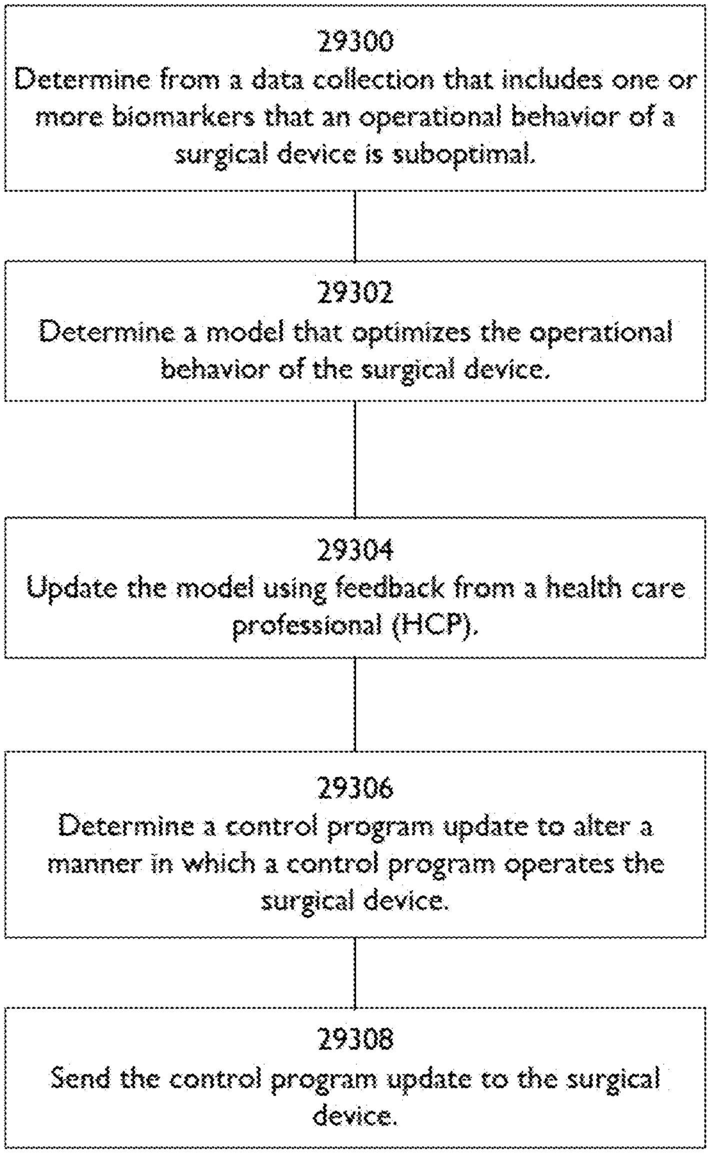

FIG. 109 depicts a method for applying machine learning to a data collection to improve a surgical outcome. The method may be implemented in a computing system. At 29300, an operational behavior of a surgical device may be determined to be suboptimal using a surgical device data and/or a biomarker from a sensing system. The operational behavior of the surgical device may be indicative of how the surgical device may potentially operate or may be operating during the operation. For example, the operational behavior of the surgical device may indicate that the surgical device is a stapler that is firing at a specific power. As another example, the operational behavior of the surgical device may indicate that the surgical device is an endocutter that may be operating at a specific parameter. The operational behavior may include one or more parameters that may control an operation of the surgical device. The operational behavior may include an indication of how the surgical device may perform, a prediction of how the surgical device may perform, an indication of how the surgical device is performing, an indication of a task being performed by the surgical device, an indication of a task being performed by a user (e.g., an HCP) holding the surgical device, and the like.

An indication that an operational behavior is suboptimal may be an indication that the operational behavior may be improved. For example, an operation of a device may be improved when there is an indication that the operational of the device is suboptimal.

The data collection may include one more biomarkers. The one or more biomarkers may be related to a patient that may be planning to go under surgery. For example, a biomarker may be a baseline heart rate for a patient. The one or more biomarkers may be related to a patient that may be undergoing surgery. For example, a surgical device may be used during the surgery on the patient and one or more biomarkers may be recorded (e.g., received from a sensing system) as the surgical device may be used. The one or more biomarkers may indicate how the surgical device may be affecting the patient. For example, it may be expected that a biomarker may be within a range when a surgical device is used. When the biomarker is outside the range, it may indicate that the surgical device may not be operating optimally. In an example, the biomarker that may be outside the range may indicate that an improvement may be made to the surgical device. In an example, the biomarker may indicate that the surgical device may be contributing to a surgical complication and the operational behavior of the surgical device may be considered suboptimal.

At 29302, a model may be determined to optimize and/or improve the operational behavior of the surgical device to improve a surgical outcome using machine learning, the surgical device data, and the biomarker. For example, the machine learning model may be trained to detect a data pattern that a second surgical device operational parameter may be correlated to an absence of a surgical complication under a physiological condition state represented by the biomarker measurement data. The model may be predictive of how a surgical device may operate, may be predictive of how a wearable device may operate, may be predictive of a surgical complication, may be predictive of a surgical outcome may be predictive of a surgical success rate, and the like. The model may diagnose a disease, for example, by indicating a probability that a disease may occur or may be occurring. The model may optimize the operational behavior of the surgical device by determining a surgical outcome and by determining one or more parameters that may be adjusted on the surgical device to improve the surgical outcome. The model may optimize the operational behavior of the surgical device by determining a surgical outcome and by determining that a control program for the surgical device may be modified, updated, and or generated to modify the operational behavior of the surgical device.

A model may be created to be trained using input data, such as surgical device operational parameters recorded during surgical procedures, biomarker measurement data recorded prior to and during surgical procedures, and surgical data such as surgical complications recorded during surgical procedures. The machine learning model may be trained to detect a data pattern that a first surgical device operational parameter may be correlated to a surgical complication under certain physiological state represented by the biomarker measurement data.

In an example, a model may be trained with data from the data collection. The model may predict one or more surgical outcomes. The model may predict one or more surgical complications. The models may be used to determine one or more parameters and/or a control program that may be used to improve and operational behavior of a surgical device to improve one or more surgical outcomes.

At 29304, the model may be updated using a feedback given by a health care processional (HCP) to improve the model. For example, the model's predictions of surgical complications and/or absence of surgical complications may be sent to an HCP for validation. In response, the HCP may provide positive or negative feedback to update the machine learning model to improve model prediction accuracy.

It may be determined that feedback from the HCP may be useful for improving the model. For example, it may be determined that data may be insufficient to provide an accurate prediction for one or more surgical outcomes. It may be determined that feedback from the HCP may be useful for improving the accuracy of a prediction for a surgical outcome. A request for feedback may be sent to the HCP. Feedback from the HCP may be received. The model may be updated using the feedback from the HCP.

At 29306, a control program update may be determined, generated, and/or configured using the model and the surgical device data to alter a manner in which a control program operates the surgical device during a surgical procedure. For example, based on the data pattern for surgical complications and the data pattern for an absence of surgical complications detected by the machine learning model, a control program update, such as an update to use the second surgical device, may be generated for the surgical device on the condition that the surgical device operational parameters and biomarker measure data during actual surgical procedures match the data pattern for surgical complications.

in an example, the control program maybe a model. The model may be associated with and or deployed on the surgical device. For example, surgical device may have artificial intelligence. It may be determined that the model on the surgical device may need to be updated to improve how the surgical device may operate. The control program update may be an improved model, training data for a deployed model, and or other data to update a model on the surgical device. For example, an improved model may be trained and the improved model may be included in a control program update such that the improved model may alter the manner in which the control program operates the surgical device.

In an example, the control program may include surgical device parameters that may change how the surgical device may operate. The surgical device may have a number of parameters that may be adjusted. By adjusting the parameters, the way in which the surgical device may operate may change. For example, the parameters may affect the firing power of a surgical stapler. As another example, the parameters may affect the power given to an endocutter. A control program update may be determined to adjust one or more parameters for the surgical device to alter the manner in which the surgical device operates.

In an example, the surgical device may include a control program, which may be firmware, that may control how the surgical device operates. For example, the control program may be software that operates the hardware on the surgical device. Updates to the control program may include parameters, updates to the firmware, optimizations to the hardware on the surgical device, optimizations to the software on the surgical device and the like. A control program update may be designed to improve, replace, update, or augment the control program that may be operating on the surgical device. For example, the control program update may be designed to provide an advanced feature that may not have been included with the control program currently operating on the surgical device. The control program update may be set to the surgical device to operate the control program on the surgical device. And the surgical device may have the advanced feature upgrade after installing the control program update.

At 29308, the control program update may be sent to the surgical device. For example, the determined control program update to use the second surgical device parameter may be sent to the surgical device for use during a surgical procedure. As another example, the control program update may update a model, a control program, and or other software that may be used by or operating on the surgical device.

A computing system and/or a method may be provided for applying machine learning to a data collection to improve a surgical outcome. The computing system may comprise a processor. The processor may be configured to perform a method and/or a number of actions. An indication may be determined. The indication may indicate that an operational behavior of a surgical device may be suboptimal or may be improved. For example, a data collection may include one or more biomarkers that may be used to determine an indication that an operational behavior of a surgical device may be suboptimal or may be improved. A model that may optimize and/or improve the operational behavior of the surgical device to improve a surgical outcome may be determined using machine learning and/or the data collection. The model may be updated using feedback given by a healthcare provider (HCP) to improve the model. A control program update may be determined and/or generated using the model and the data collection. The control program update may be configured to alter a manner in which a control program operates the surgical device during a surgical procedure. The control program update may be sent to the surgical device.

In an example, a request for feedback may be determined. The request for feedback may result in a faster learning cycle for training the model that optimize and/or improves the operational behavior of the surgical device. The request for feedback may result in a faster training cycle that may optimize and/or improve the operational behavior of the surgical device. For example, the feedback may reduce the amount of data used to train the model, may reduce the amount of time used to train the model, may reduce the amounts of information needed from a user to train the model, and the like. the request for feedback may be sent to the HCP.

In an example, it may be determined that an advanced instrument operation may reduce a complication for a patient and/or may improve a recovery rate for the patient. For example, it may be determined from the model that an advanced instrument operation may reduce a complication for a patient and/or improve a recovery rate for the patient. The control program update may be generated using the model and the data collection, for example, by altering the manner in which the control program operates the surgical device during the surgical procedure to provide the advanced instrument operation.

In an example, the model may further provide a risk level assessment and the feedback given by the HCP may further include a risk level verification that may indicate that the HCP agrees with the risk level assessment provided by the model. For example, the model may determine a risk level using one or more biomarkers for a patient and may provide the risk level 2 and HCP. The HCP may indicate that they agree with the risk level provided by the model.

In an example, the model may provide a notification level. The notification level may enable improvement in the model by seeking feedback from the HCP during the surgical procedure. The notification level may be set so as to seek feedback from the HCP without distracting the HCP during a surgery. The notification level may be set so as to prevent a surgical complication by reducing a distraction to the HCP during a surgery.

In an example, the model may provide a notification level that may reduce one or more distractions to the HCP during the surgical procedure.

In an example, the model may provide a notification level that may improve a quality of the model by seeking feedback from the HCP during the surgical procedure while minimizing one or more distractions to the HCP during the surgical procedure.

In an example, a previous model associated with the control program that may operate the surgical device during the surgery may be determined. The model that may optimize and/or improve and/or improve the operational behavior of the surgical device to improve the surgical outcome may be determined, generated, and/or trained using the machine learning, the data collection, and the previous model.

A computing system and/or a method may be provided for applying machine learning to a data collection to improve a surgical outcome. It may be determined from a data collection that may include one or more biomarkers that an operational behavior of a surgical device may be suboptimal or may be improved. A model that may optimize and/or improve the operational behavior of the surgical device and may predict a surgical complication may be determined. For example, the model may be determined using machine learning and the data collection. The model may be updated using feedback given by a healthcare provider (HCP) to improve the model. A control program update may be generated using the model and the data collection. The control program update may be configured to alter a manner in which a control program may operate the surgical device during a surgical procedure to prevent the surgical complication. The control program update may be sent to the surgical device.

In an example, the control program may be a first control program update and the control program update may be a first control program update. A second control program update may be generated using the model and the data collection. The second control program update may be configured to alter the manner in which a second control program operates a sensing system associated with a patient to monitor for the surgical complication. For example, the first control program update may change how the surgical device operates during the surgical procedure to prevent the surgical complication and the second control program update may change how the sensor system monitors the patient.

In an example, a request for feedback may be determined. The request for the feedback may be for a feedback that may result in a faster learning cycle or training cycle for determining the model that may optimize and/or improve the operational behavior of the surgical device and may predict the surgical complication.

In an example, feedback may be given by the HCP provider. The feedback may include a surgical complication verification that may indicate that the HCP agrees with the surgical complication predicted by the model.

In an example, the model may provide a risk level assessment for the surgical complication. The feedback given by the HCP may include a risk level verification that may indicate that the HCP agrees with the risk level assessment for a surgical complication provided by the model. For example, the model may predict that the patient may experience the surgical complication.

In an example, the model may provide a notification level to improve a quality of the model by seeking feedback about the surgical complication from the HCP during the surgical procedure. For example, the model may determine that it may not have enough information regarding a surgical procedure. The model may determine that feedback from the HCP may benefit the model. The model may set and/or determine the notification level such that the notification level may increase the amount of feedback provided by the HCP, for example, to improve the model.

In an example, the model may provide a notification level to prevent a surgical complication by reducing one or more distraction to the HCP during the surgical procedure.

A computing system and/or a method may be provided for applying machine learning to a data collection to improve a surgical outcome. The computing system may comprise a processor. The processor may be configured to perform a number of actions and/or the method. It may be determined that an operational behavior of a surgical device may be suboptimal or may be improved using a surgical device data and a biomarker from a sensing system. A model that improves the operational behavior of the surgical device to improve a surgical outcome may be determined using machine learning, the surgical device data, and the biomarker. The model may be updated using feedback given by an HCP to improve the model. A control program update may be generated and/or determined using the model and the surgical device data. The control program update may be configured to alter a manner in which a control program operates the surgical device during a surgical procedure.

In an example, a data collection improvement may be determined using the biomarker and the feedback. A model may be updated using the data collection improvement. The data collection improvement may be one or more of an improved data set, a data set with improved accuracy, an improved method of data collection, an improved prediction provided by data, a removal of a false positive, an improvement in data filtering, and the like.

In an example, the biomarker may be a first biomarker, and the sensing system may be a first sensing system. A sensor feedback improvement may be determined using the model and the feedback. A second biomarker may be determined from a second sensing system using the sensor feedback improvement. The model may be updated using the second biomarker. The sensor feedback improvement may be an indication that the second sensing system may provide improved biomarker tracking as compared to the first sensing system. The sensor feedback improvement may be an indication that the second biomarker may improve a diagnosis made with the first biomarker, may improve the accuracy of the first biomarker, may be complementary to the first biomarker, may confirm a prediction based on the first biomarker, may be used with the first biomarker to improve a prediction, and the like.

In an example, the surgical outcome may include one or more of a reduced complication for a patient, an improved recovery rate for the patient, a low false positive sensing issue for the sensing system, and the like.

In an example, improving a surgical outcome may include improving a surgical procedure outcome by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Figure 110:
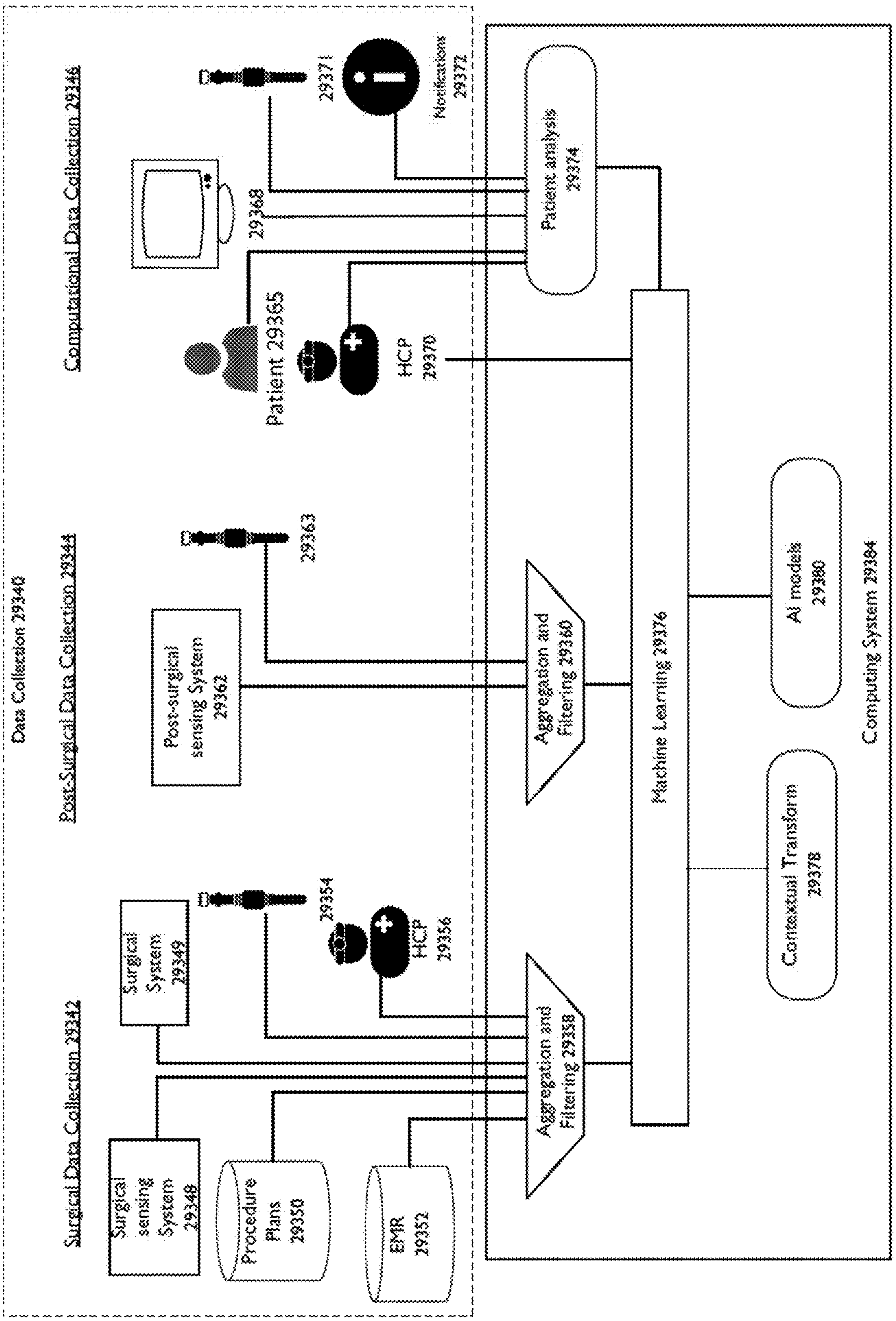

FIG. 110 depicts a flow diagram for applying machine learning to improve one or more patient monitoring measures.

The computing system 29384 may include computing hardware including a processor, memory, input/output subsystems, and the like. The processor may be configured (via application specific hardware, software, firmware, or the like) to transform received data and to derive contextualized for output. For example, the processor may include a microprocessor, a microcontroller, a FPGA, and an application-specific integrated circuit (ASIC), a system-on-a-chip (SOIC), a digital signal processing (DSP) platform, a real-time computing system, or the like. For example, processor may be configured to implement computing functions and/or modules as disclosed herein. For example, the processor may be configured for aggregation and/or filtering 29358, aggregation and/or filtering 29360, machine learning 29376, contextual transform 29378 (e.g., including real-time intra-operative processing), artificial intelligence models 29380, patient analysis 29374, and the like.

The computing system 29384 may be any device suitable for processing sensor, health record data, user input, and the like, before and during surgery, to transform the data and derive computational data for output. The computational output may include a sensor measurement. The computational data may include contextualized data. The computational data may include a context, for example, which may include additional information relevant to the present understanding and/or interpretation of the sensor measurement. For example, the context may include pre-surgery and/or pre-therapy baselines. For example, the context may include situational awareness of incorrectly connected and/or incorrectly operating surgical and/or sensing systems. For example, the context may include adjustments to products, surgical plans, and/or margins.

The computing system 29384 may be incorporated with any method suitable for implementation of the functionality disclosed herein. For example, the computing system 29384 may be incorporated as a stand-alone computing system. For example, the computing system may be incorporated into a surgical hub, such as that disclosed in FIG. 1, for example. For example, the computing system 29384 may be incorporated into a sensing system itself (e.g., sensing both pre-surgical and surgical data and providing contextualized data as an output). For example, the computing system 29384 may be incorporated into a surgical device itself (receiving both pre-surgical and surgical data and providing contextualized data and/or alerts as an output).

A data collection, such as data collection 29340 may be provided. Machine learning 29376 may use the data collection, such as data collection 29340. Data collection 29340 may be used by machine learning 29376 to train a model, verify a model, determine a model, and the like.

Data collection 29340 may include one or more data sources. For example, data collection 29340 may include surgical data collection 29342, post-surgical data collection 29344, and computational data 29346. Data collection 29340 may include one or more biomarkers. The one or more biomarkers may come from one or more computing systems, surgical sensing systems, wearable devices, displays, surgical instruments, surgical devices, sensor systems, devices, and the like. The data collection 29340 may include electronic medical records for a patient, data for a patient, data for other patients, data regarding past procedures, data regarding research for procedures, medical data, instructions from a health care provider, plans for a surgery, and the like.

Data collection 29340 may include data from a number of different sources. For example, the sources may include procedure plans database 29350, EMR 29352, surgical sensing system 29348, surgical system 29349, wearable device 29354, data from health care provider 29356, post-surgical sensing system 29362, and wearable device 29363.

Data collection 29340 may include surgical data collection 29342. Surgical data collection 29342 may include data from one or more data sources. Surgical data collection 29342 may include data that may be related a patient that may be recorded during to a surgery. Surgical data collection 29342 may include one or more biomarkers they may have been recorded for a patient during a surgery. For example, a heart rate and blood glucose level for a patient may be recorded for a patient during a surgery.

Surgical data collection 29342 may include data from surgical sensing system 29348. Surgical sensing system 29348 may include any configuration of hardware and software devices suitable for sensing and presenting patient parameters and/or biomarkers that may be relevant before, during, or after a surgical procedure. Such a surgical sensing system 29348 may include any of the sensing and monitoring systems disclosed herein, including uncontrolled patient monitoring systems, controlled patient monitoring systems, and the like. For example, surgical sensing system 29348 may include a wearable patient sensor system. The surgical sensing system 29348 may provide data suitable for establishing baselines of patient biomarkers for use in determining computational data during and/or after surgery. The surgical sensing system 29348 may incorporate or be incorporated into the sensing system 20001 as shown in FIG. 1B.

Surgical data collection 29342 may include data from wearable device 29354. Wearable device 29354 may include any configuration of hardware and software devices suitable for sensing and presenting patent parameters and/or biomarkers that may be relevant before, during, or after a surgical procedure. For example, the wearable device 29354 may provide data suitable for establishing baselines of patient biomarkers for use in determining computational data during and/or after surgery. Wearable device 29354 may include any of those disclosed herein, such as those with reference to FIG. 1B for example.

Surgical data collection 29342 may include procedure plans 29350. Procedure plans 29350 may include any data source relevant to a health procedure (e.g., relevant to a health procedure in view of a particular patient and/or facility). Procedure plan 29248 may include structured data indicative of the desired end result, the surgical tactics to be employed, the operation logistics, and the like. Procedure plan 29350 may include an accounting of the equipment to be used and/or the techniques to be used. Procedure plan 29350 may include an order. Procedure plan 29350 may include a timeline. The structured data may include defined fields and/or data tags associated corresponding values. The structured data may include codes associated with surgical steps.

Surgical data collection 29342 may include EMR 29352. EMR 29352 may include any data source relevant to a patient in view of a health procedure, such a surgical procedure. EMR 29352 may include information such as allergies and/or adverse drug reactions, chronic diseases, family medical history, illnesses and/or hospitalizations, imaging data, laboratory test results, medications and dosing, prescription record, records of surgeries and other procedures, vaccinations, observations of daily living, information collected by surgical sensing system 29348, information collected by wearable device 29354, and the like.

Surgical data collection 29342 may include data from a surgical healthcare provider, such as HCP 29356. Data from HCP 29356 may include any data relevant to a pre-surgical sensing system, a patient record, a procedure plan, and the like. Data from HCP 29356 may include data that may be relevant to an operation, configuration, and/or management of a computing system, such as computing system 29384. For example, data from HCP 29356 include feedback that may be provided to a machine learning module, such a machine learning module 29376. The data from HCP 29356 may include manually entering data that may not be received directly for a relevant source (such as manually entering a manually taken biomarker reading, for example).

Data collection 29340 may include post-surgical data collection 29344. Post-surgical data collection 29344 may include data from one or more data sources. Post-surgical data collection 29344 may include data that is related to a patient that may be recorded after a surgery. Surgical data collection 29344 may include one or more biomarkers they may have been recorded for a patient after a surgery. For example, a heart rate and blood glucose level for a patient may be recorded for a patient after a surgery to monitor post-surgical complications and/or recovery milestones.

Post-surgical data collection 29344 may include one or more data sources. Surgical data collection 29290 may include data from post-surgical sensing system 29362, post-surgical system 29361, and wearable device 29363.

Post-surgical data collection 29344 may include data from post-surgical sensing system 29362. Post-surgical sensing system 29362 may include any configuration of hardware and software devices suitable for sensing and presenting parameters patient biomarkers that may be relevant during a surgical procedure. Post-surgical sensing system 29362 may include the sensing and monitoring systems disclosed herein, including uncontrolled patient monitoring systems, environmental sensing systems, and the like.

Post-surgical data collection 29344 may include data from post-surgical sensing system 29362. post-surgical sensing system 29362 may include any configuration of hardware and software devices suitable for sensing and presenting parameters patient biomarkers that may be relevant after a surgical procedure. Post-surgical sensing system 29362 may include one or more of the sensing and monitoring systems disclosed herein, including controlled patient monitoring systems, surgeon monitoring systems, environmental sensing systems, and the like.

Post-surgical data collection 29344 may include data from wearable device 29363. Wearable device 29363 may include any configuration of hardware and software devices suitable for sensing and presenting patent parameters and/or biomarkers that may be relevant before, during, or after a surgical procedure. Such systems may be used by the patient for any amount of time after surgery, inside and outside of a medical facility. To illustrate, via an uncontrolled patient monitoring system, the patient may use a wearable heart-related sensor at during a surgical procedure. And/or, via a controlled patient monitoring system, a healthcare provider may monitor the same and/or analogous biomarkers using facility equipment during time of the surgical procedure. For example, the wearable device 29363 may provide data suitable for use in determining computational data during and/or after surgery. Wearable device 29363 may include any of those disclosed herein, such as those with reference to FIG. 1B for example.

The data received from the surgical data sources, such as surgical data collection 29342, may be subject to aggregation and/or filtering 29358. Aggregation and/or filtering 29358 may perform pre-processing on data received from surgical data collection 29342. The data received from the surgical data sources, such as post-surgical data collection 29344, may be subject to aggregation and/or filtering 29360. Aggregation and/or filtering 29360 may perform per-processing on data received from post-surgical data collection 29344.

Aggregation and/or filtering 29358 and aggregation and/or filtering 29360 may be used to prepare and format the data for use by computing system 29384. For example, aggregation and/or filtering 29358 and aggregation and/or filtering 29360 may prepare data to be processed by machine learning 29376, contextual transform 29378, artificial intelligence models 29380, and patient analysis 29374.

Processing the data received from the surgical data collection 29342 by aggregation and/or filtering 29358 may include filtering (e.g., to select sensor data from the stream of data from surgical sensing system 29348). Aggregation and/or filtering 29358 may use filtering to help reject noise in data from surgical data collection 29342. Aggregation and/or filtering 29358 may use a method to establish a baseline for a biomarker from surgical data collection 29342. Aggregation and/or filtering 29358 may perform time mapping on data from surgical data collection 29342 (e.g., to place received values from different sources in alignment with each other in regard to time). Time mapping may aid in correlation and ratio analysis, which may occur in contextual transform 29378.

Aggregation and/or filtering 29358 may translate data from surgical data collection 29342. The translation of data may include coordinating formats, coordinating data types, translating from one format to another format, translating from one data type, to another data type, accounting for a difference between a data source data format, and accounting for a data type expected by another module, such as machine learning 29376. Translating may include translating the data into a format suitable for machine learning, for artificial intelligence models, for patient analysis, for use by a surgical device control program, and/or for use by a wearable control program. Data from the surgical data collection 29342 may be translated into a notification for display, such as display on a human-interface device 29368. Data from surgical collection 29342 may be translated into data that may be included and/or used for notifications 29372.

Processing the data received from post-surgical data collection 29344 by aggregation and/or filtering 29360 may include filtering (e.g., to select sensor data from the stream of data from post-surgical sensing systems 29362). Aggregation and/or filtering 29360 may use a method to establish a baseline for a biomarker from post-surgical data collection 29344. Aggregation and/or filtering 29360 may use filtering to help reject noise in data from post-surgical data collection 29344. Aggregation and/or filtering 29263 may perform time mapping on data from post-surgical data collection 29344 (e.g., to place received values from different sources in alignment with each other in regard to time). Time mapping may aid in correlation and ratio analysis, which may occur in contextual transform 29278.

Aggregation and/or filtering 29360 may translate data from post-surgical data collection 29344. The translation of data may include coordinating formats, coordinating data types, translating from one format to another format, translating from one data type, to another data type, accounting for a difference between a data source data format, and accounting for a data type expected by another module, such as machine learning 29376. Translating may include translating the data into a format suitable for machine learning, for artificial intelligence models, for patient analysis, for use by a surgical device control program, and/or for use by a wearable control program. Data from the post-surgical data collection 29344 may be translated into a notification for display, such as display on a human-interface device 29368. Data from post-surgical collection 29344 may be translated into data that may be included and/or used for notifications 29372.

Contextual transform 29378 may operate to provide a context for data, such as surgical data collection 29342 and/or post-surgical data collection 29344. For example, contextual transform 29378 may transform data into contextualized surgical data, which may be included in computational data collection 29346. To illustrate, as an input the contextual transform may receive surgical data that includes, for example, a measurement time, a sensor system identifier, and a sensor value. Contextual transform 29378 may output contextualized surgical data. Contextual transform 29378 may output data that may be modified and/or enhanced by machine learning 29376, patient analysis 29374, and artificial intelligence models 29380.

Contextual transform 29378 may determine and/or store data that may be related to each other. Contextual transform 29378 may determine how data may be related to each other. For example, contextual transform 29378 may determine that data from surgical data collection 29342 may be related to data from post-surgical data collection 29344. Contextual transform 29378 may determine a context for the data. Context, for example, additional information relevant to the present understanding and/or interpretation of the sensor measurement.

Computational data collection 29346 may be determined and/or generated by machine learning 29376. For example, machine learning 29376 may receive data from data collection 29340, may apply a machine learning model, and may use the machine learning model to generate the computational data collection 29346.

Computational data collection 29346 may include one or more biomarkers that may be augmented and/or enhanced by a machine learning model. For example, one or more biomarkers may be modified to make the one or more biomarkers more accurate using the machine learning model. Computational data collection 29346 may include one or more predictions and/or probabilities That may be associated with a patient, a surgical outcome, a diagnosis, a morbidity, and the like.

Computation data collection 29346 may include context, for example, additional information relevant to the present understanding and/or interpretation of the sensor measurement. For example, the context may include pre-surgery and/or pre-therapy baselines. For example, the context may include situational awareness of incorrectly connected and/or incorrectly operating surgical and/or sensing systems. For example, the context may include adjustments to products, surgical plans, and/or margins.

Computational data collection 29346 may include data that may provide a context. The context may include additional information that may have been created and/determined by machine learning 29360 that may place a biomarker into a specific context for the healthcare providers. For example, computational data collection 29346 may include instructions and/or information about a baseline value for a sensor value, an alert of a deviation, relevant information from the patient's record, relevant information to a procedural element of the surgery, surgical device settings, and/or any information the healthcare provider might find relevant to have at the moment of the sensor's measurement itself. Computational data collection 29346 may include one or more data tags. The data tags may include logging data (indicating that that a specific transform or other processing has occurred).

Computational data collection 29346 may include data that may be provided by HCP 29370. For example, HCP 29370 may provide feedback regarding data provided by machine learning 29376. Computational data collection 29346 may include data that may be sent to HCP 29370. For example, HCP 29370 may receive data provided by machine learning 29376. Data from HCP 29370 may include any data relevant to a wearable device, a machine learning, a patient analysis, a contextual transform, an artificial intelligence model, and the like. For example, HCP 29370 may provide data that may be associated with wearable device 29371, a patent analysis 29374, human-interface device 29368, notifications 29372, computing system 29384, and/or any combination thereof. For example, the HCP 29370 may provide data that may trigger an interaction with the context transform 29378 and/or machine learning 29376. The data from HCP 29370 may include manually entering data not received directly for any relevant source (such as manually entering a manually taken biomarker reading, for example).

Human-interface device 29368 may include any device suitable for producing a perceptible representation of contextualize surgical data, such as contextualized surgical data 29294. The perceptible representation may include a visual indication, an audible indication, or the like. The human-interface device 29368 may include a computer display. For example, the human-interface device 29368 may include a visual representation including text and/or images on a computer display. The human-interface device 29368 may include a text-to-speech device. For example, the human-interface device 29368 may include synthesized language prompt over an audio speaker. The human-interface device 29368 may communicate the contextualized surgical data to the surgeon and/or surgical team. The human-interface device 29368 may include and/or be incorporated into any suitable device disclosed herein. For example, the human-interface device 29368 may include and/or be incorporated into any of the primary display 20023, a first non-sterile human interactive device 20027, and/or a second non-sterile human interactive device 20029, such as that disclosed in FIG. 2A for example. For example, the human-interface device 29368 may include and/or be incorporated into a human interactive device 29368, such as that disclosed in FIG. 2B. For example, the human-interface device 29368 may include and/or be incorporated into the display 20224 of a surgical instrument, such as that disclosed in FIG. 7A for example.

The notifications 29372 may include any device suitable for generating a perceptible indication that relevant contextual data is available and/or has changed. The indication may include a visual indication, an audible indication, a haptic indication, and the like. The notifications 29372 may incorporate any of the human-interface devices 27020 disclosed here. The notifications 29286 may include non-verbal and/or non-textual indications to represent contextual data is available and/or has changed. For example, the alert system may include audio tones, visual color changes, lights, and the like. For example, the notification may include a haptic tap on a wearable device, such as a smartwatch worn by the surgeon. Notifications 29372 may include contextualized data, pre-surgical data, surgical data, and/or post-surgical data. Notifications 29372 may include a request from a machine learning algorithm for a HCP to provide feedback regarding data, a recommendation, And accuracy of an artificial intelligence model, and accuracy of training data, and accuracy of machine learning, a diagnosis, an indication of a problem, data generated by machine learning, a patient analysis, a conclusion regarding a patient analysis, a modification to a surgical device control program, a surgical device control program, wearable control program, any combination thereof, and the like. For example, notifications 29372 may request that HCP 29284 provide feedback regarding machine learning module 29376.

Computational data collection 29346 may include data from wearable device 29371. Wearable device 29371 may include any configuration of hardware and software devices suitable for sensing and presenting patent parameters and/or biomarkers that may be relevant before, during, or after a surgical procedure. Such systems may be used by the patient for any amount of time prior to surgery, inside and outside of a medical facility. To illustrate, via an uncontrolled patient monitoring system, the patient may use a wearable heart-related sensor at during a surgical procedure. And/or, via a controlled patient monitoring system, a healthcare provider may monitor the same and/or analogous biomarkers using facility equipment during time of the surgical procedure. For example, the wearable device 29371 may provide data suitable for use in a contextual determination during and/or after surgery. Wearable device 29371 may include any of those disclosed herein, such as those with reference to FIG. 1B for example.

Computational data collection 29346 may include a wearable control program that may have been sent by wearable control programs 29274 to wearable device 29371. Computational data collection 29346 may include an artificial intelligence model that may be sent to wearable device 29280).

The machine learning module 29376 may perform data preparation as described herein for creating and training a model for post-surgical patient analysis using the surgical data collection 29342 and the post-surgical data collection 29340 (e.g., the dataset).

In an example, the data preparation may further include creating a data field and appending it to a (e.g., each) data record in the dataset. The data field may indicate whether there was a post-surgical complication (e.g., a surgical complication that occurred post-surgery) after a respective surgical procedure derived from post-surgical data (e.g., collected from a wearable device 29363 and/or a sensing system 29362. The new data field may serve as a desired output label for training the post-surgical patient analysis AI model 29380 with supervised machine learning for improving patient analysis 29374 (e.g., improved patient monitoring measures).

In such example, the machine learning module 29376 may perform model training, model validation, model testing for a decision tree algorithm-based post-surgical patient analysis AI model 29380. Those of skill in the art will recognize any other suitable machine learning algorithm may be used to build the model 29380. The model 29380 may learn a pattern (e.g., among other patterns) that a post-surgical complication occurs (e.g., anastomotic leak) after a colorectal surgery when a sepsis-related biomarker crosses a first threshold after a first post-surgical threshold period and subsequently crosses a second threshold after a second post-surgical threshold period. For example, a sepsis-related biomarker may be core body temperature, oxygen saturation, heart rate, heart rate variability, or tissue perfusion pressure.

Accordingly, the machine learning module 29376 may be configured to send the HCP 29370 a medium-risk notification 29372 indicating a probability of sepsis when a core body temperature measurement data is detected to have crossed a first threshold after a first post-surgical threshold period by the post-surgical patient analysis AI model 29380 based on post-surgical input data to the model 29380 from actual post-surgical patient monitoring. The machine learning module 29376 may be further configured to send the HCP 29370 a high-risk notification 29372 indicating a probability of sepsis when a core body temperature measurement data is detected to have crossed a second threshold after a second post-surgical threshold period by the model 29380. In such manner, the model 29380 may improve patient monitoring by providing indications of a progressing probability of post-surgical complications. In an example, the HCP 29370 may determine the notifications were incorrect based on the biomarker measurement data and provide feedback to the machine learning module 29376. Further, the machine learning module 29376 may be configured to send the patient 29365 similarly notifications.

In another example, the data preparation may further include using only data records for a patient with an underlying condition (e.g., type 2 diabetes mellitus (T2DM). Accordingly, post-surgical patient analysis AI model 29380 may improve patient monitoring specifically for those patients. In another example, the data preparation may further include using only post-surgical biomarker measurement data collected during exercise. Accordingly, post-surgical patient analysis AI model 29380 may improve patient monitoring specifically as it relates to biomarker monitoring during exercise (e.g., for tracking recovering milestones related to calorie burning after a bariatric surgery).

Disclosed herein are methods, systems, and apparatus for contextual transformation of data into aggregated display feeds. A sensing system, such as a wearable device, may generate a data stream. The data stream may be received by a computing system. The computing system may determine one or more biometrics from the data stream. The computing system may relate the one or more biometrics to other biometrics or data. The computing system may determine a context for the one or more biomarkers, for example, by relating the one or more biomarkers to data from another data stream. This may allow the computing system to understand and/or provide a context for the one or more biomarkers that may aid a health care provider (HCP) in diagnosing an issue and/or a disease.

A computing system for contextually transforming data into an aggregated display feed may be provided. The computing system may comprise a memory and a processor. The processor may be configured to perform a number of actions. A first biomarker may be determined from a first data stream. A second biomarker may be determined from a second data stream. It may be determined that the first biomarker and the second biomarker may be interlinked to a physiologic function and/or a morbidity. One or more cooperative measures that may be related to the physiologic function and/or morbidity may be determined, for example, using the first biomarker and/or the second biomarker. A directional measure may be generated. The directional measure may indicate a contextual summary of the one or more cooperative measures. The directional measure may be sent to a display, a user, and/or a health care provider.

A method for contextually transforming data into an aggregated display feed may be provided. A first biomarker may be determined from a first data stream. A second biomarker may be determined from a second data stream. It may be determined that the first biomarker and the second biomarker may be interlinked. For example, the first biomarker and the second biomarker may be interlinked to a physiologic function and/or a morbidity. A contextual summary may be determined, for example, using the first biomarker and/or the second biomarker. The contextual summary may be related to the physiologic function and/or the morbidity. A direction measure may be generated. The direction measure may indicate a trend associated with the contextual summary. The direction measure may be sent to a user, such as a patient, a surgeon, a health care provider (HCP), a nurse, and the like.

A computing system for securing and recording consent from a user to communicate with a health care provider. The computing system may comprise a memory and a processor. The processor may be configured to perform a number of actions. It may be determined whether an identity of a user of a sensing system can be confirmed. For example, a user may be identified, and it may be determined that the identity of the user may be confirmed using a medical record, a driver's license, a government issue identification, and the like. A state of mind of the user may be identified (e.g. a mental state and/or a cognitive state). Consent from the user may be received. The consent from the user may indicate that the user consents to share data from the sensing system with a health care provider (HCP). The consent of the user may be confirmed. For example, the consent of the user may be confirmed when the identity of the user is confirmed and the state of mind of the user indicates that the user is able to provide consent. Data from the sensing system may be sent to the HCP.

A method may be provided for securing and recording consent from a user. The consent may be associated with permission to communicate patient data with a health care provider (HCP). It may be determined whether an identity of a user of a sensing system may be confirmed. A state of mind of a user may be determined. A consent from a user may be received. The consent of the user may be a consent to share data from the sensing system, such as a wearable device, with a health care provider. The consent of the user may be confirmed. For example, the consent of the user may be confirmed when the identity of the user may be confirmed and the state of mind of the user indicates that the user is able to provide consent. Data from the sensing system may be sent to the HCP.

Examples herein may include a computer-implemented method for contextually transforming data into an aggregated display feed. The method may include determining a first biomarker from a first data stream and a second biomarker from a second data stream. The method may include determining that the first biomarker and the second biomarker are interlinked to a physiologic function or morbidity. The method may include determining one or more cooperative measures related to the physiologic function or morbidity using the first biomarker and the second biomarker. The method may include generating a directional measure to indicate a contextual summary of the one or more cooperative measure. The method may include displaying the directional measure to a health care provider.

Disclosed herein are methods, systems, and apparatus for contextual transformation of data into aggregated display feeds. A sensing system, such as a wearable device, may generate a data stream. The data stream may be received by a computing system. The computing system may determine one or more biometrics from the data stream. The computing system may relate the one or more biometrics to other biometrics or data. The computing system may determine a context for the one or more biomarkers, for example, by relating the one or more biomarkers to data from another data stream. This may allow the computing system to understand and/or provide a context for the one or more biomarkers that may aid a health care provider (HCP) in diagnosing an issue and/or a disease.

A computing system for contextually transforming data into an aggregated display feed may be provided. The computing system may comprise a memory and a processor. The processor may be configured to perform a number of actions. A first biomarker may be determined from a first data stream. A second biomarker may be determined from a second data stream. It may be determined that the first biomarker and the second biomarker may be interlinked to a physiologic function and/or a morbidity. One or more cooperative measures that may be related to the physiologic function and/or morbidity may be determined, for example, using the first biomarker and/or the second biomarker. A directional measure may be generated. The directional measure may indicate a contextual summary of the one or more cooperative measures. The directional measure may be sent to a display, a user, and/or a health care provider.

A method for contextually transforming data into an aggregated display feed may be provided. A first biomarker may be determined from a first data stream. A second biomarker may be determined from a second data stream. It may be determined that the first biomarker and the second biomarker may be interlinked. For example, the first biomarker and the second biomarker may be interlinked to a physiologic function and/or a morbidity. A contextual summary may be determined, for example, using the first biomarker and/or the second biomarker. The contextual summary may be related to the physiologic function and/or the morbidity. A direction measure may be generated. The direction measure may indicate a trend associated with the contextual summary. The direction measure may be sent to a user, such as a patient, a surgeon, a health care provider (HCP), a nurse, and the like.

A computing system for securing and recording consent from a user to communicate with a health care provider. The computing system may comprise a memory and a processor. The processor may be configured to perform a number of actions. It may be determined whether an identity of a user of a sensing system can be confirmed. For example, a user may be identified, and it may be determined that the identity of the user may be confirmed using a medical record, a driver's license, a government issue identification, and the like. A state of mind of the user may be identified (e.g., a mental state and/or a cognitive state). Consent from the user may be received. The consent from the user may indicate that the user consents to share data from the sensing system with a health care provider (HCP). The consent of the user may be confirmed. For example, the consent of the user may be confirmed when the identity of the user is confirmed and the state of mind of the user indicates that the user is able to provide consent. Data from the sensing system may be sent to the HCP.

A method may be provided for securing and recording consent from a user. The consent may be associated with permission to communicate patient data with a health care provider (HCP). It may be determined whether an identity of a user of a sensing system may be confirmed. A state of mind of a user may be determined. A consent from a user may be received. The consent of the user may be a consent to share data from the sensing system, such as a wearable device, with a health care provider. The consent of the user may be confirmed. For example, the consent of the user may be confirmed when the identity of the user may be confirmed and the state of mind of the user indicates that the user is able to provide consent. Data from the sensing system may be sent to the HCP.

As shown in FIG. 1B, a sensing system may measure data relating to various biomarkers. In an example, the sensing system may sense a biomarker in patients and/or HCPs. Biomarkers may relate to different physiologic functions and/or systems. The sensing systems described herein may sense various biomarkers, including but not limited to sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle. The sensing systems described herein may sense environment and/or light exposure.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and surgeon monitoring system. Information from the biomarkers may be determined and/or used by wearable devices.

Biomarker data and information may be sent and received as data streams. The data streams may include the sensed parameters. The data streams may be used to determine physiologic functions and/or conditions. The data streams may be contextually transformed into an aggregated data stream. A context may be determined based on the data streams. Contexts that may be determined may include but are not limited to, exercising, sleeping, and eating. For example, if the context determined is a person exercising, then an increased heart rate may be expected. For example, if the context determined is a person sleeping, additional data showing an elevated heart rate may indicate a medical issue. Physiologic functions and/or conditions may be determined based on the combination of the data streams and the determined context.

A context relating to biomarker data may be used to determine physiologic functions and/or conditions. Biomarker data may indicate multiple different physiologic functions and/or conditions. Analyzing biomarker data with a determined context may allow HCPs to accurately determine a physiologic function and/or condition. For example, a user eating may be a context. Eating may affect biomarker measurements. Eating may affect biomarker measurements such as heart rate variability and blood glucose levels. HCPs may be interested in determining whether a user is eating based on a measured heart rate variability and blood glucose levels. The context surrounding heart rate variability measurements and blood glucose measurements may be important to HCPs. Different contexts may arise with the same measurements. A context may matter because a context may indicate that a biomarker has more significance in one scenario than another scenario. For example, a measure heart rate variability measurement and a blood glucose measurement may indicate that a user may be eating, or the user may be in pain. As heart rate variability may indicate both contexts of eating and/or pain, HCPs may be interested in differentiating between whether a user is eating or experiencing pain.

A context may be determined. A context may be determined based on one or more data streams relating to biomarkers. A determined context may be tagged to a dataset. The context may be used to analyze other datasets received involving other biomarkers. An algorithm may determine context. An algorithm may determine context based on one or more received data streams.

In an example, a context may be determined based on one or more received data streams. One or more data sets may be tagged with the context. The tagged context may be used to provide information about other received data streams and/or data sets. For example, if a determined context shows that a user is eating, the context of eating may be used to analyze biomarkers that relate to eating. Heart rate variability may be affected based on the context of eating, for example. HCPs may look at heart rate variability to determine whether a user is eating. Other biomarker data streams may be filtered out based on the determined context. For example, when it is determined that a user may be eating, HCPs may look at heart rate variability to confirm whether eating is occurring. HCPs may use the context to determine that eating is occurring while determining that other physiologic functions and/or conditions, such as pain and/or stress, may not be occurring.

Context may be used to synchronize data streams. Data streams may be received from devices with internal clocks. The devices with internal clocks may not be set to a real time clock reference. The devices with internal clocks may experience clock drift. The devices with internal clocks may read different times based on calibration. The devices with internal clocks may not recalibrate themselves. The devices may send data streams that start to drift away from data streams from other devices. Drifting data streams may be synchronized based on a determined context. Transforming data into metadata that may be generalized (e.g., universal) may be used to synchronize data streams. For example, tagging heart rate variability with other data sets, may allow the determined context to synchronize the data sets.

For example, different wearable devices may cooperate with one another to provide context to the measured biomarker data. The determined context may be sent with the measured data to a computing device, such as a surgical hub, for processing. The wearable devices may cooperate with one another by pairing with each other. The wearable devices may pair with each other based on proximity to each other. A plurality of wearable devices may cooperate and provide context to measured data.

For example, the plurality of wearable devices may include a hierarchy of the wearable devices. One wearable device within the plurality may have more processing power and/or more sensors that the other wearable devices. The more powerful wearable device may pair with the other devices. The other wearable devices may send their measured data to the more powerful wearable device. The other wearable devices may include sensing systems configured to measure biomarkers and/or data different than the more powerful wearable device.

For example, the more powerful wearable device may gain insight on a context from the data received from the other wearable devices. The context may be used to differentiate between physiologic functions from biomarker data. In an example, the more powerful wearable device may be able to differentiate between heart rate variability for eating and heart rate variability for pain based on a measured glucose. The context of eating may be indicated from a change in glucose. The wearable device may determine the context of eating based on the change in glucose. The wearable device may determine the heart rate variability measurement relates to eating based on the eating context. For example, the context of eating may enable a wearable device to determine that movement measurements are associated with eating rather than exercise.

A weighted distribution may be used to determine context. A weighted distribution may be applied to one or more biomarker data streams. Biomarker data streams may carry different importance in determining physiologic function and/or conditions. The weighted distribution may be determined based on a hierarchy of devices.

For example, conflict resolution may be used to resolve conflicts between wearable devices. Wearable devices may determine differing contexts based on biomarker data. The differing contexts may exclude each other.

The conflict resolution may determine which context is accurate. For example, a first wearable device may determine a first context stating that a user is eating, and a second wearable device may determine a second context stating that a user is exercising. Conflict resolution may determine that the two contexts exclude each other. Eating may not occur while exercising, for example. Conflict resolution may determine which of the two contexts may be more accurate. Conflict resolution may use weighted distributions to determine the accurate context. Conflict resolution may use situational awareness to determine the accurate context. Conflict resolution may use machine learning to determine the accurate context.

Automated system decision making algorithms based on biomarker monitoring may be provided. The automated system decision making algorithms may include data conditioning. The automated system decision making algorithms may include validation. Data conditioning and/or validation may include importing and organization of data sets, transforming multiple data streams into actionable or contextual prioritized cues, verification of data integrity, and/or securing wearable internal and communication architecture. The automated decision-making algorithms may include machine learning algorithms.

For example, importing and organization of data sets may include data organization. Data organization may include manipulation, extraction, framework organization, decomposition, and the like. For example, importing and organization of data sets may include data inter-relationships and linking.

Transforming multiple data streams into actionable or contextual prioritized cues may include contextual transformation of data into aggregated displayed feeds. The contextual transformation of data into aggregated display feeds may include classification, prioritization, and/or inter-relational linking of separately sensed data streams. The classification, prioritization, and inter-relational linking of separately sensed data streams may coordinate into contextual aggregation streams (e.g., rich contextual aggregation streams). For example, a first sensed parameter and a second sensed parameter that are interlinked to a physiologic function and/or morbidity that produce a single directional measure may indicate the summary of the two cooperative measures. The two cooperative measures may be the first send parameter and the second sensed parameter. The parameters and the directional measure may be displayed to HCPs.

For example, the interrelationship of the one or more feeds (e.g., two feeds) may include a weighted distribution. The weighted distribution may include one feed having a higher importance than a second feed. The weighted distribution may change over a surgical procedure. The weighted distribution may change over a recovery timing. The weighted distribution may change based on procedural streps. The weighted distribution may change based on time. The weighted distribution may change based on a third feed.

In an example, one or more feeds (e.g., two data feeds) may have a means for resolving conflicting results resulting within the feeds. The conflict resolution may be based on a reliability of the data. The conflict resolution may be based on anomaly detection. The conflict resolution may be based on a predefined recovery and/or analysis.

Multiple data streams may be transformed into actionable or contextual prioritized cues may include securing consent recording and communication to HCPs. Securing consent recording and communication to HCPs may include a user. The user may be a patient, a caretaker of the patient, a nurse, a doctor, a surgeon, and/or a healthcare provider. The user may be confined and may be confirmed to be non-cognitively impaired. The user may provide consent. The consent may include consent to access, control, monitoring, and/or notification of the wearables. The consent may be given to one or more selected HCPs. The consent may include sharing one HCPs information and instructions of the patient with predefined other HCPs. Confirmation of identity may prevent adjustment of consent. Cognitive impairment may prevent adjustment of consent. A combination of confirmation of identity and cognitive impairment may prevent adjustment of consent. The prevention of adjustment of consent may include when thresholds of confirmation of identity and/or cognitive impairment are not ensured. Shared information between HCPs may include procedures, therapies, monitored biomarkers, thresholds, and/or system notification settings.

Transforming multiple data streams into actionable or contextual prioritized cues may include an active classification. The active classification may include an automatic classification of physical activities. The physical activities may include sleeping, walking, running, falling, sitting, resting, ascending stairs, descending stairs, and/or the like. The active classification may include system algorithm steps. The system algorithm steps may include recognition of possible activities. The system algorithm steps may include automatically generating a decision tree to activity options. The system algorithm steps may include classification of accuracy checking. The system algorithm steps may include anomaly detection. Anomaly detection may include support vector machines, for example. Support vector machines may include Markov models and/or Wavelet analysis.

Support vector machines may be used for health monitoring systems for anomaly detection. Anomaly detection may differentiate a detected unusual pattern of data from the normal classification and expected outliers of that classification. Anomalies may include a system error on classification. Anomalies may include an irregularity that may warrant recording but may not warrant alerting and/or notification. Anomalies that warrant recording may include occurrence, timing, related events, and/or duration. Anomalies may include critical irregularities. Critical irregularities may require immediate attention and/or trigger notification of the user and/or contacting of HCPs.

Transforming multiple data streams into actionable or contextual prioritized cues may include resolving conflicting reaction options. Resolving conflicting reaction options may be based on indeterminate data. Resolving conflicting options may use automated inclusion and/or exclusion criteria. Secondary decision criteria for context of conflicting data resolution may include an inclusion and/or exclusion criteria. The criteria may include physical aspects of a patient. The criteria may include ongoing treatments for other conditions. The ongoing treatments for other conditions may be extracted from the electronic medical records (EMR) database. The criteria may include one or more wearables data sets. The wearables data sets may provide context.

For example, exclusion criteria may use a wearable monitor. In an example, the wearable monitor may assess levels of smoke exposure prior to lung surgery. The procedure may be cancelled and/or delayed based on the exposure. The procedure may be cancelled and/or delayed based on reaching a limit of exposure. Smoke exposure may include first-hand smoke, second-hand smoke, environmental exposure, and/or any combination of the like. Smoke exposure may impact procedures. Smoke cessation may associate with improved post-operative outcomes. In an example, the wearable monitor may assess coagulation state of blood. Coagulation state of blood may be assessed based on an international normalized ration (INR) The wearable monitor may determine whether coumadin was stopped at the appropriate time. Intra-operative bleeding complications may be lessened based on when coumadin was stopped. Higher INR may associate with higher incidence of blood transfusions. Clotting times may associate with higher incidence of blood transfusions.

For example, inclusion criteria may use a wearable monitor and/or device. In an example, the wearable monitor may monitor one or more pre-operative patient variables. A pre-operative patient variable may include fasting glucose, for example. The pre-operative patient variable may impact surgical procedure. The wearable monitor may monitor one or more pre-operative patient variables to allow surgery to proceed. In an example, the wearable device may monitor temperature. The wearable device may compare temperature against a running average. The wearable device may determine the absolute value from the temperature running average value. The wearable device may determine excursion from temperature running average value. The absolute value and/or excursion from temperature running average value may predict ovulation in females. Monitoring temperature excursions, such as absolute and relative changes, in females may be used to predict ovulations. Optimal in vitro fertilization times may be determined based on ovulation.

Transforming multiple data streams into actionable or contextual prioritized cues may include a hierarchical classification of data priorities. The hierarchical classification of data priorities may include a recognition of combined behavior. Combined behavior may be recognized based on two or more cooperative data sets. The two or more cooperative data sets may create a measurable physiologic measure. The hierarchical classification of data priorities may include functional stressors. The functional stressors may be used to indicate priority. The functional stressors may be used to differentiate between multiplexed cues. The hierarchical classification of data priorities may include deviations from a baseline.

For example, a measurable physiologic measure may include stress level intensity. Stress level intensity may be recognized based on any combination of heart rate variation, heart rate variation patterns, and/or skin conductance. A measurable physiologic measure may include pain level intensity. Pain level intensity may be recognized based on any combination of sweat rate, skin conductance, and/or heart rate variability. A measurable physiologic measure may include eating. Eating may be recognized based on any combination of heart rate variability, and/or blood glucose changes. A measurable physiologic measure may include coughing and/or sneezing. Coughing and/or sneezing may be recognized based on any combination of respiration rate abrupt deviation, heart rate variability, and/or physical activity monitoring of repetitive non-adulatory motion.

A measurable physiologic measure may include physical activity. Physical activity may include a type of physical activity. Physical activity may be recognized based on movement. Movement indicating physical activity may include wrist movement. Physical activity may be recognized based on heart rate. Heart rate indicating physical activity may include elevation above baseline and/or duration. Physical activity may be recognized based on standing. Standing indicating physical activity may include accelerometer measures consistent with standing followed by a duration of movement. The accelerometer measures may use a wearable device, such a smart watch. Physical activity be recognized based on GPS tracking. GPS tracking indicating physical activity may include speed and/or distance traveled. Physical activity may be recognized based on calories burned. Calories burned indicating physical activity may include any combination of distance traveled, patient height, patient age, patient weight, and/or patient gender. Physical activity may be recognized based on sleep. Sleep indicating physical activity may include indicators of sleep. Indicators of sleep may include lack of movement for a duration of time and/or heart rate variability. A lack of movement for an hour may indicate sleep. Sleep indicating physical activity may include sleep quality and/or sleep stages. Changes in heart rate variability may indicate transitions between sleep stages. Sleep stages may include light sleep, deep sleep, and/or REM sleep. Length of time of movements may indicate sleep behavior. Sleep behavior may include rolling over. Sleep behavior may indicate sleep quality. Physical activity may be recognized by any combination of movement, heart rate, standing, GPS tracking, calories burned, and/or sleep.

For example, hierarchical classification of data priorities may include deviations from a baseline. A variety of metrics may be quantified from the patient. The metrics may be quantified prior to a planned treatment and/or surgery. A prioritized means for flagging measured behavior that deviates significantly from pre-procedure baselines may be informed. The prioritized means may be informed based on knowledge of surgery type. The prioritized means may be informed based on patient demographics. The prioritized means may be informed based on potential complications. The prioritized means may be informed based on available baseline data. The prioritized means may be informed based on any combination of knowledge of surgery type, patient demographics, potential complications, and/or available baseline data. In an example, the patient and/or HCPs may be informed. The patient and/or HCPs may be informed if a measure that is consistent with a complication violates a threshold relative to the baseline. In an example, data may be flagged without providing a notification. Data may be flagged without providing notification if a measure that is consistent with a complication violates a threshold but is consistent with the baseline.

Data conditioning and/or validation may include verification of data integrity. In an example, verification of data integrity may include confirmation of redundant data measure. Confirmation of redundant data measure may ensure validity. In an example, verification of data integrity may be performed without a pre-understanding of the range and/or values of data that may be received. Verifying data integrity without a pre-understanding of the range and/or values may include using a past history as a map. Using a past history as a map may bound the current data set and/or the bounds could be an expanding and/or contracting upper and lower bounding with a predefined variation (e.g., a predefined max variation) from point to point. Verifying data integrity without a pre-understanding of the range and/or values may differentiate out erroneous data points. For example, as the system continues to get data, if multiple data points are outside the current bounded range, the system may store those data points. If the trend continues to expand within the pre-defined max variation between data points, the bounding may be expanded. If the trend continues to expand within the pre-defined max variation between data points, the stored data may be re-inserted rather than replaced with averages from the surrounding data points. The system may learn if the sensor range is overly constrained. The system may learn if errors have been detected. If the trend continues in a predictable manner, then it may be determined that the data is real and may be kept. If the data reverts to within the original bounding range suddenly, the out of bounds data points may be removed. In an example, verification of data integrity may use a system that has a basic idea of the range of data that is expected to be received. If the system had a basic idea of what range of data is expected to be received, the system may verify data sets received. A basic idea of what range of data is expected to be received may be based on the type of measurement, the average acceptable measures, and the like. For example, the system may use a received unit of measure to determine the sensing system. For example, the system may use any combination of manufacture, model number, and/or data rate as a cue to determine the type of sensor attached. For example, the system may use data from the hub on procedure and expected measurement systems in that type of procedure. The system may use the data from the hub to differentiate between systems.

Data conditioning and/or validation may include securing wearable internal and communication architecture. Securing wearable internal and communication architecture may include access protections, user identification, confirmation of user identification, management of security issues and/or authenticity of data.

User identification may include secure identification of the user and controlled access to their settings and/or data. User identification may be used to access a specific data or affect the operation of a system resource. Verification via a second means may be used to access a specific data or affect the operation of a system resource. Confirmation of authentication may be used to access a specific data or affect the operation of a system resource. For example, a means for ensuring the user is the authorized user may be used. The means for ensuring the user is the authorized user may include mechanisms that authenticate specific patients to wearables to reduce data falsification and/or fabrication. A wearable device may be used to authenticate and/or identify a user. For example, a wearable may be used as a key. Wearables as a key to other secured treatments may be used. Wearables as a key to other secured treatments may include a system monitoring device configured to the user's last initiation. Wearables as a key to other secured treatments may include a drug delivery device and wearable interacting to ensure correct user and dosage. The drug delivery device and wearable may monitor patient after drug administration. Wearables as a key to other secured treatments may include authentication to access and monitor stored medical records.

Confirmation of user identification may include secure consent preference recording. Confirmation of user identification may include prevention of unintended changes. Consent changes may be prevented based on lack of confirmation and/or reconfirmation. Consent may require a predetermined state of mind. A state of mind may include mental capacity. Lack of mental capacity may prevent giving consent. For example, elective doctor-to-doctor and/or facility-to-facility communication of key and/or selected medical records may enable collaborative contributions and monitoring of interactive therapies. Communication of key and/or selected medical records may allow a patient to select and change which doctors and/or facilities may be allowed to contribute, or review recorded medical records. Allowing a patient to select and change doctors and/or facilities may prevent patients from forgetting to notify a physician about prescriptions or therapies that may be on-going or have been occurring that may affect diagnosis or treatments from another physician.

Secure recording of encryption and tracking of when data, events, and/or treatments may be added. Blockchain and/or blockchain encryption may be used. Blockchain encryption may build the timing and responsibility to the encryption preventing them from being changed maliciously later. Secure recording of encryption and tracking may allow the user to record who can view and when the user consents to the permission into the encryption history in case the patient is not capable of giving consent in certain conditions. For example, confirmation of user identification and state of mind for consent and recording may be used for elderly monitoring. State of mind in elderly patients may change. State of mind in elderly patients may be monitored to determine whether proper consent is still given, for example.

Figure 111:
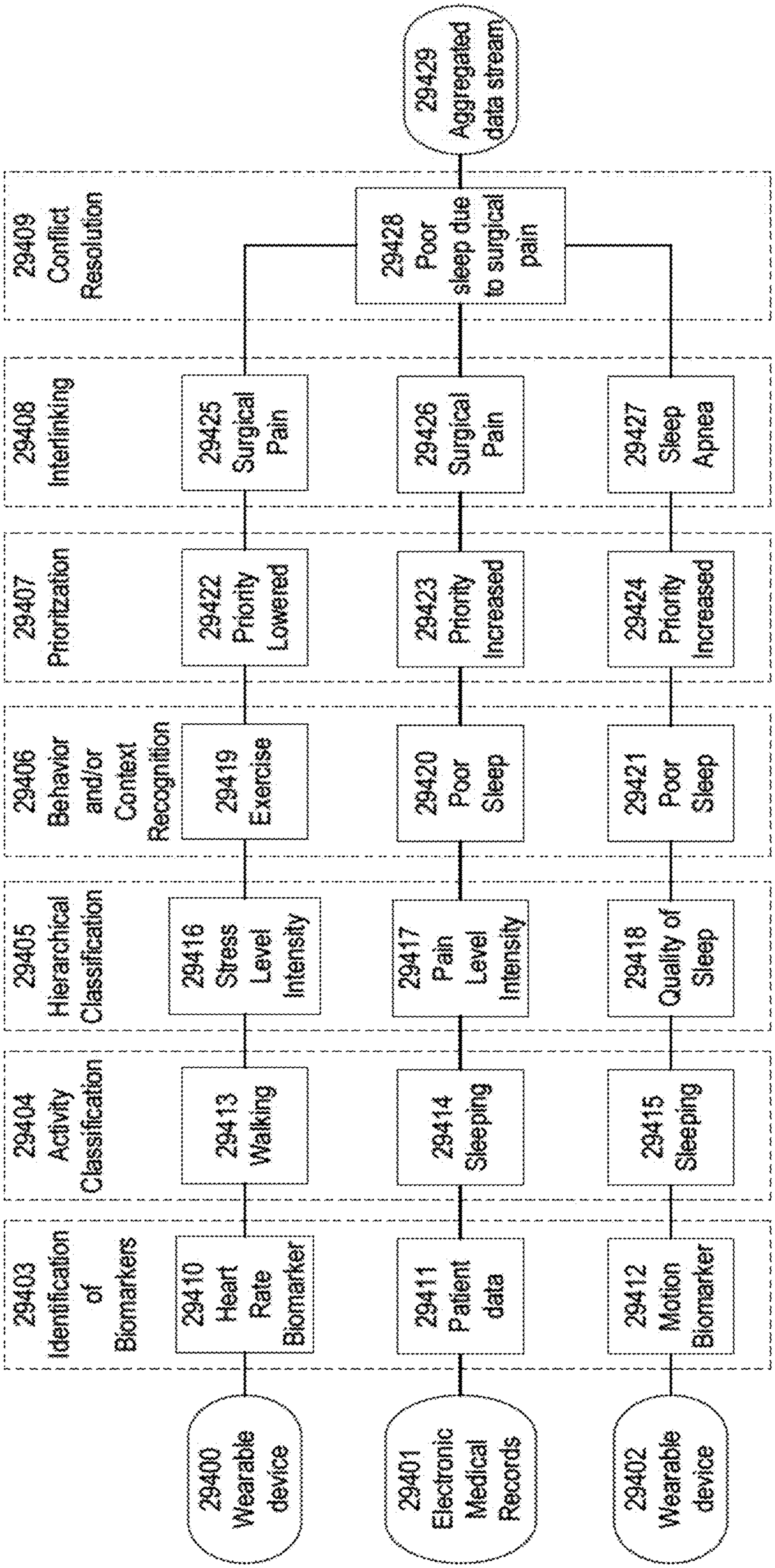

FIG. 111 depicts a flow diagram for contextually transforming data from one or more data streams into an aggregated feed, which may be an aggregated display data feed. One or more data streams may be aggregated and contextually transformed. Data streams may include data from a wearable device 29400. Data streams may include data from a database, such as electronic medical records 29401. Data streams may include a second wearable device 29402. For example, aggregation and contextual transformation may include identification of biomarkers 29403. For example, aggregation and contextual transformation may include activity classification 29404. For example, aggregation and contextual transformation may include hierarchical classification 29405. For example, aggregation and contextual transformation may include behavior and/or context recognition 29406. For example, aggregation and contextual transformation may include prioritization 29407. For example, aggregation and contextual transformation may include interlinking 29408. For example, aggregation and contextual transformation may include conflict resolution 29409. For example, aggregation and contextual transformation may include any combination of identification of biomarkers 29403, activity classification 29404, hierarchical classification 29405, behavior and/or context recognition 29406, prioritization 29407, interlinking 29408, and/or conflict resolution 29409. Aggregation and contextual transformation may include generating output, such as an aggregated data stream 29429, for example.

A first wearable device 29400 and a second wearable device 29402 may include one or more sensing systems. The one or more sensing systems may include a surgeon sensing system. The one or more sensing systems may include a patient sensing system. The wearable devices may include one or more sensing systems to monitor and detect a set of physical states and/or a set of physiological states. The wearable devices may include one or more sensing systems to monitor and detect biomarkers. In an example, a wearable device may measure a set of biomarkers.

For example, the first wearable device 29400 may monitor heart rate based on a measured set of biomarkers. The first wearable device 29400 may monitor the heart rate of a patient and/or surgeon. In another example, a wearable device may use an accelerometer to detect hand motion or shakes and determine motion. Measurement data associated with the set of biomarkers may be transmitted to another device. The wearable devices may include one or more sensing systems to monitor and detect an environment. For example, a wearable device may detect airborne chemicals, such as smoke. The wearable device may detect second-hand or third-hand smoke. In an example, a wearable device may detect sweat related biomarkers. The wearable device may monitor sweat rate in a patient based on the detected sweat related biomarkers.

The first wearable device 29400 and second wearable device 29402 may be worn. The wearable devices may be worn by a surgeon and/or patient. The wearable devices may include, but are not limited to a watch, wristband, eyeglasses, mouthguard, contact lens, tooth sensor, patch, microfluidic sensor, and/or a sock. The wearable devices may include, but are not limited to, a thermometer, microphone, accelerometer, and/or GPS.

Electronic medical records 29401 may include data and/or information. Electronic medical records 29401 may include the collection of data and/or information relating to a patient. Electronic medical records 29401 may include stored patient data over time. Electronic medical records 29401 may include patient data collected over the life of the patient. Electronic medical records 29401 may include patient data, including but not limited to, demographics, medical history, medication, allergies, immunization status, laboratory test results, radiology images, vital signs, personal statistics, patient instructions, HCPs notes, age, weight, billing information, and/or insurance information. Electronic medical records 29401 may include the most recent, up-to-date data relating to a patient.

The electronic medical records 29401 may be shared across HCPs. The electronic medical records 29401 may be shared over a network. Electronic medical records 29401 may be used in medical care. Electronic medical records 29401 may be used to provide health care for patients. Electronic medical records 29401 may be used to identify and stratify patients. In an example, electronic medical records 29401 may be used for patient analytics. The patient analytics may be used to prevent hospitalizations for high-risk patients.

For example, electronic medical records may be used to provide medical care for a patient. The electronic medical records may provide HCPs with information regarding a patient. For example, the information regarding a patient may include a notification of high blood pressure. HCPs may use the notification of high blood pressure from the electronic medical record to diagnose and/or adopt a treatment plan for a patient.

At 29403, identification of biomarkers may be used identify sleep, physical activity, heart rate variation, skin conductance, sweat, blood glucose, coughing/sneezing, stress, pain, eating, and the like. Biomarkers may be identified based on measurable indicators of a biological state or condition. For example, identification of biomarkers may include identifying biomarkers such as sleep, physical activity, heart rate, heart rate variation, skin conductance, sweat, blood glucose, coughing/sneezing, stress, pain, eating, and the like. Identification of biomarkers may be performed on one or more data streams. Identification of biomarkers may include detecting biomarkers from a wearable device, for example. Biomarkers may be identified using sensor measurements received from the wearable device. Identification of biomarkers may include detecting biomarkers from electronic medical records, for example, such as shown at 29414. Biomarkers may be identified using biomarker data found in the electronic medical records. Identification of biomarkers may select certain sensor measurements and/or biomarker data in electronic medical records to identify a biomarker. In an example, ECG and/or PPG data may be selected to identify a heart rate-related biomarker.

For example, at 29403, identification of biomarkers may include a plurality of data streams. The data streams may include one or more wearable devices. Identification of biomarkers may determine a data stream from a first wearable device 29400 involves a biomarker. The identification of biomarkers may determine that the data stream from the first wearable device 29400 involves a heart rate biomarker 29410, for example. The data stream from the first wearable device 29400 may include data pertaining to biomarkers. The data stream from the first wearable device 29400 may include data pertaining to heart rate-related biomarkers. Data pertaining to heart rate-related biomarkers may include ECG and/or PPG measurements. At 29403, data pertaining to heart rate-related biomarkers may be selected. Heart rate-related biomarkers may be identified. Heart-rate related biomarkers may be identified based on the selected data pertaining to heart rate-related biomarkers.

The data streams may include electronic medical records. Identification of biomarkers may determine a data stream from an electronic medical record 29401 includes patient data 29411. The patient data 29411 may include patient instructions and/or HCP notes. The patient data 29411 may include HCP notes including patient sleep schedule, for example. The patient data 29411 may include data relating to biomarkers. Biomarkers may be identified based on the patient data. Biomarkers, such as sleep, may be identified based on the patient data. Sleep biomarkers may be identified based on patient data showing a patient sleep schedule.

For example, at 29403, identification of biomarkers may determine a data stream from a second wearable device 29402 involves a biomarker. The identification of biomarkers may determine that the data stream from the second wearable device 29402 involves a motion biomarker 29412, for example. The data stream from the second wearable device 29402 may include data pertaining to biomarkers. The data stream from the second wearable device 29402 may include data pertaining to motion biomarkers. Data pertaining to motion biomarkers may include accelerometer, magnetometer, gyroscope, GPS, PPG and/or ECG measurements. At 29403, data pertaining to motion biomarkers may be selected. Motion biomarkers may be identified. Motion biomarkers may be identified based on the selected data pertaining to motion biomarkers. Motion biomarkers may include movement. Motion biomarkers may indicate sleep. Movement during sleep may indicate restless sleep. Machine learning may also be used for the identification of biomarkers.

At 29404, activity classification may be used. Activity classification may include identifying an activity. Activity classification may use identified biomarkers. Activity classification may use automatic classifications. Automatic classifications may identify an activity automatically. Automatic classifications may identify an activity automatically based on an identified biomarker. For example, running may be automatically classified based on certain identified biomarkers. Running may be automatically classified based on measured movement at a predetermined speed range, for example. Running may be automatically classified based on measuring a predetermined range of motion, for example, for example. Activity classification may use system algorithm steps. System algorithm steps may include recognition of activity possibilities, an automatically generated decision tree for activity options, classification accuracy checking, and/or anomaly detection. Activity classification may use a combination of automatic classification and/or algorithms. For example, one activity, such as running, may be automatically classified based on selected data but a different activity may be identified using one or more algorithms. Machine learning may also be used to assist in activity classification.

For example, at 29404, the heart rate biomarker 29410 may indicate that the user may be walking at 29413. Walking may be classified based on selected data. Heart rate biomarker 29410 may be given an activity classification of walking at 29413. Walking may be classified at 29413 based on heart rate biomarker 29410 and an additional data that may provide a context. Walking may be classified based on selected heart rate biomarkers. For example, heart rate may indicate a user is performing a physical activity, such as walking. For example, an elevated heart rate may indicate a user is walking. For example, a heart rate within a predetermined range may indicate a user is walking.

For example, at 29404, patient data 29411 may indicate that the user may be sleeping. Patient data 29411 may be given an activity classification of sleeping at 29414. Sleeping may be classified at 29414 based on patient data 29411 and an additional data that may provide a context. Sleeping may be classified based on selected data. The patient data 29411 may indicate that the patient was sleeping. The patient data 29411 may include HCP notes that a patient was sleeping at the time indicated, for example. The patient data 29411 may include HCP notes that a patient was sedated, for example. The patient data 29411 may include medication information stating that a patient was given sleep inducing medication, for example.

For example, at 29404, the motion biomarker 29412 may indicate that the user may be sleeping. Motion biomarker 29412 may be given an activity classification of sleeping at 29415. Sleeping may be classified at 29415 based on motion biomarker 29412 and an additional data that may provide a context. Sleeping may be classified based on selected data. Sleeping may be classified based on selected motion biomarkers. For example, motion may indicate that a user is sleeping. For example, limited movement may indicate that a user is sleeping. For example, movement may indicate that a user is sleeping but moving while sleeping. For example, no movement may indicate that a user is in deep sleep. For example, motion biomarkers may indicate that a user is having restless sleep.

At 29405, hierarchical classification may be used. Hierarchical classification may include hierarchical classification of biomarkers. Biomarkers may be hierarchically classified in many ways. Biomarkers may be hierarchically classified as functional stressors. Biomarkers may be hierarchically classified as functional stressors to indicate priority. Biomarkers may be hierarchically classified as function stressors to differentiate between multiplexed cues. Biomarkers may be hierarchically classified as a recognition of combined behavior. Biomarkers may be hierarchically classified as a recognition of combined behaviors by using two or more cooperative datasets. Biomarkers may be hierarchically classified as a recognition of combined behaviors by using two or more cooperative datasets to create a measurable physiologic measure. Machine learning may also be used to assist in hierarchical classification.

As shown in FIG. 111, a plurality of data streams may be contextually transformed. The contextual transformation includes the hierarchical classification of the plurality of data streams. Determining the hierarchy of the plurality of data streams may indicate contextual information. The contextual information may include physiologic outcomes relating to the data streams. Contextual information may be used to indicate the hierarchy of the plurality of data streams. In an example, hierarchical classification may occur before determining contextual information. In an example, determining contextual information may occur before hierarchical classification.

For example, at 29405, hierarchical classification may be used on the heart rate biomarker 29410 and/or walking 29413 activity classification. Hierarchical classification may be used to classify the heart rate biomarker 29410 and/or walking 29413 activity classification on a higher level. The hierarchical classification may be used on the heart rate biomarker 29410 and/or walking 29413 activity classification to output stress level intensity 29416. Stress level intensity 29416 may be prioritized. Stress level intensity 29416 may be prioritized based on the heart rate biomarker 29410 and/or walking 29413 activity classification. Stress level intensity may be a higher classification of the heart rate biomarker 29410 and/or walking 29413 activity classification. For example, higher heart rate may indicate a higher stress level intensity. For example, walking may indicate a higher stress level intensity. A hierarchical classification may also be used to identify one or more other biomarkers that may be used to clarify a context. For example, stress level intensity may be indicated by a heart rate variation, by heart rate variation patterns, skin conductance, and the like.

For example, at 29405, hierarchical classification may be used on the patient data 29411 and/or sleeping 29414 activity classification. Hierarchical classification may be used to classify the patient data 29411 and/or sleeping 29414 activity classification on a higher level. The hierarchical classification may be used on the patient data 29411 and/or sleeping 29414 activity classification to output pain level intensity 29417. Pain level intensity 29417 may be prioritized. Pain level intensity 29417 may be prioritized based on the patient data 29411 and/or sleeping 29414 activity classification. Pain level intensity may be a higher classification of the patient data 29411 and/or sleeping 29414 activity classification. For example, patient data may indicate a pain level intensity. For example, sleeping may indicate a pain level intensity. A sleeping user may not be experiencing pain. A high pain level intensity may not occur in a sleeping patient because the patient may wake up from the pain. A high pain level intensity may indicate why a patient may not be sleeping well. A hierarchical classification may be used to identify one or more other biomarkers that may be used to clarify a context. For example, pain level intensity may be indicated by a sweat rate, a skin conductance, a heart rate variability, an indication of a pain from a patient, and the like.

For example, at 29405, hierarchical classification may be used on the motion biomarker 29412 and/or sleeping 29415 activity classification. Hierarchical classification may be used to classify the motion biomarker 29412 and/or sleeping 29415 activity classification in a higher level. The hierarchical classification may be used on the motion biomarker 29412 and/or sleeping 29415 activity classification to output quality of sleep 29418. Quality of sleep 29418 may be prioritized. Quality of sleep 294192 may be prioritized based on the motion biomarker 29412 and/or sleeping 29415 activity classification. Quality of sleep may be a higher classification of the sleeping 29415 activity classification. For example, sleeping may indicate quality of sleep. Restful sleep may lead to a higher quality of sleep. Movement during sleep may indicate lower quality of sleep. A hierarchical classification may be used to identify one or more other biomarkers that may be used to clarify a context. For example, a quality of sleep may be indicated by a changes in heart rate variability, length of time of movements, and the like.

At 29406, behavior and/or context recognition may be used. Behavior and/or context recognition may be used to determine contextual information surrounding biomarkers, activities, and/or classifications. Behavior and/or context recognition may identify links between one or more biomarkers and/or patient data. For example, an increase in stress level combined with the classification of walking may indicate contextual information such as exercise. The user may be exercising which is leading to the increase in stress level and the walking classification. The biomarkers may then be analyzed in the context of exercise. Exercise may indicate that a higher stress level is not a medical emergency. For example, an increase in pain level intensity combined with the classification of sleep may indicate contextual information such as poor sleep. The user may be experiencing poor sleep accounting for movement and the sleeping classification.

For example, at 29406, behavior and/or context recognition may be used on the motion biomarker 29412, walking classification 29413, and/or stress level intensity hierarchical classification 29416. Behavior and/or context recognition may be used to determine contextual information about the user. Behavior and/or context recognition may be used to determine contextual information about the user based on the motion biomarker 29412, walking classification 29413, and/or stress level intensity hierarchical classification 29416. For example, exercise 29419 may be indicated from the behavior and/or context recognition. Exercise 29419 may be indicated based on the motion biomarker 29412, walking classification 29413, and/or stress level intensity hierarchical classification 29416.

For example, at 29406, behavior and/or context recognition may be used on the patient data 29411, sleeping classification 29414, and/or pain level intensity hierarchical classification 29417. Behavior and/or context recognition may be used to determine contextual information about the user. Behavior and/or context recognition may be used to determine contextual information about the user based on the patient data 29411, sleeping classification 29414, and/or pain level intensity hierarchical classification 29417. For example, poor sleep 29420 may be indicated from the behavior and/or context recognition. Poor sleep 29420 may be indicated based on the patient data 29411, sleeping classification 29414, and/or pain level intensity hierarchical classification 29417.

For example, at 29406, behavior and/or context recognition may be used on the motion biomarker 29412, sleeping classification 29415, and/or quality or sleep hierarchical classification 29418. Behavior and/or context recognition may be used to determine contextual information about the user. Behavior and/or context recognition may be used to determine contextual information about the user based on the motion biomarker 29412, sleeping classification 29415, and/or quality or sleep hierarchical classification 29418. For example, poor sleep 29421 may be indicated from the behavior and/or context recognition. Poor sleep 29421 may be indicated based on the motion biomarker 29412, sleeping classification 29415, and/or quality or sleep hierarchical classification 29418.

At 29407, prioritization may be used. Prioritization 29407 may be used to increase and/or lower the priority of a data stream. Prioritization 29407 may be used to modify the priority of a data stream when contextually transforming data into an aggregated feed. For example, prioritization may use multiple data streams and/or their related classifications to determine a scenario (e.g., the most likely scenario). Data that is in line with each other may be prioritized. Data that is out of line with each other may have a lowered priority. In an example, if two data streams have behavior and context for a first activity and a different data stream has a behavior and/or context for a second activity different from the first, the first two data streams may have their priority increased and the different data stream may have its priority lowered. For example, data that is in line with sleep may be prioritized and data that is out of line with sleep may have priority lowered. The data in line with sleep may be more important that the data out of line with sleep.

For example, at 29407, prioritization may be used for multiple data streams. The multiple data streams may include behavior and/or context such as exercise and poor sleep. The multiple data streams may include 3 data streams. The first data stream from a first wearable device 29400 may include behavior and/or context of exercise 29419 from a heart rate biomarker 29410. The second data stream from electronic medical records 29401 may include behavior and/or context of poor sleep 29420 from patient data 29411. The third data stream from a second wearable device 29402 may include behavior and/or context of poor sleep 29421 from a motion biomarker 29412.

In an example, prioritization may consider the three data streams. Prioritization may determine that poor sleep is the more likely scenario with the three data streams. Prioritization may increase the importance and/or priority of the data streams with the behavior and/or context for poor sleep. Prioritization may increase the importance and/or priority of the second data stream from the electronic medical records 29401 and the third data stream from the second wearable device 29402. Prioritization may increase the importance and/or priority of the second and third data stream based on the accurate behavior and/or context of poor sleep. Prioritization may lower the importance and/or priority of the data streams without a behavior and/or context for poor sleep. Prioritization may lower the importance and/or priority of the first data stream from the first wearable device 29400. Prioritization may lower the importance and/or priority of the first data stream based on the inaccurate behavior and/or context of exercise.

At 29408, interlinking may be used. Interlinking may be used to provide useful information to HCPs. Interlinking may be used to provide physiologic information and/or a morbidity. Interlinking may be used to provide physiologic information based on one or more data streams. Interlinking may be used based on identified biomarkers. Interlinking may be used based on electronic medical records. Interlinking may indicate a physiologic function and/or morbidity to HCPs. For example, interlinking may use the information that a patient just completed surgery. Interlinking may receive the knowledge that a patient just completed surgery based on electronic medical records. For example, interlinking may connect the knowledge that a patient completed surgery and/or the patient is sleeping with data streams to indicate useful information to HCPs.

For example, the first data stream from the first wearable device 29400 may indicate surgical pain 29425. Based on the context of recent surgery the patient sleeping, interlinking may indicate that the user is experiencing surgical pain 29425 while sleeping. Pain may be experienced by a patient after surgery. Pain may be indicated based on elevated heart rate. Interlinking may inform HCPs about the surgical pain 29425. For example, the second data stream from the electronic medical records 29401 may indicate surgical pain 29426. Based on the context of recent surgery and the patient sleeping, interlinking may indicate that the user is experiencing surgical pain 29426 while sleeping. Poor sleep 29420 may be used with interlinking to indicate surgical pain 29426. Interlinking may inform HCPs about the surgical pain 29426. For example, the third data stream from the second wearable device 29402 may indicate sleep apnea 29427.

At 29409, conflict resolution may be used. Conflict resolution may resolve the conflict between differing results indicated by one or more data feeds. Conflict resolution may select the data streams that accurately indicate the scenario. For example, data streams may indicate differing scenarios. Conflict resolution may use any combination of activity classification, hierarchical classification, behavior and/or context recognition, prioritization, and/or interlinking.

For example, it may be known that surgery just occurred. HCPs may want to be aware of poor sleep and/or pain occurring after surgery. Multiple data streams may indicate surgical pain and one other data stream may indicate sleep apnea, for example. The conflict between surgical pain and sleep apnea may be resolved. The conflict may be resolved based on the knowledge that surgery just occurred. The conflict may be resolved based on the desire for HCPs to be informed about poor sleep and/or pain occurring after surgery.

At 29429, the data streams may be aggregated into a data stream. The aggregated data stream 29429 may include the aggregation and contextual transformation of the plurality of data streams. The aggregated data stream 29429 may be sent to HCPs. The HCPs may use the aggregated data stream 29429. The HCPs may use the aggregated data stream to indicate the summary of multiple cooperative measures, for example.

Figure 112:
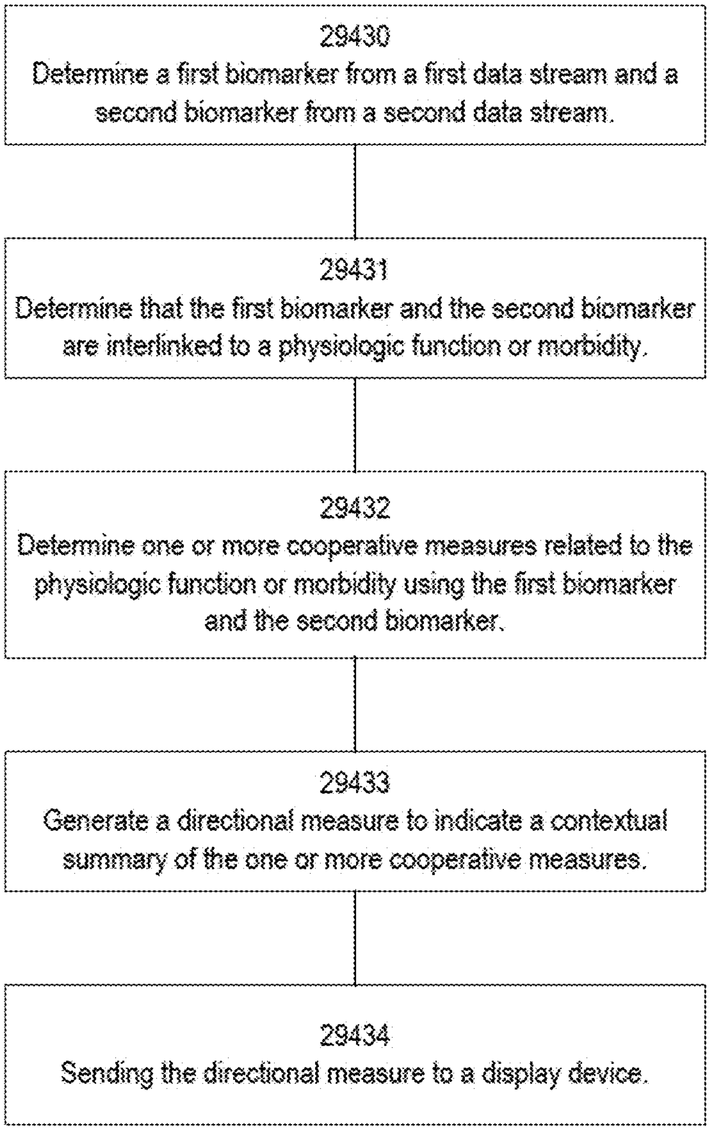

FIG. 112 depicts a method for contextually transforming data from one or more data streams into an aggregated display feed. At 29430, a first biomarker may be determined. The first biomarker may be determined from a first data stream. At 29430, a second biomarker may be determined. The second biomarker may be determined from a second data stream. At 29430, a first biomarker and a second biomarker may be determined respectively from a first data stream and a second data stream.

At 29431, a first biomarker may be determined to interlink to a physiologic function. The first biomarker may be determined to interlink to a morbidity. The first biomarker may be determined to interlink to a physiologic function and/or morbidity. A second biomarker may be determined to interlink to a physiologic function. The second biomarker may be determined to interlink to a morbidity. The second biomarker may be determined to interlink to a physiologic function and/or morbidity. The first biomarker and the second biomarker may be determined to be interlinked to a physiologic function or morbidity.

At 29120, one or more cooperative measures may be determined. The one or more cooperative measures determined may be related to a physiologic function and/or morbidity. The one or more cooperative measures related to a physiologic function and/or morbidity may be determined using the first biomarker. The one or more cooperative measures related to a physiologic function and/or morbidity may be determined using the second biomarker. The one or more cooperative measures related to a physiologic function and/or morbidity may be determined using the first and/or second biomarker.

At 29433, a directional measure may be generated. The directional measure may indicate a contextual summary. The directional measure may indicate a contextual summary of the one or more cooperative measures. A direction measure may be generated to indicate a contextual summary of the one or more cooperative measures. A directional measure may indicate a trend associated with a contextual summary. For example, a contextual summary may indicate that a patient is experiencing poor sleep due to a surgical pain, and the trend may indicate that the patient's poor sleep may continue to decrease in quality.

At 29434, the directional measure may be sent. The directional measure may be sent to a display, a computing system, a device, and/or a user.

In an example, data may be contextually transformed into an aggregated display feed. A computing device may contextually transform data into an aggregated display feed. The computing device may comprise: a memory and/or a processor. A first biomarker and a second biomarker interlinking to a physiologic function and/or a morbidity may be determined. Cooperative measures relating to the physiologic function and/or morbidity may be determined based on the first biomarker and the second biomarker. A directional measure may be generated. The directional measure may indicate a contextual summary of the one or more cooperative measures. The directional measure may be sent to a display device. In an example, the determination and/or indication as described herein may be performed by a processor and/or computing device. The processor and/or computing device may be configured to operate in any combination of the configurations as described above.

In an example, context for the first biomarker and the second biomarker may be determined. The context may be associated with a patient. The first biomarker and the second biomarker interlinking to a physiologic function and/or morbidity may be determined based on the context. For example, a first biomarker may include heart rate and a second biomarker may include core body temperature. Sleep may be determined based on the heart rate and core body temperature biomarkers. Lowered heart rate and lowered core body temperature may indicate sleep. The determination as described herein may be performed by a processor and/or computing system.

In an example, the first and second biomarker may be classified. The first and second biomarker interlinking to a physiologic function and/or morbidity may be determined. The first and second biomarker interlinking to a physiological function and/or morbidity may be determined based on the one or more classifications of the first and second biomarker. The classification and/or determination as described herein may be performed by a processor and/or computing system.

In an example, a context associated with a patient may be determined. One or more biomarkers may be prioritized. The one or more biomarkers may be prioritized based on a determined context associated with the patient. The determination and/or prioritization as described herein may be performed by a processor and/or computing system.

In an example, an aggregated display feed may be generated. The generated aggregated display feed for a patient may include a directional measure. In an example, the display device may be associated with a health care provider. The generation as described herein may be performed by a processor and/or computing system.

In an example, a weighted distribution may be determined. The weighted distribution may be applied to one or more data streams. the first biomarker and the second biomarker interlinking to a physiologic function and/or morbidity may be determined based on the determined weighted distribution. In an example, the weighted distribution may be determined based on one or more of a medical procedure that is being performed, a recovery time length, a procedural step, a time, and/or a third biomarker. The determination as described herein may be performed by a processor and/or computing system.

In an example, a first weight may be determined. The first weight may be applied to a first data stream. A second weight may be determined. The second weight may be determined to apply to a second data stream. The data streams may be prioritized. Priority for the data streams may be determined based on the applied weights. For example, the first biomarker having priority over the second biomarker may be determined based on the first weight and the second weight. In an example, the first and second biomarker interlinking to a physiologic function and/or morbidity may be determined based on the prioritization. For example, the first biomarker and the second biomarker interlinking to the physiologic function and/or morbidity may be determined based on the first biomarker having priority over the second biomarker. The determination and prioritization as described herein may be performed by a processor and/or computing system.

In an example, a conflict between one or more results indicated by one or more biomarkers may be determined. A conflict between a first result indicated by a first biomarker and a second result indicated by a second biomarker may be determined, for example. A context for a patient may be determined. Conflict resolution for the conflict may be determined based on the context for the patient. In an example, the first biomarker and the second biomarker interlinking to a physiologic function and/or morbidity may be determined based on the one or more context for the patient and the conflict resolution. In an example, conflict resolution for the conflict may be determined based on one or more of a reliability of the first data stream, a reliability of the second data stream, a detected anomaly, a predefined recovery, and/or a predefined analysis. The determination as described herein may be performed by a processor and/or computing system.

Figure 113:
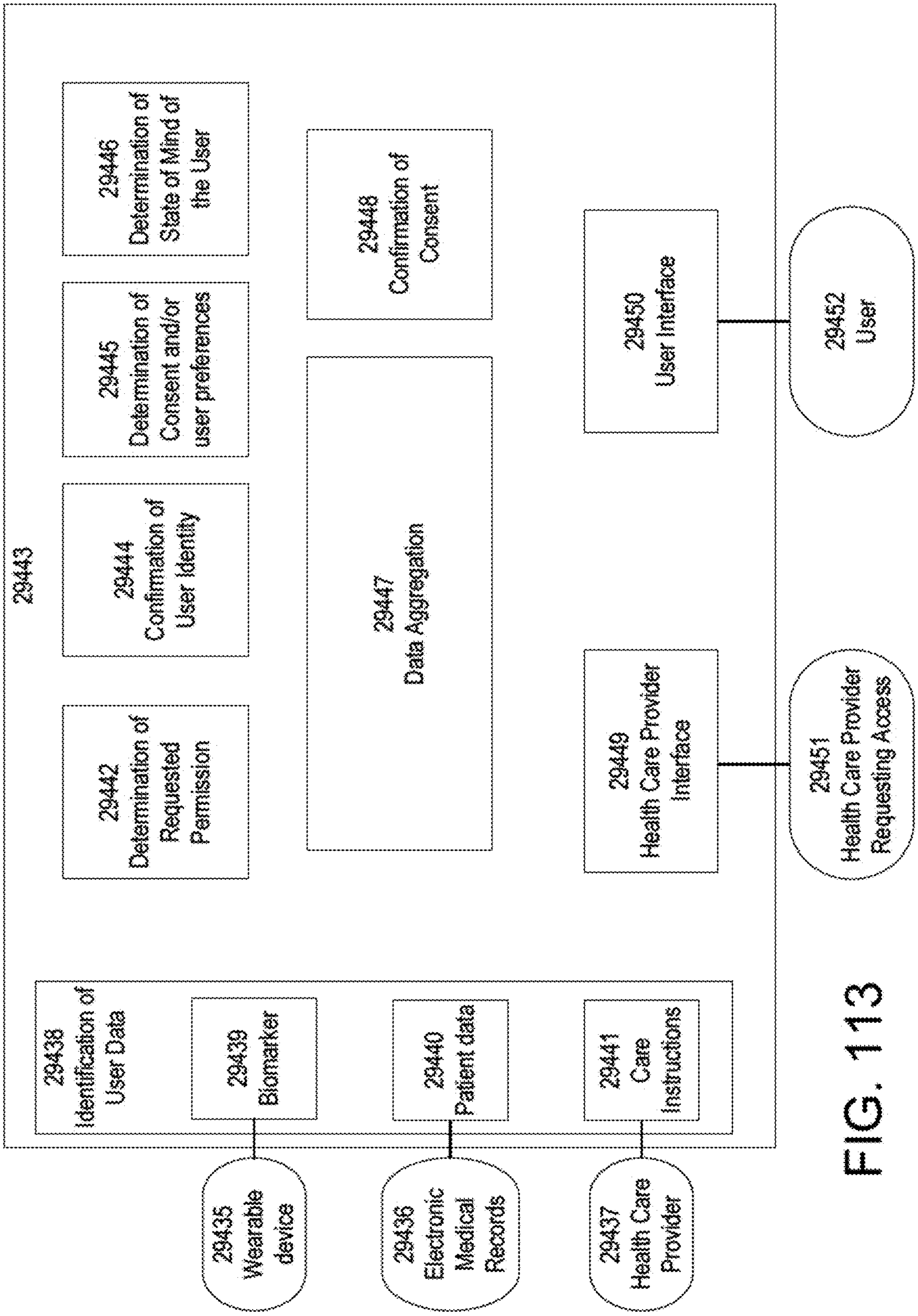

FIG. 113 depicts a block diagram of a computing system 29443 for securing consent to share data with a health care provider. The device may perform an analysis to determine whether consent may be given. The computing system 29443 may include inputs external to the device. The computing system 29443 may receive input from one or more of a wearable device 29435, electronic medical records 29436, a health care provider 29437, a health care provider requesting access 29451, and/or a user 29452. The computing system 29443 may determine whether a user may or may not give consent. The computing system 29443 may block the data from being shared if the user may not be able to give consent, for example. The computing system 29443 may block the data from being shared if the user cannot be certified, for example. The computing system 29443 may block the data from being shared if the user cannot be properly identified, for example.

The computing system 29443 may include a set of computer modules that may perform the analysis of whether the user is able to give consent. The computing system 29443 may include computer modules configured to perform one or more processes including identification of user data module 29438, determination of requestion permission module 29442, confirmation of user identity module 29444, determination of consent and/or user preferences module 29445, determination of state of mind of the user module 29446, confirmation of consent module 29448, data aggregation module 29447, health care provider interface module 29449, and/or user interface module 29450. The modules may be incorporated into a system and/or a single device. The modules may be located in the cloud, on a local server, or a combination thereof.

At 29451, a health care provider may request access to patient information and/or records. The health care provider requesting access 29451 may want to access data about the patient to understand what the patient's care instructions may include, for example. The health care provider requesting access 29451 may want to access data about the patient to monitor the patient post procedure, for example. The health care provider requesting access 29451 may use a health care provider interface 29449 to request access to the patient information. The health care provider interface 29449 may require a health care provider requesting access to provide credentials to confirm proper access to the information. The health care provider interface 29449 may prevent access to patient information based on consent permissions.

At 29452, a user may request access to patient information and/or records. The user 29452 may include the patient. The user 29452 may include the health provider caring for the patient. The user 29452 may use a user interface 29450) to request access to the patient information. The user interface 29450 may request that the user 29452 provide credentials to confirm proper access to the information. The user interface 29450 may prevent access to patient information based on consent permissions. The user interface 29450 may prevent access to a patient user based on state of mind. State of mind may include whether a patient is cognitively impaired and/or incapacitated.

At 29438, identification of user data may be performed. User data may be identified. User data include one or more data streams from external devices. Identification of user data may include receiving one or more data streams from external devices. Identification of user data may include receiving one or more data streams from a wearable device 29435, for example. Identification of user data may include receiving one or more data streams from electronic medical records 29436, for example. Identification of user data may include receiving one or more data streams from a health care provider 29437, for example. The health care provider data stream may include data such as, the operating doctor notes, instructions for patient, and/or patient notes for a different health care provider, for example. Identification of user data may include storing information from an incoming data stream relating to a specific patient.

Identification of user data may include using the one or more incoming data streams. The one or more data streams may include a biomarker 29439. The one or more data streams may include patient data 29440. The one or more data streams may include care instructions 29441. The one or more data streams may include any combination of a biomarker 29439, patient data 29440, and/or care instructions 29441. A user may be identified at 29438 based on the biomarker 29439, patient data 29440, and/or care instruction 21212. Identification of user data may include patient information including but not limited to procedures, therapies, monitored biomarkers, thresholds, and/or system notification settings. For example, identification of user data may record when incoming data streams add data, events, and/or treatments. Identification of user data may be performed when incoming data streams pertain to the specific patient. Identification of user data may include retrieving the data associated with a patient. The identification of user data may include generating an output of the data streams associated with a patient.

At 29442, determination of requested permission may be performed. Requested permissions may be determined. Requested permissions may be determined based on the type of access a health care provider requesting access and/or a user is requesting. Requested permissions may include permission to access data. Requested permissions may include permission to control data. Requested permissions may include permission to monitor data. Requested permissions may include permission to receive a notification associated with data. Requested permissions may include permission to receive a notification associated with a wearable device. Requested permissions may include any combination of the permissions described herein.

At 29444, confirmation of user identity may be performed. A user identity may be confirmed. Confirmation of user identity may include confirming the authenticity of the identity of the user and/or health care provider requesting access. Confirmation of user identity may include preventing access to a user based on failed confirmation of user identity. Confirmation of user identity may be used to prevent unauthorized access, for example. Confirmation of user identity may be used to confirm the user is who the user purports to be, for example. Confirmation of user identity may include security methods to authenticate user identity, for example. Confirmation of user identity may use security questions to authenticate the user, for example. Failed confirmation of user identity may occur when security questions are answered incorrectly, for example.

Confirmation of user identification may be requested to access a specific data. Confirmation of user identification may be required to operate a system resource. Confirmation of user identification may include one or more of user identification, verification via a second means, and/or confirmation of authentication. For example, means for ensuring the user is the authorized user may include mechanisms that authenticate specific patients to wearables. Authenticating specific patients to wearables may reduce data falsification and/or fabrication. For example, wearables may be used as a key to other secured treatments. System monitoring devices may be configured to a user's last initiation, for example. For example, a drug delivery device and a wearable may interact to ensure correct user and dosage. The interaction may continue to monitor after drug administration, for example. For example, authentication may be used to access and monitor stored medical records. For example, confirmation of user identification may include monitoring a user to ensure the user is not exchanging the system to another user.

At 29445, determination of consent and/or user preferences may be performed. Consent and/or user preferences may be determined. Consent and/or user preferences may be determined based on a user and/or health care provider requesting access having proper permissions and/or consent. Consent and/or user preferences may be determined based on a consent and/or user preferences settings. The settings may include permissions a patient and/or user may give consent. The consent and/or user preferences settings may include types of data access permissions. Data access permissions may include permission to one or more of access the data, control the data, monitor the data, receive a notification associated with the data, and/or receive a notification associated with the wearable device, and the like. The consent and/or user preferences settings may include a group of entity access permissions. Entity access permissions may include a list of entities given access permissions for at least one data access permission. Entity access permissions may include one or more of the patient, a doctor, a nurse, a health care provider, a second health care provider, and the like.

In an example, the user may set consent and/or user preference settings. For example, a user may set consent and/or user preference settings to allow a secondary health care provider access to the patient data. For example, a user may set consent and/or user preferences settings to allow the secondary health care provider to access data and monitor data. The consent and/or user preferences may be determined based on the set data access permissions to access and monitor data, for example. The consent and/or user preferences may be determined based on the secondary health care provider being set as a proper entity, for example.

At 29446, determination of state of mind of the user may be performed. A state of mind of the user may be determined. The state of mind of the user may be determined based on the cognitive ability of the user. The state of mind of the user may include cognitive impairment. Cognitive impairment may include the inability of a person to carry out normal day-to-day activities. Cognitive impairment may include the inability of a person to provide consent. Cognitive impairment may include one or more of a loss of memory, reduction in mental functions, concentration difficulties, impaired orientation to people, places, or time, and/or impairments in deductive or abstract reasoning. A patient may be cognitively impaired when in a coma, for example. A patient may be cognitively impaired when incapacitated, for example. A patient may be cognitively impaired when under the influence, for example. A patient may be cognitively impaired when under the influence of an intoxicating substance, for example.

For example, cognitive ability may be determined based on one or more of, but not limited to, a diagnosis, a neurological exam, a lab test, brain imaging, and/or a mental status test. One or more biomarkers may be used to determine cognitive ability. A diagnosis may be based on one or more of a problem with memory, a problem with mental function, a decline of mental functions over time, a decline of ability to perform daily activities, and/or an impairment compared to others of like age and education. A neurological exam may include testing for a patient's brain and/or nervous system. For example, testing for a patient's brain and/or nervous system may indicate neurological signs of cognitive impairment such as Parkinson's disease, strokes, tumors, and/or other medical conditions that can impair mental functions. For example, testing for a patient's brain and/or nervous system may include tests for reflexes, eye movements, and/or walking and balance.

A level of cognitive ability may be determined, and the level may be compared to a cognitive threshold. For example, a state of mind of a user may be requested. One or more biomarkers may be used to determine a level of cognitive of ability of the user. A cognitive threshold may be determined that may indicate an ability for a person to provide consent. The level of cognitive ability of the user may be compared to the cognitive threshold. It may be determined that the user may be of a state of mind to provide consent when the level of cognitive ability is above the cognitive threshold. It may be determined that the user may not be of a state of mind to provide consent when the level of cognitive ability for the user is below or equal to the cognitive threshold.

At 29448, confirmation of consent may be performed. Consent may be confirmed. For example, consent may be confirmed based on the determination of requested permission. Consent may be confirmed when the requested permissions determined align with the consent and/or user preferences. Consent may be denied when the requested permissions are not aligned with the consent and/or user preferences. In an example, a request to access data may be confirmed when an entity is listed as a proper entity with permission to access data in the consent and/or user preferences. In an example, a request to access data may be denied when an entity is not listed as a proper entity and/or the entity does not have the requested permission to access data.

For example, consent may be confirmed based on a confirmed user identity. Consent may be confirmed based on a confirmed user identity when a user is authenticated. A user may be authenticated when the user is confirmed to be the entity the user purports to be. Consent may be denied based on an unconfirmed user identity. An unconfirmed user identity may occur when a user is unable to properly authenticate the user's identity.

For example, consent may be confirmed based on a determination of consent and/or user preferences. Consent may be confirmed based on an entity being a proper entity listed in the determined consent and/or user preferences. Consent may be confirmed based on an entity requesting permissions that align with the determined consent and/or user preferences. Consent may be confirmed on the condition of both a proper entity and a proper request permission, for example. In an example, consent may be confirmed for a secondary health care entity requesting access to data based on the secondary health care entity being a proper entity and having proper permission to access data as listed in the consent and/or user preferences. In an example, consent may be denied for a secondary health care entity requesting access to data based on a failure to be a proper entity and/or failure to have the requested permissions as listed in the consent and/or user preferences.

For example, consent may be confirmed based on a determination of the state of mind of the user. Consent may be confirmed based on a user having a proper state of mind when giving the consent permissions. Consent may be denied based on an inability of a user to provide consent. Consent may be denied based on a user being cognitively impaired when giving the consent permissions requested, for example.

Consent may be confirmed based on one or more of determination of requested permission, confirmation of user identity, determination of consent and/or user preferences, and/or determination of state of mind of the user. Consent may be confirmed based on determination of requested permission, confirmation of user identity, determination of consent and/or user preferences, and/or determination of state of mind of the user. In an example, consent may be confirmed only on the satisfaction of determination of requested permission, confirmation of user identity, determination of consent and/or user preferences, and determination of state of mind of the user.

At 29447, data aggregation may be performed. Data aggregation may be performed as shown in FIG. 111. Data aggregation may include receiving one or more data streams. The one or more data streams may include data streams from one or more of a wearable device, electronic medical records, and/or a health care provider. The one or more data streams may include one or more of biomarker data, procedure data, therapy data, a threshold setting, and a system notification setting. Data aggregation may include the contextual transformation of one or more data streams. Data aggregation may include an output of the contextual transformation of one or more data streams. Data aggregation may include contextually transforming data into an aggregated display feed.

Data aggregation may include interlinking one or more biomarkers to a physiologic function and/or morbidity. Data aggregation may include determining one or more cooperative measures related to the physiologic function and/or morbidity. Data aggregation may include determining one or more cooperative measures related to the physiologic function and/or morbidity based on the one or more biomarkers. Data aggregation may generate a directional measure to indicate a contextual summary. Data aggregation may generate a directional measure to indicate a contextual summary of one of the one or more cooperative measures.

Data aggregation may include an output of one or more of a physiologic function and/or morbidity, cooperative measure, directional measure, and/or contextual summary. Data aggregation may include an output to patient data and/or records.

Figure 114:
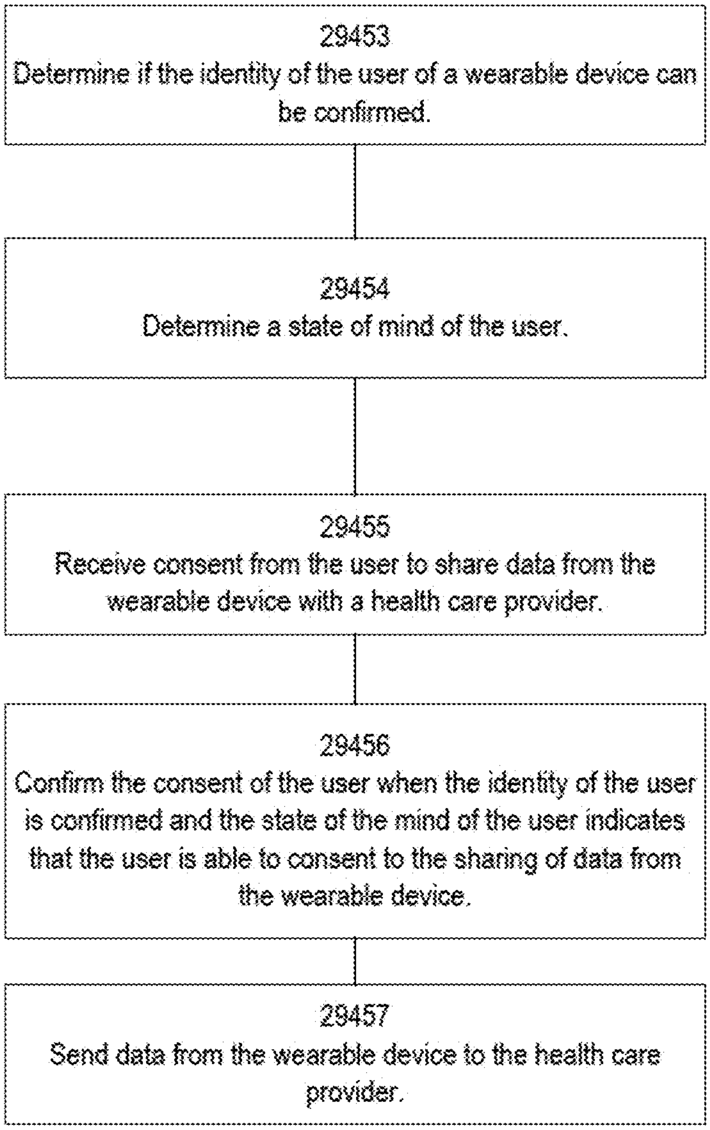

FIG. 114 depicts a method for securing consent to share data with a health care provider. At 29453, the identity of a user may be confirmed. The identity of a user of a wearable device may be confirmed. At 29454, the state of mind of a user may be determined.

At 29455, consent may be received from a user. Consent may be received from a user to share data. Consent may be received from a user to share data from a wearable device. Consent may be received from a user to share data with one or more entities. Consent may be received from a user to share data with one or more health care providers. Consent may be received from a user to share data from a wearable device with one or more entities. Consent may be received from a user to share data from a wearable device with one or more health care providers.

At 29456, consent of a user may be confirmed. Consent of the user may be confirmed when the identity of the user is confirmed. Consent of the user may be confirmed when the state of the mind of the user indicates that the user is able to consent. Consent of the user may be confirmed when the identity of the user is confirmed and the state of mind of the user indicates that the user is able to consent. Consent of the user may include consenting to the sharing of data. Consent of the user may include consenting to the sharing of data from a wearable device.

At 29457, data may be sent to one or more entities. Data may include one or more of biomarker data, procedure data, therapy data, a threshold setting, and a system notification setting. Data may be sent to one or more health care providers. Data may be sent from one or more wearable devices to one or more health care providers.

In an example, consent recording may be secured and communicated to health care providers. Consent recording may be secured and communicated to health care providers based on one or more of confirming the identity of a user, determining the state of mind of the user, receiving consent from the user to share data, confirming the consent of the user when the identity of the user is confirmed and the state of mind of the user indicates that the user is able to provide consent, and sending data to the health care provider. Whether an identity of a user can be confirmed may be determined. Whether an identity of a user of a wearable device can be confirmed may be determined. A state of mind of the user may be determined. Consent from the user to share data from the wearable device with a health care provider may be received. Consent of the user may be confirmed based on the confirmation of the identity of the user and the confirmation that the state of mind of the user indicates the user is able to provide the consent. The data may be sent from the wearable device to the health care provider. In an example, the determination, confirmation, and/or securing as described herein may be performed by a computing device and/or processor. The computing device and/or processor may be configured to operate in any combination of the configurations as described above.

In an example, the state of mind of the user may be indicated that the user is non-cognitively impaired.

In an example, the consent from the user to share the data from the wearable device with the health care provider may indicate that the health care provider as permission to one or more of access the data, control the data, monitor the data, receive a notification associated with the data, and receive a notification associated with the wearable device.

In an example, the health care provider may be a first health care provider. The consent from the user to share the data from the wearable device with the health care provider may indicate that the health care provider has permission to receive information from a second health care provider. The consent from the user to share the data from the wearable device with the health care provider may indicate that the health care provider has permission to receive patient instructions from the second health care provider.

In an example, an identification of a second health care provider may be received. The identification of a second health care provider may be received by the user.

In an example, consent may be denied. Consent of the user may be denied. Consent of the user may be denied when a state of mind of a user indicates that the cognitive ability of the user is at or below a cognitive threshold. The threshold may be set at a cognitive level that may indicate that the user is unable to be accountable for a decision.

In an example, consent may be denied. Consent of the user may be denied. Consent of the user may be denied based on the state of mind of the user. Consent of the user may be denied when the state of mind of the user indicates one or more of a cognitive impairment and an inability of the user to provide consent. In an example, consent of the user may be denied when the identity of the user is not confirmed.

In an example, the data may include one or more of biomarker data, procedure data, therapy data, a threshold setting, and a system notification setting.

A received measurement may be ordered. The measurement may be associated with a surgical sensing system. The measurement may be associated with a communications interface. The measurement may be associated with a surgical sensing system and a communications interface. The measurement may be received at a first time. A latency value may be received. The latency value may be associated with a surgical sensing system. The latency value may be associated with a communications interface. The latency value may be associated with a surgical sensing system and a communications interface. A time code may be applied. The time code may be applied to the received measurement. The time code may be applied based on the first time. The time code may be applied based on the obtained latency value. The time code may be applied based on the first time and the obtained latency value. An output may be ordered. The output may be ordered based on the received measurement. The output may be ordered based on the applied time code. The output may be ordered based on the received measurement and the applied time code.

In an example, the surgical sensing system may include one or more sensors. The surgical sensing system may include one or more sensors configured to sense at least one biomarker. The surgical sensing system may include one or more sensors configured to sense at least one environment. The surgical sensing system may include one or more sensors configured to sense one or more of a biomarker and an environment. The surgical sensing system may be configured to sense at least one surgical instrument parameter.

Examples herein may include a computer-implemented method for synchronizing data from multiple link coordinated sensing systems. The method may include receiving a measurement at a first time. The measurement may be associated with a sensing system. The measurement may be associated with a communications interface. The method may include obtaining a latency value. The latency value may be associated with the surgical sensing system. The latency value may be associated with the communications interface. The method may include applying a time code to the received measurement. The time code may be applied based on the first time and the obtained latency value. The method may include ordering an output based on the received measurement and time code.

Figure 115:
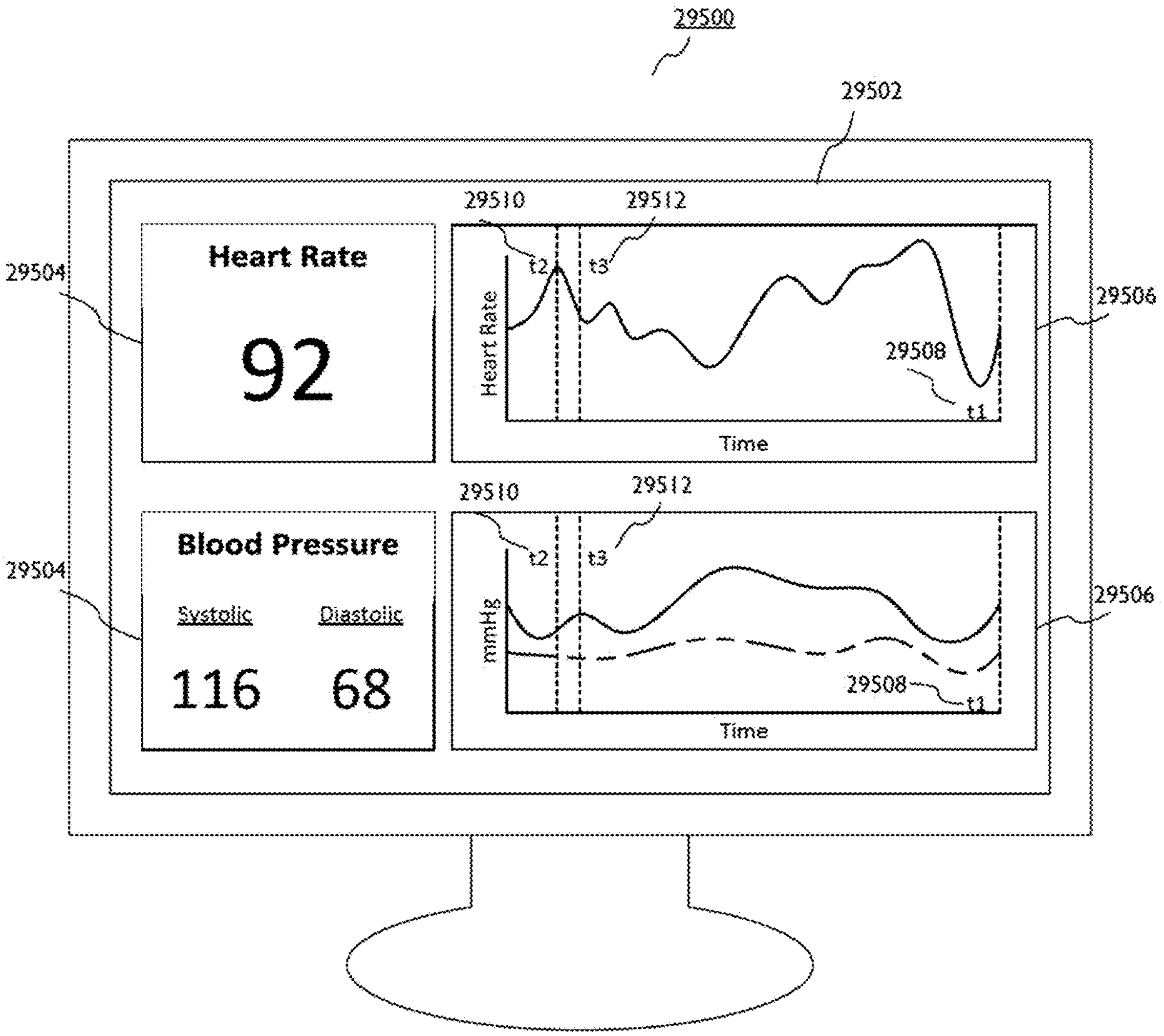

FIG. 115 shows an example display 29500. Healthcare professionals (HCPs) may be interested in data relating to surgical procedures and post-operation recovery. The display 29500 is one example in which data relating to surgical procedures and post-operation recovery may be communicated to an HCP. The data may relate to biomarkers, the environment, surgical instruments, and/or advanced energy devices. Contextual information relating to surgical procedures and post-operation recovery may be determined based on biomarkers, the environment, surgical instruments, advanced energy devices, and/or the like. Contextual information may include information relating to physiological systems and conditions.

For example, biomarkers may relate to different physiologic systems. HCP may monitor biomarkers to determine contextual information relating to surgical procedures and post-operation recovery. Biomarker sensing systems may sense biomarkers in patients and/or healthcare professionals. The biomarker sensing systems described herein may sense various biomarkers, including but not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

For example, environmental data may relate to different physiologic systems. Environmental data may include temperature, air quality, airborne chemicals, and light exposure.

HCPs may be interested in monitoring surgical instrument data during surgical procedures. The surgical instrument data may provide contextual information during the surgery. Contextual information may be determined based on other sensing system data. The sensing systems described herein may sense parameters associated with surgical tools. A surgical tool may include a surgical stapler.

Surgical sensing systems may be configured to sense data relating to surgical procedures and post-operating recovery. Surgical sensing systems may include systems configured to sense data relating to biomarkers, the environment, surgical instruments, and/or advanced energy devices. Data relating to various biomarkers may include patient or HCP biomarkers.

HCPs may be interested in analyzing received data from a surgical sensing system in context with other received data from a separate surgical sensing system. Biomarker, environment, and surgical instrument measurements may provide context to each other. Therefore, it is important for HCPs to know whether measurements from surgical sensing systems are occurring simultaneously or at different times offset from each other. HCPs may not be able to determine contextual information from multiple sensing systems if the data received from each sensing system is not synchronized with each other.

An example surgical sensing system may include a clock used to tag events with a sensing system time (e.g., a time relative to the clock of the surgical sensing system). The surgical sensing system clock may be a real-time clock (RTC). The RTC may be an integrated circuit. The RTC may measure the passage of time. The RTC may include an internal oscillator with an external crystal and/or an external frequency reference. The RTC may measure the passage of time based on the oscillator frequency. The RTC may be set using a reference clock time. In an example, the RTC may be a clock that minimizes time inaccuracies, such as drift, variability, latency differences, and/or the like.

For example, over time, clock drift may occur. Clock drift may include where the RTC desynchronizes from the reference clock time. Clock drift occurs when a RTC operates at a different rate than the reference clock. Clock drift may cause RTCs to drift apart and read different times. In an example, one or more surgical sensing systems may include an RTC set to a shared reference clock time. Over time, the one or more surgical sensing systems RTC may desynchronize from the reference clock and each read different times from each other. In an example, stream imperfections may occur using non-real-time operating systems and commodity hardware. Sensors capturing at the same frequency on different hosts may have varying data rates. The varying data rates may be due to hardware setup differences. The varying data rates may be due to local clock offsets and drifts. The varying data rates may be due to uninterruptable kernel time. The varying data rates may be due to scheduler delays. The varying data rates may be due to unpredictable disk operations.

HCPs may consider data from multiple surgical sensing systems, for example, to determine contextual information relating to surgical procedures and post-operational recovery. Assessing the relative occurrence of certain measurements from respective ones of the multiple systems and/or the accuracy of that assessment may affect such a consideration.

To illustrate, the display 29500 includes a visual representation 29502 of data signals. The visual representation 29502 may include a current measurement reading 29504 and a graphical representation 29506. The data signals may be received from various surgical sensing systems, including those that related to biomarkers, the environment, surgical instruments, and/or advanced energy devices. The received data signals may include measurements from surgical sensing systems. In an example, the data signals received may include measurements for heart rate and/or blood pressure.

The visual representation 29502 may include a current measurement reading 29504 based the most recently received measurement from a surgical sensing system. The visual representation 29502 may include a graphical representation 29506 of the measurement reading 29504 based on a hub clock time. The graphical representation 29506 may include the recent history of measurement readings 29504. As shown by FIG. 115, the measurements may include heart rate and blood pressure.

In an example a heart rate sensing system and a blood pressure sensing system may send data signals to a display 29500. The data signals may be displayed as a graphical representation 29506. The heart rate sensing system may send a heart rate measurement showing a spike at a first time 29508 based on a heart rate sensing system clock. The blood pressure sensing system may send a blood pressure measurement showing a spike at the first time 29508 based on a blood pressure sensing system clock. The heart rate sensing system clock and the blood pressure sensing system clock may be set to different reference clocks. Clocks set to different reference clocks may display different clock times. While the graphical representation may indicate that the heart rate spike occurred at the same time the blood pressure spike occurred at a first time 29508, the spikes may not have actually occurred concurrently.

In an example, a heart rate measurement and a blood pressure measurement may both spike at the same time. If the heart rate sensing system and blood pressure sensing system clocks are not set to a common reference clock, then the measurements may be displayed at different times in the visual representation 29502. For example, the heart rate measurement may show a spike at a second time 29510 and the blood pressure measurement may show a spike at a different third time 29512, despite both measurements occurring at the same time. The difference in the second time 29510 and third time 29512 may result from differing latencies. The latency may include a processing delay in the surgical sensing system and/or a transit time in sending the measurement to the display 29500. The two measurements may be offset despite occurring at the same time.

HCPs may use the visual representation 29502 to guide procedures and decision making. It is important for HCPs to know whether measurements from surgical sensing systems are occurring concurrently or asynchronously. Concurrent measurements may indicate to an HCP that the measurements are related to each other. For example, HCPs may determine certain contextual information based on concurrently spiking measurements for heart rate and blood pressure. Asynchronous measurements may indicate to an HCP that the measurements are unrelated to each other. For example, HCPs may determine measurements are unrelated to each other when one measurement spiking and the other remaining the same.

FIG. 116A is a functional block diagram of a surgical data ordering system 29514. Such a system may be used to synchronize the relative timing from multiple data feeds, for example. The synchronization of multiple data feeds together may enable correlation and monitoring of multiple systems.

For example, the synchronization may include ad hoc synchronization of data from multiple link coordinated sensing systems. A surgical hub may receive data signals. The data signals may be from at least two separate data feeds. The data signals may be unified. The data signals may be linked to procedural data. The data signals may be linked to instrument operation. The data signals may be unified and linked to create a unified fused display. HCPs may use the unified fused display.

As shown in FIG. 116A. the surgical data ordering system 29514 may be used to order received data. The surgical data ordering system 29514 may be used to order received data based on a master time clock 29516. The surgical data ordering system 29514 may include one or more surgical sensing systems 29518, a surgical hub 29520, and a downstream data system 29522. The surgical data ordering system 29514 may be configured to receive data signals from at least one surgical sensing system 29518. The surgical data ordering system 29514 may include a surgical hub 29520. The surgical hub 29520 may be in communication with one or more surgical sensing systems 29518. The surgical hub 29520 may be configured to order a received data signal from at least one surgical sensing system 29518. The surgical data ordering system 29514 may include at least one downstream data system 29522. The at least one downstream data system 29522 may include a display.

The surgical hub 29520 may include computing hardware and/or software suitable for processing and/or ordering sensor data. For example, the surgical hub 29520 may incorporate and/or be incorporated in the surgical hub 20006, disclosed herein. For example, the surgical hub 29520 may be deployed as a stand-alone unit for sensor processing. The surgical hub 29520 may be configured to gather measurement data from the one or more surgical sensing systems 29518.

The surgical hub 29520 may be configured to send notifications or requests to the one or more surgical sensing systems 29520. The surgical hub 29520 may be configured to send information to the at least one downstream data system 29522. The surgical hub 29520 may obtain a latency value. The latency value may be associated with a surgical sensing system. The latency value may be associated with a communications interface. The latency value may be associated with a combination of a surgical sensing system and a communications interface. The surgical hub 29520 may apply respective time codes to received measurements. The surgical hub 29520 may apply respective time codes to received measurements based on the master time clock 29516. The surgical hub 29520 may output one or more of the received measurements. The surgical hub 29520 may order the output.

The surgical hub 29520 may include a processing unit 29524. The surgical hub 29520 may include a master time clock 29516. The surgical hub 29520 may include a combination of a processing unit 29524 and a master time clock 29516. The surgical hub 29520 may use the processing unit 29524 to order received data signals. The surgical hub 29520 may order the received data signals based on the master time clock 29516. The surgical hub 29520 may use a combination of a processing unit 29524 and a master time clock 29516 to order received data signals. The surgical hub may include a master time log 29526. The master time log may be a data structure in memory. The surgical hub 29520 may store the ordered data signals in the master time log 29526.

The processing unit 29524 may receive one or more measurements. The processing unit 29524 may obtain a latency value. The latency value may be associated with a surgical sensing system. The latency value may be associated with a communications interface. The latency value may be associated with a combination of a surgical sensing system and a communications interface. The processing unit 29524 may apply respective time codes to received measurements. The processing unit 29524 may apply respective time codes to received measurements based on the master time clock 29516. The processing unit 29524 may output one or more of the received measurements. The processing unit 29524 may order the output. The processing unit 29524 may store the output in the master time log 29526. The processing unit 29524 may send a request to one or more surgical sensing systems 28518. The processing unit 29524 may send a request to return a data signal to one or more surgical sensing systems 28518.

The surgical hub 29520 may include a master time clock 29516. The master time clock 29516 may include any electrical and/or computing resource suitable for measuring time. For example, the master time clock 29516 may measure the passage of time. The master time clock 29516 may measure time as a real-time clock (RTC). The master time clock 29516 may measure time as a system counter, for example. The master time clock 29516 may measure time as relative time in view of a defined event. The master time clock 29516 may measure time in clock pulses. The master time clock 29516 may count clock pulses. The master time clock 29516 may measure time in seconds. The master time clock 29516 may measure time in microseconds. The master time clock 29516 may measure time in seconds and/or microseconds based on counted clock pulses. The master time clock 29516 may measure time in processor cycles. The master time clock 29516 may count processor cycles. The master time clock 29516 may be set to a time. The master time clock 29516 may be set manually. The master time clock 29516 may be set based on a reference clock. The master time clock 29516 may be set based on an RTC reference.

The master time clock 29516 may include an RTC. The master time clock 29516 may include an integrated circuit RTC. The RTC may measure the passage of time. The RTC may include an internal oscillator. The internal oscillator may include a quartz crystal, for example. The RTC may include a micromechanical resonator. The RTC may include an external frequency reference. The external frequency reference may include the power line frequency. The power line frequency may include the nominal frequency of oscillations of alternating current in a wide area synchronous grid. The RTC may measure the passage of time based on the oscillator frequency. The RTC may be software-based. The master time clock 29516 may be any RTC such as those known under the trade name Epson, Intersil, Integrated Device Technology, Maxim, NXP Semiconductors, Texas Instruments, STMicroelectonics, and/or Ricoh.

The master time log 29526 may include any information indicative of time-based measurements. For example, the master time log 29526 may include a data structure. The data structure may include a table data structure, an array, a linked list, a flat-file, a record, a delimited data stream, an XML data store, a_, and the like, for example. For example, the master time log 29526 may include one or more records. Each record may represent a respective measurement. A record may indicate relevant measurement and/or timing information, such as a sensing system ID, the measurement value itself, a time, and the like, for example. The master time log 29526 may act as a data repository. The master time log 29526 may replicate the data for logging purposes. The master time log 29526 may function as a buffer for output to the downstream system 29522.

The one or more surgical sensing system 29518 may be a surgeon sensing system and/or a patient sensing system. For example, the surgical sensing system 29518 may incorporate and/or be incorporated in the sensing system 20069, disclosed herein. The surgical sensing system 29518 may include a sensor unit. The surgical sensing system may include a data processing and communication unit. The surgical sensing system 29518 may include a sensing system clock 29528. The surgical sensing system 29518 be in communication with a surgical hub.

For example, the surgical sensing system 29518 may include one or more sensor units for measuring one or more biomarkers. The surgical sensing system 29518 may include one or more sensor units for measuring the environment. The surgical sensing system 29518 may include one or more sensor units for measuring surgical instrument parameters and energy data. The surgical sensing system 29518 may include one or more sensor units for measuring capital equipment data. For example, the surgical sensing system 29518 may include one or more sensor units for measuring biomarkers such as, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, bacteria in respiratory tract, edema, mental aspects, sweat, circulating tumor cells, autonomic tone, circadian rhythm, and/or menstrual cycle. These biomarkers may be measured using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The sensors may measure the biomarkers as described herein using one of more of the following sensing technologies: photoplethysmography, electrocardiogramalectroencephalography, colorimetry, impedimentary, potentiometry, amperometry, etc.

The surgical sensing system 29518 may measure data. The surgical sensing system 29518 may apply a sensor time to surgical sensing system events. The surgical sensing system 29518 may apply a sensor time to surgical sensing system events based on the sensor time when the data was measured. The surgical sensing system 29518 may apply a sensor time to measured data based on the sensing system clock 29528. For example, the surgical sensing system 29518 may apply a sensor time to a measurement at the time of measurement. The surgical sensing system 29518 may continuously measure data. The surgical sensing system 29518 may measure data based on a sample rate. The sample rate may be based on the sensing system clock. For example, the surgical sensing system 29518 may take a measurement after a predetermined number of clock cycles. The surgical sensing system 29518 may take a measurement after a certain time.

The surgical sensing system 29518 may send a data stream 29530 to a different device, such as a surgical hub. The data stream 29530 may include the sensed measurement 29532 itself, a sensing system ID 29534, timing information associated with the sensed information 29536, meta-data associated with the sensed measurement, and the like, for example. The surgical sensing system 29518 may be configured to send a data stream 29520) based on a received request. The surgical sensing system 29518 may be configured to select a sensed measurement to send. The surgical sensing system 29518 may apply a sensor time to a data stream based on when the measurement is sent and the sensing system clock 29528.

In an example, data feeds may be asynchronous. The data feeds may reflect one or more patient monitored parameters. The data feeds may include instrument feeds. The instrument feeds may include energy device generator data. The instrument feeds may include wireless data streams. The instrument feeds may include wireless data streams from digitally enabled surgical devices. The digitally enabled surgical devices may include a powered stapler, for example. The instrument feeds may include instrument capital equipment. The instrument capital equipment may include generators, smoke evacuators, and/or vision systems, for example.

In an example, the displayed fused data feed may show instrument power. The displayed fused data feed may show temperature. The displayed fused data feed may show progress, such as procedure progress. The displayed fused data feed may show one or more of instrument power, temperature, and progress. The displayed fused data feed may show one or more of instrument power, temperature, and progress with respect to a video feed and physiologic impacts. In an example, the fused data may aggregate datasets. The fused data may aggregate datasets to show a measure, for example. The fused data may aggregate datasets to show an outcome of a surgical task, for example.

The sensing system clock 29528 may include any electrical and/or computing resource suitable for measuring time. For example, the sensing system clock 29528 may measure the passage of time. The sensing system clock 29528 may measure time as an RTC. The sensing system clock 29528 may measure time as a system counter, for example. The sensing system clock 29528 may measure time as relative time in view of a defined event. The sensing system clock 29528 may measure time in clock pulses. The sensing system clock 29528 may count clock pulses. The sensing system clock 29528 may measure time in seconds. The sensing system clock 29528 may measure time in microseconds. The sensing system clock 29528 may measure time in seconds and/or microseconds based on counted clock pulses. The sensing system clock 29528 may be set to a time. The sensing system clock 29528 may be set manually. The sensing system clock 29528 may be set based on a reference clock. The sensing system clock 29528 may be set based on an RTC reference.

The sensing system clock 29528 may include an RTC. The sensing system clock 29528 may include an integrated circuit RTC. The RTC may measure the passage of time. The RTC may include an internal oscillator. The internal oscillator may include a quartz crystal, for example. The RTC may include a micromechanical resonator. The RTC may include an external frequency reference. The external frequency reference may include the power line frequency. The power line frequency may include the nominal frequency of oscillations of alternating current in a wide area synchronous grid. The RTC may measure the passage of time based on the oscillator frequency. The RTC may be software-based. The sensing system clock 29528 may be and RTC such as those known under the trade name Epson, Intersil, Integrated Device Technology, Maxim, NXP Semiconductors, Texas Instruments, STMicroelectonics, and/or Ricoh.

In an example, one or more surgical sensing systems 29518 may not share a common RTC reference. The master time clock 29516 may not share a common RTC reference with one or more surgical sensing systems. The one or more surgical sensing systems 29518 may be set to different RTC references. The one or more surgical sensing systems 29518 may output different times based on the non-common RTC references. The one or more surgical sensing systems 29518 may output different times than the surgical hub based on the non-common RTC references.

In an example, a surgical hub 29520 may be configured to order a received measurement 29532 from at least one surgical sensing system 29518. The surgical hub 29520 may receive a data stream 29530 from at least one surgical sensing system 29518. The data stream 29530 may include a measurement 29532, a sensing system ID 29534, one or more sensor times associated with the measurement 29536, meta-data associated with the measurement 29532, and the like. The surgical hub 29520 may apply a receipt time associated with the data stream 29530. The surgical hub 29520 may apply a receipt time associated with the data stream 29530 based on the master time clock 29516.

In an example, the surgical hub 29520 may obtain a latency value associated with the data stream 29530. The surgical hub 29520 may obtain a latency value associated with the data stream 29530 based on the one or more sensor times associated with the measurement 29536. The surgical hub 29520 may obtain a latency value associated with the data stream 29530 based on the receipt time associated with the data stream 29530. The surgical hub 29520 may obtain a latency value associated with the data stream 29530 based on any combination of the one or more sensor times and/or the receipt time.

In an example, the surgical hub 29520 may determine a time code. The surgical hub 29520 may determine a time code based on the obtained latency value. The surgical hub 29520 may determine a time code based on the master time clock 29516. The surgical hub 29520 may determine a time code based on any combination of the obtained latency value and/or master time clock 29516. The time code may be a number. The time code may be a time relative to the master clock time 29516. The time code may be a time relative to real-time. The surgical hub 29520) may apply the determined time code to a data stream 29530.

In an example, the surgical hub 29520 may provide each sensing system 29518 on a common network with a synchronized time stamp. A master time clock 29516 may record a relational matrix of each of the other clocks at a point in time. In an example, synchronization may include signal processing methods. The signal processing methods may deal with non-uniformly sampled data. The non-uniformly sampled data may include data containing large temporal gaps, for example.

In an example, the surgical hub 29520 may use a specification of data delivery rate and frequency. The surgical hub 29520 may control a sampling rate. The surgical hub 29520 may control a time indexing of data points. For example, the surgical hub 29520 may dictate when data is transmitted by the sensing system 29518 to the surgical hub 29520. The surgical hub 29520 may use a clock and trigger system. A trigger signal may be sent to a given sensing system 29518. Data may be sent back and recorded. The data may be sent back and recorded based on the trigger signal. Knowing a latency of the transmission may allow the surgical hub 29520 to set a timestamp of the system recorded event. The sensing system 29518 may be continuously measuring data. The sensing system 29518 may transmit data when prompted by the hub trigger signal.

In an example, a shift register based system may be used. The shift register based system may monitor input from multiple connections, such as sensing systems 29518. The shift register based system may sequentially output the state of each input. The shift register based system may sequentially output the state of each input based on a trigger signal. A clock signal may be used. The clock signal may proceed through the various inputs. The clock signal may proceed through the various inputs in a specified sequence. The clock signal may proceed through the various input in a specified sequence based on the frequency of the clock signal.

In an example, the combination of the trigger and the clock may dictate the capture frequency. In an example, one cycle through the shift register based system may provide a snapshot of all inputs across the specified time. A faster clock frequency may provide a higher temporal resolution across read samples. In an example the latency of a sensing system and the clock duration would enable calculation of an actual timestamp backwards in time. For example, if the transmission of the trigger signal takes 1 microsecond, the clock signal read cycle takes 1 microsecond, and the transmission of the data signal back takes 1 microsecond, the time of occurrence may be estimated to be 3 microseconds prior to obtaining the data read.

In an example, ad hoc software synchronization may used for data stream fusion and/or fixation. Data stream fusion and fixation may allow synchronization without a predefined conversion. In an example, multi-sensor data fusion and distributed signal processing may be used. The multi-sensor data fusion and distributed signal processing may be used to fuse data feeds into a global system time code. A fused signal array may be used. The fused signal array may be used to assign an augmented blocked timestamp. The augmented blocked timestamp may be used to adjust the offsets of the data feeds.

A shift with a constant delay may be experienced with fused signals. A synchronizer may be used to fuse asynchronous data. A synchronizer may be used to attach a unified timing code. The unified timing code may be an augmented timestamp. Dropped frames and/or data points may be detected based on the unified timing code. The feeds may be linked together. The feeds may be linked together based on the unified timing code. In an example, software generated block and timestamps may be used with non-real-time operating systems. Augmented timestamps may be used.

Augmented timestamps may include tolerant timestamp match, exact blockstamp match, and/or overlay timestamp match, for example. Tolerant timestamp match may be used for synchronization. Tolerant timestamp match may be used for synchronization based on a tolerance interval. Ascending timestamps matching within a tolerance interval may indicate synchronization. Tolerant timestamp match may be used for sources with equal rates. Exact blockstamp match may be used in scenarios of single source dataflow split among multiple processing pipelines subject to stream and processing imperfections. Exact blockstamp match may be used for processors with different speeds, for example. Exact blockstamp match may be used to detect dropped frames. Overlay timestamp match may use timestamp intervals. Timestamp intervals of several dataflows with different sampling rates may be grouped. Timestamp intervals of several dataflows with different sampling rates may be grouped in case of an interval overlay. An output rate of synchronized data may be higher than a rate of the fastest stream. Overlay timestamp match may be used in combination with blockstamp information about sequence integrity of the stream. Overlay timestamp may be used to synchronize streams with a large difference in frequency.

In an example, a combined blockstamp and timestamp may be augmented to a signal. The combined blockstamp and timestamp may be augmented to a signal in pipeline capture nodes. The augmented timestamp may be generated. The augmented timestamp may be generated by an incremental counter, for example. The augmented timestamp may be generated by blockstamp, for example. The augmented timestamp may be generated by a local clock, for example. The augmented timestamp may be generated by a timestamp, for example. The timestamp may allow mixing of sensor signals of different data rates. The blockstamp may allow data originating from one source, split across multiple computation nodes, to be fused in synchronicity, such as on multiple hosts or multi-core processors, for example. Statistical ad hoc regression algorithms may be used. Statistical ad hoc regression algorithms may filter estimating interframe timing. Statistical ad hoc regression algorithms may include Widrow and/or Kalman.

In an example, the surgical hub 29520 may generate an output. The surgical hub 29520 may output a received data stream 29530. The surgical hub 29520 may order the received data stream 29530. The surgical hub 29520 may order the received data stream 29530 based on the master time clock 20516. The surgical hub 29520 may order the received data stream 29530 based on an applied time code. The surgical hub 29520 may order the received data stream 29530 based on when the measurements associated with the data stream 29530 were sensed. The surgical hub 29520 may send the ordered output to the master time log 29526. The surgical hub 29520 may send the ordered output to a downstream data system 29522.

In an example, the downstream data system 29522 may receive the ordered output from the surgical hub 29520. The downstream data system 29522 may include a display, for example. The display may display the ordered data stream 29530. For example, HCPs may use the downstream data system 29522 to monitor information associated with the surgical sensing system. HCPs may use the downstream data system 29522 to monitor information associated with the surgical sensing system. HCPs may use the downstream data system 29522 to analyze a plurality of data streams from surgical sensing systems occurring at the same time. For example, HCPs may analyze the plurality of data streams from surgical sensing systems to determine contextual information regarding the surgical procedure, patient recovery, patient, and/or surgeon. HCPs may analyze a heart rate measurement spiking at the same time as a blood pressure measurement spiking, for example.

FIG. 116B is a block diagram showing an example processing unit 29538. The processing unit 29538 may receive surgical sensing system data 29540. The processing unit 29538 may order the received surgical sensing system data 29540. As shown in FIG. 116B, a timeline 29542 shows a plurality of measurements associated with different sensing systems, 29544, 29546, and 29548. The plurality of measurements may be sensed at a time 29550. The plurality of measurements may be received at a later time 29552. The plurality of measurements may be received in a different order than they were sensed. The processing unit 29538 may order the received surgical sensing system data 29540. The ordered surgical sensing system data may emulate how the measurements were sensed. The processing unit may order the received surgical sensing system data 29540 based on a master time clock 29554. The processing 29538 unit may determine a respective time code associated with respective surgical sensing system data. The processing unit 29538 may determine a respective time code associated with respective surgical sensing system data based on the master time clock 29554. At 29556, the respective time code may be applied to the respective surgical sensing system data. The surgical sensing system data may be ordered based on the applied time code.

A processing unit 29538 may include computing hardware and/or software suitable for processing and/or ordering sensor data. For example, the processing unit 29538 may incorporate and/or be incorporated in the processor module 20057. For example, the processing unit 29538 may be deployed as a stand-alone unit for sensor processing. The processing unit 29538 may be any single-core or multicore processing unit. The processing unit 29538 may be any processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with Stellaris Ware® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

A processing unit 29538 may receive an input. The processing unit 29538 may receive a data as an input. The processing unit 29538 may generate an output. The processing unit 29538 may process the data. The processing unit 29538 may generate an output based on the processed data. The processing unit 29538 may receive surgical sensing system data 29540. The processing unit 29538 may be configured to gather measurement data from one or more surgical sensing systems. The processing unit 29538 may determine a time code. The processing unit 29538 may determine a time code based on a master time clock 29554. The processing unit 29538 may apply the time code to received surgical sensing system data. The processing unit 29538 may order the received surgical sensing system data. The processing unit 29538 may order the received surgical sensing system data based on the applied time code. The processing unit 29538 may output the ordered surgical sensing system data. The processing unit 29538 may send the ordered surgical sensing system data to a downstream data system. The processing unit 29538 may send the ordered surgical sensing system data to a storage medium, such as a master time log, for example.

Surgical sensing system data 29540 may be associated with one or more surgical sensing systems. The surgical sensing system data 29540 may be sent as a data stream 29558. The surgical sensing system data 29540 may include a measurement 29560 associated with a surgical sensing system. The surgical sensing system data 29540 may include a sensing system ID 29562 associated with the surgical sensing system measurement. The surgical sensing system data 29540 may include at least one time 29564 associated with a surgical sensing system measurement. The at least one time 29564 associated with a surgical sensing system measurement may include the time when the measurement was sensed. The at least one time 29564 associated with a surgical sensing system measurement may include the time when the measurement was sent.

As shown in FIG. 116B, at 29550, a plurality of measurements, 29544, 29546, and 29548, associated with at least one surgical sensing system may be sensed. The plurality of measurements may be sensed at different times. For example, a first measurement 29544 may be sensed before a second measurement 29546 and a third measurement 29548. The second measurement 29546 may be sensed before the third measurement 29548. At 19552, the plurality of measurements may be received, such as by the processing unit 29538, for example. The plurality of measurements may be received in a different order than they were sensed. The plurality of measurements may be received in a different order than they were sensed based on different latency values associated with the surgical sensing systems. For example, the second measurement 29546 may be received before the third measurement 29548 and the first measurement 29544. The third measurement 29548 may be received before the first measurement 29544. The processing unit 29538 may order the plurality of measurements. The processing unit 29538 may order the plurality of measurements to emulate the order the measurements were sensed. The processing unit 29538 may order the plurality of the measurements to show the first measurement 29544 occurred before the second measurement 29546, which occurred before the third measurement 29548, for example.

In an example, the processing unit 29538 may include a master time clock 29554. The master time clock 29554 may incorporate and/or be incorporated into the master time clock 29516 from FIG. 116A. The processing unit 29538 may use the master time clock 29554 to order the received measurements. The processing unit 29538 may apply a received time associated with respective measurements. The processing unit 29538 may apply a received time associated with respective measurements based on the master time clock 29554. The processing unit 29538 may order the received measurements based on the received time associated with the respective measurements.

In an example, the processing unit 29538 may obtain a latency value. The processing unit 29538 may obtain a latency value associated with a received measurement. The latency value associated with a received measurement may include the time elapsed between a measurement being sensed and the measurement being received.

The processing unit 29538 may be configured to select a method of obtaining a latency value. For example, the processing unit 29538 may obtain a latency value based on apriori knowledge. In an example, the processing unit 29538 may obtain a latency value using a method of sending a request to a surgical sensing system to return a sensed measurement. In an example, the processing unit 29538 may obtain a latency value using a method of sending a request to a surgical sensing system to return the most recently sensed measurement. In an example, the processing unit 29538 may obtain a latency value using a method of sending a request to a surgical sensing system to return the next measurement sensed. In an example, the processing unit 29538 may obtain a latency value using a method of sending a request to a surgical sensing system to return a sensed measurement that is closest in time to the time the surgical sensing system receives the request. The sensed measurement closest in time may include the most recent sensed measurement and/or the next measurement the surgical sensing system senses. The surgical sensing system may be configured to determine the time remaining until a subsequent measurement is sensed based on a sampling rate. The surgical sensing system may be configured to select the closest in time sensed measurement to a received request based on the time of the most recently sensed measurement and a sampling rate.

The processing unit 29538 may determine a time code. The processing unit 29538 may determine a time code for a received measurement. The processing unit 29538 may determine a time code based on the master time clock 29554. The processing unit 29538 may determine a time code based on the obtained latency value. The processing unit 29538 may determine a time code based on the time a data stream was received. The processing unit 29538 may determine a time code based on any combination of the master time clock 29554 and/or the obtained latency. The time code may be an arbitrary number. The time code may be a time relative to the master time clock 29554. The time code may be a time relative to real-time.

At 29556, the processing unit 29538 may apply a time code. The processing unit 29538 may apply the time code to a received measurement. The processing unit 29538 may apply the time code to a received measurement associated with a surgical sensing system. The processing unit 29538 may order a received measurement based on the applied time code. The processing unit 29538 may order a plurality of received measurements based on the applied time code. The ordered measurements may emulate the order the measurements were sensed. The ordered measurements may be unified to a common time system based on the applied time code.

FIG. 117 shows a timeline 29568 illustrating an example method of obtaining a latency value 29570 associated with a surgical sensing system measurement. A surgical sensing system may sense measurements continuously. A surgical sensing system may send sensed measurements. The sensed measurements may be sent to a computing device, such as a surgical hub.

As shown in FIG. 117, the surgical sensing system may sense a measurement at a first time 29570 on the timeline 29568. The surgical sensing system may send the sensed measurement at a second time 29572 on the timeline 29568. The second time 29572 may occur after the first time 29570. The measurement may be received at a third time 29574 on the timeline 29568. The third time 29574 may occur at after the second time 29572.

The latency value 29570 may include the delay between a measurement being sensed and the measurement being received by a processing device, such as a surgical hub. The latency value 29570 may include a delay before sending the measurement 29578. The delay before sending the measurement 29578 may be the difference in time between a measurement being sensed and a measurement being sent to a processing device, such as a surgical hub. The latency value 29570 may include a transit time 29580. The transit time 29580 may be the difference in time between a measurement being sent and a measurement being received by a processing device, such as a surgical hub. The latency value 29570 may include the combination of the delay before sending the measurement 29578 and the transit time 29580.

In an example, the delay before sending the measurement 29578 may be determined. The delay before sending the measurement 29578 may be determined based on a surgical sensing system clock. The surgical sensing system clock may tag a measurement with sensor event times. The surgical sensing system clock may tag a measurement with sensor event times based on the surgical sensing system clock. The sensor event times may include any time a surgical sensing system senses a measurement. The sensor even times may include any time a surgical sensing system sends a measurement. The delay before sending the measurement may be determined by calculating the different in time between the time a measurement was sensed and the time a measurement was sent, for example.

In an example, the transit time 29580 may be determined. The transit time 29580 may be determined based on apriori knowledge FIG. 118 shows a timeline 29582 in illustrating an example method of obtaining a latency value associated with a surgical sensing system measurement. The surgical sensing system may continuously sense measurements. The surgical sensing system may receive a request to return a sensed measurement. A surgical hub may be configured to send a request. The surgical hub may be configured to send a request to return a sensed measurement. The surgical sensing system may receive a request to return a sensed measurement from a surgical hub.

In an example, as shown in FIG. 118, the surgical hub may send a request to a surgical sensing system. At 29584, the surgical hub may send a request to the surgical sensing system. The request may be a request to return a sensed measurement. At 29586, the surgical sensing system may receive the request to return the sensed measurement. At 29588, the measurement may be sensed. At 29590, the measurement may be returned. At 29592, the measurement may be received. The measurement may be received by the surgical hub.

A latency value associated with the measurement may be obtained. The latency value associated with the measurement may be obtained based on a round trip latency value 29594. The round trip latency value 29594 may be the difference in time between the time a request to return a measurement is sent and the time the measurement is received. The latency value associated with the measurement may be approximated by calculating half the round trip latency value 29594, for example.

In an example, the round trip latency value 29594 may be obtained based on a clock. The clock may include a master time clock. The surgical hub may include the master time clock. The master time clock may be an RTC. The master time clock may tag surgical hub events with hub event times. The hub event times may include times when the surgical hub sends a request to return a measurement. The hub event times may include times when the surgical hub receives sensed measurements. The round trip latency value 29594 may be calculated using the difference in the tagged time when the surgical hub sends a request to return a measurement and the tagged time when the surgical hub receives the sensed measurement.

In an example, the latency value may be obtained based on the master time clock and a surgical sensing system clock. The master time clock may tag surgical hub events with hub event times. The surgical sensing system clocks may tag surgical sensing system events with sensing system event times. The latency value may be calculated based on the hub event times and the sensing system event times. The latency value may be calculated based on the hub event times, surgical sensing system event times, a first transit time between when the surgical hub sends a request, and a second transit time between when the surgical sensing system returns a measurement and the surgical hub receives the measurement.

In an example, the surgical sensing system may be configured to continuously sense measurements. The surgical hub may be configured to send a request to the surgical sensing system. The surgical sensing system may be configured to return measurements to a surgical hub it based on the received request. The surgical sensing system may be configured to select which sensed measurement to return based on the received request. The surgical sensing system may select a measurement based on an instruction from the surgical hub request. In one example the surgical sensing system may select a measurement based on the sensing time associated with the measurements. The surgical sensing system may select a measurement that is the most recently sensed measurement relative to the request received time. The surgical sensing system may select a measurement that is the next measurement to be sensed relative to the request received time. The surgical sensing system may select a measurement that is closest in time to the request received time. The surgical sensing system may determine the measurement that is closest in time to the request received time based on the sensing time associated with the measurements and a sampling rate associated with the surgical sensing system. The surgical sensing system may determine the length of time until the next measurement will be sensed based on the sampling rate.

FIG. 119 shows a timeline 29596 illustrating an example method of selecting a sensed measurement. At 29598, the surgical hub may send a request to the surgical sensing system. At 29600, the surgical sensing system may receive the request. At 29602, the surgical sensing system may sense a first measurement. At 29604, the surgical sensing system may sense a second measurement. As shown in FIG. 119, the time the first measurement was sensed, 29602, may be earlier than the time the second measurement was sensed, 29604. The time the surgical sensing system received the request, 29600, may be later than when the first measurement was sensed, 29602, but earlier than when the second measurement was sensed, 29604. At 29606, the surgical sensing system may return a selected measurement to the surgical hub. At 29608, the surgical hub may receive the selected measurement. A round trip latency 29610 may be obtained based on the time the surgical hub sent the request and the time the surgical hub received the selected measurement.

In an example, the surgical sensing system may a select the measurement most recently sensed relative to the time the request was received from the surgical hub. As shown in FIG. 119, the most recently sensed measurement relative to the time the request was received may be the first measurement sensed at 29602. The surgical sensing system may select the first measurement sensed at 29602 to return to the surgical hub. The surgical sensing system may select the first measurement sensed at 29602 to return to the surgical hub based on a received request.

In an example, the surgical sensing system may select the measurement that will be sensed immediately after receiving a request from the surgical hub. As shown in FIG. 119, the measurement that will be sensed immediately after receiving the request may be the second measurement sensed at 29604. The surgical sensing system may select the second measurement sensed at 29604 to return to the surgical hub. The surgical sensing system may select the second measure sensed at 29604 to return to the surgical hub based on a received request.

In an example, the surgical sensing system may select the measurement that is closest to the time the request was received from the surgical hub. The sensed measurement that is closest to the time the request was received may be the sensed measurement most recently sensed. The sensed measurement that is closest to the time the request was received may be the sensed measurement that will be sensed immediately after receiving the request.

In an example, the surgical sensing system may determine the time the measurement that will be sensed after receiving the request. The surgical sensing system may determine the time the measurement that will be sensed after receiving the request based on a sampling rate 29612. The sampling rate 29612 may be the frequency at which the surgical sensing system senses measurements. The sampling rate may be the difference in time between a first measurement at 29602 and a second measurement at 29604. The surgical sensing system may calculate a first measurement delay 29614 and a second measurement delay 29616.

In an example, the measurement closer in time to when the surgical sensing system receives the request 29600 may be determined. The measurement closer in time to when the surgical sensing system receives the request 29600 may be determined based on a first delay 29614 and a second delay 29616. The measurement closer in time to when the surgical sensing system receives the request may be the lesser of the first delay and the second delay, for example. The first measurement delay 29614 may be determined. The first measurement delay 29614 may be the difference in time between when the surgical sensing system senses the first measurement 29602 and when the surgical sensing system receives the request 29600. The second measurement delay 29616 may be determined. The second measurement delay 29616 may be the difference in time between when the surgical sensing system will sense the second measurement 29604 and when the surgical sensing system receives the request 29600.

FIG. 120 depicts an example master time log 29618 with surgical sensing system data. The master time log 29618 may use a data structure in memory to store the surgical sensing system data. The surgical sensing system data may include a measurement and associated measurement meta-data. The measurement meta-data may include: a sensing system identification 29620, a measurement value 28622, a measurement received time 29624, a latency value 29626, and a time code 29628. The sensing system identification 29620 may include identification meta-data associated with a surgical sensing system. The measurement value 29624 may include the received measurement from a surgical sensing system. The measurement received time 29624 may include the time meta-data associated with the surgical sensing system data was received by the surgical hub. The latency value 29626 may include the obtained latency associated with the surgical sensing system measurement. The time code 29628 may be the value calculated by the surgical hub used to order a measurement to a common time system.

In an example, a plurality of surgical sensing systems may sense measurements. The plurality of surgical sensing systems may send the sensed measurements to a surgical hub. Each measurement may include meta-data associated with the sensed measurements. The surgical hub may tag each measurement with a measurement received time based on the master clock time when the measurement is received by the surgical hub. The surgical hub may determine a time code for each received measurement based on the measurement meta-data. The measurement meta-data used to determine a time code may include the measurement latency value and the measurement received time associated with the measurement. The surgical hub may apply the determined time code to the measurement. The surgical hub may order the plurality of measurements based on the applied time codes. As shown in FIG. 120, the order the surgical hub receives the plurality of measurements may be different than the order based on the applied time code. The order based on the applied time code may emulate when the measurements were sensed.

FIG. 121 illustrates an example method for ordering surgical sensing system data. At 29630, a measurement may be received. The measurement may be associated with a surgical sensing system. For example, a surgical data ordering system may receive the measurement associated with a surgical sensing system. For example, a surgical sensing system may sense a measurement and send the measurement to the surgical data ordering system. For example, the surgical data ordering system may send a request to the surgical sensing system to return a sensed measurement.

For example, the surgical data ordering system may send a request to the surgical sensing system to return a selected sensed measurement. The selected sensed measurement may include the most recently sensed measurement when the request is received, the next measurement that will be sensed after the request was received, and/or the sensed measurement closest in time to when the request was received. A surgical hub and/or processing unit may receive the measurement associated with the surgical sensing system as described herein.

At 29631, synchronization processing may occur. For example, the synchronization processing may include any of the techniques disclosed herein, such as latency compensation, network synchronized time stamps, master time clocks, signal processing methods, trigger signals, shift register based systems, ad hoc software synchronization, data stream fusion and/or fixation, augmented timestamps (including tolerant timestamp match, exact blockstamp match, and/or overlay timestamp match, for example), and/or the like.

In an example, at 29632, a latency value may be obtained. The latency value may be associated with the received measurement. The latency value may be associated with the surgical sensing system. The latency value may be obtained apriori. The latency value may include a delay time. The delay time may be the time elapsed between sensing the measurement and sending the measurement. The latency value may include a transit time. The transit time may be the time between sending the measurement and the measurement being received. The latency value may be obtained based on one or more of the delay time and the transit time, for example. The latency value may be obtained based on a round trip latency value. The latency value may be approximated to be half of the round trip latency value.

At 29634, a time code may be applied. The time code may be applied to a received measurement. The time code may be applied based on the latency value associated with the received measurement. The time code may be applied based on the latency value associated with the surgical sensing system. In an example, the applied time code may be based on the obtained latency and/or a measurement received time. For example, a surgical data ordering system may apply the time code to the received measurement. For example, a surgical hub and/or a processing unit may apply the time code to a received measurement.

At 29636, the received measurement may be ordered. The received measurement may be ordered based on the applied time code. A plurality of received measurements may be ordered. The plurality of received measurements may be ordered based on the applied time codes. The ordering output may include the plurality of received measurements in a different order than they were received. The ordering output may include the plurality of received measurements in a different order than they were sensed. The ordered measurements may emulate the order the plurality of measurements were sensed in. For example, the surgical data ordering system may order one or more measurements. The surgical data ordering system may order the one or more measurements based on the applied time codes.

At 29638, the ordered measurements may be entered into a master time log. The master time log may include a data structure in memory. The data structure may include a table data structure, an array, a linked list, a flat-file, a record, a delimited data stream, an XML data store, and the like, for example. The master time log may include any information indicative of time-based measurements. The master time log may include relevant measurement and/or timing information, such as a sensing system ID, the measurement value itself, a time, and the like, for example. For example, the surgical data ordering system may enter the measurements into the master time log. For example, a surgical hub and/or a processing unit may enter the ordered measurements into the master time log.

In an example, the master time log data may be sent to a downstream data system. For example, the downstream data system may include a display. The display may be used to monitor at least one surgical sensing system. The display may include a visual representation of the surgical sensing system data. The visual representation may include a current measurement reading and/or a graphical representation. The graphical representation may include the surgical sensing system measurements as a function of time. For example, the display may be used to monitor two or more surgical sensing systems on a unified time system In an example, a received measurement may be ordered. The measurement may be associated with a surgical sensing system. The measurement may be associated with a communications interface. The measurement may be associated with a surgical sensing system and a communications interface. The measurement may be received at a first time. A latency value may be received. The latency value may be associated with a surgical sensing system. The latency value may be associated with a communications interface. The latency value may be associated with a surgical sensing system and a communications interface. A time code may be applied. The time code may be applied to the received measurement. The time code may be applied based on the first time. The time code may be applied based on the obtained latency value. The time code may be applied based on the first time and the obtained latency value. An output may be ordered. The output may be ordered based on the received measurement. The output may be ordered based on the applied time code. The output may be ordered based on the received measurement and the applied time code.

In an example, the surgical sensing system may include one or more sensors. The surgical sensing system may include one or more sensors configured to sense at least one biomarker. The surgical sensing system may include one or more sensors configured to sense at least one environment. The surgical sensing system may include one or more sensors configured to sense one or more of a biomarker and an environment. The surgical sensing system may be configured to sense at least one surgical instrument parameter.

In an example, the master time log may receive a data stream. The data stream may include one or more ordered measurements, for example. The master time log may include a storage. The master time log may store the received data stream in the storage. The master time log may store the received one or more ordered measurements in the storage, for example.

In an example, the surgical sensing system may send a measurement. The surgical sensing system may send a sensed measurement. The surgical sensing system may receive a request. The surgical sensing system may receive a request to send a measurement. The surgical sensing system may receive the request at a second time. The surgical sensing system may send the sensed measurement based on the received request. The surgical sensing system may send the sensed measurement at a third time. The third time may be a later time than the second time.

In an example, the surgical sensing system may select a measurement. The surgical sensing system may select the measurement based on the time the measurement was sensed. The surgical sensing system may select a most recently sensed measurement, for example. The surgical sensing system may select the measurement based on a received request. The surgical sensing system may select a future measurement yet to be sensed for example. The surgical sensing system may select the future measurement yet to be sensed based on the received request. The surgical sensing system may select a measurement closest in time to the received request, for example.

In an example, an output may be displayed. The output may be displayed based on the master time log. The output may be displayed on a display. A visual representation may be generated based on the output. The visual representation may include a current measurement reading. The visual representation may include a graphical representation. The visual representation may be displayed.

In an example, two or more received measurements may be ordered. A first measurement may be received. The first measurement may be received at a first time. The first measurement may be associated with a first sensing system. The first measurement may be associated with a communications interface. A second measurement may be received. The second measurement may be received at a second time. The second measurement may be associated with a second sensing system. The second measurement may be associated with the communications interface. One or more latency values may be obtained. The one or more latency values may be associated with the first surgical sensing system. The one or more latency values may be associated with the second surgical sensing system. The one or more latency values may be associated with the communications interface. One or more time codes may be applied. The one or more time codes may be applied based the one or more latency values. An output may be ordered. The output may be ordered based on the first and second measurements, the output may be ordered based on the one or more time codes.

A device may be used to process surgical data. For example, the device may be used to process surgical data during a surgical procedure. The device may include a memory and a processor. The processor may be configured to retrieve a first surgical-data-processing schema from the memory. The processor may be configured to perform first processing of a first portion of incoming sensor data according to the first surgical-data-processing schema. The processor may be configured to output the result to a sensor-data channel.

The process may be configured to receive a surgical-data-processing modification command via a sensor-control channel. And the processor may save a second surgical-data-processing schema to memory according to the surgical-data-processing modification command. The second surgical-data-processing schema may be different than the first surgical-data-processing schema.

The processor may be configured to perform second processing of a second portion of the incoming sensor-data according to the second surgical-data-processing schema. The second processing may be different than the first processing. The processor may be configured to output the result to the sensor-data channel The surgical-data-processing modification command may be triggered based on changing surgical data processing requirements of the surgical procedure. And the surgical-data-processing modification command may direct changes in processing such as output frequency, output resolution, processing resource utilization, operational data transforms, and the like. The surgical-data-processing modification command and the system disclosed herein may be used to implement a variety of processing strategies for surgical sensing, including procedure specific load balancing and sensor prioritization.

A surgical-data-processing modification command may be triggered based on changing surgical data processing requirements of the surgical procedure. And the surgical-data-processing modification command may direct changes in processing such as output frequency, output resolution, processing resource utilization, operational data transforms, and the like. The surgical-data-processing modification command and the system disclosed herein may be used to implement a variety of processing strategies for surgical sensing, including procedure specific load balancing and sensor prioritization.

FIG. 122 is a flow diagram of an example method 29700 for processing surgical data during a surgical procedure. As disclosed herein, during a surgical procedure, there are many sources and/or types of surgical data (such as surgical sensor data for example). Such surgical data may be processed for immediate consumption by other surgical systems and by health care professionals. This processing may occur in real-time, near-real-time, or the like. And the surgical data systems, such as the computer-implemented patient and surgeon monitoring system 20000, disclosed herein with reference to FIG. 1A for example, may include a plurality of processing units at which various aspects of sensor processing may be performed. The methods disclosed herein, including method 29700, and the corresponding device and device combinations implementing these methods with memory and/or processors, may be used to coordinate such surgical sensor data processing. The coordination may promote aspects such as greater system efficiencies, higher system and data reliability, graceful handling of faults and failures, greater overall system flexibility and performance, and the like.

At 29702, first processing may be performed. The first processing may be performed on incoming sensor data. For example, the first processing may be performed on a first portion of the incoming sensor data. The incoming sensor data may be generated by a sensor unit sensing a physical phenomena. The incoming sensor data may be received from an external device.

The first processing may be performed according to a first surgical-data-processing schema. The first surgical-data processing schema may be retrieved from memory, for example. The first processing may be performed for output to a sensor-data channel.

At 29704, a surgical-data-processing modification command may be received. The surgical-data-processing modification command may be received, for example, via a sensor-control channel. The surgical-data-processing modification command may be received from a surgical hub, such as that disclosed herein, for example surgical hub 20006. The surgical-data-processing modification command may be triggered based on changing surgical data processing requirements of the surgical procedure.

A second surgical-data-processing schema may be generated and/or saved to memory according to the received surgical-data-processing modification command. For example, the surgical-data-processing modification command may contain information to update or modify the first surgical-data-processing schema, resulting in the second surgical-data-processing schema. For example, the surgical-data-processing modification command may contain the second surgical-data-processing schema. The second surgical-data-processing schema may be different than the first surgical-data-processing schema. For example, the second surgical-data-processing schema may include different information and/or instructions than the first surgical-data-processing schema.

At 29706, second processing may be performed. The second processing may be performed on incoming sensor data.

For example, the second processing may be performed on a second portion of the incoming sensor data. To illustrate in an actively sensing system during a surgical procedure, the first portion of the incoming sensor data may include sensor values handled before the surgical-data-processing modification command, and the second portion of the incoming sensor data may include sensor values handled after the surgical-data-processing modification command. This arrangement may be used to enable a change in processing relevant to the present values being processed. For example, this arrangement may be appropriate when an absolute value has relevance to the health care professional.

Also for example, the second processing may be performed on the first portion of the incoming sensor data. The first portion of the incoming sensor data may be stored in memory, such as a buffer, cache, data log, history, or other short-term storage, for example. This arrangement may be used to enable a change in processing relevant to a value previous processed. This arrangement may be appropriate when the present value's relation to previous values has relevance to the health care professional.

The second processing may be performed according to the second surgical-data-processing schema. The second processing may be performed for output to the sensor-data channel.

To illustrate, the surgical-data-processing modification command may be used to change sensor processing from the first processing to the second processing. For example, the change in processing may be motivated by the changing data processing needs of the systems and health care professionals in the surgery and/or by the changing data processing needs associated with the surgical procedure itself. For example, the first processing may have a different output frequency than that of the second processing. For example, the first processing may have a different output resolution than that of the second processing. For example, the first processing may be different than the second processing with regard to utilization of processing resources. For example, the first processing may be different than the second processing with regard to a data transform operation.

To illustrate, the surgical-data-processing modification command may be used to perform load balancing. For example, the surgical-data-processing modification command may be used to move a data transform operation (such as a resource intensive data transform operation for example) from one device to another in a system. For example, a surgical-data-processing modification command may be used to cause a particular device to change from a mere passthrough of sensor data to a transform other than mere passthrough. For example, the surgical-data-processing modification command may be used to cause a particular device to change from a transform other than mere passthrough to a mere passthrough of sensor data. Such actions taken by devices in-series is an example way to move processing from one device to another in a system.

The data processing approach disclosed herein, such as that illustrated by method 29700 and/or its steps, may be performed in connection with any appropriate the hardware/software data systems. For example, the hardware/software data systems disclosed herein may be used. For example, the hardware/software data systems, such as those disclosed with regard to FIGS. 7A-D for example, may be used.

For example, referring to FIG. 7A, the processor 20222 and the memory 20223 may be used for implementation. The processor 20222 may perform first processing, second processing, and reception and handling of the surgical-data-processing modification command. For example, referring to FIG. 7B, the data processing unit 20238 and the storage 20239 may be used for implementation. For example, referring to FIG. 7C, the data processing unit 20249 and the storage 20250 may be used for implementation. Also for example, the method 29700 may be performed by the sensor unit 20245 itself. For example, the sensor unit 20245 may include supplementary processing hardware and a sensor data control channel to the data processing and communications unit 20246. Such an implementation may be used, for example, with a reduced set of surgical-data-processing modification commands appropriate to the processing capabilities of the sensor unit 20245. For example, referring to FIG. 7D, the data processing unit 20253 and the storage 20259 may be used for implementation. Also for example, the method 29700 may be performed by the sensor unit 20252 itself. For example, the sensor unit 20252 may include supplementary processing hardware and a sensor data control channel to the data processing and communications unit 20253. Such an implementation may be used, for example, with a reduced set of surgical-data-processing modification commands appropriate to the processing capabilities of the sensor unit 20252.

FIG. 123 is a block diagram of an example sensor data processing system 29710. The system 29710 may include one or more surgical sensor systems 29712, 29714, a surgical sensor data processing device 29716, and one or more downstream systems 29718.

The one or more surgical sensor systems 29712, 29714 may include any of the sensor systems disclosed herein. The surgical sensor systems 29712, 29714 may include any sensing systems suitable for use in connection with a surgical procedure and/or during a surgery. For example, the surgical sensor systems 29712, 29714 may include patient monitoring systems, surgeon monitoring systems, and the like. For example, the surgical sensor systems 29712, 29714 may include environmental sensors. For example, the surgical sensor systems 29712, 29714 may include sensors associated with specific surgical instruments, such as endocutters, surgical staplers, energy devices, and the like. The surgical sensor systems 29712, 29714 may include, for example, those surgical sensing systems 20069 disclosed with reference to FIG. 5.

A surgical sensor system 29712, 29714 may measure a biomarker and communicate information about that biomarker to other devices within the system 29710. A surgical sensor system 29712, 29714 may include a respective surgical-data-processing schema 29720, 29722. The surgical-data-processing schema 29720, 29722 may include information and a corresponding data structure that defines the operation of the corresponding surgical sensor system 29712, 29714. For example, the surgical-data-processing schema 29720, 29722 may include information regarding sensor control, sensing operation, sensor data processing (such as atomic processing, stream processing, and/or composite processing), data formatting, and the like.

The surgical sensor system 29712, 29714 may communicate sensor value information over a respective sensor value data channel 29724, 29726. A sensor value data channel 29724, 29726 may include any data communications protocol suitable for transporting sensor value data, such as user datagram protocol (UDP), transmission control protocol (TCP), hypertext transfer protocol (HTTP), raw data streaming, sensor data transmission and management protocol (STMP), simple sensor interface (SSI), and the like.

To illustrate, the surgical sensor system 29712 may communicate a stream of sensor data 29728. The stream of sensor data 29728 may be communicated over a sensor value data channel 29724. The stream 29728 may include information that represents a serial listing of sensor values 29730, 29732. Each sensor value 29730, 29732 may be accompanied by corresponding metadata, such a sensor system identifier 29734, 29736, a timestamp 29738, 29740, and the like. For example, a stream 29728 may have one or more portions 29742, 29744. A portion 29742, 29744 may represent part of the stream, including one or more values, that are logically grouped together. For example, the portions may be temporally grouped, such that a first portion 29742 is communicated and/or associated with measurements in a corresponding block of time. And a second portion 29744 is communicated and/or associated with measurements in a corresponding different block of time. For example, the first and second portions may be adjacent in time. The portions 29742, 29744 may grouped by metadata for example, such that first and second portions are identified by respective metadata tags for example.

The surgical sensor system 29712, 29714 may communicate commands and related operational information over a respective sensor control channel 29746, 29748. A sensor control channel 29746, 29748 may include any data communications protocol suitable for transporting commands and related operational information, such as user datagram protocol (UDP), transmission control protocol (TCP), hypertext transfer protocol (HTTP), raw data streaming, sensor data transmission and management protocol (STMP), simple sensor interface (SSI), and the like.

The sensor value data channel 29724, 29726 and sensor control channel 29746, 29748 may include different physical communications hardware. The sensor value data channel 29724, 29726 and sensor control channel 29746, 29748 may be communicated over common physical communications hardware. The sensor value data channel 29724, 29726 and sensor control channel 29746, 29748 may include logical channels over the same physical communications hardware. The sensor value data channel 29724, 29726 and sensor control channel 29746, 29748 may receive the same treatment or different treatment from network equipment. For example, the sensor value data channel 29724, 29726 and sensor control channel 29746, 29748 may have different transport characteristics, such as latency, bandwidth, reliability, packet loss, jitter, retransmissions, acknowledgements, negative acknowledgements, and the like. In an example, the sensor value data channel 29724, 29726 may include a high bandwidth, low latency channel with no retransmissions. And the sensor control channel 29746, 29748 may have a high-reliability, reserved bandwidth channel with retransmissions.

The sensor value data channel 29724, 29726 and sensor control channel 29746, 29748 may be used to enable communication between the surgical sensor systems 29712, 29714 and the surgical sensor data processing device 29716. The surgical sensor data processing device 29716 may be configured to receive one or more incoming streams of sensor data (e.g., stream 29728) from one or more respective surgical sensor systems, process that data, and route the resulting data to one or more downstream systems 29718. The surgical sensor data processing device 29716 may be configured to communicate with the one or more downstream system 29718 via a downstream sensor value data channel 29750 and/or a downstream sensor control channel 29752.

The surgical sensor data processing device 29716 may be configured to generate commands and/or receive commands. The surgical sensor data processing device 29716 may be configured to send commands to the one or more surgical sensor systems 29712, 29714. The commands may be used to modify the operation of the surgical sensor systems 29712, 29714. For example, the commands may be used to modify the respective surgical-data-processing schema 29720, 29722 of the surgical sensor systems 29712, 29714.

The surgical sensor data processing device 29716 may have its own surgical-data-processing schema 29753. The surgical-data-processing schema 29753 may define the processing the surgical sensor data processing device 29716 performs on the one or more incoming streams. Commands (from downstream systems 29718 for example) may be used to modify the operation of the surgical sensor data processing device 29716. For example, the commands may be used to modify the surgical-data-processing schema 29753 of the surgical sensor data processing device 29716.

FIGS. 124A-C are example messaging diagrams illustrating, respectively, a processing modification at a surgical sensor system 29712, a processing modification at a surgical sensor data processing device 29716, and a processing modification at both a surgical sensor system 29712 and a surgical sensor data processing device 29716.

In FIG. 124A, the operation of a surgical sensor system 29712 is modified. One or more initialization control messages 29754 may be communicated between the surgical sensor system 29712 and the surgical sensor data processing device 29716 and/or one or more downstream systems 29718. The initialization control messages 29754 may define the initial operation of the surgical sensor system 29712. The initialization control messages 29754 may include operations such as network discovery, device discovery, service discovery, and the like. In an example, the initialization control messages 29754 may include an initial surgical-data-processing schema 29720. In an example, an initial surgical-data-processing schema 29720 may be retrieved from memory local to the surgical sensor system 29712. Such initialization control messages 29754 may be sent over a one or more sensor control channels (for example a sensor control channel 29726 and/or a downstream sensor control channel 29752).

A processor of the surgical sensor system 29712 may receive sensor data. For example, the processor of surgical sensor system 29712 may receive sensor data from an external device (such as an external sensor unit). For example, the processor of the surgical sensor system 29712 may receive sensor data from an internal subsystem (such as an internal transducer, A/D converter, processor, etc.). The surgical sensor system 29712 may process the data. The surgical sensor system 29712 may process the data according to the surgical-data-processing schema 29720. The surgical sensor system 29712 may output the stream of sensor data to the surgical sensor data processing device 29716 and/or one or more downstream systems. For example, a first portion of received sensor data may be represented in a corresponding first output portion 29756. The outputted stream of sensor data may be communicated over a sensor value data channel 29724 and/or a downstream sensor value data channel 29750.

A modification control interaction may occur. The interaction may include one or more commands and responses. For example, the surgical sensor system 29712 may receive a surgical-data-processing modification command 29758. The surgical sensor system 29712 may update the surgical-data-processing schema 29720 according to the surgical-data-processing modification command 29758. And the surgical sensor system 29712 may cease processing incoming sensor values according the processing defined by the initialization control messages 29754 and begin processing incoming sensor values according to the processing defined by the surgical-data-processing modification command 29758. And the surgical sensor system 29712 may continue to output the stream of sensor data, now under modified processing, to the surgical sensor data processing device 29716 and/or one or more downstream systems 29718. For example, a second portion of received sensor data may be represented in a corresponding second output portion 29760.

In FIG. 124B, the operation of the surgical sensor data processing device 29716 is modified. One or more initialization control messages 29762 may be communicated between the surgical sensor data processing device 29716 and one or more downstream systems 29718. The initialization control messages 29762 may define the initial operation of the surgical sensor data processing device 29716. The initialization control messages 29762 may include operations such as network discovery, device discovery, service discovery, and the like. In an example, the initialization control messages 29762 may include an initial surgical-data-processing schema 29753. In an example, an initial surgical-data-processing schema 29753 may be retrieved from memory local to the surgical sensor data processing device 29716. Such initialization control messages 29762 may be sent over a downstream sensor control channel 29752.

The surgical sensor data processing device 29716 may receive sensor data from the surgical sensor system 29712. The surgical sensor data processing device 29716 may process the data. The surgical sensor data processing device 29716 may process the data according to the surgical-data-processing schema 29753. The surgical sensor data processing device 29716 may output the stream of sensor data one or more downstream systems 29718. For example, a first portion 29764 of received sensor data may be represented in a corresponding first output portion 29766. The outputted stream of sensor data may be communicated over a downstream sensor value data channel 29750.

A modification control interaction may occur. The interaction may include one or more commands and responses. For example, the surgical sensor data processing device 29716 may receive a surgical-data-processing modification command 29768. The surgical sensor data processing device 29716 may update the surgical-data-processing schema 29753 according to the surgical-data-processing modification command 29768. And the surgical sensor data processing device 29716 may cease processing the incoming sensor values according the processing defined by the initialization control messages 29762 and begin processing incoming sensor values according to the processing defined by the surgical-data-processing modification command 29768. And surgical sensor data processing device 29716 may continue to output the stream of sensor data, now under modified processing, to one or more downstream systems 29718. For example, a second portion 29770 of received and/or generated sensor data may be represented in a corresponding second output portion 29772.

In FIG. 124C the operation of both a surgical sensor system 29712 and a surgical sensor data processing device 29716 are modified. In this example, the surgical sensor system 29712 may provide a particular data processing operation and that data processing operation may be moved from the surgical sensor system 29712 to the surgical sensor data processing device 29716. To illustrate, such a processing change may be used if the surgical sensor system 29712 were becoming overloaded, for example. Such a processing change may be used if a subsequent part of the surgical procedure required a surgical sensor system 29712 to have a higher sampling rate, for example, and off-loading some aspect of its processing to the surgical sensor data processing device 29716 would enable it to achieve that higher sampling rate.

A processor of the surgical sensor system 29712 may be receiving sensor data. For example, the processor of the surgical sensor system 29712 may receive a first portion of a surgical sensor data stream. The surgical sensor system 29712 may apply a first operation and a second operation to the first portion. The surgical sensor system 29712 may send an outputted first portion 29774. The outputted first portion 29774 may represent sensor data processed by a first and second operation.

The surgical sensor data processing device 29716 may receive the outputted first portion 29774. The surgical sensor data processing device 29716 may apply a third operation to the first portion 29774. The surgical sensor data processing device 29716 may send an outputted first portion 29776 to one or more downstream systems 29718.

Then, based on the data processing requirements of the system for example, the second operation may be moved from the surgical sensor system 29712 to the surgical sensor data processing device 29716. For example, the surgical sensor data processing device 29716 may receive a surgical-data-processing modification command from a downstream system 29718. Also for example, the surgical sensor data processing device 29716 may initiate the processing modification of its own accord.

The surgical sensor data processing device 29716 may send a surgical-data-processing modification command 29778 to the surgical sensor system 29712. The surgical-data-processing modification command 29778 may be triggered based on a load balancing operation between surgical sensor system 29712 and the surgical sensor data processing device 29716. The surgical-data-processing modification command 29778 may be triggered based on a load balancing operation between surgical sensor system 29712 and the surgical sensor data processing device 29716 which is based on changing surgical data processing requirements of the surgical procedure.

The surgical-data-processing modification command 29778 may direct the surgical sensor system 29712 to modify its surgical-data-processing schema 29720, such that the surgical sensor system 29712 would apply the first operation to a second portion of incoming sensor data and not apply the second operation to the second portion of incoming sensor data. Accordingly, the surgical sensor system 29712 may send an outputted second portion 29780. The outputted second portion 29780 may represent sensor data processed by a first operation and not the second operation.

The surgical sensor data processing device 29716 may update its surgical-data-processing schema 29753 such that the surgical sensor data processing device 29716 would apply the second operation and third operation to the second portion 29780. The surgical sensor data processing device 29716 may update its surgical-data-processing schema 29753 of its own accord. The surgical sensor data processing device 29716 may update its surgical-data-processing schema 29753 based on a surgical-data-processing modification command from a downstream system 29718. Accordingly, the surgical sensor data processing device 29716 may send an outputted second portion 29782. The outputted second portion 29780 may represent sensor data processed by the first, second, and third operation.

FIG. 125 is a block diagram of an example surgical-data-processing schema 29784. The surgical-data-processing schema 29784 may include information and a corresponding data structure that define the operation of a corresponding device, such as a corresponding surgical sensor system and/or a corresponding surgical sensor data processing device. The surgical-data-processing schema 29784 may include information regarding sensor control, sensing operation, sensor data processing (such as atomic processing, stream processing, and/or composite processing), data formatting, and the like. The surgical-data-processing schema 29784 may include such information in a structured data format. For example, structured format may be any format for storing and labeling parameters (like control, operation, and/or processing parameters). For example, structured format may be formats such as a proprietary file-type, a comma delimited file, a table, a two-dimensional array, an array of embedded arrays, JavaScript Object Notation (JSON), Extensible Markup Language (XML), a record, a tagged union, an object, a database, a database record, or the like.

An example surgical-data-processing schema 29784 may include control parameters 29786, sensing parameters 29788, atomic processing parameters 29790, stream processing parameters 29792, composite processing parameters 29794, data format parameters 29796, and the like.

The control parameters 29786 may include information regarding the overall and high-level operation of the corresponding device, such as a corresponding surgical sensor system and/or a corresponding surgical sensor data processing device. Control parameters 29786 may include a sensor identifier, a processing identifier, an initialization process key (such as a discovery key, a Trivial File Transfer Protocol (TFTP) link, or the like). The control parameters 29786 may include limits on device operation, such as limits on power consumption, processing resources, and the like. The control parameters 29786 may include communications and/or networking information, such as network types, network node identification, channel information (e.g., information that identifies and defines a corresponding sensor data channel and/or a sensor control channel), channel use information (e.g., information that identifies which channel is to be used when more than one channel for a given type is identified. For example, two sensor data channels may be defined, each to direct sensor data to a respective processing device. The channel use information in the control parameters 29786 may be used select which of those processing devices will receive the output data.), security information (such as public/private keys, authentication methods, encryption type), and the like. The control parameters 29786 may include a master process flow that defines the ordered steps (including any conditional processing) that is to be performed by the device. The master process flow may refer to operations that are further defined by other parameters in the schema 29784.

The sensing parameters 29788 may include any information that defines the operation of converting a physical phenomena to information. The sensing parameters 29788 may include transducer settings, calibration information and settings, sensing resolution, sensing frequency, sample rate, and the like.

The atomic processing parameters 29790 may include any information and/or instructions that define operations to be performed on each value of the sensed data. The atomic processing parameters 29790 may be performed on sensor values individually. The atomic processing parameters 29790 may include information identifying the one or more particular operations to be performed. The atomic processing parameters 29790) may include parameters for each of the particular operations identified. To illustrate, the atomic processing parameters 29790 may include information regarding an offset processing. The atomic processing parameters 29790 may include information that identifies the offset operation. And the atomic processing parameters 29790 may include information that specifies the offset value. Accordingly, a device processing sensor data according to such a surgical-data-processing schema 29784, would output sensor values offset by the specified offset value. Other operations that may be represented in the atomic processing parameters 29790 may include data mapping, thresholding, triggers, down sampling, and the like.

The stream processing parameters 29792 may include any information and/or instructions that define operations to be performed across a plurality of sensor values. The stream processing parameters 29792 may include information identifying the one or more particular operations to be performed. The stream processing parameters 29792 may include parameters for each of the particular operations identified. Operations that may be represented by the stream processing parameters 29792 may include running averages, hysteresis, process chains, statistical processes, filtering (such as noise filters, adaptive filters, low-pass filters, band-pass filters, high-pass filters, and the like), up sampling, and the like.

The composite processing parameters 29794 may include any information and/or instructions that define operations to be performed using values from more than one sensor. The composite processing parameters 29794 may include information identifying the one or more particular operations to be performed. The composite processing parameters 29794 may include parameters for each of the particular operations identified, such as from which sensors to take values for processing. Operations that may be represented by composite parameters 29794 may include sensor fusion operations, conditional operations, complex biomarker mapping operations, virtual sensor operations, and the like.

The data formatting parameters 29796 may include any information and/or instructions that define the data format of the output sensor value stream. The data formatting parameters 29796 may include information regarding units, timestamps, data type, data element precision, and the like.

FIG. 126 is a block diagram of an example sensor processing coordinator 29798. The sensor processing coordinator 29798 may include any hardware, software, and combination thereof suitable for generating surgical-data-processing modification commands 29800. For example, the sensor processing coordinator 29798 may include a processor and/or a memory configured to perform the operations disclosed herein. A sensor processing coordinator 29798 may be incorporated into a surgical hub for example. A sensor processing coordinator 29798 may be incorporated into other devices within a computer-implemented patient and surgeon monitoring system.

A computer-implemented patient and surgeon monitoring system may include one or more sensor processing coordinators 29798. For example, a sensor processing coordinator 29798 may have a global view of the computer-implemented patient and surgeon monitoring system and may generate the surgical-data-processing modification commands 29800 for the whole computer-implemented patient and surgeon monitoring system. Also for example, a sensor processing coordinator 29798 may have a limited view of the computer-implemented patient and surgeon monitoring system and may generate the surgical-data-processing modification commands 29800 for a portion of the computer-implemented patient and surgeon monitoring system. For example, a sensor processing coordinator 29798 may be associated with a particular set of surgical sensing systems and/or surgical sensor data processing devices.

The sensor processing coordinator 29798 may be used within the context of any sensor management system and/or protocol. For example, the sensor processing coordinator 29798 may be incorporated with distributed stream management systems, such as Digital Imaging and Communications in Medicine (DICOM) and BioSignalML markup language, and platforms such as TelegraphCQ, PIPES, Borealis, and the like.

The sensor processing coordinator 29798 may generate the surgical-data-processing modification commands 29800 based on one or more inputs. For example, the sensor processing coordinator 29798 may generate the surgical-data-processing modification commands 29800 based on sensor workload data 29802, procedure plan data 29804, surgical situational awareness data 29806, and the like.

The sensor workload data 29802 may include information that represents the current performance and/or anticipated performance of sensor processing of one or more devices in the system. For example, a surgical sensor data processing device may be utilizing 80% of its processing capacity handling data from four related surgical sensing systems. Such an input may be used by the sensor processing coordinator 29798 to determine whether to generate a surgical-data-processing modification command 29800 to modify the processing being handled by the that device.

The procedure plan data 29804 may include information that represents individual aspects of a surgery and includes information about the expected sensor demand of each aspect. For example, the procedure plan data 29804 may indicate that certain specific surgical tasks during the procedure demand more processing resources than others.

The surgical situational awareness data 29806 may include any other data available in a computer-implemented patient and surgeon monitoring system that may be used to coordinate sensor processing. To illustrate, a surgical instrument (e.g., a surgical instrument not expected from the procedural plan to be used) is turned on. Surgical situational awareness data 29806 may include an indication of the surgical instrument's identifier and an indication that the surgical instrument was activated. Such information about real-time happenings in the surgical theater may be used to by the sensor processing coordinator 29798 to determine whether to generate a surgical-data-processing modification command 29800 to modify the existing sensor processing, for example, to make additional processing capacity available to support operation of the unplanned surgical instrument.

The sensor processing coordinator 29798 may include a master sensor list 29808 and coordination plan 29810. The master sensor list 29808 may include information about the current, past, and expected sensors and devices for use during a surgical procedure. The master list 29808 may include logistical data for all of the devices in the computer-implemented patient and surgeon monitoring system. For example, the master list may include a copy of each device's surgical-data-processing schema.

The coordination plan 29810 may include information related to the operation of the sensors and devices in the computer-implemented patient and surgeon monitoring system. For example, the coordination plan 29810 may include initialization information sensors and devices. For example, the coordination plan 29810 may include mitigation processes for expected changes to the surgical data processing requirements during the surgical procedure. For example, the coordination plan 29810 may include mitigation processes that may be triggered by particular surgical situational awareness triggers. The coordination plan 29810 may include information and/or instructions to implement one or more data processing strategies in the computer-implemented patient and surgeon monitoring system.

In an example, the coordination plan 29810 may include information and/or instructions to implement a load balancing strategy. For example, the coordination plan 29801 may include instructions to, upon detection that a sensing system is near capacity, direct it to cease a portion of its operations, stream raw data to another device, and direct the other device to perform the remaining operations. For example, the coordination plan 29801 may include instructions to identify devices with additional, unused capacity that may be used to assist other devices in the system. Such sensor processing load balancing may improve overall system utilization, data processing speed, data collection rate, and communication bandwidths.

In an example, the coordination plan 29810 may include information and/or instructions to implement particular sensor processing topologies. The sensor processing coordinator may, by adjusting the identity and use of sensor data value channels and the corresponding processing for example, define different topologies and corresponding strategies. For example, the coordination plan 29810 may include information and/or instructions to direct each surgical sensing system to stream their output feeds to a single aggregation device, such as a surgical hub for example. The coordination plan may include information and/or instructions to direct each surgical sensing system to stream at their best collection and transmission rates. The surgical hub may then collect this highest-resolution, raw data and process all streams collectively. Also for example, the coordination plan may include information and/or instructions to define processing sub-units, such that devices send their data to decentralized processing points. The processing points may be defined based on processing capacity, algorithmic co-existence (e.g., pairing processing operations that are memory intensive but not processing intensive with operation that are processing intensive but not memory intensive), functional groups, and the like.

In an example, the coordination plan 29810 may include information and/or instructions to implement particular sensor-prioritization schemes. For example, certain sensor feeds may be categorized with varying degrees of criticality. For example, a two-category scheme may be implemented, such that those with the higher priority may be safely and consistently captured with at least their minimum required frequency and those with the lower priority may be captured on a best-effort basis and/or as capacity is available.

Also, for example, the coordination plan 29810 may include information and/or instructions to prioritize sensor data processing according to situation awareness data 29806 (e.g., current surgical activity and patient biomarkers) and/or procedural plan data 29804. The coordination plan 29810 may include information and/or instructions to prioritize sensor feeds that are more critical for the particular aspect of the procedure, as detected by situation awareness data 29806 and/or as set forth in the procedural plan data 28804, and to deprioritize sensor feeds that are less critical for the particular aspect of the procedure. Prioritization may include enabling higher resolutions, sampling rates, etc. for the more-critical feeds and enabling lower resolutions, sampling rates, etc. for the less-critical feeds. Such a coordination plan 29810 may maximize the utilization of available bandwidth and processing capabilities. Such a coordination plan 29810 may re-balance the computer-implemented patient and surgeon monitoring system throughout the surgery.

In an example, the coordination plan 29810 may be used to limit local processing of sensors based on biomarker or patient-specific parameters. For example, the coordination plan 29810 may be used to limit local processing of sensors based on physiological limits, for example. To illustrate, measuring heart rate variability may require a higher sampling rate than measuring merely the heart rate itself. The same sensor may be used to measure both biomarkers. But if situational awareness data 29806 and/or procedure plan data 28804 calls for heart rate and not heart rate variability, the coordination plan 29810 may include information and/or instructions to adjust the operation of the sensor down accordingly. Such a down adjustment may provide additional capacity in the processing system for other sensors, for example.

The invention claimed is:

1. A method performed by a computing system for securing and recording a consent from a user associated with a healthcare provider, the method comprising:

determining a set of biomarkers associated with the user and a set of user preferences associated with the user, wherein the set of biomarkers is obtained from a wearable device associated with the user;

determining a cognitive ability associated with the user, wherein the cognitive ability is determined based at least on the set of biomarkers;

determining a state of mind of the user, wherein the state of mind is determined by comparing the determined cognitive ability with a cognitive threshold;

obtaining, from the wearable device, data associated with the user;

receiving the consent from the user to share the data obtained from the wearable device with the healthcare provider;

determining that the at least one of the set of user preferences indicates that the user of the wearable device agrees with sharing the data obtained from the wearable device with the healthcare provider;

confirming the consent of the user, wherein the consent of the user is confirmed based on the at least one of the set of user preferences and when the state of mind of the user indicates that the user is able to provide the consent; and based on confirming the consent of the user, sending the data obtained from the wearable device to the healthcare provider.

2. The method of claim 1, wherein the state of mind of the user indicates that the user is non-cognitively impaired.

3. The method of claim 1, wherein the consent from the user indicates that the healthcare provider has permission to one or more of accessing the data, controlling the data, monitoring the data, receiving a notification associated with the data, or receiving a notification associated with the wearable device.

4. The method of claim 1, wherein the healthcare provider is a first healthcare provider and wherein the consent from the user to share the data from the wearable device with the healthcare provider further indicates that the first healthcare provider has permission to receive one or more of information from a second healthcare provider and or patient instructions from the second healthcare provider.

5. The method of claim 4, further comprising receiving an identification of the second healthcare provider from the user.

6. The method of claim 1, wherein the method further comprises denying the consent of the user when the state of mind of the user indicates that the cognitive ability associated with the user is at or below the cognitive threshold.

7. The method of claim 1, wherein the method further comprises denying the consent of the user when the state of mind of the user indicates one or more of a user cognitive impairment and or an inability of the user to provide the consent.

8. A computing system for securing a consent from a user to record measurements and communicate with a healthcare provider, the computing system comprising:

a memory, and a processor, the processor configured to:

determine whether an identity of the user of a wearable device can be confirmed;

determine a set of biomarkers associated with the user and a set of user preferences associated with the user, wherein the set of biomarkers is obtained from the wearable device;

determine a cognitive ability associated with the user, wherein the cognitive ability is determined based at least on the set of biomarkers;

determine a state of mind of the user, wherein the state of mind is determined by comparing the determined cognitive ability with a cognitive threshold;

obtain, from the wearable device, data associated with the user;

receive the consent from the user to share the data obtained from the wearable device with the healthcare provider; and confirm the consent of the user based on a determination that the identity of the user is confirmed, a determination that at least one of the set of user preferences indicates that the user of the wearable device agrees with sharing the data obtained from the wearable device with the healthcare provider, and a determination that the state of mind of the user indicates that the user is able to provide the consent.

9. The computing system of claim 8, wherein the state of mind of the user indicates that the user is non-cognitively impaired.

10. The computing system of claim 8, wherein the consent from the user to share the data from the wearable device with the healthcare provider further indicates that the healthcare provider has permission to one or more of accessing the data, controlling the data, monitor the data, receiving a notification associated with the data, or receiving a notification associated with the wearable device.

11. The computing system of claim 8, wherein the healthcare provider is a first healthcare provider and wherein the consent from the user to share the data from the wearable device with the healthcare provider further indicates that the first healthcare provider has permission to receive one or more of information from a second healthcare provider and patient instructions from the second healthcare provider.

12. The computing system of claim 11, wherein the processor is further configured to receive an identification of the second healthcare provider from the user.

13. The computing system of claim 8, wherein the processor is further configured to deny the consent of the user when the state of mind of the user indicates that the cognitive ability associated with the user is at or below the cognitive threshold.

14. The computing system of claim 8, wherein the processor is further configured to deny the consent of the user when the state of mind of the user indicates at least a user cognitive impairment, or an inability of the user to provide the consent.

15. The computing system of claim 8, wherein the processor is further configured to deny the consent of the user when the identity of the user is not confirmed.

16. A computing system for securing a consent from a user to record measurements and communicate with a healthcare provider, the computing system comprising:

a memory, and a processor, the processor configured to:

verify an identity of the user of a wearable device;

obtain, from the wearable device, data associated with the user;

obtain, from the wearable device, a set of biomarkers associated with the user;

obtain a set of user preferences associated with the user;

determine, based on a cognitive ability associated with the user and a cognitive threshold, that a state of mind of the user indicates that the user is able to provide the consent, wherein the cognitive ability is based at least on the set of biomarkers associated with the user;

receive an indication of the consent from the user to share the data obtained from the wearable device with the healthcare provider;

confirm based on the indication of the consent from the user to share the data obtained from the wearable device with the healthcare provider, at least one of the set of user preferences associated with the user, and the cognitive ability associated with the user that the user of the wearable device agrees to share the data obtained from the wearable device with the healthcare provider; and send the data obtained from the wearable device to the healthcare provider.

17. The computing system of claim 16, wherein the processor is being configured to determine that the state of mind of the user indicates that the user is able to provide the consent comprises the processor being configured to determine that the state of mind of the user indicates that the cognitive ability of the user is at or above the cognitive threshold.

18. The computing system of claim 16, wherein the processor being configured to determine that the state of mind of the user indicates that the user is able to provide the consent comprises the processor being configured to determine that one biomarker of the set of biomarkers associated with the user is at or above a threshold value.

19. The computing system of claim 16, wherein the processor being configured to determine the cognitive ability comprises the processor being configured to determine a first biomarker associated with the user and determine a second biomarker associated with the user.

20. The computing system of claim 16, wherein the processor being configured to verify the identity of the user of the wearable device comprises the processor being configured to confirm the identity of the user with at least one of a database, an electronic medical record, an identification, a photo, a voice recording, or a biomarker of the set of biomarkers.

* * * * *